(12) United States Patent
Kurtz et al.

(10) Patent No.: US 11,965,215 B2
(45) Date of Patent: Apr. 23, 2024

(54) METHODS AND SYSTEMS FOR ANALYZING NUCLEIC ACID MOLECULES

(71) Applicant: The Board of Trustees of the Leland Stanford Junior University, Stanford, CA (US)

(72) Inventors: David M. Kurtz, San Carlos, CA (US); Maximilian Diehn, San Carlos, CA (US); Arash Ash Alizadeh, San Mateo, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 18/167,804

(22) Filed: Feb. 10, 2023

(65) Prior Publication Data
US 2024/0026460 A1    Jan. 25, 2024

Related U.S. Application Data

(63) Continuation of application No. 17/646,473, filed on Dec. 29, 2021, now Pat. No. 11,613,787, which is a continuation of application No. PCT/US2020/059526, filed on Nov. 6, 2020.

(60) Provisional application No. 62/931,688, filed on Nov. 6, 2019.

(51) Int. Cl.
| | |
|---|---|
| *G16B 30/10* | (2019.01) |
| *C12N 15/10* | (2006.01) |
| *C12Q 1/6869* | (2018.01) |
| *C12Q 1/6874* | (2018.01) |
| *C12Q 1/6886* | (2018.01) |
| *G16B 20/00* | (2019.01) |
| *G16B 20/10* | (2019.01) |
| *G16B 20/20* | (2019.01) |
| *G16B 30/00* | (2019.01) |
| *G16B 35/20* | (2019.01) |
| *G16B 40/00* | (2019.01) |
| *G16H 10/40* | (2018.01) |
| *G16H 20/10* | (2018.01) |
| *G16H 50/20* | (2018.01) |
| *G16H 50/30* | (2018.01) |
| *G16H 50/70* | (2018.01) |
| *G16H 70/60* | (2018.01) |
| *G16H 10/60* | (2018.01) |

(52) U.S. Cl.
CPC ....... *C12Q 1/6886* (2013.01); *C12N 15/1089* (2013.01); *C12Q 1/6869* (2013.01); *C12Q 1/6874* (2013.01); *G16B 20/00* (2019.02); *G16B 20/10* (2019.02); *G16B 20/20* (2019.02); *G16B 30/00* (2019.02); *G16B 30/10* (2019.02); *G16B 35/20* (2019.02); *G16B 40/00* (2019.02); *G16H 10/40* (2018.01); *G16H 20/10* (2018.01); *G16H 50/20* (2018.01); *G16H 50/30* (2018.01); *G16H 50/70* (2018.01); *G16H 70/60* (2018.01); *C12Q 2600/112* (2013.01); *C12Q 2600/156* (2013.01); *C12Q 2600/158* (2013.01); *G01N 2800/7028* (2013.01); *G16H 10/60* (2018.01)

(58) Field of Classification Search
None
See application file for complete search history.

(56) References Cited

U.S. PATENT DOCUMENTS

| | | |
|---|---|---|
| 5,804,396 A  | 9/1998  | Plowman |
| 6,171,856 B1 | 1/2001  | Thigpen et al. |
| 8,105,769 B2 | 1/2012  | Bell et al. |
| 8,318,433 B2 | 11/2012 | Brenner |
| 8,580,497 B2 | 11/2013 | Stratton et al. |
| 8,722,368 B2 | 5/2014  | Casbon et al. |
| 8,741,606 B2 | 6/2014  | Casbon et al. |
| 8,835,358 B2 | 9/2014  | Fodor et al. |
| 9,035,036 B2 | 5/2015  | Bell et al. |
| 9,340,830 B2 | 5/2016  | Lipson et al. |
| 9,598,731 B2 | 3/2017  | Talasaz |
| 9,752,188 B2 | 9/2017  | Schmitt et al. |
| 9,834,822 B2 | 12/2017 | Talasaz |
| 9,840,743 B2 | 12/2017 | Talasaz |
| 9,850,523 B1 | 12/2017 | Chudova et al. |
| 9,902,992 B2 | 2/2018  | Talasaz et al. |
| 9,920,366 B2 | 3/2018  | Eltoukhy et al. |
| 10,041,127 B2 | 8/2018 | Talasaz |
| 10,450,611 B2 | 10/2019 | West et al. |
| 10,457,955 B2 | 10/2019 | Kumar et al. |
| 10,494,678 B2 | 12/2019 | Talasaz |
| 10,501,808 B2 | 12/2019 | Talasaz |

(Continued)

FOREIGN PATENT DOCUMENTS

| | | |
|---|---|---|
| BR | 112022008752 A2 | 8/2022 |
| CN | 109337983 A     | 2/2019 |

(Continued)

OTHER PUBLICATIONS

Chaudhuri et al., Early Detection of Molecular Residual Disease in Localized Lung Cancer by Circulating Tumor DNA Profiling, Cancer Discovery, vol. 7, No. 12, Dec. 2017, pp. 1394-1403.

(Continued)

*Primary Examiner* — Joseph Woitach
(74) *Attorney, Agent, or Firm* — KPPB LLP

(57) ABSTRACT

Processes and materials to detect cancer from a biopsy are described. In some cases, cell-free nucleic acids can be sequenced, and the sequencing result can be utilized to detect sequences derived from a neoplasm. Detection of somatic variants occurring in phase can indicate the presence of cancer in a diagnostic scan and a clinical intervention can be performed.

24 Claims, 86 Drawing Sheets
Specification includes a Sequence Listing.

(56) References Cited

U.S. PATENT DOCUMENTS

| | | |
|---|---|---|
| 10,501,810 B2 | 12/2019 | Talasaz |
| 10,704,085 B2 | 7/2020 | Talasaz et al. |
| 10,704,086 B2 | 7/2020 | Talasaz et al. |
| 10,738,364 B2 | 8/2020 | Talasaz |
| 11,299,783 B2 | 4/2022 | West et al. |
| 11,384,394 B2 | 7/2022 | Bartha et al. |
| 11,447,833 B2 | 9/2022 | Kurtz et al. |
| 11,613,787 B2 | 3/2023 | Kurtz et al. |
| 11,634,779 B2 | 4/2023 | Kurtz et al. |
| 11,783,912 B2 | 10/2023 | Chabon et al. |
| 2002/0015718 A1 | 2/2002 | Kruse et al. |
| 2013/0210645 A1 | 8/2013 | Volgelstein et al. |
| 2014/0227705 A1 | 8/2014 | Vogelstein et al. |
| 2014/0296081 A1 | 10/2014 | Diehn et al. |
| 2015/0024950 A1 | 1/2015 | Bielas et al. |
| 2015/0376700 A1 | 12/2015 | Schnall-Levin et al. |
| 2016/0032396 A1 | 2/2016 | Diehn et al. |
| 2017/0107576 A1 | 4/2017 | Babiarz et al. |
| 2018/0251848 A1 | 9/2018 | Diehn et al. |
| 2018/0265928 A1 | 9/2018 | Schnall-Levin et al. |
| 2019/0264257 A1 | 8/2019 | Desharnais et al. |
| 2020/0131505 A1 | 4/2020 | Green et al. |
| 2021/0025005 A1 | 1/2021 | Babiarz et al. |
| 2021/0172022 A1 | 6/2021 | Kurtz et al. |
| 2021/0366571 A1 | 11/2021 | Kurtz et al. |
| 2022/0251664 A1 | 8/2022 | Kurtz et al. |
| 2022/0375540 A1 | 11/2022 | Chabon et al. |
| 2022/0389518 A1 | 12/2022 | Kurtz et al. |
| 2023/0124070 A1 | 4/2023 | Kurtz et al. |
| 2023/0183816 A1 | 6/2023 | Kurtz et al. |
| 2023/0203597 A1 | 6/2023 | Kurtz et al. |

FOREIGN PATENT DOCUMENTS

| | | |
|---|---|---|
| CN | 113383085 A | 9/2021 |
| CN | 115443341 A | 12/2022 |
| DE | 112020005433 T5 | 10/2022 |
| EP | 3561075 A1 | 10/2019 |
| EP | 4055187 A1 | 9/2022 |
| EP | 4110397 A1 | 1/2023 |
| EP | 4110957 A2 | 1/2023 |
| GB | 2595193 A | 11/2021 |
| GB | 2595193 B | 10/2022 |
| HK | 40060652 A | 5/2022 |
| HK | 40064341 | 6/2022 |
| IN | 202217026392 | 4/2022 |
| JP | 2023501376 A | 1/2023 |
| KR | 20220094218 A | 7/2022 |
| KR | 20220145891 A | 10/2022 |
| KR | 20220157976 A | 11/2022 |
| WO | WO-2014151117 A1 | 9/2014 |
| WO | WO-2015188192 A2 | 12/2015 |
| WO | WO-2016040901 A1 | 3/2016 |
| WO | WO-2017100441 A1 | 6/2017 |
| WO | 20170161175 A1 | 9/2017 |
| WO | WO-2018231818 A1 | 12/2018 |
| WO | WO-2020154682 A2 | 7/2020 |
| WO | WO-2020204674 A2 | 10/2020 |
| WO | WO-2021003485 A1 | 1/2021 |
| WO | WO-2021092476 A1 | 5/2021 |
| WO | WO-2021173722 A1 | 9/2021 |
| WO | WO-2021173724 A1 | 9/2021 |
| WO | WO-2021173722 A3 | 10/2021 |
| WO | WO-2022236221 A1 | 11/2022 |

OTHER PUBLICATIONS

Kurtz et al., Phased Variant Enrichment for Enhanced Minimal Residual Disease Detection from Cell-Free DNA, Blood, vol. 134, Supp. 1, Nov. 13, 2019, pp. 552.

Kurtz, "Personalized Risk Assessment and Disease Monitoring in Non-Hodgkin Lymphoma From Circulating Tumor DNA", ProQuest, Dec. 2017, 258 pgs.

Abbosh et al. Abstract CT023: Phylogenetic tracking and minimal residual disease detection using ctDNA in early-stage NSCLC: A lung TRACERx study. Cancer Research, Proceedings: AACR Annual Meeting 2020; Apr. 27-28, 2020 and Jun. 22-24, 2020; Philadelphia, PA. Published Aug. 2020. Accessed Sep. 14, 2021 at: https://cancerres.aacrjournals.org/content/80/16_Supplement/CT023.4 pages.

Abbosh et al., "Early stage NSCLC—challenges to implementing ctDNA-based screening and MRD detection", Nature Reviews Clinical Oncology, vol. 15, Jul. 3, 2018, pp. 577-586.

Abbosh et al., "Phylogenetic ctDNA analysis depicts early-stage lung cancer evolution", Nature, vol. 545, Apr. 26, 2017, pp. 446-451.

Alexandrov et al., "Clock-like mutational processes in human somatic cells", Nature Genetics, vol. 47, Nov. 9, 2015, pp. 1402-1407.

Alexandrov, et al. Signatures of mutational processes in human cancer. Nature. Aug. 22, 2013;500(7463):415-421. doi: 10.1038/nature12477. Epub Aug. 14, 2013.

Alexandrov, et al. The repertoire of mutational signatures in human cancer. Nature. Feb. 2020;578(7793):94-101. doi: 10.1038/s41586-020-1943-3. Epub Feb. 5, 2020.

Alizadeh, et al. Distinct types of diffuse large B-cell lymphoma identified by gene expression profiling. Nature. Feb. 3, 2000;403(6769):503-11.

Alkodsi et al., "Distinct subtypes of diffuse large B-cell lymphoma defined by hypermutated genes", Leukemia, vol. 33, Jun. 11, 2019, pp. 2662-2672.

Bell et al., "Chromosome-scale mega-haplotypes enable digital karyotyping of cancer aneuploidy", Nucleic Acids Research, vol. 45, No. 19, Nov. 2, 2017, 13 pgs.

Bettegowda et al. Detection of Circulating Tumor DNA in Early- and Late-Stage Human Malignancies. Sci. Transl. Med. 6(224):224ra24 (2014).

Bianconi et al., "An estimation of the No. of cells in the human body", Annals of Human Biology, vol. 40, No. 6, Jul. 5, 2013, pp. 463-471.

Bozdech et al., "Expression profiling of the schizont and trophozoite stages of Plasmodium falciparum with a long-oligonucleotide microarray", Genome Biology, vol. 4, No. R9, Jan. 31, 2003, 15 pgs.

Brenner, et al. Next-generation sequencing diagnostics of bacteremia in sepsis (Next GeneSiS-Trial): Study protocol of a prospective, observational, noninterventional, multicenter, clinical trial. Medicine (Baltimore). Feb. 2018;97(6):e9868. doi: 10.1097/MD.0000000000009868.

Burns, et al. Evidence for APOBEC3B mutagenesis in multiple human cancers. Nat Genet. Sep. 2013; 45(9): 977-983. Published online Jul. 14, 2013. doi: 10.1038/ng.2701.

Chabon, et al. Circulating tumour DNA profiling reveals heterogeneity of EGFR inhibitor resistance mechanisms in lung cancer patients. Nat Commun. Jun. 10, 2016;7:11815. doi: 10.1038/ncomms11815.

Cibulskis et al. Sensitive detection of somatic point mutations in impure and heterogenous cancer samples. Nat Biotechnol 31:213-219 (2013).

Copyright Reminder: Dissertations, Stanford Libraries website, accessed on Aug. 18, 2021; Available online at: https://library.stanford.edu/using/copyright-reminder/common-situations/dissertations.

Corcoran et al., "Application of Cell-free DNA Analysis to Cancer Treatment", The New England Journal of Medicine, vol. 379, pp. 1754-1765 (2018).

De Vlaminck, et al. Circulating cell-free DNA enables noninvasive diagnosis of heart transplant rejection. Sci Transl Med. Jun. 18, 2014;6(241):241ra77. doi: 10.1126/scitranslmed.3007803.

De Vlaminck, et al. Noninvasive monitoring of infection and rejection after lung transplantation. Proc Natl Acad Sci USA. Oct. 27, 2015;112(43):13336-13341. doi: 10.1073/pnas.1517494112. Epub Oct. 12, 2015.

De Yébenes, et al. Activation-induced deaminase: light and dark sides. Trends Mol Med. Sep. 2006;12(9):432-439. doi: 10.1016/j.molmed.2006.07.001. Epub Jul. 24, 2006.

(56) References Cited

OTHER PUBLICATIONS

Deng et al., "TNER: a novel background error suppression method for mutation detection in circulating tumor Dna", Bmc Bioinformatics, vol. 19, No. 387, Oct. 20, 2018, 7 pgs.
Dewey et al. Phased whole-genome genetic risk in a family quartet using a major allele reference sequence. PLoS Genetics 7(9):e1002280 (2011).
Diaz, et al. Performance of Streck cfDNA Blood Collection Tubes for Liquid Biopsy Testing. PLoS One. Nov. 10, 2016;11(11):e0166354. doi: 10.1371/journal.pone.0166354. eCollection 2016.
Diehl et al. Circulating mutant DNA to assess tumor dynamics. Nat Med 14(9):985-990 (2008).
Dissertations and Theses. Stanford Libraries, Robin Li and Melissa M Science Library. (Website.) Accessed Sep. 11, 2021 at: https://library.stanford.edu/science/collections/chemistry-and-chemical-engineering-collection/dissertations-and-theses . 4 pages.
"Dissertations and theses", Stanford Libraries, Special Collections & University Archives, Retrieved from https://library.stanford.edu/using/copyright-reminder/ common-situations/dissertations on Jun. 21, 2021, 3 pgs.
Dou et al., "Detecting Somatic Mutations in Normal Cells", Trends Genet. Jul. 2018, 34(7):545-557. doi:10.1016/j.tig.2018.04.003.
EDissertation Requirements for Submission, Stanford University Registrar's office: Student affairs website, accessed Jun. 24, 2021 at https://registrar.stanford.edu/students/dissertation-and-thesis-submission/preparing-dissertations-electronic-submission.
"Embargo and Restriction Options", ProQuest, Retrieved from https://support.proquest.com/articledetail?id=kA0400000004JJCCA2 on Sep. 15, 2021, 4 pgs.
Fan, et al. Noninvasive diagnosis of fetal aneuploidy by shotgun sequencing DNA from maternal blood. Proc Natl Acad Sci U S A. Oct. 21, 2008; 105(42):16266-71. Epub Oct. 6, 2008.
Format Requirements for eDissertation, Stanford University, Registrar's office: Student affairs website, accessed Aug. 19, 2021 at https://registrar.stanford.edu/students/dissertation-and-thesis-submission/preparing-dissertations-electronic-submission/format.
Garcia-Murillas, et al. Mutation tracking in circulating tumor DNA predicts relapse in early breast cancer. Sci Transl Med. Aug. 26, 2015;7(302):302ra133. doi: 10.1126/scitranslmed.aab0021.
Jaeger et al., "Improved predictions of secondary structures for RNA", Proceedings of the National Academy of Sciences, vol. 86, No. 20, Oct. 1, 1989, pp. 7706-7710.
Jiang, P. et al. Lengthening and shortening of plasma DNA in hepatocellular carcinoma patients. Proc Natl Acad Sci U S A 2015;112:E1317-25.
Kalinich, et al. Cancer detection: Seeking signals in blood. Science. Feb. 23, 2018;359(6378):866-867. doi: 10.1126/science.aas9102.
Kennedy et al. Detecting ultralow-frequency mutations by Duplex Sequencing. Nature Protocols 9(11):2586-2606 (2014).
Khodabakhshi, et al. Recurrent targets of aberrant somatic hypermutation in lymphoma. Oncotarget. Nov. 2012;3(11):1308-1319. doi: 10.18632/oncotarget.653.
Kim, S. et al. Strelka2: fast and accurate calling of germline and somatic variants. Nat. Methods 15; 591-594, Jul. 16, 2018.
Koboldt, et al. VarScan 2: somatic mutation and copy number alteration discovery in cancer by exome sequencing. Genome Res. Mar. 2012;22(3):568-76. doi: 10.1101/gr.129684.111. Epub Feb. 2, 2012.
Kurtz et al., "Circulating Tumor DNA Measurements as Early Outcome Predictors in Diffuse Large B-Cell Lymphoma", Journal of Clinical Oncology: Official Journal of the American Society of Clinical Oncology, vol. 36, No. 28, Oct. 1, 2018, pp. 2845-2853.
Kurtz et al., "Noninvasive monitoring of diffuse large B-cell lymphoma by immunoglobulin high-throughput sequencing", Blood, vol. 125, No. 24, Jun. 11, 2015, pp. 3679-3687.
Kurtz et al., "Reply to J. Wang et al.", Journal of Clinical Oncology: Official Journal of the American Society of Clinical Oncology, vol. 37, No. 9, Mar. 20, 2019, pp. 755-757.
Lenz, et al. Aberrant immunoglobulin class switch recombination and switch translocations in activated B cell-like diffuse large B cell lymphoma. J Exp Med. Mar. 19, 2007;204(3):633-643. doi: 10.1084/jem.20062041. Epub Mar. 12, 2007.
Li, et al. Fast and accurate short read alignment with Burrows-Wheeler transform. Bioinformatics. Jul. 15, 2009;25(14):1754-1760. doi: 10.1093/bioinformatics/btp324. Epub May 18, 2009.
Librarian view of catalog entry for: "Personalized risk assessment and disease monitoring in non-Hodgkin lymphoma from circulating tumor DNA, David Kurtz"; date catalogued: Dec. 11, 2017. Accessed Aug. 19, 2021.
Lieber, "Mechanisms of human lymphoid chromosomal translocations", Nature Reviews Cancer, vol. 16, May 25, 2016, pp. 387-398.
Lo, et al. Prenatal Diagnosis of Fetal RhD Status by Molecular Analysis of Maternal Plasma. New England Journal of Medicine, 339:1734-1738 (Dec. 10, 1998).
Lo, et al. Presence of fetal DNA in maternal plasma and serum. The Lancet, Aug. 16, 1997, vol. 350, 485-487.
Lu et al., "BCL6 breaks occur at different AID sequence motifs in Ig-BCL6 and non-Ig-BCL6 rearrangements", Blood, vol. 121, No. 22, May 30, 2013, pp. 4551-4554.
Morin, et al. Mutational and structural analysis of diffuse large B-cell lymphoma using whole-genome sequencing. Blood. Aug. 15, 2013;122(7):1256-1265. doi: 10.1182/blood-2013-02-483727. Epub May 22, 2013.
Nakamura, et al. Analysis of the immunoglobulin heavy chain gene variable region of CD5-positive and -negative diffuse large B cell lymphoma. Leukemia. Mar. 2001; 15(3):452-457. doi: 10.1038/sj.leu.2402031.
Neelapu et al., "Axicabtagene Ciloleucel CAR T-Cell Therapy in Refractory Large B-Cell Lymphoma", The New England Journal of Medicine, vol. 377, No. 26, Dec. 28, 2017, pp. 2531-2544.
Newman et al. An ultrasensitive method for quantitating circulating tumor DNA with broad patient coverage. Nat Med. May 2014 ; 20(5): 548-554. With Supplementary Text and Figures (Supplementary Figures 1-8 and Supplementary Methods) and Supplementary Table 1 (NSCLC selector design and coordinates).
Newman, et al. An ultrasensitive method for quantitating circulating tumor DNA with broad patient coverage. Nat Med. May 2014;20(5):548-54. Epub Apr. 6, 2014.
Newman, et al. Integrated digital error suppression for improved detection of circulating tumor DNA. Nat Biotechnol. May 2016;34(5):547-555. doi: 10.1038/nbt.3520. Epub Mar. 28, 2016.
Notice of Allowance for U.S. Appl. No. 17/455,209, dated Apr. 18, 2022, 10 pgs.
Office Action for U.S. Appl. No. 17/107,668, dated Jun. 17, 2021, 27 pgs.
Office Action for U.S. Appl. No. 17/107,668, dated Oct. 21, 2021, 40 pgs.
"Pan-cancer analysis of whole genomes", The ICGC/TCGA Pan-Cancer Analysis of Whole Genomes Consortium, Nature, vol. 578, Feb. 5, 2020, pp. 82-93.
Papageorgiou et al. Fetal-specific DNA methylation ratio permits noninvasive prenatal diagnosis of trisomy 21. Nat Med. Apr. 2011;17(4):510-3. doi: 10.1038/nm.2312. Epub Mar. 6, 2011.
Pasqualucci et al. Analysis of the coding genome of diffuse large B-cell lymphoma. Nature Genet. 43(9):830-837 (2011).
Pasqualucci, et al. Hypermutation of multiple proto-oncogenes in B-cell diffuse large-cell lymphomas. Nature. Jul. 19, 2001;412(6844):341-346. doi: 10.1038/35085588.
Permission to Publish, Stanford Libraries Special Collections & University Archives website, accessed on Aug. 30, 2021; available online at: https://library.stanford.edu/spc/using-our-collections/permission-publish.
Personalized risk assessment and disease monitoring in non-Hodgkin lymphoma from circulating tumor DNA [electronic resource], Stanford University Library Searchworks Catalog entry accessed Jul. 21, 2021, available online at: https://searchworks.stanford.edu/view/12266090.
Phallen, et al. Direct detection of early-stage cancers using circulating tumor DNA. Science translational medicine 9.403 (2017): eaan2415.
Puente, et al. Non-coding recurrent mutations in chronic lymphocytic leukaemia. Nature. Oct. 22, 2015;526(7574):519-524. doi: 10.1038/nature14666. Epub Jul. 22, 2015.

(56) References Cited

OTHER PUBLICATIONS

Qian, et al. B cell super-enhancers and regulatory clusters recruit AID tumorigenic activity. Cell. Dec. 18, 2014;159(7):1524-1537.
Reading room policies & procedures, Stanford Libraries, Special Collections and University Archives website, accessed on Jul. 30, 2021, available online at: https://library.stanford.edu/spc/using-our-collections/reading-room-policies-procedures .
Reinert et al., "Analysis of Plasma Cell-Free DNA by Ultradeep Sequencing in Patients With Stages I to III Colorectal Cancer", JAMA Oncology, vol. 5, No. 8, May 9, 2019, pp. 1124-1131.
Response to Jun. 17, 2021 Office Action for U.S. Appl. No. 17/107,668, filed Sep. 17, 2021, 79 pgs.
Response to Oct. 21, 2021 Office Action for U.S. Appl. No. 17/107,668, filed Apr. 21, 2022, 101 pgs.
Restriction Requirement for U.S. Appl. No. 17/107,668, dated Apr. 26, 2021, 9 pgs.
Richter, et al. Recurrent mutation of the ID3 gene in Burkitt lymphoma identified by integrated genome, exome and transcriptome sequencing. Nat Genet. Dec. 2012;44(12):1316-1320. doi: 10.1038/ng.2469. Epub Nov. 11, 2012.
Robbiani et al., "AID Is Required for the Chromosomal Breaks in c-myc that Lead to c-myc/IgH Translocations", Cell, vol. 135, No. 6, Dec. 12, 2008, pp. 1028-1038.
Roschewski et al., "Circulating tumour DNA and CT monitoring in patients with untreated diffuse large B-cell lymphoma: a correlative biomarker study", The Lancet Oncology, vol. 16, No. 5, May 1, 2015, pp. 541-549.
Rosenthal, et al. DeconstructSigs: delineating mutational processes in single tumors distinguishes DNA repair deficiencies and patterns of carcinoma evolution. Genome Biol. Feb. 22, 2016;17:31. doi: 10.1186/s13059-016-0893-4.
Rowley, "Chromosome studies in the non-Hodgkin's lymphomas: the role of the 14;18 translocation", Journal of Clinical Oncology: Official Journal of the American Society of Clinical Oncology, vol. 6, No. 5, May 1988, pp. 919-925.
Scherer, et al. Distinct biological subtypes and patterns of genome evolution in lymphoma revealed by circulating tumor DNA. Sci Transl Med. Nov. 9, 2016;8(364):364ra155. doi: 10.1126/scitranslmed.aai8545.
Scherer et al., "High-throughput sequencing for noninvasive disease detection in hematologic malignancies", Blood, vol. 130, No. 4, Jul. 27, 2017, pp. 440-452.
Schmitt et al., "Detection of ultra-rare mutations by next-generation sequencing", Proceedings of the National Academy of Sciences, vol. 109, No. 36, Sep. 4, 2012, pp. 14508-14513.
Schmitz et al., "Burkitt lymphoma pathogenesis and therapeutic targets from structural and functional genomics", Nature, vol. 490, Aug. 12, 2012, pp. 116-120.
Schmitz, et al. Genetics and Pathogenesis of Diffuse Large B-Cell Lymphoma. N Engl J Med. Apr. 12, 2018;378(15):1396-1407. doi: 10.1056/NEJMoa1801445.
Sozzi, et al. Analysis of circulating tumor DNA in plasma at diagnosis and during follow-up of lung cancer patients. Cancer Res. Jun. 15, 2001;61(12):4675-4678.
Special Policies: Guidelines to counsel & researchers seeking discovery from Stanford Libraries, Stanford Libraries, accessed on Jun. 25, 2021; available online at: https://library.stanford.edu/using/special-policies/guidelines-counsel-researchers-seeking-discovery-stanford-libraries.
Steidl et al., "MHC class II transactivator CIITA is a recurrent gene fusion partner in lymphoid cancers", Nature, vol. 471, Mar. 2, 2011, pp. 377-381.
Sugimoto et al., "Improved Thermodynamic Parameters and Helix Initiation Factor to Predict Stability of DNA Duplexes", Nucleic Acids Research, vol. 24, No. 22, Nov. 1, 1996, pp. 4501-4505.
Thierry, et al. Clinical validation of the detection of KRAS and BRAF mutations from circulating tumor DNA. Nat Med. Apr. 2014;20(4):430-5. doi: 10.1038/nm.3511. Epub Mar. 23, 2014.
Tie, et al. Circulating tumor DNA analysis detects minimal residual disease and predicts recurrence in patients with stage II colon cancer. Sci Transl Med. Jul. 6, 2016;8(346):346ra92. doi: 10.1126/scitranslmed.aaf6219.
U.S. Appl. No. 17/455,209 Notice of Allowance dated Aug. 2, 2022.
U.S. Appl. No. 17/455,209 Notice of Allowance dated Jun. 13, 2022.
U.S. Appl. No. 17/646,472 Office Action dated Aug. 29, 2022.
U.S. Appl. No. 17/661,730 Office Action dated Aug. 22, 2022.
"Using our collections", Stanford Libraries, Special Collections & University Archives, Retrieved from https://library.stanford.edu/spc/using-our-collections on Aug. 19, 2021, 3 pgs.
Van der Auwera, G. A. et al. From FastQ data to high-confidence variant calls: the Genome Analysis Toolkit best practices pipeline. Curr. Protoc. Bioinformatics 43, Published online Oct. 15, 2013.
Vaqué, et al. B-cell lymphoma mutations: improving diagnostics and enabling targeted therapies. Haematologica. Feb. 2014;99(2):222-231. doi: 10.3324/haematol.2013.096248.
Wang, et al. Diagnosis of Pneumocystis jirovecii pneumonia with serum cell-free DNA in non-HIV-infected immunocompromised patients. Oncotarget. May 20, 20170;8(42):71946-71953. doi: 10.18632/oncotarget.18037. eCollection Sep. 22, 2017.
Ardila et al., "End-to-end lung cancer screening with three-dimensional deep learning on low-dose chest computed tomography", Nat. Med., Jun. 2019, vol. 25, No. pp. 954-961, published online May 20, 2019, doi: 10.1038/s41591-019-0447-x.
Bailey, et al. Comprehensive characterization of cancer driver genes and mutations. Cell 173.2 (2018): 371-385.
Ballenghien et al., "Patterns of cross-contamination in a multispecies population genomic project: detection, quantification, impact, and solutions", BMC Biology, vol. 15, No. 25, Mar. 29, 2017, 16 pgs.
Bandelt et al., "Contamination and sample mix-up can best explain some patterns of mtDNA instabilities in buccal cells and oral squamous cell carcinoma", BMC Cancer, vol. 9, No. 113 Apr. 16, 2009, 8 pgs.
Bentley et al., "Accurate Whole Human Genome Sequencing using Reversible Terminator Chemistry," Nature, 456(7218): 53-59 (2008).
Cancer Genome Atlas Research Network, "Comprehensive genomic characterization of squamous cell lung cancers," Nature, 489, 519-525 (2012).
"Carter et al., "Absolute quantification of somatic DNA alterations in human cancer," Nat Biotechnol, 30:413-21 (2012)."
Chan, et al. Cancer genome scanning in plasma: detection of tumor-associated copy number aberrations, single-nucleotide variants, and tumoral heterogeneity by massively parallel sequencing. Clin Chem. Jan. 2013;59(1):211-24. doi: 10.1373/clinchem.2012.196014. Epub Oct. 11, 2012.
Chaudhuri et al. Early Detection of Molecular Residual Disease in Localized Lung Cancer by Circulating Tumor DnA Profiling. Cancer Discov; 7(12); 1394-403 (2017). With Supplemental Tables Table of Contents and Table S6.
Chen et al., "AfterQC: automatic filtering, trimming, error removing and quality control for fastq data", BMC Bioinformatics, vol. 18, Suppl. 3, Mar. 14, 2017,10 pgs.
Church et al., "Results of Initial Low-Dose Computed Tomographic Screening for Lung Cancer", The National Lung Screening Trial Research Team, The New England Journal of Medicine, vol. 368, No. 21, May 23, 2013, pp. 1980-1991.
Cohen, et al., Detection and localization of surgically resectable cancers with a multi-analyte blood test. Science Feb. 23, 2018: vol. 359, Issue 6378, pp. 926-930. DOI: 10.1126/science.aar3247.
"Comprehensive molecular profiling of lung adenocarcinoma", The Cancer Genome Atlas Research Network, Nature, vol. 511, Jul. 31, 2014, pp. 543-550.
Co-pending U.S. Appl. No. 18/167,803, inventors Kurtz; David M et al., filed Feb. 10, 2023.
Costello, et al. Discovery and characterization of artifactual mutations in deep coverage targeted capture sequencing data due to oxidative DNA damage during sample preparation. Nucleic Acids Res. Apr. 1, 2013;41(6): e67. doi: 10.1093/nar/gks1443. Epub Jan. 8, 2013.

(56) References Cited

OTHER PUBLICATIONS

Cristiano et al. Genome-Wide Cell-Free DNA Fragmentation in Patients with Cancer. Nature 570 (7761):385-389. (Jun. 2019).

Dai et al. Identification of risk loci and a polygenic risk score for lung cancer: a large-scale prospective cohort study in Chinese populations. The Lancet, vol. 7, Issue 10, pp. 881-891 (Oct. 2019).

De Koning et al., "PL02.05 Effects of Volume CT Lung Cancer Screening: Mortality Results of the NELSON Randomised-Controlled Population Based Trial", Journal of Thoracic Oncology, vol. 13, No. 10, Supplement, Oct. 2018, pp. S185.

Denissenko et al., "Preferential Formation of Benzo[a]pyrene Adducts at Lung Cancer Mutational Hotspots in P53", Science, vol. 274, No. 5286, Oct. 18, 1996, pp. 430-432.

Diaconis et al., "Methods for Studying Coincidences", Journal of the American Statistical Association, vol. 84, No. 408, Dec. 1989, pp. 853-861.

Dissertations and theses, Stanford Libraries, Special Collections & University Archives website, accessed on Jun. 21, 2021, available online at: https://library.stanford.edu/spc/university-archives/dissertations-and-theses.

Doria-Rose et al., "Use of Lung Cancer Screening Tests in the United States: Results from the 2010 National Health Interview Survey", Cancer Epidemiology, Biomarkers & Prevention, vol. 21, No. 7, Jul. 1, 2012, pp. 1049-1059.

Ersek et al., "Knowledge of, Attitudes Toward, and Use of Low-Dose Computed Tomography for Lung Cancer Screening Among Family Physicians", Cancer, vol. 122, No. 15, Aug. 1, 2016, pp. 2324-2331.

Forshew, et al. Noninvasive identification and monitoring of cancer mutations by targeted deep sequencing of plasma DNA. Sci Transl Med. May 30, 2012;4(136):136ra68.

Genovese et al., "Clonal Hematopoiesis and Blood-Cancer Risk Inferred from Blood DNA Sequence", The New England Journal of Medicine, vol. 371, Dec. 25, 2014, pp. 2477-2487.

Goldstraw et al., "The IASLC Lung Cancer Staging Project: Proposals for Revision of the TNM Stage Groupings in the Forthcoming (Eighth) Edition of the TNM Classification for Lung Cancer", Journal of Thoracic Oncology, vol. 11, No. 1, Jan. 2016, pp. 39-51.

Gregory et al. Targeted single molecule mutation detection with massively parallel sequencing. Nucleic Acids Research, 2016, vol. 44, No. 3 e22. Published online Sep. 17, 2015. 11 pages.

Hainaut et al., "Somatic TP53 Mutations in the Era of Genome Sequencing", Cold Spring Harbor Perspectives in Medicine, vol. 6, No. 11, Nov. 2016, 22 pgs.

Han, et al. The Biology of Cell-free DNA Fragmentation and the Roles of DNASE1, DNASE1L3, and DFFB. Am J Hum Genet. Feb. 6, 2020;106(2):202-214. doi: 10.1016/j.ajhg.2020.01.008. Epub Jan. 30, 2020.

Hawkins et al. Indel-correcting DNA barcodes for high-throughput sequencing. PNAS, vol. 115, No. 27 (E6217-E6226) (Published online Jun. 20, 2018).

Hu et al., "False-Positive Plasma Genotyping Due to Clonal Hematopoiesis", Clinical Cancer Research, vol. 24, No. 18, Sep. 15, 2018, pp. 4437-4443.

Imperiale, et al., Multitarget stool DNA testing for colorectal-cancer screening. N Engl J Med. Apr. 2014; 370:1287-1297.

Jaiswal et al., "Age-Related Clonal Hematopoiesis Associated with Adverse Outcomes", The New England Journal of Medicine, vol. 371, No. 26, Dec. 25, 2014, pp. 2488-2498.

Jemal et al., Lung cancer screening with low-dose computed tomography in the United States—2010 to 2015. JAMA Oncol. 3(9):1278-1281 (2017).

Jensen et al., "Decision Memo for Screening for Lung Cancer with Low Dose Computed Tomography (LDCT)", Centers for Medicare & Medicaid Services, CAG-00439N, Retrieved from: https://www.cms.gov/medicare-coverage-database/view/ncacal-decision-memo.aspx?proposed=N&NCAId=274, Feb. 5, 2015, 71 pgs.

Kandoth et al., "Mutational landscape and significance across 12 major cancer types," Nature, 502:333-339 (2013).

Karczewski et al., "Variation across 141,456 human exomes and genomes reveals the spectrum of loss-of-function intolerance across human protein-coding genes", bioRxiv, doi: 10.1101/531210, Aug. 13, 2019, 44 pgs.

Kinde et al. Detection and quantification of rare mutations with massively parallel sequencing. PNAS, vol. 108, No. 23, pp. 9530-9535 (Jun. 7, 2011). With Supporting Information (10 pages).

Kircher et al., Double indexing overcomes inaccuracies in multiplex sequencing on the Illumina platform, Nucleic Acids Res., 40(1): e3 (8 pages) (2012).

Kucab et al., "A Compendium of Mutational Signatures of Environmental Agents", Cell, vol. 177, No. 4, May 2, 2019, pp. 821-836.e16.

Kurtz et al., "Dynamic Risk Profiling Using Serial Tumor Biomarkers for Personalized Outcome Prediction", Cell, vol. 178, No. 3, Jul. 25, 2019, pp. 699-713.

Lawrence, MS et al. Mutational heterogeneity in cancer and the search for new cancer genes. Nature 499(7457):214-218 (Jul. 11, 2013) Epub Jun. 16, 2013.

Leary, et al. Development of personalized tumor biomarkers using massively parallel sequencing. Sci Transl Med. Feb. 24, 2010;2(20):20ra14.

Lewis et al., "Low-Dose CT Lung Cancer Screening Practices and Attitudes among Primary Care Providers at an Academic Medical Center", Cancer Epidemiology, Biomarkers & Prevention, vol. 24, No. 4, Apr. 1, 2015, pp. 664-670.

Ley, et al. DNA sequencing of a cytogenetically normal acute myeloid leukemia genome. Nature. Nov. 6, 2008;456(7218):66-72.

Liao, G.J.W. et al., "Targeted massively parallel sequencing of maternal plasma DNA permits efficient and unbiased detection of fetal alleles," Clin. Chem. 2011, 57(1), 92-101.

Liu et al., "Biological background of the genomic variations of cf-DNA in healthy individuals", Annals of Oncology, vol. 30, No. 3, Mar. 1, 2019, pp. 464-470.

Lui, et al. Predominant hematopoietic origin of cell-free DNA in plasma and serum after sex-mismatched bone marrow transplantation. Clin Chem. Mar. 2002;48(3):421-427.

Ma et al., "Annual Number of Lung Cancer Deaths Potentially Avertable by Screening in the United States", Cancer, vol. 119, No. 7, Apr. 1, 2013, pp. 1381-1385.

Martincorena et al. Universal Patterns of Selection in Cancer and Somatic Tissues. Cell 171, 1029-1041 (Nov. 16, 2017). With Erratum.

Mermel et al., GISTIC2.0 facilitates sensitive and confident localization of the targets of focal somatic copy-number alteration in human cancers, Genome Biol, 12:R41 (2011).

Mir et al., "Short Barcodes for Next Generation Sequencing", PLoS One, vol. 8, No. 12, Dec. 2013, e82933, 8 pgs.

Moss et al. Comprehensive Human Cell-Type Methylation Atlas Reveals Origins of Circulating Cell-Free DNA in Health and Disease. Nature Communications 9(1):5068 (2018).

Mouliere et al. Enhanced Detection of Circulating Tumor DNA by Fragment Size Analysis. Science Translational Medicine 10(466):eaat4921 (2018).

PCT/US2021/019478 International Search Report and Written Opinion dated Aug. 25, 2021.

Pfeifer et al., "Tobacco smoke carcinogens, DNA damage and p53 mutations in smoking-associated cancers", Oncogene, vol. 21, No. 48, Oct. 15, 2002, pp. 7435-7451.

Pinsky et al., "Performance of Lung-RADS in the National Lung Screening Trial: A Retrospective Assessment", Annals of Internal Medicine, vol. 162, No. 7, Apr. 7, 2015, pp. 485-491.

Pinsky et al., "The National Lung Screening Trial: Results stratified by demographics, smoking history, and lung cancer histology", Cancer, vol. 119, No. 22, Nov. 15, 2013, pp. 3976-3983.

Ptashkin et al., "Prevalence of Clonal Hematopoiesis Mutations in Tumor-Only Clinical Genomic Profiling of Solid Tumors", JAMA Oncology, vol. 4, No. 11, Nov. 1, 2018, pp. 1589-1593.

Qian et al. A novel pathway-based approach improves lung cancer risk prediction using germline genetic variations. Cancer Epidemiol Biomarkers Prev. Aug. 2016 ; 25(8): 1208-1215.

(56) References Cited

OTHER PUBLICATIONS

Roberts et al. Hypermutation in human cancer genomes: footprints and mechanisms. Nature Reviews Cancer, vol. 14, pp. 786-800 (2014).
Saunders et al. Strelka: accurate somatic small-variant calling from sequenced tumor-normal sample pairs. Bioinformatic, 28(14):1811-1817 (2012).
Serpas et al. Dnase1l3 deletion causes aberrations in length and end-motif frequencies in plasma DNA. PNAS, vol. 116, No. 2, pp. 641-649 (Jan. 8, 2019). Published online Dec. 28, 2018.
Shen et al. Sensitive tumour detection and classification using plasma cell-free DNA methylomes. Nature. 2018;563:579-83.
Siegel et al. Cancer statistics, 2019. A Cancer Journal for Clinicians 69(1):7-34 (2019).
Snyder et al., Cell-free DNA comprises an in vivo nucleosome footprint that informs its tissues-of-origin. Cell. 164(1-2):57-68 (2016).
Steensma et al., "Clonal hematopoiesis of indeterminate potential and its distinction from myelodysplastic syndromes", Blood, vol. 126, No. 1, Jul. 2, 2015, pp. 9-16.
Supplementary Information for Chabon et al. Integrating genomic features for non-invasive early lung cancer detection. Nature. https://doi.org/10.1038/s41586-020-2140-0 . Published online Mar. 25, 2020. 27 pages.
Supplementary Note for Chabon et al. Integrating genomic features for non-invasive early lung cancer detection. Nature. https://doi.org/10.1038/s41586-020-2140-0 . Published online Mar. 25, 2020. 4 pages.
Swanton et al., "Prevalence of clonal hematopoiesis of indeterminate potential (CHIP) measured by an ultra-sensitive sequencing assay: Exploratory analysis of the Circulating Cancer Genome Atlas (CCGA) study", Journal of Clinical Oncology, vol. 36, No. 15, Supplement, May 20, 2018, pp. 12003.
Travis et al., "International Association for the Study of Lung Cancer/American Thoracic Society/European Respiratory Society International Multidisciplinary Classification of Lung Adenocarcinoma", Journal of Thoracic Oncology, vol. 6, No. 2, Feb. 2011, pp. 244-285.
Underhill et al. Fragment Length of Circulating Tumor DNA. Edited by David J. Kwiatkowski. PLoS Genetics 12(7):e1006162 (2016).
U.S. Appl. No. 17/646,473 Notice of Allowance dated Jan. 13, 2023.
U.S. Appl. No. 17/646,473 Notice of Allowance dated Nov. 9, 2022.
U.S. Appl. No. 17/646,473 Office Action dated Jun. 22, 2022.
U.S. Appl. No. 17/646,473 Office Action dated Oct. 17, 2022.
U.S. Appl. No. 17/661,034 Notice of Allowance dated Jun. 2, 2023.
U.S. Appl. No. 17/661,034 Office Action dated Feb. 2, 2023.
U.S. Appl. No. 17/661,730 Notice of Allowance dated Jan. 12, 2023.
U.S. Appl. No. 17/661,730 Office Action dated Dec. 1, 2022.
U.S. Appl. No. 17/820,200 Office Action dated Apr. 26, 2023.
U.S. Appl. No. 18/056,652 Office Action dated May 22, 2023.
U.S. Appl. No. 18/056,656 Office Action dated Jul. 3, 2023.
U.S. Appl. No. 18/172,957 Office Action dated Apr. 26, 2023.
Vendrell et al. Circulating Cell Free Tumor DNA Detection as a Routine Tool for Lung Cancer Patient Management. Int. J. Mol. Sci. 2017, 18, 264. 19 pages.
Vodak et al., "Sample-Index Misassignment Impacts Tumour Exome Sequencing", Scientific Reports, vol. 8, No. 5307, Mar. 28, 2018, 6 pgs.
Wagle et al. High-Throughput Detection of Actionable Genomic Alterations in Clinical Tumor Samples by Targeted, Massively Parallel Sequencing. Cancer Discov. Jan. 2012 ; 2(1): 82-93.
Weissfeld et al. Lung cancer risk prediction using common SNPs located in GWAS-identified susceptibility regions. J Thorac Oncol. Nov. 2015 ; 10(11): 1538-1545.
Wender et al., "American Cancer Society lung cancer screening guidelines", CA: A Cancer Journal for Clinicians, vol. 63, No. 2, Mar./Apr. 2013, pp. 106-117.
Xie et al., "Age-related mutations associated with clonal hematopoietic expansion and malignancies", Nature Medicine, vol. 20, No. 12, Oct. 19, 2014, pp. 1472-1478.
Young et al., "Clonal haematopoiesis harbouring AML-associated mutations is ubiquitous in healthy adults", Nature Communications, vol. 7, 12484, Aug. 22, 2016, 7 pgs.
Chicard et al. Whole-Exome Sequencing of Cell-Free DNA Reveals Temporo-spatial Heterogeneity and Identifies Treatment-Resistant Clones in Neuroblastoma. Clin Cancer Res; 24(4); 939-49 (2017).
Chiu et al. cfDNA screening and diagnosis of monogenic disorders—where are we heading? Prenatal Diagnosis 2018, 38, 52-58.
Co-pending U.S. Appl. No. 18/452,463, inventors Chabon; Jacob J. et al., filed Aug. 18, 2023.
Co-pending U.S. Appl. No. 18/481,092, inventors Kurtz; David M. et al., filed Oct. 4, 2023.
EP20885631.0 Extended European Search Report dated Sep. 27, 2023.
Spindler et al. Quantitative Cell-Free DNA, KRAS, and BRAF Mutations in Plasma from Patients with Metastatic Colorectal Cancer during Treatment with Cetuximab and Irinotecan. Clin Cancer Res; 18(4) pp. 1177-1185 (Feb. 15, 2012).
U.S. Appl. No. 17/820,200 Office Action dated Aug. 17, 2023.
U.S. Appl. No. 18/056,652 Notice of Allowance dated Sep. 14, 2023.
U.S. Appl. No. 18/056,656 Office Action dated Sep. 29, 2023.
U.S. Appl. No. 18/172,957 Office Action dated Aug. 17, 2023.

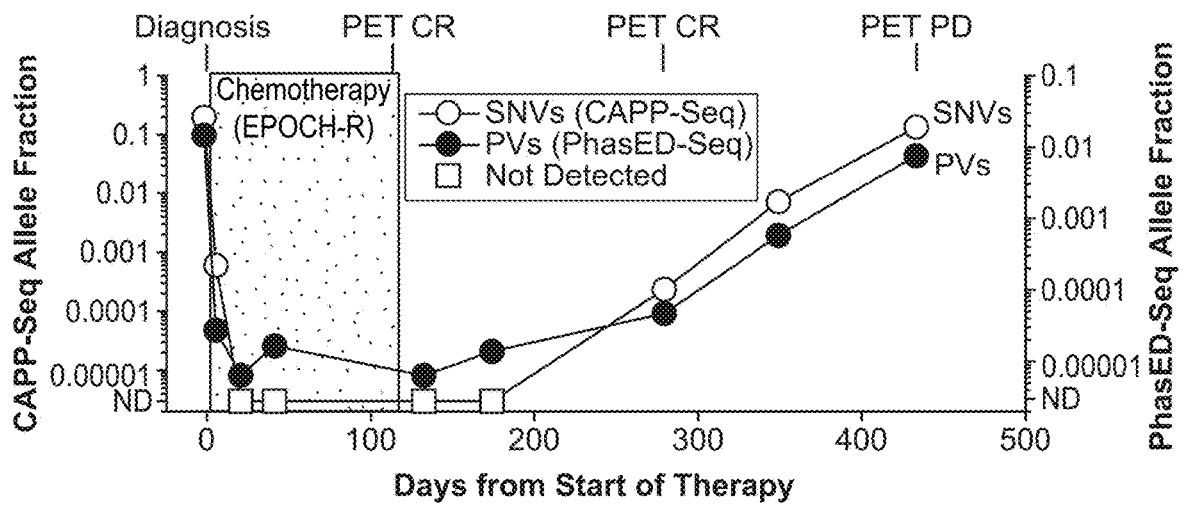
FIG. 4A
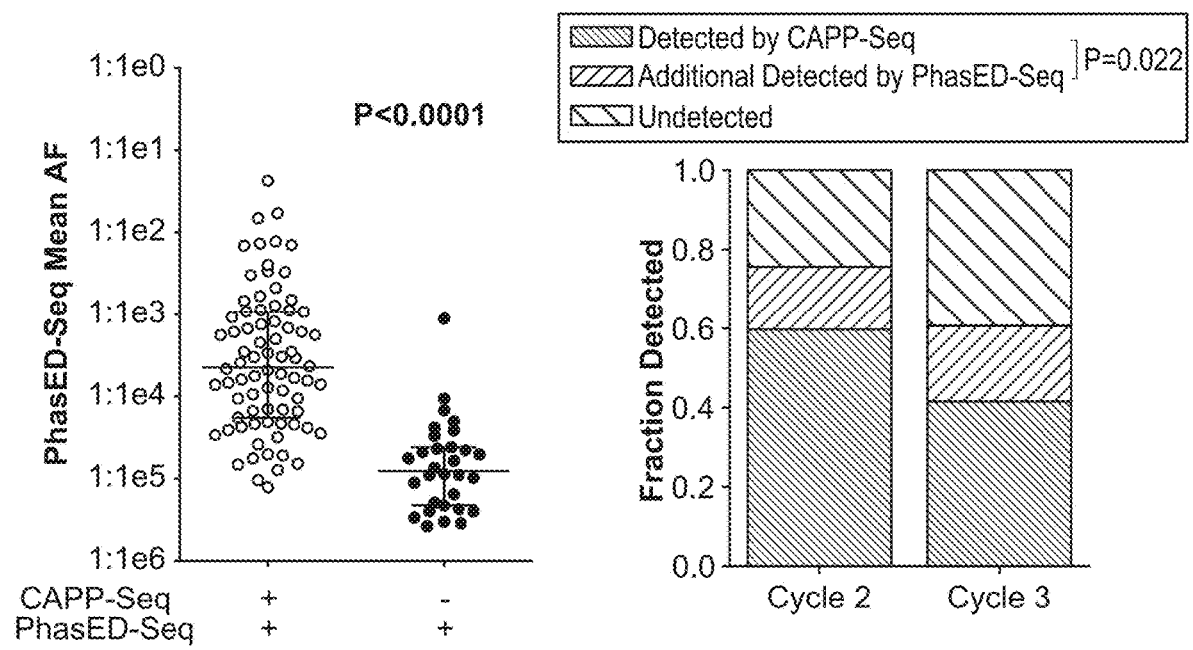
FIG. 4B
FIG. 4C

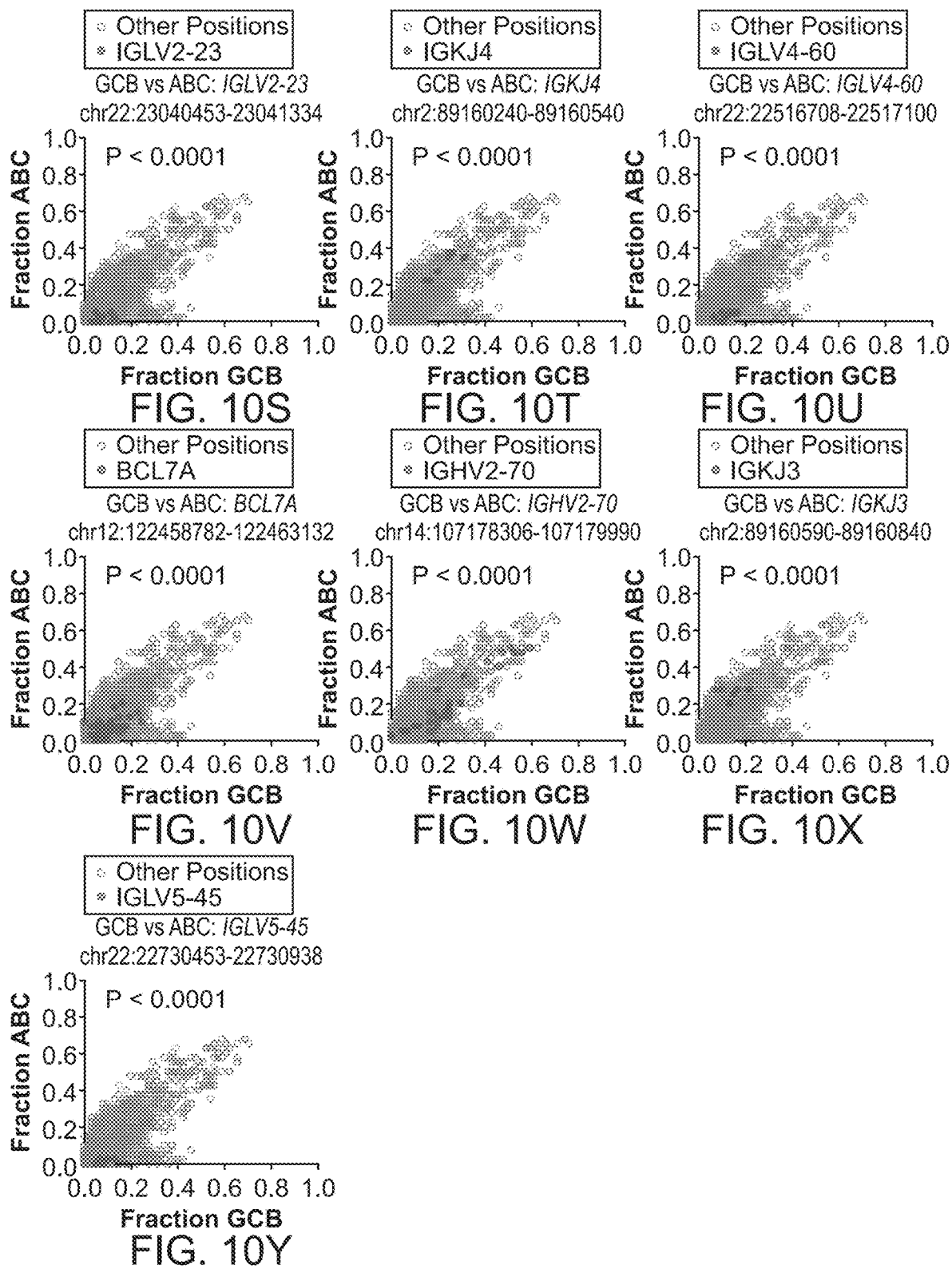

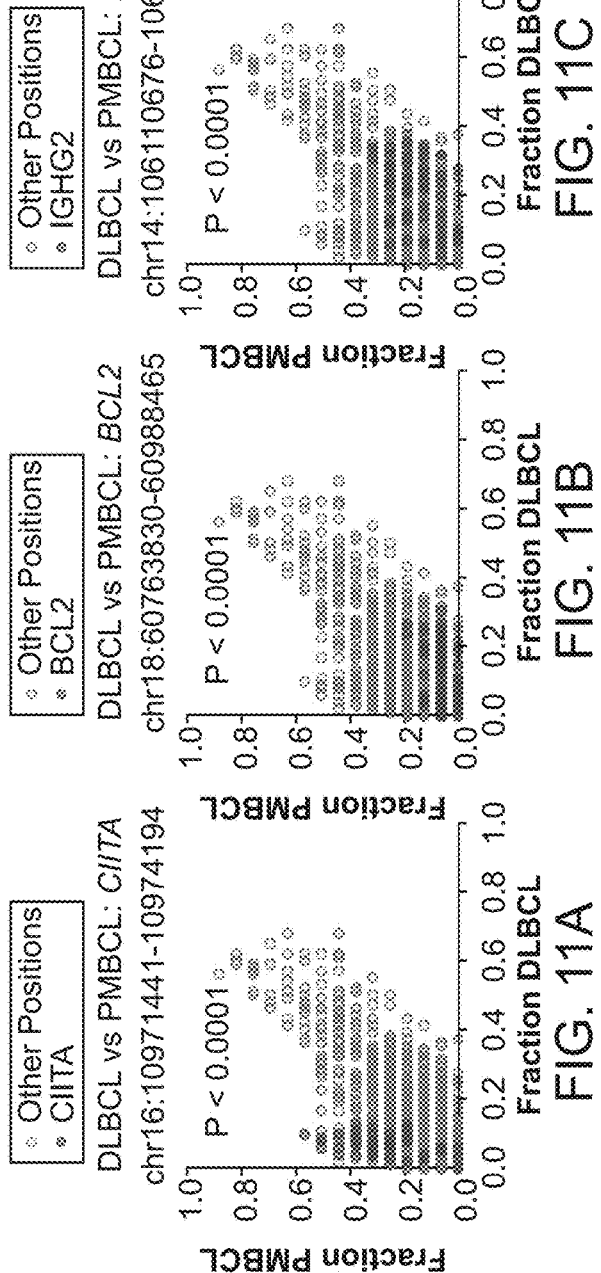
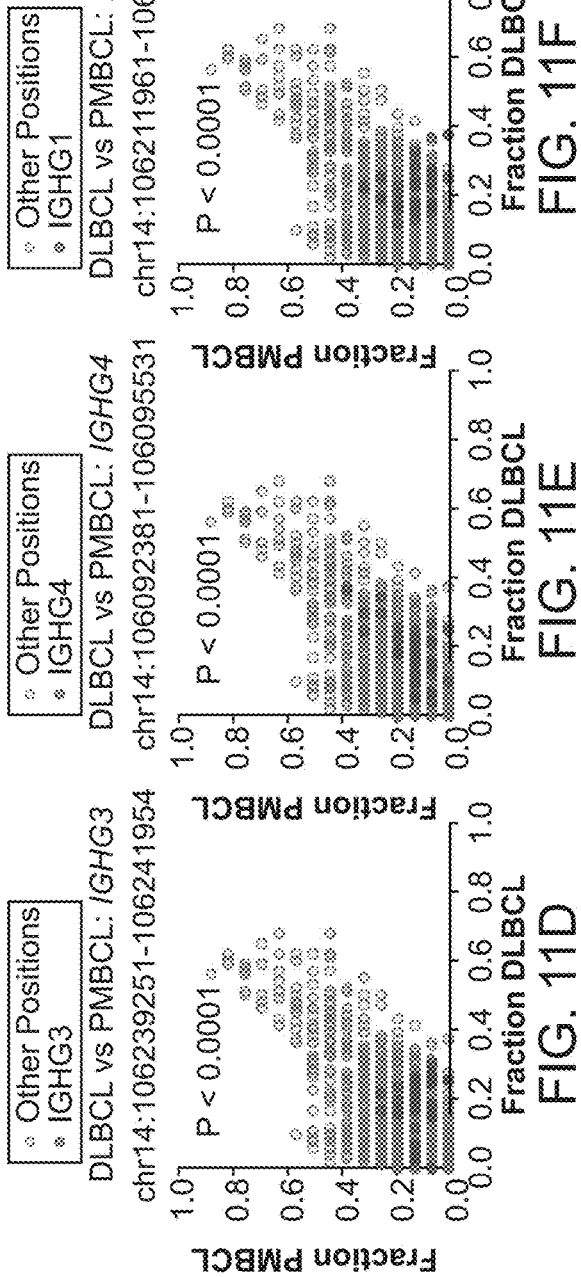
FIG. 11A FIG. 11B FIG. 11C
FIG. 11D FIG. 11E FIG. 11F

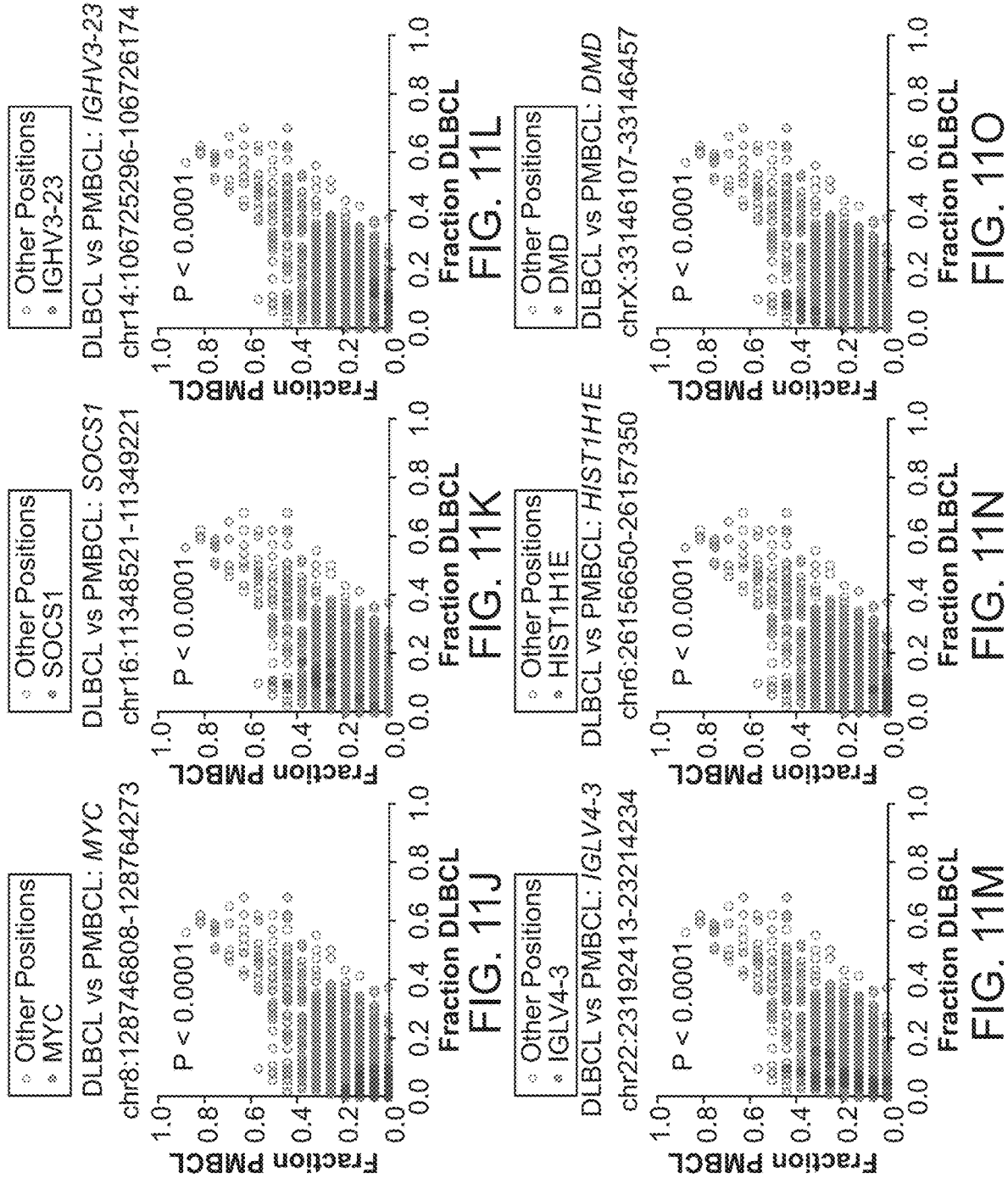

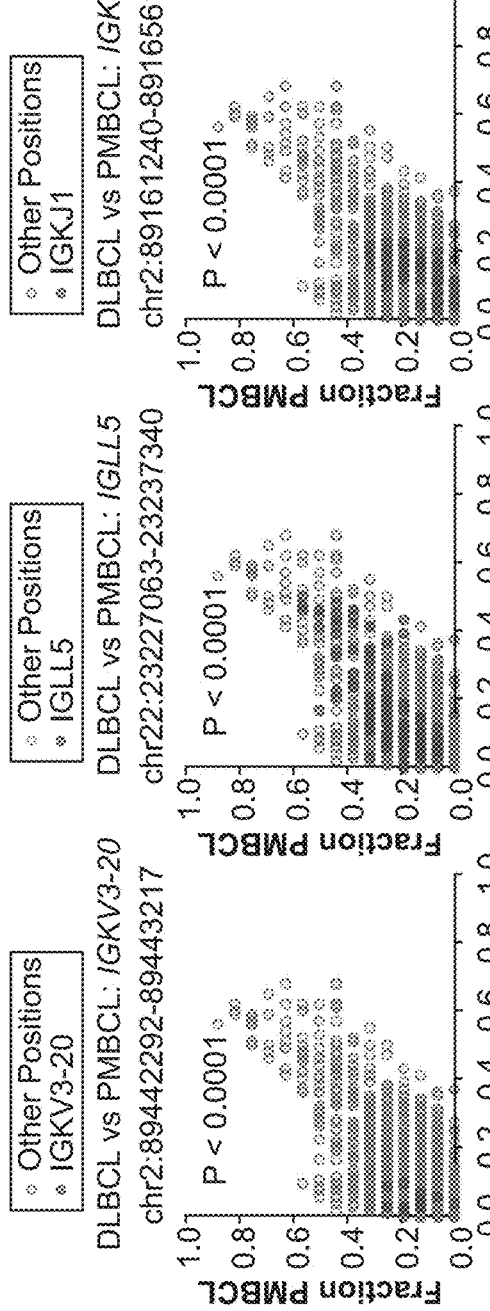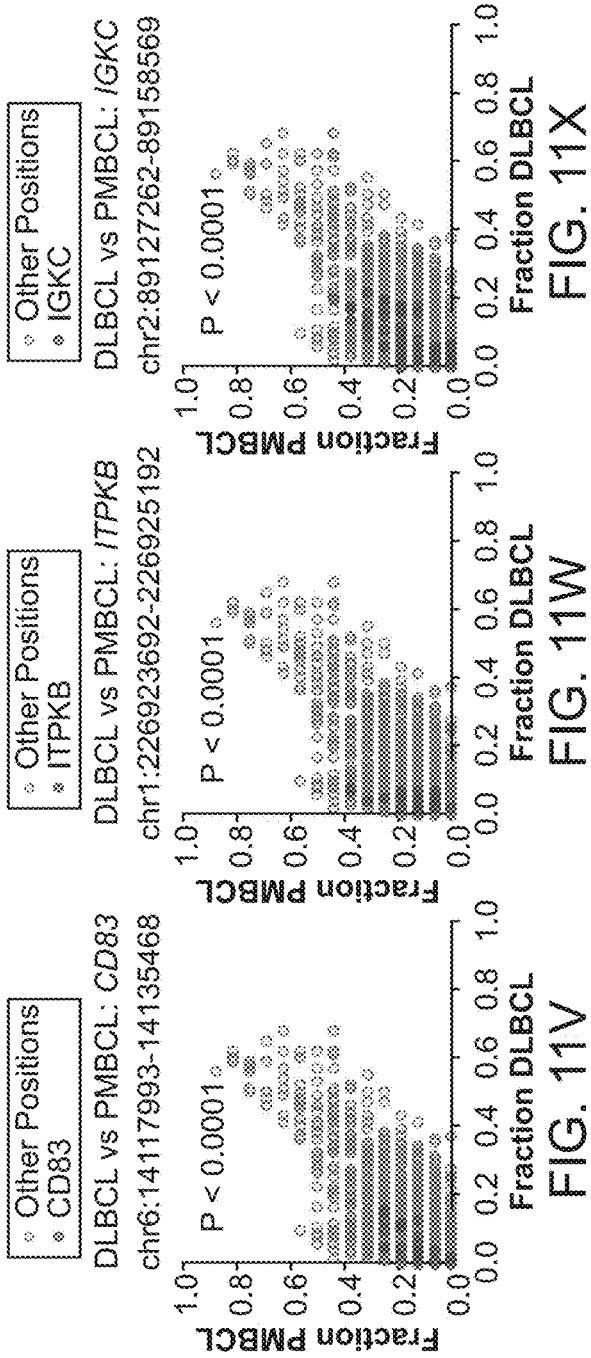

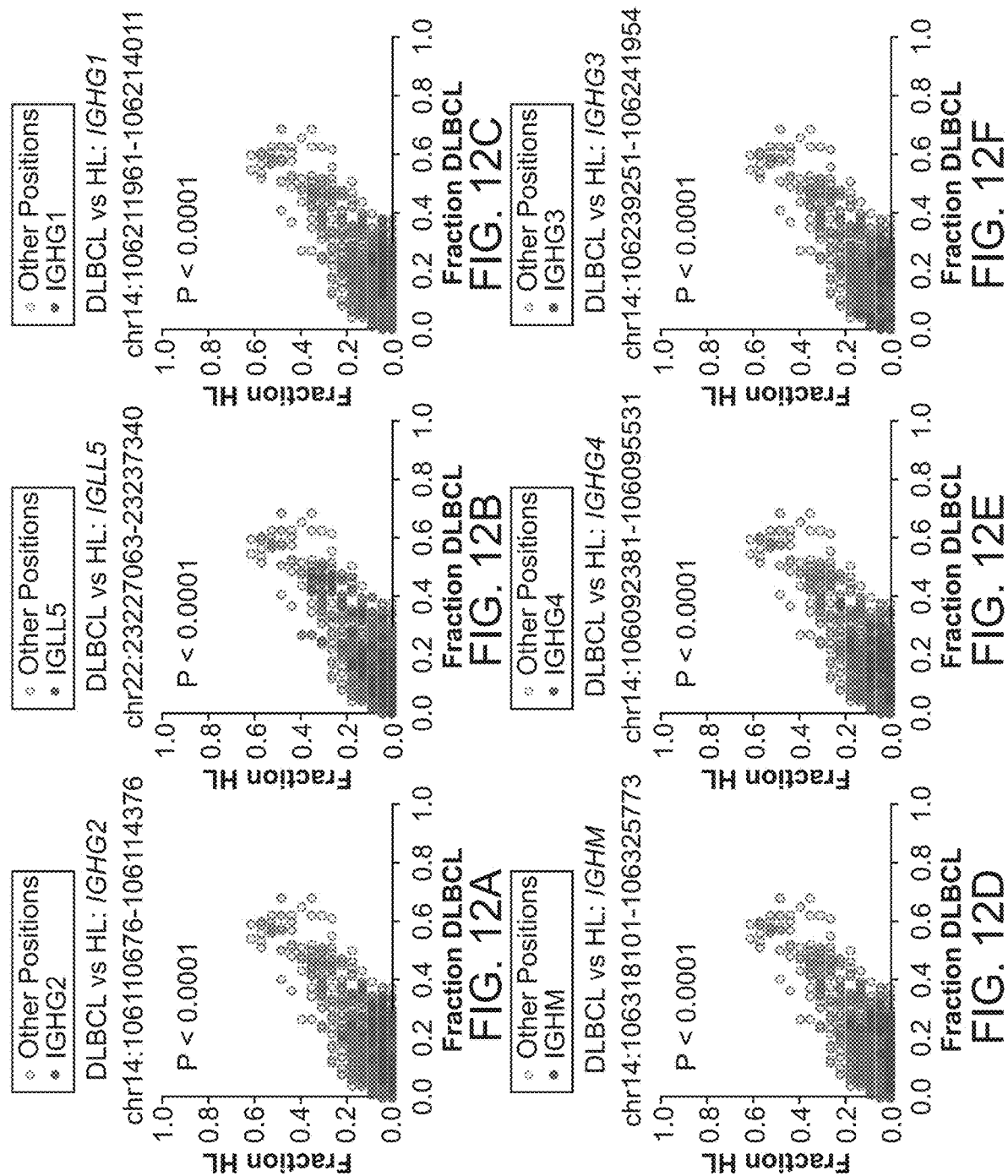

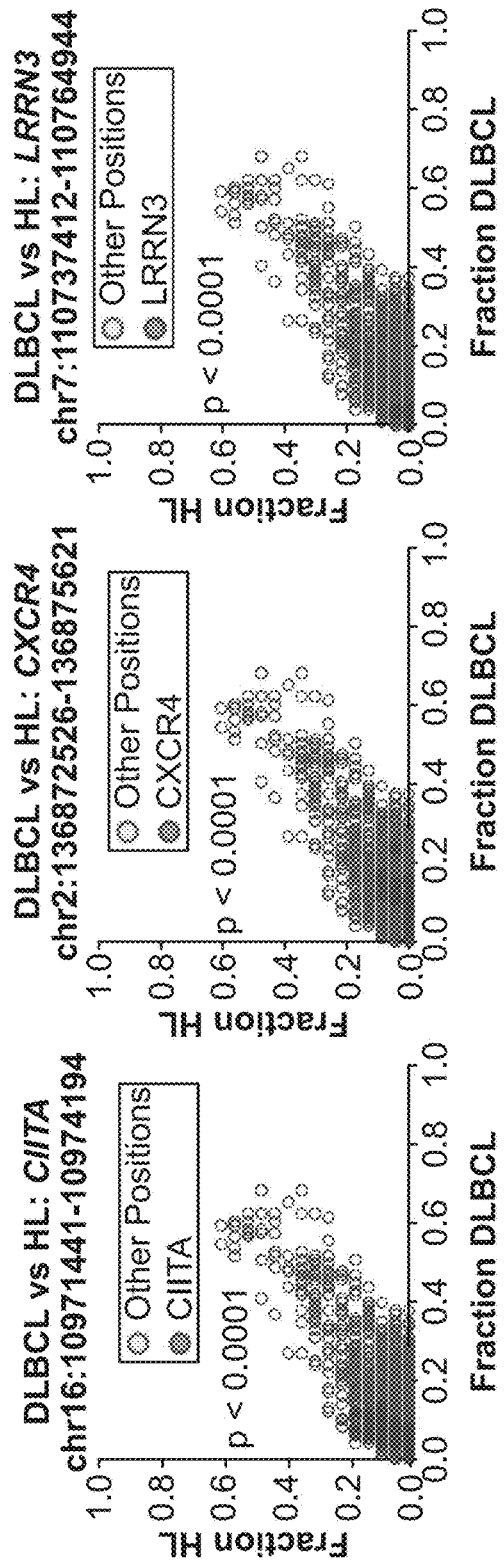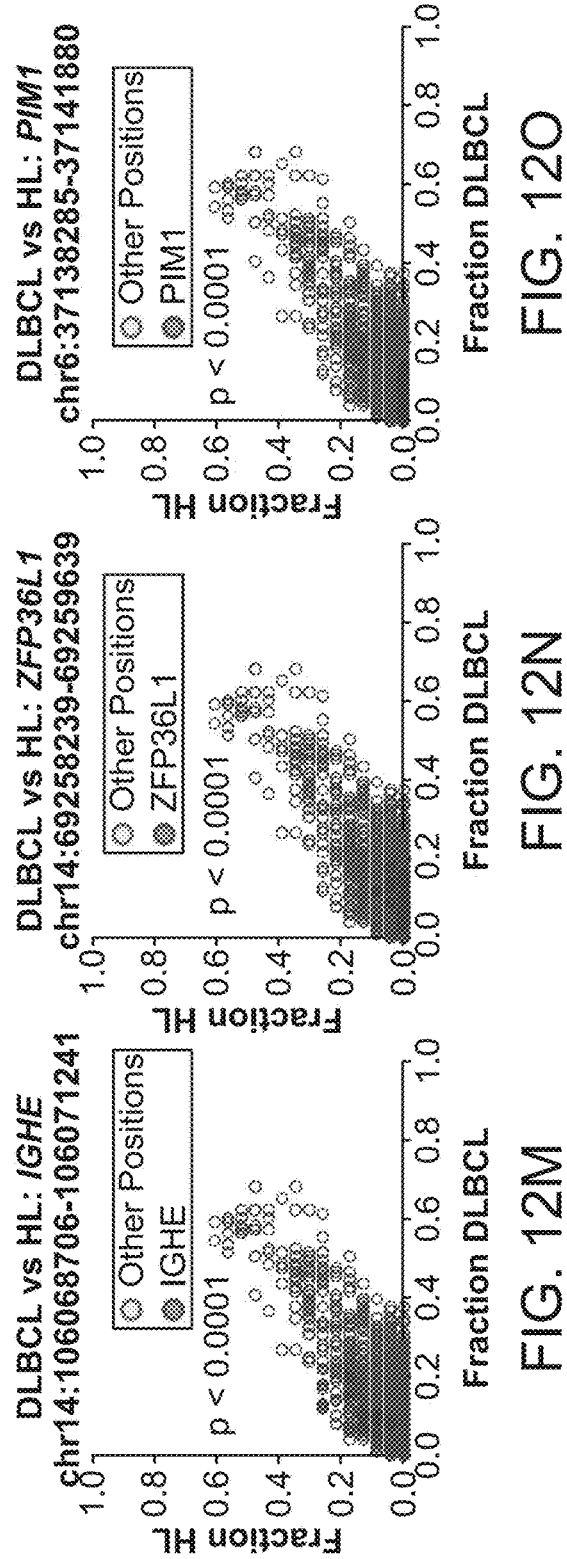

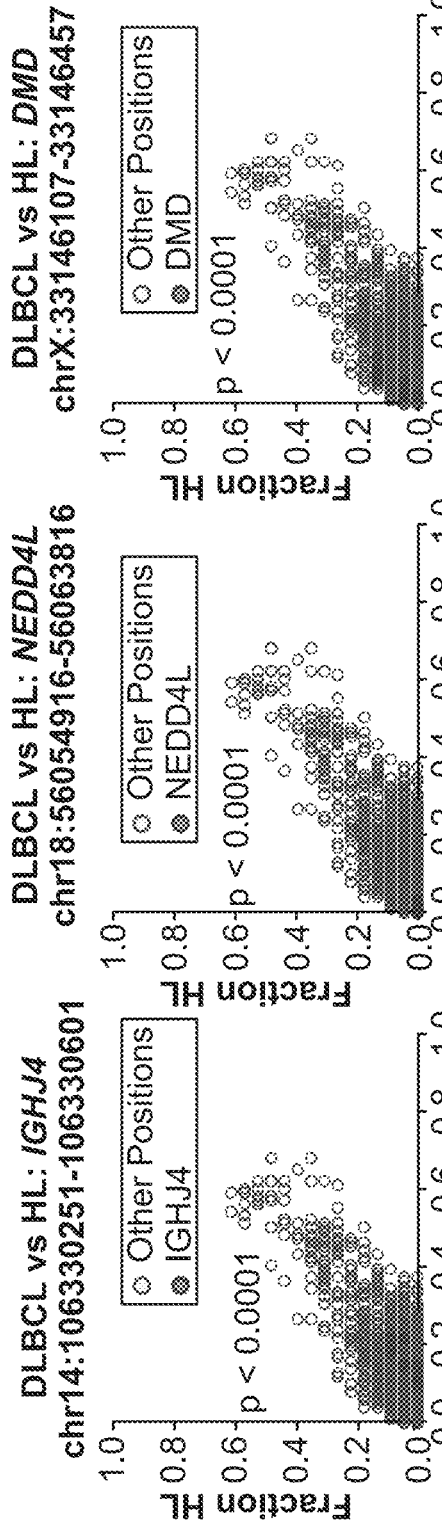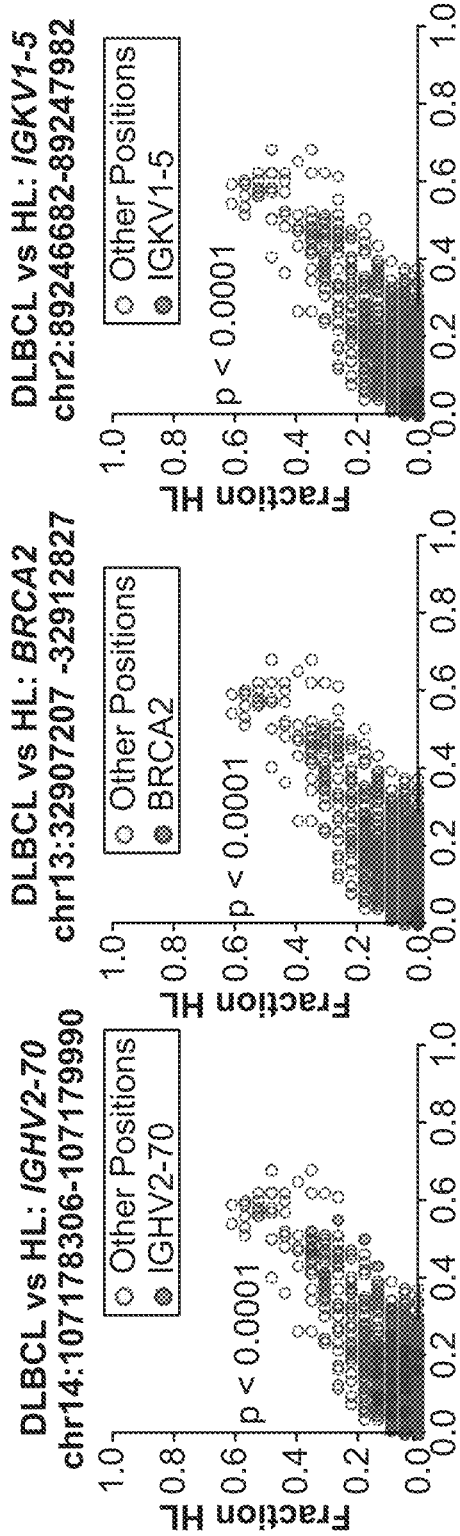

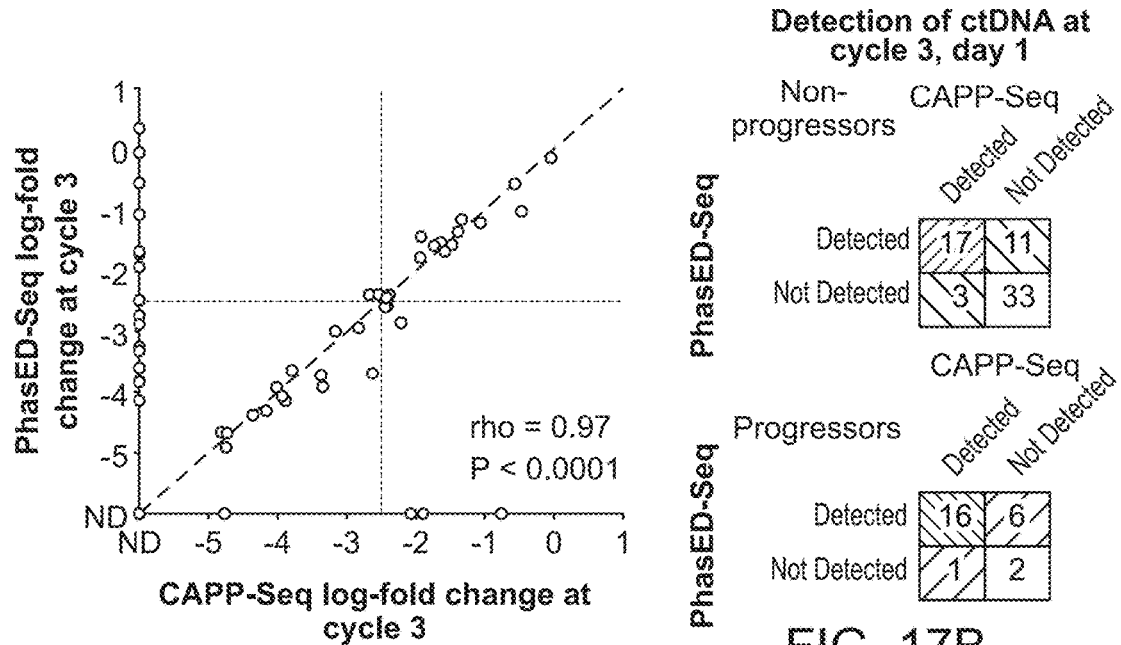
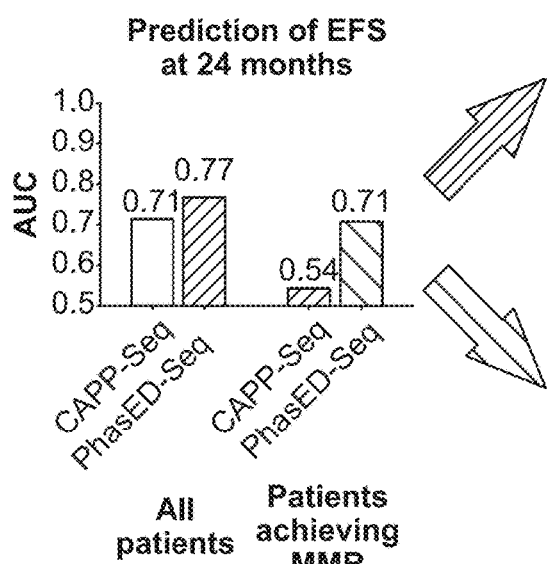
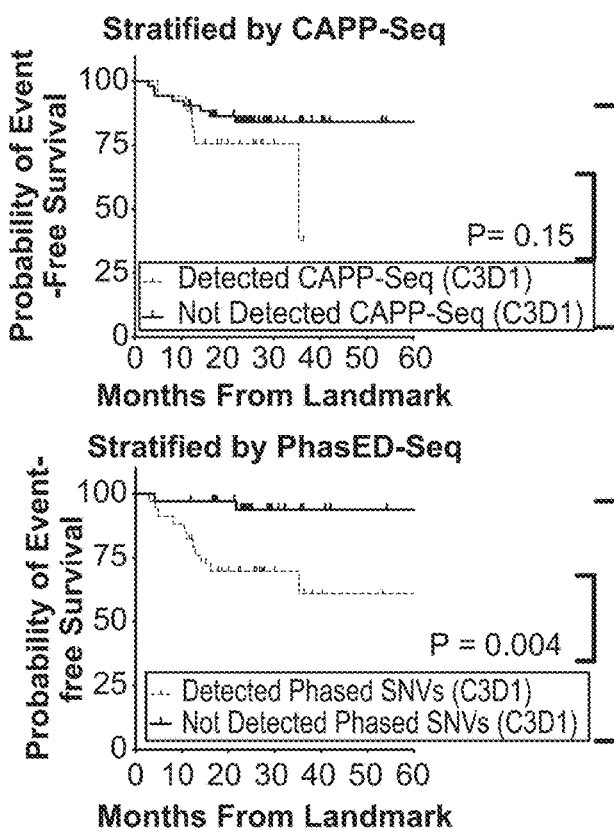
FIG. 17A
FIG. 17B
FIG. 17C
FIG. 17D

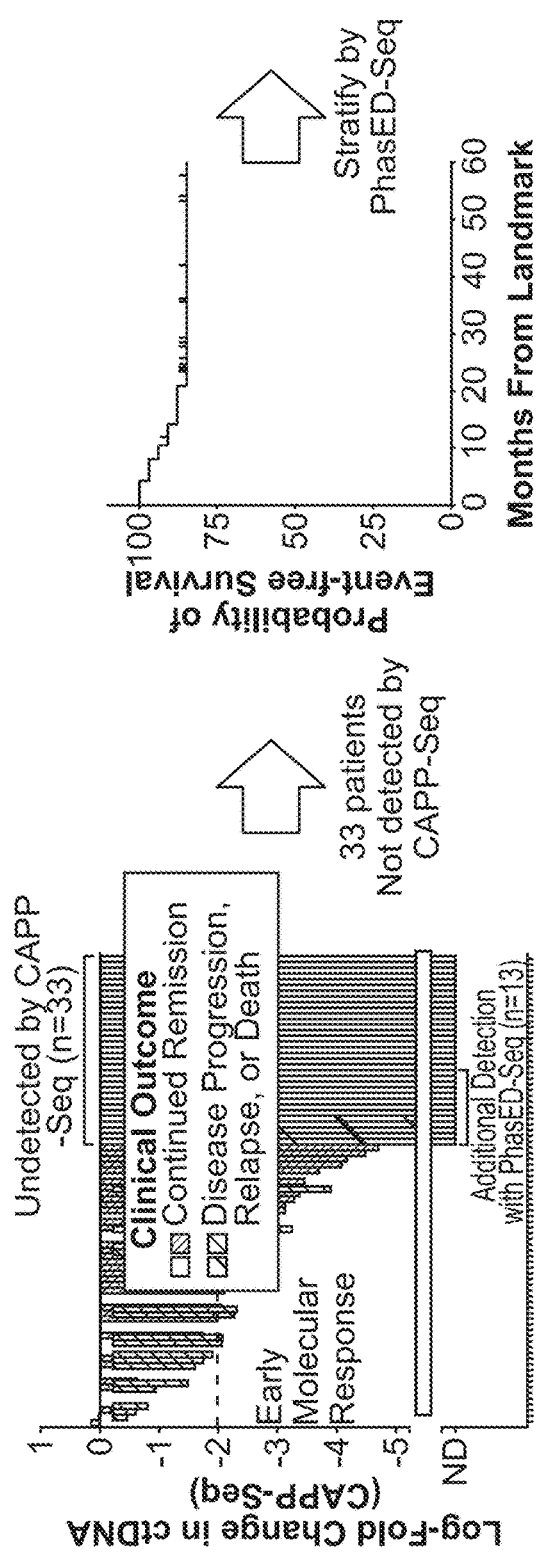
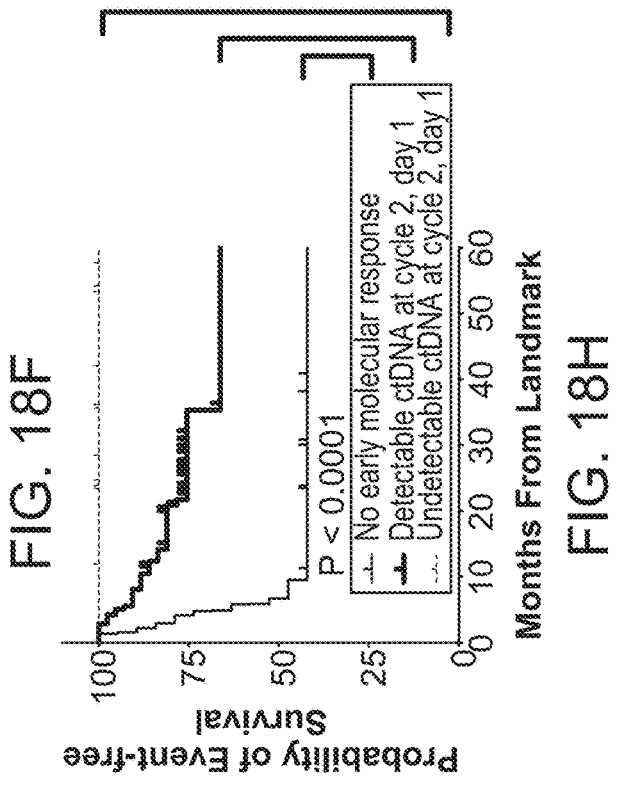
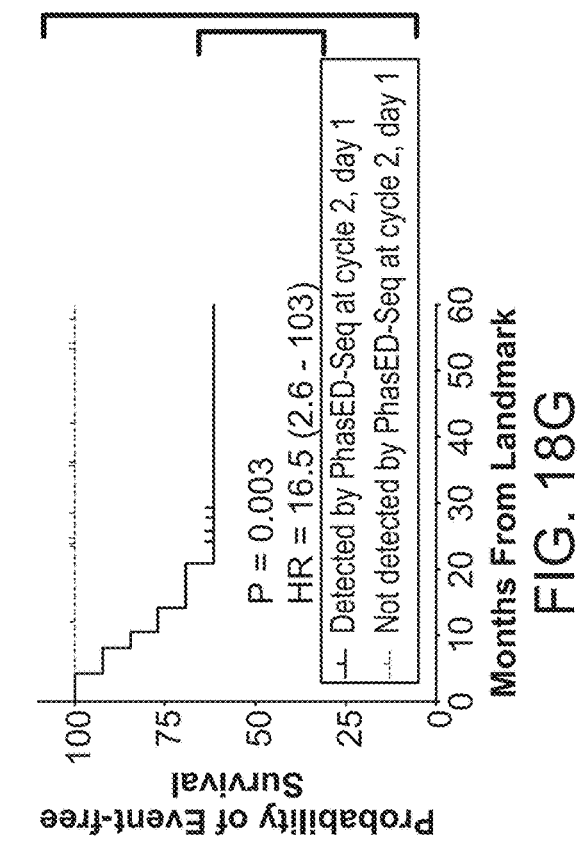
FIG. 18E
FIG. 18F
FIG. 18G
FIG. 18H

2512 — Obtaining, by a computer system, sequencing data derived from a plurality of cell-free nucleic acid molecules from a subject.

2514 — Processing, by the computer system, the sequencing data to identify one or more cell-free nucleic acid molecules of the plurality of cell-free nucleic acid molecules, wherein each of the one or more cell-free nucleic acid molecules comprises a plurality of phased variants relative to a reference genomic sequence, wherein at least about 10% of the one or more cell-free nucleic acid molecules comprises a first phased variant of the plurality of phased variants and a second phased variant of the plurality of phased variants that are separated by at least one nucleotide.

2516 — Analyzing, by the computer system, the identified one or more cell-free nucleic acid molecules to determine a condition of the subject.

2542 — Identifying the subject for treatment of the condition, wherein the subject has been determined to have the condition based on identification of one or more cell-free nucleic acid molecules from a plurality of cell-free nucleic acid molecules from the subject,
wherein each of the one or more cell-free nucleic acid molecules identified comprises a plurality of phased variants relative to a reference genomic sequence that are separated by at least one nucleotide, and
wherein a presence of the plurality of phased variants is indicative of the condition of the subject.

2544 — Subjecting the subject to the treatment based on the identification.

2562 — Providing a mixture comprising (1) a set of nucleic acid probes and (2) a plurality of cell-free nucleic acid molecules from a subject,
wherein an individual nucleic acid probe of the set of nucleic acid probes is designed to hybridize to a target cell-free nucleic acid molecule comprising a plurality of phased variants relative to a reference genomic sequence that are separated by at least one nucleotide, and
wherein the individual nucleic acid probe comprises an activatable reporter agent, activation of the activatable reporter agent being selected from the group consisting of: (i) hybridization of the individual nucleic acid probe to the plurality of phased variants and (ii) dehybridization of at least a portion of the individual nucleic acid probe that has been hybridized to the plurality of phased variants.

2564 — Detecting the reporter agent that is activated, to identify one or more cell-free nucleic acid molecules of the plurality of cell-free nucleic acid molecules, wherein each of the one or more cell-free nucleic acid molecules comprises the plurality of phased variants.

2566 — Analyzing the identified one or more cell-free nucleic acid molecules to determine a condition of the subject.

2572 — Providing a mixture comprising (1) a set of nucleic acid probes and (2) a plurality of cell-free nucleic acid molecules from a subject, wherein an individual nucleic acid probe of the set of nucleic acid probes is designed to hybridize to a target cell-free nucleic acid molecule comprising a plurality of phased variants relative to a reference genomic sequence, and wherein the individual nucleic acid probe comprises an activatable reporter agent, activation of the activatable reporter agent being selected from the group consisting of: (i) hybridization of the individual nucleic acid probe to the plurality of phased variants and (ii) dehybridization of at least a portion of the individual nucleic acid probe that has been hybridized to the plurality of phased variants.

2574 — Detecting the reporter agent that is activated, to identify one or more cell-free nucleic acid molecules of the plurality of cell-free nucleic acid molecules, wherein each of the one or more cell-free nucleic acid molecules comprises the plurality of phased variants, wherein a limit of detection of the identification step is less than about 1 out of 50,000 cell-free nucleic acid molecules of the plurality of cell-free nucleic acid molecules.

2576 — Analyzing the identified one or more cell-free nucleic acid molecules to determine a condition of the subject.

METHODS AND SYSTEMS FOR ANALYZING NUCLEIC ACID MOLECULES

CROSS-REFERENCE

This application is a continuation of U.S. patent application Ser. No. 17/646,473, filed Dec. 29, 2021, which is a continuation of PCT Patent Application No. PCT/US2020/059526, filed Nov. 6, 2020, which claims the benefit of U.S. Provisional Patent Application No. 62/931,688, filed Nov. 6, 2019, the disclosures of which are entirely incorporated herein by reference in their entirety.

GOVERNMENT RIGHTS

This invention was made with Government support under CA233975, CA241076, and CA188298 awarded by the National Institutes of Health. The Government has certain rights in the invention.

SEQUENCE LISTING

The instant application contains a Sequence Listing which has been submitted electronically in XML file format and is hereby incorporated by reference in its entirety. Said XML copy, created on Aug. 11, 2022, is named 58626-702_601_SL.xml and is 1,304,877 bytes in size.

BACKGROUND

Noninvasive blood tests that can detect somatic alterations (e.g., mutated nucleic acids) based on the analysis of cell-free nucleic acids (e.g., cell-free deoxyribonucleic acid (cfDNA) and cell-free ribonucleic acid (cfRNA)) are attractive candidates for cancer screening applications due to the relative ease of obtaining biological specimens (e.g., biological fluids). Circulating tumor nucleic acids (e.g., ctDNA or ctRNA; i.e., nucleic acids derived from cancerous cells) can be sensitive and specific biomarkers in numerous cancer subtypes. However, current methods for minimal residual disease (MRD) detection from ctDNA can be limited by one or more factors, such as low input DNA amounts and high background error rates.

Recent approaches have improved ctDNA MRD performance by tracking multiple somatic mutations with error-suppressed sequencing, resulting in detection limits as low as 4 parts in 100,000 from limited cfDNA input. Detection of residual disease during or after treatment is a powerful tool, with detectable MRD representing an adverse prognostic sign even during radiographic remission. However, current limits of detection may be insufficient to universally detect residual disease in patients destined for disease relapse or progression. This 'loss of detection' is exemplified in diffuse large B-cell lymphoma (DLBCL), where ctDNA detection after two cycles of curative-intent therapy is a strong prognostic marker. Despite this, almost one-third of patients experiencing disease progression do not have detectable ctDNA at this landmark, representing 'false-negative' tests. Similar false-negative rates in colon cancer and breast cancer have been observed.

SUMMARY

The present disclosure provides methods and systems for analyzing cell-free nucleic acids (e.g., cfDNA, cfRNA) from a subject. Methods and systems of the present disclosure can utilize sequencing results derived from the subject to detect cancer-derived nucleic acids (e.g., ctDNA, ctRNA) for, e.g., disease diagnosis, disease monitoring, or determining treatments for the subject. Methods and systems of the present disclosure can exhibit enhanced sensitivity, specificity and/or reliability of detection of cancer-derived nucleic acids.

In one aspect, the present disclosure provides a method comprising: (a) obtaining, by a computer system, sequencing data derived from a plurality of cell-free nucleic acid molecules that is obtained or derived from a subject; (b) processing, by the computer system, the sequencing data to identify one or more cell-free nucleic acid molecules of the plurality of cell-free nucleic acid molecules, wherein each of the one or more cell-free nucleic acid molecules comprises a plurality of phased variants relative to a reference genomic sequence, wherein at least about 10% of the one or more cell-free nucleic acid molecules comprises a first phased variant of the plurality of phased variants and a second phased variant of the plurality of phased variants that are separated by at least one nucleotide; and (c) analyzing, by the computer system, the identified one or more cell-free nucleic acid molecules to determine a condition of the subject.

In some embodiments of any one of the methods disclosed herein, the at least about 10% of the cell-free nucleic acid molecules comprise at least about 20%, at least about 30%, at least about 40%, at least about 50%, at least about 60%, at least about 70%, at least about 80%, at least about 90%, or about 100% of the one or more cell-free nucleic acid molecules.

In one aspect, the present disclosure provides a method comprising: (a) obtaining, by a computer system, sequencing data derived from a plurality of cell-free nucleic acid molecules that is obtained or derived from a subject; (b) processing, by the computer system, the sequencing data to identify one or more cell-free nucleic acid molecules of the plurality of cell-free nucleic acid molecules, wherein each of the one or more cell-free nucleic acid molecules comprises a plurality of phased variants relative to a reference genomic sequence that are separated by at least one nucleotide; and (c) analyzing, by the computer system, the identified one or more cell-free nucleic acid molecules to determine a condition of the subject.

In one aspect, the present disclosure provides a method comprising: (a) obtaining sequencing data derived from a plurality of cell-free nucleic acid molecules that is obtained or derived from a subject; (b) processing the sequencing data to identify one or more cell-free nucleic acid molecules of the plurality of cell-free nucleic acid molecules with a limit of detection of less than about 1 out of 50,000 observations from the sequencing data; and (c) analyzing the identified one or more cell-free nucleic acid molecules to determine a condition of the subject.

In some embodiments of any one of the methods disclosed herein, the limit of detection of the identification step is less than about 1 out of 100,000, less than about 1 out of 500,000, less than about 1 out of 1,000,000, less than about 1 out of 1,500,000, or less than about 1 out of 2,000,000 observations from the sequencing data.

In some embodiments of any one of the methods disclosed herein, each of the one or more cell-free nucleic acid molecules comprises a plurality of phased variants relative to a reference genomic sequence. In some embodiments of any one of the methods disclosed herein, a first phased variant of the plurality of phased variants and a second phased variant of the plurality of phased variants are separated by at least one nucleotide.

In some embodiments of any one of the methods disclosed herein, the processes (a) to (c) are performed by a computer system.

In some embodiments of any one of the methods disclosed herein, the sequencing data is generated based on nucleic acid amplification. In some embodiments of any one of the methods disclosed herein, the sequencing data is generated based on polymerase chain reaction. In some embodiments of any one of the methods disclosed herein, the sequencing data is generated based on amplicon sequencing.

In some embodiments of any one of the methods disclosed herein, the sequencing data is generated based on next-generation sequencing (NGS). Alternatively, in some embodiments of any one of the methods disclosed herein, the sequencing data is generated based on non-hybridization-based NGS.

In some embodiments of any one of the methods disclosed herein, the sequencing data is generated without use of molecular barcoding of at least a portion of the plurality of cell-free nucleic acid molecules. In some embodiments of any one of the methods disclosed herein, the sequencing data is obtained without use of sample barcoding of at least a portion of the plurality of cell-free nucleic acid molecules.

In some embodiments of any one of the methods disclosed herein, the sequencing data is obtained without in silico removal or suppression of (i) background error or (ii) sequencing error.

In one aspect, the present disclosure provides a method of treating a condition of a subject, the method comprising: (a) identifying the subject for treatment of the condition, wherein the subject has been determined to have the condition based on identification of one or more cell-free nucleic acid molecules from a plurality of cell-free nucleic acid molecules that is obtained or derived from the subject, wherein each of the one or more cell-free nucleic acid molecules identified comprises a plurality of phased variants relative to a reference genomic sequence that are separated by at least one nucleotide, and wherein a presence of the plurality of phased variants is indicative of the condition of the subject; and (b) subjecting the subject to the treatment based on the identification in (a).

In one aspect, the present disclosure provides a method of monitoring a progress of a condition of a subject, the method comprising: (a) determining a first state of the condition of the subject based on identification of a first set of one or more cell-free nucleic acid molecules from a first plurality of cell-free nucleic acid molecules that is obtained or derived from the subject; (b) determining a second state of the condition of the subject based on identification of a second set of one or more cell-free nucleic acid molecules from a second plurality of cell-free nucleic acid molecules that is obtained or derived from the subject, wherein the second plurality of cell-free nucleic acid molecules are obtained from the subject subsequent to obtaining the first plurality of cell-free nucleic acid molecules from the subject; and (c) determining the progress of the condition based on the first state of the condition and the second state of the condition, wherein each of the one or more cell-free nucleic acid molecules comprises a plurality of phased variants relative to a reference genomic sequence that are separated by at least one nucleotide.

In some embodiments of any one of the methods disclosed herein, the progress of the condition is worsening of the condition.

In some embodiments of any one of the methods disclosed herein, the progress of the condition is at least a partial remission of the condition.

In some embodiments of any one of the methods disclosed herein, a presence of the plurality of phased variants is indicative of the first state or the second state of the condition of the subject.

In some embodiments of any one of the methods disclosed herein, the second plurality of cell-free nucleic acid molecules is obtained from the subject at least about 1 week, at least about 2 weeks, at least about 3 weeks, at least about 4 weeks, at least about 2 months, or at least about 3 months subsequent to obtaining the first plurality of cell-free nucleic acid molecules from the subject.

In some embodiments of any one of the methods disclosed herein, the subject is subjected to a treatment for the condition (i) prior to obtaining the second plurality of cell-free nucleic acid molecules from the subject and (ii) subsequent to obtaining the first plurality of cell-free nucleic acid molecules from the subject.

In some embodiments of any one of the methods disclosed herein, the progress of the condition is indicative of minimal residual disease of the condition of the subject. In some embodiments of any one of the methods disclosed herein, the progress of the condition is indicative of tumor burden or cancer burden of the subject.

In some embodiments of any one of the methods disclosed herein, the one or more cell-free nucleic acid molecules are captured from among the plurality of cell-free nucleic acid molecules with a set of nucleic acid probes, wherein the set of nucleic acid probes is configured to hybridize to at least a portion of cell-free nucleic acid molecules comprising one or more genomic regions associated with the condition.

In one aspect, the present disclosure provides a method comprising: (a) providing a mixture comprising (1) a set of nucleic acid probes and (2) a plurality of cell-free nucleic acid molecules that is obtained or derived from a subject, wherein an individual nucleic acid probe of the set of nucleic acid probes is designed to hybridize to at least a portion of a target cell-free nucleic acid molecule comprising a plurality of phased variants relative to a reference genomic sequence that are separated by at least one nucleotide, and wherein the individual nucleic acid probe comprises an activatable reporter agent, activation of the activatable reporter agent being selected from the group consisting of: (i) hybridization of the individual nucleic acid probe to the plurality of phased variants and (ii) dehybridization of at least a portion of the individual nucleic acid probe that has been hybridized to the plurality of phased variants; (b) detecting the activatable reporter agent that is activated, to identify one or more cell-free nucleic acid molecules of the plurality of cell-free nucleic acid molecules, wherein each of the one or more cell-free nucleic acid molecules comprises the plurality of phased variants; and (c) analyzing the identified one or more cell-free nucleic acid molecules to determine a condition of the subject.

In one aspect, the present disclosure provides a method comprising: (a) providing a mixture comprising (1) a set of nucleic acid probes and (2) a plurality of cell-free nucleic acid molecules that is obtained or derived from a subject, wherein an individual nucleic acid probe of the set of nucleic acid probes is designed to hybridize to at least a portion of a target cell-free nucleic acid molecule comprising a plurality of phased variants relative to a reference genomic sequence, and wherein the individual nucleic acid probe comprises an activatable reporter agent, activation of the activatable reporter agent being selected from the group consisting of: (i) hybridization of the individual nucleic acid probe to the plurality of phased variants and (ii) dehybridization of at least a portion of the individual nucleic acid probe that has been hybridized to the plurality of phased variants; (b) detecting the activatable reporter agent that is activated, to identify one or more cell-free nucleic acid molecules of the plurality of cell-free nucleic acid molecules, wherein each of the one or more cell-free nucleic acid molecules comprises the plurality of phased variants, wherein a limit of detection of the identification step is less than about 1 out of 50,000 cell-free nucleic acid molecules of the plurality of cell-free nucleic acid molecules; and (c) analyzing the identified one or more cell-free nucleic acid molecules to determine a condition of the subject.

In some embodiments of any one of the methods disclosed herein, the limit of detection of the identification step is less than about 1 out of 100,000, less than about 1 out of 500,000, less than about 1 out of 1,000,000, less than about 1 out of 1,500,000, or less than about 1 out of 2,000,000 cell-free nucleic acid molecules of the plurality of cell-free nucleic acid molecules.

In some embodiments of any one of the methods disclosed herein, a first phased variant of the plurality of phased variants and a second phased variant of the plurality of phased variants are separated by at least one nucleotide.

In some embodiments of any one of the methods disclosed herein, the activatable reporter agent is activated upon hybridization of the individual nucleic acid probe to the plurality of phased variants.

In some embodiments of any one of the methods disclosed herein, the activatable reporter agent is activated upon dehybridization of at least a portion of the individual nucleic acid probe that has been hybridized to the plurality of phased variants.

In some embodiments of any one of the methods disclosed herein, the method further comprises mixing (1) the set of nucleic acid probes and (2) the plurality of cell-free nucleic acid molecules.

In some embodiments of any one of the methods disclosed herein, the activatable reporter agent is a fluorophore.

In some embodiments of any one of the methods disclosed herein, analyzing the identified one or more cell-free nucleic acid molecules comprises analyzing (i) the identified one or more cell-free nucleic acid molecules and (ii) other cell-free nucleic acid molecules of the plurality of cell-free nucleic acid molecules that do not comprise the plurality of phased variants as different variables.

In some embodiments of any one of the methods disclosed herein, the analyzing of the identified one or more cell-free nucleic acid molecules is not based on other cell-free nucleic acid molecules of the plurality of cell-free nucleic acid molecules that do not comprise the plurality of phased variants.

In some embodiments of any one of the methods disclosed herein, a number of the plurality of phased variants from the identified one or more cell-free nucleic acid molecules is indicative of the condition of the subject. In some embodiments, a ratio of (i) the number of the plurality of phased variants from the one or more cell-free nucleic acid molecules and (ii) a number of single nucleotide variants (SNVs) from the one or more cell-free nucleic acid molecules is indicative of the condition of the subject.

In some embodiments of any one of the methods disclosed herein, a frequency of the plurality of phased variants in the identified one or more cell-free nucleic acid molecules is indicative of the condition of the subject. In some embodiments, the frequency is indicative of a diseased cell associated with the condition. In some embodiments, the condition is diffuse large B-cell lymphoma, and wherein the frequency is indicative of whether the one or more cell-free nucleic acid molecules are derived from germinal center B-cell (GCB) or activated B-cell (ABC).

In some embodiments of any one of the methods disclosed herein, genomic origin of the identified one or more cell-free nucleic acid molecules is indicative of the condition of the subject.

In some embodiments of any one of the methods disclosed herein, the first and second phased variants are separated by at least 2, at least 3, at least 4, at least 5, at least 6, at least 7, or at least 8 nucleotides. In some embodiments of any one of the methods disclosed herein, the first and second phased variants are separated by at most about 180, at most about 170, at most about 160, at most about 150, or at most about 140 nucleotides.

In some embodiments of any one of the methods disclosed herein, at least about 10%, at least about 20%, at least about 30%, at least about 40%, or at least about 50% of the one or more cell-free nucleic acid molecules comprising a plurality of phased variants comprises a single nucleotide variant (SNV) that is at least 2 nucleotides away from an adjacent SNV.

In some embodiments of any one of the methods disclosed herein, the plurality of phased variants comprises at least 3, at least 4, at least 5, at least 10, at least 15, at least 20, or at least 25 phased variants within the same cell-free nucleic acid molecule.

In some embodiments of any one of the methods disclosed herein, the one or more cell-free nucleic acid molecules identified comprises at least 2, at least 3, at least 4, at least 5, at least 10, at least 50, at least 100, at least 500, or at least 1,000 cell-free nucleic acid molecules.

In some embodiments of any one of the methods disclosed herein, the reference genomic sequence is derived from a reference cohort. In some embodiments, the reference genomic sequence comprises a consensus sequence from the reference cohort. In some embodiments, the reference genomic sequence comprises at least a portion of hg19 human genome, hg18 genome, hg17 genome, hg16 genome, or hg38 genome.

In some embodiments of any one of the methods disclosed herein, the reference genomic sequence is derived from a sample of the subject.

In some embodiments of any one of the methods disclosed herein, the sample is a healthy sample. In some embodiments, the sample comprises a healthy cell. In some embodiments, the healthy cell comprises a healthy leukocyte.

In some embodiments of any one of the methods disclosed herein, the sample is a diseased sample. In some embodiments, the diseased sample comprises a diseased cell. In some embodiments, the diseased cell comprises a tumor cell. In some embodiments, the diseased sample comprises a solid tumor.

In some embodiments of any one of the methods disclosed herein, the set of nucleic acid probes is designed based on the plurality of phased variants that are identified by comparing (i) sequencing data from a solid tumor, lymphoma, or blood tumor of the subject and (ii) sequencing data from a healthy cell of the subject or a healthy cohort. In some embodiments, the healthy cell is from the subject. In some embodiments, the healthy cell is from the healthy cohort.

In some embodiments of any one of the methods disclosed herein, the set of nucleic acid probes are designed to hybridize to at least a portion of sequences of genomic loci associated with the condition. In some embodiments, the genomic loci associated with the condition are known to exhibit aberrant somatic hypermutation when the subject has the condition.

In some embodiments of any one of the methods disclosed herein, the set of nucleic acid probes are designed to hybridize to at least about 5%, at least about 10%, at least about 20%, at least about 30%, at least about 40%, at least about 50%, at least about 60%, at least about 70%, at least about 80%, at least about 90%, or about 100% of (i) the genomic regions identified in Table 1, (ii) the genomic regions identified in Table 3, or (iii) the genomic regions identified to have a plurality of phased variants in Table 3.

In some embodiments of any one of the methods disclosed herein, each nucleic acid probe of the set of nucleic acid probes has at least about 70%, at least about 80%, at least about 90% sequence identity, at least about 95% sequence identity, or about 100% sequence identity to a probe sequence selected from Table 6.

In some embodiments of any one of the methods disclosed herein, the set of nucleic acid probes comprises at least about 5%, at least about 10%, at least about 20%, at least about 30%, at least about 40%, at least about 50%, at least about 60%, at least about 70%, at least about 80%, or at least about 90% of probe sequences in Table 6.

In some embodiments of any one of the methods disclosed herein, the method further comprises determining that the subject has the condition or determining a degree or status of the condition of the subject, based on the identified one or more cell-free nucleic acid molecules comprising the plurality of phased variants. In some embodiments, the method further comprises determining that the one or more cell-free nucleic acid molecules are derived from a sample associated with the condition, based on performing a statistical model analysis of the identified one or more cell-free nucleic acid molecules. In some embodiments, the statistical model analysis comprises a Monte Carlo statistical analysis.

In some embodiments of any one of the methods disclosed herein, the method further comprises monitoring a progress of the condition of the subject based on the identified one or more cell-free nucleic acid molecules.

In some embodiments of any one of the methods disclosed herein, the method further comprises performing a different procedure to confirm the condition of the subject. In some embodiments, the different procedure comprises a blood test, genetic test, medical imaging, physical exam, or tissue biopsy.

In some embodiments of any one of the methods disclosed herein, the method further comprises determining a treatment for the condition of the subject based on the identified one or more cell-free nucleic acid molecules.

In some embodiments of any one of the methods disclosed herein, the subject has been subjected to a treatment for the condition prior to (a).

In some embodiments of any one of the methods disclosed herein, the treatment comprises chemotherapy, radiotherapy, chemoradiotherapy, immunotherapy, adoptive cell therapy, hormone therapy, targeted drug therapy, surgery, transplant, transfusion, or medical surveillance.

In some embodiments of any one of the methods disclosed herein, the plurality of cell-free nucleic acid molecules comprise a plurality of cell-free deoxyribonucleic acid (DNA) molecules.

In some embodiments of any one of the methods disclosed herein, condition comprises a disease.

In some embodiments of any one of the methods disclosed herein, the plurality of cell-free nucleic acid molecules are derived from a bodily sample of the subject. In some embodiments, the bodily sample comprises plasma, serum, blood, cerebrospinal fluid, lymph fluid, saliva, urine, or stool.

In some embodiments of any one of the methods disclosed herein, the subject is a mammal. In some embodiments of any one of the methods disclosed herein, the subject is a human.

In some embodiments of any one of the methods disclosed herein, the condition comprises neoplasm, cancer, or tumor. In some embodiments, the condition comprises a solid tumor. In some embodiments, the condition comprises a lymphoma. In some embodiments, the condition comprises a B-cell lymphoma. In some embodiments, the condition comprises a sub-type of B-cell lymphoma selected from the group consisting of diffuse large B-cell lymphoma, follicular lymphoma, Burkitt lymphoma, and B-cell chronic lymphocytic leukemia.

In some embodiments of any one of the methods disclosed herein, the plurality of phased variants have been previously identified as tumor-derived from sequencing a prior tumor sample or cell-free nucleic acid sample.

In one aspect, the present disclosure provides a composition comprising a bait set comprising a set of nucleic acid probes designed to capture cell-free DNA molecules derived from at least about 5% of genomic regions set forth in (i) the genomic regions identified in Table 1, (ii) the genomic regions identified in Table 3, or (iii) the genomic regions identified to have a plurality of phased variants in Table 3.

In some embodiments of any of the compositions disclosed herein, the set of nucleic acid probes are designed to pull down cell-free DNA molecules derived from at least about 10%, at least about 20%, at least about 30%, at least about 40%, at least about 50%, at least about 60%, at least about 70%, at least about 80%, at least about 90%, or about 100% of the genomic regions set forth in (i) the genomic regions identified in Table 1, (ii) the genomic regions identified in Table 3, or (iii) the genomic regions identified to have a plurality of phased variants in Table 3.

In some embodiments of any of the compositions disclosed herein, the set of nucleic acid probes are designed to capture the one or more cell-free DNA molecules derived from at most about 10%, at most about 20%, at most about 30%, at most about 40%, at most about 50%, at most about 60%, at most about 70%, at most about 80%, at most about 90%, or about 100% of the genomic regions set forth in (i) the genomic regions identified in Table 1, (ii) the genomic regions identified in Table 3, or (iii) the genomic regions identified to have a plurality of phased variants in Table 3.

In some embodiments of any of the compositions disclosed herein, the bait set comprises at most 5, at most 10, at most 50, at most 100, at most 500, at most 1000, or at most 2000 nucleic acid probes.

In some embodiments of any of the compositions disclosed herein, an individual nucleic acid probe of the set of nucleic acid probes comprises a pull-down tag.

In some embodiments of any of the compositions disclosed herein, the pull-down tag comprises a nucleic acid barcode.

In some embodiments of any of the compositions disclosed herein, the pull-down tag comprises biotin.

In some embodiments of any of the compositions disclosed herein, each of the cell-free DNA molecules is between about 100 nucleotides and about 180 nucleotides in length.

In some embodiments of any of the compositions disclosed herein, the genomic regions are associated with a condition.

In some embodiments of any of the compositions disclosed herein, the genomic regions exhibit aberrant somatic hypermutation when a subject has the condition.

In some embodiments of any of the compositions disclosed herein, the condition comprises a B-cell lymphoma. In some embodiments, the condition comprises a sub-type of B-cell lymphoma selected from the group consisting of diffuse large B-cell lymphoma, follicular lymphoma, Burkitt lymphoma, and B-cell chronic lymphocytic leukemia.

In some embodiments of any of the compositions disclosed herein, the composition further comprises a plurality of cell-free DNA molecules obtained or derived from a subject.

In one aspect, the present disclosure provides a method to perform a clinical procedure on an individual, the method comprising: (a) obtaining or having obtained a targeted sequencing result of a collection of cell-free nucleic acid molecules, wherein the collection of cell-free nucleic acid molecules are sourced from a liquid or waste biopsy of an individual, and wherein the targeting sequencing is performed utilizing nucleic acid probes to pull down sequences of genomic loci known to experience aberrant somatic hypermutation in a B-cell cancer; (b) identifying or having identified a plurality of variants in phase within the cell-free nucleic acid sequencing result; (c) determining or having determined, utilizing a statistical model and the identified phased variants, that the cell-free nucleic acid sequencing result contains nucleotides derived from a neoplasm; and (d) performing a clinical procedure on the individual to confirm the presence of the B-cell cancer, based upon determining that the cell-free nucleic acid sequencing result contains nucleic acid sequences likely derived from the B-cell cancer.

In some embodiments of any of the compositions disclosed herein, the biopsy is one of blood, serum, cerebrospinal fluid, lymph fluid, urine, or stool.

In some embodiments of any of the compositions disclosed herein, the genomic loci are selected from (i) the genomic regions identified in Table 1, (ii) the genomic regions identified in Table 3, or (iii) the genomic regions identified to have a plurality of phased variants in Table 3.

In some embodiments of any of the compositions disclosed herein, the sequences of the nucleic acid probes are selected from Table 6.

In some embodiments of any of the compositions disclosed herein, the clinical is procedure is a blood test, medical imaging, or a physical exam.

In one aspect, the present disclosure provides a method to treat an individual for a B-cell cancer, the method comprising: (a) obtaining or having obtained a targeted sequencing result of a collection of cell-free nucleic acid molecules, wherein the collection of cell-free nucleic acid molecules are sourced from a liquid or waste biopsy of an individual, and wherein the targeting sequencing is performed utilizing nucleic acid probes to pull down sequences of genomic loci known to experience aberrant somatic hypermutation in a B-cell cancer; (b) identifying or having identified a plurality of variants in phase within the cell-free nucleic acid sequencing result; (c) determining or having determined, utilizing a statistical model and the identified phased variants, that the cell-free nucleic acid sequencing result contains nucleotides derived from a neoplasm; and (d) treating the individual to curtail the B-cell cancer, based upon determining that the cell-free nucleic acid sequencing result contains nucleic acid sequences derived from the B-cell cancer.

In some embodiments of any of the compositions disclosed herein, the biopsy is one of blood, serum, cerebrospinal fluid, lymph fluid, urine or stool.

In some embodiments of any of the compositions disclosed herein, the genomic loci are selected from (i) the genomic regions identified in Table 1, (ii) the genomic regions identified in Table 3, or (iii) the genomic regions identified to have a plurality of phased variants in Table 3.

In some embodiments of any of the compositions disclosed herein, the sequences of the nucleic acid probes are selected from Table 6.

In some embodiments of any of the compositions disclosed herein, the treatment is chemotherapy, radiotherapy, immunotherapy, hormone therapy, targeted drug therapy, or medical surveillance.

In one aspect, the present disclosure provides a method to detect cancerous minimal residual disease in an individual and to treat the individual for a cancer, the method comprising: (a) obtaining or having obtained a targeted sequencing result of a collection of cell-free nucleic acid molecules, wherein the collection of cell-free nucleic acid molecules are sourced from a liquid or waste biopsy of an individual, wherein the liquid or waste biopsy is sourced after a series of treatments in order to detect minimal residual disease, and wherein the targeting sequencing is performed utilizing nucleic acid probes to pull down sequences of genomic loci determined to contain a plurality of variants in phase, as determined by a prior sequencing result on a prior biopsy derived from the cancer; (b) identifying or having identified at least one set of the plurality of variants in phase within the cell-free nucleic acid sequencing result; and (c) treating the individual to curtail the cancer, based upon determining that the cell-free nucleic acid sequencing result contains nucleic acid sequences derived from the cancer.

In some embodiments of any of the compositions disclosed herein, the liquid or waste biopsy is one of blood, serum, cerebrospinal fluid, lymph fluid, urine or stool.

In some embodiments of any of the compositions disclosed herein, the treatment is chemotherapy, radiotherapy, immunotherapy, hormone therapy, targeted drug therapy, or medical surveillance.

In one aspect, the present disclosure provides a computer program product comprising a non-transitory computer-readable medium having computer-executable code encoded therein, the computer-executable code adapted to be executed to implement any one of the methods disclosed herein.

In one aspect, the present disclosure provides a system comprising one or more computer processors and computer memory coupled thereto, wherein the computer memory comprises machine executable code that, upon execution by the one or more computer processors, implements any one of the methods disclosed herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

Various features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 1A. is a cartoon depicting the difference between detection of a single nucleotide variant (SNV) (top) and multiple variants 'in-phase' (phased variants, PVs; bottom) on individual cell-free DNA molecules. In theory, detection of a PV is a more specific event than detection of an isolated SNV. FIG. 1B. is a scatter plot showing the distribution of the number of PVs from WGS data for 24 different histologies of cancer, normalized by the total number of SNVs. Bars show the median value and interquartile range. (FL-NHL, follicular lymphoma; DLBCL-NHL, diffuse large B-cell lymphoma; Burkitt-NHL, Burkitt lymphoma; Lung-SCC, squamous cell lung cancer; Lung-Adeno, lung adenocarcinoma; Kidney-RCC, renal cell carcinoma; Bone-Osteosarc, osteosarcoma; Liver-HCC, hepatocellular carcinoma; Breast-Adeno, breast adenocarcinoma; Panc-Adeno, pancreatic adenocarcinoma; Head-SCC, head and neck squamous cell carcinoma; Ovary-Adeno, ovarian adenocarcinoma; Eso-Adeno, esophageal adenocarcinoma; Uterus-Adeno, uterine adenocarcinoma; Stomach-Adeno, stomach adenocarcinoma; CLL, chronic lymphocytic leukemia; ColoRect-Adeno, colorectal adenocarcinoma; Prost-Adeno, prostate adenocarcinoma; CNS-GBM, glioblastoma multiforme; Panc-Endocrine, pancreatic neuroendocrine tumor; Thy-Adeno, thyroid adenocarcinoma; CNS-PiloAstro, piloastrocytoma; CNS-Medullo, medulloblastoma.) FIG. 1C. is a heatmap demonstrating the enrichment in single base substitution (SBS) mutational signatures for PVs versus single SNVs across multiple cancer types. Blue represents signatures which are enriched in PVs in specific histologies; darker gray represents signatures where un-phased, single SNVs are enriched; and red represents SNVs occurring in isolation. Only signatures which have a significant difference between PVs and unphased SNVs after correcting for multiple hypotheses are shown; other signatures are grey. Signatures associated with smoking, AID/AICDA, and APOBEC are indicated. FIG. 1D. demonstrate bar plots showing the distribution of PVs occurring in stereotyped regions across the genome in B-lymphoid malignancies and lung adenocarcinoma. In this plot, the genome was divided into 1000 bp bins, and the fraction of samples of a given histology with a PV in each 1000 bp bin was calculated. Only bins that have at least a 2 percent recurrence frequency in any cancer subtype are shown. Key genomic loci are also labeled. FIG. 1E. is a comparison of duplex sequencing to phased variant sequencing. A schema comparing error-suppressed sequencing by duplex sequencing vs. recovery of phased variants. In duplex sequencing, recovery of a single SNV observed on both strands of an original DNA double-helix (i.e., in trans) is required. This requires independent recovery of two molecules by sequencing as the plus and minus strands of the original DNA molecule go through library preparation and PCR independently. In contrast, recovery of PVs requires multiple SNVs observed on the same single strand of DNA (i.e., in cis). Thus, recovery of only the plus or the minus strand (rather than both) is sufficient for identification of PVs.

FIG. 2A is a schematic of the design for PhasED-Seq. WGS data from DLBCL tumor samples were aggregated (left), and areas of recurrent putative PVs were identified (middle). An assay capturing the genomic regions most recurrently containing PVs was then designed (right), resulting in an ~7500× enrichment in PVs compared to WGS. The top right panel shows the in silico expected number of PVs per case per kilobase of panel size (y-axis) for increasing panel sizes (x-axis). The dashed line shows the selected regions in the PhasED-Seq panel. The bottom right panel shows the total number of expected PVs per case (y-axis, assessed in silico from WGS data, for increasing panel sizes (y-axis). The dark area shows the selected regions in the PhasED-Seq panel. FIG. 2B illustrate two panels showing the yield of SNVs (left) and PVs (right) for sequencing tumor DNA and matched germline by a previously established lymphoma CAPP-Seq panel or PhasED-Seq; values are assessed in silico by limiting WGS to the targeted space of interest. PVs reported in the right panel include doublet, triplet, and quadruplet phased events. FIG. 2C shows the yield of SNVs (left) and PVs (right) from experimental sequencing of tumor and/or cell-free DNA from CAPP-Seq versus PhasED-Seq, similar to FIG. 2B. FIG. 2D is a scatterplot showing the frequency of PVs by genomic location (in 1000 bp bins) for patients with DLBCL, identified either by WGS or identified by PhasED-Seq. PVs in IGH, BCL2, MYC, and BCL6 are highlighted. FIG. 2E illustrate scatterplots comparing the frequency of PVs by genomic location (in 50 bp bins) for patients with different types of lymphomas. The colored circles show the relative frequency of PVs in 50 bp bins from a specific gene of interest; the other (gray) circles show the relative frequency of PVs in 50 bp bins from the remainder of the PhasED-Seq sequencing panel. FIG. 2F illustrate volcano plots summarizing the difference in relative frequency of PVs in specific genetic loci between types of lymphoma, including ABC-DLBCL vs. GCB-DLBCL (dark Gray, left); PMBCL vs DLBCL (dark gray, middle); and HL vs. DLBCL (dark gray, right). The x-axis demonstrates the relative enrichment in PVs in a specific locus, while the y-axis demonstrates the statistical significance of this association. (Example 10).

FIG. 3A illustrates bar plot showing the performance of hybrid capture sequencing for recovery of synthetic 150 bp oligonucleotides from two loci (MYC and BCL6) with increasing degree of mutation/non-reference bases. Error bars represent the 95% confidence interval (n=3 replicates of each condition in distinct samples). FIG. 3B illustrates plot demonstrating the background error-rate (Example 10) for different types of error-suppression from 12 healthy control cell-free DNA samples sequenced on the PhasED-Seq panel. 'PhasED-Seq 2×' or 'doublets' represents detection of two mutations in-phase on the same DNA molecule; 'PhasED-Seq 3×' or 'triplets' represents detection of three mutations in-phase on the same DNA molecule. FIG. 3C illustrates bar plot showing the depth of unique molecular recovery (e.g., depth after barcode-mediated PCR duplicate removal) from sequencing data from 12 cell-free DNA samples for different types of error-suppression, including barcode deduplication, duplex sequencing, and recovery of PVs of increasing maximal distance between SNVs in-phase. FIG. 3D illustrates bar plot showing the cumulative fraction of PVs that have a maximal distance between SNVs less than the number of base-pairs shown on the x-axis. FIG. 3E illustrates a plot demonstrating the results of a limiting dilution series simulating cell-free DNA samples containing patient-specific tumor fractions of $1 \times 10^{-3}$ to $0.5 \times 10^{-6}$; cfDNA from 3 independent patients samples were used in each dilution. The same sequencing data was analyzed using a variety of error-suppression methods for recovery of expected tumor fractions, including iDES, duplex sequencing, and PhasED-Seq (both for recovery of doublet and triplet molecules). Points and error-bars represent the mean, minimum, and maximum across the three patient-specific tumor mutations considered. The difference between observed and expected tumor fractions for sample <1:10,000 were compared via paired t-test. *, P<0.05, , P<0.005, *, P<0.0005. FIG. 3F illustrates plot demonstrating the background signal for detection of tumor-specific alleles in 12 unrelated, healthy cell-free DNA samples, and the healthy cfDNA sample used for limiting dilution series (n=13 total samples). In each sample, tumor-specific SNVs or PVs from the 3 patient samples utilized in the limiting dilution experiment shown in FIG. 3E, for a total of 39 assessments were assessed. Bars represent the arithmetic mean across all 39 assessments; statistical comparison performed by Wilcoxon rank-sum test. *, P<0.05, , P<0.005, *, P<0.0005. FIG. 3G illustrates plot showing the theoretical rate of detection for a sample with a given number of PV-containing regions, according to simple binomial sampling. This plot is produced by assuming a unique sequencing depth of 5000× (line), along with a varying number of independent 150 bp PV-containing regions, from 3 regions (blue) to 67 regions (purple). Confidence envelopes consider depth from 4000-6000×; a 5% false-positive rate is also assumed. FIG. 3H illustrates plot showing the observed rate of detection (y-axis) for sample of a given true tumor fraction (x-axis), with varying numbers of PV-containing regions. For each number of tumor-reporter regions ranging from 3 to 67, this number of 150 bp windows was randomly sampled from each of 3 patient-specific PV reporter lists 25 times and used to assess tumor-detection at each dilution. Filled-in points represent 'wet' dilution series experiments, while open points represent in silico dilution experiments. Points and error-bars represent the mean, minimum, and maximum across the three patient-specific PV reporter lists used in the original sampling. FIG. 3I illustrates scatter plot compares the predicted vs observed rate of detection for samples from the dilution series shown in panels FIG. 3G and FIG. 3H. Additional details of this experiment are provided in Example 10.

FIGS. 4A-4G illustrate clinical application of PhasED-Seq for ultra-sensitive disease detection and response monitoring in DLBCL. FIG. 4A illustrates plot showing ctDNA levels for a patient with DLBCL responding to, and subsequently relapsing after, first-line immuno-chemotherapy. Levels measured by CAPP-Seq are shown in darker gray circles while levels measured by PhasED-Seq are shown in lighter gray circles. Open circles represent undetectable levels by CAPP-Seq. FIG. 4B illustrates a univariate scatter plot showing the mean tumor allele fraction measured by PhasED-Seq for clinical samples at time-points of minimal disease (i.e., after 1 or 2 cycles of therapy). The plot is divided by samples detected vs undetected by standard CAPP-Seq; P-value from Wilcoxon rank-sum test. FIG. 4C illustrates bar plot showing the fraction of DLBCL patients who have detectable ctDNA by CAPP-Seq after 1 or 2 cycles of treatment (dark gray bars), as well as the fraction of additional patients with detectable disease when adding PhasED-Seq to standard CAPP-Seq (medium gray bars). P-value represents a Fisher's Exact Test for detection by CAPP-Seq alone versus the combination of PhasED-Seq and CAPP-Seq in 171 samples after 1 or 2 cycles of treatment. FIG. 4D illustrates a waterfall plot showing the change in ctDNA levels measured by CAPP-Seq after 2 cycles of first-line therapy in patients with DLBCL. Patients with undetectable ctDNA by CAPP-Seq are shown as "ND" ("not detected"), in darker colors. The colors of the bars also indicate the eventual clinical outcomes for these patients. FIG. 4E illustrates a Kaplan-Meier plot showing the event-free survival for 52 DLBCL patients with undetectable ctDNA measured by CAPP-Seq after 2 cycles. FIG. 4F illustrates a Kaplan-Meier plot showing the event-free survival of 52 patients shown in FIG. 4E (undetectable ctDNA by CAPP-Seq) stratified by ctDNA detection via PhasED-Seq at this same time-point (cycle 3, day 1). FIG. 4G illustrates a Kaplan-Meier plot showing the event-free survival for 89 patients with DLBCL stratified by ctDNA at cycle 3, day 1 separated into 3 strata—patients failing to achieve a major molecular response (dark gray), patients with a major molecular response who still have detectable ctDNA by PhasED-Seq and/or CAPP-Seq (light grey), and patients who have a stringent molecular remission (undetectable ctDNA by PhasED-Seq and CAPP-Seq; medium gray).

FIG. 5A-C illustrate Univariate scatter plots showing the number of SNVs (FIG. 5A), PVs (FIG. 5B), and PVs, controlling for total number of SNVs (FIG. 5C), from WGS data for 24 different histologies of cancer. Bars show the median value and interquartile range. (FL-NHL, follicular lymphoma; DLBCL-NHL, diffuse large B cell lymphoma; Burkitt-NHL, Burkitt lymphoma; Lung-SCC, squamous cell lung cancer; Lung-Adeno, lung adenocarcinoma; Kidney-RCC, renal cell carcinoma; Bone-Osteosarc, osteosarcoma; Liver-HCC, hepatocellular carcinoma; Breast-Adeno, breast adenocarcinoma; Panc-Adeno, pancreatic adenocarcinoma; Head-SCC, head and neck squamous cell carcinoma; Ovary-Adeno, ovarian adenocarcinoma; Eso-Adeno, esophageal adenocarcinoma; Uterus-Adeno, uterine adenocarcinoma; Stomach-Adeno, stomach adenocarcinoma; CLL, chronic lymphocytic leukemia; ColoRect-Adeno, colorectal adenocarcinoma; Prost-Adeno, prostate adenocarcinoma; CNS-GBM, glioblastoma multiforme; Panc-Endocrine, pancreatic neuroendocrine tumor; Thy-Adeno, thyroid adenocarcinoma; CNS-PiloAstro, piloastrocytoma; CNS-Medullo, medulloblastoma).

FIG. 8A. illustrates bar plot showing the number of independent 1000 bp regions across the genome that recurrently contain PVs for DLBCL, FL, BL, and CLL (n=68, 74, 36, and 151 respectively). FIG. 8B-D illustrate plots showing the frequency of PVs for multiple lymphoid malignancies with relationships to specific genetic loci, including FIG. 8B: BCL2, FIG. 8C: MYC, and FIG. 8D: ID3. The location of the transcript for a given gene is shown below the plot in grey; exons are shown in darker gray. * indicates a region with significantly more PVs in a given cancer histology compared to all other histologies by Fisher's Exact Test (P<0.05). FIG. 8E, similar to FIG. 8B-D, these plots show the frequency of PVs across lymphoma subtypes. Here, it is shown the IGH locus, consisting of IGHV, IGHD, and IGHJ parts, for ABC and GCB subtype DLBCLs (n=25 and 25, respectively). Coding regions for Ig parts, including Ig-constant regions and V-genes, are shown. (DLBCL, diffuse large B-cell lymphoma; FL, follicular lymphoma; BL, Burkitt lymphoma; CLL, chronic lymphocytic leukemia).

FIG. 9A illustrates univariate scatter plot showing the fraction of all PVs across the genome identified by WGS (n=79) that were recovered by previously reported lymphoma CAPP-Seq panel[8] (left) compared to PhasED-Seq (right). FIG. 9B illustrates the expected yield of SNVs per case identified from WGS using a previously established lymphoma CAPP-Seq panel or the PhasED-Seq panel. FIG. 9C illustrates the expected yield of PVs per case identified from WGS using a previously established lymphoma CAPP-Seq panel or the PhasED-Seq panel. Data from three independent publicly available cohorts are shown in FIGS. 9A-9C. FIG. 9D-9F illustrate plots showing the improvement in recovery of PVs by PhasED-Seq compared to CAPP-Seq in 16 patients sequenced by both assays. This includes improvement in d) two SNVs in phase (e.g., 2× or 'doublet PVs'), e) three SNVs in phase (3× or 'triplet PVs') and f) four SNVs in phase (e.g., 4× or 'quadruplet PVs'). FIGS. 9G-9K. illustrate panels showing the number of SNVs and PVs identified for patients with different types of lymphomas. These panels show the number of g) SNVs, h) doublet PVs, i) triplet PVs, j) quadruplet PVs, and k) all PVs. *, P<0.05; , P<0.01; *, P<0.001. (DLBCL, diffuse large B-cell lymphoma; GCB, germinal center B-cell like DLBCL; ABC, activated B-cell like DLBCL; PMBCL, primary mediastinal B-cell lymphoma; HL, Hodgkin lymphoma).

FIG. 14A shows a plot of the theoretical energy of binding for typical 150-mers across the genome with increasing fraction of bases mutated from the reference genome. Mutations were spread throughout the 150-mer either clustered to one end of the sequence, clustered in the middle of the sequence, or randomly throughout the sequence. Point and error-bars represent the median and interquartile ranges from 10,000 in silico simulations. FIG. 14B illustrates a plot showing two histograms of summary metrics of the mutation rate of 151-bp windows across the PhasED-Seq panel across all patients in this study. The light gray histogram shows the maximum percent mutated in any 151-bp window for all patients in this study; the dark gray histogram shows the 95$^{th}$ percentile mutation rate across all mutated 151-bp windows. FIG. 14C is a plot showing the percentile of mutation rate across all mutated 151-bp windows across all patients in this study.

FIG. 14D illustrates heatmaps showing the relative error rate (as log 10(error rate)) for single SNVs (left, "RED"), doublet PVs (middle, "YELLOW"), and triplet PVs (right, "BLUE"). FIG. 14D demonstrates that analysis based on the plurality of phased variants (e.g., double or triplet PVs) yields a lower error rate than analysis based on single SNVs. In addition, FIG. 14D demonstrates that analysis using a higher number of phased variant sets (e.g., triplet PVs labeled as "BLUE") yields a lower error rate than analysis based on a lower number of phased variant sets (e.g., doublet PVs labeled as "YELLOW"). The error rate of single SNVs from sequencing with multiple error suppression methods is shown, including barcode deduplication, iDES, and duplex sequencing. Error rates are summarized by the type of mutation. In the case of triplet PVs, the x and y-axis of the heatmap represent the first and second type of base alteration in the PV; the third alteration is averaged over all 12 possible base changes. FIG. 14E illustrates a plot showing the error rate for doublet/2× PVs as a function of the genomic distance between the component SNVs.

FIG. 15 illustrates the detection-rate of ctDNA from pretreatment samples across 107 patients with large-B cell lymphomas by standard CAPP-Seq (green), as well as PhasED-Seq using doublets (light blue), triplets (medium blue), and quadruplets (dark blue). The specificity of ctDNA detection is also shown. In the lower two plots, the false-detection rate in 40 withheld healthy control cfDNA samples is shown. The size of each bar in these two plots shows the detection-rate for patient-specific cfDNA mutations in these 40-withheld controls, across all 107 cases. FIG. 16A illustrates table summarizing the sensitivity and specificity for ctDNA detection in pretreatment samples by CAPP-Seq and PhasED-Seq using doublets, triplets, and quadruplets, shown in panel A. Sensitivity is calculated across all 107 cases, while specificity is calculated across the 40 withheld control samples, assessing for each of the 107 independent patient-specific mutation lists, for a total of 4280 independent tests. FIG. 16B illustrates a scatterplot showing the quantity of ctDNA (measured as log 10(haploid genome equivalents/mL)) as measured by CAPP-Seq vs. PhasED-Seq in individual samples. Samples taken prior to cycle 1 of RCHOP therapy (i.e., pretreatment), prior to cycle 2, and prior to cycle 3, are shown in independent colors (blue, green, and red respectively; 278 total samples). Undetectable levels fall on the axes. Spearman correlation and P-value are shown.

FIGS. 17A-17D illustrate detection of ctDNA after two cycles of systemic therapy. FIG. 17A illustrates a scatter plot showing the log-fold change in ctDNA after 2 cycles of therapy (i.e., the Major Molecular Response or MMR) measured by CAPP-Seq or PhasED-Seq for patients receiving RCHOP therapy. Dotted lines show the previously established threshold of a 2.5-log reduction in ctDNA for MMR. Undetectable samples fall on the axes; the correlation coefficient represents a Spearman rho for the 33 samples detected by both CAPP-Seq and PhasED-Seq. FIG. 17B illustrates 2 by 2 tables summarizing the detection rate of ctDNA samples after 2 cycles of therapy by PhasED-Seq vs CAPP-Seq. Patients with eventual disease progression are shown in bottom panel, while patients without eventual disease progression are shown in upper panel. FIG. 17C illustrates bar-plots showing the area under the receiver operator curve (AUC) for classification of patients for event-free survival at 24 months based on CAPP-Seq (light colors) or PhasED-Seq (dark colors) after 2 cycles of therapy. Classification of all patient (n=89, left) and only patients achieving a MMR (n=69, right) are both shown. FIG. 17D illustrates Kaplan-Meier plots showing the event-free survival of 69 patients achieving a MMR stratified by ctDNA detection with CAPP-Seq (top) or PhasED-Seq (bottom).

FIGS. 18A-18H illustrate detection of ctDNA after one cycle of systemic therapy. FIG. 18A illustrates scatterplot showing the log-fold change in ctDNA after 1 cycle of therapy (i.e., the Early Molecular Response or EMR) measured by CAPP-Seq or PhasED-Seq for patients receiving RCHOP therapy. Dotted lines show the previously established threshold of a 2-log reduction in ctDNA for EMR. Undetectable samples fall on the axes; the correlation coefficient represents a Spearman rho for the 45 samples detected by both CAPP-Seq and PhasED-Seq. FIG. 18B illustrates 2 by 2 tables summarizing the detection rate of ctDNA samples after 1 cycle of therapy by PhasED-Seq vs CAPP-Ceq. Patients with eventual disease progression are shown in red, while patients without eventual disease progression are shown in blue. FIG. 18C illustrates bar-plots showing the area under the receiver operator curve (AUC) for classification of patients for event-free survival at 24 months based on CAPP-Seq (light colors) or PhasED-Seq (dark colors) after 1 cycle of therapy. Classification of all patient (n=82, left) and only patients achieving an EMR (n=63, right) are both shown. FIG. 18D illustrates Kaplan-Meier plots showing the event-free survival of 63 patients achieving an EMR stratified by ctDNA detection with CAPP-Seq (top) or PhasED-Seq (bottom). FIG. 18E illustrates waterfall plot showing the change in ctDNA levels measured by CAPP-Seq after 1 cycle of first-line therapy in patients with DLBCL. Patients with undetectable ctDNA by CAPP-Seq are shown as "ND" ("not detected"), in darker colors. The colors of the bars also indicate the eventual clinical outcomes for these patients. FIG. 18F illustrates a Kaplan-Meier plot showing the event-free survival for 33 DLBCL patients with undetectable ctDNA measured by CAPP-Seq after 1 cycle of therapy. FIG. 18G illustrates a Kaplan-Meier plot showing the event-free survival of 33 patients shown in FIG. 18F (undetectable ctDNA by CAPP-Seq) stratified by ctDNA detection via PhasED-Seq at this same time-point (cycle 2, day 1). FIG. 18H illustrates a Kaplan-Meier plot showing the event-free survival for 82 patients with DLBCL stratified by ctDNA at cycle 2, day 1 separated into 3 strata—patients failing to achieve an early molecular response, patients with an early molecular response who still have detectable ctDNA by PhasED-Seq and/or CAPP-Seq, and patients who have a stringent molecular remission (undetectable ctDNA by PhasED-Seq and CAPP-Seq).

FIGS. 25A-25C show example flowcharts of methods for determining a condition of a subject based on one or more cell-free nucleic acid molecules comprising a plurality of variants.

FIG. 25D shows an example flowchart of a method for treating a condition of a subject based on one or more cell-free nucleic acid molecules comprising a plurality of variants.

FIGS. 25F and 25G show example flowcharts of methods for determining a condition of a subject based on one or more cell-free nucleic acid molecules comprising a plurality of variants.

DETAILED DESCRIPTION

Figure 1A:
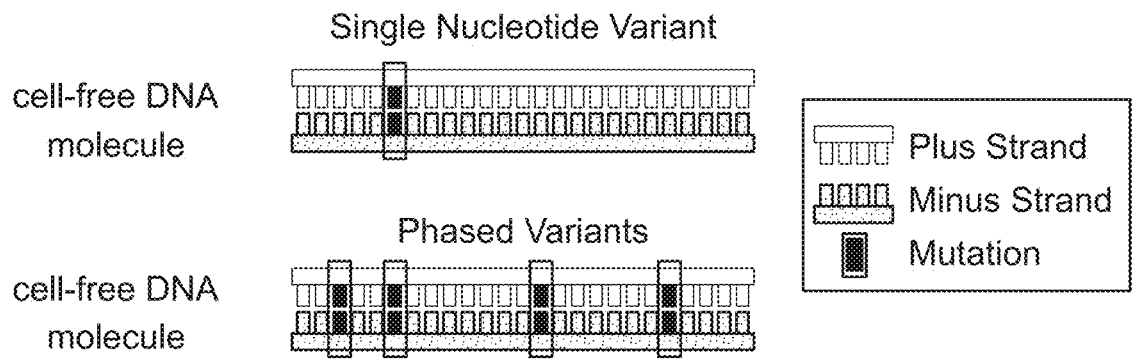
FIGS. 1A-1E illustrate discovery of phased variants and their mutational signatures via analysis of whole-genome sequencing data.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "about" or "approximately" generally mean within an acceptable error range for the particular value, which may depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value may be assumed.

The term "phased variants," "variants in phase," "PV," or "somatic variants in phase," as used interchangeably herein, generally refers to two or more mutations (e.g., SNVs or indels) that occur in cis (i.e., on the same strand of a nucleic acid molecule) within a single cell-free nucleic acid molecule. In some cases, a cell-free nucleic acid molecule can be a cell-free deoxyribonucleic acid (cfDNA) molecule. In some cases, a cfDNA molecule can be derived from a diseased tissue, such as a tumor (e.g., a circulating tumor DNA (ctDNA) molecule).

The term "biological sample" or "bodily sample," as used interchangeably herein, generally refers to a tissue or fluid sample derived from a subject. A biological sample can be directly obtained from the subject. Alternatively, a biological sample can be derived from the subject (e.g., by processing an initial biological sample obtained from the subject). The biological sample can be or can include one or more nucleic acid molecules, such as DNA or ribonucleic acid (RNA) molecules. The biological sample can be derived from any organ, tissue or biological fluid. A biological sample can comprise, for example, a bodily fluid or a solid tissue sample. An example of a solid tissue sample is a tumor sample, e.g., from a solid tumor biopsy. Non-limiting examples of bodily fluids include blood, serum, plasma, tumor cells, saliva, urine, cerebrospinal fluid, lymphatic fluid, prostatic fluid, seminal fluid, milk, sputum, stool, tears, and derivatives of these. In some cases, one or more cell-free nucleic acid molecules as disclosed herein can be derived from a biological sample.

The term "subject," as used herein, generally refers to any animal, mammal, or human. A subject can have, potentially have, or be suspected of having one or more conditions, such as a disease. In some cases, a condition of the subject can be cancer, a symptom(s) associated with cancer, or asymptomatic with respect to cancer or undiagnosed (e.g., not diagnosed for cancer). In some cases, the subject can have cancer, the subject can show a symptom(s) associated with cancer, the subject can be free from symptoms associated with cancer, or the subject may not be diagnosed with cancer. In some examples, the subject is a human.

The term "cell-free DNA" or "cfDNA," as used interchangeably herein, generally refers to DNA fragments circulating freely in a blood stream of a subject. Cell-free DNA fragments can have dinucleosomal protection (e.g., a fragment size of at least 240 base pairs ("bp")). These cfDNA fragments with dinucleosomal protection were likely not cut between the nucleosome, resulting in a longer fragment length (e.g., with a typical size distribution centered around 334 bp). Cell-free DNA fragments can have mononucleosomal protection (e.g., a fragment size of less than 240 base pairs ("bp")). These cfDNA fragments with mononucleosomal protection were likely cut between the nucleosome, resulting in a shorter fragment length (e.g., with a typical size distribution centered around 167 bp).

The term "sequencing data," as used herein, generally refers to "raw sequence reads" and/or "consensus sequences" of nucleic acids, such as cell-free nucleic acids or derivatives thereof. Raw sequence reads are the output of a DNA sequencer, and typically include redundant sequences of the same parent molecule, for example after amplification. "Consensus sequences" are sequences derived from redundant sequences of a parent molecule intended to represent the sequence of the original parent molecule. Consensus sequences can be produced by voting (wherein each majority nucleotide, e.g., the most commonly observed nucleotide at a given base position, among the sequences is the consensus nucleotide) or other approaches such as comparing to a reference genome. In some cases, consensus sequences can be produced by tagging original parent molecules with unique or non-unique molecular tags, which allow tracking of the progeny sequences (e.g., after amplification) by tracking of the tag and/or use of sequence read internal information.

The term "reference genomic sequence," as used herein, generally refers to a nucleotide sequence against which a subject's nucleotide sequences are compared.

The term "genomic region," as used herein, generally refers to any region (e.g., range of base pair locations) of a genome, e.g., an entire genome, a chromosome, a gene, or an exon. A genomic region can be a contiguous or a non-contiguous region. A "genetic locus" (or "locus") can be a portion or entirety of a genomic region (e.g., a gene, a portion of a gene, or a single nucleotide of a gene).

The term "likelihood," as used herein, generally refers to a probability, a relative probability, a presence or an absence, or a degree.

The term "liquid biopsy," as used herein, generally refers to a non-invasive or minimally invasive laboratory test or assay (e.g., of a biological sample or cell-free nucleic acids). The "liquid biopsy" assays can report detections or measurements (e.g., minor allele frequencies, gene expression, or protein expression) of one or more marker genes associated with a condition of a subject (e.g., cancer or tumor-associated marker genes).

A. Introduction

Modifications (e.g., mutations) of genomic DNA can be manifested in a formation and/or progression of one or more conditions (e.g., a disease, such as cancer or tumor) of a subject. The present disclosure provides methods and systems for analyzing cell-free nucleic acid molecules, such as cfDNA, from a subject to determine the presence or absence of a condition of the subject, prognosis of a diagnosed condition of the subject, progress of the condition of the subject over time, therapeutic treatment of a diagnosed condition of the subject, or predicted treatment outcome for a condition of the subject.

Analysis of cell-free nucleic acids, such as cfDNA, have been developed with broad applications in, e.g., prenatal testing, organ transplantation, infectious disease, and oncology. In the context of detecting or monitoring a disease of a subject, such as cancer, circulating tumor DNA (ctDNA) can be a sensitive and specific biomarker in numerous cancer types. In some cases, ctDNA can be used to detect the presence of minimal residual disease (MRD) or tumor burden after treatment, such as chemotherapies or surgical resection of solid tumors. However, the limit of detection (LOD) for ctDNA analysis can be restricted by a number of factors including (i) low input DNA amounts from a typical blood collection and (ii) background error rates from sequencing.

In some cases, ctDNA-based cancer detection can be improved by tracking multiple somatic mutations with error-suppressed sequencing, e.g., with LOD of about 2 parts in 100,000 from cfDNA input while using off-the-shelf panels or personalized assays. However, in some cases, current LOD of ctDNA of interest can be insufficient to universally detect MIRD in patients destined for disease relapse or progression. For example, such 'loss of detection' can be exemplified in diffuse large B-cell lymphoma (DLBCL). For DLBCL, interim ctDNA detection after only two cycles of curative-intent therapy can represent a major molecular response (MMR), and can be a strong prognostic marker for ultimate clinical outcomes. Despite this, nearly one-third of patients ultimately experiencing disease progression do not have detectable ctDNA at this interim landmark using available techniques (e.g., Cancer Personalized Profiling by Deep Sequencing (CAPP-Seq)), thus representing 'false-negative' measurements. Such high false-negative rates have also been observed in DLBCL patients by alternative methods, such as monitoring ctDNA through immunoglobulin gene rearrangements. Therefore, there exists a need for improved methods of ctDNA-based cancer detection with greater sensitivity.

Somatic variants detected on both of the complementary strands of parental DNA duplexes can be used to lower the LOD of ctDNA detection, thereby advantageously increasing the sensitivity of ctDNA detection. Such 'duplex sequencing' can reduce background error profile due to the requirement of two concordant events for detection of a single nucleotide variant (SNV). However, the duplex sequencing approach alone can be limited by inefficient recovery of DNA duplexes as recovery of both original strands can occur in a minority of all recovered molecules. Thus, duplex sequencing may be suboptimal and inefficient for real-world ctDNA detection with limited amount of starting sample, where input DNA from practical blood volumes (e.g., between about 4,000 to about 8,000 genomes per standard 10 milliliter (mL) blood collection tube) is limited and maximal recovery of genomes is essential.

Thus, there remains a significant unmet need for detection and analysis of ctDNA with low LOD (e.g., thereby yielding high sensitivity) for determining, for example, presence or absence of a disease of a subject, prognosis of the disease, treatment for the disease, and/or predicted outcome of the treatment.

B. Methods and Systems for Determining or Monitoring a Condition

The present disclosure describes methods and systems for detecting and analyzing cell free nucleic acids with a plurality of phased variants as a characteristic of a condition of a subject. In some aspects, the cell-free nucleic acid molecules can comprise cfDNA molecules, such as ctDNA molecules. The methods and systems disclosed herein can utilize sequencing data derived from a plurality of cell-free nucleic acid molecules of the subject to identify a subset of the plurality of cell-free nucleic acid molecules having the plurality of phased variants, thereby to determine the condition of the subject. The methods and systems disclosed herein can directly detect and, in some cases, pull down (or capture) such subset of the plurality of cell-free nucleic acid molecules that exhibit the plurality of phased variants, thereby to determine the condition of the subject with or without sequencing. The methods and systems disclosed herein can reduce background error rate often involved during detection and analysis of cell-free nucleic acid molecules, such as cfDNA.

In some aspects, methods and systems for cell-free nucleic acid sequencing and detection of cancer are provided. In some embodiments, cell-free nucleic acids (e.g., cfDNA or cfRNA) can be extracted from a liquid biopsy of an individual and prepared for sequencing. Sequencing results of the cell-free nucleic acids can be analyzed to detect somatic variants in phase (i.e., phased variants, as disclosed herein) as an indication of circulating-tumor nucleic acid (ctDNA or ctRNA) sequences (i.e., sequences that derived or are originated from nucleic acids of a cancer cell). Accordingly, in some cases, cancer can be detected in the individual by extracting a liquid biopsy from the individual and sequencing the cell-free nucleic acids derived from that liquid biopsy to detect circulating-tumor nucleic acid sequences, and the presence of circulating-tumor nucleic acid sequences can indicate that the individual has a cancer (e.g., a specific type of cancer). In some cases, a clinical intervention and/or treatment can be determined and/or performed on the individual based on the detection of the cancer.

As disclosed herein, a presence of somatic variants in phase can be a strong indication that the nucleic acids containing such phased variants are derived from a bodily sample with a condition, such as a cancerous cell (or alternatively, that the nucleic acids are from derived from a bodily sample obtained or derived from a subject with a condition, such as cancer). Detection of phased somatic variants can enhance the signal-to-noise ratio of cell-free nucleic acid detection methods (e.g., by reducing or eliminating spurious "noise" signals) as it may be unlikely that phased mutations would occur within a small genetic window that is approximately the size of a typical cell-free nucleic acid molecule (e.g., about 170 bp or less).

In some aspects, a number of genomic regions can be used as hotspots for detection of phased variants, especially in various cancers, e.g., lymphomas. In some cases, enzymes (e.g., AID, Apobec3a) can stereotypically mutagenize DNA in specific genes and locations, leading to development of particular cancers. Accordingly, cell-free nucleic acids derived from such hotspot genomic regions can be captured or targeted (e.g., with or without deep sequencing) for cancer detection and/or monitoring. Alternatively, capture or targeted sequencing can performed on regions in which phased variants have been previously detected from a cancerous source (e.g., tumor) of a particular individual in order to detect cancer in that individual.

In some aspects, capture sequencing on cell-free nucleic acids can be performed as a screening diagnostic. In some cases, a screening diagnostic can be developed and used to detect circulating-tumor nucleic acids for cancers that have stereotypical regions of phased variants. In some cases, capture sequencing on cell-free nucleic acids is performed as a diagnostic to detect MRD or tumor burden to determine if a particular disease is present during or after treatment. In some cases, capture sequencing on cell-free nucleic acids can be performed as a diagnostic to determine progress (e.g., progression or regression) of a treatment.

In some aspects, cell-free nucleic acid sequencing results can be analyzed to detect whether phased somatic single nucleotide variants (SNVs) or other mutations or variants (e.g., indels) exist within the cell-free nucleic acid sample. In some cases, the presence of particular somatic SNVs or other variants can be indicative of circulating-tumor nucleic acid sequences, and thus indicative of a tumor present in the subject. In some cases, a minimum of two variants can be detected in phase on a cell-free nucleic acid molecule. In some cases, a minimum of three variants can be detected in phase on a cell-free nucleic acid molecule. In some cases, a minimum of four variants can be detected in phase on a cell-free nucleic acid molecule. In some cases, a minimum of five or more variants can be detected in phase on a cell-free nucleic acid molecule. In some cases, the greater number of phased variants detected on a cell-free nucleic acid molecule, the greater the likelihood that the cell-free nucleic acid molecule is derived from cancer, as opposed to detecting an innocuous sequence of somatic variants that arise from molecular preparation of the sequence library or random biological errors. Accordingly, the likelihood of false-positive detection can decrease with detection of more variants in phase within a molecule (e.g., thereby increasing specificity of detection).

In some aspects, a cell-free nucleic acid sequencing result can be analyzed to detect whether an insertion or deletion of one or more nucleobases (i.e., indel) exist within the cell-free nucleic acid sample, e.g., relative to a reference genomic sequence. Without wishing to be bound by theory, in some cases, presence of indels in a cell-free nucleic acid molecule (e.g., cfDNA) can be indicative of a condition of a subject, e.g., a disease such as cancer. In some cases, a genetic variation as a result of an indel can be treated as a variant or mutation, and thus two indels can be treated a two phased variants, as disclosed herein. In some examples, within a cell-free nucleic acid molecule, a first genetic variation from a first indel (a first phase variant) and a second genetic variation from a second indel (a second phase variant) can be separated from each other by at least 1 nucleotide.

Within a single cell-free nucleic acid molecule (e.g., a single cfDNA molecule), as disclosed herein, a first phased variant can be a SNV and a second phased variant can be a part of a different small nucleotide polymorphism, e.g., another SNV or a part of a multi-nucleotide variant (MNV). A multi-nucleotide variant can be a cluster of two or more (e.g., at least 2, 3, 4, 5, or more) adjacent variants existing within the same stand of nucleic acid molecule. In some cases, the first phased variant and the second phased variant can be parts of the same MNV within the single cell-free nucleic acid molecule. In some cases, the first phased variant and the second phased variant can be from two different MNVs within the single cell-free nucleic acid molecule.

In some aspects, a statistical method can be utilized to calculate the likelihood that detected phased variants are from a cancer and not random or artificial (e.g., from sample prep or sequencing error). In some cases, a Monte Carlo sampling method can be utilized to determine the likelihood that detected phased variants are from a cancer and not random or artificial.

Aspects of the present disclosure provide identification or detection of cell-free nucleic acids (e.g., cfDNA molecule) with a plurality of phased variants, e.g., from a liquid biopsy of a subject. In some cases, a first phased variant of the plurality of phased variants and a second phased variant of the plurality of phased variants can be directly adjacent to each other (e.g., neighboring SNVs). In some cases, a first phased variant of the plurality of phased variants and a second phased variant of the plurality of phased variants can be separated by at least one nucleotide. The spacing between the first phased variant and the second phased variant can be limited by the length of the cell-free nucleic acid molecule.

Within a single cell-free nucleic acid molecule (e.g., a single cfDNA molecule), as disclosed herein, a first phased variant and a second phased variant can be separated from each other by at least or up to about 1 nucleotide, at least or up to about 2 nucleotides, at least or up to about 3 nucleotides, at least or up to about 4 nucleotides, at least or up to about 5 nucleotides, at least or up to about 6 nucleotides, at least or up to about 7 nucleotides, at least or up to about 8 nucleotides, at least or up to about 9 nucleotides, at least or up to about 10 nucleotides, at least or up to about 11 nucleotides, at least or up to about 12 nucleotides, at least or up to about 13 nucleotides, at least or up to about 14 nucleotides, at least or up to about 15 nucleotides, at least or up to about 20 nucleotides, at least or up to about 25 nucleotides, at least or up to about 30 nucleotides, at least or up to about 35 nucleotides, at least or up to about 40 nucleotides, at least or up to about 45 nucleotides, at least or up to about 50 nucleotides, at least or up to about 60 nucleotides, at least or up to about 70 nucleotides, at least or up to about 80 nucleotides, at least or up to about 90 nucleotides, at least or up to about 100 nucleotides, at least or up to about 110 nucleotides, at least or up to about 120 nucleotides, at least or up to about 130 nucleotides, at least or up to about 140 nucleotides, at least or up to about 150 nucleotides, at least or up to about 160 nucleotides, at least or up to about 170 nucleotides, or at least or up to about 180 nucleotides. Alternatively or in addition to, within a single cell-free nucleic acid molecule, a first phased variant and a second phased variant may not or need not be separated by one or more nucleotides and thus can be directly adjacent to one another.

A single cell-free nucleic acid molecule (e.g., a single cfDNA molecule), as disclosed herein, can comprise at least or up to about 2 phased variants, at least or up to about 3 phased variants, at least or up to about 4 phased variants, at least or up to about 5 phased variants, at least or up to about 6 phased variants, at least or up to about 7 phased variants, at least or up to about 8 phased variants, at least or up to about 9 phased variants, at least or up to about 10 phased variants, at least or up to about 12 phased variants, at least or up to about 12 phased variants, at least or up to about 13 phased variants, at least or up to about 14 phased variants, at least or up to about 15 phased variants, at least or up to about 20 phased variants, or at least or up to about 25 phased variants within the same molecule.

From a plurality of cell-free nucleic acid molecules obtained (e.g., from a liquid biopsy of a subject), two or more (e.g., 10 or more, 1,000 or more, 10,000 or more) cell-free nucleic acid molecules can be identified to have an average of at least or up to about 2 phased variants, at least or up to about 3 phased variants, at least or up to about 4 phased variants, at least or up to about 5 phased variants, at least or up to about 6 phased variants, at least or up to about 7 phased variants, at least or up to about 8 phased variants, at least or up to about 9 phased variants, at least or up to about 10 phased variants, at least or up to about 12 phased variants, at least or up to about 12 phased variants, at least or up to about 13 phased variants, at least or up to about 14 phased variants, at least or up to about 15 phased variants, at least or up to about 20 phased variants, or at least or up to about 25 phased variants per each cell-free nucleic acid molecule identified to comprise a plurality of phased variants.

In some cases, a plurality of cell-free nucleic acid molecules (e.g., cfDNA molecules) can be obtained from a biological sample of a subject (e.g., solid tumor or liquid biopsy). Out of the plurality of cell-free nucleic acid molecules, at least or up to 1, at least or up to 2, at least or up to 3, at least or up to 4, at least or up to 5, at least or up to 6, at least or up to 7, at least or up to 8, at least or up to 9, at least or up to 10, at least or up to 15, at least or up to 20, at least or up to 25, at least or up to 30, at least or up to 35, at least or up to 40, at least or up to 45, at least or up to 50, at least or up to 60, at least or up to 70, at least or up to 80, at least or up to 90, at least or up to 100, at least or up to 150, at least or up to 200, at least or up to 300, at least or up to 400, at least or up to 500, at least or up to 600, at least or up to 700, at least or up to 800, at least or up to 900, at least or up to 1,000, at least or up to 5,000, at least or up to, 10,000, at least or up to 50,000, or at least or up to 100,000 cell-free nucleic acid molecules can be identified, such that each identified cell-free nucleic acid molecule comprises the plurality of phased variants, as disclosed herein.

In some cases, a plurality of cell-free nucleic acid molecules (e.g., cfDNA molecules) can be obtained from a biological sample of a subject (e.g., solid tumor or liquid biopsy). Out of the plurality of cell-free nucleic acid molecules, at least or up to 1, at least or up to 2, at least or up to 3, at least or up to 4, at least or up to 5, at least or up to 6, at least or up to 7, at least or up to 8, at least or up to 9, at least or up to 10, at least or up to 15, at least or up to 20, at least or up to 25, at least or up to 30, at least or up to 35, at least or up to 40, at least or up to 45, at least or up to 50, at least or up to 60, at least or up to 70, at least or up to 80, at least or up to 90, at least or up to 100, at least or up to 150, at least or up to 200, at least or up to 300, at least or up to 400, at least or up to 500, at least or up to 600, at least or up to 700, at least or up to 800, at least or up to 900, or at least or up to 1,000 cell-free nucleic acid molecules can be identified from a target genomic region (e.g., a target genomic locus), such that each identified cell-free nucleic acid molecule comprises the plurality of phased variants, as disclosed herein.

Figure 1B:
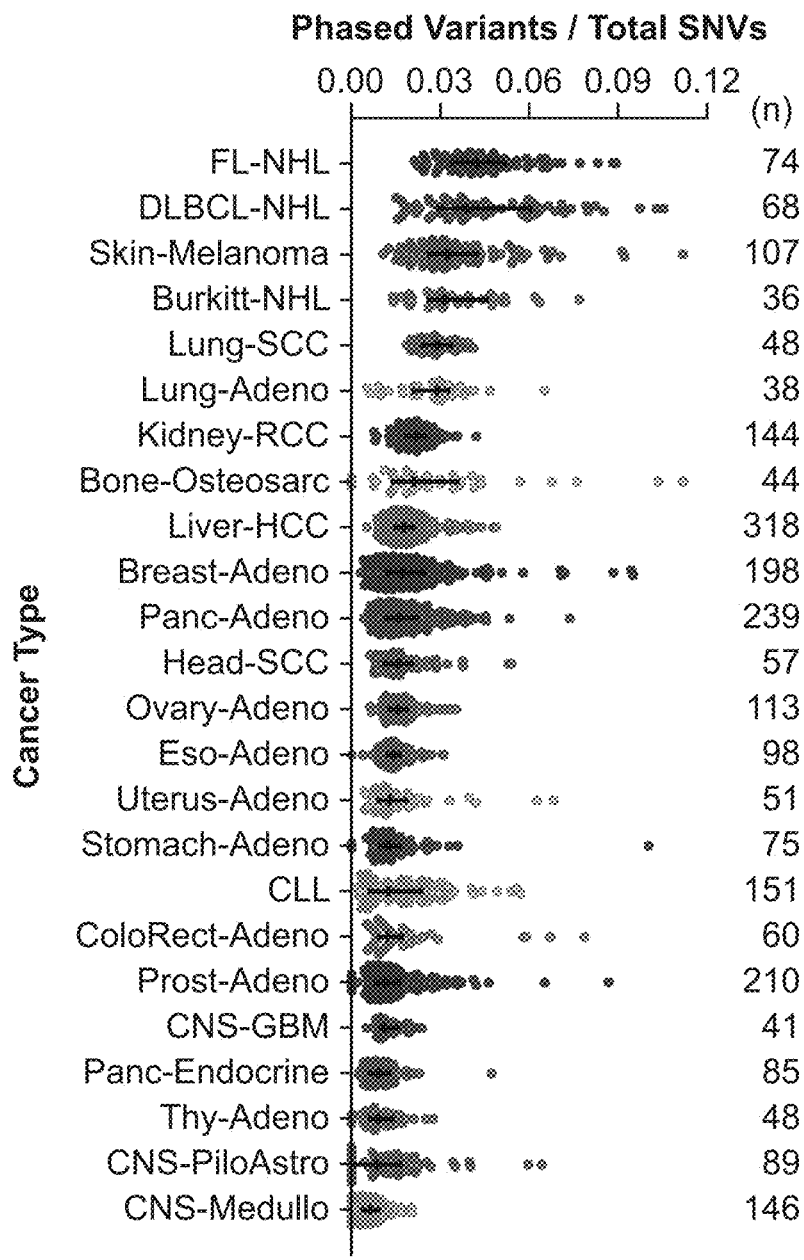
Figure 1C:
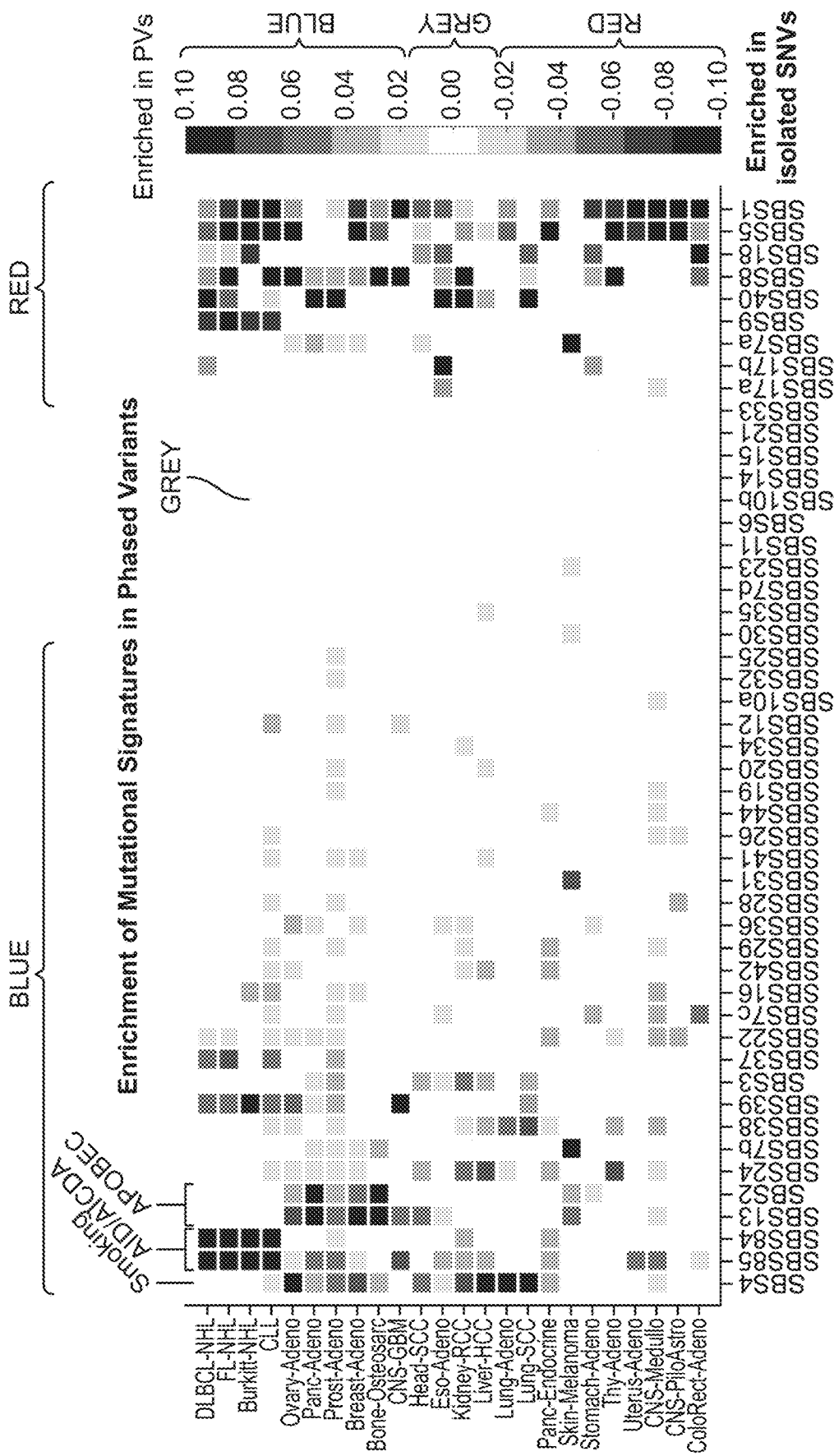
Figure 1D:
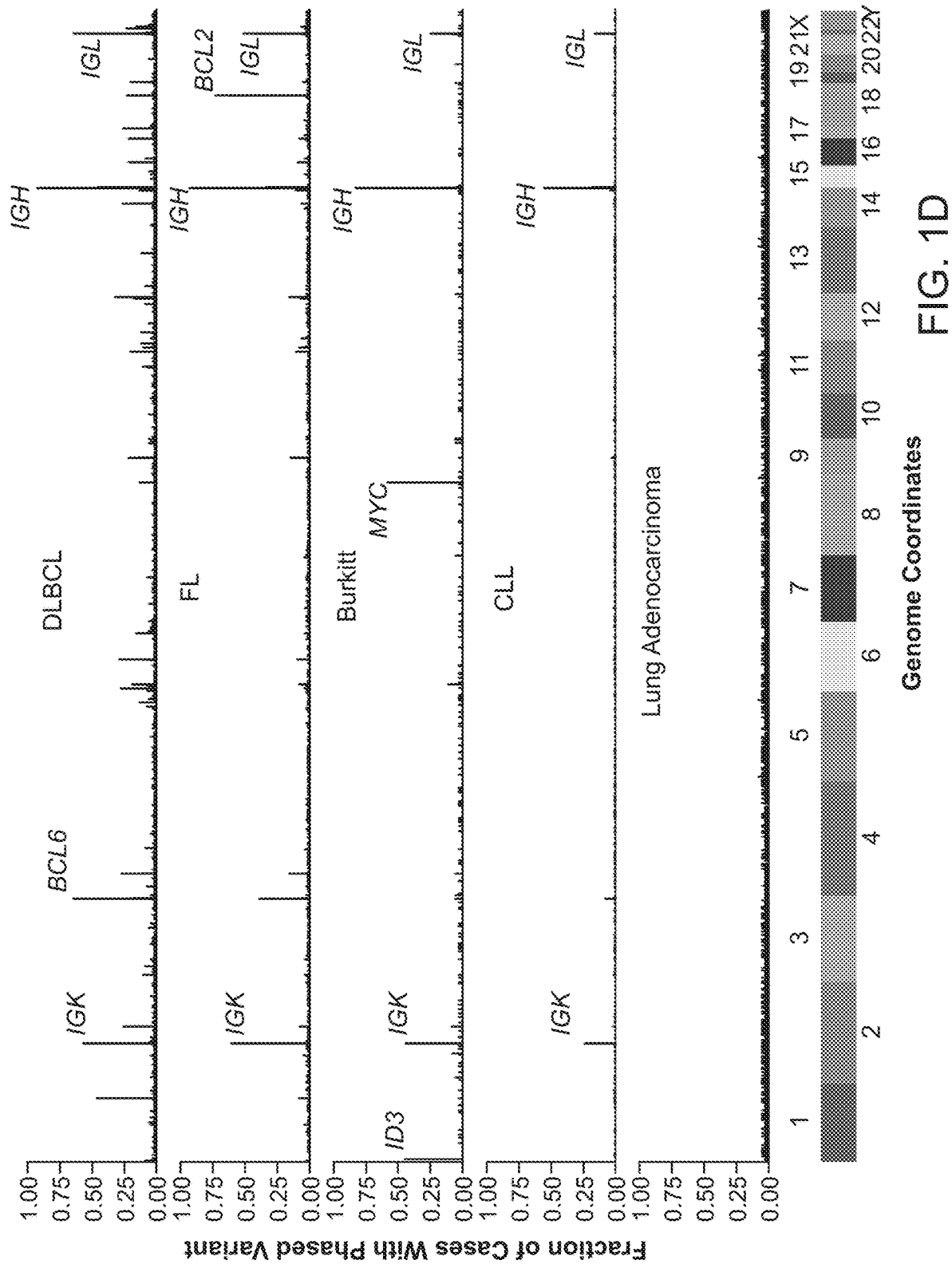
Figure 1E:
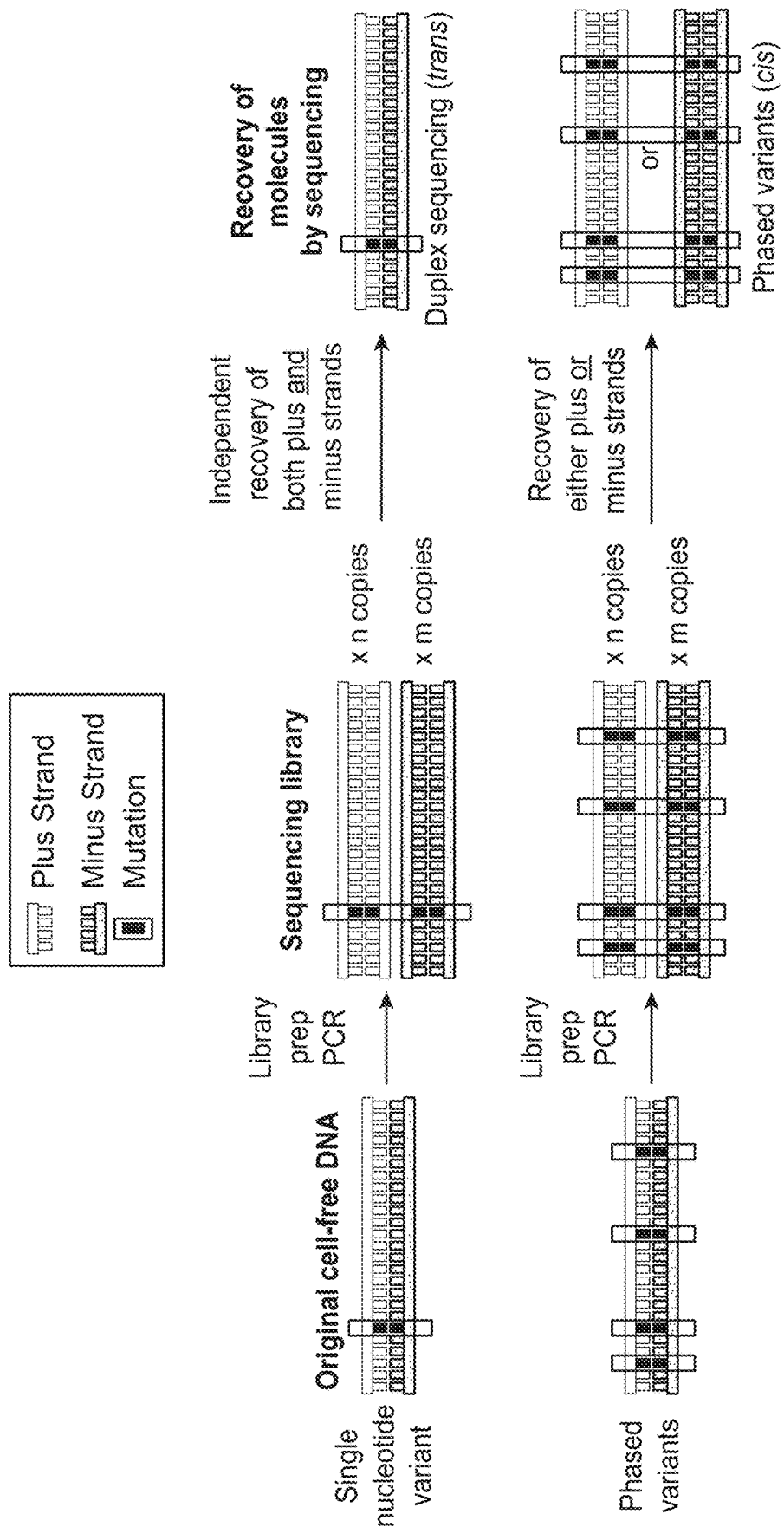

FIGS. 1A and 1E schematically illustrate examples of (i) a cfDNA molecule comprising a SNV and (ii) another cfDNA molecule comprising a plurality of phased variants. Each variant identified within the cfDNA can indicate a presence of one more genetic mutations in the cell that the cfNDA is originated from. In alternative embodiments, one or more of the phased variants may be an insertion or deletion (indel) instead of an SNV.

In one aspect, the present disclosure provides a method for determining a condition of a subject, as shown by flowchart 2510 in FIG. 25A. The method can comprise (a) obtaining, by a computer system, sequencing data derived from a plurality of cell-free nucleic acid molecules that is obtained or derived from the subject (process 2512). The method can further comprise (b) processing, by the computer system, the sequencing data to identify one or more cell-free nucleic acid molecules of the plurality of cell-free nucleic acid molecules, wherein each of the one or more cell-free nucleic acid molecules identified comprises a plurality of phased variants relative to a reference genomic sequence (process 2514). In some cases, at least a portion of the one or more cell-free nucleic acid molecules can comprise a first phased variant of the plurality of phased variants and a second phased variant of the plurality of phased variants that are separated by at least one nucleotide, as disclosed herein. The method can optionally comprise (c) analyzing, by the computer system, at least a portion of the identified one or more cell-free nucleic acid molecules to determine the condition of the subject (process 2516).

In some cases, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, at least or up to about 50%, at least or up to about 60%, at least or up to about 70%, at least or up to about 80%, at least or up to about 90%, at least or up to about 95%, at least or up to about 99%, or about 100% of the one or more cell-free nucleic acid molecules can comprise a first phased variant of the plurality of phased variants and a second phased variant of the plurality of phased variants that are separated by at least one nucleotide, as disclosed herein. In some examples, a plurality of phased variants within a single cfDNA molecule can comprise (i) a first plurality of phased variants that are separated by at least one nucleotide from one another and (ii) a second plurality of phased variants that are adjacent to one another (e.g., two phased variants within a MNV). In some examples, a plurality of phased variants within a single cfDNA molecule can consist of phased variants that are separate by at least one nucleotide from one another.

Figure 25B:
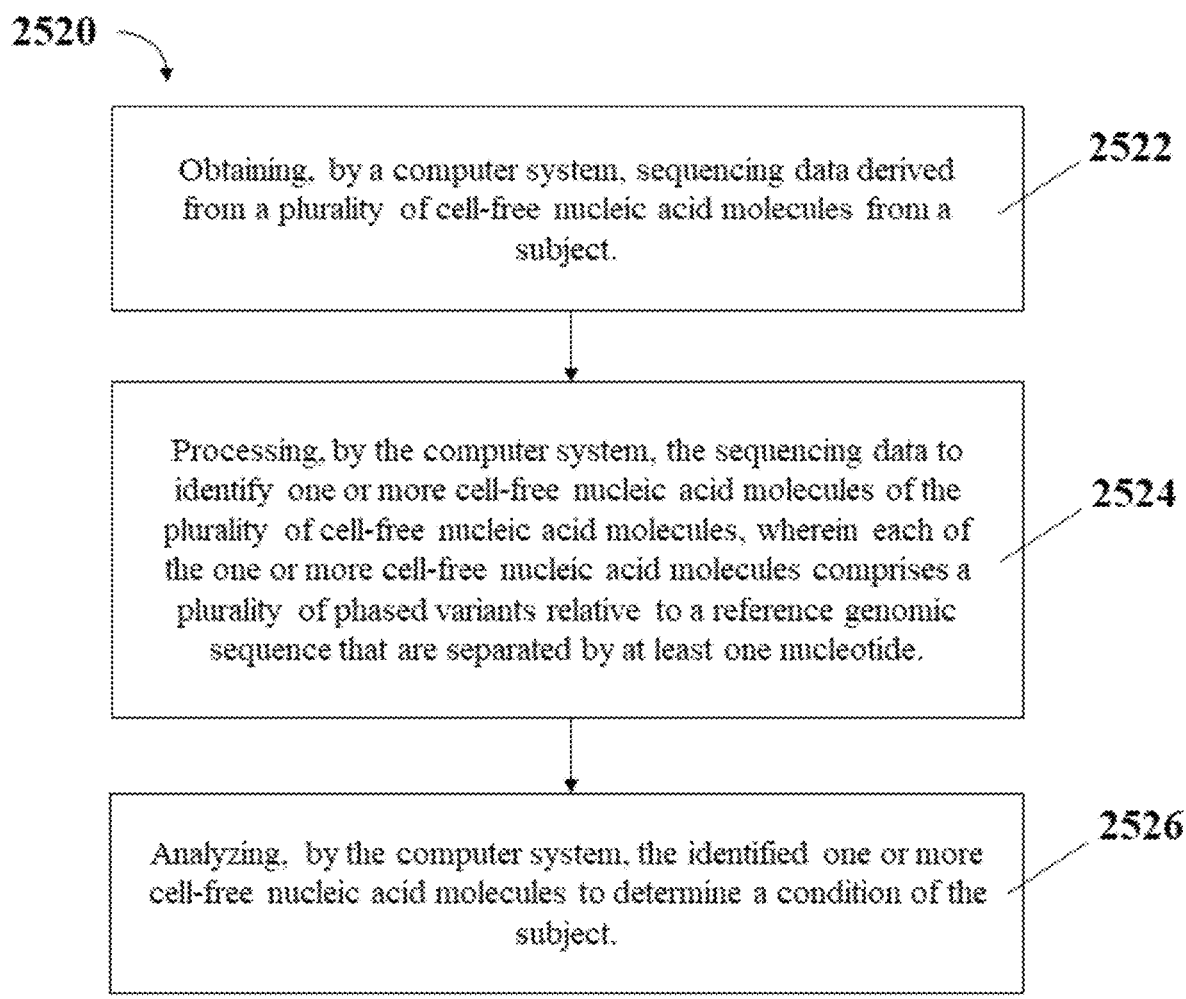

In one aspect, the present disclosure provides a method for determining a condition of the subject, as shown by flowchart 2520 in FIG. 25B. The method can comprise (a) obtaining, by a computer system, sequencing data derived from a plurality of cell-free nucleic acid molecules that is obtained or derived from a subject (process 2522). The method can further comprise (b) processing, by the computer system, the sequencing data to identify one or more cell-free nucleic acid molecules of the plurality of cell-free nucleic acid molecules, wherein each of the one or more cell-free nucleic acid molecules comprises a plurality of phased variants relative to a reference genomic sequence (process 2524). In some cases, a first phased variant of the plurality of phased variant and a second phased variant of the plurality of phased variant can be separated by at least one nucleotide, as disclosed herein. The method can optionally comprise (c) analyzing, by the computer system, at least a portion of the identified one or more cell-free nucleic acid molecules to determine the condition of the subject (process 2526).

Figure 25C:
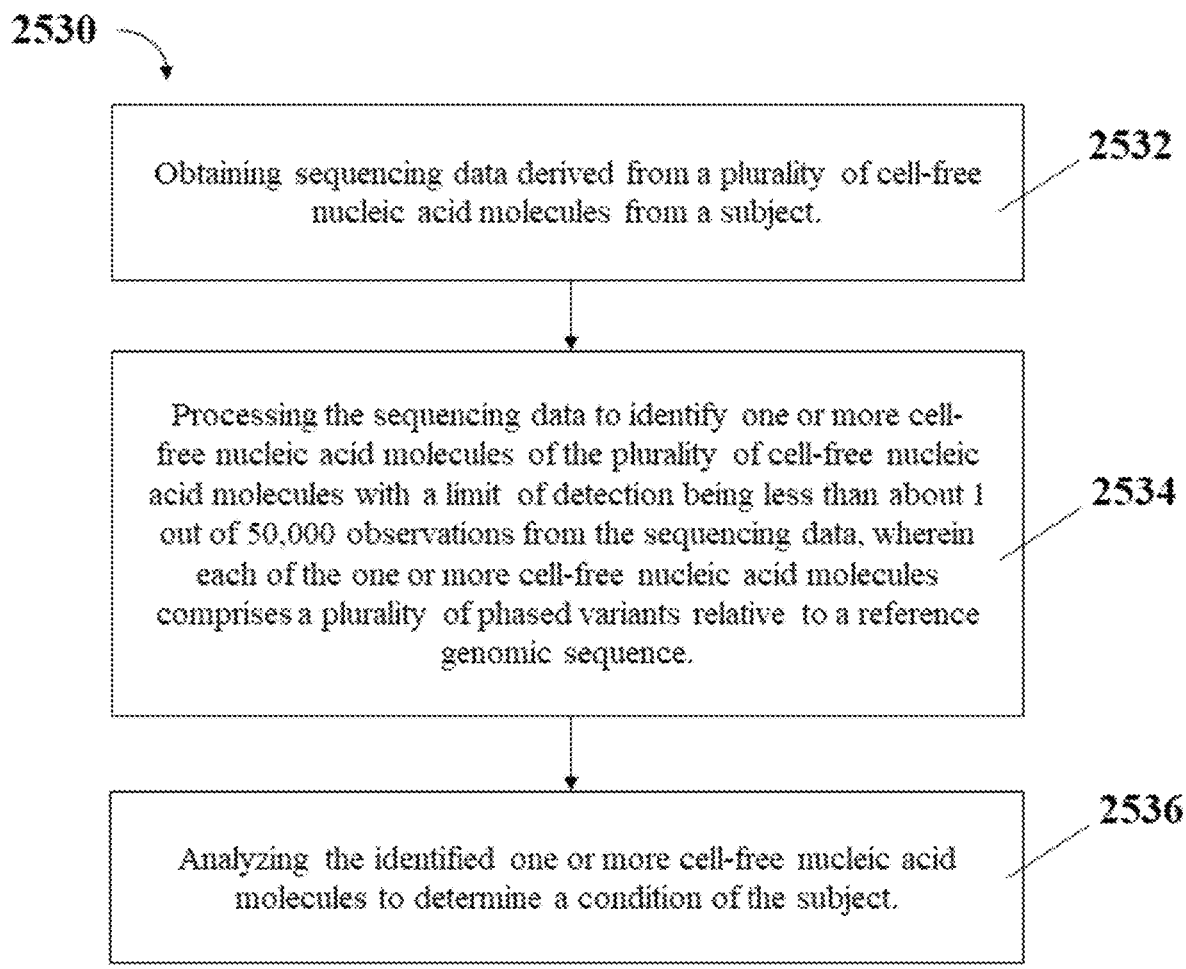

In one aspect, the present disclosure provides a method for determining a condition of a subject, as shown by flowchart 2530 in FIG. 25C. The method can comprise (a) obtaining sequencing data derived from a plurality of cell-free nucleic acid molecules that is obtained or derived from the subject (process 2532). The method can further comprise (b) processing the sequencing data to identify one or more cell-free nucleic acid molecules of the plurality of cell-free nucleic acid molecules with a LOD being less than about 1 out of 50,000 observations (or cell-free nucleic acid molecules) from the sequencing data (process 2534). In some cases, each of the one or more cell-free nucleic acid molecules comprises a plurality of phased variants relative to a reference genomic sequence. The method can optionally comprise (c) analyzing at least a portion of the identified one or more cell-free nucleic acid molecules to determine the condition of the subject (process 2536).

In some cases, the LOD of the operation of identifying the one or more cell-free nucleic acid molecules, as disclosed herein, can be less than about 1 out of 60,000, less than 1 out of 70,000, less than 10 out of 80,000, less than 1 out of 90,000, less than 1 out of 100,000, less than 1 out of 150,000, less than 1 out of 200,000, less than 1 out of 300,000, less than 1 out of 400,000, less than 1 out of 500,000, less than 1 out of 600,000, less than 1 out of 700,000, less than 1 out of 800,000, less than 1 out of 900,000, less than 1 out of 1,000,000, less than 1 out of 1,000,000, less than 1 out of 1,100,000, less than 1 out of 1,200,000, less than 1 out of 1,300,000, less than 1 out of 1,400,000, less than 1 out of 1,500,000, or less than 1 out of 2,000,000 observations from the sequencing data.

In some cases, at least one cell-free nucleic acid molecule of the identified one or more cell-free nucleic acid molecules can comprise a first phased variant of the plurality of phased variants and a second phased variant of the plurality of phased variants that are separated by at least one nucleotide, as disclosed herein.

In some cases, one or more of the operations (a) through (c) of the subject method can be performed by a computer system. In an example, all of the operations (a) through (c) of the subject method can be performed by the computer system.

The sequencing data, as disclosed herein, can be obtained from one or more sequencing methods. A sequencing method can be a first-generation sequencing method (e.g., Maxam-Gilbert sequencing, Sanger sequencing). A sequencing method can be a high-throughput sequencing method, such as next-generation sequencing (NGS) (e.g., sequencing by synthesis). A high-throughput sequencing method can sequence simultaneously (or substantially simultaneously) at least about 10,000, at least about 100,000, at least about 1 million, at least about 10 million, at least about 100 million, at least about 1 billion, or more polynucleotide molecules (e.g., cell-free nucleic acid molecules or derivatives thereof). NGS can be any generation number of sequencing technologies (e.g., second-generation sequencing technologies, third-generation sequencing technologies, fourth-generation sequencing technologies, etc.). Non-limiting examples of high-throughput sequencing methods include massively parallel signature sequencing, polony sequencing, pyrosequencing, sequencing-by-synthesis, combinatorial probe anchor synthesis (cPAS), sequencing-by-ligation (e.g., sequencing by oligonucleotide ligation and detection (SOLiD) sequencing), semiconductor sequencing (e.g., Ion Torrent semiconductor sequencing), DNA nanoball sequencing, and single-molecule sequencing, sequencing-by-hybridization.

In some embodiments of any one of the methods disclosed herein, the sequencing data can be obtained based on any of the disclosed sequencing methods that utilizes nucleic acid amplification (e.g., polymerase chain reaction (PCR)). Non-limiting examples of such sequencing methods can include 454 pyrosequencing, polony sequencing, and SoLiD sequencing. In some cases, amplicons (e.g., derivatives of the plurality of cell-free nucleic acid molecules that is obtained or derived from the subject, as disclosed herein) that correspond to a genomic region of interest (e.g., a genomic region associated with a disease) can be generated by PCR, optionally pooled, and subsequently sequenced to generating sequencing data. In some examples, because the regions of interest are amplified into amplicons by PCR before being sequenced, the nucleic acid sample is already enriched for the region of interest, and thus any additional pooling (e.g., hybridization) may not and need not be needed prior to sequencing (e.g., non-hybridization based NGS). Alternatively, pooling via hybridization can further be performed for additional enrichment prior to sequencing. Alternatively, the sequencing data can be obtained without generating PCR copies, e.g., via cPAS sequencing.

A number of embodiments utilize capture hybridization techniques to perform targeted sequencing. When performing sequencing on cell-free nucleic acids, in order to enhance resolution on particular genomic loci, library products can be captured by hybridization prior to sequencing. Capture hybridization can be particularly useful when trying to detect rare and/or somatic phased variants from a sample at particular genomic loci. In some situations, detection of rare and/or somatic phased variants is indicative of the source of nucleic acids, including nucleic acids derived from a cancer source. Accordingly, capture hybridization is a tool that can enhance detection of circulating-tumor nucleic acids within cell-free nucleic acids.

Various types of cancers repeatedly experience aberrant somatic hypermutation in particular genomic loci. For instance, the enzyme activation-induced deaminase induces aberrant somatic hypermutation in B-cells, which leads to various B-cell lymphomas, including (but not limited to) diffuse large B-cell lymphoma (DLBCL), follicular lymphoma (FL), Burkitt lymphoma (BL), and B-cell chronic lymphocytic leukemia (CLL). Accordingly, in numerous embodiments, probes are designed to pull down (or capture) genomic loci known to experience aberrant somatic hypermutation in a lymphoma. FIG. 1D and Table 1 describe a number of regions that experience aberrant somatic hypermutation in DLBCL, FL, BL and CLL. Provided in Table 6 is list of nucleic acid probes that can be utilized to pull down (or capture) genomic loci to detect aberrant somatic hypermutation in B-cell cancers.

Capture sequencing can also be performed utilizing personalized nucleic acid probes designed to detect the existence of an individual's cancer. An individual having a cancer can have their cancer biopsied and sequenced to detect somatic phased variants that have accumulated in the cancer. Based on the sequencing result, in accordance with a number of embodiments, nucleic acid probes are designed and synthesized capable of pulling down the genomic loci inclusive of the positions of where the phased variants. These personalized designed and synthesized nucleic acid probes can be utilized to detect circulating-tumor nucleic acids from a liquid biopsy of that individual. Accordingly, the personalized nucleic acid probes can be useful for determining treatment response and/or detecting MRD after treatment.

In some embodiments of any one of the methods disclosed herein, the sequencing data can be obtained based on any sequencing method that utilizes adapters. Nucleic acid samples (e.g., the plurality of cell-free nucleic acid molecules from the subject, as disclosed herein) can be conjugated with one or more adapters (or adapter sequences) for recognizing (e.g., via hybridization) of the sample or any derivatives thereof (e.g., amplicons). In some examples, the nucleic acid samples can be tagged with a molecular barcode, e.g., such that each cell-free nucleic acid molecule of the plurality of cell-free nucleic acid molecules can have a unique barcode. Alternatively or in addition to, the nucleic acid samples can be tagged with a sample barcode, e.g., such that the plurality of cell-free nucleic acid molecules from the subject (e.g., a plurality of cell-free nucleic acid molecules obtained from a specific bodily tissue of the subject) can have the same barcode.

In alternative embodiments, the methods of identifying one or more cell-free nucleic acid molecules comprising the plurality of phased variants, as disclosed herein, can be performed without molecular barcoding, without sample barcoding, or without molecular barcoding and sample barcoding, at least in part due to high specificity and low LOD achieved by relying on identifying the phased variants as opposed to, e.g., a single SNV.

In some embodiments of any one of the methods disclosed herein, the sequencing data can be obtained and analyzed without in silico removal or suppression of (i) background error and/or (ii) sequencing error, at least in part due to high specificity and low LOD achieved by relying on identifying the phased variants as opposed to, e.g., a single SNV or indel.

In some embodiments of any one of the methods disclosed herein, using the plurality of variants as a condition to identify target cell-free nucleic acid molecules with specific mutations of interest without in silico methods of error suppression can yield a background error-rate that is lower than that of (i) barcode-deduplication, (ii) integrated digital error suppression, or (iii) duplex sequencing by at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 400-fold, at least about 600-fold, at least about 800-fold, or at least about 1,000-fold. This approach may advantageously increase signal-to-noise ratio (thereby increasing sensitivity and/or specificity) of identifying target cell-free nucleic acid molecules with specific mutations of interest.

In some embodiments of any one of the methods disclosed herein, increasing a minimum number of phased variants (e.g., increasing from at least two phased variants to at least three phased variants) per cell-free nucleic acid molecule required as a condition to identify target cell-free nucleic acid molecules with specific mutations of interest can reduce the background error-rate by at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, or at least about 100-fold. This approach may advantageously increase signal-to-noise ratio (thereby increasing sensitivity and/or specificity) of identifying target cell-free nucleic acid molecules with specific mutations of interest.

In one aspect, the present disclosure provides a method of treating a condition of a subject, as shown in flowchart 2540 in FIG. 25D. The method can comprise (a) identifying the subject for treatment of the condition, wherein the subject has been determined to have the condition based on identification of one or more cell-free nucleic acid molecules from a plurality of cell-free nucleic acid molecules that is obtained or derived from the subject (Process 2542). Each of the identified one or more cell-free nucleic acid molecules can comprise a plurality of phased variants relative to a reference genomic sequence. At least a portion (e.g., partial or all) of the plurality of phased variants can be separated by at least one nucleotide, such that a first phased variant of the plurality of phased variants and a second phased variant of the plurality of phased variants are separated by at least one nucleotide, as disclosed herein. In some cases, a presence of the plurality of phased variants is indicative of the condition (e.g., a disease, such as cancer) of the subject. The method can further comprise (b) subjecting the subject to the treatment based on the step (a) (process 2544). Examples of such treatment of the condition of the subject are disclosed elsewhere in the present disclosure.

Figure 25E:
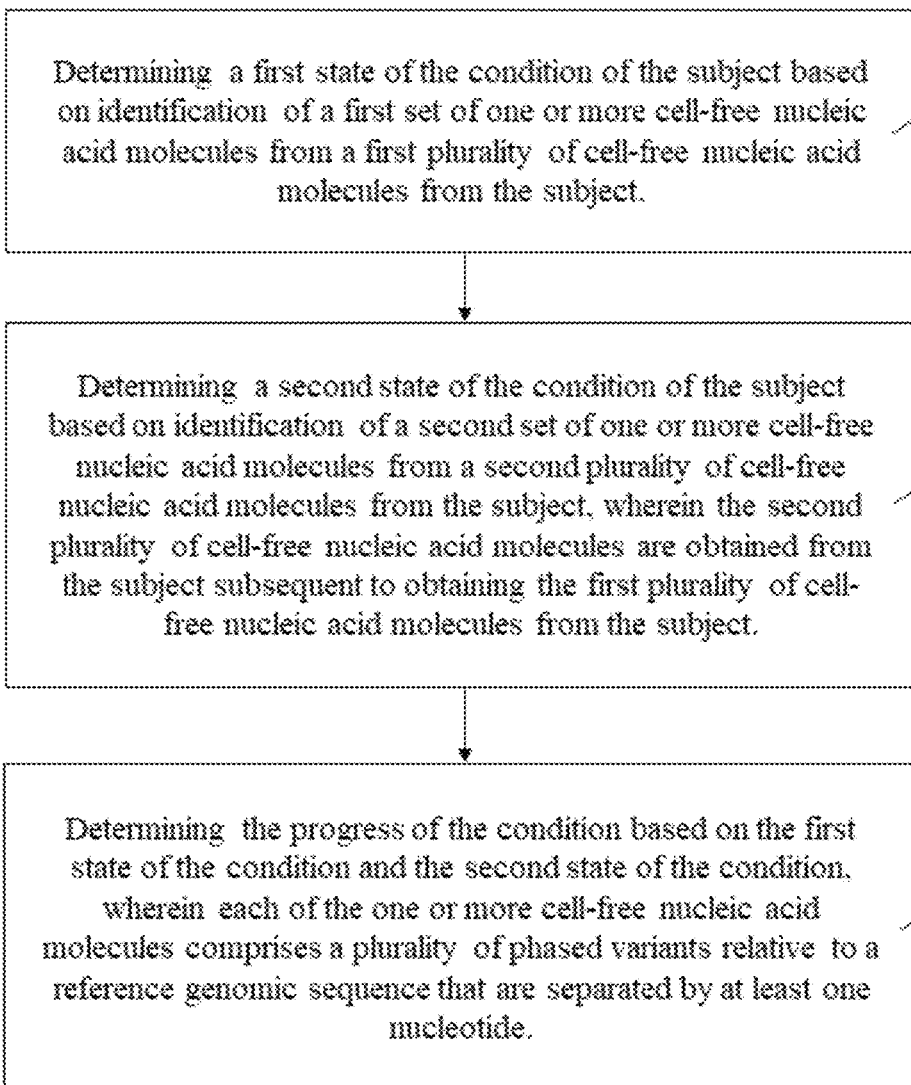
FIG. 25E shows an example flowchart of a method for determining a progress (e.g., progression or regression) of a condition of a subject based on one or more cell-free nucleic acid molecules comprising a plurality of variants.

In one aspect, the present disclosure provides a method of monitoring a progress (e.g., progression or regression) of a condition of a subject, as shown in flowchart 2550 in FIG. 25E. The method can comprise (a) determining a first state of the condition of the subject based on identification of a first set of one or more cell-free nucleic acid molecules from a first plurality of cell-free nucleic acid molecules that is obtained or derived from the subject (process 2552). The method can further comprise (b) determining a second state of the condition of the subject based on identification of a second set of one or more cell-free nucleic acid molecules from a second plurality of cell-free nucleic acid molecules that is obtained or derived from the subject (process 2554). The second plurality of cell-free nucleic acid molecules can be obtained from the subject subsequent to obtaining the first plurality of cell-free nucleic acid molecules from the subject. The method can optionally comprise (c) determining the progress (e.g., progression or regression) of the condition based at least in part on the first state of the condition and the second state of the condition (process 2556). In some cases, each of the one or more cell-free nucleic acid molecules identified (e.g., each of the first set of one or more cell-free nucleic acid molecules identified, each of the second set of one or more cell-free nucleic acid molecules identified) can comprise a plurality of phased variants relative to a reference genomic sequence. At least a portion (e.g., partial or all) of the one or more cell-free nucleic acid molecules identified can be separated by at least one nucleotide, as disclosed herein. In some cases, presence of the plurality of phased variants can be indicative of a state of the condition of the subject.

In some cases, the first plurality of cell-free nucleic acid molecules from the subject can be obtained (e.g., via blood biopsy) and analyzed to determine (e.g., diagnose) a first state of the condition (e.g., a disease, such as cancer) of the subject. The first plurality of cell-free nucleic acid molecules can be analyzed via any of the methods disclosed herein (e.g., with or without sequencing) to identify the first set of one or more cell-free nucleic acid molecules comprising the plurality of phased variants, and the presence or characteristics of the first set of one or more cell-free nucleic acid molecules can be used to determine the first state of the condition (e.g., an initial diagnosis) of the subject. Based on the determined first state of the condition, the subject can be subjected to one or more treatments (e.g., chemotherapy) as disclosed herein. Subsequent to the one or more treatments, he second plurality of cell-free nucleic acid molecules can be obtained from the subject.

In some cases, the subject can be subjected to at least or up to about 1 treatment, at least or up to about 2 treatments, at least or up to about 3 treatments, at least or up to about 4 treatments, at least or up to about 5 treatments, at least or up to about 6 treatments, at least or up to about 7 treatments, at least or up to about 8 treatments, at least or up to about 9 treatments, or at least or up to about 10 treatments based on the determined first state of the condition. In some cases, the subject can be subjected to a plurality of treatments based on the determined first state of the condition, and a first treatment of the plurality of treatments and a second treatment of the plurality of treatments can be separated by at least or up to about 1 day, at least or up to about 7 days, at least or up to about 2 weeks, at least or up to about 3 weeks, at least or up to about 4 weeks, at least or up to about 2 months, at least or up to about 3 months, at least or up to about 4 months, at least or up to about 5 months, at least or up to about 6 months, at least or up to about 12 months, at least or up to about 2 years, at least or up to about 3 years, at least or up to about 4 years, at least or up to about 5 years, or at least or up to about 10 years. The plurality of treatments for the subject can be the same. Alternatively, the plurality of treatments can be different by drug type (e.g., different chemotherapeutic drugs), drug dosage (e.g., increasing dosage, decreasing dosage), presence or absence of a co-therapeutic agent (e.g., chemotherapy and immunotherapy), modes of administration (e.g., intravenous vs oral administrations), frequency of administration (e.g., daily, weekly, monthly), etc.

In some cases, the subject may not and need not be treated for the condition between determination of the first state of the condition and determination of the second state of the condition. For example, without any intervening treatment, the second plurality of cell-free nucleic acid molecules may be contained (e.g., via liquid biopsy) from the subject to confirm whether the subject still exhibits indications of the first state of the condition.

In some cases, the second plurality of cell-free nucleic acid molecules from the subject can be obtained (e.g., via blood biopsy) at least or up to about 1 day, at least or up to about 7 days, at least or up to about 2 weeks, at least or up to about 3 weeks, at least or up to about 4 weeks, at least or up to about 2 months, at least or up to about 3 months, at least or up to about 4 months, at least or up to about 5 months, at least or up to about 6 months, at least or up to about 12 months, at least or up to about 2 years, at least or up to about 3 years, at least or up to about 4 years, at least or up to about 5 years, or at least or up to about 10 years after obtaining the first plurality of cell-free nucleic acid molecules from the subject.

In some cases, at least or up to about 2, at least or up to about 3, at least or up to about 4, at least or up to about 5, at least or up to about 6, at least or up to about 7, at least or up to about 8, at least or up to about 9, or at least or up to about 10 different samples comprising a plurality of nucleic acid molecules (e.g., at least the first plurality of cell-free nucleic acid molecules and the second plurality of cell-free nucleic acid molecules) can be obtained over time (e.g., once every month for 6 months, once every two months for a year, once every three months for a year, once every 6 months for one or more years, etc.) to monitor the progress of the condition of the subject, as disclosed herein.

In some cases, the step of determining the progress of the condition based on the first state of the condition and the second state of the condition can comprise comparing one or more characteristics of the first state and the second state of the condition, such as, for example, (i) a total number of cell-free nucleic acid molecules identified to comprise the plurality of phased variants in each state (e.g., per equal weight or volume of the biological sample of origin, per equal number of initial cell-free nucleic acid molecules analyzed, etc.), (ii) an average number of the plurality of phased variants per each cell-free nucleic acid molecule identified to comprise a plurality of phased variants (i.e., two or more phased variants), or (iii) a number of cell-free nucleic acid molecules identified to comprise the plurality of phased variants divided by a total number of cell-free nucleic acid molecules that comprise a mutation that overlaps with some of the plurality of phased variants (i.e., phased variant allele frequency). Based on such comparison, MRD of the condition (e.g., cancer or tumor) of the subject can be determined. For example, tumor burden or cancer burden of the subject can be determined based on such comparison.

In some cases, the progress of the condition can be progression or worsening of the condition. In an example, the worsening of the condition can comprise developing of a cancer from an earlier stage to a later stage, such as from stage I cancer to stage III cancer. In another example, the worsening of the condition can comprise increasing size (e.g., volume) of a solid tumor. Yet in a different example, the worsening of the condition can comprise cancer metastasis from once location to another location within the subject's body.

In some examples, (i) a total number of cell-free nucleic acid molecules identified to comprise the plurality of phased variants from the second state of the condition of the subject can be higher than (ii) a total number of cell-free nucleic acid molecules identified to comprise the plurality of phased variants from the first state of the condition of the subject by at least or up to about 0.1-fold, at least or up to about 0.2-fold, at least or up to about 0.3-fold, at least or up to about 0.4-fold, at least or up to about 0.5-fold, at least or up to about 0.6-fold, at least or up to about 0.7-fold, at least or up to about 0.8-fold, at least or up to about 0.9-fold, at least or up to about 1-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, at least or up to about 100-fold, at least or up to about 200-fold, at least or up to about 300-fold, at least or up to about 400-fold, or at least or up to about 500-fold.

In some examples, (i) an average number of the plurality of phased variants per each cell-free nucleic acid molecule identified to comprise a plurality of phased variants from the second state of the condition of the subject can be higher than (ii) an average number of the plurality of phased variants per each cell-free nucleic acid molecule identified to comprise a plurality of phased variants from the first state of the condition of the subject by at least or up to about 0.1-fold, at least or up to about 0.2-fold, at least or up to about 0.3-fold, at least or up to about 0.4-fold, at least or up to about 0.5-fold, at least or up to about 0.6-fold, at least or up to about 0.7-fold, at least or up to about 0.8-fold, at least or up to about 0.9-fold, at least or up to about 1-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, at least or up to about 100-fold, at least or up to about 200-fold, at least or up to about 300-fold, at least or up to about 400-fold, or at least or up to about 500-fold.

In some cases, the progress of the condition can be regression or at least a partial remission of the condition. In an example, the at least the partial remission of the condition can comprise downstaging of a cancer from a later stage to an earlier stage, such as from stage IV cancer to stage II cancer. Alternatively, the at least the partial remission of the condition can be full remission from cancer. In another example, the at least the partial remission of the condition can comprise decreasing size (e.g., volume) of a solid tumor.

In some examples, (i) a total number of cell-free nucleic acid molecules identified to comprise the plurality of phased variants from the second state of the condition of the subject can be lower than (ii) a total number of cell-free nucleic acid molecules identified to comprise the plurality of phased variants from the first state of the condition of the subject by at least or up to about 0.1-fold, at least or up to about 0.2-fold, at least or up to about 0.3-fold, at least or up to about 0.4-fold, at least or up to about 0.5-fold, at least or up to about 0.6-fold, at least or up to about 0.7-fold, at least or up to about 0.8-fold, at least or up to about 0.9-fold, at least or up to about 1-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, at least or up to about 100-fold, at least or up to about 200-fold, at least or up to about 300-fold, at least or up to about 400-fold, or at least or up to about 500-fold.

In some examples, (i) an average number of the plurality of phased variants per each cell-free nucleic acid molecule identified to comprise a plurality of phased variants from the second state of the condition of the subject can be lower than (ii) an average number of the plurality of phased variants per each cell-free nucleic acid molecule identified to comprise a plurality of phased variants from the first state of the condition of the subject by at least or up to about 0.1-fold, at least or up to about 0.2-fold, at least or up to about 0.3-fold, at least or up to about 0.4-fold, at least or up to about 0.5-fold, at least or up to about 0.6-fold, at least or up to about 0.7-fold, at least or up to about 0.8-fold, at least or up to about 0.9-fold, at least or up to about 1-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, at least or up to about 100-fold, at least or up to about 200-fold, at least or up to about 300-fold, at least or up to about 400-fold, or at least or up to about 500-fold.

In some cases, the progress of the condition can remain substantially the same between the two states of the condition of the subject. In some examples, (i) a total number of cell-free nucleic acid molecules identified to comprise the plurality of phased variants from the second state of the condition of the subject can be about the same as (ii) a total number of cell-free nucleic acid molecules identified to comprise the plurality of phased variants from the first state of the condition of the subject. In some examples, (i) an average number of the plurality of phased variants per each cell-free nucleic acid molecule identified to comprise a plurality of phased variants from the second state of the condition of the subject can about the same as (ii) an average number of the plurality of phased variants per each cell-free nucleic acid molecule identified to comprise a plurality of phased variants from the first state of the condition of the subject.

In some embodiments of any one of the methods disclosed herein, the one or more cell-free nucleic acid molecules comprising the plurality of phased variants can be identified from the plurality of cell-free nucleic acid molecules by one or more sequencing methods. Alternatively or in addition to, the one or more cell-free nucleic acid molecules comprising the plurality of phased variants can be identified by being pulled down from (or captured from among) the plurality of cell-free nucleic acid molecules with a set of nucleic acid probes. The pull down (or capture) method via the set of nucleic acid probes can be sufficient to identify the one or more cell-free nucleic acid molecules of interest without sequencing. In some cases, the set of nucleic acid probes can be configured to hybridize to at least a portion of cell-free nucleic acid (e.g., cfDNA) molecules from one or more genomic regions associated with the condition of the subject. As such, a presence of one or more cell-free nucleic acid molecules that have been pulled down by the set of nucleic acid probes can be an indication that the one or more cell-free nucleic acid molecules are derived from the condition (e.g., ctDNA or ctRNA). Additional details of the set of nucleic probes are disclosed elsewhere the present disclosure.

In some embodiments of any one of the methods disclosed herein, based the sequencing data derived from the plurality of cell-free nucleic acid molecules (e.g., cfDNA) that is obtained or derived from the subject, (i) the one or more cell-free nucleic acid molecules identified to comprise the plurality of phased variants can be separated, in silico, from (ii) one or more other cell-free nucleic acid molecules that are not identified to comprise the plurality of phased variants (or one or more other cell-free nucleic acid molecules that do not comprise the plurality of phased variants). In some cases, the method can further comprise generating an additional data comprising sequencing information of only (i) the one or more cell-free nucleic acid molecules identified to comprise the plurality of phased variants. In some cases, the method can further comprise generating a different data comprising sequencing information of only (ii) the one or more other cell-free nucleic acid molecules that are not identified to comprise the plurality of phased variants (or the one or more other cell-free nucleic acid molecules that do not comprise the plurality of phased variants).

In one aspect, the present disclosure provides a method for determining a condition of the subject, as shown by flowchart 2560 in FIG. 25F. The method can comprise (a) providing a mixture comprising (1) a set of nucleic acid probes and (2) a plurality of cell-free nucleic acid molecules obtained or derived from the subject (process 2562). In some cases, an individual nucleic acid probe of the set of nucleic acid probes can be designed to hybridize to a target cell-free nucleic acid molecule comprising a plurality of phased variants relative to a reference genomic sequence that are separated by at least one nucleotide. As such, a first phased variant of the plurality of phased variants and a second phased variant of the plurality of phased variants can be separated by at least one nucleotide, as disclosed herein. In some cases, the individual nucleic acid probe can comprise an activatable reporter agent. The activatable reporter agent can be activated by either one of (i) hybridization of the individual nucleic acid probe to the plurality of phased variants and (ii) dehybridization of at least a portion of the individual nucleic acid probe that has been hybridized to the plurality of phased variants. The method can further comprise (b) detecting the reporter agent that is activated, to identify one or more cell-free nucleic acid molecules of the plurality of cell-free nucleic acid molecules (process 2564). Each of the one or more cell-free nucleic acid molecules can comprise the plurality of phased variants. The method can optionally comprise (c) analyzing at least a portion of the identified one or more cell-free nucleic acid molecules to determine the condition of the subject (process 2566).

In one aspect, the present disclosure provides a method for determining a condition of the subject, as shown by flowchart 2570 in FIG. 25G. The method can comprise (a) providing a mixture comprising (1) a set of nucleic acid probes and (2) a plurality of cell-free nucleic acid molecules obtained or derived from the subject (process 2572). In some cases, an individual nucleic acid probe of the set of nucleic acid probes can be designed to hybridize to a target cell-free nucleic acid molecule comprising a plurality of phased variants relative to a reference genomic sequence. In some cases, the individual nucleic acid probe can comprise an activatable reporter agent. The activatable reporter agent can be activated by either one of (i) hybridization of the individual nucleic acid probe to the plurality of phased variants and (ii) dehybridization of at least a portion of the individual nucleic acid probe that has been hybridized to the plurality of phased variants. The method can further comprise (b) detecting the reporter agent that is activated, to identify one or more cell-free nucleic acid molecules of the plurality of cell-free nucleic acid molecules (process 2574). Each of the one or more cell-free nucleic acid molecules can comprise the plurality of phased variants, and a LOD of the identification step can be less than about 1 out of 50,000 cell-free nucleic acid molecules of the plurality of cell-free nucleic acid molecules, as disclosed herein. The method can optionally comprise (c) analyzing at least a portion of the identified one or more cell-free nucleic acid molecules to determine the condition of the subject (process 2576).

In some cases, a first phased variant of the plurality of phased variants and a second phased variant of the plurality of phased variants are separated by at least one nucleotide, as disclosed herein.

In some cases, the LOD of the step of identifying the one or more cell-free nucleic acid molecules, as disclosed herein, can be less than about 1 out of 60,000, less than 1 out of 70,000, less than 10 out of 80,000, less than 1 out of 90,000, less than 1 out of 100,000, less than 1 out of 150,000, less than 1 out of 200,000, less than 1 out of 300,000, less than 1 out of 400,000, less than 1 out of 500,000, less than 1 out of 600,000, less than 1 out of 700,000, less than 1 out of 800,000, less than 1 out of 900,000, less than 1 out of 1,000,000, less than 1 out of 1,000,000, less than 1 out of 1,100,000, less than 1 out of 1,200,000, less than 1 out of 1,300,000, less than 1 out of 1,400,000, less than 1 out of 1,500,000, less than 1 out of 2,000,000, less than 1 out of 2,500,000, less than 1 out of 3,000,000, less than 1 out of 4,000,000, or less than 1 out of 5,000,000 cell-free nucleic acid molecules of the plurality of cell-free nucleic acid molecules. Generally, a detection method with a lower LOD has a greater sensitivity of such detection.

In some embodiments of any one of the methods disclosed herein, the method can further comprise mixing (1) the set of nucleic acid probes and (2) the plurality of cell-free nucleic acid molecules.

In some embodiments of any one of the methods disclosed herein, the activatable reporter agent of a nucleic acid probe can be activated upon hybridization of the individual nucleic acid probe to the plurality of phased variants. Non-limiting examples of such nucleic acid probe can include a molecular beacon, eclipse probe, amplifluor probe, scorpions PCR primer, and light upon extension fluorogenic PCR primer (LUX primer).

Figure 26A:
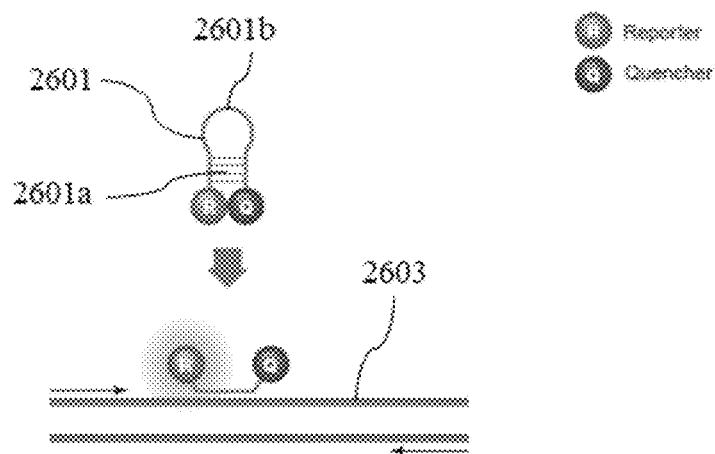
FIGS. 26A and 26B schematically illustrate different fluorescent probes for identifying one or more cell-free nucleic acid molecules comprising a plurality of phased variants.

For example, the nucleic acid probe can be a molecular beacon, as shown in FIG. 26A. The molecular beacon can be fluorescently labeled (e.g., dye-labeled) oligonucleotide probe that comprises complementarity to a target cell-free nucleic acid molecule 2603 in a region that comprises the plurality of phased variants. The molecular beacon can have a length between about 25 nucleotides to about 50 nucleotides. The molecular beacon can also be designed to be partially self-complimentary, such that it form a hairpin structure with a stem 2601a and a loop 2601b. The 5' and 3' ends of the molecular beacon probe can have complementary sequences (e.g., about 5-6 nucleotides) that form the stem structure 2601a. The loop portion 2601b of the hairpin can be designed to specifically hybridize to a portion (e.g., about 15-30 nucleotides) of the target sequence comprising two or more phased variants. The hairpin can be designed to hybridize to a portion that comprises at least 2, 3, 4, 5, or more phased variants. A fluorescent reporter molecule can be attached to the 5' end of the molecular beacon probe, and a quencher that quenches fluorescence of the fluorescent reporter can be attached to the 3' end of the molecular beacon probe. Formation of the hairpin therefore can bring the fluorescent reporter and quencher together, such that no fluorescence is emitted. However, during annealing operation of amplification reaction of the plurality of cell-free nucleic acid molecules that is obtained or derived from the subject, the loop portion of the molecular beacon can bind to its target sequence, causing the stem to denature. Thus, the reporter and quencher can be separated, abolishing quenching, and the fluorescent reporter is activated and detectable. Because fluorescence of the fluorescent reporter is emitted from the molecular beacon probe only when the probe is bound to the target sequence, the amount or level of fluorescence detected can be proportional to the amount of target in the reaction (e.g., (i) a total number of cell-free nucleic acid molecules identified to comprise the plurality of phased variants in each state or (ii) an average number of the plurality of phased variants per each cell-free nucleic acid molecule identified to comprise a plurality of phased variants, as disclosed herein).

In some embodiments of any one of the methods disclosed herein, the activatable reporter agent can be activated upon dehybridization of at least a portion of the individual nucleic acid probe that has been hybridized to the plurality of phased variants. In other words, once the individual nucleic acid probe is hybridized to target cell-free nucleic acid molecule's portion that comprises the plurality of phased variants, dehybridization of at least a portion of the individual nucleic acid prob and the target cell-free nucleic acid can activate the activatable reporter agent. Non-limiting examples of such nucleic acid probe can include a hydrolysis probe (e.g., TaqMan prob), dual hybridization probes, and QZyme PCR primer.

Figure 26B:
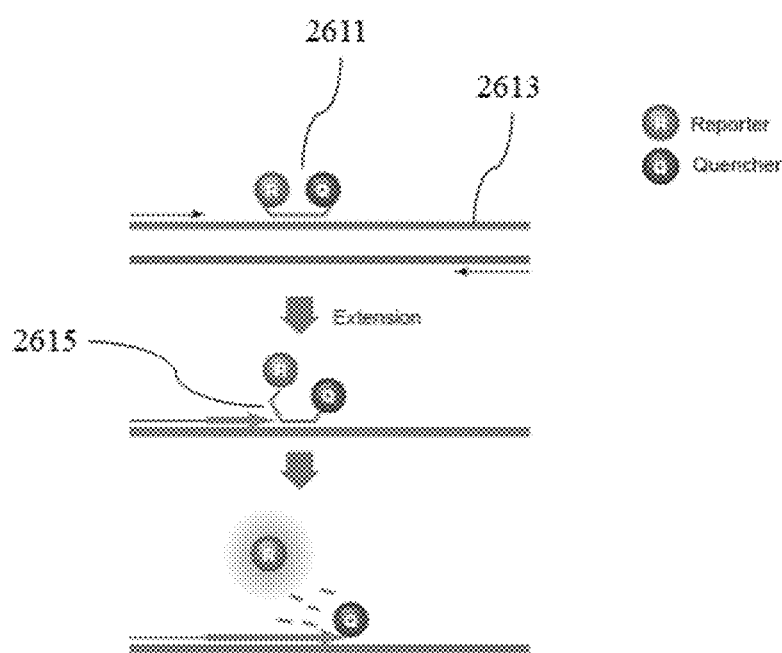

For example, the nucleic acid probe can be a hydrolysis probe, as shown in FIG. 26B. The hydrolysis probe 2611 can be a fluorescently labeled oligonucleotide probe that can specifically hybridize to a portion (e.g., between about 10 and about 25 nucleotides) of the target cell-free nucleic acid molecule 2613, wherein the hybridized portion comprises two or more phased variants. The hydrolysis probe 2611 can be labeled with a fluorescent reporter at the 5' end and a quencher at the 3' end. When the hydrolysis probe is intact (e.g., not cleaved), the fluorescence of the reporter is quenched due to its proximity to the quencher (FIG. 26B). During annealing operation of amplification reaction of the plurality of cell-free nucleic acid molecules obtained or derived from the subject, 5'→3' exonuclease activity of certain thermostable polymerases (e.g., Taq or Tth) The amplification reaction of the plurality of cell-free nucleic acid molecules obtained or derived from the subject can include a combined annealing/extension operation during which the hydrolysis probe hybridizes to the target cell-free nucleic acid molecule, and the dsDNA-specific 5'→3' exonuclease activity of a thermostable polymerase (e.g., Taq or Tth) cleaves off the fluorescent reporter from the hydrolysis probe. As a result, the fluorescent reporter is separated from the quencher, resulting in a fluorescence signal that is proportional to the amount of target in the sample (e.g., (i) a total number of cell-free nucleic acid molecules identified to comprise the plurality of phased variants in each state or (ii) an average number of the plurality of phased variants per each cell-free nucleic acid molecule identified to comprise a plurality of phased variants, as disclosed herein).

In some embodiments of any one of the methods disclosed herein, the reporter agent can comprise a fluorescent reporter. Non-limiting examples of a fluorescent reporter include fluorescein amidite (FAM, 2-[3-(dimethylamino)-6-dimethyliminio-xanthen-9-yl]benzoate TAMRA, (2E)-2-[(2E,4E)-5-(2-tert-butyl-9-ethyl-6,8,8-trimethyl-pyrano[3,2-g]quinolin-1-ium-4-yl)penta-2,4-dienylidene]-1-(6-hydroxy-6-oxo-hexyl)-3,3-dimethyl-indoline-5-sulfonate Dy 750, 6-carboxy-2',4,4',5',7,7'-hexachlorofluorescein, 4,5,6,7-Tetrachlorofluorescein TET™ sulforhodamine 101 acid chloride succinimidyl ester Texas Red-X, ALEXA Dyes, Bodipy Dyes, cyanine Dyes, Rhodamine 123 (hydrochloride), Well RED Dyes, MAX, and TEX 613. In some cases, the reporter agent further comprises a quencher, as disclosed herein. Non-limiting examples of a quencher can include Black Hole Quencher, Iowa Black Quencher, and 4-dimethylaminoazobenzene-4'-sulfonyl chloride (DABCYL).

In some embodiments of any one of the methods disclosed herein, any PCR reaction utilizing the set of nucleic acid probes can be performed using real-time PCR (qPCR). Alternatively, the PCR reaction utilizing the set of nucleic acid probes can be performed using digital PCR (dPCR).

Figure 24:
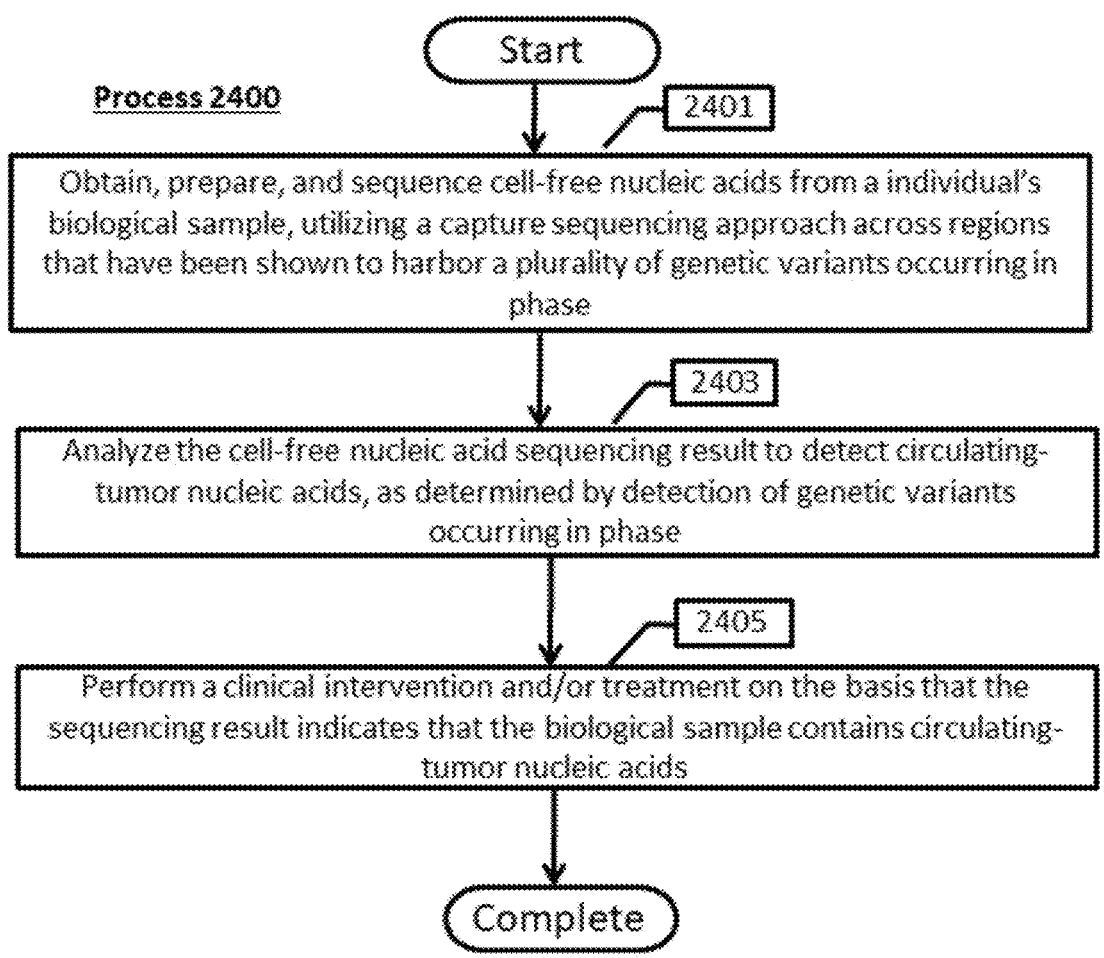
FIG. 24 illustrates a flow diagram of a process to perform a clinical intervention and/or treatment on an individual based on detecting circulating-tumor nucleic acid sequences in a sequencing result in accordance with an embodiment.

Provided in FIG. 24 is an example flowchart of a process to perform a clinical intervention and/or treatment based on detecting circulating-tumor nucleic acids in an individual's biological sample. In several embodiments, detection of circulating-tumor nucleic acids is determined by the detection of somatic variants in phase in a cell-free nucleic acid sample. In many embodiments, detection of circulating-tumor nucleic acids indicates cancer is present, and thus appropriate clinical intervention and/or treatment can be performed.

Referring to FIG. 24, process 2400 can begin with obtaining, preparing, and sequencing (2401) cell-free nucleic acids obtained from a non-invasive biopsy (e.g., liquid or waste biopsy), utilizing a capture sequencing approach across regions shown to harbor a plurality of genetic mutations or variants occurring in phase. In several embodiments, cfDNA and/or cfRNA is extracted from plasma, blood, lymph, saliva, urine, stool, and/or other appropriate bodily fluid. Cell-free nucleic acids can be isolated and purified by any appropriate means. In some embodiments, column purification is utilized (e.g., QIAamp Circulating Nucleic Acid Kit from Qiagen, Hilden, Germany). In some embodiments, isolated RNA fragments can be converted into complementary DNA for further downstream analysis.

In some embodiments, a biopsy is extracted prior to any indication of cancer. In some embodiments, a biopsy is extracted to provide an early screen in order to detect a cancer. In some embodiments, a biopsy is extracted to detect if residual cancer exists after a treatment. In some embodiments, a biopsy is extracted during treatment to determine whether the treatment is providing the desired response. Screening of any particular cancer can be performed. In some embodiments, screening is performed to detect a cancer that develops somatic phased variants in stereotypical regions in the genome, such as (for example) lymphoma. In some embodiments, screening is performed to detect a cancer in which somatic phased variants were discovered utilizing a prior extracted cancer biopsy.

In some embodiments, a biopsy is extracted from an individual with a determined risk of developing cancer, such as those with a familial history of the disorder or have determined risk factors (e.g., exposure to carcinogens). In many embodiments, a biopsy is extracted from any individual within the general population. In some embodiments, a biopsy is extracted from individuals within a particular age group with higher risk of cancer, such as, for example, aging individuals above the age of 50. In some embodiments, a biopsy is extracted from an individual diagnosed with and treated for a cancer.

In some embodiments, extracted cell-free nucleic acids are prepared for sequencing. Accordingly, cell-free nucleic acids are converted into a molecular library for sequencing. In some embodiments, adapters and/or primers are attached onto cell-free nucleic acids to facilitate sequencing. In some embodiments, targeted sequencing of particular genomic loci is to be performed, and thus particular sequences corresponding to the particular loci are captured via hybridization prior to sequencing (e.g., capture sequencing). In some embodiments, capture sequencing is performed utilizing a set of probes that pull down (or capture) regions that have been discovered to commonly harbor phased variants for a particular cancer (e.g., lymphoma). In some embodiments, capture sequencing is performed utilizing a set of probes that pull down (or capture) regions that have been discovered to harbor phased variants as determined prior by sequencing a biopsy of the cancer. More detailed discussion of capture sequencing and probes is provided in the section entitled "Capture Sequencing."

In some embodiments, any appropriate sequencing technique can be utilized that can detect phased variants indicative of circulating-tumor nucleic acids. Sequencing techniques include (but are not limited to) 454 sequencing, Illumina sequencing, SOLiD sequencing, Ion Torrent sequencing, single-read sequencing, paired-end sequencing, etc.

Process 2400 analyzes (2403) the cell-free nucleic acid sequencing result to detect circulating-tumor nucleic acid sequences, as determined by detection of somatic variants occurring in phase. Because cancers are actively growing and expanding, neoplastic cells are often releasing biomolecules (especially nucleic acids) into the vasculature, lymph, and/or waste systems. In addition, due to biophysical constraints in their local environment, neoplastic cells are often rupturing, releasing their inner cell contents into the vasculature, lymph, and/or waste systems. Accordingly, it is possible to detect distal primary tumors and/or metastases from a liquid or waste biopsy.

Detection of circulating-tumor nucleic acid sequences indicates that a cancer is present in the individual being examined. Accordingly, based on detection of circulating-tumor nucleic acids, a clinical intervention and/or treatment may be performed (2405). In a number of embodiments, a clinical procedure is performed, such as (for example) a blood test, genetic test, medical imaging, physical exam, a tumor biopsy, or any combination thereof. In several embodiments, diagnostics are preformed to determine the particular stage of cancer. In a number of embodiments, a treatment is performed, such as (for example) chemotherapy, radiotherapy, chemoradiotherapy, immunotherapy, hormone therapy, targeted drug therapy, surgery, transplant, transfusion, medical surveillance, or any combination thereof. In some embodiments, an individual is assessed and/or treated by medical professional, such as a doctor, physician, physician's assistant, nurse practitioner, nurse, caretaker, dietician, or similar.

Various embodiments of the present disclosure are directed towards utilizing detection of cancer to perform clinical interventions. In a number of embodiments, an individual has a liquid or waste biopsy screened and processed by methods described herein to indicate that the individual has cancer and thus an intervention is to be performed. Clinical interventions include clinical procedures and treatments. Clinical procedures include (but are not limited to) blood tests, genetic test, medical imaging, physical exams, and tumor biopsies. Treatments include (but are not limited to) chemotherapy, radiotherapy, chemoradiotherapy, immunotherapy, hormone therapy, targeted drug therapy, surgery, transplant, transfusion, and medical surveillance. In several embodiments, diagnostics are performed to determine the particular stage of cancer. In some embodiments, an individual is assessed and/or treated by medical professional, such as a doctor, physician, physician's assistant, nurse practitioner, nurse, caretaker, dietician, or similar.

In several embodiments as described herein a cancer can be detected utilizing a sequencing result of cell-free nucleic acids derived from blood, serum, cerebrospinal fluid, lymph fluid, urine or stool. In many embodiments, cancer is detected when a sequencing result has one or more somatic variants present in phase within a short genetic window, such as the length of a cell-free molecule (e.g., about 170 bp). In numerous embodiments, a statistical method is utilized to determine whether the presence of phased variants is derived from a cancerous source (as opposed to molecular artifact or other biological source). Various embodiments utilize a Monte Carlo sampling method as the statistical method to determine whether a sequencing result of cell-free nucleic acids includes sequences of circulating-tumor nucleic acids based on a score as determined by the presence of phased variants. Accordingly, in a number of embodiments, cell-free nucleic acids are extracted, processed, and sequenced, and the sequencing result is analyzed to detect cancer. This process is especially useful in a clinical setting to provide a diagnostic scan.

An exemplary procedure for a diagnostic scan of an individual for a B-cell cancer is as follows:
  (a) extract liquid or waste biopsy from individual,
  (b) prepare and perform targeted sequencing of cell-free nucleic acids from biopsy utilizing nucleic acid probes specific for the B-cell cancer,
  (c) detect phased variants in a sequencing results that are indicative of circulating-tumor nucleic acid sequences, and
  (d) perform clinical intervention based on detection of circulating-tumor nucleic acid sequences.

An exemplary procedure for a personalized diagnostic scan of an individual for a cancer that has been previously sequenced to detect phased variants in particular genomic loci is as follows:
  extract cancer biopsy from individual
  sequence cancer biopsy to detect phased variants that have accumulated in the cancer
    (a) design and synthesize nucleic acid probes for genomic loci that include the positions of the detected phased variants,
    (b) extract liquid or waste biopsy from individual,
    (c) prepare and perform targeted sequencing of cell-free nucleic acids from biopsy utilizing the designed and synthesized nucleic acid probes,
    (d) detect phased variants in a sequencing results that are indicative of circulating-tumor nucleic acid sequences, and
    (e) perform clinical intervention based on detection of circulating-tumor nucleic acid sequences.

In some embodiments of any one of the methods disclosed herein, at least a portion of the identified one or more cell-free nucleic acid molecules comprising the plurality of phased variants can be further analyzed for determining the condition of the subject. In such analysis, (i) the identified one or more cell-free nucleic acid molecules and (ii) other cell-free nucleic acid molecules of the plurality of cell-free nucleic acid molecules that do not comprise the plurality of phased variants can be analyzed as different variables. In some cases, a ratio of (i) a number the identified one or more cell-free nucleic acid molecules and (ii) a number of the other cell-free nucleic acid molecules of the plurality of cell-free nucleic acid molecules that do not comprise the plurality of phased variants can be used a factor to determine the condition of the subject. In some cases, comparison of (i) a position(s) of the identified one or more cell-free nucleic acid molecules relative to the reference genomic sequence and (ii) a position(s) of the other cell-free nucleic acid molecules of the plurality of cell-free nucleic acid molecules that do not comprise the plurality of phased variants relative to the reference genomic sequence can be used a factor to determine the condition of the subject.

Alternatively, in some cases, the analysis of the identified one or more cell-free nucleic acid molecules comprising the plurality of phased variants for determining the condition of the subject may not and need not be based on the other cell-free nucleic acid molecules of the plurality of cell-free nucleic acid molecules that do not comprise the plurality of phased variants. As disclosed herein, non-limiting examples of information or characteristics of the one or more cell-free nucleic acid molecules comprising the plurality of phased variants can include (i) a total number of such cell-free nucleic acid molecules and (ii) an average number of the plurality of phased variations per each nucleic acid molecule in the population of identified cell-free nucleic acid molecules.

Thus, in some embodiments of any one of the methods disclosed herein, a number of the plurality of phased variants from the one or more cell-free nucleic acid molecules that have been identified to have the plurality of phased variants can be indicative of the condition of the subject. In some cases, a ratio of (i) the number of the plurality of phased variants from the one or more cell-free nucleic acid molecules and (ii) a number of single nucleotide variants from the one or more cell-free nucleic acid molecules can be indicative of the condition of the subject. For instance, a particular condition (e.g., follicular lymphoma) can exhibit a signature ratio that is different than that of another condition (e.g., breast cancer). In some examples, for cancer or solid tumor, the ratio as disclosed herein can be between about 0.01 and about 0.20. In some examples, for cancer or solid tumor, the ratio as disclosed herein can be about 0.01, about 0.02, about 0.03, about 0.04, about 0.05, about 0.06, about 0.07, about 0.08, about 0.09, about 0.10, about 0.11, about 0.12, about 0.13, about 0.14, about 0.15, about 0.16, about 0.17, about 0.18, about 0.19, or about 0.20. In some examples, for cancer or solid tumor, the ratio as disclosed herein can be at least or up to about 0.01, at least or up to about 0.02, at least or up to about 0.03, at least or up to about 0.04, at least or up to about 0.05, at least or up to about 0.06, at least or up to about 0.07, at least or up to about 0.08, at least or up to about 0.09, at least or up to about 0.10, at least or up to about 0.11, at least or up to about 0.12, at least or up to about 0.13, at least or up to about 0.14, at least or up to about 0.15, at least or up to about 0.16, at least or up to about 0.17, at least or up to about 0.18, at least or up to about 0.19, or at least or up to about 0.20.

In some embodiments of any one of the methods disclosed herein, a frequency of the plurality of phased variants in the one or more cell-free nucleic acid molecules that have been identified can be indicative of the condition of the subject. In some cases, based on the sequencing data disclosed herein, an average frequency of the plurality of phased variant per a predetermined bin length (e.g., a bin of about 50 base pairs) within each of the identified cell-free nucleic acid molecule can be indicative of the condition of the subject. In some cases, based on the sequencing data disclosed herein, an average frequency of the plurality of phased variant per a predetermined bin length (e.g., a bin of about 50 base pairs) within each of the identified cell-free nucleic acid molecule that is associated with a particular gene (e.g., BCL2, PIM1) can be indicative of the condition of the subject. The size of the bin can be about 30, about 40, about 50, about 60, about 70, or about 80.

In some examples, a first condition (e.g., Hodgkin lymphoma or HL) can exhibit a first average frequency and a second condition (e.g., DLBCL) can exhibit a different average frequency, thereby allowing identification and/or determination of whether the subject has or is suspected of having a particular condition. In some examples, a first sub-type of a disease can exhibit a first average frequency and a second sub-type of the same disease can exhibit a different average frequency, thereby allowing identification and/or determination of whether the subject has or is suspected of having a particular sub-type of the disease. For example, the subject can have DLBCL, and one or more cell-free nucleic acid molecules derived from germinal center B-cell (GCB) DLBCL or activated B-cell (ABC) DLBCL can have different average frequency of the plurality of phased variant per a predetermined bin length, as disclosed herein.

In some example, a condition of the subject may have a predetermined number of phased variants spanning predetermined genomic loci (i.e., a predetermined frequency of phased variants). When the predetermined frequency of phased variants match a frequency of the plurality of phased variants in the one or more cell-free nucleic acid molecules that have been identified from a plurality of cell-free nucleic acid molecules from the subject, it may indicate that the subject has such condition.

In some embodiments of any one of the methods disclosed herein, the one or more cell-free nucleic acid molecules identified to comprise the plurality of phased variants can be analyzed to determine their genomic origin (e.g., which gene locus they are from). The genomic origin of the one or more cell-free nucleic acid molecules that have been identified can be indicative of the condition of the subject, as different disease can have the plurality of phased variants in different signature genes. For example, a subject can have GCB DLBCL, and one or more cell-free nucleic acid molecules originated from GCBs of the subject can have the phased variants prevalent in BCL2 gene, while one or more cell-free nucleic acid molecules originated from ABCs of the same subject may not comprise as many phased variants in the BCL2 gene as those from GCBs. On the other hand, a subject can have ABC DLBCL, and one or more cell-free nucleic acid molecules originated from ABCs of the subject can have the phased variants prevalent in PIM1 gene, while one or more cell-free nucleic acid molecules originated from GCBs of the same subject may not comprise as many phased variants in the PIM1 gene as those from ABCs.

In some embodiments of any one of the methods disclosed herein, at least or up to about 10%, at least or up to about 15%, at least or up to about 20%, at least or up to about 25%, at least or up to about 30%, at least or up to about 35%, at least or up to about 40%, at least or up to about 45%, at least or up to about 50%, at least or up to about 55%, at least or up to about 60%, at least or up to about 65%, at least or up to about 70%, at least or up to about 75%, at least or up to about 80%, at least or up to about 85%, at least or up to about 90%, at least or up to about 95%, at least or up to about 99%, or about 100% of the one or more cell-free nucleic acid molecules comprising the plurality of phased variants can comprise a single nucleotide variant (SNV) that is at least 2 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 3 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 4 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 5 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 6 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 7 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 8 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 9 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 10 nucleotides away from an adjacent SNV.

C. Reference Genomic Sequence

In some embodiments of any one of the methods disclosed herein, the reference genomic sequence can be at least a portion of a nucleic acid sequence database (i.e., a reference genome), which database is assembled from genetic data and intended to represent the genome of a reference cohort. In some cases, a reference cohort can be a collection of individuals from a specific or varying genotype, haplotype, demographics, sex, nationality, age, ethnicity, relatives, physical condition (e.g., healthy or having been diagnosed to have the same or different condition, such as a specific type of cancer), or other groupings. A reference genomic sequence as disclosed herein can be a mosaic (or a consensus sequence) of the genomes of two or more individuals. The reference genomic sequence can comprise at least a portion of a publicly available reference genome or a private reference genome. Non-limiting examples of a human reference genome include hg19, hg18, hg17, hg16, and hg38.

In some examples, the reference genomic sequence can comprise at least or up to about 500 nucleobases, at least or up to about 1 kilobase (kb), at least or up to about 2 kb, at least or up to about 3 kb, at least or up to about 4 kb, at least or up to about 5 kb, at least or up to about 6 kb, at least or up to about 7 kb, at least or up to about 8 kb, at least or up to about 9 kb, at least or up to about 10 kb, at least or up to about 20 kb, at least or up to about 30 kb, at least or up to about 40 kb, at least or up to about 50 kb, at least or up to about 60 kb, at least or up to about 70 kb, at least or up to about 80 kb, at least or up to about 90 kb, at least or up to about 100 kb, at least or up to about 200 kb, at least or up to about 300 kb, at least or up to about 400 kb, at least or up to about 500 kb, at least or up to about 600 kb, at least or up to about 700 kb, at least or up to about 800 kb, at least or up to about 900 kb, at least or up to about 1,000 kb, at least or up to about 2,000 kb, at least or up to about 3,000 kb, at least or up to about 4,000 kb, at least or up to about 5,000 kb, at least or up to about 6,000 kb, at least or up to about 7,000 kb, at least or up to about 8,000 kb, at least or up to about 9,000 kb, at least or up to about 10,000 kb, at least or up to about 20,000 kb, at least or up to about 30,000 kb, at least or up to about 40,000 kb, at least or up to about 50,000 kb, at least or up to about 60,000 kb, at least or up to about 70,000 kb, at least or up to about 80,000 kb, at least or up to about 90,000 kb, or at least or up to about 100,000 kb.

In some cases, the reference genomic sequence can be whole reference genome or a portion (e.g., a portion relevant to the condition of interest) of the genome. For example, the reference genomic sequence can consist of at least 1, 2, 3, 4, 5, or more genes that experience aberrant somatic hypermutation under certain types of cancer. In some cases, the reference genomic sequence can be a whole chromosomal sequence, or a fragment thereof. In some cases, the reference genomic sequence can comprise two or more (e.g., at least 2, 3, 4, 5, or more) different portions of the reference genome that are not adjacent to one another (e.g., within the same chromosome or from different chromosomes).

In some embodiments of any one of the methods disclosed herein, the reference genomic sequence can be at least a portion of a reference genome of a selected individual, such as a healthy individual or the subject of any of the methods as disclosed herein.

In some cases, the reference genomic sequence can be derived from an individual who is not the subject (e.g., a healthy control individual). Alternatively, in some cases, the reference genomic sequence can be derived from a sample of the subject. In some examples, the sample can be a healthy sample of the subject. The healthy sample of the subject can be any subject cell that is healthy, e.g., a healthy leukocyte. By comparing sequencing data of the plurality of cell-free nucleic acid molecules (e.g., cfDNA molecules) of the subject against at least a portion of the genomic sequence of a healthy cell of the same subject, one or more cell-free nucleic acid molecules that comprise the plurality of phased variants can be identified and analyzed, as disclosed herein. In some examples, the sample can be a diseased sample of the subject, such as a diseased cell (e.g., a tumor cell) or a solid tumor. The reference genomic sequence can be obtained from sequencing at least a portion of a diseased cell of the subject or from sequencing a plurality of cell-free nucleic acid molecules obtained from the solid tumor of the subject. Once the subject is diagnosed to have a particular condition (e.g., a disease), the reference genomic sequence of the subject that comprises the plurality of phased variants can be used to determine whether the subject still exhibits the same phased variants at future time points. In this context, any new phased variants identified between the "diseased" reference genomic sequence of the subject and new cell-free nucleic acid molecules obtained or derived from the subject can indicate a reduced degree of aberrant somatic hypermutation in particular genomic loci (e.g., at least a partial remission).

In various embodiments, diagnostic scans can be performed for any neoplasm type, including (but not limited to) acute lymphoblastic leukemia (ALL), acute myeloid leukemia (AML), anal cancer, astrocytomas, basal cell carcinoma, bile duct cancer, bladder cancer, breast cancer, Burkitt's lymphoma, cervical cancer, chronic lymphocytic leukemia (CLL) chronic myelogenous leukemia (CML), chronic myeloproliferative neoplasms, colorectal cancer, diffuse large B-cell lymphoma, endometrial cancer, ependymoma, esophageal cancer, esthesioneuroblastoma, Ewing sarcoma, fallopian tube cancer, follicular lymphoma, gallbladder cancer, gastric cancer, gastrointestinal carcinoid tumor, hairy cell leukemia, hepatocellular cancer, Hodgkin lymphoma, hypopharyngeal cancer, Kaposi sarcoma, Kidney cancer, Langerhans cell histiocytosis, laryngeal cancer, leukemia, liver cancer, lung cancer, lymphoma, melanoma, Merkel cell cancer, mesothelioma, mouth cancer, neuroblastoma, non-Hodgkin lymphoma, non-small cell lung cancer, osteosarcoma, ovarian cancer, pancreatic cancer, pancreatic neuroendocrine tumors, pharyngeal cancer, pituitary tumor, prostate cancer, rectal cancer, renal cell cancer, retinoblastoma, skin cancer, small cell lung cancer, small intestine cancer, squamous neck cancer, T-cell lymphoma, testicular cancer, thymoma, thyroid cancer, uterine cancer, vaginal cancer, and vascular tumors.

In a number of embodiments, a diagnostic scan is utilized to provide an early detection of cancer. In some embodiments, a diagnostic scan detects cancer in individuals having stage I, II, or III cancer. In some embodiments, a diagnostic scan is utilized to detect MRD or tumor burden. In some embodiments, a diagnostic scan is utilized to determine progress (e.g., progression or regression) of treatment. Based on the diagnostic scan, a clinical procedure and/or treatment may be performed.

D. Nucleic Acid Probes

In some embodiments of any one of the methods disclosed herein, the set of nucleic acid probes can be designed based on the any of the subject reference genomic sequences of the present disclosure. In some cases, the set of nucleic acid probes can be designed based on the plurality of phased variants that have been identified by comparing (i) sequencing data from a solid tumor of the subject and (ii) sequencing data from a healthy cell of the subject or a healthy cohort, as disclosed herein. The set of nucleic acid probes can be designed based on the plurality of phased variants that have been identified by comparing (i) sequencing data from a solid tumor of the subject and (ii) sequencing data from a healthy cell of the subject. The set of nucleic acid probes can be designed based on the plurality of phased variants that have been identified by comparing (i) sequencing data from a solid tumor of the subject and (ii) sequencing data from a healthy cell of a healthy cohort.

In some embodiments of any one of the methods disclosed herein, the set of nucleic acid probes are designed to hybridize to sequences of genomic loci associated with the condition. As disclosed herein, the genomic loci associated with the condition can be determined to experience or exhibit aberrant somatic hypermutation when the subject has the condition. Alternatively, the set of nucleic acid probes are designed to hybridize to sequences of stereotyped regions.

In some embodiments of any one of the methods disclosed herein, the set of nucleic acid probes can be designed to hybridize to at least about 5%, at least about 10%, at least about 20%, at least about 30%, at least about 40%, at least about 50%, at least about 60%, at least about 70%, at least about 80%, at least about 90%, at least about 95%, at least about 99%, or about 100% of the genomic regions identified in Table 1.

In some embodiments of any one of the methods disclosed herein, the set of nucleic acid probes can be designed to hybridize to at least a portion of cell-free nucleic acid (e.g., cfDNA) molecules derived from at least about 5%, at least about 10%, at least about 20%, at least about 30%, at least about 40%, at least about 50%, at least about 60%, at least about 70%, at least about 80%, at least about 90%, at least about 95%, at least about 99%, or about 100% of the genomic regions identified in Table 1.

In some embodiments of any one of the methods disclosed herein, each nucleic acid probe of the set of nucleic acid probes can have at least about 50%, at least about 55%, at least about 60%, at least about 65%, at least about 70%, at least about 75%, at least about 80%, at least about 85%, at least about 90% sequence identity, at least about 95% sequence identity, at least about 99%, or about 100% sequence identity to a probe sequence selected from Table 6.

In some embodiments of any one of the methods disclosed herein, the set of nucleic acid probes can comprise at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or about 100% of probe sequences in Table 6.

In some embodiments of any one of the methods disclosed herein, the set of nucleic acid probes can be designed to cover one or more target genomic regions comprising at least or up to about 500 nucleobases, at least or up to about 1 kilobase (kb), at least or up to about 2 kb, at least or up to about 3 kb, at least or up to about 4 kb, at least or up to about 5 kb, at least or up to about 6 kb, at least or up to about 7 kb, at least or up to about 8 kb, at least or up to about 9 kb, at least or up to about 10 kb, at least or up to about 20 kb, at least or up to about 30 kb, at least or up to about 40 kb, at least or up to about 50 kb, at least or up to about 60 kb, at least or up to about 70 kb, at least or up to about 80 kb, at least or up to about 90 kb, at least or up to about 100 kb, at least or up to about 200 kb, at least or up to about 300 kb, at least or up to about 400 kb, or at least or up to about 500 kb.

In some embodiments of any one of the methods disclosed herein, a target genomic region (e.g., a target genomic locus) of the one or more target genomic regions can comprise at most about 200 nucleobases, at most about 300 nucleobases, 400 nucleobases, at most about 500 nucleobases, at most about 600 nucleobases, at most about 700 nucleobases, at most about 800 nucleobases, at most about 900 nucleobases, at most about 1 kb, at most about 2 kb, at most about 3 kb, at most about 4 kb, at most about 5 kb, at most about 6 kb, at most about 7 kb, at most about 8 kb, at most about 9 kb, at most about 10 kb, at most about 11 kb, at most about 12 kb, at most about 13 kb, at most about 14 kb, at most about 15 kb, at most about 16 kb, at most about 17 kb, at most about 18 kb, at most about 19 kb, at most about 20 kb, at most about 25 kb, at most about 30 kb, at most about 35 kb, at most about 40 kb, at most about 45 kb, at most about 50 kb, or at most about 100 kb.

In some embodiments of any one of the methods disclosed herein, the set of nucleic acid probes can comprise at least or up to about 10, at least or up to about 20, at least or up to about 30, at least or up to about 40, at least or up to about 50, at least or up to about 60, at least or up to about 70, at least or up to about 80, at least or up to about 90, at least or up to about 100, at least or up to about 200, at least or up to about 300, at least or up to about 400, at least or up to about 500, at least or up to about 600, at least or up to about 700, at least or up to about 800, at least or up to about 900, at least or up to about 1,000, at least or up to about 2,000, at least or up to about 3,000, at least or up to about 4,000, or at least or up to about 5,000 different nucleic acid probes designed to hybridize to different target nucleic acid sequences.

In some embodiments of any one of the methods disclosed herein, the set of nucleic acid probes can have a length of at least or up to about 50, at least or up to about 55, at least or up to about 60, at least or up to about 65, at least or up to about 70, at least or up to about 75, at least or up to about 80, at least or up to about 85, at least or up to about 90, at least or up to about 95, or at least or up to about 100 nucleotides.

In one aspect, the present disclosure provides a composition comprising a bait set comprising any one of the set of nucleic acid probes disclosed herein. The composition comprising such bait set can be used for any of the methods disclosed herein. In some cases, the set of nucleic acid probes can be designed to pull down (or capture) cfDNA molecules. In some cases, the set of nucleic acid probes can be designed to pull down (or capture) cfRNA molecules.

In some embodiments, the bait set can comprise a set of nucleic acid probes designed to pull down cell-free nucleic acid (e.g., cfDNA) molecules derived from genomic regions set forth in Table 1. The set of nucleic acid probes can be designed to pull down cell-free nucleic acid molecules derived from at least or up to about 1%, at least or up to about 2%, at least or up to about 3%, at least or up to about 4%, at least or up to about 5%, at least or up to about 6%, at least or up to about 7%, at least or up to about 8%, at least or up to about 9%, at least or up to about 10%, at least or up to about 15%, at least or up to about 20%, at least or up to about 25%, at least or up to about 30%, at least or up to about 35%, at least or up to about 40%, at least or up to about 45%, at least or up to about 50%, at least or up to about 55%, at least or up to about 60%, at least or up to about 65%, at least or up to about 70%, at least or up to about 75%, at least or up to about 80%, at least or up to about 85%, at least or up to about 90%, at least or up to about 95%, at least or up to about 99%, or about 100% of the genomic regions set forth in Table 1. In some cases, the set of nucleic acid probes can be designed to pull down cfDNA molecules. In some cases, the set of nucleic acid probes can be designed to pull down cfRNA molecules.

In some embodiments of any one of the compositions disclosed herein, an individual nucleic acid probe (or each nucleic acid probe) of the set of nucleic acid probes can comprise a pull-down tag. The pull-down tag can be used to enrich a sample (e.g., a sample comprising the plurality of nucleic acid molecules obtained or derived from the subject) for a specific subset (e.g., for cell-free nucleic acid molecules comprising the plurality of phased variants as disclosed herein).

In some cases, pull-down tag can comprise a nucleic acid barcode (e.g., on either or both sides of the nucleic acid probe). By utilizing beads or substrates comprising nucleic acid sequences having complementarity to the nucleic acid barcode, the nucleic acid barcode can be used to pull-down and enrich for any nucleic acid probe that is hybridized to a target cell-free nucleic acid molecule. Alternatively or in addition to, the nucleic acid barcode can be used to identify the target cell-free nucleic acid molecule from any sequencing data (e.g., sequencing by amplification) obtained by using any of the set of nucleic acid probes disclosed herein.

In some cases, the pull-down tag can comprise an affinity target moiety that can be specifically recognized and bound by an affinity binding moiety. The affinity binding moiety specifically can bind the affinity target moiety to form an affinity pair. In some cases, by utilizing beads or substrates comprising the affinity binding moiety, the affinity target moiety can be used to pull-down and enrich for any nucleic acid probe that is hybridized to a target cell-free nucleic acid molecule. Alternatively, the pull-down tag can comprise the affinity binding moiety, while the beads/substrates can comprise the affinity target moiety. Non-limiting examples of the affinity pair can include biotin/avidin, antibody/antigen, biotin/streptavidin, metal/chelator, ligand/receptor, nucleic acid and binding protein, and complementary nucleic acids. In an example, the pull-down tag can comprise biotin.

In some embodiments of any one of the compositions disclosed herein, a length of a target cell-free nucleic acid (e.g., cfDNA) molecule that is to be pulled down by any subject nucleic acid probe can be about 100 nucleotides to about 200 nucleotides. The length of the target cell-free nucleic acid molecule can be at least about 100 nucleotides. The length of the target cell-free nucleic acid molecule can be at most about 200 nucleotides. The length of the target cell-free nucleic acid molecule can be about 100 nucleotides to about 110 nucleotides, about 100 nucleotides to about 120 nucleotides, about 100 nucleotides to about 130 nucleotides, about 100 nucleotides to about 140 nucleotides, about 100 nucleotides to about 150 nucleotides, about 100 nucleotides to about 160 nucleotides, about 100 nucleotides to about 170 nucleotides, about 100 nucleotides to about 180 nucleotides, about 100 nucleotides to about 190 nucleotides, about 100 nucleotides to about 200 nucleotides, about 110 nucleotides to about 120 nucleotides, about 110 nucleotides to about 130 nucleotides, about 110 nucleotides to about 140 nucleotides, about 110 nucleotides to about 150 nucleotides, about 110 nucleotides to about 160 nucleotides, about 110 nucleotides to about 170 nucleotides, about 110 nucleotides to about 180 nucleotides, about 110 nucleotides to about 190 nucleotides, about 110 nucleotides to about 200 nucleotides, about 120 nucleotides to about 130 nucleotides, about 120 nucleotides to about 140 nucleotides, about 120 nucleotides to about 150 nucleotides, about 120 nucleotides to about 160 nucleotides, about 120 nucleotides to about 170 nucleotides, about 120 nucleotides to about 180 nucleotides, about 120 nucleotides to about 190 nucleotides, about 120 nucleotides to about 200 nucleotides, about 130 nucleotides to about 140 nucleotides, about 130 nucleotides to about 150 nucleotides, about 130 nucleotides to about 160 nucleotides, about 130 nucleotides to about 170 nucleotides, about 130 nucleotides to about 180 nucleotides, about 130 nucleotides to about 190 nucleotides, about 130 nucleotides to about 200 nucleotides, about 140 nucleotides to about 150 nucleotides, about 140 nucleotides to about 160 nucleotides, about 140 nucleotides to about 170 nucleotides, about 140 nucleotides to about 180 nucleotides, about 140 nucleotides to about 190 nucleotides, about 140 nucleotides to about 200 nucleotides, about 150 nucleotides to about 160 nucleotides, about 150 nucleotides to about 170 nucleotides, about 150 nucleotides to about 180 nucleotides, about 150 nucleotides to about 190 nucleotides, about 150 nucleotides to about 200 nucleotides, about 160 nucleotides to about 170 nucleotides, about 160 nucleotides to about 180 nucleotides, about 160 nucleotides to about 190 nucleotides, about 160 nucleotides to about 200 nucleotides, about 170 nucleotides to about 180 nucleotides, about 170 nucleotides to about 190 nucleotides, about 170 nucleotides to about 200 nucleotides, about 180 nucleotides to about 190 nucleotides, about 180 nucleotides to about 200 nucleotides, or about 190 nucleotides to about 200 nucleotides. The length of the target cell-free nucleic acid molecule can be about 100 nucleotides, about 110 nucleotides, about 120 nucleotides, about 130 nucleotides, about 140 nucleotides, about 150 nucleotides, about 160 nucleotides, about 170 nucleotides, about 180 nucleotides, about 190 nucleotides, or about 200 nucleotides. In some examples, the length of the target cell-free nucleic acid molecule can range between about 100 nucleotides and about 180 nucleotides.

In some embodiments of any one of the compositions disclosed herein, the genomic regions can be associated with a condition. The genomic regions can be determined to exhibit aberrant somatic hypermutation when a subject has the condition. For example, the condition can comprise B-cell lymphoma or a sub-type thereof, such as diffuse large B-cell lymphoma, follicular lymphoma, Burkitt lymphoma, and B-cell chronic lymphocytic leukemia. Additional details of the condition are provided below.

In some embodiments of any one of the compositions disclosed herein, the composition further comprises the plurality of cell-free nucleic acid (e.g., cfDNA) molecules obtained or derived from the subject.

E. Diagnostic or Therapeutic Applications

A number of embodiments are directed towards performing a diagnostic scan on cell-free nucleic acids of an individual and then based on results of the scan indicating cancer, performing further clinical procedures and/or treating the individual. In accordance with various embodiments, numerous types of neoplasms can be detected.

In some embodiments of any one of the methods disclosed herein, the method can comprise determining that the subject has the condition or determining a degree or status of the condition of the subject, based on the one or more cell-free nucleic acid molecules comprising the plurality of phased variants. In some cases, the method can further comprise determining that the one or more cell-free nucleic acid molecules (each identified to comprise a plurality of phased variants) are derived from a sample associated with the condition (e.g., cancer), based on a statistical model analysis (i.e., molecular analysis). For example, the method can comprise using one or more algorithms (e.g., Monte Carlos simulation) to determine a first probability of a cell-free nucleic acid identified to have a plurality of phased variants being associated with or originated from a first condition (e.g., 80%) and a second probability of the same cell-free nucleic acid being associated with or originated from a second condition (or from a healthy cell) (e.g., 20%). In some cases, the method can comprise determining a likelihood or probability that the subject has one or more conditions based on analysis of the one or more cell-free nucleic acid molecules each identified to comprise a plurality of phased variants (i.e., macro- or global analysis). For example, the method can comprise using one or more algorithms (e.g., comprising one or more mathematical models as disclosed herein, such as binomial sampling) to analyze a plurality of cell-free nucleic acid molecules each identified to comprise a plurality of phased variants, thereby to determine a first probability of the subject having a first condition (e.g., 80%) and a second probability of the subject having a second condition (or being healthy) (e.g., 20%).

The statistical model analysis as disclosed herein can be an approximate solution by a numerical approximation such as a binomial model, a ternary model, a Monte Carlo simulation, or a finite difference method. In an example, the statistical model analysis as used herein can be a Monte Carlo statistical analysis. In another example, the statistical model analysis as used herein can be a binomial or ternary model analysis.

In some embodiments of any one of the methods disclosed herein, the method can comprise monitoring a progress of the condition of the subject based on the one or more cell-free nucleic acid molecules identified, such that each of the identified cell-free nucleic acid molecule comprises a plurality of phased variants. In some cases, the progress of the condition can be worsening of the condition, as described in the present disclosure (e.g., developing from stage I cancer to stage III cancer). In some cases, the progress of the condition can be at least a partial remission of the condition, as described in the present disclosure (e.g., downstaging from stage IV cancer to stage II cancer). Alternatively, in some cases, the progress of the condition can remain substantially the same between two different time points, as described in the present disclosure. In an example, the method can comprise determining likelihoods or probabilities of different progresses of the condition of the subject. For example, the method can comprise using one or more algorithms (e.g., comprising one or more mathematical models as disclosed herein, such as binomial sampling) to determine a first probability of the subject's condition being worse than before (e.g., 20%), a second probability of at least partial remission of the condition (e.g., 70%), and a third probability that the subject's condition is the same as before (e.g., 10%).

In some embodiments of any one of the methods disclosed herein, the method can comprise comprising performing a different procedure (e.g., follow-up diagnostic procedures) to confirm the condition of the subject, which condition has been determined and/or monitored progress thereof, as provided in the present disclosure. Non-limiting examples of a different procedure can include physical exam, medical imaging, genetic test, mammography, endoscopy, stool sampling, pap test, alpha-fetoprotein blood test, CA-125 test, prostate-specific antigen (PSA) test, biopsy extraction, bone marrow aspiration, and tumor marker detection tests. Medical imaging includes (but is not limited to) X-ray, magnetic resonance imaging (MRI), computed tomography (CT), ultrasound, and positron emission tomography (PET). Endoscopy includes (but is not limited to) bronchoscopy, colonoscopy, colposcopy, cystoscopy, esophagoscopy, gastroscopy, laparoscopy, neuroendoscopy, proctoscopy, and sigmoidoscopy.

In some embodiments of any one of the methods disclosed herein, the method can comprise determining a treatment for the condition of the subject based on the one or more cell-free nucleic acid molecules identified, each identified cell-free nucleic acid molecule comprising a plurality of phased variants. In some cases, the treatment can be determined based on (i) the determined condition of the subject and/or (ii) the determined progress of the condition of the subject. In addition, the treatment can be determined based on one or more additional factors of the following: sex, nationality, age, ethnicity, and other physical conditions of the subject. In some examples, the treatment can be determined based on one or more features of the plurality of phased variants of the identified cell-free nucleic acid molecules, as disclosed herein.

In some embodiments of any one of the methods disclosed herein, the subject may not have been subjected to any treatment for the condition, e.g., the subject may not have been diagnosed with the condition (e.g., a lymphoma). In some embodiments of any one of the methods disclosed herein, the subject may been subjected to a treatment for the condition prior to any subject method of the present disclosure. In some cases, the methods disclosed herein can be performed to monitor progress of the condition that the subject has been diagnosed with, thereby to (i) determine efficacy of the previous treatment and (ii) assess whether to keep the treatment, modify the treatment, or cancel the treatment in favor of a new treatment.

In some embodiments of any one of the methods disclosed herein, non-limiting examples of a treatment (e.g., prior treatment, new treatment to be determined based on the methods of the present disclosure, etc.) can include chemotherapy, radiotherapy, chemoradiotherapy, immunotherapy, adoptive cell therapy (e.g., chimeric antigen receptor (CAR) T cell therapy, CAR NK cell therapy, modified T cell receptor (TCR) T cell therapy, etc.) hormone therapy, targeted drug therapy, surgery, transplant, transfusion, or medical surveillance.

In some embodiments of any one of the methods disclosed herein, the condition can comprise a disease. In some embodiments of any one of the methods disclosed herein, the condition can comprise neoplasm, cancer, or tumor. In an example, the condition can comprise a solid tumor. In another example, the condition can comprise a lymphoma, such as B-cell lymphoma (BCL). Non-limiting examples of BCL can include diffuse large B-cell lymphoma (DLBCL), follicular lymphoma (FL), Burkitt lymphoma (BL), B-cell chronic lymphocytic leukemia (CLL), Marginal zone B-cell lymphoma (MZL), and Mantle cell lymphoma (MCL).

As disclosed herein, a treatment for a condition of subject can comprise administering the subject with one or more therapeutic agents. The one or more therapeutic drugs can be administered to the subject by one or more of the following: orally, intraperitoneally, intravenously, intraarterially, transdermally, intramuscularly, liposomally, via local delivery by catheter or stent, subcutaneously, intraadiposally, and intrathecally.

Non-limiting examples of the therapeutic drugs can include cytotoxic agents, chemotherapeutic agents, growth inhibitory agents, agents used in radiation therapy, anti-angiogenesis agents, apoptotic agents, anti-tubulin agents, and other agents to treat cancer, for example, anti-CD20 antibodies, anti-PD1 antibodies (e.g., Pembrolizumab) platelet derived growth factor inhibitors (e.g., GLEEVEC™ (imatinib mesylate)), a COX-2 inhibitor (e.g., celecoxib), interferons, cytokines, antagonists (e.g., neutralizing antibodies) that bind to one or more of the following targets PDGFR-β, BlyS, APRIL, BCMA receptor(s), TRAIL/Apo2, other bioactive and organic chemical agents, and the like.

Non-limiting examples of a cytotoxic agent can include radioactive isotopes (e.g., At211, I131, I125, Y90, Re186, Re188, Sm153, Bi212, P32, and radioactive isotopes of Lu), chemotherapeutic agents, e.g., methotrexate, adriamycin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin.

Non-limiting examples of a chemotherapeutic agent can include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolmelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics; dynemicin, including dynemicin A; an espiramicina; as well as neocarzinostatin chromophore and related chromoprotein enediyne antibiotic chromophores), aclacinomycins, actinomycin, anthramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; eflornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verrucarin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, for example taxanes including TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhône-Poulenc Rorer, Antony, France); chlorambucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Examples of a chemotherapeutic agent can also include "anti-hormonal agents" or "endocrine therapeutics" that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD) leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGFR); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Examples of a chemotherapeutic agent can also include antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, feMzumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1λ antibody genetically modified to recognize interleukin-12 p40 protein.

Examples of a chemotherapeutic agent can also include "tyrosine kinase inhibitors" such as an EGFR-targeting agent (e.g., small molecule, antibody, etc.); small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g., those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone); and rapamycin (sirolimus, RAPAMUNE®).

Examples of a chemotherapeutic agent can also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Examples of a chemotherapeutic agent can also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate: immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (ENBREL®), infliximab (REMICADE®), adalimumab (HUMIRA®), certolizumab pegol (CIMZIA®), golimumab (SIMPONI®), Interleukin 1 (IL-1) blockers such as anakinra (KINERET®), T-cell costimulation blockers such as abatacept (ORENCIA®), Interleukin 6 (IL-6) blockers such as tocilizumab (ACTEMERA®); Interleukin 13 (IL-13) blockers such as lebrikizumab; Interferon alpha (IFN) blockers such as rontalizumab; beta 7 integrin blockers such as rhuMAb Beta7; IgE pathway blockers such as Anti-M1 prime; Secreted homotrimeric LTa3 and membrane bound heterotrimer LTa/β2 blockers such as Anti-lymphotoxin alpha (LTa); miscellaneous investigational agents such as thioplatin, PS-341, phenylbutyrate, ET-18-OCH3, or famesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGFR); vaccines such as THERATOPE® vaccine; perifosine, COX-2 inhibitor (e.g., celecoxib or etoricoxib), proteosome inhibitor (e.g., PS341); CCI-779; tipifamib (R11577); orafenib, ABT510; Bcl-2 inhibitor such as oblimersen sodium (GENASENSE®); pixantrone; famesyltransferase inhibitors such as lonafamib (SCH 6636, SARASAR™); and pharmaceutically acceptable salts, acids or derivatives of any of the above; as well as combinations of two or more of the above.

In accordance with many embodiments, once a diagnosis of cancer is indicated, a number of treatments can be performed, including (but not limited to) surgery, resection, chemotherapy, radiation therapy, immunotherapy, targeted therapy, hormone therapy, stem cell transplant, and blood transfusion. In some embodiments, an anti-cancer and/or chemotherapeutic agent is administered, including (but not limited to) alkylating agents, platinum agents, taxanes, vinca agents, anti-estrogen drugs, aromatase inhibitors, ovarian suppression agents, endocrine/hormonal agents, bisphophonate therapy agents and targeted biological therapy agents. Medications include (but are not limited to) cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolomide, topotecan, vincristine, vinblastine, eribulin, mutamycin, capecitabine, capecitabine, anastrozole, exemestane, letrozole, leuprolide, abarelix, buserelin, goserelin, megestrol acetate, risedronate, pamidronate, ibandronate, alendronate, zoledronate, tykerb, daunorubicin, doxorubicin, epirubicin, idarubicin, valrubicin mitoxantrone, bevacizumab, cetuximab, ipilimumab, ado-trastuzumab emtansine, afatinib, aldesleukin, alectinib, alemtuzumab, atezolizumab, avelumab, axtinib, belimumab, belinostat, bevacizumab, blinatumomab, bortezomib, bosutinib, brentuximab vedotin, brigatinib, cabozantinib, canakinumab, carfilzomib, certinib, cetuximab, cobimetinib, crizotinib, dabrafenib, daratumumab, dasatinib, denosumab, dinutuximab, durvalumab, elotuzumab, enasidenib, erlotinib, everolimus, gefitinib, ibritumomab tiuxetan, ibrutinib, idelalisib, imatinib, ipilimumab, ixazomib, lapatinib, lenvatinib, midostaurin, necitumumab, neratinib, nilotinib, niraparib, nivolumab, obinutuzumab, ofatumumab, olaparib, olaratumab, osimertinib, palbociclib, panitumumab, panobinostat, pembrolizumab, pertuzumab, ponatinib, ramucirumab, regorafenib, ribociclib, rituximab, romidepsin, rucaparib, ruxolitinib, siltuximab, sipuleucel-T, sonidegib, sorafenib, temsirolimus, tocilizumab, tofacitinib, tositumomab, trametinib, trastuzumab, vandetanib, vemurafenib, venetoclax, vismodegib, vorinostat, and ziv-aflibercept. In accordance with various embodiments, an individual may be treated, by a single medication or a combination of medications described herein. A common treatment combination is cyclophosphamide, methotrexate, and 5-fluorouracil (CMF).

In some embodiments of any one of the methods disclosed herein, any of the cell-free nucleic acid molecules (e.g., cfDNA, cfRNA) can be derived from a cell. For example, a cell sample or tissue sample may be obtained from a subject and processed to remove all cells from the sample, thereby producing cell-free nucleic acid molecules derived from the sample.

In some embodiments of any one of the methods disclosed herein, a reference genomic sequence can be derived from a cell of an individual. The individual can be a healthy control or the subject who is being subjected to the methods disclosed herein for determining or monitoring progress of a condition.

A cell can be a healthy cell. Alternatively, a cell can be a diseased cell. A diseased cell can have altered metabolic, gene expression, and/or morphologic features. A diseased cell can be a cancer cell, a diabetic cell, and an apoptotic cell. A diseased cell can be a cell from a diseased subject. Exemplary diseases can include blood disorders, cancers, metabolic disorders, eye disorders, organ disorders, musculoskeletal disorders, cardiac disease, and the like.

A cell can be a mammalian cell or derived from a mammalian cell. A cell can be a rodent cell or derived from a rodent cell. A cell can be a human cell or derived from a human cell. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a pluripotent stem cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a microbe cell or derived from a microbe cell. A cell can be a fungi cell or derived from a fungi cell. A cell can be from a specific organ or tissue.

Non-limiting examples of a cell(s) can include lymphoid cells, such as B cell, T cell (Cytotoxic T cell, Natural Killer T cell, Regulatory T cell, T helper cell), Natural killer cell, cytokine induced killer (CTK) cells; myeloid cells, such as granulocytes (Basophil granulocyte, Eosinophil granulocyte, Neutrophil granulocyte/Hypersegmented neutrophil), Monocyte/Macrophage, Red blood cell (Reticulocyte), Mast cell, Thrombocyte/Megakaryocyte, Dendritic cell; cells from the endocrine system, including thyroid (Thyroid epithelial cell, Parafollicular cell), parathyroid (Parathyroid chief cell, Oxyphil cell), adrenal (Chromaffin cell), pineal (Pinealocyte) cells; cells of the nervous system, including glial cells (Astrocyte, Microglia), Magnocellular neurosecretory cell, Stellate cell, Boettcher cell, and pituitary (Gonadotrope, Corticotrope, Thyrotrope, Somatotrope, Lactotroph); cells of the Respiratory system, including Pneumocyte (Type I pneumocyte, Type II pneumocyte), Clara cell, Goblet cell, Dust cell; cells of the circulatory system, including Myocardiocyte, Pericyte; cells of the digestive system, including stomach (Gastric chief cell, Parietal cell), Goblet cell, Paneth cell, G cells, D cells, ECL cells, I cells, K cells, S cells; enteroendocrine cells, including enterochromaffin cell, APUD cell, liver (Hepatocyte, Kupffer cell), Cartilage/bone/muscle; bone cells, including Osteoblast, Osteocyte, Osteoclast, teeth (Cementoblast, Ameloblast); cartilage cells, including Chondroblast, Chondrocyte; skin cells, including Trichocyte, Keratinocyte, Melanocyte (Nevus cell); muscle cells, including Myocyte; urinary system cells, including Podocyte, Juxtaglomerular cell, Intraglomerular mesangial cell/Extraglomerular mesangial cell, Kidney proximal tubule brush border cell, *Macula densa* cell; reproductive system cells, including Spermatozoon, Sertoli cell, Leydig cell, Ovum; and other cells, including Adipocyte, Fibroblast, Tendon cell, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell), Wet stratified barrier epithelial cells, Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts), Exocrine secretory epithelial cells, Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion). Apocrine sweat gland cell (odoriferous secretion, sex-hormone sensitive), Gland of Moll in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), Paneth cell of small intestine (lysozyme secretion), Type II pneumocyte of lung (surfactant secretion), Clara cell of lung, Hormone secreting cells, Anterior pituitary cells, Somatotropes, Lactotropes, Thyrotropes, Gonadotropes, Corticotropes, Intermediate pituitary cell, Magnocellular neurosecretory cells, Gut and respiratory tract cells, Thyroid gland cells, thyroid epithelial cell, parafollicular cell, Parathyroid gland cells, Parathyroid chief cell, Oxyphil cell, Adrenal gland cells, chromaffin cells, Ley dig cell of testes, Theca interna cell of ovarian follicle, *Corpus luteum* cell of ruptured ovarian follicle, Granulosa lutein cells, Theca lutein cells, Juxtaglomerular cell (renin secretion), *Macula densa* cell of kidney, Metabolism and storage cells, Barrier function cells (Lung, Gut, Exocrine Glands and Urogenital Tract), Kidney, Type I pneumocyte (lining air space of lung), Pancreatic duct cell (centroacinar cell), Nonstriated duct cell (of sweat gland, salivary gland, mammary gland, etc.), Duct cell (of seminal vesicle, prostate gland, etc.), Epithelial cells lining closed internal body cavities, Ciliated cells with propulsive function, Extracellular matrix secretion cells, Contractile cells; Skeletal muscle cells, stem cell, Heart muscle cells, Blood and immune system cells, Erythrocyte (red blood cell), Megakaryocyte (platelet precursor), Monocyte, Connective tissue macrophage (various types), Epidermal Langerhans cell, Osteoclast (in bone), Dendritic cell (in lymphoid tissues), Microglial cell (in central nervous system), Neutrophil granulocyte, Eosinophil granulocyte, Basophil granulocyte, Mast cell, Helper T cell, Suppressor T cell, Cytotoxic T cell, Natural Killer T cell, B cell, Natural killer cell, Reticulocyte, Stem cells and committed progenitors for the blood and immune system (various types), Pluripotent stem cells, Totipotent stem cells, Induced pluripotent stem cells, adult stem cells, Sensory transducer cells, Autonomic neuron cells, Sense organ and peripheral neuron supporting cells, Central nervous system neurons and glial cells, Lens cells, Pigment cells, Melanocyte, Retinal pigmented epithelial cell, Germ cells, Oogonium/Oocyte, Spermatid, Spermatocyte, Spermatogonium cell (stem cell for spermatocyte), Spermatozoon, Nurse cells, Ovarian follicle cell, Sertoli cell (in testis), Thymus epithelial cell, Interstitial cells, and Interstitial kidney cells.

In some embodiments of any one of the methods disclosed herein, the condition can be a cancer or tumor. Non-limiting examples of such condition can include Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, *Glomus* tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, and Wilms' tumor.

In accordance with various embodiments, numerous types of neoplasms can be detected, including (but not limited to) acute lymphoblastic leukemia (ALL), acute myeloid leukemia (AML), anal cancer, astrocytomas, basal cell carcinoma, bile duct cancer, bladder cancer, breast cancer, Burkitt's lymphoma, cervical cancer, chronic lymphocytic leukemia (CLL) chronic myelogenous leukemia (CML), chronic myeloproliferative neoplasms, colorectal cancer, diffuse large B-cell lymphoma, endometrial cancer, ependymoma, esophageal cancer, esthesioneuroblastoma, Ewing sarcoma, fallopian tube cancer, follicular lymphoma, gallbladder cancer, gastric cancer, gastrointestinal carcinoid tumor, hairy cell leukemia, hepatocellular cancer, Hodgkin lymphoma, hypopharyngeal cancer, Kaposi sarcoma, Kidney cancer, Langerhans cell histiocytosis, laryngeal cancer, leukemia, liver cancer, lung cancer, lymphoma, melanoma, Merkel cell cancer, mesothelioma, mouth cancer, neuroblastoma, non-Hodgkin lymphoma, non-small cell lung cancer, osteosarcoma, ovarian cancer, pancreatic cancer, pancreatic neuroendocrine tumors, pharyngeal cancer, pituitary tumor, prostate cancer, rectal cancer, renal cell cancer, retinoblastoma, skin cancer, small cell lung cancer, small intestine cancer, squamous neck cancer, T-cell lymphoma, testicular cancer, thymoma, thyroid cancer, uterine cancer, vaginal cancer, and vascular tumors.

Many embodiments are directed to diagnostic or companion diagnostic scans performed during cancer treatment of an individual. When performing diagnostic scans during treatment, the ability of agent to treat the cancer growth can be monitored. Most anti-cancer therapeutic agents result in death and necrosis of neoplastic cells, which should release higher amounts nucleic acids from these cells into the samples being tested. Accordingly, the level of circulating-tumor nucleic acids can be monitored over time, as the level should increase during early treatments and begin to decrease as the number of cancerous cells are decreased. In some embodiments, treatments are adjusted based on the treatment effect on cancer cells. For instance, if the treatment isn't cytotoxic to neoplastic cells, a dosage amount may be increased or an agent with higher cytotoxicity can be administered. In the alternative, if cytotoxicity of cancer cells is good but unwanted side effects are high, a dosage amount can be decreased or an agent with less side effects can be administered.

Various embodiments are also directed to diagnostic scans performed after treatment of an individual to detect residual disease and/or recurrence of cancer. If a diagnostic scan indicates residual and/or recurrence of cancer, further diagnostic tests and/or treatments may be performed as described herein. If the cancer and/or individual is susceptible to recurrence, diagnostic scans can be performed frequently to monitor any potential relapse.

F. Computer Systems

In one aspect, the present disclosure provides a computer program product comprising a non-transitory computer-readable medium having computer-executable code encoded therein, the computer-executable code adapted to be executed to implement any one of the preceding methods.

The present disclosure provides computer systems that are programmed to implement methods of the disclosure. The system can, in some cases, include components such as a processor, an input module for inputting sequencing data or data derived therefrom, a computer-readable medium containing instructions that, when executed by the processor, perform an algorithm on the input regarding one or more cell-free nucleic acids molecules, and an output module providing one or more indicia associated with the condition.

Figure 27:
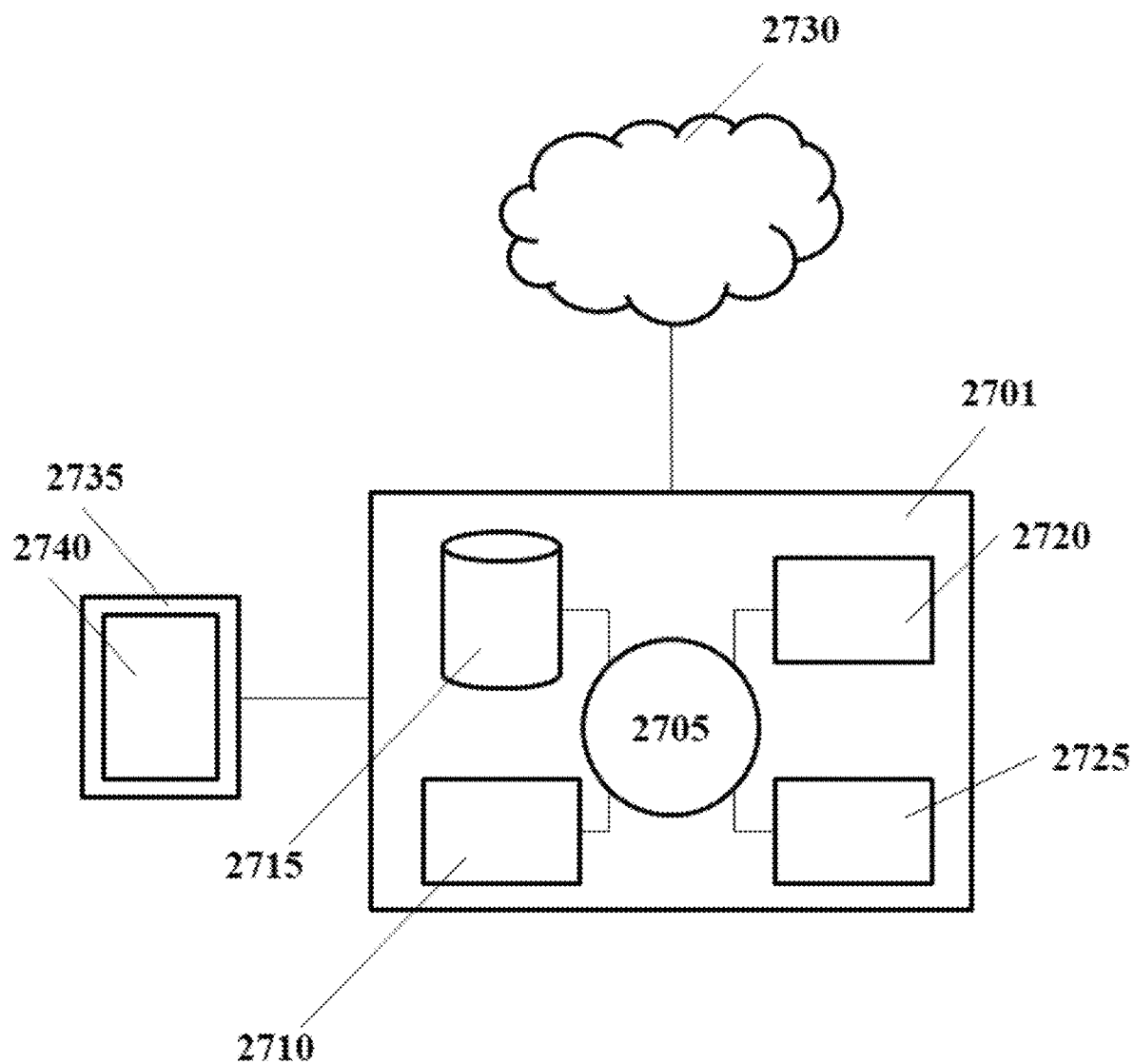
FIG. 27 shows a computer system that is programmed or otherwise configured to implement methods provided herein.

FIG. 27 shows a computer system 2701 that is programmed or otherwise configured to implement partial or all of the methods disclosed herein. The computer system 2701 can regulate various aspects of the present disclosure, such as, for example, (i) identify, from sequencing data derived from a plurality of cell-free nucleic acid molecules, one or more cell-free nucleic acid molecules comprising the plurality of phased variants, (ii) analyze any of the identified cell-free nucleic acid molecules, (iii) determine a condition of the subject based at least in part on the identified cell-free nucleic acid molecules, (iv) monitor a progress of the condition of the subject based at least in part on the identified cell-free nucleic acid molecules, (v) identify the subject based at least in part on the identified cell-free nucleic acid molecules, or (vi) determine an appropriate treatment of the condition of the subject based at least in part on the identified cell-free nucleic acid molecules. The computer system 2701 can be an electronic device of a user or a computer system that is remotely located with respect to the electronic device. The electronic device can be a mobile electronic device.

The computer system 2701 includes a central processing unit (CPU, also "processor" and "computer processor" herein) 2705, which can be a single core or multi core processor, or a plurality of processors for parallel processing. The computer system 2701 also includes memory or memory location 2710 (e.g., random-access memory, read-only memory, flash memory), electronic storage unit 2715 (e.g., hard disk), communication interface 2720 (e.g., network adapter) for communicating with one or more other systems, and peripheral devices 2725, such as cache, other memory, data storage and/or electronic display adapters. The memory 2710, storage unit 2715, interface 2720 and peripheral devices 2725 are in communication with the CPU 2705 through a communication bus (solid lines), such as a motherboard. The storage unit 2715 can be a data storage unit (or data repository) for storing data. The computer system 2701 can be operatively coupled to a computer network ("network") 2730 with the aid of the communication interface 2720. The network 2730 can be the Internet, an internet and/or extranet, or an intranet and/or extranet that is in communication with the Internet. The network 2730 in some cases is a telecommunication and/or data network. The network 2730 can include one or more computer servers, which can enable distributed computing, such as cloud computing. The network 2730, in some cases with the aid of the computer system 2701, can implement a peer-to-peer network, which may enable devices coupled to the computer system 2701 to behave as a client or a server.

The CPU 2705 can execute a sequence of machine-readable instructions, which can be embodied in a program or software. The instructions may be stored in a memory location, such as the memory 2710. The instructions can be directed to the CPU 2705, which can subsequently program or otherwise configure the CPU 2705 to implement methods of the present disclosure. Examples of operations performed by the CPU 2705 can include fetch, decode, execute, and writeback.

The CPU 2705 can be part of a circuit, such as an integrated circuit. One or more other components of the system 2701 can be included in the circuit. In some cases, the circuit is an application specific integrated circuit (ASIC).

The storage unit 2715 can store files, such as drivers, libraries and saved programs. The storage unit 2715 can store user data, e.g., user preferences and user programs. The computer system 2701 in some cases can include one or more additional data storage units that are external to the computer system 2701, such as located on a remote server that is in communication with the computer system 2701 through an intranet or the Internet.

The computer system 2701 can communicate with one or more remote computer systems through the network 2730. For instance, the computer system 2701 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2701 via the network 2730.

Methods as described herein can be implemented by way of machine (e.g., computer processor) executable code stored on an electronic storage location of the computer system 2701, such as, for example, on the memory 2710 or electronic storage unit 2715. The machine executable or machine readable code can be provided in the form of software. During use, the code can be executed by the processor 2705. In some cases, the code can be retrieved from the storage unit 2715 and stored on the memory 2710 for ready access by the processor 2705. In some situations, the electronic storage unit 2715 can be precluded, and machine-executable instructions are stored on memory 2710.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2701 can include or be in communication with an electronic display 2735 that comprises a user interface (UI) 2740 for providing, for example, (i) analysis of any of the identified cell-free nucleic acid molecules, (ii) a determined condition of the subject based at least in part on the identified cell-free nucleic acid molecules, (iii) a determined progress of the condition of the subject based at least in part on the identified cell-free nucleic acid molecules, (iv) the identified subject suspected of having the condition based at least in part on the identified cell-free nucleic acid molecules, or (v) a determined treatment of the condition of the subject based at least in part on the identified cell-free nucleic acid molecules. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2705. The algorithm can, for example, (i) identify, from sequencing data derived from a plurality of cell-free nucleic acid molecules, one or more cell-free nucleic acid molecules comprising the plurality of phased variants, (ii) analyze any of the identified cell-free nucleic acid molecules, (iii) determine a condition of the subject based at least in part on the identified cell-free nucleic acid molecules, (iv) monitor a progress of the condition of the subject based at least in part on the identified cell-free nucleic acid molecules, (v) identify the subject based at least in part on the identified cell-free nucleic acid molecules, or (vi) determine an appropriate treatment of the condition of the subject based at least in part on the identified cell-free nucleic acid molecules.

EXAMPLES

The following illustrative examples are representative of embodiments of the stimulation, systems, and methods described herein and are not meant to be limiting in any way.

Example 1: Genomic Distribution of Phased Variants

Described is an alternative to duplex sequencing for reducing the background error rate that involves detection of 'phased variants' (PVs), where two or more mutations occur in cis (i.e., on the same strand of DNA FIG. 1A and FIG. 1E). Similar to duplex sequencing, this method provides lower error profiles due to the concordant detection of two separate non-reference events in individual molecules. However, unlike duplex sequencing, both events occur on the same sequencing read-pair, thereby increasing the efficiency of genome recovery. Phased mutations are present in diverse cancer types, but occur in stereotyped portions of the genome in B-cell malignancies, likely due to on-target and aberrant somatic hypermutation (aSHM) driven by activation-induced deaminase (AID). The most common regions of aSHM in B-cell non-Hodgkin lymphomas (NHL) are identified. Described herein is phased variant Enrichment and Detection Sequencing (PhasED-Seq), a novel method to detect ctDNA through phased variants to tumor fractions on the order of parts per million. Described herein is demonstration that PhasED-Seq can meaningfully improve detection of ctDNA in clinical samples both during therapy and prior to disease relapse.

To identify malignancies where PVs may potentially improve disease detection, the frequency of PVs across cancer types were assessed. Publicly available whole-genome sequencing data was analyzed to identify sets of variants occurring at a distance of <170 bp apart, which represents the typical length of a single cfDNA fragment consisting of a single core nucleosome and associated linker. The frequency of these 'putative phased variants," (Example 10) controlling for the total number of SNVs, from 2538 tumors across 24 cancer histologies including solid tumors and hematological malignancies (FIG. 1B, FIG. 5, and Table 1) was identified and summarized. PVs were most significantly enriched in two B-cell lymphomas (DLBCL and follicular lymphoma, FL, P<0.05 vs all other histologies), a group of diseases with hypermutation driven by AID/AICDA.

Example 2: Mutational Mechanisms Underlying PVs

Figure 6A:
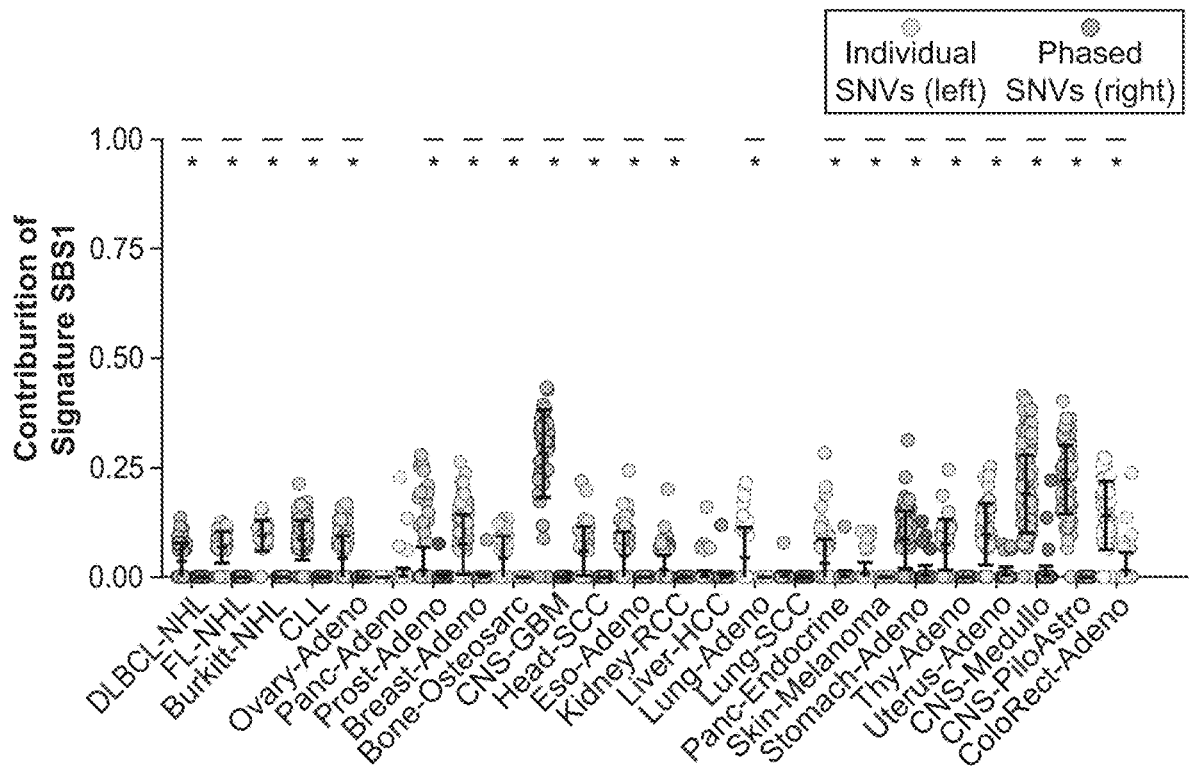
FIGS. 6A-6WW illustrate contribution of mutational signatures in phased and un-phased SNVs in WGS (FIGS. 6A-6WW.) Scatterplots showing the contribution of established single base substitution (SBS) mutational signatures to SNVs seen in PVs, shown in dark colors, and SNVs seen outside of possible phased relationships, shown in light colors, from WGS. This is presented for 49 SBS mutational signatures across 24 subtypes of cancer. Mutational signatures that show a significant difference in contribution between phased and un-phased SNVs after multiple hypothesis testing correction are indicated with a *. These figures represent the raw data summarized in FIG. 1C.
Figure 6B:
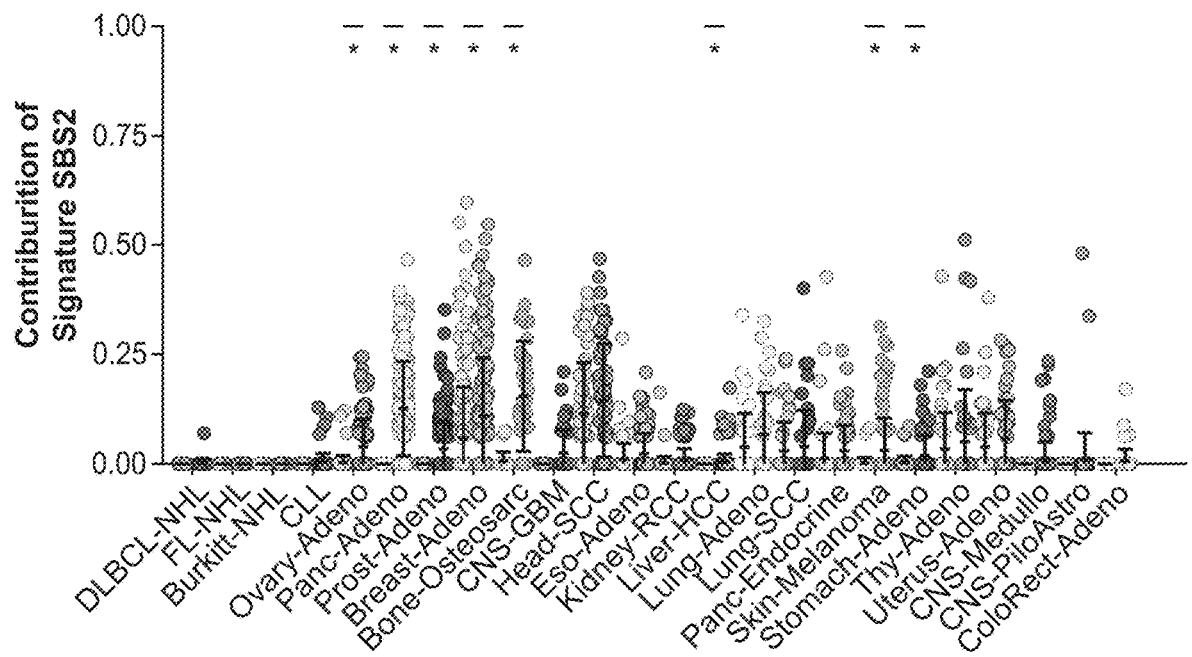
Figure 6C:
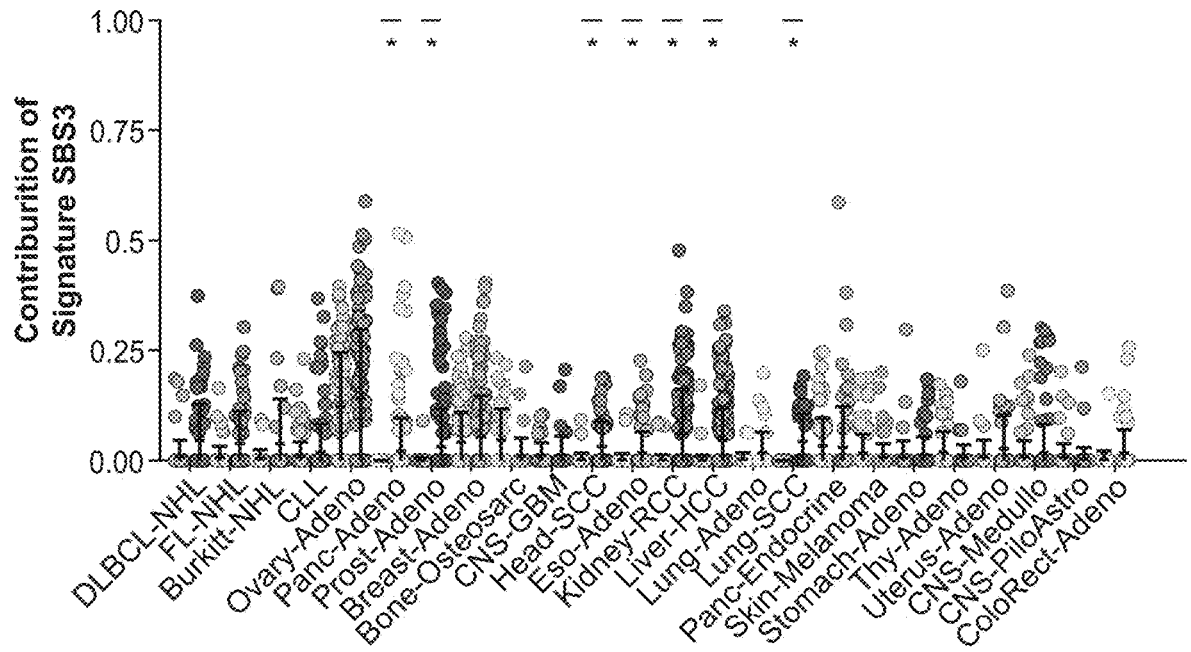
Figure 6D:
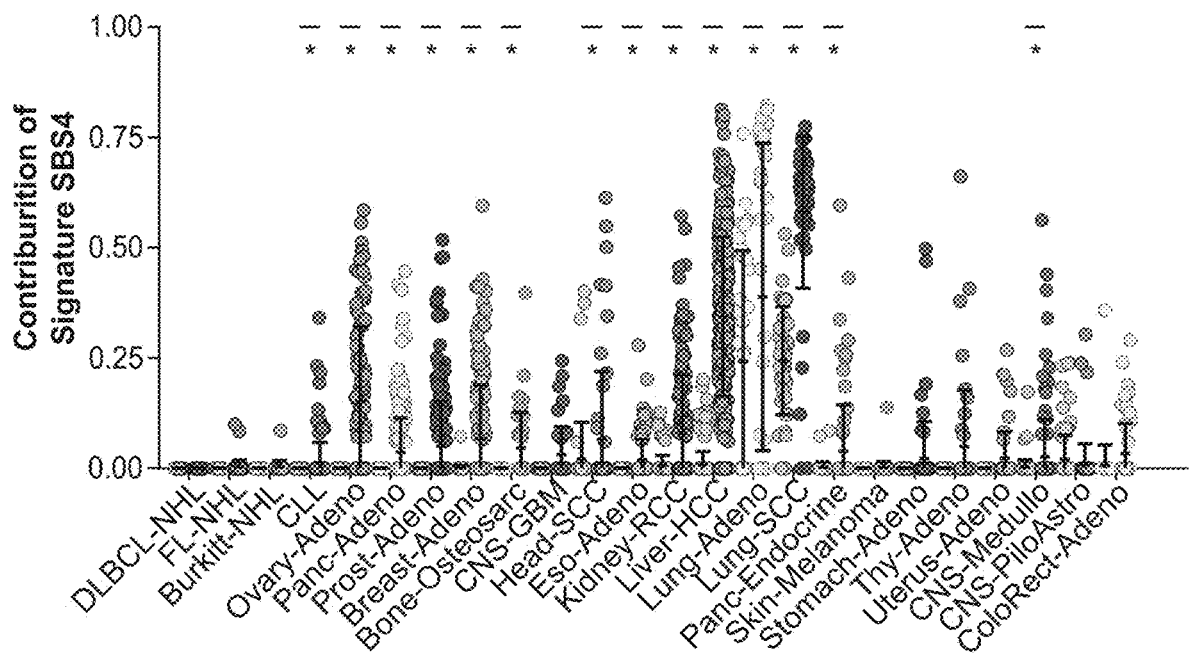
Figure 6E:
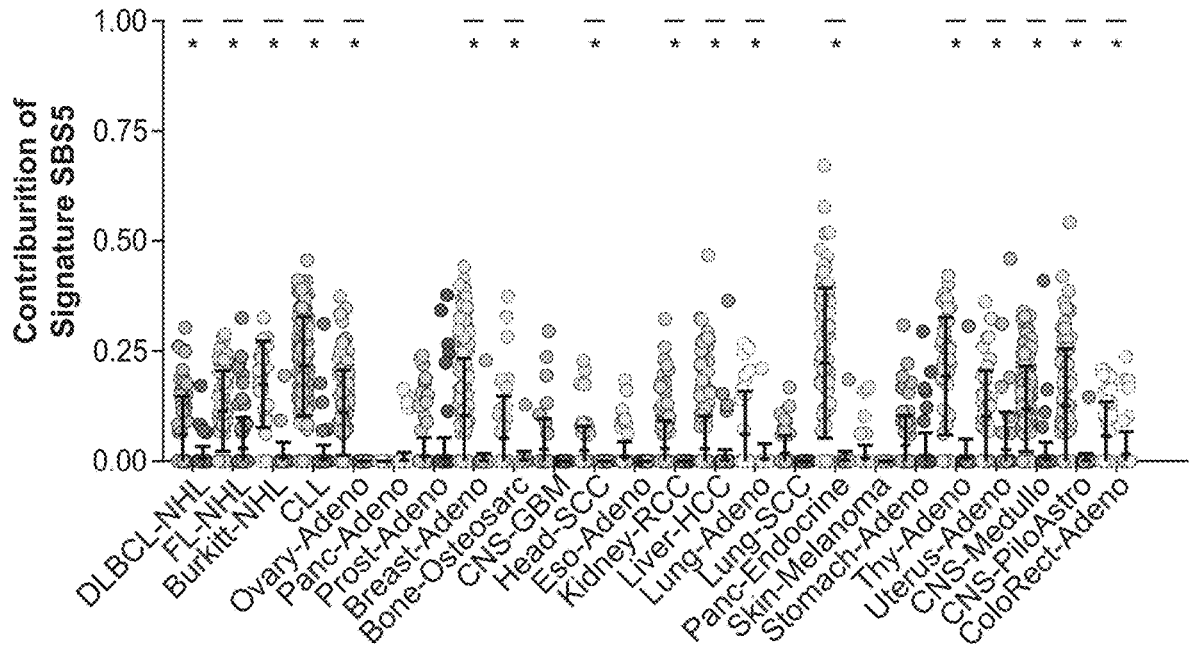
Figure 6F:
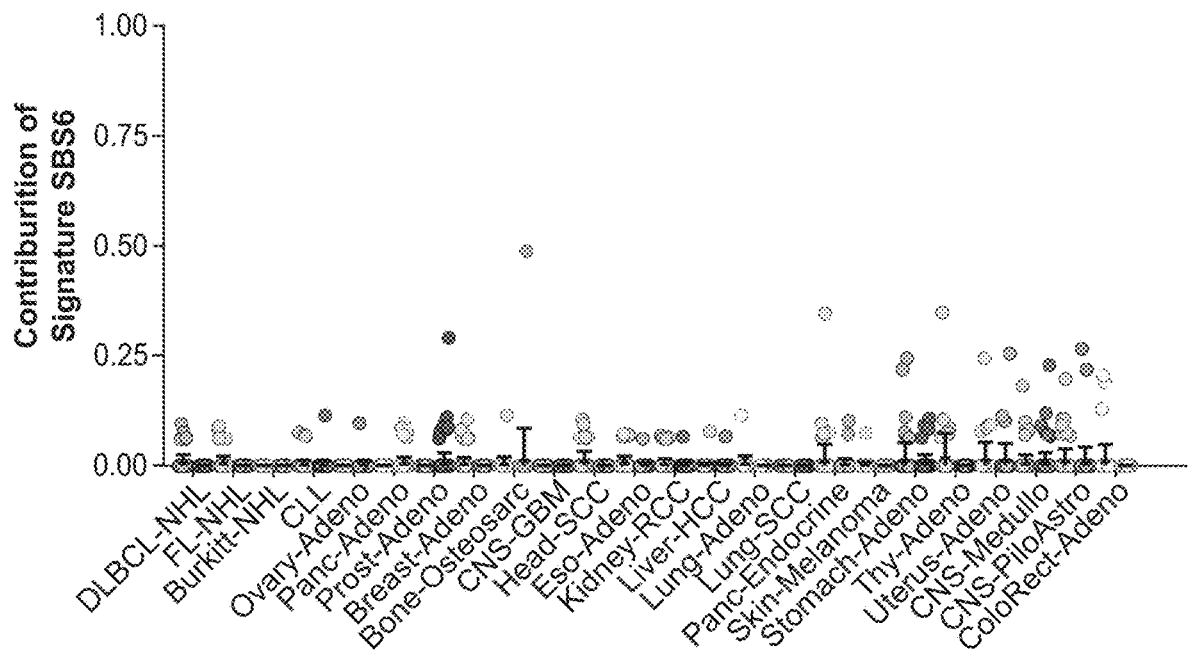
Figure 6G:
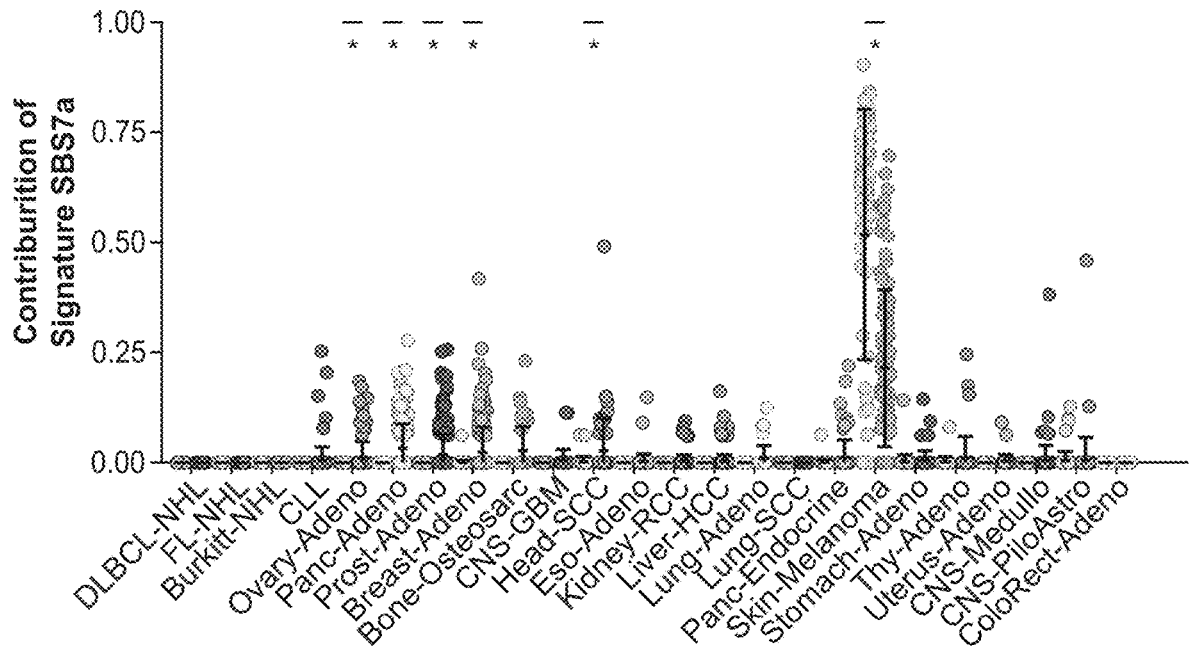
Figure 6H:
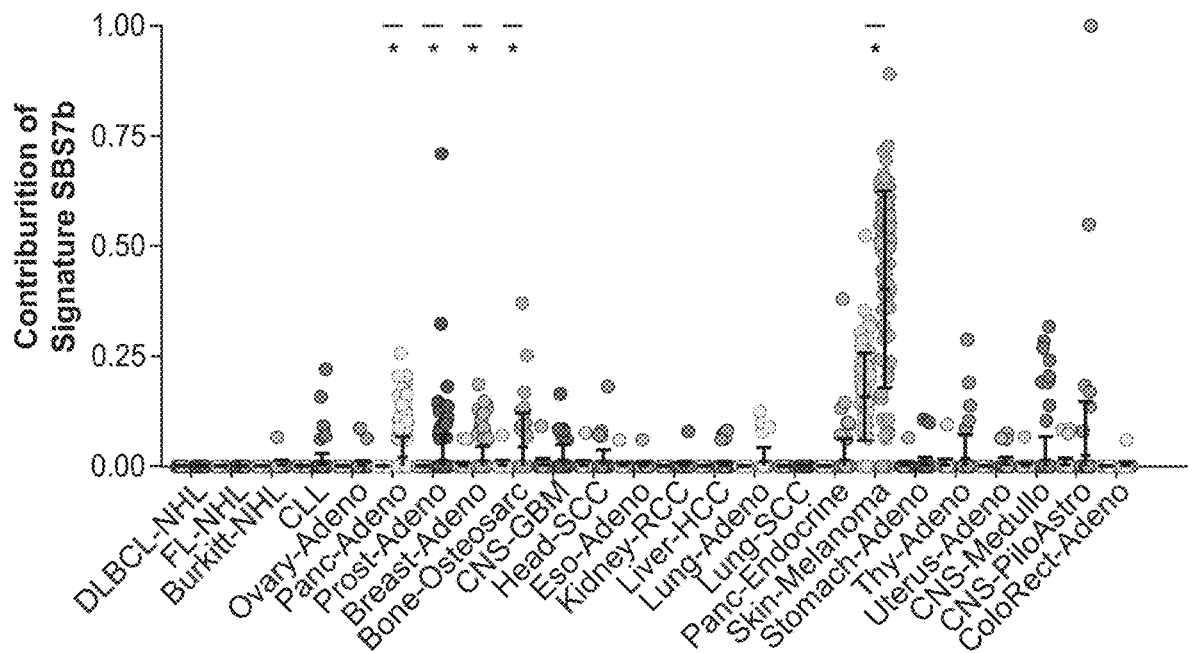
Figure 6I:
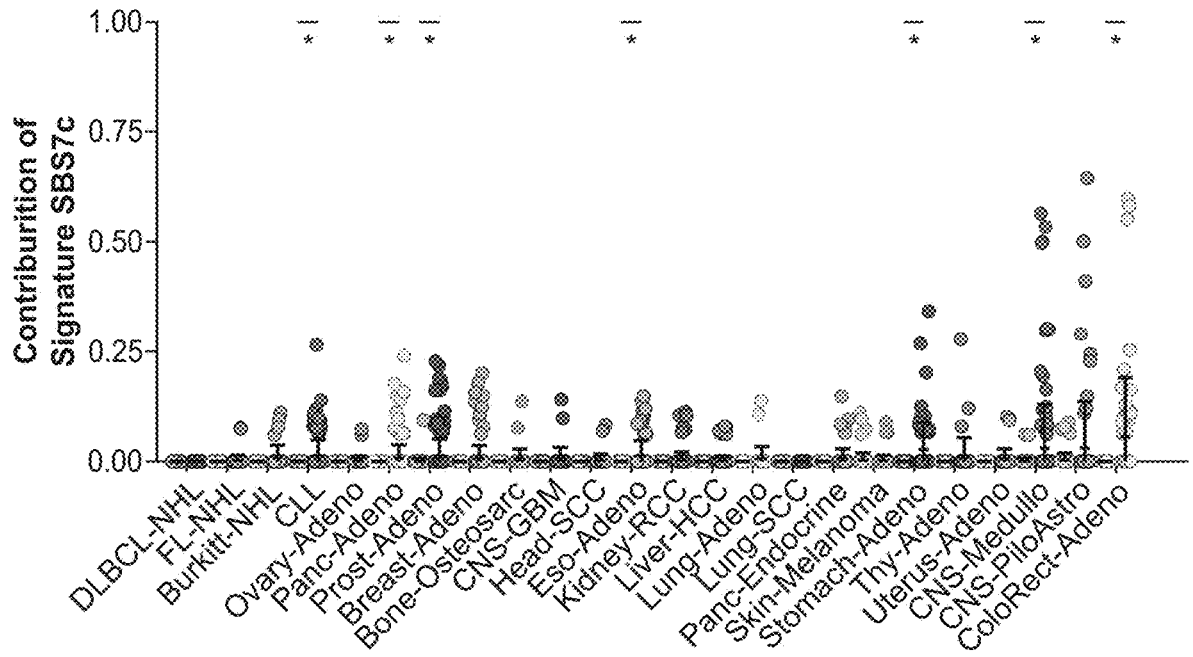
Figure 6J:
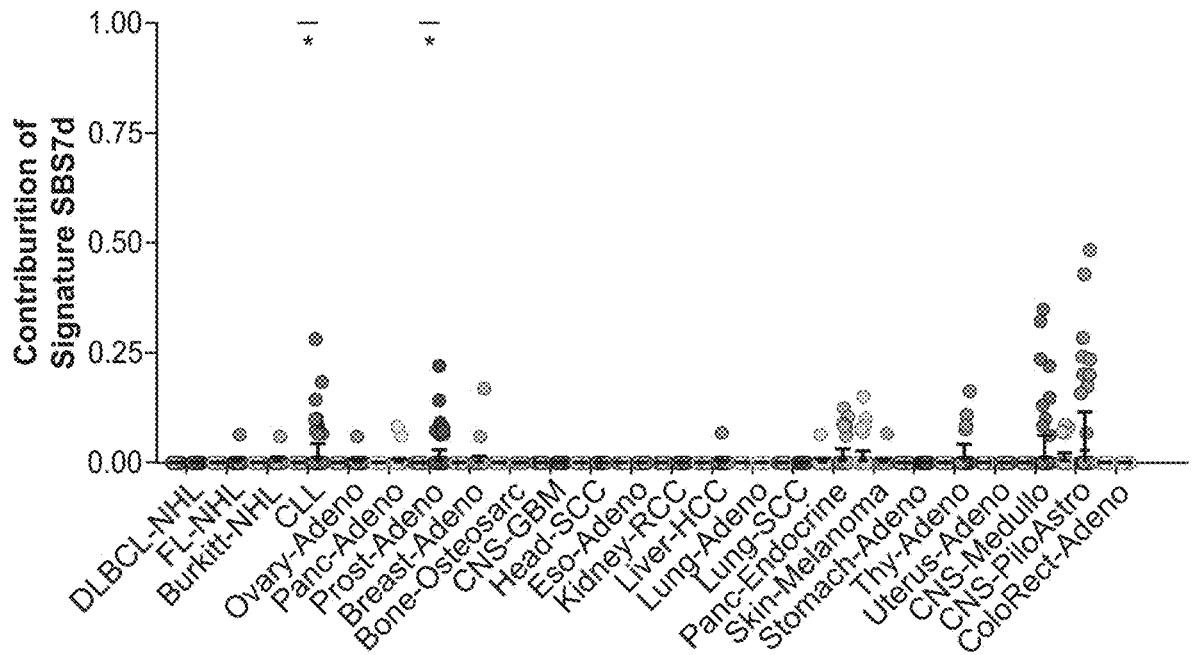
Figure 6K:
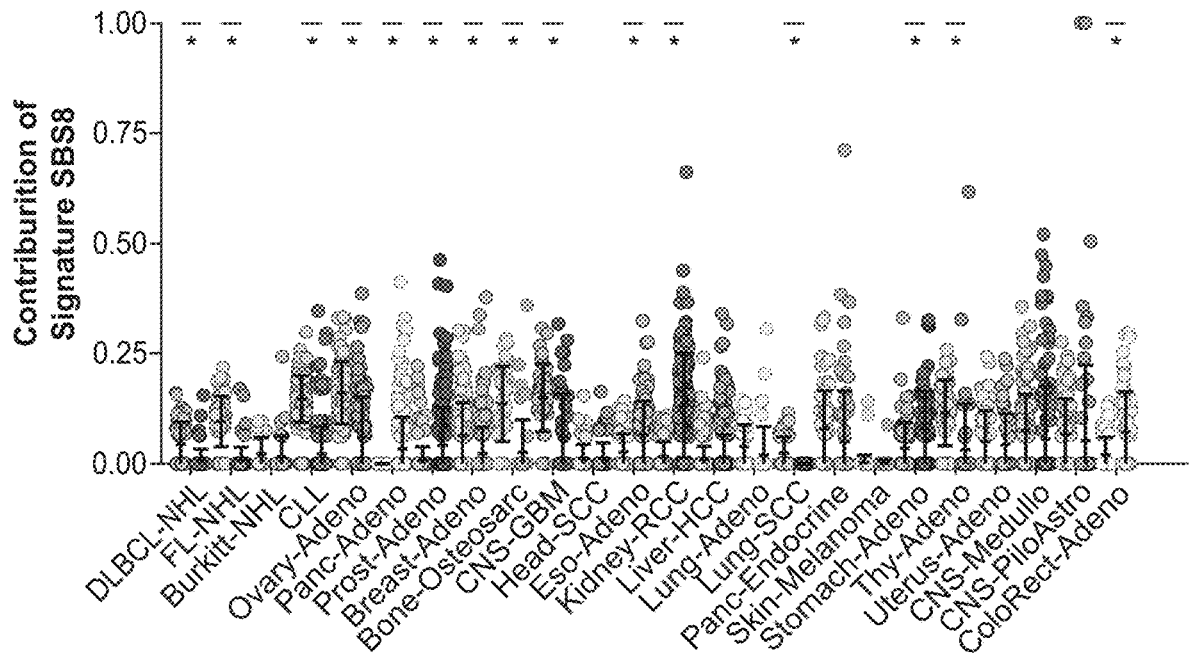
Figure 6L:
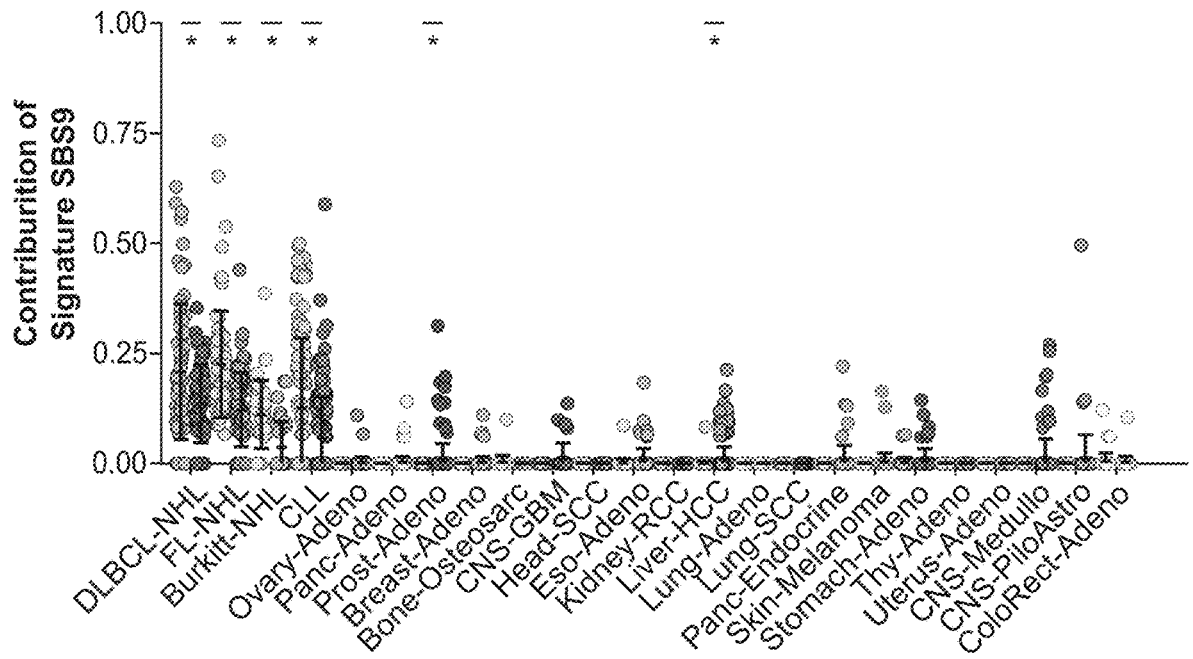
Figure 6M:
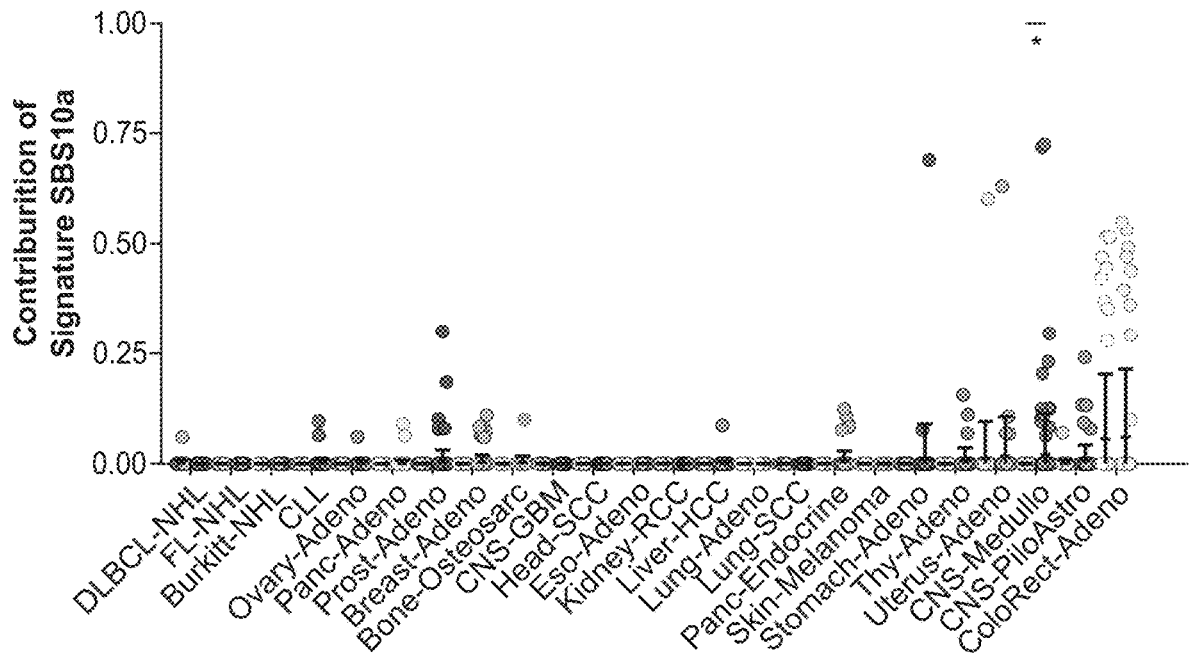
Figure 6N:
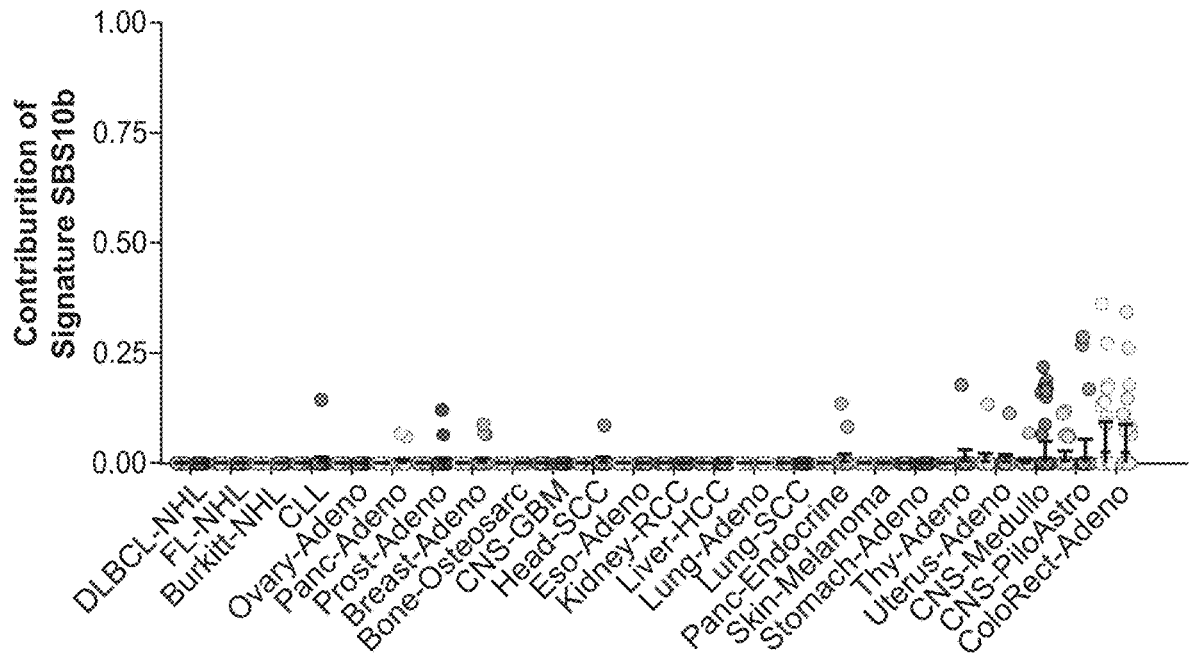
Figure 6O:
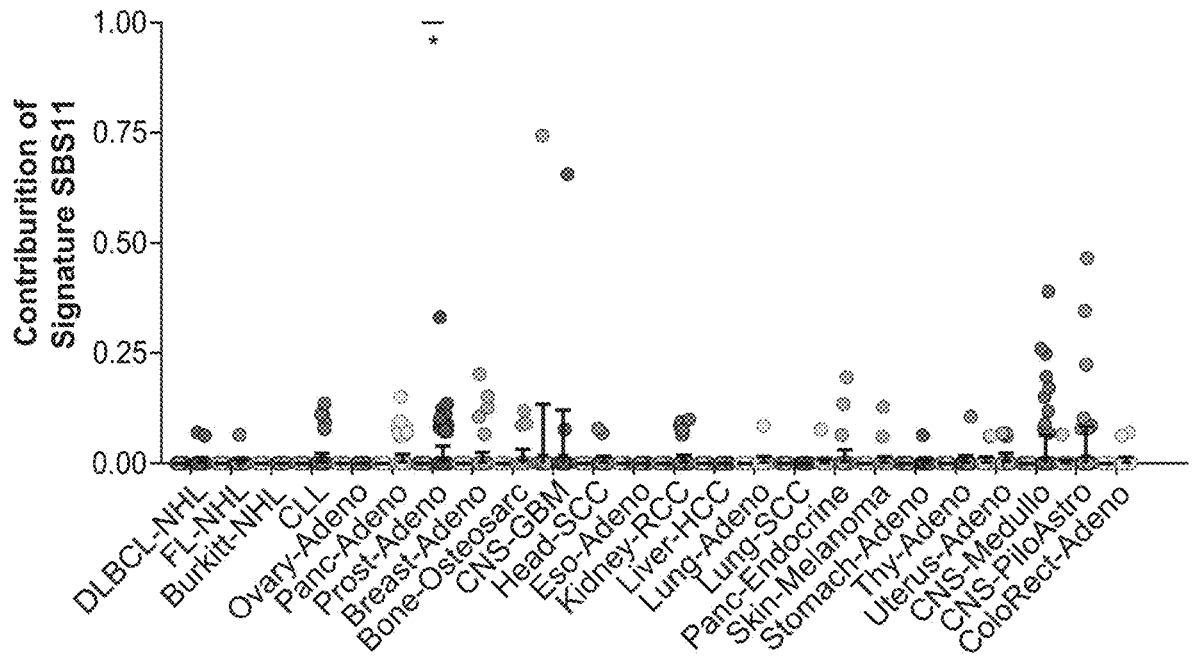
Figure 6P:
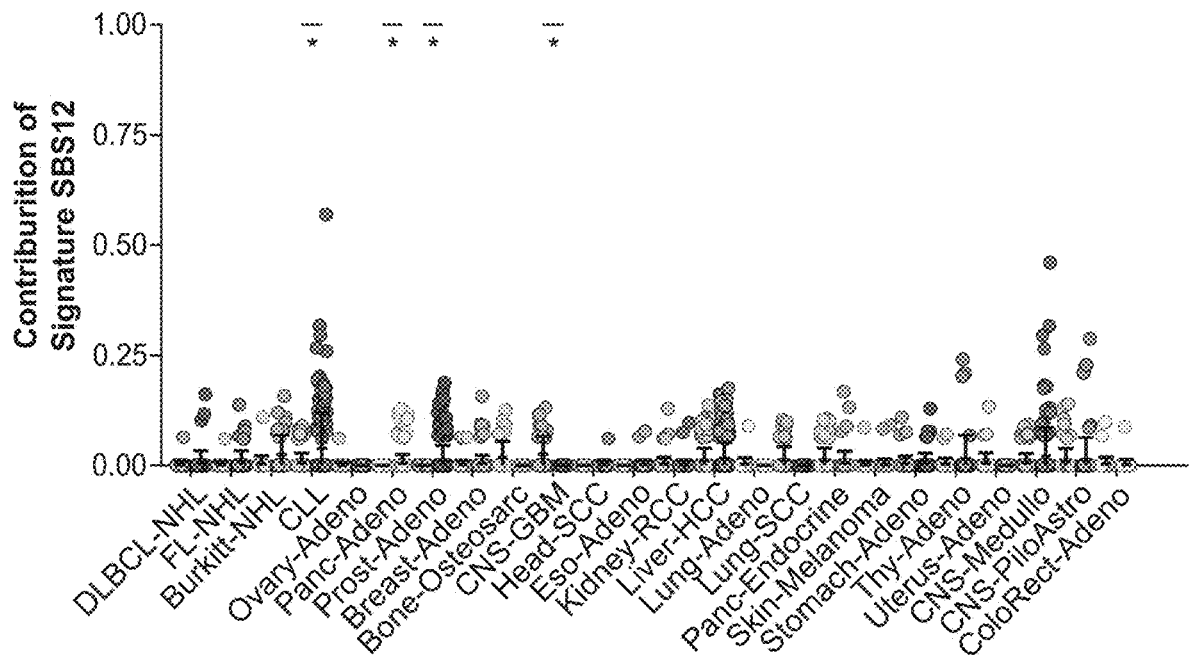
Figure 6Q:
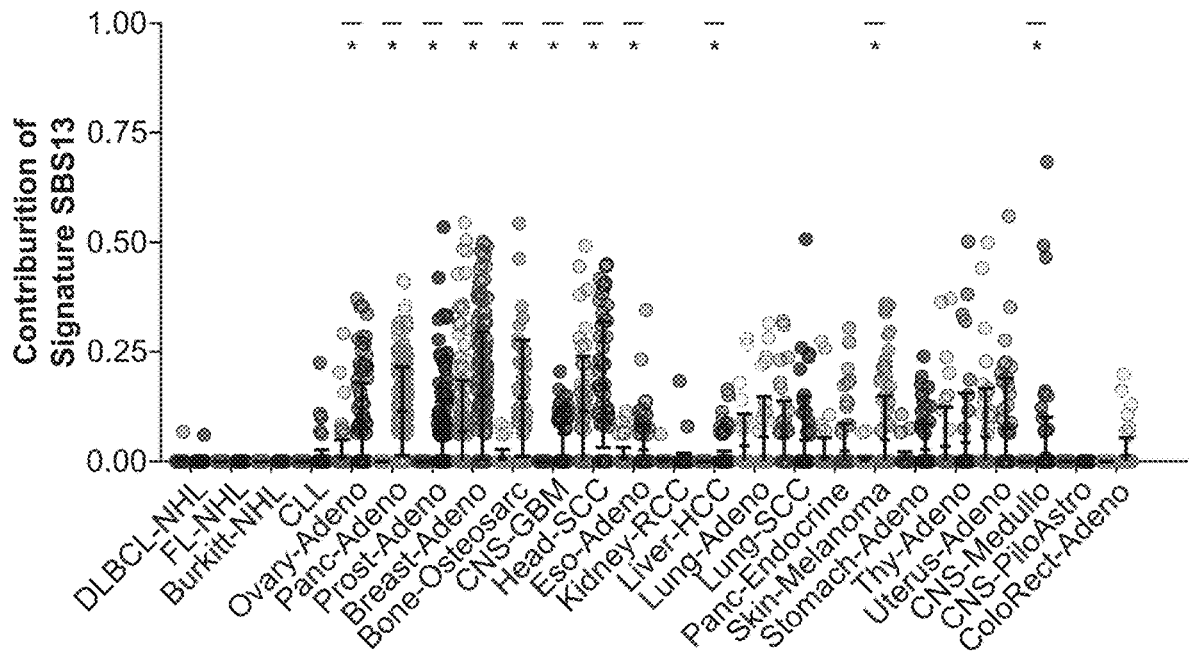
Figure 6R:
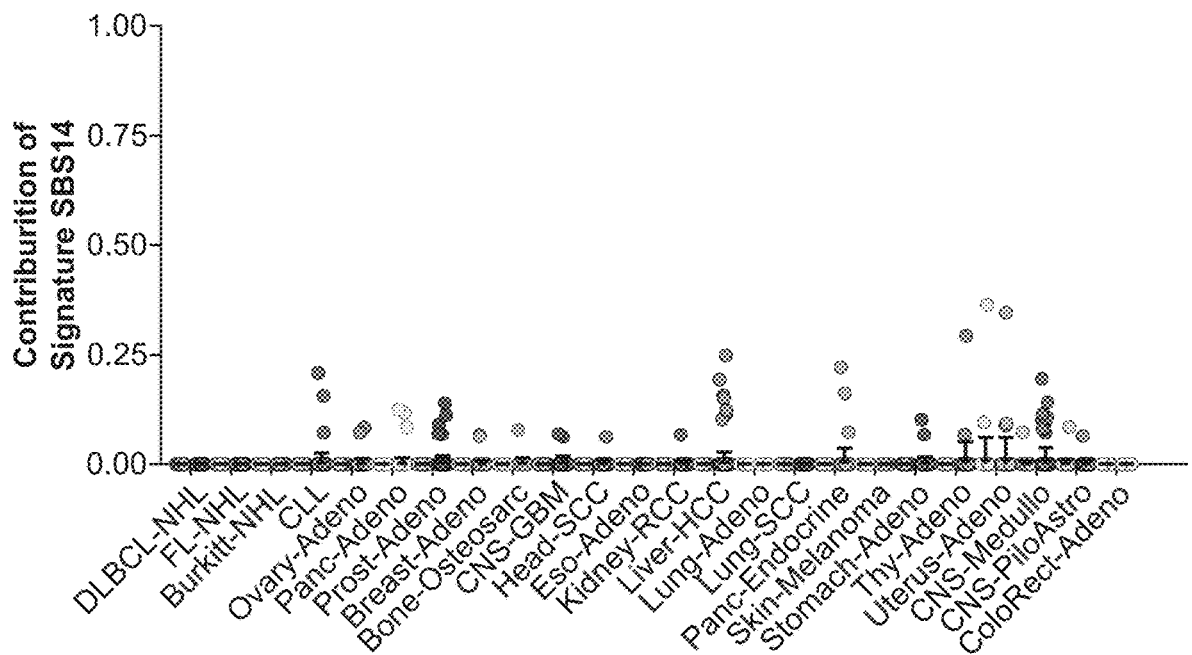
Figure 6S:
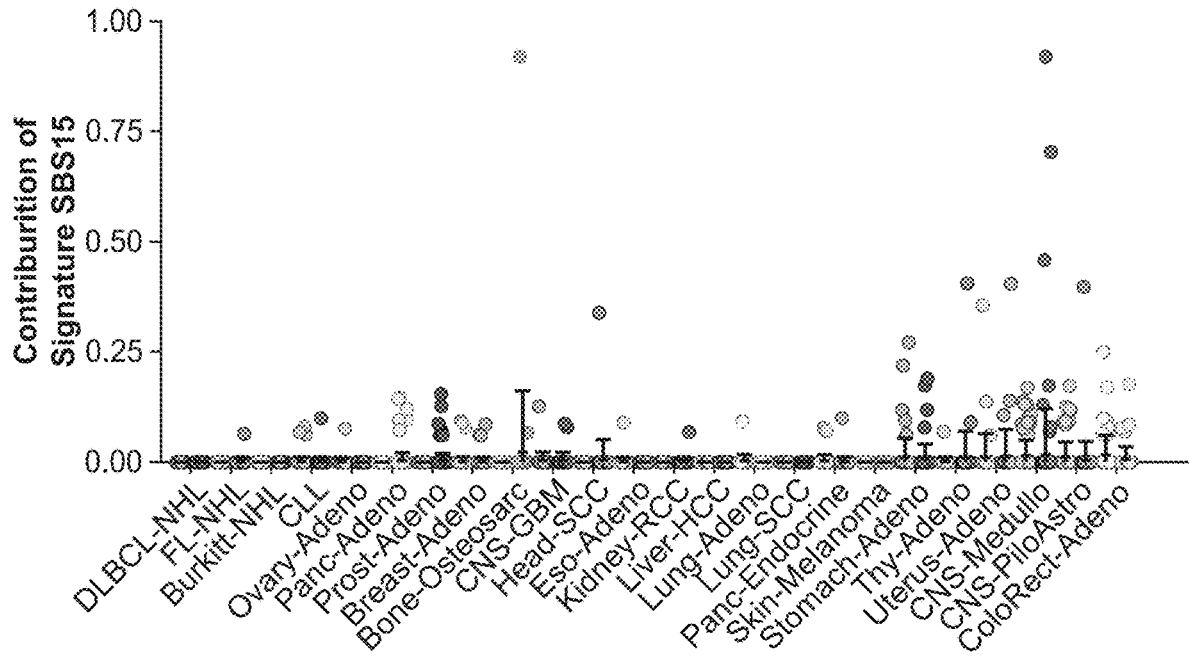
Figure 6T:
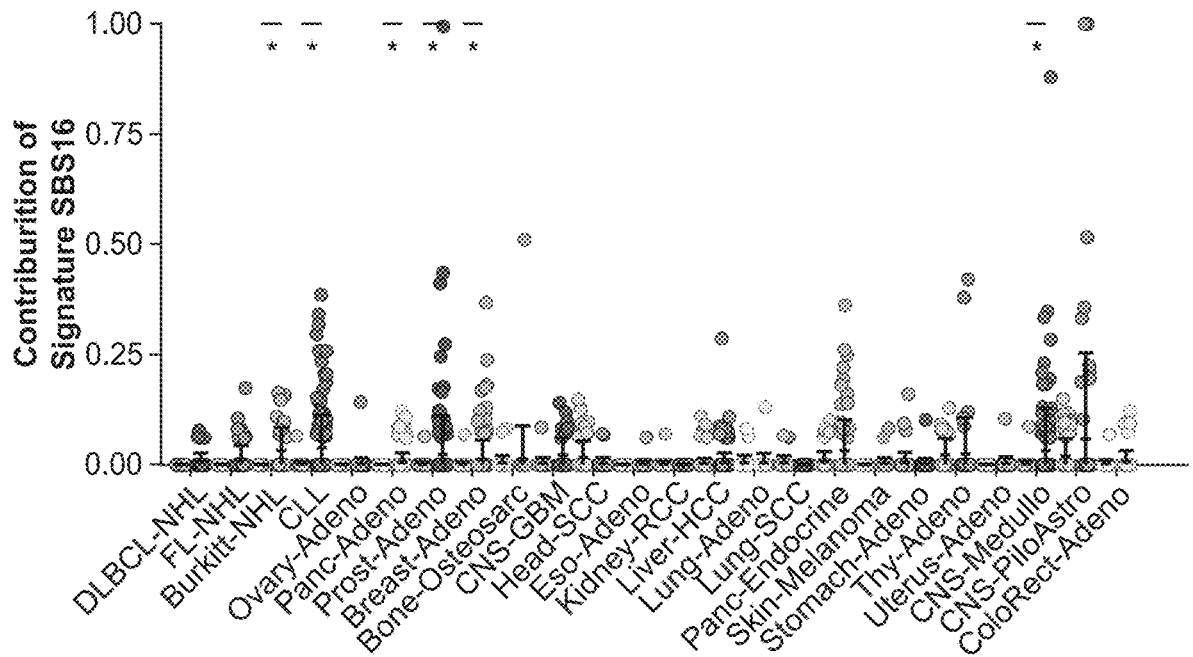
Figure 6U:
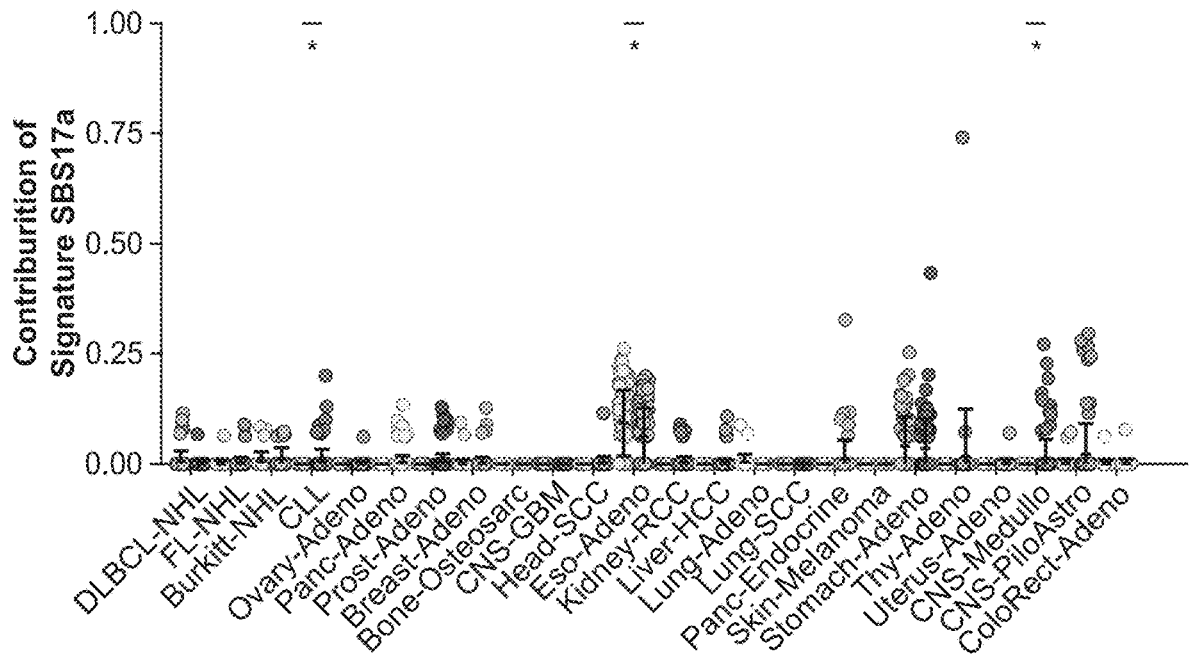
Figure 6V:
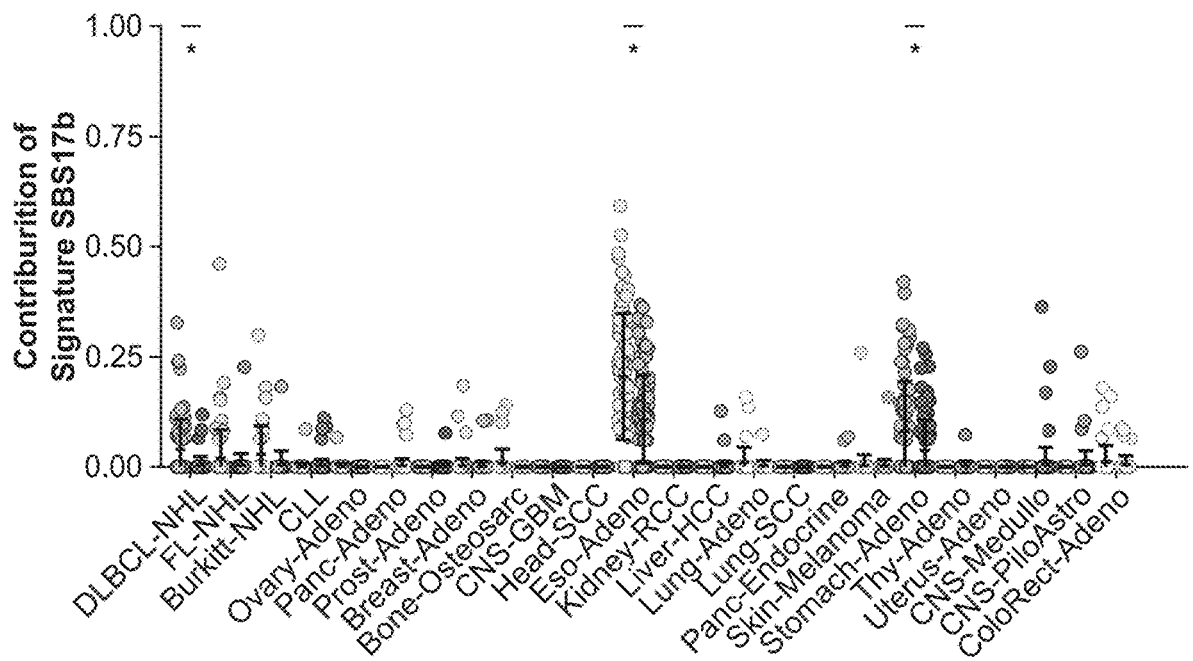
Figure 6W:
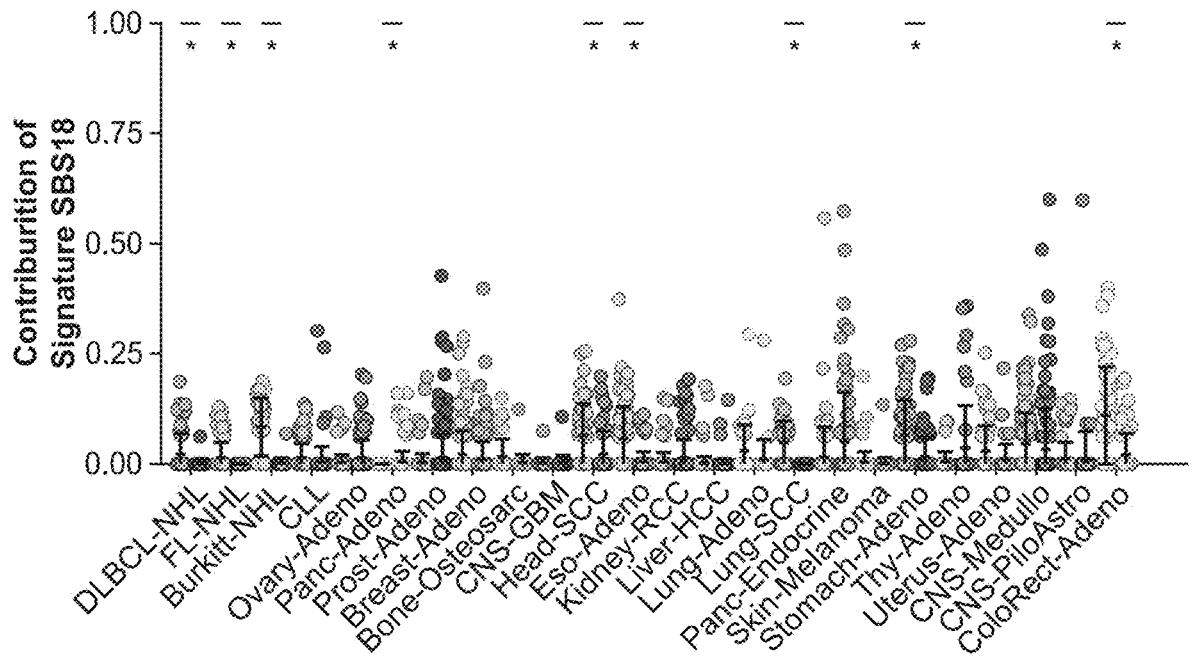
Figure 6X:
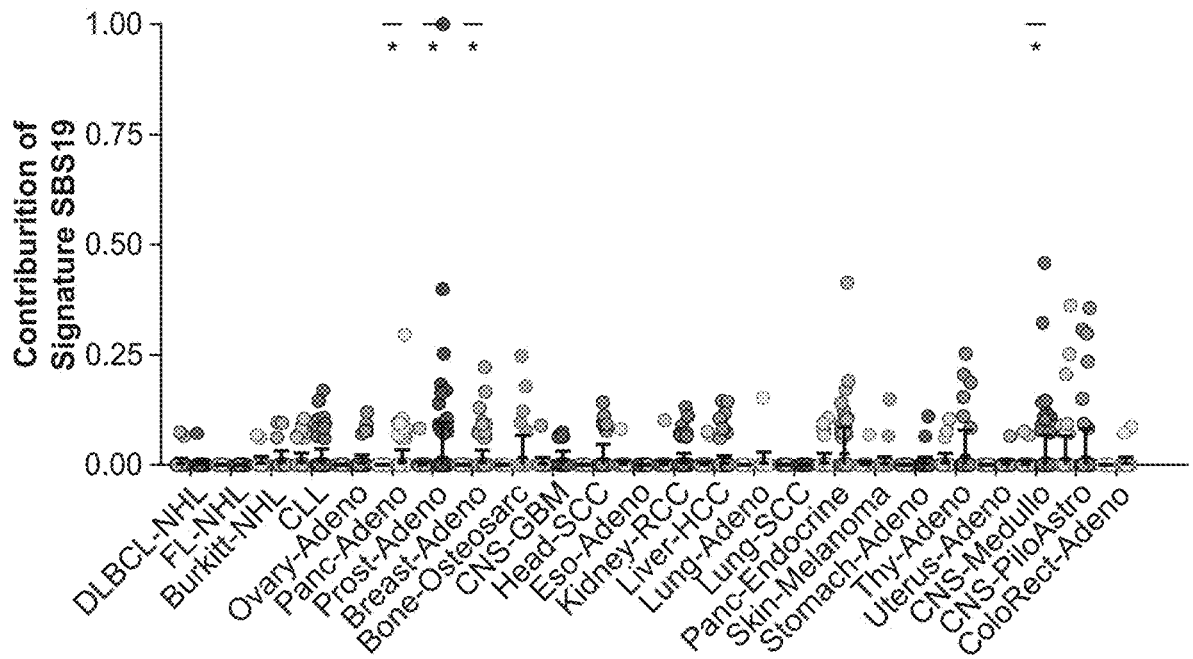
Figure 6Y:
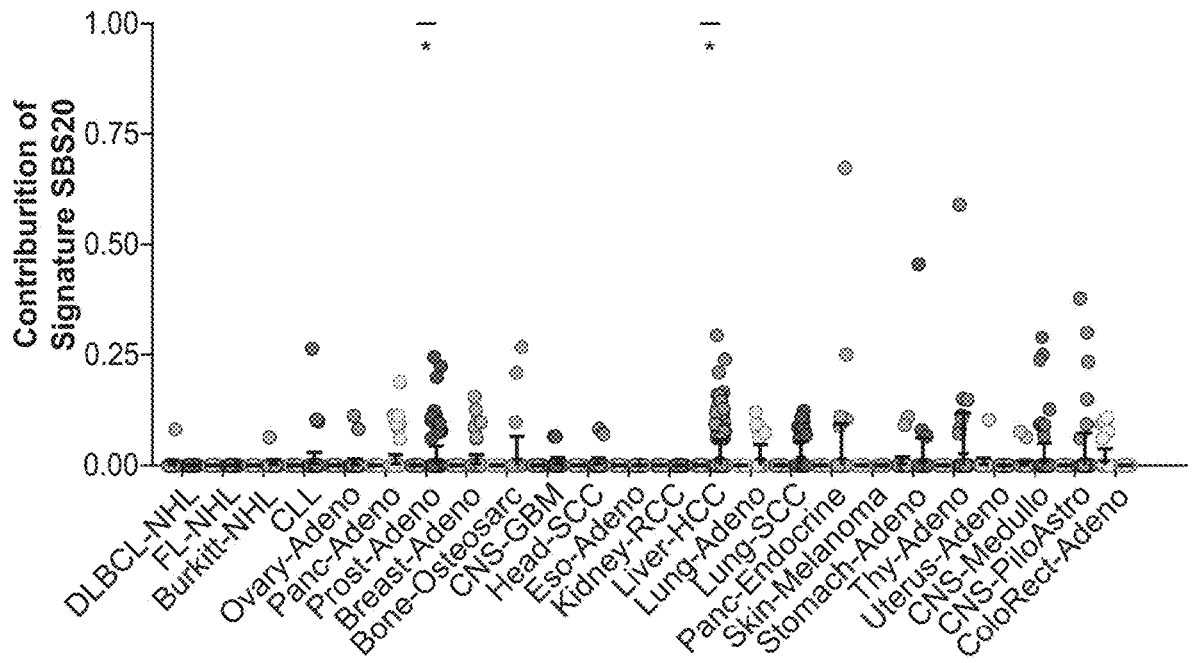
Figure 6Z:
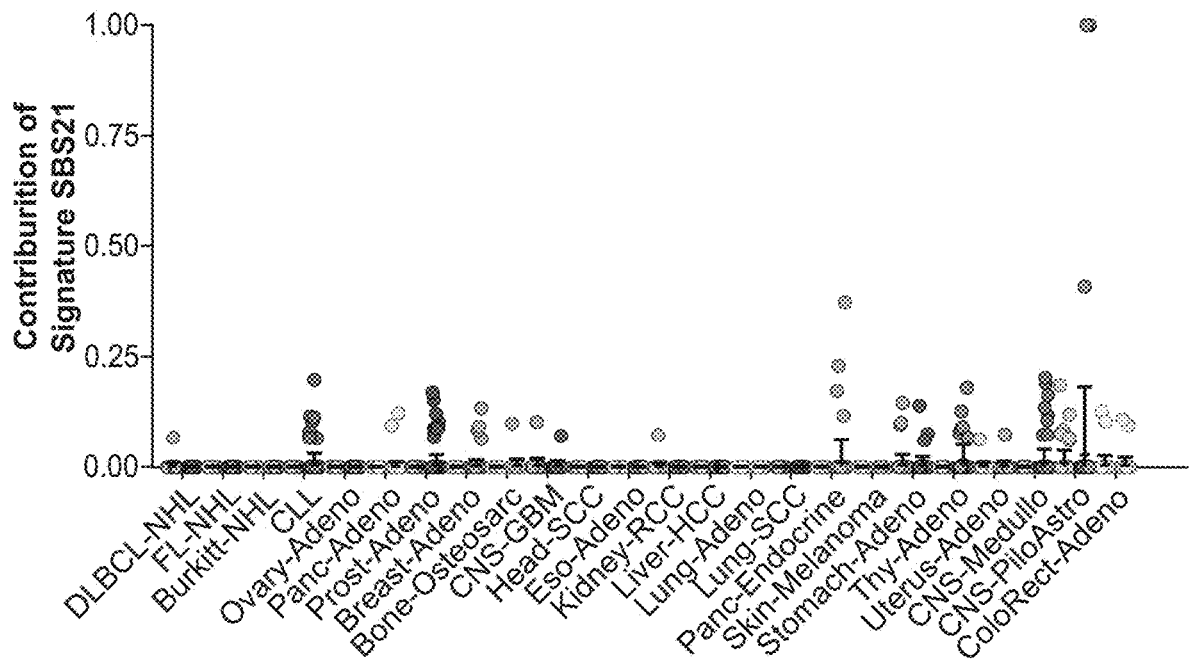
Figure 6A:
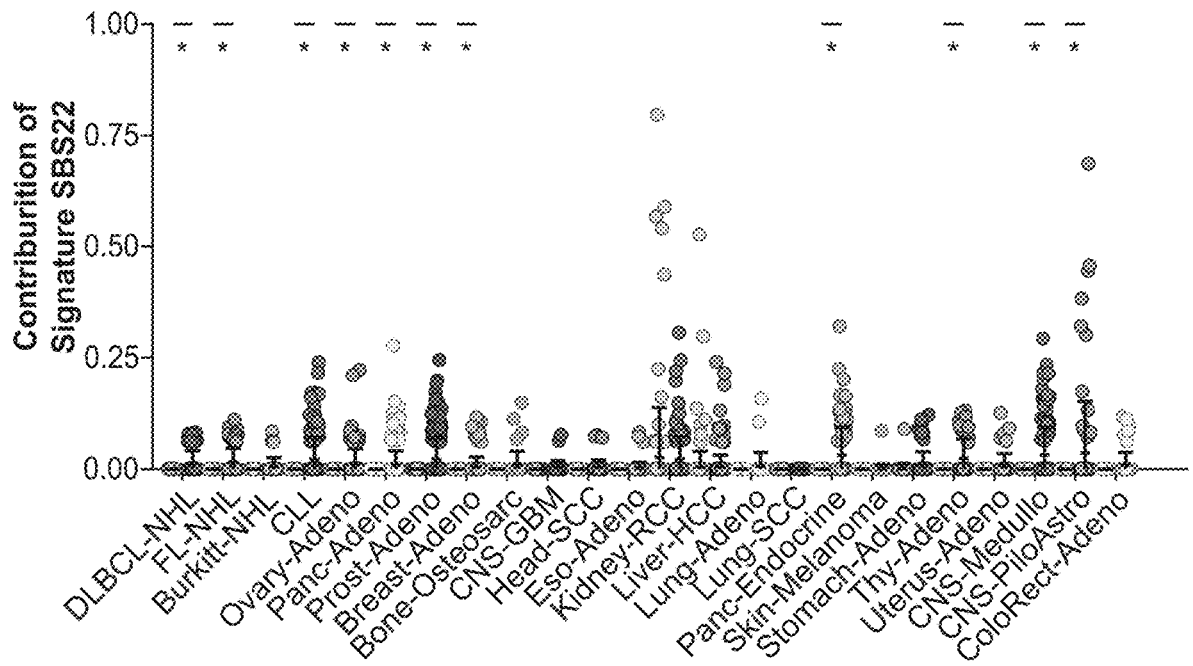
Figure 6B:
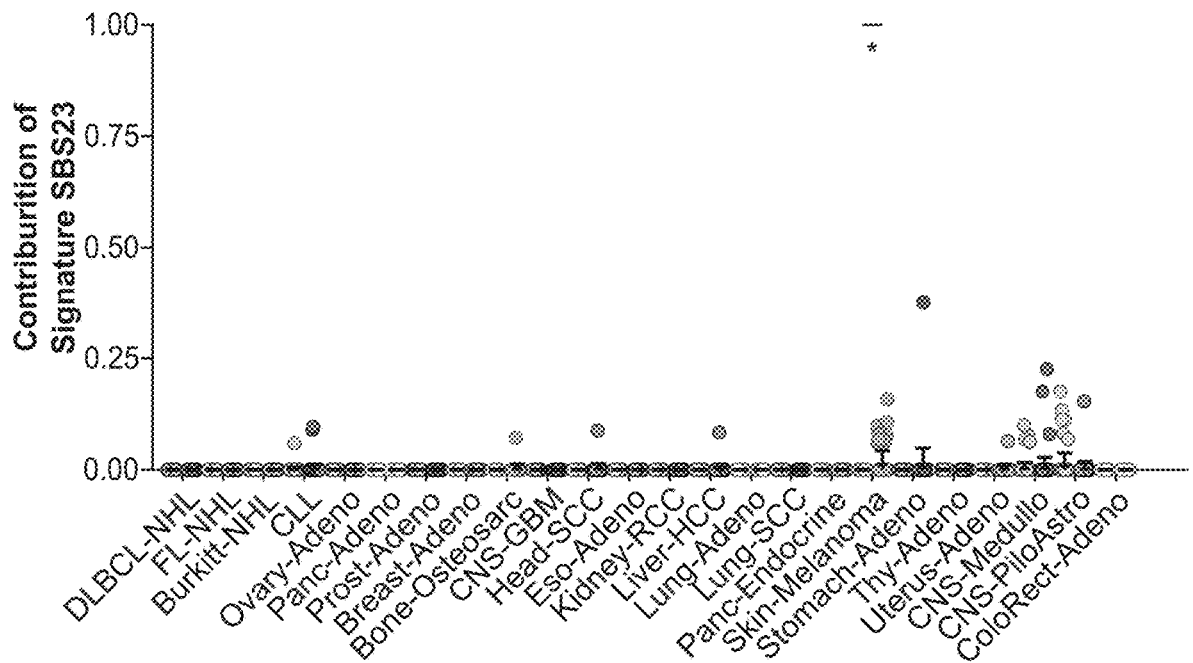
Figure 6C:
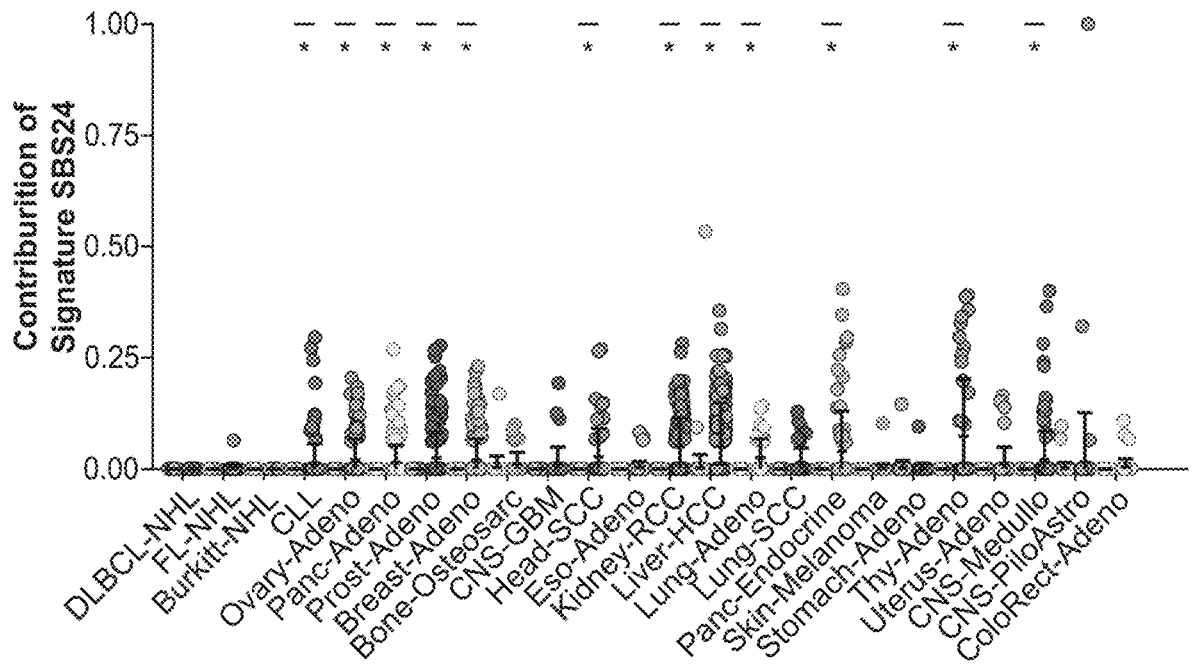
Figure 6D:
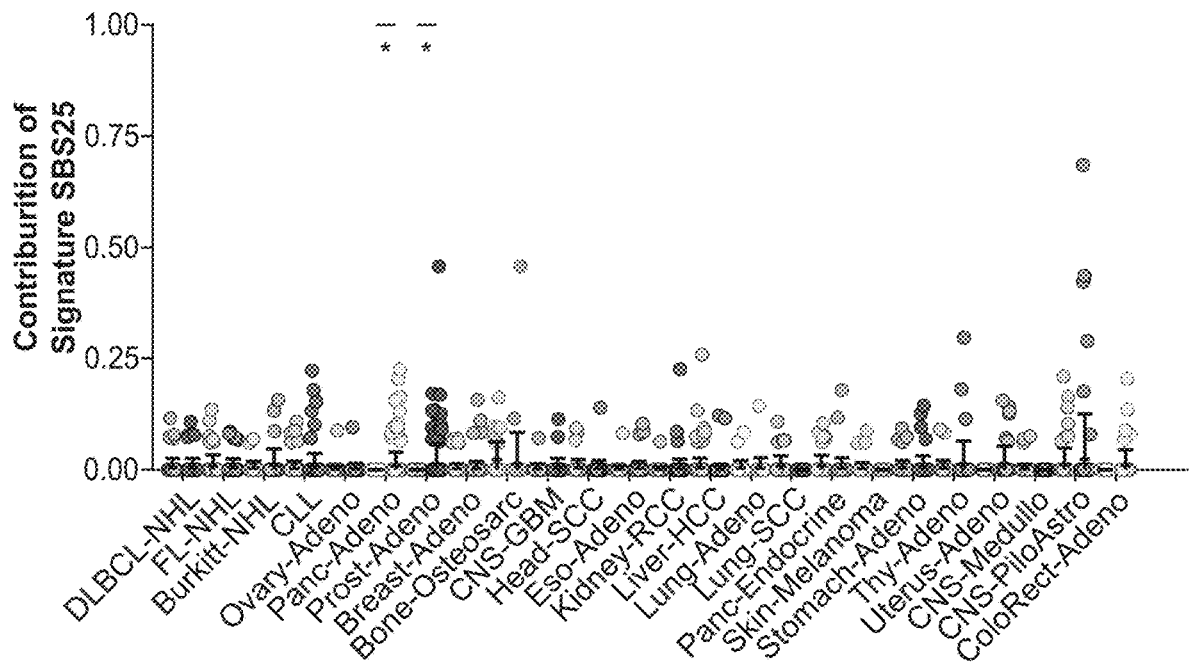
Figure 6E:
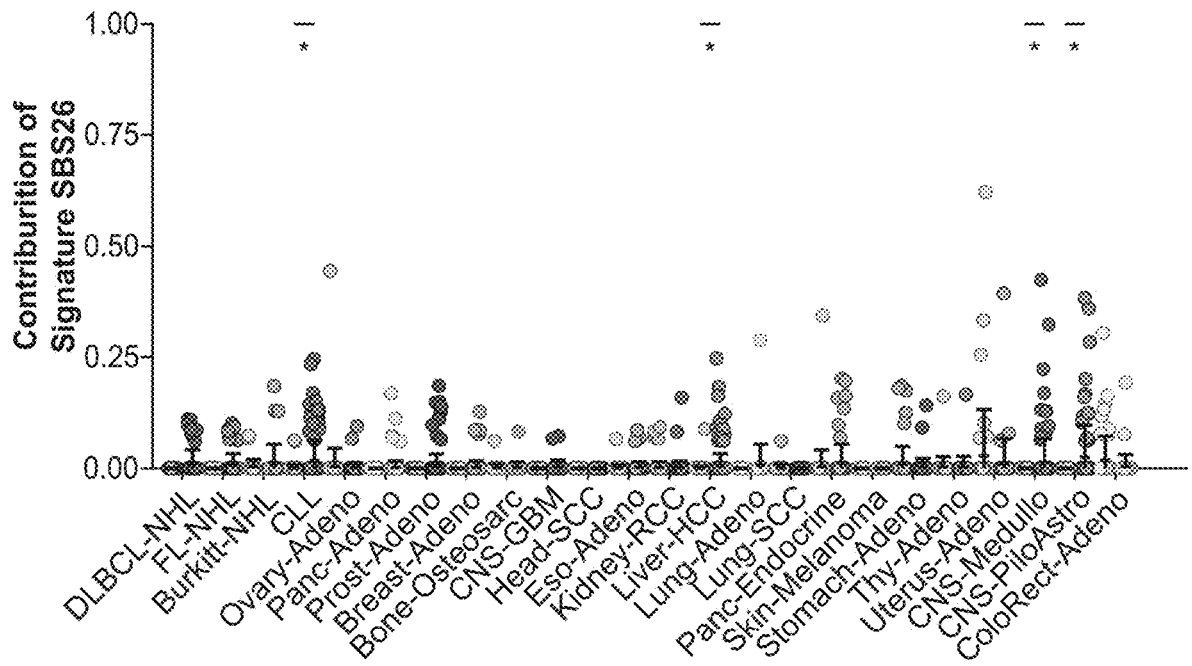
Figure 6F:
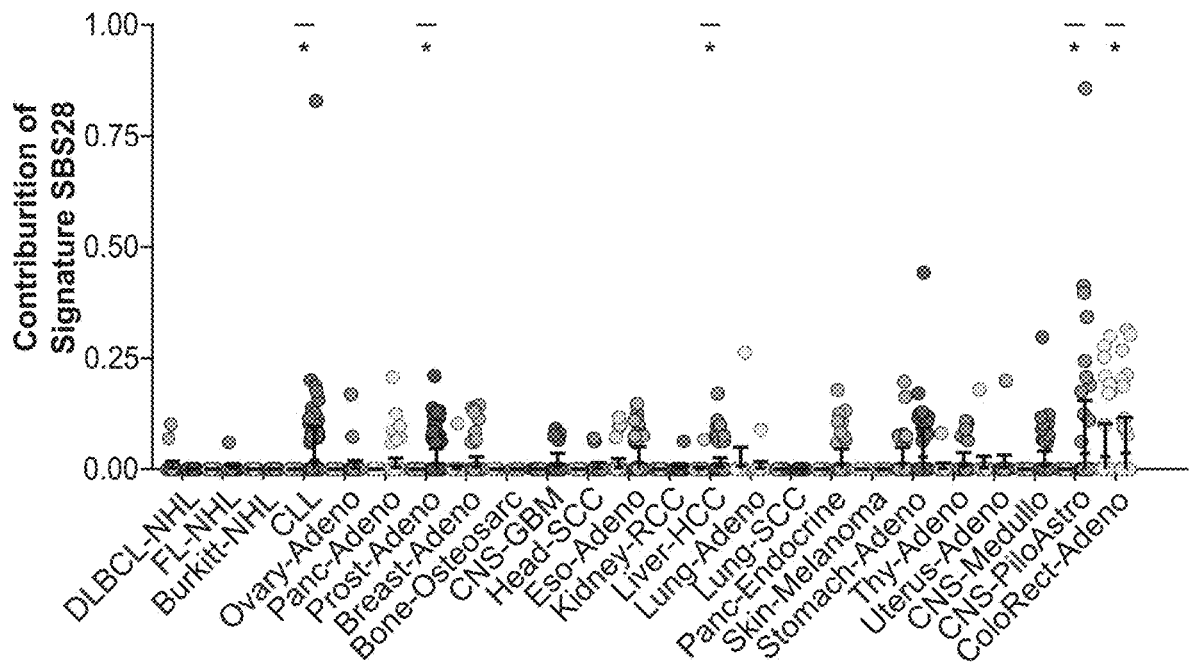
Figure 6G:
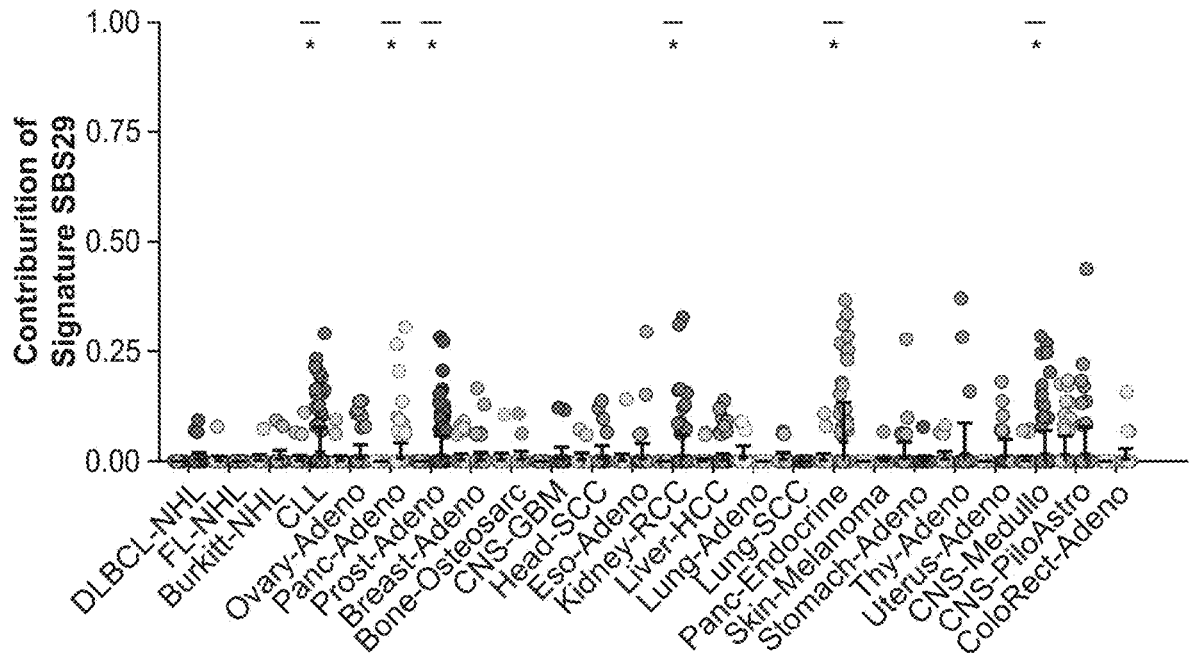
Figure 6H:
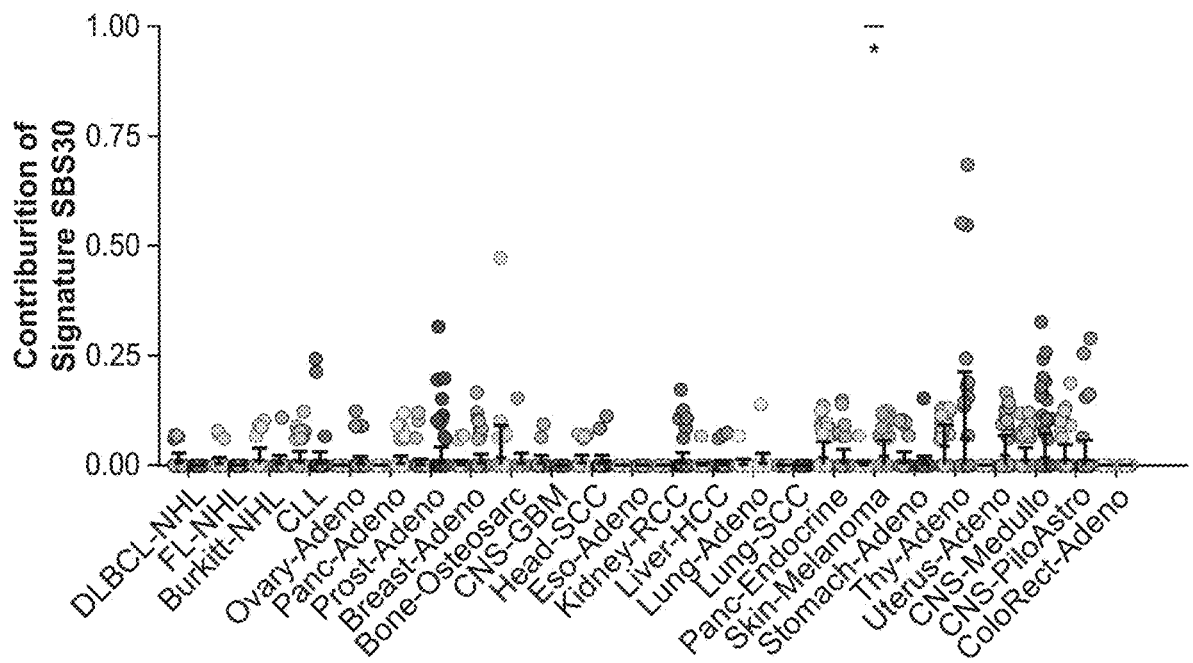
Figure 6I:
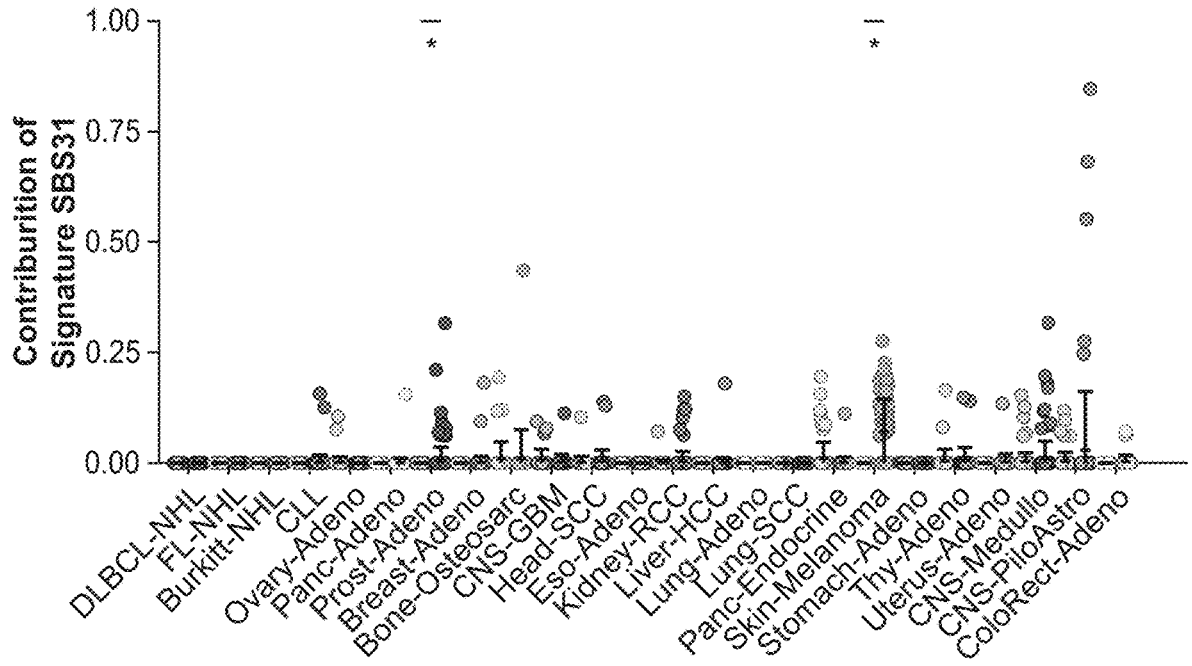
Figure 6J:
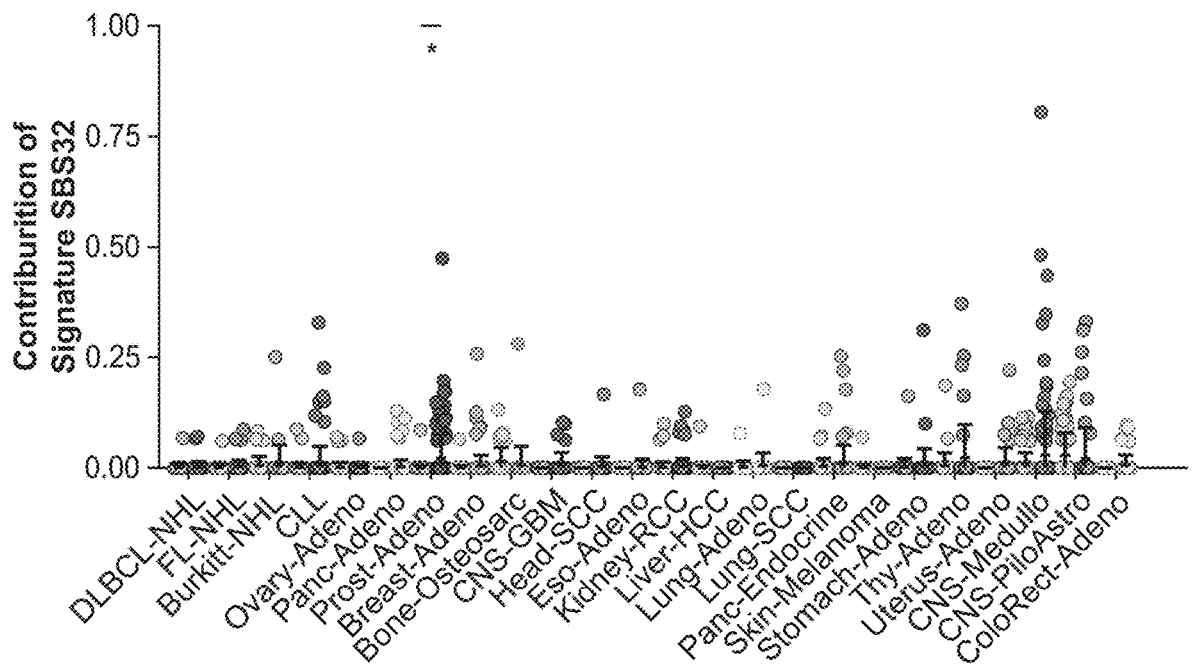
Figure 6K:
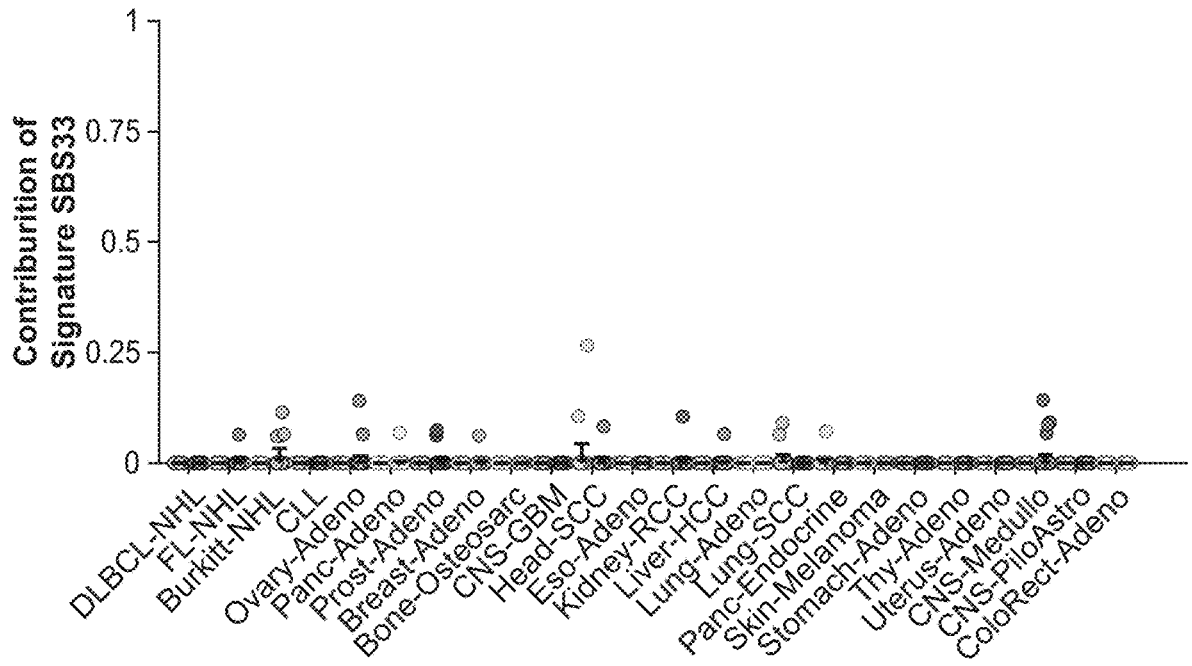
Figure 6L:
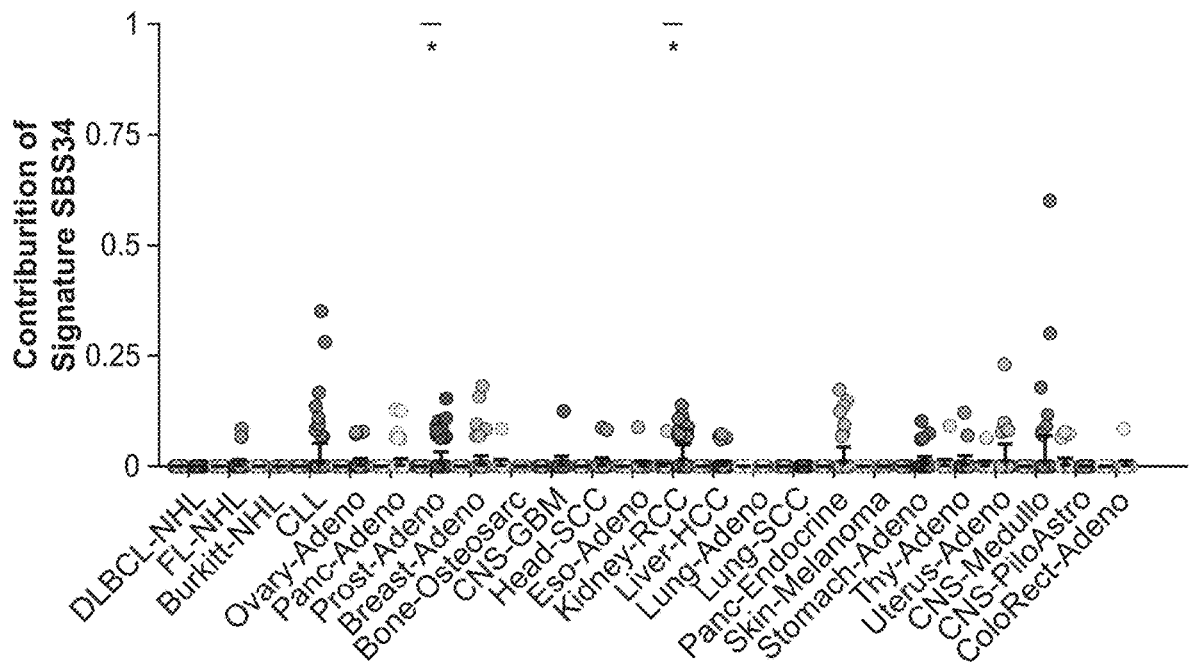
Figure 6M:
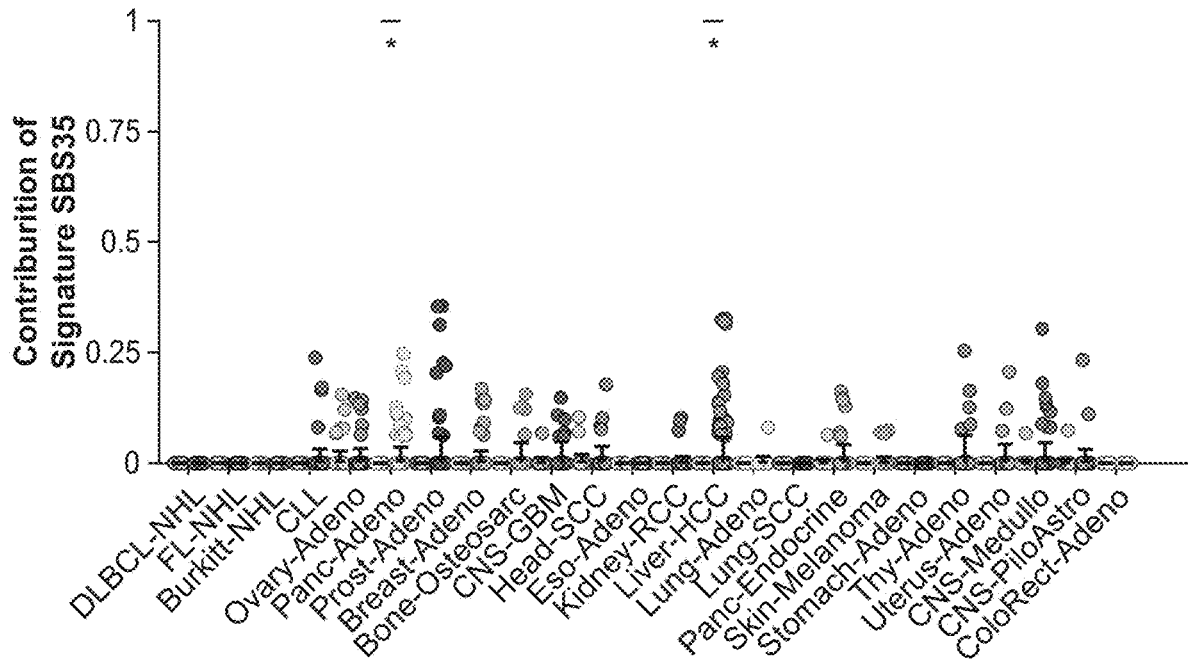
Figure 6N:
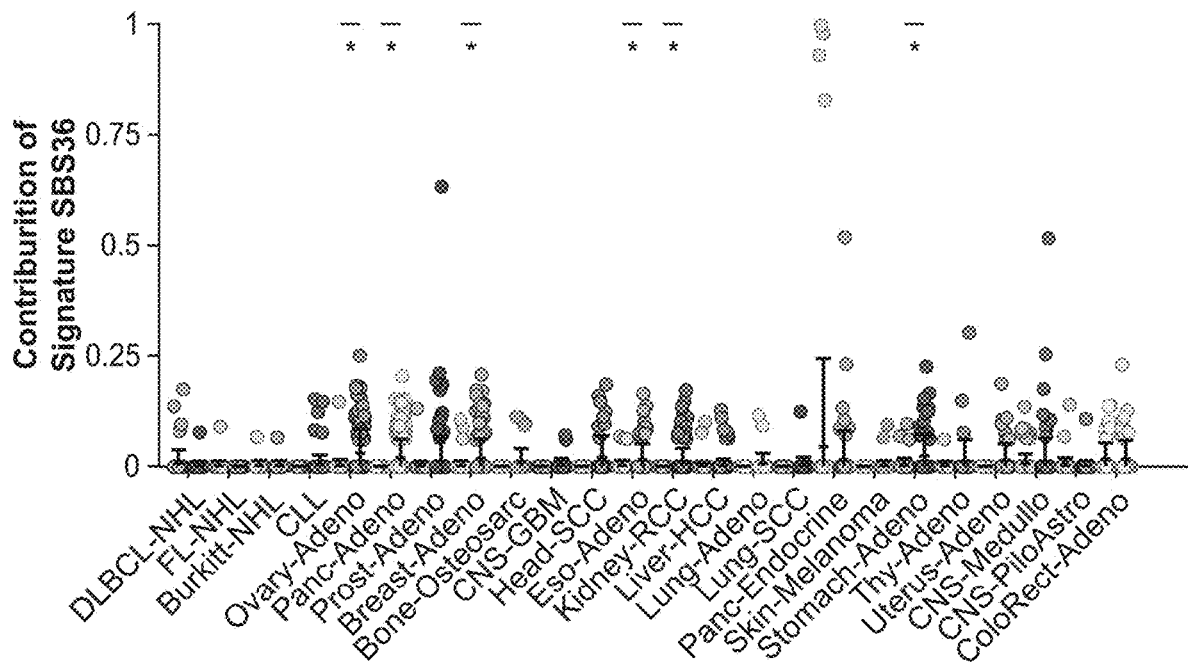
Figure 6O:
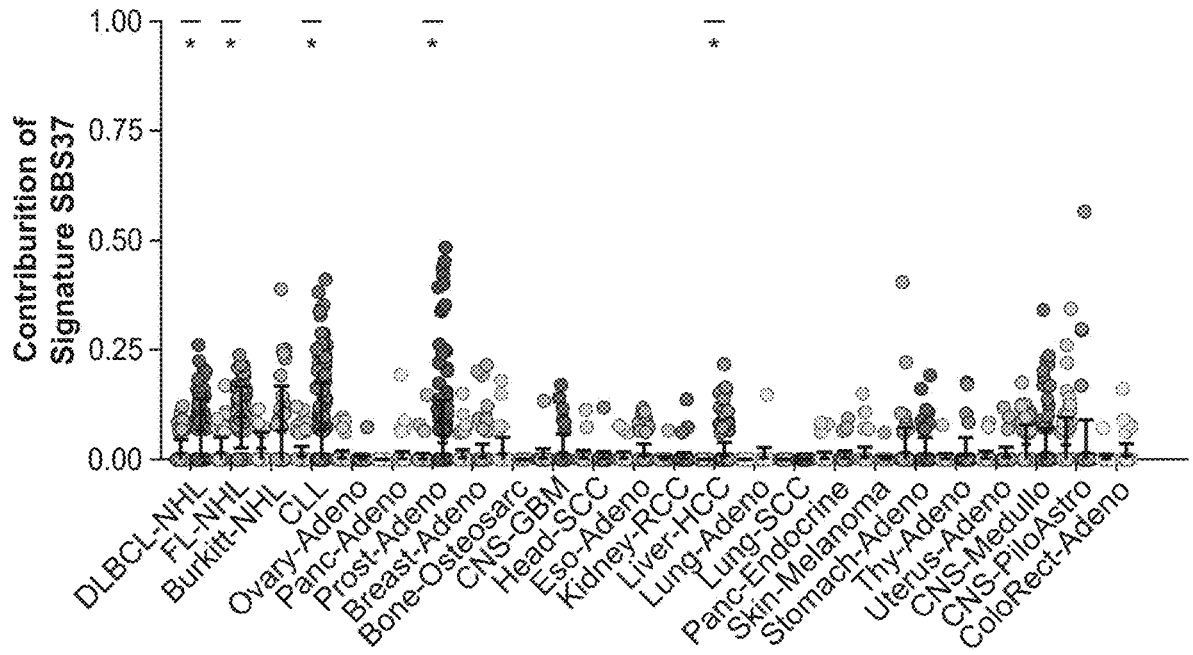
Figure 6P:
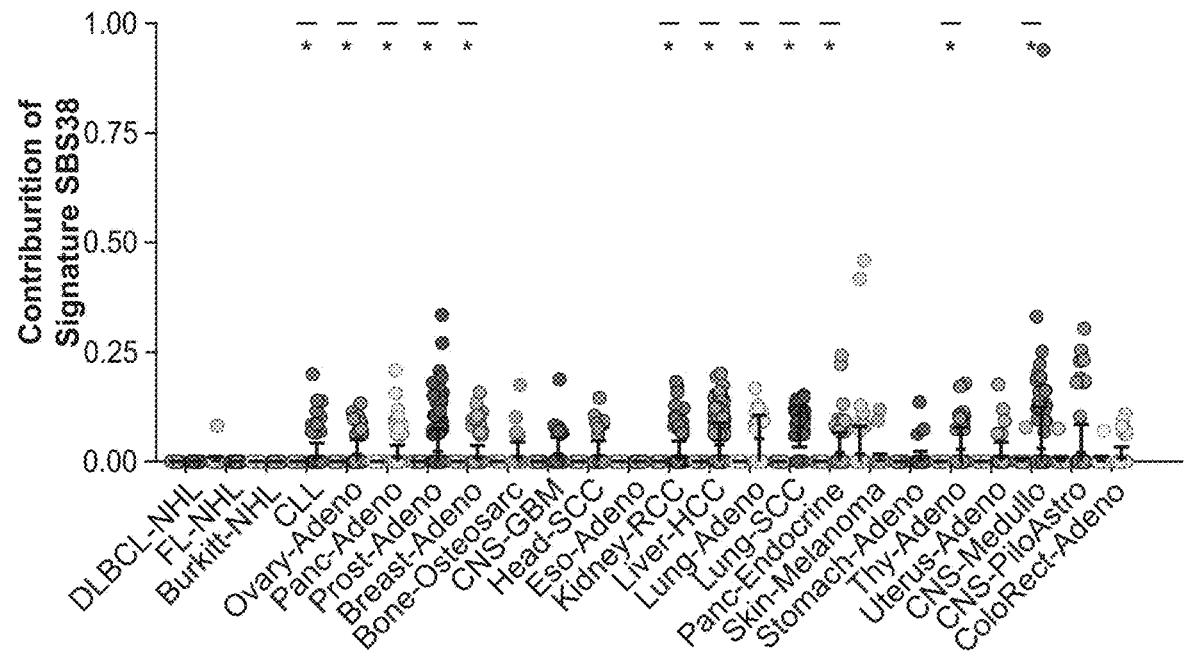
Figure 6Q:
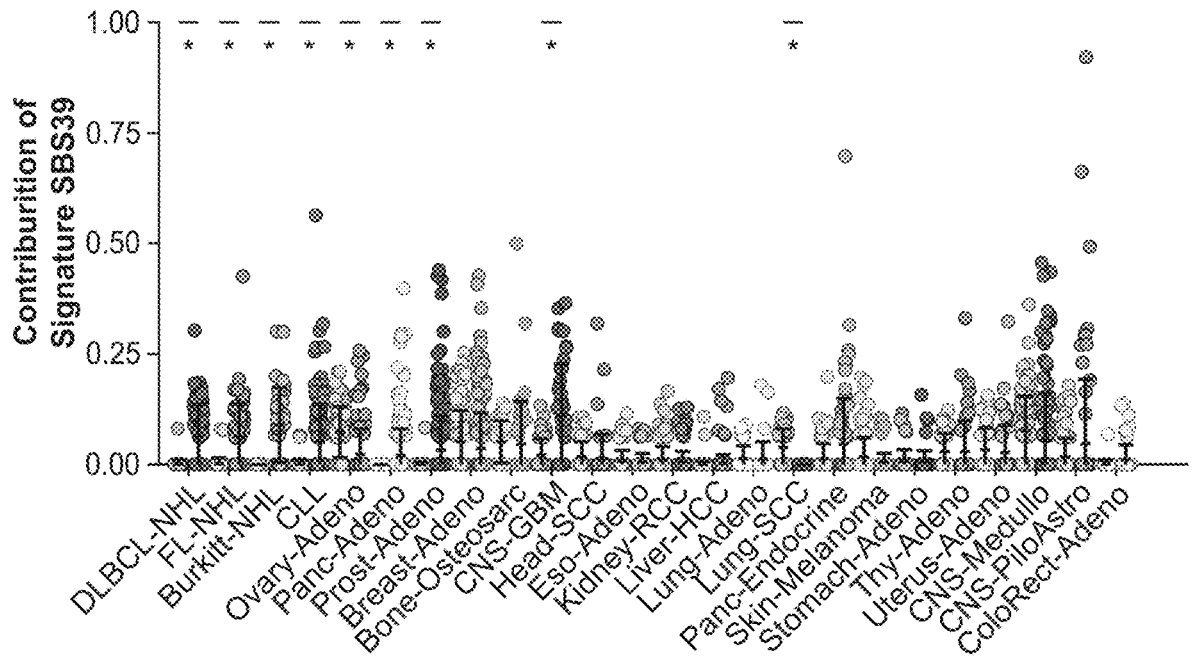
Figure 6R:
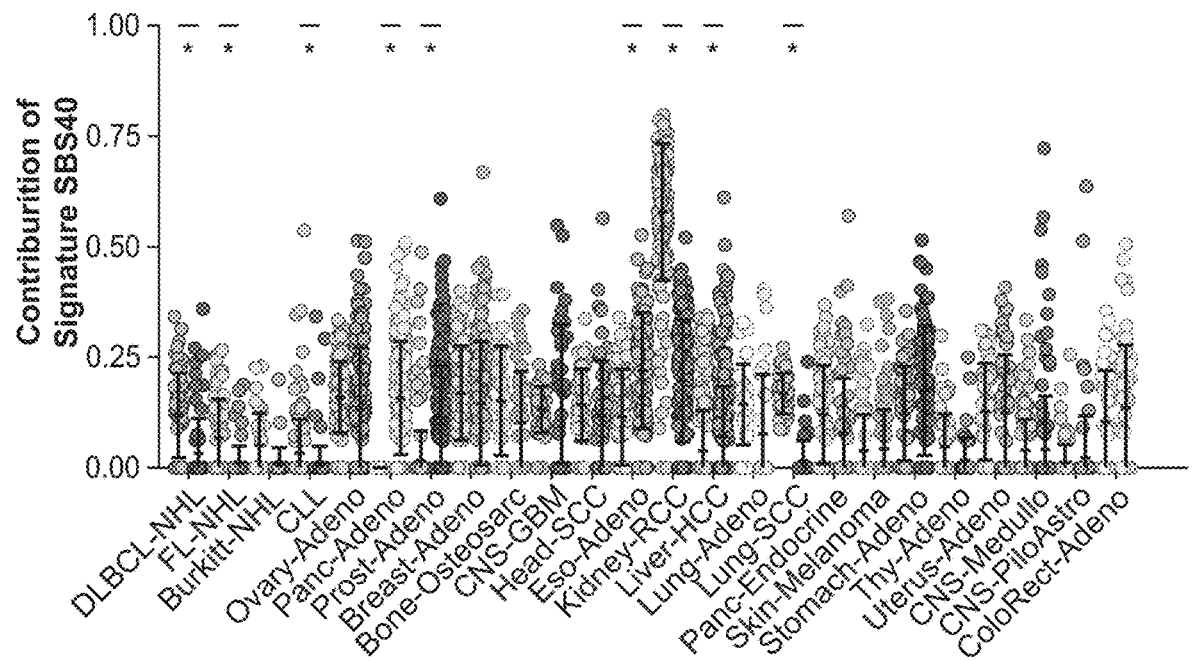
Figure 6S:
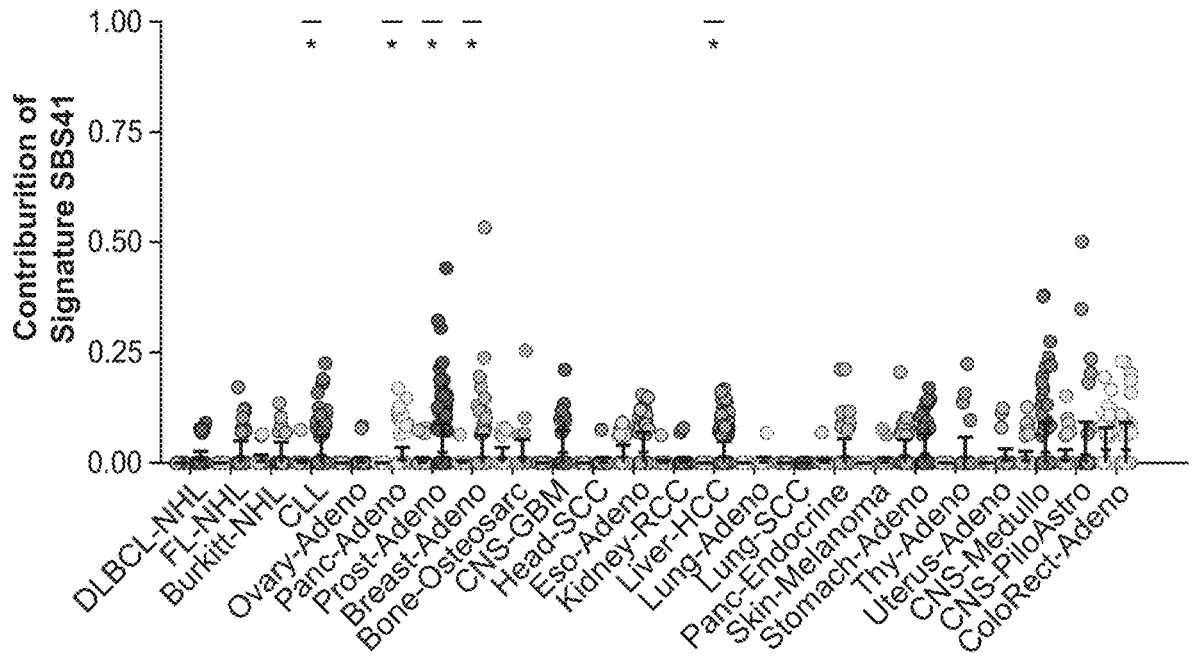
Figure 6T:
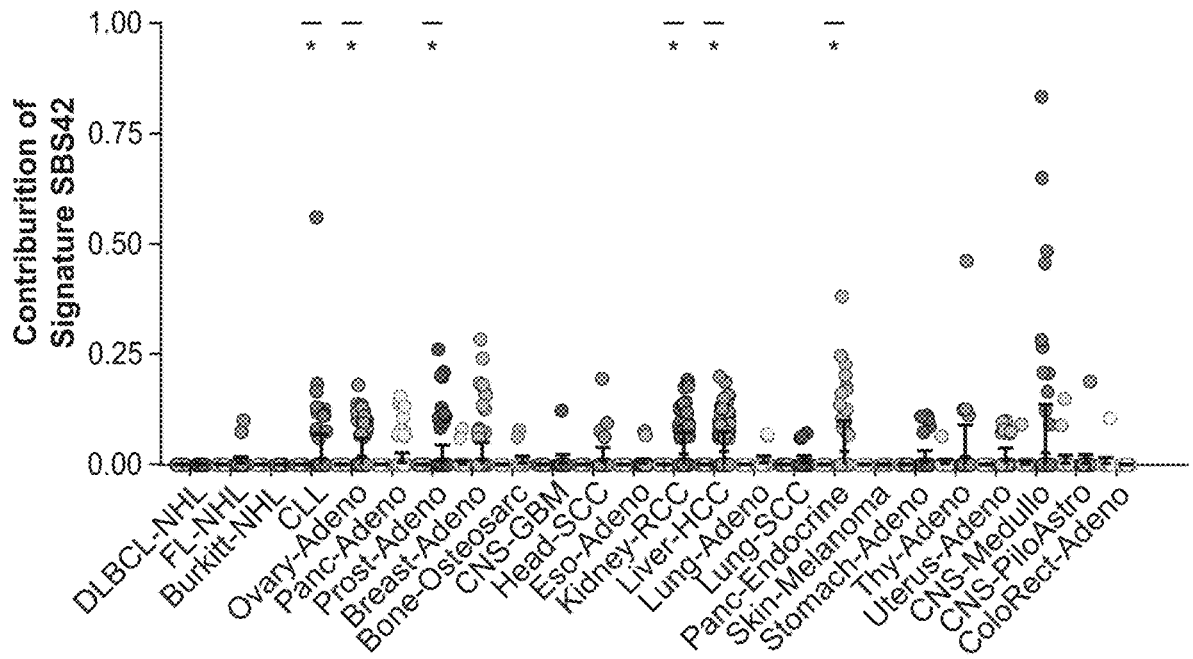
Figure 6U:
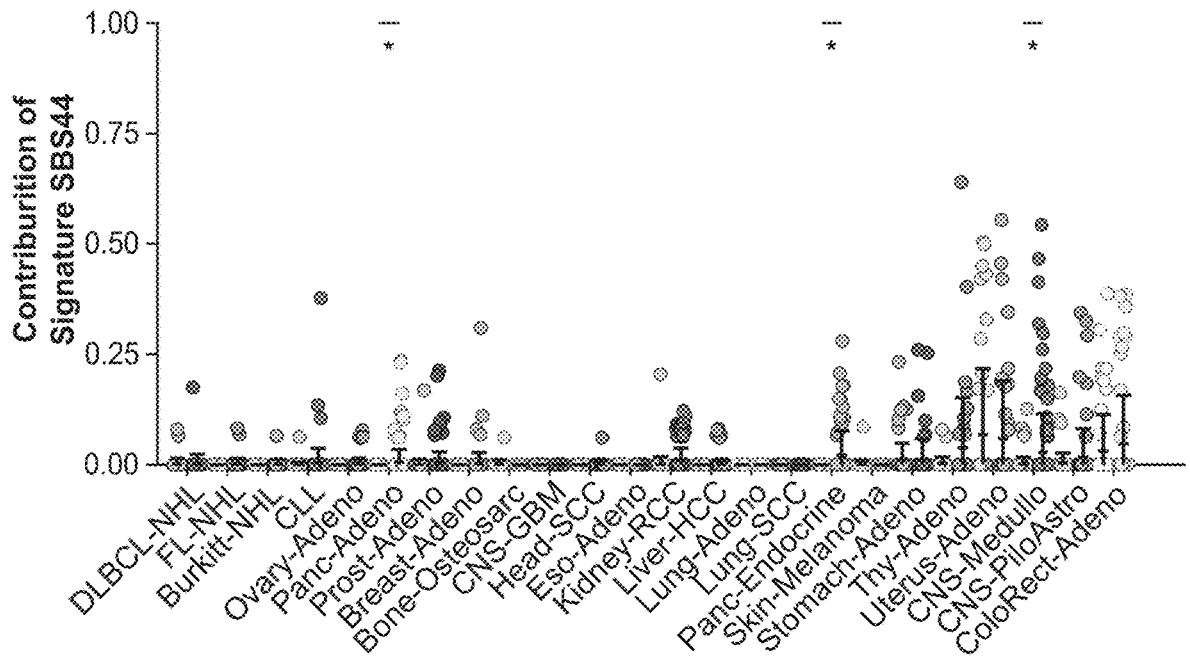
Figure 6V:
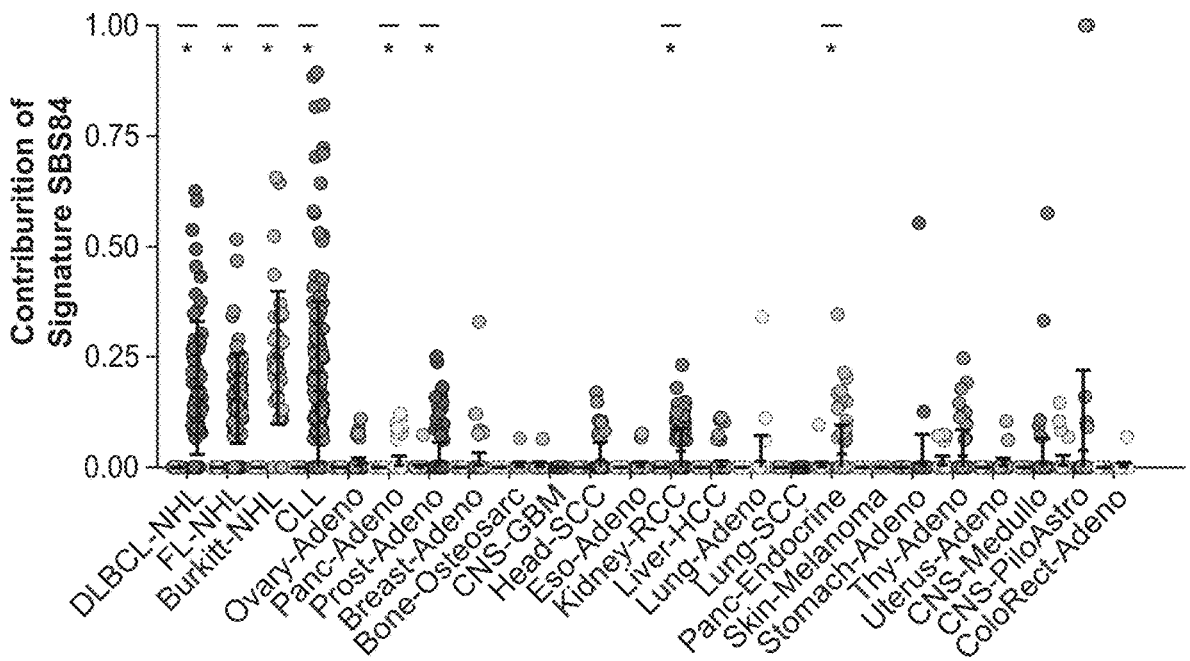
Figure 6W:
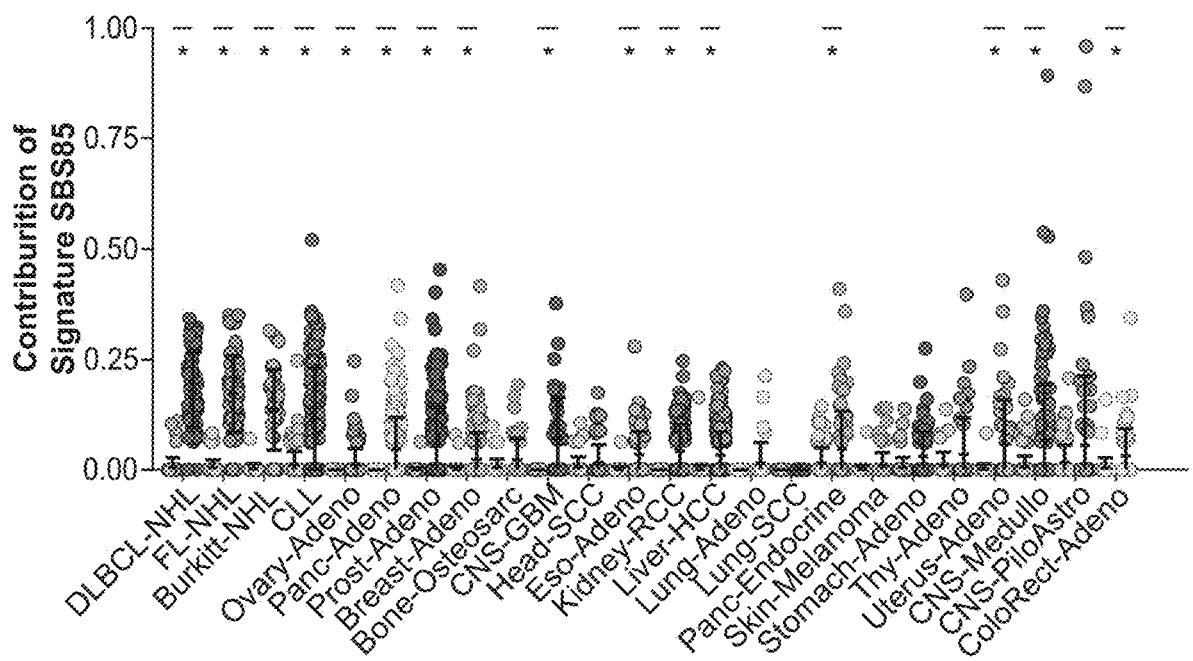

To investigate the origin of PVs, the single base substitution (SBS) mutational signatures contributing to SNVs occurring within 170 bp of another SNV, and SNVs occurring in isolation (e.g., not having another SNV within 170 bp) (Example 10) were compared. As expected, PVs were highly enriched in several mutational signatures associated with clustered mutations. Signatures of clustered mutations associated with activity of AID (SBS84 and SBS85) were significantly enriched in PVs from B-cell lymphomas and CLL, while signatures associated with activity of APOBEC3B (SBS2 and SBS13)—another mechanism of kataegis hypermutation—were significantly enriched in PVs from multiple solid cancer histologies, including ovarian, pancreatic, prostate, and breast adenocarcinomas (FIG. 1C and FIGS. 6A-6WW). Signatures of clustered mutations associated with activity of AID (SBS84 and SBS85) were enriched in PVs found in lymphomas and CLL, while signatures associated with activity of APOBEC3B (SBS2 and SBS13) were significantly enriched in breast cancer (FIG. 1C and FIGS. 6A-6WW). PVs from multiple tumor types were also associated with SBS4, a signature associated with tobacco use. Furthermore, among PVs across multiple tumor histologies, it was observed that novel enrichments in several other signatures without clearly associated mechanisms (e.g., SBS24, SBS37, SBS38, and SBS39). In contrast, aging-associated mutational signatures such as SBS1 and SBS5 were significantly enriched in isolated SNVs.

Example 3: PVs Occur in Stereotyped Genomic Regions in Lymphoid Cancers

Figure 7:
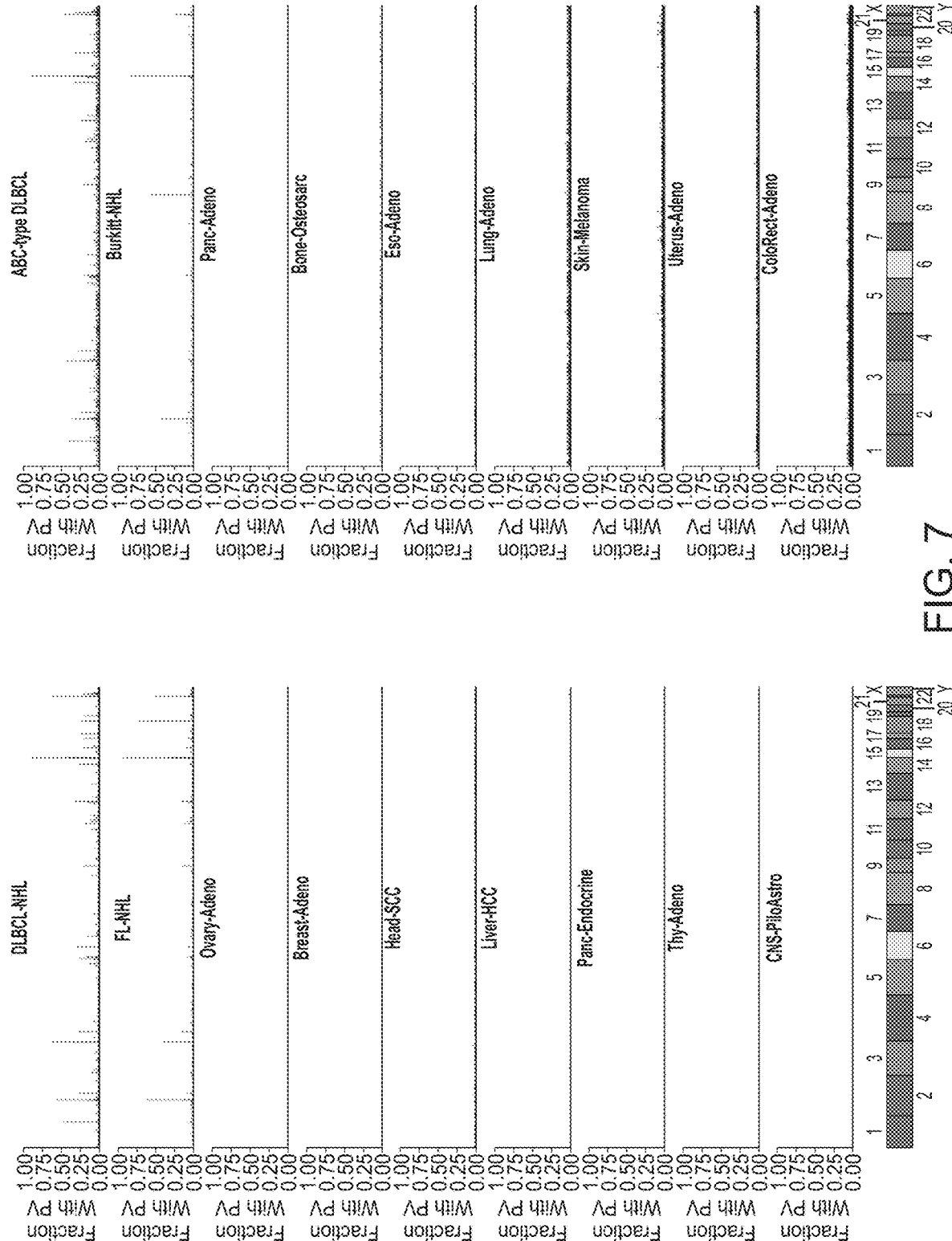
FIG. 7 illustrates distribution of PVs in stereotyped regions across the genome. Bar plots show the distribution of PVs occurring in stereotyped regions across the genome of multiple cancer types. In this plot, the genome was divided into 1000 bp bins, and the fraction of samples of a given histology with a PV in each 1000 bp bin was calculated. Only bins that have at least a 2 percent recurrence frequency in any cancer subtype are shown. Histologies shown are as in FIG. 1E; activated B-cell (ABC) and germinal center B-cell (GCB) subtypes of DLBCL are also shown.
Figure 7:
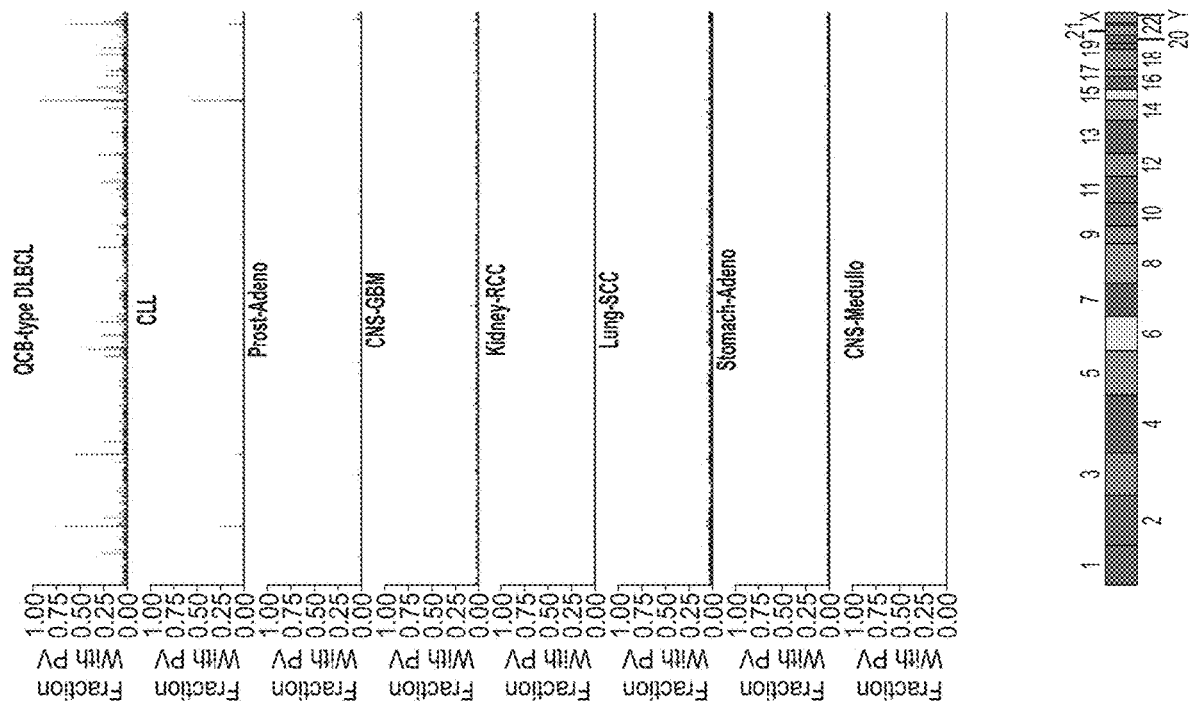

To assess the genomic distribution of putative PVs, these events were first binned into 1-kb regions to visualize their frequency across tumor types. It was observed that a strikingly stereotyped distribution of PVs in individual lymphoid neoplasms (e.g., DLBCL, FL, Burkitt lymphoma (BL), and chronic lymphocytic leukemia (CLL); FIG. 1D and FIG. 7). In contrast, non-lymphoid cancers generally did not exhibit substantial recurrence of clustered PVs in stereotyped regions. This lack of stereotype in the position of PVs was true even when considering melanomas and lung cancers, diseases with frequent PVs.

Figure 8A:
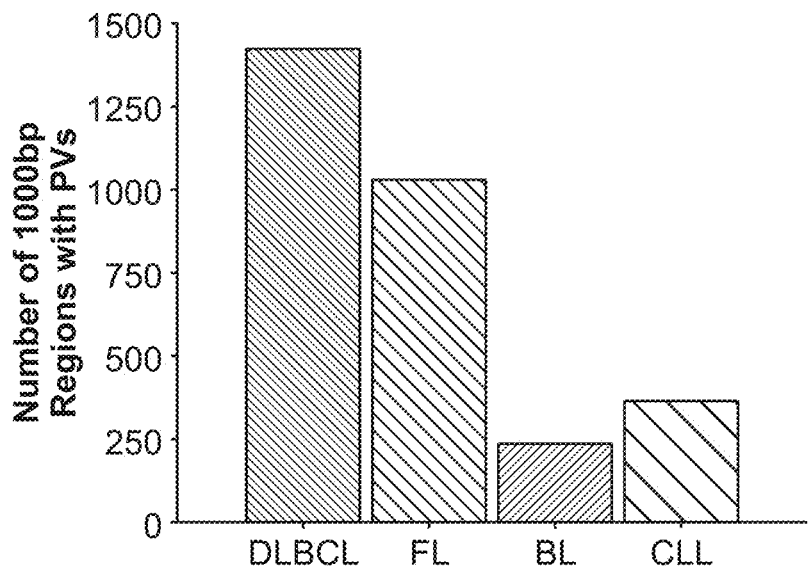
FIGS. 8A-8E illustrate quantity and genomic location of PVs from WGS in lymphoid malignancies.

Notably, the majority of hypermutated regions were shared between all three lymphoma subtypes, with the highest densities seen in known targets of aSHM including BCL2, BCL6, and MYC, as well as the immunoglobulin (Ig) loci encoding the heavy and light chains IGH, IGK, and IGL (Table 2). Strikingly, certain regions within Ig loci were densely mutated in nearly all lymphoma patients as well as in patients with CLL (FIG. 1D). Among lymphoma subtypes, DLBCL tumors harbored the most 1-kb regions recurrently containing PVs (FIG. 8A), consistent with the highest number of recurrently mutated genes being observed in this tumor type. In total, 1639 unique 1-kb regions recurrently containing PVs in B-lymphoid malignancies were identified. Among these lymphoma-associated 1-kb regions, nearly one-third fell into genomic areas previously associated with physiological or aberrant SHM in B-cells. Specifically, 19% (315/1639) were located in Ig regions, while 13% (218/1639) were in portions of 68 previously identified targets of aSHM (Table 2). While most PVs fell into noncoding regions of the genome, additional recurrently affected loci not previously described as targets of aSHM, including XBP1, LPP, and AICDA, among others, were also identified.

Figure 8B:
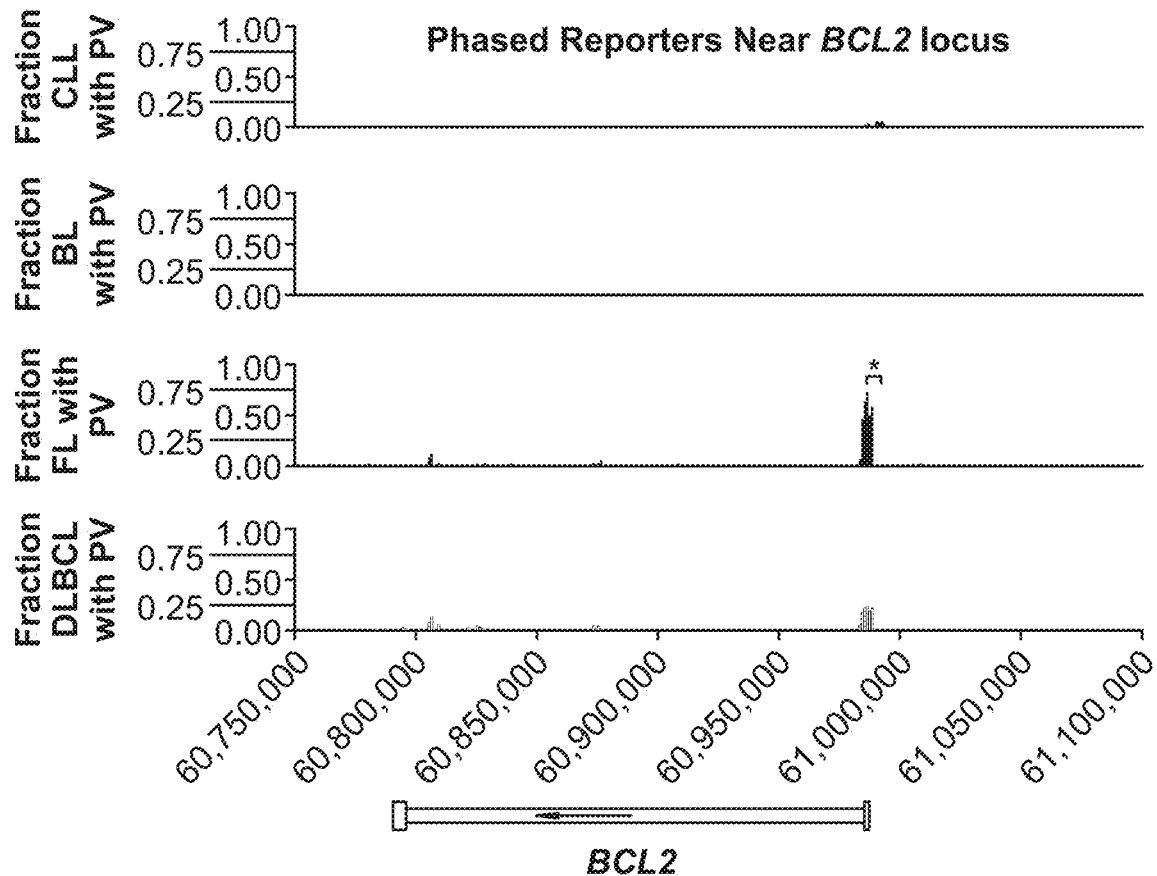
Figure 8C:
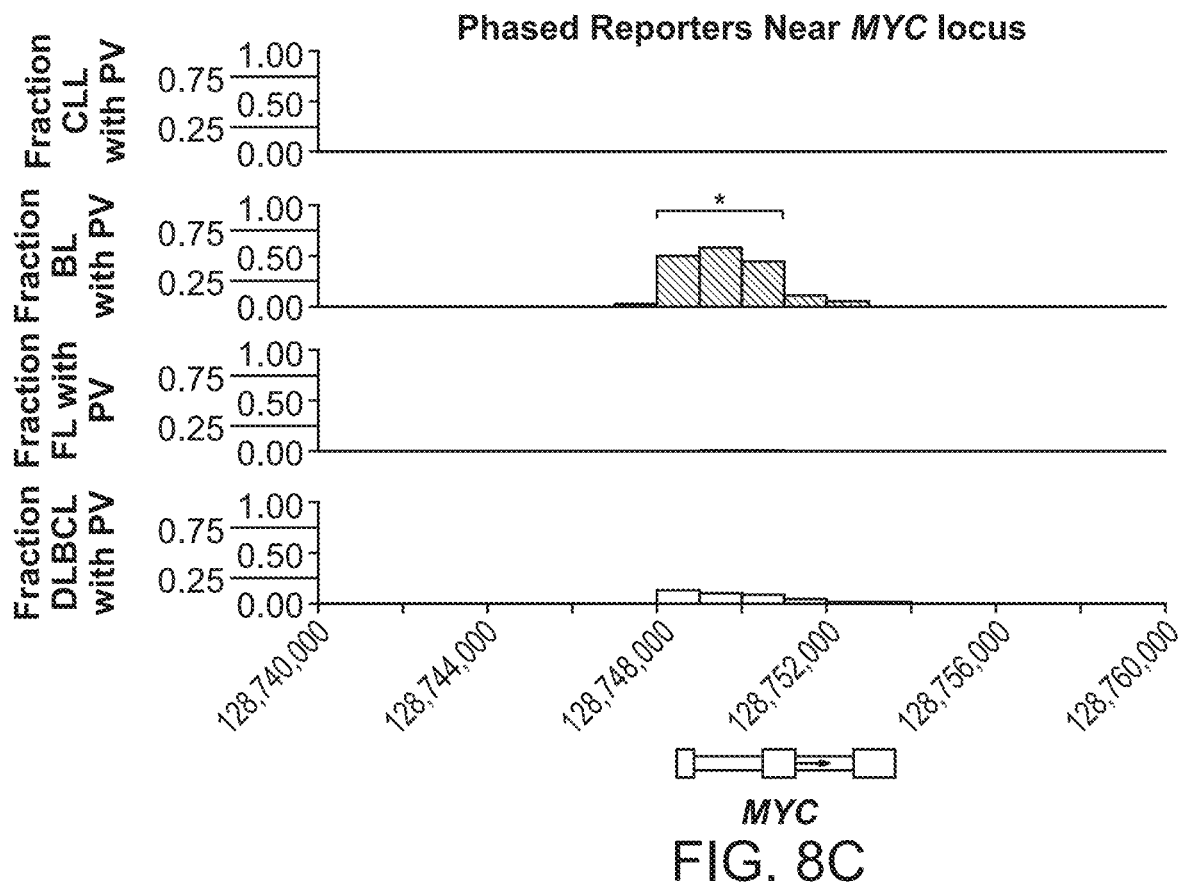
Figure 8D:
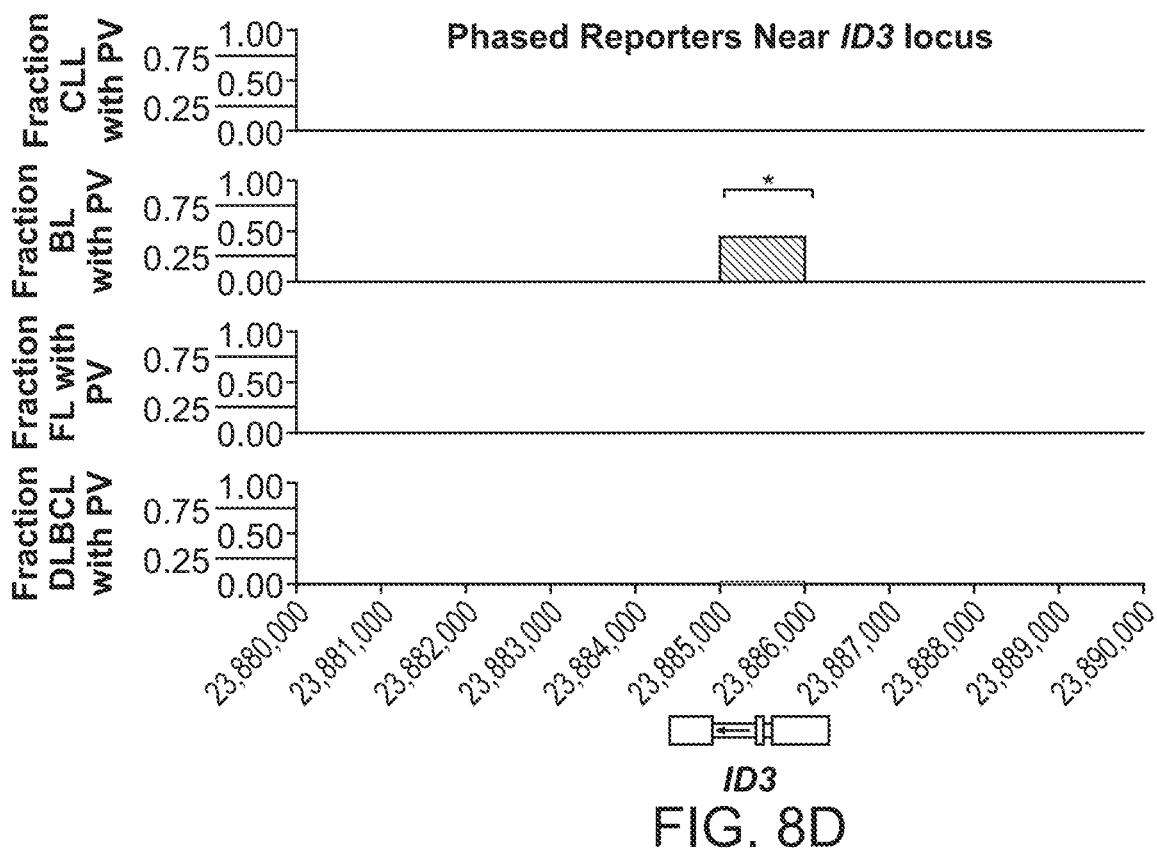
Figure 8E:
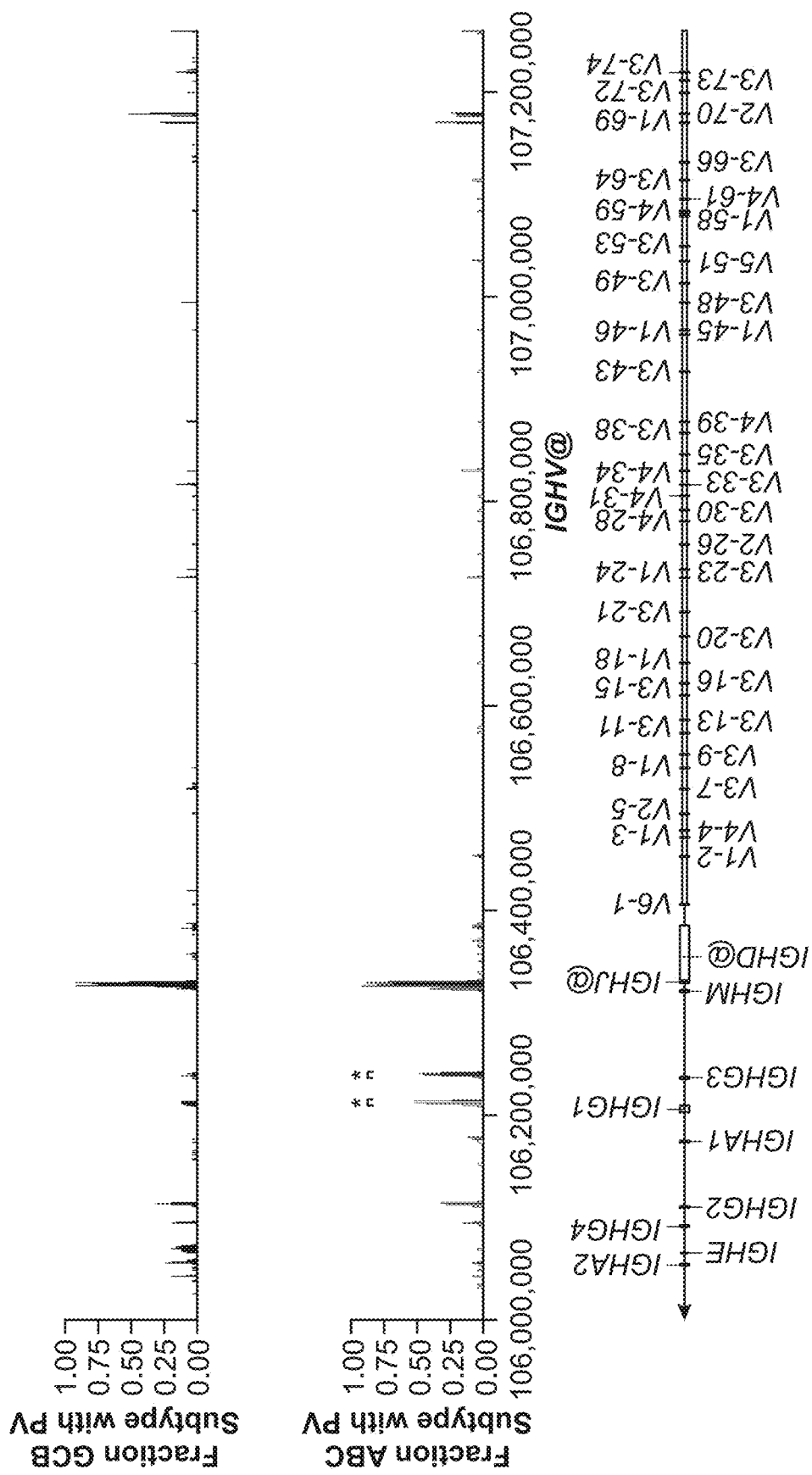

The distribution of PVs within each lymphoid malignancy correlated with oncogenic features associated with the distinct pathophysiology of the corresponding disease. For example, cases of FL—where more than 90% of tumors harbor oncogenic BCL2 fusions—were significantly more likely to contain phased variants in BCL2 than other lymphoid malignancies (FIG. 1D and FIG. 8B). Similarly, significantly more Burkitt lymphomas (BL) harbored PVs in MYC and ID3, two driver genes strongly associated with the BL pathogenesis, than other lymphoid malignancies (FIG. 1D and FIGS. 8C-8D). DLBCL molecular subtypes associated with distinct cell-of-origin also demonstrated distinct distributions of PVs (Table 2). Specifically, while germinal center B-cell like (GCB) and activated B-cell like (ABC) DLBCLs harbored similar frequencies of PVs overall (median 798 vs 516, P=0.37), significant enrichment for PVs in the telomeric IGH class-switch regions (Sγ1, and Sγ3) in ABC-DLBCLs, consistent with previous reports41 (FIG. 8E), was found. Conversely, GCB-DLBCLs harbored more phased haplotypes in centromeric IGH class switch regions (Sα2 and Sε) and in BCL2.

Example 4: Design and Validation of PhasED-Seq Panel for Lymphoma

Figure 2A:
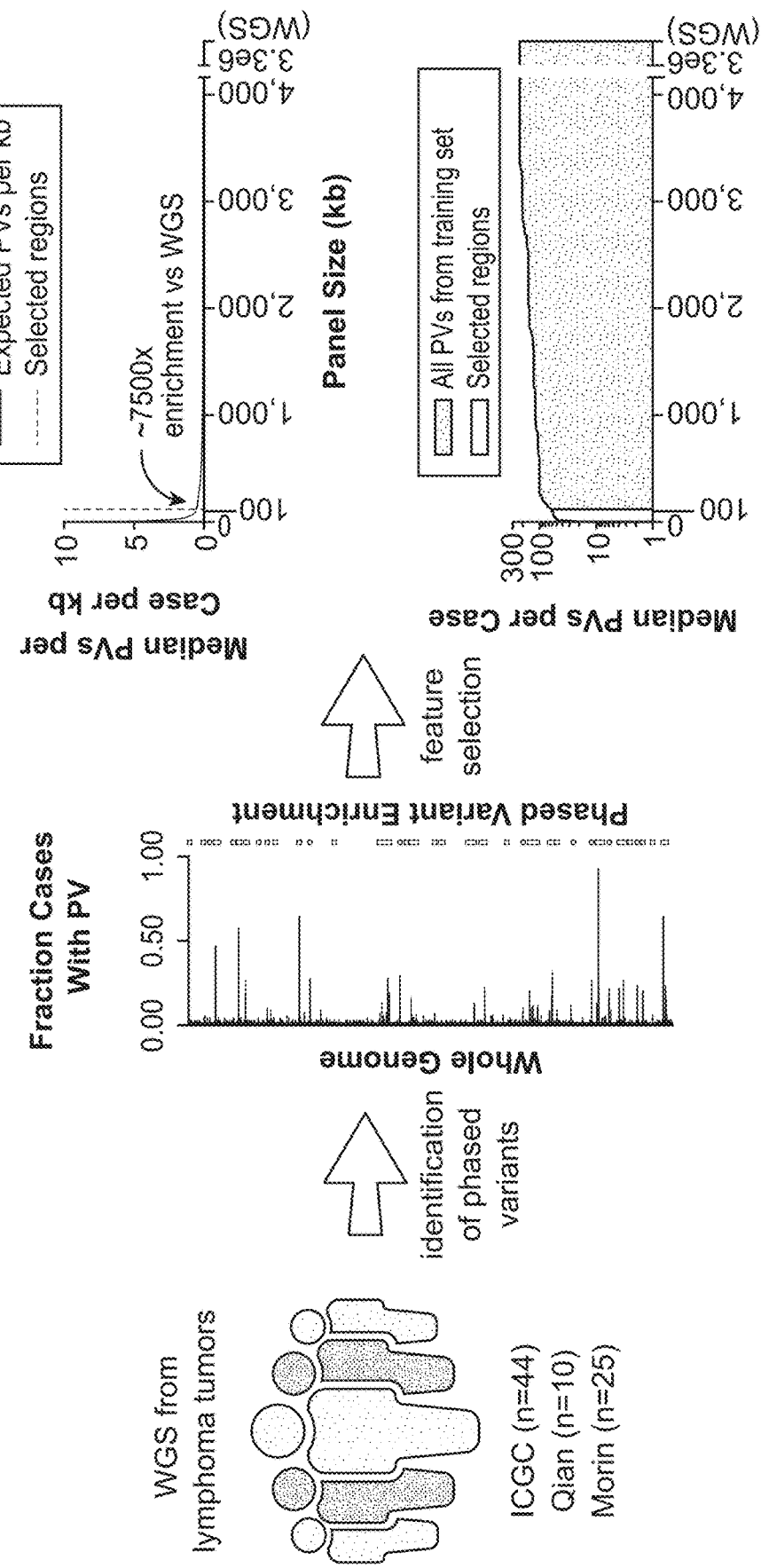
FIGS. 2A-2F illustrate design, validation, and application of phased variant enrichment sequencing.

To validate these PV-rich regions and assess their utility for disease detection from ctDNA, a sequencing panel targeting putative PVs identified within WGS from three independent cohorts of patients with DLBCL, as well as in patients with CLL (FIG. 2A and Example 10) was designed. This final Phased variant Enrichment and Detection Sequencing (PhasED-Seq) panel targeted ~115 kb of genomic space focused on PVs, along with an additional ~200 kb targeting genes that are recurrently mutated in B-NHLs (Table 3). While the 115 kb of space dedicated to PV-capture targets only 0.0035% of the human genome, it captures 26% of phased variants observed in mature B-cell neoplasms profiled by WGS (FIG. 9A), thus yielding a ~7500-fold PV enrichment by PhasED-Seq over WGS.

Figure 2B:
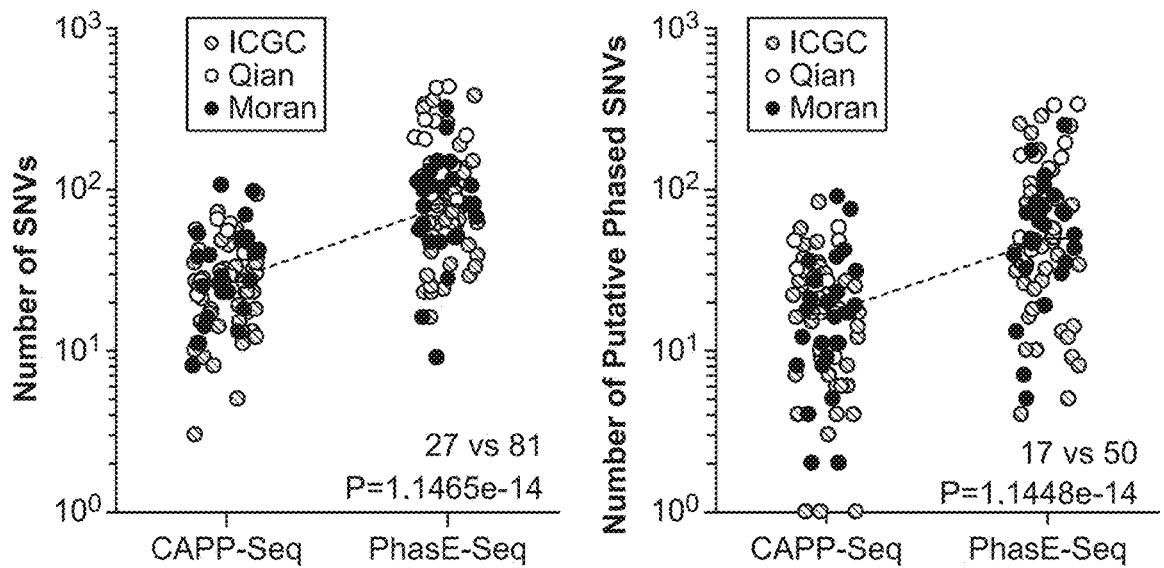
Figure 2C:
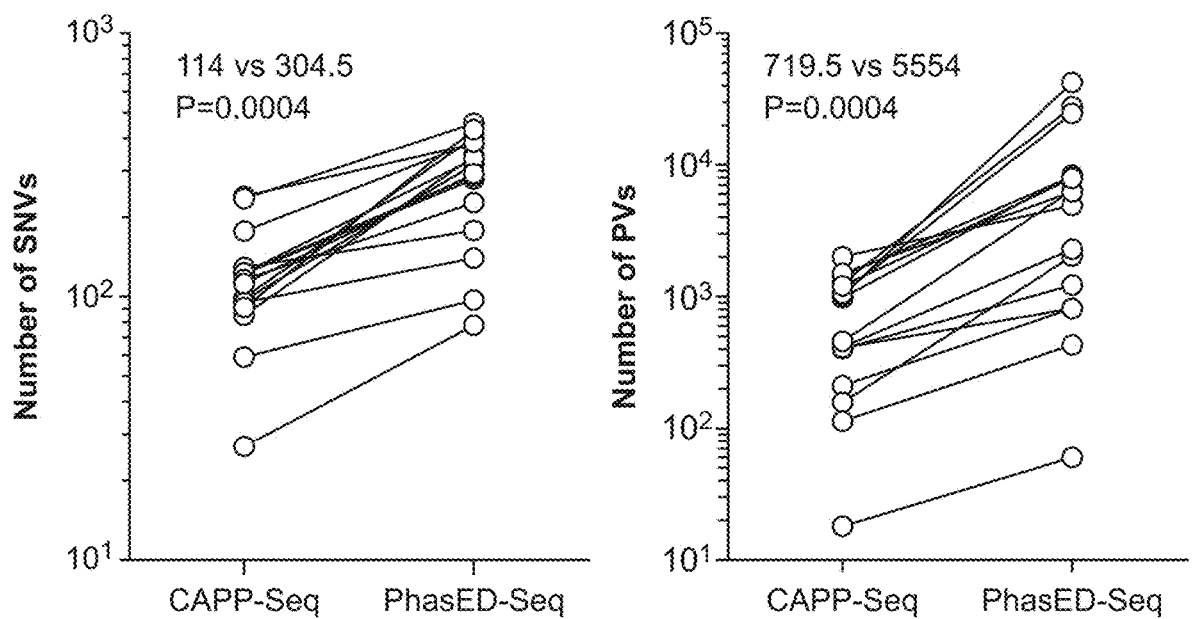
Figure 2D:
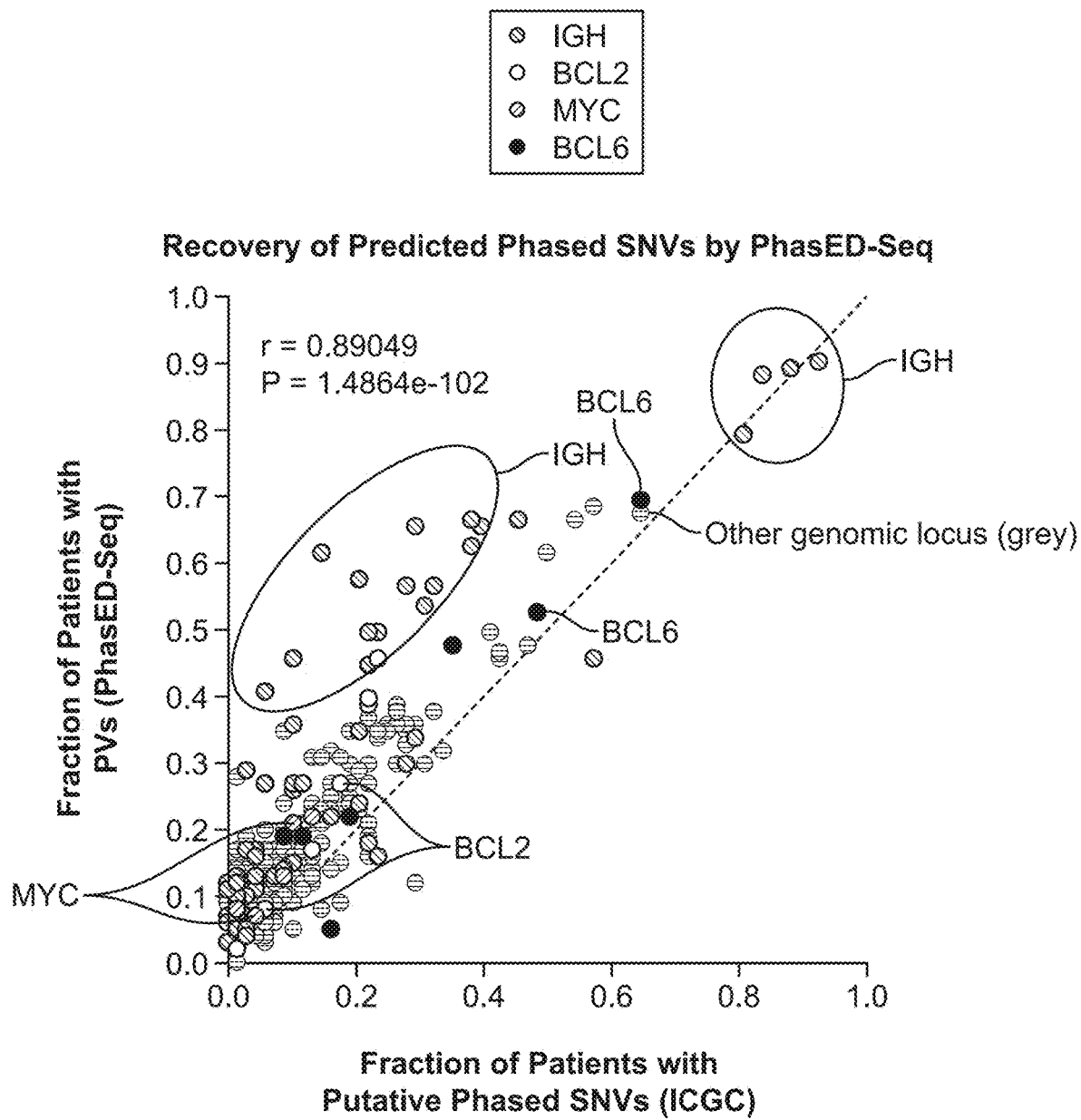
Figure 9A:
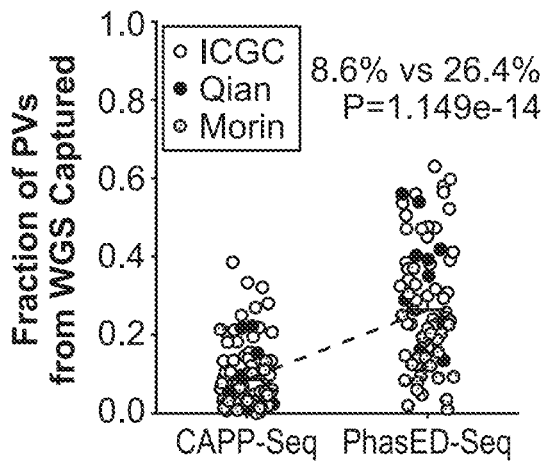
FIGS. 9A-9K illustrate performance of PhasED-Seq for recovery of PVs across lymphomas.
Figure 9B:
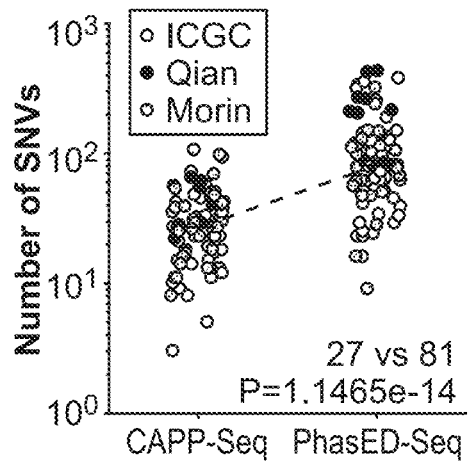
Figure 9C:
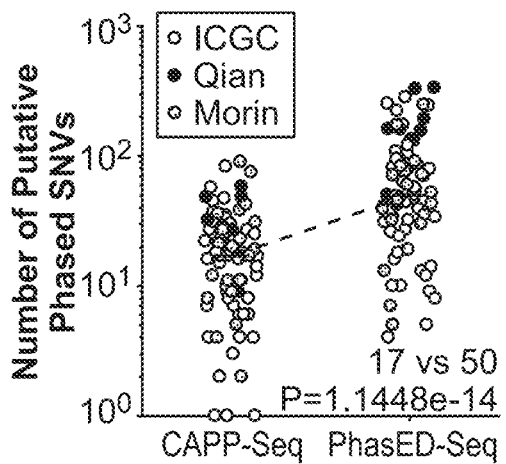
Figure 9D:
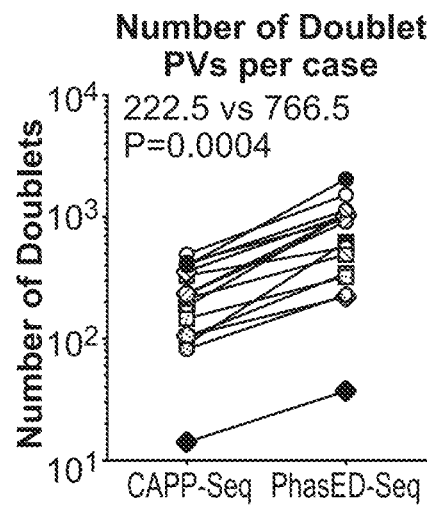
Figure 9E:
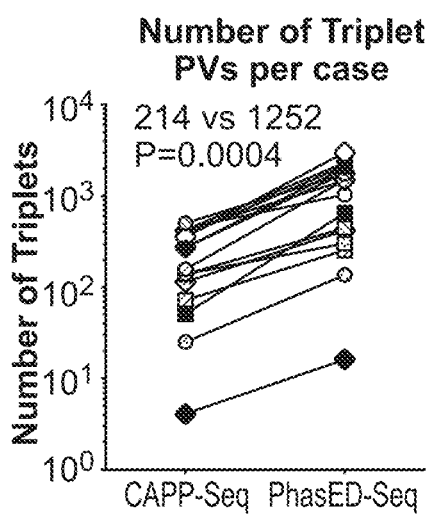
Figure 9F:
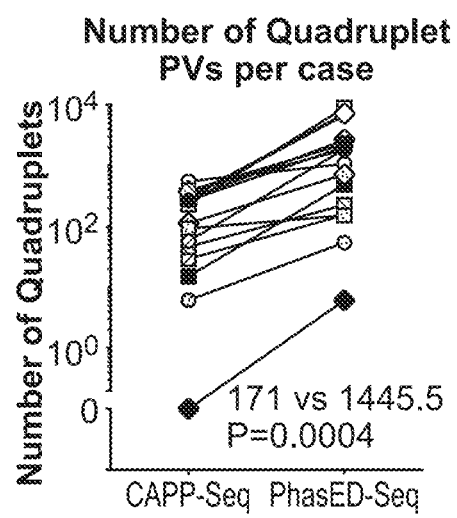
Figure 9G:
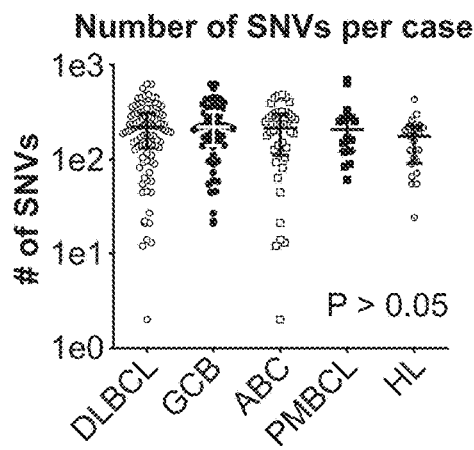
Figure 9H:
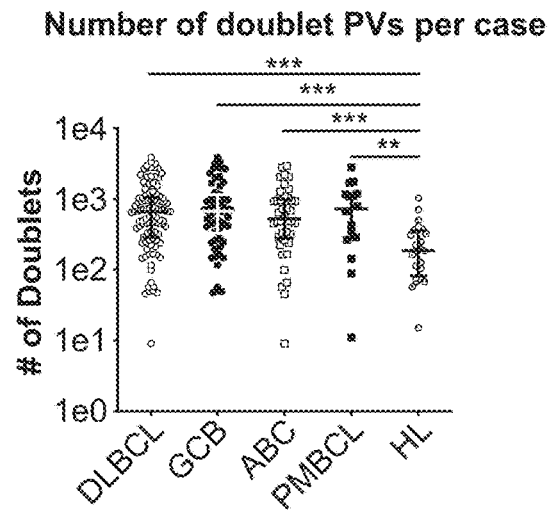
Figure 9I:
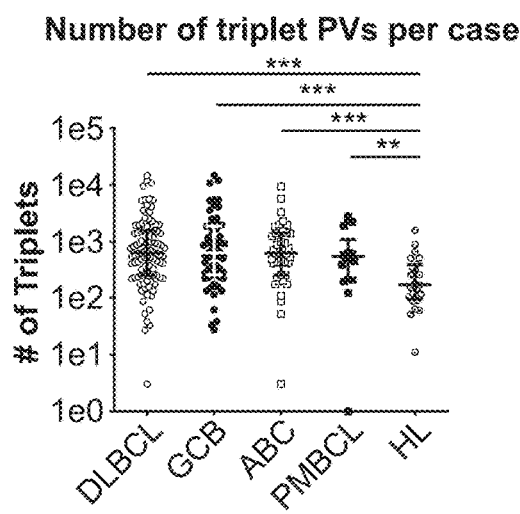
Figure 9J:
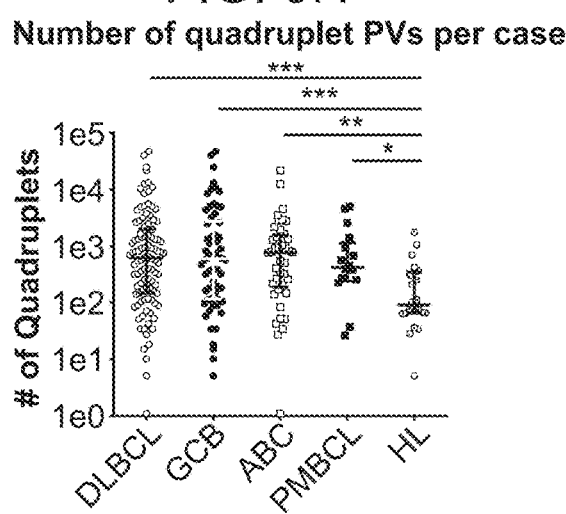
Figure 9K:
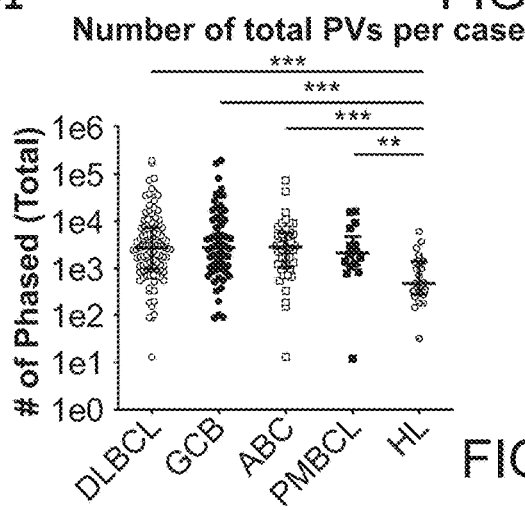
Figure 10A:
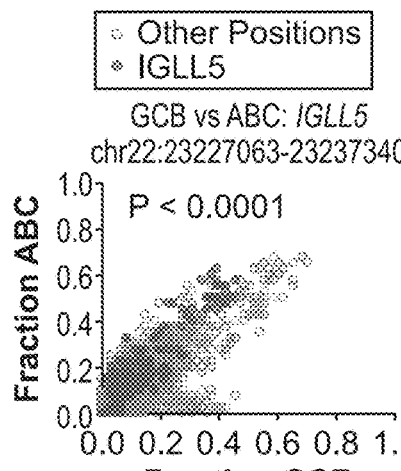
FIGS. 10A-10Y illustrate location-specific differences in PVs between ABC-DLBCL and GCB-DLBC (FIGS. 10A-10Y.) Similar to FIG. 2D, these scatterplots compare the frequency of PVs by genomic location (in 50 bp bins) for patients with different types of lymphomas; in this figure, the difference between ABC-DLBCL and GCB-DLBCL is shown. The red circles show the relative frequency of PVs in 50 bp bins from a specific gene of interest; the other (grey) circles show the relative frequency of PVs in 50 bp bins from the remainder of the PhasED-Seq sequencing panel. Only genes with a statistically significant difference in PVs between ABC-DLBCL and GCB-DLBCL are shown. P-values represent a Wilcoxon rank-sum test of 50 bp bins from a given gene against all other 50 bp bins; see Example 10.
Figure 10B:
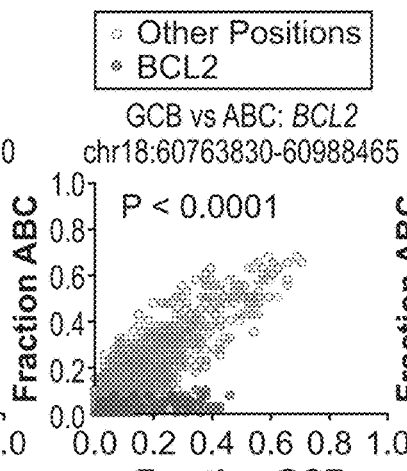
Figure 10C:
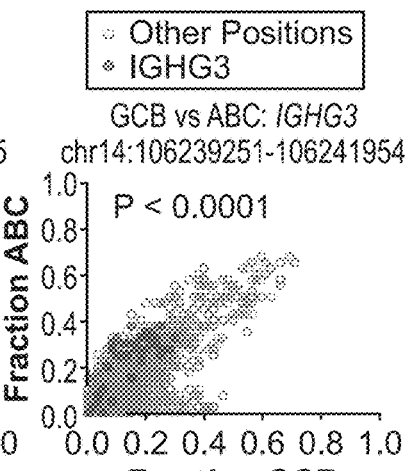
Figure 10D:
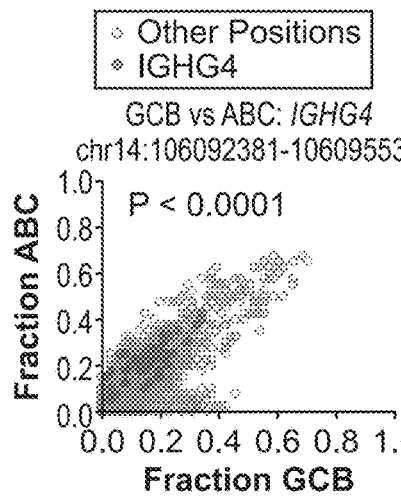
Figure 10E:
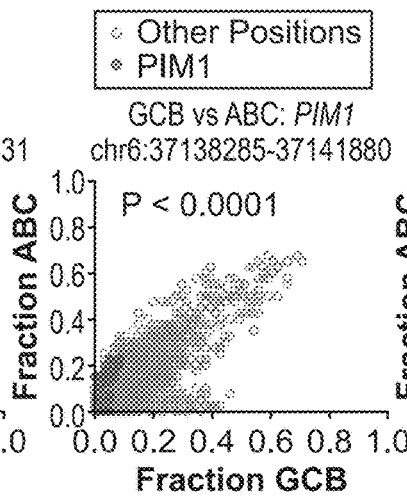
Figure 10F:
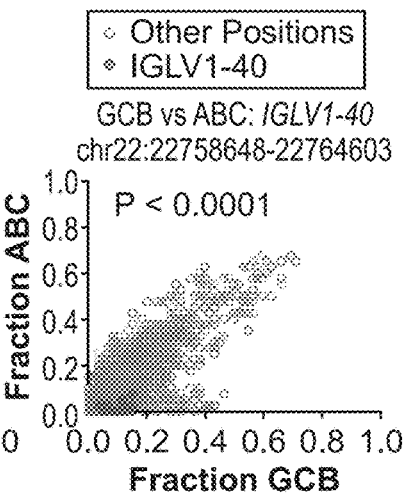
Figure 10G:
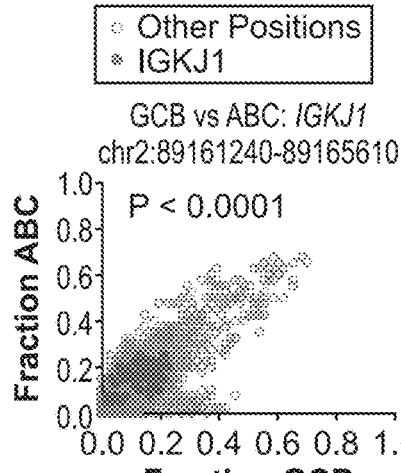
Figure 10H:
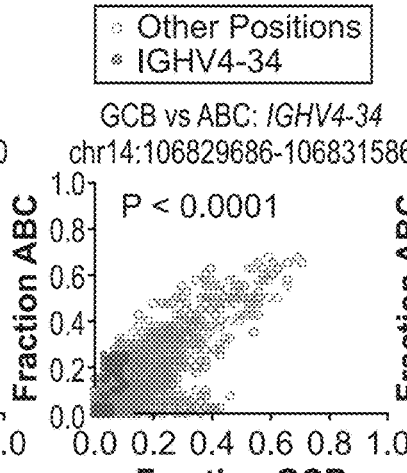
Figure 10I:
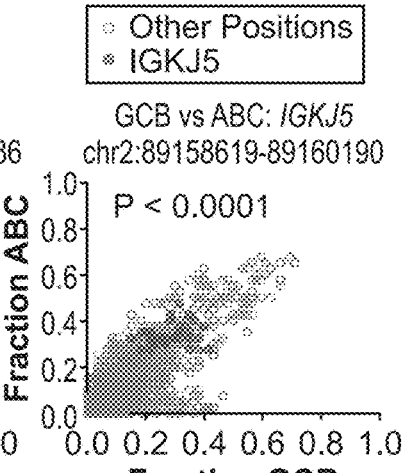
Figures 10J, 10K, 10L, 10M, 10N, 10O, 10P, 10Q, 10R:
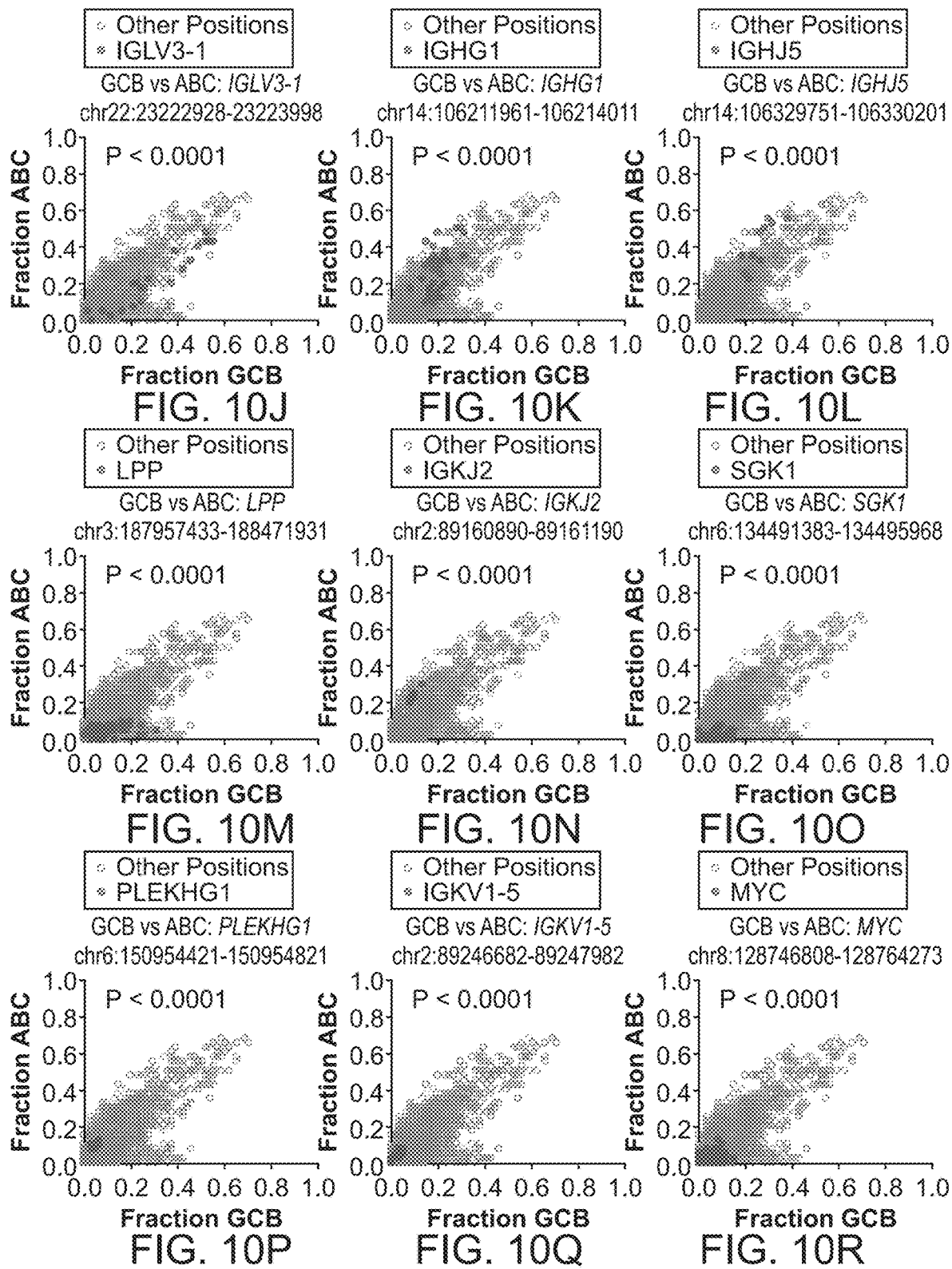

Expected SNV and PV recovery was compared to previously reported CAPP-Seq selector designed to maximize SNVs per patient in B-cell lymphomas (FIG. 9A-C). When considering diverse B-NHLs with available WGS data, PhasED-Seq recovered 3.0× more SNVs (81 vs. 27) and 2.9× more PVs (50 vs. 17) in the median case than previous CAPP-Seq panel. This observation highlights the importance of including non-coding portions of the genome for maximal mutation recovery. To validate these yield improvements experimentally, 16 pretreatment tumor or plasma DNA samples from patients with DLBCL (Table 4) were profiled. Both CAPP-Seq and PhasED-Seq panels were applied to each specimen in parallel and then sequenced them to high unique molecular depths (FIG. 2B). Compared to the expected enrichment established from WGS, similar improvements in yield of SNVs by PhasED-Seq compared to CAPP-Seq (2.7×; median 304.5 vs. 114) were observed. However, when enumerating PVs observed in individual sequenced DNA fragments, an improvement in favor of PhasED-Seq beyond the expected improvement from WGS (7.7×; median 5554 vs 719.5 PVs/case) was found. This improvement is potentially due to either 1) the higher sequencing depth in targeted sequencing which leads to improvement in rare allele detection, or 2) enumeration of higher order PVs in targeted sequencing with PhasED-Seq or CAPP-Seq, which was not accounted for in the WGS design (i.e., >2 SNVs per fragment; FIGS. 9D-9F). Furthermore, across 1-kb windows in the panel, robust correlation between the frequency of putative PVs in WGS data and PVs from targeted sequencing by PhasED-Seq across 101 DLBCL samples (FIG. 2C) was observed, further validating the frequency and distribution of PVs in B-cell malignancies.

Example 5: Differences in Phased Variants Between Lymphoma Subtypes

Figure 2E:
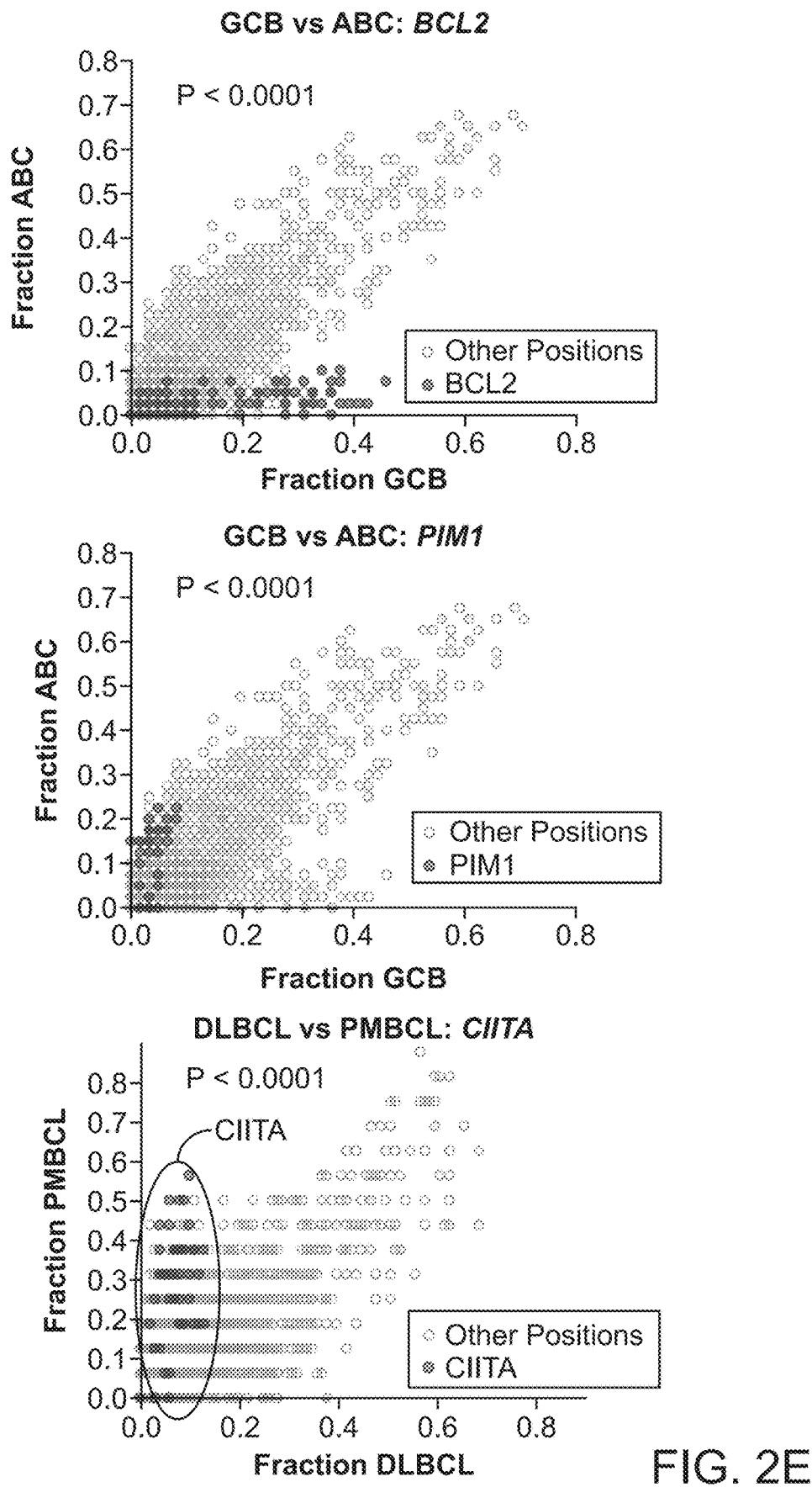
Figure 2F:
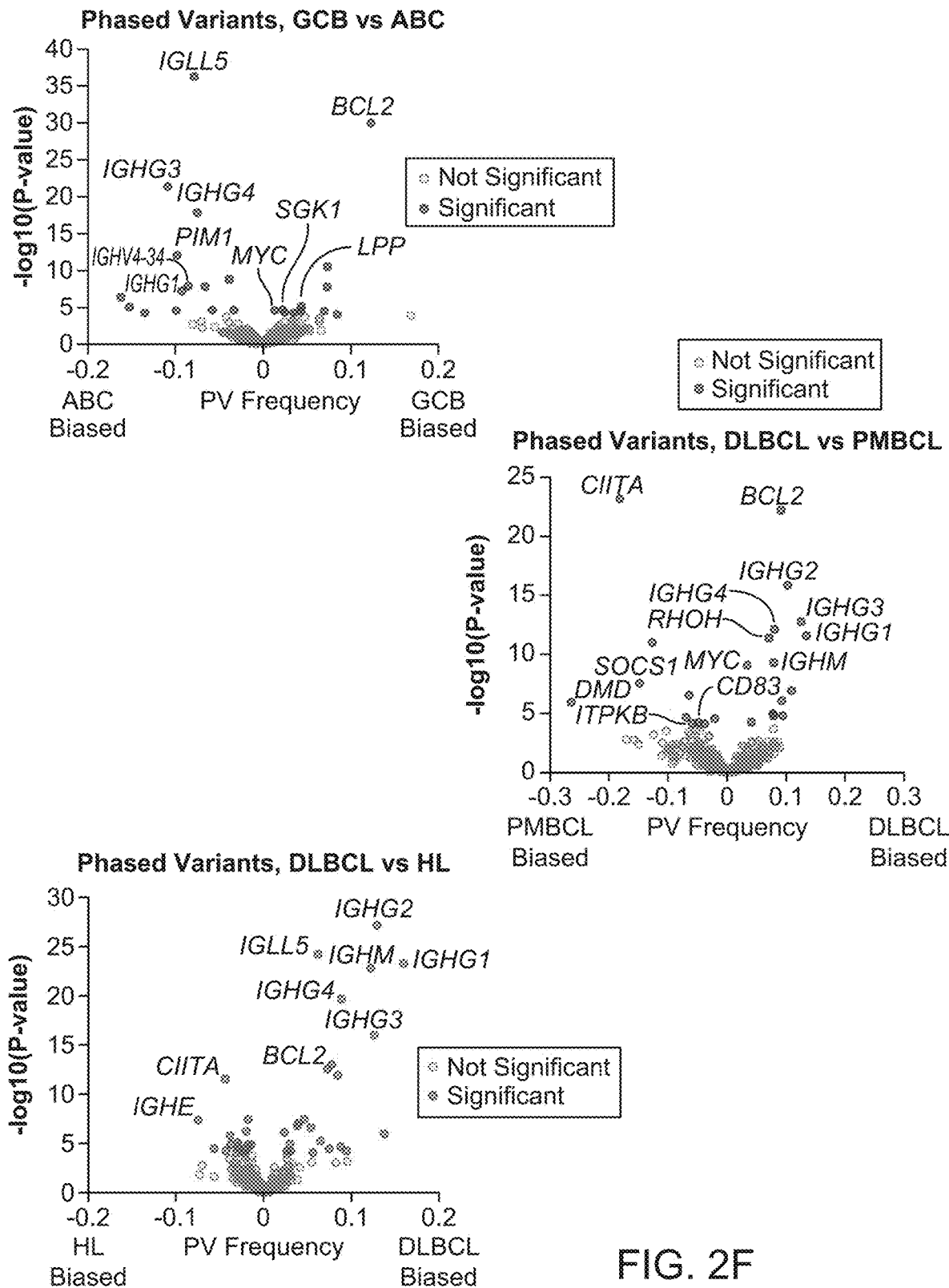
Figures 11G, 11H, 11I:
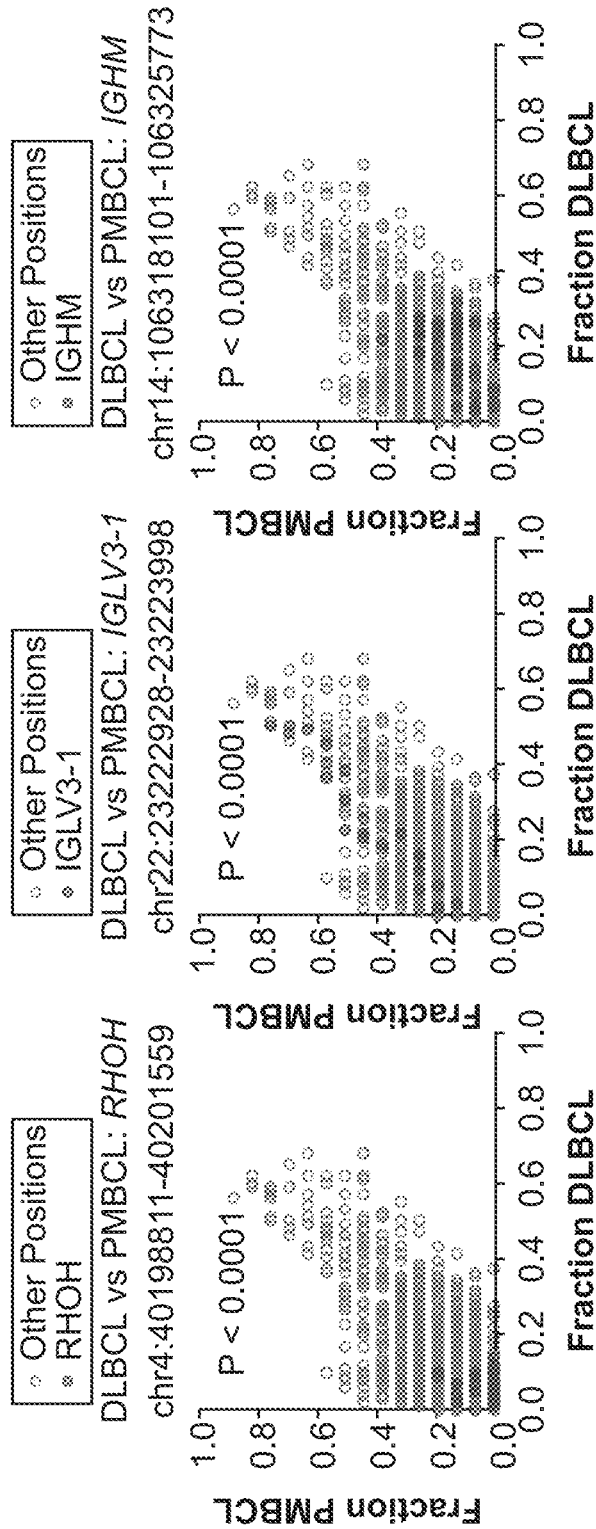
FIGS. 11A-11X illustrate Location-specific differences in PVs between DLBCL and PMBCL (FIGS. 11A-11X). Similar to FIG. 2D, these scatterplots compare the frequency of PVs by genomic location (in 50 bp bins) for patients with different types of lymphomas; in this figure, the difference between DLBCL and PMBCL is shown. The blue circles show the relative frequency of PVs in 50 bp bins from a specific gene of interest; the other (gray) circles show the relative frequency of PVs in 50 bp bins from the remainder of the PhasED-Seq sequencing panel. Only genes with a statistically significant difference in PVs between DLBCL and PMBCL are shown. P-values represent a Wilcoxon rank-sum test of 50 bp bins from a given gene against all other 50 bp bins; see Example 10.
Figures 11P, 11Q, 11R:
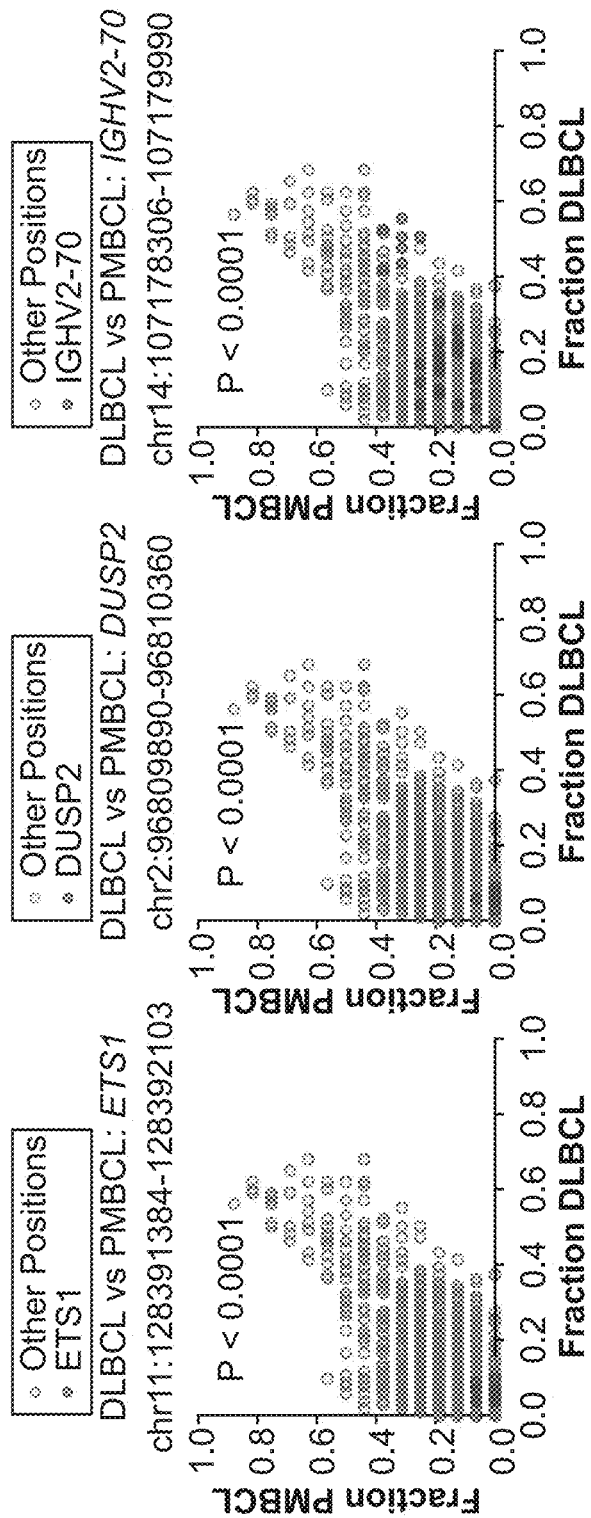
Figures 12G, 12H, 12I:
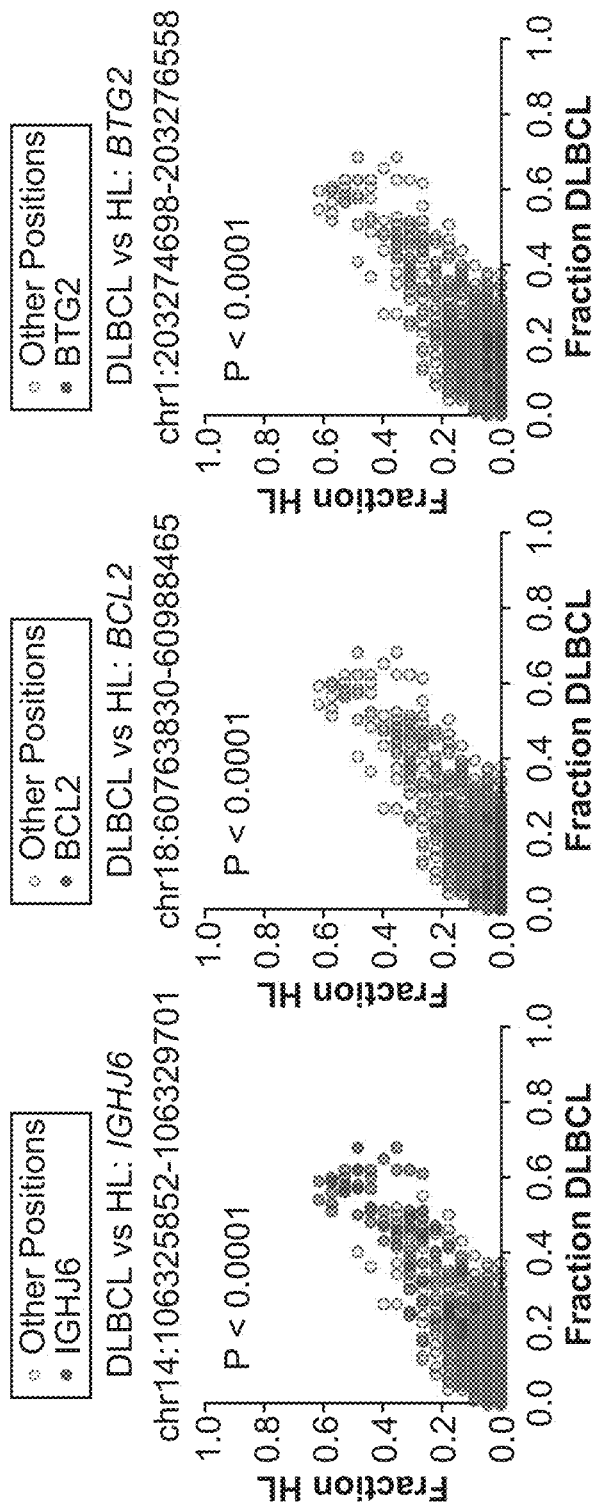
FIGS. 12A-12NN illustrate Location-specific differences in PVs between DLBCL and HL. Similar to FIG. 2D, scatterplots of FIGS. 12A-12NN compare the frequency of PVs by genomic location (in 50 bp bins) for patients with different types of lymphomas; in this figure, the difference between DLBCL and HL is shown. The green circles show the relative frequency of PVs in 50 bp bins from a specific gene of interest; the other (grey) circles show the relative frequency of PVs in 50 bp bins from the remainder of the PhasED-Seq sequencing panel. Only genes with a statistically significant difference in PVs between DLBCL and HL are shown. P-values represent a Wilcoxon rank sum test of 50 bp bins from a given gene against all other 50 bp bins; see Example 10.
Figures 12P, 12Q, 12R:
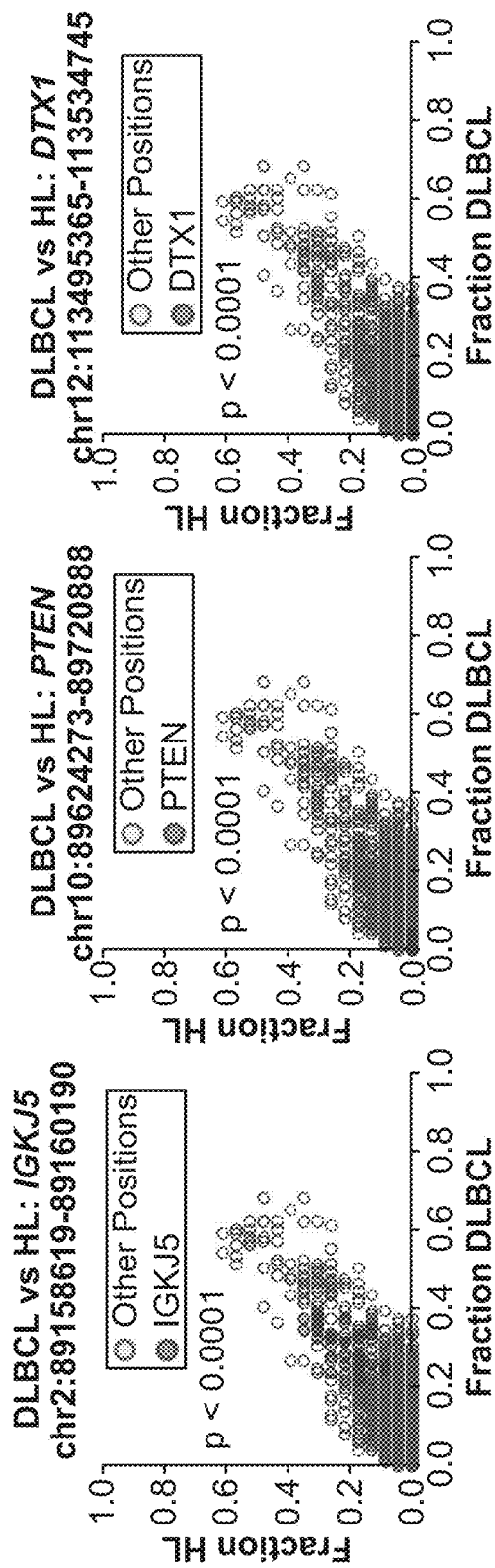
Figures 12S, 12T, 12U, 12V, 12W, 12X:
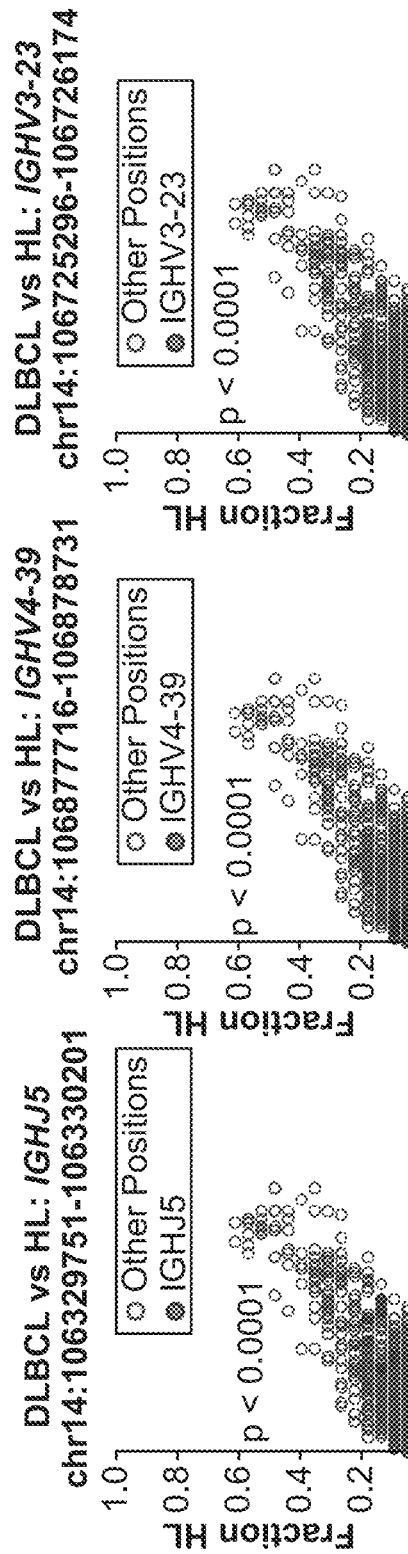
Figures 12A, 12Y, 12Z:
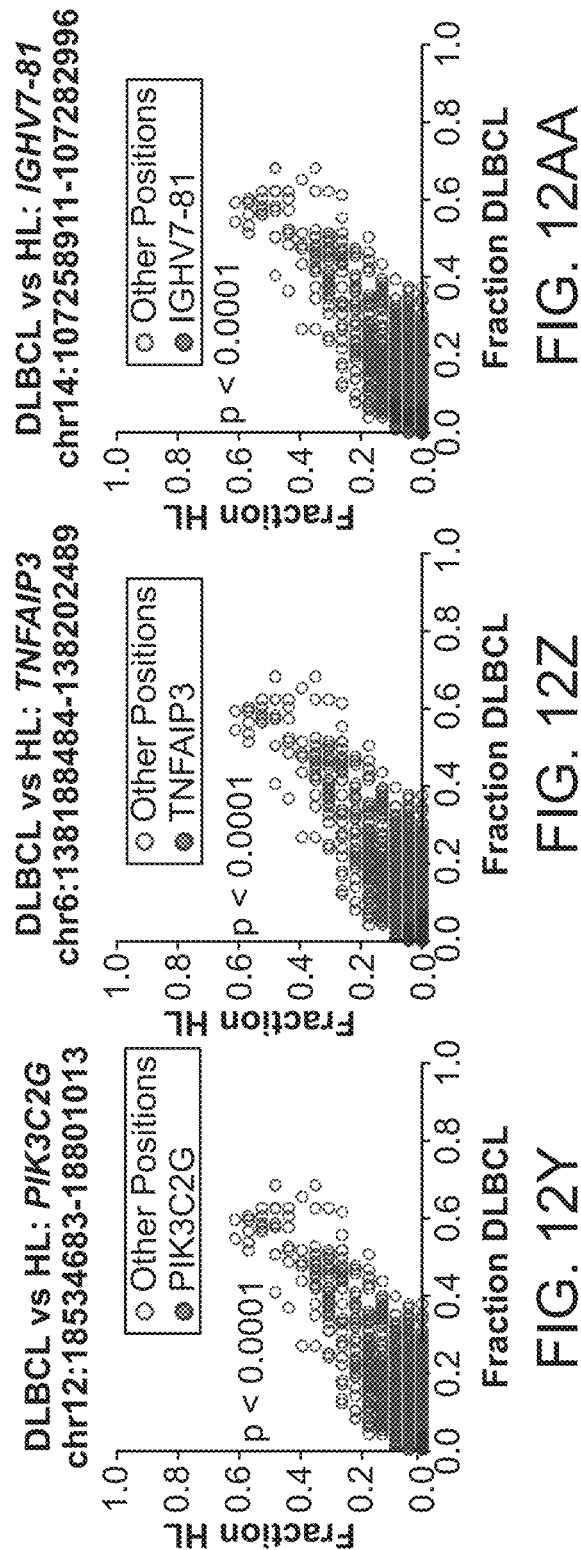
Figures 12H, 12I, 12J:
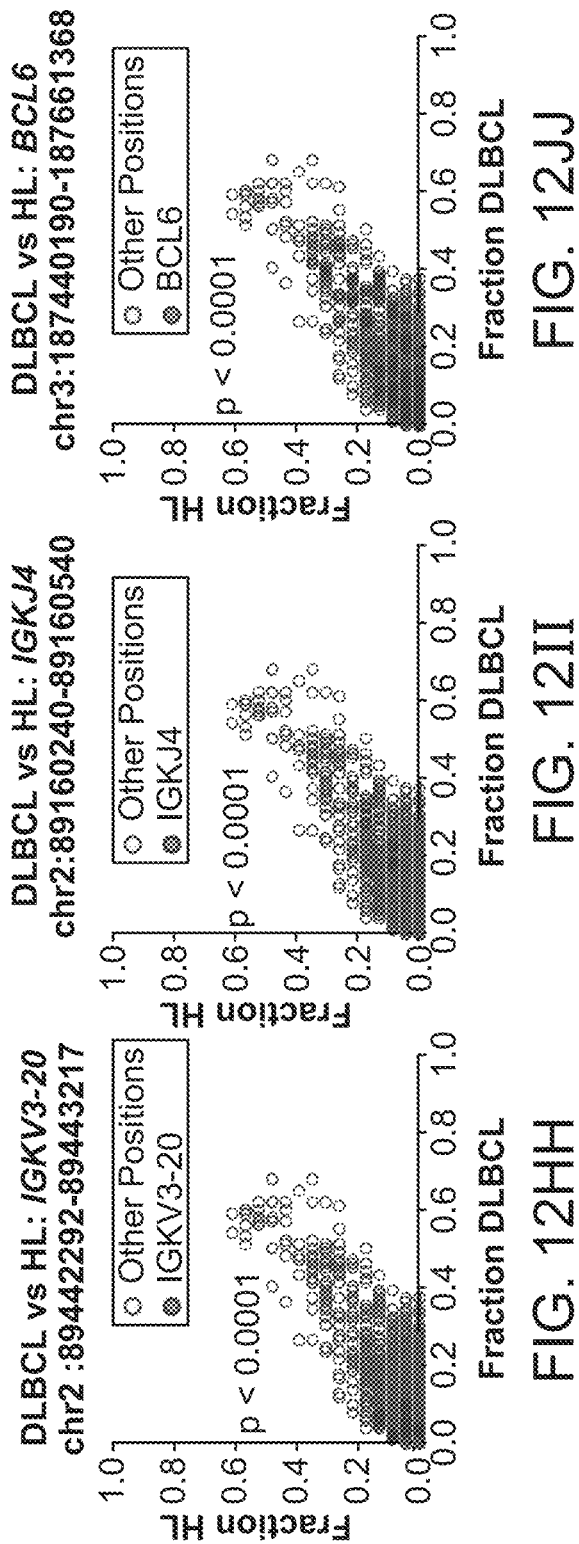
Figure 12K:
Figure 12L:
Figure 12M:
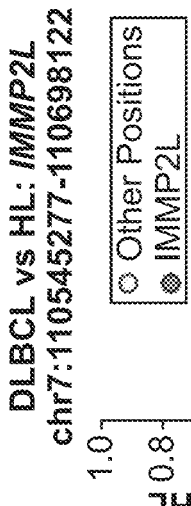
Figure 12N:
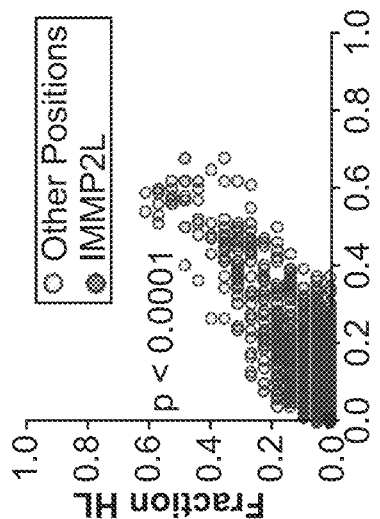
Figure 13:
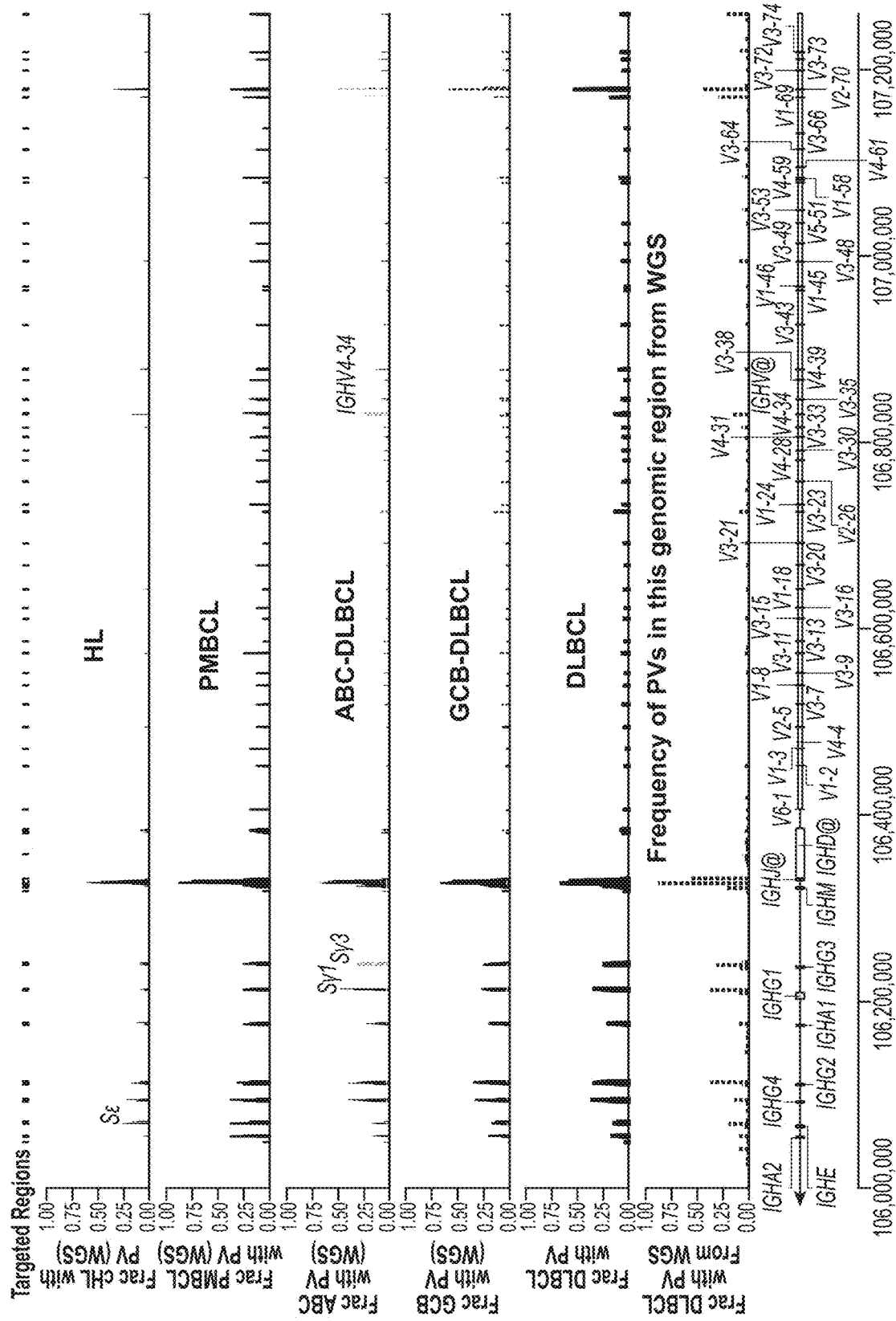
FIG. 13 illustrates differences in PVs between lymphoma types in mutations in the IGH locus. This figure shows the frequency of PVs from PhasED-Seq across the @IGH locus for different types of B-cell lymphomas. The bottom track shows the structure of the @IGH locus and gene-parts, including Ig-constant genes and V-genes. The next (outlined) track shows the frequency of PVs in this genomic region from WGS data (ICGC cohort). The remainder of the tracks show the frequency of PVs from PhasED-Seq targeted sequencing data, including 1) DLBCL, GCB-DLBCL, ABC-DLBCL, PMBCL, and HL. The regions targeted by the PhasED-Seq panel are shown at the top. Selected immunoglobulin parts with PVs enriched in specific histologies are labeled (i.e., IGHV4-34, Sε, Sγ3 and Sγ1).

Having validated the PhasED-Seq panel, the biological differences in PVs between various B-cell malignancies, including DLBCL (n=101), primary mediastinal B-cell lymphoma (PMBCL) (n=16), and classical Hodgkin lymphoma (cHL) (n=23) were examined. The number of SNVs identified per case was not significantly different between lymphoma subtypes (FIGS. 9G-9K). However, when considering mutational haplotypes, cHL had a significantly lower burden of PVs than either DLBCL or PMBCL. In addition to this quantitative disparity, differences in the genomic locations of PVs between different B-cell lymphoma subtypes were also observed (FIGS. 2D-2E and FIGS. 10-12). This included previously established biological associations in DLBCL subtypes, including more frequent PVs in BCL2 in GCB-type than ABC-type DLBCL, with the opposite association seen for PIM1. More frequent PVs in CIITA in PMBCL compared with DLBCL, a gene in which breakpoints are common in PMBCL, was also observed. Relative enrichments were also observed throughout the IGH locus, with more frequent PVs seen in Sγ3 and Sγ1 regions in ABC-DLBCL (compared with GCB-DLBCL) and interestingly, more frequent PVs in the Sε locus in cHL compared with DLBCL (FIG. 2E and FIG. 13). In total, after correcting for testing multiple hypotheses, significant relative enrichments in 25 genetic loci between ABC- and GCB-DLBCL, 24 between DLBCL and PMBCL, and 40 between DLBCL and cHL were found (FIG. 10-12).

Example 6: Recovery of Phased Variants Through PhasED-Seq

Figure 3A:
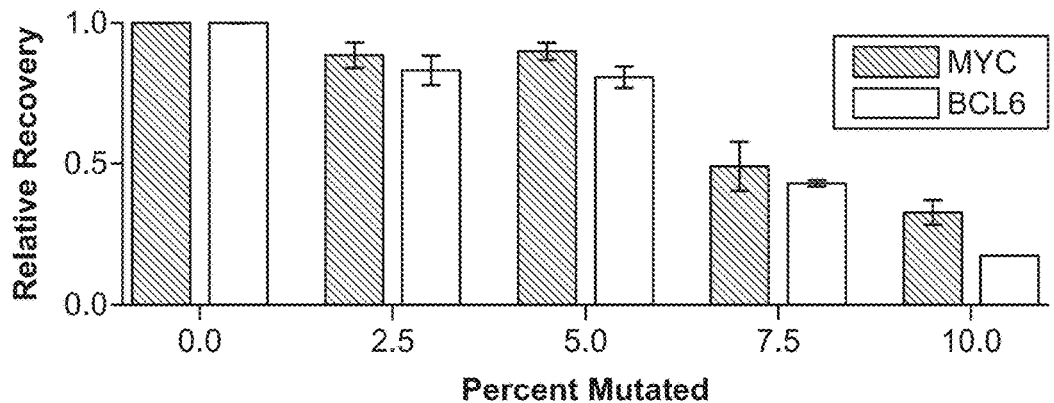
FIGS. 3A-3I illustrate technical performance of PhasED-Seq for disease detection.
Figure 14B:
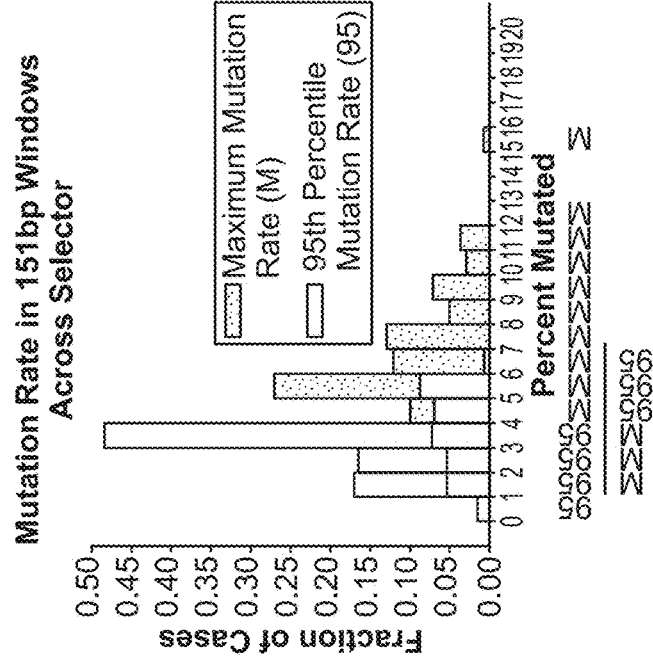
FIGS. 14A-14E illustrate Technical aspects of PhasED-Seq by hybrid-capture sequencing.
Figure 14A:
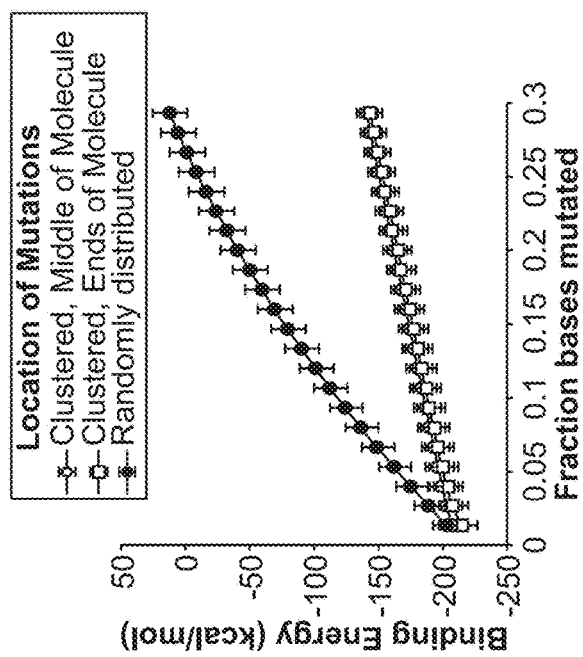
Figure 14C:
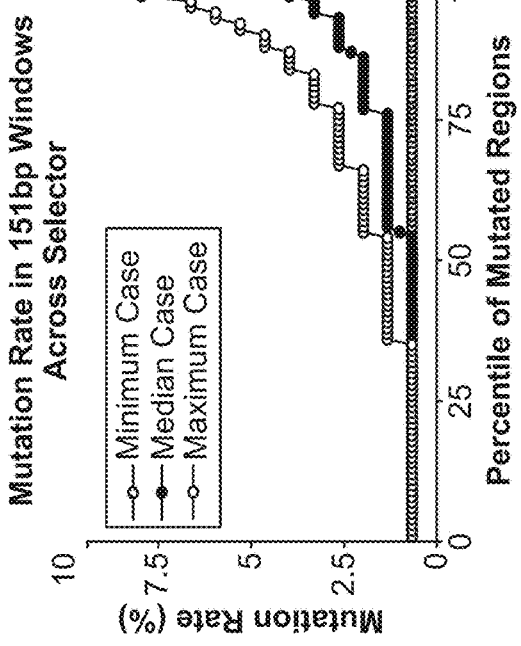

To facilitate detection of ctDNA using PVs, efficient recovery of DNA molecules is desired. Hybrid-capture sequencing is potentially sensitive to DNA mismatches, with increasing mutations decreasing hybridization efficiency. Indeed, AID hotspots can contain a 5-10% local mutation rate, with even higher rates in certain regions of IGH. To empirically assess the effect of mutation rate on capture efficiency, DNA hybridization of 150-mers with varying mutation rates in silico was simulated. As expected, predicted binding energy decreased with an increasing number of mutations (FIG. 14A). Notably, randomly distributed mutations had a greater effect on binding energy than clustered mutations. To assess the effect of this decreased binding affinity, 150-mer DNA oligonucleotides with 0 to 10% difference from the reference sequence in MYC and BCL6, two loci that are targets of aSHM were synthesized. To assess the worst-case scenario for hybridization, non-reference bases were randomly distributed rather than in clusters (Example 10). An equimolar mixture of these oligonucleotides were then captured with PhasED-Seq panel. Concordant with the in silico predictions, increased mutational rates resulted in decreased capture efficiency (FIG. 3A). Molecules with a 5% mutation rate were captured with 85% efficiency relative to fully-wildtype counterparts, while molecules with 10% mutation were captured with only 27% relative efficiency. To assess the prevalence of this degree of mutation in human tumors, the distribution of variants in panel in 140 patients with B-cell lymphomas, calculating the fraction of mutated bases in overlapping 151-bp windows (Example 10) was examined. Only 7% ($^{10}$/140) of patients had any 151-bp window exceeding 10% mutation rate (FIG. 14B-C). Indeed, in the experiment with synthetic oligonucleotides, a 5% mutation rate was recovered nearly as efficiently as the wild-type sequence. In over half of all cases considered, no locus had >5% mutation rate at any window, while in all cases >90% of windows had <5% mutations. Overall, these observations indicate that the majority of phased mutations are recoverable by efficient hybrid capture, despite hybridization biases.

Example 7: Error Profile and Limit of Detection for Phased Variant Sequencing

Figure 3B:
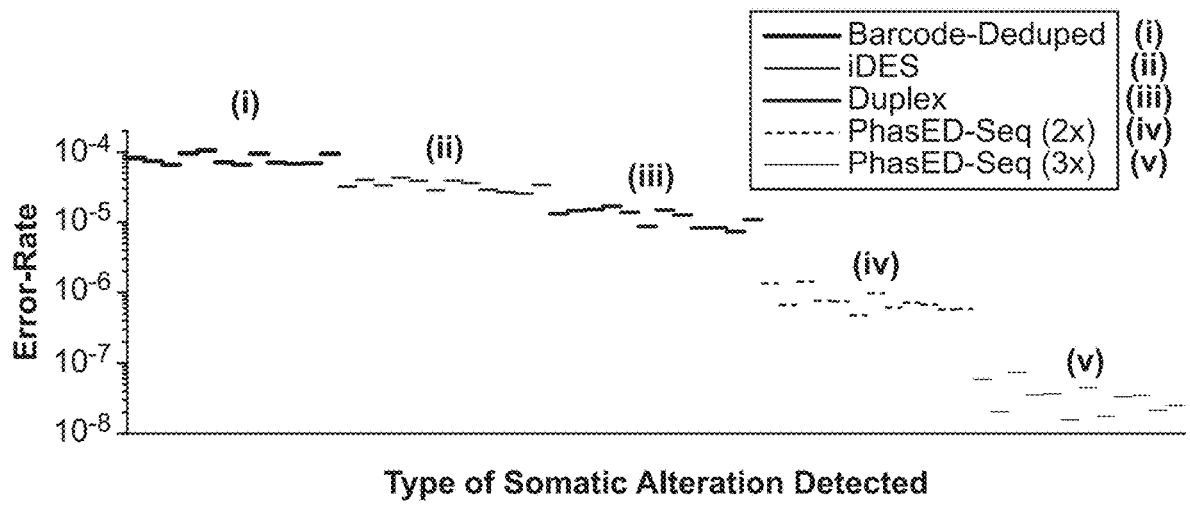
Figure 3C:
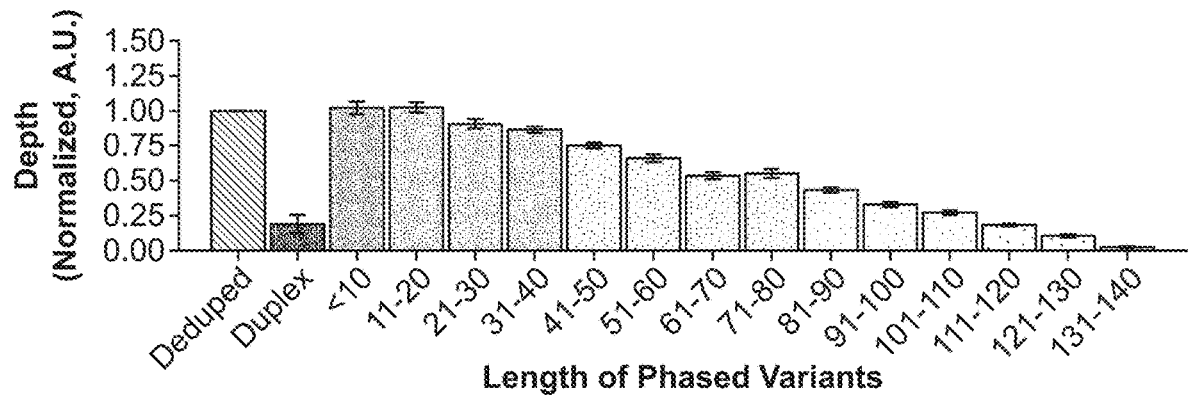
Figure 3D:
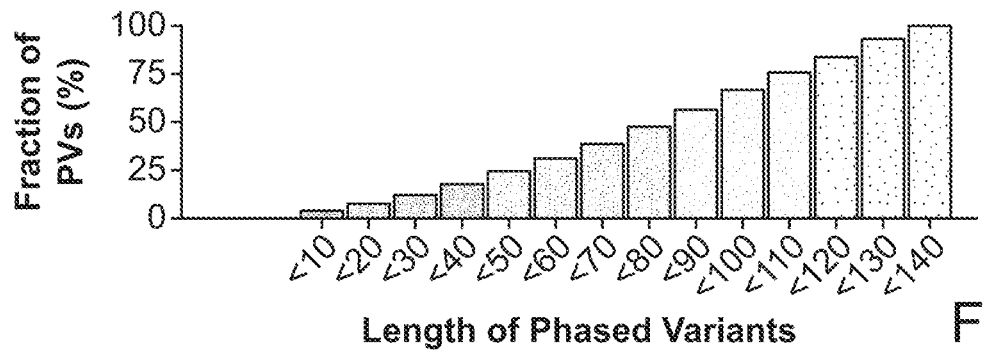
Figure 14D:
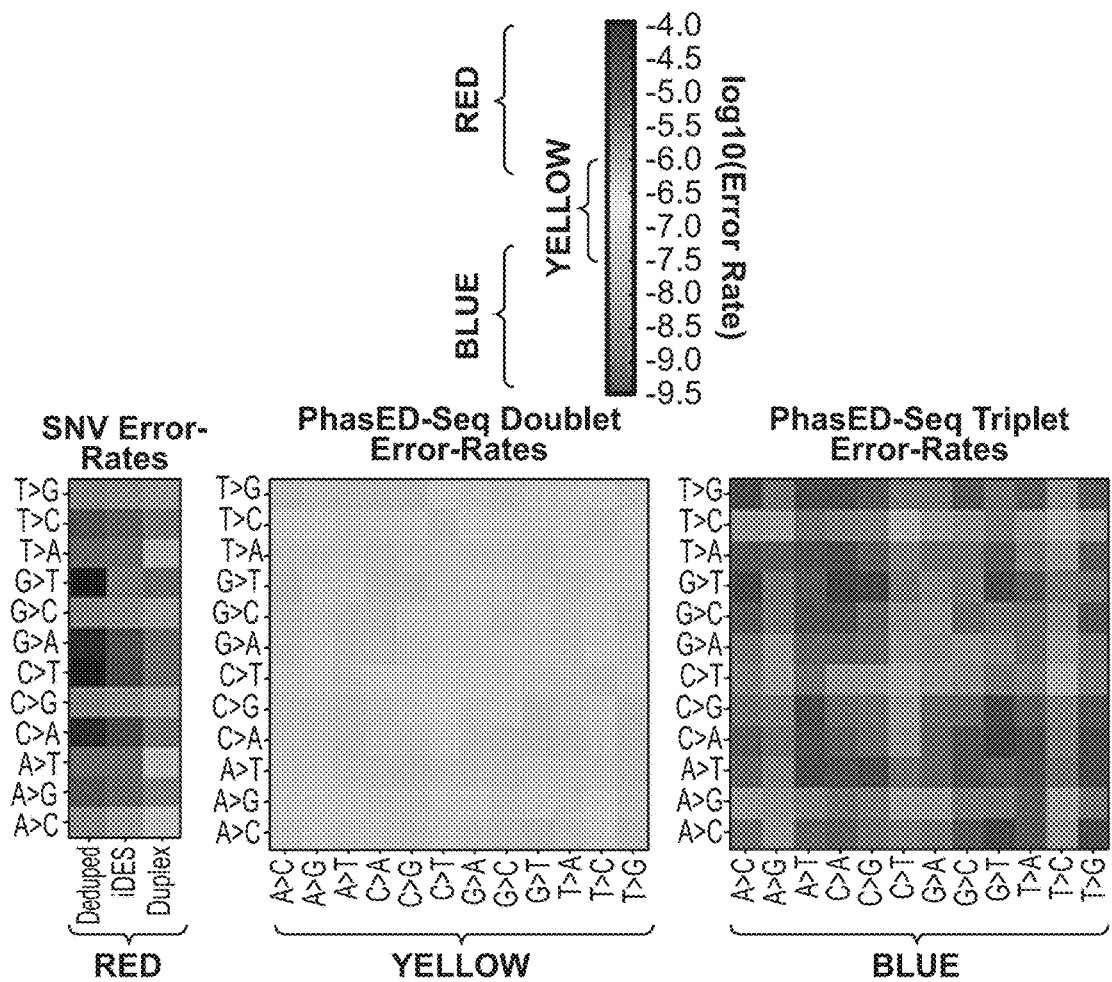
Figure 14E:
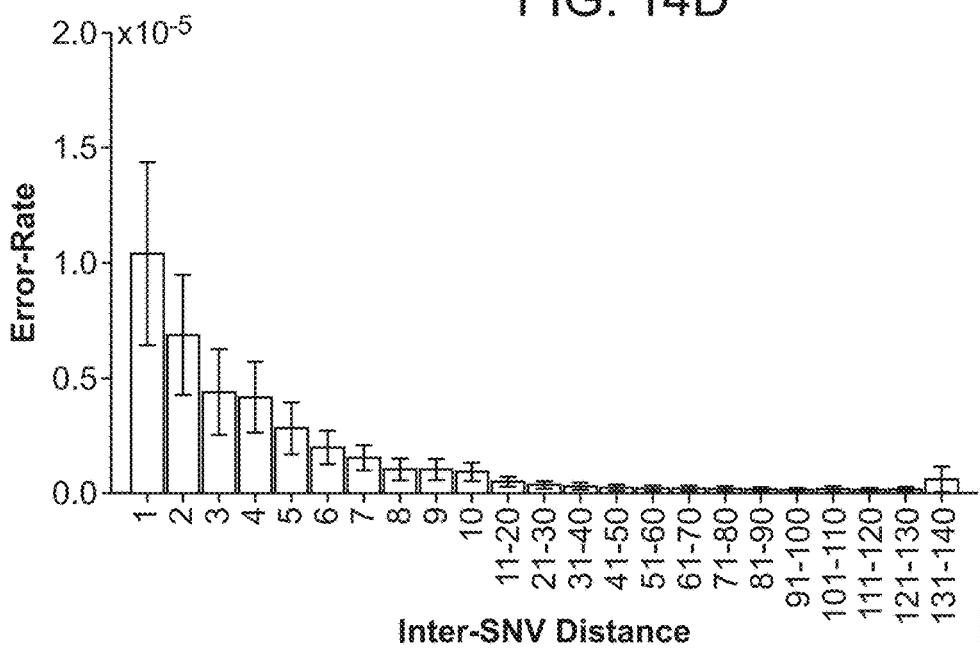

Previous methods for highly error-suppressed sequencing applied to cfDNA have utilized either a combination of molecular and in silico methods for error suppression (e.g., integrated digital error suppression, iDES) or duplex molecular recovery. However, each of these has limitations, either for detecting events at ultra-low tumor fractions or for efficient recovery of original DNA molecules, which are important considerations for cfDNA analysis where input DNA is limited. The error profile and recovery of input genomes from plasma cfDNA samples form 12 heathy adults by PhasED-Seq were compared with both iDES-CAPP-Seq and duplex sequencing. While iDES-enhanced CAPP-Seq had a lower background error profile than barcode-deduplication alone, duplex sequencing offered the lowest background error rate for non-reference single nucleotide substitutions (FIG. 3B, $3.3 \times 10^{-5}$ vs. $1.2 \times 10^{-5}$, P<0.0001). However, the rate of phased errors—e.g., multiple non-reference bases occurring on the same sequencing fragment—was significantly lower than the rate of single errors in either iDES-enhanced CAPP-Seq or duplex sequencing data. This was true for the incidence of both two (2× or 'doublet' PVs) or three (3× or 'triplet' PVs) substitutions on the same DNA molecule (FIG. 3B, $8.0 \times 10^{-7}$ and $3.4 \times 10^{-8}$ respectively, P<0.0001). Phased errors containing C to T or T to C transition substitutions were more common than other types of PVs (FIG. 14D). Notably, the rate doublet PVs errors in cfDNA was also correlated with distance between positions, with the highest PV error-rate consisting of neighboring SNVs (e.g., DNVs) and decreasing error rate with increasing distance between constituent variants (FIG. 14E). When considering unique molecular depth, duplex sequencing recovered only 19% of all unique cfDNA fragments (FIG. 3C). In contrast, the unique depth of PVs within a genomic distance of <20 bp was nearly identical to the depth of individual positions (e.g., molecules covering individual SNVs). Similarly, PVs up to 80 bps in size had depth greater than 50% of the median unique molecular depth for a sample. Importantly, almost half (48%) of all PVs were within 80 bp of each other, demonstrating their utility for disease detection from input-limited cfDNA samples (FIG. 3D).

Figure 3E:
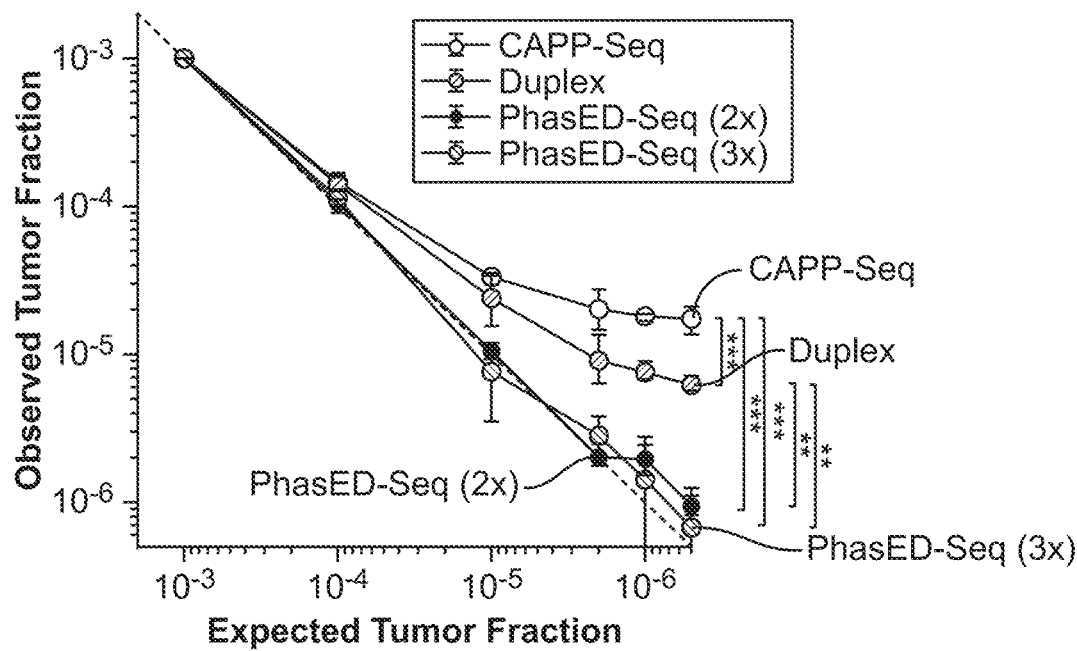
Figure 3F:
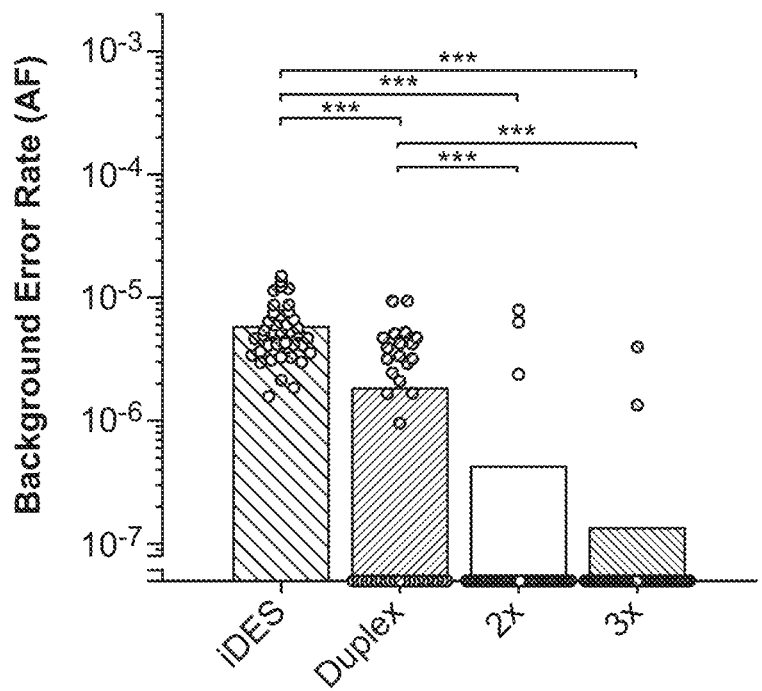
Figure 23A:
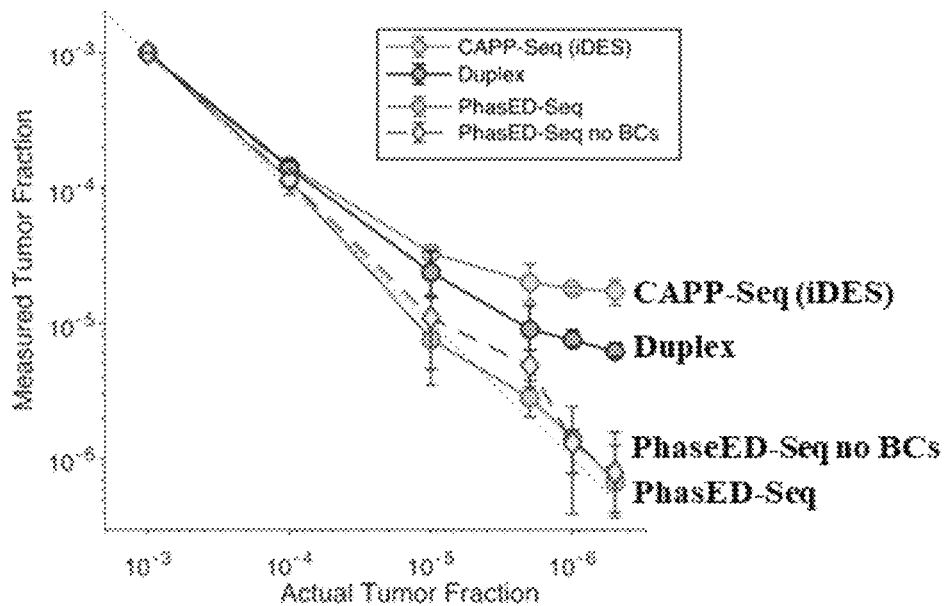
FIGS. 23A-23B illustrate that the method describe herein (e.g. method depicted yielding FIG. 3E and FIG. 3F) does not require barcode mediated error suppression.
Figure 23B:
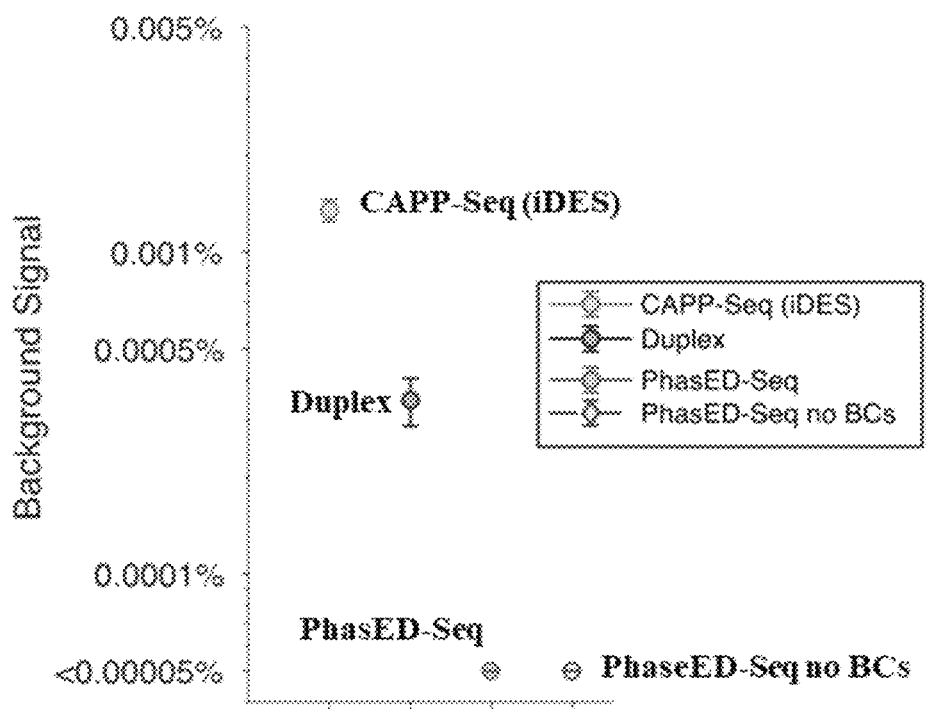

To quantitatively compare the performance of PhasED-Seq to alternative methods for ctDNA detection, limiting dilutions of ctDNA from 3 lymphoma patients into healthy control cfDNA were generated, resulting in expected tumor fractions between 0.1% and 0.00005% (1 part in 2,000,000; (Example 10). The expected tumor fraction was compared to the estimated tumor content in each of these dilutions using PhasED-Seq to track tumor-derived PVs, as well as to error-suppressed detection methods depending on individual SNVs (e.g. iDES-enhanced CAPP-Seq or duplex sequencing; FIG. 3E). All methods performed equally well down to tumor fractions of 0.01% (1 part in 10,000). However, below this level (e.g., 0.001%, 0.0002%, 0.0001%, and 0.00005%), both PhasED-Seq and duplex sequencing significantly outperformed iDES-enhanced CAPP-Seq (P<0.0001 for duplex, '2×' PhasED-Seq, and '3×' PhasED-Seq; FIG. 3E). In addition, when compared to duplex-sequencing, tracking either 2 or 3 variants in-phase (e.g., 2× and 3× PhasED-Seq) more accurately identified expected tumor content, with superior linearity down to 1 part in 2,000,000 (P=0.005 for duplex vs 2× PhasED-Seq, P=0.002 for 3× PhasED-Seq) (Example 10). Specificity of PVs by looking for evidence of tumor-derived SNVs or PVs in cfDNA samples from 12 unrelated healthy control subjects and the healthy control used for the limiting dilution was assessed. Here again, both 2×- or 3×-PhasED-Seq showed significantly lower background signal levels than did CAPP-Seq and duplex sequencing (FIG. 3F). This lower error rate and background from PVs improves the detection limit for ctDNA disease detection. In some instances, the method of sequencing-based cfDNA assays described herein (e.g. the method depicted in FIG. 3E and FIG. 3F) does not require molecular barcodes to achieve exquisite error-suppression and low limits of detection. Signal assessed by the method without barcode used limiting dilution series from 1:1,000 to 5:10,000,000, and 'blank' controls (FIGS. 23A-23B).

Figure 3G:
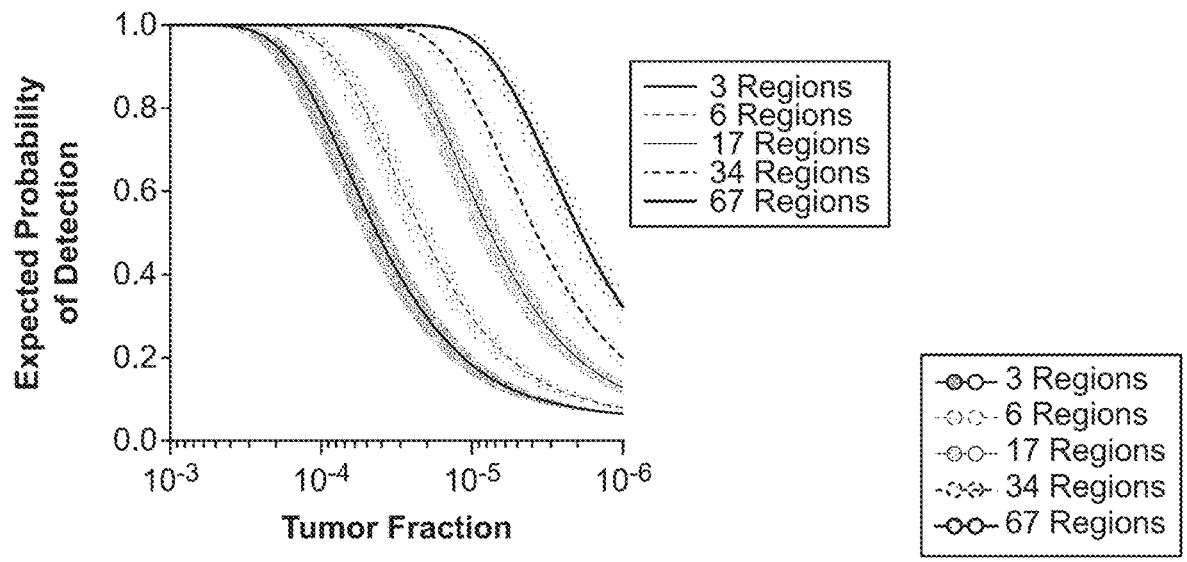
Figure 3H:
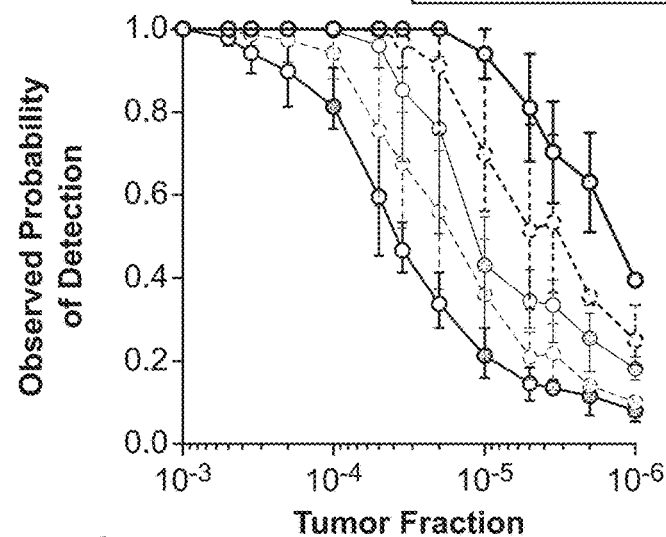
Figure 3I:
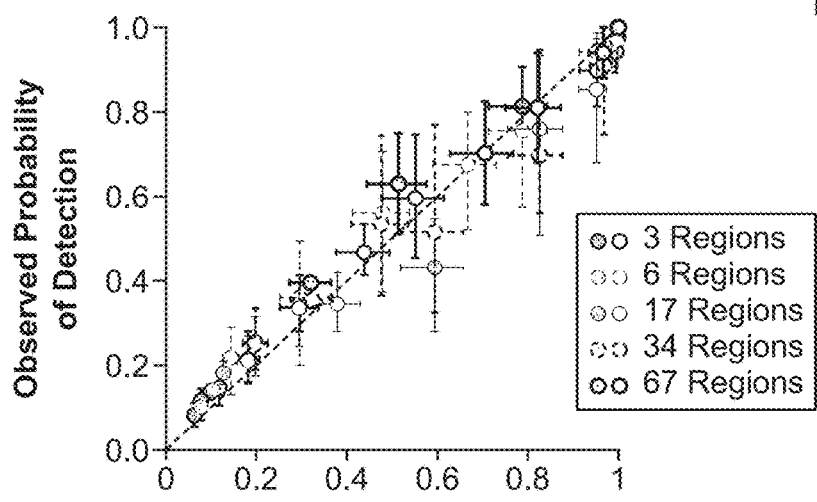

This dilution series was used to assess the limit of detection for a given number of PVs (FIGS. 3G-3I). When considering a set of PVs within 150 base pair (bp) regions, the probability of detection for a given sample may be accurately modelled by binomial sampling, considering both the depth of sequencing and the number of 150 bp regions with PVs (Example 10).

Example 8: Improvements in Detection of Low-Burden Minimal Residual Disease

To test the utility of the lower LOD afforded by PhasED-Seq for detection of ultra-low burden MRD from cfDNA, Serial cell-free DNA samples were sequenced from a patient undergoing front-line therapy for DLBCL (FIG. 4A). Using CAPP-Seq, this patient had undetectable ctDNA after only one cycle of therapy, with multiple subsequent samples during and after treatment also remaining undetectable. This patient had subsequent re-emergence of detectable ctDNA >250 days after the start of therapy, with eventual clinical and radiographic disease progression 5 months later, indicating falsely negative serial measurements with CAPP-Seq. Strikingly, all four of the plasma samples that were undetectable by CAPP-Seq during and after treatment had detectable ctDNA levels by PhasED-Seq, with mean allelic fractions as low as 6 parts in 1,000,000. This increased sensitivity improved the lead-time of disease detection by ctDNA compared to radiographic surveillance from 5 with CAPP-Seq to 10 months with PhasED-Seq.

Figures 4D, 4E, 4F, 4G:
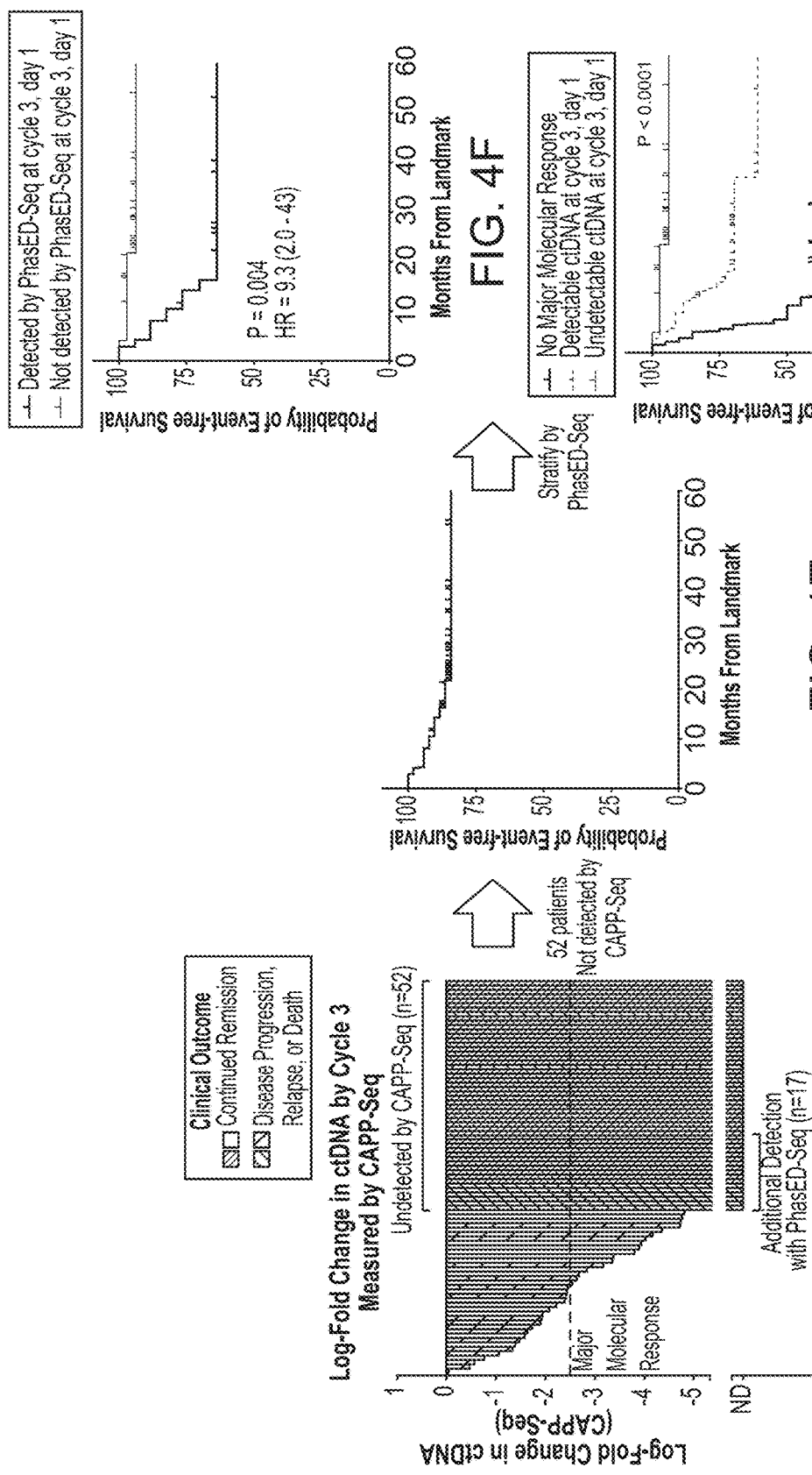
Figure 15:
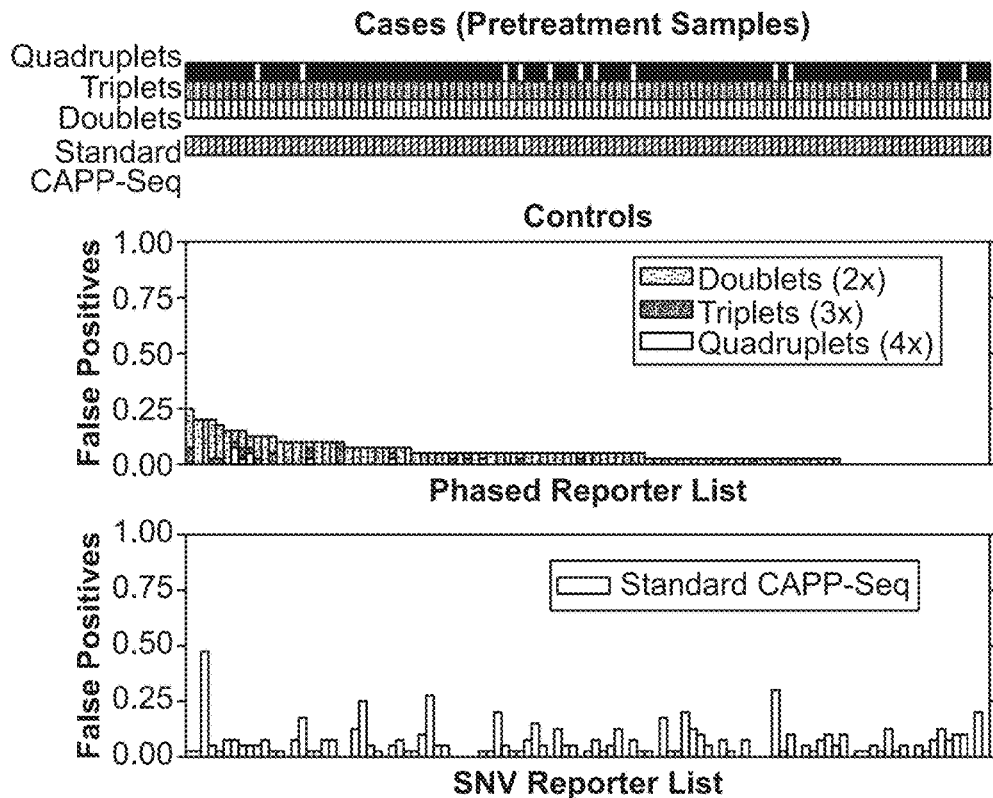
FIGS. 15 and 16A-16B illustrates comparison of ctDNA quantitation by PhasED-Seq to CAPP-Seq and clinical applications.
Figure 16A:
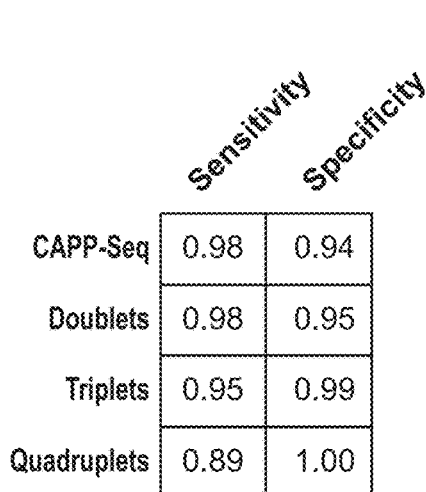
Figure 16B:
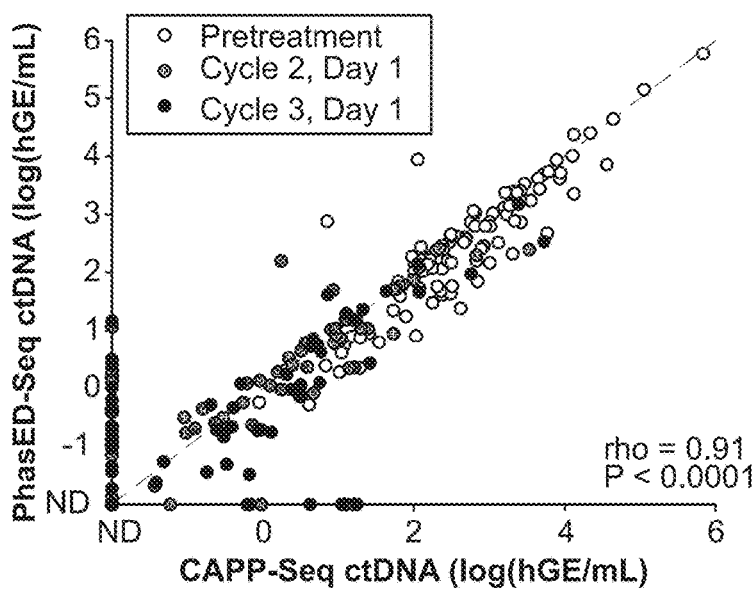
Figure 18A:
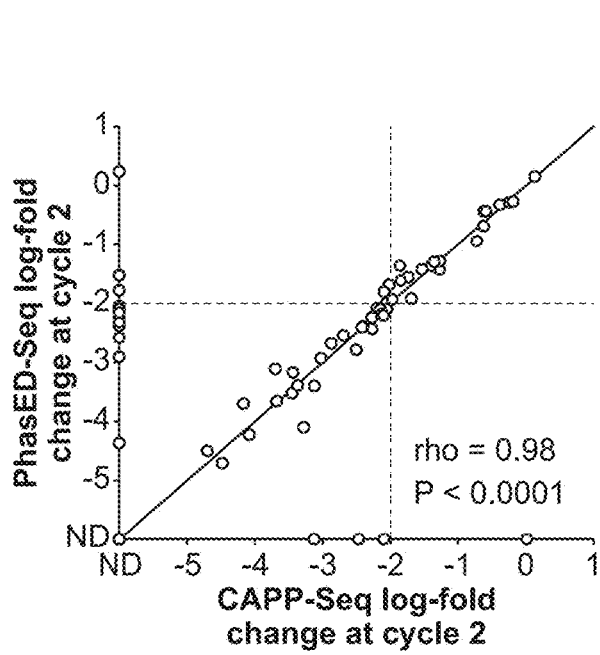
Figure 18B:
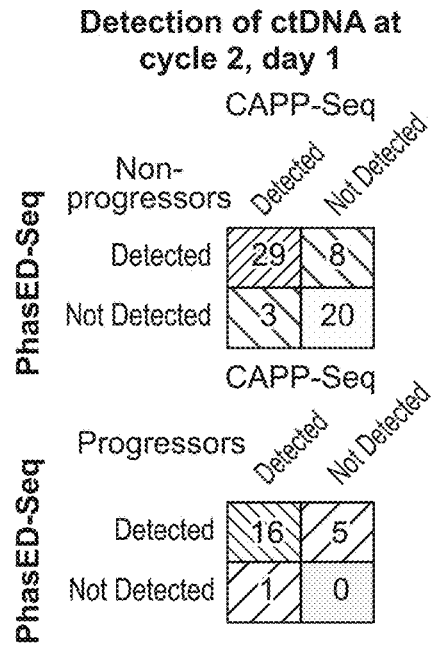
Figure 18C:
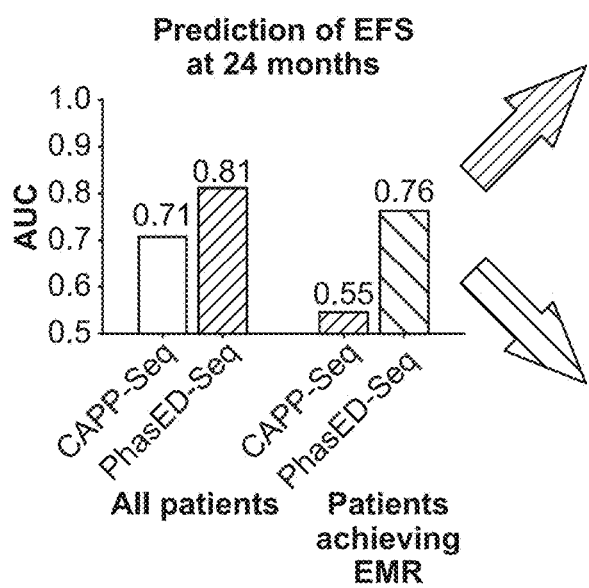
Figure 18D:
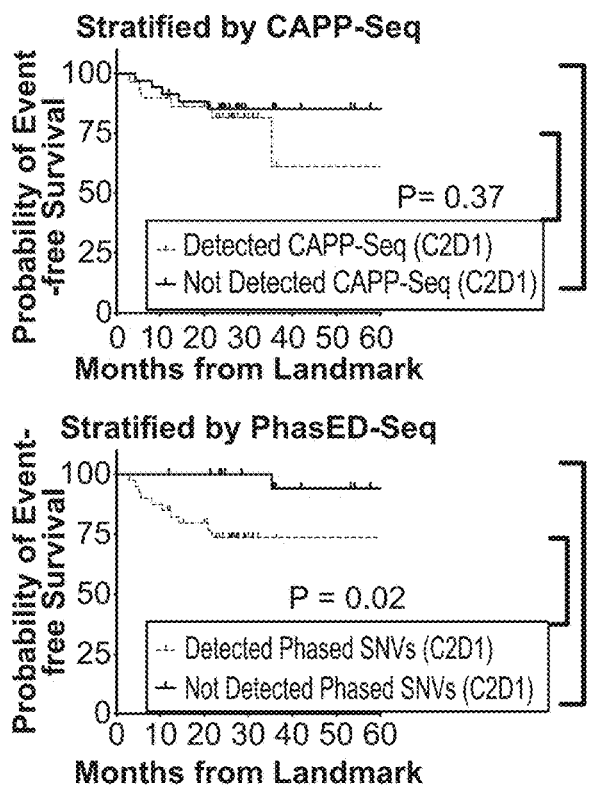

Next, the performance of PhasED-Seq ctDNA detection in a cohort of 107 patients with large B-cell lymphomas and blood samples available after 1 or 2 cycles of standard immuno-chemotherapy was next assessed. Importantly, ctDNA levels measured by PhasED-Seq were highly correlated with those measured by CAPP-Seq. In total, 443 tumor, germ-line, and cell-free DNA samples, including cfDNA prior to therapy (n=107) and after 1 or 2 cycles of treatment (n=82 and 89), were assessed. Prior to therapy, patient-specific PVs were detectable by PhaseED-Seq in 98% of samples, with 95% specificity in cfDNA from healthy controls (FIGS. 15 and 16A). Importantly, ctDNA levels measured by PhasED-Seq were highly correlated with those measured by CAPP-Seq, considering both pretreatment and post treatment samples (Spearman rho=0.91, FIG. 16B). Next, quantitative levels of ctDNA measured by PhasED-Seq and CAPP-Seq from cfDNA samples after initiation of therapy were compared. In total, 72% ($78/108$) of samples with detectable ctDNA by PhasED-Seq after 1 or 2 cycles were also detected by conventional CAPP-Seq (FIG. 4B). Among 108 samples detected by PhasED-Seq, disease burden was significantly lower for those with undetectable (28%) vs. detectable (72%) ctDNA levels using conventional CAPP-Seq, with a >10× difference in median ctDNA levels (tumor fraction $2.2 \times 10^4$ vs $1.2 \times 10^5$, P<0.001, FIG. 4B). In total, an additional 16% ($13/82$) of samples after 1 cycle of therapy and 19% ($17/89$) of samples after 2 cycles of therapy had detectable ctDNA when comparing PhasED-Seq with CAPP-Seq (FIG. 4C).

ctDNA molecular response criteria was previously described for DLBCL patients using CAPP-Seq, including Major Molecular Response (MMR), defined as a 2.5-log reduction in ctDNA after 2 cycles of therapy22. While MMR at this time-point is prognostic for outcomes, many patients have undetectable ctDNA by CAPP-Seq at this landmark (FIGS. 4D-4E). Importantly, even in patients with undetectable ctDNA by CAPP-Seq, detection of occult ultra-low ctDNA levels by PhasED-Seq was prognostic for outcomes including event-free and overall survival (FIG. 4D). Indeed, in the 89 patients with a sample available from this time-point, 58% ($52/89$) had undetectable ctDNA by CAPP-Seq at their interim MMR assessment, after completing 2 of 6 planned cycles of therapy. Using PhasED-Seq, 33% ($17/52$) of samples not detected by CAPP-Seq had evidence of ctDNA as evidenced by PVs, with levels as low as ~3:1,000,000 (FIGS. 17A-17D)—these 17 cases additionally detected by PhasED-Seq represent potential false negative tests by CAPP-Seq. Similar results were seen at the Early Molecular Response (EMR) time-point (i.e., after 1 cycle of therapy, FIGS. 18A-18H).

While detection of ctDNA in DLBCL after 1 or 2 cycles of therapy is a known adverse prognostic marker outcomes for patients with undetectable ctDNA at these time-points are heterogeneous (FIG. 4E and FIG. 18F). Importantly, even in patients with undetectable ctDNA by CAPP-Seq after 1 or 2 cycles of therapy, detection of ultra-low ctDNA levels by PhasED-Seq was strongly prognostic for outcomes including event-free survival (FIG. 4F, FIGS. 17C-D, FIGS. 18C-D, and FIG. 18G). When combining detection by PhasED-Seq with previously described MMR threshold, patients could be stratified into three groups—patients not achieving MMR, patients achieving MMR but with persistent ctDNA, and patients with undetectable ctDNA (FIG. 4G). Interestingly, while patients not achieving MMR were at especially high risk for early events despite additional planned first line therapy (e.g., within the first year of treatment), patients with persistent low levels of ctDNA appeared to have a higher risk of later relapse or progression events. In contrast, patients with undetectable ctDNA after 2 cycles of therapy by PhasED-Seq had overwhelmingly favorable outcomes, with 95% being event-free and 97% overall survival at 5 years. Similar results were seen at the EMR time-point after 1 cycle of therapy (FIG. 1811).

Example 9: Exemplary Embodiments of Mutation Detection Using Next Generation Sequencing (NGS) when the Mutation is not a Single Base Substation, but Rather a Pair of Mutations In many instances, a limitation of cfDNA tracking may be the limitation on the number of molecules available for detection. Additionally, there are multiple potential limitations on tracking tumor molecules from cell-free DNA, including not only the sequencing error profile, but also the number of molecules available for detection. The number of molecules available for detection—here termed the number of "evaluable fragments"—can be thought of as both a function of the number of recovered unique genomes (e.g., unique depth of sequencing) and the number of somatic mutations being tracked. More specifically, the number of evaluable fragments is equal to: $EF=d*n$.

Where d=the unique molecular depth considered and n=the number of somatic alterations tracked. For the typical cell-free DNA samples, less than 10,000 unique genomes are often recovered (d), requiring any sensitive method to track multiple alterations (n). Furthermore, as stated above, the major limitation for duplex sequencing is difficulty recovering sufficient unique molecular depth (d); thus, from a typical plasma sample with duplex depth of ~1,500×, even if following 100 somatic alterations, there are only 150,000 evaluable fragments. Thus, in this scenario, sensitivity is limited by the number of molecules available for detection. In contrast, other methods such as iDES-enhanced CAPP-Seq consider all molecules recovered. Here, as many as 5,000-6,000× unique haploid genomes can be recovered. Therefore, the number of evaluable fragments, tracking the same 100 somatic alterations, may be 500,000-600,000×. However, the error profile of single-stranded sequencing, even with error suppression, allows detection to levels of at best 1 part in 50,000. Therefore, methods aiming to improve on the detection limits for ctDNA must overcome both the error-profile of sequencing and the recovery of sufficient evaluable fragments to utilize said lower error-profiles.

To remedy this apparent deficiency, the method of PhasED-Seq, as described in the instant disclosure, allows for lymphoid malignancies and was applicable to other cancer histologies, (e.g., using a "personalized" approach). For a personalized approach, customized hybrid-capture oligonucleotides (or primers for PCR amplicons) were used to capture personalized somatic mutations identified from whole exome or genome sequencing. The PCAWG dataset assessed for SNVs occurring within 170 bp of each other in genomic space was re-analyzed. It was found that in 14 of 24 cancer histologies considered, the median case contained >100 possible phased variants, including in several solid tumors such as Melanoma (median 2072), lung squamous cell carcinoma (1268), lung adenocarcinoma (644.5), and colorectal adenocarcinoma (216.5).

Figure 19:
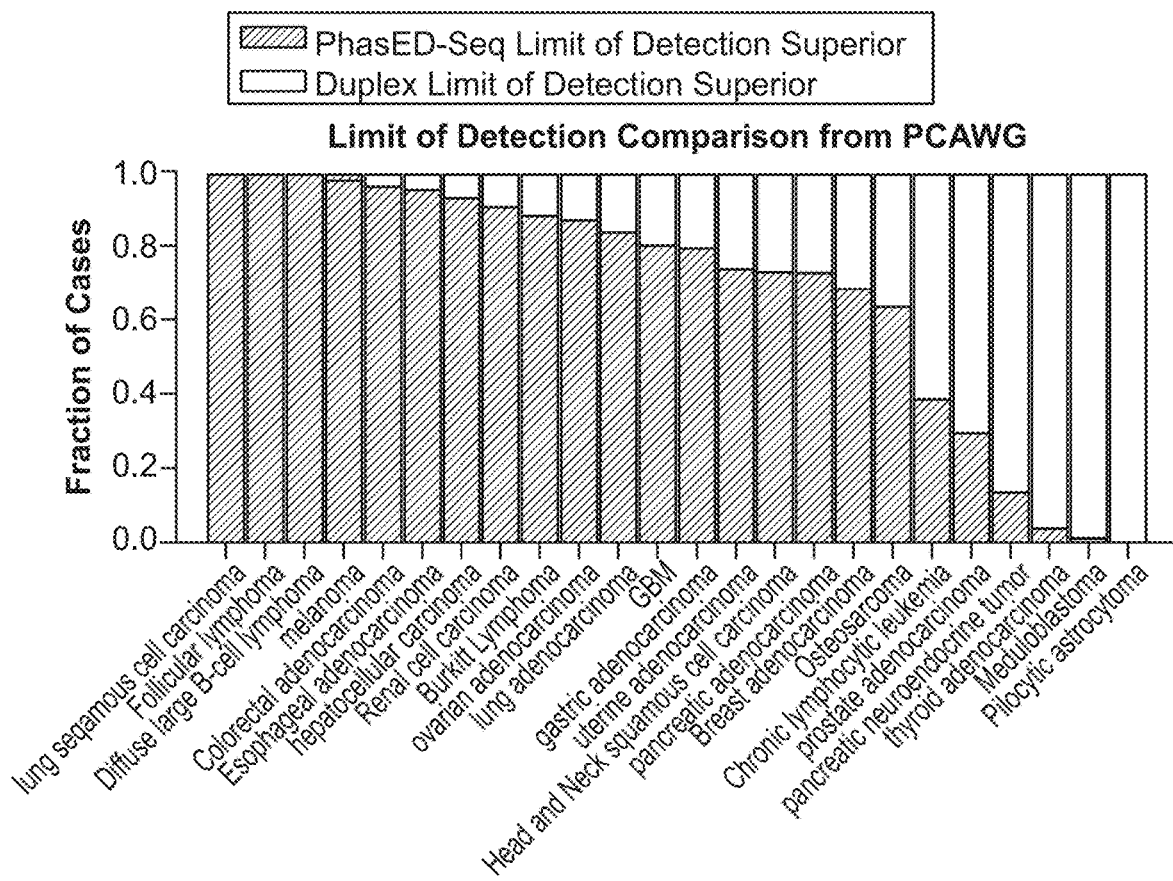
FIG. 19 illustrates a fraction of patients where PhasED-Seq would achieve a lower LOD than duplex sequencing tracking SNVs based on PCAWG data (whole genome sequencing) from which the number of SNVs and phased variants (PVs) in different tumor types was quantified.
Figure 20:
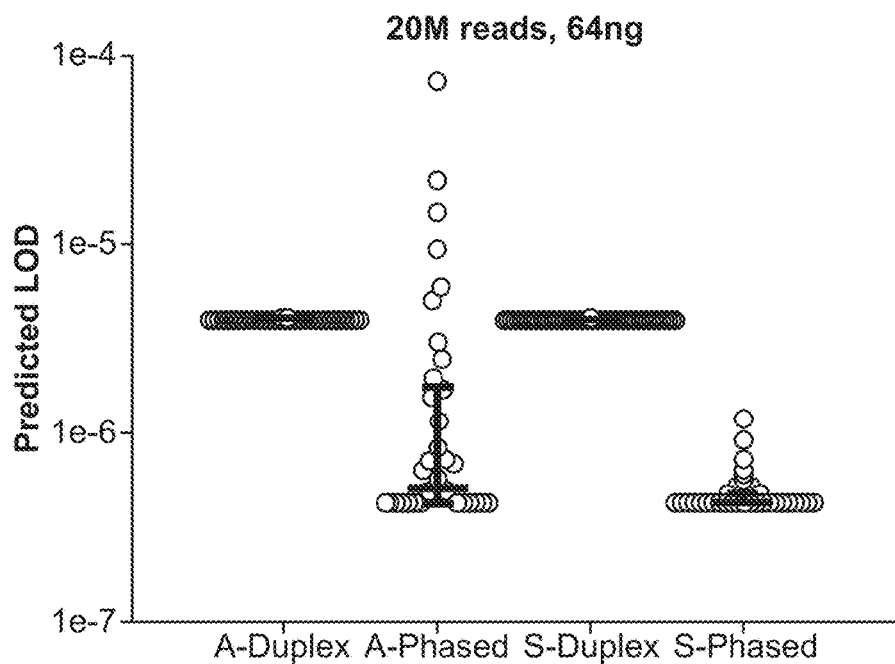
FIG. 20 illustrates improved LODs achieved in lung cancers (adenocarcinoma, abbreviated 'A', and squamous cell carcinoma, abbreviated 'S'), compared to duplex sequencing of whole genome sequencing data.

Next, the expected limit of detection in all cases in the PCAWG dataset using either duplex sequencing or PhasED-Seq was assessed. Again, the limit of detection was defined by the expected number of evaluable fragments, and thus depends on both the number of variants tracked and the expected depth of sequencing. Utilizing the data from optimized hybrid capture conditions, a model to predict the expected deduplicated (single-stranded) and duplex (double-stranded) molecular depth with a given DNA input and number of sequencing reads was constructed. Using this, along with the number of SNVs or possible PVs from the PCAWG dataset, for each case, which method would lead to a greater number of evaluable fragments, and therefore a superior limit of detection was assessed. The results of this exercise, assuming 64 nanograms (ng) of total cfDNA input and a total of 20 million sequencing reads are shown in FIG. 19. Notably, in the majority of cancer types (18/24 histologies), PhasED-Seq had a lower limit of detection than duplex sequencing. This importantly included not only B-cell lymphomas, but common solid tumors, including lung squamous cell carcinoma and adenocarcinoma, colorectal adenocarcinoma, esophageal and gastric adenocarcinoma, and breast adenocarcinoma, among others. Indeed, taking lung cancers as a specific example, an almost 10-fold lower limit of detection was found for the median squamous cell and adenocarcinoma lung cancer case using PhasED-Seq compared to duplex sequencing (FIG. 20). Both PhasED-Seq and duplex sequencing using a personalized approach had a lower limit of detection than non-personalized approaches (e.g., iDES-enhanced CAPP-Seq).

Figure 21:
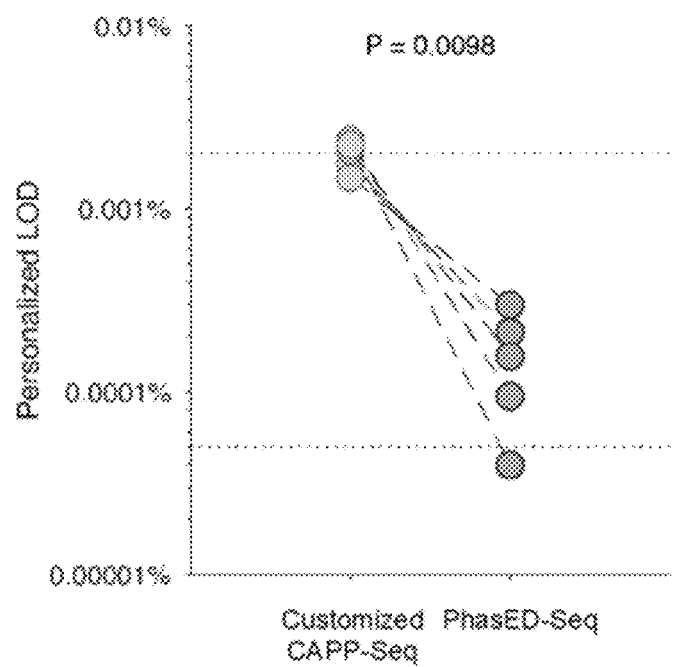
FIG. 21 illustrates empiric data from an experiment where WGS was performed on tumor tissue and custom panels were designed for 5 patients with solid tumors (5 lung cancers) to examine and compare the LODs of custom CAPP-Seq vs PhasED-Seq, showing a ~10× lower LOD using PhasED-Seq in 5/5 patients.

To further confirm the applicability of phased variants and PhasED-Seq in diverse solid tumors, WGS (20-30×) was performed on paired tumor and normal DNA to identify PVs from five solid tumor patients predicted to have low ctDNA burden prior to treatment (lung cancer (n=5)). After identifying putative PVs in each case, a set of personalized hybrid capture oligonucleotides was subsequently designed to performed targeted resequencing of tumor and normal DNA to validate candidate PVs. Finally, plasma samples were sequenced from all 5 patients to high unique molecular depth using personalized PhasED-Seq to detect ctDNA. Considering these five lung cancer cases the PhasED-Seq approach achieved a ~10-fold improvement in analytical sensitivity, achieving a median LOD of 0.00018% compared to 0.0019% using customized CAPP-Seq (FIG. 21).

Figure 22A:
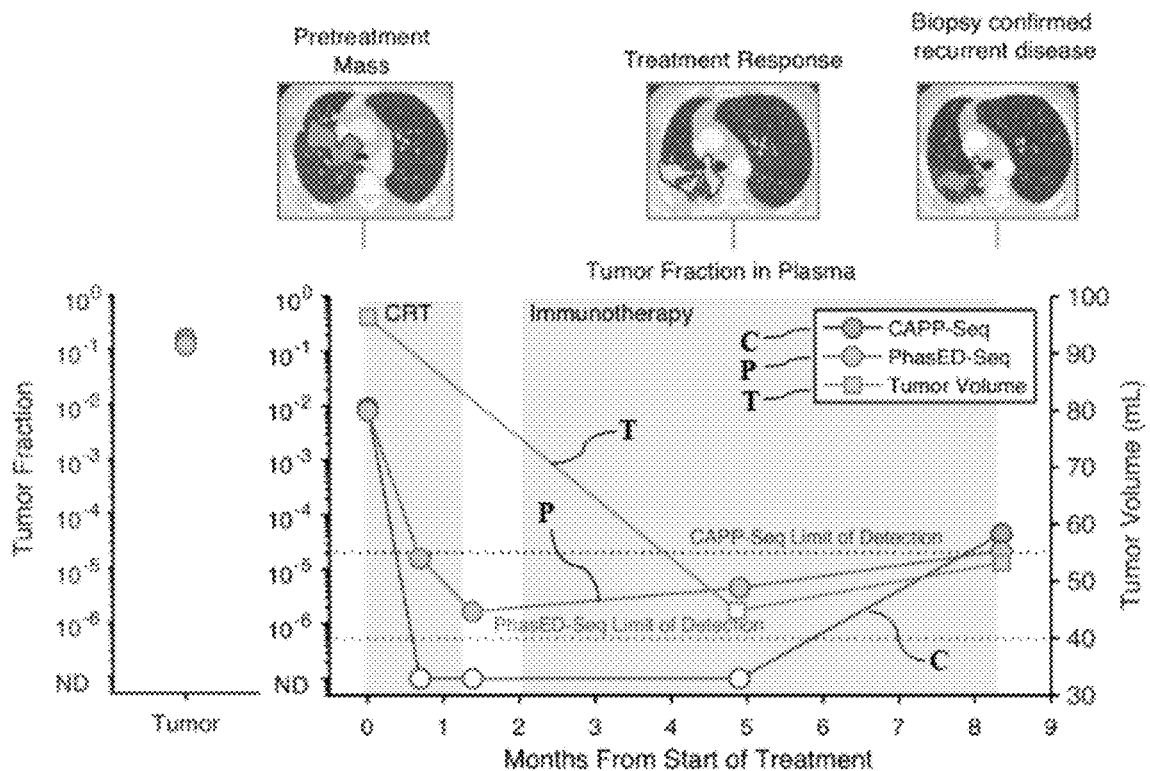
FIG. 22A illustrates proof of principle example patient vignette comparing using custom CAPP-Seq and PhasED-Seq for disease surveillance in lung cancer showing earlier detection of relapse using PhasED-Seq.
Figure 22B:
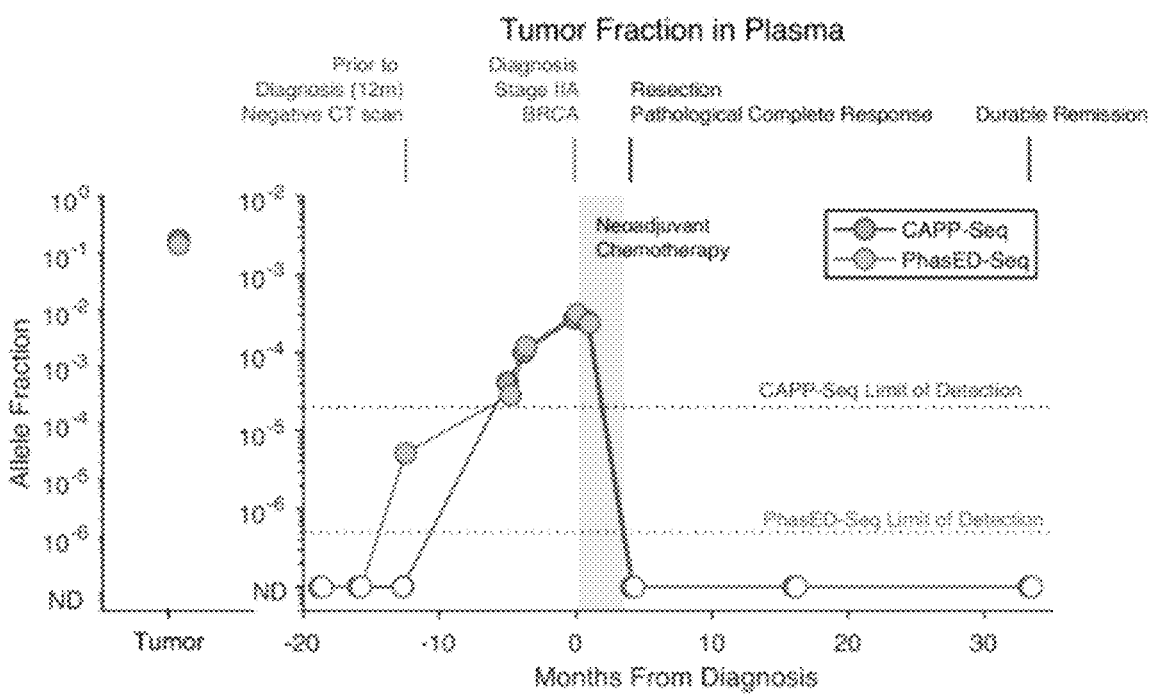
FIG. 22B illustrates proof of principle example patient vignette comparing using custom CAPP-Seq and PhasED-Seq for early detection of disease in breast cancer, showing earlier detection of disease with PhasED-Seq.

To demonstrate the clinical significance of this improved limit of detection for ctDNA from PhasED-Seq in solid tumors, serial plasma samples from a patient with stage 3 adenocarcinoma of the lung treated with chemoradiotherapy with curative intent (LUP814) were analyzed using both CAPP-Seq and PhasED-Seq. As outlined above, both CAPP-Seq and PhasED-Seq quantified a similar level of ctDNA prior to therapy (~1% tumor fraction). However, 3 subsequent samples after beginning therapy had undetectable ctDNA by standard CAPP-Seq, including samples during and after chemoradiation and during adjuvant immunotherapy with Durvalumab. Despite the lack of detectable disease by CAPP-Seq, the patient had biopsy-confirmed recurrent disease after an initial radiographic response. However, when analyzing these same samples with PhasED-Seq, molecular residual disease in 3/3 (100%) of samples was detected, with mean tumor fraction as low as 0.00016% (1.6 parts per million). Furthermore, the trend in ctDNA quantitation mirrored the patient's disease course, with an initial response to chemoradiotherapy but disease progression during immunotherapy. Importantly, this patient's disease remained detectable at all timepoints, with detectable disease at the completion of chemoradiotherapy 8 months prior to the patient's biopsy-confirmed disease progression (FIG. 22).

Figures 5A, 5B:
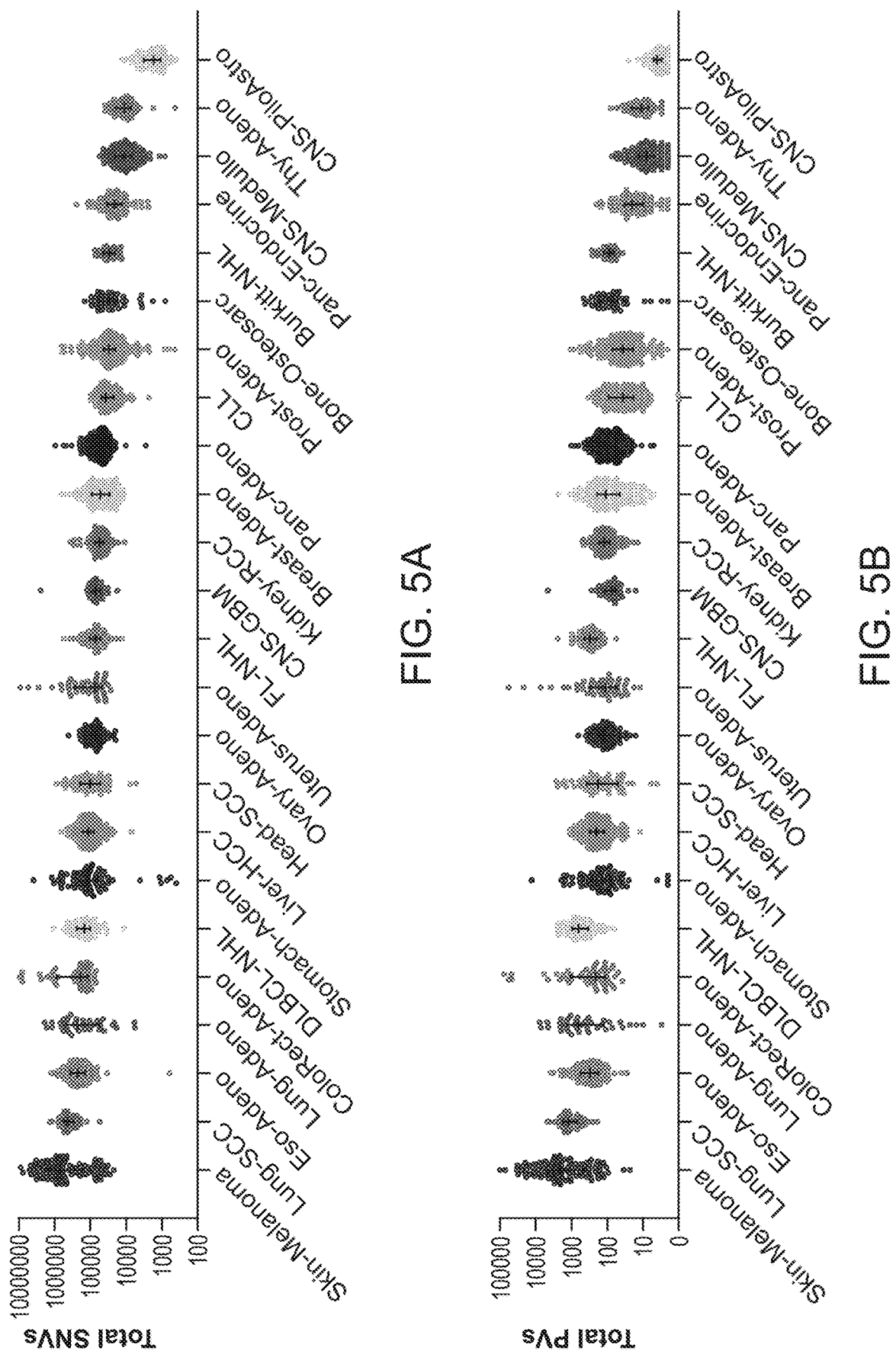
FIGS. 5A-5C illustrate enumeration of SNVs and PVs in diverse cancers from WGS.
Figure 5C:
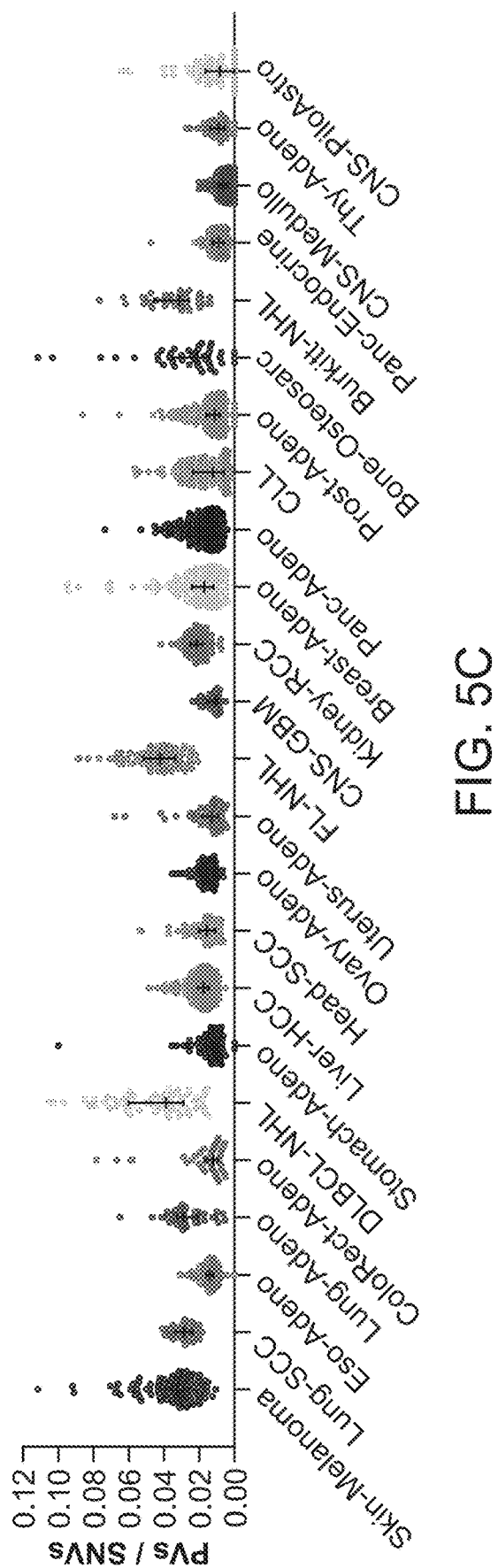

Example 10: Methods of Phased Variant Enrichment for Enhanced Disease Detection from Cell-Free DNA 10(a): Whole-Genome Sequencing Analysis 10(a)(1): Whole-Genome Sequencing Data Putative Phased Variant Identification Whole-genome sequencing data were obtained from two sources. Data for lymphoid malignancies (diffuse large B-cell lymphoma, DLBCL; follicular lymphoma, FL; Burkitt lymphoma, BL; chronic lymphocytic leukemia, CLL) were downloaded from the International Cancer Genome Consortium (ICGC) data portal on May 7, 2018. Data from all other histologies were part of the pan-Cancer analysis of whole genomes (PCAWG) and downloaded on Nov. 11, 2019. Only cancer histologies with at least 35 available cases were considered; details of the dataset considered are provided in Table 1. All samples had somatic mutations called from WGS using matched tumor and normal genotyping. Queries were limited to base substitutions obtained from WGS (single, double, triple, and oligo nucleotide variants; SNVs, DNVs, TNVs, and ONVs). Having thus identified the cases and variants of interest, the number of putative phased variants (PVs) in each tumor was next identified. To function as a PV on a single cell-free DNA (cfDNA) molecule, two variants, such as two single nucleotide variants (SNVs) generally must occur within a genomic distance less than the length of a typical cfDNA molecule (~170 bp). Therefore, putative PVs were defined as two variants occurring on the same chromosome within a genomic distance of <170 bp. DNVs, TNVs, and ONVs were considered as the set of their respective component SNVs. The number of SNVs as well as the identity of putative PVs for each case are detailed in Table 1. The raw number of SNVs and putative PVs, as well as the number of putative PVs controlling for the number of SNVs, is shown in FIG. 5A-C.

10(a)(2): Mutational Signatures of Phased Variants from WGS

To assess the mutational processes associated with phased and non-phased mutations across different cancer types/subtypes, the mutational signatures of single base substitutions (SBS) were enumerated for each WGS case described above using the R package 'deconstructSigs'. The list of SNVs for each patient was first divided into two groups: 1) SNVs contained within a possible PV; that is, with an adjacent or 'nearest neighbor' SNV <170 bp away, and 2) isolated SNVs (i.e., non-phased), defined as those occurring ≥170 bp in distance from the closest adjacent SNV. 'DeconstructSigs' was then applied using the 49 SBS signatures described in COSMIC (excluding signatures linked to possible sequencing artefacts) to assess the contribution of each SBS signature to both candidate phased SNVs and un-phased SNVs for each patient. To compare the contribution of each SBS signature to phased and isolated SNVs, a Wilcoxon signed rank test was performed to compare the relative contribution of each SBS signature between these two categories for each cancer type (FIGS. 6A-6WW). To account for multiple hypotheses, Bonferroni's correction was applied, by considering any SBS signature that differed in contribution to phased vs. un-phased SNVs to be significant if the Wilcoxon signed rank test resulted in a P-value of <0.05/49 or 0.001. The distributions of these comparisons, along with significance testing, are depicted in FIGS. 6A-6WW. A summary of this analysis is also shown in FIG. 1C using a heat-map display, where the 'heat' represents the difference between the mean contribution of the SBS signature to phased variants to the mean contribution to isolated/un-phased variants.

10(a)(3): Genomic Distribution of Phased Variants from WGS

The recurrence frequency for PVs was assessed in each cancer type across the genome within each tumor type. Specifically, the human genome (build GRCh37/hg19) was first divided into 1-kb bins (3,095,689 total bins); then, for each sample, the number of PVs (as defined above) contained in each 1-kb bin was counted. For this analysis, any PV with at least one of its constituent SNVs falling within the 1-kb bin of interest was included. The fraction of patients whose tumors harbored a PV for each cancer type within each genomic bin was then calculated. To identify 1-kb bins recurrently harboring PVs across patients, the fraction of patients containing PVs in each 1-kb bin vs. genomic coordinates (FIG. 1D and FIG. 7) was plotted; for this analysis, only bins where at least 2% of samples contained a PV in at least one cancer subtype were plotted.

10(a)(4): Identification of Recurrent 1-kb Bins with Phased Variants

To identify 1-kb bins that recurrently contain PVs in B-lymphoid malignancies, WGS data was utilized from the following diseases: DLBCL, FL, BL, and CLL. Any 1-kb bin where >1 sample from these tumor types was considered to recurrently contain PVs from B-lymphoid malignancies. The genomic coordinates of 1-kb bins containing recurrent PVs in lymphoid malignancies are enumerated in Table 2, and are plotted in FIG. 8A.

10(b): Design of PhasED-Seq Panel for B-Lymphoid Malignancies

10(b)(1): Identification of Recurrent PVs from WGS Data at Higher Resolution

Given the prevalence of recurrent putative PVs from WGS data in B-cell malignancies, a targeted sequencing approach was designed for their hybridization-mediated capture—Phased variant Enrichment Sequencing (PhasED-Seq)—to enrich these specific PV events from tumor or cell-free DNA. In addition to the ICGC data described above, WGS data was also utilized from other sources in this design, including both B-cell NHLs as well as CLL.

Previous experience with targeted sequencing from cfDNA in NHLs was also examined. Pairs of SNVs occurring at a distance of <170 bp apart in each B-cell tumor sample were identified. Then, genomic "windows" that contained PVs was identified as follows: for each chromosome, the PVs were sorted by genomic coordinates relative to reference genome. Then, the lowest (i.e., left-most) position was identified for any PV in any patient; this defined the left-hand (5') coordinate seeding a desired window of interest, to be captured from the genome. This window was then extended by growing its 3' end to capture successive PVs until a gap of ≥340 bp was reached, with 340-bp chosen as capturing two successive chromatosomal sized fragments of ~170-bp. When such a gap was reached, a new window was started, and this iterative process of adding neighboring PVs was repeated again until the next gap of ≥340 bp was reached. This resulted in a BED file of genomic windows containing all possible PVs from all samples considered. Finally, each window was additionally padded by 50 bp on each side, to enable efficient capture from flanking sequences in rare scenarios when repetitive or poorly mapping intervening sequences might preclude their direct targeting for enrichment.

Having identified the regions of interest containing putative PVs, each window was then into 170 bp segments (e.g., the approximate size of a chromatosomal cfDNA molecule). Then, the number of cases containing a PV was enumerated in each case. For each 170 bp region, the region in final sequencing panel design was included if one or more of the following criteria was met: 1) at least one patient contained a PV in the 170 bp region in 3 of 5 independent data-sets, 2) at least one patient contained a PV in the region in 2 of 5 independent data-sets if one dataset was prior CAPP-Seq experience, or 3) at least one patient contained a PV in the region in 2 of 5 independent data-sets, with a total of at least 3 patients containing a PV in the region. This resulted in 691 'tiles', with each tile representing a 170 bp genomic region. These tiles, along with an additional ~200 kb of genomic space targeting driver genes recurrently mutated in B-NHL, were combined into a unified targeted sequencing panel as previously described for both tumor and cfDNA genotyping using NimbleDesign (Roche NimbleGen). The final coordinates of this panel are provided in Table 3.

10(b)(2): Comparison of PhasED-Seq and CAPP-Seq Performance in PV Yield

To evaluate the performance of PhasED-Seq for capturing both SNVs and PVs compared to previously reported CAPP-Seq selector for B-cell lymphomas, the predicted number of both SNVs and PVs that may be recovered with each panel by limiting WGS in silico to the capture targets of each approach (FIG. 9A-C) was quantified. The predicted number of variants was then compared using the Wilcoxon signed rank test. Both CAPP-Seq and PhasED-Seq were also performed on 16 samples from patients with DLBCL. In these samples, tumor or plasma DNA, along with matched germline DNA, was sequenced. The resulting number of variants were again compared by the Wilcoxon signed rank text (FIG. 2B, and FIGS. 9D-9E). The sequencing depth for the samples included in this analysis are provided in Tables 4.

10(c): Identification of Phased Variants from Targeted Sequencing Data

10(c)(1): Patient Enrollment and Clinical Sample Collection

Patients with B-cell lymphomas undergoing front-line therapy were enrolled on this study from six centers across North America and Europe, including Stanford University, MD Anderson Cancer Center, the National Cancer Institute, University of Eastern Piedmont (Italy), Essen University Hospital (Germany), and CHU Dijon (France). In total, 343 cell-free DNA, 73 tumor, and 183 germ-line samples from 183 patients were included in this study. All patient samples were collected with written informed consent for research use and were approved by the corresponding Institutional Review Boards in accordance with the Declaration of Helsinki. Cell-free, tumor, and germ-line DNA were isolated as previously described. All radiographic imaging was performed as part of standard clinical care.

10(c)(2): Library Preparation and Sequencing

To generate sequencing libraries and targeted sequencing data, CAPP-Seq was applied as previously described. Briefly, cell-free, tumor, and germ-line DNA were used to construct sequencing libraries through end repair, A-tailing, and adapter ligation following the KAPA Hyper Prep Kit manufacturer's instructions with ligation performed overnight at 4° C. CAPP-Seq adapters with unique molecular identifiers (UMIDs) were used for barcoding of unique DNA duplexes and subsequent deduplication of sequencing read pairs. Hybrid capture was then performed (SeqCap EZ Choice; NimbleGen) using the PhasED-Seq panel described above. Affinity capture was performed according to the manufacturer's protocol, with all 47° C. hybridizations conducted on an Eppendorf thermal cycler. Following enrichment, libraries were sequenced using an Illumina HiSeq4000 instrument with 2×150 bp paired-end (PE) reads.

10(c)(3): Pre-Processing and Alignment

FASTQ files were de-multiplexed and UMIDs were extracted using a custom pipeline as previously described. Following demultiplexing, reads were aligned to the human genome (build GRCh37/hg19) using BWA ALN. Molecular barcode-mediated error suppression and background polishing (i.e., integrated digital error suppression; iDES) were then performed as previously described.

10(c)(4): Identification of Phased Variants and Allelic Quantitation

After generating UMID error-suppressed alignment files (e.g., BAM files), PVs were identified from each sample as follows. First, matched germ-line sequencing of uninvolved peripheral blood mononuclear cells (PBMCs) was performed to identify patient-specific constitutional single nucleotide polymorphisms (SNPs). These were defined as non-reference positions with a variant allele fraction (VAF) above 40% with a depth of at least 10, or a VAF of above 0.25% with a depth of at least 100. Next, PVs were identified from read-level data for a sample of interest. Following UMID-mediated error suppression, each individual paired-end (PE) read and identified all non-reference positions were using 'samtools calmd'. PE data was used rather than single reads to identify variants occurring on the same template DNA molecule, which may subsequently fall into either read 1 or read 2. Any read-pair containing ≥2 non-reference positions was considered to represent a possible somatic PV. For reads with ≥2 non-reference positions, each permutation of size ≥2 was considered independently: i.e., if 4 non-reference positions were identified in a read-pair, all combinations of 2 SNVs (i.e., 'doublet' phased variants) and all combinations of 3 SNVs (i.e., 'triplet' phased variants) were independently considered. PVs containing putative germ-line SNPs were also removed as follows: if in a given n-mer (i.e., n SNVs in phase on a given molecule) ≥n−1 of the component variants were identified as germ-line SNPs, the PV was redacted. This filtering strategy ensures that for any remaining PV, at least 2 of the component SNVs were not seen in the germ-line, as relevant for both sensitivity and specificity.

Putative somatic PVs were filtered using a heuristic blacklisting approach in considering sequencing data from 170 germ-line DNA samples serving as controls. In each of these samples, PVs were identified on read-pairs as described above, but without filtering for matched germ-line. Any PV that occurred in one or greater paired-end read, in one or more of these control samples, was included in the blacklist and removed from patient-specific somatic PV lists.

To calculate the VAF of each PV, a numerator representing the number of DNA molecules containing a PV of interest was calculated over a denominator representing the total number of DNA molecules that covered the genomic region of interest. That is, the numerator is simply the total number of deduplicated read-pairs that contain a given PV while the denominator is the number of read-pairs that span the genomic locus of a given PV.

10(c)(5): Genotyping Phased Variants from Pretreatment Samples

The above strategy resulted in a list of PVs of ≥1 read-depth in each sample. To identify PVs serving as tumor-specific somatic reporters for disease monitoring, for each case a 'best genotyping' specimen—either DNA from a tumor tissue biopsy (preferred), or pretreatment cell-free DNA was identified. After identifying all possible PVs in the 'best genotyping sample', the list for specificity was further filtered as follows. For any n-mer PV set, if ≥n−1 of the constituent SNVs were present as germ-line SNPs in the 170 control samples described above, the PV was removed. Furthermore, only PVs that meet the following criteria were considered: 1) AF>1%; 2) depth of the PV locus of ≥100 read-pairs, and 3) at least one component SNV must be in the on-target space. Finally, 4) any PV meeting these criteria was assessed for read-support in a cohort of 12 healthy control cfDNA samples. If any read-support was present in >1 of these 12 samples, the PV was removed. For genotyping from cell-free DNA samples identified as low tumor fraction by SNVs (i.e., <1% mean AF across all SNVs), the AF threshold for determining PVs was relaxed to >0.2%. This filtering resulted in the PV lists used for disease monitoring and MRD detection.

10(c)(6): Determination of Tumor Fraction in a Sample from Phased Variants

For evaluation of a sample for minimal residual disease (MRD) detection with prior knowledge of the tumor genotype, the presence of any PV identified in the best pretreatment genotyping sample in the MRD sample of interest can be assessed. Given a list of k possible tumor-derived PVs observed in the best genotyping sample, all read-pairs covering at least 1 of the k possible PVs were determined. This value, d, can be thought of as the aggregated 'informative depth' across all PVs spanned by cfDNA molecules in a PhasED-Seq experiment. It was then assessed how many of these d read-pairs actually contained 1 or more of the k possible PVs—this value, x, represents the number of tumor-derived molecules containing somatic PVs in a given sample. The number of tumor-derived molecules containing PVs divided by the informative depth—x/d—is therefore the phased-variant tumor fraction (PVAF) in a given sample. For detection of MRD in each sample, PVAF was calculated independently for doublet, triplet, and quadruplet PVs.

10(c)(7): Monte Carlo Simulation for Empirical Significance of PV Detection within a Specimen To assess the statistical significance of the detection of tumor-derived PVs in any sample, an empiric significance testing approach was implemented. A test statistic f was first defined as follows—from a given list of k possible tumor-derived PVs observed in the best genotyping sample, the arithmetic mean of allele fractions was calculated across all k PVs (allele fraction defined as the number of read-pairs containing an individual PV ($x_i$) over the number of read-pairs spanning the PV positions ($d_i$)):

$$f = \frac{\sum_{i=1}^{k} \frac{x_i}{d_i}}{k} \tag{1}$$

to assess the hypothesis that f is not significantly different from the background error-rate of similar PVs assessed from the same sample. A Monte Carlo approach was used to develop a null distribution and perform statistical testing as follows:

1. Given a set of k PVs, $\{pv_1 \ldots pv_i \ldots pv_k\}$, an 'alternate' list of PVs, $\{pv'_1 \ldots pv''_i \ldots pv'_k\}$, was generated such that for each alternate PV had the same type of base change and distance between SNVs as the test PV. For example, if a doublet PV, chr14:106329929 C>T and chr14:106329977 G>A, was identified in the genotyping sample and searched for an alternate two positions at the same genomic distance (here, 48 bp) with reference bases C and G, and assessed for read-pairs with the same types of base changes (i.e., C>T and G>A), using the heuristic search scheme below.
2. For each tumor $pv_i$ in the set of k, 50 such alternates were identified. This was performed with a random search algorithm to scan the genomic space and identify alternates. To find these 50 alternates, a random position on the same chromosome as the test $pv_i$ was identified and then searched for the same types of reference bases at the same genomic distance as described above. Synteny of observed/alternate PVs was used to control for regional variation in SHM/aSHM as well as copy number variation, as potential confounders of the null distribution. Alternate positions that were identified as a germ-line SNP, defined as having AF>5%, were excluded.
3. After identifying 50 such alternates for each $pv_i$, 10,000 random permutations of 1 alternate were generated for each of the k original PVs and calculated the phased-variant fraction f' for these alternate lists in the sample of interest being evaluated for presence of MRD, as described above.
4. An empiric P-value was calculated, defined as the fraction of times the true phased-variant fraction f is observed to be less than or equal to the alternate f' across the 10,000 random PV lists as an empirical measure of significance of MRD significance in the blood sample of interest.

While this resulting comparison is a measure of the significance for PV detection of tumor-reporter list compared to the empirically defined background PV error-rate within the sample of interest, its relationship to specificity of detection across cases and control samples was also evaluated, as described below.

10(c)(8): Assessment of Specificity of PhasED-Seq

To determine the specificity of disease and MRD detection through PhasED-Seq, patient-specific PVs from 107 patients with DLBCL were first identified using pretreatment tumor or plasma DNA along with paired germ-line samples. 40 independent plasma DNA samples were then assessed from healthy individuals for presence of these patient-specific PVs, using the Monte Carlo approach outlined above. A threshold for P-values was empirically determined from Monte Carlo such that 95% specificity was achieved for disease detection from doublet, triplet, and quadruplet PVs. The P-value threshold yielding ≥95% specificity for each size of PV was as follows: <0.041 for doublets, <1 for triplets, and <1 for quadruplets. The results of this specificity in control cfDNA analysis is shown in FIGS. 15 and 16.

10(c)(9): Calculation of Error Rates

To assess the error profile of both isolated SNVs and PVs, the non-reference base observation rate of each type of variant was examined across all reads. For isolated SNVs, the error-rate for each possible base change $e_{n1>n1'}$ was calculated as the fraction of on-target bases with reference allele n1 that are mutated to alternate allele n1', when considering all possible base-changes of the reference allele. Positions with a non-reference allele rate exceeding 5% were classified as probable germ-line events, and excluded from the error-rate analysis. A global error rate, defined as the rate of mutation from the hg19 reference allele to any alternate allele, was also calculated.

For phased variants, a similar calculation was performed. For the error-rate of a given type of phased variant composed of k constituent base-changes $\{e_{n1>n1'} \ldots e_{nk>nk'}\}$, the error-rate was calculated by determining both the number of instances of the type of base change (i.e., the numerator), as well as the number of possible instances for the base change (i.e., the denominator). To calculate the numerator, N, the number of occurrences of the PV of interest over all read-pairs was counted in a given sample. For example, to calculate the error-rate of C>T and G>A phased doublets, the number of read-pairs that include both a reference C mutated to a T as well as a reference G mutated to an A was first counted.

To calculate the denominator, D, the number of possible instances of this type of phased variant was also calculated; this was performed first for each read-pair i, and then summed over all read pairs. A PV with k components can be summarized as having certain set of reference bases $p_A$, $p_C$, $p_G$, $p_T$, where $p_N$ is the number of each reference base in the PV. Similarly, a given read pair contains a certain set of reference bases $b_A$, $b_C$, $b_G$, $b_T$, where $b_N$ is the number of each reference base in the read pair. Therefore, for each read pair in a given sample, the number of possible occurrences of PV type of interest can be calculated combinatorially as:

$$D_i = \binom{b_A}{p_A}\binom{b_C}{p_C}\binom{b_G}{p_G}\binom{b_T}{p_T} \tag{2}$$

For example, consider a read-pair with 40 reference As, 50 reference Cs, 45 reference Gs, and 35 reference Ts. The number of positions for a C>T and G>A PV is:

$$D_i = \binom{40}{0}\binom{50}{1}\binom{45}{1}\binom{35}{0} = 2250 \tag{3}$$

The aggregated denominator, D, for error rate calculation is then simply the sum of this value over all read pairs. The error rate for this type of PV is then simply ND.

10(d): Differences in Phased Variants Between Lymphoma Subtypes

To compare the distribution of phased variants in different types of lymphomas, tumor-specific PVs were identified in 101 DLBCL, 16 PMBCL, and 23 cHL patients via sequencing of tumor biopsy specimens and/or pre-treatment cell-free DNA and paired germ-line specimens. After identifying these tumor-specific PVs, their distribution was the assessed across the targeted sequencing panel. The panel was first divided into 50 bp bins; for each patient, it was then determined if each patient had evidence of a PV within the 50 bp bin, defined as having at least one component of the PV within the bin. The nearest gene to each 50 bp bin was further determined, based on GENCODEv19 annotation of the reference genome.

To assess how the distribution of PVs between subtypes of lymphoma varies at the level of specific genes, the distribution of PVs was examined across the 50 bp bins spanning each gene (or nearest gene). For example, consider a given gene with n such 50 bp bins represented in targeted sequencing panel. For each bin, it was first determined the fraction of patients, f, in each type of lymphoma with a PV falling within the 50 bp bin—i.e., determining $\{f_{type1,1}, \ldots f_{type1,n}\}$ and $\{f_{type2,1}, \ldots f_{type2,n}\}$. Then, any two histologies were then compared for the fraction of cases harboring PVs in the set of 50 bp bins assigned to each gene. These comparisons are depicted for individual genes on gene-specific plots in FIG. 2D and FIGS. 10-12.

The enrichment in PVs was statistically compared in a specific lymphoma type or subtype vs. another by calculating the difference in the fraction of patients which contain a PV in each 50 bp bin across all bins assigned to a gene (i.e., overlapping a given gene or with a given nearest gene). Specifically, for any comparison between two lymphoma types (type$_1$ and type$_2$), this set of differences in PV-rate was first identified between histologies $\{f_{type1,1} - f_{type2,1}, \ldots f_{type1,n} - f_{type2,n}\}$. This set of gene-specific differences in frequency of PVs was the compared between types of lymphoma against the distribution of all other 50 bp bins in the sequencing panel by the Wilcoxon rank sum test. For this test, the set of n 50 bp bins assigned to a given gene was compared to all other 50 bp bins (i.e., 6755–n, since there are 6755 50 bp bins in sequencing panel). This P-value, along with the mean difference in fraction of patients with a PV in each bin for each gene between histologies, is depicted as a volcano plot in FIG. 2E. To account for the global difference in rate of PVs between different histologies, the mean difference in fraction of patients with a PV between histologies was centered on 0 by subtracting the mean difference across all genes.

10(e): Hybridization Bias

To assess the effect of mutations on hybridization efficiency, the affinity of mutated molecules to wildtype capture baits in silico was first estimated by considering DNA fragments harboring 0-30% mutations across the entire fragment. For each mutation condition across this range, 10,000 regions were first randomly sampled, each 150 bp in length, from across the whole genome. These 150-mers were then mutated in silico to simulate the desired mutation rate in 3 different ways: 1) mutating 'clustered' or contiguous bases starting from the ends of a sequence, 2) mutating clustered bases started from the middle of the sequence, or 3) mutating bases selected at random positions throughout the sequence. The energy.c package was then used to calculate the theoretical binding energy (kcal/mol) between the mutated and wild-type sequences, in relying on a nearest-neighbor model employing established thermodynamic parameters (FIG. 14A).

This in silico experiment was then replicated by testing the effects of same mutation rates in vitro. Specifically, oligonucleotides (IDT) were synthesized and annealed to form DNA duplexes harboring 0-10% mutations at defined positions relative to the human reference genome sequence. These synthetic DNA molecules were then captured together at equimolar concentrations and quantified the relative capture efficiency of mutated duplexes compared to the wild-type, unmutated species (FIG. 3A). Two sets of oligonucleotide sequences were selected from coding regions of BCL6 and MYC to capture AID-mediated aberrant somatic hypermutations associated with each gene (Table 5); the preserved mappability of the mutated species was ensured by BWA ALN. These synthetic oligonucleotide duplexes were then subjected to library preparation, then captured and sequenced using PhasED-Seq, performed in triplicate using distinct samples. This allowed assessment of the relative efficiency of hybrid capture and molecular recovery as directly compared to wildtype molecules identical to the reference genome.

10(f): Assessment of Limit of Detection with Limiting Dilution Series

To empirically define the analytical sensitivity of PhasED-Seq, a limited dilution series of cell-free DNA from 3 patients that were spiked into healthy control cell-free DNA at defined concentrations was utilized. The dilution series contained samples with an expected mean tumor fraction of 0.1%, 0.01%, 0.001%, 0.0002%, 0.0001%, and 0.00005% or ranging from 1 part in 1,000 to 1 part in 2,000,000. The sequencing characteristics and ctDNA quantification via CAPP-Seq, duplex sequencing, and PhasED-Seq are provided. To compare the performance of each method, the difference was calculated, δ, between the observed and expected tumor fraction for each patient i at each dilution concentration j:

$$\delta_{i,j} = \overline{tumorfrac}_{i,j} - tumorfrac_{i,j} \qquad (4)$$

This value was calculated for patients i={1,2,3} and concentrations j={0.001%, 0.0002%, 0.0001%, 0.00005%} for each ctDNA detection method (CAPP-Seq, duplex, doublet PhasED-Seq, and triplet PhasED-Seq). The performance of each method was then compared to each other by paired t-test across this set of patients and concentrations.

10(g): Model to Predict the Probability of Detection for a Given Set of Phased Variants To build a mathematical model to predict the probability of detection for a given sample of interest, it began with the common assumption that cfDNA detection can be considered a random process based on binomial sampling. However, unlike SNVs occurring at large genomic distances apart from one another, detection of PVs can be highly inter-dependent, especially when PVs are degenerate (i.e., when two PVs share component SNVs) or occur in close proximity. To account for this, only PVs occurring >150 bp apart from each other was considered as independent 'tumor reporters'. The number of 'tumor reporters' to allow for disease detection in a given sample can thus be determined as follows. The PhasED-Seq panel was broken apart into 150 bp bins. Each PV in a given patient's reporter list was then turned into a BED coordinate, consisting of the start position (defined as the left-most component SNV) and end position (defined as the right-most component SNV). For each PV, the 150 bp bin from the PhasED-Seq selector panel containing the PV was determined; if a PV spanned two or more 150 bp bins, it was assigned to both bins. The number of independent tumor reporters was then defined as the number of separate 150 bp bins containing a tumor-specific PV.

A mathematical model was then developed comparing the expected probability of detection for a given sample at a given tumor fraction with a given number of independent tumor reporters (e.g., 150 bp bins). With a given number of tumor reporters r, at a given tumor fraction f, with a given sequencing depth d, the probability of detecting 1 or more cell-free DNA molecule containing a tumor-specific PV containing can be defined as:

$$Pr(\text{detection}) = 1 - Pr(\text{nondetection}) \qquad (5)$$

$$= 1 - \binom{d*r}{0} f^0 (1-f)^{d*r}$$

based on simple binomial sampling. However, as ctDNA detection method was trained to have a 5% false positive rate, this false positive rate term was added to the model as well:

$$Pr(\text{detection}) = 1 - Pr(\text{nondetection}) + 0.05 * Pr(\text{nondetection}) \quad (7)$$

$$Pr(\text{detection}) = 1 - 0.95 * Pr(\text{nondetection}) \quad (8)$$

$$= 1 - 0.95 * \binom{d*r}{0} f^0 (1-f)^{d*r} \quad (9)$$

FIG. 3G shows the results of this model for a range of tumor reporters r from 3 to 67 at depth d of 5000. The confidence envelope on this plot shows solutions for a range of depth d from 4000 to 6000.

To empirically validate this model assessing the probability of disease detection, samples from limiting dilution series were utilized. In this dilution series, 3 patient cfDNA samples, each containing patient-specific PVs, were spiked into healthy control cfDNA. For each list of patient specific PVs, 25 random subsamplings of the 150 bp bins containing patient-specific PVs were performed to generate reporter lists containing variable numbers of tumor-specific reporters. A maximum bin number of 67 was selected to allow sampling from all 3 patient-specific PV lists, followed by scaling down the number of bins by 2× or 3× per operation. This resulted in reporter lists containing patient-specific PVs from 3, 6, 17, 34, or 67 independent 150 bp bins. Disease detection was then assessed using each of these patient-specific PV lists of increasing size in each of 'wet' limiting dilution samples from 1:1,000 to 1:1,000,000 (FIG. 3H, closed circles). In silico mixtures was further created using sequencing reads from limiting dilution samples with varying expected tumor-content, and again assessed for the probability of disease detection using patient-specific sub-sampled PV reporter lists of varying lengths (open circles). For this experiment, both the 'wet' and 'in-silico' dilution bam files were down-sampled to achieve a depth of ~4000-6000× to correspond with modeled depth. The final mean and standard deviation of depth across all down-sampled bam files was 4214×±789. The probability of detection was summarized across all tests at a given expected tumor fraction, for a given patient-specific PV list. For each given dilution, multiple independently sampled sets of reads were considered to allow superior estimation of the true probability of detection. Specifically, the following number of replicates at each dilution indicated was considered in Table 7.

TABLE 7

Replicates at each dilution for predicting the probability of detection for a given set of phased variants.

| Dilution | Replicates | Number of Tests (Replicates * 25) | Wet or In silico |
|---|---|---|---|
| 1:1,000 | 1 | 25 | Wet |
| 5:10,000 | 3 | 75 | In silico |
| 3.5:10,000 | 3 | 75 | In silico |
| 2:10,000 | 3 | 75 | In silico |
| 1:10,000 | 3 | 75 | Wet |
| 5:100,000 | 3 | 75 | In silico |
| 3.5:100,000 | 3 | 75 | In silico |
| 2:100,000 | 3 | 75 | In silico |
| 1:100,000 | 3 | 75 | Wet |
| 5:1,000,000 | 8 | 200 | In silico |

TABLE 7-continued

Replicates at each dilution for predicting the probability of detection for a given set of phased variants.

| Dilution | Replicates | Number of Tests (Replicates * 25) | Wet or In silico |
|---|---|---|---|
| 3.5:1,000,000 | 8 | 200 | In silico |
| 2:1,000,000 | 8 | 200 | Wet |
| 1:1,000,000 | 8 | 200 | Wet |

The total number of tests, for each patient-specific PV list, is therefore the number of randomly subsampled PV lists (e.g., 25) times the number of independently downsampled bam files; this number is provided in the table above. In FIG. 3H, the points and error-bars represent the mean, minimum, and maximum across all three patients. The concordance between the predicted probability of disease detection from theoretical mathematical model and wet and in silico samples validating this model, is shown in FIG. 3I.

10(h): Statistical Analyses & Software Availability

All P-values reported in this manuscript are 2-sided unless otherwise noted. Comparisons of matched samples and populations were performed using the Wilcoxon signed rank test; comparisons of samples drawn from unrelated populations were performed using the Wilcoxon rank-sum test. Comparisons of paired samples were performed by paired t-test. Survival probabilities were estimated using the Kaplan-Meier method; survival of groups of patients based on ctDNA levels were compared using the log-rank test. Other statistical tests are noted in the manuscript text where utilized. All analyses were performed with the use of MAT-LAB, version 2018b, R Statistical Software version 3.4.1, and GraphPad Prism, version 8.0.2. The contribution of known mutational processes to phased and isolated SNVs from WGS was assessed with the deconstruct Sigs R package using the COSMIC signature set (v2) as described. Calculation of AUC accounting for survival and censorship was performed using the R 'survivalROC' package version 1.0.3 with default settings. An executable version of the PhasED-Seq software, developed in C++ 17, is available at phasedseq(dot)stanford(dot)edu.

Example 11

Additional details of the tables described throughout the present disclosure are provided herein:

TABLE 1: 1000 bp regions of interest throughout the genome containing putative phased variants (PV) in various lymphoid neoplasms. Only regions containing >1 subject with a PV are shown. Coordinates are in hg19. Regions from genes that were previously identified as targets of activation-induced deaminase (AID) are labeled. Regions that contain PVs in >5% of subjects in any histology (BL, CLL, DLBCL, FL) are also labeled. BL, Burkitt lymphoma; CLL, chronic lymphocytic leukemia; DLBCL, diffuse large B-cell lymphoma; FL, follicular lymphoma.

TABLE 2: 1000 bp regions of interest throughout the genome containing putative phased variants (PV) in the ABC and GCB subtypes of DLBCL. Only regions containing >1 subject with a PV are shown. Coordinates are in hg19. Regions from genes that were previously identified as targets of AID are labeled. ABC, activated B-cell subtype; GCB, germinal center B-cell subtype.

TABLE 3: Regions used for the PhasED-Seq capture reagent described in this paper focused on lymphoid malignancies. Coordinates are in hg19. The closest gene and the reason for inclusion (Phased Variants vs general DLBCL genotyping) is also shown.

TABLE 4: Enrichment of PVs at genetic loci throughout the PhasED-Seq targeted sequencing panel for different types of B-cell lymphomas (DLBCL including ABC and GCB subtypes, PMBCL, and cHL). The PhasED-Seq selector was binned into 50 bp bins in hg19 coordinates, and each bin was labelled by gene or nearest gene. The mean of the fraction of cases of a given histology with a PV across all 50 bp bins is shown. Significance was determined by rank-sum (Mann-Whitney U) test of 50 bp bins for a given gene against the remainder of the sequencing panel. Uncorrected P-values are shown; multiple-hypothesis testing correction was performed by Bonferroni method. DLBCL, diffuse large B-cell lymphoma; PMBCL, primary mediastinal B-cell lymphoma; cHL, classical Hodgkin lymphoma; ABC, activated B-cell DLBCL; GCB, germinal center B-cell DLBCL.

TABLE 5: Sequences of oligonucleotides synthesized to assess hybridization and molecular recovery bias with increasing mutational burden (SEQ ID NOs. 1331-1358).

TABLE 6: Nucleic acid probes for Capture Sequencing of B-cell Cancers (SEQ ID NOs. 0001-1330).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

TABLE 1

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 1 | chr1 | 756000 | 757000 | 0.028 | 0.000 | 0.015 | 0.000 | AL669831.1 | 0.47887 | 1.00000 | 0.29694 | 0 | 0 |
| 2 | chr1 | 1963000 | 1964000 | 0.028 | 0.000 | 0.015 | 0.000 | GABRD | 0.47887 | 1.00000 | 0.29694 | 0 | 0 |
| 3 | chr1 | 2052000 | 2053000 | 0.028 | 0.000 | 0.000 | 0.014 | PRKCZ | 1.00000 | 0.34615 | 1.00000 | 0 | 0 |
| 4 | chr1 | 3789000 | 3790000 | 0.000 | 0.000 | 0.029 | 0.014 | DFFB | 0.22755 | 0.54294 | 0.08726 | 0 | 0 |
| 5 | chr1 | 6614000 | 6615000 | 0.000 | 0.000 | 0.044 | 0.014 | NOL9 | 0.34966 | 0.54966 | 0.02537 | 0 | 1 |
| 6 | chr1 | 6614000 | 6615000 | 0.000 | 0.000 | 0.088 | 0.027 | NOL9 | 0.15270 | 0.09031 | 0.00058 | 1 | 1 |
| 7 | chr1 | 6661000 | 6662000 | 0.000 | 0.000 | 0.029 | 0.014 | KLHL21 | 0.60686 | 0.54294 | 0.08726 | 0 | 0 |
| 8 | chr1 | 6662000 | 6663000 | 0.000 | 0.000 | 0.044 | 0.014 | KLHL21 | 0.34948 | 0.54966 | 0.02537 | 0 | 0 |
| 9 | chr1 | 9129000 | 9130000 | 0.000 | 0.000 | 0.000 | 0.014 | SLC2A5 | 0.10727 | 0.54966 | 1.00000 | 0 | 0 |
| 10 | chr1 | 10894000 | 10895000 | 0.028 | 0.000 | 0.000 | 0.014 | C1orf127 | 1.00000 | 0.34615 | 1.00000 | 0 | 0 |
| 11 | chr1 | 17019000 | 17020000 | 0.028 | 0.000 | 0.015 | 0.014 | AL137798.1 | 1.00000 | 0.34615 | 1.00000 | 0 | 0 |
| 12 | chr1 | 17231000 | 17232000 | 0.000 | 0.000 | 0.015 | 0.014 | CROCC | 1.00000 | 1.00000 | 0.08726 | 0 | 0 |
| 13 | chr1 | 19935000 | 19936000 | 0.000 | 0.000 | 0.029 | 0.000 | MINOS1-NBL1 | 0.22755 | 0.54294 | 0.08726 | 0 | 0 |
| 14 | chr1 | 21091000 | 21092000 | 0.000 | 0.000 | 0.015 | 0.014 | HPTBP3 | 1.00000 | 1.00000 | 0.29694 | 0 | 0 |
| 15 | chr1 | 23885000 | 23886000 | 0.444 | 0.000 | 0.015 | 0.000 | ID3 | 0.47887 | 0.00000 | 0.29694 | 1 | 1 |
| 16 | chr1 | 28408000 | 28409000 | 0.000 | 0.000 | 0.029 | 0.000 | EYA3 | 0.22755 | 0.54294 | 0.08726 | 0 | 0 |
| 17 | chr1 | 32373000 | 32374000 | 0.000 | 0.000 | 0.000 | 0.014 | FTP4A2 | 0.22755 | 0.54294 | 1.00000 | 0 | 0 |
| 18 | chr1 | 36722000 | 36723000 | 0.000 | 0.012 | 0.015 | 0.014 | THRAP3 | 0.47887 | 1.00000 | 1.00000 | 0 | 0 |
| 19 | chr1 | 46576000 | 46577000 | 0.000 | 0.000 | 0.015 | 0.014 | PIK3R3 | 1.00000 | 1.00000 | 0.29694 | 0 | 0 |
| 20 | chr1 | 51965000 | 51966000 | 0.000 | 0.006 | 0.015 | 0.000 | EPS15 | 0.47887 | 0.54294 | 0.50663 | 0 | 0 |
| 21 | chr1 | 51978000 | 51979000 | 0.000 | 0.006 | 0.029 | 0.000 | EPS15 | 0.22755 | 0.54294 | 0.08726 | 0 | 0 |
| 22 | chr1 | 51983000 | 51984000 | 0.000 | 0.006 | 0.029 | 0.000 | EPS15 | 0.22755 | 0.54294 | 0.21104 | 0 | 0 |
| 23 | chr1 | 72393000 | 72394000 | 0.000 | 0.000 | 0.015 | 0.014 | NEGR1 | 1.00000 | 1.00000 | 0.29694 | 0 | 0 |
| 24 | chr1 | 73719000 | 73720000 | 0.000 | 0.000 | 0.029 | 0.000 | LRRIQ3 | 0.22755 | 0.54294 | 0.08726 | 0 | 0 |
| 25 | chr1 | 77315000 | 77316000 | 0.028 | 0.000 | 0.000 | 0.000 | ST6GALNAC5 | 1.00000 | 0.34615 | 1.00000 | 0 | 0 |
| 26 | chr1 | 81306000 | 81307000 | 0.000 | 0.006 | 0.015 | 0.014 | LPHN2 | 1.00000 | 1.00000 | 0.29694 | 0 | 0 |
| 27 | chr1 | 81527000 | 81528000 | 0.000 | 0.006 | 0.029 | 0.014 | LPHN2 | 0.22755 | 0.54294 | 0.08726 | 0 | 0 |
| 28 | chr1 | 82009000 | 82010000 | 0.028 | 0.000 | 0.015 | 0.000 | TTLL7 | 0.47887 | 1.00000 | 0.29694 | 0 | 0 |
| 29 | chr1 | 84106000 | 84107000 | 0.028 | 0.000 | 0.015 | 0.000 | HS2ST1; | 0.47887 | 1.00000 | 0.50663 | 0 | 0 |
| 30 | chr1 | 87524000 | 87525000 | 0.000 | 0.006 | 0.015 | 0.000 | HS2ST1;LOC339524; | 0.47887 | 1.00000 | 0.50663 | 0 | 0 |
| 31 | chr1 | 94551000 | 94552000 | 0.000 | 0.000 | 0.029 | 0.000 | ABCA4 | 0.22755 | 0.54294 | 0.08726 | 0 | 0 |
| 32 | chr1 | 94552000 | 94553000 | 0.000 | 0.000 | 0.029 | 0.000 | ABCA4 | 0.22755 | 0.54294 | 0.08726 | 0 | 0 |
| 33 | chr1 | 103696000 | 103697000 | 0.000 | 0.000 | 0.000 | 0.027 | COL11A1 | 0.49735 | 1.00000 | 1.00000 | 0 | 0 |
| 34 | chr1 | 116979000 | 116980000 | 0.000 | 0.000 | 0.044 | 0.041 | ATP1A1 | 1.00000 | 0.54966 | 0.02537 | 0 | 0 |
| 35 | chr1 | 149784000 | 149785000 | 0.000 | 0.000 | 0.015 | 0.014 | HIST2H3D | 1.00000 | 1.00000 | 0.29694 | 0 | 0 |
| 36 | chr1 | 149821000 | 149822000 | 0.000 | 0.000 | 0.044 | 0.000 | HIST2H2AA4 | 0.10727 | 0.54966 | 0.02537 | 1 | 0 |
| 37 | chr1 | 149857000 | 149858000 | 0.000 | 0.000 | 0.015 | 0.014 | HIST2H2BE | 1.00000 | 1.00000 | 0.29694 | 1 | 0 |
| 38 | chr1 | 149858000 | 149859000 | 0.000 | 0.000 | 0.059 | 0.000 | HIST2H2AC;HIST2H2BE; | 0.05016 | 0.29551 | 0.00730 | 0 | 1 |
| 39 | chr1 | 160616000 | 160617000 | 0.000 | 0.000 | 0.015 | 0.014 | SLAMF1 | 1.00000 | 0.54294 | 0.29694 | 0 | 0 |
| 40 | chr1 | 162711000 | 162712000 | 0.000 | 0.000 | 0.015 | 0.014 | DDR2 | 1.00000 | 0.54294 | 0.29694 | 0 | 0 |
| 41 | chr1 | 163684000 | 163685000 | 0.000 | 0.000 | 0.015 | 0.014 | NUF2 | 1.00000 | 1.00000 | 0.29694 | 0 | 0 |
| 42 | chr1 | 167598000 | 167599000 | 0.000 | 0.000 | 0.044 | 0.014 | RCSD1 | 0.34948 | 0.54966 | 0.02537 | 0 | 0 |
| 43 | chr1 | 167599000 | 167600000 | 0.000 | 0.000 | 0.029 | 0.014 | RCSD1 | 0.60686 | 0.54294 | 0.08726 | 0 | 0 |
| 44 | chr1 | 167600000 | 167601000 | 0.000 | 0.000 | 0.044 | 0.000 | RCSD1 | 0.10727 | 0.54966 | 0.02537 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAny Histology |
|---|---|---|---|---|---|---|---|---|---|---|---|---|---|
| 45 | chr1 | 174333000 | 174334000 | 0.000 | 0.000 | 0.015 | 0.014 | RABGAP1L | 1.00000 | 1.00000 | 0.29694 | 0 | 0 |
| 46 | chr1 | 187263000 | 187264000 | 0.000 | 0.000 | 0.044 | 0.000 | PLA2G4A | 0.10727 | 0.54966 | 0.02537 | 0 | 0 |
| 47 | chr1 | 187283000 | 187284000 | 0.028 | 0.000 | 0.029 | 0.000 | PLA2G4A | 0.22755 | 0.54294 | 0.08726 | 0 | 0 |
| 48 | chr1 | 187892000 | 187893000 | 0.000 | 0.000 | 0.015 | 0.000 | PLA2G4A | 0.47887 | 1.00000 | 0.29694 | 0 | 0 |
| 49 | chr1 | 195282000 | 195283000 | 0.000 | 0.000 | 0.015 | 0.014 | KCNT2 | 1.00000 | 1.00000 | 0.29694 | 0 | 0 |
| 50 | chr1 | 198591000 | 198592000 | 0.000 | 0.000 | 0.029 | 0.000 | PTPRC | 0.22755 | 0.54294 | 0.08726 | 0 | 0 |
| 51 | chr1 | 198608000 | 198609000 | 0.000 | 0.000 | 0.029 | 0.000 | PTPRC | 0.22755 | 0.54294 | 0.08726 | 0 | 0 |
| 52 | chr1 | 198609000 | 198610000 | 0.000 | 0.000 | 0.029 | 0.000 | PTPRC | 0.22755 | 0.54294 | 0.08726 | 0 | 0 |
| 53 | chr1 | 202004000 | 202005000 | 0.028 | 0.000 | 0.029 | 0.000 | ELF3 | 0.22755 | 1.00000 | 0.08726 | 0 | 0 |
| 54 | chr1 | 203273000 | 203274000 | 0.000 | 0.000 | 0.029 | 0.000 | BTG2 | 0.22755 | 0.54294 | 0.08726 | 1 | 1 |
| 55 | chr1 | 203274000 | 203275000 | 0.028 | 0.006 | 0.176 | 0.014 | BTG2 | 0.00078 | 0.00730 | 0.00000 | 1 | 1 |
| 56 | chr1 | 203275000 | 203276000 | 0.028 | 0.000 | 0.471 | 0.081 | BTG2 | 0.00000 | 0.00000 | 0.00000 | 1 | 1 |
| 57 | chr1 | 203276000 | 203277000 | 0.000 | 0.000 | 0.059 | 0.000 | BTG2 | 0.05016 | 0.65667 | 0.00730 | 0 | 0 |
| 58 | chr1 | 205780000 | 205781000 | 0.000 | 0.000 | 0.000 | 0.027 | SLC41A1 | 0.49735 | 1.00000 | 1.00000 | 0 | 0 |
| 59 | chr1 | 205781000 | 205782000 | 0.000 | 0.000 | 0.000 | 0.027 | SLC41A1 | 0.49735 | 1.00000 | 1.00000 | 0 | 0 |
| 60 | chr1 | 206283000 | 206284000 | 0.000 | 0.000 | 0.015 | 0.014 | CTSE | 1.00000 | 1.00000 | 0.29694 | 0 | 0 |
| 61 | chr1 | 206286000 | 206287000 | 0.000 | 0.000 | 0.029 | 0.027 | CTSE | 0.60686 | 0.54294 | 0.08726 | 0 | 0 |
| 62 | chr1 | 217044000 | 217045000 | 0.000 | 0.000 | 0.029 | 0.000 | ESRRG | 0.22755 | 0.54294 | 0.08726 | 0 | 0 |
| 63 | chr1 | 226924000 | 226925000 | 0.000 | 0.000 | 0.029 | 0.000 | ITPKB | 0.22755 | 0.54294 | 0.08726 | 1 | 0 |
| 64 | chr1 | 226925000 | 226926000 | 0.000 | 0.000 | 0.044 | 0.000 | ITPKB | 0.10727 | 0.54966 | 0.02537 | 1 | 0 |
| 65 | chr1 | 226926000 | 226927000 | 0.000 | 0.000 | 0.029 | 0.000 | ITPKB | 0.22755 | 0.54294 | 0.08726 | 1 | 0 |
| 66 | chr1 | 229974000 | 229975000 | 0.000 | 0.000 | 0.015 | 0.027 | URB2 | 1.00000 | 1.00000 | 0.29694 | 0 | 0 |
| 67 | chr1 | 235131000 | 235132000 | 0.000 | 0.000 | 0.029 | 0.027 | TOMM20 | 0.49735 | 0.54294 | 0.08726 | 0 | 0 |
| 68 | chr1 | 235141000 | 235142000 | 0.000 | 0.000 | 0.015 | 0.000 | TOMM20 | 1.00000 | 1.00000 | 0.29694 | 0 | 0 |
| 69 | chr1 | 238787000 | 238788000 | 0.000 | 0.000 | 0.029 | 0.000 | MTRNR2L11 | 0.22755 | 0.54294 | 0.08726 | 0 | 0 |
| 70 | chr1 | 248088000 | 248089000 | 0.000 | 0.000 | 0.015 | 0.000 | OR2T5 | 0.47887 | 1.00000 | 0.29694 | 0 | 0 |
| 71 | chr2 | 630000 | 631000 | 0.000 | 0.000 | 0.000 | 0.027 | TMEM18 | 0.49735 | 1.00000 | 1.00000 | 0 | 0 |
| 72 | chr2 | 1484000 | 1485000 | 0.000 | 0.000 | 0.000 | 0.027 | TPO | 1.00000 | 1.00000 | 1.00000 | 0 | 0 |
| 73 | chr2 | 7991000 | 7992000 | 0.056 | 0.000 | 0.000 | 0.000 | RNF144A | 1.00000 | 0.11763 | 1.00000 | 0 | 1 |
| 74 | chr2 | 121173000 | 121174000 | 0.000 | 0.000 | 0.044 | 0.014 | LPIN1 | 0.10727 | 0.54966 | 0.02537 | 0 | 0 |
| 75 | chr2 | 121175000 | 121176000 | 0.000 | 0.000 | 0.029 | 0.000 | LPIN1 | 0.22755 | 0.54294 | 0.08726 | 0 | 0 |
| 76 | chr2 | 122249000 | 122250000 | 0.000 | 0.000 | 0.029 | 0.000 | LPIN1 | 0.22755 | 0.54294 | 0.08726 | 0 | 0 |
| 77 | chr2 | 141113000 | 141114000 | 0.000 | 0.000 | 0.015 | 0.027 | FAM84A | 0.49735 | 1.00000 | 0.29694 | 0 | 0 |
| 78 | chr2 | 175777000 | 175778000 | 0.000 | 0.000 | 0.029 | 0.000 | RAD51AP2 | 0.22755 | 0.54294 | 0.08726 | 0 | 0 |
| 79 | chr2 | 192553000 | 192554000 | 0.000 | 0.000 | 0.029 | 0.000 | OSR1 | 0.22755 | 0.54294 | 0.08726 | 0 | 0 |
| 80 | chr2 | 248802000 | 248803000 | 0.000 | 0.000 | 0.015 | 0.014 | NCOA1 | 1.00000 | 1.00000 | 0.29694 | 0 | 0 |
| 81 | chr2 | 31478000 | 31479000 | 0.000 | 0.000 | 0.000 | 0.014 | EHD3 | 1.00000 | 1.00000 | 1.00000 | 0 | 0 |
| 82 | chr2 | 41728000 | 41729000 | 0.000 | 0.000 | 0.015 | 0.027 | C2orf91 | 1.00000 | 0.54294 | 0.29694 | 0 | 0 |
| 83 | chr2 | 45404000 | 45405000 | 0.000 | 0.000 | 0.000 | 0.027 | SIX2 | 0.49735 | 1.00000 | 1.00000 | 0 | 0 |
| 84 | chr2 | 47923000 | 47924000 | 0.000 | 0.000 | 0.015 | 0.014 | MSH6 | 1.00000 | 1.00000 | 0.29694 | 0 | 0 |
| 00 | chr2 | 47944000 | 47945000 | 0.000 | 0.000 | 0.029 | 0.027 | MSH6 | 0.22755 | 0.54294 | 0.08726 | 0 | 0 |
| 86 | chr2 | 51360000 | 51361000 | 0.000 | 0.000 | 0.015 | 0.014 | NRXN1 | 1.00000 | 1.00000 | 0.29694 | 0 | 0 |
| 87 | chr2 | 51655000 | 51656000 | 0.000 | 0.000 | 0.000 | 0.027 | NRXN1 | 0.49735 | 1.00000 | 1.00000 | 0 | 0 |
| 88 | chr2 | 56565000 | 56566000 | 0.000 | 0.000 | 0.029 | 0.000 | CCDC85A | 0.22755 | 0.54294 | 0.08726 | 0 | 0 |
| 89 | chr2 | 57800000 | 57801000 | 0.000 | 0.000 | 0.015 | 0.014 | VRK2 | 1.00000 | 1.00000 | 0.29694 | 0 | 0 |
| 90 | chr2 | 60779000 | 60780000 | 0.000 | 0.000 | 0.029 | 0.027 | BCL11A | 0.22755 | 0.54294 | 0.08726 | 0 | 0 |
| 91 | chr2 | 60780000 | 60781000 | 0.000 | 0.000 | 0.029 | 0.000 | BCL11A | 0.22755 | 0.54294 | 0.08726 | 0 | 0 |
| 92 | chr2 | 63802000 | 63803000 | 0.000 | 0.000 | 0.000 | 0.027 | WDPCP | 0.49735 | 1.00000 | 1.00000 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 93 | chr2 | 63827000 | 63828000 | 0.000 | 0.000 | 0.015 | 0.014 | MDH1 | 1.00000 | 1.00000 | 0.29694 | 0 | 0 |
| 94 | chr2 | 64319000 | 64320000 | 0.000 | 0.000 | 0.044 | 0.000 | PELI1 | 0.10727 | 0.54966 | 0.02537 | 0 | 0 |
| 95 | chr2 | 65593000 | 65594000 | 0.028 | 0.000 | 0.044 | 0.054 | SPRED2 | 1.00000 | 0.54966 | 0.02537 | 1 | 1 |
| 96 | chr2 | 67002000 | 67003000 | 0.000 | 0.000 | 0.029 | 0.000 | MEIS1 | 0.22755 | 1.00000 | 0.08726 | 0 | 0 |
| 97 | chr2 | 70315000 | 70316000 | 0.083 | 0.000 | 0.000 | 0.000 | PCBP1 | 1.00000 | 0.03921 | 1.00000 | 0 | 1 |
| 98 | chr2 | 79502000 | 79503000 | 0.028 | 0.000 | 0.015 | 0.000 | REG3A | 0.47887 | 1.00000 | 0.29694 | 0 | 0 |
| 99 | chr2 | 79644000 | 79645000 | 0.000 | 0.000 | 0.000 | 0.027 | CTNNA2 | 0.49735 | 1.00000 | 1.00000 | 0 | 0 |
| 100 | chr2 | 81818000 | 81819000 | 0.028 | 0.000 | 0.015 | 0.027 | CTNNA2 | 0.49735 | 1.00000 | 0.29694 | 0 | 0 |
| 101 | chr2 | 82310000 | 82311000 | 0.000 | 0.000 | 0.029 | 0.000 | CTNNA2 | 0.47887 | 1.00000 | 0.08726 | 0 | 0 |
| 102 | chr2 | 82948000 | 82949000 | 0.000 | 0.000 | 0.029 | 0.000 | SUCLG1 | 0.22755 | 1.00000 | 0.08726 | 0 | 0 |
| 103 | chr2 | 85335000 | 85336000 | 0.000 | 0.000 | 0.000 | 0.027 | TCF7L1 | 0.49735 | 1.00000 | 1.00000 | 0 | 0 |
| 104 | chr2 | 83905000 | 88906000 | 0.000 | 0.000 | 0.059 | 0.000 | EIF2AK3 | 0.05016 | 0.29551 | 0.00730 | 0 | 1 |
| 105 | chr2 | 88906000 | 88907000 | 0.000 | 0.000 | 0.074 | 0.014 | EIF2AK3 | 0.10420 | 0.16101 | 0.00953 | 0 | 1 |
| 106 | churz | 88907000 | 88908000 | 0.000 | 0.000 | 0.059 | 0.000 | EIF2AK3 | 0.05016 | 0.29551 | 0.00730 | 0 | 1 |
| 107 | chr2 | 89052000 | 89053000 | 0.000 | 0.000 | 0.015 | 0.000 | RP1A | 0.47887 | 1.00000 | 0.00730 | 0 | 0 |
| 108 | ch-2 | 89065000 | 89066000 | 0.000 | 0.006 | 0.015 | 0.027 | RP1A | 1.00000 | 1.00000 | 0.50663 | 0 | 0 |
| 109 | chr2 | 89066000 | 89067000 | 0.000 | 0.000 | 0.015 | 0.014 | RP1A | 0.03985 | 1.00000 | 0.29694 | 0 | 0 |
| 110 | chr2 | 89095000 | 89096000 | 0.000 | 0.000 | 0.015 | 0.014 | RP1A | 1.00000 | 1.00000 | 0.29694 | 0 | 0 |
| 111 | chr2 | 89127000 | 89128000 | 0.000 | 0.006 | 0.147 | 0.041 | IGKC | 0.01224 | 0.01404 | 0.00003 | 0 | 1 |
| 112 | chr2 | 89128000 | 89129000 | 0.028 | 0.006 | 0.176 | 0.041 | IGKC | 0.01224 | 0.03142 | 0.00000 | 1 | 1 |
| 113 | chr2 | 89129000 | 89130000 | 0.000 | 0.000 | 0.044 | 0.041 | IGKC | 1.00000 | 0.54966 | 0.02537 | 0 | 0 |
| 114 | chu2 | 89130000 | 89131000 | 0.000 | 0.000 | 0.059 | 0.000 | IGKC | 0.10727 | 0.54966 | 0.00730 | 0 | 0 |
| 115 | chr2 | 89131000 | 89132000 | 0.000 | 0.006 | 0.029 | 0.014 | IGKC | 0.22755 | 0.54966 | 0.08726 | 0 | 0 |
| 116 | chr2 | 89132000 | 89133000 | 0.000 | 0.000 | 0.015 | 0.014 | IGKC | 1.00000 | 1.00000 | 0.50663 | 0 | 0 |
| 117 | chr2 | 89133000 | 89134000 | 0.000 | 0.006 | 0.029 | 0.041 | IGKC | 1.00000 | 0.54294 | 0.29694 | 0 | 0 |
| 118 | chr2 | 89137000 | 89138000 | 0.000 | 0.000 | 0.044 | 0.014 | IGKC | 0.34948 | 0.54966 | 0.02537 | 0 | 0 |
| 119 | chr2 | 89138000 | 89139000 | 0.000 | 0.000 | 0.015 | 0.014 | IGKC | 1.00000 | 1.00000 | 0.29694 | 0 | 0 |
| 120 | chr2 | 89139000 | 89140000 | 0.000 | 0.000 | 0.044 | 0.014 | IGKC | 0.34948 | 0.54966 | 0.02537 | 0 | 0 |
| 121 | chr2 | 89140000 | 89141000 | 0.000 | 0.006 | 0.088 | 0.054 | IGKC | 0.52007 | 0.09031 | 0.00058 | 0 | 1 |
| 122 | chr2 | 89141000 | 89142000 | 0.000 | 0.006 | 0.103 | 0.027 | IGKC | 0.08710 | 0.09269 | 0.00099 | 0 | 1 |
| 123 | chr2 | 89142000 | 89143000 | 0.000 | 0.000 | 0.088 | 0.000 | IGKC | 0.01070 | 0.09031 | 0.00058 | 0 | 0 |
| 124 | chr2 | 89143000 | 89144000 | 0.000 | 0.000 | 0.029 | 0.014 | IGKC | 0.22755 | 0.54294 | 0.08726 | 0 | 0 |
| 125 | chr2 | 89144000 | 89145000 | 0.000 | 0.000 | 0.015 | 0.014 | IGKC | 1.00000 | 1.00000 | 0.29694 | 0 | 0 |
| 126 | chr2 | 89145000 | 89146000 | 0.000 | 0.000 | 0.029 | 0.014 | IGKC | 0.60686 | 0.54294 | 0.08726 | 0 | 0 |
| 127 | chr2 | 89146000 | 89147000 | 0.000 | 0.000 | 0.029 | 0.014 | IGKC | 0.60686 | 0.54294 | 0.08726 | 0 | 0 |
| 128 | chr2 | 89153000 | 89154000 | 0.000 | 0.000 | 0.029 | 0.000 | IGKC | 0.22755 | 0.54294 | 0.08726 | 0 | 0 |
| 129 | chr2 | 89155000 | 89156000 | 0.000 | 0.000 | 0.059 | 0.014 | IGKC | 0.19371 | 0.29551 | 0.00730 | 0 | 1 |
| 130 | chr2 | 89156000 | 89157000 | 0.000 | 0.000 | 0.103 | 0.041 | IGKC | 0.02808 | 0.09269 | 0.00016 | 0 | 1 |
| 131 | chr2 | 89157000 | 89158000 | 0.000 | 0.000 | 0.250 | 0.149 | IGKC | 0.14439 | 0.00048 | 0.00000 | 0 | 1 |
| 132 | chr2 | 89158000 | 89159000 | 0.028 | 0.019 | 0.426 | 0.270 | IGKC | 0.05462 | 0.00001 | 0.00000 | 0 | 1 |
| 133 | chr2 | 89159000 | 89160000 | 0.222 | 0.180 | 0.574 | 0.473 | IGKJ5 | 0.24418 | 0.00083 | 0.00000 | 0 | 1 |
| 134 | chr2 | 89160000 | 89161000 | 0.444 | 0.242 | 0.500 | 0.608 | IGKJ3; IGKJ4; IGKJ5; | 0.23729 | 0.68125 | 0.00019 | 0 | 1 |
| 135 | chr2 | 89161000 | 89162000 | 0.222 | 0.081 | 0.265 | 0.405 | IGKJ1; IGKJ2; IGKJI | 0.10957 | 0.81234 | 0.00049 | 0 | 1 |
| 136 | chr2 | 89162000 | 89163000 | 0.056 | 0.012 | 0.221 | 0.108 | IGKJI | 0.10913 | 0.04835 | 0.00000 | 0 | 1 |
| 137 | chr2 | 89163000 | 89164000 | 0.000 | 0.068 | 0.235 | 0.176 | IGKJI | 0.41068 | 0.00098 | 0.00117 | 0 | 1 |
| 138 | chrz | 89164000 | 89165000 | 0.028 | 0.137 | 0.294 | 0.216 | IGKJI | 0.33637 | 0.00075 | 0.00821 | 0 | 1 |
| 139 | chr2 | 89165000 | 89166000 | 0.083 | 0.143 | 0.279 | 0.216 | IGKJI | 0.43812 | 0.02316 | 0.02379 | 0 | 1 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 140 | chr2 | 89166000 | 89167000 | 0.028 | 0.012 | 0.044 | 0.027 | IGKJI | 0.67043 | 1.00000 | 0.15671 | 0 | 0 |
| 141 | chr2 | 89169000 | 89170000 | 0.000 | 0.000 | 0.015 | 0.014 | IGKJI | 1.00000 | 1.00000 | 0.29694 | 0 | 0 |
| 142 | chr2 | 89184000 | 89185000 | 0.000 | 0.006 | 0.015 | 0.054 | IGKV4-1 | 0.36833 | 1.00000 | 0.50663 | 0 | 1 |
| 143 | chr2 | 89185000 | 89186000 | 0.028 | 0.056 | 0.162 | 0.135 | IGKV4-1 | 0.81354 | 0.05349 | 0.01836 | 0 | 1 |
| 144 | chr2 | 89196000 | 89197000 | 0.000 | 0.000 | 0.059 | 0.014 | IGKV5-2 | 0.19371 | 0.29551 | 0.00730 | 0 | 0 |
| 145 | chr2 | 89197000 | 89198000 | 0.000 | 0.000 | 0.000 | 0.027 | IGKV5-2 | 0.49735 | 1.00000 | 1.00000 | 0 | 0 |
| 146 | chr2z | 89214000 | 89215000 | 0.000 | 0.012 | 0.029 | 0.000 | IGKV5-2 | 1.00000 | 1.00000 | 1.00000 | 0 | 0 |
| 147 | chr2 | 89246000 | 89247000 | 0.000 | 0.031 | 0.029 | 0.027 | IGKV1-5 | 1.00000 | 1.00000 | 1.00000 | 0 | 1 |
| 148 | chr2 | 89247000 | 89248000 | 0.028 | 0.019 | 0.118 | 0.054 | IGKV1-5 | 0.23086 | 0.54294 | 0.00321 | 0 | 1 |
| 149 | chr2 | 89248000 | 89249000 | 0.028 | 0.044 | 0.044 | 0.000 | IGKV1-5 | 0.10727 | 0.15803 | 0.02537 | 0 | 0 |
| 150 | chr2 | 89266000 | 89267000 | 0.000 | 0.000 | 0.015 | 0.014 | IGKV1-6 | 1.00000 | 1.00000 | 0.29694 | 0 | 0 |
| 151 | chr2 | 89291000 | 89292000 | 0.000 | 0.019 | 0.029 | 0.000 | IGKV1-8 | 0.22755 | 0.54294 | 0.63492 | 0 | 0 |
| 152 | chr2 | 89292000 | 89293000 | 0.000 | 0.025 | 0.044 | 0.000 | IGKV1-8 | 0.10727 | 0.54966 | 0.42650 | 0 | 0 |
| 153 | chr2 | 89326000 | 89327000 | 0.000 | 0.019 | 0.000 | 0.041 | IGKV3-11 | 0.24603 | 1.00000 | 0.55662 | 0 | 0 |
| 154 | chr2 | 89327000 | 89328000 | 0.000 | 0.012 | 0.015 | 0.027 | IGKV3-11 | 1.00000 | 1.00000 | 1.00000 | 0 | 0 |
| 155 | chr2 | 89442000 | 89443000 | 0.111 | 0.050 | 0.074 | 0.122 | IGKV3-20 | 0.40586 | 0.71556 | 0.53493 | 0 | 1 |
| 156 | chr2 | 89443000 | 89444000 | 0.000 | 0.000 | 0.015 | 0.041 | IGKV3-20 | 0.62100 | 1.00000 | 0.29694 | 0 | 0 |
| 157 | chr2 | 89476000 | 89477000 | 0.028 | 0.000 | 0.000 | 0.014 | IGKV2-24 | 1.00000 | 0.34615 | 1.00000 | 0 | 0 |
| 158 | chr2 | 89513000 | 89514000 | 0.000 | 0.000 | 0.029 | 0.000 | IGKV1-27 | 0.22755 | 0.54294 | 0.08726 | 0 | 0 |
| 159 | chr2 | 89521000 | 89522000 | 0.028 | 0.000 | 0.015 | 0.014 | IGKV2-28 | 1.00000 | 1.00000 | 0.29694 | 0 | 0 |
| 160 | chr2 | 89533000 | 89534000 | 0.028 | 0.000 | 0.044 | 0.014 | IGKV2-30 | 0.34948 | 1.00000 | 0.02537 | 0 | 0 |
| 161 | chr2 | 89534000 | 89535000 | 0.000 | 0.000 | 0.029 | 0.014 | IGKV2-30 | 0.60686 | 0.54294 | 0.08726 | 0 | 0 |
| 162 | chr2 | 89544000 | 89545000 | 0.028 | 0.012 | 0.059 | 0.014 | IGKV2-30 | 0.19371 | 0.65667 | 0.06548 | 0 | 1 |
| 163 | chr2 | 89545000 | 89546000 | 0.000 | 0.006 | 0.029 | 0.000 | IGKV2-30 | 0.22755 | 0.54294 | 0.21104 | 0 | 0 |
| 164 | chr2 | 90259000 | 90260000 | 0.028 | 0.000 | 0.015 | 0.014 | IGKV1D-8 | 1.00000 | 1.00000 | 0.29694 | 0 | 0 |
| 165 | chr2 | 90260000 | 90261000 | 0.000 | 0.000 | 0.059 | 0.014 | IGKV1D-8 | 0.19371 | 0.29551 | 0.00730 | 1 | 1 |
| 166 | chr2 | 90809000 | 90810000 | 0.000 | 0.012 | 0.044 | 0.014 | DUSP2 | 0.10727 | 0.54966 | 0.02537 | 0 | 0 |
| 167 | chr2 | 96810000 | 96811000 | 0.028 | 0.000 | 0.044 | 0.000 | DUSP2 | 0.34948 | 0.54294 | 0.08726 | 0 | 0 |
| 168 | chr2 | 96811000 | 96812000 | 0.000 | 0.000 | 0.029 | 0.014 | DUSP2 | 0.22755 | 0.54294 | 0.08726 | 0 | 0 |
| 169 | chr2 | 98611000 | 98612000 | 0.000 | 0.000 | 0.029 | 0.027 | TMEM131 | 1.00000 | 1.00000 | 0.29694 | 0 | 0 |
| 170 | chr2 | 100757000 | 100758000 | 0.000 | 0.000 | 0.044 | 0.000 | AFF3 | 1.00000 | 0.54294 | 0.08726 | 0 | 0 |
| 171 | chr2 | 100758000 | 100759000 | 0.028 | 0.000 | 0.029 | 0.027 | AFF3 | 0.34948 | 0.54966 | 0.02537 | 0 | 0 |
| 172 | chr2 | 106144000 | 106145000 | 0.000 | 0.000 | 0.029 | 0.014 | FHL2 | 0.22755 | 0.54294 | 0.08726 | 0 | 0 |
| 173 | chr2 | 111878000 | 111879000 | 0.028 | 0.000 | 0.044 | 0.014 | BCL2L11 | 0.60686 | 0.54294 | 0.08726 | 0 | 0 |
| 174 | chr2 | 111879000 | 111880000 | 0.000 | 0.000 | 0.044 | 0.014 | BCL2L11 | 0.34948 | 0.54966 | 0.02537 | 0 | 0 |
| 175 | chr2 | 112305000 | 112306000 | 0.000 | 0.000 | 0.015 | 0.014 | ANAPC1 | 1.00000 | 1.00000 | 0.29694 | 0 | 0 |
| 176 | chr2 | 116234000 | 116235000 | 0.028 | 0.000 | 0.015 | 0.014 | DPP10 | 1.00000 | 1.00000 | 0.29694 | 0 | 0 |
| 177 | chr2 | 116439000 | 116440000 | 0.000 | 0.000 | 0.000 | 0.014 | DPP10 | 1.00000 | 1.00000 | 1.00000 | 0 | 0 |
| 178 | chr2 | 124697000 | 124698000 | 0.028 | 0.000 | 0.015 | 0.000 | CNTNAP5 | 0.47887 | 1.00000 | 0.29694 | 0 | 0 |
| 179 | chr2 | 125235000 | 125236000 | 0.000 | 0.000 | 0.029 | 0.000 | CNTNAP5 | 0.22755 | 0.54294 | 0.08726 | 0 | 0 |
| 180 | chr2 | 127538000 | 127539000 | 0.028 | 0.000 | 0.015 | 0.000 | GYPC | 0.47887 | 1.00000 | 0.29694 | 0 | 0 |
| 181 | chr2 | 136874000 | 136875000 | 0.000 | 0.000 | 0.191 | 0.014 | CXCR4 | 0.00036 | 0.00372 | 0.00000 | 1 | 1 |
| 182 | chr2 | 136875000 | 136876000 | 0.083 | 0.019 | 0.265 | 0.081 | CXCR4 | 0.00626 | 0.03882 | 0.00000 | 1 | 1 |
| 183 | chr2 | 136996000 | 136997000 | 0.000 | 0.000 | 0.029 | 0.000 | CXCR4 | 0.22755 | 0.54966 | 0.08726 | 0 | 0 |
| 184 | chr2 | 137082000 | 137083000 | 0.000 | 0.000 | 0.015 | 0.014 | CXCR4 | 1.00000 | 1.00000 | 0.29694 | 1 | 0 |
| 185 | chr2 | 140951000 | 140952000 | 0.000 | 0.000 | 0.000 | 0.000 | LRP1B | 1.00000 | 1.00000 | 1.00000 | 0 | 0 |
| 186 | chr2 | 141335000 | 141336000 | 0.000 | 0.000 | 0.015 | 0.014 | LRP1B | 0.22755 | 0.54294 | 0.29694 | 0 | 0 |
| 187 | chr2 | 141770000 | 141771000 | 0.000 | 0.000 | 0.029 | 0.000 | LRP1B | 0.22755 | 0.54294 | 0.08726 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 188 | chr2 | 146445000 | 146446000 | 0.000 | 0.000 | 0.029 | 0.000 | ZEB2 | 0.22755 | 0.54294 | 0.08726 | 0 | 0 |
| 189 | chr2 | 146446000 | 146447000 | 0.000 | 0.000 | 0.029 | 0.014 | ZEB2 | 0.60686 | 0.54294 | 0.08726 | 0 | 0 |
| 190 | chr2 | 156443000 | 156444000 | 0.000 | 0.000 | 0.029 | 0.000 | KCNJ3 | 0.22755 | 0.54294 | 0.08726 | 0 | 0 |
| 191 | chr2 | 172590000 | 172591000 | 0.000 | 0.000 | 0.029 | 0.000 | DYNC1I2 | 0.22755 | 0.54294 | 0.08726 | 0 | 0 |
| 192 | chr2 | 176581000 | 176582000 | 0.028 | 0.000 | 0.000 | 0.014 | KIAA1715 | 1.00000 | 0.34615 | 1.00000 | 0 | 0 |
| 193 | chr2 | 179880000 | 179881000 | 0.000 | 0.000 | 0.015 | 0.014 | CDC141 | 1.00000 | 0.54294 | 0.29694 | 0 | 0 |
| 194 | chr2 | 180358000 | 180359000 | 0.000 | 0.000 | 0.029 | 0.000 | ZNF385B | 0.22755 | 0.54294 | 0.08726 | 0 | 0 |
| 195 | chr2 | 189285000 | 189286000 | 0.000 | 0.000 | 0.015 | 0.014 | GULP1 | 1.00000 | 0.54294 | 0.29694 | 0 | 0 |
| 196 | chr2 | 189432000 | 189433000 | 0.000 | 0.000 | 0.000 | 0.014 | GULP1 | 1.00000 | 1.00000 | 1.00000 | 0 | 0 |
| 197 | chr2 | 194115000 | 194116000 | 0.000 | 0.000 | 0.015 | 0.014 | TMEFF2 | 1.00000 | 0.54294 | 0.29694 | 0 | 0 |
| 198 | chr2 | 197035000 | 197036000 | 0.000 | 0.000 | 0.044 | 0.014 | STK17B | 0.34948 | 0.54966 | 0.02537 | 0 | 0 |
| 199 | chr2 | 197041000 | 197042000 | 0.000 | 0.000 | 0.029 | 0.000 | STK17B | 0.22755 | 0.54294 | 0.08726 | 0 | 0 |
| 200 | chr2 | 215999000 | 216000000 | 0.000 | 0.006 | 0.015 | 0.000 | ABCA12 | 0.47887 | 1.00000 | 0.50663 | 0 | 0 |
| 201 | chr2 | 216973000 | 216974000 | 0.028 | 0.000 | 0.000 | 0.014 | XRCC5 | 1.00000 | 0.34615 | 1.00000 | 0 | 0 |
| 202 | chr2 | 217247000 | 217248000 | 0.028 | 0.000 | 0.000 | 0.014 | 4-Mar-19 | 1.00000 | 0.34615 | 1.00000 | 0 | 0 |
| 203 | chr2 | 225386000 | 225387000 | 0.000 | 0.000 | 0.029 | 0.000 | CUL3 | 0.22755 | 0.54294 | 0.08726 | 0 | 0 |
| 204 | chr2 | 225524000 | 225525000 | 0.000 | 0.000 | 0.015 | 0.000 | CUL3 | 0.47887 | 0.54294 | 0.29694 | 0 | 0 |
| 205 | chr2 | 233478000 | 233479000 | 0.028 | 0.000 | 0.000 | 0.000 | EFHD1 | 1.00000 | 0.34615 | 1.00000 | 0 | 0 |
| 206 | chr2 | 233980000 | 233981000 | 0.000 | 0.000 | 0.029 | 0.000 | INPP5D | 0.22755 | 0.54294 | 0.08726 | 0 | 0 |
| 207 | chr2 | 240641000 | 240642000 | 0.000 | 0.000 | 0.000 | 0.027 | AC093802.1 | 0.49735 | 0.34615 | 1.00000 | 0 | 0 |
| 208 | chr2 | 241125000 | 241126000 | 0.000 | 0.000 | 0.000 | 0.027 | OTOS | 0.49735 | 1.00000 | 1.00000 | 0 | 0 |
| 209 | chr3 | 8739000 | 8740000 | 0.000 | 0.000 | 0.000 | 0.027 | CAV3 | 0.49735 | 1.00000 | 1.00000 | 0 | 0 |
| 210 | chr3 | 16407000 | 16408000 | 0.000 | 0.000 | 0.029 | 0.041 | RFTN1 | 0.24603 | 0.34615 | 1.00000 | 0 | 0 |
| 211 | chr3 | 16409000 | 16410000 | 0.028 | 0.006 | 0.029 | 0.000 | RFTN1 | 0.10727 | 0.54966 | 1.00000 | 1 | 0 |
| 212 | chr3 | 16419000 | 16420000 | 0.000 | 0.006 | 0.044 | 0.000 | RFTN1 | 0.10727 | 0.54966 | 0.07959 | 1 | 0 |
| 213 | chr3 | 16472000 | 16473000 | 0.028 | 0.000 | 0.015 | 0.014 | RFTN1 | 1.00000 | 0.54966 | 1.00000 | 1 | 0 |
| 214 | chr3 | 16495000 | 16496000 | 0.000 | 0.000 | 0.029 | 0.000 | RFTN1 | 0.22755 | 0.54294 | 0.08726 | 1 | 0 |
| 215 | chr3 | 16552000 | 16553000 | 0.000 | 0.012 | 0.103 | 0.014 | RFTN1 | 0.60686 | 0.09269 | 0.58408 | 1 | 0 |
| 216 | chr3 | 16554000 | 16555000 | 0.000 | 0.000 | 0.029 | 0.027 | RFTN1 | 0.08710 | 0.54294 | 0.00016 | 1 | 1 |
| 217 | chr3 | 16555000 | 16556000 | 0.000 | 0.000 | 0.029 | 0.000 | RFTN1 | 0.22755 | 0.54294 | 0.08726 | 1 | 0 |
| 218 | chr3 | 21658000 | 21659000 | 0.000 | 0.000 | 0.029 | 0.000 | ZNF385D | 0.22755 | 0.54294 | 0.08726 | 0 | 0 |
| 219 | chr3 | 25691000 | 25692000 | 0.000 | 0.000 | 0.029 | 0.000 | TOP2B | 0.22755 | 0.54294 | 0.08726 | 0 | 0 |
| 220 | chr3 | 31969000 | 31970000 | 0.000 | 0.000 | 0.029 | 0.014 | OSBPL10 | 0.10727 | 0.54966 | 0.02537 | 0 | 0 |
| 221 | chr3 | 31993000 | 31994000 | 0.000 | 0.000 | 0.044 | 0.000 | OSBPL10 | 0.10727 | 0.54966 | 0.02537 | 0 | 0 |
| 222 | chr3 | 32001000 | 32002000 | 0.000 | 0.000 | 0.088 | 0.014 | OSBPL10 | 0.05468 | 0.09031 | 0.00058 | 0 | 1 |
| 223 | chr3 | 32022000 | 32023000 | 0.000 | 0.000 | 0.029 | 0.000 | OSBPL10 | 0.22755 | 0.54294 | 0.08726 | 0 | 0 |
| 224 | chr3 | 32023000 | 32024000 | 0.000 | 0.000 | 0.029 | 0.014 | RBM5 | 0.60686 | 0.54294 | 0.08726 | 0 | 0 |
| 225 | chr3 | 50128000 | 50129000 | 0.000 | 0.000 | 0.015 | 0.000 | CACNA2D3 | 0.47887 | 1.00000 | 0.50663 | 0 | 0 |
| 226 | chr3 | 54913000 | 54914000 | 0.000 | 0.000 | 0.000 | 0.014 | ERC2 | 1.00000 | 1.00000 | 1.00000 | 0 | 0 |
| 227 | chr3 | 56074000 | 56075000 | 0.028 | 0.000 | 0.029 | 0.014 | FHIT | 0.22755 | 0.34615 | 0.08726 | 0 | 0 |
| 228 | chr3 | 59577000 | 59578000 | 0.000 | 0.000 | 0.044 | 0.000 | FHIT | 0.10727 | 0.54966 | 0.02537 | 0 | 0 |
| 229 | chr3 | 60351000 | 60352000 | 0.000 | 0.000 | 0.000 | 0.014 | FHIT | 1.00000 | 0.34615 | 1.00000 | 0 | 0 |
| 230 | chr3 | 60356000 | 60357000 | 0.028 | 0.000 | 0.015 | 0.014 | FHIT | 1.00000 | 0.54966 | 1.00000 | 0 | 0 |
| 231 | chr3 | 60357000 | 60358000 | 0.000 | 0.000 | 0.015 | 0.014 | FHIT | 1.00000 | 1.00000 | 0.29694 | 0 | 0 |
| 232 | chr3 | 60358000 | 60359000 | 0.000 | 0.000 | 0.015 | 0.014 | FHIT | 1.00000 | 1.00000 | 0.29694 | 0 | 0 |
| 233 | chr3 | 60359000 | 60360000 | 0.000 | 0.000 | 0.029 | 0.000 | FHIT | 0.22755 | 0.54294 | 0.08726 | 0 | 0 |
| 234 | chr3 | 60389000 | 60390000 | 0.000 | 0.000 | 0.015 | 0.027 | FHIT | 1.00000 | 1.00000 | 0.29694 | 0 | 0 |
| 235 | chr3 | 60392000 | 60393000 | 0.000 | 0.000 | 0.029 | 0.000 | FHIT | 0.22755 | 0.54294 | 0.08726 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAny Histology |
|---|---|---|---|---|---|---|---|---|---|---|---|---|---|
| 236 | chr3 | 60395000 | 60396000 | 0.000 | 0.000 | 0.000 | 0.027 | FHIT | 0.49735 | 1.00000 | 1.00000 | 0 | 0 |
| 237 | chr3 | 60404000 | 60405000 | 0.000 | 0.000 | 0.029 | 0.000 | FHIT | 0.22755 | 0.54294 | 0.08726 | 0 | 0 |
| 238 | chr3 | 60436000 | 60437000 | 0.000 | 0.000 | 0.000 | 0.027 | FHIT | 0.49735 | 1.00000 | 1.00000 | 0 | 0 |
| 239 | chr3 | 60437000 | 60438000 | 0.000 | 0.000 | 0.029 | 0.000 | FHIT | 0.22755 | 0.54294 | 0.08726 | 0 | 0 |
| 240 | chr3 | 60477000 | 60478000 | 0.000 | 0.000 | 0.029 | 0.014 | FHIT | 0.22755 | 0.54294 | 0.08726 | 0 | 0 |
| 241 | chr3 | 60485000 | 60486000 | 0.000 | 0.000 | 0.015 | 0.000 | FHIT | 1.00000 | 1.00000 | 0.29694 | 0 | 0 |
| 242 | chr3 | 60515000 | 60516000 | 0.000 | 0.000 | 0.015 | 0.014 | FHIT | 1.00000 | 1.00000 | 0.29694 | 0 | 0 |
| 243 | chr3 | 60535000 | 60536000 | 0.000 | 0.006 | 0.015 | 0.000 | FHIT | 0.47887 | 1.00000 | 0.50663 | 0 | 0 |
| 244 | chr3 | 60602000 | 60603000 | 0.000 | 0.000 | 0.029 | 0.014 | FHIT | 0.60686 | 0.54294 | 0.08726 | 0 | 0 |
| 245 | chr3 | 60613000 | 60614000 | 0.000 | 0.000 | 0.029 | 0.014 | FHIT | 0.60686 | 0.54294 | 0.08726 | 0 | 0 |
| 246 | chr3 | 60614000 | 60615000 | 0.000 | 0.000 | 0.029 | 0.000 | FHIT | 0.22755 | 0.54294 | 0.08726 | 0 | 0 |
| 247 | chr3 | 60632000 | 60633000 | 0.000 | 0.000 | 0.000 | 0.027 | FHIT | 0.49735 | 1.00000 | 1.00000 | 0 | 0 |
| 248 | chr3 | 60635000 | 60636000 | 0.000 | 0.000 | 0.029 | 0.014 | FHIT | 0.22755 | 0.54294 | 0.08726 | 0 | 0 |
| 249 | chr3 | 60640000 | 60641000 | 0.000 | 0.000 | 0.000 | 0.027 | FHIT | 0.49735 | 1.00000 | 1.00000 | 0 | 0 |
| 250 | chr3 | 60647000 | 60648000 | 0.000 | 0.000 | 0.015 | 0.014 | FHIT | 1.00000 | 1.00000 | 0.29694 | 0 | 0 |
| 251 | chr3 | 60648000 | 60649000 | 0.000 | 0.000 | 0.015 | 0.014 | FHIT | 1.00000 | 1.00000 | 0.29694 | 0 | 0 |
| 252 | chr3 | 60652000 | 60653000 | 0.000 | 0.000 | 0.015 | 0.027 | FHIT | 0.49735 | 1.00000 | 0.29694 | 0 | 0 |
| 253 | chr3 | 60660000 | 60661000 | 0.000 | 0.000 | 0.029 | 0.014 | FHIT | 0.60686 | 0.54294 | 0.08726 | 0 | 0 |
| 254 | chr3 | 60665000 | 60666000 | 0.000 | 0.000 | 0.015 | 0.027 | FHIT | 1.00000 | 1.00000 | 0.29694 | 0 | 0 |
| 255 | chr3 | 60666000 | 60667000 | 0.000 | 0.000 | 0.015 | 0.014 | FHIT | 1.00000 | 1.00000 | 0.29694 | 0 | 0 |
| 256 | chr3 | 60671000 | 60672000 | 0.000 | 0.000 | 0.015 | 0.041 | FHIT | 0.24603 | 1.00000 | 0.29694 | 0 | 0 |
| 257 | chr3 | 60673000 | 60674000 | 0.000 | 0.000 | 0.044 | 0.000 | FHIT | 0.10727 | 0.54966 | 0.02537 | 0 | 0 |
| 258 | chr3 | 60675000 | 60676000 | 0.000 | 0.000 | 0.015 | 0.014 | FHIT | 1.00000 | 1.00000 | 0.29694 | 0 | 0 |
| 259 | chr3 | 60678000 | 60679000 | 0.000 | 0.000 | 0.044 | 0.000 | FHIT | 0.10727 | 0.54966 | 0.02537 | 0 | 0 |
| 260 | chr3 | 60683000 | 60684000 | 0.000 | 0.000 | 0.015 | 0.027 | FHIT | 1.00000 | 1.00000 | 0.29694 | 0 | 0 |
| 261 | chr3 | 60684000 | 60685000 | 0.000 | 0.000 | 0.015 | 0.041 | FHIT | 0.62100 | 1.00000 | 0.29694 | 0 | 0 |
| 262 | chr3 | 60688000 | 60689000 | 0.000 | 0.000 | 0.015 | 0.014 | FHIT | 0.60686 | 1.00000 | 0.08726 | 0 | 0 |
| 263 | chr3 | 60717000 | 60718000 | 0.000 | 0.000 | 0.015 | 0.027 | FHIT | 1.00000 | 1.00000 | 0.29694 | 0 | 0 |
| 264 | chr3 | 60740000 | 60741000 | 0.000 | 0.000 | 0.029 | 0.000 | FHIT | 0.49735 | 1.00000 | 1.00000 | 0 | 0 |
| 265 | chr3 | 60774000 | 60775000 | 0.000 | 0.000 | 0.029 | 0.014 | FHIT | 0.22755 | 0.54294 | 0.08726 | 0 | 0 |
| 266 | chr3 | 60792000 | 60793000 | 0.000 | 0.000 | 0.000 | 0.027 | FHIT | 0.49735 | 1.00000 | 1.00000 | 0 | 0 |
| 267 | chr3 | 60806000 | 60807000 | 0.028 | 0.000 | 0.000 | 0.014 | FHIT | 1.00000 | 0.34615 | 1.00000 | 0 | 0 |
| 268 | chr3 | 60812000 | 60813000 | 0.000 | 0.000 | 0.000 | 0.027 | FHIT | 0.49735 | 1.00000 | 1.00000 | 0 | 0 |
| 269 | chr3 | 60860000 | 60861000 | 0.000 | 0.000 | 0.015 | 0.027 | FHIT | 0.49735 | 1.00000 | 1.00000 | 0 | 0 |
| 270 | chr3 | 71551000 | 71552000 | 0.000 | 0.000 | 0.015 | 0.027 | EIF4E3 | 1.00000 | 1.00000 | 0.29694 | 0 | 0 |
| 271 | chr3 | 78274000 | 78275000 | 0.000 | 0.006 | 0.015 | 0.014 | ROBO1 | 1.00000 | 1.00000 | 0.50663 | 0 | 0 |
| 272 | chr3 | 80273000 | 80274000 | 0.000 | 0.006 | 0.015 | 0.000 | ROBO1 | 0.47887 | 1.00000 | 0.29694 | 0 | 0 |
| 273 | chr3 | 83094000 | 83095000 | 0.000 | 0.000 | 0.015 | 0.000 | GBE1 | 1.00000 | 0.34615 | 1.00000 | 0 | 0 |
| 274 | chr3 | 83924000 | 83925000 | 0.028 | 0.000 | 0.000 | 0.014 | CADM2 | 1.00000 | 0.34615 | 1.00000 | 0 | 0 |
| 275 | chr3 | 84293000 | 84294000 | 0.000 | 0.000 | 0.015 | 0.014 | CADM2 | 1.00000 | 1.00000 | 0.29694 | 0 | 0 |
| 276 | chr3 | 85260000 | 85261000 | 0.000 | 0.000 | 0.044 | 0.014 | CADM2 | 0.10727 | 0.54966 | 0.02537 | 0 | 0 |
| 277 | chr3 | 85261000 | 85262000 | 0.000 | 0.000 | 0.029 | 0.000 | CADM2 | 0.22755 | 0.54294 | 0.08726 | 0 | 0 |
| 278 | chr3 | 85799000 | 85800000 | 0.000 | 0.000 | 0.029 | 0.000 | CADM2 | 0.22755 | 0.54294 | 0.08726 | 0 | 0 |
| 279 | chr3 | 86226000 | 86227000 | 0.000 | 0.000 | 0.029 | 0.000 | CADM2 | 0.22755 | 0.54294 | 0.08726 | 0 | 0 |
| 280 | chr3 | 88146000 | 88147000 | 0.000 | 0.000 | 0.029 | 0.000 | CGGBP1 | 0.22755 | 0.54294 | 0.08726 | 0 | 0 |
| 281 | chr3 | 94709000 | 94710000 | 0.000 | 0.000 | 0.015 | 0.000 | NSUN3 | 0.47887 | 1.00000 | 1.00000 | 0 | 0 |
| 282 | chr3 | 95460000 | 95461000 | 0.028 | 0.000 | 0.015 | 0.000 | MTRNR2L12 | 0.22755 | 1.00000 | 0.29694 | 0 | 0 |
| 283 | chr3 | 95724000 | 95725000 | 0.000 | 0.000 | 0.029 | 0.000 | MTRNR2L12 | 0.22755 | 0.54294 | 0.08726 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 284 | chr3 | 101569000 | 101570000 | 0.028 | 0.000 | 0.015 | 0.000 | NFKRIZ | 0.47887 | 1.00000 | 0.29694 | 0 | 0 |
| 285 | chr3 | 111851000 | 111852000 | 0.000 | 0.000 | 0.044 | 0.000 | GCSAM | 0.10727 | 0.54966 | 0.02537 | 0 | 0 |
| 286 | chr3 | 111852000 | 111853000 | 0.028 | 0.000 | 0.059 | 0.000 | GCSAM | 0.05016 | 0.29551 | 0.00730 | 0 | 1 |
| 287 | chr3 | 122377000 | 122378000 | 0.000 | 0.000 | 0.044 | 0.000 | PARP14 | 0.10727 | 1.00000 | 0.02537 | 0 | 0 |
| 288 | chr3 | 150478000 | 150479000 | 0.000 | 0.000 | 0.029 | 0.000 | SIAH2 | 0.22755 | 0.54294 | 0.08726 | 0 | 0 |
| 289 | chr3 | 150479000 | 150480000 | 0.000 | 0.000 | 0.029 | 0.000 | SIAH2 | 0.22755 | 0.54294 | 0.08726 | 0 | 0 |
| 290 | chr3 | 150480000 | 150481000 | 0.000 | 0.000 | 0.015 | 0.014 | SIAH2 | 1.00000 | 1.00000 | 0.29694 | 0 | 0 |
| 291 | chr3 | 163237000 | 163238000 | 0.000 | 0.000 | 0.000 | 0.027 | SI | 0.49735 | 1.00000 | 1.00000 | 0 | 0 |
| 292 | chr3 | 163238000 | 163239000 | 0.000 | 0.000 | 0.029 | 0.000 | SI | 0.22755 | 0.54294 | 0.08726 | 0 | 0 |
| 293 | chr3 | 163615000 | 163616000 | 0.000 | 0.000 | 0.029 | 0.000 | SI | 0.22755 | 0.54294 | 0.08726 | 0 | 0 |
| 294 | chr3 | 183270000 | 183271000 | 0.000 | 0.000 | 0.029 | 0.014 | KLHL6 | 0.60686 | 0.54294 | 0.08726 | 0 | 0 |
| 295 | chr3 | 183271000 | 183272000 | 0.000 | 0.000 | 0.029 | 0.014 | KLHL6 | 0.60686 | 0.54966 | 0.08726 | 1 | 1 |
| 296 | chr3 | 183272000 | 183273000 | 0.000 | 0.019 | 0.044 | 0.027 | KLHL6 | 0.67043 | 0.54966 | 0.36534 | 1 | 1 |
| 297 | chr3 | 183273000 | 183274000 | 0.000 | 0.000 | 0.074 | 0.027 | KLHL6 | 0.34948 | 0.54966 | 0.02537 | 1 | 1 |
| 298 | chr3 | 186648000 | 186649000 | 0.056 | 0.000 | 0.000 | 0.000 | ADIPOQ | 0.02624 | 0.02564 | 0.00009 | 0 | 0 |
| 299 | chr3 | 186714000 | 186715000 | 0.000 | 0.006 | 0.132 | 0.027 | ST6GAL1 | 0.34948 | 0.54966 | 0.02537 | 1 | 0 |
| 300 | chr3 | 186715000 | 186716000 | 0.000 | 0.000 | 0.044 | 0.014 | ST6GAL1 | 0.10420 | 0.16101 | 0.00953 | 1 | 0 |
| 301 | chr3 | 186739000 | 186740000 | 0.056 | 0.006 | 0.074 | 0.014 | ST6GAL1 | 0.25970 | 1.00000 | 0.08726 | 1 | 1 |
| 302 | chr3 | 186740000 | 186741000 | 0.000 | 0.000 | 0.029 | 0.027 | ST6GAL1 | 0.22755 | 0.54294 | 0.08726 | 1 | 1 |
| 303 | chr3 | 186742000 | 186743000 | 0.000 | 0.050 | 0.338 | 0.041 | ST6GAL1 | 0.00001 | 0.00001 | 0.00000 | 1 | 1 |
| 304 | chr3 | 186783000 | 186784000 | 0.028 | 0.025 | 0.162 | 0.000 | ST6GAL1 | 0.00019 | 0.05349 | 0.42650 | 1 | 0 |
| 305 | chr3 | 186784000 | 186785000 | 0.000 | 0.000 | 0.044 | 0.000 | ST6GAL1 | 0.10727 | 0.54966 | 0.08726 | 1 | 1 |
| 306 | chr3 | 187458000 | 187459000 | 0.000 | 0.000 | 0.029 | 0.000 | BCL6 | 0.22755 | 0.54294 | 0.08726 | 1 | 0 |
| 307 | chr3 | 187459000 | 187460000 | 0.000 | 0.000 | 0.029 | 0.000 | BCL6 | 0.22755 | 0.54294 | 0.08726 | 0 | 0 |
| 308 | chr3 | 187460000 | 187461000 | 0.000 | 0.000 | 0.088 | 0.041 | BCL6 | 0.31126 | 0.09031 | 0.00058 | 0 | 0 |
| 309 | chr3 | 187461000 | 187462000 | 0.000 | 0.081 | 0.353 | 0.122 | BCL6 | 0.00137 | 0.00001 | 0.00000 | 1 | 1 |
| 310 | chr3 | 187462000 | 187463000 | 0.056 | 0.037 | 0.647 | 0.392 | BCL6 | 0.00266 | 0.00000 | 0.00000 | 1 | 1 |
| 311 | chr3 | 187463000 | 187464000 | 0.000 | 0.037 | 0.485 | 0.230 | BCL6 | 0.00164 | 0.00000 | 0.00000 | 1 | 1 |
| 312 | chr3 | 187464000 | 187465000 | 0.028 | 0.000 | 0.162 | 0.000 | BCL6 | 0.00019 | 0.05349 | 0.00000 | 1 | 1 |
| 313 | chr3 | 187468000 | 187469000 | 0.000 | 0.000 | 0.044 | 0.014 | BCL6 | 0.10727 | 0.54966 | 0.02537 | 1 | 0 |
| 314 | chr3 | 187635000 | 187636000 | 0.000 | 0.000 | 0.029 | 0.000 | BCL6 | 0.22755 | 0.54294 | 0.08726 | 1 | 1 |
| 315 | chr3 | 187636000 | 187637000 | 0.000 | 0.019 | 0.118 | 0.054 | BCL6 | 0.23086 | 0.04825 | 0.00321 | 1 | 1 |
| 316 | chr3 | 187653000 | 187654000 | 0.000 | 0.012 | 0.191 | 0.081 | BCL6 | 0.08249 | 0.00372 | 0.00000 | 1 | 1 |
| 317 | chr3 | 187658000 | 187659000 | 0.000 | 0.000 | 0.044 | 0.000 | BCL6 | 0.10727 | 0.54966 | 1.00000 | 1 | 1 |
| 318 | chr3 | 187660000 | 187661000 | 0.028 | 0.000 | 0.044 | 0.014 | BCL6 | 0.34948 | 0.54966 | 0.02537 | 1 | 1 |
| 319 | chr3 | 187661000 | 187662000 | 0.000 | 0.000 | 0.029 | 0.000 | BCL6 | 0.22755 | 0.54294 | 0.08726 | 1 | 1 |
| 320 | chr3 | 187664000 | 187665000 | 0.000 | 0.000 | 0.044 | 0.014 | BCL6 | 0.60686 | 1.00000 | 0.08726 | 1 | 1 |
| 321 | chr3 | 187686000 | 187687000 | 0.028 | 0.006 | 0.029 | 0.014 | AC022498.1 | 1.00000 | 1.00000 | 1.00000 | 0 | 0 |
| 322 | chr3 | 187687000 | 187688000 | 0.000 | 0.000 | 0.000 | 0.014 | AC022498.1 | 1.00000 | 1.00000 | 1.00000 | 0 | 0 |
| 323 | chr3 | 187693000 | 187694000 | 0.000 | 0.006 | 0.015 | 0.014 | AC022498.1 | 0.05016 | 0.29551 | 0.29694 | 0 | 0 |
| 324 | chr3 | 187696000 | 187697000 | 0.000 | 0.006 | 0.059 | 0.000 | AC022498.1 | 0.10727 | 0.54966 | 0.02818 | 0 | 0 |
| 325 | chr3 | 187697000 | 187698000 | 0.000 | 0.000 | 0.044 | 0.014 | AC022498.1 | 0.22755 | 0.54294 | 0.02537 | 0 | 0 |
| 326 | chr3 | 187803000 | 187804000 | 0.000 | 0.000 | 0.029 | 0.000 | AC022498.1 | 0.10727 | 0.54966 | 0.08726 | 0 | 0 |
| 327 | chr3 | 187806000 | 187807000 | 0.000 | 0.000 | 0.059 | 0.014 | AC022498.1 | 0.19371 | 0.29551 | 0.00730 | 0 | 1 |
| 328 | chr3 | 187957000 | 187958000 | 0.000 | 0.006 | 0.132 | 0.014 | AC022498.1 | 0.00701 | 0.02564 | 0.00009 | 0 | 0 |
| 329 | chr3 | 187958000 | 187959000 | 0.028 | 0.025 | 0.221 | 0.095 | AC022498.1 | 0.06156 | 0.00936 | 0.00000 | 0 | 1 |
| 330 | chr3 | 187959000 | 187960000 | 0.000 | 0.012 | 0.118 | 0.000 | AC022498.1 | 0.00220 | 0.04825 | 0.00116 | 0 | 1 |
| 331 | chr3 | 187960000 | 187961000 | 0.000 | 0.000 | 0.029 | 0.000 | AC022498.1 | 0.22755 | 0.54294 | 0.08726 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 332 | chr3 | 188222000 | 188223000 | 0.000 | 0.000 | 0.029 | 0.000 | LPP | 0.22755 | 0.54294 | 0.08726 | 0 | 0 |
| 333 | chr3 | 188298000 | 188299000 | 0.000 | 0.000 | 0.015 | 0.014 | LPP | 1.00000 | 1.00000 | 0.29694 | 0 | 0 |
| 334 | chr3 | 188299000 | 188300000 | 0.000 | 0.006 | 0.088 | 0.027 | LPP | 0.15270 | 0.09031 | 0.00311 | 0 | 1 |
| 335 | chr3 | 188471000 | 188472000 | 0.000 | 0.006 | 0.191 | 0.068 | LPP | 0.04150 | 0.00372 | 0.00000 | 0 | 1 |
| 336 | chr3 | 188472000 | 188473000 | 0.000 | 0.000 | 0.044 | 0.027 | LPP | 0.67043 | 0.54966 | 0.02537 | 0 | 0 |
| 337 | chr4 | 50000 | 51000 | 0.000 | 0.000 | 0.029 | 0.000 | ZNF595; ZNF718; | 0.22755 | 0.54294 | 0.08726 | 0 | 0 |
| 338 | chr4 | 51000 | 52000 | 0.000 | 0.000 | 0.044 | 0.014 | ZNF595; ZNF718; | 0.34948 | 0.54966 | 0.02537 | 0 | 0 |
| 339 | chr4 | 54000 | 55000 | 0.000 | 0.000 | 0.029 | 0.000 | ZNF595; ZNF718; | 0.22755 | 0.54294 | 0.08726 | 0 | 0 |
| 340 | chr4 | 290000 | 291000 | 0.000 | 0.000 | 0.000 | 0.027 | ZNF732 | 1.00000 | 0.11763 | 1.00000 | 0 | 1 |
| 341 | chr4 | 385000 | 386000 | 0.000 | 0.000 | 0.029 | 0.000 | ZNF141 | 0.22755 | 0.54294 | 0.08726 | 0 | 0 |
| 342 | chr4 | 550000 | 551000 | 0.000 | 0.000 | 0.000 | 0.027 | PIGG | 0.49735 | 1.00000 | 1.00000 | 0 | 0 |
| 343 | chr4 | 2707000 | 2708000 | 0.028 | 0.000 | 0.015 | 0.000 | FAM193A | 0.47887 | 1.00000 | 0.29694 | 0 | 0 |
| 344 | chr4 | 5206000 | 5207000 | 0.000 | 0.000 | 0.029 | 0.027 | STK32B | 0.22755 | 0.54294 | 0.08726 | 0 | 0 |
| 345 | chr4 | 25863000 | 25864000 | 0.000 | 0.000 | 0.059 | 0.014 | SEL1L3 | 0.19371 | 0.29551 | 0.00730 | 0 | 1 |
| 346 | chr4 | 25864000 | 25865000 | 0.000 | 0.006 | 0.044 | 0.027 | SEL1L3 | 0.67043 | 0.54966 | 0.07959 | 0 | 0 |
| 347 | chr4 | 25865000 | 25866000 | 0.000 | 0.000 | 0.074 | 0.014 | SEL1L3 | 0.25970 | 0.16101 | 0.00208 | 0 | 1 |
| 348 | chr4 | 29657000 | 29658000 | 0.000 | 0.000 | 0.015 | 0.000 | PCDH7 | 1.00000 | 1.00000 | 0.29694 | 0 | 0 |
| 349 | chr4 | 30356000 | 30357000 | 0.000 | 0.000 | 0.015 | 0.000 | PCDH7 | 0.47887 | 1.00000 | 0.50663 | 0 | 0 |
| 350 | chr4 | 33418000 | 33419000 | 0.000 | 0.000 | 0.029 | 0.000 | PCDH7 | 0.22755 | 0.54294 | 0.08726 | 0 | 0 |
| 351 | chr4 | 33449000 | 33450000 | 0.028 | 0.000 | 0.015 | 0.000 | PCDH7 | 0.47887 | 1.00000 | 0.29694 | 0 | 0 |
| 352 | chr4 | 39348000 | 39349000 | 0.000 | 0.006 | 0.015 | 0.014 | RFC1 | 1.00000 | 1.00000 | 1.00000 | 0 | 0 |
| 353 | chr4 | 39974000 | 39975000 | 0.000 | 0.000 | 0.000 | 0.027 | PDS5A | 0.49735 | 1.00000 | 1.00000 | 0 | 0 |
| 354 | chr4 | 40194000 | 40195000 | 0.000 | 0.000 | 0.044 | 0.014 | N4BP2 | 0.67043 | 0.54966 | 0.02537 | 0 | 0 |
| 355 | chr4 | 40195000 | 40196000 | 0.000 | 0.000 | 0.015 | 0.027 | N4BP2 | 1.00000 | 1.00000 | 0.29694 | 0 | 0 |
| 356 | chr4 | 40196000 | 40197000 | 0.000 | 0.000 | 0.074 | 0.014 | N4BP2 | 0.10420 | 0.16101 | 0.00208 | 0 | 1 |
| 357 | chr4 | 40197000 | 40198000 | 0.000 | 0.000 | 0.015 | 0.027 | N4BP2 | 1.00000 | 1.00000 | 0.29694 | 0 | 0 |
| 358 | chr4 | 40198000 | 40199000 | 0.000 | 0.000 | 0.088 | 0.041 | N4BP2 | 0.31126 | 0.09031 | 0.00058 | 0 | 1 |
| 359 | chr4 | 40199000 | 40200000 | 0.056 | 0.000 | 0.279 | 0.162 | N4BP2 | 0.10628 | 0.00895 | 0.00000 | 0 | 1 |
| 360 | chr4 | 40200000 | 40201000 | 0.000 | 0.006 | 0.118 | 0.041 | RHOH | 0.11795 | 0.04825 | 0.00030 | 1 | 1 |
| 361 | chr4 | 40201000 | 40202000 | 0.000 | 0.000 | 0.088 | 0.041 | RHOH | 0.31126 | 0.09031 | 0.00058 | 1 | 1 |
| 362 | chr4 | 40202000 | 40203000 | 0.000 | 0.000 | 0.029 | 0.014 | RHOH | 0.60686 | 0.54294 | 0.08726 | 1 | 0 |
| 363 | chr4 | 40204000 | 40205000 | 0.000 | 0.000 | 0.029 | 0.000 | RHOH | 0.22755 | 0.54294 | 0.08726 | 1 | 0 |
| 364 | chr4 | 45308000 | 45309000 | 0.000 | 0.000 | 0.029 | 0.014 | GNPDA2 | 0.22755 | 0.54294 | 0.29694 | 0 | 0 |
| 365 | chr4 | 46360000 | 46361000 | 0.000 | 0.000 | 0.015 | 0.000 | GABRA2 | 1.00000 | 1.00000 | 0.29694 | 0 | 0 |
| 366 | chr4 | 62375000 | 62376000 | 0.000 | 0.000 | 0.029 | 0.000 | LPHN3 | 0.22755 | 0.54294 | 0.08726 | 0 | 0 |
| 367 | chr4 | 62530000 | 62531000 | 0.000 | 0.000 | 0.029 | 0.000 | LPHN3 | 0.22755 | 0.54294 | 0.08726 | 0 | 0 |
| 368 | chr4 | 62911000 | 62912000 | 0.000 | 0.000 | 0.029 | 0.000 | LPHN3 | 0.22755 | 0.54294 | 0.08726 | 0 | 0 |
| 369 | chr4 | 63120000 | 63121000 | 0.000 | 0.000 | 0.029 | 0.000 | LPHN3 | 0.22755 | 0.54294 | 0.08726 | 0 | 0 |
| 370 | chr4 | 64015000 | 64016000 | 0.000 | 0.000 | 0.015 | 0.014 | TECRL | 1.00000 | 0.54294 | 0.29694 | 0 | 0 |
| 371 | chr4 | 65038000 | 65039000 | 0.000 | 0.000 | 0.015 | 0.014 | TECRL | 1.00000 | 1.00000 | 0.29694 | 0 | 0 |
| 372 | chr4 | 65165000 | 65166000 | 0.000 | 0.006 | 0.000 | 0.014 | EPHA5 | 1.00000 | 1.00000 | 1.00000 | 0 | 0 |
| 373 | chr4 | 65966000 | 65967000 | 0.000 | 0.000 | 0.029 | 0.000 | EPHA5 | 0.22755 | 0.54294 | 0.08726 | 0 | 0 |
| 374 | chr4 | 66827000 | 66828000 | 0.000 | 0.000 | 0.029 | 0.000 | IGJ | 0.62100 | 1.00000 | 0.29694 | 0 | 0 |
| 375 | chr4 | 71531000 | 71532000 | 0.000 | 0.000 | 0.015 | 0.041 | IGJ | 0.49735 | 1.00000 | 1.00000 | 0 | 0 |
| 376 | chr4 | 71532000 | 71533000 | 0.000 | 0.000 | 0.000 | 0.027 | RASSF6 | 0.22755 | 0.54294 | 0.08726 | 0 | 0 |
| 377 | chr4 | 74456000 | 74457000 | 0.000 | 0.000 | 0.029 | 0.000 | RASSF6 | 0.47887 | 1.00000 | 0.50663 | 0 | 0 |
| 378 | chr4 | 74483000 | 74484000 | 0.006 | 0.006 | 0.015 | 0.000 | RASSF6 | 1.00000 | 1.00000 | 0.50663 | 0 | 0 |
| 379 | chr4 | 74484000 | 74485000 | 0.000 | 0.000 | 0.044 | 0.000 | RASSF6 | 0.10727 | 0.54966 | 0.02537 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 380 | chr4 | 74485000 | 74486000 | 0.000 | 0.000 | 0.088 | 0.000 | RASSF6 | 0.01070 | 0.09031 | 0.00058 | 0 | 1 |
| 381 | chr4 | 91886000 | 91887000 | 0.000 | 0.000 | 0.015 | 0.014 | CCSER1 | 1.00000 | 1.00000 | 0.29694 | 0 | 0 |
| 382 | chr4 | 92787000 | 92788000 | 0.000 | 0.000 | 0.029 | 0.000 | CCSER1 | 0.22755 | 0.54294 | 0.08726 | 0 | 0 |
| 383 | chr4 | 113206000 | 113207000 | 0.000 | 0.000 | 0.029 | 0.000 | TIFA | 0.22755 | 0.54294 | 0.08726 | 0 | 0 |
| 384 | chr4 | 114466000 | 114467000 | 0.000 | 0.000 | 0.029 | 0.000 | CAMK2D | 0.22755 | 0.54294 | 0.08726 | 0 | 0 |
| 385 | chr4 | 114681000 | 114682000 | 0.000 | 0.000 | 0.044 | 0.000 | CAMK2D | 0.10727 | 0.54966 | 0.02537 | 0 | 0 |
| 386 | chr4 | 117928000 | 117929000 | 0.000 | 0.000 | 0.029 | 0.000 | TRAM1L1 | 0.22755 | 0.54294 | 0.08726 | 0 | 0 |
| 387 | chr4 | 123637000 | 123638000 | 0.000 | 0.000 | 0.000 | 0.027 | BBS12 | 0.49735 | 1.00000 | 1.00000 | 0 | 0 |
| 388 | chr4 | 125227000 | 125228000 | 0.000 | 0.000 | 0.015 | 0.014 | ANKRD50 | 1.00000 | 1.00000 | 0.29694 | 0 | 0 |
| 389 | chr4 | 127371000 | 127372000 | 0.000 | 0.000 | 0.029 | 0.000 | FAT4 | 0.22755 | 0.54294 | 0.08726 | 0 | 0 |
| 390 | chr4 | 133455000 | 133456000 | 0.000 | 0.000 | 0.000 | 0.027 | PCDH10 | 0.49735 | 1.00000 | 1.00000 | 0 | 0 |
| 391 | chr4 | 134538000 | 134539000 | 0.000 | 0.000 | 0.015 | 0.014 | PCDH10 | 1.00000 | 1.00000 | 0.29694 | 0 | 0 |
| 392 | chr4 | 134743000 | 134744000 | 0.000 | 0.000 | 0.029 | 0.000 | PABPC4L | 0.22755 | 0.54294 | 0.08726 | 0 | 0 |
| 393 | chr4 | 134867000 | 134868000 | 0.000 | 0.006 | 0.029 | 0.000 | PABPC4L | 0.22755 | 0.54294 | 0.08726 | 0 | 0 |
| 394 | chr4 | 134949000 | 134950000 | 0.028 | 0.000 | 0.029 | 0.000 | PABPC4L | 0.22755 | 1.00000 | 0.08726 | 0 | 0 |
| 395 | chr4 | 135064000 | 135065000 | 0.000 | 0.000 | 0.015 | 0.014 | PABPC4L | 1.00000 | 1.00000 | 0.29694 | 0 | 0 |
| 396 | chr4 | 135077000 | 135078000 | 0.000 | 0.000 | 0.029 | 0.000 | PCDH18 | 0.22755 | 0.54294 | 0.08726 | 0 | 0 |
| 397 | chr4 | 136799000 | 136800000 | 0.028 | 0.006 | 0.000 | 0.000 | PCDH18 | 1.00000 | 0.34615 | 1.00000 | 0 | 0 |
| 398 | chr4 | 136867000 | 136868000 | 0.000 | 0.000 | 0.015 | 0.014 | NAA15 | 1.00000 | 1.00000 | 0.29694 | 0 | 0 |
| 399 | chr4 | 140236000 | 140237000 | 0.000 | 0.000 | 0.029 | 0.000 | LRBA | 1.00000 | 0.54294 | 0.29694 | 0 | 0 |
| 400 | chr4 | 151723000 | 151724000 | 0.000 | 0.000 | 0.029 | 0.000 | LRBA | 0.22755 | 0.54294 | 0.08726 | 0 | 0 |
| 401 | chr4 | 151950000 | 151951000 | 0.000 | 0.000 | 0.000 | 0.027 | SH3D19 | 0.49735 | 1.00000 | 1.00000 | 0 | 0 |
| 402 | chr4 | 152125000 | 152126000 | 0.000 | 0.000 | 0.029 | 0.000 | CTSO | 0.22755 | 0.54294 | 0.08726 | 0 | 0 |
| 403 | chr4 | 157246000 | 157247000 | 0.028 | 0.000 | 0.015 | 0.014 | 1-Mar-19 | 1.00000 | 1.00000 | 0.29694 | 0 | 0 |
| 404 | chr4 | 164532000 | 164533000 | 0.000 | 0.000 | 0.000 | 0.027 | AGA | 0.49735 | 1.00000 | 1.00000 | 0 | 0 |
| 405 | chr4 | 178732000 | 178733000 | 0.000 | 0.000 | 0.015 | 0.014 | AGA | 1.00000 | 0.34615 | 1.00000 | 0 | 0 |
| 406 | chr4 | 178885000 | 178886000 | 0.000 | 0.000 | 0.029 | 0.000 | AGA | 1.00000 | 0.54294 | 1.00000 | 0 | 0 |
| 407 | chr4 | 179898000 | 179899000 | 0.000 | 0.000 | 0.029 | 0.000 | TENM3 | 0.22755 | 0.54294 | 0.08726 | 0 | 0 |
| 408 | chr4 | 180885000 | 180886000 | 0.000 | 0.006 | 0.029 | 0.000 | TENM3 | 0.22755 | 0.54294 | 0.21104 | 0 | 0 |
| 409 | chr4 | 181554000 | 181555000 | 0.000 | 0.000 | 0.015 | 0.014 | TENM3 | 1.00000 | 1.00000 | 0.29694 | 0 | 0 |
| 410 | chr4 | 182122000 | 182123000 | 0.000 | 0.000 | 0.029 | 0.000 | AHRR | 1.00000 | 1.00000 | 1.00000 | 0 | 0 |
| 411 | chr5 | 436000 | 437000 | 0.028 | 0.000 | 0.029 | 0.000 | IRX1 | 1.00000 | 0.34615 | 0.21104 | 0 | 0 |
| 412 | chr5 | 3982000 | 3983000 | 0.000 | 0.000 | 0.029 | 0.000 | BASP1 | 0.22755 | 0.54294 | 0.08726 | 0 | 0 |
| 413 | chr5 | 17218000 | 17219000 | 0.000 | 0.000 | 0.029 | 0.000 | BASP1 | 0.22755 | 0.54294 | 0.08726 | 0 | 0 |
| 414 | chr5 | 17219000 | 17220000 | 0.000 | 0.000 | 0.029 | 0.000 | CDH18 | 1.00000 | 0.34615 | 1.00000 | 0 | 0 |
| 415 | chr5 | 18514000 | 18515000 | 0.028 | 0.000 | 0.015 | 0.014 | CDH18 | 1.00000 | 0.54294 | 0.08726 | 0 | 0 |
| 416 | chr5 | 22356000 | 22357000 | 0.000 | 0.000 | 0.029 | 0.000 | CDH12 | 0.22755 | 0.54294 | 0.08726 | 0 | 0 |
| 417 | chr5 | 22517000 | 22518000 | 0.000 | 0.000 | 0.015 | 0.014 | CDH12 | 1.00000 | 1.00000 | 0.29694 | 0 | 0 |
| 418 | chr5 | 24632000 | 24633000 | 0.000 | 0.000 | 0.029 | 0.000 | CDH10 | 0.22755 | 0.54294 | 0.08726 | 0 | 0 |
| 419 | chr5 | 25275000 | 25276000 | 0.000 | 0.000 | 0.015 | 0.014 | CDH10 | 1.00000 | 1.00000 | 0.29694 | 0 | 0 |
| 420 | chr5 | 25541000 | 25542000 | 0.000 | 0.000 | 0.029 | 0.000 | CDH10 | 0.22755 | 0.54294 | 0.08726 | 0 | 0 |
| 421 | chr5 | 26119000 | 26120000 | 0.000 | 0.000 | 0.015 | 0.014 | CDH9 | 1.00000 | 1.00000 | 0.29694 | 0 | 0 |
| 422 | chr5 | 26450000 | 26451000 | 0.000 | 0.000 | 0.029 | 0.000 | CDH9 | 0.22755 | 0.54294 | 0.08726 | 0 | 0 |
| 423 | chr5 | 29224000 | 29225000 | 0.000 | 0.000 | 0.029 | 0.000 | CDH6 | 0.22755 | 0.54294 | 0.08726 | 0 | 0 |
| 424 | chr5 | 29492000 | 29493000 | 0.000 | 0.000 | 0.029 | 0.000 | CDH6 | 0.22755 | 0.54294 | 0.08726 | 0 | 0 |
| 425 | chr5 | 29648000 | 29649000 | 0.000 | 0.000 | 0.029 | 0.000 | CDH6 | 0.22755 | 0.54294 | 0.08726 | 0 | 0 |
| 426 | chr5 | 51521000 | 51522000 | 0.000 | 0.000 | 0.044 | 0.014 | CTD-2203A3.1 | 0.34948 | 0.54966 | 0.02537 | 0 | 0 |
| 427 | chr5 | 83841000 | 83842000 | 0.000 | 0.000 | 0.029 | 0.000 | EDIL3 | 0.22755 | 0.54294 | 0.08726 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAny Histology |
|---|---|---|---|---|---|---|---|---|---|---|---|---|---|
| 428 | chr5 | 88177000 | 88178000 | 0.000 | 0.000 | 0.029 | 0.000 | MEF2C | 0.22755 | 0.54294 | 0.08726 | 0 | 0 |
| 429 | chr5 | 88178000 | 88179000 | 0.000 | 0.000 | 0.015 | 0.014 | MEF2C | 1.00000 | 1.00000 | 0.29694 | 0 | 0 |
| 430 | chr5 | 91417000 | 91418000 | 0.000 | 0.000 | 0.000 | 0.027 | ARRDC3 | 0.49735 | 1.00000 | 1.00000 | 0 | 0 |
| 431 | chr5 | 103678000 | 103679000 | 0.000 | 0.000 | 0.015 | 0.014 | NUDT12 | 1.00000 | 1.00000 | 0.29694 | 0 | 0 |
| 432 | chr5 | 123696000 | 123697000 | 0.000 | 0.000 | 0.000 | 0.027 | ZNF608 | 0.49735 | 1.00000 | 1.00000 | 1 | 0 |
| 433 | chr5 | 124079000 | 124080000 | 0.000 | 0.000 | 0.029 | 0.014 | ZNF608 | 0.60686 | 0.54294 | 0.08726 | 1 | 0 |
| 434 | chr5 | 124080000 | 124081000 | 0.000 | 0.000 | 0.029 | 0.014 | ZNF608 | 0.60686 | 0.54294 | 0.08726 | 0 | 0 |
| 435 | chr5 | 127594000 | 127595000 | 0.000 | 0.000 | 0.015 | 0.000 | FBN2 | 1.00000 | 1.00000 | 0.29694 | 0 | 0 |
| 436 | chr5 | 127875000 | 127876000 | 0.000 | 0.000 | 0.000 | 0.027 | FBN2 | 0.49735 | 1.00000 | 1.00000 | 0 | 0 |
| 437 | chr5 | 131825000 | 131826000 | 0.000 | 0.000 | 0.074 | 0.000 | IRF1 | 0.02326 | 0.16101 | 0.00208 | 0 | 1 |
| 438 | chr5 | 131826000 | 131827000 | 0.000 | 0.000 | 0.029 | 0.000 | IRF1 | 0.22755 | 0.54294 | 0.08726 | 0 | 0 |
| 439 | chr5 | 149791000 | 149792000 | 0.000 | 0.000 | 0.132 | 0.014 | CD74 | 0.00701 | 0.02564 | 0.00001 | 1 | 1 |
| 440 | chr5 | 149792000 | 149793000 | 0.000 | 0.000 | 0.015 | 0.000 | CD74 | 1.00000 | 1.00000 | 0.29694 | 0 | 0 |
| 441 | chr5 | 158380000 | 158381000 | 0.028 | 0.000 | 0.015 | 0.014 | EBF1 | 0.47887 | 1.00000 | 0.29694 | 0 | 0 |
| 442 | chr5 | 158479000 | 158480000 | 0.000 | 0.000 | 0.025 | 0.000 | EBF1 | 0.22755 | 1.00000 | 0.08726 | 0 | 0 |
| 443 | chr5 | 158526000 | 158527000 | 0.028 | 0.000 | 0.044 | 0.000 | EBF1 | 0.10727 | 1.00000 | 0.02537 | 0 | 0 |
| 444 | chr5 | 158527000 | 158528000 | 0.000 | 0.000 | 0.029 | 0.000 | EBF1 | 0.22755 | 0.54294 | 0.08726 | 0 | 0 |
| 445 | chr5 | 158528000 | 158529000 | 0.000 | 0.000 | 0.059 | 0.000 | EBF1 | 0.05016 | 0.29551 | 0.00730 | 0 | 1 |
| 446 | chr5 | 164247000 | 164248000 | 0.000 | 0.000 | 0.029 | 0.000 | MAT2B | 0.22755 | 0.54294 | 0.08726 | 0 | 0 |
| 447 | chr5 | 164441000 | 164442000 | 0.028 | 0.000 | 0.015 | 0.014 | MAT2B | 0.47887 | 1.00000 | 0.29694 | 0 | 0 |
| 448 | chr5 | 165932000 | 165933000 | 0.000 | 0.000 | 0.015 | 0.000 | TENM2 | 1.00000 | 1.00000 | 0.29694 | 0 | 0 |
| 449 | chr5 | 173300000 | 173301000 | 0.000 | 0.000 | 0.000 | 0.027 | CPEB4 | 0.49735 | 1.00000 | 1.00000 | 0 | 0 |
| 450 | chr5 | 179166000 | 179167000 | 0.000 | 0.000 | 0.015 | 0.027 | MAML1 | 1.00000 | 1.00000 | 0.29694 | 0 | 0 |
| 451 | chr6 | 180102000 | 180103000 | 0.000 | 0.000 | 0.015 | 0.014 | FLT4 | 1.00000 | 1.00000 | 0.29694 | 0 | 0 |
| 452 | chr6 | 392000 | 393000 | 0.000 | 0.000 | 0.074 | 0.000 | IRF4 | 0.02326 | 0.16101 | 0.00208 | 1 | 1 |
| 453 | chr6 | 393000 | 394000 | 0.000 | 0.000 | 0.074 | 0.027 | IRF4 | 0.02326 | 0.16101 | 0.00208 | 1 | 1 |
| 454 | chr6 | 14118000 | 14119000 | 0.000 | 0.000 | 0.279 | 0.000 | CD83 | 0.00011 | 0.00013 | 0.00000 | 1 | 1 |
| 455 | chr6 | 14119000 | 14120000 | 0.000 | 0.000 | 0.044 | 0.027 | CD83 | 0.67043 | 0.54966 | 0.02537 | 0 | 0 |
| 456 | chr6 | 18111000 | 18112000 | 0.028 | 0.000 | 0.044 | 0.000 | NHLRC1 | 0.10727 | 1.00000 | 0.02537 | 0 | 0 |
| 457 | chr6 | 18387000 | 18388000 | 0.000 | 0.000 | 0.000 | 0.027 | RNF144B | 0.49735 | 1.00000 | 1.00000 | 1 | 0 |
| 458 | chr6 | 18388000 | 18389000 | 0.000 | 0.000 | 0.000 | 0.027 | RNF144B | 0.49735 | 1.00000 | 1.00000 | 1 | 0 |
| 459 | chr6 | 19573000 | 19574000 | 0.000 | 0.000 | 0.029 | 0.014 | ID4 | 1.00000 | 0.54294 | 0.08726 | 0 | 0 |
| 460 | chr6 | 22873000 | 22874000 | 0.000 | 0.000 | 0.015 | 0.000 | HDGFL1 | 1.00000 | 1.00000 | 0.29694 | 1 | 0 |
| 461 | chr6 | 26031000 | 26032000 | 0.000 | 0.000 | 0.074 | 0.027 | HIST1H3B | 0.02326 | 0.16101 | 0.00208 | 1 | 1 |
| 462 | chr6 | 26032000 | 26033000 | 0.000 | 0.000 | 0.074 | 0.027 | HIST1H3B | 0.02326 | 0.16101 | 0.00208 | 1 | 1 |
| 463 | chr6 | 26056000 | 26057000 | 0.000 | 0.000 | 0.059 | 0.027 | HIST1H1C | 0.42627 | 0.29551 | 0.00730 | 1 | 1 |
| 464 | chr6 | 26123000 | 26124000 | 0.000 | 0.000 | 0.059 | 0.014 | HIST1H2BG | 0.19371 | 0.29551 | 0.00730 | 1 | 1 |
| 465 | chr6 | 26124000 | 26125000 | 0.000 | 0.000 | 0.074 | 0.000 | HIST1H2AC; HIST1H2BC; | 0.02326 | 0.16101 | 0.00208 | 0 | 1 |
| 466 | chr6 | 26125000 | 26126000 | 0.000 | 0.000 | 0.015 | 0.014 | HIST1H2AC | 1.00000 | 1.00000 | 0.29694 | 1 | 0 |
| 467 | chr6 | 26156000 | 26157000 | 0.000 | 0.000 | 0.074 | 0.014 | HIST1H1E | 0.10420 | 0.16101 | 0.00208 | 1 | 1 |
| 468 | chr6 | 26157000 | 26158000 | 0.000 | 0.000 | 0.029 | 0.000 | HIST1H1E | 0.60686 | 0.54294 | 0.08726 | 0 | 0 |
| 469 | chr6 | 26216000 | 26217000 | 0.000 | 0.000 | 0.029 | 0.014 | HIST1H2BG | 0.22755 | 0.54294 | 0.08726 | 0 | 0 |
| 470 | chr6 | 26234000 | 26235000 | 0.000 | 0.000 | 0.044 | 0.000 | HIST1H1D | 0.10727 | 0.54966 | 0.02537 | 0 | 0 |
| 471 | chr6 | 27101000 | 27102000 | 0.000 | 0.000 | 0.029 | 0.014 | HIST1H2AG | 0.22755 | 0.54294 | 0.08726 | 1 | 0 |
| 472 | chr6 | 27114000 | 27115000 | 0.000 | 0.000 | 0.059 | 0.000 | HIST1H2AH; HIST1H2BK; | 0.19371 | 0.29551 | 0.00730 | 0 | 1 |
| 473 | chr6 | 27792000 | 27793000 | 0.000 | 0.000 | 0.044 | 0.014 | HIST1H4J | 0.34948 | 0.54966 | 0.02537 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 474 | chr6 | 27833000 | 27834000 | 0.000 | 0.000 | 0.015 | 0.014 | HIST1H2AL | 1.00000 | 1.00000 | 0.29694 | 1 | 0 |
| 475 | chr6 | 27860000 | 27861000 | 0.000 | 0.000 | 0.029 | 0.027 | HIST1H2AM | 1.00000 | 0.54294 | 0.08726 | 1 | 0 |
| 476 | chr6 | 27861000 | 27862000 | 0.000 | 0.000 | 0.015 | 0.014 | HIST1H2BO | 1.00000 | 1.00000 | 0.29694 | 1 | 0 |
| 477 | chr6 | 29778000 | 29779000 | 0.028 | 0.000 | 0.000 | 0.014 | LOC54223 | 1.00000 | 0.34615 | 1.00000 | 0 | 0 |
| 478 | chr6 | 29780000 | 29781000 | 0.000 | 0.000 | 0.015 | 0.014 | HLA-G | 1.00000 | 1.00000 | 0.29694 | 0 | 0 |
| 479 | chr6 | 29911000 | 29912000 | 0.000 | 0.000 | 0.044 | 0.000 | HLA-A | 0.10727 | 0.54966 | 0.02537 | 1 | 0 |
| 480 | chr6 | 29927000 | 29928000 | 0.000 | 0.000 | 0.015 | 0.014 | HLA-A | 1.00000 | 1.00000 | 0.29694 | 1 | 0 |
| 481 | chr6 | 31324000 | 31325000 | 0.028 | 0.000 | 0.029 | 0.014 | HLA-B | 0.60686 | 0.54294 | 0.08726 | 1 | 0 |
| 482 | chr6 | 31325000 | 31326000 | 0.000 | 0.000 | 0.029 | 0.000 | HLA-B | 1.00000 | 1.00000 | 1.00000 | 1 | 0 |
| 483 | chr6 | 31543000 | 31544000 | 0.000 | 0.000 | 0.029 | 0.000 | TNF | 0.22755 | 0.54294 | 0.08726 | 1 | 0 |
| 484 | chr6 | 31549000 | 31550000 | 0.000 | 0.006 | 0.191 | 0.068 | LTB | 0.04150 | 0.00372 | 0.00000 | 1 | 1 |
| 485 | chr6 | 31550000 | 31551000 | 0.000 | 0.000 | 0.044 | 0.000 | LTB | 0.10727 | 0.54966 | 0.02537 | 1 | 0 |
| 486 | chr6 | 32440000 | 32441000 | 0.028 | 0.000 | 0.044 | 0.027 | HLA-DRA | 0.67043 | 0.54966 | 0.02537 | 0 | 0 |
| 487 | chr6 | 32451000 | 32452000 | 0.056 | 0.000 | 0.000 | 0.000 | HLA-DRB5 | 1.00000 | 0.11763 | 1.00000 | 0 | 1 |
| 488 | chr6 | 32452000 | 32453000 | 0.028 | 0.000 | 0.015 | 0.000 | HLA-DRB5 | 0.47887 | 1.00000 | 0.29694 | 0 | 0 |
| 489 | chr6 | 32455000 | 32456000 | 0.028 | 0.000 | 0.015 | 0.027 | HLA-DRB5 | 0.47887 | 1.00000 | 0.29694 | 0 | 0 |
| 490 | chr6 | 32457000 | 32458000 | 0.056 | 0.000 | 0.000 | 0.027 | HLA-DRB5 | 0.49735 | 1.00000 | 1.00000 | 0 | 0 |
| 491 | chr6 | 32498000 | 32499000 | 0.000 | 0.000 | 0.029 | 0.027 | HLA-DRB5 | 0.49735 | 1.00000 | 1.00000 | 0 | 0 |
| 492 | chr6 | 32505000 | 32506000 | 0.000 | 0.000 | 0.029 | 0.041 | HLA-DRB5 | 0.60686 | 0.54294 | 0.08726 | 0 | 0 |
| 493 | chr6 | 32511000 | 32512000 | 0.000 | 0.000 | 0.000 | 0.027 | HLA-DRB1 | 0.24603 | 1.00000 | 1.00000 | 0 | 0 |
| 494 | chr6 | 32522000 | 32523000 | 0.028 | 0.000 | 0.015 | 0.014 | HLA-DRB1 | 1.00000 | 1.00000 | 0.29694 | 0 | 0 |
| 495 | chr6 | 32525000 | 32526000 | 0.000 | 0.000 | 0.029 | 0.014 | HLA-DRB1 | 0.60686 | 0.54294 | 0.08726 | 0 | 0 |
| 496 | chr6 | 32526000 | 32527000 | 0.028 | 0.000 | 0.015 | 0.041 | HLA-DRB1 | 0.24603 | 1.00000 | 1.00000 | 0 | 0 |
| 497 | chr6 | 32527000 | 32528000 | 0.000 | 0.000 | 0.000 | 0.027 | HLA-DRB1 | 0.49735 | 1.00000 | 1.00000 | 0 | 0 |
| 498 | chr6 | 32548000 | 32549000 | 0.000 | 0.000 | 0.029 | 0.014 | HLA-DRB1 | 0.60686 | 0.54294 | 0.08726 | 0 | 0 |
| 499 | chr6 | 32552000 | 32553000 | 0.000 | 0.000 | 0.015 | 0.027 | HLA-DRB1 | 1.00000 | 0.27446 | 0.29694 | 0 | 1 |
| 500 | chr6 | 32557000 | 32558000 | 0.028 | 0.000 | 0.000 | 0.041 | HLA-DRB1 | 0.24603 | 0.34615 | 1.00000 | 0 | 0 |
| 501 | chr6 | 32609000 | 32610000 | 0.028 | 0.000 | 0.059 | 0.014 | HLA-DQA1 | 0.19371 | 0.65667 | 0.00730 | 0 | 1 |
| 502 | chr6 | 32630000 | 32631000 | 0.000 | 0.000 | 0.015 | 0.014 | HLA-DQB1 | 1.00000 | 1.00000 | 0.29694 | 0 | 0 |
| 503 | chr6 | 32632000 | 32633000 | 0.111 | 0.000 | 0.029 | 0.027 | HLA-DQB1 | 1.00000 | 0.00372 | 0.08726 | 0 | 1 |
| 504 | chr6 | 32727000 | 32728000 | 0.056 | 0.000 | 0.015 | 0.014 | HLA-DQB2 | 1.00000 | 0.17874 | 0.29694 | 0 | 1 |
| 505 | chr6 | 32729000 | 32730000 | 0.056 | 0.000 | 0.029 | 0.014 | HLA-DQB2 | 0.47887 | 0.27446 | 0.29694 | 0 | 1 |
| 506 | chr6 | 33048000 | 33049000 | 0.000 | 0.000 | 0.015 | 0.014 | HLA-DPB1 | 0.60686 | 0.60763 | 0.08726 | 0 | 0 |
| 507 | chr6 | 34179000 | 34180000 | 0.000 | 0.000 | 0.015 | 0.000 | HMGA1 | 1.00000 | 1.00000 | 0.29694 | 0 | 0 |
| 51.5 | chr6 | 37139000 | 37140000 | 0.000 | 0.000 | 0.029 | 0.000 | PIM1 | 0.22755 | 0.54294 | 0.08726 | 1 | 0 |
| 508 | chr6 | 37139000 | 37140000 | 0.000 | 0.000 | 0.191 | 0.041 | PIM1 | 0.08249 | 0.00372 | 0.00000 | 1 | 1 |
| 509 | chr6 | 37140000 | 37141000 | 0.000 | 0.000 | 0.088 | 0.081 | PIM1 | 0.31126 | 0.09031 | 0.00058 | 1 | 1 |
| 510 | chr6 | 58001000 | 58002000 | 0.000 | 0.000 | 0.029 | 0.014 | PRIM2 | 0.60686 | 0.54294 | 0.08726 | 0 | 0 |
| 511 | chr6 | 67923000 | 67924000 | 0.000 | 0.000 | 0.015 | 0.014 | BAI3 | 1.00000 | 1.00000 | 0.29694 | 0 | 0 |
| 512 | chr6 | 77256000 | 77257000 | 0.000 | 0.000 | 0.029 | 0.000 | IMPG1 | 0.22755 | 0.54294 | 0.08726 | 0 | 0 |
| 513 | chr6 | 81437000 | 81438000 | 0.000 | 0.000 | 0.015 | 0.014 | BCKDHB | 1.00000 | 1.00000 | 0.29694 | 0 | 0 |
| 514 | chr6 | 88468000 | 88469000 | 0.000 | 0.000 | 0.029 | 0.014 | AKIRIN2 | 1.00000 | 1.00000 | 0.08726 | 0 | 0 |
| 516 | chr6 | 88630000 | 88631000 | 0.028 | 0.000 | 0.044 | 0.000 | SPACA1 | 0.34948 | 0.54966 | 0.02537 | 0 | 0 |
| 517 | chr6 | 88876000 | 88877000 | 0.000 | 0.000 | 0.015 | 0.000 | CNR1 | 1.00000 | 1.00000 | 0.29694 | 0 | 0 |
| 518 | chr6 | 89323000 | 89324000 | 0.028 | 0.000 | 0.029 | 0.014 | RNGTT | 0.47887 | 0.54294 | 0.08726 | 0 | 0 |
| 519 | chr6 | 89338000 | 89339000 | 0.000 | 0.000 | 0.029 | 0.000 | RNGTT | 0.22755 | 0.54294 | 0.08726 | 0 | 0 |
| 520 | chr6 | 89348000 | 89349000 | 0.000 | 0.000 | 0.044 | 0.014 | RNGTT | 0.10727 | 0.54966 | 0.02537 | 0 | 0 |
| 521 | chr6 | 89470000 | 89471000 | 0.000 | 0.000 | 0.029 | 0.000 | RNGTT | 0.22755 | 0.54294 | 0.08726 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 522 | chr6 | 89471000 | 89472000 | 0.000 | 0.000 | 0.029 | 0.000 | RNGTT | 0.22755 | 0.54294 | 0.08726 | 0 | 0 |
| 523 | chr6 | 90061000 | 90062000 | 0.000 | 0.000 | 0.059 | 0.000 | UBE2J1 | 0.05016 | 0.29551 | 0.00730 | 1 | 1 |
| 524 | chr6 | 90062000 | 90063000 | 0.000 | 0.000 | 0.029 | 0.000 | UBE2J1 | 0.22755 | 0.54294 | 0.08726 | 1 | 0 |
| 525 | chr6 | 90994000 | 90995000 | 0.000 | 0.000 | 0.029 | 0.014 | MAP3K7 | 0.60686 | 0.54294 | 0.08726 | 0 | 1 |
| 526 | chr6 | 91004000 | 91005000 | 0.000 | 0.000 | 0.059 | 0.014 | MAP3K7 | 0.19371 | 0.29551 | 0.00730 | 1 | 1 |
| 527 | chr6 | 91005000 | 91006000 | 0.000 | 0.019 | 0.294 | 0.095 | MAP3K7 | 0.00279 | 0.00011 | 0.00000 | 1 | 1 |
| 528 | chr6 | 91006000 | 91007000 | 0.000 | 0.006 | 0.118 | 0.027 | MAP3K7 | 0.04838 | 0.04825 | 0.00030 | 0 | 0 |
| 529 | chr6 | 91007000 | 91008000 | 0.000 | 0.012 | 0.029 | 0.000 | MAP3K7 | 0.22755 | 0.54294 | 0.58408 | 0 | 0 |
| 530 | chr6 | 94822000 | 94823000 | 0.028 | 0.000 | 0.015 | 0.014 | EPHA7 | 0.47887 | 1.00000 | 0.29694 | 0 | 0 |
| 531 | chr6 | 107704000 | 107705000 | 0.028 | 0.000 | 0.000 | 0.000 | PDSS2 | 1.00000 | 0.34615 | 1.00000 | 0 | 0 |
| 532 | chr6 | 112885000 | 112886000 | 0.000 | 0.000 | 0.015 | 0.014 | RFPL4B | 1.00000 | 1.00000 | 0.29694 | 0 | 0 |
| 533 | chr6 | 118244000 | 118245000 | 0.000 | 0.000 | 0.015 | 0.014 | SLC35F1 | 1.00000 | 1.00000 | 0.29694 | 0 | 0 |
| 534 | chr6 | 121288000 | 121289000 | 0.000 | 0.000 | 0.000 | 0.027 | C6orf170 | 0.49735 | 1.00000 | 1.00000 | 0 | 0 |
| 535 | chr6 | 121489000 | 121490000 | 0.000 | 0.000 | 0.029 | 0.000 | C6orf170 | 0.22755 | 0.54294 | 0.08726 | 0 | 0 |
| 536 | chr6 | 123504000 | 123505000 | 0.000 | 0.006 | 0.015 | 0.000 | TRDN | 1.00000 | 1.00000 | 1.00000 | 0 | 0 |
| 537 | chr6 | 127313000 | 127314000 | 0.000 | 0.006 | 0.015 | 0.014 | RSPO3 | 0.47887 | 1.00000 | 0.50663 | 0 | 0 |
| 538 | chr6 | 133785000 | 133786000 | 0.000 | 0.000 | 0.029 | 0.000 | EYA4 | 0.22755 | 0.54294 | 0.08726 | 1 | 1 |
| 539 | chr6 | 134491000 | 134492000 | 0.000 | 0.000 | 0.029 | 0.000 | SGK1 | 0.22755 | 0.54294 | 0.08726 | 1 | 0 |
| 540 | chr6 | 134492000 | 134493000 | 0.000 | 0.000 | 0.044 | 0.014 | SGK1 | 0.34948 | 0.54966 | 0.02537 | 1 | 0 |
| 541 | chr6 | 134493000 | 134494000 | 0.000 | 0.000 | 0.029 | 0.000 | SGK1 | 0.22755 | 0.54294 | 0.08726 | 1 | 0 |
| 542 | chr6 | 134494000 | 134495000 | 0.000 | 0.000 | 0.029 | 0.000 | SGK1 | 0.22755 | 0.54294 | 0.08726 | 1 | 0 |
| 543 | chr6 | 134495000 | 134496000 | 0.028 | 0.000 | 0.162 | 0.041 | SGK1 | 0.02233 | 0.01471 | 0.00000 | 1 | 1 |
| 544 | chr6 | 134496000 | 134497000 | 0.000 | 0.000 | 0.029 | 0.000 | SGK1 | 0.22755 | 0.54294 | 0.08726 | 1 | 0 |
| 545 | chr6 | 142046000 | 142047000 | 0.000 | 0.000 | 0.059 | 0.000 | NMBR | 0.05016 | 0.29551 | 0.00730 | 1 | 1 |
| 546 | chr6 | 147860000 | 147861000 | 0.028 | 0.000 | 0.015 | 0.014 | SAMD5 | 0.47887 | 1.00000 | 0.08726 | 0 | 0 |
| 547 | chr6 | 150954000 | 150955000 | 0.000 | 0.000 | 0.044 | 0.014 | PLEKHG1 | 0.34948 | 0.54966 | 0.02537 | 0 | 0 |
| 548 | chr6 | 159238000 | 159239000 | 0.000 | 0.012 | 0.044 | 0.000 | EZR | 0.34948 | 0.54966 | 0.15671 | 0 | 0 |
| 549 | chr6 | 159239000 | 159240000 | 0.000 | 0.000 | 0.029 | 0.014 | EZR | 0.60686 | 0.54294 | 0.08726 | 0 | 0 |
| 550 | chr6 | 159240000 | 159241000 | 0.000 | 0.000 | 0.059 | 0.000 | EZR | 0.05016 | 0.29551 | 0.00730 | 0 | 0 |
| 551 | chr6 | 159464000 | 159465000 | 0.028 | 0.000 | 0.015 | 0.014 | TAGAP | 0.47887 | 1.00000 | 0.29694 | 0 | 0 |
| 552 | chr6 | 159465000 | 159466000 | 0.000 | 0.000 | 0.029 | 0.000 | TAGAP | 0.22755 | 0.54294 | 0.08726 | 0 | 0 |
| 553 | chr6 | 161265000 | 161266000 | 0.028 | 0.000 | 0.000 | 0.027 | PLG | 0.49735 | 0.34615 | 1.00000 | 0 | 0 |
| 554 | chr6 | 161833000 | 161834000 | 0.000 | 0.000 | 0.000 | 0.027 | PARK2 | 0.49735 | 0.34615 | 1.00000 | 0 | 0 |
| 555 | chr6 | 162712000 | 162713000 | 0.000 | 0.000 | 0.029 | 0.014 | PARK2 | 0.60686 | 0.54294 | 0.08726 | 0 | 0 |
| 556 | chr6 | 164941000 | 164942000 | 0.000 | 0.000 | 0.015 | 0.014 | C6orf118 | 1.00000 | 1.00000 | 0.29694 | 0 | 0 |
| 557 | chr6 | 168813000 | 168814000 | 0.028 | 0.000 | 0.029 | 0.000 | SMOC2 | 0.22755 | 0.54294 | 0.08726 | 0 | 0 |
| 558 | chr7 | 1898000 | 1899000 | 0.000 | 0.000 | 0.029 | 0.014 | AC110781.3 | 0.47887 | 0.54294 | 0.08726 | 0 | 0 |
| 559 | chr7 | 1963000 | 1964000 | 0.000 | 0.000 | 0.015 | 0.000 | MAD1L1 | 1.00000 | 1.00000 | 0.29694 | 0 | 0 |
| 560 | chr7 | 2080000 | 2081000 | 0.000 | 0.000 | 0.015 | 0.014 | MAD1L1 | 1.00000 | 1.00000 | 0.29694 | 0 | 0 |
| 561 | chr7 | 5568000 | 5569000 | 0.000 | 0.000 | 0.059 | 0.014 | ACTB | 0.19371 | 0.29551 | 0.00730 | 1 | 1 |
| 562 | chr7 | 5569000 | 5570000 | 0.000 | 0.000 | 0.059 | 0.014 | ACTB | 0.19371 | 0.29551 | 0.00730 | 1 | 0 |
| 563 | chr7 | 5570000 | 5571000 | 0.000 | 0.000 | 0.015 | 0.027 | ACTB | 1.00000 | 1.00000 | 0.29694 | 0 | 0 |
| 564 | chr7 | 9933000 | 9934000 | 0.028 | 0.000 | 0.029 | 0.014 | NDUFA4 | 0.60686 | 0.54294 | 0.08726 | 0 | 0 |
| 565 | chr7 | 13017000 | 13018000 | 0.000 | 0.000 | 0.015 | 0.014 | ARL4A | 0.47887 | 1.00000 | 0.29694 | 0 | 0 |
| 566 | chr7 | 13346000 | 13347000 | 0.000 | 0.000 | 0.000 | 0.027 | ETV1 | 0.49735 | 1.00000 | 1.00000 | 1 | 0 |
| 567 | chr7 | 15459000 | 15460000 | 0.000 | 0.000 | 0.015 | 0.027 | AGMO | 1.00000 | 1.00000 | 1.00000 | 0 | 0 |
| 568 | chr7 | 16382000 | 16383000 | 0.000 | 0.000 | 0.015 | 0.014 | ISPD | 1.00000 | 1.00000 | 0.29694 | 0 | 0 |
| 569 | chr7 | 28600000 | 28601000 | 0.000 | 0.000 | 0.015 | 0.000 | CREB5 | 0.47887 | 1.00000 | 0.29694 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAny Histology |
|---|---|---|---|---|---|---|---|---|---|---|---|---|---|
| 570 | chr7 | 40846000 | 40847000 | 0.000 | 0.000 | 0.015 | 0.041 | C7orf10 | 0.62100 | 1.00000 | 0.29694 | 0 | 0 |
| 571 | chr7 | 50349000 | 50350000 | 0.000 | 0.000 | 0.059 | 0.014 | IKZF1 | 0.19371 | 0.29551 | 0.00730 | 0 | 1 |
| 572 | chr7 | 50350000 | 50351000 | 0.000 | 0.000 | 0.044 | 0.000 | IKZF1 | 0.10727 | 0.54966 | 0.02537 | 0 | 0 |
| 573 | chr7 | 53335000 | 53336000 | 0.000 | 0.000 | 0.000 | 0.027 | POM121L12 | 0.49735 | 1.00000 | 1.00000 | 0 | 0 |
| 574 | chr7 | 57713000 | 57714000 | 0.000 | 0.000 | 0.029 | 0.000 | ZNF716 | 0.22755 | 1.00000 | 0.08726 | 0 | 0 |
| 575 | chr7 | 62475000 | 62476000 | 0.000 | 0.000 | 0.015 | 0.027 | AC006455.1 | 0.22755 | 0.54294 | 0.08726 | 0 | 0 |
| 576 | chr7 | 70669000 | 70670000 | 0.000 | 0.000 | 0.029 | 0.000 | WBSCR17 | 1.00000 | 1.00000 | 0.08726 | 0 | 0 |
| 577 | chr7 | 71553000 | 71554000 | 0.000 | 0.000 | 0.015 | 0.014 | CALN1 | 0.22755 | 0.54294 | 0.29694 | 0 | 0 |
| 578 | chr7 | 79847000 | 79848000 | 0.000 | 0.000 | 0.015 | 0.014 | GNAI1 | 1.00000 | 1.00000 | 0.29694 | 0 | 0 |
| 579 | chr7 | 80694000 | 80695000 | 0.000 | 0.000 | 0.029 | 0.000 | AC005008.2 | 0.22755 | 0.54294 | 0.08726 | 0 | 0 |
| 580 | chr7 | 81556000 | 81557000 | 0.000 | 0.000 | 0.000 | 0.027 | CACNA2D1 | 0.49735 | 1.00000 | 1.00000 | 0 | 0 |
| 581 | chr7 | 84127000 | 84128000 | 0.028 | 0.000 | 0.015 | 0.000 | SEMA3A | 0.47887 | 1.00000 | 0.29694 | 0 | 0 |
| 582 | chr7 | 84247000 | 84248000 | 0.000 | 0.000 | 0.029 | 0.000 | SEMA3D | 0.22755 | 0.54294 | 0.08726 | 0 | 0 |
| 583 | chr7 | 84257000 | 84258000 | 0.028 | 0.000 | 0.015 | 0.000 | SEMA3D | 0.47887 | 1.00000 | 0.29694 | 0 | 0 |
| 584 | chr7 | 86914000 | 86915000 | 0.000 | 0.000 | 0.015 | 0.014 | CROT | 1.00000 | 1.00000 | 0.29694 | 0 | 0 |
| 585 | chr7 | 90356000 | 90357000 | 0.000 | 0.000 | 0.029 | 0.000 | CDK14 | 0.22755 | 0.54294 | 0.08726 | 0 | 0 |
| 586 | chr7 | 93304000 | 93305000 | 0.000 | 0.000 | 0.029 | 0.000 | CALCR | 0.22755 | 0.54294 | 0.08726 | 0 | 0 |
| 587 | chr7 | 93682000 | 93683000 | 0.000 | 0.000 | 0.015 | 0.014 | BET1 | 1.00000 | 1.00000 | 0.29694 | 0 | 0 |
| 588 | chr7 | 102644000 | 102645000 | 0.028 | 0.000 | 0.000 | 0.000 | FBXL13 | 1.00000 | 0.34615 | 1.00000 | 0 | 0 |
| 589 | chr7 | 105699000 | 105700000 | 0.000 | 0.000 | 0.015 | 0.027 | CDHR3 | 1.00000 | 1.00000 | 0.29694 | 0 | 0 |
| 590 | chr7 | 110521000 | 110522000 | 0.000 | 0.000 | 0.029 | 0.000 | IMMP2L | 0.22755 | 0.54294 | 0.08726 | 0 | 0 |
| 591 | chr7 | 110543000 | 110544000 | 0.000 | 0.000 | 0.015 | 0.000 | IMMP2L | 0.22755 | 0.54294 | 0.29694 | 0 | 0 |
| 592 | chr7 | 110545000 | 110546000 | 0.000 | 0.000 | 0.015 | 0.000 | IMMP2L | 1.00000 | 1.00000 | 0.29694 | 0 | 0 |
| 593 | chr7 | 110597000 | 110598000 | 0.000 | 0.000 | 0.015 | 0.000 | IMMP2L | 0.22755 | 0.54294 | 0.29694 | 0 | 0 |
| 594 | chr7 | 110601000 | 110602000 | 0.000 | 0.000 | 0.029 | 0.000 | IMMP2L | 0.22755 | 0.54294 | 0.08726 | 0 | 0 |
| 595 | chr7 | 110602000 | 110603000 | 0.000 | 0.000 | 0.029 | 0.000 | IMMP2L | 0.22755 | 0.54294 | 0.08726 | 0 | 0 |
| 596 | chr7 | 110609000 | 110610000 | 0.000 | 0.000 | 0.029 | 0.000 | IMMP2L | 1.00000 | 1.00000 | 0.29694 | 0 | 0 |
| 597 | chr7 | 110610000 | 110611000 | 0.000 | 0.000 | 0.044 | 0.000 | IMMP2L | 0.10727 | 0.54966 | 0.02537 | 0 | 0 |
| 598 | chr7 | 110617000 | 110618000 | 0.000 | 0.000 | 0.029 | 0.000 | IMMP2L | 0.22755 | 0.54294 | 0.08726 | 0 | 0 |
| 599 | chr7 | 110618000 | 110619000 | 0.000 | 0.000 | 0.044 | 0.000 | IMMP2L | 0.10727 | 0.54966 | 0.02537 | 0 | 0 |
| 600 | chr7 | 110619000 | 110620000 | 0.000 | 0.000 | 0.029 | 0.000 | IMMP2L | 0.22755 | 0.54294 | 0.08726 | 0 | 0 |
| 601 | chr7 | 110621000 | 110622000 | 0.000 | 0.000 | 0.029 | 0.014 | IMMP2L | 1.00000 | 1.00000 | 0.08726 | 0 | 0 |
| 602 | chr7 | 110628000 | 110629000 | 0.000 | 0.000 | 0.029 | 0.000 | IMMP2L | 0.22755 | 0.54294 | 0.08726 | 0 | 0 |
| 603 | chr7 | 110629000 | 110630000 | 0.000 | 0.000 | 0.015 | 0.027 | IMMP2L | 1.00000 | 1.00000 | 0.29694 | 0 | 0 |
| 604 | chr7 | 110631000 | 110632000 | 0.000 | 0.000 | 0.044 | 0.000 | IMMP2L | 0.10727 | 0.54966 | 0.02537 | 0 | 0 |
| 605 | chr7 | 110632000 | 110633000 | 0.000 | 0.000 | 0.029 | 0.014 | IMMP2L | 0.60686 | 1.00000 | 0.08726 | 0 | 0 |
| 606 | chr7 | 110636000 | 110637000 | 0.000 | 0.000 | 0.029 | 0.014 | IMMP2L | 0.60686 | 0.54966 | 0.08726 | 0 | 0 |
| 607 | chr7 | 110637000 | 110638000 | 0.000 | 0.000 | 0.029 | 0.014 | IMMP2L | 0.60686 | 0.54966 | 0.08726 | 0 | 0 |
| 608 | chr7 | 110638000 | 110639000 | 0.000 | 0.000 | 0.029 | 0.027 | IMMP2L | 1.00000 | 1.00000 | 0.08726 | 0 | 0 |
| 609 | chr7 | 110639000 | 110640000 | 0.000 | 0.000 | 0.044 | 0.000 | IMMP2L | 0.10727 | 0.54966 | 0.02537 | 0 | 0 |
| 610 | chr7 | 110641000 | 110642000 | 0.000 | 0.000 | 0.029 | 0.014 | IMMP2L | 0.22755 | 0.54294 | 0.08726 | 0 | 0 |
| 611 | chr7 | 110650000 | 110651000 | 0.000 | 0.000 | 0.029 | 0.000 | IMMP2L | 0.22755 | 0.54294 | 0.08726 | 0 | 0 |
| 612 | chr7 | 110651000 | 110652000 | 0.000 | 0.000 | 0.029 | 0.014 | IMMP2L | 0.60686 | 0.54294 | 0.08726 | 0 | 0 |
| 613 | chr7 | 110666000 | 110667000 | 0.000 | 0.006 | 0.000 | 0.027 | IMMP2L | 0.49735 | 1.00000 | 1.00000 | 0 | 0 |
| 614 | chr7 | 110671000 | 110672000 | 0.000 | 0.000 | 0.029 | 0.014 | IMMP2L | 0.22755 | 0.54294 | 0.08726 | 0 | 0 |
| 615 | chr7 | 110677000 | 110678000 | 0.000 | 0.000 | 0.029 | 0.014 | IMMP2L | 0.60686 | 0.54294 | 0.08726 | 0 | 0 |
| 616 | chr7 | 110679000 | 110680000 | 0.000 | 0.000 | 0.029 | 0.000 | IMMP2L | 0.22755 | 0.54294 | 0.08726 | 0 | 0 |
| 617 | chr7 | 110680000 | 110681000 | 0.000 | 0.000 | 0.074 | 0.000 | IMMP2L | 0.02326 | 0.16101 | 0.00208 | 0 | 1 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAny Histology |
|---|---|---|---|---|---|---|---|---|---|---|---|---|---|
| 618 | chr7 | 110685000 | 110686000 | 0.000 | 0.000 | 0.029 | 0.000 | LRRN3 | 0.22755 | 0.54294 | 0.08726 | 0 | 0 |
| 619 | chr7 | 110686000 | 110687000 | 0.028 | 0.000 | 0.044 | 0.027 | LRRN3 | 0.67043 | 1.00000 | 0.02537 | 0 | 0 |
| 620 | chr7 | 110688000 | 110689000 | 0.000 | 0.000 | 0.029 | 0.000 | LRRN3 | 0.22755 | 0.54294 | 0.08726 | 0 | 1 |
| 621 | chr7 | 110699000 | 110700000 | 0.000 | 0.000 | 0.059 | 0.000 | LRRN3 | 0.05016 | 0.29551 | 0.00730 | 0 | 0 |
| 622 | chr7 | 110700000 | 110701000 | 0.000 | 0.000 | 0.029 | 0.000 | LRRN3 | 0.22755 | 0.54294 | 0.08726 | 0 | 0 |
| 623 | chr7 | 110709000 | 110710000 | 0.000 | 0.000 | 0.029 | 0.000 | LRRN3 | 0.22755 | 0.54294 | 0.08726 | 0 | 0 |
| 624 | chr7 | 110711000 | 110712000 | 0.000 | 0.000 | 0.044 | 0.014 | LRRN3 | 0.10727 | 0.54966 | 0.02537 | 0 | 0 |
| 625 | chr7 | 110714000 | 110715000 | 0.000 | 0.000 | 0.015 | 0.000 | LRRN3 | 1.00000 | 1.00000 | 0.29694 | 0 | 0 |
| 626 | chr7 | 110727000 | 110728000 | 0.000 | 0.000 | 0.029 | 0.014 | LRRN3 | 0.22755 | 0.54294 | 0.08726 | 0 | 0 |
| 627 | chr7 | 110728000 | 110729000 | 0.000 | 0.000 | 0.015 | 0.014 | LRRN3 | 1.00000 | 1.00000 | 0.29694 | 0 | 0 |
| 628 | chr7 | 110729000 | 110730000 | 0.000 | 0.000 | 0.029 | 0.000 | LRRN3 | 0.60686 | 0.54294 | 0.08726 | 0 | 0 |
| 629 | chr7 | 110734000 | 110735000 | 0.000 | 0.000 | 0.015 | 0.014 | LRRN3 | 1.00000 | 1.00000 | 0.29694 | 0 | 0 |
| 630 | chr7 | 110737000 | 110738000 | 0.000 | 0.000 | 0.015 | 0.027 | LRRN3 | 1.00000 | 1.00000 | 0.29694 | 0 | 0 |
| 631 | chr7 | 110740000 | 110741000 | 0.000 | 0.000 | 0.029 | 0.027 | LRRN3 | 1.00000 | 0.54294 | 0.08726 | 0 | 0 |
| 632 | chr7 | 110744000 | 110745000 | 0.000 | 0.000 | 0.029 | 0.014 | LRRN3 | 0.22755 | 0.54294 | 0.08726 | 0 | 0 |
| 633 | chr7 | 110746000 | 110747000 | 0.000 | 0.000 | 0.029 | 0.000 | LRRN3 | 0.60686 | 0.54294 | 0.08726 | 0 | 0 |
| 634 | chr7 | 110747000 | 110748000 | 0.000 | 0.000 | 0.044 | 0.014 | LRRN3 | 0.22755 | 0.54294 | 0.02537 | 0 | 0 |
| 635 | chr7 | 110748000 | 110749000 | 0.000 | 0.000 | 0.029 | 0.000 | LRRN3 | 0.22755 | 0.54294 | 0.08726 | 0 | 0 |
| 636 | chr7 | 110755000 | 110756000 | 0.000 | 0.000 | 0.044 | 0.000 | LRRN3 | 0.10727 | 0.54966 | 0.02537 | 0 | 0 |
| 637 | chr7 | 110764000 | 110765000 | 0.000 | 0.000 | 0.029 | 0.014 | LRRN3 | 0.22755 | 0.54294 | 0.08726 | 0 | 0 |
| 638 | chr7 | 110767000 | 110768000 | 0.000 | 0.000 | 0.029 | 0.000 | LRRN3 | 0.60686 | 0.54294 | 0.08726 | 0 | 0 |
| 639 | chr7 | 110769000 | 110770000 | 0.000 | 0.000 | 0.044 | 0.000 | LRRN3 | 0.10727 | 0.54966 | 0.02537 | 0 | 0 |
| 640 | chr7 | 110771000 | 110772000 | 0.000 | 0.000 | 0.029 | 0.014 | LRRN3 | 0.60686 | 0.54294 | 0.08726 | 0 | 0 |
| 641 | chr7 | 110779000 | 110780000 | 0.000 | 0.000 | 0.015 | 0.027 | LRRN3 | 1.00000 | 1.00000 | 0.29694 | 0 | 0 |
| 642 | chr7 | 110780000 | 110781000 | 0.000 | 0.000 | 0.029 | 0.000 | LRRN3 | 0.22755 | 0.54294 | 0.08726 | 0 | 0 |
| 643 | chr7 | 110783000 | 110784000 | 0.000 | 0.000 | 0.044 | 0.000 | LRRN3 | 0.10727 | 0.54966 | 0.02537 | 0 | 0 |
| 644 | chr7 | 110785000 | 110786000 | 0.000 | 0.000 | 0.029 | 0.000 | LRRN3 | 0.22755 | 0.54294 | 0.08726 | 0 | 0 |
| 645 | chr7 | 110801000 | 110802000 | 0.000 | 0.000 | 0.015 | 0.027 | LRRN3 | 1.00000 | 1.00000 | 0.29694 | 0 | 0 |
| 646 | chr7 | 110802000 | 110803000 | 0.000 | 0.000 | 0.029 | 0.000 | LRRN3 | 0.22755 | 0.54294 | 0.08726 | 0 | 0 |
| 647 | chr7 | 110810000 | 110811000 | 0.000 | 0.000 | 0.029 | 0.014 | LRRN3 | 0.22755 | 0.54294 | 0.08726 | 0 | 0 |
| 648 | chr7 | 110816000 | 110817000 | 0.000 | 0.000 | 0.044 | 0.000 | LRRN3 | 0.10727 | 0.54966 | 0.02537 | 0 | 0 |
| 649 | chr7 | 110821000 | 110822000 | 0.000 | 0.000 | 0.029 | 0.000 | LRRN3 | 0.60686 | 0.54294 | 0.08726 | 0 | 0 |
| 650 | chr7 | 110824000 | 110825000 | 0.000 | 0.000 | 0.029 | 0.000 | LRRN3 | 0.22755 | 0.54294 | 0.08726 | 0 | 0 |
| 651 | chr7 | 110827000 | 110828000 | 0.000 | 0.000 | 0.015 | 0.014 | LRRN3 | 1.00000 | 1.00000 | 0.29694 | 0 | 0 |
| 652 | chr7 | 110836000 | 110837000 | 0.000 | 0.000 | 0.044 | 0.000 | LRRN3 | 1.00000 | 0.54966 | 0.02537 | 0 | 0 |
| 653 | chr7 | 110847000 | 110848000 | 0.000 | 0.000 | 0.029 | 0.014 | LRRN3 | 0.22755 | 0.54294 | 0.08726 | 0 | 0 |
| 654 | chr7 | 111567000 | 111568000 | 0.028 | 0.000 | 0.000 | 0.014 | DOCK4 | 1.00000 | 0.34615 | 1.00000 | 0 | 0 |
| 655 | chr7 | 119056000 | 119057000 | 0.000 | 0.000 | 0.015 | 0.014 | KCND2 | 1.00000 | 1.00000 | 0.29694 | 0 | 0 |
| 656 | chr7 | 121380000 | 121381000 | 0.000 | 0.006 | 0.015 | 0.014 | PTPRZ1 | 1.00000 | 1.00000 | 0.50663 | 0 | 0 |
| 657 | chr7 | 123887000 | 123888000 | 0.000 | 0.000 | 0.029 | 0.000 | TMEM229A | 0.22755 | 0.54294 | 0.08726 | 0 | 0 |
| 658 | chr7 | 125262000 | 125263000 | 0.000 | 0.000 | 0.015 | 0.014 | POT1 | 1.00000 | 1.00000 | 0.29694 | 0 | 0 |
| 659 | chr7 | 145723000 | 145724000 | 0.000 | 0.000 | 0.029 | 0.014 | CNTNAP2 | 0.22755 | 0.54294 | 0.08726 | 0 | 0 |
| 660 | chr7 | 148508000 | 148509000 | 0.000 | 0.000 | 0.000 | 0.041 | EZH2 | 0.24603 | 1.00000 | 1.00000 | 0 | 0 |
| 661 | chr7 | 155127000 | 155128000 | 0.000 | 0.000 | 0.000 | 0.027 | BLACE | 0.49735 | 1.00000 | 1.00000 | 0 | 0 |
| 662 | chr7 | 157162000 | 157163000 | 0.056 | 0.000 | 0.000 | 0.000 | DNAJB6 | 1.00000 | 0.11763 | 1.00000 | 0 | 1 |
| 663 | chr7 | 158684000 | 158685000 | 0.000 | 0.000 | 0.015 | 0.014 | WDR60 | 1.00000 | 1.00000 | 1.00000 | 0 | 0 |
| 664 | chr8 | 1646000 | 1647000 | 0.000 | 0.000 | 0.015 | 0.027 | DLGAP2 | 1.00000 | 1.00000 | 0.29694 | 0 | 0 |
| 665 | chr8 | 5558000 | 5559000 | 0.000 | 0.000 | 0.029 | 0.000 | MCPH1 | 0.22755 | 0.54294 | 0.08726 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAny Histology |
|---|---|---|---|---|---|---|---|---|---|---|---|---|---|
| 666 | chr8 | 5612000 | 5613000 | 0.000 | 0.000 | 0.000 | 0.027 | MCPH1 | 0.49735 | 1.00000 | 1.00000 | 0 | 0 |
| 667 | chr8 | 8602000 | 8603000 | 0.000 | 0.000 | 0.029 | 0.014 | MFHAS1 | 0.60686 | 0.54294 | 0.08726 | 0 | 0 |
| 668 | chr8 | 8706000 | 8707000 | 0.000 | 0.000 | 0.029 | 0.000 | MFHAS1 | 0.22755 | 0.54294 | 0.08726 | 0 | 0 |
| 669 | chr8 | 8717000 | 8718000 | 0.000 | 0.000 | 0.029 | 0.000 | MFHAS1 | 0.22755 | 0.54294 | 0.08726 | 0 | 0 |
| 670 | chr8 | 11352000 | 11353000 | 0.000 | 0.000 | 0.029 | 0.014 | BLK | 0.60686 | 0.54294 | 0.08726 | 0 | 0 |
| 671 | chr8 | 14080000 | 14081000 | 0.000 | 0.000 | 0.015 | 0.014 | SGCZ | 1.00000 | 1.00000 | 0.29694 | 0 | 0 |
| 672 | chr8 | 14796000 | 14797000 | 0.000 | 0.006 | 0.015 | 0.014 | SGCZ | 0.47887 | 1.00000 | 0.50663 | 0 | 0 |
| 673 | chr8 | 16090000 | 16091000 | 0.000 | 0.000 | 0.015 | 0.000 | MSR1 | 1.00000 | 1.00000 | 0.29694 | 0 | 0 |
| 674 | chr8 | 16187000 | 16188000 | 0.028 | 0.000 | 0.015 | 0.014 | MSR1 | 0.47887 | 1.00000 | 0.29694 | 0 | 0 |
| 675 | chr8 | 23101000 | 23102000 | 0.000 | 0.000 | 0.015 | 0.014 | CHMP7 | 1.00000 | 1.00000 | 0.29694 | 0 | 0 |
| 676 | chr8 | 24207000 | 24208000 | 0.000 | 0.000 | 0.029 | 0.000 | ADAM28 | 0.22755 | 0.54294 | 0.08726 | 0 | 0 |
| 677 | chr8 | 29155000 | 29156000 | 0.028 | 0.000 | 0.000 | 0.014 | KIF13B | 1.00000 | 0.34615 | 1.00000 | 0 | 0 |
| 678 | chr8 | 35657000 | 35658000 | 0.000 | 0.000 | 0.029 | 0.000 | AC012215.1 | 0.22755 | 0.54294 | 0.08726 | 0 | 0 |
| 679 | chr8 | 38759000 | 38760000 | 0.000 | 0.000 | 0.029 | 0.000 | PLEKHA2 | 0.22755 | 0.54294 | 0.08726 | 0 | 0 |
| 680 | chr8 | 54986000 | 54987000 | 0.000 | 0.000 | 0.029 | 0.000 | LYPLA1 | 0.22755 | 0.54294 | 0.08726 | 0 | 0 |
| 681 | chr8 | 60031000 | 60032000 | 0.000 | 0.000 | 0.015 | 0.014 | TOX | 1.00000 | 1.00000 | 0.29694 | 0 | 0 |
| 682 | chr8 | 67525000 | 67526000 | 0.000 | 0.000 | 0.015 | 0.000 | MYBL1 | 1.00000 | 1.00000 | 0.29694 | 0 | 0 |
| 683 | chr8 | 77105000 | 77106000 | 0.000 | 0.000 | 0.029 | 0.000 | ZFHX4 | 0.22755 | 0.54294 | 0.08726 | 0 | 0 |
| 684 | chr8 | 78400000 | 78401000 | 0.000 | 0.000 | 0.029 | 0.000 | PEX2 | 0.22755 | 0.54294 | 0.08726 | 0 | 0 |
| 685 | chr8 | 90322000 | 90323000 | 0.000 | 0.000 | 0.029 | 0.000 | RIPK2 | 0.22755 | 0.54294 | 0.08726 | 0 | 0 |
| 686 | chr8 | 93199000 | 93200000 | 0.000 | 0.000 | 0.015 | 0.014 | RUNX1T1 | 1.00000 | 1.00000 | 0.29694 | 0 | 0 |
| 687 | chr8 | 94618000 | 94619000 | 0.028 | 0.000 | 0.015 | 0.000 | FAM92A1 | 0.47887 | 0.54294 | 0.29694 | 0 | 0 |
| 688 | chr8 | 110586000 | 110587000 | 0.000 | 0.000 | 0.029 | 0.000 | SYBU | 0.22755 | 0.54294 | 0.08726 | 0 | 0 |
| 689 | chr8 | 126687000 | 126688000 | 0.028 | 0.000 | 0.015 | 0.014 | TRIB1 | 1.00000 | 1.00000 | 0.29694 | 0 | 0 |
| 690 | chr8 | 128748000 | 128749000 | 0.500 | 0.000 | 0.132 | 0.000 | MYC | 0.00099 | 0.00010 | 0.00001 | 1 | 1 |
| 691 | chr8 | 128749000 | 128750000 | 0.583 | 0.000 | 0.103 | 0.014 | MYC | 0.02808 | 0.00000 | 0.00016 | 1 | 1 |
| 692 | chr8 | 128750000 | 128751000 | 0.444 | 0.000 | 0.088 | 0.014 | MYC | 0.05468 | 0.00007 | 0.00058 | 1 | 1 |
| 693 | chr8 | 128751000 | 128752000 | 0.111 | 0.000 | 0.044 | 0.014 | MYC | 0.10727 | 0.23165 | 0.02537 | 1 | 1 |
| 694 | chr8 | 128752000 | 128753000 | 0.056 | 0.000 | 0.015 | 0.014 | FAM135B | 0.47887 | 0.27446 | 0.29694 | 0 | 0 |
| 695 | chr8 | 137918000 | 137919000 | 0.028 | 0.000 | 0.015 | 0.000 | FAM135B | 0.47887 | 1.00000 | 0.29694 | 0 | 0 |
| 696 | chr8 | 138274000 | 138275000 | 0.000 | 0.000 | 0.000 | 0.027 | ISNARE1 | 0.49735 | 1.00000 | 1.00000 | 0 | 0 |
| 697 | chr8 | 143183000 | 143184000 | 0.028 | 0.000 | 0.015 | 0.000 | C8orf31 | 0.47887 | 1.00000 | 0.29694 | 0 | 0 |
| 698 | chr8 | 144123000 | 144124000 | 0.000 | 0.000 | 0.029 | 0.014 | UHRF2 | 0.60686 | 0.54294 | 0.08726 | 0 | 0 |
| 699 | chr9 | 6411000 | 6412000 | 0.000 | 0.000 | 0.029 | 0.000 | UHRF2 | 0.22755 | 0.54294 | 0.08726 | 0 | 0 |
| 700 | chr9 | 6413000 | 6414000 | 0.000 | 0.000 | 0.015 | 0.014 | UHRF2 | 1.00000 | 1.00000 | 0.29694 | 0 | 0 |
| 701 | chr9 | 6414000 | 6415000 | 0.000 | 0.000 | 0.029 | 0.014 | PTPRD | 0.60686 | 0.54294 | 0.08726 | 0 | 0 |
| 702 | chr9 | 9928000 | 9929000 | 0.000 | 0.000 | 0.000 | 0.027 | NFIB | 0.49735 | 1.00000 | 1.00000 | 0 | 0 |
| 703 | chr9 | 13965000 | 13966000 | 0.000 | 0.000 | 0.029 | 0.014 | DMRTA1 | 0.60686 | 0.54294 | 0.08726 | 0 | 0 |
| 704 | chr9 | 22824000 | 22825000 | 0.000 | 0.000 | 0.015 | 0.014 | TUSC1 | 0.22755 | 0.54294 | 0.08726 | 0 | 0 |
| 705 | chr9 | 25260000 | 25261000 | 0.000 | 0.000 | 0.015 | 0.014 | LINGO2 | 0.22755 | 0.54294 | 0.08726 | 0 | 0 |
| 706 | chr9 | 29890000 | 29891000 | 0.000 | 0.000 | 0.015 | 0.014 | ACO1 | 1.00000 | 1.00000 | 0.29694 | 0 | 0 |
| 707 | chr9 | 30656000 | 30657000 | 0.000 | 0.006 | 0.015 | 0.000 | PAX5 | 0.47887 | 1.00000 | 0.50663 | 1 | 0 |
| 708 | chr9 | 37003000 | 37004000 | 0.000 | 0.000 | 0.015 | 0.014 | PAX5 | 1.00000 | 1.00000 | 0.29694 | 1 | 0 |
| 709 | chr9 | 37005000 | 37006000 | 0.000 | 0.000 | 0.015 | 0.014 | PAX5 | 1.00000 | 1.00000 | 0.29694 | 1 | 0 |
| 710 | chr9 | 37024000 | 37025000 | 0.000 | 0.006 | 0.044 | 0.027 | PAX5 | 0.67043 | 0.54966 | 0.02564 | 1 | 0 |
| 711 | chr9 | 37025000 | 37026000 | 0.000 | 0.000 | 0.132 | 0.054 | PAX5 | 0.14640 | 0.02564 | 0.00000 | 1 | 1 |
| 712 | chr9 | 37026000 | 37027000 | 0.000 | 0.006 | 0.221 | 0.108 | PAX5 | 0.10913 | 0.00107 | 0.00001 | 1 | 1 |
| 713 | chr9 | 37027000 | 37028000 | 0.000 | 0.000 | 0.029 | 0.014 | PAX5 | 0.60686 | 0.54294 | 0.08726 | 1 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 714 | chr9 | 37033000 | 37034000 | 0.000 | 0.000 | 0.044 | 0.014 | PAX5 | 0.34948 | 0.54966 | 0.02537 | 1 | 0 |
| 715 | chr9 | 37034000 | 37035000 | 0.000 | 0.000 | 0.074 | 0.041 | PAX5 | 0.47996 | 0.16101 | 0.00208 | 1 | 1 |
| 716 | chr9 | 37035000 | 37036000 | 0.000 | 0.000 | 0.015 | 0.014 | PAX5 | 1.00000 | 1.00000 | 0.29694 | 1 | 0 |
| 717 | chr9 | 37196000 | 37197000 | 0.000 | 0.000 | 0.029 | 0.014 | ZCCHC7 | 0.60686 | 0.54294 | 0.08726 | 0 | 0 |
| 718 | chr9 | 37197000 | 37198000 | 0.000 | 0.000 | 0.029 | 0.000 | ZCCHC7 | 0.22755 | 0.54294 | 0.08726 | 0 | 0 |
| 719 | chr9 | 37293000 | 37294000 | 0.000 | 0.000 | 0.029 | 0.027 | ZCCHC7 | 1.00000 | 0.54294 | 0.08726 | 0 | 0 |
| 720 | chr9 | 37294000 | 37295000 | 0.000 | 0.000 | 0.044 | 0.027 | ZCCHC7 | 0.67043 | 0.54966 | 0.02537 | 0 | 0 |
| 721 | chr9 | 37327000 | 37328000 | 0.000 | 0.000 | 0.015 | 0.014 | ZCCHC7 | 1.00000 | 1.00000 | 0.29694 | 0 | 0 |
| 722 | chr9 | 37336000 | 37337000 | 0.000 | 0.000 | 0.044 | 0.014 | ZCCHC7 | 0.34948 | 0.54966 | 0.02537 | 0 | 0 |
| 723 | chr9 | 37337000 | 37338000 | 0.000 | 0.012 | 0.015 | 0.041 | ZCCHC7 | 0.62100 | 1.00000 | 1.00000 | 0 | 0 |
| 724 | chr9 | 37338000 | 37339000 | 0.000 | 0.000 | 0.029 | 0.014 | ZCCHC7 | 0.60686 | 0.54294 | 0.08726 | 0 | 1 |
| 725 | chr9 | 37369000 | 37370000 | 0.000 | 0.000 | 0.029 | 0.000 | ZCCHC7 | 0.22755 | 0.54294 | 0.08726 | 0 | 0 |
| 726 | chr9 | 37371000 | 37372000 | 0.028 | 0.025 | 0.118 | 0.068 | ZCCHC7 | 0.38669 | 0.15803 | 0.00732 | 0 | 1 |
| 727 | chr9 | 37372000 | 37373000 | 0.000 | 0.000 | 0.015 | 0.014 | ZCCHC7 | 1.00000 | 1.00000 | 0.29694 | 0 | 0 |
| 728 | chr9 | 37383000 | 37384000 | 0.000 | 0.000 | 0.059 | 0.027 | ZCCHC7 | 0.42627 | 0.29551 | 0.00730 | 0 | 1 |
| 729 | chr9 | 37384000 | 37385000 | 0.000 | 0.000 | 0.059 | 0.054 | ZCCHC7 | 1.00000 | 0.29551 | 0.00730 | 0 | 0 |
| 730 | chr9 | 37385000 | 37386000 | 0.000 | 0.000 | 0.029 | 0.014 | ZCCHC7 | 0.60686 | 0.54294 | 0.08726 | 0 | 0 |
| 731 | chr9 | 37387000 | 37388000 | 0.000 | 0.000 | 0.059 | 0.014 | ZCCHC7 | 0.19371 | 0.29551 | 0.00730 | 0 | 1 |
| 732 | chr9 | 37397000 | 37398000 | 0.000 | 0.000 | 0.044 | 0.000 | ZCCHC7 | 0.10727 | 0.54966 | 0.02537 | 0 | 0 |
| 733 | chr9 | 37398000 | 37399000 | 0.000 | 0.000 | 0.029 | 0.014 | GRHPR | 0.22755 | 0.54294 | 0.08726 | 0 | 0 |
| 734 | chr9 | 37399000 | 37400000 | 0.000 | 0.000 | 0.029 | 0.014 | GRHPR | 0.22755 | 0.54294 | 0.08726 | 0 | 0 |
| 735 | chr9 | 37402000 | 37403000 | 0.000 | 0.000 | 0.029 | 0.014 | GRHPR | 0.22755 | 0.54294 | 0.21104 | 0 | 0 |
| 736 | chr9 | 37406000 | 37407000 | 0.000 | 0.000 | 0.015 | 0.014 | GRHPR | 1.00000 | 1.00000 | 0.29694 | 0 | 0 |
| 737 | chr9 | 37407000 | 37408000 | 0.056 | 0.000 | 0.132 | 0.149 | GRHPR | 0.81382 | 0.02564 | 0.00001 | 0 | 1 |
| 738 | chr9 | 37408000 | 37409000 | 0.000 | 0.006 | 0.029 | 0.027 | GRHPR | 1.00000 | 0.54294 | 0.21104 | 0 | 0 |
| 739 | chr9 | 37410000 | 37411000 | 0.000 | 0.000 | 0.029 | 0.000 | GRHPR | 0.22755 | 0.54294 | 0.08726 | 0 | 0 |
| 740 | chr9 | 37424000 | 37425000 | 0.000 | 0.000 | 0.044 | 0.000 | GRHPR | 0.10727 | 0.54966 | 0.02537 | 0 | 0 |
| 741 | chr9 | 37425000 | 37426000 | 0.000 | 0.000 | 0.029 | 0.014 | GRHPR | 0.22755 | 0.54294 | 0.08726 | 0 | 0 |
| 742 | chr9 | 112811000 | 112812000 | 0.000 | 0.000 | 0.059 | 0.014 | AKAP2 | 0.19371 | 0.29551 | 0.00730 | 0 | 1 |
| 743 | chr9 | 117037000 | 117038000 | 0.000 | 0.000 | 0.000 | 0.014 | COL27A1 | 1.00000 | 1.00000 | 1.00000 | 0 | 0 |
| 744 | chr9 | 119779000 | 119780000 | 0.000 | 0.000 | 0.044 | 0.014 | ASTN2 | 0.10727 | 0.54966 | 0.02537 | 0 | 0 |
| 745 | chr9 | 126232000 | 126233000 | 0.056 | 0.000 | 0.000 | 0.000 | DENND1A | 1.00000 | 0.11763 | 1.00000 | 0 | 1 |
| 746 | chr9 | 130741000 | 130742000 | 0.056 | 0.000 | 0.000 | 0.014 | FAM102A | 0.60686 | 0.11763 | 1.00000 | 0 | 1 |
| 747 | chr9 | 130742000 | 130743000 | 0.000 | 0.000 | 0.059 | 0.000 | FAM102A | 0.05016 | 0.29551 | 0.00730 | 1 | 0 |
| 748 | chr9 | 132767000 | 132768000 | 0.000 | 0.006 | 0.059 | 0.027 | FNBP1 | 0.42627 | 0.29551 | 0.00730 | 1 | 0 |
| 749 | chr9 | 132785000 | 132786000 | 0.000 | 0.000 | 0.015 | 0.014 | FNBP1 | 1.00000 | 1.00000 | 0.29694 | 0 | 0 |
| 750 | chr9 | 132803000 | 132804000 | 0.000 | 0.000 | 0.029 | 0.014 | FNBP1 | 0.22755 | 0.54294 | 0.08726 | 0 | 0 |
| 751 | chr9 | 132804000 | 132805000 | 0.000 | 0.000 | 0.015 | 0.000 | FNBP1 | 1.00000 | 1.00000 | 0.29694 | 0 | 0 |
| 752 | chr9 | 134551000 | 134552000 | 0.000 | 0.000 | 0.029 | 0.027 | RAPGEF1 | 1.00000 | 0.54294 | 0.08726 | 0 | 0 |
| 753 | chr9 | 138874000 | 138875000 | 0.056 | 0.000 | 0.029 | 0.014 | UBAC1 | 0.60686 | 0.60763 | 0.08726 | 0 | 1 |
| 754 | chr10 | 3333000 | 3334000 | 0.000 | 0.000 | 0.000 | 0.027 | PITRM1 | 0.49735 | 1.00000 | 1.00000 | 0 | 0 |
| 755 | chr10 | 5707000 | 5708000 | 0.000 | 0.000 | 0.029 | 0.014 | ASB13 | 0.60686 | 0.54294 | 0.08726 | 0 | 0 |
| 756 | chr10 | 5728000 | 5729000 | 0.000 | 0.006 | 0.000 | 0.014 | ASB13 | 0.47887 | 1.00000 | 0.50663 | 0 | 0 |
| 757 | chr10 | 15393000 | 15394000 | 0.028 | 0.000 | 0.015 | 0.000 | FAM171A1 | 0.47887 | 1.00000 | 0.29694 | 0 | 0 |
| 758 | chr10 | 20796000 | 20797000 | 0.000 | 0.006 | 0.015 | 0.000 | PLXDC2 | 0.47887 | 1.00000 | 0.50663 | 0 | 0 |
| 759 | chr10 | 35424000 | 35425000 | 0.000 | 0.000 | 0.029 | 0.000 | CREM | 0.22755 | 0.54294 | 0.08726 | 0 | 0 |
| 760 | chr10 | 56678000 | 56679000 | 0.000 | 0.000 | 0.000 | 0.027 | PCDH15 | 0.49735 | 1.00000 | 1.00000 | 0 | 0 |
| 761 | chr10 | 63440000 | 63441000 | 0.028 | 0.000 | 0.015 | 0.000 | C10orf107 | 0.47887 | 1.00000 | 0.29694 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAny Histology |
|---|---|---|---|---|---|---|---|---|---|---|---|---|---|
| 762 | chr10 | 63659000 | 63660000 | 0.000 | 0.000 | 0.044 | 0.014 | ARID5B | 0.34948 | 0.54966 | 0.02537 | 1 | 0 |
| 763 | chr10 | 63660000 | 63661000 | 0.000 | 0.000 | 0.059 | 0.014 | ARID5B | 0.19371 | 0.29551 | 0.00730 | 1 | 1 |
| 764 | chr10 | 63662000 | 63663000 | 0.000 | 0.000 | 0.029 | 0.014 | ARID5B | 0.60686 | 0.54294 | 0.08726 | 1 | 0 |
| 765 | chr10 | 63720000 | 63721000 | 0.000 | 0.000 | 0.029 | 0.000 | ARID5B | 0.22755 | 0.54294 | 0.08726 | 1 | 0 |
| 766 | chr10 | 63803000 | 63804000 | 0.000 | 0.000 | 0.000 | 0.027 | ARID5B | 0.49735 | 1.00000 | 1.00000 | 1 | 0 |
| 767 | chr10 | 63809000 | 63810000 | 0.000 | 0.000 | 0.015 | 0.014 | ARID5B | 1.00000 | 1.00000 | 0.29694 | 1 | 0 |
| 768 | chr10 | 63810000 | 63811000 | 0.000 | 0.000 | 0.000 | 0.027 | ARID5B | 0.49735 | 1.00000 | 1.00000 | 1 | 0 |
| 769 | chr10 | 67907000 | 67908000 | 0.000 | 0.006 | 0.015 | 0.000 | CTNNA3 | 0.47887 | 1.00000 | 0.50663 | 0 | 0 |
| 770 | chr10 | 68474000 | 68475000 | 0.000 | 0.000 | 0.000 | 0.027 | CTNNA3 | 0.49735 | 1.00000 | 1.00000 | 0 | 0 |
| 771 | chr10 | 98510000 | 98511000 | 0.000 | 0.000 | 0.029 | 0.000 | PIK3AP1 | 0.22755 | 0.54294 | 0.08726 | 0 | 0 |
| 772 | chr10 | 101384000 | 101385000 | 0.028 | 0.000 | 0.015 | 0.014 | SLC25A28 | 1.00000 | 1.00000 | 0.29694 | 0 | 0 |
| 773 | chr10 | 108276000 | 108277000 | 0.000 | 0.000 | 0.029 | 0.000 | SORCS1 | 0.22755 | 0.54294 | 0.08726 | 0 | 0 |
| 774 | chr10 | 113473000 | 113474000 | 0.028 | 0.000 | 0.015 | 0.000 | GPAM | 0.47887 | 1.00000 | 0.29694 | 0 | 0 |
| 775 | chr10 | 113636000 | 113637000 | 0.000 | 0.000 | 0.029 | 0.000 | GPAM | 0.22755 | 0.54294 | 0.08726 | 0 | 0 |
| 776 | chr10 | 116458000 | 116459000 | 0.000 | 0.000 | 0.044 | 0.014 | ABLIM1 | 0.10727 | 0.54966 | 0.02537 | 0 | 0 |
| 777 | chr10 | 121623000 | 121624000 | 0.000 | 0.000 | 0.029 | 0.000 | MCMBP | 0.22755 | 0.54294 | 0.08726 | 0 | 0 |
| 778 | chr10 | 132973000 | 132974000 | 0.000 | 0.000 | 0.015 | 0.027 | TCERG1L | 1.00000 | 1.00000 | 0.29694 | 0 | 0 |
| 779 | chr10 | 134326000 | 134327000 | 0.028 | 0.000 | 0.015 | 0.000 | INPP5A | 0.47887 | 1.00000 | 0.08726 | 0 | 0 |
| 780 | chr11 | 871000 | 872000 | 0.000 | 0.000 | 0.029 | 0.000 | CHID1 | 0.22755 | 1.00000 | 0.29694 | 0 | 0 |
| 781 | chr11 | 1149000 | 1150000 | 0.028 | 0.000 | 0.015 | 0.000 | MUC5AC | 0.47887 | 1.00000 | 0.29694 | 0 | 0 |
| 782 | chr11 | 25065000 | 25066000 | 0.000 | 0.000 | 0.029 | 0.000 | LUZP2 | 0.22755 | 0.54294 | 0.08726 | 0 | 0 |
| 783 | chr11 | 25289000 | 25290000 | 0.028 | 0.000 | 0.029 | 0.000 | LUZP2 | 0.22755 | 0.54294 | 0.08726 | 0 | 0 |
| 784 | chr11 | 27216000 | 27217000 | 0.028 | 0.000 | 0.000 | 0.014 | BBOX1 | 0.60686 | 1.00000 | 1.00000 | 0 | 0 |
| 785 | chr11 | 28849000 | 28850000 | 0.000 | 0.000 | 0.000 | 0.027 | METTL15 | 0.49735 | 1.00000 | 1.00000 | 0 | 0 |
| 786 | chr11 | 29253000 | 29254000 | 0.000 | 0.000 | 0.029 | 0.000 | KCNA4 | 0.22755 | 0.54294 | 0.08726 | 0 | 0 |
| 787 | chr11 | 29900000 | 29901000 | 0.000 | 0.000 | 0.029 | 0.000 | KCNA4 | 0.22755 | 0.54294 | 0.08726 | 0 | 0 |
| 788 | chr11 | 40626000 | 40627000 | 0.000 | 0.000 | 0.029 | 0.000 | LRRC4C | 0.22755 | 0.54294 | 0.08726 | 0 | 0 |
| 789 | chr11 | 40845000 | 40846000 | 0.000 | 0.000 | 0.025 | 0.000 | LRRC4C | 0.22755 | 0.54294 | 0.08726 | 0 | 0 |
| 790 | chr11 | 40868000 | 40869000 | 0.000 | 0.000 | 0.029 | 0.000 | LRRC4C | 0.22755 | 0.54294 | 0.08726 | 0 | 0 |
| 791 | chr11 | 41066000 | 41067000 | 0.000 | 0.000 | 0.015 | 0.000 | AP15 | 0.47887 | 0.54294 | 0.29694 | 0 | 0 |
| 792 | chr11 | 41844000 | 41845000 | 0.028 | 0.000 | 0.029 | 0.014 | SLC43A3 | 0.60686 | 1.00000 | 0.08726 | 0 | 0 |
| 793 | chr11 | 57171000 | 57172000 | 0.000 | 0.000 | 0.074 | 0.014 | MS4A1 | 0.10420 | 0.54294 | 0.00208 | 1 | 1 |
| 794 | chr11 | 60224000 | 60225000 | 0.000 | 0.000 | 0.074 | 0.027 | FRMD8 | 0.25970 | 0.16101 | 0.00208 | 0 | 1 |
| 795 | chr11 | 65190000 | 65191000 | 0.000 | 0.000 | 0.103 | 0.014 | FRMD8 | 0.02808 | 0.09269 | 0.00016 | 0 | 1 |
| 796 | chr11 | 65191000 | 65192000 | 0.000 | 0.000 | 0.029 | 0.014 | SCYL1 | 0.60686 | 0.54294 | 0.08726 | 0 | 0 |
| 797 | chr11 | 65266000 | 65267000 | 0.028 | 0.000 | 0.029 | 0.000 | SCYL1 | 0.00488 | 0.09269 | 0.00016 | 0 | 0 |
| 798 | chr11 | 65267000 | 65268000 | 0.000 | 0.000 | 0.103 | 0.000 | EED | 0.22755 | 0.54294 | 0.08726 | 0 | 0 |
| 799 | chr11 | 85963000 | 85964000 | 0.000 | 0.000 | 0.029 | 0.000 | FAT3 | 0.22755 | 0.54294 | 0.08726 | 0 | 0 |
| 800 | chr11 | 92261000 | 92262000 | 0.000 | 0.000 | 0.000 | 0.027 | YAP1 | 0.49735 | 1.00000 | 1.00000 | 0 | 0 |
| 801 | chr11 | 102117000 | 102118000 | 0.000 | 0.012 | 0.206 | 0.108 | BIRC3 | 0.16270 | 0.00197 | 0.00000 | 1 | 1 |
| 802 | chr11 | 102188000 | 102189000 | 0.000 | 0.000 | 0.059 | 0.000 | BIRC3 | 0.05016 | 0.29551 | 0.00730 | 1 | 1 |
| 803 | chr11 | 102189000 | 102190000 | 0.000 | 0.000 | 0.015 | 0.014 | ELMOD1 | 0.47887 | 1.00000 | 1.00000 | 0 | 0 |
| 804 | chr11 | 104974000 | 104975000 | 0.028 | 0.000 | 0.015 | 0.014 | DDX10 | 1.00000 | 1.00000 | 0.29694 | 0 | 0 |
| 805 | chr11 | 108781000 | 108782000 | 0.000 | 0.000 | 0.015 | 0.014 | DDX10 | 1.00000 | 1.00000 | 0.29694 | 0 | 0 |
| 806 | chr11 | 108975000 | 108976000 | 0.000 | 0.000 | 0.015 | 0.000 | C11orf87 | 0.47887 | 1.00000 | 0.29694 | 0 | 0 |
| 807 | chr11 | 109066000 | 109067000 | 0.028 | 0.000 | 0.015 | 0.014 | POU2AF1 | 0.60686 | 0.54294 | 0.08726 | 1 | 0 |
| 808 | chr11 | 111248000 | 111249000 | 0.000 | 0.000 | 0.029 | 0.014 | POU2AF1 | 0.60686 | 0.54294 | 0.08726 | 1 | 0 |
| 809 | chr11 | 111249000 | 111250000 | 0.000 | 0.012 | 0.103 | 0.081 | POU2AF1 | 0.77363 | 0.09269 | 0.00337 | 1 | 1 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAny Histology |
|---|---|---|---|---|---|---|---|---|---|---|---|---|---|
| 810 | chr1 | 115761000 | 115762000 | 0.028 | 0.000 | 0.015 | 0.041 | CADM1 | 0.62100 | 1.00000 | 0.29694 | 0 | 0 |
| 811 | chr1 | 118723000 | 118724000 | 0.000 | 0.000 | 0.029 | 0.000 | CXCR5 | 0.22755 | 0.54294 | 0.08726 | 0 | 0 |
| 812 | chr1 | 126496000 | 126497000 | 0.028 | 0.000 | 0.015 | 0.014 | KIRREL3 | 1.00000 | 1.00000 | 0.29694 | 0 | 0 |
| 813 | chr1 | 128390000 | 128391000 | 0.000 | 0.000 | 0.044 | 0.014 | ETS1 | 0.34948 | 0.54966 | 0.02537 | 0 | 1 |
| 814 | chr1 | 128391000 | 128392000 | 0.000 | 0.000 | 0.118 | 0.014 | ETS1 | 0.01415 | 0.04825 | 0.00004 | 1 | 0 |
| 815 | chr2 | 6554000 | 6555000 | 0.000 | 0.000 | 0.029 | 0.000 | CD27 | 0.22755 | 0.54294 | 0.08726 | 0 | 0 |
| 816 | chr2 | 8762000 | 8763000 | 0.000 | 0.000 | 0.015 | 0.014 | AICDA | 1.00000 | 1.00000 | 0.29694 | 0 | 0 |
| 817 | chr2 | 8763000 | 8764000 | 0.000 | 0.000 | 0.044 | 0.041 | AICDA | 0.44431 | 0.54966 | 0.02537 | 0 | 1 |
| 818 | chr2 | 8764000 | 8765000 | 0.000 | 0.000 | 0.029 | 0.068 | AICDA | 1.00000 | 1.00000 | 0.08726 | 0 | 0 |
| 819 | chr2 | 8765000 | 8766000 | 0.000 | 0.000 | 0.015 | 0.027 | AICDA | 1.00000 | 1.00000 | 0.29694 | 0 | 0 |
| 820 | chr2 | 9823000 | 9824000 | 0.000 | 0.000 | 0.015 | 0.014 | CLEC2D | 1.00000 | 1.00000 | 0.29694 | 0 | 0 |
| 821 | chr2 | 11710000 | 11711000 | 0.000 | 0.000 | 0.029 | 0.014 | ETV6 | 0.22755 | 0.54294 | 0.08726 | 0 | 0 |
| 822 | chr2 | 11803000 | 11804000 | 0.000 | 0.000 | 0.015 | 0.014 | ETV6 | 1.00000 | 1.00000 | 0.29694 | 1 | 0 |
| 823 | chr2 | 14923000 | 14924000 | 0.000 | 0.000 | 0.015 | 0.014 | HIST4H4 | 1.00000 | 1.00000 | 0.29694 | 1 | 0 |
| 824 | chr2 | 16717000 | 16718000 | 0.000 | 0.000 | 0.000 | 0.027 | LMO3 | 0.49735 | 1.00000 | 1.00000 | 0 | 0 |
| 825 | chr2 | 23805000 | 23806000 | 0.000 | 0.000 | 0.029 | 0.000 | SOX5 | 0.22755 | 0.54294 | 0.08726 | 0 | 0 |
| 826 | chr2 | 25149000 | 25150000 | 0.000 | 0.000 | 0.029 | 0.014 | C12orf77 | 0.22755 | 0.54294 | 0.08726 | 0 | 0 |
| 827 | chr2 | 25151000 | 25152000 | 0.000 | 0.000 | 0.015 | 0.014 | C12orf77 | 1.00000 | 1.00000 | 0.29694 | 0 | 0 |
| 828 | chr2 | 25174000 | 25175000 | 0.000 | 0.000 | 0.044 | 0.014 | C12orf77 | 0.10727 | 0.54966 | 0.02537 | 0 | 0 |
| 829 | chr2 | 25205000 | 25206000 | 0.000 | 0.006 | 0.015 | 0.014 | LRMP | 0.47887 | 1.00000 | 0.50663 | 0 | 0 |
| 830 | chr2 | 25206000 | 25207000 | 0.000 | 0.006 | 0.103 | 0.014 | LRMP | 0.02808 | 0.09269 | 0.00099 | 1 | 1 |
| 831 | chr2 | 25207000 | 25208000 | 0.000 | 0.006 | 0.118 | 0.014 | LRMP | 0.01415 | 0.04825 | 0.00030 | 1 | 1 |
| 832 | chr2 | 25208000 | 25209000 | 0.000 | 0.000 | 0.029 | 0.014 | LRMP | 0.60686 | 0.54294 | 0.08726 | 0 | 0 |
| 833 | chr2 | 25665000 | 25666000 | 0.028 | 0.000 | 0.015 | 0.000 | IFITD1 | 0.47887 | 1.00000 | 0.29694 | 0 | 0 |
| 834 | chr2 | 38920000 | 38921000 | 0.000 | 0.000 | 0.029 | 0.014 | CPNE8 | 0.22755 | 0.54294 | 0.08726 | 0 | 0 |
| 835 | chr2 | 48027000 | 48028000 | 0.028 | 0.006 | 0.059 | 0.027 | RPAP3 | 0.42627 | 0.65667 | 0.00730 | 0 | 0 |
| 836 | chr2 | 57496000 | 57497000 | 0.000 | 0.000 | 0.015 | 0.014 | STAT6 | 1.00000 | 1.00000 | 0.29694 | 0 | 0 |
| 837 | chr2 | 69203000 | 69204000 | 0.000 | 0.006 | 0.015 | 0.000 | MDM2 | 0.47887 | 1.00000 | 0.50663 | 0 | 0 |
| 838 | chr2 | 76202000 | 76203000 | 0.028 | 0.000 | 0.000 | 0.027 | PHLDA1 | 0.49735 | 1.00000 | 1.00000 | 0 | 1 |
| 839 | chr2 | 79270000 | 79271000 | 0.000 | 0.000 | 0.029 | 0.027 | SYT1 | 1.00000 | 0.54294 | 0.08726 | 0 | 0 |
| 840 | chr2 | 82572000 | 82573000 | 0.000 | 0.000 | 0.015 | 0.014 | CCDC59 | 1.00000 | 1.00000 | 0.29694 | 0 | 0 |
| 841 | chr2 | 84837000 | 84838000 | 0.000 | 0.000 | 0.000 | 0.014 | SLC6A15 | 0.49735 | 1.00000 | 1.00000 | 0 | 1 |
| 842 | chr2 | 86114000 | 86115000 | 0.000 | 0.000 | 0.029 | 0.000 | RASSF9 | 0.22755 | 0.54294 | 0.08726 | 0 | 0 |
| 843 | chr2 | 86115000 | 86116000 | 0.000 | 0.000 | 0.029 | 0.000 | RASSF9 | 0.22755 | 0.54294 | 0.08726 | 0 | 0 |
| 844 | chr2 | 92539000 | 92540000 | 0.000 | 0.006 | 0.088 | 0.027 | BTG1 | 0.15270 | 0.09031 | 0.00058 | 1 | 1 |
| 845 | chr2 | 96030000 | 96031000 | 0.000 | 0.006 | 0.074 | 0.014 | BTG1 | 0.10420 | 0.16101 | 0.00208 | 0 | 1 |
| 846 | chr2 | 110171000 | 110172000 | 0.000 | 0.000 | 0.015 | 0.000 | NTN4 | 0.47887 | 1.00000 | 0.29694 | 0 | 0 |
| 847 | chr2 | 109810000 | 109810000 | 0.000 | 0.000 | 0.015 | 0.000 | FAM222A | 0.47887 | 1.00000 | 0.50663 | 0 | 0 |
| 848 | chr2 | 113493000 | 113494000 | 0.000 | 0.000 | 0.000 | 0.014 | PPTC7 | 1.00000 | 1.00000 | 0.29694 | 0 | 0 |
| 849 | chr2 | 113494000 | 113495000 | 0.000 | 0.000 | 0.059 | 0.000 | DTX1 | 0.05016 | 0.29551 | 0.00730 | 1 | 1 |
| 850 | chr2 | 113495000 | 113496000 | 0.000 | 0.000 | 0.176 | 0.041 | DTX1 | 0.01224 | 0.00730 | 0.00000 | 1 | 0 |
| 851 | chr2 | 113496000 | 113497000 | 0.000 | 0.000 | 0.162 | 0.068 | DTX1 | 0.11004 | 0.01471 | 0.00000 | 1 | 1 |
| 852 | chr2 | 113497000 | 113498000 | 0.000 | 0.000 | 0.132 | 0.054 | DTX1 | 0.14640 | 0.02564 | 0.00001 | 1 | 1 |
| 853 | chr2 | 113499000 | 113500000 | 0.000 | 0.000 | 0.074 | 0.000 | DTX1 | 0.02326 | 0.16101 | 0.00208 | 1 | 1 |
| 854 | chr2 | 113512000 | 113513000 | 0.000 | 0.006 | 0.029 | 0.014 | DTX1 | 0.22755 | 0.54294 | 0.08726 | 1 | 1 |
| 855 | chr2 | 113499000 | 113500000 | 0.000 | 0.000 | 0.029 | 0.027 | DTX1 | 0.22755 | 0.54294 | 0.08726 | 1 | 1 |
| 856 | chr2 | 115966000 | 115967000 | 0.000 | 0.000 | 0.000 | 0.027 | MED13L | 0.49735 | 1.00000 | 1.00000 | 0 | 0 |
| 857 | chr2 | 122432000 | 122433000 | 0.000 | 0.000 | 0.029 | 0.000 | WDR66 | 0.22755 | 0.54294 | 0.08726 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAny Histology |
|---|---|---|---|---|---|---|---|---|---|---|---|---|---|
| 858 | chr2 | 122433000 | 122434000 | 0.000 | 0.000 | 0.059 | 0.014 | WDR66 | 0.19371 | 0.29551 | 0.00730 | 0 | 1 |
| 859 | chr2 | 122447000 | 122448000 | 0.000 | 0.000 | 0.000 | 0.027 | WDR66 | 0.49735 | 1.00000 | 1.00000 | 0 | 0 |
| 860 | chr2 | 122458000 | 122459000 | 0.000 | 0.006 | 0.118 | 0.068 | BCL7A | 0.38669 | 0.04825 | 0.00030 | 1 | 1 |
| 861 | chr2 | 122459000 | 122460000 | 0.000 | 0.006 | 0.324 | 0.108 | BCL7A | 0.00197 | 0.00003 | 0.00000 | 1 | 1 |
| 862 | chr2 | 122460000 | 122461000 | 0.000 | 0.006 | 0.176 | 0.081 | BCL7A | 0.12879 | 0.00730 | 0.00000 | 1 | 1 |
| 863 | chr2 | 122461000 | 122462000 | 0.000 | 0.006 | 0.279 | 0.162 | BCL7A | 0.10628 | 0.00013 | 0.00000 | 1 | 1 |
| 864 | chr2 | 122462000 | 122463000 | 0.000 | 0.012 | 0.191 | 0.027 | BCL7A | 0.00186 | 0.00372 | 0.00000 | 1 | 1 |
| 865 | chr2 | 122463000 | 122464000 | 0.000 | 0.012 | 0.132 | 0.054 | BCL7A | 0.14640 | 0.02564 | 0.00038 | 1 | 1 |
| 866 | chr2 | 124054000 | 124055000 | 0.028 | 0.000 | 0.015 | 0.014 | TMED2 | 1.00000 | 1.00000 | 0.29694 | 0 | 0 |
| 867 | chr2 | 127965000 | 127966000 | 0.000 | 0.000 | 0.000 | 0.027 | TMEM132C | 0.49735 | 1.00000 | 1.00000 | 0 | 1 |
| 868 | chr2 | 131303000 | 131304000 | 0.056 | 0.000 | 0.015 | 0.014 | STX2 | 1.00000 | 0.27446 | 0.29694 | 0 | 0 |
| 869 | chr2 | 131649000 | 131650000 | 0.000 | 0.000 | 0.000 | 0.027 | GPR133 | 0.49735 | 1.00000 | 1.00000 | 0 | 0 |
| 870 | chr2 | 133306000 | 133307000 | 0.028 | 0.000 | 0.015 | 0.027 | ANKLE2 | 1.00000 | 0.54294 | 0.29694 | 0 | 0 |
| 871 | chr3 | 21913000 | 21914000 | 0.028 | 0.000 | 0.029 | 0.000 | ZDHHC20 | 0.22755 | 0.54294 | 0.08726 | 0 | 0 |
| 872 | chr3 | 32116000 | 32117000 | 0.028 | 0.000 | 0.029 | 0.027 | RXFP2 | 0.47887 | 1.00000 | 0.29694 | 0 | 0 |
| 873 | chr3 | 35498000 | 35499000 | 0.000 | 0.000 | 0.015 | 0.027 | NBEA | 1.00000 | 1.00000 | 0.29694 | 0 | 0 |
| 874 | chr3 | 38371000 | 38372000 | 0.028 | 0.000 | 0.015 | 0.000 | TRPC4 | 0.47887 | 0.54294 | 0.29694 | 0 | 0 |
| 875 | chr3 | 38630000 | 38631000 | 0.028 | 0.000 | 0.029 | 0.000 | TRPC4 | 0.22755 | 0.54294 | 0.08726 | 0 | 0 |
| 876 | chr3 | 41156000 | 41157000 | 0.000 | 0.000 | 0.015 | 0.000 | FOXO1 | 1.00000 | 1.00000 | 0.29694 | 1 | 0 |
| 877 | chr3 | 41240000 | 41241000 | 0.028 | 0.000 | 0.029 | 0.000 | FOXO1 | 0.22755 | 0.54294 | 0.08726 | 1 | 0 |
| 878 | chr3 | 46958000 | 46959000 | 0.028 | 0.000 | 0.029 | 0.000 | KIAA0226L | 0.22755 | 0.54294 | 0.08726 | 0 | 0 |
| 879 | chr3 | 46959000 | 46960000 | 0.028 | 0.000 | 0.029 | 0.000 | KIAA0226L | 0.22755 | 0.54294 | 0.08726 | 0 | 0 |
| 880 | chr3 | 46960000 | 46961000 | 0.000 | 0.000 | 0.088 | 0.027 | KIAA0226L | 0.15270 | 0.09031 | 0.00058 | 0 | 1 |
| 881 | chr3 | 46961000 | 46962000 | 0.000 | 0.000 | 0.015 | 0.014 | KIAA0226L | 1.00000 | 1.00000 | 0.29694 | 0 | 0 |
| 882 | chr3 | 46962000 | 46963000 | 0.028 | 0.000 | 0.015 | 0.014 | KIAA0226L | 0.47887 | 0.54294 | 0.08726 | 0 | 0 |
| 883 | chr3 | 55239000 | 55240000 | 0.000 | 0.000 | 0.029 | 0.027 | OLFM4 | 0.22755 | 0.54294 | 0.08726 | 0 | 0 |
| 884 | chr3 | 55386000 | 55387000 | 0.000 | 0.000 | 0.029 | 0.000 | OLFM4 | 0.22755 | 0.54294 | 0.08726 | 0 | 0 |
| 885 | chr3 | 55598000 | 55599000 | 0.000 | 0.000 | 0.029 | 0.000 | OLFM4 | 0.22755 | 0.54294 | 0.08726 | 0 | 0 |
| 886 | chr3 | 57222000 | 57223000 | 0.000 | 0.000 | 0.029 | 0.000 | PRR20A; PRR20DPRR20BPRR20E; | 0.22755 | 0.54294 | 0.08726 | 0 | 0 |
| 887 | chr3 | 61343000 | 61344000 | 0.000 | 0.000 | 0.015 | 0.000 | TDRD3 | 0.47887 | 1.00000 | 0.29694 | 0 | 0 |
| 888 | chr3 | 62830000 | 62831000 | 0.000 | 0.000 | 0.000 | 0.027 | PCDH20 | 0.49735 | 1.00000 | 1.00000 | 0 | 0 |
| 889 | chr3 | 63049000 | 63050000 | 0.000 | 0.000 | 0.029 | 0.000 | PCDH20 | 0.22755 | 0.54294 | 0.08726 | 0 | 0 |
| 890 | chr3 | 63157000 | 63158000 | 0.000 | 0.000 | 0.015 | 0.000 | AL445989.1 | 0.47887 | 1.00000 | 0.29694 | 0 | 0 |
| 891 | chr3 | 63214000 | 63215000 | 0.028 | 0.000 | 0.015 | 0.000 | AL445989.1 | 0.47887 | 0.54294 | 0.29694 | 0 | 0 |
| 892 | chr3 | 64802000 | 64803000 | 0.000 | 0.000 | 0.015 | 0.014 | AL445989.1 | 1.00000 | 1.00000 | 0.29694 | 0 | 0 |
| 893 | chr3 | 65637000 | 65638000 | 0.000 | 0.000 | 0.029 | 0.000 | PCDH9 | 0.22755 | 0.54294 | 0.08726 | 0 | 0 |
| 894 | chr3 | 68656000 | 68657000 | 0.000 | 0.000 | 0.029 | 0.027 | PCDH9 | 0.49735 | 0.54294 | 1.00000 | 0 | 0 |
| 895 | chr3 | 69418000 | 69419000 | 0.000 | 0.000 | 0.014 | 0.014 | KLHL1 | 0.60686 | 1.00000 | 0.08726 | 0 | 0 |
| 896 | chr3 | 70956000 | 70957000 | 0.000 | 0.012 | 0.015 | 0.000 | KLHL1 | 0.47887 | 0.54294 | 1.00000 | 0 | 0 |
| 897 | chr3 | 74542000 | 74543000 | 0.000 | 0.000 | 0.029 | 0.000 | KLF12 | 0.22755 | 0.54294 | 0.08726 | 0 | 0 |
| 898 | chr3 | 75983000 | 75984000 | 0.000 | 0.000 | 0.074 | 0.014 | TBC1D4 | 0.10420 | 0.16101 | 0.00208 | 0 | 0 |
| 899 | chr3 | 75984000 | 75985000 | 0.000 | 0.000 | 0.118 | 0.027 | TBC1D4 | 0.04838 | 0.04825 | 0.00004 | 0 | 1 |
| 900 | chr3 | 83450000 | 83451000 | 0.000 | 0.000 | 0.029 | 0.000 | SLITRK1 | 0.22755 | 0.54294 | 0.08726 | 0 | 0 |
| 901 | chr3 | 84641000 | 84642000 | 0.000 | 0.000 | 0.015 | 0.014 | SLITRK1 | 1.00000 | 1.00000 | 0.29694 | 0 | 0 |
| 902 | chr3 | 87793000 | 87794000 | 0.000 | 0.000 | 0.015 | 0.014 | SLITRK5 | 1.00000 | 1.00000 | 0.29694 | 0 | 0 |
| 903 | chr3 | 91480000 | 91481000 | 0.000 | 0.000 | 0.000 | 0.027 | GPC5 | 0.49735 | 1.00000 | 1.00000 | 0 | 0 |
| 904 | chr3 | 106081000 | 106082000 | 0.000 | 0.000 | 0.015 | 0.014 | DAOA | 1.00000 | 1.00000 | 0.29694 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 905 | chr13 | 114786000 | 114787000 | 0.000 | 0.000 | 0.015 | 0.027 | RASA3 | 1.00000 | 1.00000 | 0.29694 | 0 | 0 |
| 906 | chr13 | 114916000 | 114917000 | 0.028 | 0.000 | 0.000 | 0.014 | RASA3 | 1.00000 | 0.34615 | 1.00000 | 0 | 0 |
| 907 | chr14 | 22948000 | 22949000 | 0.000 | 0.000 | 0.029 | 0.000 | TRAJ56 | 0.22755 | 0.54294 | 0.08726 | 0 | 0 |
| 908 | chr14 | 22949000 | 22950000 | 0.000 | 0.000 | 0.044 | 0.000 | TRAJ56 | 0.10727 | 0.54966 | 0.02537 | 0 | 0 |
| 909 | chr14 | 22950000 | 22951000 | 0.000 | 0.000 | 0.029 | 0.014 | TRAJ54 | 0.22755 | 0.54294 | 0.08726 | 0 | 0 |
| 910 | chr14 | 22977000 | 22978000 | 0.000 | 0.000 | 0.015 | 0.014 | TRAJ33 | 1.00000 | 1.00000 | 1.00000 | 0 | 0 |
| 911 | chr14 | 27286000 | 27287000 | 0.000 | 0.000 | 0.029 | 0.000 | NOVA1 | 0.22755 | 0.54294 | 0.08726 | 0 | 0 |
| 912 | chr14 | 28645000 | 28646000 | 0.000 | 0.000 | 0.000 | 0.027 | FOXG1 | 0.49735 | 1.00000 | 1.00000 | 0 | 0 |
| 913 | chr14 | 49407000 | 49408000 | 0.000 | 0.000 | 0.000 | 0.041 | RPS29 | 0.24603 | 1.00000 | 1.00000 | 0 | 0 |
| 914 | chr14 | 50864000 | 50865000 | 0.000 | 0.000 | 0.029 | 0.000 | CDKL1 | 0.22755 | 0.54294 | 0.08726 | 0 | 0 |
| 915 | chr14 | 54812000 | 54813000 | 0.000 | 0.000 | 0.000 | 0.027 | CDKN3 | 0.49735 | 1.00000 | 1.00000 | 0 | 0 |
| 916 | chr14 | 55348000 | 55349000 | 0.000 | 0.000 | 0.029 | 0.000 | GCH1 | 0.22755 | 0.54294 | 0.08726 | 0 | 0 |
| 917 | chr14 | 59827000 | 59828000 | 0.000 | 0.012 | 0.029 | 0.068 | DAAM1 | 1.00000 | 0.54294 | 0.29694 | 0 | 0 |
| 918 | chr14 | 63143000 | 63144000 | 0.000 | 0.000 | 0.015 | 0.014 | KCNH5 | 1.00000 | 1.00000 | 0.29694 | 0 | 0 |
| 919 | chr14 | 64194000 | 64195000 | 0.000 | 0.000 | 0.015 | 0.014 | SGPP1 | 1.00000 | 1.00000 | 0.29694 | 0 | 1 |
| 920 | chr14 | 69258000 | 69259000 | 0.000 | 0.006 | 0.191 | 0.027 | ZFP36L1 | 0.00186 | 0.00372 | 0.00000 | 1 | 1 |
| 921 | chr14 | 69259000 | 69260000 | 0.000 | 0.012 | 0.265 | 0.068 | ZFP36L1 | 0.00244 | 0.00024 | 0.00000 | 1 | 1 |
| 922 | chr14 | 78418000 | 78419000 | 0.000 | 0.000 | 0.029 | 0.000 | ADCK1 | 1.00000 | 0.54294 | 0.29694 | 0 | 0 |
| 923 | chr14 | 81685000 | 81686000 | 0.028 | 0.000 | 0.015 | 0.000 | GTF2A1 | 0.01415 | 0.04825 | 0.00004 | 1 | 1 |
| 924 | chr14 | 84420000 | 84421000 | 0.000 | 0.006 | 0.118 | 0.108 | FLRT2 | 0.47887 | 1.00000 | 0.50663 | 0 | 0 |
| 925 | chr14 | 91883000 | 91884000 | 0.028 | 0.037 | 0.132 | 0.054 | CCDC88C | 0.79702 | 0.15881 | 0.01566 | 0 | 0 |
| 926 | chr14 | 94941000 | 94942000 | 0.028 | 0.025 | 0.088 | 0.027 | SERPINA9 | 0.52007 | 0.41714 | 0.06858 | 0 | 0 |
| 927 | chr14 | 94942000 | 94943000 | 0.000 | 0.000 | 0.000 | 0.014 | SERPINA9 | 0.49735 | 1.00000 | 0.21104 | 1 | 0 |
| 928 | chr14 | 96179000 | 96180000 | 0.000 | 0.000 | 0.015 | 0.014 | TCL1A | 1.00000 | 1.00000 | 0.29694 | 1 | 1 |
| 929 | chr14 | 96180000 | 96181000 | 0.028 | 0.006 | 0.044 | 0.014 | TCL1A | 0.34948 | 0.54966 | 0.02537 | 1 | 0 |
| 930 | chr14 | 101597000 | 101598000 | 0.000 | 0.000 | 0.015 | 0.014 | AL117190.3 | 1.00000 | 1.00000 | 0.29694 | 1 | 0 |
| 931 | chr14 | 102285000 | 102286000 | 0.000 | 0.019 | 0.103 | 0.041 | PPP2R5C | 0.19468 | 0.09269 | 0.00855 | 0 | 0 |
| 932 | chr14 | 105954000 | 105955000 | 0.000 | 0.000 | 0.015 | 0.000 | CRIP1 | 1.00000 | 1.00000 | 0.50663 | 0 | 1 |
| 933 | chr14 | 106031000 | 106032000 | 0.000 | 0.006 | 0.029 | 0.014 | IGHA2 | 0.60686 | 0.54294 | 0.08726 | 0 | 0 |
| 934 | chr14 | 106042000 | 106043000 | 0.056 | 0.000 | 0.103 | 0.027 | IGHA2 | 0.08710 | 0.49207 | 0.00016 | 0 | 1 |
| 935 | chr14 | 106048000 | 106049000 | 0.056 | 0.006 | 0.074 | 0.027 | IGHA2 | 0.25970 | 1.00000 | 0.00953 | 0 | 0 |
| 936 | chr14 | 106054000 | 106055000 | 0.000 | 0.000 | 0.059 | 0.000 | IGHA2 | 0.05016 | 0.29551 | 0.00730 | 0 | 1 |
| 937 | chr14 | 106055000 | 106056000 | 0.000 | 0.000 | 0.029 | 0.014 | IGHA2 | 0.22755 | 0.54294 | 0.08726 | 0 | 0 |
| 938 | chr14 | 106056000 | 106057000 | 0.000 | 0.006 | 0.059 | 0.000 | IGHA2 | 0.05016 | 0.29551 | 0.00730 | 0 | 1 |
| 939 | chr14 | 106057000 | 106058000 | 0.000 | 0.000 | 0.044 | 0.014 | IGHE | 0.34948 | 0.54966 | 0.02537 | 0 | 0 |
| 940 | chr14 | 106058000 | 106059000 | 0.000 | 0.000 | 0.103 | 0.027 | IGHE | 0.08710 | 0.09269 | 0.00016 | 0 | 1 |
| 941 | chr14 | 106066000 | 106067000 | 0.000 | 0.006 | 0.206 | 0.216 | IGHE | 1.00000 | 0.00197 | 0.00000 | 0 | 1 |
| 942 | chr14 | 106067000 | 106068000 | 0.000 | 0.000 | 0.088 | 0.068 | IGHE | 0.75773 | 0.09031 | 0.00058 | 0 | 1 |
| 943 | chr14 | 106069000 | 106070000 | 0.000 | 0.000 | 0.074 | 0.068 | IGHE | 1.00000 | 0.16101 | 0.00208 | 0 | 0 |
| 944 | chr14 | 106070000 | 106071000 | 0.000 | 0.000 | 0.029 | 0.014 | IGHE | 0.60686 | 0.54294 | 0.08726 | 0 | 0 |
| 945 | chr14 | 106071000 | 106072000 | 0.000 | 0.000 | 0.015 | 0.027 | IGHE | 1.00000 | 1.00000 | 0.29694 | 0 | 0 |
| 946 | chr14 | 106072000 | 106073000 | 0.000 | 0.000 | 0.103 | 0.027 | IGHG4 | 0.60686 | 0.54294 | 0.08726 | 0 | 0 |
| 947 | chr14 | 106082000 | 106083000 | 0.000 | 0.000 | 0.015 | 0.000 | IGHG4 | 1.00000 | 1.00000 | 0.00016 | 0 | 1 |
| 948 | chr14 | 106083000 | 106084000 | 0.000 | 0.000 | 0.029 | 0.014 | IGHG4 | 0.22755 | 0.54294 | 0.08726 | 0 | 0 |
| 949 | chr14 | 106092000 | 106093000 | 0.000 | 0.006 | 0.147 | 0.027 | IGHG4 | 0.01393 | 0.01404 | 0.00003 | 0 | 1 |
| 950 | chr14 | 106094000 | 106095000 | 0.000 | 0.006 | 0.103 | 0.081 | IGHG4 | 0.77363 | 0.09269 | 0.00016 | 0 | 0 |
| 951 | chr14 | 106095000 | 106096000 | 0.000 | 0.000 | 0.074 | 0.014 | IGHG2 | 0.10420 | 0.16101 | 0.00208 | 0 | 1 |
| 952 | chr14 | 106110000 | 106111000 | 0.000 | 0.000 | 0.074 | 0.014 | IGHG2 | 0.10420 | 0.16101 | 0.00208 | 0 | 1 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAny Histology |
|---|---|---|---|---|---|---|---|---|---|---|---|---|---|
| 953 | chr14 | 106111000 | 106112000 | 0.000 | 0.000 | 0.015 | 0.014 | IGHG2 | 1.00000 | 1.00000 | 0.29694 | 0 | 0 |
| 954 | chr14 | 106112000 | 106113000 | 0.000 | 0.056 | 0.294 | 0.257 | IGHG2 | 0.70749 | 0.00011 | 0.00000 | 0 | 1 |
| 955 | chr14 | 106113000 | 106114000 | 0.028 | 0.068 | 0.397 | 0.284 | IGHG2 | 0.16121 | 0.00002 | 0.00000 | 0 | 1 |
| 956 | chr14 | 106114000 | 106115000 | 0.000 | 0.000 | 0.279 | 0.122 | IGHG2 | 0.02111 | 0.00013 | 0.08726 | 0 | 0 |
| 957 | chr14 | 106146000 | 106147000 | 0.000 | 0.006 | 0.029 | 0.000 | IGHA1 | 0.22755 | 0.54294 | 0.54294 | 0 | 0 |
| 958 | chr14 | 106150000 | 106151000 | 0.000 | 0.006 | 0.015 | 0.014 | IGHA1 | 1.00000 | 1.00000 | 0.50663 | 0 | 0 |
| 959 | chr14 | 106152000 | 106153000 | 0.000 | 0.000 | 0.015 | 0.027 | IGHA1 | 1.00000 | 1.00000 | 0.50663 | 0 | 0 |
| 960 | chr14 | 106161000 | 106162000 | 0.000 | 0.006 | 0.015 | 0.014 | IGHA1 | 1.00000 | 1.00000 | 0.29694 | 0 | 0 |
| 961 | chr14 | 106173000 | 106174000 | 0.028 | 0.006 | 0.029 | 0.027 | IGHA1 | 1.00000 | 1.00000 | 0.21104 | 0 | 0 |
| 962 | chr14 | 106174000 | 106175000 | 0.000 | 0.006 | 0.029 | 0.000 | IGHA1 | 0.22755 | 0.54294 | 0.21104 | 0 | 0 |
| 963 | chr14 | 106175000 | 106176000 | 0.028 | 0.006 | 0.059 | 0.014 | IGHA1 | 0.19371 | 0.65667 | 0.02818 | 0 | 1 |
| 964 | chr14 | 106176000 | 106177000 | 0.139 | 0.031 | 0.103 | 0.068 | IGHA1 | 0.55139 | 0.74810 | 0.04551 | 0 | 1 |
| 965 | chr14 | 106177000 | 106178000 | 0.000 | 0.019 | 0.059 | 0.027 | IGHA1 | 0.42627 | 0.29551 | 0.20027 | 0 | 1 |
| 966 | chr14 | 106178000 | 106179000 | 0.000 | 0.016 | 0.059 | 0.014 | IGHA1 | 0.19371 | 0.29551 | 0.02818 | 0 | 1 |
| 967 | chr14 | 106208000 | 106209000 | 0.028 | 0.000 | 0.103 | 0.014 | IGHA1 | 0.08710 | 0.09269 | 0.00016 | 0 | 1 |
| 968 | chr14 | 106209000 | 106210000 | 0.000 | 0.006 | 0.118 | 0.054 | IGHG1 | 0.23086 | 0.04825 | 0.00030 | 0 | 1 |
| 969 | chr14 | 106210000 | 106211000 | 0.000 | 0.006 | 0.118 | 0.068 | IGHG1 | 0.38669 | 0.04825 | 0.00004 | 0 | 1 |
| 970 | chr14 | 106211000 | 106212000 | 0.000 | 0.056 | 0.149 | 0.149 | IGHG1 | 0.20587 | 0.00098 | 0.00025 | 0 | 1 |
| 971 | chr14 | 106212000 | 106213000 | 0.028 | 0.106 | 0.309 | 0.270 | IGHG1 | 0.71144 | 0.00070 | 0.00035 | 0 | 1 |
| 972 | chr14 | 106213000 | 106214000 | 0.056 | 0.068 | 0.382 | 0.216 | IGHG1 | 0.04243 | 0.00034 | 0.00000 | 0 | 1 |
| 973 | chr14 | 106214000 | 106215000 | 0.000 | 0.000 | 0.147 | 0.000 | IGHG1 | 0.00044 | 0.01404 | 0.00000 | 0 | 1 |
| 974 | chr14 | 106237000 | 106238000 | 0.000 | 0.000 | 0.088 | 0.000 | IGHG3 | 0.01070 | 0.09031 | 0.00058 | 0 | 1 |
| 975 | chr14 | 106238000 | 106239000 | 0.000 | 0.000 | 0.176 | 0.027 | IGHG3 | 0.003 70 | 0.00730 | 0.00000 | 0 | 1 |
| 976 | chr14 | 106239000 | 106240000 | 0.056 | 0.062 | 0.206 | 0.135 | IGHG3 | 0.27339 | 0.04910 | 0.00349 | 0 | 1 |
| 977 | chr14 | 106240000 | 106241000 | 0.028 | 0.130 | 0.324 | 0.230 | IGHG3 | 0.25971 | 0.04825 | 0.00136 | 0 | 1 |
| 978 | chr14 | 106241000 | 106242000 | 0.000 | 0.025 | 0.221 | 0.081 | IGHG3 | 0.03144 | 0.00034 | 0.00000 | 0 | 1 |
| 979 | chr14 | 106242000 | 106243000 | 0.000 | 0.000 | 0.044 | 0.014 | IGHG3 | 0.34948 | 0.00107 | 0.00000 | 0 | 0 |
| 980 | chr14 | 106221000 | 106222000 | 0.000 | 0.000 | 0.059 | 0.000 | IGHM | 0.05016 | 0.54966 | 0.02537 | 0 | 1 |
| 981 | chr14 | 106322000 | 106323000 | 0.000 | 0.006 | 0.221 | 0.054 | IGHM | 0.00556 | 0.29551 | 0.00730 | 0 | 1 |
| 982 | chr14 | 106323000 | 106324000 | 0.000 | 0.062 | 0.235 | 0.162 | IGHM | 0.29797 | 0.00107 | 0.00000 | 0 | 1 |
| 983 | chr14 | 106324000 | 106325000 | 0.250 | 0.193 | 0.221 | 0.284 | IGHM | 0.44266 | 0.02782 | 0.00040 | 0 | 1 |
| 984 | chr14 | 106325000 | 106326000 | 0.694 | 0.335 | 0.279 | 0.365 | IGHM | 0.28848 | 0.80827 | 0.00000 | 0 | 1 |
| 985 | chr14 | 106326000 | 106327000 | 0.833 | 0.540 | 0.838 | 0.838 | IGHJ6 | 1.00000 | 0.00006 | 0.71834 | 0 | 1 |
| 986 | chr14 | 106327000 | 106328000 | 0.333 | 0.335 | 0.926 | 0.905 | IGHJ6 | 0.76698 | 1.00000 | 0.44111 | 0 | 1 |
| 987 | chr14 | 106328000 | 106329000 | 0.250 | 0.248 | 0.809 | 0.730 | IGHJ6 | 0.32171 | 0.00000 | 0.00001 | 0 | 1 |
| 988 | chr14 | 106329000 | 106330000 | 0.694 | 0.441 | 0.882 | 0.932 | IGHJ6 | 0.38669 | 0.00000 | 0.00000 | 0 | 1 |
| 989 | chr14 | 106330000 | 106331000 | 0.694 | 0.298 | 0.574 | 0.649 | IGHJ3; IGHJ4; IGHJ5; IGHJ7-27; IGHJ1; IGHJ2; | 0.39187 | 0.03086 | 0.00000 | 0 | 1 |
| 990 | chr14 | 106331000 | 106332000 | 0.028 | 0.012 | 0.044 | 0.027 | | 0.67043 | 0.29080 | 0.00017 | 0 | 0 |
| | | | | | | | | | | 1.00000 | 0.15671 | | |
| 991 | chr14 | 106338000 | 106339000 | 0.028 | 0.006 | 0.000 | 0.000 | IGHD7-27 | 1.00000 | 0.34615 | 2.00000 | 0 | 0 |
| 992 | chr14 | 106350000 | 106351000 | 0.000 | 0.006 | 0.029 | 0.000 | IGHD4-23 | 0.22755 | 0.54294 | 0.21104 | 0 | 0 |
| 993 | chr14 | 106352000 | 106353000 | 0.000 | 0.000 | 0.029 | 0.000 | IGHD3-22 | 0.22755 | 0.54294 | 0.08726 | 0 | 0 |
| 994 | chr14 | 106354000 | 106355000 | 0.000 | 0.006 | 0.029 | 0.000 | IGHD2-21 | 0.22755 | 0.54294 | 0.21104 | 0 | 0 |
| 995 | chr14 | 106355000 | 106356000 | 0.000 | 0.000 | 0.015 | 0.000 | IGHD2-21 | 0.47887 | 1.00000 | 0.50663 | 0 | 0 |
| 996 | chr14 | 106357000 | 106358000 | 0.028 | 0.000 | 0.044 | 0.000 | IGHD2-21 | 0.10727 | 0.54966 | 0.02537 | 0 | 0 |
| 997 | chr14 | 106358000 | 106359000 | 0.000 | 0.006 | 0.059 | 0.000 | IGHD1-20; IGHD6-19; | 0.05016 | 0.65667 | 0.00730 | 0 | 1 |
| 998 | chr14 | 106358000 | 106359000 | 0.028 | 0.006 | 0.029 | 0.000 | IGHD5-18 | 0.22755 | 0.54294 | 0.21104 | 0 | 0 |
| 999 | chr14 | 106362000 | 106363000 | 0.000 | 0.006 | 0.000 | 0.000 | IGHD3-16 | 1.00000 | 0.34615 | 1.00000 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 1000 | chr14 | 106364000 | 106365000 | 0.000 | 0.000 | 0.029 | 0.000 | IGHD2-15 | 0.22755 | 0.54294 | 0.08726 | 0 | 0 |
| 1001 | chr14 | 106367000 | 106368000 | 0.000 | 0.000 | 0.029 | 0.000 | IGHD6-13 | 0.22755 | 0.54294 | 0.08726 | 0 | 0 |
| 1002 | chr14 | 106370000 | 106371000 | 0.000 | 0.012 | 0.044 | 0.014 | IGHD3-10; IGHD3-9; | 0.34948 | 0.54966 | 0.15671 | 0 | 0 |
| 1003 | chr14 | 106371000 | 106372000 | 0.000 | 0.012 | 0.029 | 0.014 | IGHD3-9 | 0.60686 | 0.54294 | 0.58408 | 0 | 0 |
| 1004 | chr14 | 106372000 | 106373000 | 0.000 | 0.006 | 0.015 | 0.000 | IGHD2-8 | 0.47887 | 1.00000 | 0.50663 | 0 | 0 |
| 1005 | chr14 | 106375000 | 106376000 | 0.000 | 0.019 | 0.000 | 0.000 | IGHD1-7 | 0.47887 | 1.00000 | 1.00000 | 0 | 0 |
| 1006 | chr14 | 106376000 | 106377000 | 0.000 | 0.012 | 0.015 | 0.000 | IGHD6-6 | 0.47887 | 1.00000 | 1.00000 | 0 | 0 |
| 1007 | chr14 | 106380000 | 106381000 | 0.000 | 0.031 | 0.000 | 0.000 | IGHD3-3 | 1.00000 | 1.00000 | 0.32529 | 0 | 0 |
| 1008 | chr14 | 106381000 | 106382000 | 0.000 | 0.031 | 0.000 | 0.000 | IGHD2-2 | 1.00000 | 1.00000 | 0.32529 | 0 | 0 |
| 1009 | chr14 | 106382000 | 106383000 | 0.000 | 0.037 | 0.044 | 0.014 | IGHD2-2 | 0.34948 | 0.54966 | 0.72719 | 0 | 0 |
| 1010 | chr14 | 106383000 | 106384000 | 0.000 | 0.000 | 0.044 | 0.014 | IGHD2-2 | 0.34948 | 0.54966 | 0.02537 | 0 | 0 |
| 1011 | chr14 | 106384000 | 106385000 | 0.000 | 0.012 | 0.044 | 0.014 | IGHD1-1 | 0.34948 | 0.54966 | 0.15671 | 0 | 0 |
| 1012 | chr14 | 106385000 | 106386000 | 0.000 | 0.000 | 0.029 | 0.014 | IGHD1-1 | 0.60686 | 0.54294 | 0.08726 | 0 | 0 |
| 1013 | chr14 | 106387000 | 106388000 | 0.000 | 0.000 | 0.029 | 0.014 | KIAA0125 | 0.60686 | 0.54294 | 0.08726 | 0 | 0 |
| 1014 | chr14 | 106405000 | 106406000 | 0.000 | 0.006 | 0.015 | 0.014 | IGHV6-1 | 1.00000 | 1.00000 | 0.50663 | 0 | 0 |
| 1015 | chr14 | 106406000 | 106407000 | 0.000 | 0.006 | 0.015 | 0.014 | IGHV6-1 | 1.00000 | 1.00000 | 0.50663 | 0 | 0 |
| 1016 | chr14 | 106419000 | 106420000 | 0.000 | 0.006 | 0.015 | 0.000 | IGHV6-1 | 0.47887 | 1.00000 | 0.50663 | 0 | 0 |
| 1017 | chr14 | 106452000 | 106453000 | 0.000 | 0.006 | 0.029 | 0.000 | IGHV1-2 | 0.22755 | 0.54294 | 0.21104 | 0 | 0 |
| 1018 | chr14 | 106453000 | 106454000 | 0.000 | 0.006 | 0.044 | 0.000 | IGHV1-2 | 0.10727 | 0.54966 | 0.07959 | 0 | 0 |
| 1019 | chr14 | 106454000 | 106455000 | 0.000 | 0.000 | 0.029 | 0.014 | IGHV1-2 | 0.22755 | 0.54294 | 0.08726 | 0 | 0 |
| 1020 | chr14 | 106494000 | 106495000 | 0.000 | 0.019 | 0.000 | 0.014 | IGHV2-5 | 1.00000 | 1.00000 | 0.55662 | 0 | 0 |
| 1021 | chr14 | 106518000 | 106519000 | 0.028 | 0.037 | 0.000 | 0.054 | IGHV3-7 | 0.12104 | 0.34615 | 0.18288 | 0 | 1 |
| 1022 | chr14 | 106519000 | 106520000 | 0.000 | 0.012 | 0.000 | 0.027 | IGHV3-7 | 0.49735 | 1.00000 | 1.00000 | 0 | 0 |
| 1023 | chr14 | 106539000 | 106540000 | 0.000 | 0.031 | 0.015 | 0.000 | IGHV1-8 | 0.47887 | 1.00000 | 0.67240 | 0 | 0 |
| 1024 | chr14 | 106552000 | 106553000 | 0.000 | 0.006 | 0.029 | 0.014 | IGHV3-9 | 0.60686 | 0.54294 | 0.21104 | 0 | 0 |
| 1025 | chr14 | 106573000 | 106574000 | 0.000 | 0.019 | 0.029 | 0.068 | IGHV3-11 | 0.44431 | 0.54294 | 0.63492 | 0 | 0 |
| 1026 | chr14 | 106574000 | 106575000 | 0.000 | 0.006 | 0.029 | 0.041 | IGHV3-11 | 1.00000 | 0.54294 | 0.21104 | 0 | 0 |
| 1027 | chr14 | 106578000 | 106579000 | 0.000 | 0.006 | 0.015 | 0.027 | IGHV3-11 | 1.00000 | 1.00000 | 0.29694 | 0 | 0 |
| 1028 | chr14 | 106579000 | 106580000 | 0.000 | 0.000 | 0.015 | 0.027 | IGHV3-11 | 0.22755 | 1.00000 | 0.29694 | 0 | 0 |
| 1029 | chr14 | 106610000 | 106611000 | 0.056 | 0.012 | 0.029 | 0.000 | IGHV3-15 | 1.00000 | 0.60763 | 0.58408 | 0 | 0 |
| 1030 | chr14 | 106641000 | 106642000 | 0.000 | 0.019 | 0.015 | 0.000 | IGHV1-18 | 0.47887 | 1.00000 | 1.00000 | 0 | 0 |
| 1031 | chr14 | 106642000 | 106643000 | 0.000 | 0.012 | 0.015 | 0.000 | IGHV1-18 | 0.47887 | 1.00000 | 1.00000 | 0 | 0 |
| 1032 | chr14 | 106691000 | 106692000 | 0.000 | 0.012 | 0.029 | 0.027 | IGHV3-21 | 1.00000 | 0.54294 | 0.58408 | 0 | 0 |
| 1033 | chr14 | 106692000 | 106693000 | 0.000 | 0.006 | 0.015 | 0.041 | IGHV3-21 | 0.62100 | 1.00000 | 0.50663 | 0 | 0 |
| 1034 | chr14 | 106725000 | 106726000 | 0.083 | 0.068 | 0.103 | 0.135 | IGHV3-23 | 0.61250 | 1.00000 | 0.42238 | 0 | 0 |
| 1035 | chr14 | 106726000 | 106727000 | 0.028 | 0.019 | 0.088 | 0.095 | IGHV3-23 | 1.00000 | 0.41714 | 0.02173 | 0 | 1 |
| 1036 | chr14 | 106733000 | 106734000 | 0.028 | 0.006 | 0.015 | 0.027 | IGHV1-24 | 0.47887 | 1.00000 | 0.50663 | 0 | 0 |
| 1037 | chr14 | 106757000 | 106758000 | 0.056 | 0.000 | 0.015 | 0.000 | IGHV2-26 | 1.00000 | 0.27446 | 0.29694 | 0 | 0 |
| 1038 | chr14 | 106758000 | 106759000 | 0.056 | 0.000 | 0.000 | 0.000 | IGHV2-26 | 1.00000 | 0.11763 | 1.00000 | 0 | 1 |
| 1039 | chr14 | 106791000 | 106792000 | 0.056 | 0.006 | 0.015 | 0.000 | IGHV3-30 | 0.47887 | 0.27446 | 0.50663 | 0 | 1 |
| 1040 | chr14 | 106804000 | 106805000 | 0.000 | 0.006 | 0.029 | 0.000 | IGHV4-31 | 0.22755 | 0.54294 | 0.21104 | 0 | 1 |
| 1041 | chr14 | 106805000 | 106806000 | 0.000 | 0.006 | 0.044 | 0.014 | IGHV4-31 | 0.34948 | 0.54966 | 0.07959 | 0 | 1 |
| 1042 | chr14 | 106806000 | 106807000 | 0.000 | 0.006 | 0.015 | 0.000 | IGHV4-31 | 0.47887 | 1.00000 | 0.50663 | 0 | 0 |
| 1043 | chr14 | 106815000 | 106816000 | 0.000 | 0.012 | 0.044 | 0.027 | IGHV3-33 | 0.67043 | 0.54966 | 0.15671 | 0 | 0 |
| 1044 | chr14 | 106816000 | 106817000 | 0.000 | 0.006 | 0.074 | 0.014 | IGHV3-33 | 0.10420 | 0.16101 | 0.00953 | 0 | 1 |
| 1045 | chr14 | 106817000 | 106818000 | 0.000 | 0.006 | 0.029 | 0.000 | IGHV3-33 | 0.22755 | 0.54294 | 0.08726 | 0 | 0 |
| 1046 | chr14 | 106829000 | 106830000 | 0.167 | 0.050 | 0.162 | 0.135 | IGHV4-34 | 0.81354 | 1.00000 | 0.00804 | 0 | 1 |
| 1047 | chr14 | 106830000 | 106831000 | 0.028 | 0.043 | 0.118 | 0.135 | IGHV4-34 | 0.80514 | 0.15803 | 0.07447 | 0 | 1 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 1048 | chr14 | 106877000 | 106878000 | 0.056 | 0.006 | 0.015 | 0.041 | IGHV4-39 | 0.62100 | 0.27446 | 0.50663 | 0 | 1 |
| 1049 | chr14 | 106878000 | 106879000 | 0.028 | 0.012 | 0.044 | 0.041 | IGHV4-39 | 1.00000 | 1.00000 | 0.15671 | 0 | 0 |
| 1050 | chr14 | 106967000 | 106968000 | 0.056 | 0.000 | 0.015 | 0.000 | IGHV1-46 | 0.47887 | 0.27446 | 0.29694 | 0 | 1 |
| 1051 | chr14 | 106994000 | 106995000 | 0.028 | 0.012 | 0.088 | 0.122 | IGHV3-48 | 0.59201 | 0.41714 | 0.00949 | 0 | 0 |
| 1052 | chr14 | 106995000 | 106996000 | 0.000 | 0.000 | 0.000 | 0.027 | IGHV3-48 | 0.49735 | 1.00000 | 1.00000 | 0 | 0 |
| 1053 | chr14 | 107034000 | 107035000 | 0.028 | 0.000 | 0.000 | 0.014 | IGHV5-51 | 1.00000 | 0.34615 | 1.00000 | 0 | 0 |
| 1054 | chr14 | 107035000 | 107036000 | 0.000 | 0.006 | 0.029 | 0.014 | IGHV5-51 | 0.60686 | 0.54294 | 0.21104 | 0 | 0 |
| 1055 | chr14 | 107048000 | 107049000 | 0.028 | 0.006 | 0.000 | 0.000 | IGHV3-53 | 1.00000 | 0.34615 | 1.00000 | 0 | 0 |
| 1056 | chr14 | 107049000 | 107050000 | 0.000 | 0.012 | 0.044 | 0.027 | IGHV3-53 | 0.67043 | 0.54966 | 0.15671 | 0 | 0 |
| 1057 | chr14 | 107083000 | 107084000 | 0.000 | 0.006 | 0.044 | 0.054 | IGHV4-59 | 1.00000 | 0.54966 | 0.07959 | 0 | 1 |
| 1058 | chr14 | 107084000 | 107085000 | 0.000 | 0.006 | 0.029 | 0.027 | IGHV4-59 | 1.00000 | 0.54294 | 0.21104 | 0 | 0 |
| 1059 | chr14 | 107095000 | 107096000 | 0.000 | 0.006 | 0.015 | 0.000 | IGHV4-61 | 0.47887 | 1.00000 | 0.50663 | 0 | 1 |
| 1060 | chr14 | 107113000 | 107114000 | 0.000 | 0.000 | 0.029 | 0.000 | IGHV3-64 | 0.22755 | 0.54294 | 0.08726 | 0 | 0 |
| 1061 | chr14 | 107114000 | 107115000 | 0.000 | 0.000 | 0.029 | 0.000 | IGHV3-64 | 0.22755 | 0.54294 | 0.08726 | 0 | 0 |
| 1062 | chr14 | 107169000 | 107170000 | 0.056 | 0.068 | 0.206 | 0.041 | IGHV1-69 | 0.00346 | 0.04910 | 0.00442 | 1 | 1 |
| 1063 | chr14 | 107170000 | 107171000 | 0.028 | 0.075 | 0.294 | 0.095 | IGHV1-69 | 0.00279 | 0.00075 | 0.00004 | 0 | 1 |
| 1064 | chr14 | 107176000 | 107177000 | 0.028 | 0.006 | 0.118 | 0.027 | IGHV2-70 | 0.04838 | 0.15803 | 0.00030 | 0 | 1 |
| 1065 | chr14 | 107177000 | 107178000 | 0.000 | 0.000 | 0.044 | 0.014 | IGHV2-70 | 0.67043 | 0.54966 | 0.02537 | 0 | 0 |
| 1066 | chr14 | 107178000 | 107179000 | 0.056 | 0.161 | 0.456 | 0.284 | IGHV2-70 | 0.03781 | 0.00002 | 0.00001 | 0 | 1 |
| 1067 | chr14 | 107179000 | 107180000 | 0.056 | 0.180 | 0.382 | 0.338 | IGHV2-70 | 0.60350 | 0.00034 | 0.00206 | 0 | 1 |
| 1068 | chr14 | 107183000 | 107184000 | 0.000 | 0.006 | 0.029 | 0.000 | IGHV3-72 | 0.22755 | 0.54294 | 0.21104 | 0 | 0 |
| 1069 | chr14 | 107199000 | 107200000 | 0.000 | 0.012 | 0.015 | 0.000 | IGHV3-72 | 0.47887 | 1.00000 | 1.00000 | 0 | 0 |
| 1070 | chr14 | 107218000 | 107219000 | 0.028 | 0.012 | 0.015 | 0.000 | IGHV3-74 | 0.47887 | 1.00000 | 1.00000 | 0 | 0 |
| 1071 | chr14 | 107219000 | 107220000 | 0.000 | 0.012 | 0.074 | 0.027 | IGHV3-74 | 0.25970 | 0.16101 | 0.02559 | 0 | 1 |
| 1072 | chr14 | 107221000 | 107222000 | 0.000 | 0.000 | 0.059 | 0.000 | IGHV3-74 | 0.05016 | 0.29551 | 0.00730 | 0 | 0 |
| 1073 | chr14 | 107232000 | 107233000 | 0.028 | 0.000 | 0.029 | 0.000 | IGHV3-74 | 0.22755 | 0.54294 | 0.08726 | 0 | 0 |
| 1074 | chr14 | 107253000 | 107254000 | 0.000 | 0.000 | 0.044 | 0.014 | IGHV7-81 | 0.67043 | 0.54966 | 0.02537 | 0 | 0 |
| 1075 | chr14 | 107258000 | 107259000 | 0.000 | 0.000 | 0.015 | 0.014 | IGHV7-81 | 0.34948 | 1.00000 | 0.29694 | 0 | 0 |
| 1076 | chr14 | 107259000 | 107260000 | 0.000 | 0.025 | 0.235 | 0.027 | IGHV7-81 | 1.00000 | 1.00000 | 0.00000 | 0 | 1 |
| 1077 | chr15 | 45003000 | 45004000 | 0.000 | 0.000 | 0.044 | 0.000 | B2M | 0.00021 | 0.00098 | 0.02537 | 0 | 0 |
| 1078 | chr15 | 45007000 | 45008000 | 0.000 | 0.000 | 0.044 | 0.000 | B2M | 0.10727 | 0.54966 | 0.02537 | 0 | 0 |
| 1079 | chr15 | 45814000 | 45815000 | 0.000 | 0.000 | 0.015 | 0.014 | SLC30A4 | 0.10727 | 0.54966 | 0.29694 | 0 | 0 |
| 1080 | chr15 | 59664000 | 59665000 | 0.000 | 0.000 | 0.044 | 0.041 | MYO1E | 1.00000 | 1.00000 | 0.02537 | 0 | 0 |
| 1081 | chr15 | 65588000 | 65589000 | 0.000 | 0.000 | 0.015 | 0.014 | PARP16 | 1.00000 | 0.54966 | 0.29694 | 0 | 0 |
| 1082 | chr15 | 78332000 | 78333000 | 0.028 | 0.000 | 0.000 | 0.014 | TBC1D2B | 1.00000 | 0.34615 | 1.00000 | 0 | 0 |
| 1083 | chr15 | 83227000 | 83228000 | 0.000 | 0.000 | 0.029 | 0.000 | CPEB1 | 0.22755 | 0.54294 | 0.08726 | 0 | 0 |
| 1084 | chr15 | 86226000 | 86227000 | 0.000 | 0.000 | 0.044 | 0.000 | AKAP13 | 0.10727 | 0.54966 | 0.02537 | 0 | 0 |
| 1085 | chr15 | 86233000 | 86234000 | 0.000 | 0.000 | 0.029 | 0.014 | AKAP13 | 0.60686 | 0.54294 | 0.08726 | 0 | 0 |
| 1086 | chr15 | 86245000 | 86246000 | 0.000 | 0.000 | 0.059 | 0.000 | AKAP13 | 0.05016 | 0.29551 | 0.00730 | 0 | 1 |
| 1087 | chr16 | 368000 | 369000 | 0.000 | 0.000 | 0.015 | 0.014 | AXIN1 | 1.00000 | 1.00000 | 0.29694 | 0 | 0 |
| 1088 | chr16 | 3788000 | 3789000 | 0.000 | 0.000 | 0.015 | 0.041 | CREBBP | 1.00000 | 1.00000 | 0.29694 | 0 | 1 |
| 1089 | chr16 | 10971000 | 10972000 | 0.000 | 0.000 | 0.162 | 0.081 | CHTA | 0.02233 | 0.01471 | 0.00000 | 1 | 1 |
| 1090 | chr16 | 10972000 | 10973000 | 0.000 | 0.000 | 0.191 | 0.081 | CHTA | 0.08249 | 0.00372 | 0.00000 | 1 | 1 |
| 1091 | chr16 | 10973000 | 10974000 | 0.000 | 0.000 | 0.162 | 0.095 | CHTA | 0.31342 | 0.01471 | 0.00000 | 1 | 1 |
| 1092 | chr16 | 10974000 | 10975000 | 0.000 | 0.000 | 0.059 | 0.000 | CHTA | 0.05016 | 0.29551 | 0.00730 | 0 | 0 |
| 1093 | chr16 | 11348000 | 11349000 | 0.000 | 0.000 | 0.191 | 0.027 | SOCS1 | 0.00186 | 0.00372 | 0.00000 | 1 | 1 |
| 1094 | chr16 | 11349000 | 11350000 | 0.000 | 0.000 | 0.221 | 0.041 | SOCS1 | 0.00179 | 0.00107 | 0.00000 | 1 | 1 |
| 1095 | chr16 | 21167000 | 21168000 | 0.000 | 0.000 | 0.015 | 0.014 | DNAH3 | 1.00000 | 1.00000 | 0.29694 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 1096 | chr6 | 27325000 | 27326000 | 0.000 | 0.000 | 0.029 | 0.041 | CTD-3203P2.2 | 1.00000 | 0.54294 | 0.08726 | 0 | 0 |
| 1097 | chr6 | 27326000 | 27327000 | 0.000 | 0.000 | 0.088 | 0.041 | CTD-3203P2.2 | 0.31126 | 0.09031 | 0.00058 | 0 | 1 |
| 1098 | chr6 | 27327000 | 27328000 | 0.000 | 0.000 | 0.029 | 0.000 | IL4R | 0.22755 | 0.54294 | 0.08726 | 0 | 0 |
| 1099 | chr6 | 27414000 | 27415000 | 0.000 | 0.000 | 0.029 | 0.000 | IL21R | 0.22755 | 0.54294 | 0.08726 | 0 | 0 |
| 1100 | chr6 | 29248000 | 29249000 | 0.000 | 0.000 | 0.029 | 0.000 | 61E3.4 | 0.22755 | 0.54294 | 0.08726 | 0 | 0 |
| 1101 | chr6 | 31910000 | 31911000 | 0.000 | 0.000 | 0.015 | 0.014 | ZNF267 | 1.00000 | 1.00000 | 0.29694 | 0 | 0 |
| 1102 | chr6 | 46821000 | 46822000 | 0.000 | 0.000 | 0.015 | 0.014 | C16orf87 | 1.00000 | 1.00000 | 0.29694 | 0 | 0 |
| 1103 | chr6 | 50985000 | 50986000 | 0.000 | 0.000 | 0.015 | 0.014 | CYLD | 1.00000 | 1.00000 | 0.29694 | 0 | 0 |
| 1104 | chr6 | 64351000 | 64352000 | 0.000 | 0.000 | 0.029 | 0.014 | CDH11 | 0.60686 | 0.54294 | 0.08726 | 0 | 0 |
| 1105 | chr6 | 78398000 | 78399000 | 0.000 | 0.000 | 0.000 | 0.027 | WWOX | 0.49735 | 1.00000 | 1.00000 | 0 | 0 |
| 1106 | chr6 | 78615000 | 78616000 | 0.000 | 0.000 | 0.015 | 0.000 | WWOX | 1.00000 | 1.00000 | 0.29694 | 0 | 0 |
| 1107 | chr6 | 78753000 | 78754000 | 0.000 | 0.000 | 0.015 | 0.014 | WWOX | 1.00000 | 1.00000 | 0.29694 | 0 | 0 |
| 1108 | chr6 | 78811000 | 78812000 | 0.000 | 0.000 | 0.000 | 0.027 | WWOX | 0.49735 | 1.00000 | 1.00000 | 0 | 0 |
| 1109 | chr6 | 79988000 | 79989000 | 0.000 | 0.000 | 0.015 | 0.014 | MAF | 1.00000 | 1.00000 | 0.29694 | 0 | 0 |
| 1110 | chr6 | 81836000 | 81837000 | 0.000 | 0.000 | 0.029 | 0.000 | PLCG2 | 0.22755 | 0.54294 | 0.08726 | 0 | 0 |
| 1111 | chr6 | 85932000 | 85933000 | 0.000 | 0.000 | 0.059 | 0.027 | IRF8 | 0.42627 | 0.29551 | 0.00730 | 1 | 0 |
| 1112 | chr6 | 85933000 | 85934000 | 0.000 | 0.012 | 0.221 | 0.081 | IRF8 | 0.03144 | 0.00107 | 0.00000 | 1 | 1 |
| 1113 | chr6 | 85934000 | 85935000 | 0.000 | 0.006 | 0.015 | 0.027 | IRF8 | 1.00000 | 1.00000 | 0.50663 | 1 | 1 |
| 1114 | chr6 | 85936000 | 85937000 | 0.000 | 0.000 | 0.029 | 0.014 | IRF8 | 0.60686 | 0.54294 | 0.08726 | 0 | 0 |
| 1115 | chr6 | 88441000 | 88442000 | 0.000 | 0.000 | 0.015 | 0.014 | ZNF469 | 1.00000 | 1.00000 | 0.29694 | 0 | 0 |
| 1116 | chr7 | 3598000 | 3599000 | 0.000 | 0.000 | 0.029 | 0.014 | P2RX5; P2RX5-TAX1BP3P2RX5; | 0.60686 | 0.54294 | 0.08726 | 0 | 0 |
| 1117 | chr7 | 17286000 | 17287000 | 0.000 | 0.000 | 0.029 | 0.000 | SMCR9 | 0.22755 | 0.54294 | 0.08726 | 0 | 0 |
| 1118 | chr7 | 21194000 | 21195000 | 0.000 | 0.000 | 0.015 | 0.041 | MAP2K3 | 0.62100 | 1.00000 | 0.29694 | 0 | 0 |
| 1119 | chr7 | 29646000 | 29647000 | 0.000 | 0.000 | 0.029 | 0.014 | EVI2A | 0.60686 | 0.54294 | 0.08726 | 0 | 0 |
| 1120 | chr7 | 38020000 | 38021000 | 0.000 | 0.000 | 0.029 | 0.000 | IKZF3 | 0.22755 | 0.54294 | 0.08726 | 0 | 0 |
| 1121 | chr7 | 43662000 | 43663000 | 0.000 | 0.000 | 0.029 | 0.000 | PLEKHM1 | 0.22755 | 0.54294 | 0.08726 | 0 | 0 |
| 1122 | chr7 | 56408000 | 56409000 | 0.000 | 0.006 | 0.059 | 0.027 | BZRAP1 | 0.42627 | 0.29551 | 0.02818 | 0 | 0 |
| 1123 | chr7 | 56409000 | 56410000 | 0.028 | 0.000 | 0.265 | 0.014 | BZRAP1 | 0.00005 | 0.00024 | 0.00000 | 1 | 1 |
| 1124 | chr7 | 57916000 | 57917000 | 0.000 | 0.000 | 0.029 | 0.014 | VMP1 | 0.60686 | 0.54294 | 0.08726 | 0 | 0 |
| 1125 | chr7 | 57917000 | 57918000 | 0.000 | 0.000 | 0.029 | 0.000 | VMP1 | 0.22755 | 0.54294 | 0.08726 | 0 | 0 |
| 1126 | chr7 | 62007000 | 62008000 | 0.000 | 0.000 | 0.029 | 0.000 | CD79B | 0.22755 | 0.54294 | 0.08726 | 0 | 0 |
| 1127 | chr7 | 62008000 | 62009000 | 0.000 | 0.000 | 0.044 | 0.014 | CD79B | 0.34948 | 0.54966 | 0.02537 | 1 | 1 |
| 1128 | chr7 | 63067000 | 63068000 | 0.000 | 0.000 | 0.015 | 0.014 | GNA13 | 1.00000 | 1.00000 | 0.29694 | 0 | 0 |
| 1129 | chr7 | 65676000 | 65677000 | 0.000 | 0.000 | 0.029 | 0.000 | PITPNC1 | 0.22755 | 0.54294 | 0.08726 | 0 | 0 |
| 1130 | chr7 | 69365000 | 69366000 | 0.000 | 0.006 | 0.015 | 0.014 | AC007461.1 | 1.00000 | 1.00000 | 0.29694 | 0 | 0 |
| 1131 | chr7 | 70083000 | 70084000 | 0.000 | 0.000 | 0.000 | 0.014 | SOX9 | 1.00000 | 1.00000 | 1.00000 | 0 | 0 |
| 1132 | chr7 | 74733000 | 74734000 | 0.000 | 0.000 | 0.015 | 0.027 | SRSF2 | 0.49735 | 1.00000 | 1.00000 | 0 | 0 |
| 1133 | chr7 | 75447000 | 75448000 | 0.000 | 0.000 | 0.044 | 0.000 | 9-Sep-19 | 0.10727 | 0.54966 | 0.02537 | 0 | 0 |
| 1134 | chr7 | 75448000 | 75449000 | 0.000 | 0.000 | 0.044 | 0.000 | 9-Sep-19 | 0.10727 | 0.54966 | 0.02537 | 0 | 0 |
| 1135 | chr7 | 76775000 | 76776000 | 0.000 | 0.000 | 0.015 | 0.027 | CYTH1 | 0.49735 | 1.00000 | 1.00000 | 0 | 0 |
| 1136 | chr7 | 80928000 | 80929000 | 0.000 | 0.000 | 0.015 | 0.014 | B3GNTL1 | 1.00000 | 1.00000 | 0.29694 | 0 | 0 |
| 1137 | chr7 | 80976000 | 80977000 | 0.000 | 0.000 | 0.015 | 0.014 | B3GNTL1 | 1.00000 | 1.00000 | 0.29694 | 0 | 0 |
| 1138 | chr18 | 2709000 | 2710000 | 0.000 | 0.000 | 0.000 | 0.027 | SMCHD1 | 1.00000 | 1.00000 | 1.00000 | 0 | 0 |
| 1139 | chr18 | 3600000 | 3601000 | 0.000 | 0.000 | 0.029 | 0.014 | DLGAP1 | 1.00000 | 1.00000 | 0.29694 | 0 | 0 |
| 1140 | chr18 | 12062000 | 12063000 | 0.000 | 0.000 | 0.000 | 0.041 | ANKRD62 | 0.24603 | 1.00000 | 1.00000 | 0 | 0 |
| 1141 | chr18 | 27771000 | 27772000 | 0.000 | 0.000 | 0.029 | 0.000 | DSC3 | 0.22755 | 0.54294 | 0.08726 | 0 | 0 |
| 1142 | chr18 | 28066000 | 28067000 | 0.000 | 0.000 | 0.029 | 0.000 | DSC3 | 0.22755 | 0.54294 | 0.08726 | 0 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 1143 | chr18 | 30349000 | 30350000 | 0.000 | 0.000 | 0.000 | 0.027 | AC012123.1; KLHL14; | 0.49735 | 1.00000 | 1.00000 | 0 | 0 |
| 1144 | chr18 | 36806000 | 36807000 | 0.000 | 0.000 | 0.029 | 0.000 | CELF4 | 0.22755 | 0.54294 | 0.08726 | 0 | 0 |
| 1145 | chr18 | 37751000 | 37752000 | 0.000 | 0.000 | 0.015 | 0.014 | PIK3C3 | 1.00000 | 1.00000 | 0.29694 | 0 | 0 |
| 1146 | chr18 | 38672000 | 38673000 | 0.028 | 0.000 | 0.000 | 0.014 | PIK3C3 | 1.00000 | 0.34615 | 1.00000 | 0 | 0 |
| 1147 | chr18 | 42168000 | 42169000 | 0.028 | 0.000 | 0.000 | 0.014 | SETBP1 | 1.00000 | 0.34615 | 1.00000 | 0 | 0 |
| 1148 | chr18 | 51952000 | 51953000 | 0.000 | 0.000 | 0.029 | 0.000 | C18orf54 | 0.22755 | 0.54294 | 0.08726 | 0 | 0 |
| 1149 | chr18 | 52447000 | 52448000 | 0.000 | 0.000 | 0.015 | 0.014 | RAB27B | 1.00000 | 1.00000 | 0.29694 | 0 | 0 |
| 1150 | chr18 | 52988000 | 52989000 | 0.000 | 0.000 | 0.029 | 0.000 | TCF4 | 0.22755 | 0.54294 | 0.08726 | 0 | 0 |
| 1151 | chr18 | 54653000 | 54654000 | 0.000 | 0.000 | 0.000 | 0.027 | WDR7 | 0.49735 | 1.00000 | 1.00000 | 0 | 0 |
| 1152 | chr18 | 60794000 | 60795000 | 0.000 | 0.000 | 0.029 | 0.000 | BCL2 | 0.22755 | 0.54294 | 0.08726 | 1 | 1 |
| 1153 | chr18 | 60805000 | 60806000 | 0.000 | 0.006 | 0.074 | 0.081 | BCL2 | 1.00000 | 0.16101 | 0.00208 | 1 | 0 |
| 1154 | chr18 | 60806000 | 60807000 | 0.000 | 0.000 | 0.132 | 0.122 | BCL2 | 1.00000 | 0.02564 | 0.00009 | 1 | 0 |
| 1155 | chr18 | 60809000 | 60810000 | 0.000 | 0.000 | 0.059 | 0.027 | BCL2 | 0.42627 | 0.29551 | 0.00730 | 1 | 0 |
| 1156 | chr18 | 60821000 | 60822000 | 0.000 | 0.000 | 0.029 | 0.000 | BCL2 | 0.22755 | 0.54294 | 0.08726 | 1 | 0 |
| 1157 | chr18 | 60825000 | 60826000 | 0.000 | 0.000 | 0.044 | 0.027 | BCL2 | 0.67043 | 0.54966 | 0.02537 | 1 | 0 |
| 1158 | chr18 | 60826000 | 60827000 | 0.000 | 0.000 | 0.029 | 0.027 | BCL2 | 0.22755 | 0.54294 | 0.08726 | 1 | 0 |
| 1159 | chr18 | 60828000 | 60829000 | 0.000 | 0.000 | 0.015 | 0.000 | BCL2 | 1.00000 | 1.00000 | 0.08726 | 1 | 0 |
| 1160 | chr18 | 60874000 | 60875000 | 0.000 | 0.000 | 0.044 | 0.027 | BCL2 | 0.67043 | 0.54966 | 0.02537 | 1 | 0 |
| 1161 | chr18 | 60875000 | 60876000 | 0.000 | 0.000 | 0.044 | 0.027 | BCL2 | 0.67043 | 0.54966 | 0.02537 | 1 | 0 |
| 1162 | chr18 | 60876000 | 60877000 | 0.000 | 0.000 | 0.015 | 0.054 | BCL2 | 0.36833 | 1.00000 | 0.29694 | 1 | 0 |
| 1163 | chr18 | 60983000 | 60984000 | 0.000 | 0.006 | 0.059 | 0.068 | BCL2 | 1.00000 | 0.29551 | 0.02818 | 1 | 0 |
| 1164 | chr18 | 60984000 | 60985000 | 0.000 | 0.012 | 0.176 | 0.459 | BCL2 | 0.00034 | 0.00730 | 0.00001 | 1 | 1 |
| 1165 | chr18 | 60985000 | 60986000 | 0.000 | 0.000 | 0.221 | 0.635 | BCL2 | 0.00000 | 0.00107 | 0.00000 | 1 | 1 |
| 1166 | chr18 | 60986000 | 60987000 | 0.000 | 0.019 | 0.235 | 0.730 | BCL2 | 0.00000 | 0.00098 | 0.00000 | 1 | 1 |
| 1167 | chr18 | 60987000 | 60988000 | 0.000 | 0.019 | 0.191 | 0.500 | BCL2 | 0.00019 | 0.00372 | 0.00001 | 1 | 1 |
| 1168 | chr18 | 60988000 | 60989000 | 0.000 | 0.012 | 0.221 | 0.595 | BCL2 | 0.00000 | 0.00107 | 0.00000 | 1 | 1 |
| 1169 | chr18 | 61810000 | 61811000 | 0.000 | 0.000 | 0.015 | 0.014 | SERPINB8 | 1.00000 | 1.00000 | 0.29694 | 0 | 0 |
| 1170 | chr18 | 63080000 | 63081000 | 0.000 | 0.000 | 0.029 | 0.000 | CDH7 | 0.22755 | 0.54294 | 0.08726 | 0 | 0 |
| 1171 | chr18 | 63791000 | 63792000 | 0.000 | 0.000 | 0.015 | 0.014 | CDH7 | 1.00000 | 1.00000 | 0.29694 | 0 | 0 |
| 1172 | chr18 | 63875000 | 63876000 | 0.000 | 0.000 | 0.029 | 0.014 | CDH19 | 0.47887 | 0.54294 | 0.08726 | 0 | 0 |
| 1173 | chr18 | 64643000 | 64644000 | 0.000 | 0.000 | 0.029 | 0.000 | CDH19 | 0.22755 | 0.54294 | 0.08726 | 0 | 0 |
| 1174 | chr18 | 65863000 | 65864000 | 0.000 | 0.000 | 0.000 | 0.027 | TMX3 | 0.49735 | 1.00000 | 1.00000 | 0 | 0 |
| 1175 | chr18 | 66328000 | 66329000 | 0.000 | 0.000 | 0.015 | 0.000 | TMX3 | 1.00000 | 1.00000 | 0.29694 | 0 | 0 |
| 1176 | chr18 | 70462000 | 70463000 | 0.000 | 0.000 | 0.015 | 0.014 | NETO1 | 1.00000 | 1.00000 | 0.29694 | 0 | 0 |
| 1177 | chr18 | 73767000 | 73768000 | 0.000 | 0.000 | 0.015 | 0.014 | ZNF516 | 1.00000 | 1.00000 | 0.29694 | 0 | 0 |
| 1178 | chr1s | 76515000 | 76516000 | 0.000 | 0.000 | 0.029 | 0.000 | SALL3 | 0.22755 | 0.54294 | 0.08726 | 0 | 0 |
| 1179 | chr18 | 76724000 | 76725000 | 0.000 | 0.000 | 0.015 | 0.014 | SALL3 | 1.00000 | 1.00000 | 0.29694 | 0 | 0 |
| 1180 | chr18 | 76725000 | 76726000 | 0.000 | 0.000 | 0.015 | 0.014 | SALL3 | 1.00000 | 1.00000 | 0.29694 | 0 | 0 |
| 1181 | chr19 | 1612000 | 1613000 | 0.056 | 0.000 | 0.000 | 0.027 | TCF3 | 1.00000 | 0.11763 | 1.00000 | 0 | 1 |
| 1182 | chr19 | 2476000 | 2477000 | 0.000 | 0.000 | 0.015 | 0.014 | GADD45B | 0.22755 | 0.54294 | 0.08726 | 0 | 0 |
| 1183 | chr19 | 10304000 | 10305000 | 0.000 | 0.000 | 0.059 | 0.000 | DNMT1 | 0.05016 | 0.29551 | 0.00730 | 1 | 0 |
| 1184 | chr19 | 10305000 | 10306000 | 0.000 | 0.000 | 0.044 | 0.000 | DNMT1 | 0.10727 | 0.54966 | 0.02537 | 0 | 0 |
| 1185 | chr19 | 10335000 | 10336000 | 0.000 | 0.000 | 0.015 | 0.014 | SIPR2 | 1.00000 | 1.00000 | 0.29694 | 0 | 0 |
| 1186 | chr19 | 10340000 | 10341000 | 0.000 | 0.000 | 0.118 | 0.041 | SIPR2 | 0.11795 | 0.04825 | 0.00004 | 0 | 0 |
| 1187 | chr19 | 10341000 | 10342000 | 0.000 | 0.012 | 0.206 | 0.054 | SIPR2 | 0.01013 | 0.00197 | 0.00000 | 0 | 1 |
| 1188 | chr19 | 16030000 | 16031000 | 0.000 | 0.000 | 0.015 | 0.000 | CYP4F11 | 1.00000 | 1.00000 | 0.29694 | 0 | 0 |
| 1189 | chr19 | 16436000 | 16437000 | 0.028 | 0.000 | 0.029 | 0.014 | KLF2 | 0.60686 | 0.54294 | 0.08726 | 1 | 0 |
| 1190 | chr19 | 20889000 | 20890000 | 0.000 | 0.006 | 0.015 | 0.000 | ZNF626 | 0.47887 | 1.00000 | 0.50663 | 0 | 0 |

TABLE 1-continued

| # | Chromosome | Region Start | Region End | BL | CLL | DLBCL | FL | ClosestGene | Fisher_p_DLBCL vs Fisher_p_DLBCL v Fisher_p_DLBCL vs_FL | Fisher_p_DLBCL vs_BL | Fisher_p_DLBCL vs_CLL | Previously Identified | overSPctInAny Histology |
|---|---|---|---|---|---|---|---|---|---|---|---|---|---|
| 1191 | chr19 | 21073000 | 21074000 | 0.000 | 0.000 | 0.015 | 0.027 | ZNF85 | 1.00000 | 1.00000 | 0.29694 | 0 | 0 |
| 1192 | chr19 | 21092000 | 21093000 | 0.000 | 0.000 | 0.029 | 0.000 | ZNF85 | 0.22755 | 0.54294 | 0.08726 | 0 | 0 |
| 1193 | chr19 | 23841000 | 23842000 | 0.000 | 0.000 | 0.015 | 0.027 | ZNF675 | 1.00000 | 1.00000 | 0.29694 | 0 | 0 |
| 1194 | chr19 | 29256000 | 29257000 | 0.000 | 0.000 | 0.029 | 0.000 | UQCRFS1 | 0.22755 | 0.54294 | 0.08726 | 0 | 0 |
| 1195 | chr19 | 44183000 | 44184000 | 0.000 | 0.000 | 0.029 | 0.000 | PLAUR | 0.22755 | 0.54294 | 0.08726 | 0 | 0 |
| 1196 | chr19 | 50399000 | 50400000 | 0.000 | 0.000 | 0.029 | 0.000 | IL4I1 | 0.22755 | 0.54294 | 0.08726 | 0 | 0 |
| 1197 | chr19 | 53419000 | 53420000 | 0.028 | 0.000 | 0.015 | 0.014 | ZNF321P; ZNF816; ZNF321PZNF321PZNF816-ZNF816-ZNF321P; | 1.00000 | 1.00000 | 0.29694 | 0 | 0 |
| 1198 | chr20 | 15470000 | 15471000 | 0.028 | 0.006 | 0.000 | 0.000 | MACROD2 | 1.00000 | 0.34615 | 1.00000 | 0 | 0 |
| 1199 | chr20 | 23359000 | 23360000 | 0.056 | 0.000 | 0.000 | 0.000 | NAPB | 1.00000 | 0.11763 | 1.00000 | 0 | 1 |
| 1200 | chr20 | 23912000 | 23913000 | 0.000 | 0.000 | 0.027 | 0.027 | CST5 | 0.49735 | 1.00000 | 1.00000 | 0 | 0 |
| 1201 | chr20 | 46131000 | 46132000 | 0.000 | 0.000 | 0.059 | 0.014 | NCOA3 | 0.19371 | 0.29551 | 0.00730 | 1 | 1 |
| 1202 | chr20 | 49127000 | 49128000 | 0.000 | 0.000 | 0.029 | 0.014 | PTPN1 | 0.60686 | 0.54294 | 0.08726 | 0 | 0 |
| 1203 | chr20 | 49648000 | 49649000 | 0.000 | 0.000 | 0.029 | 0.000 | KCNG1 | 0.22755 | 0.54294 | 0.08726 | 0 | 0 |
| 1204 | chr20 | 61607000 | 61608000 | 0.000 | 0.000 | 0.000 | 0.027 | SLC17A9 | 0.49735 | 1.00000 | 1.00000 | 0 | 0 |
| 1205 | chr21 | 21597000 | 21598000 | 0.000 | 0.000 | 0.029 | 0.000 | NCAM2 | 0.22755 | 0.54294 | 0.08726 | 0 | 0 |
| 1206 | chr21 | 23458000 | 23459000 | 0.000 | 0.000 | 0.029 | 0.000 | NCAM2 | 0.22755 | 0.54294 | 0.08726 | 0 | 0 |
| 1207 | chr21 | 24998000 | 24999000 | 0.000 | 0.000 | 0.029 | 0.000 | MRPL39 | 0.22755 | 0.54294 | 0.08726 | 0 | 0 |
| 1208 | chr21 | 26935000 | 26936000 | 0.000 | 0.000 | 0.015 | 0.014 | MRPL39 | 1.00000 | 1.00000 | 0.29694 | 0 | 0 |
| 1209 | chr21 | 35779000 | 35780000 | 0.000 | 0.000 | 0.000 | 0.027 | SMIM11 | 0.49735 | 1.00000 | 1.00000 | 0 | 0 |
| 1210 | chr21 | 38779000 | 38780000 | 0.028 | 0.000 | 0.029 | 0.000 | DYRK1A | 0.49735 | 1.00000 | 1.00000 | 0 | 0 |
| 1211 | chr21 | 43254000 | 43255000 | 0.000 | 0.000 | 0.029 | 0.027 | PRDM15 | 0.22755 | 0.54294 | 0.08726 | 0 | 0 |
| 1212 | chr21 | 44612000 | 44613000 | 0.000 | 0.012 | 0.044 | 0.068 | CRYAA | 0.49735 | 1.00000 | 1.00000 | 0 | 0 |
| 1213 | chr21 | 45381000 | 45382000 | 0.000 | 0.012 | 0.015 | 0.027 | AGPAT3 | 0.22755 | 0.54294 | 0.08726 | 0 | 0 |
| 1214 | chr21 | 46058000 | 46059000 | 0.028 | 0.031 | 0.029 | 0.068 | KRTAP10-10 | 1.00000 | 1.00000 | 1.00000 | 0 | 0 |
| 1215 | chr22 | 19050000 | 19051000 | 0.000 | 0.000 | 0.015 | 0.027 | DGCR2 | 0.49735 | 1.00000 | 0.29694 | 0 | 0 |
| 1216 | chr22 | 20212000 | 20213000 | 0.000 | 0.006 | 0.029 | 0.014 | RTN4R | 0.60686 | 0.54294 | 1.00000 | 0 | 0 |
| 1217 | chr22 | 20708000 | 20709000 | 0.000 | 0.000 | 0.029 | 0.014 | FAM230A | 0.22755 | 0.54294 | 0.08726 | 0 | 0 |
| 1218 | chr22 | 21994000 | 21995000 | 0.028 | 0.019 | 0.015 | 0.054 | SDF2L1 | 0.47887 | 1.00000 | 0.29694 | 0 | 0 |
| 1219 | chr22 | 22379000 | 22380000 | 0.000 | 0.006 | 0.029 | 0.014 | IGLV4-69 | 1.00000 | 0.54294 | 0.08726 | 0 | 0 |
| 1220 | chr22 | 22380000 | 22381000 | 0.000 | 0.012 | 0.044 | 0.068 | IGLV4-69 | 0.72064 | 0.54966 | 0.15671 | 0 | 1 |
| 1221 | chr22 | 22381000 | 22382000 | 0.000 | 0.012 | 0.015 | 0.027 | IGLV4-69 | 0.49735 | 1.00000 | 1.00000 | 0 | 0 |
| 1222 | chr22 | 22385000 | 22386000 | 0.028 | 0.031 | 0.029 | 0.068 | IGLV4-69 | 1.00000 | 1.00000 | 1.00000 | 0 | 1 |
| 1223 | chr22 | 22452000 | 22453000 | 0.000 | 0.012 | 0.015 | 0.014 | IGLV8-61 | 0.44431 | 1.00000 | 1.00000 | 0 | 0 |
| 1224 | chr22 | 22453000 | 22454000 | 0.000 | 0.012 | 0.015 | 0.014 | IGLV8-61 | 1.00000 | 1.00000 | 0.08726 | 0 | 0 |
| 1225 | chr22 | 22516000 | 22517000 | 0.000 | 0.025 | 0.015 | 0.054 | IGLV4-60 | 0.36833 | 0.54294 | 1.00000 | 0 | 1 |
| 1226 | chr22 | 22517000 | 22518000 | 0.000 | 0.019 | 0.000 | 0.014 | IGLV4-60 | 1.00000 | 1.00000 | 0.29694 | 0 | 0 |
| 1227 | chr22 | 22550000 | 22551000 | 0.056 | 0.006 | 0.044 | 0.054 | IGLV6-57 | 1.00000 | 1.00000 | 0.55662 | 0 | 1 |
| 1228 | chr22 | 22569000 | 22570000 | 0.000 | 0.006 | 0.015 | 0.014 | IGLV10-54 | 1.00000 | 1.00000 | 0.07959 | 0 | 1 |
| 1229 | chr22 | 22676000 | 22677000 | 0.000 | 0.000 | 0.015 | 0.000 | IGLV1-51 | 0.47887 | 1.00000 | 0.50663 | 0 | 0 |
| 1230 | chr22 | 22677000 | 22678000 | 0.083 | 0.012 | 0.015 | 0.014 | IGLV1-51 | 1.00000 | 0.11840 | 0.29694 | 0 | 1 |
| 1231 | chr22 | 22707000 | 22708000 | 0.028 | 0.006 | 0.044 | 0.014 | IGLV5-48 | 0.34948 | 1.00000 | 1.00000 | 0 | 0 |
| 1232 | chr22 | 22712000 | 22713000 | 0.083 | 0.012 | 0.088 | 0.041 | IGLV1-47 | 0.31126 | 1.00000 | 0.07959 | 0 | 1 |
| 1233 | chr22 | 22723000 | 22724000 | 0.000 | 0.006 | 0.015 | 0.027 | IGLV7-46 | 1.00000 | 1.00000 | 0.00949 | 0 | 1 |
| 1234 | chr22 | 22724000 | 22725000 | 0.028 | 0.012 | 0.088 | 0.041 | IGLV7-46 | 0.31126 | 0.41714 | 0.50663 | 0 | 1 |
| 1235 | chr22 | 22730000 | 22731000 | 0.000 | 0.006 | 0.059 | 0.054 | IGLV5-45 | 1.00000 | 0.29551 | 0.02818 | 0 | 1 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 1236 | chr22 | 22731000 | 22732000 | 0.000 | 0.006 | 0.029 | 0.000 | IGLV5-45 | 0.22755 | 0.54294 | 0.21104 | 0 | 0 |
| 1237 | chr22 | 22735000 | 22736000 | 0.028 | 0.037 | 0.059 | 0.068 | IGLV1-44 | 1.00000 | 0.65667 | 0.48849 | 0 | 1 |
| 1238 | chr22 | 22749000 | 22750000 | 0.000 | 0.006 | 0.059 | 0.027 | IGLV7-43 | 0.42627 | 0.29551 | 0.02818 | 0 | 0 |
| 1239 | chr22 | 22758000 | 22759000 | 0.028 | 0.006 | 0.029 | 0.014 | IGLV1-40 | 0.60686 | 1.00000 | 0.21104 | 0 | 1 |
| 1240 | chr22 | 22759000 | 22760000 | 0.056 | 0.006 | 0.044 | 0.027 | IGLV1-40 | 0.67043 | 1.00000 | 0.07959 | 0 | 1 |
| 1241 | chr22 | 22764000 | 22765000 | 0.111 | 0.006 | 0.044 | 0.068 | IGLV1-40 | 0.72064 | 0.23165 | 0.07959 | 0 | 1 |
| 1242 | chr22 | 22765000 | 22766000 | 0.000 | 0.062 | 0.015 | 0.000 | IGLV3-25 | 0.47887 | 2.00000 | 0.50663 | 0 | 0 |
| 1243 | chr22 | 22828000 | 22829000 | 0.028 | 0.062 | 0.132 | 0.108 | IGLV3-25 | 0.79702 | 0.15881 | 0.11274 | 0 | 1 |
| 1244 | chr22 | 23029000 | 23030000 | 0.000 | 0.000 | 0.015 | 0.014 | IGLV2-23 | 1.00000 | 1.00000 | 0.29694 | 0 | 0 |
| 1245 | chr22 | 23035000 | 23036000 | 0.000 | 0.000 | 0.000 | 0.027 | IGLV2-23 | 0.49735 | 1.00000 | 1.00000 | 0 | 0 |
| 1246 | chr22 | 23039000 | 23040000 | 0.000 | 0.043 | 0.103 | 0.054 | IGLV2-23 | 0.35266 | 0.09269 | 0.12716 | 0 | 1 |
| 1247 | chr22 | 23040000 | 23041000 | 0.000 | 0.006 | 0.044 | 0.000 | IGLV2-23 | 0.10727 | 0.54966 | 0.07959 | 0 | 0 |
| 1248 | chr22 | 23041000 | 23042000 | 0.028 | 0.056 | 0.059 | 0.014 | IGLV3-21 | 0.19371 | 0.65667 | 1.00000 | 0 | 1 |
| 1249 | chr22 | 23055000 | 23056000 | 0.000 | 0.000 | 0.074 | 0.041 | IGLV3-19 | 0.47996 | 0.16101 | 0.00208 | 0 | 1 |
| 1250 | chr22 | 23063000 | 23064000 | 0.000 | 0.000 | 0.059 | 0.041 | IGLV3-16 | 0.70990 | 0.29551 | 0.00730 | 0 | 1 |
| 1251 | chr22 | 23090000 | 23091000 | 0.000 | 0.019 | 0.044 | 0.054 | IGLV2-14 | 1.00000 | 0.54966 | 0.36534 | 0 | 0 |
| 1252 | chr22 | 23100000 | 23101000 | 0.028 | 0.031 | 0.074 | 0.081 | IGLV2-14 | 1.00000 | 0.66188 | 0.16714 | 0 | 1 |
| 1253 | chr22 | 23101000 | 23102000 | 0.000 | 0.000 | 0.015 | 0.027 | IGLV3-12 | 1.00000 | 1.00000 | 0.29694 | 0 | 0 |
| 1254 | chr22 | 23114000 | 23115000 | 0.000 | 0.000 | 0.029 | 0.014 | IGLV2-11 | 0.60686 | 0.54294 | 0.08726 | 0 | 0 |
| 1255 | chr22 | 23134000 | 23135000 | 0.000 | 0.019 | 0.074 | 0.027 | IGLV3-10 | 0.25970 | 0.16101 | 0.05242 | 0 | 1 |
| 1256 | chr22 | 23154000 | 23155000 | 0.000 | 0.006 | 0.000 | 0.014 | IGLV3-9 | 1.00000 | 1.00000 | 1.00000 | 0 | 0 |
| 1257 | chr22 | 23161000 | 23162000 | 0.000 | 0.012 | 0.000 | 0.014 | IGLV3-9 | 1.00000 | 1.00000 | 1.00000 | 0 | 0 |
| 1258 | chr22 | 23162000 | 23163000 | 0.000 | 0.012 | 0.000 | 0.041 | IGLV2-8 | 0.24603 | 1.00000 | 1.00000 | 0 | 0 |
| 1259 | chr22 | 23165000 | 23166000 | 0.000 | 0.006 | 0.088 | 0.041 | IGLV4-3 | 0.31126 | 0.09031 | 0.00311 | 0 | 1 |
| 1260 | chr22 | 23192000 | 23193000 | 0.000 | 0.000 | 0.015 | 0.000 | IGLV4-3 | 0.47887 | 1.00000 | 0.50663 | 0 | 0 |
| 1261 | chr22 | 23197000 | 23198000 | 0.028 | 0.025 | 0.147 | 0.068 | IGLV4-3 | 0.17231 | 0.01404 | 0.00108 | 0 | 1 |
| 1262 | chr22 | 23198000 | 23199000 | 0.000 | 0.031 | 0.221 | 0.068 | IGLV4-3 | 0.01424 | 0.00107 | 0.00002 | 0 | 1 |
| 1263 | chr22 | 23199000 | 23200000 | 0.000 | 0.000 | 0.029 | 0.000 | IGLV4-3 | 0.22755 | 0.54294 | 0.08726 | 0 | 0 |
| 1264 | chr22 | 23203000 | 23204000 | 0.056 | 0.000 | 0.059 | 0.041 | IGLV4-3 | 0.70990 | 1.00000 | 0.00730 | 0 | 1 |
| 1265 | chr22 | 23204000 | 23205000 | 0.000 | 0.000 | 0.015 | 0.027 | IGLV4-3 | 1.00000 | 1.00000 | 0.29694 | 0 | 0 |
| 1266 | chr22 | 23205000 | 23206000 | 0.000 | 0.000 | 0.029 | 0.000 | IGLV4-3 | 0.22755 | 0.54294 | 0.08726 | 0 | 0 |
| 1267 | chr22 | 23207000 | 23208000 | 0.000 | 0.000 | 0.029 | 0.000 | IGLV4-3 | 0.22755 | 0.54294 | 0.08726 | 0 | 0 |
| 1268 | chr22 | 23209000 | 23210000 | 0.000 | 0.000 | 0.088 | 0.027 | IGLV4-3 | 0.15270 | 0.09031 | 0.00058 | 0 | 1 |
| 1269 | chr22 | 23213000 | 23214000 | 0.000 | 0.000 | 0.074 | 0.027 | IGLV4-3 | 0.25970 | 0.16101 | 0.00208 | 0 | 1 |
| 1270 | chr22 | 23214000 | 23215000 | 0.000 | 0.000 | 0.044 | 0.000 | IGLV4-3 | 0.10727 | 0.54966 | 0.02537 | 0 | 0 |
| 1271 | chr22 | 23219000 | 23220000 | 0.000 | 0.000 | 0.059 | 0.014 | IGLV3-1 | 0.05016 | 0.29551 | 0.00730 | 0 | 1 |
| 1272 | chr22 | 23220000 | 23221000 | 0.000 | 0.006 | 0.147 | 0.014 | IGLV3-1 | 0.00342 | 0.01404 | 0.00003 | 0 | 1 |
| 1273 | chr22 | 23222000 | 23223000 | 0.033 | 0.149 | 0.544 | 0.432 | IGLV3-1 | 0.23940 | 0.54966 | 0.00000 | 0 | 1 |
| 1274 | chr22 | 23223000 | 23224000 | 0.000 | 0.000 | 0.118 | 0.068 | IGLV3-1 | 0.04838 | 0.04825 | 0.00000 | 0 | 1 |
| 1275 | chr22 | 23225000 | 23226000 | 0.000 | 0.000 | 0.221 | 0.027 | IGLV3-1 | 0.01424 | 0.00107 | 0.00004 | 0 | 1 |
| 1276 | chr22 | 23226000 | 23227000 | 0.000 | 0.000 | 0.029 | 0.000 | IGLV3-1 | 0.22755 | 0.54294 | 0.08726 | 0 | 0 |
| 1277 | chr22 | 23227000 | 23228000 | 0.028 | 0.056 | 0.412 | 0.257 | IGLL5 | 0.07371 | 1.00000 | 0.00001 | 0 | 1 |
| 1278 | chr22 | 23228000 | 23229000 | 0.028 | 0.019 | 0.309 | 0.095 | IGLL5 | 0.00152 | 0.00070 | 0.00000 | 0 | 1 |
| 1279 | chr22 | 23229000 | 23230000 | 0.000 | 0.000 | 0.118 | 0.041 | IGLL5 | 0.11795 | 0.04825 | 0.00000 | 0 | 1 |
| 1280 | chr22 | 23230000 | 23231000 | 0.222 | 0.161 | 0.647 | 0.514 | IGLL5 | 0.12719 | 0.00007 | 0.00000 | 0 | 1 |
| 1281 | chr22 | 23231000 | 23232000 | 0.250 | 0.155 | 0.647 | 0.514 | IGLL5 | 0.12719 | 0.00017 | 0.00000 | 0 | 1 |
| 1282 | chr22 | 23232000 | 23233000 | 0.000 | 0.012 | 0.426 | 0.162 | IGLL5 | 0.00075 | 0.00000 | 0.00000 | 0 | 1 |
| 1283 | chr22 | 23233000 | 23234000 | 0.000 | 0.006 | 0.162 | 0.054 | IGLJ1 | 0.05410 | 0.01471 | 0.00001 | 0 | 1 |
| 1284 | chr22 | 23234000 | 23235000 | 0.056 | 0.000 | 0.147 | 0.041 | IGLJ1 | 0.03985 | 0.20979 | 0.00000 | 0 | 1 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 1284 | chr22 | 23235000 | 23236000 | 0.056 | 0.031 | 0.176 | 0.068 | IGLJ1; IGLL5; | 0.06843 | 0.13046 | 0.00035 | 0 | 1 |
| 1285 | chr22 | 23236000 | 23237000 | 0.111 | 0.043 | 0.250 | 0.095 | IGLJ1; IGLL5; | 0.02356 | 0.12484 | 0.00001 | 0 | 1 |
| 1286 | chr22 | 23237000 | 23238000 | 0.083 | 0.006 | 0.103 | 0.054 | IGLC1; IGLL5; | 0.35266 | 1.00000 | 0.00099 | 0 | 1 |
| 1287 | chr22 | 23241000 | 23242000 | 0.028 | 0.012 | 0.074 | 0.000 | IGLJ2 | 0.02326 | 0.66188 | 0.02559 | 0 | 0 |
| 1288 | chr22 | 23242000 | 23243000 | 0.028 | 0.050 | 0.147 | 0.108 | IGLC2 | 0.61516 | 0.09212 | 0.02792 | 0 | 0 |
| 1289 | chr22 | 23243000 | 23244000 | 0.000 | 0.000 | 0.029 | 0.000 | IGLC2 | 0.22755 | 1.00000 | 0.08726 | 0 | 0 |
| 1290 | chr22 | 23244000 | 23245000 | 0.000 | 0.012 | 0.015 | 0.014 | IGLC2 | 1.00000 | 1.00000 | 1.00000 | 0 | 0 |
| 1291 | chr22 | 23247000 | 23248000 | 0.111 | 0.099 | 0.088 | 0.122 | IGLJ3 | 0.59201 | 0.73481 | 1.00000 | 1 | 1 |
| 1292 | chr22 | 23248000 | 23249000 | 0.000 | 0.012 | 0.015 | 0.027 | IGLC3 | 1.00000 | 1.00000 | 1.00000 | 0 | 0 |
| 1293 | chr22 | 23249000 | 23250000 | 0.000 | 0.006 | 0.029 | 0.027 | IGLC3 | 1.00000 | 0.54294 | 0.21104 | 0 | 0 |
| 1294 | chr22 | 23260000 | 23261000 | 0.000 | 0.025 | 0.015 | 0.000 | IGLJ6 | 0.47887 | 1.00000 | 1.00000 | 0 | 0 |
| 1295 | chr22 | 23261000 | 23262000 | 0.000 | 0.012 | 0.015 | 0.014 | IGLJ6 | 1.00000 | 1.00000 | 1.00000 | 0 | 0 |
| 1296 | chr22 | 23263000 | 23264000 | 0.000 | 0.006 | 0.044 | 0.014 | IGLJ7 | 0.34948 | 0.54966 | 0.07959 | 0 | 0 |
| 1297 | chr22 | 23264000 | 23265000 | 0.000 | 0.006 | 0.044 | 0.027 | IGLC7 | 0.67043 | 0.54966 | 0.07959 | 0 | 0 |
| 1298 | chr22 | 23273000 | 23274000 | 0.000 | 0.000 | 0.044 | 0.000 | IGLC7 | 0.10727 | 0.54294 | 0.02537 | 0 | 0 |
| 1299 | chr22 | 23277000 | 23278000 | 0.000 | 0.006 | 0.029 | 0.014 | IGLC7 | 0.60686 | 0.54966 | 0.08726 | 0 | 0 |
| 1300 | chr22 | 23278000 | 23279000 | 0.000 | 0.000 | 0.059 | 0.014 | IGLC7 | 0.19371 | 0.29551 | 0.02818 | 0 | 0 |
| 1301 | chr22 | 23281000 | 23282000 | 0.000 | 0.006 | 0.029 | 0.014 | IGLC7 | 0.60686 | 0.54294 | 0.08726 | 0 | 0 |
| 1302 | chr22 | 23282000 | 23283000 | 0.028 | 0.000 | 0.147 | 0.027 | IGLC7 | 0.01393 | 0.01404 | 0.00003 | 0 | 1 |
| 1303 | chr22 | 23284000 | 23285000 | 0.000 | 0.006 | 0.029 | 0.000 | IGLC7 | 0.22755 | 0.54294 | 0.08726 | 0 | 0 |
| 1304 | chr22 | 23523000 | 23524000 | 0.000 | 0.000 | 0.015 | 0.041 | BCR | 0.62100 | 1.00000 | 0.29694 | 0 | 0 |
| 1305 | chr22 | 23524000 | 23525000 | 0.000 | 0.000 | 0.029 | 0.014 | BCR | 0.60686 | 0.54294 | 0.08726 | 0 | 0 |
| 1306 | chr22 | 27236000 | 27237000 | 0.028 | 0.000 | 0.029 | 0.000 | CRYBA4 | 0.22755 | 1.00000 | 0.08726 | 0 | 0 |
| 1307 | chr22 | 29195000 | 29196000 | 0.000 | 0.000 | 0.088 | 0.000 | XBP1 | 0.01070 | 0.09031 | 0.00058 | 0 | 1 |
| 1308 | chr22 | 29196000 | 29197000 | 0.000 | 0.000 | 0.059 | 0.000 | XBP1 | 0.70990 | 0.29551 | 0.00730 | 1 | 1 |
| 1309 | chr22 | 31826000 | 31827000 | 0.000 | 0.000 | 0.029 | 0.000 | DRG1 | 0.22755 | 0.54294 | 0.08726 | 0 | 0 |
| 1310 | chr22 | 32982000 | 32983000 | 0.028 | 0.006 | 0.015 | 0.027 | SYN3 | 0.47887 | 1.00000 | 1.00000 | 0 | 0 |
| 1311 | chr22 | 39852000 | 39853000 | 0.000 | 0.000 | 0.029 | 0.000 | TAB1 | 0.22755 | 0.54294 | 0.08726 | 0 | 0 |
| 1312 | chr22 | 39854000 | 39855000 | 0.000 | 0.000 | 0.029 | 0.000 | TAB1 | 0.22755 | 0.54294 | 0.08726 | 0 | 0 |
| 1313 | chr22 | 43360000 | 43361000 | 0.000 | 0.000 | 0.029 | 0.000 | PACSIN2 | 0.22755 | 0.54294 | 0.08726 | 0 | 0 |
| 1314 | chr22 | 47186000 | 47187000 | 0.000 | 0.000 | 0.029 | 0.000 | TBC1D22A | 0.22755 | 0.54294 | 0.08726 | 0 | 0 |
| 1315 | chr22 | 47738000 | 47739000 | 0.000 | 0.000 | 0.000 | 0.027 | LL22NC03-75H12.2 | 0.49735 | 1.00000 | 1.00000 | 0 | 0 |
| 1316 | chr22 | 50336000 | 50337000 | 0.028 | 0.000 | 0.015 | 0.000 | CRELD2 | 0.47887 | 1.00000 | 0.29694 | 0 | 0 |
| 1317 | chrX | 228000 | 229000 | 0.000 | 0.000 | 0.000 | 0.027 | GTPBP6 | 0.49735 | 1.00000 | 1.00000 | 0 | 0 |
| 1318 | chrX | 1514000 | 1515000 | 0.000 | 0.000 | 0.015 | 0.014 | SLC25A6 | 1.00000 | 1.00000 | 0.29694 | 0 | 0 |
| 1319 | chrX | 1611000 | 1612000 | 0.000 | 0.000 | 0.029 | 0.041 | P2RY8 | 0.22755 | 0.54294 | 0.08726 | 0 | 0 |
| 1320 | chrX | 12993000 | 12994000 | 0.000 | 0.000 | 0.235 | 0.027 | TMSB4X | 0.00091 | 0.00098 | 0.00000 | 1 | 1 |
| 1321 | chrX | 12994000 | 12995000 | 0.000 | 0.000 | 0.221 | 0.027 | TMSB4X | 0.00045 | 0.00107 | 0.00000 | 1 | 1 |
| 1322 | chrX | 13419000 | 13420000 | 0.028 | 0.000 | 0.029 | 0.027 | ATXN3L | 1.00000 | 1.00000 | 0.08726 | 0 | 0 |
| 1323 | chrX | 27031000 | 27032000 | 0.000 | 0.006 | 0.059 | 0.000 | DCAF8L2 | 0.05016 | 0.29551 | 0.00730 | 0 | 1 |
| 1324 | chrX | 32315000 | 32316000 | 0.028 | 0.000 | 0.000 | 0.027 | DMD | 0.49735 | 0.34615 | 1.00000 | 0 | 0 |
| 1325 | chrX | 32317000 | 32318000 | 0.000 | 0.000 | 0.029 | 0.014 | DMD | 1.00000 | 1.00000 | 1.00000 | 1 | 0 |
| 1326 | chrX | 33144000 | 33145000 | 0.000 | 0.000 | 0.029 | 0.014 | DMD | 0.60686 | 0.54294 | 0.08726 | 1 | 0 |
| 1327 | chrX | 33145000 | 33146000 | 0.000 | 0.000 | 0.044 | 0.027 | DMD | 0.67043 | 0.54966 | 0.02537 | 1 | 0 |
| 1328 | chrX | 33146000 | 33147000 | 0.000 | 0.000 | 0.162 | 0.068 | DMD | 0.11004 | 0.01471 | 0.00000 | 1 | 1 |
| 1329 | chrX | 41366000 | 41367000 | 0.000 | 0.000 | 0.015 | 0.027 | CASK | 1.00000 | 1.00000 | 0.29694 | 0 | 0 |
| 1330 | chrX | 42802000 | 42803000 | 0.000 | 0.000 | 0.074 | 0.027 | MAOA | 0.25970 | 0.16101 | 0.00208 | 0 | 1 |
| 1331 | chrX | 48775000 | 48776000 | 0.000 | 0.000 | 0.044 | 0.014 | PIM2 | 0.34948 | 0.54966 | 0.02537 | 1 | 0 |

TABLE 1-continued

| # | Chromosome | Region Start | Region End | BL | CLL | DLBCL | FL | ClosestGene | Fisher_p_DLBCL_vs_FL | Fisher_p_DLBCL_vs_BL | Fisher_p_DLBCL_vs_CLL | Previously Identified | overSPctInAnyHistology |
|---|---|---|---|---|---|---|---|---|---|---|---|---|---|
| 1332 | chrX | 48776000 | 48777000 | 0.000 | 0.000 | 0.029 | 0.014 | PIM2 | 0.60686 | 0.54294 | 0.08726 | 1 | 0 |
| 1333 | chrX | 64071000 | 64072000 | 0.000 | 0.000 | 0.059 | 0.014 | ZC4H2 | 0.19371 | 0.29551 | 0.00730 | 0 | 0 |
| 1334 | chrX | 67030000 | 67031000 | 0.028 | 0.000 | 0.015 | 0.000 | AR | 0.47887 | 1.00000 | 0.29694 | 0 | 0 |
| 1335 | chrX | 80258000 | 80259000 | 0.000 | 0.000 | 0.000 | 0.027 | HMGN5 | 0.49735 | 1.00000 | 1.00000 | 0 | 0 |
| 1336 | chrX | 81172000 | 81173000 | 0.000 | 0.000 | 0.015 | 0.027 | SH3BGRL | 1.00000 | 1.00000 | 0.29694 | 0 | 0 |
| 1337 | chrX | 87742000 | 87743000 | 0.000 | 0.000 | 0.029 | 0.000 | CPXCR1 | 0.22755 | 0.54294 | 0.08726 | 0 | 0 |
| 1338 | chrX | 87831000 | 87832000 | 0.000 | 0.000 | 0.000 | 0.027 | CPXCR1 | 0.49735 | 1.00000 | 1.00000 | 0 | 0 |
| 1339 | chrX | 88263000 | 88264000 | 0.000 | 0.000 | 0.029 | 0.027 | CPXCR1 | 0.49735 | 1.00000 | 1.00000 | 0 | 0 |
| 1340 | chrX | 88458000 | 88459000 | 0.000 | 0.000 | 0.000 | 0.027 | NAP1L3 | 0.22755 | 0.54294 | 0.29694 | 0 | 0 |
| 1341 | chrX | 92647000 | 92648000 | 0.000 | 0.000 | 0.015 | 0.027 | FAM133A | 0.49735 | 1.00000 | 1.00000 | 0 | 0 |
| 1342 | chrX | 93279000 | 93280000 | 0.000 | 0.000 | 0.015 | 0.014 | FAM133A | 1.00000 | 1.00000 | 0.29694 | 0 | 0 |
| 1343 | chrX | 94079000 | 94080000 | 0.000 | 0.000 | 0.015 | 0.014 | IL1RAPL2 | 1.00000 | 1.00000 | 0.29694 | 0 | 0 |
| 1344 | chrX | 104006000 | 104007000 | 0.000 | 0.000 | 0.015 | 0.014 | IL1RAPL2 | 1.00000 | 1.00000 | 0.29694 | 0 | 0 |
| 1345 | chrX | 104269000 | 104270000 | 0.000 | 0.000 | 0.000 | 0.027 | RIPPLY1 | 0.49735 | 1.00000 | 1.00000 | 0 | 0 |
| 1346 | chrX | 106132000 | 106133000 | 0.000 | 0.000 | 0.015 | 0.000 | HTR2C | 0.47887 | 1.00000 | 0.50663 | 0 | 0 |
| 1347 | chrX | 113095000 | 113096000 | 0.000 | 0.006 | 0.015 | 0.014 | CXorf61 | 1.00000 | 1.00000 | 0.29694 | 0 | 0 |
| 1348 | chrX | 115676000 | 115677000 | 0.000 | 0.000 | 0.015 | 0.000 | DCAF12L2 | 0.22755 | 0.54294 | 0.08726 | 0 | 0 |
| 1349 | chrX | 124996000 | 124997000 | 0.000 | 0.000 | 0.029 | 0.000 | DCAF12L1 | 0.22755 | 0.54294 | 0.08726 | 0 | 0 |
| 1350 | chrX | 125708000 | 125709000 | 0.000 | 0.000 | 0.015 | 0.014 | SMARCA1 | 1.00000 | 1.00000 | 0.29694 | 0 | 0 |
| 1351 | chrX | 128565000 | 128566000 | 0.000 | 0.000 | 0.015 | 0.027 | RBMX2 | 1.00000 | 1.00000 | 0.29694 | 0 | 0 |
| 1352 | chrX | 129643000 | 129644000 | 0.000 | 0.000 | 0.029 | 0.014 | CT45A3; CT45A4; SPANXD; SPANXE; | 0.60686 | 0.54294 | 0.08726 | 0 | 0 |
| 1353 | chrX | 134903000 | 134904000 | 0.000 | 0.000 | 0.029 | 0.000 | | 0.22755 | 0.54294 | 0.08726 | 0 | 0 |
| 1354 | chrX | 140846000 | 140847000 | 0.000 | 0.000 | 0.000 | 0.027 | SPANXN1 | 0.49735 | 1.00000 | 1.00000 | 0 | 0 |
| 1355 | chrX | 143750000 | 143751000 | 0.000 | 0.000 | 0.000 | 0.027 | TMEM257 | 0.49735 | 0.34615 | 1.00000 | 0 | 0 |
| 1356 | chrX | 145016000 | 145017000 | 0.028 | 0.000 | 0.000 | 0.027 | | | | | | |

TABLE 2

| # | Chromosome | Region Start | Region End | ABC-subtype | GCB-subtype | ClosestGene | p_ABC_vs_GCB | Previously Identified |
|---|---|---|---|---|---|---|---|---|
| 1 | chr1 | 756000 | 757000 | 0.040 | 0.000 | AL669831.1 | 1.00000 | 0 |
| 2 | chr1 | 1963000 | 1964000 | 0.000 | 0.000 | GABRD | 1.00000 | 0 |
| 3 | chr1 | 2052000 | 2053000 | 0.000 | 0.040 | PRKCZ | 1.00000 | 0 |
| 4 | chr1 | 3789000 | 3790000 | 0.000 | 0.000 | DFFB | 1.00000 | 0 |
| 5 | chr1 | 6613000 | 6614000 | 0.000 | 0.000 | NOL9 | 1.00000 | 1 |
| 6 | chr1 | 6614000 | 6615000 | 0.120 | 0.040 | NOL9 | 0.60921 | 1 |
| 7 | chr1 | 6661000 | 6662000 | 0.000 | 0.000 | KLHL21 | 1.00000 | 0 |
| 8 | chr1 | 6662000 | 6663000 | 0.120 | 0.000 | KLHL21 | 0.23469 | 0 |
| 9 | chr1 | 9129000 | 9130000 | 0.000 | 0.080 | SLC2A5 | 0.48980 | 0 |
| 10 | chr1 | 10894000 | 10895000 | 0.000 | 0.000 | C1orf127 | 1.00000 | 0 |
| 11 | chr1 | 17019000 | 17020000 | 0.000 | 0.000 | AL137798.1 | 1.00000 | 0 |
| 12 | chr1 | 17231000 | 17232000 | 0.040 | 0.000 | CROCC | 1.00000 | 0 |
| 13 | chr1 | 19935000 | 19936000 | 0.080 | 0.000 | MINOS1-NBL1 | 0.48980 | 0 |
| 14 | chr1 | 21091000 | 21092000 | 0.040 | 0.000 | HP1BP3 | 1.00000 | 0 |
| 15 | chr1 | 23885000 | 23886000 | 0.080 | 0.040 | ID3 | 1.00000 | 1 |
| 16 | chr1 | 28408000 | 28409000 | 0.000 | 0.040 | EYA3 | 1.00000 | 0 |
| 17 | chr1 | 32373000 | 32374000 | 0.000 | 0.040 | PTP4A2 | 1.00000 | 0 |
| 18 | chr1 | 36722000 | 36723000 | 0.040 | 0.000 | THRAP3 | 1.00000 | 0 |
| 19 | chr1 | 46576000 | 46577000 | 0.040 | 0.000 | PIK3R3 | 1.00000 | 0 |
| 20 | chr1 | 51965000 | 51966000 | 0.000 | 0.040 | EPS15 | 1.00000 | 0 |
| 21 | chr1 | 51978000 | 51979000 | 0.040 | 0.080 | EPS15 | 1.00000 | 0 |
| 22 | chr1 | 51983000 | 51984000 | 0.040 | 0.000 | EPS15 | 1.00000 | 0 |
| 23 | chr1 | 72393000 | 72394000 | 0.040 | 0.000 | NEGR1 | 1.00000 | 0 |
| 24 | chr1 | 73719000 | 73720000 | 0.040 | 0.040 | LRRIQ3 | 1.00000 | 0 |
| 25 | chr1 | 77315000 | 77316000 | 0.000 | 0.040 | ST6GALNAC5 | 1.00000 | 0 |
| 26 | chr1 | 81306000 | 81307000 | 0.040 | 0.000 | LPHN2 | 1.00000 | 0 |
| 27 | chr1 | 81527000 | 81528000 | 0.000 | 0.000 | LPHN2 | 1.00000 | 0 |
| 28 | chr1 | 82009000 | 82010000 | 0.000 | 0.000 | LPHN2 | 1.00000 | 0 |
| 29 | chr1 | 84106000 | 84107000 | 0.040 | 0.000 | TTLL7 | 1.00000 | 0 |
| 30 | chr1 | 87524000 | 87525000 | 0.000 | 0.040 | HS2ST1; HS2ST1 LOC339524; | 1.00000 | 0 |
| 31 | chr1 | 94551000 | 94552000 | 0.000 | 0.040 | ABCA4 | 1.00000 | 0 |
| 32 | chr1 | 94552000 | 94553000 | 0.000 | 0.040 | ABCA4 | 1.00000 | 0 |
| 33 | chr1 | 103696000 | 103697000 | 0.000 | 0.000 | COL11A1 | 1.00000 | 0 |
| 34 | chr1 | 116979000 | 116980000 | 0.000 | 0.040 | ATP1A1 | 1.00000 | 0 |
| 35 | chr1 | 149784000 | 149785000 | 0.040 | 0.040 | HIST2H3D | 1.00000 | 1 |
| 36 | chr1 | 149821000 | 149822000 | 0.040 | 0.000 | HIST2H2AA4 | 1.00000 | 1 |
| 37 | chr1 | 149857000 | 149858000 | 0.000 | 0.040 | HIST2H2BE | 1.00000 | 1 |
| 38 | chr1 | 149858000 | 149859000 | 0.080 | 0.040 | HIST2H2AC; HIST2H2BE; | 1.00000 | 0 |
| 39 | chr1 | 160616000 | 160617000 | 0.040 | 0.040 | SLAMF1 | 1.00000 | 0 |
| 40 | chr1 | 162711000 | 162712000 | 0.040 | 0.000 | DDR2 | 1.00000 | 0 |
| 41 | chr1 | 163684000 | 163685000 | 0.040 | 0.000 | NUF2 | 1.00000 | 0 |
| 42 | chr1 | 167598000 | 167599000 | 0.080 | 0.000 | RCSD1 | 0.48980 | 0 |
| 43 | chr1 | 167599000 | 167600000 | 0.040 | 0.000 | RCSD1 | 1.00000 | 0 |
| 44 | chr1 | 167600000 | 167601000 | 0.040 | 0.040 | RCSD1 | 1.00000 | 0 |
| 45 | chr1 | 174333000 | 174334000 | 0.040 | 0.000 | RABGAP1L | 1.00000 | 0 |
| 46 | chr1 | 187263000 | 187264000 | 0.000 | 0.000 | PLA2G4A | 1.00000 | 0 |
| 47 | chr1 | 187283000 | 187284000 | 0.040 | 0.000 | PLA2G4A | 1.00000 | 0 |
| 48 | chr1 | 187892000 | 187893000 | 0.040 | 0.000 | PLA2G4A | 1.00000 | 0 |
| 49 | chr1 | 195282000 | 195283000 | 0.000 | 0.040 | KCNT2 | 1.00000 | 0 |
| 50 | chr1 | 198591000 | 198592000 | 0.000 | 0.040 | PTPRC | 1.00000 | 0 |
| 51 | chr1 | 198608000 | 198609000 | 0.040 | 0.000 | PTPRC | 1.00000 | 0 |
| 52 | chr1 | 198609000 | 198610000 | 0.080 | 0.000 | PTPRC | 0.48980 | 0 |
| 53 | chr1 | 202004000 | 202005000 | 0.040 | 0.040 | ELF3 | 1.00000 | 0 |
| 54 | chr1 | 203273000 | 203274000 | 0.040 | 0.000 | BTG2 | 1.00000 | 1 |
| 55 | chr1 | 203274000 | 203275000 | 0.160 | 0.160 | BTG2 | 1.00000 | 1 |
| 56 | chr1 | 203275000 | 203276000 | 0.400 | 0.280 | BTG2 | 0.55122 | 1 |
| 57 | chr1 | 203276000 | 203277000 | 0.080 | 0.040 | BTG2 | 1.00000 | 1 |
| 58 | chr1 | 205780000 | 205781000 | 0.000 | 0.000 | SLC41A1 | 1.00000 | 0 |
| 59 | chr1 | 205781000 | 205782000 | 0.000 | 0.000 | SLC41A1 | 1.00000 | 0 |
| 60 | chr1 | 206283000 | 206284000 | 0.000 | 0.040 | CTSE | 1.00000 | 0 |
| 61 | chr] | 206286000 | 206287000 | 0.040 | 0.000 | CTSE | 1.00000 | 0 |
| 62 | chr1 | 217044000 | 217045000 | 0.040 | 0.000 | ESRRG | 1.00000 | 0 |
| 63 | chr1 | 226924000 | 226925000 | 0.080 | 0.120 | ITPKB | 1.00000 | 1 |
| 64 | chr1 | 226925000 | 226926000 | 0.120 | 0.000 | ITPKB | 0.23469 | 1 |
| 65 | chr1 | 226926000 | 226927000 | 0.120 | 0.000 | ITPKB | 0.23469 | 1 |
| 66 | chr1 | 229974000 | 229975000 | 0.040 | 0.040 | URB2 | 1.00000 | 0 |
| 67 | chr1 | 235131000 | 235132000 | 0.000 | 0.000 | TOMM20 | 1.00000 | 0 |
| 68 | chr1 | 235141000 | 235142000 | 0.040 | 0.000 | TOMM20 | 1.00000 | 0 |
| 69 | chr1 | 238787000 | 238788000 | 0.040 | 0.000 | MTRNR2L11 | 1.00000 | 0 |
| 70 | chr1 | 248088000 | 248089000 | 0.040 | 0.000 | OR2T8 | 1.00000 | 0 |
| 71 | chr2 | 630000 | 631000 | 0.000 | 0.000 | TMEM18 | 1.00000 | 0 |
| 72 | chr2 | 1484000 | 1485000 | 0.000 | 0.000 | TPO | 1.00000 | 0 |
| 73 | chr2 | 7991000 | 7992000 | 0.000 | 0.040 | RNF144A | 1.00000 | 0 |
| 74 | chr2 | 12173000 | 12174000 | 0.000 | 0.040 | LPIN1 | 1.00000 | 0 |
| 75 | chr2 | 12175000 | 12176000 | 0.000 | 0.000 | LPIN1 | 1.00000 | 0 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 76 | chr2 | 12249000 | 12250000 | 0.000 | 0.040 | LPIN1 | 1.00000 | 0 |
| 77 | chr2 | 14113000 | 14114000 | 0.000 | 0.000 | FAM84A | 1.00000 | 0 |
| 78 | chr2 | 17577000 | 17578000 | 0.000 | 0.040 | RAD51AP2 | 1.00000 | 0 |
| 79 | chr2 | 19253000 | 19254000 | 0.000 | 0.000 | OSR1 | 1.00000 | 0 |
| 80 | chr2 | 24802000 | 24803000 | 0.040 | 0.000 | NCOA1 | 1.00000 | 0 |
| 81 | chr2 | 31478000 | 31479000 | 0.040 | 0.000 | EHD3 | 1.00000 | 0 |
| 82 | chr2 | 41728000 | 41729000 | 0.040 | 0.000 | C2orf91 | 1.00000 | 0 |
| 83 | chr2 | 45404000 | 45405000 | 0.000 | 0.000 | SIX2 | 1.00000 | 0 |
| 84 | chr2 | 47923000 | 47924000 | 0.000 | 0.040 | MSH6 | 1.00000 | 0 |
| 85 | chr2 | 47944000 | 47945000 | 0.000 | 0.000 | MSH6 | 1.00000 | 0 |
| 86 | chr2 | 51360000 | 51361000 | 0.040 | 0.000 | NRXN1 | 1.00000 | 0 |
| 87 | chr2 | 51655000 | 51656000 | 0.000 | 0.000 | NRXN1 | 1.00000 | 0 |
| 88 | chr2 | 56565000 | 56566000 | 0.040 | 0.000 | CCDC85A | 1.00000 | 0 |
| 89 | chr2 | 57800000 | 57801000 | 0.040 | 0.000 | VRK2 | 1.00000 | 0 |
| 90 | chr2 | 60779000 | 60780000 | 0.000 | 0.040 | BCL11A | 1.00000 | 0 |
| 91 | chr2 | 60780000 | 60781000 | 0.080 | 0.000 | BCL11A | 0.48980 | 0 |
| 92 | chr2 | 63802000 | 63803000 | 0.000 | 0.000 | WDPCP | 1.00000 | 0 |
| 93 | chr2 | 63827000 | 63828000 | 0.000 | 0.040 | MDH1 | 1.00000 | 0 |
| 94 | chr2 | 64319000 | 64320000 | 0.000 | 0.040 | PELI1 | 1.00000 | 0 |
| 95 | chr2 | 65593000 | 65594000 | 0.000 | 0.040 | SPRED2 | 1.00000 | 1 |
| 96 | chr2 | 67002000 | 67003000 | 0.040 | 0.040 | MEIS1 | 1.00000 | 0 |
| 97 | chr2 | 70315000 | 70316000 | 0.040 | 0.000 | PCBP1 | 1.00000 | 0 |
| 98 | chr2 | 79502000 | 79503000 | 0.000 | 0.000 | REG3A | 1.00000 | 0 |
| 99 | chr2 | 79644000 | 79645000 | 0.000 | 0.000 | CTNNA2 | 1.00000 | 0 |
| 100 | chr2 | 81818000 | 81819000 | 0.000 | 0.000 | CTNNA2 | 1.00000 | 0 |
| 101 | chr2 | 82310000 | 82311000 | 0.000 | 0.000 | CTNNA2 | 1.00000 | 0 |
| 102 | chr2 | 82948000 | 82949000 | 0.000 | 0.040 | SUCLG1 | 1.00000 | 0 |
| 103 | chr2 | 85335000 | 85336000 | 0.000 | 0.000 | TCF7L1 | 1.00000 | 0 |
| 104 | chr2 | 88905000 | 88906000 | 0.080 | 0.000 | EIF2AK3 | 0.48980 | 0 |
| 105 | chr2 | 88906000 | 88907000 | 0.160 | 0.040 | EIF2AK3 | 0.34868 | 0 |
| 106 | chr2 | 88907000 | 88908000 | 0.040 | 0.040 | EIF2AK3 | 1.00000 | 0 |
| 107 | chr2 | 89052000 | 89053000 | 0.000 | 0.080 | RPIA | 0.48980 | 0 |
| 108 | chr2 | 89065000 | 89066000 | 0.000 | 0.000 | RPIA | 1.00000 | 0 |
| 109 | chr2 | 89066000 | 89067000 | 0.040 | 0.000 | RPIA | 1.00000 | 0 |
| 110 | chr2 | 89095000 | 89096000 | 0.000 | 0.040 | RPIA | 1.00000 | 0 |
| 111 | chr2 | 89127000 | 89128000 | 0.120 | 0.080 | IGKC | 1.00000 | 0 |
| 112 | chr2 | 89128000 | 89129000 | 0.160 | 0.160 | IGKC | 1.00000 | 0 |
| 113 | chr2 | 89129000 | 89130000 | 0.120 | 0.000 | IGKC | 0.23469 | 0 |
| 114 | chr2 | 89130000 | 89131000 | 0.080 | 0.000 | IGKC | 0.48980 | 0 |
| 115 | chr2 | 89131000 | 89132000 | 0.040 | 0.040 | IGKC | 1.00000 | 0 |
| 116 | chr2 | 89132000 | 89133000 | 0.040 | 0.000 | IGKC | 1.00000 | 0 |
| 117 | chr2 | 89133000 | 89134000 | 0.000 | 0.040 | IGKC | 1.00000 | 0 |
| 118 | chr2 | 89137000 | 89138000 | 0.000 | 0.040 | IGKC | 1.00000 | 0 |
| 119 | chr2 | 89138000 | 89139000 | 0.040 | 0.000 | IGKC | 1.00000 | 0 |
| 120 | chr2 | 89139000 | 89140000 | 0.000 | 0.040 | IGKC | 1.00000 | 0 |
| 121 | chr2 | 89140000 | 89141000 | 0.040 | 0.120 | IGKC | 0.60921 | 0 |
| 122 | chr2 | 89141000 | 89142000 | 0.080 | 0.120 | IGKC | 1.00000 | 0 |
| 123 | chr2 | 89142000 | 89143000 | 0.040 | 0.200 | IGKC | 0.18946 | 0 |
| 124 | chr2 | 89143000 | 89144000 | 0.000 | 0.080 | IGKC | 0.48980 | 0 |
| 125 | chr2 | 89144000 | 89145000 | 0.040 | 0.040 | IGKC | 1.00000 | 0 |
| 126 | chr2 | 89145000 | 89146000 | 0.040 | 0.000 | IGKC | 1.00000 | 0 |
| 127 | chr2 | 89146000 | 89147000 | 0.000 | 0.000 | IGKC | 1.00000 | 0 |
| 128 | chr2 | 89153000 | 89154000 | 0.000 | 0.000 | IGKC | 1.00000 | 0 |
| 129 | chr2 | 89155000 | 89156000 | 0.080 | 0.080 | IGKC | 1.00000 | 0 |
| 130 | chr2 | 89156000 | 89157000 | 0.120 | 0.000 | IGKC | 0.23469 | 0 |
| 131 | chr2 | 89157000 | 89158000 | 0.240 | 0.160 | IGKC | 0.72520 | 0 |
| 132 | chr2 | 89158000 | 89159000 | 0.240 | 0.280 | IGKC | 1.00000 | 0 |
| 133 | chr2 | 89159000 | 89160000 | 0.360 | 0.640 | IGKJ5 | 0.08874 | 0 |
| 134 | chr2 | 89160000 | 89161000 | 0.320 | 0.680 | IGKJ3; IGKJ4; IGKJ5; | 0.02271 | 0 |
| 135 | chr2 | 89161000 | 89162000 | 0.240 | 0.320 | IGKJ1; IGKJ2; | 0.75361 | 0 |
| 136 | chr2 | 89162000 | 89163000 | 0.200 | 0.200 | IGKJ1 | 1.00000 | 0 |
| 137 | chr2 | 89163000 | 89164000 | 0.120 | 0.240 | IGKJ1 | 0.46349 | 0 |
| 138 | chr2 | 89164000 | 89165000 | 0.160 | 0.280 | IGKJ1 | 0.49620 | 0 |
| 139 | chr2 | 89165000 | 89166000 | 0.160 | 0.360 | IGKJ1 | 0.19633 | 0 |
| 140 | chr2 | 89166000 | 89167000 | 0.000 | 0.040 | IGKJ1 | 1.00000 | 0 |
| 141 | chr2 | 89169000 | 89170000 | 0.000 | 0.040 | IGKJ1 | 1.00000 | 0 |
| 142 | chr2 | 89184000 | 89185000 | 0.000 | 0.000 | IGKV4-1 | 1.00000 | 0 |
| 143 | chr2 | 89185000 | 89186000 | 0.120 | 0.320 | IGKV4-1 | 0.17062 | 0 |
| 144 | chr2 | 89196000 | 89197000 | 0.000 | 0.160 | IGKV5-2 | 0.10986 | 0 |
| 145 | chr2 | 89197000 | 89198000 | 0.000 | 0.040 | IGKV5-2 | 1.00000 | 0 |
| 146 | chr2 | 89214000 | 89215000 | 0.000 | 0.040 | IGKV5-2 | 1.00000 | 0 |
| 147 | chr2 | 89246000 | 89247000 | 0.040 | 0.000 | IGKV1-5 | 1.00000 | 0 |
| 148 | chr2 | 89247000 | 89248000 | 0.160 | 0.000 | IGKV1-5 | 0.10986 | 0 |
| 149 | chr2 | 89248000 | 89249000 | 0.040 | 0.000 | IGKV1-5 | 1.00000 | 0 |
| 150 | chr2 | 89266000 | 89267000 | 0.000 | 0.040 | IGKV1-6 | 1.00000 | 0 |
| 151 | chr2 | 89291000 | 89292000 | 0.040 | 0.040 | IGKV1-8 | 1.00000 | 0 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 152 | chr2 | 89292000 | 89293000 | 0.000 | 0.040 | IGKV1-8 | 1.00000 | 0 |
| 153 | chr2 | 89326000 | 89327000 | 0.040 | 0.000 | IGKV3-11 | 1.00000 | 0 |
| 154 | chr2 | 89327000 | 89328000 | 0.040 | 0.000 | IGKV3-11 | 1.00000 | 0 |
| 155 | chr2 | 89442000 | 89443000 | 0.040 | 0.160 | IGKV3-20 | 0.34868 | 0 |
| 156 | chr2 | 89443000 | 89444000 | 0.040 | 0.000 | IGKV3-20 | 1.00000 | 0 |
| 157 | chr2 | 89476000 | 89477000 | 0.000 | 0.000 | IGKV2-24 | 1.00000 | 0 |
| 158 | chr2 | 89513000 | 89514000 | 0.040 | 0.000 | IGKV1-27 | 1.00000 | 0 |
| 159 | chr2 | 89521000 | 89522000 | 0.040 | 0.040 | IGKV2-28 | 1.00000 | 0 |
| 160 | chr2 | 89533000 | 89534000 | 0.040 | 0.000 | IGKV2-30 | 1.00000 | 0 |
| 161 | chr2 | 89534000 | 89535000 | 0.080 | 0.000 | IGKV2-30 | 0.48980 | 0 |
| 162 | chr2 | 89544000 | 89545000 | 0.000 | 0.080 | IGKV2-30 | 0.48980 | 0 |
| 163 | chr2 | 89545000 | 89546000 | 0.040 | 0.000 | IGKV2-30 | 1.00000 | 0 |
| 164 | chr2 | 90259000 | 90260000 | 0.040 | 0.000 | IGKV1D-8 | 1.00000 | 0 |
| 165 | chr2 | 90260000 | 90261000 | 0.120 | 0.000 | IGKV1D-8 | 0.23469 | 0 |
| 166 | chr2 | 96809000 | 96810000 | 0.040 | 0.080 | DUSP2 | 1.00000 | 1 |
| 167 | chr2 | 96810000 | 96811000 | 0.080 | 0.120 | DUSP2 | 1.00000 | 1 |
| 168 | chr2 | 96811000 | 96812000 | 0.000 | 0.080 | DUSP2 | 0.48980 | 1 |
| 169 | chr2 | 98611000 | 98612000 | 0.000 | 0.040 | TMEM131 | 1.00000 | 0 |
| 170 | chr2 | 100757000 | 100758000 | 0.080 | 0.000 | AFF3 | 0.48980 | 0 |
| 171 | chr2 | 100758000 | 100759000 | 0.120 | 0.000 | AFF3 | 0.23469 | 0 |
| 172 | chr2 | 106144000 | 106145000 | 0.000 | 0.080 | FHL2 | 0.48980 | 0 |
| 173 | chr2 | 111878000 | 111879000 | 0.000 | 0.120 | BCL2L11 | 0.23469 | 0 |
| 174 | chr2 | 111879000 | 111880000 | 0.040 | 0.120 | BCL2L11 | 0.60921 | 0 |
| 175 | chr2 | 112305000 | 112306000 | 0.000 | 0.040 | ANAPC1 | 1.00000 | 0 |
| 176 | chr2 | 116234000 | 116235000 | 0.040 | 0.000 | DPP10 | 1.00000 | 0 |
| 177 | chr2 | 116439000 | 116440000 | 0.040 | 0.000 | DPP10 | 1.00000 | 0 |
| 178 | chr2 | 124697000 | 124698000 | 0.000 | 0.040 | CNTNAP5 | 1.00000 | 0 |
| 179 | chr2 | 125235000 | 125236000 | 0.000 | 0.000 | CNTNAP5 | 1.00000 | 0 |
| 180 | chr2 | 127538000 | 127539000 | 0.000 | 0.000 | GYPC | 1.00000 | 0 |
| 181 | chr2 | 136874000 | 136875000 | 0.200 | 0.120 | CXCR4 | 0.70194 | 1 |
| 182 | chr2 | 136875000 | 136876000 | 0.240 | 0.240 | CXCR4 | 1.00000 | 1 |
| 183 | chr2 | 136996000 | 136997000 | 0.000 | 0.040 | CXCR4 | 1.00000 | 1 |
| 184 | chr2 | 137082000 | 137083000 | 0.040 | 0.000 | CXCR4 | 1.00000 | 1 |
| 185 | chr2 | 140951000 | 140952000 | 0.040 | 0.000 | LRP1B | 1.00000 | 0 |
| 186 | chr2 | 141335000 | 141336000 | 0.040 | 0.000 | LRP1B | 1.00000 | 0 |
| 187 | chr2 | 141770000 | 141771000 | 0.000 | 0.000 | LRP1B | 1.00000 | 0 |
| 188 | chr2 | 146445000 | 146446000 | 0.000 | 0.000 | ZEB2 | 1.00000 | 0 |
| 189 | chr2 | 146446000 | 146447000 | 0.000 | 0.080 | ZEB2 | 0.48980 | 0 |
| 190 | chr2 | 156443000 | 156444000 | 0.000 | 0.000 | KCNJ3 | 1.00000 | 0 |
| 191 | chr2 | 172590000 | 172591000 | 0.040 | 0.000 | DYNC1I2 | 1.00000 | 0 |
| 192 | chr2 | 176581000 | 176582000 | 0.000 | 0.000 | KIAA1715 | 1.00000 | 0 |
| 193 | chr2 | 179880000 | 179881000 | 0.000 | 0.040 | CCDC141 | 1.00000 | 0 |
| 194 | chr2 | 180358000 | 180359000 | 0.040 | 0.000 | ZNF385B | 1.00000 | 0 |
| 195 | chr2 | 189285000 | 189286000 | 0.040 | 0.000 | GULP1 | 1.00000 | 0 |
| 196 | chr2 | 189432000 | 189433000 | 0.000 | 0.040 | GULP1 | 1.00000 | 0 |
| 197 | chr2 | 194115000 | 194116000 | 0.040 | 0.000 | TMEFF2 | 1.00000 | 0 |
| 198 | chr2 | 197035000 | 197036000 | 0.040 | 0.080 | STK17B | 1.00000 | 0 |
| 199 | chr2 | 197041000 | 197042000 | 0.080 | 0.000 | STK17B | 0.48980 | 0 |
| 200 | chr2 | 215999000 | 216000000 | 0.040 | 0.000 | ABCA12 | 1.00000 | 0 |
| 201 | chr2 | 216973000 | 216974000 | 0.000 | 0.000 | XRCC5 | 1.00000 | 0 |
| 202 | chr2 | 217247000 | 217248000 | 0.000 | 0.000 | 4 Mar. 2019 | 1.00000 | 0 |
| 203 | chr2 | 225386000 | 225387000 | 0.040 | 0.000 | CUL3 | 1.00000 | 0 |
| 204 | chr2 | 225524000 | 225525000 | 0.000 | 0.040 | CUL3 | 1.00000 | 0 |
| 205 | chr2 | 233478000 | 233479000 | 0.040 | 0.000 | EFHD1 | 1.00000 | 0 |
| 206 | chr2 | 233980000 | 233981000 | 0.000 | 0.080 | INPP5D | 0.48980 | 0 |
| 207 | chr2 | 240641000 | 240642000 | 0.000 | 0.000 | AC093802.1 | 1.00000 | 0 |
| 208 | chr2 | 241125000 | 241126000 | 0.000 | 0.000 | OTOS | 1.00000 | 0 |
| 209 | chr3 | 8739000 | 8740000 | 0.000 | 0.000 | CAV3 | 1.00000 | 0 |
| 210 | chr3 | 16407000 | 16408000 | 0.000 | 0.000 | RFTN1 | 1.00000 | 1 |
| 211 | chr3 | 16409000 | 16410000 | 0.000 | 0.000 | RFTN1 | 1.00000 | 1 |
| 212 | chr3 | 16419000 | 16420000 | 0.040 | 0.080 | RFTN1 | 1.00000 | 1 |
| 213 | chr3 | 16472000 | 16473000 | 0.040 | 0.000 | RFTN1 | 1.00000 | 1 |
| 214 | chr3 | 16495000 | 16496000 | 0.000 | 0.080 | RFTN1 | 0.48980 | 1 |
| 215 | chr3 | 16552000 | 16553000 | 0.000 | 0.080 | RFTN1 | 0.48980 | 1 |
| 216 | chr3 | 16554000 | 16555000 | 0.120 | 0.120 | RFTN1 | 1.00000 | 1 |
| 217 | chr3 | 16555000 | 16556000 | 0.000 | 0.040 | RFTN1 | 1.00000 | 1 |
| 218 | chr3 | 21658000 | 21659000 | 0.040 | 0.000 | ZNF385D | 1.00000 | 0 |
| 219 | chr3 | 25691000 | 25692000 | 0.040 | 0.040 | TOP2B | 1.00000 | 0 |
| 220 | chr3 | 31969000 | 31970000 | 0.000 | 0.040 | OSBPL10 | 1.00000 | 1 |
| 221 | chr3 | 31993000 | 31994000 | 0.040 | 0.000 | OSBPL10 | 1.00000 | 1 |
| 222 | chr3 | 32001000 | 32002000 | 0.080 | 0.040 | OSBPL10 | 1.00000 | 1 |
| 223 | chr3 | 32022000 | 32023000 | 0.120 | 0.080 | OSBPL10 | 1.00000 | 1 |
| 224 | chr3 | 32023000 | 32024000 | 0.080 | 0.000 | OSBPL10 | 0.48980 | 1 |
| 225 | chr3 | 50128000 | 50129000 | 0.000 | 0.040 | RBM5 | 1.00000 | 0 |
| 226 | chr3 | 54913000 | 54914000 | 0.040 | 0.000 | CACNA2D3 | 1.00000 | 0 |
| 227 | chr3 | 56074000 | 56075000 | 0.040 | 0.040 | ERC2 | 1.00000 | 0 |
| 228 | chr3 | 59577000 | 59578000 | 0.000 | 0.000 | FHIT | 1.00000 | 0 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 229 | chr3 | 60351000 | 60352000 | 0.000 | 0.040 | FHIT | 1.00000 | 0 |
| 230 | chr3 | 60356000 | 60357000 | 0.000 | 0.000 | FHIT | 1.00000 | 0 |
| 231 | chr3 | 60357000 | 60358000 | 0.040 | 0.000 | FHIT | 1.00000 | 0 |
| 232 | chr3 | 60358000 | 60359000 | 0.040 | 0.000 | FHIT | 1.00000 | 0 |
| 233 | chr3 | 60359000 | 60360000 | 0.000 | 0.000 | FHIT | 1.00000 | 0 |
| 234 | chr3 | 60389000 | 60390000 | 0.000 | 0.040 | FHIT | 1.00000 | 0 |
| 235 | chr3 | 60392000 | 60393000 | 0.040 | 0.000 | FHIT | 1.00000 | 0 |
| 236 | chr3 | 60395000 | 60396000 | 0.000 | 0.000 | FHIT | 1.00000 | 0 |
| 237 | chr3 | 60404000 | 60405000 | 0.040 | 0.000 | FHIT | 1.00000 | 0 |
| 238 | chr3 | 60436000 | 60437000 | 0.000 | 0.000 | FHIT | 1.00000 | 0 |
| 239 | chr3 | 60437000 | 60438000 | 0.000 | 0.040 | FHIT | 1.00000 | 0 |
| 240 | chr3 | 60477000 | 60478000 | 0.040 | 0.040 | FHIT | 1.00000 | 0 |
| 241 | chr3 | 60485000 | 60486000 | 0.040 | 0.000 | FHIT | 1.00000 | 0 |
| 242 | chr3 | 60515000 | 60516000 | 0.000 | 0.040 | FHIT | 1.00000 | 0 |
| 243 | chr3 | 60535000 | 60536000 | 0.040 | 0.000 | FHIT | 1.00000 | 0 |
| 244 | chr3 | 60602000 | 60603000 | 0.000 | 0.000 | FHIT | 1.00000 | 0 |
| 245 | chr3 | 60613000 | 60614000 | 0.000 | 0.040 | FHIT | 1.00000 | 0 |
| 246 | chr3 | 60614000 | 60615000 | 0.000 | 0.040 | FHIT | 1.00000 | 0 |
| 247 | chr3 | 60632000 | 60633000 | 0.000 | 0.000 | FHIT | 1.00000 | 0 |
| 248 | chr3 | 60635000 | 60636000 | 0.000 | 0.000 | FHIT | 1.00000 | 0 |
| 249 | chr3 | 60640000 | 60641000 | 0.000 | 0.000 | FHIT | 1.00000 | 0 |
| 250 | chr3 | 60647000 | 60648000 | 0.000 | 0.040 | FHIT | 1.00000 | 0 |
| 251 | chr3 | 60648000 | 60649000 | 0.000 | 0.040 | FHIT | 1.00000 | 0 |
| 252 | chr3 | 60652000 | 60653000 | 0.000 | 0.000 | FHIT | 1.00000 | 0 |
| 253 | chr3 | 60660000 | 60661000 | 0.040 | 0.000 | FHIT | 1.00000 | 0 |
| 254 | chr3 | 60665000 | 60666000 | 0.000 | 0.040 | FHIT | 1.00000 | 0 |
| 255 | chr3 | 60666000 | 60667000 | 0.000 | 0.040 | FHIT | 1.00000 | 0 |
| 256 | chr3 | 60671000 | 60672000 | 0.000 | 0.000 | FHIT | 1.00000 | 0 |
| 257 | chr3 | 60673000 | 60674000 | 0.040 | 0.000 | FHIT | 1.00000 | 0 |
| 258 | chr3 | 60675000 | 60676000 | 0.000 | 0.040 | FHIT | 1.00000 | 0 |
| 259 | chr3 | 60678000 | 60679000 | 0.000 | 0.040 | FHIT | 1.00000 | 0 |
| 260 | chr3 | 60683000 | 60684000 | 0.000 | 0.000 | FHIT | 1.00000 | 0 |
| 261 | chr3 | 60684000 | 60685000 | 0.000 | 0.040 | FHIT | 1.00000 | 0 |
| 262 | chr3 | 60688000 | 60689000 | 0.040 | 0.000 | FHIT | 1.00000 | 0 |
| 263 | chr3 | 60717000 | 60718000 | 0.000 | 0.000 | FHIT | 1.00000 | 0 |
| 264 | chr3 | 60740000 | 60741000 | 0.040 | 0.000 | FHIT | 1.00000 | 0 |
| 265 | chr3 | 60774000 | 60775000 | 0.000 | 0.040 | FHIT | 1.00000 | 0 |
| 266 | chr3 | 60792000 | 60793000 | 0.000 | 0.000 | FHIT | 1.00000 | 0 |
| 267 | chr3 | 60806000 | 60807000 | 0.040 | 0.000 | FHIT | 1.00000 | 0 |
| 268 | chr3 | 60812000 | 60813000 | 0.000 | 0.000 | FHIT | 1.00000 | 0 |
| 269 | chr3 | 60860000 | 60861000 | 0.000 | 0.000 | FHIT | 1.00000 | 0 |
| 270 | chr3 | 71551000 | 71552000 | 0.040 | 0.000 | EIF4E3 | 1.00000 | 0 |
| 271 | chr3 | 78274000 | 78275000 | 0.000 | 0.040 | ROBO1 | 1.00000 | 0 |
| 272 | chr3 | 80273000 | 80274000 | 0.000 | 0.000 | ROBO1 | 1.00000 | 0 |
| 273 | chr3 | 83094000 | 83095000 | 0.000 | 0.000 | GBE1 | 1.00000 | 0 |
| 274 | chr3 | 83924000 | 83925000 | 0.000 | 0.000 | CADM2 | 1.00000 | 0 |
| 275 | chr3 | 84293000 | 84294000 | 0.000 | 0.040 | CADM2 | 1.00000 | 0 |
| 276 | chr3 | 85260000 | 85261000 | 0.000 | 0.040 | CADM2 | 1.00000 | 0 |
| 277 | chr3 | 85261000 | 85262000 | 0.000 | 0.000 | CADM2 | 1.00000 | 0 |
| 278 | chr3 | 85799000 | 85800000 | 0.040 | 0.000 | CADM2 | 1.00000 | 0 |
| 279 | chr3 | 86226000 | 86227000 | 0.000 | 0.000 | CADM2 | 1.00000 | 0 |
| 280 | chr3 | 88146000 | 88147000 | 0.040 | 0.000 | CGGBP1 | 1.00000 | 0 |
| 281 | chr3 | 94709000 | 94710000 | 0.000 | 0.000 | NSUN3 | 1.00000 | 0 |
| 282 | chr3 | 95460000 | 95461000 | 0.000 | 0.000 | MTRNR2L12 | 1.00000 | 0 |
| 283 | chr3 | 95724000 | 95725000 | 0.080 | 0.000 | MTRNR2L12 | 0.48980 | 0 |
| 284 | chr3 | 101569000 | 101570000 | 0.000 | 0.040 | NFKBIZ | 1.00000 | 0 |
| 285 | chr3 | 111851000 | 111852000 | 0.000 | 0.000 | GCSAM | 1.00000 | 0 |
| 286 | chr3 | 111852000 | 111853000 | 0.040 | 0.040 | GCSAM | 1.00000 | 0 |
| 287 | chr3 | 122377000 | 122378000 | 0.080 | 0.040 | PARP14 | 1.00000 | 0 |
| 288 | chr3 | 150478000 | 150479000 | 0.000 | 0.000 | SIAH2 | 1.00000 | 0 |
| 289 | chr3 | 150479000 | 150480000 | 0.000 | 0.040 | SIAH2 | 1.00000 | 0 |
| 290 | chr3 | 150480000 | 150481000 | 0.000 | 0.120 | SIAH2 | 0.23469 | 0 |
| 291 | chr3 | 163237000 | 163238000 | 0.000 | 0.000 | SI | 1.00000 | 0 |
| 292 | chr3 | 163238000 | 163239000 | 0.000 | 0.000 | SI | 1.00000 | 0 |
| 293 | chr3 | 163615000 | 163616000 | 0.040 | 0.040 | SI | 1.00000 | 0 |
| 294 | chr3 | 183270000 | 183271000 | 0.000 | 0.000 | KLHL6 | 1.00000 | 0 |
| 295 | chr3 | 183271000 | 183272000 | 0.000 | 0.040 | KLHL6 | 1.00000 | 0 |
| 296 | chr3 | 183272000 | 183273000 | 0.000 | 0.120 | KLHL6 | 0.23469 | 0 |
| 297 | chr3 | 183273000 | 183274000 | 0.000 | 0.040 | KLHL6 | 1.00000 | 0 |
| 298 | chr3 | 186648000 | 186649000 | 0.000 | 0.040 | ADIPOQ | 1.00000 | 0 |
| 299 | chr3 | 186714000 | 186715000 | 0.080 | 0.160 | ST6GAL1 | 0.66710 | 1 |
| 300 | chr3 | 186715000 | 186716000 | 0.080 | 0.000 | ST6GAL1 | 0.48980 | 1 |
| 301 | chr3 | 186739000 | 186740000 | 0.120 | 0.040 | ST6GAL1 | 0.60921 | 1 |
| 302 | chr3 | 186740000 | 186741000 | 0.160 | 0.080 | ST6GAL1 | 0.66710 | 1 |
| 303 | chr3 | 186742000 | 186743000 | 0.000 | 0.000 | ST6GAL1 | 1.00000 | 1 |
| 304 | chr3 | 186783000 | 186784000 | 0.160 | 0.240 | ST6GAL1 | 0.72520 | 1 |
| 305 | chr3 | 86784000 | 186785000 | 0.040 | 0.040 | ST6GAL1 | 1.00000 | 1 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 306 | chr3 | 187458000 | 187459000 | 0.000 | 0.000 | BCL6 | 1.00000 | 1 |
| 307 | chr3 | 187459000 | 187460000 | 0.000 | 0.000 | BCL6 | 1.00000 | 1 |
| 308 | chr3 | 187460000 | 187461000 | 0.040 | 0.040 | BCL6 | 1.00000 | 1 |
| 309 | chr3 | 187461000 | 187462000 | 0.240 | 0.360 | BCL6 | 0.53803 | 1 |
| 310 | chr3 | 187462000 | 187463000 | 0.440 | 0.560 | BCL6 | 0.57214 | 1 |
| 311 | chr3 | 187463000 | 187464000 | 0.360 | 0.440 | BCL6 | 0.77329 | 1 |
| 312 | chr3 | 187464000 | 187465000 | 0.200 | 0.200 | BCL6 | 1.00000 | 1 |
| 313 | chr3 | 187468000 | 187469000 | 0.120 | 0.000 | BCL6 | 0.23469 | 1 |
| 314 | chr3 | 187635000 | 187636000 | 0.040 | 0.000 | BCL6 | 1.00000 | 1 |
| 315 | chr3 | 187636000 | 187637000 | 0.000 | 0.000 | BCL6 | 1.00000 | 1 |
| 316 | chr3 | 187653000 | 187654000 | 0.040 | 0.040 | BCL6 | 1.00000 | 1 |
| 317 | chr3 | 187658000 | 187659000 | 0.000 | 0.040 | BCL6 | 1.00000 | 1 |
| 318 | chr3 | 187660000 | 187661000 | 0.040 | 0.160 | BCL6 | 0.34868 | 1 |
| 319 | chr3 | 187661000 | 187662000 | 0.040 | 0.240 | BCL6 | 0.09828 | 1 |
| 320 | chr3 | 187664000 | 187665000 | 0.040 | 0.080 | BCL6 | 1.00000 | 1 |
| 321 | chr3 | 187686000 | 187687000 | 0.040 | 0.000 | AC022498.1 | 1.00000 | 0 |
| 322 | chr3 | 187687000 | 187688000 | 0.000 | 0.040 | AC022498.1 | 1.00000 | 0 |
| 323 | chr3 | 187693000 | 187694000 | 0.040 | 0.040 | AC022498.1 | 1.00000 | 0 |
| 324 | chr3 | 187696000 | 187697000 | 0.040 | 0.000 | AC022498.1 | 1.00000 | 0 |
| 325 | chr3 | 187697000 | 187698000 | 0.040 | 0.000 | AC022498.1 | 1.00000 | 0 |
| 326 | chr3 | 187803000 | 187804000 | 0.000 | 0.000 | AC022498.1 | 1.00000 | 0 |
| 327 | chr3 | 187806000 | 187807000 | 0.080 | 0.080 | AC022498.1 | 1.00000 | 0 |
| 328 | chr3 | 187957000 | 187958000 | 0.120 | 0.160 | AC022498.1 | 1.00000 | 0 |
| 329 | chr3 | 187958000 | 187959000 | 0.240 | 0.280 | AC022498.1 | 1.00000 | 0 |
| 330 | chr3 | 187959000 | 187960000 | 0.120 | 0.040 | AC022498.1 | 0.60921 | 0 |
| 331 | chr3 | 187960000 | 187961000 | 0.000 | 0.040 | AC022498.1 | 1.00000 | 0 |
| 332 | chr3 | 188222000 | 188223000 | 0.000 | 0.000 | LPP | 1.00000 | 0 |
| 333 | chr3 | 188298000 | 188299000 | 0.040 | 0.000 | LPP | 1.00000 | 0 |
| 334 | chr3 | 188299000 | 188300000 | 0.080 | 0.080 | LPP | 1.00000 | 0 |
| 335 | chr3 | 188471000 | 188472000 | 0.120 | 0.240 | LPP | 0.46349 | 0 |
| 336 | chr3 | 188472000 | 188473000 | 0.000 | 0.080 | LPP | 0.48980 | 0 |
| 337 | chr4 | 50000 | 51000 | 0.080 | 0.000 | ZNF595; ZNF718; | 0.48980 | 0 |
| 338 | chr4 | 51000 | 52000 | 0.120 | 0.040 | ZNF595; ZNF718; | 0.60921 | 0 |
| 339 | chr4 | 54000 | 55000 | 0.080 | 0.000 | ZNF595; ZNF718; | 0.48980 | 0 |
| 340 | chr4 | 290000 | 291000 | 0.000 | 0.000 | ZNF732 | 1.00000 | 0 |
| 341 | chr4 | 385000 | 386000 | 0.080 | 0.000 | ZNF141 | 0.48980 | 0 |
| 342 | chr4 | 550000 | 551000 | 0.000 | 0.000 | PIGG | 1.00000 | 0 |
| 343 | chr4 | 2707000 | 2708000 | 0.000 | 0.040 | FAM193A | 1.00000 | 0 |
| 344 | chr4 | 5206000 | 5207000 | 0.080 | 0.000 | STK32B | 0.48980 | 0 |
| 345 | chr4 | 25863000 | 25864000 | 0.080 | 0.040 | SEL1L3 | 1.00000 | 0 |
| 346 | chr4 | 25864000 | 25865000 | 0.000 | 0.040 | SEL1L3 | 1.00000 | 0 |
| 347 | chr4 | 25865000 | 25866000 | 0.040 | 0.000 | SEL1L3 | 1.00000 | 0 |
| 348 | chr4 | 29657000 | 29658000 | 0.040 | 0.000 | PCDH7 | 1.00000 | 0 |
| 349 | chr4 | 30356000 | 30357000 | 0.040 | 0.000 | PCDH7 | 1.00000 | 0 |
| 350 | chr4 | 33418000 | 33419000 | 0.000 | 0.000 | PCDH7 | 1.00000 | 0 |
| 351 | chr4 | 33449000 | 33450000 | 0.000 | 0.040 | PCDH7 | 1.00000 | 0 |
| 352 | chr4 | 39348000 | 39349000 | 0.000 | 0.040 | RFC1 | 1.00000 | 0 |
| 353 | chr4 | 39974000 | 39975000 | 0.000 | 0.000 | PDS5A | 1.00000 | 0 |
| 354 | chr4 | 40194000 | 40195000 | 0.000 | 0.120 | N4BP2 | 0.23469 | 0 |
| 355 | chr4 | 40195000 | 40196000 | 0.000 | 0.040 | N4BP2 | 1.00000 | 0 |
| 356 | chr4 | 40196000 | 40197000 | 0.040 | 0.000 | N4BP2 | 1.00000 | 0 |
| 357 | chr4 | 40197000 | 40198000 | 0.000 | 0.000 | N4BP2 | 1.00000 | 0 |
| 358 | chr4 | 40198000 | 40199000 | 0.120 | 0.080 | N4BP2 | 1.00000 | 0 |
| 359 | chr4 | 40199000 | 40200000 | 0.280 | 0.240 | N4BP2 | 1.00000 | 0 |
| 360 | chr4 | 40200000 | 40201000 | 0.080 | 0.080 | RHOH | 1.00000 | 1 |
| 361 | chr4 | 40201000 | 40202000 | 0.120 | 0.120 | RHOH | 1.00000 | 1 |
| 362 | chr4 | 40202000 | 40203000 | 0.080 | 0.000 | RHOH | 0.48980 | 1 |
| 363 | chr4 | 40204000 | 40205000 | 0.000 | 0.040 | RHOH | 1.00000 | 1 |
| 364 | chr4 | 45308000 | 45309000 | 0.000 | 0.000 | GNPDA2 | 1.00000 | 0 |
| 365 | chr4 | 46360000 | 46361000 | 0.000 | 0.040 | GABRA2 | 1.00000 | 0 |
| 366 | chr4 | 62375000 | 62376000 | 0.000 | 0.000 | LPHN3 | 1.00000 | 0 |
| 367 | chr4 | 62530000 | 62531000 | 0.000 | 0.000 | LPHN3 | 1.00000 | 0 |
| 368 | chr4 | 62911000 | 62912000 | 0.000 | 0.040 | LPHN3 | 1.00000 | 0 |
| 369 | chr4 | 63120000 | 63121000 | 0.040 | 0.040 | LPHN3 | 1.00000 | 0 |
| 370 | chr4 | 64015000 | 64016000 | 0.000 | 0.000 | LPHN3 | 1.00000 | 0 |
| 371 | chr4 | 65038000 | 65039000 | 0.040 | 0.000 | TECRL | 1.00000 | 0 |
| 372 | chr4 | 65165000 | 65166000 | 0.000 | 0.040 | TECRL | 1.00000 | 0 |
| 373 | chr4 | 65966000 | 65967000 | 0.000 | 0.040 | EPHA5 | 1.00000 | 0 |
| 374 | chr4 | 66827000 | 66828000 | 0.000 | 0.080 | EPHA5 | 0.48980 | 0 |
| 375 | chr4 | 71531000 | 71532000 | 0.000 | 0.040 | IGJ | 1.00000 | 0 |
| 376 | chr4 | 71532000 | 71533000 | 0.000 | 0.000 | IGJ | 1.00000 | 0 |
| 377 | chr4 | 74456000 | 74457000 | 0.040 | 0.000 | RASSF6 | 1.00000 | 0 |
| 378 | chr4 | 74483000 | 74484000 | 0.040 | 0.000 | RASSF6 | 1.00000 | 0 |
| 379 | chr4 | 74484000 | 74485000 | 0.040 | 0.000 | RASSF6 | 1.00000 | 0 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 380 | chr4 | 74485000 | 74486000 | 0.120 | 0.000 | RASSF6 | 0.23469 | 0 |
| 381 | chr4 | 91886000 | 91887000 | 0.040 | 0.000 | CCSER1 | 1.00000 | 0 |
| 382 | chr4 | 92787000 | 92788000 | 0.000 | 0.040 | CCSER1 | 1.00000 | 0 |
| 383 | chr4 | 113206000 | 113207000 | 0.000 | 0.000 | TIFA | 1.00000 | 0 |
| 384 | chr4 | 114466000 | 114467000 | 0.000 | 0.000 | CAMK2D | 1.00000 | 0 |
| 385 | chr4 | 114681000 | 114682000 | 0.000 | 0.080 | CAMK2D | 0.48980 | 0 |
| 386 | chr4 | 117928000 | 117929000 | 0.040 | 0.000 | TRAM1L1 | 1.00000 | 0 |
| 387 | chr4 | 123637000 | 123638000 | 0.000 | 0.000 | BBS12 | 1.00000 | 0 |
| 388 | chr4 | 125227000 | 125228000 | 0.040 | 0.000 | ANKRD50 | 1.00000 | 0 |
| 389 | chr4 | 127371000 | 127372000 | 0.000 | 0.000 | FAT4 | 1.00000 | 0 |
| 390 | chr4 | 133455000 | 133456000 | 0.000 | 0.000 | PCDH10 | 1.00000 | 0 |
| 391 | chr4 | 134538000 | 134539000 | 0.000 | 0.040 | PCDH10 | 1.00000 | 0 |
| 392 | chr4 | 134743000 | 134744000 | 0.040 | 0.040 | PABPC4L | 1.00000 | 0 |
| 393 | chr4 | 134867000 | 134868000 | 0.000 | 0.000 | PABPC4L | 1.00000 | 0 |
| 394 | chr4 | 134949000 | 134950000 | 0.080 | 0.000 | PABPC4L | 0.48980 | 0 |
| 395 | chr4 | 135064000 | 135065000 | 0.040 | 0.000 | PABPC4L | 1.00000 | 0 |
| 396 | chr4 | 135077000 | 135078000 | 0.000 | 0.000 | PABPC4L | 1.00000 | 0 |
| 397 | chr4 | 136799000 | 136800000 | 0.000 | 0.000 | PCDH18 | 1.00000 | 0 |
| 398 | chr4 | 136867000 | 136868000 | 0.000 | 0.040 | PCDH18 | 1.00000 | 0 |
| 399 | chr4 | 140236000 | 140237000 | 0.040 | 0.000 | NAA15 | 1.00000 | 0 |
| 400 | chr4 | 151723000 | 151724000 | 0.000 | 0.000 | LRBA | 1.00000 | 0 |
| 401 | chr4 | 151950000 | 151951000 | 0.000 | 0.000 | LRBA | 1.00000 | 0 |
| 402 | chr4 | 152125000 | 152126000 | 0.040 | 0.040 | SH3D19 | 1.00000 | 0 |
| 403 | chr4 | 157246000 | 157247000 | 0.040 | 0.000 | CTSO | 1.00000 | 0 |
| 404 | chr4 | 164532000 | 164533000 | 0.000 | 0.000 | 1 Mar. 2019 | 1.00000 | 0 |
| 405 | chr4 | 178732000 | 178733000 | 0.040 | 0.040 | AGA | 1.00000 | 0 |
| 406 | chr4 | 178885000 | 178886000 | 0.040 | 0.000 | AGA | 1.00000 | 0 |
| 407 | chr4 | 179898000 | 179899000 | 0.000 | 0.040 | AGA | 1.00000 | 0 |
| 408 | chr4 | 180885000 | 180886000 | 0.040 | 0.000 | TENM3 | 1.00000 | 0 |
| 409 | chr4 | 181554000 | 181555000 | 0.000 | 0.040 | TENM3 | 1.00000 | 0 |
| 410 | chr4 | 182122000 | 182123000 | 0.000 | 0.040 | TENM3 | 1.00000 | 0 |
| 411 | chr5 | 436000 | 437000 | 0.000 | 0.000 | AHRR | 1.00000 | 0 |
| 412 | chr5 | 3982000 | 3983000 | 0.040 | 0.000 | IRX1 | 1.00000 | 0 |
| 413 | chr5 | 17218000 | 17219000 | 0.040 | 0.000 | BASP1 | 1.00000 | 0 |
| 414 | chr5 | 17219000 | 17220000 | 0.080 | 0.000 | BASP1 | 0.48980 | 0 |
| 415 | chr5 | 18514000 | 18515000 | 0.040 | 0.000 | CDH18 | 1.00000 | 0 |
| 416 | chr5 | 22356000 | 22357000 | 0.040 | 0.000 | CDH12 | 1.00000 | 0 |
| 417 | chr5 | 22517000 | 22518000 | 0.040 | 0.000 | CDH12 | 1.00000 | 0 |
| 418 | chr5 | 24632000 | 24633000 | 0.000 | 0.000 | CDH10 | 1.00000 | 0 |
| 419 | chr5 | 25275000 | 25276000 | 0.000 | 0.040 | CDH10 | 1.00000 | 0 |
| 420 | chr5 | 25541000 | 25542000 | 0.000 | 0.000 | CDH10 | 1.00000 | 0 |
| 421 | chr5 | 26119000 | 26120000 | 0.000 | 0.080 | CDH9 | 0.48980 | 0 |
| 422 | chr5 | 26450000 | 26451000 | 0.000 | 0.000 | CDH9 | 1.00000 | 0 |
| 423 | chr5 | 29224000 | 29225000 | 0.080 | 0.000 | CDH6 | 0.48980 | 0 |
| 424 | chr5 | 29492000 | 29493000 | 0.000 | 0.000 | CDH6 | 1.00000 | 0 |
| 425 | chr5 | 29648000 | 29649000 | 0.000 | 0.000 | CDH6 | 1.00000 | 0 |
| 426 | chr5 | 51521000 | 51522000 | 0.000 | 0.040 | CTD-2203A3.1 | 1.00000 | 0 |
| 427 | chr5 | 83841000 | 83842000 | 0.040 | 0.000 | EDIL3 | 1.00000 | 0 |
| 428 | chr5 | 88177000 | 88178000 | 0.040 | 0.000 | MEF2C | 1.00000 | 0 |
| 429 | chr5 | 88178000 | 88179000 | 0.040 | 0.000 | MEF2C | 1.00000 | 0 |
| 430 | chr5 | 91417000 | 91418000 | 0.000 | 0.000 | ARRDC3 | 1.00000 | 0 |
| 431 | chr5 | 103678000 | 103679000 | 0.040 | 0.000 | NUDT12 | 1.00000 | 0 |
| 432 | chr5 | 123696000 | 123697000 | 0.000 | 0.000 | ZNF608 | 1.00000 | 1 |
| 433 | chr5 | 124079000 | 124080000 | 0.000 | 0.040 | ZNF608 | 1.00000 | 1 |
| 434 | chr5 | 124080000 | 124081000 | 0.040 | 0.000 | ZNF608 | 1.00000 | 1 |
| 435 | chr5 | 127594000 | 127595000 | 0.000 | 0.040 | FBN2 | 1.00000 | 0 |
| 436 | chr5 | 127875000 | 127876000 | 0.000 | 0.000 | FBN2 | 1.00000 | 0 |
| 437 | chr5 | 131825000 | 131826000 | 0.120 | 0.040 | IRF1 | 0.60921 | 0 |
| 438 | chr5 | 131826000 | 131827000 | 0.040 | 0.040 | IRF1 | 1.00000 | 0 |
| 439 | chr5 | 149791000 | 149792000 | 0.160 | 0.240 | CD74 | 0.72520 | 1 |
| 440 | chr5 | 149792000 | 149793000 | 0.040 | 0.080 | CD74 | 1.00000 | 1 |
| 441 | chr5 | 158380000 | 158381000 | 0.000 | 0.080 | EBF1 | 0.48980 | 0 |
| 442 | chr5 | 158479000 | 158480000 | 0.000 | 0.000 | EBF1 | 1.00000 | 0 |
| 443 | chr5 | 158526000 | 158527000 | 0.040 | 0.080 | EBF1 | 1.00000 | 0 |
| 444 | chr5 | 158527000 | 158528000 | 0.040 | 0.040 | EBF1 | 1.00000 | 0 |
| 445 | chr5 | 158528000 | 158529000 | 0.040 | 0.040 | EBF1 | 1.00000 | 0 |
| 446 | chr5 | 164247000 | 164248000 | 0.040 | 0.040 | MAT2B | 1.00000 | 0 |
| 447 | chr5 | 164441000 | 164442000 | 0.000 | 0.000 | MAT2B | 1.00000 | 0 |
| 448 | chr5 | 165932000 | 165933000 | 0.000 | 0.000 | TENM2 | 1.00000 | 0 |
| 449 | chr5 | 173300000 | 173301000 | 0.000 | 0.000 | CPEB4 | 1.00000 | 0 |
| 450 | chr5 | 179166000 | 179167000 | 0.040 | 0.040 | MAML1 | 1.00000 | 0 |
| 451 | chr5 | 180102000 | 180103000 | 0.040 | 0.000 | FLT4 | 1.00000 | 0 |
| 452 | chr6 | 392000 | 393000 | 0.120 | 0.080 | IRF4 | 1.00000 | 1 |
| 453 | chr6 | 393000 | 394000 | 0.080 | 0.080 | IRF4 | 1.00000 | 1 |
| 454 | chr6 | 14118000 | 14119000 | 0.160 | 0.440 | CD83 | 0.06222 | 1 |
| 455 | chr6 | 14119000 | 14120000 | 0.000 | 0.120 | CD83 | 0.23469 | 1 |
| 456 | chr6 | 18111000 | 18112000 | 0.000 | 0.080 | NHLRC1 | 0.48980 | 0 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 457 | chr6 | 18387000 | 18388000 | 0.000 | 0.040 | RNF144B | 1.00000 | 1 |
| 458 | chr6 | 18388000 | 18389000 | 0.000 | 0.040 | RNF144B | 1.00000 | 1 |
| 459 | chr6 | 19573000 | 19574000 | 0.040 | 0.040 | ID4 | 1.00000 | 0 |
| 460 | chr6 | 22873000 | 22874000 | 0.040 | 0.000 | HDGFL1 | 1.00000 | 0 |
| 461 | chr6 | 26031000 | 26032000 | 0.000 | 0.040 | HIST1H3B | 1.00000 | 1 |
| 462 | chr6 | 26032000 | 26033000 | 0.000 | 0.040 | HIST1H3B | 1.00000 | 1 |
| 463 | chr6 | 26056000 | 26057000 | 0.120 | 0.040 | HIST1H1C | 0.60921 | 1 |
| 464 | chr6 | 26123000 | 26124000 | 0.120 | 0.040 | HIST1H2BC | 0.60921 | 1 |
| 465 | chr6 | 26124000 | 26125000 | 0.120 | 0.080 | HIST1H2AC; HIST1H2BC; | 1.00000 | 0 |
| 466 | chr6 | 26125000 | 26126000 | 0.000 | 0.040 | HIST1H2AC | 1.00000 | 1 |
| 467 | chr6 | 26156000 | 26157000 | 0.120 | 0.080 | HIST1H1E | 1.00000 | 1 |
| 468 | chr6 | 26157000 | 26158000 | 0.080 | 0.040 | HIST1H1E | 1.00000 | 1 |
| 469 | chr6 | 26216000 | 26217000 | 0.040 | 0.040 | HIST1H2BG | 1.00000 | 1 |
| 470 | chr6 | 26234000 | 26235000 | 0.080 | 0.040 | HIST1H1D | 1.00000 | 0 |
| 471 | chr6 | 27101000 | 27102000 | 0.040 | 0.000 | HIST1H2AG | 1.00000 | 1 |
| 472 | chr6 | 27114000 | 27115000 | 0.080 | 0.040 | HIST1H2AH; HIST1H2BK; | 1.00000 | 0 |
| 473 | chr6 | 27792000 | 27793000 | 0.120 | 0.040 | HIST1H4J | 0.60921 | 0 |
| 474 | chr6 | 27833000 | 27834000 | 0.040 | 0.000 | HIST1H2AL | 1.00000 | 1 |
| 475 | chr6 | 27860000 | 27861000 | 0.000 | 0.080 | HIST1H2AM | 0.48980 | 1 |
| 476 | chr6 | 27861000 | 27862000 | 0.000 | 0.040 | HIST1H2BO | 1.00000 | 1 |
| 477 | chr6 | 29778000 | 29779000 | 0.000 | 0.040 | LOC554223 | 1.00000 | 0 |
| 478 | chr6 | 29780000 | 29781000 | 0.040 | 0.000 | HLA-G | 1.00000 | 0 |
| 479 | chr6 | 29911000 | 29912000 | 0.080 | 0.040 | HLA-A | 1.00000 | 0 |
| 480 | chr6 | 29927000 | 29928000 | 0.040 | 0.000 | HLA-A | 1.00000 | 0 |
| 481 | chr6 | 31324000 | 31325000 | 0.040 | 0.040 | HLA-B | 1.00000 | 1 |
| 482 | chr6 | 31325000 | 31326000 | 0.000 | 0.000 | HLA-B | 1.00000 | 1 |
| 483 | chr6 | 31543000 | 31544000 | 0.080 | 0.000 | TNF | 0.48980 | 1 |
| 484 | chr6 | 31549000 | 31550000 | 0.200 | 0.240 | LTB | 1.00000 | 1 |
| 485 | chr6 | 31550000 | 31551000 | 0.040 | 0.040 | LTB | 1.00000 | 1 |
| 486 | chr6 | 32440000 | 32441000 | 0.120 | 0.000 | HLA-DRA | 0.23469 | 0 |
| 487 | chr6 | 32451000 | 32452000 | 0.040 | 0.000 | HLA-DRB5 | 1.00000 | 0 |
| 488 | chr6 | 32452000 | 32453000 | 0.080 | 0.000 | HLA-DRB5 | 0.48980 | 0 |
| 489 | chr6 | 32455000 | 32456000 | 0.040 | 0.040 | HLA-DRB5 | 1.00000 | 0 |
| 490 | chr6 | 32457000 | 32458000 | 0.000 | 0.000 | HLA-DRB5 | 1.00000 | 0 |
| 491 | chr6 | 32498000 | 32499000 | 0.000 | 0.040 | HLA-DRB5 | 1.00000 | 0 |
| 492 | chr6 | 32505000 | 32506000 | 0.040 | 0.000 | HLA-DRB5 | 1.00000 | 0 |
| 493 | chr6 | 32511000 | 32512000 | 0.000 | 0.000 | HLA-DRB5 | 1.00000 | 0 |
| 494 | chr6 | 32522000 | 32523000 | 0.040 | 0.000 | HLA-DRB1 | 1.00000 | 0 |
| 495 | chr6 | 32525000 | 32526000 | 0.040 | 0.000 | HLA-DRB1 | 1.00000 | 0 |
| 496 | chr6 | 32526000 | 32527000 | 0.000 | 0.000 | HLA-DRB1 | 1.00000 | 0 |
| 497 | chr6 | 32527000 | 32528000 | 0.000 | 0.000 | HLA-DRB1 | 1.00000 | 0 |
| 498 | chr6 | 32548000 | 32549000 | 0.000 | 0.000 | HLA-DRB1 | 1.00000 | 0 |
| 499 | chr6 | 32552000 | 32553000 | 0.040 | 0.000 | HLA-DRB1 | 1.00000 | 0 |
| 500 | chr6 | 32557000 | 32558000 | 0.000 | 0.080 | HLA-DRB1 | 0.48980 | 0 |
| 501 | chr6 | 32609000 | 32610000 | 0.000 | 0.040 | HLA-DQA1 | 1.00000 | 0 |
| 502 | chr6 | 32630000 | 32631000 | 0.000 | 0.040 | HLA-DQB1 | 1.00000 | 0 |
| 503 | chr6 | 32632000 | 32633000 | 0.080 | 0.040 | HLA-DQB1 | 1.00000 | 0 |
| 504 | chr6 | 32727000 | 32728000 | 0.040 | 0.040 | HLA-DQB2 | 1.00000 | 0 |
| 505 | chr6 | 32729000 | 32730000 | 0.000 | 0.040 | HLA-DQB2 | 1.00000 | 0 |
| 506 | chr6 | 33048000 | 33049000 | 0.000 | 0.040 | HLA-DPB1 | 1.00000 | 0 |
| 507 | chr6 | 34179000 | 34180000 | 0.000 | 0.040 | HMGA1 | 1.00000 | 0 |
| 508 | chr6 | 37138000 | 37139000 | 0.200 | 0.200 | PIM1 | 1.00000 | 1 |
| 509 | chr6 | 37139000 | 37140000 | 0.120 | 0.120 | PIM1 | 1.00000 | 1 |
| 510 | chr6 | 37140000 | 37141000 | 0.040 | 0.000 | PIM1 | 1.00000 | 1 |
| 511 | chr6 | 58001000 | 58002000 | 0.040 | 0.000 | PRIM2 | 1.00000 | 0 |
| 512 | chr6 | 67923000 | 67924000 | 0.040 | 0.000 | BAI3 | 1.00000 | 0 |
| 513 | chr6 | 77256000 | 77257000 | 0.040 | 0.000 | IMPG1 | 1.00000 | 0 |
| 514 | chr6 | 81437000 | 81438000 | 0.040 | 0.000 | BCKDHB | 1.00000 | 0 |
| 515 | chr6 | 88468000 | 88469000 | 0.000 | 0.040 | AKIRIN2 | 1.00000 | 0 |
| 516 | chr6 | 88630000 | 88631000 | 0.040 | 0.080 | SPACA1 | 1.00000 | 0 |
| 517 | chr6 | 88876000 | 88877000 | 0.000 | 0.000 | CNR1 | 1.00000 | 0 |
| 518 | chr6 | 89323000 | 89324000 | 0.000 | 0.000 | RNGTT | 1.00000 | 0 |
| 519 | chr6 | 89338000 | 89339000 | 0.080 | 0.000 | RNGTT | 0.48980 | 0 |
| 520 | chr6 | 89348000 | 89349000 | 0.080 | 0.000 | RNGTT | 0.48980 | 0 |
| 521 | chr6 | 89470000 | 89471000 | 0.080 | 0.000 | RNGTT | 0.48980 | 0 |
| 522 | chr6 | 89471000 | 89472000 | 0.000 | 0.000 | RNGTT | 1.00000 | 0 |
| 523 | chr6 | 90061000 | 90062000 | 0.040 | 0.040 | UBE2J1 | 1.00000 | 1 |
| 524 | chr6 | 90062000 | 90063000 | 0.040 | 0.000 | UBE2J1 | 1.00000 | 1 |
| 525 | chr6 | 90994000 | 90995000 | 0.000 | 0.080 | MAP3K7 | 0.48980 | 0 |
| 526 | chr6 | 91004000 | 91005000 | 0.040 | 0.040 | MAP3K7 | 1.00000 | 0 |
| 527 | chr6 | 91005000 | 91006000 | 0.120 | 0.280 | MAP3K7 | 0.28902 | 0 |
| 528 | chr6 | 91006000 | 91007000 | 0.040 | 0.120 | MAP3K7 | 0.60921 | 0 |
| 529 | chr6 | 91007000 | 91008000 | 0.000 | 0.040 | MAP3K7 | 1.00000 | 0 |
| 530 | chr6 | 94822000 | 94823000 | 0.000 | 0.040 | EPHA7 | 1.00000 | 0 |
| 531 | chr6 | 107704000 | 107705000 | 0.000 | 0.000 | PDSS2 | 1.00000 | 0 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 532 | chr6 | 112885000 | 112886000 | 0.040 | 0.000 | RFPL4B | 1.00000 | 0 |
| 533 | chr6 | 118244000 | 118245000 | 0.040 | 0.000 | SLC35F1 | 1.00000 | 0 |
| 534 | chr6 | 121288000 | 121289000 | 0.000 | 0.000 | C6orf170 | 1.00000 | 0 |
| 535 | chr6 | 121489000 | 121490000 | 0.000 | 0.080 | C6orf170 | 0.48980 | 0 |
| 536 | chr6 | 123504000 | 123505000 | 0.040 | 0.000 | TRDN | 1.00000 | 0 |
| 537 | chr6 | 127313000 | 127314000 | 0.040 | 0.000 | RSPO3 | 1.00000 | 0 |
| 538 | chr6 | 133785000 | 133786000 | 0.080 | 0.000 | EYA4 | 0.48980 | 0 |
| 539 | chr6 | 134491000 | 134492000 | 0.000 | 0.080 | SGK1 | 0.48980 | 1 |
| 540 | chr6 | 134492000 | 134493000 | 0.080 | 0.040 | SGK1 | 1.00000 | 1 |
| 541 | chr6 | 134493000 | 134494000 | 0.040 | 0.080 | SGK1 | 1.00000 | 1 |
| 542 | chr6 | 134494000 | 134495000 | 0.040 | 0.080 | SGK1 | 1.00000 | 1 |
| 543 | chr6 | 134495000 | 134496000 | 0.160 | 0.280 | SGK1 | 0.49620 | 1 |
| 544 | chr6 | 134496000 | 134497000 | 0.000 | 0.200 | SGK1 | 0.05015 | 1 |
| 545 | chr6 | 142046000 | 142047000 | 0.000 | 0.080 | NMBR | 0.48980 | 0 |
| 546 | chr6 | 147860000 | 147861000 | 0.000 | 0.040 | SAMD5 | 1.00000 | 0 |
| 547 | chr6 | 150954000 | 150955000 | 0.040 | 0.040 | PLEKHG1 | 1.00000 | 0 |
| 548 | chr6 | 159238000 | 159239000 | 0.000 | 0.080 | EZR | 0.48980 | 0 |
| 549 | chr6 | 159239000 | 159240000 | 0.040 | 0.000 | EZR | 1.00000 | 0 |
| 550 | chr6 | 159240000 | 159241000 | 0.040 | 0.000 | EZR | 1.00000 | 0 |
| 551 | chr6 | 159464000 | 159465000 | 0.040 | 0.000 | TAGAP | 1.00000 | 0 |
| 552 | chr6 | 159465000 | 159466000 | 0.040 | 0.000 | TAGAP | 1.00000 | 0 |
| 553 | chr6 | 161265000 | 161266000 | 0.000 | 0.040 | PLG | 1.00000 | 0 |
| 554 | chr6 | 161833000 | 161834000 | 0.000 | 0.000 | PARK2 | 1.00000 | 0 |
| 555 | chr6 | 162712000 | 162713000 | 0.000 | 0.000 | PARK2 | 1.00000 | 0 |
| 556 | chr6 | 164941000 | 164942000 | 0.000 | 0.000 | C6orf118 | 1.00000 | 0 |
| 557 | chr6 | 168813000 | 168814000 | 0.000 | 0.000 | SMOC2 | 1.00000 | 0 |
| 558 | chr7 | 1898000 | 1899000 | 0.040 | 0.040 | AC110781.3 | 1.00000 | 0 |
| 559 | chr7 | 1963000 | 1964000 | 0.040 | 0.000 | MAD1L1 | 1.00000 | 0 |
| 560 | chr7 | 2080000 | 2081000 | 0.000 | 0.040 | MAD1L1 | 1.00000 | 0 |
| 561 | chr7 | 5568000 | 5569000 | 0.040 | 0.080 | ACTB | 1.00000 | 1 |
| 562 | chr7 | 5569000 | 5570000 | 0.040 | 0.120 | ACTB | 0.60921 | 1 |
| 563 | chr7 | 5570000 | 5571000 | 0.040 | 0.040 | ACTB | 1.00000 | 1 |
| 564 | chr7 | 9933000 | 9934000 | 0.040 | 0.040 | NDUFA4 | 1.00000 | 0 |
| 565 | chr7 | 13017000 | 13018000 | 0.000 | 0.040 | ARL4A | 1.00000 | 0 |
| 566 | chr7 | 13346000 | 13347000 | 0.000 | 0.000 | ETV1 | 1.00000 | 0 |
| 567 | chr7 | 15459000 | 15460000 | 0.000 | 0.000 | AGMO | 1.00000 | 0 |
| 568 | chr7 | 16382000 | 16383000 | 0.040 | 0.000 | ISPD | 1.00000 | 0 |
| 569 | chr7 | 28600000 | 28601000 | 0.040 | 0.000 | CREB5 | 1.00000 | 0 |
| 570 | chr7 | 40846000 | 40847000 | 0.040 | 0.000 | C7orf10 | 1.00000 | 0 |
| 571 | chr7 | 50349000 | 50350000 | 0.040 | 0.040 | IKZF1 | 1.00000 | 0 |
| 572 | chr7 | 50350000 | 50351000 | 0.080 | 0.040 | IKZF1 | 1.00000 | 0 |
| 573 | chr7 | 53335000 | 53336000 | 0.000 | 0.000 | POM121L12 | 1.00000 | 0 |
| 574 | chr7 | 57713000 | 57714000 | 0.080 | 0.040 | ZNF716 | 1.00000 | 0 |
| 575 | chr7 | 62475000 | 62476000 | 0.040 | 0.040 | AC006455.1 | 1.00000 | 0 |
| 576 | chr7 | 70669000 | 70670000 | 0.040 | 0.000 | WBSCR17 | 1.00000 | 0 |
| 577 | chr7 | 71553000 | 71554000 | 0.000 | 0.040 | CALN1 | 1.00000 | 0 |
| 578 | chr7 | 79847000 | 79848000 | 0.040 | 0.000 | GNAI1 | 1.00000 | 0 |
| 579 | chr7 | 80694000 | 80695000 | 0.040 | 0.000 | AC005008.2 | 1.00000 | 0 |
| 580 | chr7 | 81556000 | 81557000 | 0.000 | 0.000 | CACNA2D1 | 1.00000 | 0 |
| 581 | chr7 | 84127000 | 84128000 | 0.040 | 0.000 | SEMA3A | 1.00000 | 0 |
| 582 | chr7 | 84247000 | 84248000 | 0.000 | 0.040 | SEMA3D | 1.00000 | 0 |
| 583 | chr7 | 84257000 | 84258000 | 0.000 | 0.000 | SEMA3D | 1.00000 | 0 |
| 584 | chr7 | 86914000 | 86915000 | 0.000 | 0.040 | CROT | 1.00000 | 0 |
| 585 | chr7 | 90356000 | 90357000 | 0.000 | 0.040 | CDK14 | 1.00000 | 0 |
| 586 | chr7 | 93304000 | 93305000 | 0.000 | 0.000 | CALCR | 1.00000 | 0 |
| 587 | chr7 | 93682000 | 93683000 | 0.040 | 0.000 | BET1 | 1.00000 | 0 |
| 588 | chr7 | 102644000 | 102645000 | 0.000 | 0.000 | FBXL13 | 1.00000 | 0 |
| 589 | chr7 | 105699000 | 105700000 | 0.000 | 0.040 | CDHR3 | 1.00000 | 0 |
| 590 | chr7 | 110521000 | 110522000 | 0.040 | 0.040 | IMMP2L | 1.00000 | 0 |
| 591 | chr7 | 110543000 | 110544000 | 0.040 | 0.000 | IMMP2L | 1.00000 | 0 |
| 592 | chr7 | 110545000 | 110546000 | 0.040 | 0.000 | IMMP2L | 1.00000 | 0 |
| 593 | chr7 | 110597000 | 110598000 | 0.000 | 0.040 | IMMP2l | 1.00000 | 0 |
| 594 | chr7 | 110601000 | 110602000 | 0.000 | 0.000 | IMMP2L | 1.00000 | 0 |
| 595 | chr7 | 110602000 | 110603000 | 0.040 | 0.000 | IMMP2L | 1.00000 | 0 |
| 596 | chr7 | 110609000 | 110610000 | 0.040 | 0.000 | IMMP2L | 1.00000 | 0 |
| 597 | chr7 | 110610000 | 110611000 | 0.040 | 0.000 | IMMP2L | 1.00000 | 0 |
| 598 | chr7 | 110617000 | 110618000 | 0.040 | 0.000 | IMMP2L | 1.00000 | 0 |
| 599 | chr7 | 110618000 | 110619000 | 0.000 | 0.000 | IMMP2L | 1.00000 | 0 |
| 600 | chr7 | 110619000 | 110620000 | 0.040 | 0.000 | IMMP2L | 1.00000 | 0 |
| 601 | chr7 | 110621000 | 110622000 | 0.000 | 0.040 | IMMP2L | 1.00000 | 0 |
| 602 | chr7 | 110628000 | 110629000 | 0.040 | 0.000 | IMMP2L | 1.00000 | 0 |
| 603 | chr7 | 110629000 | 110630000 | 0.000 | 0.000 | IMMP2L | 1.00000 | 0 |
| 604 | chr7 | 110631000 | 110632000 | 0.000 | 0.040 | IMMP2L | 1.00000 | 0 |
| 605 | chr7 | 110632000 | 110633000 | 0.040 | 0.000 | IMMP2L | 1.00000 | 0 |
| 606 | chr7 | 110636000 | 110637000 | 0.040 | 0.000 | IMMP2L | 1.00000 | 0 |
| 607 | chr7 | 110637000 | 110638000 | 0.000 | 0.000 | IMMP2L | 1.00000 | 0 |
| 608 | chr7 | 110638000 | 110639000 | 0.000 | 0.040 | IMMP2L | 1.00000 | 0 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 609 | chr7 | 110639000 | 110640000 | 0.000 | 0.000 | IMMP2L | 1.00000 | 0 |
| 610 | chr7 | 110641000 | 110642000 | 0.000 | 0.000 | IMMP2L | 1.00000 | 0 |
| 611 | chr7 | 110650000 | 110651000 | 0.000 | 0.000 | IMMP2L | 1.00000 | 0 |
| 612 | chr7 | 110651000 | 110652000 | 0.000 | 0.040 | IMMP2L | 1.00000 | 0 |
| 613 | chr7 | 110666000 | 110667000 | 0.000 | 0.000 | IMMP2L | 1.00000 | 0 |
| 614 | chr7 | 110671000 | 110672000 | 0.000 | 0.080 | IMMP2L | 0.48980 | 0 |
| 615 | chr7 | 110677000 | 110678000 | 0.000 | 0.000 | IMMP2L | 1.00000 | 0 |
| 616 | chr7 | 110679000 | 110680000 | 0.000 | 0.000 | IMMP2L | 1.00000 | 0 |
| 617 | chr7 | 110680000 | 110681000 | 0.000 | 0.000 | IMMP2L | 1.00000 | 0 |
| 618 | chr7 | 110685000 | 110686000 | 0.000 | 0.000 | LRRN3 | 1.00000 | 0 |
| 619 | chr7 | 110686000 | 110687000 | 0.000 | 0.040 | LRRN3 | 1.00000 | 0 |
| 620 | chr7 | 110688000 | 110689000 | 0.000 | 0.000 | LRRN3 | 1.00000 | 0 |
| 621 | chr7 | 110699000 | 110700000 | 0.080 | 0.000 | LRRN3 | 0.48980 | 0 |
| 622 | chr7 | 110700000 | 110701000 | 0.000 | 0.040 | LRRN3 | 1.00000 | 0 |
| 623 | chr7 | 110709000 | 110710000 | 0.040 | 0.040 | LRRN3 | 1.00000 | 0 |
| 624 | chr7 | 110711000 | 110712000 | 0.000 | 0.040 | LRRN3 | 1.00000 | 0 |
| 625 | chr7 | 110714000 | 110715000 | 0.000 | 0.040 | LRRN3 | 1.00000 | 0 |
| 626 | chr7 | 110727000 | 110728000 | 0.000 | 0.040 | LRRN3 | 1.00000 | 0 |
| 627 | chr7 | 110728000 | 110729000 | 0.040 | 0.000 | LRRN3 | 1.00000 | 0 |
| 628 | chr7 | 110729000 | 110730000 | 0.000 | 0.040 | LRRN3 | 1.00000 | 0 |
| 629 | chr7 | 110734000 | 110735000 | 0.000 | 0.040 | LRRN3 | 1.00000 | 0 |
| 630 | chr7 | 110737000 | 110738000 | 0.000 | 0.000 | LRRN3 | 1.00000 | 0 |
| 631 | chr7 | 110740000 | 110741000 | 0.040 | 0.080 | LRRN3 | 1.00000 | 0 |
| 632 | chr7 | 110744000 | 110745000 | 0.000 | 0.000 | LRRN3 | 1.00000 | 0 |
| 633 | chr7 | 110746000 | 110747000 | 0.000 | 0.040 | LRRN3 | 1.00000 | 0 |
| 634 | chr7 | 110747000 | 110748000 | 0.000 | 0.000 | LRRN3 | 1.00000 | 0 |
| 635 | chr7 | 110748000 | 110749000 | 0.000 | 0.000 | LRRN3 | 1.00000 | 0 |
| 636 | chr7 | 110755000 | 110756000 | 0.000 | 0.000 | LRRN3 | 1.00000 | 0 |
| 637 | chr7 | 110764000 | 110765000 | 0.000 | 0.000 | LRRN3 | 1.00000 | 0 |
| 638 | chr7 | 110767000 | 110768000 | 0.040 | 0.000 | LRRN3 | 1.00000 | 0 |
| 639 | chr7 | 110769000 | 110770000 | 0.000 | 0.040 | LRRN3 | 1.00000 | 0 |
| 640 | chr7 | 110771000 | 110772000 | 0.040 | 0.040 | LRRN3 | 1.00000 | 0 |
| 641 | chr7 | 110779000 | 110780000 | 0.000 | 0.000 | LRRN3 | 1.00000 | 0 |
| 642 | chr7 | 110780000 | 110781000 | 0.000 | 0.040 | LRRN3 | 1.00000 | 0 |
| 643 | chr7 | 110783000 | 110784000 | 0.000 | 0.040 | LRRN3 | 1.00000 | 0 |
| 644 | chr7 | 110785000 | 110786000 | 0.000 | 0.080 | LRRN3 | 0.48980 | 0 |
| 645 | chr7 | 110801000 | 110802000 | 0.000 | 0.040 | LRRN3 | 1.00000 | 0 |
| 646 | chr7 | 110802000 | 110803000 | 0.000 | 0.040 | LRRN3 | 1.00000 | 0 |
| 647 | chr7 | 110810000 | 110811000 | 0.000 | 0.000 | LRRN3 | 1.00000 | 0 |
| 648 | chr7 | 110816000 | 110817000 | 0.000 | 0.000 | LRRN3 | 1.00000 | 0 |
| 649 | chr7 | 110821000 | 110822000 | 0.000 | 0.040 | LRRN3 | 1.00000 | 0 |
| 650 | chr7 | 110824000 | 110825000 | 0.000 | 0.000 | LRRN3 | 1.00000 | 0 |
| 651 | chr7 | 110827000 | 110828000 | 0.040 | 0.000 | LRRN3 | 1.00000 | 0 |
| 652 | chr7 | 110836000 | 110837000 | 0.040 | 0.040 | LRRN3 | 1.00000 | 0 |
| 653 | chr7 | 110847000 | 110848000 | 0.000 | 0.040 | LRRN3 | 1.00000 | 0 |
| 654 | chr7 | 111567000 | 111568000 | 0.000 | 0.000 | DOCK4 | 1.00000 | 0 |
| 655 | chr7 | 119056000 | 119057000 | 0.040 | 0.000 | KCND2 | 1.00000 | 0 |
| 656 | chr7 | 121380000 | 121381000 | 0.040 | 0.000 | PTPRZ1 | 1.00000 | 0 |
| 657 | chr7 | 123887000 | 123888000 | 0.000 | 0.000 | TMEM229A | 1.00000 | 0 |
| 658 | chr7 | 125262000 | 125263000 | 0.000 | 0.040 | POT1 | 1.00000 | 0 |
| 659 | chr7 | 145723000 | 145724000 | 0.000 | 0.000 | CNTNAP2 | 1.00000 | 0 |
| 660 | chr7 | 148508000 | 148509000 | 0.000 | 0.000 | EZH2 | 1.00000 | 0 |
| 661 | chr7 | 155127000 | 155128000 | 0.000 | 0.000 | BLACE | 1.00000 | 0 |
| 662 | chr7 | 157162000 | 157163000 | 0.040 | 0.000 | DNAJB6 | 1.00000 | 0 |
| 663 | chr7 | 158684000 | 158685000 | 0.000 | 0.040 | WDR60 | 1.00000 | 0 |
| 664 | chr8 | 1646000 | 1647000 | 0.000 | 0.040 | DLGAP2 | 1.00000 | 0 |
| 665 | chr8 | 5558000 | 5559000 | 0.000 | 0.040 | MCPH1 | 1.00000 | 0 |
| 666 | chr8 | 5612000 | 5613000 | 0.000 | 0.000 | MCPH1 | 1.00000 | 0 |
| 667 | chr8 | 8602000 | 8603000 | 0.000 | 0.120 | MFHAS1 | 0.23469 | 0 |
| 668 | chr8 | 8706000 | 8707000 | 0.000 | 0.000 | MFHAS1 | 1.00000 | 0 |
| 669 | chr8 | 8717000 | 8718000 | 0.000 | 0.040 | MFHAS1 | 1.00000 | 0 |
| 670 | chr8 | 11352000 | 11353000 | 0.040 | 0.040 | BLK | 1.00000 | 0 |
| 671 | chr8 | 14080000 | 14081000 | 0.000 | 0.040 | SGCZ | 1.00000 | 0 |
| 672 | chr8 | 14796000 | 14797000 | 0.040 | 0.000 | SGCZ | 1.00000 | 0 |
| 673 | chr8 | 16090000 | 16091000 | 0.000 | 0.040 | MSR1 | 1.00000 | 0 |
| 674 | chr8 | 16187000 | 16188000 | 0.000 | 0.080 | MSR1 | 0.48980 | 0 |
| 675 | chr8 | 23101000 | 23102000 | 0.000 | 0.040 | CHMP7 | 1.00000 | 0 |
| 676 | chr8 | 24207000 | 24208000 | 0.000 | 0.000 | ADAM28 | 1.00000 | 0 |
| 677 | chr8 | 29155000 | 29156000 | 0.000 | 0.040 | KIF13B | 1.00000 | 0 |
| 678 | chr8 | 35657000 | 35658000 | 0.000 | 0.000 | AC012215.1 | 1.00000 | 0 |
| 679 | chr8 | 38759000 | 38760000 | 0.040 | 0.000 | PLEKHA2 | 1.00000 | 0 |
| 680 | chr8 | 54986000 | 54987000 | 0.040 | 0.000 | LYPLA1 | 1.00000 | 0 |
| 681 | chr8 | 60031000 | 60032000 | 0.040 | 0.000 | TOX | 1.00000 | 0 |
| 682 | chr8 | 67525000 | 67526000 | 0.040 | 0.000 | MYBL1 | 1.00000 | 0 |
| 683 | chr8 | 77105000 | 77106000 | 0.000 | 0.000 | ZFHX4 | 1.00000 | 0 |
| 684 | chr8 | 78400000 | 78401000 | 0.000 | 0.040 | PEX2 | 1.00000 | 0 |
| 685 | chr8 | 90322000 | 90323000 | 0.040 | 0.000 | RIPK2 | 1.00000 | 0 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 686 | chr8 | 93199000 | 93200000 | 0.000 | 0.040 | RUNX1T1 | 1.00000 | 0 |
| 687 | chr8 | 94618000 | 94619000 | 0.000 | 0.040 | FAM92A1 | 1.00000 | 0 |
| 688 | chr8 | 110586000 | 110587000 | 0.000 | 0.040 | SYBU | 1.00000 | 0 |
| 689 | chr8 | 126687000 | 126688000 | 0.000 | 0.000 | TRIB1 | 1.00000 | 0 |
| 690 | chr8 | 128748000 | 128749000 | 0.080 | 0.280 | MYC | 0.13833 | 1 |
| 691 | chr8 | 128749000 | 128750000 | 0.080 | 0.320 | MYC | 0.07375 | 1 |
| 692 | chr8 | 128750000 | 128751000 | 0.080 | 0.120 | MYC | 1.00000 | 1 |
| 693 | chr8 | 128751000 | 128752000 | 0.040 | 0.080 | MYC | 1.00000 | 1 |
| 694 | chr8 | 128752000 | 128753000 | 0.040 | 0.000 | MYC | 1.00000 | 1 |
| 695 | chr8 | 137918000 | 137919000 | 0.000 | 0.040 | FAM135B | 1.00000 | 0 |
| 696 | chr8 | 138274000 | 138275000 | 0.000 | 0.000 | FAM135B | 1.00000 | 0 |
| 697 | chr8 | 143183000 | 143184000 | 0.000 | 0.040 | TSNARE1 | 1.00000 | 0 |
| 698 | chr8 | 144123000 | 144124000 | 0.000 | 0.040 | C8orf31 | 1.00000 | 0 |
| 699 | chr9 | 6411000 | 6412000 | 0.040 | 0.040 | UHRF2 | 1.00000 | 0 |
| 700 | chr9 | 6413000 | 6414000 | 0.040 | 0.040 | UHRF2 | 1.00000 | 0 |
| 701 | chr9 | 6414000 | 6415000 | 0.000 | 0.040 | UHRF2 | 1.00000 | 0 |
| 702 | chr9 | 9928000 | 9929000 | 0.000 | 0.000 | PTPRD | 1.00000 | 0 |
| 703 | chr9 | 13965000 | 13966000 | 0.040 | 0.000 | NFIB | 1.00000 | 0 |
| 704 | chr9 | 22824000 | 22825000 | 0.040 | 0.000 | DMRTA1 | 1.00000 | 0 |
| 705 | chr9 | 25260000 | 25261000 | 0.040 | 0.000 | TUSC1 | 1.00000 | 0 |
| 706 | chr9 | 29890000 | 29891000 | 0.040 | 0.000 | LINGO2 | 1.00000 | 0 |
| 707 | chr9 | 30656000 | 30657000 | 0.000 | 0.040 | ACO1 | 1.00000 | 0 |
| 708 | chr9 | 37003000 | 37004000 | 0.040 | 0.000 | PAX5 | 1.00000 | 1 |
| 709 | chr9 | 37005000 | 37006000 | 0.040 | 0.000 | PAX5 | 1.00000 | 1 |
| 710 | chr9 | 37024000 | 37025000 | 0.040 | 0.040 | PAX5 | 1.00000 | 1 |
| 711 | chr9 | 37025000 | 37026000 | 0.160 | 0.120 | PAX5 | 1.00000 | 1 |
| 712 | chr9 | 37026000 | 37027000 | 0.240 | 0.120 | PAX5 | 0.46349 | 1 |
| 713 | chr9 | 37027000 | 37028000 | 0.080 | 0.040 | PAX5 | 1.00000 | 1 |
| 714 | chr9 | 37033000 | 37034000 | 0.120 | 0.040 | PAX5 | 0.60921 | 1 |
| 715 | chr9 | 37034000 | 37035000 | 0.120 | 0.040 | PAX5 | 0.60921 | 1 |
| 716 | chr9 | 37035000 | 37036000 | 0.000 | 0.040 | PAX5 | 1.00000 | 1 |
| 717 | chr9 | 37196000 | 37197000 | 0.040 | 0.000 | ZCCHC7 | 1.00000 | 0 |
| 718 | chr9 | 37197000 | 37198000 | 0.040 | 0.000 | ZCCHC7 | 1.00000 | 0 |
| 719 | chr9 | 37293000 | 37294000 | 0.000 | 0.000 | ZCCHC7 | 1.00000 | 0 |
| 720 | chr9 | 37294000 | 37295000 | 0.080 | 0.000 | ZCCHC7 | 0.48980 | 0 |
| 721 | chr9 | 37327000 | 37328000 | 0.040 | 0.000 | ZCCHC7 | 1.00000 | 0 |
| 722 | chr9 | 37336000 | 37337000 | 0.080 | 0.000 | ZCCHC7 | 0.48980 | 0 |
| 723 | chr9 | 37337000 | 37338000 | 0.000 | 0.000 | ZCCHC7 | 1.00000 | 0 |
| 724 | chr9 | 37338000 | 37339000 | 0.000 | 0.040 | ZCCHC7 | 1.00000 | 0 |
| 725 | chr9 | 37369000 | 37370000 | 0.040 | 0.000 | ZCCHC7 | 1.00000 | 0 |
| 726 | chr9 | 37371000 | 37372000 | 0.080 | 0.080 | ZCCHC7 | 1.00000 | 0 |
| 727 | chr9 | 37372000 | 37373000 | 0.000 | 0.000 | ZCCHC7 | 1.00000 | 0 |
| 728 | chr9 | 37383000 | 37384000 | 0.080 | 0.080 | ZCCHC7 | 1.00000 | 0 |
| 729 | chr9 | 37384000 | 37385000 | 0.120 | 0.040 | ZCCHC7 | 0.60921 | 0 |
| 730 | chr9 | 37385000 | 37386000 | 0.040 | 0.000 | ZCCHC7 | 1.00000 | 0 |
| 731 | chr9 | 37387000 | 37388000 | 0.080 | 0.040 | ZCCHC7 | 1.00000 | 0 |
| 732 | chr9 | 37397000 | 37398000 | 0.040 | 0.120 | GRHPR | 0.60921 | 0 |
| 733 | chr9 | 37398000 | 37399000 | 0.040 | 0.000 | GRHPR | 1.00000 | 0 |
| 734 | chr9 | 37399000 | 37400000 | 0.080 | 0.000 | GRHPR | 0.48980 | 0 |
| 735 | chr9 | 37402000 | 37403000 | 0.000 | 0.040 | GRHPR | 1.00000 | 0 |
| 736 | chr9 | 37406000 | 37407000 | 0.000 | 0.040 | GRHPR | 1.00000 | 0 |
| 737 | chr9 | 37407000 | 37408000 | 0.200 | 0.080 | GRHPR | 0.41743 | 0 |
| 738 | chr9 | 37408000 | 37409000 | 0.080 | 0.000 | GRHPR | 0.48980 | 0 |
| 739 | chr9 | 37410000 | 37411000 | 0.000 | 0.000 | GRHPR | 1.00000 | 0 |
| 740 | chr9 | 37424000 | 37425000 | 0.040 | 0.040 | GRHPR | 1.00000 | 0 |
| 741 | chr9 | 37425000 | 37426000 | 0.000 | 0.040 | GRHPR | 1.00000 | 0 |
| 742 | chr9 | 112811000 | 112812000 | 0.080 | 0.080 | AKAP2 | 1.00000 | 0 |
| 743 | chr9 | 117037000 | 117038000 | 0.000 | 0.040 | COL27A1 | 1.00000 | 0 |
| 744 | chr9 | 119779000 | 119780000 | 0.040 | 0.000 | ASTN2 | 1.00000 | 0 |
| 745 | chr9 | 126232000 | 126233000 | 0.040 | 0.000 | DENND1A | 1.00000 | 0 |
| 746 | chr9 | 130741000 | 130742000 | 0.040 | 0.000 | FAM102A | 1.00000 | 1 |
| 747 | chr9 | 130742000 | 130743000 | 0.040 | 0.080 | FAM102A | 1.00000 | 1 |
| 748 | chr9 | 132767000 | 132768000 | 0.000 | 0.040 | FNBP1 | 1.00000 | 0 |
| 749 | chr9 | 132785000 | 132786000 | 0.000 | 0.040 | FNBP1 | 1.00000 | 0 |
| 750 | chr9 | 132803000 | 132804000 | 0.000 | 0.040 | FNBP1 | 1.00000 | 0 |
| 751 | chr9 | 132804000 | 132805000 | 0.040 | 0.120 | FNBP1 | 0.60921 | 0 |
| 752 | chr9 | 134551000 | 134552000 | 0.040 | 0.000 | RAPGEF1 | 1.00000 | 0 |
| 753 | chr9 | 138874000 | 138875000 | 0.000 | 0.040 | UBAC1 | 1.00000 | 0 |
| 754 | chr10 | 3333000 | 3334000 | 0.000 | 0.000 | PITRM1 | 1.00000 | 0 |
| 755 | chr10 | 5707000 | 5708000 | 0.040 | 0.040 | ASB13 | 1.00000 | 0 |
| 756 | chr10 | 5728000 | 5729000 | 0.000 | 0.040 | ASB13 | 1.00000 | 0 |
| 757 | chr10 | 15393000 | 15394000 | 0.000 | 0.000 | FAM171A1 | 1.00000 | 0 |
| 758 | chr10 | 20796000 | 20797000 | 0.040 | 0.000 | PLXDC2 | 1.00000 | 0 |
| 759 | chr10 | 35424000 | 35425000 | 0.000 | 0.000 | CREM | 1.00000 | 0 |
| 760 | chr10 | 56678000 | 56679000 | 0.000 | 0.000 | PCDH15 | 1.00000 | 0 |
| 761 | chr10 | 63440000 | 63441000 | 0.000 | 0.040 | C10orf107 | 1.00000 | 0 |
| 762 | chr10 | 63659000 | 63660000 | 0.040 | 0.000 | ARID5B | 1.00000 | 1 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 763 | chr10 | 63660000 | 63661000 | 0.040 | 0.080 | ARID5B | 1.00000 | 1 |
| 764 | chr10 | 63662000 | 63663000 | 0.000 | 0.000 | ARID5B | 1.00000 | 1 |
| 765 | chr10 | 63720000 | 63721000 | 0.000 | 0.000 | ARID5B | 1.00000 | 1 |
| 766 | chr10 | 63803000 | 63804000 | 0.000 | 0.000 | ARID5B | 1.00000 | 1 |
| 767 | chr10 | 63809000 | 63810000 | 0.000 | 0.080 | ARID5B | 0.48980 | 1 |
| 768 | chr10 | 63810000 | 63811000 | 0.000 | 0.040 | ARID5B | 1.00000 | 1 |
| 769 | chr10 | 67907000 | 67908000 | 0.000 | 0.040 | CTNNA3 | 1.00000 | 0 |
| 770 | chr10 | 68474000 | 68475000 | 0.000 | 0.000 | CTNNA3 | 1.00000 | 0 |
| 771 | chr10 | 98510000 | 98511000 | 0.080 | 0.000 | PIK3AP1 | 0.48980 | 0 |
| 772 | chr10 | 101384000 | 101385000 | 0.000 | 0.000 | SLC25A28 | 1.00000 | 0 |
| 773 | chr10 | 108276000 | 108277000 | 0.040 | 0.000 | SORCS1 | 1.00000 | 0 |
| 774 | chr10 | 113473000 | 113474000 | 0.040 | 0.040 | GPAM | 1.00000 | 0 |
| 775 | chr10 | 113636000 | 113637000 | 0.040 | 0.000 | GPAM | 1.00000 | 0 |
| 776 | chr10 | 116458000 | 116459000 | 0.000 | 0.040 | ABLIM1 | 1.00000 | 0 |
| 777 | chr10 | 121623000 | 121624000 | 0.040 | 0.000 | MCMBP | 1.00000 | 0 |
| 778 | chr10 | 132973000 | 132974000 | 0.040 | 0.000 | TCERG1L | 1.00000 | 0 |
| 779 | chr10 | 134326000 | 134327000 | 0.000 | 0.000 | INPP5A | 1.00000 | 0 |
| 780 | chr11 | 871000 | 872000 | 0.040 | 0.040 | CHID1 | 1.00000 | 0 |
| 781 | chr11 | 1149000 | 1150000 | 0.000 | 0.000 | MUC5AC | 1.00000 | 0 |
| 782 | chr11 | 25065000 | 25066000 | 0.040 | 0.000 | LUZP2 | 1.00000 | 0 |
| 783 | chr11 | 25289000 | 25290000 | 0.040 | 0.040 | LUZP2 | 1.00000 | 0 |
| 784 | chr11 | 27216000 | 27217000 | 0.000 | 0.040 | BBOX1 | 1.00000 | 0 |
| 785 | chr11 | 28849000 | 28850000 | 0.000 | 0.000 | METTL15 | 1.00000 | 0 |
| 786 | chr11 | 29253000 | 29254000 | 0.040 | 0.000 | KCNA4 | 1.00000 | 0 |
| 787 | chr11 | 29900000 | 29901000 | 0.000 | 0.000 | KCNA4 | 1.00000 | 0 |
| 788 | chr11 | 40626000 | 40627000 | 0.000 | 0.000 | LRRC4C | 1.00000 | 0 |
| 789 | chr11 | 40845000 | 40846000 | 0.000 | 0.000 | LRRC4C | 1.00000 | 0 |
| 790 | chr11 | 40868000 | 40869000 | 0.000 | 0.000 | LRRC4C | 1.00000 | 0 |
| 791 | chr11 | 41066000 | 41067000 | 0.000 | 0.000 | LRRC4C | 1.00000 | 0 |
| 792 | chr11 | 41844000 | 41845000 | 0.000 | 0.000 | API5 | 1.00000 | 0 |
| 793 | chr11 | 57171000 | 57172000 | 0.040 | 0.000 | SLC43A3 | 1.00000 | 0 |
| 794 | chr11 | 60224000 | 60225000 | 0.040 | 0.080 | MS4A1 | 1.00000 | 1 |
| 795 | chr11 | 65190000 | 65191000 | 0.080 | 0.120 | FRMD8 | 1.00000 | 0 |
| 796 | chr11 | 65191000 | 65192000 | 0.080 | 0.120 | FRMD8 | 1.00000 | 0 |
| 797 | chr11 | 65266000 | 65267000 | 0.000 | 0.040 | SCYL1 | 1.00000 | 0 |
| 798 | chr11 | 65267000 | 65268000 | 0.120 | 0.040 | SCYL1 | 0.60921 | 0 |
| 799 | chr11 | 85963000 | 85964000 | 0.000 | 0.000 | EED | 1.00000 | 0 |
| 800 | chr11 | 92261000 | 92262000 | 0.000 | 0.040 | FAT3 | 1.00000 | 0 |
| 801 | chr11 | 102117000 | 102118000 | 0.000 | 0.000 | YAP1 | 1.00000 | 0 |
| 802 | chr11 | 102188000 | 102189000 | 0.200 | 0.280 | BIRC3 | 0.74164 | 1 |
| 803 | chr11 | 102189000 | 102190000 | 0.040 | 0.080 | BIRC3 | 1.00000 | 1 |
| 804 | chr11 | 107497000 | 107498000 | 0.000 | 0.000 | ELMOD1 | 1.00000 | 0 |
| 805 | chr11 | 108781000 | 108782000 | 0.000 | 0.040 | DDX10 | 1.00000 | 0 |
| 806 | chr11 | 108975000 | 108976000 | 0.040 | 0.000 | DDX10 | 1.00000 | 0 |
| 807 | chr11 | 109066000 | 109067000 | 0.000 | 0.000 | C11orf87 | 1.00000 | 0 |
| 808 | chr11 | 111248000 | 111249000 | 0.000 | 0.040 | POU2AF1 | 1.00000 | 1 |
| 809 | chr11 | 111249000 | 111250000 | 0.120 | 0.160 | POU2AF1 | 1.00000 | 1 |
| 810 | chr11 | 115761000 | 115762000 | 0.000 | 0.040 | CADM1 | 1.00000 | 0 |
| 811 | chr11 | 118723000 | 118724000 | 0.040 | 0.000 | CXCR5 | 1.00000 | 0 |
| 812 | chr11 | 126496000 | 126497000 | 0.040 | 0.000 | KIRREL3 | 1.00000 | 0 |
| 813 | chr11 | 128390000 | 128391000 | 0.000 | 0.040 | ETS1 | 1.00000 | 1 |
| 814 | chr11 | 128391000 | 128392000 | 0.160 | 0.040 | ETS1 | 0.34868 | 1 |
| 815 | chr12 | 6554000 | 6555000 | 0.000 | 0.040 | CD27 | 1.00000 | 0 |
| 816 | chr12 | 8762000 | 8763000 | 0.040 | 0.000 | AICDA | 1.00000 | 0 |
| 817 | chr12 | 8763000 | 8764000 | 0.080 | 0.040 | AICDA | 1.00000 | 0 |
| 818 | chr12 | 8764000 | 8765000 | 0.080 | 0.000 | AICDA | 0.48980 | 0 |
| 819 | chr12 | 8765000 | 8766000 | 0.040 | 0.000 | AICDA | 1.00000 | 0 |
| 820 | chr12 | 9823000 | 9824000 | 0.040 | 0.000 | CLEC2D | 1.00000 | 0 |
| 821 | chr12 | 11710000 | 11711000 | 0.000 | 0.040 | ETV6 | 1.00000 | 1 |
| 822 | chr12 | 11803000 | 11804000 | 0.040 | 0.000 | ETV6 | 1.00000 | 1 |
| 823 | chr12 | 14923000 | 14924000 | 0.040 | 0.040 | HIST4H4 | 1.00000 | 1 |
| 824 | chr12 | 16717000 | 16718000 | 0.000 | 0.000 | LMO3 | 1.00000 | 0 |
| 825 | chr12 | 23805000 | 23806000 | 0.000 | 0.040 | SOX5 | 1.00000 | 0 |
| 826 | chr12 | 25149000 | 25150000 | 0.000 | 0.040 | C12orf77 | 1.00000 | 0 |
| 827 | chr12 | 25151000 | 25152000 | 0.000 | 0.040 | C12orf77 | 1.00000 | 0 |
| 828 | chr12 | 25174000 | 25175000 | 0.040 | 0.040 | C12orf77 | 1.00000 | 0 |
| 829 | chr12 | 25205000 | 25206000 | 0.040 | 0.040 | LRMP | 1.00000 | 1 |
| 830 | chr12 | 25206000 | 25207000 | 0.080 | 0.120 | LRMP | 1.00000 | 1 |
| 831 | chr12 | 25207000 | 25208000 | 0.080 | 0.120 | LRMP | 1.00000 | 1 |
| 832 | chr12 | 25208000 | 25209000 | 0.000 | 0.040 | LRMP | 1.00000 | 1 |
| 833 | chr12 | 25665000 | 25666000 | 0.000 | 0.000 | IFLTD1 | 1.00000 | 0 |
| 834 | chr12 | 38920000 | 38921000 | 0.000 | 0.000 | CPNE8 | 1.00000 | 0 |
| 835 | chr12 | 48027000 | 48028000 | 0.080 | 0.080 | RPAP3 | 1.00000 | 0 |
| 836 | chr12 | 57496000 | 57497000 | 0.040 | 0.000 | STAT6 | 1.00000 | 0 |
| 837 | chr12 | 69203000 | 69204000 | 0.000 | 0.040 | MDM2 | 1.00000 | 0 |
| 838 | chr12 | 76202000 | 76203000 | 0.000 | 0.000 | PHLDA1 | 1.00000 | 0 |
| 839 | chr12 | 79270000 | 79271000 | 0.000 | 0.000 | SYT1 | 1.00000 | 0 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 840 | chr12 | 82572000 | 82573000 | 0.040 | 0.000 | CCDC59 | 1.00000 | 0 |
| 841 | chr12 | 84837000 | 84838000 | 0.000 | 0.000 | SLC6A15 | 1.00000 | 0 |
| 842 | chr12 | 86114000 | 86115000 | 0.040 | 0.000 | RASSF9 | 1.00000 | 0 |
| 843 | chr12 | 86115000 | 86116000 | 0.040 | 0.000 | RASSF9 | 1.00000 | 0 |
| 844 | chr12 | 92538000 | 92539000 | 0.080 | 0.080 | BTG1 | 1.00000 | 1 |
| 845 | chr12 | 92539000 | 92540000 | 0.080 | 0.040 | BTG1 | 1.00000 | 1 |
| 846 | chr12 | 96030000 | 96031000 | 0.000 | 0.040 | NTN4 | 1.00000 | 0 |
| 847 | chr12 | 110171000 | 110172000 | 0.000 | 0.040 | FAM222A | 1.00000 | 0 |
| 848 | chr12 | 110980000 | 110981000 | 0.000 | 0.040 | PPTC7 | 1.00000 | 0 |
| 849 | chr12 | 113493000 | 113494000 | 0.080 | 0.040 | DTX1 | 0.48980 | 1 |
| 850 | chr12 | 113494000 | 113495000 | 0.240 | 0.040 | DTX1 | 0.09828 | 1 |
| 851 | chr12 | 113495000 | 113496000 | 0.160 | 0.080 | DTX1 | 0.66710 | 1 |
| 852 | chr12 | 113496000 | 113497000 | 0.160 | 0.040 | DTX1 | 0.34868 | 1 |
| 853 | chr12 | 113497000 | 113498000 | 0.080 | 0.040 | DTX1 | 1.00000 | 1 |
| 854 | chr12 | 113499000 | 113500000 | 0.000 | 0.000 | DTX1 | 1.00000 | 1 |
| 855 | chr12 | 113512000 | 113513000 | 0.000 | 0.000 | DTX1 | 1.00000 | 1 |
| 856 | chr12 | 115966000 | 115967000 | 0.000 | 0.000 | MED13L | 1.00000 | 0 |
| 857 | chr12 | 122432000 | 122433000 | 0.040 | 0.000 | WDR66 | 1.00000 | 0 |
| 858 | chr12 | 122433000 | 122434000 | 0.080 | 0.000 | WDR66 | 0.48980 | 0 |
| 859 | chr12 | 122447000 | 122448000 | 0.000 | 0.040 | WDR66 | 1.00000 | 0 |
| 860 | chr12 | 122458000 | 122459000 | 0.080 | 0.120 | BCL7A | 1.00000 | 1 |
| 861 | chr12 | 122459000 | 122460000 | 0.240 | 0.320 | BCL7A | 0.75361 | 1 |
| 862 | chr12 | 122460000 | 122461000 | 0.120 | 0.280 | BCL7A | 0.28902 | 1 |
| 863 | chr12 | 122461000 | 122462000 | 0.240 | 0.240 | BCL7A | 1.00000 | 1 |
| 864 | chr12 | 122462000 | 122463000 | 0.160 | 0.200 | BCL7A | 1.00000 | 1 |
| 865 | chr12 | 122463000 | 122464000 | 0.120 | 0.200 | BCL7A | 0.70194 | 1 |
| 866 | chr12 | 124054000 | 124055000 | 0.000 | 0.080 | TMED2 | 0.48980 | 0 |
| 867 | chr12 | 127965000 | 127966000 | 0.000 | 0.000 | TMEM132C | 1.00000 | 0 |
| 868 | chr12 | 131303000 | 131304000 | 0.000 | 0.120 | STX2 | 0.23469 | 0 |
| 869 | chr12 | 131649000 | 131650000 | 0.000 | 0.000 | GPR133 | 1.00000 | 0 |
| 870 | chr12 | 133306000 | 133307000 | 0.000 | 0.000 | ANKLE2 | 1.00000 | 0 |
| 871 | chr13 | 21913000 | 21914000 | 0.040 | 0.040 | ZDHHC20 | 1.00000 | 0 |
| 872 | chr13 | 32116000 | 32117000 | 0.040 | 0.040 | RXFP2 | 1.00000 | 0 |
| 873 | chr13 | 35498000 | 35499000 | 0.000 | 0.000 | NBEA | 1.00000 | 0 |
| 874 | chr13 | 38371000 | 38372000 | 0.040 | 0.000 | TRPC4 | 1.00000 | 0 |
| 875 | chr13 | 38630000 | 38631000 | 0.040 | 0.000 | TRPC4 | 1.00000 | 0 |
| 876 | chr13 | 41156000 | 41157000 | 0.000 | 0.040 | FOXO1 | 1.00000 | 1 |
| 877 | chr13 | 41240000 | 41241000 | 0.000 | 0.040 | FOXO1 | 1.00000 | 1 |
| 878 | chr13 | 46958000 | 46959000 | 0.000 | 0.000 | KIAA0226L | 1.00000 | 0 |
| 879 | chr13 | 46959000 | 46960000 | 0.040 | 0.000 | KIAA0226L | 1.00000 | 0 |
| 880 | chr13 | 46960000 | 46961000 | 0.160 | 0.040 | KIAA0226L | 0.34868 | 0 |
| 881 | chr13 | 46961000 | 46962000 | 0.000 | 0.040 | KIAA0226L | 1.00000 | 0 |
| 882 | chr13 | 46962000 | 46963000 | 0.000 | 0.040 | KIAA0226L | 1.00000 | 0 |
| 883 | chr13 | 55239000 | 55240000 | 0.040 | 0.000 | OLFM4 | 1.00000 | 0 |
| 884 | chr13 | 55386000 | 55387000 | 0.040 | 0.000 | OLFM4 | 1.00000 | 0 |
| 885 | chr13 | 55598000 | 55599000 | 0.000 | 0.000 | OLFM4 | 1.00000 | 0 |
| 886 | chr13 | 57222000 | 57223000 | 0.000 | 0.040 | PRR20A; PRR20D PRR20B PRR20E; | 1.00000 | 0 |
| 887 | chr13 | 61343000 | 61344000 | 0.000 | 0.000 | TDRD3 | 1.00000 | 0 |
| 888 | chr13 | 62830000 | 62831000 | 0.000 | 0.000 | PCDH20 | 1.00000 | 0 |
| 889 | chr13 | 63049000 | 63050000 | 0.080 | 0.000 | PCDH20 | 0.48980 | 0 |
| 890 | chr13 | 63157000 | 63158000 | 0.000 | 0.000 | AL445989.1 | 1.00000 | 0 |
| 891 | chr13 | 63214000 | 63215000 | 0.040 | 0.000 | AL445989.1 | 1.00000 | 0 |
| 892 | chr13 | 64802000 | 64803000 | 0.040 | 0.040 | AL445989.1 | 1.00000 | 0 |
| 893 | chr13 | 65637000 | 65638000 | 0.000 | 0.040 | PCDH9 | 1.00000 | 0 |
| 894 | chr13 | 68656000 | 68657000 | 0.000 | 0.000 | PCDH9 | 1.00000 | 0 |
| 895 | chr13 | 69418000 | 69419000 | 0.000 | 0.000 | KLHL1 | 1.00000 | 0 |
| 896 | chr13 | 70956000 | 70957000 | 0.040 | 0.000 | KLHL1 | 1.00000 | 0 |
| 897 | chr13 | 74542000 | 74543000 | 0.000 | 0.040 | KLF12 | 1.00000 | 0 |
| 898 | chr13 | 75983000 | 75984000 | 0.000 | 0.040 | TBC1D4 | 1.00000 | 0 |
| 899 | chr13 | 75984000 | 75985000 | 0.000 | 0.160 | TBC1D4 | 0.10986 | 0 |
| 900 | chr13 | 83450000 | 83451000 | 0.000 | 0.000 | SLITRK1 | 1.00000 | 0 |
| 901 | chr13 | 84641000 | 84642000 | 0.040 | 0.000 | SLITRK1 | 1.00000 | 0 |
| 902 | chr13 | 87793000 | 87794000 | 0.040 | 0.000 | SLITRK5 | 1.00000 | 0 |
| 903 | chr13 | 91480000 | 91481000 | 0.000 | 0.000 | GPC5 | 1.00000 | 0 |
| 904 | chr13 | 106081000 | 106082000 | 0.040 | 0.000 | DAOA | 1.00000 | 0 |
| 905 | chr13 | 114786000 | 114787000 | 0.040 | 0.000 | RASA3 | 1.00000 | 0 |
| 906 | chr13 | 114916000 | 114917000 | 0.000 | 0.000 | RASA3 | 1.00000 | 0 |
| 907 | chr14 | 22948000 | 22949000 | 0.040 | 0.000 | TRAJ56 | 1.00000 | 0 |
| 908 | chr14 | 22949000 | 22950000 | 0.040 | 0.000 | TRAJ56 | 1.00000 | 0 |
| 909 | chr14 | 22950000 | 22951000 | 0.040 | 0.000 | TRAJ54 | 1.00000 | 0 |
| 910 | chr14 | 22977000 | 22978000 | 0.000 | 0.040 | TRAJ33 | 1.00000 | 0 |
| 911 | chr14 | 27286000 | 27287000 | 0.000 | 0.000 | NOVA1 | 1.00000 | 0 |
| 912 | chr14 | 28645000 | 28646000 | 0.000 | 0.000 | FOXG1 | 1.00000 | 0 |
| 913 | chr14 | 49407000 | 49408000 | 0.000 | 0.000 | RPS29 | 1.00000 | 0 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 914 | chr14 | 50864000 | 50865000 | 0.000 | 0.000 | CDKL1 | 1.00000 | 0 |
| 915 | chr14 | 54812000 | 54813000 | 0.000 | 0.000 | CDKN3 | 1.00000 | 0 |
| 916 | chr14 | 55348000 | 55349000 | 0.040 | 0.000 | GCH1 | 1.00000 | 0 |
| 917 | chr14 | 59827000 | 59828000 | 0.000 | 0.040 | DAAM1 | 1.00000 | 0 |
| 918 | chr14 | 63143000 | 63144000 | 0.000 | 0.040 | KCNH5 | 1.00000 | 0 |
| 919 | chr14 | 64194000 | 64195000 | 0.000 | 0.040 | SGPP1 | 1.00000 | 0 |
| 920 | chr14 | 69258000 | 69259000 | 0.240 | 0.200 | ZFP36L1 | 1.00000 | 1 |
| 921 | chr14 | 69259000 | 69260000 | 0.360 | 0.240 | ZFP36L1 | 0.53803 | 1 |
| 922 | chr14 | 78418000 | 78419000 | 0.000 | 0.040 | ADCK1 | 1.00000 | 0 |
| 923 | chr14 | 81685000 | 81686000 | 0.000 | 0.040 | GTF2A1 | 1.00000 | 0 |
| 924 | chr14 | 84420000 | 84421000 | 0.040 | 0.000 | FLRT2 | 1.00000 | 0 |
| 925 | chr14 | 91883000 | 91884000 | 0.040 | 0.000 | CCDC88C | 1.00000 | 0 |
| 926 | chr14 | 94941000 | 94942000 | 0.000 | 0.120 | SERPINA9 | 0.23469 | 1 |
| 927 | chr14 | 94942000 | 94943000 | 0.040 | 0.200 | SERPINA9 | 0.18946 | 1 |
| 928 | chr14 | 96179000 | 96180000 | 0.160 | 0.120 | TCL1A | 1.00000 | 1 |
| 929 | chr14 | 96180000 | 96181000 | 0.080 | 0.160 | TCL1A | 0.66710 | 1 |
| 930 | chr14 | 101597000 | 101598000 | 0.000 | 0.000 | AL117190.3 | 1.00000 | 0 |
| 931 | chr14 | 102285000 | 102286000 | 0.040 | 0.000 | PPP2R5C | 1.00000 | 0 |
| 932 | chr14 | 105954000 | 105955000 | 0.040 | 0.040 | CRIP1 | 1.00000 | 0 |
| 933 | chr14 | 106031000 | 106032000 | 0.040 | 0.000 | IGHA2 | 1.00000 | 0 |
| 934 | chr14 | 106042000 | 106043000 | 0.080 | 0.200 | IGHA2 | 0.41743 | 0 |
| 935 | chr14 | 106048000 | 106049000 | 0.040 | 0.040 | IGHA2 | 1.00000 | 0 |
| 936 | chr14 | 106054000 | 106055000 | 0.040 | 0.040 | IGHA2 | 1.00000 | 0 |
| 937 | chr14 | 106055000 | 106056000 | 0.080 | 0.240 | IGHA2 | 0.24672 | 0 |
| 938 | chr14 | 106056000 | 106057000 | 0.040 | 0.200 | IGHA2 | 0.18946 | 0 |
| 939 | chr14 | 106057000 | 106058000 | 0.000 | 0.080 | IGHA2 | 0.48980 | 0 |
| 940 | chr14 | 106058000 | 106059000 | 0.000 | 0.080 | IGHA2 | 0.48980 | 0 |
| 941 | chr14 | 06066000 | 106067000 | 0.000 | 0.120 | IGHE | 0.23469 | 0 |
| 942 | chr14 | 106067000 | 106068000 | 0.000 | 0.120 | IGHE | 0.23469 | 0 |
| 943 | chr14 | 106068000 | 106069000 | 0.040 | 0.120 | IGHE | 0.60921 | 0 |
| 944 | chr14 | 106069000 | 106070000 | 0.040 | 0.200 | IGHE | 0.18946 | 0 |
| 945 | chr14 | 106070000 | 106071000 | 0.000 | 0.160 | IGHE | 0.10986 | 0 |
| 946 | chr14 | 106071000 | 106072000 | 0.000 | 0.160 | IGHE | 0.10986 | 0 |
| 947 | chr14 | 106072000 | 106073000 | 0.000 | 0.120 | IGHE | 0.23469 | 0 |
| 948 | chr14 | 106082000 | 106083000 | 0.000 | 0.000 | IGHG4 | 1.00000 | 0 |
| 949 | chr14 | 106092000 | 106093000 | 0.040 | 0.000 | IGHG4 | 1.00000 | 0 |
| 950 | chr14 | 106094000 | 106095000 | 0.160 | 0.200 | IGHG4 | 1.00000 | 0 |
| 951 | chr14 | 106095000 | 106096000 | 0.080 | 0.160 | IGHG4 | 0.66710 | 0 |
| 952 | chr14 | 106110000 | 106111000 | 0.080 | 0.040 | IGHG2 | 1.00000 | 0 |
| 953 | chr14 | 106111000 | 106112000 | 0.000 | 0.040 | IGHG2 | 1.00000 | 0 |
| 954 | chr14 | 106112000 | 106113000 | 0.280 | 0.200 | IGHG2 | 0.74164 | 0 |
| 955 | chr14 | 106113000 | 106114000 | 0.240 | 0.320 | IGHG2 | 0.75361 | 0 |
| 956 | chr14 | 106114000 | 106115000 | 0.320 | 0.200 | IGHG2 | 0.52019 | 0 |
| 957 | chr14 | 106146000 | 106147000 | 0.000 | 0.000 | IGHA1 | 1.00000 | 0 |
| 958 | chr14 | 106151000 | 106152000 | 0.040 | 0.000 | IGHA1 | 1.00000 | 0 |
| 959 | chr14 | 106152000 | 106153000 | 0.040 | 0.000 | IGHA1 | 1.00000 | 0 |
| 960 | chr14 | 106161000 | 106162000 | 0.000 | 0.040 | IGHA1 | 1.00000 | 0 |
| 961 | chr14 | 106173000 | 106174000 | 0.040 | 0.040 | IGHA1 | 1.00000 | 0 |
| 962 | chr14 | 106174000 | 106175000 | 0.040 | 0.000 | IGHA1 | 1.00000 | 0 |
| 963 | chr14 | 106175000 | 106176000 | 0.040 | 0.000 | IGHA1 | 1.00000 | 0 |
| 964 | chr14 | 106176000 | 106177000 | 0.080 | 0.040 | IGHA1 | 1.00000 | 0 |
| 965 | chr14 | 106177000 | 106178000 | 0.000 | 0.000 | IGHA1 | 1.00000 | 0 |
| 966 | chr14 | 106178000 | 106179000 | 0.120 | 0.000 | IGHA1 | 0.23469 | 0 |
| 967 | chr14 | 106208000 | 106209000 | 0.040 | 0.040 | IGHG1 | 1.00000 | 0 |
| 968 | chr14 | 106209000 | 106210000 | 0.160 | 0.080 | IGHG1 | 0.66710 | 0 |
| 969 | chr14 | 106210000 | 106211000 | 0.160 | 0.120 | IGHG1 | 1.00000 | 0 |
| 970 | chr14 | 106211000 | 106212000 | 0.440 | 0.120 | IGHG1 | 0.02548 | 0 |
| 971 | chr14 | 106212000 | 106213000 | 0.520 | 0.120 | IGHG1 | 0.00544 | 0 |
| 972 | chr14 | 106213000 | 106214000 | 0.520 | 0.120 | IGHG1 | 0.00544 | 0 |
| 973 | chr14 | 106214000 | 106215000 | 0.240 | 0.000 | IGHG1 | 0.02229 | 0 |
| 974 | chr14 | 106237000 | 106238000 | 0.080 | 0.040 | IGHG3 | 1.00000 | 0 |
| 975 | chr14 | 106238000 | 106239000 | 0.320 | 0.120 | IGHG3 | 0.17062 | 0 |
| 976 | chr14 | 106239000 | 106240000 | 0.440 | 0.040 | IGHG3 | 0.00192 | 0 |
| 977 | chr14 | 106240000 | 06241000 | 0.480 | 0.080 | IGHG3 | 0.00361 | 0 |
| 978 | chr14 | 106241000 | 106242000 | 0.320 | 0.040 | IGHG3 | 0.02322 | 0 |
| 979 | chr14 | 106242000 | 106243000 | 0.040 | 0.000 | IGHG3 | 1.00000 | 0 |
| 980 | chr14 | 106321000 | 106322000 | 0.040 | 0.000 | IGHM | 1.00000 | 0 |
| 981 | chr14 | 106322000 | 106323000 | 0.240 | 0.040 | IGHM | 0.09828 | 0 |
| 982 | chr14 | 106323000 | 106324000 | 0.400 | 0.160 | IGHM | 0.11366 | 0 |
| 983 | chr14 | 106324000 | 106325000 | 0.320 | 0.120 | IGHM | 0.17062 | 0 |
| 984 | chr14 | 106325000 | 106326000 | 0.160 | 0.320 | IGHM | 0.32089 | 0 |
| 985 | chr14 | 106326000 | 106327000 | 0.920 | 0.920 | IGHJ6 | 1.00000 | 0 |
| 986 | chr14 | 106327000 | 106328000 | 0.800 | 0.760 | IGHJ6 | 1.00000 | 0 |
| 987 | chr14 | 106328000 | 106329000 | 0.680 | 0.800 | IGHJ6 | 0.52019 | 0 |
| 988 | chr14 | 106329000 | 106330000 | 0.880 | 0.920 | IGHJ6 | 1.00000 | 0 |
| 989 | chr14 | 106330000 | 106331000 | 0.720 | 0.520 | IGHJ3; IGHJ4; IGHJ5; | 0.24363 | 0 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 990 | chr14 | 106331000 | 106332000 | 0.120 | 0.080 | IGHD7-27; IGHJ1; IGHJ2 | 1.00000 | 0 |
| 991 | chr14 | 106338000 | 106339000 | 0.040 | 0.000 | IGHD7-27 | 1.00000 | 0 |
| 992 | chr14 | 106350000 | 106351000 | 0.040 | 0.000 | IGHD4-23 | 1.00000 | 0 |
| 993 | chr14 | 106352000 | 106353000 | 0.000 | 0.040 | IGHD3-22 | 1.00000 | 0 |
| 994 | chr14 | 106353000 | 106354000 | 0.000 | 0.000 | IGHD2-21 | 1.00000 | 0 |
| 995 | chr14 | 106354000 | 106355000 | 0.000 | 0.040 | IGHD2-21 | 1.00000 | 0 |
| 996 | chr14 | 106355000 | 106356000 | 0.000 | 0.040 | IGHD2-21 | 1.00000 | 0 |
| 997 | chr14 | 106357000 | 106358000 | 0.040 | 0.080 | IGHD1-20; IGHD6-19; | 1.00000 | 0 |
| 998 | chr14 | 106358000 | 106359000 | 0.000 | 0.040 | IGHD5-18 | 1.00000 | 0 |
| 999 | chr14 | 106362000 | 106363000 | 0.000 | 0.000 | IGHD3-16 | 1.00000 | 0 |
| 1000 | chr14 | 106364000 | 106365000 | 0.040 | 0.000 | IGHD2-15 | 1.00000 | 0 |
| 1001 | chr14 | 106367000 | 106368000 | 0.040 | 0.000 | IGHD6-13 | 1.00000 | 0 |
| 1002 | chr14 | 106370000 | 106371000 | 0.080 | 0.000 | IGHD3-10; IGHD3-9; | 0.48980 | 0 |
| 1003 | chr14 | 106371000 | 106372000 | 0.040 | 0.000 | IGHD3-9 | 1.00000 | 0 |
| 1004 | chr14 | 106372000 | 106373000 | 0.040 | 0.000 | IGHD2-8 | 1.00000 | 0 |
| 1005 | chr14 | 106375000 | 106376000 | 0.000 | 0.000 | IGHD1-7 | 1.00000 | 0 |
| 1006 | chr14 | 106376000 | 106377000 | 0.000 | 0.040 | IGHD6-6 | 1.00000 | 0 |
| 1007 | chr14 | 106380000 | 106381000 | 0.000 | 0.040 | IGHD3-3 | 1.00000 | 0 |
| 1008 | chr14 | 106381000 | 106382000 | 0.000 | 0.040 | IGHD2-2 | 1.00000 | 0 |
| 1009 | chr14 | 106382000 | 106383000 | 0.040 | 0.120 | IGHD2-2 | 0.60921 | 0 |
| 1010 | chr14 | 106383000 | 106384000 | 0.080 | 0.040 | IGHD2-2 | 1.00000 | 0 |
| 1011 | chr14 | 106384000 | 106385000 | 0.040 | 0.040 | IGHD1-1 | 1.00000 | 0 |
| 1012 | chr14 | 106385000 | 106386000 | 0.080 | 0.040 | IGHD1-1 | 1.00000 | 0 |
| 1013 | chr14 | 106387000 | 106388000 | 0.040 | 0.080 | KIAA0125 | 1.00000 | 0 |
| 1014 | chr14 | 106405000 | 106406000 | 0.000 | 0.040 | IGHV6-1 | 1.00000 | 0 |
| 1015 | chr14 | 106406000 | 106407000 | 0.000 | 0.040 | IGHV6-1 | 1.00000 | 0 |
| 1016 | chr14 | 106419000 | 106420000 | 0.000 | 0.080 | IGHV6-1 | 0.48980 | 0 |
| 1017 | chr14 | 106452000 | 106453000 | 0.040 | 0.000 | IGHV1-2 | 1.00000 | 0 |
| 1018 | chr14 | 106453000 | 106454000 | 0.080 | 0.000 | IGHV1-2 | 0.48980 | 0 |
| 1019 | chr14 | 106454000 | 106455000 | 0.040 | 0.000 | IGHV1-2 | 1.00000 | 0 |
| 1020 | chr14 | 106494000 | 106495000 | 0.000 | 0.040 | IGHV2-5 | 1.00000 | 0 |
| 1021 | chr14 | 106518000 | 106519000 | 0.000 | 0.080 | IGHV3-7 | 0.48980 | 0 |
| 1022 | chr14 | 106519000 | 106520000 | 0.000 | 0.080 | IGHV3-7 | 0.48980 | 0 |
| 1023 | chr14 | 106539000 | 106540000 | 0.000 | 0.040 | IGHV1-8 | 1.00000 | 0 |
| 1024 | chr14 | 106552000 | 106553000 | 0.000 | 0.000 | IGHV3-9 | 1.00000 | 0 |
| 1025 | chr14 | 106573000 | 106574000 | 0.040 | 0.000 | IGHV3-11 | 1.00000 | 0 |
| 1026 | chr14 | 106574000 | 106575000 | 0.040 | 0.000 | IGHV3-11 | 1.00000 | 0 |
| 1027 | chr14 | 106578000 | 106579000 | 0.040 | 0.000 | IGHV3-11 | 1.00000 | 0 |
| 1028 | chr14 | 106579000 | 106580000 | 0.040 | 0.000 | IGHV3-11 | 1.00000 | 0 |
| 1029 | chr14 | 106610000 | 106611000 | 0.000 | 0.000 | IGHV3-15 | 1.00000 | 0 |
| 1030 | chr14 | 106641000 | 106642000 | 0.040 | 0.040 | IGHV1-18 | 1.00000 | 0 |
| 1031 | chr14 | 106642000 | 106643000 | 0.040 | 0.000 | IGHV1-18 | 1.00000 | 0 |
| 1032 | chr14 | 106691000 | 106692000 | 0.000 | 0.000 | IGHV3-21 | 1.00000 | 0 |
| 1033 | chr14 | 106692000 | 106693000 | 0.000 | 0.040 | IGHV3-21 | 1.00000 | 0 |
| 1034 | chr14 | 106725000 | 106726000 | 0.120 | 0.160 | IGHV3-23 | 1.00000 | 0 |
| 1035 | chr14 | 106726000 | 106727000 | 0.040 | 0.080 | IGHV3-23 | 1.00000 | 0 |
| 1036 | chr14 | 106733000 | 106734000 | 0.000 | 0.080 | IGHV1-24 | 0.48980 | 0 |
| 1037 | chr14 | 106757000 | 106758000 | 0.000 | 0.040 | IGHV2-26 | 1.00000 | 0 |
| 1038 | chr14 | 106758000 | 106759000 | 0.000 | 0.040 | IGHV2-26 | 1.00000 | 0 |
| 1039 | chr14 | 106791000 | 106792000 | 0.040 | 0.040 | IGHV3-30 | 1.00000 | 0 |
| 1040 | chr14 | 106804000 | 106805000 | 0.040 | 0.040 | IGHV4-31 | 1.00000 | 0 |
| 1041 | chr14 | 106805000 | 106806000 | 0.040 | 0.040 | IGHV4-31 | 1.00000 | 0 |
| 1042 | chr14 | 106806000 | 106807000 | 0.000 | 0.000 | IGHV4-31 | 1.00000 | 0 |
| 1043 | chr14 | 106815000 | 106816000 | 0.000 | 0.040 | IGHV3-33 | 1.00000 | 0 |
| 1044 | chr14 | 106816000 | 106817000 | 0.000 | 0.160 | IGHV3-33 | 0.10986 | 0 |
| 1045 | chr14 | 106817000 | 106818000 | 0.000 | 0.080 | IGHV3-33 | 0.48980 | 0 |
| 1046 | chr14 | 106829000 | 106830000 | 0.160 | 0.080 | IGHV4-34 | 0.66710 | 0 |
| 1047 | chr14 | 106830000 | 106831000 | 0.160 | 0.000 | IGHV4-34 | 0.10986 | 0 |
| 1048 | chr14 | 106877000 | 106878000 | 0.040 | 0.080 | IGHV4-39 | 1.00000 | 0 |
| 1049 | chr14 | 106878000 | 106879000 | 0.000 | 0.080 | IGHV4-39 | 0.48980 | 0 |
| 1050 | chr14 | 106967000 | 106968000 | 0.040 | 0.040 | IGHV1-46 | 1.00000 | 0 |
| 1051 | chr14 | 106994000 | 106995000 | 0.000 | 0.120 | IGHV3-48 | 0.23469 | 0 |
| 1052 | chr14 | 106995000 | 106996000 | 0.000 | 0.000 | IGHV3-48 | 1.00000 | 0 |
| 1053 | chr14 | 107034000 | 107035000 | 0.040 | 0.000 | IGHV5-51 | 1.00000 | 0 |
| 1054 | chr14 | 107035000 | 107036000 | 0.080 | 0.000 | IGHV5-51 | 0.48980 | 0 |
| 1055 | chr14 | 107048000 | 107049000 | 0.000 | 0.000 | IGHV3-53 | 1.00000 | 0 |
| 1056 | chr14 | 107049000 | 107050000 | 0.000 | 0.000 | IGHV3-53 | 1.00000 | 0 |
| 1057 | chr14 | 107083000 | 107084000 | 0.040 | 0.040 | IGHV4-59 | 1.00000 | 0 |
| 1058 | chr14 | 107084000 | 107085000 | 0.000 | 0.040 | IGHV4-59 | 1.00000 | 0 |
| 1059 | chr14 | 107095000 | 107096000 | 0.040 | 0.000 | IGHV4-61 | 1.00000 | 0 |
| 1060 | chr14 | 107113000 | 107114000 | 0.080 | 0.000 | IGHV3-64 | 0.48980 | 0 |
| 1061 | chr14 | 107114000 | 107115000 | 0.080 | 0.000 | IGHV3-64 | 0.48980 | 0 |
| 1062 | chr14 | 107169000 | 107170000 | 0.200 | 0.240 | IGHV1-69 | 1.00000 | 0 |
| 1063 | chr14 | 107170000 | 107171000 | 0.360 | 0.280 | IGHV1-69 | 0.76241 | 0 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 1064 | chr14 | 107176000 | 107177000 | 0.200 | 0.200 | IGHV2-70 | 1.00000 | 0 |
| 1065 | chr14 | 107177000 | 107178000 | 0.080 | 0.040 | IGHV2-70 | 1.00000 | 0 |
| 1066 | chr14 | 107178000 | 107179000 | 0.200 | 0.520 | IGHV2-70 | 0.03776 | 0 |
| 1067 | chr14 | 107179000 | 107180000 | 0.240 | 0.360 | IGHV2-70 | 0.53803 | 0 |
| 1068 | chr14 | 107183000 | 107184000 | 0.000 | 0.000 | IGHV2-70 | 1.00000 | 0 |
| 1069 | chr14 | 107199000 | 107200000 | 0.000 | 0.080 | IGHV3-72 | 0.48980 | 0 |
| 1070 | chr14 | 107218000 | 107219000 | 0.000 | 0.080 | IGHV3-74 | 0.48980 | 0 |
| 1071 | chr14 | 107219000 | 107220000 | 0.000 | 0.160 | IGHV3-74 | 0.10986 | 0 |
| 1072 | chr14 | 107221000 | 107222000 | 0.000 | 0.080 | IGHV3-74 | 0.48980 | 0 |
| 1073 | chr14 | 107232000 | 107233000 | 0.000 | 0.000 | IGHV3-74 | 1.00000 | 0 |
| 1074 | chr14 | 107253000 | 107254000 | 0.000 | 0.000 | IGHV7-81 | 1.00000 | 0 |
| 1075 | chr14 | 107258000 | 107259000 | 0.000 | 0.040 | IGHV7-81 | 1.00000 | 0 |
| 1076 | chr14 | 107259000 | 107260000 | 0.160 | 0.200 | IGHV7-81 | 1.00000 | 0 |
| 1077 | chr15 | 45003000 | 45004000 | 0.040 | 0.040 | B2M | 1.00000 | 0 |
| 1078 | chr15 | 45007000 | 45008000 | 0.000 | 0.000 | B2M | 1.00000 | 0 |
| 1079 | chr15 | 45814000 | 45815000 | 0.000 | 0.040 | SLC30A4 | 1.00000 | 0 |
| 1080 | chr15 | 59664000 | 59665000 | 0.000 | 0.080 | MYO1E | 0.48980 | 0 |
| 1081 | chr15 | 65588000 | 65589000 | 0.040 | 0.000 | PARP16 | 1.00000 | 0 |
| 1082 | chr15 | 78332000 | 78333000 | 0.000 | 0.000 | TBC1D2B | 1.00000 | 0 |
| 1083 | chr15 | 83227000 | 83228000 | 0.000 | 0.040 | CPEB1 | 1.00000 | 0 |
| 1084 | chr15 | 86226000 | 86227000 | 0.040 | 0.040 | AKAP13 | 1.00000 | 0 |
| 1085 | chr15 | 86233000 | 86234000 | 0.040 | 0.000 | AKAP13 | 1.00000 | 0 |
| 1086 | chr15 | 86245000 | 86246000 | 0.080 | 0.120 | AKAP13 | 1.00000 | 0 |
| 1087 | chr16 | 368000 | 369000 | 0.000 | 0.040 | AXIN1 | 1.00000 | 0 |
| 1088 | chr16 | 3788000 | 3789000 | 0.040 | 0.000 | CREBBP | 1.00000 | 0 |
| 1089 | chr16 | 10971000 | 10972000 | 0.080 | 0.120 | CIITA | 1.00000 | 1 |
| 1090 | chr16 | 10972000 | 10973000 | 0.120 | 0.320 | CIITA | 0.17062 | 1 |
| 1091 | chr16 | 10973000 | 10974000 | 0.120 | 0.240 | CIITA | 0.46349 | 1 |
| 1092 | chr16 | 10974000 | 10975000 | 0.080 | 0.120 | CIITA | 1.00000 | 1 |
| 1093 | chr16 | 11348000 | 11349000 | 0.080 | 0.200 | SOCS1 | 0.41743 | 1 |
| 1094 | chr16 | 11349000 | 11350000 | 0.120 | 0.240 | SOCS1 | 0.46349 | 1 |
| 1095 | chr16 | 21167000 | 21168000 | 0.040 | 0.000 | DNAH3 | 1.00000 | 0 |
| 1096 | chr16 | 27325000 | 27326000 | 0.000 | 0.040 | CTD-3203P2.2 | 1.00000 | 0 |
| 1097 | chr16 | 27326000 | 27327000 | 0.080 | 0.080 | CTD-3203P2.2 | 1.00000 | 0 |
| 1098 | chr16 | 27327000 | 27328000 | 0.000 | 0.000 | IL4R | 1.00000 | 0 |
| 1099 | chr16 | 27414000 | 27415000 | 0.040 | 0.000 | IL21R | 1.00000 | 0 |
| 1100 | chr16 | 29248000 | 29249000 | 0.000 | 0.000 | 61E3.4 | 1.00000 | 0 |
| 1101 | chr16 | 31910000 | 31911000 | 0.040 | 0.000 | ZNF267 | 1.00000 | 0 |
| 1102 | chr16 | 46821000 | 46822000 | 0.000 | 0.040 | C16orf87 | 1.00000 | 0 |
| 1103 | chr16 | 50985000 | 50986000 | 0.040 | 0.000 | CYLD | 1.00000 | 0 |
| 1104 | chr16 | 64351000 | 64352000 | 0.000 | 0.040 | CDH11 | 1.00000 | 0 |
| 1105 | chr16 | 78398000 | 78399000 | 0.000 | 0.000 | WWOX | 1.00000 | 0 |
| 1106 | chr16 | 78615000 | 78616000 | 0.040 | 0.000 | WWOX | 1.00000 | 0 |
| 1107 | chr16 | 78753000 | 78754000 | 0.000 | 0.040 | WWOX | 1.00000 | 0 |
| 1108 | chr16 | 78811000 | 78812000 | 0.000 | 0.040 | WWOX | 1.00000 | 0 |
| 1109 | chr16 | 79988000 | 79989000 | 0.000 | 0.040 | MAF | 1.00000 | 0 |
| 1110 | chr16 | 81836000 | 81837000 | 0.000 | 0.000 | PLCG2 | 1.00000 | 0 |
| 1111 | chr16 | 85932000 | 85933000 | 0.040 | 0.040 | IRF8 | 1.00000 | 1 |
| 1112 | chr16 | 85933000 | 85934000 | 0.080 | 0.240 | IRF8 | 0.24672 | 1 |
| 1113 | chr16 | 85934000 | 85935000 | 0.040 | 0.000 | IRF8 | 1.00000 | 1 |
| 1114 | chr16 | 85936000 | 85937000 | 0.000 | 0.000 | IRF8 | 1.00000 | 1 |
| 1115 | chr16 | 88441000 | 88442000 | 0.040 | 0.000 | ZNF469 | 1.00000 | 0 |
| 1116 | chr17 | 3598000 | 3599000 | 0.040 | 0.040 | P2RX5; P2RX5-TAX1BP3P2RX5; | 1.00000 | 0 |
| 1117 | chr17 | 17286000 | 17287000 | 0.080 | 0.000 | SMCR9 | 0.48980 | 0 |
| 1118 | chr17 | 21194000 | 21195000 | 0.000 | 0.040 | MAP2K3 | 1.00000 | 0 |
| 1119 | chr17 | 29646000 | 29647000 | 0.000 | 0.000 | EVI2A | 1.00000 | 0 |
| 1120 | chr17 | 38020000 | 38021000 | 0.000 | 0.040 | IKZF3 | 1.00000 | 0 |
| 1121 | chr17 | 43662000 | 43663000 | 0.040 | 0.00€ | PLEKHM1 | 1.00000 | 0 |
| 1122 | chr17 | 56408000 | 56409000 | 0.120 | 0.040 | BZRAP1 | 0.60921 | 0 |
| 1123 | chr17 | 56409000 | 56410000 | 0.360 | 0.200 | BZRAP1 | 0.34513 | 0 |
| 1124 | chr17 | 57916000 | 57917000 | 0.040 | 0.080 | VMP1 | 1.00000 | 1 |
| 1125 | chr17 | 57917000 | 57918000 | 0.040 | 0.080 | VMP1 | 1.00000 | 1 |
| 1126 | chr17 | 62007000 | 62008000 | 0.040 | 0.000 | CD79B | 1.00000 | 0 |
| 1127 | chr17 | 62008000 | 62009000 | 0.040 | 0.000 | CD79B | 1.00000 | 0 |
| 1128 | chr17 | 63067000 | 63068000 | 0.000 | 0.000 | GNA13 | 1.00000 | 0 |
| 1129 | chr17 | 65676000 | 65677000 | 0.040 | 0.000 | PITPNC1 | 1.00000 | 0 |
| 1130 | chr17 | 69365000 | 69366000 | 0.000 | 0.040 | AC007461.1 | 1.00000 | 0 |
| 1131 | chr17 | 70083000 | 70084000 | 0.000 | 0.000 | SOX9 | 1.00000 | 0 |
| 1132 | chr17 | 74733000 | 74734000 | 0.000 | 0.000 | SRSF2 | 1.00000 | 0 |
| 1133 | chr17 | 75447000 | 75448000 | 0.080 | 0.000 | 9 Sep. 2019 | 0.48980 | 0 |
| 1134 | chr17 | 75448000 | 75449000 | 0.040 | 0.000 | 9 Sep. 2019 | 1.00000 | 0 |
| 1135 | chr17 | 76775000 | 76776000 | 0.000 | 0.000 | CYTH1 | 1.00000 | 0 |
| 1136 | chr17 | 80928000 | 80929000 | 0.000 | 0.000 | B3GNTL1 | 1.00000 | 0 |
| 1137 | chr17 | 80976000 | 80977000 | 0.000 | 0.040 | B3GNTL1 | 1.00000 | 0 |
| 1138 | chr18 | 2709000 | 2710000 | 0.000 | 0.000 | SMCHD1 | 1.00000 | 0 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 1139 | chr18 | 3600000 | 3601000 | 0.040 | 0.000 | DLGAP1 | 1.00000 | 0 |
| 1140 | chr18 | 12062000 | 12063000 | 0.000 | 0.000 | ANKRD62 | 1.00000 | 0 |
| 1141 | chr18 | 27771000 | 27772000 | 0.040 | 0.000 | DSC3 | 1.00000 | 0 |
| 1142 | chr18 | 28066000 | 28067000 | 0.000 | 0.040 | DSC3 | 1.00000 | 0 |
| 1143 | chr18 | 30349000 | 30350000 | 0.000 | 0.000 | AC012123.1; KLHL14; | 1.00000 | 0 |
| 1144 | chr18 | 36806000 | 36807000 | 0.040 | 0.000 | CELF4 | 1.00000 | 0 |
| 1145 | chr18 | 37751000 | 37752000 | 0.000 | 0.040 | PIK3C3 | 1.00000 | 0 |
| 1146 | chr18 | 38672000 | 38673000 | 0.000 | 0.040 | PIK3C3 | 1.00000 | 0 |
| 1147 | chr18 | 42168000 | 42169000 | 0.000 | 0.000 | SETBP1 | 1.00000 | 0 |
| 1148 | chr18 | 51952000 | 51953000 | 0.040 | 0.000 | C18orf54 | 1.00000 | 0 |
| 1149 | chr18 | 52447000 | 52448000 | 0.000 | 0.080 | RAB27B | 0.48980 | 0 |
| 1150 | chr18 | 52988000 | 52989000 | 0.040 | 0.000 | TCF4 | 1.00000 | 0 |
| 1151 | chr18 | 54653000 | 54654000 | 0.000 | 0.000 | WDR7 | 1.00000 | 0 |
| 1152 | chr18 | 60794000 | 60795000 | 0.000 | 0.080 | BCL2 | 0.48980 | 1 |
| 1153 | chr18 | 60805000 | 60806000 | 0.000 | 0.000 | BCL2 | 1.00000 | 1 |
| 1154 | chr18 | 60806000 | 60807000 | 0.000 | 0.120 | BCL2 | 0.23469 | 1 |
| 1155 | chr18 | 60809000 | 60810000 | 0.000 | 0.080 | BCL2 | 0.48980 | 1 |
| 1156 | chr18 | 60821000 | 60822000 | 0.000 | 0.040 | BCL2 | 1.00000 | 1 |
| 1157 | chr18 | 60825000 | 60826000 | 0.000 | 0.080 | BCL2 | 0.48980 | 1 |
| 1158 | chr18 | 60826000 | 60827000 | 0.000 | 0.040 | BCL2 | 1.00000 | 1 |
| 1159 | chr18 | 60828000 | 60829000 | 0.000 | 0.000 | BCL2 | 1.00000 | 1 |
| 1160 | chr18 | 60873000 | 60874000 | 0.000 | 0.040 | BCL2 | 1.00000 | 1 |
| 1161 | chr18 | 60875000 | 60876000 | 0.000 | 0.000 | BCL2 | 1.00000 | 1 |
| 1162 | chr18 | 60876000 | 60877000 | 0.000 | 0.040 | BCL2 | 1.00000 | 1 |
| 1163 | chr18 | 60983000 | 60984000 | 0.000 | 0.040 | BCL2 | 1.00000 | 1 |
| 1164 | chr18 | 60984000 | 60985000 | 0.000 | 0.240 | BCL2 | 0.02229 | 1 |
| 1165 | chr18 | 60985000 | 60986000 | 0.040 | 0.320 | BCL2 | 0.02322 | 1 |
| 1166 | chr18 | 60986000 | 60987000 | 0.080 | 0.320 | BCL2 | 0.07375 | 1 |
| 1167 | chr18 | 60987000 | 60988000 | 0.080 | 0.320 | BCL2 | 0.07375 | 1 |
| 1168 | chr18 | 60988000 | 60989000 | 0.080 | 0.280 | BCL2 | 0.13833 | 1 |
| 1169 | chr18 | 61810000 | 61811000 | 0.040 | 0.000 | SERPINB8 | 1.00000 | 0 |
| 1170 | chr18 | 63080000 | 63081000 | 0.000 | 0.000 | CDH7 | 1.00000 | 0 |
| 1171 | chr18 | 63791000 | 63792000 | 0.000 | 0.000 | CDH7 | 1.00000 | 0 |
| 1172 | chr18 | 63875000 | 63876000 | 0.040 | 0.000 | CDH19 | 1.00000 | 0 |
| 1173 | chr18 | 64643000 | 64644000 | 0.000 | 0.000 | CDH19 | 1.00000 | 0 |
| 1174 | chr18 | 65863000 | 65864000 | 0.000 | 0.000 | TMX3 | 1.00000 | 0 |
| 1175 | chr18 | 66328000 | 66329000 | 0.040 | 0.000 | TMX3 | 1.00000 | 0 |
| 1176 | chr18 | 70462000 | 70463000 | 0.000 | 0.040 | NETO1 | 1.00000 | 0 |
| 1177 | chr18 | 73767000 | 73768000 | 0.040 | 0.000 | ZNF516 | 1.00000 | 0 |
| 1178 | chr18 | 76515000 | 76516000 | 0.040 | 0.000 | SALL3 | 1.00000 | 0 |
| 1179 | chr18 | 76724000 | 76725000 | 0.040 | 0.000 | SALL3 | 1.00000 | 0 |
| 1180 | chr18 | 76725000 | 76726000 | 0.040 | 0.000 | SALL3 | 1.00000 | 0 |
| 1181 | chr19 | 1612000 | 1613000 | 0.000 | 0.040 | TCF3 | 1.00000 | 0 |
| 1182 | chr19 | 2476000 | 2477000 | 0.040 | 0.040 | GADD45B | 1.00000 | 1 |
| 1183 | chr19 | 10304000 | 10305000 | 0.040 | 0.080 | DNMT1 | 1.00000 | 0 |
| 1184 | chr19 | 10305000 | 10306000 | 0.000 | 0.080 | DNMT1 | 0.48980 | 0 |
| 1185 | chr19 | 10335000 | 10336000 | 0.000 | 0.040 | S1PR2 | 1.00000 | 1 |
| 1186 | chr19 | 10340000 | 10341000 | 0.080 | 0.160 | S1PR2 | 0.66710 | 1 |
| 1187 | chr19 | 10341000 | 10342000 | 0.120 | 0.280 | S1PR2 | 0.28902 | 1 |
| 1188 | chr19 | 16030000 | 16031000 | 0.000 | 0.000 | CYP4F11 | 1.00000 | 0 |
| 1189 | chr19 | 16436000 | 16437000 | 0.040 | 0.000 | KLF2 | 1.00000 | 1 |
| 1190 | chr19 | 20889000 | 20890000 | 0.000 | 0.040 | ZNF626 | 1.00000 | 0 |
| 1191 | chr19 | 21073000 | 21074000 | 0.040 | 0.000 | ZNF85 | 1.00000 | 0 |
| 1192 | chr19 | 21092000 | 21093000 | 0.000 | 0.040 | ZNF85 | 1.00000 | 0 |
| 1193 | chr19 | 23841000 | 23842000 | 0.040 | 0.000 | ZNF675 | 1.00000 | 0 |
| 1194 | chr19 | 29256000 | 29257000 | 0.040 | 0.000 | UQCRFS1 | 1.00000 | 0 |
| 1195 | chr19 | 44183000 | 44184000 | 0.040 | 0.000 | PLAUR | 1.00000 | 0 |
| 1196 | chr19 | 50399000 | 50400000 | 0.040 | 0.040 | IL4I1 | 1.00000 | 0 |
| 1197 | chr19 | 53419000 | 53420000 | 0.000 | 0.000 | ZNF321P; ZNF816; ZNF816-ZNF321P ZNF321P ZNF816-ZNF321P; | 1.00000 | 0 |
| 1198 | chr20 | 15470000 | 15471000 | 0.000 | 0.040 | MACROD2 | 1.00000 | 0 |
| 1199 | chr20 | 23359000 | 23360000 | 0.000 | 0.000 | NAPB | 1.00000 | 0 |
| 1200 | chr20 | 23912000 | 23913000 | 0.000 | 0.000 | CST5 | 1.00000 | 0 |
| 1201 | chr20 | 46131000 | 46132000 | 0.040 | 0.120 | NCOA3 | 0.60921 | 1 |
| 1202 | chr20 | 49127000 | 49128000 | 0.000 | 0.000 | PTPN1 | 1.00000 | 0 |
| 1203 | chr20 | 49648000 | 49649000 | 0.040 | 0.000 | KCNG1 | 1.00000 | 0 |
| 1204 | chr20 | 61607000 | 61608000 | 0.000 | 0.000 | SLC17A9 | 1.00000 | 0 |
| 1205 | chr21 | 21597000 | 21598000 | 0.000 | 0.000 | NCAM2 | 1.00000 | 0 |
| 1206 | chr21 | 23458000 | 23459000 | 0.000 | 0.040 | NCAM2 | 1.00000 | 0 |
| 1207 | chr21 | 24998000 | 24999000 | 0.000 | 0.040 | MRPL39 | 1.00000 | 0 |
| 1208 | chr21 | 26935000 | 26936000 | 0.000 | 0.080 | MRPL39 | 0.48980 | 0 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 1209 | chr21 | 35779000 | 35780000 | 0.000 | 0.000 | SMIM11 | 1.00000 | 0 |
| 1210 | chr21 | 38779000 | 38780000 | 0.000 | 0.000 | DYRK1A | 1.00000 | 0 |
| 1211 | chr21 | 43254000 | 43255000 | 0.000 | 0.040 | PRDM15 | 1.00000 | 0 |
| 1212 | chr21 | 44612000 | 44613000 | 0.000 | 0.000 | CRYAA | 1.00000 | 0 |
| 1213 | chr21 | 45381000 | 45382000 | 0.040 | 0.000 | AGPAT3 | 1.00000 | 0 |
| 1214 | chr21 | 46058000 | 46059000 | 0.000 | 0.000 | KRTAP10-10 | 1.00000 | 0 |
| 1215 | chr22 | 19050000 | 19051000 | 0.000 | 0.000 | DGCR2 | 1.00000 | 0 |
| 1216 | chr22 | 20212000 | 20213000 | 0.040 | 0.000 | RTN4R | 1.00000 | 0 |
| 1217 | chr22 | 20708000 | 20709000 | 0.040 | 0.040 | FAM230A | 1.00000 | 0 |
| 1218 | chr22 | 21994000 | 21995000 | 0.000 | 0.000 | SDF2L1 | 1.00000 | 0 |
| 1219 | chr22 | 22379000 | 22380000 | 0.040 | 0.040 | IGLV4-69 | 1.00000 | 0 |
| 1220 | chr22 | 22380000 | 22381000 | 0.040 | 0.080 | IGLV4-69 | 1.00000 | 0 |
| 1221 | chr22 | 22381000 | 22382000 | 0.040 | 0.040 | IGLV4-69 | 1.00000 | 0 |
| 1222 | chr22 | 22385000 | 22386000 | 0.040 | 0.080 | IGLV4-69 | 1.00000 | 0 |
| 1223 | chr22 | 22452000 | 22453000 | 0.000 | 0.040 | IGLV8-61 | 1.00000 | 0 |
| 1224 | chr22 | 22453000 | 22454000 | 0.000 | 0.040 | IGLV8-61 | 1.00000 | 0 |
| 1225 | chr22 | 22516000 | 22517000 | 0.000 | 0.160 | IGLV4-60 | 0.10986 | 0 |
| 1226 | chr22 | 22517000 | 22518000 | 0.000 | 0.080 | IGLV4-60 | 0.48980 | 0 |
| 1227 | chr22 | 22550000 | 22551000 | 0.160 | 0.000 | IGLV6-57 | 0.10986 | 0 |
| 1228 | chr22 | 22569000 | 22570000 | 0.040 | 0.000 | IGLV10-54 | 1.00000 | 0 |
| 1229 | chr22 | 22676000 | 22677000 | 0.040 | 0.000 | IGLV1-51 | 1.00000 | 0 |
| 1230 | chr22 | 22677000 | 22678000 | 0.040 | 0.000 | IGLV1-51 | 1.00000 | 0 |
| 1231 | chr22 | 22707000 | 22708000 | 0.040 | 0.080 | IGLV5-48 | 1.00000 | 0 |
| 1232 | chr22 | 22712000 | 22713000 | 0.160 | 0.040 | IGLV1-47 | 0.34868 | 0 |
| 1233 | chr22 | 22723000 | 22724000 | 0.000 | 0.000 | IGLV7-46 | 1.00000 | 0 |
| 1234 | chr22 | 22724000 | 22725000 | 0.080 | 0.040 | IGLV7-46 | 1.00000 | 0 |
| 1235 | chr22 | 22730000 | 22731000 | 0.040 | 0.040 | IGLV5-45 | 1.00000 | 0 |
| 1236 | chr22 | 22731000 | 22732000 | 0.000 | 0.000 | IGLV5-45 | 1.00000 | 0 |
| 1237 | chr22 | 22735000 | 22736000 | 0.080 | 0.120 | IGLV1-44 | 1.00000 | 0 |
| 1238 | chr22 | 22749000 | 22750000 | 0.120 | 0.040 | IGLV7-43 | 0.60921 | 0 |
| 1239 | chr22 | 22758000 | 22759000 | 0.080 | 0.040 | IGLV1-40 | 1.00000 | 0 |
| 1240 | chr22 | 22759000 | 22760000 | 0.080 | 0.080 | IGLV1-40 | 1.00000 | 0 |
| 1241 | chr22 | 22764000 | 22765000 | 0.120 | 0.080 | IGLV1-40 | 1.00000 | 0 |
| 1242 | chr22 | 23028000 | 23029000 | 0.000 | 0.040 | IGLV3-25 | 1.00000 | 0 |
| 1243 | chr22 | 23029000 | 23030000 | 0.040 | 0.120 | IGLV3-25 | 0.60921 | 0 |
| 1244 | chr22 | 23035000 | 23036000 | 0.000 | 0.040 | IGLV2-23 | 1.00000 | 0 |
| 1245 | chr22 | 23039000 | 23040000 | 0.000 | 0.000 | IGLV2-23 | 1.00000 | 0 |
| 1246 | chr22 | 23040000 | 23041000 | 0.120 | 0.040 | IGLV2-23 | 0.60921 | 0 |
| 1247 | chr22 | 23041000 | 23042000 | 0.040 | 0.000 | IGLV2-23 | 1.00000 | 0 |
| 1248 | chr22 | 23055000 | 23056000 | 0.040 | 0.000 | IGLV3-21 | 1.00000 | 0 |
| 1249 | chr22 | 23063000 | 23064000 | 0.040 | 0.000 | IGLV3-19 | 1.00000 | 0 |
| 1250 | chr22 | 23090000 | 23091000 | 0.120 | 0.000 | IGLV3-16 | 0.23469 | 0 |
| 1251 | chr22 | 23100000 | 23101000 | 0.040 | 0.000 | IGLV2-14 | 1.00000 | 0 |
| 1252 | chr22 | 23101000 | 23102000 | 0.120 | 0.040 | IGLV2-14 | 0.60921 | 0 |
| 1253 | chr22 | 23114000 | 23115000 | 0.000 | 0.000 | IGLV3-12 | 1.00000 | 0 |
| 1254 | chr22 | 23134000 | 23135000 | 0.000 | 0.000 | IGLV2-11 | 1.00000 | 0 |
| 1255 | chr22 | 23154000 | 23155000 | 0.120 | 0.000 | IGLV3-10 | 0.23469 | 0 |
| 1256 | chr22 | 23161000 | 23162000 | 0.000 | 0.000 | IGLV3-9 | 1.00000 | 0 |
| 1257 | chr22 | 23162000 | 23163000 | 0.000 | 0.000 | IGLV3-9 | 1.00000 | 0 |
| 1258 | chr22 | 23165000 | 23166000 | 0.000 | 0.000 | IGLV2-8 | 1.00000 | 0 |
| 1259 | chr22 | 23192000 | 23193000 | 0.080 | 0.080 | IGLV4-3 | 1.00000 | 0 |
| 1260 | chr22 | 23197000 | 23198000 | 0.040 | 0.000 | IGLV4-3 | 1.00000 | 0 |
| 1261 | chr22 | 23198000 | 23199000 | 0.160 | 0.040 | IGLV4-3 | 0.34868 | 0 |
| 1262 | chr22 | 23199000 | 23200000 | 0.200 | 0.200 | IGLV4-3 | 1.00000 | 0 |
| 1263 | chr22 | 23203000 | 23204000 | 0.000 | 0.000 | IGLV4-3 | 1.00000 | 0 |
| 1264 | chr22 | 23204000 | 23205000 | 0.080 | 0.000 | IGLV4-3 | 0.48980 | 0 |
| 1265 | chr22 | 23205000 | 23206000 | 0.000 | 0.000 | IGLV4-3 | 1.00000 | 0 |
| 1266 | chr22 | 23207000 | 23208000 | 0.000 | 0.040 | IGLV4-3 | 1.00000 | 0 |
| 1267 | chr22 | 23209000 | 23210000 | 0.000 | 0.040 | IGLV4-3 | 1.00000 | 0 |
| 1268 | chr22 | 23213000 | 23214000 | 0.120 | 0.040 | IGLV4-3 | 0.60921 | 0 |
| 1269 | chr22 | 23214000 | 23215000 | 0.040 | 0.040 | IGLV4-3 | 1.00000 | 0 |
| 1270 | chr22 | 23219000 | 23220000 | 0.080 | 0.000 | IGLV3-1 | 0.48980 | 0 |
| 1271 | chr22 | 23220000 | 23221000 | 0.080 | 0.000 | IGLV3-1 | 0.48980 | 0 |
| 1272 | chr22 | 23222000 | 23223000 | 0.040 | 0.120 | IGLV3-1 | 0.60921 | 0 |
| 1273 | chr22 | 23223000 | 23224000 | 0.320 | 0.520 | IGLV3-1 | 0.25159 | 0 |
| 1274 | chr22 | 23224000 | 23225000 | 0.080 | 0.080 | IGLV3-1 | 1.00000 | 0 |
| 1275 | chr22 | 23226000 | 23227000 | 0.120 | 0.000 | IGLV3-1 | 0.23469 | 0 |
| 1276 | chr22 | 23227000 | 23228000 | 0.200 | 0.360 | IGLL5 | 0.34513 | 0 |
| 1277 | chr22 | 23228000 | 23229000 | 0.240 | 0.200 | IGLL5 | 1.00000 | 0 |
| 1278 | chr22 | 23229000 | 23230000 | 0.040 | 0.160 | IGLL5 | 0.34868 | 0 |
| 1279 | chr22 | 23230000 | 23231000 | 0.440 | 0.600 | IGLL5 | 0.39610 | 0 |
| 1280 | chr22 | 23231000 | 23232000 | 0.480 | 0.440 | IGLL5 | 1.00000 | 0 |
| 1281 | chr22 | 23232000 | 23233000 | 0.320 | 0.240 | IGLL5 | 0.75361 | 0 |
| 1282 | chr22 | 23233000 | 23234000 | 0.200 | 0.040 | IGLJ1 | 0.18946 | 0 |
| 1283 | chr22 | 23234000 | 23235000 | 0.200 | 0.080 | IGLJ1 | 0.41743 | 0 |
| 1284 | chr22 | 23235000 | 23236000 | 0.320 | 0.080 | IGLJ1; IGLL5; | 0.07375 | 0 |
| 1285 | chr22 | 23236000 | 23237000 | 0.240 | 0.200 | IGLJ1; IGLL5; | 1.00000 | 0 |

TABLE 2-continued

| # | Chromosome | Region Start | Region End | ABC-subtype | GCB-subtype | ClosestGene | p_ABC_vs_GCB | Previously Identified |
|---|---|---|---|---|---|---|---|---|
| 1286 | chr22 | 23237000 | 23238000 | 0.040 | 0.160 | IGLC1; IGLL5; | 0.34868 | 0 |
| 1287 | chr22 | 23241000 | 23242000 | 0.040 | 0.040 | IGLJ2 | 1.00000 | 0 |
| 1288 | chr22 | 23242000 | 23243000 | 0.120 | 0.040 | IGLC2 | 0.60921 | 0 |
| 1289 | chr22 | 23243000 | 23244000 | 0.080 | 0.040 | IGLC2 | 1.00000 | 0 |
| 1290 | chr22 | 23244000 | 23245000 | 0.000 | 0.040 | IGLC2 | 1.00000 | 0 |
| 1291 | chr22 | 23247000 | 23248000 | 0.280 | 0.160 | IGLJ3 | 0.49620 | 0 |
| 1292 | chr22 | 23248000 | 23249000 | 0.040 | 0.000 | IGLC3 | 1.00000 | 0 |
| 1293 | chr22 | 23249000 | 23250000 | 0.040 | 0.000 | IGLC3 | 1.00000 | 0 |
| 1294 | chr22 | 23260000 | 23261000 | 0.000 | 0.000 | IGLJ6 | 1.00000 | 0 |
| 1295 | chr22 | 23261000 | 23262000 | 0.000 | 0.000 | IGLJ6 | 1.00000 | 0 |
| 1296 | chr22 | 23263000 | 23264000 | 0.000 | 0.040 | IGLJ7 | 1.00000 | 0 |
| 1297 | chr22 | 23264000 | 23265000 | 0.000 | 0.040 | IGLC7 | 1.00000 | 0 |
| 1298 | chr22 | 23273000 | 23274000 | 0.000 | 0.040 | IGLC7 | 1.00000 | 0 |
| 1299 | chr22 | 23277000 | 23278000 | 0.040 | 0.040 | IGLC7 | 1.00000 | 0 |
| 1300 | chr22 | 23278000 | 23279000 | 0.000 | 0.120 | IGLC7 | 0.23469 | 0 |
| 1301 | chr22 | 23281000 | 23282000 | 0.040 | 0.000 | IGLC7 | 1.00000 | 0 |
| 1302 | chr22 | 23282000 | 23283000 | 0.080 | 0.160 | IGLC7 | 0.66710 | 0 |
| 1303 | chr22 | 23284000 | 23285000 | 0.000 | 0.000 | IGLC7 | 1.00000 | 0 |
| 1304 | chr22 | 23523000 | 23524000 | 0.000 | 0.080 | BCR | 0.48980 | 0 |
| 1305 | chr22 | 23524000 | 23525000 | 0.000 | 0.000 | BCR | 1.00000 | 0 |
| 1306 | chr22 | 27236000 | 27237000 | 0.000 | 0.000 | CRYBA4 | 1.00000 | 0 |
| 1307 | chr22 | 29195000 | 29196000 | 0.040 | 0.040 | XBP1 | 1.00000 | 0 |
| 1308 | chr22 | 29196000 | 29197000 | 0.040 | 0.040 | XBP1 | 1.00000 | 0 |
| 1309 | chr22 | 31826000 | 31827000 | 0.040 | 0.000 | DRG1 | 1.00000 | 0 |
| 1310 | chr22 | 32982000 | 32983000 | 0.000 | 0.040 | SYN3 | 1.00000 | 0 |
| 1311 | chr22 | 39852000 | 39853000 | 0.040 | 0.000 | TAB1 | 1.00000 | 0 |
| 1312 | chr22 | 39854000 | 39855000 | 0.000 | 0.000 | TAB1 | 1.00000 | 0 |
| 1313 | chr22 | 43360000 | 43361000 | 0.000 | 0.000 | PACSIN2 | 1.00000 | 0 |
| 1314 | chr22 | 47186000 | 47187000 | 0.000 | 0.000 | TBC1D22A | 1.00000 | 0 |
| 1315 | chr22 | 47738000 | 47739000 | 0.000 | 0.000 | LL22NC03-75H12.2 | 1.00000 | 0 |
| 1316 | chr22 | 50336000 | 50337000 | 0.000 | 0.000 | CRELD2 | 1.00000 | 0 |
| 1317 | chrX | 228000 | 229000 | 0.000 | 0.000 | GTPBP6 | 1.00000 | 0 |
| 1318 | chrX | 1514000 | 1515000 | 0.000 | 0.040 | SLC25A6 | 1.00000 | 0 |
| 1319 | chrX | 1611000 | 1612000 | 0.040 | 0.040 | P2RY8 | 1.00000 | 1 |
| 1320 | chrX | 12993000 | 12994000 | 0.320 | 0.280 | TMSB4X | 1.00000 | 1 |
| 1321 | chrX | 12994000 | 12995000 | 0.200 | 0.160 | TMSB4X | 1.00000 | 1 |
| 1322 | chrX | 13419000 | 13420000 | 0.000 | 0.040 | ATXN3L | 1.00000 | 0 |
| 1323 | chrX | 27031000 | 27032000 | 0.080 | 0.040 | DCAF8L2 | 1.00000 | 0 |
| 1324 | chrX | 32315000 | 32316000 | 0.000 | 0.000 | DMD | 1.00000 | 1 |
| 1325 | chrX | 32317000 | 32318000 | 0.000 | 0.000 | DMD | 1.00000 | 1 |
| 1326 | chrX | 33144000 | 33145000 | 0.000 | 0.000 | DMD | 1.00000 | 1 |
| 1327 | chrX | 33145000 | 33146000 | 0.000 | 0.040 | DMD | 1.00000 | 1 |
| 1328 | chrX | 33146000 | 33147000 | 0.080 | 0.120 | DMD | 1.00000 | 1 |
| 1329 | chrX | 41366000 | 41367000 | 0.040 | 0.000 | CASK | 1.00000 | 0 |
| 1330 | chrX | 42802000 | 42803000 | 0.080 | 0.120 | MAOA | 1.00000 | 0 |
| 1331 | chrX | 48775000 | 48776000 | 0.120 | 0.040 | PIM2 | 0.60921 | 1 |
| 1332 | chrX | 48776000 | 48777000 | 0.080 | 0.000 | PIM2 | 0.48980 | 1 |
| 1333 | chrX | 64071000 | 64072000 | 0.120 | 0.080 | ZC4H2 | 1.00000 | 0 |
| 1334 | chrX | 67030000 | 67031000 | 0.000 | 0.000 | AR | 1.00000 | 0 |
| 1335 | chrX | 80258000 | 80259000 | 0.000 | 0.000 | HMGN5 | 1.00000 | 0 |
| 1336 | chrX | 81172000 | 81173000 | 0.040 | 0.000 | SH3BGRL | 1.00000 | 0 |
| 1337 | chrX | 87742000 | 87743000 | 0.040 | 0.000 | CPXCR1 | 1.00000 | 0 |
| 1338 | chrX | 87831000 | 87832000 | 0.000 | 0.000 | CPXCR1 | 1.00000 | 0 |
| 1339 | chrX | 88263000 | 88264000 | 0.000 | 0.000 | CPXCR1 | 1.00000 | 0 |
| 1340 | chrX | 88458000 | 88459000 | 0.040 | 0.000 | CPXCR1 | 1.00000 | 0 |
| 1341 | chrX | 92647000 | 92648000 | 0.000 | 0.000 | NAPIL3 | 1.00000 | 0 |
| 1342 | chrX | 93279000 | 93280000 | 0.040 | 0.000 | FAM133A | 1.00000 | 0 |
| 1343 | chrX | 94079000 | 94080000 | 0.040 | 0.000 | FAM133A | 1.00000 | 0 |
| 1344 | chrX | 104006000 | 104007000 | 0.040 | 0.000 | IL1RAPL2 | 1.00000 | 0 |
| 1345 | chrX | 104269000 | 104270000 | 0.040 | 0.000 | IL1RAPL2 | 1.00000 | 0 |
| 1346 | chrX | 106132000 | 106133000 | 0.000 | 0.000 | RIPPLY1 | 1.00000 | 0 |
| 1347 | chrX | 113095000 | 113096000 | 0.000 | 0.040 | HTR2C | 1.00000 | 0 |
| 1348 | chrX | 115676000 | 115677000 | 0.040 | 0.000 | CXorf61 | 1.00000 | 0 |
| 1349 | chrX | 124996000 | 124997000 | 0.000 | 0.000 | DCAF12L2 | 1.00000 | 0 |
| 1350 | chrX | 125708000 | 125709000 | 0.000 | 0.000 | DCAF12L1 | 1.00000 | 0 |
| 1351 | chrX | 128565000 | 128566000 | 0.040 | 0.040 | SMARCA1 | 1.00000 | 0 |
| 1352 | chrX | 129643000 | 129644000 | 0.000 | 0.040 | RBMX2 | 1.00000 | 0 |
| 1353 | chrX | 134903000 | 134904000 | 0.000 | 0.000 | CT45A3; CT45A4; | 1.00000 | 0 |
| 1354 | chrX | 140846000 | 140847000 | 0.040 | 0.000 | SPANXD; SPANXE; | 1.00000 | 0 |
| 1355 | chrX | 143750000 | 143751000 | 0.000 | 0.000 | SPANXN1 | 1.00000 | 0 |
| 1356 | chrX | 145016000 | 145017000 | 0.040 | 0.000 | TMEM257 | 1.00000 | 0 |

TABLE 3

| # | Chromosome | Region Start | Region End | Closest Gene | Reason for Inclusion |
|---|---|---|---|---|---|
| 1 | chr1 | 2306311 | 2306832 | MORN1 | Genotyping |
| 2 | chr1 | 2334441 | 2334664 | RER1 | Genotyping |
| 3 | chr1 | 2334671 | 2335161 | RER1 | Genotyping |
| 4 | chr1 | 2488006 | 2488247 | TNFRSF14 | Phased Variants |
| 5 | chr1 | 2489111 | 2489330 | TNFRSF14 | Genotyping |
| 6 | chr1 | 2489726 | 2489973 | TNFRSF14 | Genotyping |
| 7 | chr1 | 2491206 | 2491455 | TNFRSF14 | Genotyping |
| 8 | chr1 | 2492036 | 2492175 | TNFRSF14 | Genotyping |
| 9 | chr1 | 2493051 | 2493333 | TNFRSF14 | Genotyping |
| 10 | chr1 | 2494241 | 2494376 | TNFRSF14 | Genotyping |
| 11 | chr1 | 2494556 | 2494745 | TNFRSF14 | Genotyping |
| 12 | chr1 | 3547350 | 3547715 | WRAP73 | Genotyping |
| 13 | chr1 | 3747620 | 3747798 | CEP104 | Genotyping |
| 14 | chr1 | 3800045 | 3800148 | DFFB | Genotyping |
| 15 | chr1 | 3800155 | 3800363 | DFFB | Genotyping |
| 16 | chr1 | 4472438 | 4472621 | AJAP1 | Genotyping |
| 17 | chr1 | 4476348 | 4476627 | AJAP1 | Genotyping |
| 18 | chr1 | 9784432 | 9784540 | PIK3CD | Genotyping |
| 19 | chr1 | 23885407 | 23885541 | ID3 | Genotyping |
| 20 | chr1 | 23885582 | 23885938 | ID3 | Genotyping |
| 21 | chr1 | 27059146 | 27059321 | ARID1A | Genotyping |
| 22 | chr1 | 27101071 | 27101294 | ARID1A | Genotyping |
| 23 | chr1 | 27101401 | 27101613 | ARID1A | Genotyping |
| 24 | chr1 | 27105466 | 27105671 | ARID1A | Genotyping |
| 25 | chr1 | 27106311 | 27106523 | ARID1A | Genotyping |
| 26 | chr1 | 27106711 | 27106920 | ARID1A | Genotyping |
| 27 | chr1 | 29069531 | 29070185 | YTHDF2 | Genotyping |
| 28 | chr1 | 34404022 | 34404171 | CSMD2 | Phased Variants |
| 29 | chr1 | 35472492 | 35472739 | ZMYM6 | Genotyping |
| 30 | chr1 | 61553802 | 61554330 | NFIA | Genotyping |
| 31 | chr1 | 72334891 | 72335045 | NEGR1 | Phased Variants |
| 32 | chr1 | 72335051 | 72335120 | NEGR1 | Phased Variants |
| 33 | chr1 | 85733207 | 85733640 | BCL10 | Phased Variants |
| 34 | chr1 | 85736272 | 85736619 | BCL10 | Genotyping |
| 35 | chr1 | 85741932 | 85742068 | BCL10 | Genotyping |
| 36 | chr1 | 86591437 | 86591909 | COL24A1 | Genotyping |
| 37 | chr1 | 107866871 | 107867579 | NTNG1 | Genotyping |
| 38 | chr1 | 109649126 | 109649304 | C1orf194 | Genotyping |
| 39 | chr1 | 109822181 | 109822805 | PSRC1 | Genotyping |
| 40 | chr1 | 110561141 | 110561757 | AHCYL1 | Genotyping |
| 41 | chr1 | 111441722 | 111442219 | CD53 | Genotyping |
| 42 | chr1 | 111715727 | 111715908 | CEPT1 | Genotyping |
| 43 | chr1 | 117078642 | 117078856 | CD58 | Genotyping |
| 44 | chr1 | 117086927 | 117087172 | CD58 | Genotyping |
| 45 | chr1 | 120457960 | 120459297 | NOTCH2 | Genotyping |
| 46 | chr1 | 160319283 | 160319532 | NCSTN | Genotyping |
| 47 | chr1 | 181452914 | 181453131 | CACNA1E | Genotyping |
| 48 | chr1 | 185833555 | 185833832 | HMCN1 | Genotyping |
| 49 | chr1 | 185972790 | 185973006 | HMCN1 | Genotyping |
| 50 | chr1 | 186062580 | 186062797 | HMCN1 | Genotyping |
| 51 | chr1 | 186083050 | 186083301 | HMCN1 | Genotyping |
| 52 | chr1 | 186143590 | 186143828 | HMCN1 | Genotyping |
| 53 | chr1 | 186158895 | 186159102 | HMCN1 | Genotyping |
| 54 | chr1 | 190067139 | 190068194 | FAM5C | Genotyping |
| 55 | chr1 | 201038552 | 201038756 | CACNA1S | Genotyping |
| 56 | chr1 | 203274697 | 203275926 | BTG2 | Phased Variants |
| 57 | chr1 | 203276207 | 203276586 | BTG2 | Genotyping |
| 58 | chr1 | 226923691 | 226925200 | ITPKB | Phased Variants |
| 59 | chr1 | 227842646 | 227842718 | ZNF678 | Genotyping |
| 60 | chr2 | 1652010 | 1652858 | PXDN | Genotyping |
| 61 | chr2 | 48027958 | 48028159 | MSH6 | Genotyping |
| 62 | chr2 | 48059883 | 48060051 | FBXO11 | Genotyping |
| 63 | chr2 | 48065973 | 48066184 | FBXO11 | Genotyping |
| 64 | chr2 | 55237198 | 55237610 | RTN4 | Genotyping |
| 65 | chr2 | 56149510 | 56150116 | EFEMP1 | Genotyping |
| 66 | chr2 | 58520800 | 58521222 | FANCL | Genotyping |
| 67 | chr2 | 59821914 | 59822083 | BCL11A | Genotyping |
| 68 | chr2 | 60773084 | 60773479 | BCL11A | Genotyping |
| 69 | chr2 | 61118794 | 61118998 | REL | Genotyping |
| 70 | chr2 | 61145504 | 61145785 | REL | Genotyping |
| 71 | chr2 | 61148869 | 61149644 | REL | Genotyping |
| 72 | chr2 | 61441169 | 61441870 | USP34 | Genotyping |
| 73 | chr2 | 61719434 | 61719642 | XPO1 | Genotyping |
| 74 | chr2 | 62934009 | 62934460 | EHBP1 | Genotyping |
| 75 | chr2 | 63217829 | 63218002 | EHBP1 | Genotyping |
| 76 | chr2 | 63335242 | 63335600 | WDPCP | Genotyping |
| 77 | chr2 | 63631157 | 63631817 | WDPCP | Genotyping |
| 78 | chr2 | 63826277 | 63826429 | MDH1 | Genotyping |

TABLE 3-continued

| # | Chromosome | Region Start | Region End | Closest Gene | Reason for Inclusion |
|---|---|---|---|---|---|
| 79 | chr2 | 65258145 | 65258367 | SLC1A4 | Phased Variants |
| 80 | chr2 | 65593035 | 65593153 | SPRED2 | Phased Variants |
| 81 | chr2 | 65593180 | 65593250 | SPRED2 | Phased Variants |
| 82 | chr2 | 77746602 | 77746988 | LRRTM4 | Genotyping |
| 83 | chr2 | 80801235 | 80801513 | CTNNA2 | Genotyping |
| 84 | chr2 | 88906681 | 88906861 | EIF2AK3 | Phased Variants |
| 85 | chr2 | 89127261 | 89127335 | IGKC | Phased Variants |
| 86 | chr2 | 89127461 | 89127946 | IGKC | Phased Variants |
| 87 | chr2 | 89128431 | 89128574 | IGKC | Phased Variants |
| 88 | chr2 | 89131726 | 89132295 | IGKC | Phased Variants |
| 89 | chr2 | 89140556 | 89140755 | IGKC | Phased Variants |
| 90 | chr2 | 89140886 | 89141350 | IGKC | Phased Variants |
| 91 | chr2 | 89157326 | 89157609 | IGKC | Phased Variants |
| 92 | chr2 | 89157626 | 89158011 | IGKC | Phased Variants |
| 93 | chr2 | 89158036 | 89158938 | IGKC | Phased Variants |
| 94 | chr2 | 89158941 | 89159493 | IGKJ5 | Phased Variants |
| 95 | chr2 | 89159511 | 89161445 | IGKJ1 | Phased Variants |
| 96 | chr2 | 89161926 | 89162149 | IGKJ1 | Phased Variants |
| 97 | chr2 | 89162776 | 89163285 | IGKJ1 | Phased Variants |
| 98 | chr2 | 89163306 | 89163837 | IGKJ1 | Phased Variants |
| 99 | chr2 | 89163861 | 89164838 | IGKJ1 | Phased Variants |
| 100 | chr2 | 89164866 | 89165181 | IGKJ1 | Phased Variants |
| 101 | chr2 | 89165191 | 89165644 | IGKJ1 | Phased Variants |
| 102 | chr2 | 89184966 | 89185186 | IGKV4-1 | Phased Variants |
| 103 | chr2 | 89185196 | 89185704 | IGKV4-1 | Phased Variants |
| 104 | chr2 | 89196226 | 89196411 | IGKV5-2 | Phased Variants |
| 105 | chr2 | 89196851 | 89197324 | IGKV5-2 | Phased Variants |
| 106 | chr2 | 89214836 | 89215040 | IGKV5-2 | Phased Variants |
| 107 | chr2 | 89246681 | 89246772 | IGKV1-5 | Phased Variants |
| 108 | chr2 | 89246786 | 89246857 | IGKV1-5 | Phased Variants |
| 109 | chr2 | 89246911 | 89247053 | IGKV1-5 | Phased Variants |
| 110 | chr2 | 89247096 | 89247215 | IGKV1-5 | Phased Variants |
| 111 | chr2 | 89247526 | 89247628 | IGKV1-5 | Phased Variants |
| 112 | chr2 | 89247641 | 89247735 | IGKV1-5 | Phased Variants |
| 113 | chr2 | 89247831 | 89248010 | IGKV1-5 | Phased Variants |
| 114 | chr2 | 89265756 | 89265829 | IGKV1-6 | Genotyping |
| 115 | chr2 | 89265936 | 89266013 | IGKV1-6 | Genotyping |
| 116 | chr2 | 89291906 | 89291981 | IGKV1-8 | Phased Variants |
| 117 | chr2 | 89292131 | 89292217 | IGKV1-8 | Phased Variants |
| 118 | chr2 | 89442291 | 89442561 | IGKV3-20 | Phased Variants |
| 119 | chr2 | 89442616 | 89443259 | IGKV3-20 | Phased Variants |
| 120 | chr2 | 89475781 | 89476009 | IGKV2-24 | Genotyping |
| 121 | chr2 | 89476041 | 89476122 | IGKV2-24 | Genotyping |
| 122 | chr2 | 89544331 | 89544608 | IGKV2-30 | Genotyping |
| 123 | chr2 | 89544656 | 89544899 | IGKV2-30 | Phased Variants |
| 124 | chr2 | 89976276 | 89976426 | IGKV2D-30 | Genotyping |
| 125 | chr2 | 89986776 | 89987023 | IGKV2D-29 | Genotyping |
| 126 | chr2 | 89987031 | 89987108 | IGKV2D-29 | Genotyping |
| 127 | chr2 | 90025206 | 90025289 | IGKV2D-26 | Genotyping |
| 128 | chr2 | 90025296 | 90025378 | IGKV2D-26 | Genotyping |
| 129 | chr2 | 90025471 | 90025554 | IGKV2D-26 | Genotyping |
| 130 | chr2 | 90077981 | 90078054 | IGKV3D-20 | Genotyping |
| 131 | chr2 | 90078136 | 90078222 | IGKV3D-20 | Genotyping |
| 132 | chr2 | 90078251 | 90078335 | IGKV3D-20 | Genotyping |
| 133 | chr2 | 90121891 | 90122008 | IGKV1D-17 | Genotyping |
| 134 | chr2 | 90122021 | 90122157 | IGKV1D-17 | Genotyping |
| 135 | chr2 | 90212016 | 90212093 | IGKV3D-11 | Genotyping |
| 136 | chr2 | 90212196 | 90212278 | IGKV3D-11 | Genotyping |
| 137 | chr2 | 90249151 | 90249275 | IGKV1D-43 | Genotyping |
| 138 | chr2 | 90249346 | 90249419 | IGKV1D-43 | Genotyping |
| 139 | chr2 | 90259931 | 90260059 | IGKV1D-8 | Genotyping |
| 140 | chr2 | 90260181 | 90260258 | IGKV1D-8 | Genotyping |
| 141 | chr2 | 96809889 | 96810144 | DUSP2 | Genotyping |
| 142 | chr2 | 96810164 | 96810374 | DUSP2 | Phased Variants |
| 143 | chr2 | 100758483 | 100758660 | AFF3 | Phased Variants |
| 144 | chr2 | 103148733 | 103148948 | SLC9A4 | Genotyping |
| 145 | chr2 | 117951919 | 117952057 | DDX18 | Phased Variants |
| 146 | chr2 | 136872525 | 136872740 | CXCR4 | Genotyping |
| 147 | chr2 | 136874415 | 136874797 | CXCR4 | Phased Variants |
| 148 | chr2 | 136874920 | 136875662 | CXCR4 | Phased Variants |
| 149 | chr2 | 141245127 | 141245373 | LRP1B | Genotyping |
| 150 | chr2 | 145162401 | 145162624 | ZEB2 | Genotyping |
| 151 | chr2 | 145187091 | 145187638 | ZEB2 | Genotyping |
| 152 | chr2 | 145270956 | 145271394 | ZEB2 | Genotyping |
| 153 | chr2 | 145275631 | 145275744 | ZEB2 | Genotyping |
| 154 | chr2 | 145275756 | 145276174 | ZEB2 | Genotyping |
| 155 | chr2 | 145278026 | 145278305 | ZEB2 | Genotyping |
| 156 | chr2 | 145278311 | 145278659 | ZEB2 | Genotyping |

TABLE 3-continued

| # | Chromosome | Region Start | Region End | Closest Gene | Reason for Inclusion |
|---|---|---|---|---|---|
| 157 | chr2 | 145692901 | 145693081 | ZEB2 | Genotyping |
| 158 | chr2 | 148680516 | 148680692 | ACVR2A | Genotyping |
| 159 | chr2 | 169781120 | 169781352 | ABCB11 | Genotyping |
| 160 | chr2 | 170101185 | 170101401 | LRP2 | Genotyping |
| 161 | chr2 | 198950434 | 198951003 | PLCL1 | Genotyping |
| 162 | chr2 | 242793232 | 242793447 | PDCD1 | Genotyping |
| 163 | chr2 | 242794037 | 242794192 | PDCD1 | Genotyping |
| 164 | chr2 | 242794317 | 242794537 | PDCD1 | Genotyping |
| 165 | chr2 | 242794822 | 242795040 | PDCD1 | Genotyping |
| 166 | chr2 | 242800887 | 242801093 | PDCD1 | Genotyping |
| 167 | chr3 | 7620223 | 7620990 | GRM7 | Genotyping |
| 168 | chr3 | 16419204 | 16419479 | RFTN1 | Phased Variants |
| 169 | chr3 | 38180129 | 38180549 | MYD88 | Genotyping |
| 170 | chr3 | 38181334 | 38181509 | MYD88 | Genotyping |
| 171 | chr3 | 38181854 | 38182099 | MYD88 | Genotyping |
| 172 | chr3 | 38182194 | 38182407 | MYD88 | Genotyping |
| 173 | chr3 | 38182554 | 38182844 | MYD88 | Genotyping |
| 174 | chr3 | 49397608 | 49397717 | RHOA | Genotyping |
| 175 | chr3 | 49397718 | 49397827 | RHOA | Genotyping |
| 176 | chr3 | 49399903 | 49400084 | RHOA | Genotyping |
| 177 | chr3 | 49405833 | 49406013 | RHOA | Genotyping |
| 178 | chr3 | 49412838 | 49413046 | RHOA | Genotyping |
| 179 | chr3 | 64547204 | 64547477 | ADAMTS9 | Genotyping |
| 180 | chr3 | 64579889 | 64580094 | ADAMTS9 | Genotyping |
| 181 | chr3 | 71551101 | 71551497 | EIF4E3 | Phased Variants |
| 182 | chr3 | 140281598 | 140281875 | CLSTN2 | Genotyping |
| 183 | chr3 | 164730700 | 164730888 | SI | Genotyping |
| 184 | chr3 | 165548198 | 165548680 | BCHE | Genotyping |
| 185 | chr3 | 176750699 | 176750928 | TBL1XR1 | Genotyping |
| 186 | chr3 | 176767759 | 176767977 | TBL1XR1 | Genotyping |
| 187 | chr3 | 176769304 | 176769543 | TBL1XR1 | Genotyping |
| 188 | chr3 | 176771659 | 176771732 | TBL1XR1 | Genotyping |
| 189 | chr3 | 183209758 | 183209937 | KLHL6 | Genotyping |
| 190 | chr3 | 183210258 | 183210544 | KLHL6 | Genotyping |
| 191 | chr3 | 183272308 | 183272521 | KLHL6 | Phased Variants |
| 192 | chr3 | 183273063 | 183273456 | KLHL6 | Phased Variants |
| 193 | chr3 | 184580663 | 184580872 | VPS8 | Genotyping |
| 194 | chr3 | 185146278 | 185146873 | MAP3K13 | Genotyping |
| 195 | chr3 | 185197923 | 185198317 | MAP3K13 | Genotyping |
| 196 | chr3 | 185236908 | 185237109 | LIPH | Genotyping |
| 197 | chr3 | 185446223 | 185446389 | C3orf65 | Genotyping |
| 198 | chr3 | 185538773 | 185538951 | IGF2BP2 | Genotyping |
| 199 | chr3 | 185697423 | 185697669 | TRA2B | Genotyping |
| 200 | chr3 | 186714604 | 186715001 | ST6GAL1 | Phased Variants |
| 201 | chr3 | 186782529 | 186782790 | ST6GAL1 | Phased Variants |
| 202 | chr3 | 186783389 | 186784291 | ST6GAL1 | Phased Variants |
| 203 | chr3 | 187440189 | 187440445 | BCL6 | Genotyping |
| 204 | chr3 | 187442669 | 187442920 | BCL6 | Genotyping |
| 205 | chr3 | 187443239 | 187443438 | BCL6 | Genotyping |
| 206 | chr3 | 187446814 | 187447831 | BCL6 | Genotyping |
| 207 | chr3 | 187449434 | 187449655 | BCL6 | Genotyping |
| 208 | chr3 | 187451284 | 187451667 | BCL6 | Genotyping |
| 209 | chr3 | 187460134 | 187460530 | BCL6 | Phased Variants |
| 210 | chr3 | 187460824 | 187461302 | BCL6 | Phased Variants |
| 211 | chr3 | 187461319 | 187461381 | BCL6 | Phased Variants |
| 212 | chr3 | 187461454 | 187461918 | BCL6 | Phased Variants |
| 213 | chr3 | 187461924 | 187462343 | BCL6 | Phased Variants |
| 214 | chr3 | 187462374 | 187462887 | BCL6 | Phased Variants |
| 215 | chr3 | 187462924 | 187462999 | BCL6 | Phased Variants |
| 216 | chr3 | 187463004 | 187463525 | BCL6 | Phased Variants |
| 217 | chr3 | 187463709 | 187463781 | BCL6 | Phased Variants |
| 218 | chr3 | 187463794 | 187464109 | BCL6 | Phased Variants |
| 219 | chr3 | 187619334 | 187619708 | BCL6 | Phased Variants |
| 220 | chr3 | 187660817 | 187661390 | BCL6 | Phased Variants |
| 221 | chr3 | 187957432 | 187957507 | AC022498.1 | Phased Variants |
| 222 | chr3 | 187957512 | 187957754 | AC022498.1 | Phased Variants |
| 223 | chr3 | 187957767 | 187958110 | AC022498.1 | Phased Variants |
| 224 | chr3 | 187958282 | 187958675 | AC022498.1 | Phased Variants |
| 225 | chr3 | 187958787 | 187959184 | AC022498.1 | Phased Variants |
| 226 | chr3 | 187959462 | 187959686 | AC022498.1 | Phased Variants |
| 227 | chr3 | 188299217 | 188299605 | LPP | Phased Variants |
| 228 | chr3 | 188471412 | 188471549 | LPP | Phased Variants |
| 229 | chr3 | 188471567 | 188471937 | LPP | Phased Variants |
| 230 | chr4 | 7728456 | 7728661 | SORCS2 | Genotyping |
| 231 | chr4 | 40198810 | 40199653 | N4BP2 | Phased Variants |
| 232 | chr4 | 40199660 | 40199873 | N4BP2 | Phased Variants |
| 233 | chr4 | 40199990 | 40200211 | N4BP2 | Phased Variants |
| 234 | chr4 | 40200505 | 40200727 | RHOH | Phased Variants |

TABLE 3-continued

| # | Chromosome | Region Start | Region End | Closest Gene | Reason for Inclusion |
|---|---|---|---|---|---|
| 235 | chr4 | 40200730 | 40201571 | RHOH | Phased Variants |
| 236 | chr4 | 80327792 | 80328151 | GK2 | Genotyping |
| 237 | chr4 | 88011077 | 88011285 | AFF1 | Genotyping |
| 238 | chr4 | 106157604 | 106157813 | TET2 | Genotyping |
| 239 | chr4 | 134727698 | 134727916 | PABPC4L | Phased Variants |
| 240 | chr4 | 153249285 | 153249507 | FBXW7 | Genotyping |
| 241 | chr4 | 154624670 | 154625050 | TLR2 | Genotyping |
| 242 | chr4 | 187509884 | 187510410 | FAT1 | Genotyping |
| 243 | chr4 | 187557779 | 187557985 | FAT1 | Genotyping |
| 244 | chr4 | 188924114 | 188924897 | ZFP42 | Genotyping |
| 245 | chr5 | 5182145 | 5182494 | ADAMTS16 | Genotyping |
| 246 | chr5 | 11110990 | 11111137 | CTNND2 | Genotyping |
| 247 | chr5 | 11236740 | 11236956 | CTNND2 | Genotyping |
| 248 | chr5 | 11364700 | 11364923 | CTNND2 | Genotyping |
| 249 | chr5 | 11397080 | 11397377 | CTNND2 | Genotyping |
| 250 | chr5 | 11411600 | 11411807 | CTNND2 | Genotyping |
| 251 | chr5 | 13864465 | 13864696 | DNAH5 | Genotyping |
| 252 | chr5 | 21783415 | 21783668 | CDH12 | Genotyping |
| 253 | chr5 | 54964698 | 54964921 | SLC38A9 | Phased Variants |
| 254 | chr5 | 67590966 | 67591183 | PIK3R1 | Genotyping |
| 255 | chr5 | 75913716 | 75914448 | F2RL2 | Genotyping |
| 256 | chr5 | 83258967 | 83259183 | EDIL3 | Genotyping |
| 257 | chr5 | 112176756 | 112176958 | APC | Genotyping |
| 258 | chr5 | 124079827 | 124080721 | ZNF608 | Phased Variants |
| 259 | chr5 | 131825017 | 131825239 | IRF1 | Genotyping |
| 260 | chr5 | 135381969 | 135382218 | TGFBI | Genotyping |
| 261 | chr5 | 137801487 | 137801637 | EGR1 | Genotyping |
| 262 | chr5 | 137801697 | 137801804 | EGR1 | Genotyping |
| 263 | chr5 | 140208033 | 140208874 | PCDHA6 | Genotyping |
| 264 | chr5 | 158527642 | 158528019 | EBF1 | Phased Variants |
| 265 | chr5 | 176522449 | 176522613 | FGFR4 | Genotyping |
| 266 | chr6 | 392760 | 392967 | IRF4 | Phased Variants |
| 267 | chr6 | 393090 | 393309 | IRF4 | Phased Variants |
| 268 | chr6 | 394815 | 395025 | IRF4 | Genotyping |
| 269 | chr6 | 14117992 | 14118654 | CD83 | Phased Variants |
| 270 | chr6 | 14131732 | 14132021 | CD83 | Genotyping |
| 271 | chr6 | 14133857 | 14133996 | CD83 | Genotyping |
| 272 | chr6 | 14135317 | 14135496 | CD83 | Genotyping |
| 273 | chr6 | 26020709 | 26020958 | HIST1H3A | Genotyping |
| 274 | chr6 | 26032014 | 26032217 | HIST1H3B | Genotyping |
| 275 | chr6 | 26045744 | 26046077 | HIST1H3C | Genotyping |
| 276 | chr6 | 26056034 | 26056315 | HIST1H1C | Genotyping |
| 277 | chr6 | 26056319 | 26056558 | HIST1H1C | Genotyping |
| 278 | chr6 | 26123614 | 26123778 | HIST1H2BC | Phased Variants |
| 279 | chr6 | 26123879 | 26124098 | HIST1H2BC | Genotyping |
| 280 | chr6 | 26124544 | 26124640 | HIST1H2AC | Genotyping |
| 281 | chr6 | 26124714 | 26124889 | HIST1H2AC | Genotyping |
| 282 | chr6 | 26156649 | 26157377 | HIST1H1E | Phased Variants |
| 283 | chr6 | 26158529 | 26158608 | HIST1H2BD | Genotyping |
| 284 | chr6 | 26158739 | 26158835 | HIST1H2BD | Genotyping |
| 285 | chr6 | 26197104 | 26197182 | HIST1H3D | Genotyping |
| 286 | chr6 | 26197189 | 26197465 | HIST1H3D | Genotyping |
| 287 | chr6 | 26216779 | 26216920 | HIST1H2BG | Genotyping |
| 288 | chr6 | 26217214 | 26217431 | HIST1H2AE | Genotyping |
| 289 | chr6 | 26234654 | 26234976 | HIST1H1D | Genotyping |
| 290 | chr6 | 26250459 | 26250537 | HIST1H3F | Genotyping |
| 291 | chr6 | 26250594 | 26250703 | HIST1H3F | Genotyping |
| 292 | chr6 | 26252154 | 26252232 | HIST1H2BH | Genotyping |
| 293 | chr6 | 27100079 | 27100185 | HIST1H2BJ | Genotyping |
| 294 | chr6 | 27100939 | 27101039 | HIST1H2AG | Genotyping |
| 295 | chr6 | 27101159 | 27101300 | HIST1H2AG | Genotyping |
| 296 | chr6 | 27114004 | 27114216 | HIST1H2BK | Phased Variants |
| 297 | chr6 | 27114319 | 27114396 | HIST1H2BK | Genotyping |
| 298 | chr6 | 27114494 | 27114592 | HIST1H2BK | Genotyping |
| 299 | chr6 | 27277284 | 27277495 | POM121L2 | Genotyping |
| 300 | chr6 | 27777783 | 27777900 | HIST1H3H | Genotyping |
| 301 | chr6 | 27777928 | 27778106 | HIST1H3H | Genotyping |
| 302 | chr6 | 27782718 | 27782926 | HIST1H2BM | Genotyping |
| 303 | chr6 | 27799168 | 27799381 | HIST1H4K | Genotyping |
| 304 | chr6 | 27833408 | 27833516 | HIST1H2AL | Genotyping |
| 305 | chr6 | 27834968 | 27835075 | HIST1H1B | Genotyping |
| 306 | chr6 | 27839658 | 27839805 | HIST1H3I | Genotyping |
| 307 | chr6 | 27860479 | 27860659 | HIST1H2AM | Genotyping |
| 308 | chr6 | 27860794 | 27860938 | HIST1H2AM | Genotyping |
| 309 | chr6 | 27861244 | 27861344 | HIST1H2BO | Genotyping |
| 310 | chr6 | 27861399 | 27861485 | HIST1H2BO | Genotyping |
| 311 | chr6 | 37138284 | 37139559 | PIM1 | Phased Variants |
| 312 | chr6 | 37140749 | 37140956 | PIM1 | Genotyping |

TABLE 3-continued

| # | Chromosome | Region Start | Region End | Closest Gene | Reason for Inclusion |
|---|---|---|---|---|---|
| 313 | chr6 | 37141679 | 37141903 | PIMI | Genotyping |
| 314 | chr6 | 41903611 | 41903834 | CCND3 | Genotyping |
| 315 | chr6 | 41904271 | 41904477 | CCND3 | Genotyping |
| 316 | chr6 | 41904941 | 41905155 | CCND3 | Genotyping |
| 317 | chr6 | 41908071 | 41908365 | CCND3 | Genotyping |
| 318 | chr6 | 41909196 | 41909441 | CCND3 | Genotyping |
| 319 | chr6 | 75965846 | 75966046 | TMEM30A | Genotyping |
| 320 | chr6 | 75969006 | 75969288 | TMEM30A | Genotyping |
| 321 | chr6 | 91004618 | 91004828 | MAP3K7 | Phased Variants |
| 322 | chr6 | 91005793 | 91005998 | MAP3K7 | Phased Variants |
| 323 | chr6 | 94120219 | 94120743 | EPHA7 | Genotyping |
| 324 | chr6 | 106534266 | 106534477 | PRDM1 | Genotyping |
| 325 | chr6 | 106536046 | 106536340 | PRDM1 | Genotyping |
| 326 | chr6 | 106543466 | 106543637 | PRDM1 | Genotyping |
| 327 | chr6 | 106547146 | 106547437 | PRDM1 | Genotyping |
| 328 | chr6 | 106552761 | 106552932 | PRDM1 | Genotyping |
| 329 | chr6 | 106552961 | 106553841 | PRDM1 | Genotyping |
| 330 | chr6 | 106554221 | 106554400 | PRDM1 | Genotyping |
| 331 | chr6 | 106554766 | 106555383 | PRDM1 | Genotyping |
| 332 | chr6 | 108040228 | 108040856 | SCML4 | Genotyping |
| 333 | chr6 | 108041553 | 108042219 | SCML4 | Genotyping |
| 334 | chr6 | 110777718 | 110778244 | SLC22A16 | Genotyping |
| 335 | chr6 | 134491382 | 134491589 | SGK1 | Genotyping |
| 336 | chr6 | 134491892 | 134492111 | SGK1 | Genotyping |
| 337 | chr6 | 134492132 | 134492333 | SGK1 | Genotyping |
| 338 | chr6 | 134492717 | 134492923 | SGK1 | Genotyping |
| 339 | chr6 | 134493307 | 134493474 | SGK1 | Genotyping |
| 340 | chr6 | 134493732 | 134494308 | SGK1 | Phased Variants |
| 341 | chr6 | 134494342 | 134494514 | SGK1 | Genotyping |
| 342 | chr6 | 134494552 | 134494718 | SGK1 | Phased Variants |
| 343 | chr6 | 134494722 | 134494795 | SGK1 | Phased Variants |
| 344 | chr6 | 134494967 | 134495974 | SGK1 | Phased Variants |
| 345 | chr6 | 138188483 | 138188650 | TNFAIP3 | Genotyping |
| 346 | chr6 | 138192338 | 138192683 | TNFAIP3 | Genotyping |
| 347 | chr6 | 138195963 | 138196172 | TNFAIP3 | Genotyping |
| 348 | chr6 | 138196803 | 138197021 | TNFAIP3 | Genotyping |
| 349 | chr6 | 138197108 | 138197313 | TNFAIP3 | Genotyping |
| 350 | chr6 | 138198193 | 138198407 | TNFAIP3 | Genotyping |
| 351 | chr6 | 138199548 | 138200525 | TNFAIP3 | Genotyping |
| 352 | chr6 | 138201178 | 138201404 | TNFAIP3 | Genotyping |
| 353 | chr6 | 138202138 | 138202494 | TNFAIP3 | Genotyping |
| 354 | chr6 | 150954420 | 150954823 | PLEKHG1 | Phased Variants |
| 355 | chr6 | 59238415 | 159238794 | EZR | Phased Variants |
| 356 | chr7 | 2963818 | 2963952 | CARD11 | Genotyping |
| 357 | chr7 | 2963953 | 2964056 | CARD11 | Genotyping |
| 358 | chr7 | 2969593 | 2969738 | CARD11 | Genotyping |
| 359 | chr7 | 2976668 | 2976876 | CARD11 | Genotyping |
| 360 | chr7 | 2977493 | 2977712 | CARD11 | Genotyping |
| 361 | chr7 | 2978258 | 2978502 | CARD11 | Genotyping |
| 362 | chr7 | 2979398 | 2979601 | CARD11 | Genotyping |
| 363 | chr7 | 2983918 | 2984199 | CARD11 | Genotyping |
| 364 | chr7 | 2985403 | 2985610 | CARD11 | Genotyping |
| 365 | chr7 | 2987163 | 2987382 | CARD11 | Genotyping |
| 366 | chr7 | 5569095 | 5569200 | ACTB | Genotyping |
| 367 | chr7 | 5569210 | 5569359 | ACTB | Genotyping |
| 368 | chr7 | 80285799 | 80286074 | CD36 | Genotyping |
| 369 | chr7 | 82387830 | 82388061 | PCLO | Genotyping |
| 370 | chr7 | 82453520 | 82453733 | PCLO | Genotyping |
| 371 | chr7 | 82763800 | 82764050 | PCLO | Genotyping |
| 372 | chr7 | 82784490 | 82784643 | PCLO | Genotyping |
| 373 | chr7 | 106508490 | 106509161 | PIK3CG | Genotyping |
| 374 | chr7 | 110545276 | 110545445 | IMMP2L | Phased Variants |
| 375 | chr7 | 110697971 | 110698144 | LRRN3 | Phased Variants |
| 376 | chr7 | 110737411 | 110737634 | LRRN3 | Phased Variants |
| 377 | chr7 | 110746681 | 110746893 | LRRN3 | Phased Variants |
| 378 | chr7 | 110762936 | 110764629 | LRRN3 | Genotyping |
| 379 | chr7 | 110764636 | 110764981 | LRRN3 | Genotyping |
| 380 | chr7 | 119915406 | 119915800 | KCND2 | Genotyping |
| 381 | chr7 | 122634905 | 122635140 | TAS2R16 | Genotyping |
| 382 | chr7 | 140453012 | 140453121 | BRAF | Genotyping |
| 383 | chr7 | 140453162 | 140453268 | BRAF | Genotyping |
| 384 | chr7 | 146997183 | 146997422 | CNTNAP2 | Genotyping |
| 385 | chr7 | 148506318 | 148506416 | EZH2 | Genotyping |
| 386 | chr7 | 148506448 | 148506551 | EZH2 | Genotyping |
| 387 | chr7 | 148508658 | 148508867 | EZH2 | Genotyping |
| 388 | chr7 | 148513738 | 148513900 | EZH2 | Genotyping |
| 389 | chr7 | 148523533 | 148523743 | EZH2 | Genotyping |
| 390 | chr7 | 151943421 | 151943500 | KMT2C | Phased Variants |

TABLE 3-continued

| # | Chromosome | Region Start | Region End | Closest Gene | Reason for Inclusion |
|---|---|---|---|---|---|
| 391 | chr8 | 623880 | 624090 | ERICH1 | Genotyping |
| 392 | chr8 | 3141724 | 3141942 | CSMD1 | Genotyping |
| 393 | chr8 | 4494931 | 4495105 | CSMD1 | Genotyping |
| 394 | chr8 | 8748687 | 8749284 | MFHAS1 | Genotyping |
| 395 | chr8 | 8750067 | 8750281 | MFHAS1 | Genotyping |
| 396 | chr8 | 18729445 | 18729937 | PSD3 | Genotyping |
| 397 | chr8 | 75898190 | 75898400 | CRISPLD1 | Genotyping |
| 398 | chr8 | 101730376 | 101730457 | PABPC1 | Genotyping |
| 399 | chr8 | 103663491 | 103664160 | KLF10 | Genotyping |
| 400 | chr8 | 104897561 | 104898479 | RIMS2 | Genotyping |
| 401 | chr8 | 113308014 | 113308283 | CSMD3 | Genotyping |
| 402 | chr8 | 113364624 | 113364791 | CSMD3 | Genotyping |
| 403 | chr8 | 113568994 | 113569205 | CSMD3 | Genotyping |
| 404 | chr8 | 116616145 | 116616886 | TRPS1 | Genotyping |
| 405 | chr8 | 122626847 | 122627163 | HAS2 | Genotyping |
| 406 | chr8 | 128492947 | 128493338 | POU5F1B | Genotyping |
| 407 | chr8 | 128746807 | 128748893 | MYC | Genotyping |
| 408 | chr8 | 128748902 | 128749969 | MYC | Genotyping |
| 409 | chr8 | 128750367 | 128751183 | MYC | Phased Variants |
| 410 | chr8 | 128752612 | 128753235 | MYC | Genotyping |
| 411 | chr8 | 128754007 | 128754731 | MYC | Genotyping |
| 412 | chr8 | 128754752 | 128756424 | MYC | Genotyping |
| 413 | chr8 | 128756707 | 128756931 | MYC | Genotyping |
| 414 | chr8 | 128756947 | 128757361 | MYC | Genotyping |
| 415 | chr8 | 128757737 | 128757921 | MYC | Genotyping |
| 416 | chr8 | 128764072 | 128764292 | MYC | Genotyping |
| 417 | chr8 | 128951724 | 128951896 | TMEM75 | Genotyping |
| 418 | chr8 | 130692149 | 130692503 | GSDMC | Genotyping |
| 419 | chr8 | 130760594 | 130761023 | GSDMC | Genotyping |
| 420 | chr8 | 131373024 | 131373443 | ASAP1 | Genotyping |
| 421 | chr& | 136569669 | 136569842 | KHDRBS3 | Genotyping |
| 422 | chr8 | 136659204 | 136659414 | KHDRBS3 | Genotyping |
| 423 | chr8 | 137101252 | 137101464 | KHDRBS3 | Genotyping |
| 424 | chr8 | 137528187 | 137528570 | KHDRBS3 | Genotyping |
| 425 | chr8 | 138849937 | 138850149 | FAM135B | Genotyping |
| 426 | chr8 | 139600457 | 139601255 | COL22A1 | Genotyping |
| 427 | chr8 | 139601392 | 139601569 | COL22A1 | Genotyping |
| 428 | chr9 | 5450474 | 5450616 | CD274 | Genotyping |
| 429 | chr9 | 5456059 | 5456200 | CD274 | Genotyping |
| 430 | chr9 | 5457054 | 5457446 | CD274 | Genotyping |
| 431 | chr9 | 5462809 | 5463160 | CD274 | Genotyping |
| 432 | chr9 | 5465489 | 5465622 | CD274 | Genotyping |
| 433 | chr9 | 5466724 | 5466867 | CD274 | Genotyping |
| 434 | chr9 | 5467814 | 5468022 | CD274 | Genotyping |
| 435 | chr9 | 5510589 | 5510804 | PDCD1LG2 | Genotyping |
| 436 | chr9 | 5522484 | 5522636 | PDCD1LG2 | Genotyping |
| 437 | chr9 | 5534764 | 5535047 | PDCD1LG2 | Genotyping |
| 438 | chr9 | 5549309 | 5549627 | PDCD1LG2 | Genotyping |
| 439 | chr9 | 5557589 | 5557762 | PDCD1LG2 | Genotyping |
| 440 | chr9 | 5563119 | 5563251 | PDCD1LG2 | Genotyping |
| 441 | chr9 | $569929 | 5570140 | PDCD1LG2 | Genotyping |
| 442 | chr9 | 13222185 | 13222409 | MPDZ | Genotyping |
| 443 | chr9 | 16435498 | 16436307 | BNC2 | Genotyping |
| 444 | chr9 | 19957356 | 19958178 | SLC24A2 | Genotyping |
| 445 | chr9 | 20820916 | 20821095 | FOCAD | Genotyping |
| 446 | chr9 | 20946676 | 20946849 | FOCAD | Genotyping |
| 447 | chr9 | 21808814 | 21808891 | MTAP | Genotyping |
| 448 | chr9 | 21808894 | 21808973 | MTAP | Genotyping |
| 449 | chr9 | 21859249 | 21859469 | MTAP | Genotyping |
| 450 | chr9 | 21970834 | 21971023 | CDKN2A | Genotyping |
| 451 | chr9 | 21971069 | 21971170 | CDKN2A | Genotyping |
| 452 | chr9 | 21974409 | 21974881 | CDKN2A | Genotyping |
| 453 | chr9 | 21989304 | 21989976 | CDKN2A | Genotyping |
| 454 | chr9 | 21994084 | 21994405 | CDKN2A | Genotyping |
| 455 | chr9 | 22005929 | 22006067 | CDKN2B | Genotyping |
| 456 | chr9 | 22006109 | 22006187 | CDKN2B | Genotyping |
| 457 | chr9 | 22008649 | 22009012 | CDKN2B | Genotyping |
| 458 | chr9 | 24545399 | 24545922 | IZUMO3 | Genotyping |
| 459 | chr9 | 24905444 | 24905729 | IZUMO3 | Genotyping |
| 460 | chr9 | 27950144 | 27950532 | LINGO2 | Genotyping |
| 461 | chr9 | 37024919 | 37025642 | PAX5 | Phased Variants |
| 462 | chr9 | 37025829 | 37025996 | PAX5 | Phased Variants |
| 463 | chr9 | 37026269 | 37027015 | PAX5 | Phased Variants |
| 464 | chr9 | 37033619 | 37033797 | PAX5 | Phased Variants |
| 465 | chr9 | 37293169 | 37293378 | ZCCHC7 | Phased Variants |
| 466 | chr9 | 37371494 | 37371879 | ZCCHC7 | Phased Variants |
| 467 | chr9 | 37384684 | 37384911 | ZCCHC7 | Phased Variants |
| 468 | chr9 | 37407369 | 37407588 | GRHPR | Phased Variants |

TABLE 3-continued

| # | Chromosome | Region Start | Region End | Closest Gene | Reason for Inclusion |
|---|---|---|---|---|---|
| 469 | chr9 | 78686579 | 78686854 | PCSK5 | Genotyping |
| 470 | chr9 | 139390582 | 139390950 | NOTCH1 | Genotyping |
| 471 | chr9 | 139390952 | 139391172 | NOTCH1 | Genotyping |
| 472 | chr9 | 139402662 | 139402868 | NOTCH1 | Genotyping |
| 473 | chr10 | 5755066 | 5755273 | FAM208B | Phased Variants |
| 474 | chr10 | 89500957 | 89501139 | PAPSS2 | Genotyping |
| 475 | chr10 | 89603602 | 89604077 | KLLN | Genotyping |
| 476 | chr10 | 89624272 | 89624350 | PTEN | Genotyping |
| 477 | chr10 | 89653752 | 89653825 | PTEN | Genotyping |
| 478 | chr10 | 89653832 | 89653909 | PTEN | Genotyping |
| 479 | chr10 | 89685272 | 89685379 | PTEN | Genotyping |
| 480 | chr10 | 89690752 | 89690894 | PTEN | Genotyping |
| 481 | chr10 | 89692737 | 89692810 | PTEN | Genotyping |
| 482 | chr10 | 89692877 | 89692951 | PTEN | Genotyping |
| 483 | chr10 | 89692972 | 89693037 | PTEN | Genotyping |
| 484 | chr10 | 89711837 | 89711966 | PTEN | Genotyping |
| 485 | chr10 | 89711982 | 89712058 | PTEN | Genotyping |
| 486 | chr10 | 89717577 | 89717714 | PTEN | Genotyping |
| 487 | chr10 | 89717742 | 89717811 | PTEN | Genotyping |
| 488 | chr10 | 89720637 | 89720904 | PTEN | Genotyping |
| 489 | chr10 | 90074239 | 90074419 | RNLS | Genotyping |
| 490 | chr10 | 90537736 | 90538027 | LIPN | Genotyping |
| 491 | chr10 | 90579966 | 90580319 | LIPM | Genotyping |
| 492 | chr10 | 90699126 | 90699647 | ACTA2 | Genotyping |
| 493 | chr10 | 90773866 | 90774076 | FAS | Genotyping |
| 494 | chr10 | 91092211 | 91092423 | IFIT3 | Genotyping |
| 495 | chr10 | 91358986 | 91359298 | PANK1 | Genotyping |
| 496 | chr10 | 131640289 | 131640505 | EBF3 | Genotyping |
| 497 | chr11 | 58978692 | 58978791 | MPEG1 | Genotyping |
| 498 | chr11 | 58978927 | 58979095 | MPEG1 | Genotyping |
| 499 | chr11 | 58979112 | 58979365 | MPEG1 | Genotyping |
| 500 | chr11 | 65190342 | 65190557 | FRMD8 | Phased Variants |
| 501 | chr11 | 65266552 | 65266924 | SCYL1 | Phased Variants |
| 502 | chr11 | 65267397 | 65267603 | SCYL1 | Phased Variants |
| 503 | chr11 | 65623422 | 65623506 | CFL1 | Genotyping |
| 504 | chr11 | 69346691 | 69346940 | CCND1 | Genotyping |
| 505 | chr11 | 102188381 | 102188945 | BIRC3 | Phased Variants |
| 506 | chr11 | 111234536 | 111235068 | POU2AF1 | Genotyping |
| 507 | chr11 | 111249311 | 111249530 | POU2AF1 | Phased Variants |
| 508 | chr11 | 111613196 | 111613432 | PPP2R1B | Genotyping |
| 509 | chr11 | 111781036 | 111781641 | CRYAB | Genotyping |
| 510 | chr11 | 111904096 | 111904291 | DLAT | Genotyping |
| 511 | chr11 | 112405016 | 112405330 | AP002884.2 | Genotyping |
| 512 | chr11 | 112405341 | 112405621 | AP002884.2 | Genotyping |
| 513 | chr11 | 117101043 | 117101217 | PCSK7 | Genotyping |
| 514 | chr11 | 117712683 | 117712997 | FXYD6 | Genotyping |
| 515 | chr11 | 118754793 | 118755011 | CXCR5 | Phased Variants |
| 516 | chr11 | 118764838 | 118765408 | CXCR5 | Genotyping |
| 517 | chr11 | 118967323 | 118968029 | DPAGT1 | Genotyping |
| 518 | chr11 | 120127163 | 120127588 | POU2F3 | Genotyping |
| 519 | chr11 | 120189028 | 120189629 | POU2F3 | Genotyping |
| 520 | chr11 | 125472640 | 125472915 | STT3A | Genotyping |
| 521 | chr11 | 128391383 | 128391629 | ETS1 | Phased Variants |
| 522 | chr11 | 128391648 | 128392132 | ETS1 | Phased Variants |
| 523 | chr11 | 129739778 | 129740102 | NFRKB | Genotyping |
| 524 | chr11 | 131747549 | 131748030 | NTM | Genotyping |
| 525 | chr11 | 134027789 | 134027980 | NCAPD3 | Genotyping |
| 526 | chr11 | 134118684 | 134118873 | THYN1 | Genotyping |
| 527 | chr11 | 134129469 | 134130211 | ACAD8 | Genotyping |
| 528 | chr11 | 134130464 | 134131097 | ACAD8 | Genotyping |
| 529 | chr11 | 134133389 | 134133972 | ACAD8 | Genotyping |
| 530 | chr12 | 6439713 | 6439920 | TNFRSF1A | Genotyping |
| 531 | chr12 | 15813487 | 15813687 | EPS8 | Genotyping |
| 532 | chr12 | 18534682 | 18534856 | PIK3C2G | Genotyping |
| 533 | chr12 | 18544037 | 18544241 | PIK3C2G | Genotyping |
| 534 | chr12 | 18573807 | 18574017 | PIK3C2G | Genotyping |
| 535 | chr12 | 18699197 | 18699459 | PIK3C2G | Genotyping |
| 536 | chr12 | 18747397 | 18747562 | PIK3C2G | Genotyping |
| 537 | chr12 | 18800762 | 18801046 | PIK3C2G | Genotyping |
| 538 | chr12 | 18891267 | 18891560 | CAPZA3 | Genotyping |
| 539 | chr12 | 25205888 | 25206105 | LRMP | Phased Variants |
| 540 | chr12 | 25206398 | 25206616 | LRMP | Phased Variants |
| 541 | chr12 | 25206748 | 25206877 | LRMP | Phased Variants |
| 542 | chr12 | 25207088 | 25207474 | LRMP | Phased Variants |
| 543 | chr12 | 25398218 | 25398299 | KRAS | Genotyping |
| 544 | chr12 | 48190731 | 48190983 | HDAC7 | Genotyping |
| 545 | chr12 | 49415991 | 49416144 | KMT2D | Genotyping |
| 546 | chr12 | 49418306 | 49418550 | KMT2D | Genotyping |

TABLE 3-continued

| # | Chromosome | Region Start | Region End | Closest Gene | Reason for Inclusion |
|---|---|---|---|---|---|
| 547 | chr12 | 49420531 | 49420750 | KMT2D | Genotyping |
| 548 | chr12 | 49426451 | 49426592 | KMT2D | Genotyping |
| 549 | chr12 | 49427886 | 49428116 | KMT2D | Genotyping |
| 550 | chr12 | 49433331 | 49433507 | KMT2D | Genotyping |
| 551 | chr12 | 49437926 | 49438391 | KMT2D | Genotyping |
| 552 | chr12 | 49444391 | 49444595 | KMT2D | Genotyping |
| 553 | chr12 | 49447196 | 49447491 | KMT2D | Genotyping |
| 554 | chr12 | 57496552 | 57496735 | STAT6 | Genotyping |
| 555 | chr12 | 57498222 | 57498396 | STAT6 | Genotyping |
| 556 | chr12 | 57498912 | 57499150 | STAT6 | Genotyping |
| 557 | chr12 | 86198698 | 86199622 | RASSF9 | Genotyping |
| 558 | chr12 | 92537875 | 92538647 | BTG1 | Phased Variants |
| 559 | chr12 | 92538790 | 92539374 | BTG1 | Phased Variants |
| 560 | chr12 | 113495364 | 113496458 | DTX1 | Phased Variants |
| 561 | chr12 | 113496509 | 113496679 | DTX1 | Phased Variants |
| 562 | chr12 | 113496694 | 113496945 | DTX1 | Phased Variants |
| 563 | chr12 | 113497059 | 113497278 | DTX1 | Phased Variants |
| 564 | chr12 | 113515199 | 113515658 | DTX1 | Genotyping |
| 565 | chr12 | 113515664 | 113515934 | DTX1 | Genotyping |
| 566 | chr12 | 113530924 | 113531055 | DTX1 | Genotyping |
| 567 | chr12 | 113531319 | 113531531 | DTX1 | Genotyping |
| 568 | chr12 | 113531799 | 113531930 | DTX1 | Genotyping |
| 569 | chr12 | 113532569 | 113532781 | DTX1 | Genotyping |
| 570 | chr12 | 113532809 | 113533032 | DTX1 | Genotyping |
| 571 | chr12 | 113533099 | 113533237 | DTX1 | Genotyping |
| 572 | chr12 | 113534494 | 113534778 | DTX1 | Genotyping |
| 573 | chr12 | 122458781 | 122459524 | BCL7A | Phased Variants |
| 574 | chr12 | 122460811 | 122461193 | BCL7A | Phased Variants |
| 575 | chr12 | 122461316 | 122461882 | BCL7A | Phased Variants |
| 576 | chr12 | 122462001 | 122462210 | BCL7A | Phased Variants |
| 577 | chr12 | 122462716 | 122462935 | BCL7A | Phased Variants |
| 578 | chr12 | 122463031 | 122463137 | BCL7A | Phased Variants |
| 579 | chr13 | 32907206 | 32907376 | BRCA2 | Genotyping |
| 580 | chr13 | 32912226 | 32912828 | BRCA2 | Genotyping |
| 581 | chr13 | 41133662 | 41133842 | FOXO1 | Genotyping |
| 582 | chr13 | 41133922 | 41135026 | FOXO1 | Genotyping |
| 583 | chr13 | 41239682 | 41239755 | FOXO1 | Genotyping |
| 584 | chr13 | 41239827 | 41240356 | FOXO1 | Genotyping |
| 585 | chr13 | 41240362 | 41240788 | FOXO1 | Genotyping |
| 586 | chr13 | 46959165 | 46959379 | KIAA0226L | Phased Variants |
| 587 | chr13 | 46961680 | 46962067 | KIAA0226L | Phased Variants |
| 588 | chr13 | 51915233 | 51915552 | SERPINE3 | Genotyping |
| 589 | chr13 | 58207131 | 58209129 | PCDH17 | Genotyping |
| 590 | chr13 | 84453542 | 84455255 | SLITRK1 | Genotyping |
| 591 | chr13 | 113516229 | 113516436 | ATP11A | Phased Variants |
| 592 | chr14 | 23344697 | 23345206 | LRP10 | Genotyping |
| 593 | chr14 | 32615405 | 32615617 | ARHGAP5 | Genotyping |
| 594 | chr14 | 35873671 | 35873838 | NFKBIA | Genotyping |
| 595 | chr14 | 64330252 | 64330462 | SYNE2 | Phased Variants |
| 596 | chr14 | 69258238 | 69259642 | ZFP36L1 | Phased Variants |
| 597 | chr14 | 84420586 | 84420796 | FLRT2 | Phased Variants |
| 598 | chr14 | 96179592 | 96180295 | TCL1A | Phased Variants |
| 599 | chr14 | 106048955 | 106049032 | IGHA2 | Phased Variants |
| 600 | chr14 | 106054695 | 106055541 | IGHA2 | Genotyping |
| 601 | chr14 | 106055740 | 106055827 | IGHA2 | Genotyping |
| 602 | chr14 | 106055910 | 106055995 | IGHA2 | Genotyping |
| 603 | chr14 | 106056035 | 106056121 | IGHA2 | Genotyping |
| 604 | chr14 | 106068705 | 106068911 | IGHE | Phased Variants |
| 605 | chr14 | 06069045 | 106069384 | IGHE | Phased Variants |
| 606 | chr14 | 106071060 | 106071135 | IGHE | Phased Variants |
| 607 | chr14 | 106071190 | 106071271 | IGHE | Phased Variants |
| 608 | chr14 | 106092380 | 106092608 | IGHG4 | Genotyping |
| 609 | chr14 | 106092670 | 106093406 | IGHG4 | Genotyping |
| 610 | chr14 | 106093435 | 106093575 | IGHG4 | Genotyping |
| 611 | chr14 | 106093610 | 106094215 | IGHG4 | Genotyping |
| 612 | chr14 | 106094235 | 106094479 | IGHG4 | Genotyping |
| 613 | chr14 | 106094580 | 106094654 | IGHG4 | Genotyping |
| 614 | chr14 | 106094675 | 106094915 | IGHG4 | Genotyping |
| 615 | chr14 | 106095335 | 106095417 | IGHG4 | Phased Variants |
| 616 | chr14 | 106095480 | 106095560 | IGHG4 | Phased Variants |
| 617 | chr14 | 106110675 | 106110814 | IGHG2 | Phased Variants |
| 618 | chr14 | 106110830 | 106110904 | IGHG2 | Phased Variants |
| 619 | chr14 | 106110950 | 106111025 | IGHG2 | Phased Variants |
| 620 | chr14 | 106111100 | 106111311 | IGHG2 | Genotyping |
| 621 | chr14 | 106111390 | 106112121 | IGHG2 | Genotyping |
| 622 | chr14 | 106112160 | 106112302 | IGHG2 | Genotyping |
| 623 | chr14 | 106112335 | 106113010 | IGHG2 | Phased Variants |
| 624 | chr14 | 106113020 | 106113438 | IGHG2 | Phased Variants |

TABLE 3-continued

| # | Chromosome | Region Start | Region End | Closest Gene | Reason for Inclusion |
|---|---|---|---|---|---|
| 625 | chr14 | 106113450 | 106113625 | IGHG2 | Phased Variants |
| 626 | chr14 | 106113695 | 106113901 | IGHG2 | Phased Variants |
| 627 | chr14 | 106113905 | 106113984 | IGHG2 | Phased Variants |
| 628 | chr14 | 106114175 | 106114414 | IGHG2 | Phased Variants |
| 629 | chr14 | 106174970 | 106175819 | IGHA1 | Genotyping |
| 630 | chr14 | 106175820 | 106176042 | IGHA1 | Genotyping |
| 631 | chr14 | 106176070 | 106176217 | IGHA1 | Genotyping |
| 632 | chr14 | 106176235 | 106176320 | IGHA1 | Genotyping |
| 633 | chr14 | 106176375 | 106176932 | IGHA1 | Phased Variants |
| 634 | chr14 | 106176985 | 106177069 | IGHA1 | Phased Variants |
| 635 | chr14 | 106177425 | 106177536 | IGHA1 | Genotyping |
| 636 | chr14 | 106211960 | 106212864 | IGHG1 | Phased Variants |
| 637 | chr14 | 106212870 | 106212948 | IGHG1 | Phased Variants |
| 638 | chr14 | 106212980 | 106213124 | IGHG1 | Phased Variants |
| 639 | chr14 | 106213125 | 106213200 | IGHG1 | Phased Variants |
| 640 | chr14 | 106213210 | 106213525 | IGHG1 | Phased Variants |
| 641 | chr14 | 106213660 | 106214042 | IGHG1 | Phased Variants |
| 642 | chr14 | 106239250 | 106239357 | IGHG3 | Phased Variants |
| 643 | chr14 | 106239455 | 106239900 | IGHG3 | Phased Variants |
| 644 | chr14 | 106239990 | 106240155 | IGHG3 | Phased Variants |
| 645 | chr14 | 106240170 | 106240815 | IGHG3 | Phased Variants |
| 646 | chr14 | 106240820 | 106240892 | IGHG3 | Phased Variants |
| 647 | chr14 | 106240915 | 106241118 | IGHG3 | Phased Variants |
| 648 | chr14 | 106241200 | 106241278 | IGHG3 | Phased Variants |
| 649 | chr14 | 106241345 | 106241627 | IGHG3 | Phased Variants |
| 650 | chr14 | 106241630 | 106241705 | IGHG3 | Genotyping |
| 651 | chr14 | 106241710 | 106241975 | IGHG3 | Genotyping |
| 652 | chr14 | 106318100 | 106318327 | IGHM | Phased Variants |
| 653 | chr14 | 106322055 | 106322271 | IGHM | Phased Variants |
| 654 | chr14 | 106322905 | 106323129 | IGHM | Phased Variants |
| 655 | chr14 | 106323470 | 106323656 | IGHM | Phased Variants |
| 656 | chr14 | 106323805 | 106323896 | IGHM | Phased Variants |
| 657 | chr14 | 106324010 | 106324087 | IGHM | Phased Variants |
| 658 | chr14 | 106324155 | 106324245 | IGHM | Phased Variants |
| 659 | chr14 | 106324290 | 106324369 | IGHM | Phased Variants |
| 660 | chr14 | 106324490 | 106324577 | IGHM | Phased Variants |
| 661 | chr14 | 106324750 | 106325340 | IGHM | Phased Variants |
| 662 | chr14 | 106325360 | 106325513 | IGHM | Phased Variants |
| 663 | chr14 | 106325515 | 106325791 | IGHM | Phased Variants |
| 664 | chr14 | 106325820 | 106326095 | IGHJ6 | Phased Variants |
| 665 | chr14 | 106326245 | 106326338 | IGHJ6 | Phased Variants |
| 666 | chr14 | 106326450 | 106331808 | IGHD7-27 | Phased Variants |
| 667 | chr14 | 106357890 | 106357967 | IGHD6-19 | Phased Variants |
| 668 | chr14 | 106380360 | 106380541 | IGHD3-3 | Phased Variants |
| 669 | chr14 | 106380550 | 106380901 | IGHD3-3 | Phased Variants |
| 670 | chr14 | 106380910 | 106381109 | IGHD3-3 | Phased Variants |
| 671 | chr14 | 106381275 | 106381351 | IGHD3-3 | Phased Variants |
| 672 | chr14 | 106381485 | 106381633 | IGHD2-2 | Phased Variants |
| 673 | chr14 | 106381655 | 106381724 | IGHD2-2 | Phased Variants |
| 674 | chr14 | 106381890 | 106381968 | IGHD2-2 | Phased Variants |
| 675 | chr14 | 106381990 | 106382161 | IGHD2-2 | Phased Variants |
| 676 | chr14 | 106382325 | 106382403 | IGHD2-2 | Phased Variants |
| 677 | chr14 | 106382905 | 106383014 | IGHD2-2 | Phased Variants |
| 678 | chr14 | 106383030 | 106383140 | IGHD2-2 | Phased Variants |
| 679 | chr14 | 106383980 | 106384142 | IGHD1-1 | Phased Variants |
| 680 | chr14 | 106384630 | 106384702 | IGHD1-1 | Phased Variants |
| 681 | chr14 | 106384720 | 106384798 | IGHD1-1 | Phased Variants |
| 682 | chr14 | 106384825 | 106384957 | IGHD1-1 | Phased Variants |
| 683 | chr14 | 106405615 | 106405963 | IGHV6-1 | Genotyping |
| 684 | chr14 | 106452660 | 106452748 | IGHV1-2 | Genotyping |
| 685 | chr14 | 106452755 | 106452907 | IGHV1-2 | Genotyping |
| 686 | chr14 | 106452940 | 106453023 | IGHV1-2 | Genotyping |
| 687 | chr14 | 106471395 | 106471476 | IGHV1-3 | Genotyping |
| 688 | chr14 | 106471510 | 106471609 | IGHV1-3 | Genotyping |
| 689 | chr14 | 106494090 | 106494168 | IGHV2-5 | Phased Variants |
| 690 | chr14 | 106494210 | 106494365 | IGHV2-5 | Phased Variants |
| 691 | chr14 | 106494445 | 106494553 | IGHV2-5 | Phased Variants |
| 692 | chr14 | 106494565 | 106494640 | IGHV2-5 | Phased Variants |
| 693 | chr14 | 106494650 | 106494806 | IGHV2-5 | Phased Variants |
| 694 | chr14 | 106518495 | 106518570 | IGHV3-7 | Phased Variants |
| 695 | chr14 | 106518855 | 106518962 | IGHV3-7 | Phased Variants |
| 696 | chr14 | 106518970 | 106519111 | IGHV3-7 | Phased Variants |
| 697 | chr14 | 106539175 | 106539315 | IGHV1-8 | Genotyping |
| 698 | chr14 | 106552365 | 106552502 | IGHV3-9 | Genotyping |
| 699 | chr14 | 106573315 | 106573414 | IGHV3-11 | Genotyping |
| 700 | chr14 | 106573445 | 106573524 | IGHV3-11 | Genotyping |
| 701 | chr14 | 106573540 | 106573645 | IGHV3-11 | Phased Variants |
| 702 | chr14 | 106573685 | 106574021 | IGHV3-11 | Phased Variants |

TABLE 3-continued

| # | Chromosome | Region Start | Region End | Closest Gene | Reason for Inclusion |
|---|---|---|---|---|---|
| 703 | chr14 | 106586200 | 106586343 | IGHV3-13 | Genotyping |
| 704 | chr14 | 106610380 | 106610479 | IGHV3-15 | Genotyping |
| 705 | chr14 | 106610480 | 106610557 | IGHV3-15 | Genotyping |
| 706 | chr14 | 106610690 | 106610765 | IGHV3-15 | Phased Variants |
| 707 | chr14 | 106621885 | 106622026 | IGHV3-16 | Genotyping |
| 708 | chr14 | 106622035 | 106622108 | IGHV3-16 | Genotyping |
| 709 | chr14 | 106641655 | 106641789 | IGHV1-18 | Genotyping |
| 710 | chr14 | 106642110 | 106642265 | IGHV1-18 | Phased Variants |
| 711 | chr14 | 106667545 | 106667628 | IGHV3-20 | Genotyping |
| 712 | chr14 | 106667675 | 106667750 | IGHV3-20 | Genotyping |
| 713 | chr14 | 106667805 | 106667882 | IGHV3-20 | Genotyping |
| 714 | chr14 | 106691755 | 106691904 | IGHV3-21 | Genotyping |
| 715 | chr14 | 106725295 | 106725442 | IGHV3-23 | Phased Variants |
| 716 | chr14 | 106725550 | 106725663 | IGHV3-23 | Phased Variants |
| 717 | chr14 | 106725780 | 106725952 | IGHV3-23 | Phased Variants |
| 718 | chr14 | 106725995 | 106726188 | IGHV3-23 | Phased Variants |
| 719 | chr14 | 106732970 | 106733077 | IGHV1-24 | Phased Variants |
| 720 | chr14 | 106733185 | 106733270 | IGHV1-24 | Phased Variants |
| 721 | chr14 | 106733275 | 106733487 | IGHV1-24 | Phased Variants |
| 722 | chr14 | 106757725 | 106757888 | IGHV2-26 | Genotyping |
| 723 | chr14 | 106758470 | 106758653 | IGHV2-26 | Phased Variants |
| 724 | chr14 | 106780610 | 106780752 | IGHV4-28 | Genotyping |
| 725 | chr14 | 106791090 | 106791169 | IGHV3-30 | Phased Variants |
| 726 | chr14 | 106805290 | 106805428 | IGHV4-31 | Genotyping |
| 727 | chr14 | 106805945 | 106806076 | IGHV4-31 | Phased Variants |
| 728 | chr14 | 106806120 | 106806219 | IGHV4-31 | Phased Variants |
| 729 | chr14 | 106815805 | 106815910 | IGHV3-33 | Phased Variants |
| 730 | chr14 | 106829685 | 106829757 | IGHV4-34 | Phased Variants |
| 731 | chr14 | 106829765 | 106829986 | IGHV4-34 | Phased Variants |
| 732 | chr14 | 106830125 | 106830196 | IGHV4-34 | Phased Variants |
| 733 | chr14 | 106830240 | 106830312 | IGHV4-34 | Phased Variants |
| 734 | chr14 | 106830315 | 106830884 | IGHV4-34 | Phased Variants |
| 735 | chr14 | 106831185 | 106831594 | IGHV4-34 | Phased Variants |
| 736 | chr14 | 106845300 | 106845540 | IGHV3-35 | Genotyping |
| 737 | chr14 | 106846385 | 106846557 | IGHV3-35 | Phased Variants |
| 738 | chr14 | 106866380 | 106866461 | IGHV3-38 | Genotyping |
| 739 | chr14 | 106866475 | 106866638 | IGHV3-38 | Genotyping |
| 740 | chr14 | 106877715 | 106877858 | IGHV4-39 | Phased Variants |
| 741 | chr14 | 106877930 | 106878498 | IGHV4-39 | Phased Variants |
| 742 | chr14 | 106878540 | 106878612 | IGHV4-39 | Phased Variants |
| 743 | chr14 | 106878680 | 106878759 | IGHV4-39 | Phased Variants |
| 744 | chr14 | 106926180 | 106926405 | IGHV3-43 | Genotyping |
| 745 | chr14 | 106962965 | 106963167 | IGHV1-45 | Genotyping |
| 746 | chr14 | 106963170 | 106963280 | IGHV1-45 | Genotyping |
| 747 | chr14 | 106967130 | 106967209 | IGHV1-46 | Genotyping |
| 748 | chr14 | 106967315 | 106967397 | IGHV1-46 | Genotyping |
| 749 | chr14 | 106994300 | 106994376 | IGHV3-48 | Phased Variants |
| 750 | chr14 | 106994430 | 106994534 | IGHV3-48 | Phased Variants |
| 751 | chr14 | 106994545 | 106994618 | IGHV3-48 | Phased Variants |
| 752 | chr14 | 106994660 | 106994745 | IGHV3-48 | Phased Variants |
| 753 | chr14 | 106994760 | 106994904 | IGHV3-48 | Phased Variants |
| 754 | chr14 | 107013035 | 107013204 | IGHV3-49 | Genotyping |
| 755 | chr14 | 107034665 | 107034845 | IGHV5-51 | Genotyping |
| 756 | chr14 | 107034955 | 107035097 | IGHV5-51 | Genotyping |
| 757 | chr14 | 107078455 | 107078631 | IGHV1-58 | Genotyping |
| 758 | chr14 | 107083565 | 107083726 | IGHV4-59 | Phased Variants |
| 759 | chr14 | 107083790 | 107083923 | IGHV4-59 | Phased Variants |
| 760 | chr14 | 107113405 | 107113560 | IGHV3-64 | Phased Variants |
| 761 | chr14 | 107113820 | 107113922 | IGHV3-64 | Phased Variants |
| 762 | chr14 | 107114095 | 107114238 | IGHV3-64 | Phased Variants |
| 763 | chr14 | 107136755 | 107136899 | IGHV3-66 | Phased Variants |
| 764 | chr14 | 107169645 | 107169841 | IGHV1-69 | Phased Variants |
| 765 | chr14 | 107169970 | 107170195 | IGHV1-69 | Phased Variants |
| 766 | chr14 | 107170220 | 107170472 | IGHV1-69 | Phased Variants |
| 767 | chr14 | 107170475 | 107170563 | IGHV1-69 | Phased Variants |
| 768 | chr14 | 107170660 | 107170871 | IGHV1-69 | Phased Variants |
| 769 | chr14 | 107178305 | 107178377 | IGHV2-70 | Phased Variants |
| 770 | chr14 | 107178415 | 107178869 | IGHV2-70 | Phased Variants |
| 771 | chr14 | 107178880 | 107179116 | IGHV2-70 | Phased Variants |
| 772 | chr14 | 107179130 | 107179339 | IGHV2-70 | Phased Variants |
| 773 | chr14 | 107179360 | 107180001 | IGHV2-70 | Phased Variants |
| 774 | chr14 | 107199020 | 107199094 | IGHV3-72 | Genotyping |
| 775 | chr14 | 107199095 | 107199173 | IGHV3-72 | Genotyping |
| 776 | chr14 | 107210955 | 107211159 | IGHV3-73 | Genotyping |
| 777 | chr14 | 107218755 | 107218891 | IGHV3-74 | Genotyping |
| 778 | chr14 | 107258910 | 107259078 | IGHV7-81 | Phased Variants |
| 779 | chr14 | 107259100 | 107259206 | IGHV7-81 | Phased Variants |
| 780 | chr14 | 107259235 | 107259444 | IGHV7-81 | Phased Variants |

TABLE 3-continued

| # | Chromosome | Region Start | Region End | Closest Gene | Reason for Inclusion |
|---|---|---|---|---|---|
| 781 | chr14 | 107259555 | 107259635 | IGHV7-81 | Phased Variants |
| 782 | chr14 | 107282770 | 107282884 | IGHV7-81 | Genotyping |
| 783 | chr14 | 107282945 | 107283018 | IGHV7-81 | Genotyping |
| 784 | chr15 | 45003678 | 45003861 | B2M | Genotyping |
| 785 | chr15 | 45007718 | 45007927 | B2M | Genotyping |
| 786 | chr15 | 45008463 | 45008603 | B2M | Genotyping |
| 787 | chr15 | 66727354 | 66727536 | MAP2K1 | Genotyping |
| 788 | chr15 | 66729014 | 66729123 | MAP2K1 | Genotyping |
| 789 | chr15 | 66729139 | 66729292 | MAP2K1 | Genotyping |
| 790 | chr15 | 86312062 | 86312565 | KLHL25 | Genotyping |
| 791 | chr16 | 2812096 | 2812786 | SRRM2 | Genotyping |
| 792 | chr16 | 3779106 | 3779320 | CREBBP | Genotyping |
| 793 | chr16 | 3781171 | 3781464 | CREBBP | Genotyping |
| 794 | chr16 | 3781756 | 3781972 | CREBBP | Genotyping |
| 795 | chr16 | 3786011 | 3786223 | CREBBP | Genotyping |
| 796 | chr16 | 3786591 | 3786885 | CREBBP | Genotyping |
| 797 | chr16 | 3788511 | 3788716 | CREBBP | Genotyping |
| 798 | chr16 | 3789521 | 3789770 | CREBBP | Genotyping |
| 799 | chr16 | 3790376 | 3790580 | CREBBP | Genotyping |
| 800 | chr16 | 3794846 | 3794994 | CREBBP | Genotyping |
| 801 | chr16 | 3808801 | 3809009 | CREBBP | Genotyping |
| 802 | chr16 | 3817706 | 3817915 | CREBBP | Genotyping |
| 803 | chr16 | 3823711 | 3823942 | CREBBP | Genotyping |
| 804 | chr16 | 3824536 | 3824719 | CREBBP | Genotyping |
| 805 | chr16 | 3832716 | 3832942 | CREBBP | Genotyping |
| 806 | chr16 | 3900236 | 3900462 | CREBBP | Genotyping |
| 807 | chr16 | 3900561 | 3900914 | CREBBP | Genotyping |
| 808 | chr16 | 10971440 | 10973882 | CIITA | Phased Variants |
| 809 | chr16 | 10973885 | 10974203 | CIITA | Phased Variants |
| 810 | chr16 | 11348520 | 11349249 | SOCS1 | Phased Variants |
| 811 | chr16 | 30093722 | 30093935 | PPP4C | Genotyping |
| 812 | chr16 | 33523607 | 33523675 | IGHV3OR16-12 | Phased Variants |
| 813 | chr16 | 81946175 | 81946356 | PLCG2 | Genotyping |
| 814 | chr16 | 81953055 | 81953307 | PLCG2 | Genotyping |
| 815 | chr16 | 81962120 | 81962263 | PLCG2 | Genotyping |
| 816 | chr16 | 85933003 | 85933569 | IRF8 | Phased Variants |
| 817 | chr16 | 85936563 | 85936836 | IRF8 | Genotyping |
| 818 | chr16 | 85942563 | 85942821 | IRF8 | Genotyping |
| 819 | chr16 | 85945108 | 85945330 | IRF8 | Genotyping |
| 820 | chr16 | 85946708 | 85946887 | IRF8 | Genotyping |
| 821 | chr16 | 85948018 | 85948170 | IRF8 | Genotyping |
| 822 | chr16 | 85951993 | 85952448 | IRF8 | Genotyping |
| 823 | chr16 | 85953683 | 85953837 | IRF8 | Genotyping |
| 824 | chr16 | 85954723 | 85954937 | IRF8 | Genotyping |
| 825 | chr17 | 5366796 | 5367031 | DHX33 | Genotyping |
| 826 | chr17 | 7576949 | 7577197 | TP53 | Genotyping |
| 827 | chr17 | 7577444 | 7577683 | TP53 | Genotyping |
| 828 | chr17 | 7578129 | 7578336 | TP53 | Genotyping |
| 829 | chr17 | 7578344 | 7578591 | TP53 | Genotyping |
| 830 | chr17 | 7579259 | 7579428 | TP53 | Genotyping |
| 831 | chr17 | 18001529 | 18001704 | DRG2 | Genotyping |
| 832 | chr17 | 18022119 | 18022791 | MYO15A | Genotyping |
| 833 | chr17 | 40467709 | 40467857 | STAT3 | Genotyping |
| 834 | chr17 | 40469104 | 40469321 | STAT3 | Genotyping |
| 835 | chr17 | 40474309 | 40474530 | STAT3 | Genotyping |
| 836 | chr17 | 40474974 | 40475190 | STAT3 | Genotyping |
| 837 | chr17 | 40475254 | 40475394 | STAT3 | Genotyping |
| 838 | chr17 | 40478074 | 40478252 | STAT3 | Genotyping |
| 839 | chr17 | 40485844 | 40486132 | STAT3 | Genotyping |
| 840 | chr17 | 40489754 | 40489903 | STAT3 | Genotyping |
| 841 | chr17 | 40491284 | 40491489 | STAT3 | Genotyping |
| 842 | chr17 | 41847058 | 41847241 | DUSP3 | Genotyping |
| 843 | chr17 | 51900441 | 51900897 | KIF2B | Genotyping |
| 844 | chr17 | 56408574 | 56408755 | BZRAP1 | Phased Variants |
| 845 | chr17 | 56408884 | 56409615 | BZRAP1 | Phased Variants |
| 846 | chr17 | 62006520 | 62006919 | CD79B | Genotyping |
| 847 | chr17 | 62007105 | 62007279 | CD79B | Genotyping |
| 848 | chr17 | 62007410 | 62007761 | CD79B | Genotyping |
| 849 | chr17 | 62008645 | 62008786 | CD79B | Genotyping |
| 850 | chr17 | 62009505 | 62009659 | CD79B | Genotyping |
| 851 | chr17 | 63010240 | 63010308 | GNA13 | Phased Variants |
| 852 | chr17 | 63010315 | 63010973 | GNA13 | Phased Variants |
| 853 | chr17 | 63014313 | 63014461 | GNA13 | Genotyping |
| 854 | chr17 | 63049573 | 63049774 | GNA13 | Genotyping |
| 855 | chr17 | 63052443 | 63052678 | GNA13 | Genotyping |
| 856 | chr17 | 75447868 | 75448421 | 9-Sep | Phased Variants |
| 857 | chr17 | 78343503 | 78343715 | RNF213 | Genotyping |
| 858 | chr17 | 79478953 | 79479026 | ACTG1 | Genotyping |

TABLE 3-continued

| # | Chromosome | Region Start | Region End | Closest Gene | Reason for Inclusion |
|---|---|---|---|---|---|
| 859 | chr18 | 1477565 | 1477666 | ADCYAP1 | Phased Variants |
| 860 | chr18 | 6947104 | 6947347 | LAMA1 | Genotyping |
| 861 | chr18 | 6980464 | 6980680 | LAMA1 | Genotyping |
| 862 | chr18 | 13825915 | 13826461 | MC5R | Genotyping |
| 863 | chr18 | 30349775 | 30350300 | AC012123.1 | Phased Variants |
| 864 | chr18 | 48231684 | 48232112 | MAPK4 | Genotyping |
| 865 | chr18 | 48327694 | 48327901 | MRO | Genotyping |
| 866 | chr18 | 48512954 | 48513347 | ELAC1 | Genotyping |
| 867 | chr18 | 48591759 | 48592011 | SMAD4 | Genotyping |
| 868 | chr18 | 48593364 | 48593571 | SMAD4 | Genotyping |
| 869 | chr18 | 48604604 | 48604852 | SMAD4 | Genotyping |
| 870 | chr18 | 48703169 | 48703965 | MEX3C | Genotyping |
| 871 | chr18 | 53804515 | 53804796 | TXNL1 | Genotyping |
| 872 | chr18 | 55274405 | 55274580 | NARS | Genotyping |
| 873 | chr18 | 55319680 | 55319999 | ATP8B1 | Genotyping |
| 874 | chr18 | 55329690 | 55329857 | ATP8B1 | Genotyping |
| 875 | chr18 | 55359005 | 55359259 | ATP8B1 | Genotyping |
| 876 | chr18 | 56054915 | 56055594 | NEDD4L | Genotyping |
| 877 | chr18 | 56063365 | 56063826 | NEDD4L | Genotyping |
| 878 | chr18 | 60763829 | 60764032 | BCL2 | Genotyping |
| 879 | chr18 | 60764299 | 60764540 | BCL2 | Genotyping |
| 880 | chr18 | 60774414 | 60774660 | BCL2 | Genotyping |
| 881 | chr18 | 60793369 | 60793654 | BCL2 | Genotyping |
| 882 | chr18 | 60795829 | 60796006 | BCL2 | Genotyping |
| 883 | chr18 | 60806264 | 60806836 | BCL2 | Phased Variants |
| 884 | chr18 | 60983784 | 60983991 | BCL2 | Phased Variants |
| 885 | chr18 | 60984454 | 60986731 | BCL2 | Phased Variants |
| 886 | chr18 | 60986844 | 60987047 | BCL2 | Phased Variants |
| 887 | chr18 | 60987964 | 60988511 | BCL2 | Phased Variants |
| 888 | chr18 | 64172116 | 64172531 | CDH19 | Genotyping |
| 889 | chr18 | 64176241 | 64176518 | CDH19 | Genotyping |
| 890 | chr18 | 64239166 | 64239357 | CDH19 | Genotyping |
| 891 | chr18 | 65179856 | 65181824 | DSEL | Genotyping |
| 892 | chr18 | 73944893 | 73945380 | ZNF516 | Genotyping |
| 893 | chr18 | 75683734 | 75684502 | GALR1 | Genotyping |
| 894 | chr18 | 77092820 | 77093034 | ATP9B | Genotyping |
| 895 | chr18 | 77170715 | 77171032 | NFATC1 | Genotyping |
| 896 | chr18 | 77208755 | 77208996 | NFATC1 | Genotyping |
| 897 | chr18 | 77227415 | 77227661 | NFATC1 | Genotyping |
| 898 | chr18 | 77288040 | 77288611 | NFATC1 | Genotyping |
| 899 | chr18 | 77794425 | 77795130 | RBFA | Genotyping |
| 900 | chr19 | 1376440 | 1376662 | MUM1 | Genotyping |
| 901 | chr19 | 6586161 | 6586445 | CD70 | Genotyping |
| 902 | chr19 | 6590026 | 6590238 | CD70 | Genotyping |
| 903 | chr19 | 6590786 | 6591079 | CD70 | Genotyping |
| 904 | chr19 | 8028408 | 8028583 | ELAVL1 | Genotyping |
| 905 | chr19 | 10334563 | 10335187 | S1PR2 | Genotyping |
| 906 | chr19 | 10335308 | 10335585 | S1PR2 | Genotyping |
| 907 | chr19 | 10340823 | 10341376 | S1PR2 | Phased Variants |
| 908 | chr19 | 10341833 | 10341984 | S1PR2 | Genotyping |
| 909 | chr19 | 12902574 | 12902861 | JUNB | Genotyping |
| 910 | chr19 | 19256469 | 19256851 | MEF2B | Genotyping |
| 911 | chr19 | 19257044 | 19257222 | MEF2B | Genotyping |
| 912 | chr19 | 19257339 | 19257480 | MEF2B | Genotyping |
| 913 | chr19 | 19257489 | 19257741 | MEF2B | Genotyping |
| 914 | chr19 | 19257824 | 19258036 | MEF2B | Genotyping |
| 915 | chr19 | 19258484 | 19258662 | MEF2B | Genotyping |
| 916 | chr19 | 19259984 | 19260176 | MEF2B | Genotyping |
| 917 | chr19 | 19261414 | 19261588 | MEF2B | Genotyping |
| 918 | chr19 | 19293309 | 19293478 | MEF2BNB | Genotyping |
| 919 | chr19 | 42599890 | 42600121 | POU2F2 | Genotyping |
| 920 | chr19 | 51525626 | 51525937 | KLK11 | Genotyping |
| 921 | chr19 | 51559441 | 51560040 | KLK13 | Genotyping |
| 922 | chr19 | 51561771 | 51561943 | KLK13 | Genotyping |
| 923 | chr19 | 52381611 | 52381786 | ZNF577 | Genotyping |
| 924 | chr19 | 52403336 | 52403586 | ZNF649 | Genotyping |
| 925 | chr19 | 52961146 | 52961224 | ZNF534 | Genotyping |
| 926 | chr19 | 52961226 | 52961578 | ZNF534 | Genotyping |
| 927 | chr19 | 53598586 | 53599055 | ZNF160 | Genotyping |
| 928 | chr20 | 23028372 | 23028858 | THBD | Genotyping |
| 929 | chr20 | 25003526 | 25003774 | ACSS1 | Genotyping |
| 930 | chr20 | 46131072 | 46131213 | NCOA3 | Phased Variants |
| 931 | chr20 | 46131217 | 46131287 | NCOA3 | Phased Variants |
| 932 | chr21 | 18981233 | 18981504 | BTG3 | Genotyping |
| 933 | chr21 | 28213258 | 28213536 | ADAMTS1 | Genotyping |
| 934 | chr21 | 28216763 | 28217005 | ADAMTS1 | Genotyping |
| 935 | chr22 | 22380472 | 22381038 | IGLV4-69 | Phased Variants |
| 936 | chr22 | 22385622 | 22385767 | IGLV4-69 | Genotyping |

TABLE 3-continued

| # | Chromosome | Region Start | Region End | Closest Gene | Reason for Inclusion |
|---|---|---|---|---|---|
| 937 | chr22 | 22385777 | 22385898 | IGLV4-69 | Genotyping |
| 938 | chr22 | 22453287 | 22453502 | IGLV8-61 | Genotyping |
| 939 | chr22 | 22453527 | 22453608 | IGLV8-61 | Genotyping |
| 940 | chr22 | 22516707 | 22516785 | IGLV4-60 | Phased Variants |
| 941 | chr22 | 22516827 | 22517113 | IGLV4-60 | Phased Variants |
| 942 | chr22 | 22550337 | 22550812 | IGLV6-57 | Genotyping |
| 943 | chr22 | 22556227 | 22556630 | IGLV11-55 | Genotyping |
| 944 | chr22 | 22569332 | 22569655 | IGLV10-54 | Genotyping |
| 945 | chr22 | 22673242 | 22673607 | IGLV5-52 | Genotyping |
| 946 | chr22 | 22677077 | 22677216 | IGLV1-51 | Phased Variants |
| 947 | chr22 | 22677227 | 22677337 | IGLV1-51 | Genotyping |
| 948 | chr22 | 22681927 | 22682007 | IGLV1-50 | Genotyping |
| 949 | chr22 | 22682097 | 22682213 | IGLV1-50 | Genotyping |
| 950 | chr22 | 22697727 | 22698123 | IGLV9-49 | Genotyping |
| 951 | chr22 | 22707427 | 22707509 | IGLV5-48 | Genotyping |
| 952 | chr22 | 22707517 | 22707658 | IGLV5-48 | Phased Variants |
| 953 | chr22 | 22707742 | 22707823 | IGLV5-48 | Genotyping |
| 954 | chr22 | 22712077 | 22712496 | IGLV1-47 | Phased Variants |
| 955 | chr22 | 22712512 | 22712625 | IGLV1-47 | Genotyping |
| 956 | chr22 | 22723897 | 22724189 | IGLV7-46 | Phased Variants |
| 957 | chr22 | 22724207 | 22724494 | IGLV7-46 | Phased Variants |
| 958 | chr22 | 22730452 | 22730552 | IGLV5-45 | Phased Variants |
| 959 | chr22 | 22730607 | 22730756 | IGLV5-45 | Phased Variants |
| 960 | chr22 | 22730887 | 22730955 | IGLV5-45 | Phased Variants |
| 961 | chr22 | 22735417 | 22735604 | IGLV1-44 | Phased Variants |
| 962 | chr22 | 22735792 | 22735878 | IGLV1-44 | Phased Variants |
| 963 | chr22 | 22749602 | 22749701 | IGLV7-43 | Phased Variants |
| 964 | chr22 | 22749732 | 22749853 | IGLV7-43 | Phased Variants |
| 965 | chr22 | 22749857 | 22749939 | IGLV7-43 | Phased Variants |
| 966 | chr22 | 22749942 | 22750074 | IGLV7-43 | Phased Variants |
| 967 | chr22 | 22750092 | 22750342 | IGLV7-43 | Phased Variants |
| 968 | chr22 | 22758647 | 22759294 | IGLV1-40 | Phased Variants |
| 969 | chr22 | 22759297 | 22759377 | IGLV1-40 | Phased Variants |
| 970 | chr22 | 22764167 | 22764309 | IGLV1-40 | Phased Variants |
| 971 | chr22 | 22764367 | 22764450 | IGLV1-40 | Phased Variants |
| 972 | chr22 | 22764552 | 22764634 | IGLV1-40 | Phased Variants |
| 973 | chr22 | 22782037 | 22782325 | IGLV5-37 | Genotyping |
| 974 | chr22 | 22786477 | 22786702 | IGLV1-36 | Genotyping |
| 975 | chr22 | 22786727 | 22786842 | IGLV1-36 | Genotyping |
| 976 | chr22 | 22930852 | 22931173 | IGLV2-33 | Genotyping |
| 977 | chr22 | 22937192 | 22937341 | IGLV3-32 | Genotyping |
| 978 | chr22 | 22937347 | 22937548 | IGLV3-32 | Genotyping |
| 979 | chr22 | 23010977 | 23011143 | IGLV3-27 | Genotyping |
| 980 | chr22 | 23011172 | 23011316 | IGLV3-27 | Genotyping |
| 981 | chr22 | 23029497 | 23029581 | IGLV3-25 | Genotyping |
| 982 | chr22 | 23029622 | 23029778 | IGLV3-25 | Genotyping |
| 983 | chr22 | 23040452 | 23040527 | IGLV2-23 | Phased Variants |
| 984 | chr22 | 23040592 | 23040811 | IGLV2-23 | Phased Variants |
| 985 | chr22 | 23040852 | 23041365 | IGLV2-23 | Phased Variants |
| 986 | chr22 | 23047067 | 23047329 | IGLV3-22 | Genotyping |
| 987 | chr22 | 23055367 | 23055445 | IGLV3-21 | Genotyping |
| 988 | chr22 | 23055497 | 23055577 | IGLV3-21 | Phased Variants |
| 989 | chr22 | 23055727 | 23055857 | IGLV3-21 | Phased Variants |
| 990 | chr22 | 23063307 | 23063661 | IGLV3-19 | Genotyping |
| 991 | chr22 | 23077337 | 23077435 | IGLV2-18 | Genotyping |
| 992 | chr22 | 23077537 | 23077615 | IGLV2-18 | Genotyping |
| 993 | chr22 | 23090122 | 23090205 | IGLV3-16 | Genotyping |
| 994 | chr22 | 23090287 | 23090372 | IGLV3-16 | Genotyping |
| 995 | chr22 | 23101392 | 23101473 | IGLV2-14 | Phased Variants |
| 996 | chr22 | 23101532 | 23101605 | IGLV2-14 | Phased Variants |
| 997 | chr22 | 23101652 | 23101735 | IGLV2-14 | Genotyping |
| 998 | chr22 | 23114792 | 23114874 | IGLV3-12 | Genotyping |
| 999 | chr22 | 23114947 | 23115052 | IGLV3-12 | Genotyping |
| 1000 | chr22 | 23135152 | 23135230 | IGLV2-11 | Genotyping |
| 1001 | chr22 | 23135247 | 23135399 | IGLV2-11 | Genotyping |
| 1002 | chr22 | 23135437 | 23135521 | IGLV2-11 | Genotyping |
| 1003 | chr22 | 23154347 | 23154477 | IGLV3-10 | Phased Variants |
| 1004 | chr22 | 23154597 | 23154815 | IGLV3-10 | Phased Variants |
| 1005 | chr22 | 23161917 | 23162052 | IGLV3-9 | Genotyping |
| 1006 | chr22 | 23162072 | 23162290 | IGLV3-9 | Genotyping |
| 1007 | chr22 | 23165422 | 23165496 | IGLV2-8 | Phased Variants |
| 1008 | chr22 | 2316SS42 | 23165680 | IGLV2-8 | Phased Variants |
| 1009 | chr22 | 23165727 | 23165811 | IGLV2-8 | Phased Variants |
| 1010 | chr22 | 23192412 | 23192818 | IGLV4-3 | Phased Variants |
| 1011 | chr22 | 23197917 | 23198053 | IGLV4-3 | Phased Variants |
| 1012 | chr22 | 23198067 | 23198475 | IGLV4-3 | Phased Variants |
| 1013 | chr22 | 23198587 | 23198732 | IGLV4-3 | Phased Variants |
| 1014 | chr22 | 23198797 | 23198869 | IGLV4-3 | Phased Variants |

TABLE 3-continued

| # | Chromosome | Region Start | Region End | Closest Gene | Reason for Inclusion |
|---|---|---|---|---|---|
| 1015 | chr22 | 23199022 | 23199127 | IGLV4-3 | Phased Variants |
| 1016 | chr22 | 23199182 | 23199261 | IGLV4-3 | Phased Variants |
| 1017 | chr22 | 23199277 | 23199671 | IGLV4-3 | Phased Variants |
| 1018 | chr22 | 23213857 | 23214141 | IGLV4-3 | Genotyping |
| 1019 | chr22 | 23214167 | 23214249 | IGLV4-3 | Genotyping |
| 1020 | chr22 | 23222927 | 23223065 | IGLV3-1 | Phased Variants |
| 1021 | chr22 | 23223077 | 23223319 | IGLV3-1 | Phased Variants |
| 1022 | chr22 | 23223327 | 23224010 | IGLV3-1 | Phased Variants |
| 1023 | chr22 | 23227062 | 23227279 | IGLL5 | Phased Variants |
| 1024 | chr22 | 23227567 | 23227896 | IGLL5 | Phased Variants |
| 1025 | chr22 | 23227897 | 23228624 | IGLL5 | Phased Variants |
| 1026 | chr22 | 23229332 | 23229550 | IGLL5 | Phased Variants |
| 1027 | chr22 | 23229562 | 23229739 | IGLL5 | Phased Variants |
| 1028 | chr22 | 23230012 | 23231063 | IGLL5 | Phased Variants |
| 1029 | chr22 | 23231072 | 23231764 | IGLL5 | Phased Variants |
| 1030 | chr22 | 23231927 | 23232005 | IGLL5 | Phased Variants |
| 1031 | chr22 | 23232062 | 23232346 | IGLL5 | Phased Variants |
| 1032 | chr22 | 23232362 | 23232465 | IGLL5 | Phased Variants |
| 1033 | chr22 | 23232517 | 23232737 | IGLL5 | Phased Variants |
| 1034 | chr22 | 23234612 | 23235837 | IGLJ1 | Phased Variants |
| 1035 | chr22 | 23235847 | 23236276 | IGLJ1 | Phased Variants |
| 1036 | chr22 | 23236277 | 23236378 | IGLJ1 | Phased Variants |
| 1037 | chr22 | 23236387 | 23236526 | IGLJ1 | Phased Variants |
| 1038 | chr22 | 23236557 | 23236851 | IGLJ1 | Phased Variants |
| 1039 | chr22 | 23236877 | 23237366 | IGLC1 | Phased Variants |
| 1040 | chr22 | 23241762 | 23241835 | IGLJ2 | Genotyping |
| 1041 | chr22 | 23242602 | 23242981 | IGLC2 | Phased Variants |
| 1042 | chr22 | 23244157 | 23244373 | IGLC2 | Phased Variants |
| 1043 | chr22 | 23247137 | 23247209 | IGLJ3 | Genotyping |
| 1044 | chr22 | 23247257 | 23247444 | IGLJ3 | Phased Variants |
| 1045 | chr22 | 23247467 | 23247630 | IGLJ3 | Phased Variants |
| 1046 | chr22 | 23248182 | 23248404 | IGLC3 | Phased Variants |
| 1047 | chr22 | 23252687 | 23252824 | IGLJ4 | Genotyping |
| 1048 | chr22 | 23256362 | 23256504 | IGLJ5 | Genotyping |
| 1049 | chr22 | 23260267 | 23260399 | IGLJ6 | Genotyping |
| 1050 | chr22 | 23263507 | 23263653 | IGLJ7 | Genotyping |
| 1051 | chr22 | 23263872 | 23264263 | IGLJ7 | Phased Variants |
| 1052 | chr22 | 23278157 | 23278381 | IGLC7 | Phased Variants |
| 1053 | chr22 | 23282767 | 23282839 | IGLC7 | Phased Variants |
| 1054 | chr22 | 23282842 | 23282956 | IGLC7 | Phased Variants |
| 1055 | chr22 | 23523567 | 23524204 | BCR | Genotyping |
| 1056 | chr22 | 23524212 | 23524419 | BCR | Genotyping |
| 1057 | chr22 | 23610547 | 23610791 | BCR | Genotyping |
| 1058 | chr22 | 29191136 | 29191455 | XBP1 | Genotyping |
| 1059 | chr22 | 29191461 | 29191746 | XBP1 | Genotyping |
| 1060 | chr22 | 29192006 | 29192215 | XBP1 | Genotyping |
| 1061 | chr22 | 29193041 | 29193205 | XBP1 | Genotyping |
| 1062 | chr22 | 29196261 | 29196547 | XBP1 | Genotyping |
| 1063 | chr22 | 41513340 | 41513562 | EP300 | Genotyping |
| 1064 | chr22 | 41525845 | 41526047 | EP300 | Genotyping |
| 1065 | chr22 | 41527440 | 41527664 | EP300 | Genotyping |
| 1066 | chr22 | 41536110 | 41536291 | EP300 | Genotyping |
| 1067 | chr22 | 41545740 | 41545940 | EP300 | Genotyping |
| 1068 | chr22 | 41545995 | 41546223 | EP300 | Genotyping |
| 1069 | chr22 | 41565485 | 41565650 | EP300 | Genotyping |
| 1070 | chr22 | 41566385 | 41566592 | EP300 | Genotyping |
| 1071 | chr22 | 41568480 | 41568693 | EP300 | Genotyping |
| 1072 | chr22 | 41569600 | 41569814 | EP300 | Genotyping |
| 1073 | chr22 | 41572225 | 41572436 | EP300 | Genotyping |
| 1074 | chr22 | 41572800 | 41573022 | EP300 | Genotyping |
| 1075 | chr22 | 41573300 | 41573515 | EP300 | Genotyping |
| 1076 | chr22 | 41574255 | 41574486 | EP300 | Genotyping |
| 1077 | chr22 | 41574685 | 41574904 | EP300 | Genotyping |
| 1078 | chr22 | 47570209 | 47570414 | TBC1D22A | Phased Variants |
| 1079 | chrX | 1584324 | 1585521 | P2RY8 | Genotyping |
| 1080 | chrX | 1655789 | 1656029 | AKAP17A | Genotyping |
| 1081 | chrX | 12993264 | 12993539 | TMSB4X | Phased Variants |

TABLE 3-continued

| # | Chromosome | Region Start | Region End | Closest Gene | Reason for Inclusion |
|---|---|---|---|---|---|
| 1082 | chrX | 12993544 | 12994173 | TMSB4X | Phased Variants |
| 1083 | chrX | 12994289 | 12994397 | TMSB4X | Phased Variants |
| 1084 | chrX | 12994444 | 12994514 | TMSB4X | Phased Variants |
| 1085 | chrX | 33146106 | 33146490 | DMD | Phased Variants |
| 1086 | chrX | 35820576 | 35821268 | MAGEB16 | Genotyping |
| 1087 | chrX | 70347816 | 70348034 | MED12 | Genotyping |
| 1088 | chrX | 70612661 | 70612778 | TAF1 | Genotyping |
| 1089 | chrX | 73962123 | 73963110 | KIAA2022 | Genotyping |
| 1090 | chrX | 86772953 | 86773345 | KLHL4 | Genotyping |
| 1091 | chrX | 90026453 | 90026652 | PABPC5 | Phased Variants |
| 1092 | chrX | 100610984 | 100611308 | BTK | Genotyping |
| 1093 | chrX | 119509280 | 119509492 | ATP1B4 | Genotyping |
| 1094 | chrX | 141291052 | 141291326 | MAGEC2 | Genotyping |
| 1095 | chrX | 141291357 | 141291566 | MAGEC2 | Genotyping |
| 1096 | chrX | 153997383 | 153997622 | DKC1 | Genotyping |

TABLE 4

| # | Chromosome | Region Start | Region End | Number of 50 bp bins | Gene | Mean frac DLBCL with PV | Mean frac GCB with PV | Mean frac ABC with PV | Mean frac PMBCL with PV | Mean frac CHIL with PV | ranksumP ABCvsGCB | ranksumP PMBCLvsDLBCL | ranksumP CHLv&DLBCL |
|---|---|---|---|---|---|---|---|---|---|---|---|---|---|
| 1 | chr22 | 23227063 | 23237340 | 135 | IGLL5 | 0.184 | 0.158 | 0.224 | 0.242 | 0.088 | 0.00000 | 0.00003 | 0.00000 |
| 2 | chr18 | 60763830 | 60988465 | 104 | BCL2 | 0.111 | 0.165 | 0.029 | 0.056 | 0.004 | 0.00000 | 0.00000 | 0.00000 |
| 3 | chr14 | 106239251 | 106241954 | 49 | IGHG3 | 0.193 | 0.155 | 0.251 | 0.105 | 0.032 | 0.00000 | 0.00000 | 0.00000 |
| 4 | chr14 | 106092381 | 106095531 | 51 | IGHG4 | 0.179 | 0.155 | 0.217 | 0.136 | 0.056 | 0.00000 | 0.00000 | 0.00000 |
| 5 | chr6 | 37138285 | 37141880 | 36 | PIM1 | 0.073 | 0.039 | 0.124 | 0.068 | 0.000 | 0.00000 | 0.00251 | 0.00000 |
| 6 | chr22 | 22758648 | 22764603 | 22 | IGLV1-40 | 0.064 | 0.098 | 0.013 | 0.102 | 0.109 | 0.00000 | 0.46986 | 0.00001 |
| 7 | chr2 | 89161240 | 89165610 | 66 | IGKJ1 | 0.144 | 0.134 | 0.160 | 0.140 | 0.012 | 0.00000 | 0.00000 | 0.36296 |
| 8 | chr14 | 106829686 | 106831586 | 30 | IGHV4-34 | 0.077 | 0.049 | 0.121 | 0.100 | 0.219 | 0.00000 | 0.10144 | 0.01432 |
| 9 | chr2 | 89158619 | 89160190 | 32 | IGKJ5 | 0.307 | 0.286 | 0.339 | 0.350 | 0.208 | 0.00000 | 0.28398 | 0.00000 |
| 10 | chr22 | 23222928 | 23223998 | 22 | IGLV3-1 | 0.266 | 0.300 | 0.215 | 0.429 | 0.266 | 0.00000 | 0.00000 | 0.22589 |
| 11 | chr14 | 106211961 | 106214011 | 39 | IGHG1 | 0.229 | 0.197 | 0.277 | 0.131 | 0.035 | 0.00000 | 0.00000 | 0.00000 |
| 12 | chr14 | 106329751 | 106330201 | 10 | IGHJ5 | 0.320 | 0.261 | 0.410 | 0.375 | 0.148 | 0.00000 | 0.00000 | 0.00000 |
| 13 | chr3 | 187957433 | 188471931 | 54 | LPP | 0.080 | 0.102 | 0.046 | 0.168 | 0.062 | 0.00001 | 0.00027 | 0.00345 |
| 14 | chr2 | 89160890 | 89161190 | 7 | IGKJ2 | 0.151 | 0.096 | 0.236 | 0.116 | 0.062 | 0.00001 | 0.02569 | 0.00086 |
| 15 | chr6 | 134491383 | 134495968 | 64 | SGK1 | 0.039 | 0.053 | 0.018 | 0.075 | 0.001 | 0.00002 | 0.58192 | 0.99403 |
| 16 | chr6 | 150954421 | 150954821 | 9 | PLEKHG1 | 0.067 | 0.049 | 0.094 | 0.063 | 0.000 | 0.00002 | 0.11666 | 0.00114 |
| 17 | chr2 | 89246682 | 89247982 | 18 | IGKV1-5 | 0.031 | 0.023 | 0.043 | 0.097 | 0.024 | 0.00003 | 0.01798 | 0.00005 |
| 18 | chr18 | 128746808 | 128764273 | 164 | MYC | 0.037 | 0.047 | 0.021 | 0.039 | 0.001 | 0.00003 | 0.00000 | 0.86966 |
| 19 | chr22 | 23040453 | 23041334 | 17 | IGLV2-23 | 0.051 | 0.073 | 0.018 | 0.088 | 0.005 | 0.00003 | 0.77724 | 0.04594 |
| 20 | chr2 | 89160240 | 89160540 | 7 | IGKJ4 | 0.259 | 0.225 | 0.311 | 0.241 | 0.130 | 0.00003 | 0.04157 | 0.00006 |
| 21 | chr22 | 22516708 | 22517100 | 8 | IGLV4-60 | 0.084 | 0.117 | 0.034 | 0.078 | 0.022 | 0.00003 | 0.17854 | 0.01628 |
| 22 | chr12 | 122458782 | 122463132 | 48 | BCL7A | 0.091 | 0.106 | 0.068 | 0.173 | 0.041 | 0.00005 | 0.00033 | 0.01552 |
| 23 | chr14 | 107178306 | 107179990 | 33 | IGHV2-70 | 0.224 | 0.242 | 0.195 | 0.182 | 0.115 | 0.00006 | 0.00002 | 0.00004 |
| 24 | chr2 | 89160590 | 89160840 | 6 | IGKJ3 | 0.185 | 0.137 | 0.258 | 0.135 | 0.109 | 0.00006 | 0.00291 | 0.00284 |
| 25 | chr22 | 22730453 | 22730938 | 7 | IGLV5-45 | 0.069 | 0.108 | 0.011 | 0.107 | 0.019 | 0.00010 | 0.70241 | 0.37522 |
| 26 | chr22 | 23248183 | 23248383 | 5 | IGLC3 | 0.164 | 0.236 | 0.055 | 0.113 | 0.035 | 0.00014 | 0.00837 | 0.00072 |
| 27 | chr2 | 89127262 | 89158569 | 66 | IGKC | 0.089 | 0.077 | 0.107 | 0.164 | 0.041 | 0.00022 | 0.00008 | 0.04625 |
| 28 | chr9 | 37293170 | 37384885 | 18 | ZCCHC7 | 0.055 | 0.075 | 0.025 | 0.069 | 0.002 | 0.00023 | 0.36871 | 0.42872 |
| 29 | chr14 | 106732971 | 106733441 | 9 | IGHV1-24 | 0.036 | 0.060 | 0.000 | 0.090 | 0.000 | 0.00026 | 0.33149 | 0.77291 |
| 30 | chr2 | 89184967 | 89185677 | 15 | IGKV4-1 | 0.103 | 0.133 | 0.057 | 0.133 | 0.078 | 0.00035 | 0.83189 | 0.36813 |
| 31 | chr2 | 59821915 | 106325773 | 12 | BCL11A | 0.035 | 0.053 | 0.008 | 0.089 | 0.000 | 0.00075 | 0.19138 | 0.80319 |
| 32 | chr20 | 46131073 | 46131277 | 5 | NCOA3 | 0.071 | 0.102 | 0.025 | 0.266 | 0.000 | 0.00085 | 0.00670 | 0.02848 |
| 33 | chr22 | 23165423 | 23165766 | 6 | IGLV2-8 | 0.045 | 0.022 | 0.079 | 0.025 | 0.009 | 0.00090 | 0.90873 | 0.01148 |
| 34 | chr8 | 87488688 | 8750268 | 17 | MFHASI | 0.033 | 0.051 | 0.004 | 0.083 | 0.043 | 0.00099 | 0.48925 | 0.69644 |
| 35 | chr19 | 52961147 | 52961549 | 9 | ZNF534 | 0.029 | 0.018 | 0.044 | 0.289 | 0.082 | 0.00113 | 0.75367 | 0.44231 |
| 36 | chr9 | 16435499 | 16436299 | 17 | BNC2 | 0.034 | 0.049 | 0.012 | 0.063 | 0.000 | 0.00119 | 0.51920 | 0.84956 |
| 37 | chr22 | 23264173 | 23282921 | 11 | IGLC7 | 0.041 | 0.061 | 0.011 | 0.077 | 0.000 | 0.00129 | 0.00884 | 0.29860 |
| 38 | chr14 | 106318101 | 106325773 | 50 | IGHM | 0.181 | 0.175 | 0.190 | 0.131 | 0.000 | 0.00192 | 0.00000 | 0.00000 |
| 39 | chr22 | 23235813 | 23235973 | 4 | IGLJ1 | 0.059 | 0.033 | 0.100 | 0.139 | 0.024 | 0.00225 | 0.00168 | 0.05724 |
| 40 | chr16 | 11348521 | 11349221 | 15 | SOCS1 | 0.071 | 0.102 | 0.025 | 0.266 | 0.000 | 0.00303 | 0.00000 | 0.07342 |
| 41 | chr16 | 10971441 | 10974194 | 56 | CHITA | 0.108 | 0.126 | 0.080 | 0.292 | 0.046 | 0.00307 | 0.00000 | 0.00000 |
| 42 | chr5 | 13864466 | 13864666 | 5 | DNAHS | 0.072 | 0.084 | 0.054 | 0.289 | 0.082 | 0.00408 | 0.40676 | 0.90937 |
| 43 | chr6 | 27777784 | 27778062 | 6 | HISTITH3H | 0.034 | 0.056 | 0.000 | 0.088 | 0.000 | 0.00488 | 0.21081 | 0.62256 |
| 44 | chr22 | 23192413 | 23214234 | 46 | IGLV4-3 | 0.041 | 0.025 | 0.067 | 0.042 | 0.000 | 0.00501 | 0.00000 | 0.65960 |
| 45 | chr14 | 106330251 | 106330601 | 00 | IGHJ4 | 0.061 | 0.074 | 0.042 | 0.162 | 0.025 | 0.00606 | 0.43909 | 0.00002 |
| 46 | chr14 | 106877716 | 106878731 | 18 | IGHV4-39 | 0.166 | 0.143 | 0.200 | 0.180 | 0.043 | 0.00685 | 0.08333 | 0.45229 |
| 47 | chr10 | 90773867 | 90774067 | 5 | FAS | 0.050 | 0.064 | 0.028 | 0.059 | 0.053 | 0.00715 | 0.19681 | 0.45229 |

TABLE 4-continued

| # | Chromosome | Region Start | Region End | Number of 50 bp bins | Gene | Mean frac DLBCL with PV | Mean frac GCB with PV | Mean frac ABC with PV | Mean frac PMBCL with PV | Mean frac CHIL with PV | ranksumP ABCvsGCB | ranksumP PMBCLvsDLBCL | ranksumP CHLvsDLBCL |
|---|---|---|---|---|---|---|---|---|---|---|---|---|---|
| 48 | chr22 | 22723898 | 22724466 | 12 | IGLV7-46 | 0.057 | 0.081 | 0.021 | 0.094 | 0.000 | 0.00728 | 0.81618 | 0.00596 |
| 49 | chr5 | 137801488 | 137801798 | 6 | EGR1 | 0.031 | 0.052 | 0.000 | 0.167 | 0.000 | 0.00799 | 0.01126 | 0.75859 |
| 50 | chr22 | 23242603 | 23244358 | 13 | IGLC2 | 0.139 | 0.164 | 0.100 | 0.163 | 0.094 | 0.00835 | 0.72971 | 0.51511 |
| 51 | chr22 | 22930853 | 22931153 | 7 | IGLV2-33 | 0.030 | 0.021 | 0.043 | 0.045 | 0.000 | 0.00870 | 0.55261 | 0.56841 |
| 52 | chr14 | 106325852 | 106329701 | 73 | IGHJ6 | 0.474 | 0.471 | 0.478 | 0.470 | 0.362 | 0.00948 | 0.02862 | 0.00000 |
| 53 | chr3 | 185697424 | 185697624 | 5 | TRA2B | 0.040 | 0.059 | 0.010 | 0.075 | 0.000 | 0.00954 | 0.90180 | 0.48859 |
| 54 | chr6 | 26056035 | 26056539 | 11 | HIST1H1C | 0.059 | 0.079 | 0.027 | 0.017 | 0.000 | 0.00967 | 0.00022 | 0.00680 |
| 55 | chr3 | 71551102 | 71551452 | 8 | FOXP1 | 0.015 | 0.006 | 0.028 | 0.031 | 0.011 | 0.00999 | 0.57172 | 0.00116 |
| 56 | chr3 | 187440190 | 187661368 | 137 | BCL6 | 0.106 | 0.116 | 0.089 | 0.126 | 0.044 | 0.01002 | 0.04210 | 0.00007 |
| 57 | chr11 | 128391384 | 128392103 | 15 | ETS1 | 0.061 | 0.059 | 0.065 | 0.021 | 0.000 | 0.01042 | 0.00001 | 0.00039 |
| 58 | chr13 | 46959166 | 46962031 | 13 | KIAA0226L | 0.034 | 0.029 | 0.042 | 0.067 | 0.000 | 0.01112 | 0.97915 | 0.84801 |
| 59 | chr11 | 118754794 | 118765389 | 17 | CXCR5 | 0.035 | 0.029 | 0.044 | 0.077 | 0.000 | 0.01378 | 0.40303 | 0.93788 |
| 60 | chr17 | 62006521 | 62009656 | 27 | CD79B | 0.041 | 0.039 | 0.044 | 0.083 | 0.002 | 0.01401 | 0.66941 | 0.59741 |
| 61 | chr1 | 2334442 | 2335149 | 15 | RER1 | 0.019 | 0.016 | 0.023 | 0.088 | 0.000 | 0.01514 | 0.02024 | 0.00677 |
| 62 | chr8 | 139600458 | 139601543 | 20 | COL22A1 | 0.031 | 0.043 | 0.011 | 0.078 | 0.000 | 0.01532 | 0.28495 | 0.48626 |
| 63 | chr1 | 34404023 | 34404123 | 3 | CSMD2 | 0.073 | 0.104 | 0.025 | 0.042 | 0.000 | 0.01556 | 0.06834 | 0.05288 |
| 64 | chr6 | 26216780 | 26216880 | 3 | HIST1H2BG | 0.040 | 0.066 | 0.000 | 0.063 | 0.000 | 0.01575 | 0.79954 | 0.58401 |
| 65 | chr18 | 52381612 | 52381762 | 4 | ZNF577 | 0.032 | 0.053 | 0.008 | 0.063 | 0.000 | 0.01627 | 0.93639 | 0.94029 |
| 66 | chr11 | 65265553 | 65267598 | 13 | SCYL1 | 0.030 | 0.045 | 0.008 | 0.048 | 0.003 | 0.01646 | 0.43210 | 0.34042 |
| 67 | chr22 | 23029498 | 23029739 | 5 | IGLV3-25 | 0.085 | 0.108 | 0.050 | 0.113 | 0.043 | 0.01712 | 0.97583 | 0.80122 |
| 68 | chr9 | 78686580 | 78686830 | 6 | PCSK5 | 0.035 | 0.052 | 0.008 | 0.073 | 0.000 | 0.01813 | 0.77106 | 0.87235 |
| 69 | chr14 | 106048956 | 106056101 | 25 | IGHA2 | 0.071 | 0.071 | 0.072 | 0.180 | 0.007 | 0.01828 | 0.00255 | 0.02269 |
| 70 | chr11 | 69258239 | 69259639 | 29 | ZFP36L1 | 0.088 | 0.103 | 0.065 | 0.159 | 0.013 | 0.01945 | 0.03212 | 0.00000 |
| 71 | chr5 | 75913717 | 75914417 | 15 | F2RL2 | 0.030 | 0.044 | 0.010 | 0.108 | 0.043 | 0.01980 | 0.01754 | 0.55332 |
| 72 | chr14 | 106926181 | 106926381 | 5 | IGHV3-43 | 0.038 | 0.056 | 0.010 | 0.038 | 0.000 | 0.01981 | 0.22178 | 0.96725 |
| 73 | chr6 | 27782719 | 27782919 | 5 | HIST1H2BM | 0.032 | 0.052 | 0.000 | 0.000 | 0.000 | 0.02014 | 0.01525 | 0.81176 |
| 74 | chr2 | 100758484 | 100758634 | 4 | AFF3 | 0.037 | 0.025 | 0.056 | 0.078 | 0.033 | 0.02064 | 0.69126 | 0.04169 |
| 75 | chr8 | 136569670 | 137528538 | 22 | KHDRBS3 | 0.029 | 0.041 | 0.011 | 0.065 | 0.000 | 0.02090 | 0.60391 | 0.32890 |
| 76 | chr6 | 392761 | 395016 | 15 | IRF4 | 0.035 | 0.031 | 0.042 | 0.021 | 0.000 | 0.02146 | 0.00420 | 0.95404 |
| 77 | chr8 | 3141725 | 4495082 | 9 | CSMD1 | 0.034 | 0.051 | 0.008 | 0.076 | 0.000 | 0.02188 | 0.57834 | 0.96296 |
| 78 | chr14 | 106330651 | 106331101 | 10 | IGHJ3 | 0.057 | 0.075 | 0.030 | 0.150 | 0.009 | 0.02210 | 0.00851 | 0.25752 |
| 79 | chr16 | 30093723 | 30093923 | 3 | PPP4C | 0.034 | 0.023 | 0.050 | 0.050 | 0.000 | 0.02254 | 0.59983 | 0.95843 |
| 80 | chr12 | 92537876 | 92539341 | 28 | BTG1 | 0.058 | 0.057 | 0.059 | 0.074 | 0.012 | 0.02452 | 0.27041 | 0.12731 |
| 81 | chr17 | 5366797 | 5366997 | 5 | DHX33 | 0.022 | 0.010 | 0.040 | 0.025 | 0.000 | 0.02494 | 0.30467 | 0.19851 |
| 82 | chr22 | 22697728 | 22698078 | 8 | IGLV9-49 | 0.041 | 0.035 | 0.050 | 0.047 | 0.000 | 0.02532 | 0.32106 | 0.47874 |
| 83 | chr22 | 23256463 | 23256463 | 3 | IGLJS | 0.059 | 0.082 | 0.025 | 0.042 | 0.000 | 0.02682 | 0.15950 | 0.08878 |
| 84 | chr5 | 176522450 | 176522600 | 4 | FGFR4 | 0.037 | 0.025 | 0.056 | 0.063 | 0.000 | 0.02722 | 0.79786 | 0.74613 |
| 85 | chr13 | 113516230 | 113516430 | 5 | ATP11A | 0.050 | 0.069 | 0.020 | 0.113 | 0.000 | 0.02729 | 0.27017 | 0.10654 |
| 86 | chr14 | 106331551 | 106331651 | 3 | IGHJ1 | 0.046 | 0.033 | 0.067 | 0.104 | 0.029 | 0.02734 | 0.59010 | 0.16336 |
| 87 | chr2 | 179519200 | 179520020 | 3 | DDX18 | 0.033 | 0.055 | 0.000 | 0.063 | 0.000 | 0.02815 | 0.98381 | 0.97542 |
| 88 | chr14 | 107210956 | 107211156 | 5 | IGHV3-73 | 0.046 | 0.023 | 0.065 | 0.113 | 0.000 | 0.02872 | 0.30080 | 0.42892 |
| 89 | chr12 | 6439714 | 6439914 | 5 | TNFRSF1A | 0.038 | 0.033 | 0.010 | 0.050 | 0.012 | 0.02933 | 0.46779 | 0.82988 |
| 90 | chr2 | 136872526 | 136875621 | 28 | CXCR4 | 0.022 | 0.010 | 0.040 | 0.025 | 0.000 | 0.02494 | 0.30467 | 0.19851 |
| 91 | chr3 | 165548199 | 165548649 | 10 | BCHE | 0.012 | 0.008 | 0.018 | 0.081 | 0.025 | 0.03118 | 0.04749 | 0.00000 |
| 92 | chr4 | 188924115 | 188924865 | 16 | ZFP42 | 0.033 | 0.055 | 0.014 | 0.066 | 0.000 | 0.03190 | 0.98381 | 0.62135 |
| 93 | chr20 | 25035527 | 25003727 | 5 | ACSS1 | 0.032 | 0.049 | 0.005 | 0.050 | 0.000 | 0.03215 | 0.46779 | 0.87436 |
| 94 | chr14 | 106994301 | 106994899 | 11 | IGHV3-48 | 0.041 | 0.036 | 0.048 | 0.138 | 0.043 | 0.03245 | 0.00337 | 0.00000 |
| 95 | chr16 | 3779107 | 3900912 | 82 | CREBBP | 0.035 | 0.043 | 0.022 | 0.125 | 0.001 | 0.03490 | 0.04749 | 0.00001 |
| 96 | chr2 | 89544332 | 89544880 | 11 | IGKV2-30 | 0.029 | 0.042 | 0.009 | 0.091 | 0.000 | 0.03816 | 0.14785 | 0.41409 |

TABLE 4-continued

| # | Chromosome | Region Start | Region End | Number of 50 bp bins | Gene | Mean frac DLBCL with PV | Mean frac GCB with PV | Mean frac ABC with PV | Mean frac PMBCL with PV | Mean frac CHIL with PV | ranksumP ABCvsGCB | ranksumP PMBCLvsDLBCL | ranksumP CHLv&DLBCL |
|---|---|---|---|---|---|---|---|---|---|---|---|---|---|
| 97 | chr5 | 112176757 | 112176957 | 5 | APC | 0.028 | 0.046 | 0.000 | 0.088 | 0.000 | 0.03821 | 0.23210 | 0.50694 |
| 98 | chr3 | 185146279 | 185198274 | 20 | MAP3K13 | 0.022 | 0.033 | 0.006 | 0.103 | 0.000 | 0.03855 | 0.00439 | 0.01617 |
| 99 | chr1 | 129739779 | 129740079 | 7 | NFRKB | 0.037 | 0.030 | 0.046 | 0.054 | 0.000 | 0.03877 | 0.49619 | 0.72943 |
| 100 | chr12 | 86198699 | 86199599 | 19 | RASSF9 | 0.035 | 0.047 | 0.017 | 0.066 | 0.000 | 0.04167 | 0.79797 | 0.81991 |
| 101 | chr12 | 15813488 | 15813638 | 4 | EPS8 | 0.035 | 0.025 | 0.050 | 0.031 | 0.000 | 0.04189 | 0.24118 | 0.93977 |
| 102 | chr2 | 63826278 | 63826428 | 4 | MDH1 | 0.017 | 0.008 | 0.031 | 0.203 | 0.043 | 0.04203 | 0.00443 | 0.12932 |
| 103 | chr14 | 107083566 | 107083891 | 7 | IGHV4-59 | 0.040 | 0.054 | 0.018 | 0.179 | 0.000 | 0.04206 | 0.00035 | 0.00040 |
| 104 | chr22 | 22735418 | 22735843 | 6 | IGLV1-44 | 0.059 | 0.079 | 0.029 | 0.073 | 0.000 | 0.04311 | 0.62445 | 0.18113 |
| 105 | chr12 | 18891268 | 18891518 | 6 | CAPZA3 | 0.012 | 0.005 | 0.021 | 0.125 | 0.000 | 0.04368 | 0.00589 | 0.00868 |
| 106 | chr14 | 106174971 | 106177526 | 44 | IGHA1 | 0.117 | 0.117 | 0.116 | 0.125 | 0.027 | 0.04581 | 0.05495 | 0.00009 |
| 107 | chr3 | 58207132 | 58209082 | 40 | PCDH17 | 0.038 | 0.047 | 0.024 | 0.092 | 0.000 | 0.04705 | 0.03043 | 0.23893 |
| 108 | chr6 | 26156650 | 26157350 | 15 | HIST1H1E | 0.064 | 0.077 | 0.045 | 0.008 | 0.000 | 0.04776 | 0.00000 | 0.00658 |
| 109 | chr8 | 75898191 | 75898391 | 5 | CRISPLD1 | 0.012 | 0.007 | 0.020 | 0.050 | 0.000 | 0.04779 | 0.61717 | 0.01894 |
| 110 | chr9 | 37024920 | 37033770 | 38 | PAX5 | 0.059 | 0.060 | 0.059 | 0.107 | 0.015 | 0.04840 | 0.84733 | 0.06185 |
| 111 | chr17 | 18001530 | 18001680 | 4 | DRG2 | 0.015 | 0.008 | 0.025 | 0.031 | 0.000 | 0.04924 | 0.70570 | 0.06008 |
| 112 | chr10 | 91092212 | 91092412 | 5 | IFIT3 | 0.026 | 0.016 | 0.040 | 0.050 | 0.000 | 0.05027 | 0.89626 | 0.41400 |
| 113 | chr2 | 56149511 | 56150111 | 13 | EFEMP1 | 0.030 | 0.029 | 0.031 | 0.115 | 0.000 | 0.05115 | 0.00217 | 0.49133 |
| 114 | chr6 | 26032015 | 26032215 | 5 | HIST1H3B | 0.030 | 0.046 | 0.005 | 0.013 | 0.000 | 0.05360 | 0.05680 | 0.72269 |
| 115 | chrX | 1584325 | 1655990 | 29 | P2RY8 | 0.031 | 0.041 | 0.016 | 0.031 | 0.001 | 0.05546 | 0.01173 | 0.29622 |
| 116 | chr4 | 187509885 | 187557980 | 16 | FAT1 | 0.028 | 0.039 | 0.013 | 0.094 | 0.000 | 0.05661 | 0.05492 | 0.36536 |
| 117 | chr5 | 1110991 | 1411801 | 24 | CTNND2 | 0.031 | 0.040 | 0.016 | 0.060 | 0.000 | 0.05690 | 0.95068 | 0.19315 |
| 118 | chr14 | 106110676 | 106114376 | 65 | IGHG2 | 0.213 | 0.210 | 0.217 | 0.147 | 0.049 | 0.05698 | 0.00000 | 0.00000 |
| 119 | chr1 | 4472439 | 4476599 | 10 | AJAP1 | 0.030 | 0.026 | 0.035 | 0.031 | 0.000 | 0.05889 | 0.10905 | 0.59078 |
| 120 | chr1 | 110561142 | 110561742 | 13 | AHCYL1 | 0.019 | 0.018 | 0.021 | 0.058 | 0.000 | 0.05908 | 0.58438 | 0.01312 |
| 121 | chr14 | 106725296 | 106726174 | 14 | IGHV3-23 | 0.099 | 0.111 | 0.080 | 0.027 | 0.000 | 0.05952 | 0.00000 | 0.00001 |
| 122 | chr1 | 111715728 | 111715878 | 4 | CEPT1 | 0.022 | 0.016 | 0.031 | 0.047 | 0.000 | 0.06085 | 0.91905 | 0.26127 |
| 123 | chr1 | 118967324 | 118968024 | 15 | DPAGT1 | 0.032 | 0.044 | 0.013 | 0.102 | 0.000 | 0.06151 | 0.19789 | 0.69126 |
| 124 | chr2 | 55237199 | 55237599 | 9 | RTN4 | 0.047 | 0.060 | 0.028 | 0.045 | 0.019 | 0.06228 | 0.41365 | 0.17702 |
| 125 | chr11 | 111781037 | 111781637 | 13 | CRYAB | 0.025 | 0.037 | 0.008 | 0.063 | 0.000 | 0.06377 | 0.11838 | 0.14383 |
| 126 | chr14 | 106573316 | 106574003 | 13 | IGHV3-11 | 0.041 | 0.054 | 0.021 | 0.082 | 0.007 | 0.06792 | 0.84332 | 0.93964 |
| 127 | chr18 | 48231685 | 48232085 | 9 | MAPK4 | 0.022 | 0.020 | 0.025 | 0.082 | 0.000 | 0.07104 | 0.07945 | 0.10112 |
| 128 | chr2 | 62934010 | 63217980 | 14 | EHBP1 | 0.030 | 0.042 | 0.013 | 0.021 | 0.012 | 0.07190 | 0.51773 | 0.62080 |
| 129 | chr22 | 22677078 | 22677289 | 5 | IGLV1-51 | 0.046 | 0.066 | 0.015 | 0.113 | 0.000 | 0.07234 | 0.37625 | 0.20872 |
| 130 | chr7 | 119915407 | 119915757 | 8 | KCND2 | 0.038 | 0.053 | 0.016 | 0.039 | 0.000 | 0.07723 | 0.12619 | 0.48614 |
| 131 | chr22 | 23154348 | 23154798 | 8 | IGLV3-10 | 0.024 | 0.020 | 0.028 | 0.102 | 0.000 | 0.07866 | 0.03037 | 0.15798 |
| 132 | chr6 | 26045745 | 26046045 | 7 | HIST1H3C | 0.030 | 0.026 | 0.036 | 0.045 | 0.000 | 0.08101 | 0.46457 | 0.03046 |
| 133 | chr10 | 131640290 | 131640490 | 5 | EBF3 | 0.040 | 0.036 | 0.045 | 0.100 | 0.000 | 0.08357 | 0.26942 | 0.76490 |
| 134 | chr1 | 109822182 | 109822782 | 13 | PSRC1 | 0.027 | 0.038 | 0.012 | 0.072 | 0.000 | 0.08367 | 0.51165 | 0.24502 |
| 135 | chr17 | 18022120 | 18022770 | 14 | MYO15A | 0.039 | 0.036 | 0.043 | 0.085 | 0.000 | 0.08686 | 0.51095 | 0.37846 |
| 136 | chr16 | 85933004 | 85954924 | 56 | IRF8 | 0.037 | 0.047 | 0.024 | 0.065 | 0.012 | 0.08712 | 0.41154 | 0.04982 |
| 137 | chr2 | 89986777 | 89987085 | 7 | IGKV2D-29 | 0.024 | 0.021 | 0.029 | 0.045 | 0.000 | 0.09053 | 0.66530 | 0.22260 |
| 138 | chr2 | 90249152 | 90249397 | 5 | IGKV1D-43 | 0.040 | 0.033 | 0.050 | 0.063 | 0.009 | 0.09076 | 0.87053 | 0.96927 |
| 139 | chr2 | 242793233 | 242801088 | 24 | PDCD1 | 0.047 | 0.048 | 0.046 | 0.083 | 0.000 | 0.09248 | 0.64737 | 0.01000 |
| 140 | chr6 | 27100080 | 27100180 | 3 | HIST1H2BJ | 0.033 | 0.027 | 0.042 | 0.000 | 0.029 | 0.09735 | 0.05014 | 0.09524 |
| 141 | chr11 | 110545277 | 110698122 | 8 | IMMP2L | 0.004 | 0.002 | 0.006 | 0.063 | 0.000 | 0.10148 | 0.15804 | 0.00010 |
| 142 | chr1 | 111441723 | 111442173 | 10 | CD53 | 0.027 | 0.038 | 0.010 | 0.100 | 0.000 | 0.10715 | 0.04221 | 0.30553 |
| 143 | chrX | 70612662 | 70612762 | 3 | TAF1 | 0.007 | 0.000 | 0.017 | 0.063 | 0.000 | 0.10731 | 0.45417 | 0.02634 |
| 144 | chr21 | 18981234 | 18981484 | 6 | BTG3 | 0.020 | 0.033 | 0.000 | 0.073 | 0.000 | 0.10744 | 0.29340 | 0.11987 |
| 145 | chr14 | 107113406 | 107114196 | 10 | IGHV3-64 | 0.015 | 0.013 | 0.018 | 0.050 | 0.000 | 0.10843 | 0.80649 | 0.00490 |

TABLE 4-continued

| # | Chromosome | Region Start | Region End | Number of 50 bp bins | Gene | Mean frac DLBCL with PV | Mean frac GCB with PV | Mean frac ABC with PV | Mean frac PMBCL with PV | Mean frac CHIL with PV | ranksumP ABCvsGCB | ranksumP PMBCLvsDLBCL | ranksumP CHLvsDLBCL |
|---|---|---|---|---|---|---|---|---|---|---|---|---|---|
| 146 | chr22 | 22380473 | 22385883 | 18 | IGLV4-69 | 0.044 | 0.054 | 0.029 | 0.073 | 0.000 | 0.10860 | 0.97247 | 0.18279 |
| 147 | chr9 | 5510590 | 5570130 | 34 | PDCDILG2 | 0.026 | 0.028 | 0.024 | 0.057 | 0.000 | 0.11075 | 0.98596 | 0.05983 |
| 148 | chr1 | 27059147 | 27106912 | 29 | ARID1A | 0.035 | 0.043 | 0.023 | 0.073 | 0.006 | 0.11182 | 0.58280 | 0.43378 |
| 149 | chr13 | 32907207 | 32912827 | 17 | BRCA2 | 0.013 | 0.013 | 0.013 | 0.088 | 0.000 | 0.11539 | 0.00502 | 0.00005 |
| 150 | chr8 | 48703170 | 48703920 | 16 | MEX3C | 0.022 | 0.023 | 0.022 | 0.059 | 0.000 | 0.11749 | 0.74407 | 0.02655 |
| 151 | chr1 | 203274698 | 203276558 | 33 | BTG2 | 0.131 | 0.129 | 0.133 | 0.133 | 0.012 | 0.11791 | 0.01136 | 0.00000 |
| 152 | chr8 | 128492948 | 128493298 | 8 | POU5F1B | 0.022 | 0.035 | 0.003 | 0.047 | 0.000 | 0.11971 | 0.87638 | 0.11243 |
| 153 | chr6 | 27834969 | 27835069 | 3 | HIST1H1B | 0.043 | 0.038 | 0.050 | 0.042 | 0.000 | 0.12081 | 0.31080 | 0.40430 |
| 154 | chr22 | 23010978 | 23011307 | 7 | IGLV3-27 | 0.045 | 0.059 | 0.025 | 0.045 | 0.000 | 0.12123 | 0.15843 | 0.35845 |
| 155 | chr1 | 117078643 | 117087128 | 10 | CD58 | 0.022 | 0.021 | 0.023 | 0.025 | 0.000 | 0.12266 | 0.14627 | 0.06157 |
| 156 | chr4 | 106380361 | 106381326 | 17 | IGHD3-3 | 0.040 | 0.040 | 0.040 | 0.022 | 0.010 | 0.12443 | 0.00226 | 0.54240 |
| 157 | chr12 | 49415992 | 49447447 | 47 | KMT2D | 0.029 | 0.031 | 0.026 | 0.097 | 0.000 | 0.12454 | 0.00102 | 0.09879 |
| 158 | chr22 | 22782038 | 22782288 | 6 | IGLV5-37 | 0.051 | 0.066 | 0.029 | 0.052 | 0.000 | 0.12900 | 0.22779 | 0.08945 |
| 159 | chr8 | 18729446 | 18729896 | 10 | PSD3 | 0.036 | 0.048 | 0.018 | 0.100 | 0.000 | 0.12911 | 0.49227 | 0.67922 |
| 160 | chr14 | 106552366 | 106552466 | 3 | IGHV3-9 | 0.020 | 0.011 | 0.033 | 0.063 | 0.000 | 0.12919 | 0.69275 | 0.24178 |
| 161 | chrX | 35820577 | 35821227 | 14 | MAGEB16 | 0.021 | 0.032 | 0.005 | 0.080 | 0.000 | 0.13076 | 0.08392 | 0.03514 |
| 162 | chr16 | 81946176 | 81962221 | 13 | PLCG2 | 0.027 | 0.028 | 0.027 | 0.058 | 0.000 | 0.13686 | 0.98920 | 0.29436 |
| 163 | chr22 | 22712078 | 22712594 | 11 | IGLV1-47 | 0.050 | 0.063 | 0.032 | 0.108 | 0.000 | 0.13854 | 0.36497 | 0.04398 |
| 164 | chr3 | 16419205 | 16419455 | 6 | RFTN1 | 0.050 | 0.046 | 0.054 | 0.063 | 0.000 | 0.14045 | 0.43890 | 0.10024 |
| 165 | chr11 | 111613197 | 111613397 | 5 | PPP2R1B | 0.026 | 0.039 | 0.005 | 0.000 | 0.000 | 0.14058 | 0.02490 | 0.46424 |
| 166 | chr14 | 106331151 | 106331501 | 8 | IGHJ2 | 0.048 | 0.047 | 0.050 | 0.102 | 0.027 | 0.14335 | 0.33135 | 0.15651 |
| 167 | chr1 | 226923692 | 226925192 | 31 | ITPKB | 0.044 | 0.053 | 0.031 | 0.139 | 0.000 | 0.14412 | 0.00007 | 0.03739 |
| 168 | chr1 | 27100940 | 27101260 | 5 | HIST1H2AG | 0.024 | 0.020 | 0.030 | 0.038 | 0.000 | 0.14525 | 0.54138 | 0.28737 |
| 169 | chr10 | 91358987 | 91359287 | 7 | PANK1 | 0.021 | 0.019 | 0.025 | 0.107 | 0.000 | 0.15224 | 0.01412 | 0.10864 |
| 170 | chr14 | 32615406 | 32615606 | 5 | ARHGAP5 | 0.020 | 0.033 | 0.000 | 0.100 | 0.000 | 0.15384 | 0.16273 | 0.16433 |
| 171 | chrX | 119509281 | 119509481 | 5 | ATP1B4 | 0.016 | 0.013 | 0.020 | 0.088 | 0.000 | 0.15508 | 0.23890 | 0.07712 |
| 172 | chr8 | 77794426 | 77795126 | 15 | RBFA | 0.014 | 0.014 | 0.013 | 0.075 | 0.000 | 0.15663 | 0.08296 | 0.00029 |
| 173 | chr10 | 89624273 | 89720888 | 32 | PTEN | 0.015 | 0.016 | 0.013 | 0.023 | 0.000 | 0.15837 | 0.04633 | 0.00000 |
| 174 | chr14 | 64330253 | 54330453 | 5 | SYNE2 | 0.006 | 0.003 | 0.010 | 0.000 | 0.000 | 0.15837 | 0.74245 | 0.00357 |
| 175 | chr9 | 24545400 | 24905695 | 17 | IZUMO3 | 0.030 | 0.039 | 0.016 | 0.037 | 0.000 | 0.15955 | 0.10765 | 0.43759 |
| 176 | chr5 | 54964699 | 54964899 | 5 | SLC38A9 | 0.002 | 0.000 | 0.005 | 0.013 | 0.000 | 0.16320 | 0.46997 | 0.00144 |
| 177 | chr10 | 101730377 | 101730427 | 2 | PABPC1 | 0.015 | 0.008 | 0.025 | 0.000 | 0.000 | 0.16455 | 0.26379 | 0.18377 |
| 178 | chr8 | 131373025 | 131373425 | 9 | ASAP1 | 0.030 | 0.040 | 0.014 | 0.028 | 0.000 | 0.16655 | 0.08650 | 0.59884 |
| 179 | chr22 | 23101393 | 23101730 | 6 | IGLV2-14 | 0.048 | 0.044 | 0.054 | 0.073 | 0.022 | 0.16893 | 0.83695 | 0.56495 |
| 180 | chr1 | 109649127 | 109649277 | 4 | C1orf194 | 0.047 | 0.045 | 0.050 | 0.078 | 0.022 | 0.17014 | 0.88867 | 0.40591 |
| 181 | chr1 | 65623423 | 65623473 | 2 | CFL1 | 0.025 | 0.014 | 0.000 | 0.031 | 0.000 | 0.17060 | 0.58174 | 0.54924 |
| 182 | chr22 | 22707428 | 22707793 | 7 | IGLV5-48 | 0.035 | 0.041 | 0.018 | 0.071 | 0.000 | 0.17227 | 0.95304 | 0.82874 |
| 183 | chr14 | 106331701 | 106331801 | 3 | IGHD7-27 | 0.026 | 0.047 | 0.033 | 0.125 | 0.000 | 0.17412 | 0.05590 | 0.56584 |
| 184 | chr14 | 96179593 | 96180293 | 15 | TCL1A | 0.050 | 0.022 | 0.050 | 0.071 | 0.000 | 0.17445 | 0.59106 | 0.01278 |
| 185 | chr22 | 23063308 | 23063658 | 8 | IGLV3-19 | 0.031 | 0.029 | 0.034 | 0.039 | 0.000 | 0.17496 | 0.31060 | 0.64225 |
| 186 | chr17 | 7576950 | 7579410 | 24 | TP53 | 0.040 | 0.051 | 0.023 | 0.107 | 0.000 | 0.17822 | 0.03641 | 0.51953 |
| 187 | chr2 | 148680517 | 148680667 | 4 | ACVR2A | 0.025 | 0.037 | 0.006 | 0.031 | 0.000 | 0.18073 | 0.41320 | 0.38140 |
| 188 | chr19 | 10334564 | 10341984 | 35 | SIPR2 | 0.064 | 0.077 | 0.044 | 0.104 | 0.002 | 0.18105 | 0.40386 | 0.00014 |
| 189 | chr6 | 108040229 | 108042204 | 27 | SCML4 | 0.025 | 0.026 | 0.023 | 0.060 | 0.005 | 0.18315 | 0.54097 | 0.01195 |
| 190 | chr6 | 27277285 | 27277485 | 5 | POM121L2 | 0.042 | 0.039 | 0.045 | 0.050 | 0.000 | 0.18414 | 0.38135 | 0.41604 |
| 191 | chr3 | 186714605 | 186784290 | 33 | ST6GAL1 | 0.084 | 0.091 | 0.072 | 0.087 | 0.018 | 0.18556 | 0.01425 | 0.00007 |
| 192 | chr19 | 12902575 | 12902825 | 6 | JUNB | 0.053 | 0.052 | 0.054 | 0.010 | 0.000 | 0.18604 | 0.00259 | 0.04452 |
| 193 | chr14 | 107199021 | 107199172 | 4 | IGHV3-72 | 0.045 | 0.041 | 0.050 | 0.000 | 0.000 | 0.18636 | 0.00860 | 0.27305 |
| 194 | chr11 | 102188382 | 102188932 | 12 | BIRC3 | 0.104 | 0.123 | 0.075 | 0.104 | 0.043 | 0.18760 | 0.23061 | 0.02703 |

TABLE 4-continued

| # | Chromosome | Region Start | Region End | Number of 50 bp bins | Gene | Mean frac DLBCL with PV | Mean frac GCB with PV | Mean frac ABC with PV | Mean frac PMBCL with PV | Mean frac CHIL with PV | ranksumP ABCvsGCB | ranksumP PMBCLvsDLBCL | ranksumP CHLvsDLBCL |
|---|---|---|---|---|---|---|---|---|---|---|---|---|---|
| 195 | chr1 | 185833556 | 186159096 | 32 | HMCN1 | 0.021 | 0.023 | 0.018 | 0.074 | 0.000 | 0.18799 | 0.04332 | 0.00092 |
| 196 | chr12 | 18534683 | 18801013 | 30 | PIK3C2G | 0.017 | 0.020 | 0.013 | 0.054 | 0.000 | 0.18947 | 0.52931 | 0.00001 |
| 197 | chrX | 100610985 | 100611285 | 7 | BTK | 0.021 | 0.021 | 0.021 | 0.116 | 0.000 | 0.18957 | 0.01363 | 0.10957 |
| 198 | chr18 | 64172117 | 64239317 | 19 | CDH19 | 0.023 | 0.032 | 0.009 | 0.072 | 0.002 | 0.19120 | 0.37384 | 0.02195 |
| 199 | chr2 | 1652011 | 1652811 | 17 | PXDN | 0.045 | 0.054 | 0.031 | 0.092 | 0.000 | 0.19342 | 0.57240 | 0.03398 |
| 200 | chr11 | 111904097 | 111904247 | 4 | DLAT | 0.037 | 0.049 | 0.019 | 0.016 | 0.000 | 0.19688 | 0.06546 | 0.70963 |
| 201 | chr22 | 22556228 | 22556628 | 9 | IGLV11-55 | 0.039 | 0.038 | 0.039 | 0.111 | 0.000 | 0.19910 | 0.04960 | 0.53925 |
| 202 | chr2 | 103148734 | 103148934 | 5 | SLC9A4 | 0.024 | 0.036 | 0.005 | 0.063 | 0.000 | 0.20039 | 0.78808 | 0.29891 |
| 203 | chr2 | 48027959 | 48028159 | 5 | MSH6 | 0.012 | 0.010 | 0.015 | 0.000 | 0.000 | 0.20189 | 0.09865 | 0.01894 |
| 204 | chr4 | 134727699 | 134727899 | 5 | PABPC4L | 0.012 | 0.010 | 0.015 | 0.150 | 0.000 | 0.20189 | 0.02007 | 0.01894 |
| 205 | chr11 | 134027790 | 134027940 | 4 | NCAPD3 | 0.047 | 0.061 | 0.025 | 0.078 | 0.000 | 0.20429 | 0.99130 | 0.21830 |
| 206 | chr2 | 77746603 | 77746953 | 8 | LRRTM4 | 0.026 | 0.037 | 0.009 | 0.047 | 0.006 | 0.20711 | 0.60835 | 0.35208 |
| 207 | chr1 | 160319284 | 160319484 | 5 | NCSTN | 0.044 | 0.039 | 0.050 | 0.025 | 0.000 | 0.21582 | 0.05416 | 0.28073 |
| 208 | chr18 | 65179857 | 65181807 | 40 | DSEL | 0.021 | 0.029 | 0.009 | 0.073 | 0.000 | 0.21609 | 0.19591 | 0.00018 |
| 209 | chr15 | 45003679 | 45008564 | 12 | B2M | 0.035 | 0.046 | 0.017 | 0.031 | 0.007 | 0.21616 | 0.04427 | 0.31773 |
| 210 | chr1 | 29069532 | 29070182 | 14 | YTHDF2 | 0.043 | 0.052 | 0.030 | 0.040 | 0.000 | 0.21620 | 0.03795 | 0.84925 |
| 211 | chr4 | 80327793 | 80328143 | 8 | GK2 | 0.030 | 0.041 | 0.013 | 0.117 | 0.000 | 0.21872 | 0.01766 | 0.70075 |
| 212 | chr5 | 158527643 | 158527993 | 8 | EBF1 | 0.052 | 0.064 | 0.034 | 0.055 | 0.000 | 0.22009 | 0.11870 | 0.13982 |
| 213 | chr1 | 3747621 | 3747771 | 4 | CEP104 | 0.025 | 0.037 | 0.006 | 0.109 | 0.000 | 0.22034 | 0.26105 | 0.39687 |
| 214 | chr2 | 48059884 | 48066174 | 9 | FBXO11 | 0.014 | 0.015 | 0.014 | 0.063 | 0.000 | 0.22199 | 0.44292 | 0.00401 |
| 215 | chrX | 33146107 | 33146457 | 8 | DMD | 0.059 | 0.059 | 0.059 | 0.359 | 0.082 | 0.22404 | 0.00000 | 0.00004 |
| 216 | chr6 | 26124545 | 26124865 | 6 | HIST1H2AC | 0.051 | 0.063 | 0.033 | 0.010 | 0.000 | 0.22855 | 0.00394 | 0.11588 |
| 217 | chr14 | 106791091 | 106791141 | 2 | IGHV3-30 | 0.045 | 0.041 | 0.050 | 0.063 | 0.000 | 0.24046 | 0.72117 | 0.43844 |
| 218 | chr3 | 183209759 | 183273414 | 23 | KLHL6 | 0.036 | 0.036 | 0.036 | 0.052 | 0.006 | 0.24437 | 0.12177 | 0.41139 |
| 219 | chr17 | 79478954 | 79479004 | 2 | ACTG1 | 0.005 | 0.000 | 0.013 | 0.125 | 0.043 | 0.24604 | 0.05674 | 0.01689 |
| 220 | chr22 | 47570210 | 47570410 | 5 | TBC1D22A | 0.030 | 0.043 | 0.010 | 0.175 | 0.000 | 0.24818 | 0.00334 | 0.70762 |
| 221 | chr6 | 27799169 | 27799369 | 5 | HIST1H4K | 0.022 | 0.033 | 0.005 | 0.038 | 0.000 | 0.24904 | 0.54640 | 0.19851 |
| 222 | chr2 | 65258146 | 65258346 | 5 | SLC1A4 | 0.018 | 0.030 | 0.000 | 0.050 | 0.000 | 0.25016 | 0.78384 | 0.08170 |
| 223 | chr14 | 106586201 | 106586301 | 3 | IGHV3-13 | 0.033 | 0.027 | 0.042 | 0.021 | 0.000 | 0.25073 | 0.17545 | 0.97542 |
| 224 | chr14 | 26158530 | 26158790 | 4 | HIST1H2BD | 0.030 | 0.041 | 0.013 | 0.016 | 0.000 | 0.25147 | 0.13295 | 0.69509 |
| 225 | chr14 | 106691756 | 106691856 | 3 | IGHV3-21 | 0.053 | 0.066 | 0.033 | 0.042 | 0.000 | 0.25208 | 0.23957 | 0.18828 |
| 226 | chr10 | 90579967 | 90580317 | 8 | LIPM | 0.035 | 0.035 | 0.034 | 0.047 | 0.000 | 0.25854 | 0.32941 | 0.85606 |
| 227 | chr7 | 82387831 | 82784641 | 19 | PCLO | 0.035 | 0.044 | 0.022 | 0.049 | 0.000 | 0.25896 | 0.17138 | 0.85294 |
| 228 | chr22 | 23090123 | 23090338 | 4 | IGLV3-16 | 0.030 | 0.041 | 0.013 | 0.063 | 0.065 | 0.26082 | 0.88005 | 0.00186 |
| 229 | chr2 | 89475782 | 89476114 | 7 | IGKV2-24 | 0.044 | 0.042 | 0.046 | 0.125 | 0.000 | 0.26354 | 0.03650 | 0.25182 |
| 230 | chr2 | 90121892 | 90122155 | 6 | IGKV1D-17 | 0.030 | 0.041 | 0.013 | 0.083 | 0.006 | 0.26708 | 0.50393 | 0.47148 |
| 231 | chr14 | 107034666 | 107035056 | 7 | IGHV5-51 | 0.038 | 0.049 | 0.021 | 0.071 | 0.000 | 0.26981 | 0.83901 | 0.54622 |
| 232 | chr6 | 26217215 | 26217415 | 5 | HIST1HLAE | 0.024 | 0.023 | 0.025 | 0.038 | 0.000 | 0.26983 | 0.53539 | 0.29891 |
| 233 | chr14 | 84420587 | 84420787 | 5 | FLRT2 | 0.000 | 0.000 | 0.000 | 0.025 | 0.015 | 0.27098 | 0.90753 | 0.00089 |
| 234 | chr4 | 40198811 | 40201559 | 49 | RHOH | 0.062 | 0.068 | 0.053 | 0.028 | 0.000 | 0.27123 | 0.00000 | 0.12156 |
| 235 | chr14 | 106539176 | 106539276 | 3 | IGHV1-8 | 0.040 | 0.038 | 0.042 | 0.063 | 0.000 | 0.27246 | 0.79783 | 0.70059 |
| 236 | chr5 | 83258968 | 83259168 | 5 | EDIL3 | 0.022 | 0.033 | 0.005 | 0.063 | 0.000 | 0.27662 | 0.67082 | 0.19851 |
| 237 | chrX | 70347817 | 70348017 | 5 | MED12 | 0.022 | 0.027 | 0.013 | 0.075 | 0.000 | 0.27662 | 0.38460 | 0.19851 |
| 238 | chr18 | 48512955 | 48513305 | 8 | ELAC1 | 0.026 | 0.033 | 0.025 | 0.102 | 0.057 | 0.27685 | 0.05230 | 0.35208 |
| 239 | chrX | 12993265 | 12994487 | 23 | TMSB4X | 0.098 | 0.108 | 0.083 | 0.177 | 0.000 | 0.27705 | 0.03023 | 0.53439 |
| 240 | chr19 | 6586162 | 6591037 | 17 | CD70 | 0.052 | 0.064 | 0.035 | 0.121 | 0.000 | 0.27742 | 0.02768 | 0.05558 |
| 241 | chr9 | 13222186 | 13222386 | 5 | MPDZ | 0.018 | 0.016 | 0.020 | 0.050 | 0.000 | 0.27845 | 0.92556 | 0.10149 |
| 242 | chr19 | 8028409 | 8028559 | 4 | ELAVL1 | 0.037 | 0.049 | 0.019 | 0.094 | 0.000 | 0.28231 | 0.39328 | 0.68881 |
| 243 | chr17 | 63010241 | 63052644 | 28 | GNA13 | 0.033 | 0.035 | 0.029 | 0.051 | 0.005 | 0.29192 | 0.20921 | 0.55174 |

TABLE 4-continued

| # | Chromosome | Region Start | Region End | Number of 50 bp bins | Gene | Mean frac DLBCL with PV | Mean frac GCB with PV | Mean frac ABC with PV | Mean frac PMBCL with PV | Mean frac CHIL with PV | ranksumP ABCvsGCB | ranksumP PMBCLvsDLBCL | ranksumP CHLv&DLBCL |
|---|---|---|---|---|---|---|---|---|---|---|---|---|---|
| 244 | chr6 | 75965847 | 75969257 | 10 | TMEM30A | 0.017 | 0.018 | 0.015 | 0.063 | 0.000 | 0.29877 | 0.61973 | 0.01289 |
| 245 | chr2 | 61118795 | 61149620 | 27 | REL | 0.024 | 0.030 | 0.014 | 0.053 | 0.006 | 0.29909 | 0.79282 | 0.00093 |
| 246 | chr8 | 103663492 | 103664142 | 14 | KLF10 | 0.032 | 0.034 | 0.029 | 0.103 | 0.000 | 0.29943 | 0.04753 | 0.77217 |
| 247 | chr7 | 122634906 | 122635106 | 5 | TAS2R16 | 0.040 | 0.036 | 0.045 | 0.050 | 0.000 | 0.30121 | 0.42497 | 0.50451 |
| 248 | chr7 | 106508491 | 106509141 | 14 | PIK3CG | 0.043 | 0.044 | 0.04] | 0.058 | 0.000 | 0.30584 | 0.28865 | 0.12742 |
| 249 | chr19 | 1376441 | 1376641 | 5 | MUM1 | 0.053 | 0.066 | 0.035 | 0.063 | 0.000 | 0.30591 | 0.40617 | 0.10207 |
| 250 | chr10 | 90074240 | 90074390 | 4 | RNLS | 0.012 | 0.012 | 0.013 | 0.141 | 0.050 | 0.30697 | 0.04146 | 0.05611 |
| 251 | chr17 | 56408575 | 56409585 | 19 | BZRAP1 | 0.107 | 0.116 | 0.095 | 0.122 | 0.000 | 0.31066 | 0.24386 | 0.00835 |
| 252 | chr18 | 48327695 | 48327895 | 5 | MRO | 0.034 | 0.033 | 0.035 | 0.088 | 0.000 | 0.32051 | 0.36874 | 0.94107 |
| 253 | chr2 | 90212017 | 90212247 | 4 | IGKV3D-11 | 0.000 | 0.000 | 0.000 | 0.063 | 0.000 | 0.32488 | 0.18259 | 0.00295 |
| 254 | chr3 | 164730701 | 164730851 | 4 | SI | 0.000 | 0.000 | 0.000 | 0.031 | 0.000 | 0.32488 | 0.89232 | 0.00295 |
| 255 | chr18 | 75683735 | 75684485 | 16 | GALR1 | 0.025 | 0.026 | 0.023 | 0.055 | 0.000 | 0.32688 | 0.88862 | 0.08570 |
| 256 | chr10 | 90699127 | 90699627 | 11 | ACTA2 | 0.022 | 0.030 | 0.009 | 0.074 | 0.000 | 0.32826 | 0.22549 | 0.05225 |
| 257 | chr7 | 146997184 | 146997384 | 5 | CNTNAP2 | 0.020 | 0.030 | 0.005 | 0.063 | 0.000 | 0.33654 | 0.72508 | 0.12531 |
| 258 | chr10 | 90537737 | 90537987 | 6 | LIPN | 0.021 | 0.022 | 0.021 | 0.063 | 0.000 | 0.33950 | 0.63054 | 0.15262 |
| 259 | chr8 | 116616146 | 116616846 | 15 | TRPS1 | 0.033 | 0.042 | 0.020 | 0.088 | 0.000 | 0.34027 | 0.10857 | 0.96046 |
| 260 | chro | 14117993 | 14135468 | 27 | CD83 | 0.061 | 0.069 | 0.049 | 0.146 | 0.006 | 0.34145 | 0.00006 | 0.25221 |
| 261 | chr14 | 106610381 | 106610741 | 6 | IGHV3-15 | 0.036 | 0.046 | 0.021 | 0.042 | 0.000 | 0.34253 | 0.25513 | 0.68243 |
| 262 | chr14 | 106962966 | 106963269 | 7 | IGHV1-45 | 0.023 | 0.023 | 0.021 | 0.036 | 0.000 | 0.34439 | 0.45188 | 0.16111 |
| 263 | chr6 | 27833409 | 27833509 | 3 | HIST1H2AL | 0.017 | 0.027 | 0.000 | 0.042 | 0.000 | 0.34503 | 0.82367 | 0.13637 |
| 264 | chr7 | 2963819 | 2987364 | 44 | CARD11 | 0.047 | 0.055 | 0.035 | 0.075 | 0.006 | 0.34677 | 0.68708 | 0.00272 |
| 265 | chr14 | 134118685 | 134118835 | 4 | THYN1 | 0.017 | 0.016 | 0.019 | 0.094 | 0.000 | 0.35301 | 0.26225 | 0.10870 |
| 266 | chr14 | 107258911 | 107282996 | 17 | IGHV7-81 | 0.031 | 0.040 | 0.019 | 0.088 | 0.026 | 0.35469 | 0.15903 | 0.00002 |
| 267 | chrX | 73962124 | 73963074 | 20 | KIAA2022 | 0.020 | 0.028 | 0.009 | 0.103 | 0.000 | 0.35514 | 0.00284 | 0.00632 |
| 268 | chr3 | 185236909 | 185237109 | 5 | LIPH | 0.022 | 0.033 | 0.005 | 0.038 | 0.000 | 0.35786 | 0.57454 | 0.20093 |
| 269 | chr3 | 64547205 | 64580090 | 11 | ADAMTS9 | 0.028 | 0.030 | 0.025 | 0.091 | 0.000 | 0.35888 | 0.08153 | 0.38328 |
| 270 | chr14 | 106405616 | 106405916 | 7 | IGHV6-1 | 0.028 | 0.037 | 0.014 | 0.098 | 0.000 | 0.36129 | 0.28061 | 0.53891 |
| 271 | chr11 | 117712684 | 117712984 | 7 | FXYD6 | 0.035 | 0.035 | 0.036 | 0.045 | 0.000 | 0.36200 | 0.39501 | 0.93264 |
| 272 | chr8 | 130692150 | 130760995 | 17 | GSDMC | 0.029 | 0.037 | 0.018 | 0.051 | 0.000 | 0.36490 | 0.59248 | 0.38946 |
| 273 | chr22 | 22749603 | 22750309 | 14 | IGLV7-43 | 0.021 | 0.022 | 0.018 | 0.067 | 0.000 | 0.36721 | 0.26604 | 0.01881 |
| 274 | chr22 | 23135153 | 23135508 | 7 | IGLV2-11 | 0.020 | 0.021 | 0.018 | 0.098 | 0.000 | 0.36740 | 0.03964 | 0.07222 |
| 275 | chr6 | 26234655 | 26234955 | 7 | HIST1H1D | 0.042 | 0.044 | 0.039 | 0.018 | 0.024 | 0.36786 | 0.01092 | 0.23508 |
| 276 | chr1 | 112405017 | 112405578 | 12 | C11orf34 | 0.029 | 0.037 | 0.017 | 0.099 | 0.000 | 0.36795 | 0.03866 | 0.51208 |
| 277 | chr1 | 2488007 | 2494707 | 36 | TNFRSF14 | 0.035 | 0.042 | 0.024 | 0.082 | 0.006 | 0.37037 | 0.15033 | 0.73903 |
| 278 | chr18 | 48591760 | 48604805 | 16 | SMAD4 | 0.019 | 0.020 | 0.016 | 0.035 | 0.000 | 0.37088 | 0.36837 | 0.00422 |
| 279 | chr18 | 55274406 | 55274556 | 4 | NARS | 0.015 | 0.025 | 0.000 | 0.047 | 0.000 | 0.37631 | 0.84014 | 0.07298 |
| 280 | chrX | 90026454 | 90026604 | 4 | PABPC5 | 0.015 | 0.020 | 0.000 | 0.031 | 0.000 | 0.37790 | 0.70713 | 0.06008 |
| 281 | chr8 | 623881 | 624081 | 5 | ERICH1 | 0.020 | 0.025 | 0.020 | 0.025 | 0.000 | 0.38591 | 0.34374 | 0.13521 |
| 282 | chr18 | 1477566 | 1477666 | 3 | ADCYAP1 | 0.043 | 0.055 | 0.046 | 0.000 | 0.000 | 0.38723 | 0.02764 | 0.48180 |
| 283 | chr12 | 48190732 | 48190982 | 6 | HDAC7 | 0.020 | 0.041 | 0.018 | 0.021 | 0.000 | 0.38786 | 0.03087 | 0.34087 |
| 284 | chr14 | 106381486 | 106383981 | 18 | IGHD2-2 | 0.029 | 0.032 | 0.025 | 0.059 | 0.024 | 0.39274 | 0.82914 | 0.00001 |
| 285 | chr5 | 135381970 | 135382170 | 5 | TGFB1 | 0.034 | 0.030 | 0.040 | 0.038 | 0.000 | 0.39274 | 0.28309 | 0.98151 |
| 286 | chr3 | 184580664 | 184580864 | 5 | VPS8 | 0.006 | 0.007 | 0.005 | 0.075 | 0.000 | 0.40112 | 0.15248 | 0.00357 |
| 287 | chr14 | 106805291 | 106806190 | 8 | IGHV4-31 | 0.038 | 0.041 | 0.034 | 0.117 | 0.000 | 0.40201 | 0.02655 | 0.49158 |
| 288 | chr22 | 23077338 | 23077588 | 4 | IGLV2-18 | 0.025 | 0.025 | 0.025 | 0.063 | 0.000 | 0.40450 | 0.82223 | 0.42774 |
| 289 | chr11 | 134129470 | 134133940 | 40 | ACAD8 | 0.027 | 0.034 | 0.016 | 0.063 | 0.000 | 0.40456 | 0.61602 | 0.02024 |
| 290 | chr1 | 190067140 | 190068190 | 22 | FAM5C | 0.028 | 0.035 | 0.017 | 0.077 | 0.000 | 0.40678 | 0.18209 | 0.12955 |
| 291 | chr19 | 52403337 | 52403537 | 5 | ZNF649 | 0.026 | 0.026 | 0.025 | 0.075 | 0.000 | 0.41027 | 0.52307 | 0.41005 |
| 292 | chr15 | 66727355 | 66729281 | 10 | MAP2K1 | 0.035 | 0.044 | 0.020 | 0.069 | 0.000 | 0.41169 | 0.93852 | 0.81159 |

TABLE 4-continued

| # | Chromosome | Region Start | Region End | Number of 50 bp bins | Gene | Mean frac DLBCL with PV | Mean frac GCB with PV | Mean frac ABC with PV | Mean frac PMBCL with PV | Mean frac CHIL with PV | ranksumP ABCvsGCB | ranksumP PMBCLvsDLBCL | ranksumP CHLvsDLBCL |
|---|---|---|---|---|---|---|---|---|---|---|---|---|---|
| 293 | chr6 | 94120220 | 94120720 | 11 | EPHA7 | 0.024 | 0.027 | 0.020 | 0.119 | 0.000 | 0.41348 | 0.00251 | 0.10186 |
| 294 | chr20 | 23028373 | 23028823 | 10 | THBD | 0.044 | 0.052 | 0.030 | 0.075 | 0.009 | 0.41401 | 0.97196 | 0.91852 |
| 295 | chr19 | 42599891 | 42600091 | 5 | POU2F2 | 0.038 | 0.049 | 0.020 | 0.125 | 0.000 | 0.41703 | 0.03149 | 0.68257 |
| 296 | chrX | 86772954 | 86773304 | 8 | KLHL4 | 0.026 | 0.035 | 0.013 | 0.086 | 0.000 | 0.41822 | 0.64743 | 0.29530 |
| 297 | chr9 | 37407370 | 37407570 | 5 | GRHPR | 0.046 | 0.056 | 0.030 | 0.113 | 0.000 | 0.42725 | 0.84925 | 0.34749 |
| 298 | chrY | 20820917 | 20946827 | 8 | FOCAD | 0.015 | 0.016 | 0.013 | 0.078 | 0.000 | 0.43273 | 0.41122 | 0.00842 |
| 299 | chr6 | 91004619 | 91005994 | 10 | BACH2 | 0.051 | 0.061 | 0.038 | 0.100 | 0.017 | 0.43292 | 0.62927 | 0.61655 |
| 300 | chr9 | 139390583 | 139402863 | 17 | NOTCH1 | 0.038 | 0.045 | 0.028 | 0.140 | 0.000 | 0.44217 | 0.00038 | 0.66264 |
| 301 | chr14 | 106452661 | 106453001 | 7 | IGHV1-2 | 0.020 | 0.021 | 0.018 | 0.080 | 0.000 | 0.44604 | 0.33603 | 0.09047 |
| 302 | chr6 | 26020710 | 26020910 | 5 | HIST1H3A | 0.036 | 0.036 | 0.035 | 0.000 | 0.000 | 0.44876 | 0.01256 | 0.96541 |
| 303 | chr9 | 27950145 | 27950495 | 8 | LINGO2 | 0.022 | 0.031 | 0.009 | 0.117 | 0.000 | 0.45177 | 0.00957 | 0.11783 |
| 304 | chr7 | 80285800 | 80286050 | 6 | CD36 | 0.013 | 0.022 | 0.000 | 0.135 | 0.000 | 0.45506 | 0.00452 | 0.01644 |
| 305 | chr18 | 13825916 | 13826416 | 11 | MC5R | 0.035 | 0.043 | 0.023 | 0.085 | 0.000 | 0.45807 | 0.35320 | 0.85391 |
| 306 | chr9 | 5450475 | 5468015 | 33 | CD274 | 0.026 | 0.029 | 0.020 | 0.049 | 0.000 | 0.46045 | 0.38390 | 0.02293 |
| 307 | chr3 | 185446224 | 185538924 | 8 | IGF2BP2 | 0.019 | 0.027 | 0.006 | 0.102 | 0.000 | 0.47564 | 0.05373 | 0.03579 |
| 308 | chr1 | 3800046 | 3800353 | 7 | DFFB | 0.042 | 0.044 | 0.039 | 0.107 | 0.000 | 0.47590 | 0.05983 | 0.43666 |
| 309 | chr22 | 23055368 | 23055828 | 7 | IGLV3-21 | 0.034 | 0.035 | 0.032 | 0.107 | 0.000 | 0.47614 | 0.96231 | 0.90440 |
| 310 | chr6 | 27114005 | 27114545 | 9 | HIST1H2BK | 0.023 | 0.031 | 0.011 | 0.021 | 0.000 | 0.48388 | 0.19555 | 0.14560 |
| 311 | chr14 | 107013036 | 107013186 | 4 | IGHV3-49 | 0.020 | 0.029 | 0.006 | 0.109 | 0.000 | 0.48557 | 0.09402 | 0.17265 |
| 312 | chr22 | 22453288 | 22453563 | 6 | IGLV8-61 | 0.053 | 0.055 | 0.050 | 0.083 | 0.022 | 0.48646 | 0.45288 | 0.04559 |
| 313 | chr14 | 106357891 | 106357941 | 2 | IGHD6-19 | 0.000 | 0.000 | 0.000 | 0.000 | 0.000 | 0.48646 | 0.05020 | 0.03556 |
| 314 | chr16 | 33523608 | 33523658 | 2 | IGHV3OR16-12 | 0.000 | 0.000 | 0.000 | 0.125 | 0.000 | 0.48646 | 0.10655 | 0.02436 |
| 315 | chr7 | 151943422 | 151943472 | 2 | KMT2C | 0.000 | 0.000 | 0.000 | 0.125 | 0.000 | 0.49420 | 0.05467 | 0.03556 |
| 316 | chr22 | 23114793 | 23115048 | 5 | IGLV3-12 | 0.018 | 0.026 | 0.005 | 0.000 | 0.000 | 0.50036 | 0.00472 | 0.09497 |
| 317 | chr2 | 80801236 | 80801486 | 6 | CNNA2 | 0.017 | 0.025 | 0.004 | 0.146 | 0.000 | 0.50251 | 0.65174 | 0.03774 |
| 318 | chr22 | 23161918 | 23162288 | 8 | IGLV3-9 | 0.036 | 0.039 | 0.031 | 0.063 | 0.000 | 0.50409 | 0.06246 | 0.76665 |
| 319 | chr12 | 113495365 | 113534745 | 80 | DTX1 | 0.058 | 0.065 | 0.047 | 0.075 | 0.009 | 0.51163 | 0.10472 | 0.00000 |
| 320 | chr1] | 65190343 | 65190543 | 5 | FRMD8 | 0.050 | 0.049 | 0.050 | 0.038 | 0.000 | 0.51321 | 0.66087 | 0.60740 |
| 321 | chr14 | 106967131 | 106967366 | 4 | IGHV1-46 | 0.022 | 0.033 | 0.006 | 0.063 | 0.027 | 0.51555 | 0.36573 | 0.32094 |
| 322 | chr2 | 25205889 | 25207439 | 21 | LRMP | 0.038 | 0.041 | 0.033 | 0.080 | 0.000 | 0.51984 | 0.19368 | 0.00948 |
| 323 | chr14 | 106780611 | 106780711 | 3 | IGHV4-28 | 0.036 | 0.038 | 0.033 | 0.125 | 0.000 | 0.52233 | 0.24640 | 0.92185 |
| 324 | chr1 | 125472641 | 125472891 | 6 | STT3A | 0.046 | 0.055 | 0.033 | 0.052 | 0.019 | 0.53028 | 0.04449 | 0.20117 |
| 325 | chr11 | 69346692 | 69346892 | 5 | CCND1 | 0.024 | 0.026 | 0.020 | 0.113 | 0.000 | 0.53207 | 0.03239 | 0.30659 |
| 326 | chr13 | 51915234 | 51915534 | 7 | SERPINE3 | 0.035 | 0.044 | 0.021 | 0.152 | 0.000 | 0.53308 | 0.16100 | 0.74664 |
| 327 | chr5 | 21783416 | 21783666 | 6 | CDH12 | 0.020 | 0.022 | 0.017 | 0.083 | 0.000 | 0.53493 | 0.26379 | 0.13344 |
| 328 | chr12 | 25398219 | 25398269 | 2 | KRAS | 0.015 | 0.025 | 0.000 | 0.000 | 0.000 | 0.53686 | 0.60987 | 0.18377 |
| 329 | chr1 | 85733208 | 85742033 | 19 | BCL10 | 0.021 | 0.025 | 0.016 | 0.056 | 0.000 | 0.53874 | 0.17297 | 0.00831 |
| 330 | chr1 | 107866872 | 107867572 | 15 | NDNG1 | 0.013 | 0.015 | 0.010 | 0.063 | 0.000 | 0.53960 | 0.54478 | 0.00018 |
| 331 | chr1 | 86591438 | 86591888 | 10 | COL24A1 | 0.029 | 0.036 | 0.018 | 0.075 | 0.000 | 0.54851 | 0.49213 | 0.46033 |
| 332 | chr18 | 30349776 | 30350276 | 11 | KLHL14 | 0.033 | 0.036 | 0.030 | 0.091 | 0.019 | 0.54949 | 0.55397 | 0.94697 |
| 333 | chr14 | 106641656 | 106642261 | 7 | IGHV1-18 | 0.023 | 0.026 | 0.018 | 0.063 | 0.000 | 0.55999 | 0.86764 | 0.01550 |
| 334 | chr17 | 78343504 | 78343704 | 5 | RNF213 | 0.014 | 0.016 | 0.010 | 0.038 | 0.000 | 0.56418 | 0.22789 | 0.04664 |
| 335 | chr1 | 120457961 | 120459261 | 27 | NOTCH2 | 0.036 | 0.039 | 0.031 | 0.053 | 0.000 | 0.56498 | 0.51376 | 0.63380 |
| 336 | chr17 | 40467710 | 40491485 | 39 | STAT3 | 0.034 | 0.040 | 0.023 | 0.059 | 0.000 | 0.56578 | 0.26379 | 0.71754 |
| 337 | chr9 | 19957357 | 19958157 | 17 | SLC24A2 | 0.020 | 0.025 | 0.022 | 0.063 | 0.000 | 0.56926 | 0.75617 | 0.22788 |
| 338 | chr3 | 38180130 | 38182805 | 29 | MYD88 | 0.027 | 0.031 | 0.033 | 0.073 | 0.000 | 0.56966 | 0.70668 | 0.03867 |
| 339 | chr18 | 73944894 | 73945344 | 10 | ZNF516 | 0.045 | 0.053 | 0.008 | 0.056 | 0.000 | 0.56966 | 0.67544 | 0.01359 |
| 340 | chr7 | 140453013 | 140453254 | 5 | BRAF | 0.018 | 0.020 | 0.000 | 0.075 | 0.000 | 0.57311 | 0.30182 | 0.01894 |
| 341 | chr6 | 159238416 | 159238766 | 8 | EZR | 0.050 | 0.057 | 0.038 | 0.016 | 0.000 | 0.57311 | 0.00246 | 0.08463 |

TABLE 4-continued

| # | Chromosome | Region Start | Region End | Number of 50 bp bins | Gene | Mean frac DLBCL with PV | Mean frac GCB with PV | Mean frac ABC with PV | Mean frac PMBCL with PV | Mean frac CHIL with PV | ranksumP ABCvsGCB | ranksumP PMBCLvsDLBCL | ranksumP CHLvsDLBCL |
|---|---|---|---|---|---|---|---|---|---|---|---|---|---|
| 342 | chr18 | 77092821 | 77093021 | 5 | ATP9B | 0.008 | 0.010 | 0.005 | 0.075 | 0.000 | 0.57396 | 0.16232 | 0.00549 |
| 343 | chr22 | 23523568 | 23610748 | 22 | BCR | 0.038 | 0.045 | 0.028 | 0.097 | 0.000 | 0.57399 | 0.04814 | 0.27043 |
| 344 | chr22 | 22673243 | 22673593 | 8 | IGLV5-52 | 0.027 | 0.035 | 0.016 | 0.117 | 0.000 | 0.57479 | 0.00701 | 0.30927 |
| 345 | chr4 | 88011078 | 88011278 | 5 | AFF1 | 0.014 | 0.016 | 0.010 | 0.038 | 0.000 | 0.57733 | 0.89980 | 0.03303 |
| 346 | chr1 | 131747550 | 131748000 | 9 | NTM | 0.029 | 0.036 | 0.018 | 0.119 | 0.000 | 0.57801 | 0.02773 | 0.42832 |
| 347 | chr2 | 90077982 | 90078316 | 6 | IGKV3D-20 | 0.025 | 0.033 | 0.013 | 0.031 | 0.000 | 0.57996 | 0.26904 | 0.32350 |
| 348 | chr2 | 96809890 | 96810360 | 10 | DUSP2 | 0.063 | 0.066 | 0.060 | 0.006 | 0.000 | 0.58190 | 0.00002 | 0.00216 |
| 349 | chr2 | 89265757 | 89265987 | 4 | IGKV1-6 | 0.010 | 0.012 | 0.006 | 0.047 | 0.000 | 0.59812 | 0.84325 | 0.02299 |
| 350 | chr19 | 53598587 | 53599037 | 10 | ZNF160 | 0.024 | 0.031 | 0.013 | 0.063 | 0.000 | 0.60291 | 0.98122 | 0.12855 |
| 351 | chr2 | 63335243 | 63631808 | 22 | WDPCP | 0.026 | 0.033 | 0.016 | 0.091 | 0.000 | 0.60661 | 0.01199 | 0.09457 |
| 352 | chr9 | 21808815 | 21859450 | 9 | MTAP | 0.019 | 0.026 | 0.008 | 0.042 | 0.000 | 0.61688 | 0.80480 | 0.03120 |
| 353 | chr6 | 27860480 | 27860895 | 7 | HISTIH2AM | 0.030 | 0.033 | 0.025 | 0.045 | 0.000 | 0.61920 | 0.45404 | 0.60865 |
| 354 | chr6 | 27839659 | 27839759 | 3 | HISTIH31 | 0.036 | 0.038 | 0.033 | 0.021 | 0.000 | 0.62267 | 0.15955 | 0.75106 |
| 355 | chr6 | 26252155 | 26252205 | 2 | HISTIH2BH | 0.015 | 0.016 | 0.013 | 0.063 | 0.000 | 0.62577 | 0.55784 | 0.18377 |
| 356 | chr19 | 19256470 | 19293460 | 41 | MEF2B | 0.040 | 0.045 | 0.032 | 0.091 | 0.029 | 0.62683 | 0.04274 | 0.29098 |
| 357 | chr14 | 107169646 | 107170861 | 21 | IGHV1-69 | 0.091 | 0.098 | 0.082 | 0.107 | 0.000 | 0.63032 | 0.38178 | 0.00266 |
| 358 | chr8 | 113308015 | 113569195 | 15 | CSMD3 | 0.013 | 0.020 | 0.003 | 0.046 | 0.000 | 0.63047 | 0.85436 | 0.00010 |
| 359 | chr22 | 22550338 | 22550788 | 10 | IGLV6-57 | 0.042 | 0.049 | 0.030 | 0.131 | 0.017 | 0.64049 | 0.04005 | 0.29687 |
| 360 | chr4 | 153249286 | 153249486 | 5 | FBXW7 | 0.026 | 0.026 | 0.025 | 0.038 | 0.000 | 0.64551 | 0.50853 | 0.39977 |
| 361 | chr11 | 120127164 | 120189629 | 22 | POU2F3 | 0.027 | 0.033 | 0.018 | 0.091 | 0.000 | 0.64824 | 0.02013 | 0.09628 |
| 362 | chr12 | 57496553 | 57499113 | 13 | STAT6 | 0.046 | 0.054 | 0.035 | 0.072 | 0.013 | 0.65115 | 0.71967 | 0.94722 |
| 363 | chr22 | 22937193 | 22937499 | 7 | IGLV3-32 | 0.018 | 0.026 | 0.007 | 0.063 | 0.000 | 0.65348 | 0.49810 | 0.05644 |
| 364 | chr2 | 138184484 | 138202489 | 64 | TNFAIP3 | 0.024 | 0.020 | 0.018 | 0.035 | 0.004 | 0.65552 | 0.00591 | 0.00002 |
| 365 | chr6 | 138849938 | 138850138 | 5 | FAM135B | 0.020 | 0.023 | 0.015 | 0.038 | 0.000 | 0.65643 | 0.70665 | 0.12531 |
| 366 | chr14 | 107218756 | 107218856 | 3 | IGHV3-74 | 0.073 | 0.082 | 0.058 | 0.104 | 0.058 | 0.66142 | 0.98960 | 0.26299 |
| 367 | chr14 | 23344698 | 23345198 | 11 | LRP10 | 0.059 | 0.063 | 0.052 | 0.034 | 0.000 | 0.66215 | 0.00576 | 0.01137 |
| 368 | chr14 | 106866381 | 106866595 | 5 | IGHV3-38 | 0.032 | 0.033 | 0.030 | 0.163 | 0.014 | 0.66584 | 0.01626 | 0.86538 |
| 369 | chr1 | 3547351 | 3547701 | 8 | WRAP73 | 0.024 | 0.027 | 0.019 | 0.063 | 0.000 | 0.66789 | 0.68610 | 0.19690 |
| 370 | chr21 | 28213259 | 28216964 | 11 | ADAMTS1 | 0.028 | 0.036 | 0.016 | 0.108 | 0.012 | 0.67094 | 0.03930 | 0.06299 |
| 371 | chr2 | 169781121 | 169781321 | 5 | ABCB11 | 0.016 | 0.023 | 0.005 | 0.125 | 0.000 | 0.67664 | 0.00990 | 0.06041 |
| 372 | chr22 | 41513341 | 41574886 | 72 | EP300 | 0.031 | 0.037 | 0.022 | 0.067 | 0.000 | 0.67996 | 0.51033 | 0.09373 |
| 373 | chr2 | 56054916 | 56063816 | 24 | NEDD4L | 0.016 | 0.020 | 0.009 | 0.031 | 0.000 | 0.68133 | 0.24138 | 0.00003 |
| 374 | chr14 | 106845301 | 106846536 | 9 | IGHV3-35 | 0.055 | 0.064 | 0.042 | 0.097 | 0.000 | 0.68499 | 0.76566 | 0.05591 |
| 375 | chr14 | 107136756 | 107136856 | 3 | IGHV3-66 | 0.030 | 0.038 | 0.017 | 0.021 | 0.000 | 0.68512 | 0.22171 | 0.79848 |
| 376 | chr14 | 23047068 | 23047318 | 6 | IGHV3-22 | 0.043 | 0.049 | 0.033 | 0.042 | 0.014 | 0.68905 | 0.16524 | 0.80319 |
| 377 | chr22 | 22786478 | 22786803 | 7 | IGLV1-36 | 0.040 | 0.047 | 0.029 | 0.080 | 0.000 | 0.69080 | 0.82010 | 0.41665 |
| 378 | chr8 | 122626848 | 122627148 | 7 | HAS2 | 0.030 | 0.033 | 0.025 | 0.063 | 0.000 | 0.70243 | 0.90117 | 0.66520 |
| 379 | chrs | 131825018 | 131825218 | 5 | IRF1 | 0.026 | 0.022 | 0.020 | 0.138 | 0.000 | 0.70868 | 0.00725 | 0.42851 |
| 380 | chr22 | 23252688 | 23252788 | 3 | IGLJ4 | 0.020 | 0.022 | 0.017 | 0.021 | 0.000 | 0.71377 | 0.39782 | 0.24178 |
| 381 | chr14 | 107078456 | 107078606 | 4 | IGHV1-58 | 0.050 | 0.053 | 0.044 | 0.063 | 0.000 | 0.71737 | 0.53128 | 0.17192 |
| 382 | chr4 | 154624671 | 154625021 | 8 | TLR2 | 0.017 | 0.020 | 0.013 | 0.125 | 0.007 | 0.72168 | 0.00257 | 0.03397 |
| 383 | chr2 | 89196227 | 89215037 | 19 | IGKV5-2 | 0.024 | 0.028 | 0.017 | 0.036 | 0.000 | 0.73228 | 0.12196 | 0.02080 |
| 384 | chr18 | 55319681 | 55359256 | 17 | ATP8B1 | 0.028 | 0.031 | 0.024 | 0.044 | 0.014 | 0.73256 | 0.29761 | 0.29755 |
| 385 | chr1 | 61553803 | 61554303 | 11 | NFIA | 0.030 | 0.033 | 0.025 | 0.097 | 0.000 | 0.73331 | 0.11994 | 0.58902 |
| 386 | chr10 | 89603603 | 89604053 | 10 | KLLN | 0.024 | 0.028 | 0.018 | 0.044 | 0.000 | 0.73666 | 0.57207 | 0.12653 |
| 387 | chr22 | 23247138 | 23247609 | 9 | IGLJ3 | 0.165 | 0.169 | 0.158 | 0.153 | 0.048 | 0.73794 | 0.02871 | 0.00093 |
| 388 | chr1 | 117101044 | 117101194 | 4 | PCSK7 | 0.042 | 0.049 | 0.031 | 0.016 | 0.000 | 0.73868 | 0.05815 | 0.47968 |
| 389 | chr6 | 27861245 | 27861450 | 4 | HISTIH2BO | 0.037 | 0.045 | 0.025 | 0.031 | 0.000 | 0.74033 | 0.21815 | 0.85767 |
| 390 | chr2 | 61441170 | 61441870 | 15 | USP34 | 0.025 | 0.028 | 0.020 | 0.042 | 0.000 | 0.74279 | 0.23146 | 0.11749 |

TABLE 4-continued

| # | Chromosome | Region Start | Region End | Number of 50 bp bins | Gene | Mean frac DLBCL with PV | Mean frac GCB with PV | Mean frac ABC with PV | Mean frac PMBCL with PV | Mean frac CHIL with PV | ranksumP ABCvsGCB | ranksumP PMBCLvsDLBCL | ranksumP CHLvsDLBCL |
|---|---|---|---|---|---|---|---|---|---|---|---|---|---|
| 391 | chr1 | 111234537 | 111249512 | 16 | POU2AF1 | 0.030 | 0.034 | 0.023 | 0.105 | 0.008 | 0.74326 | 0.02352 | 0.08875 |
| 392 | chr5 | 5182146 | 5182446 | 7 | ADAMTS16 | 0.038 | 0.044 | 0.029 | 0.107 | 0.000 | 0.75162 | 0.19189 | 0.54007 |
| 393 | chr14 | 106667546 | 106667856 | 6 | IGHV3-20 | 0.021 | 0.025 | 0.017 | 0.063 | 0.008 | 0.75404 | 0.64784 | 0.15262 |
| 394 | chr2 | 145162402 | 145693052 | 53 | ZEB2 | 0.041 | 0.046 | 0.032 | 0.048 | 0.008 | 0.76200 | 0.00643 | 0.47223 |
| 395 | chr14 | 106494091 | 106494768 | 12 | IGHV2-5 | 0.027 | 0.034 | 0.017 | 0.063 | 0.014 | 0.76623 | 0.78849 | 0.01259 |
| 396 | chr2 | 65593036 | 65593213 | 4 | SPRED2 | 0.057 | 0.061 | 0.050 | 0.250 | 0.033 | 0.77068 | 0.00195 | 0.40243 |
| 397 | chr2 | 141245128 | 141245328 | 5 | LRPIB | 0.010 | 0.016 | 0.000 | 0.088 | 0.000 | 0.77497 | 0.10161 | 0.00830 |
| 398 | chr22 | 23241763 | 23241813 | 2 | IGLJ2 | 0.030 | 0.033 | 0.025 | 0.094 | 0.000 | 0.77602 | 0.38252 | 0.80404 |
| 399 | chrX | 153997384 | 153997584 | 5 | DKC1 | 0.042 | 0.046 | 0.035 | 0.075 | 0.000 | 0.77946 | 0.93861 | 0.49207 |
| 400 | chr10 | 5755067 | 5755267 | 5 | FAM208B | 0.016 | 0.020 | 0.010 | 0.000 | 0.000 | 0.77955 | 0.06988 | 0.04606 |
| 401 | chr1 | 35472493 | 35472693 | 5 | ZMYM6 | 0.016 | 0.020 | 0.010 | 0.025 | 0.000 | 0.77955 | 0.46246 | 0.04606 |
| 402 | chr6 | 26250460 | 26250695 | 5 | HISTIH3F | 0.028 | 0.033 | 0.020 | 0.013 | 0.000 | 0.78052 | 0.07461 | 0.50252 |
| 403 | chr3 | 176750700 | 176771710 | 17 | TBLIXR1 | 0.020 | 0.024 | 0.013 | 0.051 | 0.003 | 0.78556 | 0.88935 | 0.00559 |
| 404 | chr18 | 77170716 | 77288591 | 29 | NFATC1 | 0.038 | 0.043 | 0.031 | 0.082 | 0.000 | 0.78831 | 0.61891 | 0.47180 |
| 405 | chr13 | 41133663 | 41240784 | 49 | FOXO1 | 0.025 | 0.031 | 0.016 | 0.042 | 0.000 | 0.78900 | 0.09626 | 0.00465 |
| 406 | chr8 | 128951725 | 128951875 | 4 | TMEM75 | 0.042 | 0.049 | 0.031 | 0.016 | 0.000 | 0.78980 | 0.05059 | 0.43332 |
| 407 | chr22 | 22681928 | 22682198 | 5 | IGLV1-50 | 0.020 | 0.026 | 0.010 | 0.088 | 0.000 | 0.79643 | 0.39142 | 0.12531 |
| 408 | chr2 | 89976277 | 89976377 | 3 | IGKV2D-30 | 0.066 | 0.071 | 0.058 | 0.125 | 0.000 | 0.79654 | 0.28677 | 0.06295 |
| 409 | chr14 | 106757726 | 106758621 | 8 | IGHV2-26 | 0.026 | 0.033 | 0.016 | 0.039 | 0.000 | 0.80101 | 0.48691 | 0.27328 |
| 410 | chr1 | 2306312 | 2306812 | 11 | MORN1 | 0.028 | 0.034 | 0.018 | 0.102 | 0.000 | 0.80151 | 0.03618 | 0.25568 |
| 411 | chr14 | 106384031 | 106384926 | 9 | IGHD1-1 | 0.039 | 0.046 | 0.028 | 0.132 | 0.024 | 0.81269 | 0.00673 | 0.00968 |
| 412 | chr8 | 104897562 | 104898462 | 19 | RIMS2 | 0.030 | 0.036 | 0.021 | 0.099 | 0.000 | 0.81294 | 0.04875 | 0.36772 |
| 413 | chr10 | 89500958 | 89501108 | 4 | PAPSS2 | 0.025 | 0.029 | 0.019 | 0.047 | 0.000 | 0.81562 | 0.75051 | 0.38140 |
| 414 | chr1 | 201038553 | 201038753 | 5 | CACNAIS | 0.034 | 0.033 | 0.035 | 0.113 | 0.000 | 0.82537 | 0.08167 | 0.99310 |
| 415 | chr13 | 84453543 | 84455243 | 35 | SLITRK1 | 0.034 | 0.039 | 0.026 | 0.073 | 0.003 | 0.82863 | 0.60871 | 0.95353 |
| 416 | chr22 | 23263508 | 23264123 | 9 | IGLJ7 | 0.062 | 0.069 | 0.050 | 0.042 | 0.000 | 0.84212 | 0.02446 | 0.00290 |
| 417 | chr5 | 140208034 | 140208834 | 17 | PCDHA6 | 0.026 | 0.031 | 0.019 | 0.051 | 0.000 | 0.84499 | 0.73711 | 0.13168 |
| 418 | chr1 | 23885408 | 23885899 | 10 | ID3 | 0.015 | 0.020 | 0.008 | 0.081 | 0.000 | 0.84648 | 0.06666 | 0.00452 |
| 419 | chr14 | 106518496 | 106519064 | 7 | IGHV3-7 | 0.035 | 0.040 | 0.029 | 0.054 | 0.000 | 0.84779 | 0.54879 | 0.79096 |
| 420 | chr9 | 22005930 | 22009000 | 13 | CDKN2B | 0.031 | 0.035 | 0.025 | 0.038 | 0.000 | 0.85460 | 0.20627 | 0.52500 |
| 421 | chr11 | 58978693 | 58979345 | 11 | MPEG1 | 0.032 | 0.036 | 0.025 | 0.080 | 0.000 | 0.85627 | 0.50475 | 0.70735 |
| 422 | chr7 | 227842647 | 227842697 | 2 | ZNF678 | 0.010 | 0.016 | 0.000 | 0.156 | 0.000 | 0.85664 | 0.04034 | 0.09510 |
| 423 | chr6 | 106534267 | 106555367 | 60 | PRDMI | 0.031 | 0.036 | 0.023 | 0.065 | 0.000 | 0.86083 | 0.99103 | 0.15072 |
| 424 | chr2 | 198950435 | 198950985 | 12 | PLCL1 | 0.021 | 0.027 | 0.013 | 0.094 | 0.000 | 0.86126 | 0.14473 | 0.05072 |
| 425 | chr18 | 6947105 | 6980665 | 1 | LAMA1 | 0.027 | 0.033 | 0.018 | 0.094 | 0.000 | 0.86312 | 0.22629 | 0.28027 |
| 426 | chr6 | 26197105 | 26197462 | 8 | HISTIH3D | 0.021 | 0.027 | 0.013 | 0.000 | 0.000 | 0.86860 | 0.00995 | 0.09168 |
| 427 | chr19 | 51525627 | 51525927 | 7 | KLK11 | 0.028 | 0.033 | 0.021 | 0.089 | 0.000 | 0.87219 | 0.14799 | 0.45199 |
| 428 | chr2 | 61719435 | 61719635 | 5 | XPO1 | 0.012 | 0.016 | 0.005 | 0.000 | 0.000 | 0.87795 | 0.09496 | 0.02531 |
| 429 | chrX | 141291053 | 141291534 | 10 | MAGEC2 | 0.019 | 0.023 | 0.013 | 0.081 | 0.050 | 0.88059 | 0.07959 | 0.02755 |
| 430 | chr14 | 35873672 | 35873822 | 4 | NFKBIA | 0.035 | 0.041 | 0.025 | 0.000 | 0.000 | 0.88608 | 0.02331 | 0.96205 |
| 431 | chr2 | 89443292 | 89443217 | 19 | IGKV3-20 | 0.042 | 0.047 | 0.036 | 0.148 | 0.000 | 0.88638 | 0.00002 | 0.00006 |
| 432 | chr1 | 72334892 | 72335098 | 5 | NEGR1 | 0.014 | 0.020 | 0.005 | 0.025 | 0.000 | 0.89151 | 0.51822 | 0.02712 |
| 433 | chr1 | 9784433 | 9784533 | 3 | PIK3CD | 0.007 | 0.011 | 0.000 | 0.083 | 0.000 | 0.89564 | 0.14993 | 0.02634 |
| 434 | chr1 | 170101186 | 170101386 | 5 | LRP2 | 0.032 | 0.036 | 0.025 | 0.100 | 0.002 | 0.90183 | 0.18901 | 0.76737 |
| 435 | chr1 | 110737412 | 110764944 | 61 | LRRN3 | 0.019 | 0.024 | 0.011 | 0.086 | 0.000 | 0.90333 | 0.00080 | 0.00000 |
| 436 | chr3 | 7620224 | 7620974 | 16 | GRM7 | 0.032 | 0.038 | 0.023 | 0.078 | 0.000 | 0.90702 | 0.28646 | 0.77891 |
| 437 | chr22 | 22569333 | 22569633 | 7 | IGLV10-54 | 0.031 | 0.037 | 0.021 | 0.063 | 0.000 | 0.90702 | 0.86839 | 0.77523 |
| 438 | chr17 | 75447869 | 75448419 | 12 | 9-Sep | 0.03] | 0.037 | 0.021 | 0.036 | 0.000 | 0.90976 | 0.14194 | 0.64487 |
| 439 | chr7 | 148506319 | 148523734 | 19 | EZH2 | 0.019 | 0.025 | 0.011 | 0.082 | 0.000 | 0.91143 | 0.05741 | 0.00268 |

TABLE 4-continued

| # | Chromosome | Region Start | Region End | Number of 50 bp bins | Gene | Mean frac DLBCL with PV | Mean frac GCB with PV | Mean frac ABC with PV | Mean frac PMBCL with PV | Mean frac CHL with PV | ranksumP ABCvsGCB | ranksumP PMBCLvsDLBCL | ranksumP CHLvsDLBCL |
|---|---|---|---|---|---|---|---|---|---|---|---|---|---|
| 440 | chr14 | 106621886 | 106622095 | 5 | IGHV3-16 | 0.024 | 0.030 | 0.015 | 0.063 | 0.000 | 0.91521 | 0.67996 | 0.28737 |
| 441 | chr1 | 181452915 | 181453115 | 5 | CACNA1E | 0.032 | 0.036 | 0.025 | 0.025 | 0.000 | 0.91767 | 0.14135 | 0.76209 |
| 442 | chr2 | 58520801 | 58521201 | 9 | FANCL | 0.029 | 0.035 | 0.019 | 0.069 | 0.000 | 0.92005 | 0.73186 | 0.57669 |
| 443 | chr19 | 51559442 | 51561922 | 16 | KLK13 | 0.032 | 0.038 | 0.023 | 0.113 | 0.000 | 0.92076 | 0.04033 | 0.89701 |
| 444 | chr16 | 2812097 | 2812747 | 14 | SRRM2 | 0.056 | 0.062 | 0.046 | 0.045 | 0.000 | 0.92192 | 0.02154 | 0.01164 |
| 445 | chr0 | 41903612 | 41909397 | 26 | CCND3 | 0.041 | 0.047 | 0.033 | 0.058 | 0.000 | 0.92504 | 0.14949 | 0.21095 |
| 446 | chr14 | 106068706 | 106071241 | 16 | IGHE | 0.118 | 0.124 | 0.108 | 0.215 | 0.158 | 0.92648 | 0.00059 | 0.00000 |
| 447 | chr6 | 110777719 | 110778219 | 11 | SLC22A16 | 0.027 | 0.033 | 0.018 | 0.034 | 0.000 | 0.92796 | 0.19315 | 0.23193 |
| 448 | chr9 | 21970835 | 21994385 | 37 | CDKN2A | 0.027 | 0.031 | 0.020 | 0.039 | 0.000 | 0.92888 | 0.04082 | 0.03393 |
| 449 | chr2 | 90025207 | 90025522 | 6 | IGKV2D-26 | 0.012 | 0.016 | 0.004 | 0.031 | 0.000 | 0.92990 | 0.73921 | 0.01161 |
| 450 | chr4 | 7728457 | 7728657 | 5 | SORCS2 | 0.034 | 0.039 | 0.025 | 0.038 | 0.000 | 0.93035 | 0.30875 | 0.99310 |
| 451 | chr? | 5569096 | 5569356 | 6 | ACTB | 0.048 | 0.055 | 0.038 | 0.208 | 0.007 | 0.93481 | 0.00069 | 0.95055 |
| 452 | chr3 | 140281599 | 140281849 | 6 | CLSTN2 | 0.036 | 0.038 | 0.033 | 0.031 | 0.000 | 0.94099 | 0.11813 | 0.72422 |
| 453 | chr2 | 89291907 | 89292182 | 4 | IGKV1-8 | 0.020 | 0.025 | 0.013 | 0.047 | 0.022 | 0.94155 | 0.86146 | 0.00511 |
| 454 | chr22 | 23260268 | 23260368 | 3 | IGLJ6 | 0.043 | 0.049 | 0.033 | 0.063 | 0.000 | 0.94574 | 0.74604 | 0.48180 |
| 455 | chr14 | 106815806 | 106815906 | 3 | IGHV3-33 | 0.059 | 0.066 | 0.050 | 0.063 | 0.043 | 0.94598 | 0.41907 | 0.10857 |
| 456 | chr6 | 26123615 | 26124080 | 9 | HIST1H2BC | 0.031 | 0.036 | 0.022 | 0.028 | 0.000 | 0.95616 | 0.07091 | 0.75304 |
| 457 | chr3 | 49379609 | 49413039 | 18 | RHOA | 0.030 | 0.035 | 0.022 | 0.045 | 0.003 | 0.95622 | 0.26281 | 0.40030 |
| 458 | chr22 | 29191137 | 29196512 | 28 | XBP1 | 0.032 | 0.039 | 0.022 | 0.085 | 0.003 | 0.95630 | 0.05799 | 0.16891 |
| 459 | chr14 | 106471396 | 106471580 | 4 | IGHV1-3 | 0.007 | 0.012 | 0.000 | 0.141 | 0.000 | 0.95914 | 0.00935 | 0.01524 |
| 460 | chr17 | 41847059 | 41847209 | 4 | DUSP3 | 0.032 | 0.037 | 0.025 | 0.094 | 0.000 | 0.96078 | 0.74050 | 0.94029 |
| 461 | chr17 | 51900442 | 51900892 | 10 | KIF2B | 0.035 | 0.039 | 0.028 | 0.088 | 0.000 | 0.96080 | 0.24029 | 0.71768 |
| 462 | chr15 | 86312063 | 86312563 | 11 | KLHL25 | 0.032 | 0.037 | 0.025 | 0.074 | 0.000 | 0.96521 | 0.83987 | 0.74482 |
| 463 | chr18 | 53804516 | 53804766 | 6 | TXNL1 | 0.036 | 0.041 | 0.029 | 0.115 | 0.009 | 0.96529 | 0.05667 | 0.84317 |
| 464 | chr5 | 67590967 | 67591167 | 5 | PIK3R1 | 0.018 | 0.023 | 0.010 | 0.075 | 0.000 | 0.97792 | 0.39415 | 0.02207 |
| 465 | chr5 | 124079828 | 124080678 | 18 | ZNF608 | 0.026 | 0.031 | 0.019 | 0.063 | 0.000 | 0.98245 | 0.74836 | 0.14794 |
| 466 | chr2 | 90259932 | 90260232 | 5 | IGKV1D-8 | 0.034 | 0.039 | 0.025 | 0.163 | 0.000 | 0.98690 | 0.17514 | 0.96394 |
| 467 | chr2 | 88906682 | 88906832 | 4 | EIF2AK3 | 0.059 | 0.066 | 0.050 | 0.063 | 0.000 | 0.98750 | 0.34568 | 0.07429 |
| 468 | chr4 | 106157605 | 106157805 | 5 | TET2 | 0.018 | 0.023 | 0.010 | 0.075 | 0.000 | 0.99542 | 0.34309 | 0.09635 |

TABLE 5

| Reference Coordinates | Nearest Gene | Percent Non-Reference | Total Non-Reference Bases | Plus Strand Oligonucleotide | SEQ ID NOS: |
|---|---|---|---|---|---|
| chr8:128,750,550-128,750,699 | MYC | 0 | 0 | CGACTACGACTCGTGCAGCCGTATTTCTACTGCGACGAGGAGGAGAACTT CTACCAGCAGCAGCAGCAGCGAGCTGCAGCCCTGGCGCCCAGCGAGG ATATCTGGAAGAAATTCGAGCTGCTGCCCACCCCGCCCTGTCCCTAG | 1331 |
| chr8:128,750,550-128,750,699 | MYC | 2.5 | 4 | CGACTACGACTCGTGCAGCCGTAGTTCTACTGCGACGAGGAGGAAAACT TCTACCAGCAGCAGCAGCAGCGAGCTGCAGCCCTGGCGCCCAGCGAGG GATATCTGGAAGAACTTCGAGCTGCTGCCCACCCCGCCCTGTCCCTAG | 1332 |
| chr8:128,750,550-128,750,699 | MYC | 5 | 8 | CGACTACGACTCGTGCAGCCGTAGTTCTACTGCGACGAGGAGGAATACTT CTACCAGCAGCGCCAGAGCGAGCTGCAGCCCTGGCGCCCAGCGAGG GTATCTGGAAGAACTTCGAGCTACTGCCCACCCCCGTGTCCCTAG | 1333 |
| chr8:128,750,550-128,750,699 | MYC | 7.5 | 11 | CGACTACGACTCGTTGCAGCCGTAGTTCTACTGCGACGAGGAGGAATACTT CTACCAGCAGCCGCAGAGCGAGCTGCAGCCCTGGCGCCCAGCGAGG GTATCTGGAAGAACTTCGAGCTACAGCCCCACCCCGTGTCCCTAG | 1334 |
| chr8:128,750,550-128,750,699 | MYC | 10 | 15 | CGACTACGACTCGTTGCAGCCGTAGATTCTACTGCGAGGAGGAATACTT CTACCTGCAGCAGCCGCAGAGCGAGCTGCAGCGCCTGGCGCCCAGCGAGC GTATCTGGAAGAACTTCGAGCTACAGCCCCACCCCCGTGTCCCTAG | 1335 |
| chr8:128,750,550-128,750,699 | MYC | 12.5 | 19 | CGACAACGACTCGTTGCACCCGTAGATCTACTGCGACGAGGAGGAATACTT CTACCTGCAGCAGCCGCAGAGCGAGCTGCAGCGCCTGGCGCCCAGCGAGC GTATCTGAAAGAACTTCGAGCTACAGCCCACCGCCCCTTGTCCCTAG | 1336 |
| chr8:128,750,550-128,750,699 | MYC | 15 | 23 | CGACAACGACTCGTTGCACCCGTAGATCTACTGCGACGAGGAGGAATACTT CTACCTGCAGCAGCCGCAGAGCGAGCTGCAGCGCCTGGCGCCCAGCGAGC GTATCTGAAAGAACTTCGAGCTACAGCCCACCGCCCTTGTCCCTAG | 1337 |
| chr3:187,443,281-187,443,430 | BCL6 | 0 | 0 | GCTCACCTGTACAAATCTGGCTCCGCAGTTTCGCATTTGTAGGGCTTCTCT CCAGAGTGAATTCGAGTGTGGGTTTTCAGTTGGCTGGCCGGTTGAACTGG GCCCCACAGATGTTGCAACGATAGGGTTTCTCACCTATTACCAAGAA | 1338 |
| chr3:187,443,281-187,443,430 | BCL6 | 2.5 | 4 | GCTCACCTGTACAAATCTGCCTCCGCAGTTTCGCATTTGTAGGGCTCTCT CCAGAGTGAATTCGAGTGTGGGTTTTCAGTTGGCTGGCCGGTTGAACTGG GCCCCACAGATGTTGCAACGCTAGGGTTTCTCACCTATTACCAGAA | 1339 |
| chr3:187,443,281-187,443,430 | BCL6 | 5 | 8 | GCTCACCTGTACAAATCTGCCTCCGCAGTTTCGCCTTTGTAGGGCTCCTCT CCAGAGTGAATTCGAGTGTAGGTTTTCAAGTTGGCTGGGCGGTTACCAGGA GCCCCACGATGTTGCAACGCTAGGGTTTCTCACCTATTACCAAGAA | 1340 |
| chr3:187,443,281-187,443,430 | BCL6 | 7.5 | 11 | GCTCACCTGTACAAATCTGCCTCCGCGTTTCGCCTTTTAGGGCTCCTCT CCGAGTGAATTCGAGTGTAGGTTTTCAAGTTGGCTGGGCGGTTGAACTGG GCCCCACCGATGTTGCAACGCTAGGGTTTCTCACCTATTTCCAAGAA | 1341 |
| chr3:187,443,281-187,443,430 | BCL6 | 10 | 15 | GCTCACCTGTACAAGTCTGCCTCCGCCGGTTACGCCTTTTTAGGGCTCCTCT CCGAGTGAATTCGAGTGTAGGTTTTCAAGTTGGCTGGGCGGTTGAACTGG GCTCCACCGACGTTCAACGGATTCTCACCTATTTCCAAGAA | 1342 |

TABLE 5-continued

| Reference Coordinates | Nearest Gene | Percent Non-Reference | Total Non-Reference Bases | Plus Strand Oligonucleotide | SEQ ID NOS: |
|---|---|---|---|---|---|
| chr3:187,443,281-187,443,430 | BCL6 | 12.5 | 19 | GCTCACCTGGACAAGTCTGCCTCCGCCGGTTACGACTTTTAGGGCTCCTCTCCAGAGTGAATTCGAGTGTAGGCTTTCAAGTTGGCTGGGCGGTTGAACTGGGCTCCACGGCTGTTGCAACGCTAGGGATTCTCACCTATTTCCAAGAA | 1343 |
| chr3:187,443,281-187,443,430 | BCL6 | 15 | 23 | GCTCACCTGGACAAGTCTGCCTCCGCCGGTTACGACTTTTAGGGCACCTCTCCAGAGTGAATTCGAGTGTAGGCTTTCAAGTTGGCTGGGAGCTTGAACTGGGCTGCACGGCTGTTGCAACGCTAGGGATTCTCACCTATTTCCAAGAA | 1344 |
| — | — | — | — | Minus Strand Oligonucleotide | — |
| chr8:128,750,550-128,750,699 | MYC | 0 | 0 | CTAGGGGACAGGGGCGGGGTGGGCAGCAGCTCGAATTCTTCCAGATATCCTCGCTGGGCGCCCGGGGCTGCAGCTCGCTCTGCTGCTGCTGGTAGAAGTTCCTCCTCCGTCGCAGTAGAAATACGGCTGCACCGAGTCGTAGTCG | 1345 |
| chr8:128,750,550-128,750,699 | MYC | 2.5 | 4 | CTAGGGGACAGGGGCGGGGTGGGCAGCAGCTCGAAGTTCTTCCAGATATCCTCGCTGGGCGCCAGGGGCTGCAGCTCGCTCTGCTGCTGCTGGTAGAAGTTTCCTCCTCGTCGCAGTAGAACTACGGCTGCACCGAGTCGTAGTCG | 1346 |
| chr8:128,750,550-128,750,699 | MYC | 5 | 8 | CTAGGGGACAGGGGCGGGGTGGGCAGTAGCTCGAAGTTCTTCCAGATACCCTCGCTGGGCGCCAGGGGCTGCAGCTCGCTCTGCCGCTGCTGGTAGAAGTAATTCCTCCTCGTCGCAGTAGAACTACGGCTGCACCGAGTCGTAGTCG | 1347 |
| chr8:128,750,550-128,750,699 | MYC | 7.5 | 11 | CTAGGGGACAGGGGCGGGGTGGGCTGTAGCTCGAAGTTCTTCCAGATACCCTCGCTGGGCGCCAGGGCGCTGCAGCTCGCCTCTGCCGCTGCTGGTAGAAGTAATTCCTCCTCGTCGCAGTAGAACTACGGCTGCAACGAGTCGTAGTCG | 1348 |
| chr8:128,750,550-128,750,699 | MYC | 10 | 15 | CTAGGGGACAAGGGCGGCCGTGGGCTGTAGCTCGAAGTTCTTCCAGATACGCTCGCTGGGCGCCAGGGCGCTGCAGCTCGCCTCTGCCGCTGCTGCAGGTAGAAGTAATTCCTCCTCGTCGCAGTAGATCTACGGCTGCAACGAGTCGTAGTCG | 1349 |
| chr8:128,750,550-128,750,699 | MYC | 12.5 | 19 | CTAGGGACAAGGGCGGCCGTGGGCTGTAGCTCGAAGTTCTTTCAGATACGCTCGCTGGGCGCCAGGGCGCTGCAGCTCGCCTCTGCCGCTGCAGGTAGAAGTAATTCCTCCTGCCGCTAGATCTACGGCTGCAACGAGTCGTTGTCG | 1350 |
| chr8:128,750,550-128,750,699 | MYC | 15 | 23 | CTAGGCGACAAGGGCGGCCGTGGGCTGTAGCTCGAAGTTCTTTCAGATACGCTCGGTGGGCCCCAGGCGCTCGCAGACGCTCGCCGCGTGCTGCAGGTAGAAGTAATTCCTCCTCGTCGCAGTAGATCTACGGGTGCAACGAGTCGCTGTCG | 1351 |
| chr3:187,443,281-187,443,430 | BCL6 | 0 | 0 | TTCTTGGTAATAGTGAGAAACCTATCTGTCAACATCTGTGGGCCCAGTTCAACCGGCCAGCCAACCTGAAAACCCACTCGAATTCACTCTGGAGAGAAGCCCTACAAATGCGAAACCTGCGGAGCCAGATTTGTACAGGTGAGC | 1352 |

TABLE 5-continued

| Reference Coordinates | Nearest Gene | Percent Non-Reference | Total Non-Reference Bases | Plus Strand Oligonucleotide | SEQ ID NOS: |
|---|---|---|---|---|---|
| chr3:187,443,281-187,443,430 | BCL6 | 2.5 | 4 | TTCTTGGTAATAGTGAGAATGTGAGAAACCCTAGCGTTGCAACATCTGTGGGCCCAGTTCAACCGCCCAGCCAACATGCGAAACCTGAAAACCACACTCGAATTCACTCTGGAGGAGCCCTACAAATGCGAAACCTGCGGAGGCAGATTTGTACAGGTGAGC | 1353 |
| chr3:187,443,281-187,443,430 | BCL6 | 5 | 8 | TTCTTGGTAATAGTGAGAATGTGAGAAACCCTAGCGTTGCAACATCCGTGGGGCCCAGTTCAACCGCCCAGCCAACTTGAAAACCTACACTCGAATTCACTCTGGAGAGGAGCCCTACAAAGCGAAACCTGCGGAGGCAGATTTGTACAGGTGAGC | 1354 |
| chr3:187,443,281-187,443,430 | BCL6 | 7.5 | 11 | TTCTTGGAAATAGTGAGAATGTGAGAAACCCTAGCGTTGCAACATCCGTGGGGCCCAGTTCAACCGCCCAGCCAACTTGAAAACCTACACTCGAATTCACTCTGGAGAGGAGCCCTAAAAGGCGAAACCGGCCGGAGGCAGATTTGTACAGGTGAGC | 1355 |
| chr3:187,443,281-187,443,430 | BCL6 | 10 | 15 | TTCTTGGAAATAGTGAGAATCCCTAGCGTTGCAACATCCGTGGAGCCCAGTTCAACCGCCCAGCCAACTTGAAAACCTACACTCGAATTCACTCTGGAGAGGAGCCCTAAAAGGCGTACCGGCCGGAGGCAGAGCTGTACAGGTGAGC | 1356 |
| chr3:187,443,281-187,443,430 | BCL6 | 12.5 | 19 | TTCTTGGAAATAGTGAGAATCCCTAGCGTTGCAACAGCCGTGAGCCCAGTTCAACCGCCCAGCCAACTTGAAAGCTACACTCGAATTCACTCTGGAGAGGAGCCCTAAAAGTGTACCGGCCGGAGGCAGACTTGTCCAGGTGAGC | 1357 |
| chr3:187,443,281-187,443,430 | BCL6 | 15 | 23 | TTCTTGGAAATAGTGAGAATCCCTAGCGTTGCAACAGCCGTGCAGCCCAGTTCAAGCTCCCAGCCAACTTGAAAGCTACACTCGAATTCACTCTGGAGAGGTGCCCTAAAAGTGTACCGGCCGGAGGCAGACTTGTCCAGGTGAGC | 1358 |

TABLE 6

| Name | Sequence | SEQ ID NOs. |
|---|---|---|
| TNFRSF14_chr1:2488006-2488106 | TCTCTTCTGGCCACCACAGCCGCAGCAATGGCGCTGAGTTCCTCTGCTGAGTTCATCCTGCTAGCTGGGTTC CCCAGCTGCCGGTCTGAGCCTGAGGCATG | 1 |
| TNFRSF14_chr1:2488106-2488206 | GAGCCTCCTGGAGACTGGGGGCCTCTCCTGGAGATCCACCCCAAAACGACGTCTTGAGGCTGGTGA GCCCCGAGCCTCCTCTCCGTCTGCTCGCA | 2 |
| TNFRSF14_chr1:2488206-2488306 | GATCCCAGTTCTGACCCCAGGGCCTCCCACAGATCTCTTCCCCATGCCCCTGTCCTGCCGTTGCTGCTC CGGCGTCCAGCCCGTCCCCCTGCTCCTGG | 3 |
| CSMD2_chr1:34404022-34404122 | CCATGTTGCTGCTGGCTTACTTGGCATTTCCCATGATCTGCTGGCTTATTTGGCATTTCCCATGATCCC CTGCTGCTGGTTTACTTGGCATTCCCTA | 4 |
| CSMD2_chr1:34404122-34404222 | TGATCCCATGTTGCTGGTTTACTTAGCATTTCCCATGATCCCATGTTGCTGGCTTACTTGGCATTCCCATG ATACCATGTTGCTGGCTTACTTGGCATT | 5 |
| NEGR1_chr1:72334891-72334991 | ATAGATTAGAGGAAGGAATTCTAGATGAATTAAGTAAATGAGTTATTTAAGTCAACTAATACAAGTCCT CAAAACTTTGATTATATAGAGAGCTAAACT | 6 |
| NEGR1_chr1:72334991-72335091 | GATAAATATAGACAAAATATAGTGAGCCTATAAATTAAAGCTATACTATGATGAAAAATAAATGAATAT TGTGAAATAGCCAAAATACTAAAATACAG | 7 |
| NEGR1_chr1:72335051-72335151 | AATGAATAATTGTGAAATAGCCAAAATACTAAAATACAGCTATAAGTTAAAATAAAATAAATCTGAATAAAA AATGTAGGAGGGAAAAGTGATTACCTTACC | 8 |
| BCL10_chr1:85733207-85733307 | GACATGCATCAAATGTAAACAAAATGATTACAGCCATTTTATAAAAAGTCATATTCTTTAAAACATTTTTG TCATCATTAAAAATTAAAAGGCAATAAAG | 9 |
| BCL10_chr1:85733307-85733407 | TGTCATTGTCGTGAAACAGTACGTGATCTTAAGGAGGAAGAACATCTCACTAGAGTTTGCACAAGTTCCTT CTTCTTCCTAACTGTAGATCTGGTGGCAAAG | 10 |
| BCL10_chr1:85733407-85733507 | GAGGAGCCCCCTGGGTCTCCCAGTTCTGCTGTCTGGAAGTGTAGTTGAAGAGAAGATGGTATTTCAGTTCTGCCTAC TTCTAGAACAGGCAAATTCAGAGAAGATT | 11 |
| BCL10_chr1:85733507-85733607 | AGTAGAAAAAAAGGGCTCGTCGTCGTCTGATTCTCCTTCTGGATGGTACATGACAGTGGATGCCCTCAGTTTT TCAGAGAAATTACTTCTCATCTGAATTTGAT | 12 |
| BCL10_chr1:85733607-85733707 | CTGGAGAGGTGTTCGTGCGCTCCATCTGACAAAAGGTTCACAACTGCTACATTTTAGTCCTACAATAAAATT ATTCAGATGTAAATGAAAAGTAACTAAA | 13 |
| BTG2_chr1:203274697-203274797 | ACCCGAGACCTTCACTGAGCCCGAGCGCGCCGACATGAGCCACCACGGGAAGGGAACCGACATGCTCCC GGAGATCGCCGCCGCCGGTGGGCTTCCTCTCC | 14 |
| BTG2_chr1:203274797-203274897 | AGCCTCCTTGAGGACCCCGGGGCTGCGTGAGCGAGCAGAGGCTTAAGGTCTTCAGCGGGGCGCTTCCAGGAG GCACTCACCAGGTGAGCGCATGCCGAGGGCC | 15 |
| BTG2_chr1:203274897-203274997 | TGGCGCACCGGGGGTCGGCCCCATCCCTGCCAGGGCCGTCTTTCTTCTACTCCTGCGCAGGGTGACCC ACGGGACGCAGCTTTGGGACTCGGTGGCCCT | 16 |

TABLE 6-continued

| Name | Sequence | SEQ ID NOs. |
|---|---|---|
| BTG2_chr1:203274997-203275097 | CCTCCGACCCCCGGGGCGGCCCGCAGTCCCAGTTTCCTGGTCCTCCTCCCCAGCCTGTGCTCGGGTCTCGGCCGTGGCGGTTCTGATGGGGCGCGCC | 17 |
| BTG2_chr1:203275097-203275197 | CCTCTACGCTCTCGGAGGCGCAGACCCTGGTCCAGCCCCAGTCCCCAGCTTATGCCCCTGTCTCATTACGGGCTCGTCTCCTCGCTGGAC | 18 |
| BTG2_chr1:203275197-203275297 | CCTCGAGATCTTAAGACCCTCGATGATGTGTTGTGCGGGCCGCCCGGTCGGGCTCGGAGGGGTCCCGATGAGGGAAGAAGGTGCAGTCGAGCCTTTTCAACAA | 19 |
| BTG2_chr1:203275297-203275397 | TTTTGGAGTCCCAGTGCGGTTCTTCCTGCCGGTCTGCCGGTGCGCTGTGCCTGGGGTAGTCCACTGGTTGCTGACTGGCTTCAAGTTGGAATTTGGGCCCCT | 20 |
| BTG2_chr1:203275397-203275497 | TTGTGTTATCTTTGGTTCCCCTTAGCCATCTGCCACCTATTGTGTAGGGAGGAGAGCCTCGTAGCTCGTGACCCTGCCGTGCGGCCTTCAAGTTGGGA | 21 |
| BTG2_chr1:203275497-203275597 | GGTGAAGAGATAAGCAGCCGCTCGCTGGCTGGGGAGAGAACCTCTCCCAGCTGTTTCTAGCTGGTTACTGTCAGTTTTGGGAAGCGATAGCCATCTCG | 22 |
| BTG2_chr1:203275597-203275697 | GAACGACACCCACAGAACCCTGCCTTTGAGGAAAAACAGATGTTTCATCAAAACAACCCAGTTTTCACTCCCTTAGGCACTGCTAAGGAAGGTTCTGA | 23 |
| BTG2_chr1:203275697-203275797 | CTCTTCTGAAGGAAGCAGAGGAACACAGGGTGGGAGGTCCAGTGACTTGCTGTGTGGACCCAACAATGTTGGCAGCCCTTCCTGGCCCTGAAACTTCAGCTC | 24 |
| BTG2_chr1:203275797-203275897 | ACAGGTCTCCAGAGGCCCTGCCTGGACATGCCAGTCCCAGTCACACCCTTGCTTGGGGTGTGCCAAAAGCAATACACTGGCCACTAGAGAGTA | 25 |
| BTG2_chr1:203275897-203275997 | CCCTAGAGCTCTAGAATCCCCTCCCAACGCACACACACACACACACACTCTCTCTCCACACACACACTCAGTCACACACACACACACAC | 26 |
| ITPKB_chr1:226923691-226923791 | CTTTCAGATCTTTCGCAGCGTCCCAACAGGGCAAAGGCTCCAGCATTCTGCCAGAAGGAATTCCCGCTCCACATTCCCGGTCCCCGGCTGTGCTGAGGG | 27 |
| ITPKB_chr1:226923791-226923891 | GCTGCCCCCAAGCAAGCCAGCGTTGGGAGACCCTCCCCTCCACTCTGTCGGAGAGCTGCCAACGCCCCCGCCCACGGGGCCCCACTTCGGGCCTCTCA | 28 |
| ITPKB_chr1:226923891-226923991 | GGGCCTACGGAGGCCAGGCCCTGGGCAGCCTCGGACCAGCTCAGGGAATCAGAGGACTCTGCGCTTTGCACGCTCACAGTCGTCTCTCCTGGCCTTTTGC | 29 |
| ITPKB_chr1:226923991-226924091 | CCACTTCAGGCTGTCTCACTGCCCAGAACTGCCCCTGCCTCTCCACCAGGCCTCTGGGGCTGAGGTCCTCAACCATGCCAGGCAGATATCCTTTCCCCATCTTCCCAGGGGTTCTCCATCGCGGGCCCGCCCTTTCTGGGC | 30 |
| ITPKB_chr1:226924091-226924191 | TGGGCTTGTCTCACTGCCCAGAAACTGCTGCCCCTGCCTCTTCCACCAGGGCCTCTGGGGCTGAGGTCCTCAAGCTCACGGGCTCTCCAGACGGCTCAGTG | 31 |
| ITPKB_chr1:226924191-226924291 | AGGGCAAGATCCTGTGGACGGTGTGGCCCAGTGATGTAACTCTCGCTGCCACTTCCGTGGCCATCGTAAGCTAGCTCCGAACAGCCCAATGAGGGAG | 32 |
| ITPKB_chr1:226924291-226924391 | CTAGGCAGCTCCCAGTTCCCGGGTAGGAGAGAGCCCTTTGTCAATTTCCATAGCTGGGTGAGCCACAGCGGGACTGGCAGGGATACCCTTCTCCAT | 33 |

TABLE 6-continued

| Name | Sequence | SEQ ID NOs. |
|---|---|---|
| ITPKB_chr1:226924391-226924491 | CCTTACAAAGCGGATGACCCTGAGCCTCTGATCCTGTAGGGCAGCCCGGCCGGAAGAGTGGCATT CCTTTCTTCACCTGCGAGGAGCATAGGCTG | 34 |
| ITPKB_chr1:226924491-226924591 | GGCCCTCCTTTCCTCCCGGAGTCGGTTCCTGAAGTCTCTGGACATTGCTCCCCCAGACTTTGTCCTCCG TTCCTGCTCCGGGCGCCCTGAACCAGGA | 35 |
| ITPKB_chr1:226924591-226924691 | CCCTTCCAGGGGCTGACTGCTGCTGCGAAGGGCACGGGAGGGCGAGCGAGCCCTGCCCAAACGCG GGCTGCCGGGGCGCTTGAATGGCCGGAGCTCTG | 36 |
| ITPKB_chr1:226924691-226924791 | TGCCTGGATGCGCGCCTCAAACATGCCACCTTTCTGGTTCACCTGCACTTCTGCAACTCGCGCTGCAAGA TCCGCAGCTTCCTCTTGGCCTCCTCCGGC | 37 |
| ITPKB_chr1:226924791-226924891 | CCTGGCGGGGAGAGGGTACCGCTGCCACCACCTGCTGCCGGTCCCCTGCGGGCGACCAGCCCAACTTG GGCTGCTCACGCTACTGCCGCTGCTGCCGC | 38 |
| ITPKB_chr1:226924891-226924991 | TGCCACTGCCGCTGCTACTATTCAGCCTGCGCCGGACCTCCCCAGCCCTCCGGGGCTCCGGGGCTCCTCG GGGGACAGCGACTCGGCTGGGGGAAGAG | 39 |
| ITPKB_chr1:226924991-226925091 | GAAAGAGGCGCCTCTCCCGGGCTGAAAACGTGCCGGGCTTCAGCACTGCCCTCCTCGGGGGCGGGGG CGTCCGCTGCCACTGGGCCCTGGGGCCCGG | 40 |
| ITPKB_chr1:226925091-226925191 | CCGCTCCTTCATCTCGTTGGCGTTATTCATGATCAGGCCTATTGAGCGCATAGCAGTACACAGCCATAGT ACTGGGTCCCGCTGCCCGCCGCGCCGCGG | 41 |
| ITPKB_chr1:226925191-226925291 | CTCCCGCTTCCTGCTCCCGCCGCCGCCGGCTCCCTCCCGGCTCAGCCCCGGAGGCCCGGCAG CCGCGGCTTCCGCGCGATGGGGCGGCA | 42 |
| SLC1A4_chr2:65258145-65258245 | AAGTGCGAAGGAAGTGTCAGGCTGGATGTCAAAATGAACACCTTGGAGAACTGGATGATGAACAGACG GTAAAAATCAGCTAAACATCAGAGAAAATGG | 43 |
| SLC1A4_chr2:65258245-65258345 | AGGAAGAGGTCAAAACTGTGAACAGGAACTAGAAGAAGTGTAGCAGAAAAGACTTGTCACAAACTTC GAGAGATTTGGAGAAATGATGTCAAAACAC | 44 |
| SLC1A4_chr2:65258345-65258445 | ATCTTCCTCAAGCCATGCTGAGTATCTCTGATTTGGTTAATTTCTTGGTAAGTGTTCCAAGTACAGACAA CAAAGCAGAAAAGCACTGATTACAGGGAA | 45 |
| SPRED2_chr2:65593035-65593135 | TATGCAGAATGATCCTTCAGATCATGTGAACGCTATAATTAAATGTTGCTACCAAATCCCACTACCCTTT CTCCACCTAGAAAAGTTAATGCATGAA | 46 |
| SPRED2_chr2:65593135-65593235 | TTCAGTATGAGCAACATTGTGATTTATAAAACAAACAAACAAACAAAACCACCCTATTCAC TCCGTAGGGAATAAAGCTTTCTTGCATTA | 47 |
| SPRED2_chr2:65593180-65593280 | AACAAACAAAACCCCACCCTATTCACTCCGTAGGGGAATAAAGCTTTCTTGCATTAAGTCACGCATCATGG GGGTAGGAAAAGCACAGTACTGAAAGAA | 48 |
| EIF2AK3_chr2:88906681-88906781 | GTGAAGTGATCCAAATGTAGCCAGAGATCCTAAAGAAAAAACGATGCTCATGTGTTACAAAACAAATT TTAAGGCAATCAGTGAGGAATCACAGACAA | 49 |

TABLE 6-continued

| Name | Sequence | SEQ ID NOs. |
|---|---|---|
| EIF2AK3_chr2:88906781-88906881 | ATTTCCTTAGTGCTTTATCAAGGTTGAATCTGAATATAAATTACTAGAGGAAAGCAAATCAGATTTCACATCTGAAAATTAAAACAAAATTCTTAGCT | 50 |
| IGKC_chr2:89127261-89127361 | AGGCAACAAAATGAGATCCTGTCCCTAGAAAACATTTCAAAAAATTAACAGCATGGTTGACGCACACTTGTAGCCCTAGCTACTTGGGAGGCTGAGTGGGA | 51 |
| IGKC_chr2:89127461-89127561 | AAGAACTTAAGCAGACTAGGATATAAAGTATAGGAGCGTATTGTGTACAGGAACGGGAAATACTGTTTCCTGGATCTTTTGTTTCACTTACGCACACACC | 52 |
| IGKC_chr2:89127561-89127661 | CACACCCCCAGTAGTGTACCAGGTTGCGATGGAAATCTCTCTTTCTGTGATGAGTTTGTGAAGCCCTTGCTCCAGCATGCCTCCTTCCTGCCCA | 53 |
| IGKC_chr2:89127661-89127761 | CCCCTGACCATTCCTTCCCTTCACAGACTGTCCCCATGGGTAGGCCACAGCCCAGCACAGGCCCCAGCCTGGCGGCTGCAGCAGGAGCCCCATCCCAGG | 54 |
| IGKC_chr2:89127761-89127861 | GCCTGAGGGGCCATGCGGGGGTCTGGGTGGGAGTGGGAACCGCTGGGAAGGTGAAGGGAAATATGGTGAGATGACAGGCCCGTGTCAGGGAGAGTGGG | 55 |
| IGKC_chr2:89127861-89127961 | AGGAGCCCTGGAGTGCCTACCTCTGTGTGGGCTGGAACTTCTCGGGACACTCCCTGTATCCGAGCTAGGTCTTCCACACGCATGCTACTACCCCAAGTGCCACAGCTGGAG | 56 |
| IGKC_chr2:89128431-89128531 | TCATCTCCCACTGGATAACAGTGTTGTCGGAGCACTGGGCAGTGCAGCCCTCCCGGGATGGGTCCAGACTCCTGACTGAAGTCATTTAAGGGGG | 57 |
| IGKC_chr2:89128531-89128631 | TCCTTGGCACTCATAAGCACTCACAGAATGGGCTGGCAGTGCGTATCACAGTTAATGCTCTATAAAACCATCATGGCTTTTCCATGGTAAGGCCAGTGCCAATCCGTCAAGCAAG | 58 |
| IGKC_chr2:89131726-89131826 | ACTGCTTAGAGCTCTCAGCCTACGATGGCGTATCACAGTTAATGCTCTACCACCCCAAAGCCACTACTGACTCTGGGAGACCAGCTAGTAAGCCTCAAATCGCTGCAAGCAAG | 59 |
| IGKC_chr2:89131826-89131926 | GCTTCATTATATGAGAGTTTCTGCTGTCTCCTGAGCCCATCTCACCCAAAGCCACTACTGACTCTGTATCGTGAACGTTCCCAGGCCACAAACCAGCAAAGCACCAGT | 60 |
| IGKC_chr2:89131926-89132026 | TATAGTTAGAGCTGCATTATAAAGTGCCAGAGGACATTTCTTTGCAGTGAGATGTGTATCGTGAACGTTTGGGGCCTGTGCTCGCCTAGTCCTCATCTT | 61 |
| IGKC_chr2:89132026-89132126 | TGCTTTTCTAGGTACACAAAGCCATCCATGGCTGCAAATGTTAGCTGGGCTGGCTCCCTACTTGCCTCAAGCCCCTTCATAGACCCTTCAGGACATG | 62 |
| IGKC_chr2:89132126-89132226 | CTTTTCTCTGGACGTTACAGACAGGTCCTCAGAGGTCAGAGACGAGTTGTCCTAGGGAGCAGGAGGCTTCCTAGGGAGGTCAGACTCCAAATAGTGAAT | 63 |
| IGKC_chr2:89132226-89132326 | ATGCAAAAATGCAGCTGCAGATCATGAGGAGTCGCCCTGGCTGCCACTAGGGCTCCCACAGTGCGCTGCCAACCTGCTGCCCGTGCCAGAAACTCT | 64 |
| IGKC_chr2:89140556-89140656 | CAACTGTGCCCTGCACTGTTAGGGCCCTTGTCAAAACAACACATTTCTCAGTGATTCTGAGACTCTTTCTCTTATCTATAGAAGTCATAACTCAAGAGTA | 65 |

TABLE 6-continued

| Name | Sequence | SEQ ID NOs. |
|---|---|---|
| IGKC_chr2:89140656-89140756 | AAATCATACCAATATTTTACATAAACCCTAGAATTTTATAGATCTATTATTTCTTTTAGAGTACATATTG GAAGTAACTTCACAAGGAACATTTCTT | 66 |
| IGKC_chr2:89140886-89140986 | TCTGGTCAAACCACTCCACAAATAAAGTGGACTGATCCTCTTGACTGTGTAAGTGCCATTGTGT GCACAGAGCTGGTGAGAACGGCCATGGTG | 67 |
| IGKC_chr2:89140986-89141086 | CTAGGTGGGGTGGTGTTGGTGGAGTTGGACTAGATTATCTGGGATCATGCGAAATGAAATTCATTTCT AGCTGGCTGGCTTCAGAAGGTGCCATCTCC | 68 |
| IGKC_chr2:89141086-89141186 | TATTTTTATATGAAGCGTGCTTTTGGAACTCAGGGCAACGAAGGGTGGTGCTGCACAAGGACAGCAGA AGAGTGAGCTGACTGGTCCCTGAAATCGCA | 69 |
| IGKC_chr2:89141186-89141286 | GTTGGAAAGTGGATTACCAGTGCAGTAGAACTCTTCACGGAGGCCTGACCATCAGGTCTAATGGTGTTG TTCCAGGTGGGTGGTCATGTGAGCAAAAA | 70 |
| IGKC_chr2:89141286-89141386 | TATTTGAAATCAGCGAGCACGTACCTGAGAGATGACTTTTCCACTTGGGCTAGTCTTCTTGATATTTCTGGT CCTGTTTCTTCATCTGTAAACTGGGTTAG | 71 |
| IGKC_chr2:89157326-89157426 | AAGGAGACCAAGAGCGTATTAAAATCTTGATGTTTTGAGTTTTCTTCCTAGTCTTCCCCCTATTCCTTAAT AAAGTTCTAAATTGTTTTGTTGGAGCTCT | 72 |
| IGKC_chr2:89157426-89157526 | TTGCAGCCATTCTGAGGGCTTGCATGCTTTTCTGACCTTGCAGTAAACTCAATGCTTTAGGCAAAGAATG GCCACGTCATCCGACCCCCTCAGAGTTTA | 73 |
| IGKC_chr2:89157526-89157626 | GAATTCAGAACAGGTCTGAAGAGACCAGGCAGCGGCTGAGTCAAGGAAAGCCTCCGTCCGTTTATTT CCCCTGTGCCTCTTCCAGGACTGTGCTGG | 74 |
| IGKC_chr2:89157626-89157726 | ATAACAGGCTCCCGGGGTTACTTGGCTGGGCTAAAACCTCCCTGAGAGCAGGCCCTGAGCCC TGCCTCTGCGCCTGGGTGGTGTCAGCCCCT | 75 |
| IGKC_chr2:89157726-89157826 | CCACCCTTCTGACTGTTCCAGCAACTCTCTAAGCCCTCCCAAAGGCCTGTAACCATATGCAGCA ATTTCAGCCATACCAGGAGAGTCAACT | 76 |
| IGKC_chr2:89157826-89157926 | GTAATCTTGGCCACCTGCCTAAGAGGAAGTGCTAGTTCACTTCTGACCCTCAGCAACTGCCAGGTGGC CTCTTGGAAATCCCCCTCTGGGGGATTCCA | 77 |
| IGKC_chr2:89157926-89158026 | CCCGTTGGGTGGGAGAGCAGTAGTTAAAATGTAAAATAAGAATCTTTTGCTGGGAGAGTCAACAGATAG GGAGAAGTCAGCTGATAACAGAAATAGTTT | 78 |
| IGKC_chr2:89158036-89158136 | TAAAACTAACTTCACTGTTAACCAAGCAGTTCAACATGAAAGACTGAATCTCTTATGTTTAATATTTTCTT CTCTTTTAATCTTCATAACTAATTTTTT | 79 |
| IGKC_chr2:89158136-89158236 | CAGATAATTGTATAAAATAACCATGGTAGCAAAATAATGTGATCACTGGAAAATAAGCAGGGAAAACA TGCTATGAAGATACTCCTATCTGGGTGAATT | 80 |
| IGKC_chr2:89158236-89158336 | CTTTGATAGCTTTACATTTTTCATCTGCATTTAAACATTAAACAGTTAAATGTATTTGACATGAAATTATT TCAAGTTATCTTATTAGTTTTAATGAGAGT | 81 |

TABLE 6-continued

| Name | Sequence | SEQ ID NOs. |
|---|---|---|
| IGKC_chr2:89158336-89158436 | TTAAAAAGTGTTTAAAAGAGTTTTCAAAAGGCTCTAAAAATCATTTTGAAATAGTTTAAAACAGTTTGAAT CGTTGTAAGTTAGTTTTAATAGAGCTTTA | 82 |
| IGKC_chr2:89158436-89158536 | AAAAGGCCCTAAAATAGTCCTATCAAGTTGTTGCAGACCAAAATAATCTCCTTAAATATCACTTTTGAGAT CAGCTGGGTAAACAGCAGCAACACAATG | 83 |
| IGKC_chr2:89158536-89158636 | ACAAATCATTAAACTATTTTAGAGATTAATGAAATAAAATACTCAGATTAAAATTTCCTATCACAGAATT AAGGTACTGGAAAATATGTTTAAGTTTTT | 84 |
| IGKC_chr2:89158636-89158736 | ATTAATCACATTGCTATAGGTTTTAGATATTTTGTACAACTGAAATAAAATCACACACTGGCAGCTACATTT TTGAAAGTTAAAACATGTCACGAATAT | 85 |
| IGKJ5_chr2:89158736-89158836 | ATCTTATTTTAAAATCAGTTAATATACCTTAATGGTATTTAATGCCAAATTCAAAGTGAATTGATCAAGCC CTCAGTGCCAGGTCATGGGTGTGATTTT | 86 |
| IGKJ5_chr2:89158836-89158936 | TACTCTGAAAGAATTACATATTTCTTTCTTTTTGGTTGAGCTTTTGTTATTTAAATACATTTGATGAGAGG ATATTGAAATAATTAAATAGCACTGAAAA | 87 |
| IGKJ5_chr2:89158936-89159036 | AAAAAAGCTTTAAATTATTTACAATCCCCTAATGGAAATTTTCACTAATGAGAATATCATAATGAATGTGA ATTTTATTTCTGAAATCTCTAATAAATCA | 88 |
| IGKJ5_chr2:89159036-89159141 | AAGCTTTAAATTATTATTACAATCCCCTAATGGAAATTTTCACTAATGAGAATATCATAATGAATGTGAATTTT ATTTCTGAAATCTCTAATAAATCAGTCTT | 89 |
| IGKJ5_chr2:89159041-89159141 | CTCCCTGGTTTTCCCAGCTCAGCGCCCATTACGTTCTGTCTCTCTTTCCCTTAGTGGCATTATTGTATCAC TGTGCATCAGGAAAGCTGGCTCACGGCAG | 90 |
| IGKJ5_chr2:89159141-89159241 | CATCAATGGGCAGACACAGGGTGGCCACGGCCACTAGCGCGGCAAGGCCGGCTGCCCCAAGAGCGCGGTGG CATGGCCACCAAAGCCACTCAATCGAGAAAG | 91 |
| IGKJ5_chr2:89159241-89159341 | ACCGCGGCTCTGTCTACAGCTCCGGTGCCACGCCTTCTTGGCAGAGAATAAAAATGTAGACAAGTAATAA CAGAGGATAAATGAAAGACATACTCTTTAA | 92 |
| IGKJ5_chr2:89159341-89159441 | AATATTCCTATTTTTTTCCACAGACCCACGGTCATTAAAAAATGCAATTATTACTTTTTTCATTTAAACA CATTTCTTTTGAGATTGAGCTTTTGGGAA | 93 |
| IGKJ5_chr2:89159441-89159541 | TAACCACCTTTCCACCATTACAATAAGAGATAAATTTCACGTTTAGTCTAATGTACAAATTGGATTTTTAAA AAATGAGCTCTATCTGTGAAGCCCTTATT | 94 |
| IGKJ5_chr2:89159511-89159611 | AAAATGAGCTCTATCTGTGAAGCCCTTATTCCTATAGAATGTGTCTTTTTGAGTTTATTACTTATTACAGA CTCTAAAAACAACATTGCTCTGATTTTC | 95 |
| IGKJ5_chr2:89159611-89159711 | AAGTAAGCTGCCTCTTCACATAGCAAATAGGTACACTTCACTTTTCACTTTTCTCCTGATTTTTCTTAGGGCGTGCTA TTGATTTTTATTGTCTGACAAATAA | 96 |
| IGKJ5_chr2:89159711-89159811 | TTTTATCAAACAAAAGGGAGAAAGACTAAAAATGTATTTTCCACTTTTCTGTATCATGCATAATCAGCAA CAACCAATTACAATATTGGCAAGAGTGAA | 97 |

TABLE 6-continued

| Name | Sequence | SEQ ID NOs. |
|---|---|---|
| IGKJ5_chr2:89159811-89159911 | CAAAATAAATTACTTTGCTCCTTAGAAATACAAGGGTTCCTTTTAGTACACTTTTTTTTTACTTTGTGTCATTCAGTTTAGAGCAATTAATC | 98 |
| IGKJ5_chr2:89159911-89160011 | TTTTTTCTCCAAATCCATTTTTGAAGCTGAGTTTAACTTTTGCAACCCATGCAAATCTTAAATGCCCTCATTTACCAATCTTTACCAAACTCCTATTT | 99 |
| IGKJ5_chr2:89160011-89160111 | AAGCCTCTAAAAGTCAATACTGGCCATCAGACCCAAATTCAGAAGACAATAGTGAAAAATTACTTACGTTTAATCTCCAGTCGTGTCCCTTGGCGAAG | 100 |
| IGKJ5_chr2:89160111-89160211 | GTGATCCACAGTGTTAACTTAATTACTTTCCCCTTAACAAAAATCTCTTTTGCTGTTAATATCACTAACCTGACCGATGCAGAGAAAATCTTGCAATTG | 101 |
| IGKJ4_chr2:89160211-89160311 | AGATGCCTCACTTAACTGGCTAGCGCTTGGCTGTTCCTTAAGATGAACTAATTTTCTATCCCTTACTCATCTGACTTTTTGAAAGAATCTGGTACTCTTT | 102 |
| IGKJ4_chr2:89160311-89160411 | GGAATTGACCTGAGCTAATATCTCAAACACAAAAACGCTCCAAATTTAAAACCTTATAAGAAAAAGCATTAGGAAAGTGCACTTACGTTTGATCTCCACC | 103 |
| IGKJ4_chr2:89160411-89160511 | TTGGTCCCTCCGCCGAAAGTGAGCCACAGTGAGGGATCTCACCCTTTCCCCTCAACAAAAACCTCTCTTGAAGCCAATCATATGAGATAGGCTGCTTGTT | 104 |
| IGKJ4_chr2:89160511-89160611 | CAGAGAAAAATTAGCTATTTCTTCCCCATGAATCCTATTCTCTCTCAAACCCAATGATTCGTCTATTTGCTCAGCTTTTTAAGTTCATT | 105 |
| IGKJ3_chr2:89160611-89160711 | TTCTGGTGTCCTGCTATTTACTTCTGGGTCACCAGTTTATTCAACCAAAATATCACAAAACTTGCAAATGATACAATGGCACTAAAATCTCACGAAT | 106 |
| IGKJ3_chr2:89160711-89160811 | AATTGAGACAGATGTACTTACGTTTGATATCCACTTTGGTCCCAGGGCCGAAAGTGAATCACAGTGATTCGTCTTAACTTTTCCCTTTACAAAAACCTCC | 107 |
| IGKJ3_chr2:89160811-89160911 | CTGAAAGCTCAGCTACCTGGGAATGAAGTTTGTTAGATCCCTGGCATCCGACTTGATTTGATTTAGAAAATCTTAAAAATTAGCCACAAGCTAGCCTGTGTGAACAATTTCCCCTC | 108 |
| IGKJ2_chr2:89160911-89161011 | CTCTGTACCTACCTGGGAATGAAGTTTGTTAGATCCCTGGCATCCGACTAATGAAAATCCACACAAGGAACAAAGTAAACTAATTAGCAACAGTGA | 109 |
| IGKJ2_chr2:89161011-89161111 | AGAATCAGTGGAAAAAGTACTTACGTTTGATCTCCAGCTTGGTCCCCTGGCCAAAAGTGTACACACAATGGTTCCTCTTAACTTCCCTCCTATACAAAA | 110 |
| IGKJ2_chr2:89161111-89161211 | ACTCCCTTTCTGACAATGACCAAGGCTCTGTCCAGAGACATGTTATGTTCCCAGGACATTTCTGAAGCTATTACTTAGACAACAAGTTATTCTCACCCAATG | 111 |
| IGKJ1_chr2:89161211-89161311 | ACTGAATCTTGCTTGCTCTTCAAAGAAAAATGTGCAATCAATTCTCGAGTTTGACTACAGACTTATCTTTATCTTTTCCCTGAAGGATATCAGAGGCTGAT | 112 |
| IGKJ1_chr2:89161311-89161411 | TGCAGAGTCACCTTATAGATCACTTCATAGACACAGGGAACAGAAGACACAGACAACTGAGGAAGCAAAGTTTAAATTCTACTCACGTTTGATTTCCACC | 113 |

TABLE 6-continued

| Name | Sequence | SEQ ID NOs. |
|---|---|---|
| IGKI1_chr2:89161411-89161511 | TTGGTCCCTTGGCCGAACGTCCACCACAGTGAGAGCTCTCCATTGTCTTGCTGAACAAAACCCTTCTCAC CAAAGGGAACACAGAGTCCTGGGTCAGCTG | 114 |
| IGKI1_chr2:89161926-89162026 | ATCAACTTAAGGCTCATAACTTTGAAATGCATTTTGAAATGTAGCTCCAGATGGTATACGAAACCAAAGT GAAGACTAATAGAAGTAGAAAAGTAGACTTT | 115 |
| IGKI1_chr2:89162026-89162126 | ACTTGGTTGGTTTGTCTGTTTTCACAGACACAGAAGAGCTCAGCTCTTTACTGAGCTGACCAGGCGCATG CCATCTTTGGAGCTGCCATGGAGTGCCCAGT | 116 |
| IGKI1_chr2:89162126-89162226 | GTTCCATAGTGTTTCCATAGTAATCTCATCAACAACTGAAGACCTTTTCAGTATTTTCTTTTGAGTCCA GCTCCATTTTTGCAGCCTTGTATCTCTCT | 117 |
| IGKI1_chr2:89162776-89162876 | CCGCGCCCAGCCAGTGCCTGTTTATTTTACCTGCTTTCAGATTCTCTTCTACCCTTCTAAATTATAAGCT GTTTGATGTTTTATTTGCCCTGTATTG | 118 |
| IGKI1_chr2:89162876-89162976 | GGAGGCTCCGTCCAGTATCTTTACTTAGCAAATGCTTAACAAACATTTTCAGAATAAACATATAACTACA CCTAATTGAAAGTCAATAATAGATCAGAGA | 119 |
| IGKI1_chr2:89162976-89163076 | TGCTATCATAGACCAAAGACTAATACTGACTGCCACACAGTAACTTTTACAACAGAAATCATAACTACA ATTCTAAAGATTAGGGGTAGGTTTATTTGA | 120 |
| IGKI1_chr2:89163076-89163176 | TTCTGTCACTGGCAGCTTTGCTAGTTGCCTTGAATAGCAGAATTAGACATTGTCTCACCAGAAGATGAGG AAGGAGAGGGATCAAGTTAGAGTGGAGA | 121 |
| IGKI1_chr2:89163176-89163276 | GTTAACATTGGCAAGTGAAATTTAATGCAAAATAGCTGACCAAGGCATAGTCCTTTTTAAAGGGGA CACAAAGTGATTTTCTGCAGACATAAC | 122 |
| IGKI1_chr2:89163276-89163376 | GCAATACCAATCATAAAGGGTGACATTTATTGAGCACTTACTAAGTGCCAGACATTGTACATGGATCATC ACATTTAATTATTCCCAAGACTCTATGAAC | 123 |
| IGKI1_chr2:89163306-89163406 | TGAGCACTTACTAAGTGCCAGACATTGTACATGGATCATCATCATTTAATTATTCCCAAGACTCTATGAACT AGGAACTAATATATCCCCTACTTTGTAG | 124 |
| IGKI1_chr2:89163406-89163506 | GTGCAAAAACTTGAGGGCAGAGAGGTCAAGGAACTGGCTTATGGCAGTAAGTGGCAGAGCTGTGACCTA AACTCAGATCCCATGTTTTTAACTGAACTAT | 125 |
| IGKI1_chr2:89163506-89163606 | ATGCAGATTATACTCCAGGAGTAAAGTCACTCAACGGAAGCAACAAGCTGACAGGGAATGCTGGGATG GGGGAAGGTAAAAGGAACTCCTTAGACTGGG | 126 |
| IGKI1_chr2:89163606-89163706 | ATAAGTGTGTACAGACGTATGTATAAGACTACACACATGGAAAATATTGTTTAAAGAGTGAAAATAACTAAA ATCCTCATTAATAGGAGTTTGGTTAAACTG | 127 |
| IGKI1_chr2:89163706-89163806 | TGCTAGAGCTTTACAATGTAGCACAAAGCAGACATTAAGGGGAAGACGTAGACTTCTATATAGTTACGTG GAAGGTGTTTGTGAAAATGCAGGTCACTGA | 128 |
| IGKI1_chr2:89163806-89163906 | AGAGTATGTGTGTGAGATATCATGATCCCATCTACATTGAATATATATGTATATAAATACGGGCTGAAT TTTAAAGACATAAATTGCTTGGTAGTT | 129 |

TABLE 6-continued

| Name | Sequence | SEQ ID NOs. |
|---|---|---|
| IGKJ1_chr2:89163861-89163961 | AAATACGGGCTGAATTTAAAAGACATAAATTGTGCTTGGTAGTTATCTCCTGGGATTGCAGAGGAGGAACAATGACACTTTATGCCATTCCTCCTACT | 130 |
| IGKJ1_chr2:89163961-89164061 | CTTCTGTATGGTGATGTGAATATATTCATTTATAGTTTTTAGAAATAATAAAACTGTACTAATTTTGAAAAACAGTAAACTCTGACATTGCCTATTAGC | 131 |
| IGKJ1_chr2:89164061-89164161 | ATTCTCGATATTCCTGTGCAATGCATAAACATAACTTTTAAAAGATATGTACACACATGTGTGAGTTTTCTTTGTCAAATACTTTTCTATAATCTTTAA | 132 |
| IGKJ1_chr2:89164161-89164261 | ATCAAGCATGCCAAAAAGTAAAAGTTTCCTGTTTCAGTGTAGGAGATAGTCGTCTGCAAAGGAAAGAGATGTAGGGGATAGAACAGGAATGAAAAAG | 133 |
| IGKJ1_chr2:89164261-89164361 | ATGACTGAGCTGTTCGAGGGACTTATGTTCCTAAGTGAGCTAATTGGAAATCTAATATGAACAGTGCAACCGAATAACTATTGTAAAGCAGTATTTGTAA | 134 |
| IGKJ1_chr2:89164361-89164461 | ACAATAAAAGATGATTATCATAAGTACCATTGTTGCAAAAACTATTTTTATTGATCACATGCAGTGGTGATCTGTAGGAATGATTGTGTGATGTTTGCTG | 135 |
| IGKJ1_chr2:89164461-89164561 | TAACATAAATGAAACATGGGAAGTGGCTGAGATCTTTAGGATGTGTGGTTCATTTTTTGAAAGCAAATGTTGTCTCAGAAGCATCTGTGAGACTCTG | 136 |
| IGKJ1_chr2:89164561-89164661 | CCAGGATCCACCGTTCTACAAAATATCTGTGATGGACATTGATAAGATTGATCTGTTGAGGAAAGGCAAGGTGTCAGTAAGATAGTCTGAGAGCTTCTG | 137 |
| IGKJ1_chr2:89164661-89164761 | GATTTCATGTAAAAGATGCTGAAATAGAATTTCTTGGGGACATTCCAACTAACTCATCACTGAAGGTGCTTACATTGACCCTCAGCAAAGTTAGA | 138 |
| IGKJ1_chr2:89164761-89164861 | TTATCAGAAAAAAAATAAACTGCTGTGAGGGGACAGGAAGGAAAGTCAGGGAGGGAGGGGGCAAGGAGAGAAAGAGCGAGAGAGGAGAGAAAGA | 139 |
| IGKJ1_chr2:89164866-89164966 | AGAGAGGAGAGAGAGCAAGTACACACTTCAATGCACATCTATAAATCATCCTGAAAACTACTGATAAATTATTTTAGCAATGTTCCTCAGATGTAA | 140 |
| IGKJ1_chr2:89164966-89165066 | CATTTGAAGAAATATCATTTTGCTTTTTATTTGGCATAATTTACTAGCCAATTTAGGAAGTTCCCCTCACATCAGTAACATACAGTACATCACCCAGTA | 141 |
| IGKJ1_chr2:89165066-89165166 | TGTCAGAGGACACAAATGGCATAAGTTTGCCTTTTGCAAGGTTTGAGGGATGGCCATTTCCCTACCTGACTCAGGAAAGTCTGTAGCTGATATCCATCTTC | 142 |
| IGKJ1_chr2:89165166-89165266 | AAGTTTGTGGTTCTTCTCTATATATATATTTGAGCTCAGCAGTCATGCTGGAGTCCAGAGTAGGTGATTCTTTCTGCTTTGCTTTAGCTTGACTCCTC | 143 |
| IGKJ1_chr2:89165191-89165291 | TATATAATTTGAGCTCAGCAGTCATGCTGGAGTCCAGAGTAGGTGATTCTTTCTGCTTTAGCTTGACTCCTCCTTAAGATTGTAACTCTCAGTTTACA | 144 |
| IGKJ1_chr2:89165291-89165391 | TTTTTTGTCAGACGTAAGCTGACATTCCACAAGGAGGAGGAAATTCTGTGTTCACATCCAGTGTGCTTGGAACCTGATTGGTTGTCATTCTTCCAG | 145 |

TABLE 6-continued

| Name | Sequence | SEQ ID NOs. |
|---|---|---|
| IGKJ1_chr2:89165391-89165491 | CTAGTTTGTCACGAGTGGATATCTGTCCTGGATTCCCAAGGATCAAGGCTGCCCCATTAGCCAGGAAGTAGGGAGATAGAGGAGGTCACTTGAGAAAGAG | 146 |
| IGKl_chr2:89165491-89165591 | CTGCTTCTTTGCCGCCTCCAGGTTGTGTCTGTTTCCTCTCATATCTGAAGACAGATGCTGGCAGAAGCAAAGTCCTTTGTCCGGCCACGTGCAAATGC | 147 |
| IGKl_chr2:89165591-89165691 | ATGGAACATAAATATGAACAGAGATTCTGTCCCACTCTAGAAAATGTAGATGTTCATCTTGTTTCAAGGGGACAGTGAAGGCTGCAGGTGTTTTTGAC | 148 |
| IGKV4-1_chr2:89184966-89185066 | CTTTTGTACTCACTGGTTGTTTTTGCATAGGCCCCTCCAGGCCACGACCAGCTGTTTGGATTTTATAAACGGGCCGTTTGCATTGTGAACTGAGCTACAA | 149 |
| IGKV4-1_chr2:89185066-89185166 | CAGGCAGGCAGGGCAGCAAGATGGTGTTGCAGACCCAGGTCTTCATTTCTCTGTTGCTCTCTGGATCTCTGGTGAGGAATTAAAAAGTGCCACAGTCTTTT | 150 |
| IGKV4-1_chr2:89185166-89185266 | CAGAGTAATATCTGTAGAAATAAAAAAATTAAGATATAGTTGGAAATAATGACTATTTCCAATATGGATCCAATTATCTGCTGACTTATAATACTAC | 151 |
| IGKV4-1_chr2:89185266-89185296 | ATTAAGATATAGTTGGAAATAATGACTATTTCCAATATGGATCCAATTATCTGCTGACTTATAATACTACTAGAAAGCAAATTTAAATGACATATTTCAA | 152 |
| IGKV4-1_chr2:89185296-89185396 | TTATATTTGAGACAGCGTGTATAAGTTTATGTATAATCATTGTCCATTACTGACTACAGGTGCCTACGGGGACATCGTGATGACCCAGTCTCCAGACTCC | 153 |
| IGKV4-1_chr2:89185396-89185496 | CTGGCTGTCTTCTGGGCGAGAGGGCCACCATCAACTGCAAGTCCAGCCAGTGTTTTATACAGCTCCAACAATAAGAACTACTTAGCTTGGTACCAGC | 154 |
| IGKV4-1_chr2:89185496-89185596 | AGAAACCAGGACAGCCTCCTAAGCTGCTCATTTACTGGGCATCTACCCGGGAATCCGGGGTCCCTGACCGATTCAGTGCAGCGGGTCTGGGACAGATTT | 155 |
| IGKV4-1_chr2:89185596-89185696 | CACTCTCACCATCAGCAGCCTGCAGGCTGAAGATGTGGCAGTTTATTACTGTCAGCAATATTATAGTACTCCTCCACAGTGCTTCAGCCTGGAACACAA | 156 |
| IGKV4-1_chr2:89185696-89185796 | ACCTCCTCCCCATACGTGGGCCAGTAGGTCTTTGCTGCAGCAGCTGCTTCCTCCTGCACAGCCCCAACATGCATGCTTCCTCTGTGTGTTGGGGAGG | 157 |
| IGKV4-1_chr2:89196226-89196326 | AATACATGAAAACAACTACCGAAATGTTATGAAATTATAGTTTAGTAGAACTAACAAGTGCATTAATGCAAAGAAAAGTAGGGCTCCAGTAATCAGGGAA | 158 |
| IGKV5-2_chr2:89196326-89196426 | CCAAGTGTGCATTGTAAAAGTGCAGCCTCTAACACTGGGTTTCATCACAAGTAACGAACAGGATGCCTGATGCAGGGAAAAAAGAAAGGCAATTGTT | 159 |
| IGKV5-2_chr2:89196426-89196951 | GATCTCTGGTAAGAGAAAACACTTCCTCTCTCGTGCACCAAGTCCCCTGCATATCCACAAAAATAATATATTTTCATAAGGAATTGATTTTCCTCATT | 160 |
| IGKV5-2_chr2:89196951-89197051 | CTCTGCAAATATGATGCATTTGATTTATGTTTTTACTTGCTCCATAATCAGATACCAGGGCAGAAACGACACTCACGGACTCCAGCATTCATGTCA | 161 |

TABLE 6-continued

| Name | Sequence | SEQ ID NOs. |
|---|---|---|
| IGKV5-2_chr2:89197051-89197151 | GCGACTCCAGGAGACAAAGTCAACATTCCTGCAAAGCCAGCCAAGACATTGATGATGATATGAACTGGT ACCAACAGAAAACAGGAGAAGCTGCTATTT | 162 |
| IGKV5-2_chr2:89197151-89197251 | TCATTATTCAAGAAGCTACTACTTCTGTTCCTGGAATCCCACCTCGATTCAGTTGGCTATGAGCGGGTATGAACA GATTTTACCCTCACAATTAATAACATAGA | 163 |
| IGKV5-2_chr2:89197251-89197351 | ATCTGAGAGATGCTGCATATTACTTCTGTCTACAACATGATATAATTCCCTCTCACAGTTGATACACCCTGTTA CAAAAACCTCCAAGTTCTCTCAGTGGGAT | 164 |
| IGKV5-2_chr2:89214836-89214936 | GCCCTCTGTCCTGGAGACACGGCCAAGGAGGCTGGAGACTGGGGTCAGCACAATGTCCCCATTGCAGCCTG AAATGATAAAGACAGATAAATTATATCAGA | 165 |
| IGKV5-2_chr2:89214936-89215036 | TATACTGAGACTGTCCCCATGTAGGCCATGCATTGGTGACACTTGTAACCACAGTCATATGCAACATCTTG AGTAACCAGAAAACAAAAGATAACTGGGG | 166 |
| IGKV5-2_chr2:89215036-89215136 | AACTTACAACCTACAATGAGTGCCCTAAATCCAACAACCAAGAATCCAGAGACACAAAAAACAATGATGG CCACATGAGTTTGCCCGATGTTTCCCTATA | 167 |
| IGKV1-5_chr2:89246681-89246781 | TACCAACACCATCAGAGTGTGGCTGCATCTGAGGACCACTCTCAGCTGATGAGAGGCATCAGGAGGAGCAG CTGGGGCAGCCCCTGCCTCACACATCTGCTT | 168 |
| IGKV1-5_chr2:89246786-89246886 | GGGGTTTATGTTCGGGTGTGTATAACACTGTGGGAGAATAACTATTATACTGTTGGCAGTAATAAGTTGCAA AATCATCAGGCTGCAGGCTGCTGATGGTGA | 169 |
| IGKV1-5_chr2:89246911-89247011 | GCCGCTGAACCTTGATGGGACCCCACTTTCTAAACTAGAGCGCCTTATAGATCAGGAGCTTAGGGGCTTTCC CTGGTTTCTGCTGATACCAGGCCAACCAG | 170 |
| IGKV1-5_chr2:89247011-89247111 | CTACTAATACTCTGACTGGCCCCGGCAACGTGATGGTGACTCTGTCTCCACAGATGCAGATCAGACAGGGTGGAAG GAGACTGGGTCATCTGGATGTCACATTTGG | 171 |
| IGKV1-5_chr2:89247096-89247196 | GGATGTGTCACATTTGGCACCTGAGAATTGGAAAATAGAAACACAAATATTCATACTATTGATCATATTAGG AAGACTTCCCTGAATAACCAGGCAGTACTG | 172 |
| IGKV1-5_chr2:89247196-89247296 | AGCACACTGGGCTGAGTAAATTCCTAGTGTTCTCCTTCCTTACCTGGGAGCCAGAGCAGCAGGAGCCCCA GGAGCTGAGCGGGGACCCTCATGTCCATGC | 173 |
| IGKV1-5_chr2:89247526-89247626 | GGGACTATTTATTATGAGAAACAATTTTTAGGTATTTTTTGAGAATTTTAAATATTCCTCAGGAGCCGA TAGAGTAATGTATTTCATTGGTGTATCAG | 174 |
| IGKV1-5_chr2:89247626-89247726 | GATTATTTAGGAGAGAATATTCTTGTTTGTAGGAAACACATAGTAGTAAAAATGTTAGATGGTAGGATTCTCAAGT CTTCAAAAGACTCTCATTAAGAATTCCGGGTA | 175 |
| IGKV1-5_chr2:89247641-89247741 | TATTCTTGTTTGTTAGGAAACACATAGTAGTAAAAATGTTAGATGGTAGGATTCTCAAGTCTTCAAAAGACTCTCA TAAGATTCCGGGTAGGGAAGGGGTAATT | 176 |
| IGKV1-5_chr2:89247831-89247931 | TGTAAGTATTAGGTAATGGTGTTATGCCTTTGTTCTTACTAGTATTAGATCAAGCAATTTATTACAGATAT ACAAAGATGATACCGTGTGTCTTCCATGC | 177 |

TABLE 6-continued

| Name | Sequence | SEQ ID NOs. |
|---|---|---|
| IGKV1-5_chr2:89247931-89248031 | ATGCAGCACTCACAGATCCACCACTATCAAGAGAACTGCAGGTCTCTTTAATACCCAGAGACTAAATGAGGT GCACCTTATTCTTGTTTGTTTGGGTACCTTCAT | 178 |
| IGKV1-8_chr2:89291906-89292006 | TTGGGTGTGTAACACTGTGGAGGGTAACTATAATACTGTTGACAGTAATAAGTTGCAAAATCTTCAGAC TGCAGGCAGCTGATGGTGAGAGTGAAATCT | 179 |
| IGKV1-8_chr2:89292131-89292231 | CTGACTCGCCCGACAAGTGATGTGACTCTGTCCCTAGATGCAGAGAATGAGGATGGAGACTGGGTC ATCCGGATGGCACATCTGGCACCTGAGATT | 180 |
| IGKV3-20_chr2:89442291-89442391 | CTTTCCCCTGGACACAAAGACACAGGGTGCCTGGAGACTGCGTCAACACAATTTCCCGTGTATCTGAGA TTGGAAATAAAACAGAAAAGTCACCCATGT | 181 |
| IGKV3-20_chr2:89442391-89442491 | AATCTAAATCAAACCATTGTCTTCCCAGAAGAGCCAGAATTATTGCTTTATATTGAGCTTTAATTATTGT ATTGACTGAGCAGAGTTGCCAGGTAACAG | 182 |
| IGKV3-20_chr2:89442491-89442591 | GACTTGAGAGGGTTTTCACTGACATGCAAAACCATCCCCTCACCTGGGACCCAGAGTAGCAG GAGGAAGAGAAGCTGCCTGGGGTTTCCAT | 183 |
| IGKV3-20_chr2:89442616-89442716 | AGCTCTTCTCCAGAGCTCTGACCAGCATTGATATGGGCTCTGACTGCAGGGCGGCTGGGAGGGACAT GCAAAGCAGCTGGGGCGGGTGCTGGGCTTG | 184 |
| IGKV3-20_chr2:89442716-89442816 | CAGCTGCAGAGACAATCTGCCTCCCCTTTCTGCTCTCAGCAGCCCATGCCCAGGTGATGATCAGGCCAGAAAA GGCCGTTGGCTCAGTCTGAGGGTAGAACTT | 185 |
| IGKV3-20_chr2:89442816-89442916 | CTCCCCTGCGGCCACAGAATTAACCCTGTCCTTTGTCTCACCATCACCTAGATTGAGCCACAGAAT GTTGGTACAAGTCTGTTAGAAACAAAAT | 186 |
| IGKV3-20_chr2:89443016-89443116 | AGAAGGCTGTGGTTTCATTTTCTGCTCCAACTTGTGCCCAGTCAGCTCCCTAAATGCATGATGG ATCAGGTTGAAAGGAAGAGTCTATTACAA | 187 |
| IGKV3-20_chr2:89443116-89443216 | CTTTATCTTCCGGATATACTTGTATTTTACTTGTTAGTGATCTTTCCTGAGGGTCCAGAAGCTGTCTCCATTCT TTGCAGAAATTAAAGAGCTAACATTTCAA | 188 |
| IGKV3-20_chr2:89443216-89443316 | TTAACCTCAGCACTGTGGGTGTGAGGACTTTCACAACTGCACAGATAAGTGAGACCTGGGCTCCAAATCC TCAGGGTAGTGATACCATTTCCCTAAAGAC | 189 |
| IGKV3-20_chr2:89443316-89443416 | AGAAGATGGTTTTGTCCATGCAGGCAAAGAACTATTTCTTGGGTGATCCTCTAAACTATCCAGTCTTTTTA TTCTGTATAGCTGGTATAGTTTACCCTTA | 190 |
| IGKV2-30_chr2:89544656-89544756 | GGCTATATATGTATTTGTTCATATTTCAAAATACACAGTTTCAAAATGGAACTCAAGGGATCCAAGGCTC AAAGGGGTCTCCAGAAGACCCCACACCAT | 191 |
| IGKV2-30_chr2:89544756-89544856 | CCCCTTTCTGTCAGTCTTCCCCAGAGCACAGATCCTTGTTTCGCTTGAATCTTCCACTCTCACAGAT CTGATCATCACATGCCCCACTCTGGAGG | 192 |
| IGKV2-30_chr2:89544856-89544956 | ACAACATGTCATGTCCAATACAGGAAAGGAACACACATAGAGTGTAGTGAGACCCCAGAGATACT GTTGTTAGGGCAGTGGGCCCCAGAACTCA | 193 |

TABLE 6-continued

| Name | Sequence | SEQ ID NOs. |
|---|---|---|
| DUSP2_chr2:96810164-96810264 | GGAGCAGCAGCGGGTGGAGACCCCATGGGCTGGCCGAGACAAGAGGACTCCTCAGCCAGTCCTCCTGACCTCGAGACAGGTCTCAGGAATGTGCGGAGGAC | 194 |
| DUSP2_chr2:96810264-96810364 | ACACCGGGACATACATTTCCCTTCATGCTCCCAACATACACATGCAAACATACAGACCCATACAGGCACGCGCGAGCCAGCCATGCCCCACCCCCTCCC | 195 |
| DUSP2_chr2:96810364-96810464 | CCAACACACACGTATAAAGTGTGTATATGGGCAAACTGCTCGCATCCCAAATGCAGGCTCTTTCCCTAGAGGCGCCCAGTCGGCGCGGGAG | 196 |
| AFF3_chr2:100758483-100758583 | AAGCTCACTCACTGGGGCCATTGACTGGATCCAGTCTGTGGCCATGTCATGTTTCTATTTTTGAGGTTATAGCTAATGAGCAACATGAGGTTAAGACA | 197 |
| AFF3_chr2:100758583-100758683 | CACTTTTCATAAGGCCCCAGCAGCATCATAAATATGTGTGAGCATGTTCACACTTCAGGTTATGTCTTCTTTATGTGCACCCTCTACCACACACAC | 198 |
| DDX18_chr2:117951919-117952019 | GCCAAGAACCACGACTCTCTAATTTACTTCCCAGCAGGTATTCAGTGCATAATAGTTCCTACTTAGAAGTATCATATTTGCCAAACACAAGTGATAC | 199 |
| DDX18_chr2:117952019-117952119 | CCAAAATGAGGTAAGTTCCTGTTTTCCAGTGAGATCTTTTGTTGTTGTTGTTGTTGTTGTTGTTGTTGTTGTCGATGTTGTGTTTTGTTTTGGTCT | 200 |
| CXCR4_chr2:136874415-136874515 | CCGGGTCGTCCAGCCCGGGCCGCCGGCGGCTGCCCATACACCCACGCCAACCGCCCCGCAAGCAGCCTGCAGGGGCTCCGCGCTGGGCACACCAAGCCAGGCT | 201 |
| CXCR4_chr2:136874515-136874615 | CTGTCCCACAGGTGCTGGGGAGCGACTGGGCGGCTCCGCGCGAGCGTCTTTGAATTGCGCGCCTGCAGGAAACCAAAACTCCCTAGCAAGAGGGT | 202 |
| CXCR4_chr2:136874615-136874715 | TTCAAAAGTTTCTGGAAACCACCGACACGGTTAAACATCACAACTGGACTCGGAGAGAAGCCAAACGGGTTTCCCCACTTGCACCTGCCAGTCTTCGCGCGG | 203 |
| CXCR4_chr2:136874715-136874815 | CGACCTGGCAGCCCAGGTGCGGTCTTAACCGCCCCCCGCCCCTCACCCCGTACCCGCTCCTATCCCCGGAGCGCAAATCTCAGGGCTGGCAGCTGCGCGGT | 204 |
| CXCR4_chr2:136874920-136875020 | GGAAGGTTTTCCCCTCAAACCCAAAGCGCGGGGCGGATCAACTCCTAGCTGCTGCCACCACTCGATCCCCTCAGAGGATCGGCGCGTGGGTCCACCC | 205 |
| CXCR4_chr2:136875020-136875120 | GCCTCTCCCGCCCTCTGCCTACTGTGCTGGGAGACTGGCACGCTCCGTCGGCCGCCACAGAGTTTAACAAACACGCACCCAGTGTCAAGAACAGTCACCA | 206 |
| CXCR4_chr2:136875120-136875220 | GGGCTTAACCCGAAGTTAAAGCGGGCGCAATCTCCTCCTGGGAACTCAGCCCCCAGGCACGCGCCCTCCGCCTCTAAATTCAGACAATGTAACTCGCTC | 207 |
| CXCR4_chr2:136875220-136875320 | CAAGACAATCCCCGCCTTCCCAAGGAAGAGACCCGGTTGGTCTGAGTCCCGAGGCAGCGCGCACGCCTTCTCTGCACTTGTGCACAGAATGTCTTTACGTTTG | 208 |
| CXCR4_chr2:136875320-136875420 | CAAACAGCGTGCAAGCCGCGCGCGGACTCAAGGGGAGACACATGAGCCACTGAACGCTCTTTCCAGTCGTTTCTCCTCGACTCACAGAGA | 209 |

TABLE 6-continued

| Name | Sequence | SEQ ID NOs. |
|---|---|---|
| CXCR4_chr2:136875420-136875520 | AAAAGATTCCAATCCTGCTCCCCCCACCCAGCACTATATAGGCATGGTCAAGAAAACTCCTTTCGGTGACCCTTTTTGGAGTACGGGTACCTCC | 210 |
| CXCR4_chr2:136875520-136875620 | AATGTCCTGGCCGCTTCGCCCGCTCTGCCGCTCGGAGAGGGGCTGCGCTCTAAGTTCAAACGTTTGTACATTTATGACAAAGCAGGTTGAAACTGACTTACACTGA | 211 |
| CXCR4_chr2:136875620-136875720 | TCCCCTCCATGGTAACCGCTGGTTCTCCAGATGCGGTGCTGGCTACTGGAGCACTCAGGGCCCTCGGCGTCACTTTGCTACCTGCTGCCGCAGCCAACAAACTG | 212 |
| RFTN1_chr3:16419204-16419304 | CCCATTGCTGACATATACTTACTCCCTGAGAGTGGCTCTTTCATGCACCCTCCAAGGGGTTGCTCTCCGGTCCATCCAGTGTCTTGCTGCTCACCCCCTGTGGTGAA | 213 |
| RFTN1_chr3:16419304-16419404 | AGTTCTCCACCATCTCCCTCTCCGGAGGGTGAGCTGGGCTGTGCTGGCAGTCCCCTCTGGGGCCTGAGCTGGGCTCTGGGCTTTGGTTTCTCC | 214 |
| RFTN1_chr3:16419404-16419504 | CAGCCGGAGCACTGCACACATCCCCAGTCCCCGTTTCTCATTCTCCAGTGACGCGTGATCCCCACGTGCGTTTTTTGCATCTCTGGCATCCTCGGTGCT | 215 |
| EIF4E3_chr3:71551101-71551201 | ATTTGCAGGTTATATCTGGATGGTGGCACGACAGCCGCCTGGAACACAGAAGTTGGGAGGCTGACGCTCATCAGGAAGGCTCTTTTGGGGAGCCAGGA | 216 |
| EIF4E3_chr3:71551201-71551301 | AGAGTCCCCCAGAAGCCACTTGGCACCCTATCTATAACAAGTTGCTCTTTAAGAATCATGGGAACTCCAGAATCATTTTCACAAATACCTTCCACTCAT | 217 |
| EIF4E3_chr3:71551301-71551401 | GATTCAATTAAAATGCAGAAAAACACAAACCTTCCGTTCCCACTGGCAAACTGGGTCTAGCTAACTGAGCACAGCTAGCACAAGGCAGGCCCCCTGCTAGC | 218 |
| EIF4E3_chr3:71551401-71551501 | AGGGCAAGTGGCGCCCGTCCCAAGGCCCAGGGGAGCCTCTGCAGCTCCCGAAGGACGGTCAAGTGAACAGAGAGCTGGCTGCCATCTGGGTTCTT | 219 |
| KLHL6_chr3:183272308-183272408 | ATGAGATCACCAGTTATCGTAACTAGAGGGCCTCTCCCATCTAAAGCATCTTTGTAACTGCTTTCCCTTTCCCCACACTGCCTACACATAAAGAAGCCCC | 220 |
| KLHL6_chr3:183272408-183272508 | TAATTTGTAACAAGTCATTTGCAACTCCAGAGAGAGGGCCACATCCTTTTCTCTATGTCTGTTGATTAACAAAGACAACATTATGTTTCCAACACCAG | 221 |
| KLHL6_chr3:183272508-183272608 | TCAGACCAAGGGGGAAAAAGTCCCCATGACTTCCAGTAATTTTCCATCCTTTGGAACAAGGAAATATACACAAAAGGTTTACTATAGAATGTAAGCATTG | 222 |
| KLHL6_chr3:183273063-183273163 | AACTGTTCAAGATTGGGCTTCACACTAACACACACCTCTTCCTTTGCACTTGCACCCCATTTGACTCTGGTCCTAGGCATGCTGACCTGAAATAGTTGCTG | 223 |
| KLHL6_chr3:183273163-183273263 | GCTGCGGCAAGCACCACCGCGGTGGCAGGAGAATTCCTGAATGTCCACACACAAGATGACATCTGTCAGAGCGTTTCCATTCCGCAGGGTTTCCAGGCCAT | 224 |
| KLHL6_chr3:183273263-183273363 | TCTGAAGAATTAAGGAGAGTCCCGCGTCGTCAAATTTGACCTTTTCCCATTTAAGATCTCGACCAAGTCTCCTGTTTTCTGGGAGGGCTCATCTGTAGA | 225 |

TABLE 6-continued

| Name | Sequence | SEQ ID NOs. |
|---|---|---|
| KLHL6_chr3:183273363-183273463 | AGGTGCCAGGGGCCCTTCCAAACTCTTCTGACCACATCACCCATGGTCCAGGCGCCCCTTTGTCCTGCCATCAACATCGAGACTGAAGGAGCGCCCAAG | 226 |
| ST6GAL1_chr3:186714604-186714704 | CCTTCCTGTTGGCCACTACATACGTGTCCCCCGCTTCTTGCCCTCTGCTTGGGTCCCTGCTACACTGGTATCCTGCACTTTCCACCTTGTATTGCCA | 227 |
| ST6GAL1_chr3:186714704-186714804 | GTTTGTTTCCAAGGCCATCTCCACTTTGAGCTTGTTCATGACCACCTCACACAGCACACTTGGTCTGTGTGGTGGTTTGAGGGGTTCTGTCTGTACACTG | 228 |
| ST6GAL1_chr3:186714804-186714904 | TGCTTTGGCTGTCTGTGTTGGAGGCGGGCAGGTGGGAAGGAAGAAATGTATTCTTGGGAGATTTGTTTTAGAGACATGAGACATGAAAATAGTTAAGTAAT | 229 |
| ST6GAL1_chr3:186714904-186715004 | AATATAATATGGAGGCATGGACTATCAGAGAGGCAGGCAGGACTGCCCAACCTCCTCACTGGGCACGTTACGCTACTTCCTCCTGACCTCTATAGTCC | 230 |
| ST6GAL1_chr3:186782529-186782629 | CTATCATTGCCCTTTCTTACCTTGATATCCTAAAAGCTGGTGTCGTCTCTCTATCTTTTGTCCTGGTCAGTTATCCTAACTATTTTGTCTCTGTTT | 231 |
| ST6GAL1_chr3:186782629-186782729 | CTGTGGATTAGTAAACGGGGTCCCCACCCCCACTCCACAAGGAGAACATCTGCCACCCAGAAGTCACTGAGAGAATAGCTGTTGCTTTGGTAGAATTCTG | 232 |
| ST6GAL1_chr3:186782729-186782829 | CCTCTGAGTGGCTTTGTCTTTTCCAGACGGAGAGGTCTCCTGACAGCAGCTCTCTCTTCTTTTTCTTTTTTTTTTTCAGACGAGTTTGCTCTTGC | 233 |
| ST6GAL1_chr3:186783389-186783489 | CTTCCTGTACCCTGTGGGCCTGAGAGGAGGACAATGGACAAGAAGACCCAGTGGCTTCCTTGGAAGCTTTGTGCTAGCTGGAGAGAAGACCTACTT | 234 |
| ST6GAL1_chr3:186783489-186783589 | CCTATATGCCTAGCAACAGTCCACACTGACTGACTGCAACCAGGACATTTCCAGATTACTCAGTGGGGCTTATCTTGAAATAATAGTTGATGCCATTTG | 235 |
| ST6GAL1_chr3:186783589-186783689 | TTAAATAATTATTATATACCATCTAAGGGTCTTTACATGCCTTCTCTCATTGATCTTCATGGCAAACCCTGTGAGGTATGACCACCACCATTTTAC | 236 |
| ST6GAL1_chr3:186783689-186783789 | CTCAGAACTCAGGCTCCCAGAGTTTAAGTTGCTCACAGGAGCCCAGAAAGTAAGCGACAGAGAGTGGGATTTGGTTCTAGGTGTTTGCCACCAGCACTTTA | 237 |
| ST6GAL1_chr3:186783789-186783889 | AATCACCAAAGCTTTCTGGAAGCTCCAACTTTCTTCTCAAGATACTGAAAGACAGGTATCTGATGGGTTGGCAGGGCGGTGGGAGGTGGGCGAGATT | 238 |
| ST6GAL1_chr3:186783889-186783989 | TCCATCACAACGGGTCTAAAACCAGCGATGGTGAGCTTGGGTGATTTTGATGGAACCCCTGCCATACAGTCTATTAATTCATAATTGGAGCTAAAATTT | 239 |
| ST6GAL1_chr3:186783989-186784089 | AATCATGATGGCAATCATGAGTTCTGGGGCTTCTTGATTTGGGCCAGCAGACACAGTCTCAGTCACTAGTTCTCCGAATCAGAGAAGGATGCCTTCAGG | 240 |
| ST6GAL1_chr3:186784089-186784189 | CTGTGTCTTCACATGGCTTTCCTCTGCGTGGTGGAAAGAGAGAGCTCTGCGGGTCTCTTCTTGTTGTAAGGACACTGGCCCCATTGGATTAGGGCCC | 241 |

TABLE 6-continued

| Name | Sequence | SEQ ID NOs. |
|---|---|---|
| ST6GAL1_chr3:186784189-186784289 | CACCACATGACACATTTAATCCTTAATTACCTCCCTCACAGCCCTATTTCCAAACAGGGTATTAGTCACATTAGGGATTAGGGCTTCAACATAGGAATTCT | 242 |
| ST6GAL1_chr3:186784289-186784389 | GGGGGCCACACAATTCAGTCTATAACAGAGGGAAAACAGATTTGAGAGAAAAAGTCCAAATATGCACAGTGGTATATCTGAAGATGTGCGTGCGTGC | 243 |
| BCL6_chr3:187460134-187460234 | TCAAGGGCTCAGCAAACGACAACTTAAGCATTTAGAGTCCCATCCCTATCCACCAAACCAGAGATAAGTTAGTCTTTTCAAGAAAGCATTGTATAAAAC | 244 |
| BCL6_chr3:187460234-187460334 | CCTTCAAAACTGAAAAGAGAAGAGAAAAGGGGCAATTGGAGAATTCCCACTTTTTCGGCTGTCTCCTTCAAGTCGCCCAGTTTTATGAACAGCATCTAGCCTT | 245 |
| BCL6_chr3:187460334-187460434 | ACTGTCTACTATCAACAACCCTTAAAACTAGCCAATGCTTCGGCCTCTAGTATTGGAAAGTCTTCCAAATAGGATACTGGAAACTTCTATTTATAAGCTTG | 246 |
| BCL6_chr3:187460434-187460534 | GGGTGGCCGGCGGGCGGGAGGTGGAGAGAGAGTTGCCATCTACAGGTTTCTATTTTGGCCTGAAGACTCAACTGCAGTCATTAGAGTAAGGGAATGCC | 247 |
| BCL6_chr3:187460824-187460924 | TTATTTATTAAAACCACACACCTTGCAAAGAAAAAGGGAAACTGGAGCAGTCTCTGTAGAGGAAGCCGTGGCATCGCTCAGAGCCACAAACTGTATTTC | 248 |
| BCL6_chr3:187460924-187461024 | TAAACAGCCCTTTCCCTGGTTCCCTCTCTCCTGCCCCACTTTTTTAAAATCCAGACTGTAAAAAACACATCTACTGACACTCACTTACTTTAAAAAA | 249 |
| BCL6_chr3:187461024-187461124 | GAAGAGAAAAAGTAAAGCGTTACAAGACTTTCCTCCTGGAAACTATAAACTGAAAAAAAAATCCATAAAAGATTAAATCCTGGCGGTTGTGGGGTGCG | 250 |
| BCL6_chr3:187461124-187461224 | GGGGCCCGGCGGGAGGGGGCGCCGAGTGGAGATTGGCTCTCTGAGGTGGTCAGGGCCCTGTGACAGCTTGGGACTTTCAGCACTCTGGTTTGGGGTCATT | 251 |
| BCL6_chr3:187461224-187461324 | TATCTGCTCAACTGTCAGGACCCCCCCCCAAACCCCAGCCACCAACCATCGTAGAAGGGAACACACACAGAGGGTCTTTTTTCATTTTTTT | 252 |
| BCL6_chr3:187461319-187461419 | TTTTTAAAAATCGGTTTGGTTGTGTTTTGTTTCATGGGGAGCTTTAAAACTCATTATTGCACACTAGTTCCATTTTTCGCCAGGGTTCCAATAA | 253 |
| BCL6_chr3:187461454-187461554 | CAAGACATTTACCACGTCACTACATCCGGCAGCGGGTGGCCCCTAGCTCCTGCCCCCGCCCTTTCTCCCGCCGCCCCGGAGCTCAGCCGA | 254 |
| BCL6_chr3:187461554-187461654 | TTTCTGAGGCTCCAACTCTACCCACTCCCTCCCCGGCCGCCCGCGCGCCTTCCCCCATTCTTACTCCCTCGAGGAGAGCCACCAGGTTGCAAATCCA | 255 |
| BCL6_chr3:187461654-187461754 | ACCAACCTCGCAATCTATTTTGCAAAATCACTCACAAAGATCTCCCTTTCGCGCCCCGCTCCTCCGCGCCGGGTCCCCTCAGCCACGGCCACA | 256 |
| BCL6_chr3:187461754-187461854 | AAGTGCCCTTCTCCTCCTGAGTCTTGCACATAAGGAACGCGGGCTGGGGCTCTGTTCGTCTTTCCTCGCCCAAGGTAAGGACCTCGGGAATCTGAA | 257 |

TABLE 6-continued

| Name | Sequence | SEQ ID NOs. |
|---|---|---|
| BCL6_chr3:187461854-187461954 | GCCTGGCGTCCACTACGTCAGGCCCGAGTTCCCTTTTACAGAGCTTGCACCATGGAAAAAATAAAA TAAAATTTAGGAAAGGAGGCAACAGCCAT | 258 |
| BCL6_chr3:187461924-187462024 | TAAAATTTAGGAAAGGAGGCAACAGCCATTGGGAGCCAACACAGAGTCACGCAGCGCCCAAATACAA ACACCGCAGCGCCAGAATCCCGCCACTT | 259 |
| BCL6_chr3:187462024-187462124 | TCTCGTTCTCCCAGGCTGTCTGTGAGGTTCCCTGAGTCCCCCGCACACTGAAAGGCATGCCAGGTGCA GTGCGCACCCCTTTCCCACCCACCCCAAG | 260 |
| BCL6_chr3:187462124-187462224 | AAGCCCTGTCTCCCGCCATCAGTTCTCTTCCTCGGGATGAGCAGGGAGAGCGCGCGGAGTTCCGACTCCC TCGACTACAACCAAGAAGAATAATTTTCA | 261 |
| BCL6_chr3:187462224-187462324 | AAGTGTTCAACATCCCCGCCCCCAAGTCCCCAAAACACAGGGGCAGGGAACACCAAAACACTCGGCTCT CATTAGGAAGATCACGGCTCTGAAAGGAAA | 262 |
| BCL6_chr3:187462324-187462424 | TAGTAGACACGATACTTCATCTCATCTGATTTATGACCAAAAAAACAAAAAACCCAAAGAGTTC GCTTGCATTTTTTCCTTCCAAATCTCGTT | 263 |
| BCL6_chr3:187462424-187462474 | AACAAAAACCCAAAGAGTTCGCTTGCATTTTTTCCTTCCAAATCTCGTTCGGCTCGAAGGCAGGGAATCT AAAAGACCCGAGGCGATGGAAGAGACCA | 264 |
| BCL6_chr3:187462474-187462574 | GCGGGGCGAGCCAGCCAGCCTCCTTTTTGCCTCCCGGAGTTACCCAGAAGGACAGGGGAAGGGAA GGAAGAGAGGCCAGGAAAAAGAGGAGGGAG | 265 |
| BCL6_chr3:187462574-187462674 | GGAAGCGGAGGCCAGGAGCCAGGAGCCAAGGAAAGCAGTTTGCAAGCGAGGAGAAAAGAGGGAAAAAACAC AGCCGCACGAATCCAGAGAGATCACAAGCCGT | 266 |
| BCL6_chr3:187462674-187462774 | ACGCAAGCAGCAGCAGAAAGAGCGAGAGCGCGAGCGCGCGTCCTCTCCGGTCTGGGGCCAGACAGCC CCCAGACTAGCCGAATCACCCCCCAAGCAC | 267 |
| BCL6_chr3:187462774-187462874 | TGTCTCGTCGTCTCTGTCTCCGGCCGCCCCCCTAATTCCCCTCCTTCCTTCCTCCACCTCCTTTCCAAAAACC AAACAACAAGGAGGGTGGCAAAAG | 268 |
| BCL6_chr3:187462874-187462974 | CCTCCCAAACCGGCTGATTCACTCAAGACAACAATAATAATAATACATAACAATCTATATCCTA TGGTGGAGACGTGGGACTAATCTTCGG | 269 |
| BCL6_chr3:187462924-187463024 | ACATAACAATCTATATCCTATGGTGGAGACGTGGGACTAATCTTCGGCATTATTTTAACACCTGACA GCTAGAATAAATAAATATACATTTATA | 270 |
| BCL6_chr3:187463004-187463104 | AATAAAATATATACATTTATATCAATAGATACACATAGAAAACTTGGAGCCAAAGCATTTGGCAAGAGCGG AAAAAAAAAGAATTAAAAGGTAAAATAATG | 271 |
| BCL6_chr3:187463104-187463204 | ATCATGAGCAGCCGGCGGCGGCAGCGGCACCAGCGGCAACAGCGGCGGCAGTAGCAGCAGCAGC GGCGGCAACAGCAATAATCACCTGTGT | 272 |
| BCL6_chr3:187463204-187463304 | CCGGCCCTTTCCTAGAAACTTCTTGCATCACCACTTCTAAGAACCCCAGTTCTAAGAATCAACAGAGCTCAA TTCTCGGAATTTGAGCTTCGGACTTTACC | 273 |

TABLE 6-continued

| Name | Sequence | SEQ ID NOs. |
|---|---|---|
| BCL6_chr3:187463304-187463404 | ACTGCTACGTGGCAGGGAGGACTTGGTGTCAGCTCTCCGAGATTTTACTGCCCCTGGCCAACCAAAAG CCCTCAAAGCCACAGATTTTTCACTGGC | 274 |
| BCL6_chr3:187463404-187463504 | CGGCATATTTCGAGGTCCTCATAAGCAGAGCGTCTCGGATTTGGAGGTTCCGGTTCGAGGCTCGAGGGGC CTGAAGGTGGCTCTCCCCTCCCGGGCCAA | 275 |
| BCL6_chr3:187463504-187463604 | GACGATGGTATGGCCTGCTCCCGCCACCATCACGTGGCCTCCTCCTCTGTGACGTCGGCGCCTCGTAG CAAAGCTCGGCCTCTGGAATTCTGAGAAC | 276 |
| BCL6_chr3:187463709-187463809 | GCACAAAAGGGAGCGAGAGGTTTGAACCACTGGGAAAAGTATGTTATATATAGTAGGGTTAGAGAGG CGAGTAAGAGAAAATAAATAAAATAAACA | 277 |
| BCL6_chr3:187463794-187463894 | AAAATAAAATAAAACATCACAGTCTCTTCCAACTAGAATATTAGGCACCACAGAGAAAATATTGCCAAGC AGTTTTCGGTGGGTTCATTTGCTTTATTTT | 278 |
| BCL6_chr3:187463894-187463994 | TATTTAGGACAGGGGTTTTTGCTGTGTTCTGGGTTTTTTCTTTCTGGTGTGGCTTGGGATTTTTGGT TTCTGTATTTTGATGGTTTATGGATTTT | 279 |
| BCL6_chr3:187463994-187464094 | TGCTTCTGATTTTTGCCTTTTGCAAGTTGTGTGTGTTACGTAAATCACAGGATCGCATCGGTTGGATTT TTTTGTACGTGCCCTTTCTTTCCCCTATCT | 280 |
| BCL6_chr3:187464094-187464194 | AATCCCTCAAGCGTTTAAAGATGTATTATATTCAATACTAATACTATTGAAAGAAGCTTAAATTTTGGCC ATATGTAACAATCCCAGCCCCCACTTTT | 281 |
| BCL6_chr3:187619334-187619434 | ATTATCATCATCACCACCACAATCCCTGCCTGGAGACCAAGAGAATTCAAACAGGTCAGCACCTCTAA TGCTGTATAGAACATTGACCCTACTGTCT | 282 |
| BCL6_chr3:187619434-187619534 | CCCAGTTCCTGAGGATGGTGTGATAATAACATCTCAGAGTTCTGTAGTTTCTTCCACCACTGTGCAGGTG TGGTTGGTGGGAGCAATGCCCTGGATGGA | 283 |
| BCL6_chr3:187619534-187619634 | TAAGCCAAGCTCCTTGTGTCCTGGCAGATAAATAAACAAGGTGAACCCTCAATCCGTGTAGCAGGAGTTCCAGA CAAACTCACTTTGCATGGAAGGACACTAAC | 284 |
| BCL6_chr3:187619634-187619734 | CCTTCCAGGTGCATGGAAATATTTGTAGTTTTTACTGTCTCCCCCTTCCTCCACTGCCTCATCTTTTTGT TTTTTCCCCTGTCGAGACTATTTGCTCTG | 285 |
| BCL6_chr3:187660817-187660917 | CCTTTCCAACACTGGCCTGCTTAGGGACTCACCGTCTGCACTCCGCCGTGCACAGGTGGAACTGAGTTCAG ATGAGGGAGAATTGCTTTCCATTGTTCAG | 286 |
| BCL6_chr3:187660917-187661017 | TAGGCTTTTGTAATTTCTAGTTTTGCTTACCTTTCCTACTCCACCACACACAAAACAGTGTGAGCTTTCT CATTCTAGTGCATAAACACAGGTCGGTC | 287 |
| BCL6_chr3:187661017-187661117 | AATACCCACCACAAGTGTTCAAAAGGTGAGCTGGCATTGCTGCCCAACTGGGCATTATTATGTCCCTTCTGTCCC TGCCCATCCAGGCTTGCCTTCCTCGGCAAC | 288 |
| BCL6_chr3:187661117-187661217 | CTTTTCTAGCTTGAATTGTACTGTGACTTCCTTCTCACGGACCACTCCCGGAGACTGGTGAAAGTTGGGCCCA TGCTTGAAGCCTCTGCTTCTAAATCATGT | 289 |

TABLE 6-continued

| Name | Sequence | SEQ ID NOs. |
|---|---|---|
| BCL6_chr3:187661217-187661317 | TTTCCATAAAGTCTCCCTCATGCTGCTTCCACCTTCTCCTATTTGGAATTACTGGTGGGCTCTTCCACTGTCCCATAGCAAGTGTTCTATACATTC | 290 |
| BCL6_chr3:187661317-187661417 | TGAAGGCACATTTGAATATATACTTTGTCATGGTTGCTTGGACCATGTCGTCTTTTCCAAGTAGGCTGTGAACATTCAGTGGCATGGATCATACCGTGC | 291 |
| AC022498.1_chr3:187957432-187957532 | CCCATTGTTCAAAGAAGCATTATGGAGTCTCCAAAAGCCATTGGCCAGGTGTGTCTGTGACTTCCTTAGCCTGGAAATAAACAAATAAACAAGCACAA | 292 |
| AC022498.1_chr3:187957512-187957612 | AAACAAATAAACAAGCACAAATTAGAAGTCTTTGCCCTATTACTGCACTATTAGTAGTTGATTGCGCAACATCATGCAAAAGTCACTTTAATTTATCTGG | 293 |
| AC022498.1_chr3:187957612-187957712 | CAGGTCTCTATGTAAACACCAATACAGTCAAGAGGGCTTGGATGGGTATTGCTTTCATTTCTAATGAAATTTCAGGCCTTCTAGGGTAGGATATCAAAATT | 294 |
| AC022498.1_chr3:187957712-187957812 | GGTAGATCATTTGCAATTTATTTTATCCCAAACACCTCACTTTACAGTCAGAGAAACTGAGGCCCAGAGAAGTAAAATGAGTTGCTCAAGGTCTCAGAGA | 295 |
| AC022498.1_chr3:187957812-187957867 | ACTGAGGCCCAGAGAAGTAAAATGAGTTGCTCAAGGTCTCAGAGAGCAGCAAGAAATAGAGATGGGACTTGAGCACCTAGATCTCTGGTATTGCTGTCCTGTA | 296 |
| AC022498.1_chr3:187957867-187957967 | GTTCATGGAGCTGGCAGATGGATACATCTGTACCTGTGACCTGGATGATGGAGAGACTGCTGCGACCCTTCAGAGGATCTCATCCAAGGTGGGGTTTATGTGTAA | 297 |
| AC022498.1_chr3:187957967-187958067 | ATGATATCTGTGTGTTTCATTTTCCTTTCATAAACTAATTAAAAATCCTTTTGGTATCAAATTTTAAGCCAAAAAGTAGTGAGGGGAACATGGGTAGG | 298 |
| AC022498.1_chr3:187958067-187958167 | AATAGCTTACAGCTTGCCTAACAAGGTTGTTGACTGCATAAGAGTCAGGAGTTTGGGTAAGAGTGTGTGTGTGTGTGTGTGTGTGTGTGTGTGTATTGAGTAGTT | 299 |
| AC022498.1_chr3:187958282-187958382 | CGTACTGAATTTGACTGCTTTATTTTGTAGGGAAGGAAGAAACTGATGCCTAGAGTAGTGAGAGCTTTATTCAAACTCATTCCACTGTTATTGAGTAGTT | 300 |
| AC022498.1_chr3:187958382-187958482 | AGGATATTAGACCAACCAGCAACATATTTGGGTAGAAACTTTCATATAAAAAGCTAATCATAACTATCCAATCATGTCAACTAGTAAGGCTGCTCAGGTGGG | 301 |
| AC022498.1_chr3:187958482-187958582 | ATAACACATCAACCTTCTTTGGGATTCTTCCCTCAGACACATGGTTTTGGTGGGAGGAGCATGGCAAGGGAGGGGCGAGCTCCAATGCAGGGCTGCTCTGT | 302 |
| AC022498.1_chr3:187958582-187958682 | CCTCGGCGACCTGAGCAGCACACACAGCAGAGATCAGAGAACACTCTTAGTGAATGAGACCTCCCTATTGGCTATATTAAAGTAATGCTCTGAAAAGTTCC | 303 |
| AC022498.1_chr3:187958787-187958887 | TATGTATGCATAGTCTAAAGTGATGATTTTAGAGGTAGCAAGACAGTGAAGAATGTCCCTACATGTGAAATGGGCACAGTTTTATCAGGGAAGTGTCAATA | 304 |
| AC022498.1_chr3:187958887-187958987 | GAGGGTTAATGTTCCACGTAGTTGCTGCAAGAATGATAAGTGGTCATGGGGATAGCCTGACACTCTAGGAGCAAGAAGGTGGTGGGTATGGATAGAACTAC | 305 |

TABLE 6-continued

| Name | Sequence | SEQ ID NOs. |
|---|---|---|
| AC022498.1_chr3:187958987-187959087 | TGATATAGCATGAATCCAACCTGCTGTTATCTGCGCAGGCCTCTCTGCAGCTGTTTGCCCTGAAGTACATG CTGTACGTTTCTCCAGCTGATCCTGCATG | 306 |
| AC022498.1_chr3:187959087-187959187 | ACTGGGTATAAACGCCTGTCCGCTGTGTGCTGGACAGCCCCAGACACCCTCGGCAGCCTGCTGTGTTTGT GTGAGACATGCTGTGTTAGGGATTTAAGCA | 307 |
| AC022498.1_chr3:187959462-187959562 | ACAGCTTTCTCATCTACAATGGACAACCTATTTTTAAAGAATCTTCAGAGAGTCGTTGACTTTGTTATAACT ACTACTATATACGTAATTTCAGATGATAG | 308 |
| AC022498.1_chr3:187959562-187959662 | AATTGAAAATTTAACTTGTTTTTCTAGAAAGAGTTTATTTTCCCTATAACTTCAAAGAGTAATGGTGGGGA GTAGGACATTCTGAAAATAAGAGAAACA | 309 |
| AC022498.1_chr3:187959662-187959762 | TGTCAAATGAATTTCTGACTTCCAGCTAGGCATATGGAATAAAGGTCTTTATTCCAGTGACCTCTGCTCAT TGGAAAACTTTGGGCTGGTAGATTTCATG | 310 |
| LPP_chr3:188299217-188299317 | TCTCTTGCATTCTTAACTTGCAATTTAGTACTGTTTATATCTGCTTGAAGGTTAGAGACATTCGACTAAA TGGTCTTTTTCTCCACATTGCTGTCATTCA | 311 |
| LPP_chr3:188299317-188299417 | TTAATGTCCTGGTCCTGACTTTACTCATTGACCACAGGACAAGTGGCTCAACTCTCCTGCCACTACCC AGGCTGTTAGTCCTGTTGGGAGGCTCAGG | 312 |
| LPP_chr3:188299417-188299517 | GCCCAACTCACTCACTCCATCGTAATCTCATCTCCATTCAGCTGCGAGCCTCTACAGCCCTCCTGGTTATACCCTGG ATCTTATCATTGCTTCGCTCTATTTTACC | 313 |
| LPP_chr3:188299517-188299617 | TCCTAAATCGTAAAAATTAAAACCAGCTCGGAACACAACCCCCTCATTCTTCCAGCACTCTCTCTCATTCA GGTAACTCCTATTCTACTTTTCTTCAGCA | 314 |
| LPP_chr3:188471412-188471512 | TTGTTTTTTTTACTTTACCTTAATTCTCTTTTGACTAAGATGTAAAATGTTCTTAATGTGACTGTCT CCGAAACTGTTTTGTCTACCACTCA | 315 |
| LPP_chr3:188471512-188471612 | TCCTAGTGGCAGTCCATTGATCTTTTCTGTTGCAGAGGGAAAACAAGAGAGGAAACAGACATTGGAGCCACCTTTC TATTTGTAGAGGGAAAACAAGAGAGG | 316 |
| LPP_chr3:188471567-188471667 | TGTGAGTGTGTATATGTATTTGTAGAGGGAAAAACAAGAGAGGAAAACAGACATTGGAGCCACCTTTC CCCCACTAGCCACGTACCCTGTTGAACCTTC | 317 |
| LPP_chr3:188471667-188471767 | AAGCCTCTCATAGAATCAGATATACAACAAGCACAGTGCACAGAACTACATGTCCTACAGTCCAGCTTT TAAGATATGATAAAACTCTTGTTATTCACA | 318 |
| LPP_chr3:188471767-188471867 | GAGCTAAATGGCAATAACCATAGGAGAGATTGCATATTGCTACATTATGTAAAGACCAGAGTCCCAAGAAAAT AGTGAGAACTCAGTTTGATGTATGATGTGA | 319 |
| LPP_chr3:188471867-188471967 | TATGTGATATCTTACTTTACATGGCTAACAGTTGACATTCTTTGTGGATTCTATATTGTCTAAGGCTACAG AAGAGCCATATGATAAATTCATCGGCAAC | 320 |
| N4BP2_chr4:40198810-40198910 | CAGTGAAAAGGCTTGGGCCGCTTTGTTTTCCACCTGCTTTGTTGAACAAATTTGATTTCCGAGTCAGTC ATTTTACTGTCAAGACATTTCTTCGGCAT | 321 |

TABLE 6-continued

| Name | Sequence | SEQ ID NOs. |
|---|---|---|
| N4BP2_chr4:40198910-40199010 | TCTGCAACAGGTAAGGATTTGCTTCCTTAAAAGTATTTCTTTGGTGTCAAAAGAAATTTTCTAATTTTATTTAGCTTTTACTCTAGGCCAAACATCGT | 322 |
| N4BP2_chr4:40199010-40199110 | AATGACTTCTGAGCTACCTGCTGTAAGTGTAGAATCAATTTACAGGGGACGGGGTCGGGGGGTGAGTGTTGCTTTGATATTCACTGCCCCCTCCACAC | 323 |
| N4BP2_chr4:40199110-40199210 | AGTCCTAACAAGATTTTTGAAACATGAAAAGTTACAAATAGTTGGCTTTTGGTTTTCCAGATATTCTAGAGAATGCATATGCTTGTGACTGTGGCTGAGC | 324 |
| N4BP2_chr4:40199210-40199310 | TCAACTGTATGATGGTAGTTTAAATACTACCCAAGGTTTGATGAAGTAAATCTAAAGATGCTCTAAGTTGTGCAAATATCAATTTTAAAGTTGTCTAGTTCA | 325 |
| N4BP2_chr4:40199310-40199410 | GAAAAGAAACAGAACCGAAGTCTAAATGATGTAGATTTCAATCTGGAATTTCTAGCTTGTGTTTTTTCACCTATTGCCAATGTTAATGACCATTTCCCAAA | 326 |
| N4BP2_chr4:40199410-40199510 | AGTGCTCTATGATGTATAACATGTATTTTTAATTAAATTTAATCTTTCTTCTGAGGTGGTTTGATTGGAGATATGCTACGAGGTACCAGTCAGTAGCC | 327 |
| N4BP2_chr4:40199510-40199610 | TGAGTTGTAACTAAACAAAGTTTGGGAAATCACCCGGTTTTAAGTGTCTTTACTAAATGAAAGTTGCCATTGACGTATTCAAGCAGGCAACAAGTAGTTGT | 328 |
| N4BP2_chr4:40199610-40199710 | GTCCCCTTATTGGTTCTAAGCTGGTGCCGTGGAGGATATAAAGAGAAATATTTTAAAATCTCTACTTTGAAGGACCCTATAATCTGGTAGTTGTGATAAG | 329 |
| N4BP2_chr4:40199710-40199760 | TTTAAAAATCTCTACTTTGAAGGACCCTATAATCTGTGTAGTTGTGATAAGAAGTAAAATTTAGGAAGCAATGCAAGATGAGAATTCAGTGATGAGTGGGG | 330 |
| N4BP2_chr4:40199760-40199860 | CAGCACAGGCTTGAAGAGCTTCTGAATTCCATGGAGGGGGCCTGGGGCAAACTGGAGTTGTCAGGAAGATCTGGGCTTTGGAAGAATGCCAAGTGTCG | 331 |
| N4BP2_chr4:40199860-40199960 | GTAGAAGGAGAAGGGGCAGGTGATTTCAGACTGGGAGGAGACCTTGTGGCAAAGGCACAAAGGCGAGACTGACCTGGAGATGATAAGGCCAGTTGAAGAGA | 332 |
| N4BP2_chr4:40199960-40200090 | ACATTGCAGGAAATCAGATTAGACAGTTAGGGTGTGAGACACAAAAGCGAGGACCTTGCAGGCACTGGGGAGAAGTGACCCCATTCAATAGTCCTTGGTCT | 333 |
| N4BP2_chr4:40200090-40200190 | CCTTCTGCCCTGCCTGCGCTCGCTTCCTCCGGCTCTCCACGGCACCAGCAGAATTCCATGTGAGAGGGAGCTTGTCGAGCGTTGGCCTTCCCACTTGGGGCTG | 334 |
| N4BP2_chr4:40200190-40200290 | CTTTTCTGCATCCTGTGCCTGGCTGTGGGCCTCCATTTGCCCTCTTTGCCCTTTCCCTCCCCTTGCCCATTTGCCCTCTGTCTTCCCTTAGGACATCATTTATGCAGAGAAAGGTTCGTGTGGCTCGGGGT | 335 |
| RHOH_chr4:40200505-40200605 | GGACGTGTTTAGAGAGTCAGTAGATCAGTATCATAATTAATTCAGACACTTTTTTTCTGGACCATAAAAATATCTGAACCCATATAATAACAAACATACAGCACGGT | 336 |
| RHOH_chr4:40200605-40200705 | GAATAAGAACCAACTTTTGAGCCAGATCACTTTGAGCATGGAATCCCCATTCTATCATTCTATCATTTCTGGGCTGTGGGAACCTCAGACAAGTTACTTAA | 337 |

TABLE 6-continued

| Name | Sequence | SEQ ID NOs. |
|---|---|---|
| RHOH_chr4:40200705-40200805 | CTTCTTCAATGCTCAGATTAAAAAAAAATTCACAAAATATCTCTAATAACAGTAATAATAACTGAAAAT ACCTACCTCAGAGGGTTGTCGTAGAGATCA | 338 |
| RHOH_chr4:40200730-40200830 | AAAATTCACAAAATATCTCTAATAACAGTAATAATAACTGAAAAATACCTACCTCAGAGGGTTGTCGTAGA GATCAAATGAGATAAAAATATGTAAAGCAT | 339 |
| RHOH_chr4:40200830-40200930 | GTAGCCTAGTGCTGACTGCCAAAAAAAATCTCCAATAGATGCAACTCTTATGATTCTTATTAAGGACTTG GCTATTGCCACAAATGAAGGTGTTATGAG | 340 |
| RHOH_chr4:40200930-40201030 | CCCTGGCTTAAGAGCAAGAAGCCTGCAAAGCTAACTCTCCTAATCCCAACATTCCTTTCCAGGGAAAGTA GGGTGACAGGTGAGGCTGGGAATTAACGT | 341 |
| RHOH_chr4:40201030-40201130 | TTTTTGAGCACCACCAAATATGGACAAGGCACAGGGGTTGGGTGTTTTCTGAGTGAGAATACATATGAAAGAA GGAAAACAAACTTGGAAACCGCTATTTTAA | 342 |
| RHOH_chr4:40201130-40201230 | GCCATTTGGTAACAGTTTCTCTAGCTTATGAGATGAGAGAGGTCCTCCAGTATCCGCTGCATTACTTGTG GGCCTCCTTGGTTGACGTCGCTCTCTGAA | 343 |
| RHOH_chr4:40201230-40201330 | CGCTTGGGGTGGAATTCTAGAGTGCTTTTCATTAGAGGCACAGAGAGCATGACCTTTCTTCTTCCTGCCAGTT TAAATTAAATTATTTATCTTACAATGTG | 344 |
| RHOH_chr4:40201330-40201430 | TTAATTTTAGTGCTAGCAAGGCACAGCTAAAATTCCATTTCTACTTAGGAGTGGGGATCATTGTGGCAGT GAGTGCTTATTTGGGTTTGGGATGCTTGA | 345 |
| RHOH_chr4:40201430-40201530 | TCTGGGTGAAAGCCAGATTAAAAAGCATCCTCCTTCCCCATTCCACTCTCTAGGTTATAAATATTTTTT GGATTAAAAGCCTCCTTTAAAAAAATGCA | 346 |
| RHOH_chr4:40201530-40201630 | AATCACCTGGCATGTTAATTGTGCAGGGGATTCCTAATTATGTGCAGATGACGTGAGTCACACGGTG ATAGTGTTCCTTCTAGAGTCCCACTGTGT | 347 |
| PABPC4L_chr4:134727698-134727798 | ACTAGGGCTTCATCCTGTGTAATTGAAAAATATGTCACACGTGGTGATGAGAATCTATTGAGGAACATG GGCAGTTTGAAATAATATATGCAATGTATG | 348 |
| PABPC4L_chr4:134727798-134727898 | ACTAGTTTATATATAATGAAAGGAAGTATTTAAAAAGATAGAAATGACATAGACTAATCTAATTGAGAAATAT GAAAGTCTAACAGAAATGATTGCTTGTGAA | 349 |
| PABPC4L_chr4:134727898-134727998 | ATTTTATGAAGAGAAATCCACAGATAAAATTCTCCACCTTGATCTATGTAATCCGAAATTTAGATGTTAAAAAT ATGTTGATTCTGAAAATTTATATTTATTC | 350 |
| SLC38A9_chr5:54964698-54964798 | TTTGGTATGAATAGGTCAAAAACAAGTCACCATTAACTGACAGGAAGCACAGAGATTCTCAATTAGTTTTG GCAAAGACATTATTTTATAAATATGAGTTT | 351 |
| SLC38A9_chr5:54964798-54964898 | TTAAATGATTCTTATGAAGAAACTAGCACCAAAGTGAATGCACTCTGCAAATAACTCCCAGCTTCTCTGA ATTTCAAAAGCAGCCACTAAATATTATTAG | 352 |
| SLC38A9_chr5:54964898-54964998 | CAAATCAATTTAGCTGAAAGCATGAATTACAGAAGTAAATCTTTAGGTACAAAGTAGACAGCTGACACA CATGTAGCATATACACACTAGTTGATCTGCC | 353 |

TABLE 6-continued

| Name | Sequence | SEQ ID NOs. |
|---|---|---|
| ZNF608_chr5:124079827-124079927 | TTCCTTCTTTTACCAACATAGAGTTTCCCATGAGCCCTGAATCCGGGGCACTTTTGCTAACTTCCCCTGCAG CGGCGACGCTGCCACTCCCAGTGCCCCG | 354 |
| ZNF608_chr5:124079927-124080027 | CAGTGGAAGGGCTCGCGCCACCTCCATTGCTTGGCCCCAAAGCCATAGAGGTGCCCCCCGGAAGGGG CCTGGCTGCCACTGCCATTCTGTGGCCCT | 355 |
| ZNF608_chr5:124080027-124080127 | GAAGCAGGTCGTGCTTGTCTTCCTGGATTTCCCCGCATCCTTATCCCGCTTGGCGCCTCGGCTGCTCTGG CTTTTACCTGGCTTCTCCTCTTTGCTTTT | 356 |
| ZNF608_chr5:124080127-124080227 | CCCACAGGAGCCTGCCCCCGCGTGGGCGGCAGAGGTGCTGGTGCTGGTGCTGTACTATTGCTGTTTGGGTTGCCG CTGCCGCCGCTGCTCACACTTTGACCCAGC | 357 |
| ZNF608_chr5:124080227-124080327 | GCTGAATTCATGCCAGTTGCCTCTCCAGGGCGCCCTTGGACTTCCTGCCTCTTGCCAGTGCTGCTGATCTC GGGAATCCCATACAAGGCAGCAGAAGGCA | 358 |
| ZNF608_chr5:124080327-124080427 | GAGATTTATTAGCATCCTTAGAAGTTTACTCTCTTTTCACTTTTGATTTGCTGGTCTCTTTGTGAATTCC CCTGGGGAGCAGAGGCCTGAACAGAAGC | 359 |
| ZNF608_chr5:124080427-124080527 | AAATTTTAGGCACCATCAGCTAAGGCTGCGTAGCACCAGCCCCACTGGAGGCCGGACCTTCCACAATCTTG GAGTTGCTGCTACTAGTGGTGGTGGAA | 360 |
| ZNF608_chr5:124080527-124080627 | TTATTCATCTCAAATTTCTGTCTGTCTTCTCAAATCAGCCGTCCAAATCAATTATTAAATTCCAACCCG ATTTCCCAATCATCGCCCACTGTCATAAG | 361 |
| ZNF608_chr5:124080627-124080727 | TATCAACTGTATTTGGATCCACACCTTTCCTGCAGTAGAAATGTTCACTGACATCTGAAGATGAGCTCT CTAGAATAAAATCCGATGAACTTTTCTT | 362 |
| EBF1_chr5:158527642-158527742 | TTCCTCAGGAATTTGAGCTGGGGATCTGCATCCTGGGCCATTGCAGTCTTTAGCATCCTCGCCGCGCCCTG AGCGCGCTGGAGGCTCGCAGGCTGCGCC | 363 |
| EBF1_chr5:158527742-158527842 | TCCCAGGGCTGATGCCGCGTCCGCGTCTCCTCCGCCCGTTCTGGGACGTCGGGGACAAAAGTGAGGAGGACGGGA GAGCCCGGCGGGGACAGAAAGCAGGAGGACGCGCGTC | 364 |
| EBF1_chr5:158527842-158527942 | CCAGGTGCCCACCTCTTCGCTTTGAGGCGGGGCGGTGGGATGGAATGAGAATGGGTGCGCGAGGTCGGGGCTG GTAACTCTCGGAGGGGCACGGCCCTCCACGC | 365 |
| EBF1_chr5:158527942-158528042 | TGGGAGGGATGAATGGACACGCTGGGCCTGGGCCCCGGCAAATGAGGCGCTGTGGGTCCCCAGGAAGTGGGGTACCA GGCTCTACTCCCACCCCGGCCTCTGAAACGC | 366 |
| IRF4_chr6:392760-392860 | GGCCAGGAGGGTGCCGCTGGGTGGGAGAGAGGGTGCAAGACGCGGCGTCGGGAGCCTTTG GGCTGCCGGGTGCCGTTACAGGAGAGCAGGCGG | 367 |
| IRF4_chr6:392860-392960 | GTAGGAGGCCTTCGCGGGCCGAGCTCGGAAGGCGGACGCTGTGCCCGCCAGGGGATGCCCGGGC CGGCCGCGAAGGTGCCTTCTTCCGGGGCCC | 368 |
| IRF4_chr6:392960-393060 | GGACGACCCTGACACGCACGCGCGCCCTTCCGCAGCCTCAAAGACTCCGGGGCCTCGTGGTCACTGGCGC AGGGGATCGGGGCGGGGGTGCCCGGAGTGCG | 369 |

TABLE 6-continued

| Name | Sequence | SEQ ID NOs. |
|---|---|---|
| IRF4_chr6:393090-393190 | CCCGCAGTGCAGAGCAAGAGCGGCGGAGGACCCCCGGGCGCGGCGCGGACGCGGCGGGGCATGAACC TGGAGGGCGGCGGCCGAGGCGGAGAGTTCGG | 370 |
| IRF4_chr6:393190-393290 | CATGAGCGGCGGTGAGCTGCGGCAACGGAAGCTCCGCAGTGCTGATCGACCAGATCGACGCGGCAA GTACCCCGGGCTGGTGTGGAGAACGAGGAG | 371 |
| IRF4_chr6:393290-393390 | AAGAGCATCTTCCGCATCCCTGAAGCACGCGGCAAGCAGGACTACAACCGCGAGGAGACGCCGCG CTCTTCAAGGTCTCCGGCCTCGGGAGCCGGC | 372 |
| CD83_chr6:14117992-14118092 | CCCGCGCCCACAGCTCTGCAGCTCGTGCAGCGGCGCGCAGCGCTCCAGCCCATGTCGCGCGGCCTCCAGCT TCTGCTCCTGAGCTGCGGTAGGGCTCGCGA | 373 |
| CD83_chr6:14118092-14118192 | GCGGCCTGTCTGCCCCTGTCGCCCCCCGCCCCCTCCAGACACCCCCTCCCGTCGTCGTTGCTCACGACGCG CTCTCTTTCTTTGTAGCCTACAGCCTGG | 374 |
| CD83_chr6:14118192-14118292 | CTCCCCGCGACGCCGGAGGTGAAGGTGGCTTGCTCCGAAGATGTGGACTTGCCCTGCACGCCCCCTGGGA TCCGCAGGTTCCCTACACGTCTCCTGGGT | 375 |
| CD83_chr6:14118292-14118392 | CAAGGTAGGTGCTGCGATACCCCACGGGGCTTCTCCCCGACTGAACTTGGAGTACCCAGCCTCCGTCGCGCCTCCCCCACCC CCCTAGGCTGGCGACCCTCGTGTGCCA | 376 |
| CD83_chr6:14118392-14118492 | GGTGGGGGCGAGGGGCCTCTCCCAGACCTCAATCCCCTTCCTCGTCACTGAAGGTGGCCTGAGATGAATGATCCACTTAAG CATCCGCATCCAGGTACAGGGCCGAATTAG | 377 |
| CD83_chr6:14118492-14118592 | GTTTTGCTCTCCCAGACCTCAATCCCCTTCCTCGTCACTGAAGGTGGCCTGAGATGAATGATCCACTTAAG ATGTTTTGAAGGGCAGAGACTCATTT | 378 |
| CD83_chr6:14118592-14118692 | GGATTAATTCTGAGGCCACCTGGTTGTGGCCAGCAGGTCAGGAAGAAAGCAACAGGGACCTAGAT TTGGGCATTGGACAGGGGGAATGTCTCCAGA | 379 |
| HIST1H2BC_chr6:26123614-26123714 | CTCTCCAGTTCCTATATTCTAATACCCCTCCGCCGCCAAATAAAATTTGGCGTCTGCCCACAGCTCTTTTA GTGGTATCTGGGTGGCTCTTAAAGAGC | 380 |
| HIST1H2BC_chr6:26123714-26123814 | CTTTGGGGTTAGGTGTTAAGACGCTTACTTGGAAATGTTTACTTGGACTGGTTGTACTTGGTGACGGCTTG GTGCCCTCCGACACGGCCGTCTTGGCCAG | 381 |
| HIST1H1E_chr6:26156649-26156749 | CTCCGGCCCCTGCCGAGAAGACTCCCGTGAAGAAGAAGGCCCCCAAGTCTGCCAGTGCGGCCAAGCGCA AGCGTCTGGGCCCCCGGTGTCCGAGCTCAT | 382 |
| HIST1H1E_chr6:26156749-26156849 | TACTAAAGCTGTTGCCGCCTCCAAGGAGCGCAGCGGCGTATCTTTGGCCGCTCTCAAGAAAGCGCTGGCA GCCGCTGGCTATGACGTGGAGAAGAACAAC | 383 |
| HIST1H1E_chr6:26156849-26156949 | AGCGCCATCAAGCTGGGTCTCAAGAGCCTTGGTGAGCAAGGGACACCCTGGTGCAGACCAAGGGCACCCGG GCGTCGGGTTCCTTCAAACTCAACAAGAAGG | 384 |
| HIST1H1E_chr6:26156949-26157049 | CGGCCTCTGGGAAGCAAGCCTAAGCCTAAAAAGGCAGGCGCGGCCAAGCCAAGAAGCCAGCAGGAG CGGCGAAGAAGCCCAAGAAGGCGACGCGGGC | 385 |

TABLE 6-continued

| Name | Sequence | SEQ ID NOs. |
|---|---|---|
| HIST1H1E_chr6:26157049-26157149 | GGCCACCCCGAAGAGACCCAAGAAGGCGCCAAGAGACCCAAGAAGAAGGCGAAGAGAGCCGCTGCAGCTGCTGAGC CAAAAAGCGAAAAGCCCGAAAAAGGCGAAA | 386 |
| HIST1H1E_chr6:26157149-26157249 | GCAGCCAAGCCAAAAAGGCGCCAAGAGCCCAAGAGGCGAAGAGCCCAAAGCAGTTAAACCCAAGGCGGCTAAA CCAAAGACCGCCAAGCCAAGGCAGCCAAGC | 387 |
| HIST1H1E_chr6:26157249-26157349 | CAAAGAAGGCGGCAGCCAAGAAAAAGTAGAAGTTCCTTTGGCCAACTGCTTAGAAGCCAACACAACC CAAAGGCTCTTTTCAGAGCACCACCCACCGCTC | 388 |
| HIST1H1E_chr6:26157349-26157449 | TCAGTAAAAGAGTCGTTGTTCACTATTAGGGGGCTGGCTTCGGGAAAAACGTGCTAAGCAGGGGCGGGTCT CCCGGACAAAGTCGGGGAGGAGAGTGGGA | 389 |
| HIST1H2BK_chr6:27114004-27114104 | CTCCTTAGCCAGATCGATTACAAGCACTGCATTACTCAGTGTGATAAGATCATGATAATCCCTTTA AAAAGATCGCCCGAATTTAAGCCTGGATT | 390 |
| HIST1H2BK_chr6:27114104-27114204 | AGGAACACGTGTTTACAGCTCTAATATCGATAATTTAAGTGGCTCTTAAAAGAGCCTTTGGGGTTGGGCT TTAAGACGCTTACTTGGCAAGTTTACTTAG | 391 |
| HIST1H2BK_chr6:27114204-27114304 | CGCTGGTGCTACTTGGTGACGGCCTTGGTGCCCTTCGGACACGGCGTGCTTGGCCAACTCCCCGGGCAGCAG CAGGCGCACGGCCGTCTGATCTCCCTGGA | 392 |
| PIM1_chr6:37138284-37138384 | CCCCGGGTCTCCGGTCTGCGGCAGTCCTCCTGGGCAGCTCCTCCTGCCGCCAACATCTGGAGGTTGGGATG CTCTTGTCCAAATCAACTCGCTTGCCCAC | 393 |
| PIM1_chr6:37138384-37138484 | CTGCGCGCCGCCCCTGCCAACGACCTGCACGCGCCACCAAGCTGGCGCCCGGTGAGAGCACCCCGCCTCC GGCCCGGGATGCGGGGCGGCGGCGGGATC | 394 |
| PIM1_chr6:37138484-37138584 | TCCTGGGTGGGAGCTGGCGGCTCGCGGGCCGGCACTGAGTCCCCGTGCTCCCCCTTTCCTAGGCAAGG AGAAGGAGCCCCTGGAGTCCAGTACCAGG | 395 |
| PIM1_chr6:37138584-37138684 | TGGGCCCCTACTGGGCAGCAGCGGCGGCCTTCGGCTCGGTCTACTCAGGCATCCGCGTCTCCGACAACTTGCC GGTGAGTGGGCGCCCGCGGTGGGGAGGGC | 396 |
| PIM1_chr6:37138684-37138784 | GCGCCGGGCGGGGCGGGGCGCACGGGCTGTCTTTAGCCCGGACGAGGGAACCTGACGCGAGACCCTGGGCTTC CAGGTGGCCATCAAACACGTGGAGAAGGACC | 397 |
| PIM1_chr6:37138784-37138884 | GGATTTCCGACTGGGAGAGCTGGTGAGTGCCCTGCAGGAGGCCACCCCCAGGATGAGTGGGTGGGTGA GGGGCGCCCCGACTCCCGCCTAACGCGGC | 398 |
| PIM1_chr6:37138884-37138984 | CCCCTCGCCCTGCCCAGCCTAATGCACTCGAGTGCCCATGGAAGTGGTCTGCTGAAGAAGTGAGCTCG GGTTTCCGGCGTCATTAGGCTCCTGGAC | 399 |
| PIM1_chr6:37138984-37139084 | TGGTTCGAGAGGCCGACAGTTTCTTCCTGATCCTGAGAGGCCCGAGCCGGTGCAAGATCTCTTCGACT TCATCACGGAAAGGGAGCCCTGCAAGAGG | 400 |
| PIM1_chr6:37139084-37139184 | AGCTGGCCGCGACTTCTTCTGGCAGTGCTGGAGGCCGTGCGGCACTGCCACAACTGCGGGTGCTCCA CCCGCGACATCAAGGACGAAAACATCCTTAT | 401 |

TABLE 6-continued

| Name | Sequence | SEQ ID NOs. |
|---|---|---|
| PIM1_chr6:37139184-37139284 | CGACCTCAATCGGGCGAGCTCAAGCTCATCGACTTCGGGTCGGGGCGCTGCTCAAGGACACCGTCTAC ACGGACTTCGATGGTGAGCCAGGCCCGGGA | 402 |
| PIM1_chr6:37139284-37139384 | GGGAGCTGCCCAGTGACTCGGCCCGCCCCGGCGCCCAGTCCGGAGGCCTCGGCCAGTCCCGCGCCAGCC TTTTGTAAAGGTCATTGGGCCGCCTGGCTC | 403 |
| PIM1_chr6:37139384-37139484 | GATGCTAGCCGGGGTGGGACGCAGGAGAGCCTCCCAGCGTAGTAAAGCCGGGATTTTCAGCCAGCTGA ACCTGTAATGTTTCTGCATGATTTATTCT | 404 |
| PIM1_chr6:37139484-37139584 | TCAAGTGGAATTCAGTTAGTTGCCAGGCTTTCCCGATGAATAAGAGGTTGTGGGCAACCGGCGTAGCCCA GATTTTCTAAAGTCTGACCCAGTTTCCCC | 405 |
| MAP3K7_chr6:91004618-91004718 | CTCTAAACAGACAAAAGCAAAATATCTCATTAGGCATCATCTCCGCCAAGGTTCCCACTAGGCAGGAAAG GATTTTTATCTAAAGTAATTACCCTTTTA | 406 |
| MAP3K7_chr6:91004718-91004818 | GTTAAATACACTCAACAGATGAAATTTACAGAGAGTGAGAGACTGCAGCACTAGAACAGCGAAGGTGAAA ACCAGGAACGCGCGTCTCGCCGCCCGCGGG | 407 |
| MAP3K7_chr6:91004818-91004918 | CCCGCCGGAGACTGCGGGTCCGTCTCGCGGTGGGGCGCGCCCCGGTCTCCCTCTCGTTTCCTGGAGGCCACA GGTCACGGCGACGGCGGTGACCGGAGAGC | 408 |
| MAP3K7_chr6:91005793-91005893 | CGGGTCTGACAGTGCTGCGGCTGCGCGGAGACGCGCGCCGCCTCCTGCAGCCCGCCCCATGCCTGACTT ATTACTCTCGCTCCTCCTCCCTGCTGT | 409 |
| MAP3K7_chr6:91005893-91005993 | TCCAAAACACCCTTCGACGCCAGCAAAATACAATGCGCCTCGGCCGCCGTAAACAGCCGGAGGGAGAG CACACATTCGGCGCGGCCGGCGCCGCCGCTC | 410 |
| MAP3K7_chr6:91005993-91006093 | GGCTCCCACCCCCTTCCCGTTCCCTGCTACGTCTCCTTTATACCAAAACTGTAGCCTCGAAGAGCTCTCAGGCTGCGC GCCCGGGCCGCGGGGCTCCCTTCCCGCGCC | 411 |
| SGK1_chr6:134493732-134493832 | TATGAAACAGCCAGTGCTACGTCTCCTTTATACCAAAACTGTAGCCTCGAAGAGCTCTCAGGCTTACCTAT AAACGATGTTCAGTGAATGCAGTAGCCC | 412 |
| SGK1_chr6:134493832-134493932 | AAGGCACTGGCTATTTCAGCAGCAGCATAGAAACGAGCCCGTGGTTCCAGGAAGCAGCGTTCCCTCTGGAGAT GGTAGAACAACTGCAGGAGACAACAAAG | 413 |
| SGK1_chr6:134493932-134494032 | TCATTCTGGGTTGCAAATGACTATTTAATTAGTTTTGACATACACAGCAAAAGAACAACTGCAGGAAGTGGC CCCAAGTAATCTATTAACTATAAACCTGAC | 414 |
| SGK1_chr6:134494032-134494132 | AGGTTGAAGGAAATGCTATTCTGGTAACATTCTCCCCACCAAAAATCTTTGAAAACTTTTTTCTCAAACT AAAACAAAGCAGGCTGTGCAGAGACACTA | 415 |
| SGK1_chr6:134494132-134494232 | AGAGTTGACTTCTTATCCCCCCTGCTCACCTCTCCACCATTAATGTAGTCTAGGACAAAGTACAATTGTCA GCAGTCTGGAAAGAAGTGAAGGCCCAC | 416 |
| SGK1_chr6:134494232-134494332 | CAGGAAAGGGTGCTTCACATTCTTCAACAGAACATTCCGCTCCGACATAATATGCTTCTCCTAGGAAAT GACGATTCAGATTTAGTTGCATGTTTCAAC | 417 |

TABLE 6-continued

| Name | Sequence | SEQ ID NOs. |
|---|---|---|
| SGK1_chr6:134494552-134494652 | GAGGACATGAAGGAAGTGTACCAAAAGATCTTCAGATTTGAAATTACCTTTCCAAAACTGCCCTTTCCGATCACTTTCAAGAAGTGAAAGTCAGATGTT | 418 |
| SGK1_chr6:134494652-134494752 | TAGCATGAGGATTGGACGACGGGCCAAGGTTGATTTGCTGAGAAGGACTTGGCTAGAAAAAAAAAAAAGAATTTCTTTAATACCATTGCTTCAAAGGA | 419 |
| SGK1_chr6:134494722-134494822 | AATTTCTTTAATACCATTGCTTCAAAGGAAGACATCTATAACATAAACGATGTAGAAAATGTTACATCTACAAATGACTGATGCAAATGACCATACATC | 420 |
| SGK1_chr6:134494967-134495067 | AATAAAATAATACTCTGACTCAATACTTAAAATATTTATATCACTTGTTATGCCATAATGAAGCATTCTGCCTTTGATACTAATTTCTAGAAATGCTATTT | 421 |
| SGK1_chr6:134495067-134495167 | TAATCCATTAATGTAGGAATAATAACTGACTCCCTTACAGTTCTCCACAGATGCACGGCACATACAAAAACTTACTGGAGGAGAAGGGTTGGCATTCATA | 422 |
| SGK1_chr6:134495167-134495267 | AGCTCAGGCTCCTGAGGTTGGGAGATCTTCAAGATGGACTGAACTTCAGGGCTGCAGGGAATAAAGGGCACGATTTAGAATCCAGCTCGCCACTAGGGGG | 423 |
| SGK1_chr6:134495267-134495367 | CACACCAACATCAAAAGTGAGTTTCTGGCTCTACCGACTTCTACCCGACTTCTACCCCGGATAATTCACTGTTTAAACTGAAAATACCCCAATACATTAGTCAGTTAAAGAA | 424 |
| SGK1_chr6:134495367-134495467 | AATAATAAACCCCATTAAATACAGAAATAAGGATTGTTGCTCATGGAGAAGGCCGTGAATTCGGCCAACACGAACCATTTATCTTACATCCAGTTCA | 425 |
| SGK1_chr6:134495467-134495567 | AGCCAAATCAGCAAATTAACTTTAATGTTTAAAATGTCAAATATTAGAATTTAAGGAGAAATGAGATCCCCACCCCAGAAGAGTCTTCGCCTTCC | 426 |
| SGK1_chr6:134495567-134495667 | CGATAAACGCCGTGATGAGAATGTTTACCGCTGGCAAATTCAAACATACTAGTTATTTCCTCAAATCCGGTCAAACTTACTGTTTGCATGCATAGGAGT | 427 |
| SGK1_chr6:134495667-134495767 | TATTGGCAATCTTCTGAATAAAGTCGTTCAGACCCATCTCAGACTTCAAAAAAATTTCATGAAAGCTGTGGATGAAGGAGGGAGAAATAAAGAAACGTTTAGACGGCTT | 428 |
| SGK1_chr6:134495767-134495867 | CATAAGCTTCCGGCGCCACACACTAATTCTGATCCGGGACTTTCAAAAAATTTCCACTTTGCGTCTCCTGGAGCAGAAGTCCCCGCAAGATTCCTGCACTC | 429 |
| SGK1_chr6:134495867-134495967 | ACCGATGAGAATTGCCACCATGCCCCTCATCCTGGAGTAAGTGAGGGTGCCCCTTAGCAGCCTCAGTTTTCACCGTCATCACCGCGGGGACAGAAA | 430 |
| SGK1_chr6:134495967-134496067 | GACGTTAGCGCTCAAAGACCGGCTCGGCGGAATGCGCCAGGCCGCGCGCTCGGCCTTATAAAAAGGCACCGCCCGGGGGGGCCTGCGCGACAG | 431 |
| PLEKHG1_chr6:150954420-150954520 | AGGGTGAGGAGAGTCACCAGGTAAAGATGGGTTGGAAGGACCTGGCAGCAGAGCAGGGAGCAGGACCCCAGTCCAGGGCAGGGAAGCGGGAGTCTG | 432 |
| PLEKHG1_chr6:150954520-150954620 | GGCAGAGCTGATTCCAGGCAGCTCAGTATTGCTGGCCTGTGCATCCTGAGACTTATCCGAGTCGCAGGTGAAGCTGGTGGGAATCAGGCAGAGTGCAGAG | 433 |

TABLE 6-continued

| Name | Sequence | SEQ ID NOs. |
|---|---|---|
| PLEKHG1_chr6:150954620-150954720 | CTTTAGCTGGGGCAGGGTTAGCCAAGAGCCTGTCATGAGCTGCTCTCTGGGCACTGGAAACATAAGTCTGGAGGCTTGCTGCAGCTGCAGATAAAG | 434 |
| PLEKHG1_chr6:150954720-150954820 | ATGCAGGGCCTCTGACGATGGGGCCTTAGTCATCTCAGAGGTGGTGCAGAGGGTAGAAGCCTGACTGGGGTCAGAGATGAGGAGGAGAGGGTCAGAA | 435 |
| PLEKHG1_chr6:150954820-150954920 | ACAGTGATTCTAAACCAATTTGTTGAGGCAGAAGATACTAAATGCCAGAGGAGAGAGGGAGCGTAGGCTCTAAAGGGGAAGCTTGTTAGGAATGA | 436 |
| EZR_chr6:159238415-159238515 | AGACAGAGGCGCAGGCACCAGCCTTTCATCAGCTGACCAGGAGTGCTCGGCCCGGCCTGCCAGGAACCTCTTATCAAACTCCACCGGCTGCCTGCATCTA | 437 |
| EZR_chr6:159238515-159238615 | CAATTCAAGTCCATGGCTAACCTTCTGTTAGACACAGAAATTCTGCTGCAGCCAGCAAGTTTGCTGGTGTACAGGGCACCCGCTTCATGGGCCTAGTAGGA | 438 |
| EZR_chr6:159238615-159238715 | AGCGAAGCTGAAAGGCAACTTCCGAAAGCCAGTCTCCTCTCCCAAACGCCCTTTAATATCTCCCCAGTTGGATCTGGGCGCCTGTGGTTTCGGACCCTT | 439 |
| EZR_chr6:159238715-159238815 | AGGAGCTCTGAGAACTGTGTGTGGTCGGAAGCCATCTGAGTCTCCCTGTGATTGGACTTTTTAAGAAACTTCTAAGTTGTATTACTATACCCTTTA | 440 |
| IMMP2L_chr7:110545276-110545376 | TTCCCTGTCATATGACTTCCATCCTCAGCACTTCACAATATTATCATTAATGTTTAAATCATTGTCAAGTCTGTGATTGCCTTAGAGATTTATTAAGAATA | 441 |
| IMMP2L_chr7:110545376-110545476 | ACATGCTAGGATTAGGAAAGTTTAACTTTTACCATCCTAAAATTGAGATTTTTGAAAACTGTCTTATCCCCATTAAAGAAAAATAAAGGATGAAT | 442 |
| LRRN3_chr7:110697971-110698071 | TATACATACCTGCACATATACAGCACATATGTATATGTGTCTGTATTATATGTATTAAATGAAGATTATCCACATTTGTTCTTTAGGATCTTCAGCAG | 443 |
| LRRN3_chr7:110698071-110698171 | CTCTCTTCCCATCACAATAGAAAGGCCTGAGCTAACATTTCCATTTCTGCAAAAGGCAGATTTTGTTCAATTAAAATATAATGCCTTAAATTTCCACA | 444 |
| LRRN3_chr7:110737411-110737511 | GACATTTAAAGAGACTTCGTTTTCACTGTGATAAACAGGTTTGATTTGGACTTATAACTTTTTTCTAAAATTATCAAAATTAATAACGACTATAATGAAATA | 445 |
| LRRN3_chr7:110737511-110737611 | GAGGCAAATATATTTTAGAGGATTCATTCCTTGGGGTAACATTTGTTCTATAATTTATAGTCTCATAATGTTGAGAGATTAAAGCATTTAAATAACATTGTC | 446 |
| LRRN3_chr7:110737611-110737711 | AACTAACTTTCAGCTTACCTTTCTTAAGGAAAAAAAACAAAAAAAATGTTAAAAAAATGTTAAAAATAGACATGTATTTTCAAACATACAATTCATGTTTTATGTCATTA | 447 |
| LRRN3_chr7:110746681-110746781 | AAGAGATGTGAGGGACTTATAAATAATATTAAGATAATAACAGGAATTAAAGTCTCGGTGTGTGAAAATACTGTATATCTAGGATGCCACATAAAAACTGCCCT | 448 |
| LRRN3_chr7:110746781-110746881 | TACAGATCTTGCAGGAAAGTACCTGACTATACTGTATAAGACTTCGTCTGCTACCATTTAATCATACCAAAAAAAATGAATCAACACCAAATAGATT | 449 |

TABLE 6-continued

| Name | Sequence | SEQ ID NOs. |
|---|---|---|
| LRRN3_chr7:110746881-110746981 | TCTTTTCCACTGTTCTCAATTTAAAAATAATTGGAGAAATGTGCTTTGTTTAGAGAGTAAAGGAAAAC ATTCATTCAATAGTACCATGCAGAATGAT | 450 |
| KMT2C_chr7:151943421-151943521 | CAGAAAAATAGAAGATTATCATCGGATTTGGGAATCAAAGACAGCTCAGCAAAATACTAGGACATGGC TCATATAGATGAATAAGCCTGGAAATACA | 451 |
| MYC_chr8:128750367-128750467 | CTTTAGGGGATAGCTCTCAAGGGAGAGGTTCGGGACTGTGCGCGCACTGTGCGCGCCAGGTTTC CGCACCAAGACCCCTTTAACTCAAGACTGC | 452 |
| MYC_chr8:128750467-128750567 | CTCCCGCTTTGTGTGCCCCGCTCCAGCAGCCTCCCGGACGATGCCCCTCAACGTTAGCTTCACCAACAGG AACTATGACCTCGACTACGACTCGGTGCA | 453 |
| MYC_chr8:128750567-128750667 | GCCGTATTTCTACTGCGACGAGGAGGAGAACTTCTACCAGCAGCAGCAGCGAGCTGCAGCCCCG GCGCCCAGCGAGGATATCTGGAAGAAATTC | 454 |
| MYC_chr8:128750667-128750767 | GAGCTGCTGCCCACCCCGCCCCTGTCCCCTAGCCGCCTCCCGGCTCTGCTCGCCCTCACGTTGCGGT CACACCCTTCTCCCTTCGGGAGACAACG | 455 |
| MYC_chr8:128750767-128750867 | ACGGCGGTGGCGGAGCTTCTCCACGGCCGACACAGCTGGAGATGGTGACCGAGCTGCTGTGGAGGAGACA TGGTGAACCAGAGTTTCATCTGCCCTCCTACCAG | 456 |
| MYC_chr8:128750867-128750967 | CGACGAGACCTTCATCATCAAAAACATCATCATCCAGGATGTATGTGGAGACGGGTTCTGGCCCGCCGCCAAG CTCGTCTCAGAGAAGCTGGCCTCTACCAG | 457 |
| MYC_chr8:128750967-128751067 | GCTGCGCGCAAAGACAGCGGCAGCCCGAACCCCGCGGCCACAGCGTCTGCTCCACCTCCAGCTTGT ACCTGCAGGATCTGAGCGCCGCGCCTCAG | 458 |
| MYC_chr8:128751067-128751167 | AGTGCATCGACCCCTCGGTCTTCCCCTACCCTCTCAACGACAGCAGCTCGCCCAAGTCCTGCGCCTCG CAAGACTCCAGCGCCTTCTCTCCGTCCTC | 459 |
| MYC_chr8:128751167-128751267 | GGATTCTCTGCTCCTCGACGGAGTCCTCCCCGCAGGGCAGCAGCCCCCGAGCCCTGGTGCTGCTCCATGAGGAG ACACCGCCCACCACCAGCGACTCTGT | 460 |
| PAX5_chr9:37024919-37025019 | GCTCCCCATCTGTCCCACAGTTGCTCTTGGCTGAGCCAAGGCTTGCTCACCTCTCAGAGACATTGCCT AACTGGTTTGTTTTGGGCTTACATTGCAA | 461 |
| PAX5_chr9:37025019-37025119 | GATCAGTTCCTCCCCAGAGCCAGGCTGGAGTCCGAGGCAGCAGAAAAGGCTGTGGAGGGCACTGGGGCTCACC ACAGACTGGAAACCGGTTGGGCGCAGGCCCC | 462 |
| PAX5_chr9:37025119-37025219 | AAACCTTGAGGAATCGTTTGGGCTGGGACCAGAACAGGGGGCTCCTCTGCACAGAGAGCTCCCCACCGTTT GGTGGATTACTTCAGACTCAGAAAATTGAC | 463 |
| PAX5_chr9:37025219-37025319 | ACAAAGAGAAACTGACCTGCCCGCAGCCAGCCCTGGCTGCCTACACAGAGCTTTCCCCTGCTTGCCAGCC ACTCAGCACTGCCTGGCAGACACGGACATG | 464 |
| PAX5_chr9:37025319-37025419 | CTCGCCCCGGAAGCTCACCTTCACTCCAGCCGGGTCTCTGCTGCCTTTGTTAAATAGGGGACCTGCGGCT AGGAAAGCTGGATCCCAGGCTGTTGGGAT | 465 |

TABLE 6-continued

| Name | Sequence | SEQ ID NOs. |
|---|---|---|
| PAX5_chr9:37025419-37025519 | GGGGGGAGCGGGGTGGAGGACCAGGCATGGGGACGACGGCTCCTAGCCCGGAGCAACTCCCTGACCTGAAGCCCGAGAGACCCCGAGCGGCACCCGAGC | 466 |
| PAX5_chr9:37025519-37025619 | CGAGGCTGCCGAAGCCTGTCACCTTCCTCCAGCCTGGCTCTGCAGCAAACAGAAGGAAACGCGATTCGTTCCACTTGGAATTTCCTTGAAATCTCCGAA | 467 |
| PAX5_chr9:37025619-37025719 | TCTAATCCGGCGTTAACTCACCGTGAGAGGAGCGCTCATCTCACAGGAGGCTGTGGTAATGGGTGAATTGGCAGGATCCCTGCGGGCCAGGCAGCCAGGC | 468 |
| PAX5_chr9:37025829-37025929 | TTTTCGTTTCTTATCCTCTTTTTTTAAAGGGGAGAAGCCATGAGAAAAGGCGTCTCCAGAGAAGGAGCCCCAATGGGGTCTTTAAGGGTCTCTGTATGAAC | 469 |
| PAX5_chr9:37025929-37026029 | TGGCCGGCTCCTAAGCAGAAGTGAACTGAAATCCGCTACTTCCTTGATTTTTCAAAGCCCCCTCCTCAACTCCAGGACGCCTTTGGAGCCCTAGCCCC | 470 |
| PAX5_chr9:37026269-37026369 | TGTCGCCCGCCGAGCCTTGAAAGGCTCGAGTCTGCGCCAAGCTACCGCGTTGCCGGAGGCGGGATTCCCAGTGCCTCAGCCCGGGCGGCCAAGTGCGT | 471 |
| PAX5_chr9:37026369-37026469 | TGTTTCAGGTCCCCTGGGATCCCTGCACTTTGCAAAGTTAGCTGCGCGGCTGCAGAGGTCCGAGATCCTTCCGGCCTTAGTACCTGACCACGGTC | 472 |
| PAX5_chr9:37026469-37026569 | CGGCACCCCAACCCGGTTCCCGGGAGAGTTGAAGAAGCCAGCTCGCCGCCTACTTACTATGCATGGATGCAAACGGGTCGTGCTTACAGTGTATTTC | 473 |
| PAX5_chr9:37026569-37026669 | CATCGGGGCGCTCCAGATCGCAGGCCGCGCCCTCCCGGCGCCAAGGGCTGCCCAGGGCGGATAGGGAGCCTCGCCACCAGGCCAGGCAC | 474 |
| PAX5_chr9:37026669-37026769 | TGTGCGAGCTGGGCTCAGAAAACACTGCTGGAGCTTCGGGGTCTCTCTCAGAGCCTCCCTGCTGGAGACCGCCCGGAGCTGCCGGAGAGGCCGGAAATG | 475 |
| PAX5_chr9:37026769-37026869 | GTCGTAGCGCACCCGGGCGCTTCGGGGGCATAGCGTAGGGGCCCGCCTCCGGGACAGCCAGCAGCCCCGGGCAGCTCCAGGAAGGAGCAGCTTTGAGGAGGCCGC | 476 |
| PAX5_chr9:37026869-37026969 | GGCCAAGCGCCCCGCGCTTCGGGGGCATAGCGTAGGGGCCCGCCTCCGGGACAGCCAGCAGCCCCGGCCCCAGGAAGGAGCAGCTTTGAGGAGGCCGC | 477 |
| PAX5_chr9:37026969-37027069 | CGGAACAATCGGCCCCTTGACTTCACTCAGGGGGCGGAGAGACCCGGGGGCTGCCAGGCTGGTTCCGCGGCCTCGATGCTTCTGAGGTCCCTCCTCGACCC | 478 |
| PAX5_chr9:37033619-37033719 | CACACAGGCAAACAACTTTTGGACACAAACTCATATATTTTACATCTTTTAAAAATACATATACTGTAATGAACACACTGAGTCCCTTATATAAACACA | 479 |
| PAX5_chr9:37033719-37033819 | CAGGCCCTAACTTGCAGACCCCCGGAAGGACGCCAGCGTGAACATTCAGAAACAGAGAAAAACACAGACAAACTCACAGATATTTGGACTGATGCAGAAG | 480 |
| ZCCHC7_chr9:37293169-37293269 | ACAGTTTGAAGTGTGAGCCTGAACATGTTTGATCTAAGGTCTGGAGGAAGATGTGAAGCAAATCTGACCTAAAAAAATTATAGGAAAAAAGCAAATTGT | 481 |

TABLE 6-continued

| Name | Sequence | SEQ ID NOs. |
|---|---|---|
| ZCCHC7_chr9:37293269-37293369 | TCTGGATTTGTTTCACCAAGGAACAAGTAAGCAGAGAACCAGACACTGGAGAAAAAGGAGTCAGGAAGTAGACAAGGAAATGTTAAAAGAAATATAG | 482 |
| ZCCHC7_chr9:37293369-37293469 | GATAACTGAAAGAATGTAGCTTCCAGATTGCTAGCTATCAGCAGATAGATAGAAACTTTTATACAGCCTTTAAATCTTCCCTAGAAACCTTTTAAAGT | 483 |
| ZCCHC7_chr9:37371494-37371594 | CAAGGGCCTGCCAGGATGAGAACGGGCAAACCTGGCCAAGGTGACCCTATTAGGGACTACCCCTCCTAGGGACAGCACTCAGGGCCGTTCCCAATCACCCC | 484 |
| ZCCHC7_chr9:37371594-37371694 | GGATTTCCTGTCTCTGTCTCCTGCCACACCTCCTTTTGATCTACCCCCAAGACACCCCTACCTTTTTATTCTGTGAAAATTTACTCATGCTGTGGGC | 485 |
| ZCCHC7_chr9:37371694-37371794 | CCTGCTGGAAATGCCCTCCTACTGTTTCCCAAACCCGTCAGAAATTCCACGGGAAACTCCCTTCCCTTCTGCTGCAGGCACCGTCACTGTGTCTCTC | 486 |
| ZCCHC7_chr9:37371794-37371894 | AGCTCTGCCCCCCAGCCTCTGAGTACCACCTTATCCTAGCCCTTAGCTACTGGCTTGTCATTGGGGACCAAGGTCACGTTCTTCAGCCTCCCACAGAAGCCTGGGA | 487 |
| ZCCHC7_chr9:37384684-37384784 | AGGCACACTCGCCCCCAGCTCTCTCAAGGCTCTGGGTCTCAGAAGCAGGTCTAGGCTCTCTCCCCCTGCCCCAGTCCACCGTCACTCAGACCAAGAAGCCCTAAACAAACGCTGCAGGTGA | 488 |
| ZCCHC7_chr9:37384784-37384884 | TTAGCAGAGCTCTCTCTGTCAAGACAGGTGAGTTTATGGAAGAGGACTCTTGGCATCAGCACCTGGGCAAGGTGGGTGGAGTGGCCTAAACAAACGCTGCAGGTGA | 489 |
| ZCCHC7_chr9:37384884-37384984 | GGCTCCCGAGCCCTGACATGAGATGTTTATGGAAGAGGACTCTTGGCATCAGCACCTGGGCAAGGTGGGTAGAGGCAGGAGTGGGCAAATGGGAAAGTCT | 490 |
| GRHPR_chr9:37407369-37407469 | GGAGAGCCGTTTGAGATTCACCAGGTGAATGAACCCCGGTTTTTTCTGGGTAACAGTCGAATGTGAATTACTTATTTTCACAAGCTCTTGACATGTTC | 491 |
| GRHPR_chr9:37407469-37407569 | CGTCAAATTGCTGTTCCCAAAGAGTGGACTCTGGTGACATATAAGTGTGTGGGACCATTGCATCTTACCCCAGAGATCCACTCCTGATCTGGCATTATT | 492 |
| GRHPR_chr9:37407569-37407669 | CAAAATCTGCTGAATTCAAAAGATCTGTACTTCCTGCTCACCAGGTCTGAAAAGAAAAAGAAAAAGAAGAAGGAAAGACTACACCTGACAAAAGAC | 493 |
| FAM208B_chr10:5755066-5755166 | TTCACGGTTCTTCTTTAGTTTTATCTGAAATACATTTGTAAGCTTAGGGTGCAATTTGATTAAAACAGTTTTCTTTAGTGTCAATAATGGCCTTTACTA | 494 |
| FAM208B_chr10:5755166-5755266 | GAGTGAATGGAGATATTTTCCATTCTGGATTATCGTTTAATCGAAACTTTGTTTCCTGTGGAATTTTTCTGGTTTAAGTTATTTGATTTGGGAGATAAAT | 495 |
| FAM208B_chr10:5755266-5755366 | CATGTAACTAATAAACTTTGGCATCCTGGTTAACTGAAATTGCTTCATTCAATATTTGAAGACTGAAATCTGTATTGTTGCCTGTCCTAACCTAAATTATGGG | 496 |
| FRMD8_chr11:65190342-65190442 | GGACAGACAGGAGAGATGACTGAGTTAGATGAGACCAGGGGGCGGGCTGGGGGTGCGAGAAGGAAGCTTGGCAAGGAGACTAGGTCTAGGGGGACCACA | 497 |

TABLE 6-continued

| Name | Sequence | SEQ ID NOs. |
|---|---|---|
| FRMD8_chr11:65190442-65190542 | GTGGGGCAGGCTGCATGGAAAATATCCGCAGGGTCCCCCAGGCAGAACAGCCACGCTCCAGGCCAGGCT GTCCCTACTGCCTGGTGAGGGGGAACTTGA | 498 |
| FRMD8_chr11:65190542-65190642 | CCTCTGGGAGGGCGCGCCTCTTGCATAGCTGAGCGAGCCCGGTGCCTGGTCTGTGTGGAAGGAGGAA GGCAGGGAGAGGTAGAAGGGGTGGAGGAGTC | 499 |
| SCYL1_chr11:65266552-65266652 | GGGGCAGGCGGAGCTTGAGGAAACCGCAGATAAGTTTTTCTCTTGAAAGATAGAGATTAATACAACT ACTTAAAAAATATAGTCAATAGGTTACTAA | 500 |
| SCYL1_chr11:65266652-65266752 | GATATTGCTTAGCGTTAAGTTTTTTAACGTAATTTTAAGATTTTAAGAGAAAAATGAAGACTT AGAAGAGTAGCATGAGGAAGGAAAAGATA | 501 |
| SCYL1_chr11:65266752-65266852 | AAAGGTTTCTAAAACATGACGGAGGTTGAGATGAAGCTTCTTCATGGAGTAAAAAAATGTATTTAAAAGAA AATTGAGAGAAAGGACTACAGAGCCCCGAA | 502 |
| SCYL1_chr11:65266852-65266952 | TTAATACCAATAGAAGGGCAATGCTCTTTTAGATTAAAATGAAGGTGACTTAAACAGCTTAAAGTTTAGTTT AAAAGTTGTAGGTGATTAAAATAATTTGAA | 503 |
| SCYL1_chr11:65267397-65267497 | TTGGAGAGTATAGAAGATAGAAAAATATAAAGCCAAAAAATTGGATAAAATAGCACTGAAAAAATGAGG AAATTATTGGTAACCAATTTATTTTTAAAAGC | 504 |
| SCYL1_chr11:65267497-65267597 | CCATCAATTAATTTCTGGTGTGCAGAAGTTAGAAGTAAAGCTTAGAGATGAGGGTGTTTACGTAG ACCAGAACCAATTTGAAGAATACTTGAAG | 505 |
| SCYL1_chr11:65267597-65267697 | CTAGAAGGGGAAGTTGTTAAAAATCACATCAAAAAGCTACTAAAAGGACTGGTGTAATTTAAAAAAAA CTAAGGCAGAAGGCTTTTGAAGAGTTAGAA | 506 |
| BIRC3_chr11:102188381-102188481 | TGGTGTAAGAGATGTGCCAGCGGCTGGCCGAGGGCCTAGATAGTTCCAGGTGCCTAGAGCCCGGGCGCTCAGAGAGT TGAGAGTCAGTGGGTGGGGCGCAGTTATCAA | 507 |
| BIRC3_chr11:102188481-102188581 | ACACCAGGGCCCAAAAGCAGGCTTCAGGACTTCCAGGTGCTGCTCCAAATAAATTTCAGGACAGAGCCTAAGCA CCAGTGGAATTGTGAAGTTGTGGCATTTTG | 508 |
| BIRC3_chr11:102188581-102188681 | ATTTCGGTTGCCAAGAGTTATCACTGGGCCTTTGCCAGGTAGGAAGCGGTGGTAGGAAGACAGCAGTTTTTGGTGTCTTCCTGGT GAGCTCTGGCACACAGGAAGTAAAACGT | 509 |
| BIRC3_chr11:102188681-102188781 | TTAATGAGCAAATGGACCCATGTTTCCAAGCGGTGGTAGGAAGCGGTAGGAAGACAGCAGTTTTGGTGTCTTCCTGGT GATCAGCAGGAAACCTAGTAGTGCTCTTA | 510 |
| BIRC3_chr11:102188781-102188881 | CTCTGATCAATACATTGTCGAAGGCATGTCCTGATCGTAACGCTAACATTTACATGTATTTTTCACGTTTAATTATGACTTTAT TTGCTATTATTATTGCTAACATTAAGTA | 511 |
| BIRC3_chr11:102188881-102188981 | CTGCTACCTGCTATGTGCTAGGTTTGTCTCTGAAGACTTTACATGTATTTTTCACGTTTAATTATCATAATC TTAAGAACCAGGTACCATAATTATCTCC | 512 |
| POU2AF1_chr11:111249311-111249411 | GGGAAAAAGAATGACGAAAGGCAAGACAGTGAGCAAGTGAGGACACGCTTCACCGAGCCAGATCTCCA CTCCTCCCAGGGTATCCACAGGGACAAGTCA | 513 |

TABLE 6-continued

| Name | Sequence | SEQ ID NOs. |
|---|---|---|
| POU2AF1_chr11:111249411-111249511 | CACCTGGCAGAAAGCTAAGTCACTCAGCTAGAAACAGGCCCAGGGAATTCAACAGAGGCTGAAGAGCCACTGCTTATGGAAATAAAGCCCCTCCTGTAA | 514 |
| POU2AF1_chr11:111249511-111249611 | AGAACTGCATGCTTTTCCCTCCCAACCCCAAACCCTAAACCCATCTGGCTTTTGTTGTGTGAATCATAAACTGCCCTTTCTTCACCACAGTGATTCATG | 515 |
| CXCR5_chr11:118754793-118754893 | AATCCTCTCCACTGTGATCTGTAAAATCTAGACAGTCAGTCAGCTCAGTCAGTTTAAGAGTTTATTTTCCATTCTGTGGAAGAAGCAGATAAGGAGA | 516 |
| CXCR5_chr11:118754893-118754993 | GCTGCTGTCCTTAGGAGACATCCTTTAGGAAGCTGAAGACACGGGTTCAGGCCCTGCATCCTCCTCTGAGTGCTATGTGACTGGGAACAGGATACT | 517 |
| CXCR5_chr11:118754993-118755093 | TCACCTCTTCCATTCTTTCTCTCTTTCTTCTTAGGGTCGGAATATGAACTAGACAGGAAAGTACTTTGAGGTTTTCTTACCGTAAGGAGGCTGGCATT | 518 |
| ETS1_chr11:128391383-128391483 | GGGCCCTCCACCCAGCCTCAGTTCTATGGGGACGTGGAGTCAGGCGATGATGTCCTGAGGCAGCGTCCATCTCCCTTAACATTAAGGAATAAAGCC | 519 |
| ETS1_chr11:128391483-128391583 | AGAGGGTTCTCGCTCATTTGGGAAATAAAAAGCAGGAAATGGGGCGCTGGAAATTCTATAAGCTTTTCCCCACACTCACAAAACACAGCTGTGAAA | 520 |
| ETS1_chr11:128391583-128391683 | ATAAATACCACACCCCCCAACCAGGGTCTAGGGCTGCCAACAGTCCTCCTCCTCCTCCTCCTTCTCCTCCTCGTCCTCCAGATCCAGCTGCCAA | 521 |
| ETS1_chr11:128391683-128391748 | CCTTCTCCTCCTCGTCCTCCAGATCCAGCTGCCAACAGCATCCCCCGCTCCTGAAGAAATGCACCGCCAGAAGGGAACGGCGAAAGGGGAAGAAGTCC | 522 |
| ETS1_chr11:128391748-128391848 | AGGGGACCCCCGGCCTCTGGCCCGAGAGCTTGGGTGGGGGCCTCGGCCCGTCGCCATCACCCGGGGAGGGGAAAAGCTCCAGTTTGCAGTTACTGTGTTTTTG | 523 |
| ETS1_chr11:128391848-128391948 | ATGATGGTGAGAGTCGGCTTGAGATCGACGGCCGCTTCATGTGCCAGGAGTGGGGACGTACGGGATGGTAGCAAGTTTGCAGTTACTGTGTTTTTC | 524 |
| ETS1_chr11:128391948-128392048 | TTTTTAATGAGAATTAGTAACAGGGGGAAGGGACGGGGAAATCCGACTTTCTTCCCAAAAATCTCAAATTCCCGCTGCCTTTCTTTCTTCCCCGCGCCG | 525 |
| ETS1_chr11:128392048-128392148 | GACGGTGCGCGCGCCCGGCACTCCAGGGGAAGTTGGCACTTTGCGCGAAGTGACGCGCTCGGGTCCCAGCCTCGCCCGGCCGCCCGCTCCTCCTGCC | 526 |
| LRMP_chr12:25205888-25205988 | GAGTGAGTAGCAAATATCATTTATGACCCAGTTTTTGTCCACCCTCCAGGCGGGCATAGGACTACAGACATTTTTCTAGATTACAGCTAGGATATATT | 527 |
| LRMP_chr12:25205988-25206088 | CCTGAGTTTATGACAATGAAATGGTTGAAGAGGCAATATTGTGGGGCTTTCAGAGAGGTTTGCTGAGTGGCTAGGTGCATGCATGGGTTTAACCATTAA | 528 |
| LRMP_chr12:25206088-25206188 | CTTCCCTTTTGCCTTTTATTATAAGCTGGTTTGTCGTGCTGTTTTTCTTTTAAAATTAATTAAAACTTCTCAAAATTCTAAAGTAAACAAG | 529 |

TABLE 6-continued

| Name | Sequence | SEQ ID NOs. |
|---|---|---|
| LRMP_chr12:25206398-25206498 | GCATTCTCTACATACATCTACATACATATTTGCATTTTAAAAATTGAATATTTGTCATTTTTCTGTATTA CCCAAAAGTATATAAACAGTTACCAGAG | 530 |
| LRMP_chr12:25206498-25206598 | ATTTATGTGAGAGAGACAGTTGTCACATTACAGATGTCAGATTAGCTATAAAATTGTTTCATTCTAGAAACC TAATATGTAAAATAACCTTACTTATT | 531 |
| LRMP_chr12:25206598-25206698 | TAGCCATTATCAGACACAATTGCTTTTGTTCAGCCAGTTTCTTGTTCTAGCAGTATAAATATTCTTTTATAG AAAGTTACTTGTTTGAGAAATAAACAT | 532 |
| LRMP_chr12:25206698-25206848 | ATAAGCTTAAGGTAGGCTAGAGATGAAAAATTTCAGACTTGTGTTTGATTTATTGTACCCTTTCT ACTATTATCTGACAAGCTATTTAGGAGT | 533 |
| LRMP_chr12:25206848-25206948 | TTAAGAAATAGTCTAGTTTTAAAATAGCAATGTTTGCCGGACACAGTGGCTCACCCCTGTAATCCAGC ATTTTGGAGGCCGAGGTGGGCAGATTGCT | 534 |
| LRMP_chr12:25206948-25207188 | GAATTGCCAGTTTTCAATATTCTGATTCACTCTGTTAAGCTAGTAAGGCAGTCTTTAAATTACACAGTCT GTGTGTTATTTTACTACTGCTCAGAGGGC | 535 |
| LRMP_chr12:25207188-25207288 | ATTGGAGAGAGGTTCCCTTGTGATTAGAACTGTTCATGTTGAGACATGAATCATAAGGCATTCCAAAGTTG GTTTAAGGTGTGTCGCTTTAGACACTGTG | 536 |
| LRMP_chr12:25207288-25207388 | CCCAGGACTATTCTTTTGCTCCAGTTTGCCTTTTGATTAAATCAATATTATACCTGAGTTTATAAACTAC TAAGAATTTGTTCCCCTTCCTCACTGTG | 537 |
| LRMP_chr12:25207388-25207488 | ATTTTCTTGCAGTATTTTCTTAGAAGATCAACTTTAATAACTTACCCCAAAGTGCACGTTCTTGATATTA TGAACTTGCTATTGTTGTCTTCCCAGTTT | 538 |
| BTG1_chr12:92537875-92537975 | TATTGTAGTTTTTGGAAGGGCTCGTTCTGCCCAAGAGAAGTTCCTCCTTACAGCTGATTCGGCTGTCTACC ATTTGCACGTTGGTGCTGTTTTGAGTGCT | 539 |
| BTG1_chr12:92537975-92538075 | ACCTCCTCCTGCTGGTGAGGCTTCATACAGCACACAGATGGAGCCATCTCCTCCAATTCTGTAGGACACTTCAT AGGGGTCAACCCAGAGTGTGAGTTCACTT | 540 |
| BTG1_chr12:92538075-92538175 | GGGAGAAGCCTGAACAGCTCCTGACTGCTCAGTCCAATCCGCTGTGCCTGTCCAATCAGGAGGATCCA TTTTATGGTTGATGCGAATACAACGGTAAC | 541 |
| BTG1_chr12:92538175-92538275 | CCGATCCCTTGCATGGCTTTTCTGGGAACCAGTGATGTTTATAATGTCTATAGAAGAAAGAGAACAG AGAAACACGCTTAGGATCGTTAGCTCCCA | 542 |
| BTG1_chr12:92538275-92538375 | CTGCGGATTCCTCCTACCCCAGGCTCCTTTGAGGAGGCGAAAATGAAAACTATCAACTTTTAAAATGTCCA GGATTGCATCCGTTGTTGTGCATGTGCGG | 543 |
| BTG1_chr12:92538375-92538475 | GGATGGAAAAAGCGGGCAGGGTTTTAGAAATAACACAGTAGTACCGGACAAAACAATCTCCAGGAACCA ACCGGTTGAGCCGCCAAAACAGGAATCAGGC | 544 |
| BTG1_chr12:92538475-92538575 | GCGCAGCCTCGGCCAGTCGGGAAGCCACTGGCACCTATGGCCAGGCGAGAAACTGTTTACTTTCTCCACC CCACCCCAGATGCACACAATGGAGTTGATG | 545 |

TABLE 6-continued

| Name | Sequence | SEQ ID NOs. |
|---|---|---|
| BTG1_chr12:92538575-92538675 | GCTTTGGAGATGAGAAGCGCCACCGGACTGTTAACCCCGAAGGGAAGAAAAACAAGCAACCCTAAACCA CGCTCTGGGCAGGGCTGTTAATTGTGCCGGT | 546 |
| BTG1_chr12:92538790-92538890 | ACGCAACGGTTGAGGGGCTGAGGAAAGGGACGTCGAACCCACCCCAGCCCACGGCTCCTTTGTCCC CAAATCCGCCGACGGTCCTCGGACCGCAGC | 547 |
| BTG1_chr12:92538890-92538990 | TCCCGCCTCGGTGCGCTTAAGTTTCTTTGTTGCGTGTTGTTCCTCCGTTTTGCCAGCTGGGGGG AAGGGGGCGCCCTCCGTCCAGCCCCTAA | 548 |
| BTG1_chr12:92538990-92539090 | AGCCTCGCGGGGAACCGCTGTTAGCGGCCACCCAGCGCAACCACACCGCCGGTCCCGCGGCGGGGCCCAAGC GCGACCCGGCCCGGGGCGCTGCCGAGGTTCC | 549 |
| BTG1_chr12:92539090-92539190 | CGCAGCCCCGACGGCCGGACTCTGACCCAGGATGTGGGGCCCGTCCCTCCGACGCCCTCGCCCTGCT CACCTGCCAGCAGCTCCTGCAGGCTCGGC | 550 |
| BTG1_chr12:92539190-92539290 | TGAAGGTCTGCAGCTGTCGCTCCTCGTGAGCCCCCTTGGTGCCGGAGAAACTTGGAGATGAAGGACACCGGC GGCGGCGATCTCGCCTATCATGGTGGCGGC | 551 |
| BTG1_chr12:92539290-92539390 | CCGGTGTAGAAGGGATGCATGGGGCGCGTGCGGGGGCGCGTGGGCGCTGGGGCTCGGCGCGGCGC GGCCCCGACGGGCCGGAGCAGCCACCCCGGGCT | 552 |
| DTX1_chr12:113495364-113495464 | ACGCCGACACCCCCTCCCCGCCGTCGTTCGCGCCACCCAGGCCTTCGAGGACACCGTGAGAGGGAAAAG GGGCAGGAGCCCCCCTTCGGCAGGAGCC | 553 |
| DTX1_chr12:113495464-113495564 | GTCGGAGAAGGGGCCCAGACGGAGGGAGGCGAGAAGCCCCACTGAAGCCCTGTGTCGGGGAAGAGGGACC CGCAGTTGGGAGTGCAAAGGGCTGGCTGAGAG | 554 |
| DTX1_chr12:113495564-113495664 | CCGCAGGAGCAGGCTGGGCCCAGGCTCCTGGGTGACAGGCCCGAGGGGGGCCAAGGACTTTAGAGCTGTTTCCTCC AAGAGACAACACCGAAGAGGCTGGACCTCGA | 555 |
| DTX1_chr12:113495664-113495764 | ACAGGGGCGGCTGCCTCACTCCCTACCTACCTGAGCCAGCCCGAGGGGCCAAGGACTTTAGAGCTGTTTCCTCC GGCATAAGAGAGACACACTTGCTTTCCAGGGC | 556 |
| DTX1_chr12:113495764-113495864 | AGCACCCTTTATCGGAGAAGGCTCTACAGGGAAGGGTCTTTTGCAGCCTGATGGCCATCCCACATTCCT TTAACGAGGTCTCTAGGCCTCAGAGAGAA | 557 |
| DTX1_chr12:113495864-113495964 | CCCAGAGTTAGAAAGGAGGCCAGACGTCCTTGCTGTCCCCCTGGGGAGAGGAAGTTGCCCCTGCTG CCAGGCCCAGGAGGAGCTGGGCTGCAATA | 558 |
| DTX1_chr12:113495964-113496064 | GTGGGGGACCTGCCCCTGAGGCAGTGCGGGGCCATGTGCGGCCAGGCCACGTGGGCTGATGCCTGTG AATGGTCTGGGCTTCCACCGCAGAACGTGG | 559 |
| DTX1_chr12:113496064-113496164 | CCCGGGTGGTGGTGGAGTGGCTGCTGAATGAGCACAGCGCTGGCGGCCCTACACGGCCACCGTGCCA CCACATTGAGAACGTGCTGAAGGAGGAGCGC | 560 |
| DTX1_chr12:113496164-113496264 | TCGCGGTTCCGTGGTCCTGGGCAGGTGGACGCCCAGCTTGTGCCCTACATCATCGACCTGCAGTCCATG CACCAGTTTCGCCAGGACACAGTTGAGCAG | 561 |

TABLE 6-continued

| Name | Sequence | SEQ ID NOs. |
|---|---|---|
| DTX1_chr12:113496264-113496364 | ACACCCACCCATGCCACCCGCCCCGCGAGCCATCACTACCTTGCAGCGTAGGATGCTGAAAATCCCAGTAAATCTGCTGATGCCAAATCCCTTCCCA | 562 |
| DTX1_chr12:113496364-113496464 | TCTCCCTGCCTCACCTCCAGAAAAACAGGGCAGTCTAACCTTGTCCAGTTTAAGACTTGGATTCCAATGCAGCCTCTGAGCAAGCTGTAGGGCCTTGAGC | 563 |
| DTX1_chr12:113496509-113496609 | GGGTAGATCAATATCTCCACAGCTGAGTGAGGATTAAATAAAATTGTCTCACTGAGCACAGAACCTAGAACAGCAGTAGCATGGGATTGTAGAATAAG | 564 |
| DTX1_chr12:113496609-113496709 | GGCTTTACAGTGCACTTCCTCATTTGATTTTTCCCAAGAATCACAGGCAGTAAGTCTCTGTATTGTTGTATTATTATGAGTCCCATTTTATAGATGAAGAA | 565 |
| DTX1_chr12:113496694-113496794 | TTTATAGATGAAGAAACCGAGTCTCCCAGAAGCTGAGTGATTTAAACTCAGAGCTGGGATTTAAACCCAGGCGGTTGAGTTCCAGAACCAAAGTTCTTAA | 566 |
| DTX1_chr12:113496794-113496894 | CTGGTATCCTATACTGGCTCCAAGTGTTGGTTTGTGGGGTGGAGTCGTGCTGGTGTAATTAATTGGGGATGGGGGCGTTGGTGGTTGTTGATGGTGGG | 567 |
| DTX1_chr12:113496894-113496994 | TGAGGTGCAATGAGGAGAGACAGTGTTAGCGGTTGTCTGTTGGTGGTGACTCAGTGATAGTATTGATGGTGGTGGGGTCTTGGTGACAATGGAGGGATG | 568 |
| DTX1_chr12:113496994-113497159 | TGTTGGTTGACATTGATGATGTTGTGTTGGTGGTGGTGCTGGAAGTGGTGTGATGGGGTGGTGATGATGGAAGAAATGAGAGAATGTTGGTGCAGTCTT | 569 |
| DTX1_chr12:113497059-113497159 | CGTGGCCATGTGCTGTGGTCGTAGCCCTGTGTGGCTGTTACTTAGTGGTATTGGTGATCCTGTTGTGGTTGTAATGATGGATTTGTCATCGTTGGGGAGA | 570 |
| DTX1_chr12:113497159-113497259 | TTGGTGGTAATGTGATGCTGATGATGGAGATAAAATCGATGAGGTCCCACTCTCAGGCCTACTCTCTTTTGTTCTGAGATTTGTCATCGTTGGGAGA | 571 |
| DTX1_chr12:113497259-113497359 | TGAAATGGCTGCTGTGCGGCTGTCATCTCCAGGCCCGCTGACACTTGGGCGCACTCTGATCATCGCAGATTTCTCCTTCATTCTGGGCGCGCATTAGCTCTGGT | 572 |
| BCL7A_chr12:122458781-122458881 | CCCGCCGGTTCCGCTGCAGCTGAACAGCAAGATGCGGCACCCAGGTTACCCTGATCATCGCAGATTTCTCCCGGGGCTCTGTTCTGAGGCCTCAAAAGT | 573 |
| BCL7A_chr12:122458881-122458981 | GCTCCTTGTAGATGGGACCAGGGGTCATTTGGGCAGTAGCAGCGCCTCGGTCTCCAGTCTGGTACTGAACTCAGGAATGGCTTAAGGTGAAATCGTGGTCCT | 574 |
| BCL7A_chr12:122458981-122459081 | CTGGTGAAGCTCAGCGAAGACCCCCTCGCCTTGTTTATGACAAGAGAGAACTTCTGGGGGCGGGAGGAAGAGTCCCTGTTTACGATGCTGATCATTGAGC | 575 |
| BCL7A_chr12:122459081-122459181 | TTTTGCTGAGCAGAAAACTCTTTAGTACTCAAGGTCGAGAGTCTCTGTGGTCTGCCTGGCACCAGGCACCTTCCTACAACCCTAGTTTTCCAAAAGAC | 576 |
| BCL7A_chr12:122459181-122459281 | AAAGCCTGGGGACAGGCACGTCCTAGCTCGCATTTGAACAGGGCGCAGCAGAGATGCGCGATGCCCAACTCTTTCCAAGAGCACCTCGCGTCCC | 577 |

TABLE 6-continued

| Name | Sequence | SEQ ID NOs. |
|---|---|---|
| BCL7A_chr12:122459381-122459481 | GAACCGGTGCCTTCAACTCGGAGAAGTCAAGAGACCCGCAAGAAACTTGCACGACTGCACCCGCCGCGC GCTCTGGGGGCTGGGCAGGGGCAGCTGGGC | 578 |
| BCL7A_chr12:122459481-122459581 | TGGCTCCCGGGAACGGACCCCCCCGCGCCCCGCAGACCGGCTGTCTCCCATGGACCCCTCGGCACCTG CAGCCTCCGAGGAAGGGTCAGCGCGCTGT | 579 |
| BCL7A_chr12:122460811-122460911 | GGGGGGCTCGGGCCAGCCGATGTTTTTGGCCAGAAGCCGTTCGTCTCGGCGCGCGGCTGCCTCTCCACAC CGGGAGCTCGTGTTTGTTTGCGGAGGGAG | 580 |
| BCL7A_chr12:122460911-122461011 | CTGTTGTTTTTGTTCTCTGCACCGGGGAGAGGGGGAGACTTGGTGGCGGCCAGGCTGTTTTCGGATCAC ATTAGCGTCCGCCCGCGTGGCCCGGTCGA | 581 |
| BCL7A_chr12:122461011-122461111 | CATTAAGGGGATCGAACCTTTCCGCGCCTCGTCGGGGTCTGCTCGGAATCGGCCCTGGGCCAGGCCCG AGGCGCAAGCAGATCGCCAGGTTGGGTCAG | 582 |
| BCL7A_chr12:122461111-122461211 | AGTTGTTGAAAACTCCCCGCTGCCTGATTTCAACTTTATTATTTTTTCCACGCCTTCACTGGGGTCCCGG AGGGAGAGGAGCCGCCAACGCTGGCT | 583 |
| BCL7A_chr12:122461316-122461416 | AGTAGCGCCTCGTTCTCTAAAAGCCACTGGGGGCGAGCCTCCGGTGTGGCGGTGTCACAAGTTAGCTGTC CTTTCTGAGTCAAACCCAACACAAAAGGCA | 584 |
| BCL7A_chr12:122461416-122461516 | AGAGGAAAAATCAATAAAGTCCACGTGTCTCCCCGGCCTGCTCTCCATGGAAAGGGCTGGCTGCGATGCCGGATG CCCGCCCGTGGGCTTTTGGCTCCAGTG | 585 |
| BCL7A_chr12:122461516-122461616 | GGACAAAGAATTTTCAGAACCGTGAGAAGGGAGGCTTTCCAAAGTTGAGATTCAAGTCGTCGGTGTCTC GGGAGCTCCCCTGGTACACAGGGTGCCCGG | 586 |
| BCL7A_chr12:122461616-122461716 | TGCCCGACTGGAGCCATTTAAAAATGCAGAAACAGCTGCAGGCCAACACACACGCTGGAAAACAAC CCGCAGCCCCTCTACTGTGGGATTCCCGC | 587 |
| BCL7A_chr12:122461716-122461816 | GGGAAGCCCGGAGTTGCTCCCCTCTTCTCTGCTCGAGGAGGCGTGGGGCCTCGTGTCTCAGGTTCCCGCT GTCCCTTCTGTCCGGCCTGGAGGTTGGG | 588 |
| BCL7A_chr12:122461816-122461916 | AACAGCCGCAAGCCGCCCTTTCTCCTGACCCCGGGACCAGGCCTGTAGTTGGAGCTTGAGGGGCTGTACCTCTG GGACAGAGGGCTCCTGCACCCTGACAGCTGC | 589 |
| BCL7A_chr12:122462001-122462101 | GGAGGCCTTCCTGAAGACCTCAGGCTTTGGGATCTCATGTGTCCAGCTTCCAGTTCACTTCGTTGCCGACCT CGCCTCCCTGGGTTTGGGAAACAACACAT | 590 |
| BCL7A_chr12:122462101-122462201 | CGTGTCTCTGAAGACCTCAGGCTTTGGGATCTCATGTGTCCAGCTTCACTTCGTTGCCGCGACCT TGGGCATATCATTGTCACTTCTCTAACCA | 591 |
| BCL7A_chr12:122462201-122462301 | TGGTGACCCGGGGTTTTGTGCTTCCAGTTCCCCTCGGGTTATTGAGGACGATTGAGGTCATGCCTC CGAGAGCACCCGCCCCTGGGCGCAGGAGG | 592 |
| BCL7A_chr12:122462716-122462816 | AATGCAAATTTAACAGGCACCCTGTATTTTACCCAGAGGAAGCCGAAGTGTTTGGCAGATCATTTGGC CCCATGAGCCTTGGGTGGGTTTCTCCTCAG | 593 |

TABLE 6-continued

| Name | Sequence | SEQ ID NOs. |
|---|---|---|
| BCL7A_chr12:122462816-122462916 | CCCTAGTGACCCCTAAAATTACCCCCCGAGACCCACCACCTGTCCCCTGATGCTTCCCCACCCCGGAAAAAGCTGTGGCCTCCCTCCCTCATTTGGGCAG | 594 |
| BCL7A_chr12:122462916-122463016 | GCTGCCTCCTGTTCTCTTTTCTGTGTTTCAGCAAGGCAGGCCAGTGGAGGTGAGGTGACCAGAAGATGGCTAAAGGGAAAACAAAATGGTGGGCCTCT | 595 |
| BCL7A_chr12:122463031-122463131 | CCAGGGTTTGGGGGCCCCTGTGCTGGTGAGGAGAAGAGACCCCAGGGCGATGCTAGGAGACGAAAGCTTGGGCTGCAGCGTAAGCTTGGAGGCCCGCTGC | 596 |
| BCL7A_chr12:122463131-122463231 | GGTGGCTCACGCTGTAATCCCAGAGCTTTGGGAGGCTGAGACAGGAGGATTGCTTGAGCCCAGGAGTTTGAGACCAGCCTGGGTCTCAAACCAAAAAAA | 597 |
| KIAA0226L_chr13:46959165-46959265 | TAAATATAATTTAACGCCAATCTGAGAAAAAATGACTTATTAGCTGTGTGATTTTGAGCAATGCTCTTAACCTCCCCATGAAGGATGGTGAGAACGA | 598 |
| KIAA0226L_chr13:46959265-46959365 | ACAGAATTGTAGCACGTCTGTATCAGTCTGGTACAACATGTCCTATGAAGGTTAGCTTTATTATCACCATCATTATTATTGCAGAAGACTTTCAGTTCAGA | 599 |
| KIAA0226L_chr13:46959365-46959465 | ATAAGAGACACAGTTACAGAGACCTGTTTTATTTTCCAGCTTCTTAACTGAGTCATCTTTCAGCTCCTTTTAATTAAAAGAAAAACAATCAGAGAT | 600 |
| KIAA0226L_chr13:46961680-46961780 | TCAAAGACCTGGCAGAGATCTTCCAACCCCAGATGCCCCCAGCAGCGCAGTATTAGCAGTCATACAATTGCCTGAAATGAAGAATGAGTAATCTGAT | 601 |
| KIAA0226L_chr13:46961780-46961880 | GAGTCGGCCTGAAATGCACCTGCAACTTACCCGGAACGTGAGCTGTCTCTCTCTGACCTTGCTGGCTGCTTCACCTGGAGTCTGAGTCCGACTCATGT | 602 |
| KIAA0226L_chr13:46961880-46961980 | AGCACTTCACTGTCTCCGCTTAGTTTAGCCTTCACTGTCAGCAACTCGTCAGCAGCCTTGTCCTCTTGCAGCGAAGGTTTGGAATCCCATCACGGGTGTGCAGTG | 603 |
| KIAA0226L_chr13:46961980-46962080 | GTTAGTCCTGAGATCATGGTGGTGCTAGGAGGAACCTGCCAACCAATACAGAAAGTTGTCACGAATAGAAACCTAAGCTCTGGCCGCGGCGGTGGTTCAA | 604 |
| ATP11A_chr13:113516229-113516329 | AGATATACTGTTCTAGACATGTGTCTGAAAGGAATCCTGCAAATTCTGTCTTATTGAACAGGCATAAGGTGTCACGTCAGGCGTAAGGTGTCACAGCAGG | 605 |
| ATP11A_chr13:113516329-113516429 | CGTAAGGCGTCACCTCAGGCGTAAGGTGTCACAGCAGGTAAGGCATCACGTCAGGCGTAAGGCGTCACGTCAGGCGTAAGGCGTCACAAGCTCGGTGA | 606 |
| ATP11A_chr13:113516429-113516529 | ACGTCAGGGTGCCTTGTCTTCTCGTTGCTTCAGAAGCAGCATGTGGCAGCATCTCTGTGCCTATGACGATATTGCAGTGAATATGAGA | 607 |
| SYNE2_chr14:64330252-64330352 | AATTGTACATTTCAACAACAATAAATAAGCTGTTCAAGACTGTCTCCCATGCCTCCAAAACAAATAAAACCCCCACAACTCAAATGCATATAAGCTGTT | 608 |
| SYNE2_chr14:64330352-64330452 | ACTATATAGTTATAATGGTGAGTTATAGCACCAGTGTATGATGGGATTGTTGATAGAATAATGCATATTAGAGCTTTTAGTTCAAAAATTTGAGATAGTGATTCA | 609 |

TABLE 6-continued

| Name | Sequence | SEQ ID NOs. |
|---|---|---|
| SYNE2_chr14:64330452-64330552 | GAAAGAAAAAAGGAATGATTATCATGAATTCTGTTTATTAGAATTCTGTTTATTAAAGAGTTAAAGATATGTTTTATTTTTTATCTTTATTATCATTA | 610 |
| ZFP36L1_chr14:69258238-69258338 | AATTCTAATGTTGGTCCCTTAGGATCCAGCAGGGGGGACCGGGAATCTGTAACTGCAACCACCCCACCGAGAGGATTACAGGAGCGGAGTCGAGAGCTGG | 611 |
| ZFP36L1_chr14:69258338-69258438 | TTCCCAACAATGAGGTTCATTTAAAAAGTCGTCGAGGGGGGGAGGGGAGGGGCCAAAGAAAGAAATAGATCAAAGAGCGGGAGAGTCGAGAAAGAAGGAAGAAA | 612 |
| ZFP36L1_chr14:69258438-69258538 | TGTTGGGGAGCGCTGGCAGCCGGCCTGGCAAGTGAGTTTGGGAATGTGCAGGGAGGGAAGGAAGCTGAAAAATTCAAACTTTTTAAATGCTACTCTTCA | 613 |
| ZFP36L1_chr14:69258538-69258638 | GCTCCTCGGCGTCCCTGCACCCCAACCCTGCAGCCTGCCCCTCGGGCGTTGGGCAGCTGCACCAACAGGAGCAGCAAGCTGGGAAAACAGAGCAACATGACCCGAC | 614 |
| ZFP36L1_chr14:69258638-69258738 | GTGTTAAGAGAAGGCAAAACACTTCAGCAATTAAAACACTTAAAAAGTAGCCCAGCAGCTTCACCCTTTCAAATTGGGAGGGGGAGGTTGGAAAGAAATTTAACAACAT | 615 |
| ZFP36L1_chr14:69258738-69258838 | CCATAGACTTTTGCTATGTACATTTAAACCGCAGTCCTGGAACATTCCGAGTTTAAAACTTGCTTTTTCAACACTGGCTGACAAGCAACATGTTTTAAGG | 616 |
| ZFP36L1_chr14:69258838-69258938 | AGCCCCCCCATTAAATCCTTACTCGCGGACTCTCGAGTTCAAGCCACCAGCATTTTGTCGCCACCTCCCCCCCAACCCCGCCCCGCAATCGATGAGCGCAAT | 617 |
| ZFP36L1_chr14:69258938-69259038 | GCTCGGCAACAACAGGTAAGCGGGTCAACCTGCAAATGCCTCTTTCACCCCAAAGTTTGCTGACGATCGGCTATCGCGGGAAGAAGCCCAACGGAGCTAGG | 618 |
| ZFP36L1_chr14:69259038-69259138 | GCCGACTCAAGCCCACTGCAAACTTGTTCTGCAACATCTTTTTGAATCACAACTTGGCCTTTCTTCCTCGCATATCCCCAGCTCCCCCAAAGAGTGGA | 619 |
| ZFP36L1_chr14:69259138-69259238 | GGAAAACATTGTCCCGAGACTCACTTCCCGAGGGACCTCCCAACCCCCACGGGTGGGTAATGCCGCTGACAGACCTAGGGCGCAGACTGGGAA | 620 |
| ZFP36L1_chr14:69259238-69259338 | CCCGATCAGACAGCAAGCCTGGATCCAGCAGCACGTTACGTAAAACAGGATCGCCCAAAACTTGTCCCAATCCCAGCCCTCCCCCCGAAGCCCCGGG | 621 |
| ZFP36L1_chr14:69259338-69259438 | CTGCCCTGCCAGGCAAACTTCGCCCCTCAAAACCCGGCCTCCAGATTCACATGTAATCCCCCAGCAACTGTTGAAACTCAAAGGGTGGGAAGGACGG | 622 |
| ZFP36L1_chr14:69259438-69259538 | GGCCAAATTCCTTCAAACTTGGGAGAAATGCCGGAGGGAGAGAAAAGAAATCATCTCGCTGCACCACTTTTCCCCATTGCCTTTCCAAGACCCAAACTTTTGGGGG | 623 |
| ZFP36L1_chr14:69259538-69259638 | TTCTTTCTTAAGGCAAAAAGAAAAAGACTTTTGAAAAGCAAAATGCTCCGCCCCCCCCCTTTACCTTGCATAAAACTTCGCTCAAGTCGAAGATGGTGGCAGAC | 624 |
| ZFP36L1_chr14:69259638-69259738 | ACGAGGTGGTGGTCATCCTGTGCGTTCGCGCGAGCCAGGGGCGAGGATCGTGTGTCGCGAAGGTCCCGGTGCGGGGAAGGCGCAGCCCTTCCTGTCT | 625 |

TABLE 6-continued

| Name | Sequence | SEQ ID NOs. |
|---|---|---|
| FLRT2_chr14:84420586-84420686 | TTATTTTTTTATATTAAGATTTATTCTAAATTTGATTCTTCTAAATATAGTATATATTTAGTATATATAATGCACCCTCTTACCTAATGATCATTT | 626 |
| FLRT2_chr14:84420686-84420786 | CTAAATAATCATAACAACATCGAGTAAAACATGTAATAACACATATTATTATTAAGATAAGTATAAGAAAATATAATAATAAATTGTCCCTGTTCTAAAA | 627 |
| FLRT2_chr14:84420786-84420886 | GGTAATTATATAATGCTGAATGTGTCAGAGGCATTCGAACCAGAGTGACTCCATTTTGAGTGAGGGCTAGGAAAATGAGGCTGAGACTTGCTGGGATGCA | 628 |
| TCL1A_chr14:96179592-96179692 | TTTTAATTTTATGCTTTCTTCTTCAGTGTATGTTTGGAGAGAGTTTGAACATTTTTGACTTCTTTTTCATTGAGTAAATCCAAATACTTGTAAAGACTTATC | 629 |
| TCL1A_chr14:96179692-96179792 | TATTTCTTTAACAAAAACTTAACATGGATTAAGGACCCATCTTAAGGCATCACACATTAAAAAAGTCAATATTGATTCAATACCGGCCTTATACTACGA | 630 |
| TCL1A_chr14:96179792-96179892 | CATCACTTGTTAAATTTGTTTTCTAAATAAAGCCAGAGGTAGTGGAAAATACTTCACACTCTAGGCCAGTGTTTGCTATGCCTGGTTGACCCTAAACTG | 631 |
| TCL1A_chr14:96179892-96179992 | TTGAGGGTTCTTTTTAAAAATACAGATTTCTGGGACCCACCTGAGAAGTTTCAAGATGATTCCGATAATCGGCCATAATGGATGAGTCACTTAGAGATACCCATTTTTAAG | 632 |
| TCL1A_chr14:96179992-96180092 | GATTAGGACCCCAGAAGCCCAGAAATGCCTGCTGTAGTCAACATTATAGTCACACTCCACAGGCACTGGGTCCACCCCTTTGACCGACATTCCTTTGCGG | 633 |
| TCL1A_chr14:96180092-96180192 | TTTTCCCACCCCTTCTTCCCTGCCTGGAGAACTTCCTATTCATCCTCCAGAGCCCGGCTCAAAGTGGCTTCATCTGTGGGGATCCTCCCCTGCCCCATAGTGA | 634 |
| TCL1A_chr14:96180192-96180292 | GTGCTCCTTGAGTCCTCCGCCTTCCGCCTTCCTAGGGCATCCCAAGCTCCCAGGGATCTCCTGCCTGCCTCGCCATCCGCTCCAAAGCTGGCTGACCTCGATGGT | 635 |
| TCL1A_chr14:96180292-96180392 | TAAGGGCAGCCAGGCGTCGTCCTGTCTTCTCGTCCAAATACACGAACTTCTCCCAGGCCCCACAGGCGGTCGGGTGGTGACTGCCTCCCGAGTGTCGGG | 636 |
| IGHA2_chr14:106048955-106049055 | AGGAATCAGATTTCAAAATGAATGTATAAGAAAAGAACCGGGAGTCAGTGATCAGGAACAGGGGATCCATGCATCTGGTCCAGGGCTTCAGCCGGTCAGGAG | 637 |
| IGHE_chr14:106068705-106068805 | CCCTGGCCTGGAGTCCCAAGTCCCCAGCCCATCCTGCCCCTGGAGCCCAGTTTAGCTTGGTCTTGAAGTCTGCTCTAGGTACCCCCAAAATACAGTATC | 638 |
| IGHE_chr14:106068805-106068905 | CAGCCCCGCCTCTGCCCACCGGGACAGCCAAGTTCAGCTGAGACTGGCCTACCGGGGGAGTCGCCCTCTGAAGTTCACTCTAAGCCAGCCTGGTTCAGCCT | 639 |
| IGHE_chr14:106068905-106069005 | GGGCCAGGTCAGCCCAGGACCTCCCCTTGCAGGCAGCAAACTCTTATTTCAGTCCAGCCAGTCAACCAGCTTGCTTCTGACTCAGCTCCTCTTAGCCAG | 640 |
| IGHE_chr14:106069045-106069145 | TTAGCTCAGCAAAGCTGACCTAAAGTAGCCACCTCACCCCCAGCTTCATCCAGATGAATACAGTCCAGATCAGCTTAGTCAGTTAAGCCTAGCTAGTA | 641 |

TABLE 6-continued

| Name | Sequence | SEQ ID NOs. |
|---|---|---|
| IGHE_chr14:106069145-106069245 | GTTAAATCCAGTTACGACCAGTTCAACTAATCCTGCTCAGGCCTGCTCAGCCCCAGTGAACCCAGTTTAGCCGAGGCCAGGCCAGCCCAGCTGAA | 642 |
| IGHE_chr14:106069245-106069345 | TACAGTTGCCCAGTCTAGCTCAGCCCTCAGCCACTGCCCAGTTTAGCTGAGCTCAGCCTGGCCCAGCCCAGCTCATATCAGCCCATTCAGCTGAAC | 643 |
| IGHE_chr14:106069345-106069445 | AGTTTGACCCAGTCTAACCCACCAGCTCTGACCCGTCTCAGCTGAACCCAGCCCAGCCCAGCCCAGCAAACCCAGTTTAGCCTAGCTCAGCTCAGCCCATTTC | 644 |
| IGHE_chr14:106071060-106071160 | CCTGCTCCTAGGGGTGGCAGGCAGTCTGACCAGCTCTGACCCTGCCCCAGCCCTAGCCCTGCCCCAGCGTGGGGTCTCTGACCTTCTTGGTCTTGGGCCCAGCCAAGATTCCCAGCCC | 645 |
| IGHE_chr14:106071190-106071290 | TTCTAGTTTTCTGTCCCATGCAGGGAAGGATGCCTAGAGTCCACGCAGTGACCAAGAAGCTTGGTTGATGCTGTGAGGGTGGCCCAGAGAGTCCCC | 646 |
| IGHG4_chr14:106095335-106095435 | CACCTGCTGTCTCCTTGGTCTGGCTGAGAGGAGGGCCCTACGGCCAGCTCTGCTGACCCTGCCCTGGGCTCTGGTGATGCTGCCGGCCTGGACAAGCCCT | 647 |
| IGHG4_chr14:106095480-106095580 | GAGCTCAGGTGCTGTCGTGCCCATCCTGCACCAGCCGGTTCTGCCGCATCCCGTCATGTTCCTCGTGCTCCCAGCCCCGGTCGTCCTGAGGCC | 648 |
| IGHG4_chr14:106110675-106110775 | TGAGCATGAGTGGGGCGGGCAGAGGCCTTCCGGTGAGGAGACAGATGGGGCTTGCCTTGCCTGCCCCTGGGCTGGGCTGCACAGCCGGGGTGCCTGCTCCAGGC | 649 |
| IGHG2_chr14:106110775-106110875 | AGGAGGGCTGAGCCTGGCTTCCAGCAGACACCCTCCCCTGAGCTGGCCTTCTCACCAACTGTCTTGTCCACCTTGGTGTTGCTGGGTTGTGATCTAC | 650 |
| IGHG2_chr14:106110830-106110930 | ACCAACTGTCTTGTCCACCTTGGTGTTGCTGGGCTTGTGATCTACGTTGCAGTGTAGGTCTGGGTGCCGAAGTTGCTGAGGCACGGTCACCAGGCAG | 651 |
| IGHG2_chr14:106110950-106111050 | GGACTGTAGGACTGCGGGAAGTGTGCACGCGCTGAGTTCCACGACACCGTCACCGGTTCGGGGAAGTAGTCTTTGACCAGGAG | 652 |
| IGHG2_chr14:106112335-106112435 | TGCTACACTGCCCTGCCACCACTCCACTCAGTTCATTGTGCTGGTGGCCCTTGGCTCCTGGCAGCCCATCTTGCTCCTTCTGGGGCGCCAGCCTCAGAGG | 653 |
| IGHG2_chr14:106112435-106112535 | CCTTCCTGCCTAGGGTCCGCTGGGGCCAGCCCTGAGAGCTCAGCCCACACCTGCCCTCCTGGTCTCAAGCACACATTCCCCTGCAG | 654 |
| IGHG2_chr14:106112535-106112635 | CCCGAGCCCTGGAATGCTTCCCTTCTCCATCCCAGCTCACCCTTGCAACTGCTCAGTGGATGGGCTCACACTCCCCTTCCTGCACCAGGAGGCTGCA | 655 |
| IGHG2_chr14:106112635-106112735 | CTGCACTTTCACCAGCCCTGCTGTCTGCCAGCAACTACCCAGCTCCTGCCAAAATCTAGGAGCTGAGTGATGCCTCCCACCGGCCCTGCTCACCT | 656 |
| IGHG2_chr14:106112735-106112835 | GTGGTTGCTTGCCCTGCCCTGAGCTTCCTGAGTGCCTGTCCCCTGCTCCTGCCTCCTCGTCCCCACCGCCCTGCTCACCTGTGGCTGCTCTGATTCCCTGAGGCT | 657 |

TABLE 6-continued

| Name | Sequence | SEQ ID NOs. |
|---|---|---|
| IGHG2_chr14:106112835-106112935 | AAGCCTCAGTCCTGCTCACCTTCTGATGCTCTCCTCTGTCCCCTGAGCTCCAGGGGCTGTCCCCTGCTCGT CCTGCCCTCCTACCTGCCCCTGCTTACCTG | 658 |
| IGHG2_chr14:106112935-106113035 | AGGGTGCTGCTGCCCTGGTGCTCTGAGCTCCAGGGGCTGTCCCCTGCTTCCCCTGCTTCCTACCAGCCCCTG CTCACCTGGGCTGTCTCTGCCCTGGTCC | 659 |
| IGHG2_chr14:106113020-106113120 | CTCTGCCCTGGTCCTCCCTGAGCTCCAGGGGCTCCCCTGCTCTTCCTGCCCCCACCAGCCCCTGTTCACCTT CAGATGCCTCCCCCTGTCCCCTGAAGT | 660 |
| IGHG2_chr14:106113120-106113220 | CCCAGAGCTGCCCTGTTCCTCCTGGCTCCAGCCCCGTGCTCTCACCTGCTGCTCTGCCCTGGTCC CGAGTTCCAGGGGCTGCACCCTGTTCGCC | 661 |
| IGHG2_chr14:106113220-106113320 | CACCTCCCACTAGCCATGCCAGTCTTGATGCTCTGTCTCCTGGTCCCCTGAGCTCCAGGAGCTGTCCCCTA CTCGTCCTGCCACCCACCAGCCCCTGCTC | 662 |
| IGHG2_chr14:106113320-106113420 | ACCTGAGGCCACTGAGGCTGCTCTGCCCTGGTCTCCCCTGAGCTCCAGGGTCTTCCCCCTGCTCATCCTGCCT CCCACCTGCCCTTGTTCACCTTCAGTTGC | 663 |
| IGHG2_chr14:106113420-106113520 | TCTGCCCTGGTCTGCTGCTGAGAGGTGCCCCTGCCCTGCTCACCTGTGCTGCTCGGTGTACCCTGCTCACCTGT GGTGCTCGGTCCTGGTACCCTGCTCCCT | 664 |
| IGHG2_chr14:106113450-106113550 | GCCCCCTGCTCTTCTGCCCCACCTGCCCTGCTCACCTGTGCTGCTCAGGTGTCCTGGTACCCTGAACTCCA ATGCCCCCTGCTCTCACTCTGCCCTC | 665 |
| IGHG2_chr14:106113550-106113650 | CTCAACCCGGAGCAGCAATGTCACTCAGTGTTGCCCCCTGCTCTGTTCCCCTGTCCTGTCCAGGT TTGGGCTGTTTTTCTGGCCCTCATTTTTGT | 666 |
| IGHG2_chr14:106113695-106113795 | TGTCCAGTCAGGTCTCCCAACAGAGCCCCTTGCCTCTGCTTCTCTGCTGGGTGAGCTCCAGAT CCTCCCGTCCCTGCCACTGCTCCTGCTCTG | 667 |
| IGHG2_chr14:106113795-106113895 | GAAGCCTCCAGAACCTCAGCTCCTCCAGTGGACTCTTCCCTCCATCTGTGCACTCAGCACAGCTCTCCC CCTCACCCCTCCCCTGCCCCAGCCTGCT | 668 |
| IGHG2_chr14:106113895-106113995 | GCACTCTGGGCCTTTCTGGGCTTCCCTGGACTCTTCCCTCCATCTGTGCACTCAGCAGCTCTCCCACTCCGC TCCACTCCGCTGCTGACCACAGCCCTGC | 669 |
| IGHG2_chr14:106113905-106114005 | CCTTTCTGGGCTTCCCTGGACTCTTCCCTCCATCTGTGCACTCAGCAGCTCTCCCCACTCCGC TGCTGACCACAGCCCTGCTCTCCCCGCCAG | 670 |
| IGHG2_chr14:106114175-106114275 | CCCAGGCCAGACACTGTGACCCTGCCTGGCTCCAGGCTCCAGTGATGCTGTGGCTGGACAAGCCCTCGTTC ACCTGGGGCCTCTCTCCTCCTCCTGTTCT | 671 |
| IGHG2_chr14:106114275-106114375 | ACTGCCTCCTCCTCAGCTCAGTCCTGGTGGCCATCACCCCACGGCCTGTCGCCGCATCCCGT CAGGTTCCTCGTCGTCCCAGCCTGGTCGT | 672 |
| IGHG2_chr14:106114375-106114475 | CATGGAGGCCTCAGTCAGCCTCTGGTGTGTCCTGCCCTGTTGGCCTTGGAAGCCCCTGCCCACGGTCCCGT CATCTTTGCACTGGGTGGGCGTTGGTGCCT | 673 |

TABLE 6-continued

| Name | Sequence | SEQ ID NOs. |
|---|---|---|
| IGHA1_chr14:106176375-106176475 | AGTCAGCCCAGCTAGTCCAGCCCAGCAGTCAGCCCAGTTAGCCCAGTCAGTCC AGTCAGCTCAGTCCACTTAAGCTCACCCA | 674 |
| IGHA1_chr14:106176475-106176575 | GGTCAGCTCCGTCCAGTCAGCCCAGCTAGCCCAGCTTAGCCCAGTCAACACAGTCAGCCCA GCTCAGCCTAGCCCAGCCCAGTCAGCACA | 675 |
| IGHA1_chr14:106176575-106176675 | GGTCAGACCAGCTCAGTACAGCTCAGTCAGCCCAGATCAGTCCAACCCAGCGCAGTCCAACCCA GCCCAGCTCAGCTCATCCAAGCCTAGCTCA | 676 |
| IGHA1_chr14:106176675-106176775 | GCTCAGCCCAGCCCAGGTCAGCCCAGGTCAGCCCAGCCCAGCCGAACCCAGCTCAGCCCCAGGTCAACCCAATTCAGCTCA GCTCAGCCCAGGTCAACCCAACCAAGCTCA | 677 |
| IGHA1_chr14:106176775-106176875 | CAGCCTAGCCCAGTCCAGCTCAGCCCAGCTCAGCCCAGTCAGCTCAATCCACCTAAGCTCAC CCAGCTCAGCCCAGTCTGGCTCAGCTTAG | 678 |
| IGHA1_chr14:106176875-106176975 | GTCAGCCCAGCCCAGCTAGCCCAGATCAGTCCAGCTTAGCCCAGCTCAGCCCCAGGTCAG CCCAGCTCAGCTCAGCCCAGCCAGCTCAG | 679 |
| IGHA1_chr14:106176985-106177085 | CCCAGCCCAGCTCAGCGCAGCCCAGCTAGTCACCCCAGCCCAGGTCAGCTCAGCTTAGCCAGCTCAGCCCAG CCCAACTCAGCTCAGCCCAGCTCAGCCCAA | 680 |
| IGHG1_chr14:106211960-106212060 | TCTGAGTCTCCAGGGGCTGCCCAGCTCTCCCCTGTCTCCCACCTGCTCTCCCACCGGCCCTGTCTTCCCACTGCAGCTGCTCTGC CCTGGCTCCCTGAGGCTGAGCCTCAGTG | 681 |
| IGHG1_chr14:106212060-106212160 | TGCTCACCTTCTGTGAGCTCTGATGCTCTCCCCTTGTCCCCTGAGTCTCCAGGGGCTGACCCCTGATCTTTCTGCTTCCTAC CTGCCCCTGCTGCTCACCTGGCTGCTCTG | 682 |
| IGHG1_chr14:106212160-106212260 | CCCTGATCCCTGCTCGGCTCTGAGGCTCCAGGAGCTCCTGCTCTTCCTGCCCTGCTCACCTGTG TGATGCTCTGCCCTGGTCTCCTGAGGTC AATCGCCCTGGCTCTCTGAGGTCCAGGGG | 683 |
| IGHG1_chr14:106212260-106212360 | CTGCCCCCTGCTGCTCGGCCACCACCAGCCATGCTGACGTTGTGATGCTCTGCCCTGGTCTCCTGAGGTC CAGGGGCTGTCCCCTGCTTATTCTGCCTC | 684 |
| IGHG1_chr14:106212360-106212460 | CCACCTGCCCCCTTCCTCACCTGAGGCTCTTCTGCCCTGGTGCTCTGAGCTCGAGCTCCAAAAGCTGCCCACCTGCTCC TCCTGCTTCCTACCAGCCCCTGCTCTCCT | 685 |
| IGHG1_chr14:106212460-106212560 | GTGGATGATCTGCCTGGCTCTGAGCTCCAGGGGCTGCCCACCTGCTCCCCATGCTCCCACCTGCCCC TGCTGACCTGCGGCTGCTCTGCCTTGGCT | 686 |
| IGHG1_chr14:106212560-106212660 | CCCTGAGCTCCAGGAGCTTCCCCCTGCTCATCCTGCCCCCCACTGGCCCCTGTTCACCTTCAGATGCCCTC CCTGGTCCCCTGAAGTCAGGAGCTGCCC | 687 |
| IGHG1_chr14:106212660-106212760 | CCTGTTCCTCCCGCTCCCAGCCCGTGCTCACCTGCGGCTGCTCTGCCTGGTCCCCTGAGTTCAGG GGCTGCCCCTGCTCGCCCACCTCCCACT | 688 |
| IGHG1_chr14:106212760-106212860 | AGCCATGCTCACCTCCTGATGCTCTGTCCTGGTCCCCTGAGCTCCAGGGGCTGCCCCTGCTTGCCCATCT CCCACTAGCACTCTCACCTTCACCTTCTGATGCT | 689 |

TABLE 6-continued

| Name | Sequence | SEQ ID NOs. |
|---|---|---|
| IGHG1_chr14:106212860-106212960 | CTGCCCTGGTCTCCCTGAGCTCCAGGGTCTTCCCCCTGCTCATCCTGCGCCCAGCCCCTGCTCACCTGAGGCTGCTCTGCCCTGGTCCCCTGAGCTC | 690 |
| IGHG1_chr14:106212870-106212970 | CCCCTGAGCTCCAGGGTCTTCCCCCTGCTCATCCTGCGCCCACCAGCCCCTGCTCACCTGAGGCTGCTCTGCCCTGGTCTCCCTGAGCTCCAGGAGGTGC | 691 |
| IGHG1_chr14:106212980-106213080 | TTCTGCCCCCACCTGCCCTGCCTCACCTGGGCTGCTGGTCCTGGTGCTCGAGCTCCAATGCTGCTCCCTGCTCACTCTGCCCCTCCCTCAACCCGGGCA | 692 |
| IGHG1_chr14:106213080-106213180 | GCAATGTCACTCAGGTCACTGTTGCCCCCCTGCCTGTCCTGTCCTCGGCACCCTTCGTCTGTCCAGGTTTGGGCTGTTTTTCTGCCCTCATTTTTGATTTTGCAGCACTT | 693 |
| IGHG1_chr14:106213125-106213225 | CCTCTGTCCAGGTTTGGGCTGTTTTTCTGCCCTCATTTTTGATTTTGCAGACACTTGGCGTGTTCCCTATGCTGTGGAGCAGCCCCAGTGTCCAGTCAGGT | 694 |
| IGHG1_chr14:106213210-106213310 | AGTGTCCAGTCAGGTCTCCCAACAGAGCCCCTTGCCCTTGCCCATGTGCCCTCTGAATGAGCTCCCGGATCCTCCTGTCCCTGCACTGCTCCTGCTC | 695 |
| IGHG1_chr14:106213310-106213410 | TGGAAGCTCTCTGAACCTCAGCTCCTCAGTGGCCTCTGTGCTCTGTGGGTCAGTCCCCGTGGTCACTCAGCACGGAGCCTCAGCCCTTCCCCTGCCCCAGGCCT | 696 |
| IGHG1_chr14:106213410-106213510 | GCTGCACTTCTGGGCCTTTCTGGGCTCCTGACTCTTCCCTTCTCCCGCCCGTGCACTCAGCACACTCTCCCCTCTGCCCTGACCTGAGCCCC | 697 |
| IGHG1_chr14:106213510-106213610 | TGCTCCCCGCCAGGAGTGCCCCAAACCCCATCAGCTGGCTCTGAGCCCAGCACTGCTGACCCCTGCCCTGGGCTCCTGCCTCTGCCCTGGCTTCC | 698 |
| IGHG1_chr14:106213660-106213760 | ACCTGCTGTCCTTGGTCCTGGCTGAGAGGAGGGCCCACGGGCCAGCACTGCTGACCCCTGCCCTGGGCTCCGGTGATGCTGCCGGCCTGGACAAGCCCCTC | 699 |
| IGHG1_chr14:106213760-106213860 | CGTTCACCTGGGGCCCTCTCTCCCCTCGCTCTGCCCAGCCCGGTCGTCCTGGAGGCCTCAGTCAGCCTCTGGTGTGTCCTGCCCGCATCACCCCACCGCCGGCTCTGCCCGGTC | 700 |
| IGHG1_chr14:106213860-106213960 | CCAGTCATGTTCCTGCCACTGGGCGTGGGCATCCGTCGTGCCTGAAGGCTGCCACCTCCCCGTGCCTGGCTCCGCTTGGTGTTGGCTTGGAAGCCCCTGCCCCACGGTC | 701 |
| IGHG1_chr14:106213960-106214060 | CCCGTCGTCGCGACTGGGGTGGGCATCGGTGCTGCTCCCTGACCCCCAGCCTCCATGTGGGGCCGGCCTGACCCCA | 702 |
| IGHG3_chr14:106239250-106239350 | CACTGCACTTTCACCAGCCCTGCTGCTCTCCTGAGCTCTGCTGCCGGCAACTACCCAGCTCTGCCAAAGTCTAGGAGCTGCGGTGCTGCCTCCCCACCGTCCCCTGCTCAC | 703 |
| IGHG3_chr14:106239350-106239450 | CTGTGGCTGCTCTGCCTGGTGCTCTGAGCTCCAGGAGATGCCCCTGCTCCTCCTCCTGCCCCCCACCTGCCCCTGCTCACCTGCAGCGGCTCTGCCCTGGT | 704 |
| IGHG3_chr14:106239455-106239555 | GAGCTCCAAGAGCTGCCCCTGCTCCTCTCCCCTGTCCCCTGACCCTGCTCCTGCTGTTTGCCTATGGCTGCTCTGCCCTTGTCCCCTGAGCTCCAGGAGCTGCCCC | 705 |

TABLE 6-continued

| Name | Sequence | SEQ ID NOs. |
|---|---|---|
| IGHG3_chr14:106239555-106239655 | TGCTCATTCTGCGCCACCTGCCCCTGTTCACCTGGCTGCTCTTCCCTGTCTCTGAGCTCCATGAGC TGCCCCTTGCTCCTCCTGCTTCCACCA | 706 |
| IGHG3_chr14:106239655-106239755 | GCCCCTGCTCACCTACCGATGATCTTCCCCGGCTGCTCTGAGCTCCAGGGGCTGCCCACCTGCTACCCCTGC TTCCACCAGCCCTGCTTACCTGCAGCTG | 707 |
| IGHG3_chr14:106239755-106239855 | CTCTGCCCTGGCTGGCAGAGCTGCAGAAGCTGCCCCCTGCTCTGCAACCTCTGCAACCTCTGCGACTGCTCTGCCCTGGTCCTCTCATCTT CTGATGTTCCCCCTGTTCCCTGAGCTCC | 708 |
| IGHG3_chr14:106239855-106239955 | AGGAGCTGCCCCCTACTCGTTCTACCTCCACCAACCCGTGCTCCTGCCCCTCACCTGCCTGCTGCCCTGGTCCCC TGAGCTCCAGGGGCTGCCCCCTGCTCGC | 709 |
| IGHG3_chr14:106239990-106240090 | TGCCCTGATCCCTGAGCTCCAGGACTGCCCCTGCTCGTCGTTCACCTGCCCCTCACCTGCCCCTGCTCACTGAG GCTGCTCTGCCCTGGTCCCCTGAGCTAAA | 710 |
| IGHG3_chr14:106240090-106240170 | GGGGCTGCCCCCTTACTCATCCTGCCTCCCACCAGCCCTGCTCACCTTCTGATGCCCTCCCCTGGTCCCTG AGCTCCAGGGGCTGCCCCCTGAGCTCGTG | 711 |
| IGHG3_chr14:106240170-106240270 | GGGCTGCCCCCTGCTCCTGCTCCCACCAGCCCTGCTCACCTGCTCACTGCAGCTACACTGCCCTGGTTCCCTG AGCTCCAGGAGCTGCCACCTGTCCAGCTG | 712 |
| IGHG3_chr14:106240270-106240370 | GCCTTCCACCAGCCCTGCTCACTGCCCTGCTCAGCTACACTGCCCTGGTTCCCTGAGCTCCGGGAGCTGCCGCCTG CTTGTCCTGCCTCCACCAGCCCTGCTC | 713 |
| IGHG3_chr14:106240370-106240470 | ACCTGTGGCTACACTGCCCTGGTGCCCCTGAGCTCCAGGAGCTGCCCCTGCTTGCCCATCTTCCACTGAGC CCTGCTCACCTGCAACTGCTCTGCCCTGG | 714 |
| IGHG3_chr14:106240470-106240570 | CTCTATGAGCTCCAGGGCTGCAGGGGCTGCCCCTGCTCGTCCTGCTCCACCTGCCCTGCGCACTGTGGCTGCCTC CTCACCTGTGGCTGCTCTGCCCTGGTCCC | 715 |
| IGHG3_chr14:106240570-106240670 | CTCAGCTTCCAGGGTCTTCCTGCCTCCACCTGCCCTGCCCTGCACCTGTGGCTGCTTGGTCCCTGTTCACCTTCAGATGCTCTCCC GTGTCCCCTGAGCTCCAGGAGCTGCCC | 716 |
| IGHG3_chr14:106240670-106240770 | CCTGTTCTTCCTGCCTCCCACCTGCCCTGCCCTGTGCACCTGTGGCTGCTTGCCCCTGTCCTGGTCCCTGAACTCCAATGC CTGCCCCCTGCTCACTCTGCCCCTCC | 717 |
| IGHG3_chr14:106240770-106240870 | AACCTGGGGCAGCAAGTCACTCGGTCCTGTTGCCCCTGCCCTGTCCTGGCACCCCTCTGGCACCCTCTGTCCAGGTTT AGGCTGTTTTTCTTGCCTCATTTTGTTT | 718 |
| IGHG3_chr14:106240820-106240920 | TGGCACCCTCTGTCTCAGTTTAGGCTGTTTTTCTTGCCTCATTTTGTTTTTGCAGCACTTGGCGTGTTCCC TATGCTGTGGAGCAGCCCCAGTGTCCAG | 719 |
| IGHG3_chr14:106240915-106241015 | TCCAGTCAGGTCTCCCAACAGAGCCCCTTGCCCTTGCCCATGCCCATGTGCCCCTCCTGGATGAGCTCCGGATCC TCCGTCCCTGCACTGCTCCTGCTCTGGA | 720 |
| IGHG3_chr14:106241015-106241115 | AGCCCTCCAGAACCTCCAGCTCCTCAGTGCCCTCTGCTCGCTCGCTGGGTCAGTTCCCTGAACGCACGAGCCT CAGCCCCTCCCCTTCGCCCTTGCCCCAGGCCTGCTG | 721 |

TABLE 6-continued

| Name | Sequence | SEQ ID NOs. |
|---|---|---|
| IGHG3_chr14:106241115-106241215 | CACTCTGGGCCTTTCTGGGCCTCCCTGGACTCTTCCCTCCTCCCGCCCGTGCACTCAGCAGCTCTCCCCT CCTCTCCGCTGCTGACCACCAGCCCTGCT | 722 |
| IGHG3_chr14:106241200-106241300 | GACCACAGCCCTGCTCCCCGGCCAGCAGGTGCCCAACCCATCAGCTGGCTCTGAGCCCAGCCCTGTGC CTCCCCTGTCCCTGCCTCTGCCTCTGGGCT | 723 |
| IGHG3_chr14:106241345-106241445 | GCTCTGCTCCCAGCTCACCTGCTGTCCTTGGTCCTGGCTGAGAGGAGGCCCTACGGCCAGCTCTGCTGAC CCTGCCCTGGGCTCCGGTGATGCTGCCGG | 724 |
| IGHG3_chr14:106241445-106241545 | CCTGGACAAGCCCCTGCGTTCACCTGGGACCCTCTCCTCCTGCCTTCTGTGCCTCCTGAGCTCAGGTC GGTCATGCCCATCCTGGCATCACCCCCATG | 725 |
| IGHG3_chr14:106241545-106241645 | GCTGGCTCTGCCCCATCCCGTCATGTTCCTCCACACTCCCAGCCCGTCGTCCTGGAGGCCTCAGTCAGCCT CTGGTGTGTCCTGCCCGTTGGCTTGGAA | 726 |
| IGHM_chr14:106318100-106318200 | GGGTAGAGCCCACCTCGTGGCCTGCAAGCCAGCCAGCCCTGCCGGTCGAGAAGGAAGCCTGTGAGA GCACACAACTGGAGGCCGGACGGGAAGAGA | 727 |
| IGHM_chr14:106318200-106318300 | AACACGTGCCAACAGGCCACGCAGGCCAGGCCAGAGACCCCAGAGACCCAGAGGCAGCGCCCCTTTGAGTTCCTCTCT CTGGTCTCCGATGTTCTTCGTTGGGATCA | 728 |
| IGHM_chr14:106318300-106318400 | TTTCACTTACAGGCAACAAGAGACAGTGTGAAATGCTTTCCCTGTGGTCGGGAGGGAGCCGGGGCAGAG ATGACCCCAGTGGGGTGGTGTGGGGCTCCG | 729 |
| IGHM_chr14:106322055-106322155 | CTTTGCACACCACGTGTTCTCTGTGCCTGCATGACGTCCTTGGAAGGCAGCACCTGTGAGGTGGCT GCGTACTTGCCCCCTCTCAGGACTGATGG | 730 |
| IGHM_chr14:106322155-106322255 | GAAGCCCCGGGTGCTGCTGATGTCAGAGTTGTTCTTGTATTTCCAGGAGAAAAGGGTTGGGGCCGATGCACTCCCT AAGTCCTGTGCGAGGCAGCCAACGGCCACG | 731 |
| IGHM_chr14:106322255-106322355 | CTGCTCGTATCCCTGAAGTCTCCCCAGGCAGACAACCCAGGCCTGGGAGTGAGTATAGGGAGGGTGGGT GAGGACCCGGAACCAGTGTAGACTCAGCTGA | 732 |
| IGHM_chr14:106322905-106323005 | ACTTCAGCTACCATCTATGTCCAACAAGATCATGAAGATTGGCCCAGCTCAGCTGCCCATGTCCTCCAGTTCATCCCACCCC AGGCCAGCTCAATCCAGTTCATCCCAGCC | 733 |
| IGHM_chr14:106323005-106323105 | GGCTATCCAGCTCAATCTATGTCCAACAAGATCATGAAGATTGGCCCAGCTGCCCAGTGCCCATGTCCTCCAGTTCATCCCAGCCC AGGCCAGCTCAATCCAGTTCATCCCAGCC | 734 |
| IGHM_chr14:106323105-106323205 | CAGGCCAGCTCAATCCAGCCCCAGCCCCAGCTCAGCCCCCAACCTGCGCAAAGCCAAGCTCAGCTCAGCCCAACT CAGATGAGCTCAGACCAGCTCAGCC | 735 |
| IGHM_chr14:106323470-106323570 | CAGCTCAGCTCAGCCCAGCCCAGCCAGCCAGCCAGCCAGCTCGCTCAACCTTGCTCGCTCAACCTTAGCCCAGCAGCCCAGCCCA GCTCAATCCAGCCTGGCTCAGCCCAGCCC | 736 |
| IGHM_chr14:106323570-106323670 | AGCCCAGTTTGGCTCAACCCAGCTTGGCTCAGCCCAGCCCAGGTCAGCCTGGCTCAACTCAGCCCAGCCCAGCCC AGCTCTGCTCAACCCAGCTCTGCTCAACTC | 737 |

TABLE 6-continued

| Name | Sequence | SEQ ID NOs. |
|---|---|---|
| IGHM_chr14:106323805-106323905 | AGCCCAGCTCATCCCAGTCAGCCCAGCCCAGCCTAGCTTAGCTCAACCCAGTCAGCTCAGTTCAGCTCA GCCCTGCTCAGCACAGCACAGCAGAGCCC | 738 |
| IGHM_chr14:106324010-106324110 | AGCCCGATCGGCTCAACCCAGTCAGCTTAGCTCAGCCCCAGTCAGCCCAGTTAACTCAGCCCAGTCAGCCC AGTTAACTCAGCCCAGCCCAGCCCAGCT | 739 |
| IGHM_chr14:106324155-106324255 | TCAGCCCCAGTTCAGCCCAGCTCAGCCCAGCCTAGCTTGGCTCAACACAGCTCAGCCTCAGCCAGCC CAGACCAGCTCAGCTCAGCCCAGTCCAGT | 740 |
| IGHM_chr14:106324290-106324390 | CAACCCAGCCAGCCCCAACCCAGCCTCGGCTTAACCCAGCTCAGCCCAGCTCGGCTCAGCCTCAACT CAGCCCAGCCCAGCTCAACCCAGCCCAGTT | 741 |
| IGHM_chr14:106324490-106324590 | CAGCTCAGCTGAGCCCAGCCCAGCCCAGTCCGGCTCAGCTCAGCCCCGCCCACTCAGCCCAGCTCAGCT CAGCCCAGCTCAGCCCAGCCTCAGCTTAGCC | 742 |
| IGHM_chr14:106324750-106324850 | CAGCCCAGATCATCCCAGCTCAGCTCAGCTCGGTTCAGCTCAGCTCAGCCTCGGCTTAGCCCCAGCTCAACCCAGTCC AGTCAGCCCAGCCTGGACCACCCAGCCC | 743 |
| IGHM_chr14:106324850-106324950 | AGTCAGCTCAGCCCAGTCATCCCAGCTCTGGTTCAGCTCAGCTCAGCTCAGCCCAGTCTGCTCAACCCA GCCCAAATCAGCTCAGCCCCAGGTC | 744 |
| IGHM_chr14:106324950-106325050 | ATCCAGCTCAGCCCAGCACAGCAGCTCATTCAGCTCAGCTCAGCTCAGCCTAGTCAGCTCAGTTGAGTC AGTCAACTCAGCCCAATCCAGCTGGCTC | 745 |
| IGHM_chr14:106325050-106325150 | AGCCCAGCTCACCCTAGCTCAGCTTAGCTCAGCCCAACTCAACCCAGCCCAGCTTGCCAACCCAGCTCA GCTCAGCCCAGCCCAGTTAGCCAGCCC | 746 |
| IGHM_chr14:106325150-106325250 | AGCCTCGGCTTAGCTCTGCTCAGCTCGGCCCTCAGCCCTCAGCCCCGTTCAGCCCAGTTCAGCTCAGTCA GCTCAGCCCCAGTTCAGCTCAGCTCTGTT | 747 |
| IGHM_chr14:106325250-106325350 | AGTCAGCCCAGCGTAGCTCAGTCAGTCAGCCCAGCCAGGTTAGCTCAGCCCCAGTTAGCCTTAGCCTGATACA ACCTGCTCAGCCCAGTTCAGCTCGGCTCA | 748 |
| IGHM_chr14:106325360-106325460 | GCCCAGCGTAGTCAGTCAGTTCAGCTCAGCTGAGCCCAGCCCAGGTTAGCTCAGCCCCAGTTCAGGTCAGCTCAACTC AGCCCAAACCAGCTCGGCTCGGCCCAGCTC | 749 |
| IGHM_chr14:106325460-106325560 | ACCCTAGTTCAGCTTAGCTCAGCCCAGCCCAGCCCAGCCTCGGCTTAGCTCTGCTCAGCCCAGGTTA GCCCAGCCCAGCCTCGGCTTAGCTCTGCT | 750 |
| IGHM_chr14:106325515-106325615 | AGCCAGCCCAGGTTAGCCCAGCCCAGCCCAGCCTCGGCTTAGCCCGTTCAGCTCAGCTCAGCTCAGCCC CAGCCCAGCCCAGCTCGGCTTAGCTCTGCTCAGC | 751 |
| IGHM_chr14:106325615-106325715 | TCCGGCCCCTGCTCCCGCCTCAGCCCGTTCAGCCCAGTTCAGCTCAGCTCAGCCTCAGCCTCAGCCCAGCCCC TGGTTAGCTCAGCCCAGCTAAGCTCAGCT | 752 |
| IGHM_chr14:106325715-106325815 | CGGCTCAGCTCTGCTGAGCTCGGCCCAGTTGGCTCAGCCCGACACAGCCTGCTCAGCCCAGTTCAGCTC GGCTCAGCCCAGCCCAGCTAGTC | 753 |

TABLE 6-continued

| Name | Sequence | SEQ ID NOs. |
|---|---|---|
| IGHJ6_chr14:106325820-106325920 | AGTTGAGCCCAGCCCAGGTTAGCTCAGCCCCAGGTTAGCTCAGCCTCAGCCTCTGCCCAGGTTAGCTCAGCCCCAGTCCAGTTCAGGTTAGCTCAGC | 754 |
| IGHJ6_chr14:106325920-106326020 | CCAGCTCAGCTCTGCCCCAGGTTAGCTCAGCCCCCAGGTTAGCTCAGCCCTCAGCCTTCAGCCCAGGTTAGCTCAACCTGG | 755 |
| IGHJ6_chr14:106326020-106326120 | CTCAGCTCAGCTCAGCTTGGCTCAGCCCAGCCAGCACGCTCAGCCTCTCAGCTCTGGCTCAGCTCAGCCCAGCCCAGCCCAGCTCAGCTCAGCCCCGC | 756 |
| IGHJ6_chr14:106326245-106326345 | CCAGCTCAGCAGCGCAGCCCAGCTCAGCTCAGCCCTAGCCTTGCTCGGCCCAGCTCAGCTCAGCCCAGCTCAGCCCAGCCTTGCTCAGCCCCAGCTCAGC | 757 |
| IGHJ6_chr14:106326450-106326550 | TCAGCCCAGCCTCGCCCAGCTCAGCCCAGCTTAGTGCAGCCAAGCCCAGCTCAGCTCACCTGTGCAACTTAGCCCAGCTCAGCTCAGCT | 758 |
| IGHJ6_chr14:106326550-106326650 | CAACCCAGTTCAACTCAGCCCAGTTCAGCTCAGCTCACCCCAGCCTTCAGCCTTGTTTAGTCTAGGTCAGCTTAGTCAGTTTGCCATCTGAGTCCATT | 759 |
| IGHJ6_chr14:106326650-106326750 | CTGAAAGCTGGATGGAGTTGTCATGGCCAGAAATGGTCAGCCCACCAGACCTGCTTGTCTCAGCTAAAGCCATCTCATTGCCAGGTTCCTGCACAGCCAG | 760 |
| IGHJ6_chr14:106326750-106326850 | GCTGGCTTCCATCTTTTGTCTCCCCTTACTTGATACCCACCCCAGTTCCCTGCAGTCCTGCCAGCGCCACCTGGGTTTTGGTTCCAAAGCATTACCAATCAT | 761 |
| IGHJ6_chr14:106326850-106326950 | TACCACCCTCCACTACCTGGGTGGAATATTCTTTGCTGTTTAAAGTCATTAAACATCTTGAGAATGAGACCAAGAATTAGGAGCCTGTGCTGTGAT | 762 |
| IGHJ6_chr14:106326950-106327050 | AAAAATGAGCAGGTCCCCTTGCTCTAGAAGTGCAGCATATCTTCTGCACCAAGAGGAGGGTATTGAGATGCTCAGAGCCTCCACCTTCCCGGAGCATCC | 763 |
| IGHJ6_chr14:106327050-106327150 | CCTTCCCTTCTGAGTCTGCAGTAAACCCCTGCCTTTAAATTCCCTCTAGAATAACAGTCATCATTGGAAACAACCAAGAAATGCATTTATCTGAATTTGCC | 764 |
| IGHJ6_chr14:106327150-106327250 | ACTTAAAATTCTGCCATTTACCATAAATCGCTTTGGAAGGCATGGGTACTTTCAAGGGTGCGATGATGACCTACAGTCAATGACTTAGACAAGGGCGAT | 765 |
| IGHJ6_chr14:106327250-106327350 | GCCAGTGGGGCTTGGTATGTTCAAGCATCATTACCCATGCCATCCCATTCAGAGGTTGTGGAGCAGCTCGTGCGACCTCTCCTTCCAAATGGGCTTTA | 766 |
| IGHJ6_chr14:106327350-106327450 | GGGAAAGTTAAATGGGAGTGACCCAGACAATGTCACTCAAAAGACTCACATAAATGAGTCTCCTGCTCTTCATCAAGCAATTAAGACCAGTTCCCCTTC | 767 |
| IGHJ6_chr14:106327450-106327550 | TAGTGGAAATAAGACGTCAAATACAAAGTTTAAGAGAAGCAAATGCAGCAGCGCGGCTGCTCCTGTCTCTTACCATGTCGGGCGCCTGGTCACTGCGAGC | 768 |
| IGHJ6_chr14:106327550-106327650 | CTTGCAAAGCTTTGGCATGGAATCATTCCTCCAAGTCCATTAACAAGGGCTGGGGCCTGAGCAGCAGTCGGCCCGGCAGCAGAAGCCACGCATCCCAGC | 769 |

TABLE 6-continued

| Name | Sequence | SEQ ID NOs. |
|---|---|---|
| IGHJ6_chr14:106327650-106327750 | TCTGGGTAGTCCGGGGAGACCCAAAGCCCAGGCCGGGCCTGGCAGCCACCCTCCCAGAGCCTCCGCTAGG CCAGTCCTGCTGACGCCGCCATCGGTGATTC | 770 |
| IGHJ6_chr14:106327750-106327850 | GGAACAGAATCTGTCCTTCTAAGGTGTCTCCACAGTCCTGCTTCAGCACTATCTGATTGAGTTTTCTCTT ATGCCACCAACTAACATGCTTAACTGAAA | 771 |
| IGHJ6_chr14:106327850-106327950 | TAATTCAGGATAATGATGCACATTTTACCTAAAAACTTATCCTAAAGTGAGTAGTTGAAAAGTGGTCTTGA AAAATACTAAAATGAAGGCCACTCTATCAG | 772 |
| IGHJ6_chr14:106327950-106328050 | AATATCAAAGTGTTTCTCCTTAATCACAAGAGAAAACGAGTTAACCTAAAAAGATTGTGAACACAGTCA TTATGAAAATAATGCTCTGAGGTATCGAAA | 773 |
| IGHJ6_chr14:106328050-106328150 | AAGTATTTGAGATTAGTTATCACATGAAGGGATAACAAGCTAATTTAAAAAACTTTTTGAAATACAGTCAT AAACTCTCCCTAAGACTGTTTAATTTCTTA | 774 |
| IGHJ6_chr14:106328150-106328250 | AACATCTTACTTTAAAAATGAATGCAGTTTAGAAGTTGATATGCTGTTTGCACAAACTAGCAGTTGATAA GCTAAGATTGGAAATGAAATTCAGATAGTT | 775 |
| IGHJ6_chr14:106328250-106328350 | AAAAAAGCCTTTTCAGTTTCGTCAGCCTCCGCCTTATTTTAGAAAACGCAAATTGTCCAGGTGTTGTTTTG CTCAGTAGAGCACTTTCAGATCTGGGCCT | 776 |
| IGHJ6_chr14:106328350-106328450 | GGGCAAAACCACCTCTTCACAACCAGAAGTGATAAATTTACCAATTGTGTTTTTTGCTTCTTCCTAAAATAGA CTCGCGGTGACCTGCTTCCTGCCACCT | 777 |
| IGHJ6_chr14:106328450-106328550 | GCTGTGGGTGCCGGAGACCCCCATGCAGCAGCCATCTTGACTGTTCTCTAATTCATCATCTGCTTCCAGCTTCGCTCAA TTAATTAAAAAAATAACTTGATTTATGA | 778 |
| IGHJ6_chr14:106328550-106328650 | TGGTCAAAACGCAGTCCCGCATCGGGGCCGACAGCACTGTGCTAGTATTTCTTAGCTGAGCTTGCTTTGGC CTCAATTCCAGACACATATCACTCATGGG | 779 |
| IGHJ6_chr14:106328650-106328750 | TGTTAATCAAATGATAAGAATTTCAAATACTTGGACAGTTAAAAAAATTAATAATACTTGAAAATCTCCAC ATTTTAAGTCATAATTTTCTTAACCATT | 780 |
| IGHJ6_chr14:106328750-106328850 | TTTTCTCAGAAGCCACTTCAAACATATCCTGTCTTTTAACAGTAAGCATGCCTTCCTAAGATAACAATCCTT TTCTCTTGGAAACCAGCTTCAAGGCACTG | 781 |
| IGHJ6_chr14:106328850-106328950 | AGGTCCTGGAGCCTCCCTAAGCCCTGTCAGGACGGCAGCCAGCCGTTTCTGGGCTACCCTGCCCCAACC CTGCTCTCATCAGACGCGGGCTACGCGT | 782 |
| IGHJ6_chr14:106328950-106329050 | CCCTCCTCTGCTGATTCACCCACTCCGACAGTTCTCTTCTTCCAGCCAATAAAGAATTAAGATGCAGGTTGA CACAGCGCACCACCTCATAATTCTAAAGAA | 783 |
| IGHJ6_chr14:106329050-106329150 | AATATTTCACGATTCGCTGCTGTGCAGCGATCTTGCAGTCTTGCAGTCCTACAGACACCGCTCCTGAGACACATTCCTC AGCCATCACTAAGACCCCTGGTTTGTTCA | 784 |
| IGHJ6_chr14:106329150-106329250 | GGCATCTCGTCCAAATGTGGCTCCCCAGGCCCCCAGGCTCAGTTACTCCATCAGACGCACCCAACCTGAGT CCCATTTTCCAAAGGCATCGGAAAATCCA | 785 |

TABLE 6-continued

| Name | Sequence | SEQ ID NOs. |
|---|---|---|
| IGHJ6_chr14:106329250-106329350 | CAGAGGGTTCCCAGATCTTCAAGGCACCCCAGTGCCCGTCCCCTTCCTGCCAGTCCGCCCAGGTCCCCTCGG AACATGCCCCGAGGACCAACCTGCAATGC | 786 |
| IGHJ6_chr14:106329350-106329450 | TCAGGAAACCCCACAGCAGTAGCAGAGAAAACAAAGGCCCTAGAGTGGCCATTCTTACCTGAGGAGACGG TGACCGTGCTCCCTTTGCCCCGACGTTCCAT | 787 |
| IGHJ6_chr14:106329450-106329550 | GTAGTAGTAGTAATCACAATGCAGAGAATGTCCATTCTCACCCCACAAAACCCAGCCACCCAGA GACCTTCTGTCTCCGGGCGTCACATGGAAG | 788 |
| IGHJ6_chr14:106329550-106329650 | CTGACTGTCCGTGCCCTGTCCTGCCCTTCTCATGGAACCCCTCTGCTGGCCTCCCACGTACCCCACATTCT GGCCTGACCCCTCAGAAGCCAGACCACTG | 789 |
| IGHJ6_chr14:106329650-106329750 | TCGGCCTGGGAAGTCCAACTGCAAGCAGACGAGCGCTGCTAAGTCACCCCCAGGAGTCCAAAAACCCCGGGG GGCACCCGTCCCAGAGAGCGGGTGCCTTGGA | 790 |
| IGHJ6_chr14:106329750-106329850 | GCGGGACAGAGTCCCACCACGCAATCATCACGACAGCCCCTGAGAATGCTCCAGTGAAGCGGAGAGAG GTCACCCCAGACCAGCCGAAGGAGCCCCCA | 791 |
| IGHJ6_chr14:106329850-106329950 | GCTGCCGACATCTGTGGCCGGACTTGGGAGGACAGGCTGGGTTCCCATTCGAAGGGTCCCTCTCCCGG CTTTCTTTCTGACCTCCAAAATGCCTCCA | 792 |
| IGHJ5_chr14:106329950-106330050 | AGACTCTGACCCTGAACCAGTTGTCACATTGTGACAACAATGCCAGGACCCCAGGAAGAACTGGCGCCC CACCTGAGGAGACGGTGACCAGGGTTCCT | 793 |
| IGHJ5_chr14:106330050-106330150 | GGCCCCAGGGGGTCGAACCAGTTCCTGGCAGGGCCCGGAGGACCCCTGGGGTCTGAGAGGACT CGCTACGTCCCTGGGACCCCTCTCAGATGA | 794 |
| IGHJ5_chr14:106330150-106330250 | GCCCGGGGAGGGCCCGGAGGGCGTCTGGGCTCAGGAGGAAGGAG | 795 |
| IGHJ4_chr14:106330250-106330350 | CATCTGGAGCCCTTGCCCCTCCTGTCTGTGGCCGCTGTTGCCTCAGGGCATCTCCTGAGCCCCCCAGGAT GCTCCGGGGCTCTCTTGGCAGGAGACCCA | 796 |
| IGHJ4_chr14:106330350-106330450 | GCACCCTTATTTCCCCCAGAATGCAGCAAAATGCCCTTCAGAGTTAAAGCAGGAGAGGTTGTGAGGAC TCACCTGAGGAGACGGTGACCAGGGTTCCC | 797 |
| IGHJ4_chr14:106330450-106330550 | TGGCCCCAGTAGTCAAAGTAGTCACATTGTGGGAGGCCCCATTAAGGGGTGCACAAAAACCTGACTCTCC GACTGTCCGGGCCGGCCGTGCCAGCCAGC | 798 |
| IGHJ4_chr14:106330550-106330650 | CCCGTGTCCCAAGGTCATTTTGTCCCCAGCACACAAGCATGACTCTGCCACCCTTTGCCCCAGCAGCAGAGT CCCAGTTCCAAAGAAAGCCCTTCTGCTG | 799 |
| IGHJ3_chr14:106330650-106330750 | AACGTGGTCCCAAACAGCCGGAGAAGGAGCCCCGGAGGGCCCCACATGGCCCAGCGCAGACCCAAGGAGC CCCGGACATTATCTCCCAGCTCCAGGACAG | 800 |
| IGHJ3_chr14:106330750-106330850 | AGGACGCGTGGGCCCAGAGAAAGGAGGCAGAAGGAAAGCCATCTTACCTGAAGAGACGGTGACCATTGTC CCTTGGCCCCAGATATCAAAAGCATCACACA | 801 |

TABLE 6-continued

| Name | Sequence | SEQ ID NOs. |
|---|---|---|
| IGHJ3_chr14:106330850-106330950 | GGGACACAGTCCCTGTTCCTGCCCAGACACAAACCTGTGCCCGTGCAGGACACTCGATGGGTCACATGG CCCAAGCACAGAGCAGGCAGCCGGCGTC | 802 |
| IGHJ3_chr14:106330950-106331050 | CCTGTCCCCAGCCACACAGACCCCTGGCTGAGACCCAGGCAGGAGGGTGACGTTCCAGGGAGACG GTGGCCGGGCTGCCCTGGCCCCAGTGCTCCA | 803 |
| IGHJ3_chr14:106331050-106331150 | AGCACTTGTAGCCACACTAAAGCGCAGCCTGTCCCCGGCCACATGAACAGCGCCCAGCCCCAGCC CAGGCTCTGCCCACAACTTCTCCTTCCCGT | 804 |
| IGHJ2_chr14:106331150-106331250 | CCCTGCCCTCCGGCCTGCTTGCTACCTGTGGAGGGTCCCTGACGGGGCTGAAGCCCAGCGGGGTCCCTGCC TGTCCTTGGGGGCTCCAGCTGCCCCAGGG | 805 |
| IGHJ2_chr14:106331250-106331350 | CTAAGTGACAGCAGGGGTCTGGCATGCAGCCCATGGCGGAGACCCCAGGGATGGCAGCTGGTGTGGCCTC AGGCCAGACCCCAGGCCGGCTGCAGACCCCA | 806 |
| IGHJ2_chr14:106331350-106331450 | GATACCTGGCCTGGTGCCTGGACAGAGAAGACTGGGAGGGGCTGCAGTGGGACTCACTGAGGAGACA GTGACCAGGGTGCCACGGCCCAGAGATCGA | 807 |
| IGHJ2_chr14:106331450-106331550 | AGTACCAGTAGCACAGCCTCTGCCTCCTGCTTCTCCAATACAAAACACCCTCGCCCCTCCTGCCGAC CTCCTTTGCTGACACCTGTCCCCAAGTC | 808 |
| IGHJ1_chr14:106331550-106331650 | TGAAGCCAAAGCCTCCTGCCTGGCCAGTACACCTGGCTCCCCGCTATCCCCAGACAGCAGACTCACCTGA GGAGACGGTGACCAGGGTGCCCTGGCCCA | 809 |
| IGHJ1_chr14:106331650-106331750 | GTGCTGGAAGTATTCAGCCACCGTGAGTCAGCCCTGAGCCAGGGCTACAGAAACCCACAGCCCGGGGTC CCGGGGAGCATGTTTTTGTAGAGCTGCC | 810 |
| IGHD7-27_chr14:106331750-106331850 | AATCACTGTGTCCCCAGTTAGCACAGTGGTTCCAGCTCAGCCAAAACCCTGCGGCTGGTAGGGGCCTG TGGGGCTGGGGGCTGATGTGGCTGCGTCT | 811 |
| IGHD6-19_chr14:106357890-106357990 | TGCTGGGTCTGTCCTCTGTGGGAGGGGCTGCTACCCAGGCCCAGGACTGCAGTGAGGGCTACTGAGGG GCTTTTGGGTCTGCCCTGAGCCGCTGTGGG | 812 |
| IGHD3-3_chr14:106380360-106380460 | GCTTCTCAGGTTCACTGCGGGGACACTCGGGTCTGCCCCTGGCTTAGGTGGACAGTGTCCGTGCCACCTG TGCCCTGAGGCTCCATTTCAGGCTGATATC | 813 |
| IGHD3-3_chr14:106380460-106380560 | TGTCTGTATTGTCCCCACCCGTGCATGGCCATGCTCTTTTGGGTTTATAAATTGCCCCAAATCACCCAG GCATCATTCAGGCTTTTTATATTCCCTGG | 814 |
| IGHD3-3_chr14:106380550-106380650 | TATTCCCTGGGCCACCAGGTGCCTCCACCCAGAAAGCTGAGATGTGGGAGGTTCTAGAGTCATTCTGCAA CCCTGGATGAGCCCCTGCAGCCTCAGTGCT | 815 |
| IGHD3-3_chr14:106380650-106380750 | ACTGAGGTTCCAGCCAAGACCTGGAGCAGGTGCAGATGAGGCCTGAGGCCAGGTGAAGCCCAGGCCAGGT GAGGTCCAGGCCCAGTGAGGCCCAGGTCAGAT | 816 |
| IGHD3-3_chr14:106380750-106380850 | GAGGCCCAGGTCAGGTGAAGCCCAGGTGAAGTCAGGCCCAGGTGAACCCAGTCAGGTGAGGCCCAGATCATGTGAGCT CAGGACAGGCAAGGTCCAAGTCAGGTGAGGC | 817 |

TABLE 6-continued

| Name | Sequence | SEQ ID NOs. |
|---|---|---|
| IGHD3-3_chr14:106380850-106380950 | CGAGCTCAGGTCAGGTGAAGCCCAGAGTGAGGTCTAGGCCAGGTGAGGTCCAGGCCAGGTGAGGTCCAGGTCAGGTGAGGCCCAGGTCAGGTCAAGGCTGAGGTA | 818 |
| IGHD3-3_chr14:106380910-106381010 | TCCAGGTCAGGTGAGGCCCAGGTCAGGCAAGGCTGAGGTGATGTATGAGACTTCTGTAATTTCAGTTGGTGCCAACCCTGCCTGGTGTCCCTGCCCT | 819 |
| IGHD3-3_chr14:106381010-106381110 | CCTCCCAGCCATGCTCTGTGCCTGCCAGAATGCCAGCGGCCCCTGCTGCTGCACAGTGCTGGCTGTGTGAGGAGCTGGGCTCTGCCTCCCTGTGCATGGGCGTCC | 820 |
| IGHD3-3_chr14:106381275-106381375 | GCCTGCAGCCTGTCTCCGGGATGCCCAGGGAGGTGAGTGCCACCACCATATCAGGCCTTTCTCTTTAAAGTCATTTCTTTGGGGATACATCATCAATGTCT | 821 |
| IGHD3-3_chr14:106381485-106381585 | TCTAAACACAGTCTGTGTGCATTTTCCTCTCTTGCAATTTAGAATTTAACTGCTGTTTTCAAGGTACTGTAATGTATTTGTTCTCTTCTTGTTAGGAGA | 822 |
| IGHD2-2_chr14:106381585-106381685 | CTTGCCAACCCTGTGTGTCTCAGTTCATACCCTCTTCCTCCCAGTAGAAGTAACGACCACTGTGTTTATGTGATCATCCTTTTCTTGATTTTCCTTAT | 823 |
| IGHD2-2_chr14:106381655-106381755 | TGTGATCATCCTTTTCTTGATTTTCCTTATAGTTTCCTTCAGATGGCTGTTTGTTGCTTCATTCTCAGTTTGGGCTATGACAAATTTTGCCGGCTGTAAATTTTATTTAGAA | 824 |
| IGHD2-2_chr14:106381890-106381990 | CTGCCATCGTCTTATTTGCCTGTTTTCCTTCAGATGGCTGTTTGTTGCTTCATTCTCAGTTTGGGCTATGACAAACATATGTTCTGCACATCTTTGCCCATGA | 825 |
| IGHD2-2_chr14:106381990-106382090 | GGCTCTCAGGGAGGGCTCTGGAGCTGGACTGCCTGCAGGGCTCTGCTTTGTTGCAGGAGTTCCTGCCAAGGCTTTTCAGAGTGTCTGTGCCCAGCCTG | 826 |
| IGHD2-2_chr14:106382090-106382190 | AAGTACACACTGTACTTTGCCCTTGCATCAGGCACTTTCCTTGTGCTTGCTCCACATTCTGGAGAATTTATTCAGATCTGTGCTGCAA | 827 |
| IGHD2-2_chr14:106382325-106382425 | CTTCCCCACACTGTCTCCTCCTGGGCTCACTCCCAGCAGCTTGCTGGAAGTACTTCATCAGATCTTGAACACCAGTTTATGAACTATCTGCACAGGAAGCACAGAAACAGCAAAAGCCCTG | 828 |
| IGHD2-2_chr14:106382905-106383005 | TTGCGTGGACCCTGTTTTGGTCAAGGGAAGTACTTGCTGGTGAAGGAGACCTCCCCTCCTTTCTTCTCAGGAGCCCCCTCGATGCCGTTGCCTGGTG | 829 |
| IGHD2-2_chr14:106383005-106383105 | TTTCTCAGGGCTGGTGCTGCCCTGTCGGGGGCTCAGCAGTGTCTGCCCGTTCGCCAGTGTCTGTTCTGTTTCCACGCGGTGTTCTGGGGCCGCCTTCCACGCGGTCTCGGGGATGTCAGCGGCTCG | 830 |
| IGHD2-2_chr14:106383030-106383130 | CAGCAGTGTCTGCCCTGTTCCAGGTGGGAATGTGGGTCTGTTCTGTTTCCACGCGGTGTTCTGGGGCCGCCAGTGAGGGGCTCCGGGATGTCAGCGGCTGG | 831 |
| IGHD2-2_chr14:106383130-106383230 | TCTCTGTCCCTATGGTCTGGGCTCCGGTTCACTGCTCCGTTCACTGCTCCCCCTCCAGGTCGGCTCACTGACTCAGTTACTATCCAGCGGGCTCCGTGCTCCGTGCTGTTCAGTG | 832 |
| IGHD2-2_chr14:106383980-106384080 | GGGAGCAAATGAGAGGAAGTGGCAGCGGCCCGAGTGCCAGGCGGTCCCAGTTTGGGGTTGATCTTTGTGAACAGCTCCCTGGCCCGTGTGTAAGTGG | 833 |

TABLE 6-continued

| Name | Sequence | SEQ ID NOs. |
|---|---|---|
| IGHD1-1_chr14:106384080-106384180 | TCGGGGGAGGCACGGAGTCTGAGCTACAAGCGGTGGCAGGAAGGCAGGTCCCAGTCTTGGGGTCTGGAGCTTATCTTCTTCCTGTGAACTGAGTGTG | 834 |
| IGHD1-1_chr14:106384630-106384730 | ATGGAGGACCTGCCTCGGATGACACCCCTATCTTAAGAAGGTCATGTGGGTTCCAGTGGGAGGAAGGGAAGTGGGCCACCTCCTGGGGGTCTTCCACC | 835 |
| IGHD1-1_chr14:106384720-106384820 | GTCTTCACCCCACCCCACCCTCAGCCTGGGGCCTCTGTGATTCCTCTGTGACAGACCCCAAAGTCTGTGCTGCCGCAGGGCAGGAAGGAAGGGCTGTGG | 836 |
| IGHD1-1_chr14:106384825-106384925 | TCCAGGTTTGGGGCCACAGTGGTGTTCCCTAAGCCCGAGTCTCTGTCTCATGGGCCCGCAGCAGGTCCTGAGTGAGGGACAGAGACCGGGGCGGGGTC | 837 |
| IGHD1-1_chr14:106384925-106385025 | TTTTGGTCCTGGTGGACTCTGGGTGGATTCAGTGGGGAGTCATCAGGGTCGTGTCCCCAGGGTACTGGGGTGTCTCTGCTCCTGGAGTCGGCTCTGG | 838 |
| IGHV2-5_chr14:106494090-106494190 | CCTGGGTTTTGTACAGGAGGTGCCCTGGGCTGTCTCTTTGTGCTGTGTGCACAGTAATATGTGGCTGTGTCCACAGGGTCCATGTTGTCATTGTAA | 839 |
| IGHV2-5_chr14:106494210-106494310 | GTGTCCTTGGTGATGGTGAGCCTGCTCTCAGAGATGGGCTGTAGCGTCGTGAGCAGTAATCATTCCAATAAATGAGTGCAAGCCACTCCAGGGCCTTTCCAGTGGG | 840 |
| IGHV2-5_chr14:106494310-106494410 | GCTGACGGATCAGCCAGCCACCACCTCACTAGTCTGAGTGAGAAGAACCCAGAGAAGGTGCAGTCAGCGTGAGGGTCTGTGGGTTTCACCAGCGTAGG | 841 |
| IGHV2-5_chr14:106494445-106494545 | CTGTGGAGAAAGCATAAGAAGATGAAGCCCACAGAAACTGATGTTTCACCCGTGAAGGAGTCCCTGACCACCAGCACTCACATGAAGGGATGTC | 842 |
| IGHV2-5_chr14:106494545-106494645 | AGCAGCAGGAGCGTGGAGCAAAGTGTGTCATGTGGGCACAGGAGTCACTGAGCTGGGACCTGTGCTCGGCTTTTTCAACCCAGAGGACGGCTTTTTCAACCCAGAGGAGGTGAGCT | 843 |
| IGHV2-5_chr14:106494565-106494665 | AAGTGTGTCCATGTGGGCACAGGAGTCACTGAGCTGGGACCTGTGCTCGGCTTTTTCAACCCAGAGGAGGGCTGAGCTGGTGAGATTTGCATTCCCC | 844 |
| IGHV2-5_chr14:106494650-106494750 | AGATTTGCATTCCCTACTTCCCTACTGTGCCCTACTCTATGGGATGGAGTCAGGTTTCAGGACTCAGGAGGGTGTTGCATCGTGTGAGGACCAGTGATAGTAA | 845 |
| IGHV2-5_chr14:106494750-106494850 | CATGATCAGTGTAATTCAGATGGCATTAATCTAAGGCTGGGCAAGTAGATTCTGAGTAGAAGTCTTTCAGAAGTCATGATTATGAGGTCATGTTGGTCT | 846 |
| IGHV3-7_chr14:106518495-106518595 | GCCCTTCACAGAGTCCACATAGTATTTCTCACTTCCATTCTTGCTTTATGTTGGCCACCCACTTCCAGCCCCCTTCCCTGGAGCCTGGCGGACCCAGCTCATC | 847 |
| IGHV3-7_chr14:106518855-106518955 | TGAGTCCTCTGTGCTCAGTGCTGATCACCAAGTGGAAAAGGCCTTGGAGTCCAGGGCTAAGGCTCCTCTCTGAGACCTGCAGGGTCAGGGTTGGGTTGGTT | 848 |
| IGHV3-7_chr14:106518955-106519055 | TTTCATCAGTAGAGGGAGGGCCCTATTTGCATGTCTCCTACTATATAAGAAGCTCTAGTGGGATGCTGGAGGAATAGGCTGTACCATATAAGAAGACGGT | 849 |

TABLE 6-continued

| Name | Sequence | SEQ ID NOs. |
|---|---|---|
| IGHV3-7_chr14:106518970-106519070 | AGGGCCCTATTTGCATGTCTCCTACTATATAAGAAGCTCTAGTGGGATGCTGAGGAATAGGCTGTACCCATATAAGAAGACGTGCTCTGCAGAAGTTT | 850 |
| IGHV3-7_chr14:106519070-106519170 | GCTGACAATGATGGTATTTGGAAAATATGCTGTCTTATGAAATTGTGCTGTGATAAACACTTTGCCCTGATCACCCTATTACATTTTTTAAAAAATGTGT | 851 |
| IGHV3-11_chr14:106573540-106573640 | CAAACAGAGACAACCTAGTCAGAATCTCAGAAACTGCCACATATATTCACTGCTTATCTCACTCACGTCCACTCAATGTCTCTAGTTCTCCATAAATCACCTTTTA | 852 |
| IGHV3-11_chr14:106573640-106573740 | TAATAGCAACAAGGAAAACCCAGCTGATCAGCCCAAACTCCATGGTGAGTCCTCTGTGTTCAGTGCTGATCACCGAATGGAAACTCTGGGAATTCTGGGGCT | 853 |
| IGHV3-11_chr14:106573685-106573785 | GTCCTCTGTGTTCAGTGCTGATCACCGAATGGAAACTCCTGGGAATTCTGGGGCTCTCCTCCCAGAGCTGCAGGGTCTGGGCTCGGCTGGTTTT | 854 |
| IGHV3-11_chr14:106573785-106573885 | TATCAGCAGAGGGAGGGCCCTATTTGCATGTCTCCTACTATATAGAAGCTCTAGTGGGACGCTGAGGAGAGGGCAGTGCCAGAGCAGATGAGAGGGT | 855 |
| IGHV3-11_chr14:106573885-106573985 | CCCGAAAACACTGGAGGTAATCCTATCTCCAGGAAAATATAACTTCAGATTTATGTGATTGTGACTTGATGATCAATTAGCAGTCATCATCTTATTTAA | 856 |
| IGHV3-11_chr14:106573985-106574085 | TGTTTTACATATTTCAGAATATATTCAGTGCAAGTGTCAATGTTACATTTTTAGAGAAGATGAATTACATACATAACAGACAGTGTCAATGTCTCA | 857 |
| IGHV3-15_chr14:106610690-106610790 | ACTCACACTTAATCTCTCTAGTTCTCCATAAATCACCTTTAAAAATAGCAGCAGACAAATACATGACGACACACACCAAACTCCATGGTGAGTCCTCTGTGTC | 858 |
| IGHV1-18_chr14:106642110-106642210 | GATGCTATTTAATAGCCCAATTCCTGACCCAGAGTGCCATCCCCTGAACTCTGTGTTGACAGAGCTTCCCCCACTGGAGAACATTGTAGAAGCTGAGGGTTCAAGCCGTAAT | 859 |
| IGHV1-18_chr14:106642210-106642310 | CCTGTTAGAGGCCACGCATCCCAATTCCTGCGTAGTATGTGCTACCACCACTAATAGTCGAGACCCACTCCAGCCCCAAGCTCCCCCAGGACACACCTCACTTA | 860 |
| IGHV3-23_chr14:106725295-106725395 | GGGCCCTTCACGAGTCTGCTAAGGTGAATCCAGAGGCTGCACAGGAGAGTCTCAGGGACCCCCCAGGCTGTACCAATTCCCTGGAGCCTGGCGACCCAGCTCAT | 861 |
| IGHV3-23_chr14:106725395-106725495 | GGCATAGCTGCTAAAGGTGAATCCAGAGGCTGCACAGGAGAGTCTCAGGGACCCCCCAGGCTGTACCAAGCCTCCCCCAGACTCCAACAGCTGCACCTCA | 862 |
| IGHV3-23_chr14:106725550-106725650 | ACTGTTCTCTCACTCTTATCCATTCACACTCCAATTTTTCTATTTCCCATGAATTACCTTTTAAAATAGCCACAAGAAAAAGCCAGCTCAGCCCAAACT | 863 |
| IGHV3-23_chr14:106725650-106725750 | CCATGGTGAGTTCTCTCTGTTCAGTCCTGATCACCAAATGAAAAACACCTGAAAATCCCAGGGCTGGGCTCCTCTCTCAGAGCTGCAGGGTCAGGGCTGGG | 864 |
| IGHV3-23_chr14:106725780-106725880 | TTTGCATATCTCCTACTATATAGTAAGCTCTGGGGTGAGAGGCCTTTGGAGATAGTGGGCTCAGAGCATGTCAGAATGTCCTCGGGAGATCTGTGATA | 865 |

TABLE 6-continued

| Name | Sequence | SEQ ID NOs. |
|---|---|---|
| IGHV3-23_chr14:106725880-106725980 | TTGAAAGCATTGGGAAATTGTGCTTTCCTATTGTCAGTTGTTTGTTTGTGATAAACTTAAACCTAAAAATCTTATAATTTTGTAATTTTTATTT | 866 |
| IGHV3-23_chr14:106725995-106726095 | GAGGTACCATAGATCTACATAAACTGCATATTTTAAAGTTAGCACCAATACATCTTTATTTTTACATACGCAGAGAACCATGGTATAGTATCAATA | 867 |
| IGHV3-23_chr14:106726095-106726195 | TTATTTCCATGTTAAAGATGAAAAATATCAGCAAAAGCACAGTGGGTTTTACAATGTCCCAGTGCTCACTTTTGGTCAGAGTGAGCCTGGCATCTG | 868 |
| IGHV1-24_chr14:106732970-106733070 | TCCTACATAATGACAGTGCTACACATCTTTCCATTGCTGTTTTACTCAATTACTCAACCCATTTTCTAAACAGATTTAAACTTCATAAATCCTGTCATCTC | 869 |
| IGHV1-24_chr14:106733070-106733170 | CTCAGCTTCAGCACAGCTGCCTCATTCCTCAGGGTTTCTGACGCTCCAGGATGTGGGTTTTCACACTGTGTCTGTTGCACAGTAATACACGGCCGTGTC | 870 |
| IGHV1-24_chr14:106733185-106733285 | GCTCAGCTTCCATGTAGGCTGTGTCTGTAGAATGTGTCCCAGGTGACTCTGCCCTGGAACTTCTGTGCGTAGATTGTTTCACCATCTTCAGGATCA | 871 |
| IGHV1-24_chr14:106733275-106733375 | TTCAGGATCAAAACCTCCATCCACTCCAAGCCCTTTTCCAGGAGCCTGTCGCACCCAGTGTCATGGATAATTCAGTGAGGGTGTATCCGAAACCTTGCAG | 872 |
| IGHV1-24_chr14:106733375-106733475 | GAGACCTTCACTGAGGCCCCAGGCTCTTTCACCTCAGCCCCCAGACTGTACCAGCTGGACTCTGGGCGTGGGTGCCTGTGGAGGACAGAGAGGAGTGGATGA | 873 |
| IGHV1-24_chr14:106733475-106733575 | GACACCACTTAACTGGACCCAGTCCCCTCATCAGCCTGGAACTCAGGATTCTCTTGCCTGTAGCTGCTGCCACCAAGAGAGATCCTCCAGTGCAGT | 874 |
| IGHV2-26_chr14:106758470-106758570 | GAGGGTGGGAATCTGGGAGAGACAAGGGCTTCCCATAAGTGTTCTGATAAAAATCTCTTGTTTAGGGGGAAAGTGATGATTTTTTTGAATGATAGAGA | 875 |
| IGHV2-26_chr14:106758570-106758670 | ATACATCACCCAAACATTTAAAAATGTATTGTGTAAAGAAGTGTAAATGCCATCTCAGCCATTTACACACTGCAGACACACAGCTTATTAGTGTGCCTG | 876 |
| IGHV3-30_chr14:106791090-106791190 | TGGTGAATCGGCCCTTCACGGAGTCTGCATAGTATTATTACTTCCATCATATGATATAACTGCCACCCACTCCAGCCCCTTGCCTGAGCCTGGCGAC | 877 |
| IGHV4-31_chr14:106805945-106806045 | ACAATCACTTGAGTTCAGACACACCAGGATTCACTTAAGTGTTATTTTTAGTTCAGAACCTCTATCAGGTTTAGAGGGAATCGCTCTGTCCCAGGAGTGG | 878 |
| IGHV4-31_chr14:106806045-106806145 | ATCTTACAATAGCAAACGGTCTTAGAAAAACCAACATAATCTACAGCGGAGACCTCAGCATGGCAAGCAAGGAATCACTAAAGCCACCAGGAGATCCGG | 879 |
| IGHV4-31_chr14:106806120-106806220 | CACTAAAGCCACCAGGGAGATCCGGATGCACTGATACGATCCAGAAAACATAGCGAGTCCGGGAACTGATGCCGACTTTGAGGCAGCCTCTTTTTTTTTT | 880 |
| IGHV3-33_chr14:106815805-106815905 | GATGGTGAATCGGCCCTTCACGGAGTCTGCCATAGTATTTATTACTTCCATCATACCATATAACTGCCACCCACTCCAGCCCCTTGCCTGAGCCTGGCGG | 881 |

TABLE 6-continued

| Name | Sequence | SEQ ID NOs. |
|---|---|---|
| IGHV3-33_chr14:106815905-106816005 | ACCCAGTGCATGCCATAGCTACTGAAGGTGAATCCAGACGCTGCACAGCGAGAGTCTCAGGGACCTCCCAG GCTGGACCACGCCTCCCCAGACTCCACCA | 882 |
| IGHV4-34_chr14:106829685-106829785 | CTCGACTCTTGAGGGACCGGTTGTAGTTGGTGCTTCCACTATGATTCCCCATTCCACTCCCAGCCCC TTCCCTGGGGGCTGGCGATCCAGCTCCA | 883 |
| IGHV4-34_chr14:106829765-106829865 | GGCTGGCCGATCCAGCTCCAGTAGTAACCACTGAAGGACCCACCATAGACAGCGCAGGTGAGGGACAGG GTCTCCGAAGGCTTCAACAGTCCTGCGCCCC | 884 |
| IGHV4-34_chr14:106829865-106829965 | ACTGCTGTAGCTGCCACTGGGACTGGACAGGACCCCTGTGAACAGAGAAACCCACAGTGAGCCCTGGGATCAGA GGCGACATCTCATATCTTCATATCCGATTC | 885 |
| IGHV4-34_chr14:106829965-106830065 | CTGAGACACTCACATCTGGGAGCTGCCACCAGGAGGAGAAGAACCACAGGTGTTTCATGTTCTTGTGCA GGAGGTCCATGACTCTCAGAAAGCACTTCC | 886 |
| IGHV4-34_chr14:106830125-106830225 | GAGGATTTGCATGTGGGTGGTGCCTTTGTATGGATAGGTAAAAAGGGATGAGGGAGGCCCCAGTCTTTTG GGCTCACCCTGGGAGGTGTATGCTGGCTGT | 887 |
| IGHV4-34_chr14:106830240-106830340 | AGTTCTCTTCCTCTGGCCTCCCCTCCACCAAACCCAGAGTCTCCTCTTCTTCCAGTAGGAAATGTGCTGAAGG AGCTGGTCTGGGAGACAAGTGTGATCATG | 888 |
| IGHV4-34_chr14:106830315-106830415 | GGTCTGGGAGGAGACAAGTGTGATCATGAGATCAAAGACAGATTTTGAATACAGTTAATACTGTTCTACATTT AAAGATTCATATAACACCAACCATACACCC | 889 |
| IGHV4-34_chr14:106830415-106830515 | AAGTTCACCTAAATTGTCATTTACCCCTTCAGACATATTGAAACAGCTGCTGAGTGTGTAATAATCACAGTGA ATTGAGACAAACCTGGATCCATGCAATGTG | 890 |
| IGHV4-34_chr14:106830515-106830615 | TACTGTAGTTCAGAACATCCATCATGGTTAGAAGGATGCTACCTGTCCCAGGAAGTCCTGGTTATTTTTAAAT AGTACCTGAGAGCTGCCCTTCTGAGACCT | 891 |
| IGHV4-34_chr14:106830615-106830715 | TTTGAAATTTGAGATTGTGTGTGAGATCTCAGGAGATCTCAGGAGAGGTAGTAGAATATATCCATCCTTCTCAATGTG TAACCCTGAGAATATGGCCTGACCTCTAA | 892 |
| IGHV4-34_chr14:106830715-106830815 | ACATTTCTGTGTGAAAGATGTACATTGGGATACAGTGACAGCTTCAGATGAAAACTCTATAGTACAT CAGCACTGGAGGATAGTTCATCACCAAGA | 893 |
| IGHV4-34_chr14:106830815-106830915 | TTAGTGAAATTACCTTTCCTGGGAACCAGAGAGGACCTTCGTGAGCTCTACCCTCTGAGAGAACAAGGAA CTCTGGTTCTTCCCTGACAGGTCACACCTG | 894 |
| IGHV4-34_chr14:106831185-106831285 | AACAAGTGGGCTGGCCTTCTATGAGACAGAGGGAAAAGAGACAGAGTCAATATCCAGAGCGAGGTGA GCTCCTTACCTACCTACCAGGTGGTCTCTGG | 895 |
| IGHV4-34_chr14:106831285-106831385 | GCCATTTGTTTGAGCAGACCCAGAAGTACCTTCCTCACCCCTCAGGAGGATTATGAACATTGAGAGAAACT GAGATACTTTTTTATTTACAGGGAATATT | 896 |
| IGHV4-34_chr14:106831385-106831485 | TCATCGCGTGTTTACATCTACCTGGTGTGTACAGGGATGCTAGGATGTGCTCATACAGAAGAGCAA GAATTATATTCGTGAAGAAAACCAAAG | 897 |

TABLE 6-continued

| Name | Sequence | SEQ ID NOs. |
|---|---|---|
| IGHV4-34_chr14:106831485-106831585 | AGCTTCTGAATTTGTAGTATTGTTTGCTGCAAATGTGTCAGTTCACTAGATCATGTTATGCTGCTAGAAG AAAAACTTCCCAACATTGTCATGGAGACA | 898 |
| IGHV4-34_chr14:106831585-106831685 | AAATGCAAAACAGTGTAAAGATTCAACTGAGATTCCCTTGAAAATCACCAGTAATGAACAGGCCAAAGAA ATCAACCATTGTGGAAAGAGTGGTCATTAAG | 899 |
| IGHV3-35_chr14:106846385-106846485 | CCCAGTGTCACCTTACACATCCTGCAGGTCACCTCACCCAAGGTCACCTCACACATCCACCAGGTCACCTCACACCTCGTAAATCCCC CACCTCAGACACACCCTGGTCACCTCATA | 900 |
| IGHV3-35_chr14:106846485-106846585 | CATACGTCAGGTCACCTCACCTCACGCTCACCTCACCCAAGGTCACCTCACCCCGCAGGTCACCTCGTAAATCCCC AGGTCACCACATACATGCACCAGTTCACC | 901 |
| IGHV4-39_chr14:106877715-106877815 | CTCTTGAGGGACGGGTTGTAGTAGGTGCTCCCACTATAATAGATACTCCCAATCCACTCCAGCCCCTTCCC TGGGGGCTGGGCGGATCCAGCCCCAGTAGT | 902 |
| IGHV4-39_chr14:106877815-106877915 | AACTACTACTGCTCGATGGAGCCACCAGAGACAGTGCAGGTGAGGGACAGGGTCTCCGAAGGCTTCACCA GTCCTGGGCCCTGACTCCTGCAGCTGCAGCTG | 903 |
| IGHV4-39_chr14:106877930-106878030 | GAACAGAAAAACCCACAGTGAGCCCTGGATCGAGAGGCAGCCTCCCATATCTCCATGCTCTGCATCCTAGA AACACTCACATCTGGGAGCCGCCACCAGCA | 904 |
| IGHV4-39_chr14:106878030-106878130 | GGAGGAAGAACCACAGGTGCTTCATTTTCTTGCACATGAGATCCATGACTCTCAGAAAGCATTTCCCTTAT GAGTTGGACCTGAATTTAAGGAAATGTGT | 905 |
| IGHV4-39_chr14:106878130-106878230 | GGTGGCTTCCTGTGGGCCCTAAGTGAGGATTTGCATGGGGGTGGTGCGTTTGTACGGAGCAGTGAAAAG GGATGAGAGGCGCCAGTCTTTTGAGCTC | 906 |
| IGHV4-39_chr14:106878230-106878330 | ACCCTGGGAGGAGAAATGCTGGCTGCCCTTTGAGAACTCAGTTCTCTTCTTGGGCCTCCCCTCCAAGC CCAGAGTCCTCTTCTTCCAGGTAAAGAGA | 907 |
| IGHV4-39_chr14:106878330-106878430 | TGTGTCTGAAGGAGCTGGTCTGAGAGATCAGTGTGATCCTCGGATCAAGGACAGATTTTGGAATAGGGTCAG TACTGTTCAACCCTTAAAGATTCATATAAA | 908 |
| IGHV4-39_chr14:106878430-106878530 | ACCCACCACACACACCCAGGCCATCTAAATAGTCATTTACCCTTTCAGACACATTGAAACAAGCTGAATGT AATAATGACAGTGACTTCAAACAATACTG | 909 |
| IGHV4-39_chr14:106878540-106878640 | ATGTTTATTGTAGTTCAGAACATCCACCATGGTTACAGGGAAGCTCACTGTCCCTGGAAGTGGGTCATTTT TTAAAAGCACCTGAGAGCTGTCCTTCTGT | 910 |
| IGHV4-39_chr14:106878680-106878780 | AAGGTAGTGGGACATATCTCCATACTTCTCAATGTGTGACCTTGAAGATGTGTCCTGCCCCTCTAAACACTT CTGATTGAAAATATGTAGATTGGGGATTA | 911 |
| IGHV3-48_chr14:106994300-106994400 | GTGCAAATGCCTTGGAATCCAGGGCTAAGGCACCACCTCTCTGAGAGCTCCAGGGTCAGGGTTGGGTTT TCATCAGTAGAGGGAGGGCCCTATTTGCAT | 912 |
| IGHV3-48_chr14:106994430-106994530 | GGACCCTTGAGGAGTAGGCTGTACCCAGATAAGACGACGGTGCCCTGTAGAAGTTTGCTGGCAATGATTG CATTTGGAAAATATGCTGTCTTATTATGAA | 913 |

TABLE 6-continued

| Name | Sequence | SEQ ID NOs. |
|---|---|---|
| IGHV3-48_chr14:106994530-106994630 | ATTGTGCTGTGATAAACACTTGCACTAATCACCCTATTTCATTTCATTTTAAATATTCATGTAAACTATGTTCTGTAGGAGACAATATTTTCTCCATTTACAGA | 914 |
| IGHV3-48_chr14:106994545-106994645 | ACACTTTGCACTAATCACCCTATTTCATTTCATTTTAAATATTCATGTAAACTATGTTCTGTAGGAGACAATATTTTCTCCATTTACAGAAGTGAAGTAAACCC | 915 |
| IGHV3-48_chr14:106994660-106994760 | CTGTATGCATCTAGGAGCTCATGTCTGGGATGAGTGAACCCCGGTATCTGGCCCTGTGCTCTTCATCACTGTCTCTGACATCCCCCTAAACCAACTCCAG | 916 |
| IGHV3-48_chr14:106994760-106994860 | GACAAAGCTGGATGTGTCTAGTGTTTTTATCAGAACCCACTTTCCGTAATAAGAGCATGTGTGGTTTTGCTGCCCTCCAGCACTCTTCTGAAAATATGGA | 917 |
| IGHV3-48_chr14:106994860-106994960 | GAGAACTAGGATCCAGGCACATTAATTTTCAGGTACTTCTGACATTGAACTTATTTTTCTATCTTTCTATTACTCTTTCCTTGTCTAAGTTTCCATTTG | 918 |
| IGHV4-59_chr14:107083565-107083665 | AGAGAGACCCACAGTGAGCCCTGGGATCAGAGGACCACCTCCCATATCCCATGTCTGGATCCCTGAGATACTCACATCTGGGAGCTGCCACCAGGAGAAGG | 919 |
| IGHV4-59_chr14:107083665-107083765 | AAGAACCACAGATGTTTCATGTTCTTGCACAGAGGTCCAGGACTCTCAGAAAGTATTTCCATGTGAGCTGGAACCTGAATTTAAGGAAATGTGTGGTG | 920 |
| IGHV4-59_chr14:107083790-107083890 | ATTTGCATGTGGGTGGTGCCTTTGTATGGAGAGGTGAAAAAGGAGGAGGGGAGCCCCAGTCTTTTGGGCTCGCCCTGGGAGTAGGATCGTGCTGTGCCC | 921 |
| IGHV4-59_chr14:107083890-107083990 | TTTTGAGAACTCAGTTGTTCTTCTTGGGGTCTCCCCTCCCAAGCCCAGAGTCCTCTCTTCAGGTAAAGAGACGTGCTGAAGGACCTGGTCTGTGCCCC | 922 |
| IGHV3-64_chr14:107113405-107113505 | CTGACAGTGGTGACCATGGTTGACCATGCTTGAGAACTTTCATCTCCTGTGAGGATCAATCTGCATTTTCTGCATAGGAGAATAGGTTTTCATATTAAAACAATCAT | 923 |
| IGHV3-64_chr14:107113505-107113605 | TTTTAAAAAATATGTAGAAATGACCCTAGTAATCACAGAGTTCCGAACTTAGGTTCAGTAGTAGAGAAACTTTAAGAAGATGAAGTCCCACATCGTGACAGGAAA | 924 |
| IGHV3-64_chr14:107113820-107113920 | TGGAAGATGGTGAATCTGCCCTTCACAGAGTCTGCATATAATGTCTACCCCCATTACTACTAATAGCTGAAACATATTCCAGTCCCTCCCTGAGCCTG | 925 |
| IGHV3-64_chr14:107113920-107114020 | GCCGACCCAGTGCATAGCATAGCTACTGAAGGTGAATCCAGAGGCTGCACAGGAGAGTCCAGGACCCCCCAGGCTGGACCAAGCCTTCCCCCAGACTCC | 926 |
| IGHV3-64_chr14:107114095-107114195 | TTCTTCACTCATGTCCACTCACACTCAATATCTCTATTTCCTCATGAATCACCTTTAAAAATAGCAACAAGGAAAACCCAGCTCAGCCCAAACTCCATC | 927 |
| IGHV3-64_chr14:107114195-107114295 | ATGACTCTTCTGTGTTCAGTGCTGATCACCAAATGAAAAACACCTGGGAATCCCAGGGCGGGGGCTCCTCTCCCAGAGCTGCGGAGTCAGGGCTGGGCTGG | 928 |
| IGHV3-66_chr14:107136755-107136855 | TAGGGCACATCCTTCCCATCCACTCAAGCCCTTGTGCATGGCCTGGCGCACCTAGTGCATAGAGTAACTGGTGAAGGTAGGTGTATCCACAAGTCTTGC | 929 |

TABLE 6-continued

| Name | Sequence | SEQ ID NOs. |
|---|---|---|
| IGHV3-66_chr14:107136855-107136955 | AGGAGACTTTCACTGATGCCCCAGCCTTCTTCATCTCATCCCAGACTGCACCAGCTGCACCTGGGACTGG<br>GCACCTGTGGAGAGGACACGGGAGTGGAT | 930 |
| IGHV1-69_chr14:107169645-107169745 | GAAAACTTGTTCACAGTAGCACCTTCATGGAATGTTTGTATCAACGTTATAGAGTGTGGCCTTTTCCACTC<br>TGTGAATTTGGCTTATATTACGACTCTTG | 931 |
| IGHV1-69_chr14:107169745-107169845 | AATGGAATATTTATCTTAAAATTAGAGTATGCTGTCTTGTTTCTACTGTTCTTTTTTCTCAAATATATAACCC<br>ATTTTGTAAACAGCCTTAAACCTAATAA | 932 |
| IGHV1-69_chr14:107169970-107170070 | CTGCTCAGCTCTCATGTAGGCTGTGTCTGTGGATTTGTCCGCGTAATCGTGACTCTGCCCTGGAACTTCTG<br>TGCGTAGTTTGCTGTACCAAAGATAGGGA | 933 |
| IGHV1-69_chr14:107170070-107170170 | TGATCCCTCCCATCCACTCAAGCCCTTGTCCAGGGGCCTGTCGCACCCAGCTGATAGCATAGCTGCTGAAG<br>GTGCCCTCCAGAAGCCTTGCAGGAGACCTT | 934 |
| IGHV1-69_chr14:107170170-107170270 | CACCGAGGACCCAGGCTTCTTCACCTCAGCCCTGCACTGCACCCAGCTGCACCTGGGACTGGACACCTGTG<br>GAGAGGACACAGGGGTGAATAAAATCTCT | 935 |
| IGHV1-69_chr14:107170220-107170320 | CCTGGGACTGGACACCTGTGGAGAGGACACAGGGGTGAATAAAATCTCTTTAACTAAACCAGGATCCCT<br>TCCTCAGCCTTAGGACTAGGAGAAGCCCTTA | 936 |
| IGHV1-69_chr14:107170320-107170420 | CCTGTAGCTGCTGCTGCCACCACAAAGAGAGAACCTCCAGTTCCAGTCCATGGTCAGTGATGAGCTGTCCCAGGG<br>GCTTCTTCAGAGAGGAATGTGGTTGTTAT | 937 |
| IGHV1-69_chr14:107170420-107170520 | GTGATGCTCTCAGGGCACCACCAATATATCTATATTTATCTCAGAAGACCTCAGTTATTTGCATATGCATGAG<br>GCAGGGTATTTCACAGCTCAAAGCCTGAT | 938 |
| IGHV1-69_chr14:107170475-107170575 | TTTGCATATGCATGAGGCAGGGTATTTCACAGCTCAAAGCCTGATCTAGGATGAGAAAGAAAACACAGAT<br>GCCACATCAGCTGTACAAGTGTGGGATGCT | 939 |
| IGHV1-69_chr14:107170660-107170760 | CAGAACAAACCCAACCCCAGGATGCACTCCTCACTGTGAACCCACATTTTATTGGCCTAAAGATTACCTG<br>GGTTTTTGTGGGACCATTGCTGTCTCTG | 940 |
| IGHV1-69_chr14:107170760-107170860 | ACATTGAGCAGGCACCTAGACCCATCCTGTCCCATTAGGAACACTCAGAGCTCACTGGTAACACTGAAA<br>AGGTGGCCACTCGTTACCCTACATGAGTGT | 941 |
| IGHV1-69_chr14:107170860-107170960 | CCAGCAGGACCCATGGAGAGTTCTGAGATCTGCTGGGCACTCCCAAGACAGGGTCCCCAGCACTTTCCTG<br>AGGGTCCTGACCTCGGTCCTTCAGTGG | 942 |
| IGHV2-70_chr14:107178305-107178405 | TTATCCATTTCTATGTGTCTTTTTGAAAATGTCTACTCATGTCCTTTGCTCATTTTAACGGAGTTATTTGGT<br>TCTTGTTGCTGTCTGTTGTTGTAGAGTTG | 943 |
| IGHV2-70_chr14:107178415-107178515 | TTGCAAATTCTTCATATTAGTTCCCGTGTCACAGGCAAAGTGTGCAAAAGTTTTCTGTCATTCTGTAAATTG<br>CGTATTCACTCTGTGTTGTGAAAAAAT | 944 |
| IGHV2-70_chr14:107178515-107178615 | TATTTAGGTTAATTAAATCTCATCTGTCTATTTTTTTTAGTAGGACCTTTCATGCTGAATCTTTGTC<br>AAACAGGATACAGCTTCTGCTTGCATGA | 945 |

TABLE 6-continued

| Name | Sequence | SEQ ID NOs. |
|---|---|---|
| IGHV2-70_chr14:107178615-107178715 | ACCACTAACAGGGGACATGCCATTTATTAGTAAAGAAAAAGGAGGAAAACAAGGCTTGAGTCAGATGGGGATGGGAAACGCACGCCCTGGGCAGGAAAT | 946 |
| IGHV2-70_chr14:107178715-107178815 | GGCATCTCAGCCACCACTATCCTGTTCTGCAGAAGTGGGAGGGAGCACCACTGAAAAACACCTGGGTTCTTGTACAGGAAGCGCCCTGGGCTGTGTCT | 947 |
| IGHV2-70_chr14:107178815-107178915 | GTGTATCCGTGCACAATAATACGTGGCTGTCCACAGGGTCCATGTTGGTCATTGTAAGGACCACCTGGTTTTTGGAGGTGTCCTTGGAGATGGTGAG | 948 |
| IGHV2-70_chr14:107178880-107178980 | ACCTGGTTTTTGGAGGTGTCCTTGGAGATGGTGAGCCTGGTCTTCAGAGATGTGCTGTAGTATTTATCATCATCCAATCAATGAGTGCAAGCCACTCCA | 949 |
| IGHV2-70_chr14:107178980-107179080 | GGGCCTTCCCTGGGGGTGACGATCCAGCTCACACACATTCCACTAGTGCTGAGTGAGAACCCAGAGAAGGTGCAGGTCAGTGTGAGGGTCTGTGTGGG | 950 |
| IGHV2-70_chr14:107179080-107179180 | TTTCACCAGCGCAGGACCAGACTCCCTCAAGGTGACCTGGGATAAGACCCCGTGGATAAGAACATAAGAAGATGAAGCCACAAGGAGAATAGATTT | 951 |
| IGHV2-70_chr14:107179130-107179230 | CTGTGGAGAAGACATAAGAGATGAAGCCACAAAGGAGAGAATAGATTTTTTGCTTCTGAAGTACTACCTGACCAGCACTCACAGGACGGGACAGTC | 952 |
| IGHV2-70_chr14:107179230-107179330 | AGTAGCAGGAGCCGTGGAACAAAGTATGTCCATGGTGGAGAGAGCCAGGATTCACTGAGCGAGGCCCCTGTCCTCGTCTTTTGAACCCAGGGAGGGTGAGCTG | 953 |
| IGHV2-70_chr14:107179330-107179430 | GTGGAGATTTGCATCCCCTCATCTGAGCCCTACTCTATGGGTGCACTCAGGTCTCAGGACTCAGTAGGGGAGTGCATCTGTGGTGAGGAGCAGTGAGCC | 954 |
| IGHV2-70_chr14:107179430-107179560 | TACTCTATGGGGTGCACTCAGGTCTCAGGACTCAGTAGGGGAGTGCATCTGTGGTGAGGAGCAGTGAGCCCTCAGGTGTGGGGGTCCACGTGTGCTCTCC | 955 |
| IGHV2-70_chr14:107179460-107179560 | ATCAGGGAATCTATCTCATTTCAGCACCACCATGCCTCTCAGTCAGTCTCTCTGCTTCTACAGACAGGATCTTCTTCGATGCTCCCGCACCGACA | 956 |
| IGHV2-70_chr14:107179560-107179660 | TGCAACCTTCTGTTTTAGTCCTAGAGATTAGAGTAGAAATCAAGAGAGCTGCCGTTCCTCCTCCTTCAAGAATAATGATGGTGGGCATCTGGGGGC | 957 |
| IGHV2-70_chr14:107179660-107179760 | AAGGGGCTCCCCACAAGCATTCTGATCAAAATCCTCTTTGATTATGGGAAAAGTGATGAATTTGTGTAAAAAAATTGGAGAGAATAAATAAGAAAATAC | 958 |
| IGHV2-70_chr14:107179760-107179860 | AGTTACAAGTAATTATGTAAAGAAGTGTGTCTTAGCAGTGTGTGTCACACAGCTGCATTCCTAGAGGCATGTTCCATGAAAATCGATGTTGTCCTTG | 959 |
| IGHV2-70_chr14:107179860-107179960 | TGCCCCGTCAGTTCTGTGGAGAGTAGACTCGCATGAATGACTTCCCTTTTCCAGCCCATGAATGAATGACGGATGCTTTGGACAAGGAATTGGAAGACTC | 960 |
| IGHV2-70_chr14:107179960-107180060 | CTGAGGGAGCAGCAGGCTGACTGTTGCAGCCTTGCTCGCACCTGACTGGATGTGTCTGTGCTCATAAGGCCCGTGGAAACTCATCAATCCAGGTTC | 961 |

TABLE 6-continued

| Name | Sequence | SEQ ID NOs. |
|---|---|---|
| IGHV7-81_chr14:107258910-107259010 | CAAAAAGGGGTTAAATGATTTTGGAAAAGTAAGTAGAGAAATAAAAGAGGAGGAGTAAGAGCGGACAGAAGGGAGGAAGGCAAGCAATGATGAAC | 962 |
| IGHV7-81_chr14:107259010-107259110 | TGTGTAAAATTTCACTAATTAAAAGACTATTATATTGAAGAGGTGCCTATTAGGCAGCCTTTTGATGTTAACCATGTAATATACACCATGAACAACCTT | 963 |
| IGHV7-81_chr14:107259100-107259200 | GAACAACCTTGTAGAACACACAAGAGCCCCCTCAGAGAACTGATGGTCAGTCTCCCATCCAGTTGCCTTAGGGGTTAGGAACGCTCCCATGTTGTTC | 964 |
| IGHV7-81_chr14:107259200-107259300 | TCTGGTTTTTGCTCCTGAGGACACAAACAGCCAGTGTTTCCTCCCCGATGAATAGAGAGGCCCCTGGGGAGGGTGTCTGCAGCTCACTCTGCACCT | 965 |
| IGHV7-81_chr14:107259235-107259335 | GTTTCCTCCCCGATGAATAGAGAGGCCCCTGGGGAGGGTGTCTGGCAGTCACTCTGCACCTGCACCGCGGAAGGTTTAGAATGGTCCCTCTCACAC | 966 |
| IGHV7-81_chr14:107259335-107259435 | AATAATACATGGCGGCGTCCGAGGCCTTCAGGCTGCTCCACTCAGGTAGGCCGTGCTGCTGGAGCTGTCGGCTGAGATGGTGACGTGGCCTTGGAAGGA | 967 |
| IGHV7-81_chr14:107259435-107259535 | TGGGCTGTATCTGGTATCAGAGTTCCCAGATAGATGCTCCCCATCCACTCCAGTTCTTTTCCCGGGCATCTGGCGCACCCAGTGGATCCAGTAGCTGGTA | 968 |
| IGHV7-81_chr14:107259535-107259655 | ACAGGAGATCCTCCAGAGACTCCCCGGGTCTTTTCACCTCTGCTGCAGACTGCACCTCCGCAAAGCACCTGTGTGGAGACACAAATTTG | 969 |
| CIITA_chr16:10971440-10971540 | GTGTCTGGAGTATGAACCATGTATCAGCACCGAAAGGTTCTAGAAGTTCAGACTTTCGGGCAGTGTGTCACTAACTCTCAGCATGCTGGCCTGCCTGCC | 970 |
| CIITA_chr16:10971540-10971640 | CACAGCAAGGTCTCTTCTCCGCTCCCCTTTGGGTAAATACTGAGGGGTGCCTCTGCAGGACGGGACCTCTGCCAGACTCCACTCCATACCCAGAGAAGCAGGG | 971 |
| CIITA_chr16:10971640-10971740 | AAACCAAAATTGGAGTCAGCCTTGAGGTGTAGCTGTTGAGCCCTCAGCAGCTGGGGAGAGCTGGCGGATGCTGCCTCCCCCAGTTTCCTAATGTGTT | 972 |
| CIITA_chr16:10971740-10971840 | GTTTAAAAGGGTCAGGGAGGACGGGGAACAGATGGTGGGAAAGCACAGTGCAGAGACACCTGGCACCGGCTCTGAAGGCAGCATGGCAGCTACACCGTTGG | 973 |
| CIITA_chr16:10971840-10971940 | CTGGGAAGGGTGCCCCTGAAGAAGTCGTTTACATTCTGAGTCAATTTCCTGGAGTGTACAATGGACCTGTGGGAAAGCCTGTATGAAGGGTAATG | 974 |
| CIITA_chr16:10971940-10972040 | ATGAGGAGGGACCTAGCACAGTGTCCAATATTTTATAGGAACTGGAATTGAGCTCATAGGAGCTCAATTTTATTGGCATTGCTGTTGTTGGATGGTTAAAGGG | 975 |
| CIITA_chr16:10972040-10972140 | GTGGTATCCCTTTTCTCAGACTCCCCTGAAATGTATGTTTGCTTTGAACCCAGAGACTGATGACAGGTCTGCCGGTGTGGTTGGGTGCAGCCTTAAGTT | 976 |
| CIITA_chr16:10972140-10972240 | GCTACGGACGAAAGTGTTGAGGGGAGAAGTCAGAGGTAACCTTGCCCCCTCCCTCAATTCCAGATGAGGAAATTCAGGCCTGAAAGGGAAAGTGACCAC | 977 |

TABLE 6-continued

| Name | Sequence | SEQ ID NOs. |
|---|---|---|
| CIITA_chr16:10972240-10972340 | CTCAAAGTCTCATGCCTTGGAGGACCCAGCAGGAATCCAAGACCCTGAAAAGGACCGGCAGGGCTCTTG CCACGGCTGGGGCTGTGGTCATGGTAACAC | 978 |
| CIITA_chr16:10972340-10972440 | AGTTTTCCATCCATGAAGGTACCTGAGGGATTTTCTTCTCCCTAGGGCCAGCATCAGAGGAGTGA ATAGCTCAGTTAGCTCATCTCAGGGGCCAT | 979 |
| CIITA_chr16:10972440-10972540 | GTGCCCTCGGAGGTGGTTTGCCACTTTCACGGTTGGACTGAGTTGGAGAGAAACAGAGACCCACCCAGGG GTGGGGACAAGCTCCCTGCAACTCAGGACT | 980 |
| CIITA_chr16:10972540-10972640 | TGCAGATCACTTGCCCCAAGTGGCTCCCTAGCTCCTGGCTCCTCGCCTGAGTCCTCGGGACTCTCCCGAAGT GGGGCTGGCCACTGTGAGGAACCGACTCG | 981 |
| CIITA_chr16:10972640-10972740 | AGGCAGGGACCCTCTTGGATGCCCCAGGCAGTTGGGATGCCACTTCTGATAAAGCACGTGGTGCCACAGT AGGTGCTTGGTTGCTCCACAGCCTGGCCCG | 982 |
| CIITA_chr16:10972740-10972840 | AGCTCAGCCCTGCAGAAAGAAAGTGAAAGGAAAAAGAACTGCGGGAGGCGGGAGTAGGATGACC AGCGGACGAGCTGCCACAGACTTGCCCGCGGCC | 983 |
| CIITA_chr16:10972840-10972940 | CCAGAGCTGGCGGAGGGAGAGCACCAGCAGCCGCGCGGGAACACAGCGGTAGGTGAC CAAAGTCTCCTCTGTAACCCCTAAGGTCGGGC | 984 |
| CIITA_chr16:10972940-10973040 | TGAGAATCGAGGCTCCAGACTGTCAGTACTTGCTCAAGGTCACACAGCAAGTCTGGAGGATGGGGG GATGCAATATGCAAAATGTAGGGCCGGAAA | 985 |
| CIITA_chr16:10973040-10973140 | CACCTCGTTTCCAGCATCCCCGACATCTCGCGCGCCCTTCTTGTACGCCAGATTTGGACCAGGCGTTGGCTT GCTGTGCCCAGAGCTCCACCCTTGGCCGACTCCG | 986 |
| CIITA_chr16:10973140-10973240 | GGTGGCAGGAAAGCCTGGCGGCAGCTTCTGCAGAGAAGCCCGAGACTGGGAGCGCGGAGCAGAC ACACTCCCCGCCACCCTTGGCCGACTCCG | 987 |
| CIITA_chr16:10973240-10973340 | CGCGCCCCGGATCCGCAGAGGTGCGCGCCCTTCTTGTACGCCAGATTTGGACCAGGGCCCGCCGTTCCC TGAGCTTCACTTTCCCTGTTGGGTCATATT | 988 |
| CIITA_chr16:10973340-10973440 | CCATCTCTTAACTCTGGAATCTTGGGTATTGGGCTCTCCAGGCGGGGGCCCTGCTCAGGGAGGCAGTAGG GAGCCAAACCTTTAACCAGAGGATGGGATA | 989 |
| CIITA_chr16:10973440-10973540 | AGTCCTCAACTCTCGTTGAACATCTTGGCGAAGGTGTGTTGTTGGGAGGGGTGGGAGGGATCCCC CGGACTGAACCGATCTCTTGATCTCTCACT | 990 |
| CIITA_chr16:10973540-10973640 | TCTCTACCTCGCTTTGGGCCCTGAGTCACACCCTCTAAGGAGAGAGGCTAAAGCGCCCGGAAAGCCAG CGTGCGAATGCCCGGGTGGGAGTGGGAGAT | 991 |
| CIITA_chr16:10973640-10973740 | TGGAATCTCCCTGGGGTCAGGAAAGCCGGAATCGGAGCCACCATGCTTAGCTTAGCTGGAACTCTTAAA AGCCGCGTCCTCCTGAGTCCCACAGCCCC | 992 |
| CIITA_chr16:10973740-10973840 | TCTCCACCCTAGGTGGCACAGGAGAGTGGCAAAAGCCTAGAAGTTCAAGGCATGGCTCCCTCCCCAGCC GCAGCCTGGAGTGTCTAACTTTGGCAGGAA | 993 |

TABLE 6-continued

| Name | Sequence | SEQ ID NOs. |
|---|---|---|
| CIITA_chr16:10973840-10973940 | GTCTTCCGTTTCTGCTCCCCATCCAGAGAAAAAAATAAATAATACTTCTCCGGAGTGAGATTAAGGAAACAGGTACTTCTTCCTCTTGGAGAAAGAGGA | 994 |
| CIITA_chr16:10973885-10973985 | CTTCTCCGGAGTGAGATTAAGGAAACAGGTACTTCTTCCTCTTGGAGAAAGAGGAGCCAAAGGAACTTGACTCCAACAAATGATCACCTTGCAAACCCCC | 995 |
| CIITA_chr16:10973985-10974085 | GGCTCCCTTAGGGGATGACCTGTCTCCAACAATCTCAGAGCGTTTGAGGCAGGGTCTTTGAGATGACTGAGTGGGGAATCCCAGGCTCCCCACACAT | 996 |
| CIITA_chr16:10974085-10974185 | GAACATCACCTGGATGGATGATCAACCTGTTCAGGATGTAGGTTCCCGGGGCTCACCCCCAGGCCCGGTTGCTAGGCCTGGGGTGAGGCTGAGATCCTGAGG | 997 |
| CIITA_chr16:10974185-10974285 | TTAAACCATCTATCCAGGTGACTCCAATGTTCGTTTGTGGGGCAAAAGTCCCTCAAGTCAGAGACACTGGGAGGGCGCTGATGTGGTCTCATCTCTTTAC | 998 |
| SOCS1_chr16:11348520-11348620 | CAAGAGGTGAGAAGGGGTCTGCGGCCTCGTCTCCAGCCCGAGGGCGGGAGGCGCCTCGCCCCTACACCCATCCGCTCCCTCCAACCCAGGCCGGGGAGGGT | 999 |
| SOCS1_chr16:11348620-11348720 | ACCCACATGGTTCCAGGCAAGTAATAACAAAATAACACGGATCATCCCAGTTAATGCTGCGTGCACGCGGGCGCTGCCGGTCAAATCTGAAGGGAAGA | 1000 |
| SOCS1_chr16:11348720-11348820 | GCTTCAGGTAGTCGCGGACGGGGTTGAGGGGATGCGAGCCAGGTTCTCCGGGCCCACGGTGGCCACGATGCCTGGCGCACACGTCCTCGCAGCGGC | 1001 |
| SOCS1_chr16:11348820-11348920 | CGCACGCGGCGCTGGCCCAGCGGGGCCCCCAGCATGCGGCGCCGCACGTAGTCTGCTCCAGCTCGAAGAGGCAGTGCAAGCTCTGAAGCTGC | 1002 |
| SOCS1_chr16:11348920-11349020 | CATCCAGGTGAAAGCGGCCGGCTGAAAGTGCACGCGGATGCTCGTGGGTCCCGAGGCCATCTTCACGCTAAGGGCGAAAAAGCAGTTCCGCTGGCGCT | 1003 |
| SOCS1_chr16:11349020-11349120 | GTCGCGCACCAGGAAGTGCCCACGGGCTGCCCCCGGCTAATCGGCGTGCAACGAATGTGCGGAAGTGCGTGTCGCCGGGCCCCAGTAGAATCCGAGGCGTCCAGGAGC | 1004 |
| SOCS1_chr16:11349120-11349220 | GCGCTGCGCGCCGGAAGGTGCCCGCGGGGACCGCGGGGACACGGCCGCG | 1005 |
| SOCS1_chr16:11349220-11349320 | GGCCGCGGGGGACTGCCATTGTCGGCTGCCACCTGCTGTGGAGAGGAGGAAGGTTCTGGCCGCCGTCGGGCTCTGCTG | 1006 |
| IGHV3OR16-12_chr16:33523607-33523707 | TTTAAATCACCCAAATCAAAATAATTTATCTTCATTAATAAATAATCATCAGAAGTTTAACTAATTTTTACTTTATAATACTAGGTTTAAAAATTCTT | 1007 |
| IRF8_chr16:85933003-85933103 | AATCTGAATGCCCAAGTCGTTGATTGTCGTTTGCCTGTTTCCAAAGATTGGTAGAATAGATGCCTTTTAAAAATCTCATTTTCTTTAAATCTGTTTAC | 1008 |
| IRF8_chr16:85933103-85933203 | ATGGAAAAACGTTAGGAGAGCTCATATAATGAACGGCAATAGCAACCCCCTATCTTGAAACGCGCTCATCATCCCACTGAAATTCTACCACGTGGAATAA | 1009 |

TABLE 6-continued

| Name | Sequence | SEQ ID NOs. |
|---|---|---|
| IRF8_chr16:85933203-85933303 | TGCTTGGAGGGTCAGAGTTGTGGAACTGCCAATAACCAGTCGTTACTGAGGGTTAGTTGTGAAGGAGGGGACAGACTGCTTCTAAAATTCTGTTTAAT | 1010 |
| IRF8_chr16:85933303-85933403 | GACAGTCAATTAAGATTTCTGAGTCTGCTTGAGGGCCTTTGCTTCCATCAGCCCAGTCGTCCTTGGCAAGAGAGTCTGTATATGGCCACAGCTCAC | 1011 |
| IRF8_chr16:85933403-85933503 | AAAAGCATTGTTTGAAAAAATTTATTGAAAGAACATTGTTTGTAAAATGAGTCCAATACATAGGACAGACTTTCCTAAGGTGAGATGTGTTACTTACCC | 1012 |
| IRF8_chr16:85933503-85933603 | AGAGCTGTGAAAGCTTTACGGATGGAAACTAGAGACTGAATTTTCAGAATTTTAAGAAGTCTCCCCAACCAATGGCCCCCACTTTCTTTTTTAAAC | 1013 |
| BZRAP1_chr17:56408574-56408674 | GGGCGTGATCTCCGAAGCCCACAGTACACTCATCCATAAAGTAGGAAACACTACACCCTCCAGTGCTGTTAGTAGTGCTTTCTACTTTATGGGTGACTGCA | 1014 |
| BZRAP1_chr17:56408674-56408774 | TGTCTGTCTGTCCGTCGGCGTGTACTCTTCAGGCTGCCCAGGCCTCTGACTCCTGCTCCAAGAGCCCCCCAGCCCTTCCTTGGCTTCCTAAGATCCC | 1015 |
| BZRAP1_chr17:56408884-56408984 | CCCTCTTCCCTTCCCCCTAAAGGCTTCCAGCCACGCTAGCCACCCTCAGCGTCCAAATGAGGCAGCCACCAGCTCCCCCTCTGGAGGCCTCTGGTCTCCCAGTTCTGTG | 1016 |
| BZRAP1_chr17:56408984-56409084 | AACCCCTGGCTGCCGCTTCCAGCCACGCTAGCCACCCTCAGCGTCCAAATGAGGCAGCCACCAGCTCCCCTGCCAAGGTCTGGTCTCCCAGTCCACCC | 1017 |
| BZRAP1_chr17:56409084-56409184 | AACCGTGAGGTCCTGACTGCCCAGAGCCTCAGTCCCCACCCTTCAGCCTCCCCACCAGCCCAAGATCCTGACCCCCCAGGGCCTAAGTCCCCAGCCTCCC | 1018 |
| BZRAP1_chr17:56409184-56409284 | CAACAGCCCAGGGTCCTGACCCCCCCAGGGCCTCAGGGCCCTGGCCTCCCAGCCCAGCCCAAGGTCTTGAACACACCAGGGCCTCAATTCCCAGCCTCCCAC | 1019 |
| BZRAP1_chr17:56409284-56409384 | CAGCTCAAGGTCCTGACTCCCCCAGAGCCTCAGTCCCAGCGCCTCCATAGCAGCCCAAGTCCTGACCCCCCAGGGCCTCAGTCCCCAGTCCCCAGGAGGCCCAGC | 1020 |
| BZRAP1_chr17:56409384-56409484 | CCCAAAGTTCCTGACTCCCCAGAGCCTTGATTCTCGGCCTCCCCCACCAGCCCAAAGTCCTGACTCCCTCACTGCCCTGCTGTTCCCCTGGCAGGAGCCCAA | 1021 |
| BZRAP1_chr17:56409484-56409584 | GGCTATCCCAACAACAAAATGTGGCCATGTGGGCGGAGGAAGAGGCTGGCGCCCCTTGAGACACTGGTCCCACTTCTCAGCCTCTGCGTACCCTCTGCCA | 1022 |
| BZRAP1_chr17:56409584-56409684 | TCCCGCCTTACTCTCCAGCCTCCTCTTCCTTGGACACCTCTTTCCCCGCCTGGGGTCCCGGAGCCATTTTACCTTCCTTCACTAGAGAGGGTTTCAAGGCG | 1023 |
| GNA13_chr17:63010240-63010340 | CTAAGATTTTCAAGAAGTTAAACGTAGAATTAAGATTGTTCTAATTCTGGTGTAAACTGCTATTTAAAAAACAAAACAAAACAGAAAACATCAAAAACA | 1024 |
| GNA13_chr17:63010315-63010415 | AAACAAACAGAAAACATCAAAAACACAAAAAGATATTAAAACAGCAAGTCTTTTGTACATCACTGTAGCATAAGCTGCTTGAGGTTGTCATGCAGAATAG | 1025 |

TABLE 6-continued

| Name | Sequence | SEQ ID NOs. |
|---|---|---|
| GNA13_chr17:63010415-63010515 | TATCCTTCACGTCACGGAAAACAAGGCGGATGTTCTCCGTGTTGATAGCAGTGGTGAAGTGGTGGTATAA GGGCTTCTGTTGCTGGTCCCGGCGTTTGTT | 1026 |
| GNA13_chr17:63010515-63010615 | CCCGGAAACATTCCACCAGGAATTTTGGACGTCTCTTAAGCAGTGGGGATCCCCTCAAATTCTAGGAAA TAGTCTTTGATGCTCACAATTTGCACCTTC | 1027 |
| GNA13_chr17:63010615-63010715 | TCCTCAAGCAAGTCTGTCTTGTTTAAGAACAGAATTATGGAGACATTGCTGAAACCCGGTTATTGACGA TTGTTTCAAAAATGTTCAGAGACTCTGTAA | 1028 |
| GNA13_chr17:63010715-63010815 | GGCGATTGGTCAGTGGATCTTCCATAAGCACCTGGTCAAATTCACTTGAGGAGAAACAAGGAAAAGTATTGA TGTCACACTGTCGAAACATTCAAACCAACG | 1029 |
| GNA13_chr17:63010815-63010915 | TTTTCCTTTCTGATCCTCTGACCACCTACATCAACCATTTTGAAAGGAACATTTTTATTTCAAAGTCGTATTC ATGGATGCCTTTGGTGGGTCTCTCGGCA | 1030 |
| GNA13_chr17:63010915-63011015 | AGCAGAATATCTTGTTGTGATGGAATATAATCCTGGAAAAGAAAAAACTTGTTTTATACCTATTAATCCCG AAGTAATGCGAATTTTTAATGGACTACTA | 1031 |
| 43717_chr17:75447868-75447968 | TGTAAATATTTGGCCAACTAAGCTGAGTGGCTAAGTTCTCCTGCTGCCCGGAGCTTCTTGGAACATGTTTC CTTTTCGCAAGGGGTTCCCTGGCTTCCA | 1032 |
| 43717_chr17:75447968-75448068 | GGAGGGGCCAGGAGAGAATTCGAATTGGCCACCGCCTTTCTCTAAAATCACTCCGCTCAAGTTATCACCCCT CTGGGCTCCCGGAGACCCGGCTGGCTGGAGG | 1033 |
| 43717_chr17:75448068-75448168 | CTGGAGATAGTCTCAATGCTCGAAATGCCGTAACCGAAGCTCCCCGGCGCCGGACTCGGGATCCAGGG AGCTGCTGCCAGCGCAGCTTGGATTCC | 1034 |
| 43717_chr17:75448168-75448268 | TGGATGTGTTGGATATGTGCAGGGCGTTCCTGGGAGGAGCCATGTCAGTGAGCAGGGCTGAGGATGTGCTGGCGGGCTG GTCTGCCGTGCGTCTTTGCTTCTCTACAATGGC | 1035 |
| 43717_chr17:75448268-75448368 | ATGCTGCCGTCGCCATGCAGAGGCATGTCAGTGAGGGCTCAGGTGAGCAGGGGCTGAGGGATCTCCCTAACGGACCTGCT TTCAGAGGGTCTTTTCATGCTGGGAGAACC | 1036 |
| 43717_chr17:75448368-75448468 | CCAAGAGACTAAATCATGCAGCCAACGGGGTGGTCCCCGGCCTTAGTAAGTACCGCCTTAGTAAGTACCACTTAGT TAGGCAATGCCATCTGCTCCTGAAACGCCGT | 1037 |
| 43717_chr17:75448468-75448568 | CAGCCTCCTTAGTACCGCCTTAGTAAGTACCACTTAGTACTACCACCACGCCTGGCTAATTTCGTATTTTTTTTTTTAG AGTACCTCCTTAGTAAGTACCACTTAGT | 1038 |
| ADCYAP1_chr18:1477565-1477665 | AAGTACCCTCCTTAGTAAGTACCACTTAGTACTACCACACGCCTGGCTAATTTCGTATTTTTTTTTTTAG TAGAGACAGGGTTTCTCCATATTGGTCA | 1039 |
| ADCYAP1_chr18:1477665-1477765 | AGGTCAGGGCGCATATGCGGGTCTCGCGGTCGTCGTGCTCCAGCCACGCCACAGCACGGACATCTGGAAGAGCG CCAGCTCCGACTCCACGGGGCGGCAGCG | 1040 |
| AC012123.1_chr18:30349775-30349875 | AGTCCAGCAGGGCGCATCTCCTGAAGTTGAGCAGCAGCAGACATCCTCCACCAGGTACTTGTTGGCCAG CTTCTTGGTCTCTCCAGGCCGTGCAGCGC | 1041 |
| AC012123.1_chr18:30349875-30349975 | | |

TABLE 6-continued

| Name | Sequence | SEQ ID NOs. |
|---|---|---|
| KLHL14_chr18:30349975-30350075 | GGCGATCTTGCACCTGCTTGTAGTTCTGCACCGAGATCTGTCGTTGAGGAACTGCACGCAGAGCTTGGTGACCTGGGGATGTGCAGGATCTTGCTG | 1042 |
| KLHL14_chr18:30350075-30350175 | ACCGACAGCACCTCCTCCACCGTGTCCAGGGACAGGGTCACGTTGGCCGTGTAGAGGTACTCGAGCACCAGGCGCAGCCCGATGGACAGCAGCCCTGCA | 1043 |
| KLHL14_chr18:30350175-30350275 | GCACCAGGTTGTTGATGGCCCGGGGGCTGGTCAGCAGCTTGTCGTCGGGGAGGAAGGAAGGAGTCCCGGGCTCCTCCTGCGCGGCGGTGCTGCTCTG | 1044 |
| KLHL14_chr18:30350275-30350375 | TGACGGCTGCTGCTGCGCGCGGCTGCTGCTGTGGTCCTTGGGGGCCCCCAGGCCCTGTCCTGCCGCGCCGACCCCTCCCCGAGGGGGGTGCTGGAGAAGAGC | 1045 |
| BCL2_chr18:60806264-60806364 | GAGACTTCAGCGCCGGAGCTGGCTATTCCAGAGATGGACCTCAGAGGATTCCTTAGTCTAATTACCTTCTGGGCTGGGGTAGAAGATGGTCTCGAGGGAA | 1046 |
| BCL2_chr18:60806364-60806464 | GCACAGAACCAAGTTCCCTACTGCCGCACTAGCTATGCAAATACTGCAGGGCACCTGTGGGCTCATGTCCCTCCTGCAAGAGGTGTGGTCAGTCCAGTA | 1047 |
| BCL2_chr18:60806464-60806564 | ATTCAAAAGACGTACTTCTGAAATAGGTGGAGAAATGCATTTATAGCAAAAGTGCTAAAAATATGTTAATAGTTATGCTATTTGGTTCACCAGGTTAGT | 1048 |
| BCL2_chr18:60806564-60806664 | GTAATAAACCATAACAAGACTAAAGGCCGTATCTATATGACCTTGAAATCTCATCTTCAGCGGCTTATTCATTCAGTAACAAACTATTTTGTA | 1049 |
| BCL2_chr18:60806664-60806764 | AGGTGCTGAGTATTAGCTTAAAGCTAAATAGACACATGCCCTGCCCTATAGTAACTGCTTGGTAATATTCCCAGTGCTTCCATGGCCATTGCCCAGCAGTGCCTTGCCAGG | 1050 |
| BCL2_chr18:60806764-60806864 | TCTTAGTACTGAATTCAAAGACACTTGTGTCTTGTCTGCAGGCCCCATTTGCCCAGCAGTGGCATTTTAGTTAATCTTACTTAGAGAACAGGCCCATGCTCCTGTCCTCAT | 1051 |
| BCL2_chr18:60983784-60983884 | CAAACAAACAATTTGGTCAAATAAGATCAGATGTTCACATCAATCATCTACTTTTCTTGGCCTTTTCTCTATTGGTTAAACACCAAACAGTGCATCATATATT | 1052 |
| BCL2_chr18:60983884-60983984 | TGTCAACTTTGTCAAATAAGATCAGATGTTCACATCAATCATCTACTTTTCTTGGCCTTTTCTCTATTGGCCTCCTAGTATGAGCACACTTTGTAAAA | 1053 |
| BCL2_chr18:60983984-60984084 | TGTAATAAAAACATGGTGTGCTTCTTGACATCTAAATCCACTTGCAGTAATTTCTAGGCTTTTTGCTCCTGTTAGGTCCTATAAATAATGACATTAGT | 1054 |
| BCL2_chr18:60984454-60984554 | ATAGATACCTAGATGCAAATTTTTTCAGCCGACCACACAAAATTAGGTCCACTCTGAGTGGTGAAAACAAAAGATTCTAACATTCTAGCAAACTGGTAAA | 1055 |
| BCL2_chr18:60984554-60984654 | CCATACACAAATTTATAGATACAAAGAATGCAGCCAGCCGATGCAAATTCTGTCACTGACAAGGTAGCAAGCCATAGCCCTGATACTCCTCAGGACACCTCATC | 1056 |
| BCL2_chr18:60984654-60984754 | ACGCCCACTGGGAACATGGCACACACTGGAGATTCCAGTCCAAGGACTTTGGAATGTCAACTTAGCTCTTTACAAAACAACTAAGTTTTTCAGGGAAA | 1057 |

TABLE 6-continued

| Name | Sequence | SEQ ID NOs. |
|---|---|---|
| BCL2_chr18:60984754-60984854 | AGACTTACATTGGTTTCCTCTTTTGGAAAATTTTACCGATTGATGATGCCCTTGGTCTTCTGTGGAGTCT<br>ATTCTTCAATCGGGTTGTTCTTCCAATTT | 1058 |
| BCL2_chr18:60984854-60984954 | TAGTGTACAACGGGCTTGTTTCAGGGGAGCTTGTTTGGGATGCAGACTGTCAAGACCCAACCTGGTATCT<br>GGTTCATAAGCAGTCCCTGAAACCTCCCTC | 1059 |
| BCL2_chr18:60984954-60985054 | CGGTTCCAACAAGCTGCTCAAGCCAGGAAACGTGGTCTGCTCGGGACTCCTGGACCTTCAGCTTGAGAAAC<br>ACTGAAGGGGTACCATTTACCACCACATCC | 1060 |
| BCL2_chr18:60985054-60985154 | TACTGGATTACAAACGTAGATCTTTGGATCTCCACGACTAGCAAGCAAGTAAAGACTTTTAGATGCA<br>GGCGTTATCGGTCAGGTTGGGAGTGAACGC | 1061 |
| BCL2_chr18:60985154-60985254 | TTTGTCCAGAGAGGAGGTAGGGACGCCGGAAGCAACAACTCTGATTTATTTCGCCGGCTTCCACAGCC<br>TCCCATTGCCCCAGGAGCCCACCCGCACTC | 1062 |
| BCL2_chr18:60985254-60985354 | CAACCCCCGCCATCTCGGACCTGTGGCCTTCAGCCCCAGACTCACATCACCCAAGTGCACCTACCCAGCCTCCGT<br>TATCCTGGATCCAGGTGTGCAGGTGCCGG | 1063 |
| BCL2_chr18:60985354-60985454 | TTCAGGTACTCAGTCATCCACAGGGCGATGTTGTCCACCAGGGCGACATCTCCCGGTTGACGCTCTCCAC<br>ACACATGACCCACCGAACTCAAAGAAGG | 1064 |
| BCL2_chr18:60985454-60985554 | CCACAATCTCCTCCCCAGTTCACCCCGTCCTAAAGACTCCTCCACCACGTGGCAAAGCGTCCCCGCGG<br>GTGAAGGCCGTCAGGTGCAGCTGGCTGGA | 1065 |
| BCL2_chr18:60985554-60985654 | CATCTCGGCGAAGTCGCGGCGGTAGCGCGGGAGAAGTCGTCGCCGGCCTGGCGCGAGGGTCAGGTGGAC<br>CACAGGTGGCACCCGGGCTGAGCGCAGGCCC | 1066 |
| BCL2_chr18:60985654-60985754 | GCGGCGGCGCCGCCCGGGGGCAGCCGGGGTCTGCAGCGGAGGTCCTGGCGACCGGGTCCCGGGATGCGGCT<br>GGATGGGGCGTGTGCCCGGGCTGGGAGGAGA | 1067 |
| BCL2_chr18:60985754-60985854 | AGATGCCCGGTGCGGGGCGGCGCCCCGGGGGCGGGCGCCCCACATCTCCCGCATCCCACTCGTAGCCCCT<br>CTGCACAGCTTATAATGGATGTACTTCAT | 1068 |
| BCL2_chr18:60985854-60985954 | CACTATCTCCCGGTTATCGTACCCTGTTCTCCCAGCTGCGCCATCCTTCCCAGAGAAAAGCAACGGGG<br>GCCAACGGCACCTTCGCCCCAGCTCCCAC | 1069 |
| BCL2_chr18:60985954-60986054 | CCCACGCGCCCCAGAGAAAGAGAGGAGTTATAATCCAGCTATTTTATTGGATGTGCTTGCATTCTTGG<br>ACGAGGGGTGTCTTCAATCACGCGGAACA | 1070 |
| BCL2_chr18:60986054-60986154 | CTTGATTCTGGTGTTTCCCCTTGGCATGAGATGCAGGAAATTTTATTCCAATTCTTTCGGATCTTTATT<br>TCATGAGGCACGTTATTATTAGTAAGTA | 1071 |
| BCL2_chr18:60986154-60986254 | TTGTTAATTAATATCAGTTACACTTCCTCTGTGATGCTGAAAGGTTAAAGAAAAAACAAACTAATAAGTAAAAAA<br>TCAGGTGCGTTTCCCTGTACACACTGAGTG | 1072 |
| BCL2_chr18:60986254-60986354 | AAAGCAGGGCATACACACTACAAGTAACACGGCTAAAAAGATGTATTAAGCTGCCTGGAAATTAAATTT<br>ACTCGAATGCACTTTAAGTAAAAATCTCA | 1073 |

TABLE 6-continued

| Name | Sequence | SEQ ID NOs. |
|---|---|---|
| BCL2_chr18:60986354-60986454 | AAGGTTTCCATTGAAAGTTACATTAAACCAATTTCCTGTGCAGAGAACTTACTTGTATTTTTAAGTACAGCATGATCCTCTGTCAAGTTTCCTTTTGT | 1074 |
| BCL2_chr18:60986454-60986554 | AAAACCAAAACAAATGCATAAGGCAACGATCCCATCAATCTTCAGCACTCTCCAGTTATAGCTGATTGAAACTTCCCAATGAATCAGGAGTCGCGGGGA | 1075 |
| BCL2_chr18:60986554-60986654 | GAGGGAGTAAAAATTAGGAGGAGATTTCCAGATCGATTCCCAGACTTCTGCTTCACAGAAAATGTCAATCCGCAGGAATCCCAACCGGAGATCTCAAGAGCTC | 1076 |
| BCL2_chr18:60986654-60986754 | GAGAAAAAAAAAGGCAGCGGCGGCGGCAGATGAATTACAATTTTCAGTCCGTATTCGCAGAAGTCCTGTGATGTTTTCCCCTTCTCGGCAATTTACAC | 1077 |
| BCL2_chr18:60986844-60986944 | TGAAGGAGCCGGGGACGGGGACAGGAGATCCTCTTCTGATTAAACTCCGAACAGCAAATGCATTTTCCGAAAAGCTGCTGGATAAATGAAGGCAGGACGCG | 1078 |
| BCL2_chr18:60986944-60987044 | CCTGGCCCCCGGTGCCCAGCGCTAGAAGCCCCGCTGTGTGGTGCGGCGAGGGGTGGGGAGAAGGAGGTGGTGGGGAGGGTTTATTTTTCCCTC | 1079 |
| BCL2_chr18:60987044-60987144 | TTTTCCTAAAAGATGACTGCTACGAAGTTCTCCCCCCTGGACCCTTTCTAGCCGTGTATGTGGAGAGTGTGTGTCGCCTGGACCCTTTTCTAGCCACCCCGCCTCCGGCCTGCGCACCCTTTC | 1080 |
| BCL2_chr18:60987964-60988064 | GTGTGTGTCTCGCCTGACCTTGTTTACCGGCGCTCGGCCGCCGCGGGGGAAGACCCAGGCCAATGCCGCCCCCCACCCGCCCAGCAGTGGACCTCAGCGGTGTACACGCGCCTACG | 1081 |
| BCL2_chr18:60988064-60988164 | ACACACACCACGTTGTGTTACCGGCGCTCGGCCGCCGCGGGGGAAGACCCAGGCCAATGCCGCCCCCGAGCGTGGTGTTTACTTTCCCCAGCAGTGGACCTCAGCGGTCCGCGACTACA | 1082 |
| BCL2_chr18:60988164-60988264 | CTGTGAAGACAGGTGACTCTGCACGTTTTAAGCAAATGTCTAGGGACGCCCAGACCTAGTCCGTGACCCATGCAGAACTCAGCAAGTAGCTTCCTAGGTGTCCGCGCACTACA | 1083 |
| BCL2_chr18:60988264-60988364 | CACGCACGCGCATCCCCGCCCCGTGTCCCACCTGAACACCTAGTCCGTGACCCCAGGCCCATGCAGAACTCAGCGCTCCAGGAAGGGGTTTATCAGGGCTTT | 1084 |
| BCL2_chr18:60988364-60988464 | ACGACAGTTGAAGTCAATGTTTCCCTCTGTCCCTAACACCTTTTACACTGGTTTAGTGCTACACGATGAGGACTTCCATATAGTAACTTTCAGGCCCAC | 1085 |
| BCL2_chr18:60988464-60988564 | CGTCCTAACGCTGGGGTGGGTGGGCTCCTAAAGGTCTCCACCTTTGCCTGCCAATCCTAGTTGCCGCACTTTCTCAAATGCCGGTATCCACGCTCGCTCGC | 1086 |
| S1PR2_chr19:10340823-10340923 | GTGTCTTCCATGGAGGATGGCAGCAGAGACACCCCGTGCTGCTGGCCCGACACTCTCGGCCTCCTTATCTGTTTAGGAATGCCGGTATCCACGCTCGC | 1087 |
| S1PR2_chr19:10340923-10341023 | GCCGGAGCCACGCCTCCTCTCCCCCCCGCCCCGAGACGCCACACGCGCGGGGCCCCCAGTCTCCAAGCGGCACTGGAAGGATTCCTCTCCGTCCGC | 1088 |
| S1PR2_chr19:10341023-10341123 | CAGGGGTCCCGCCTCGAGATTCTGGGAAGACTTGGGGGTGGGGACCAGATCGCAGCAGCAGCTGCACCGCGAGTTCCGGCCTGGCCGTGTCGCCCCACG | 1089 |

TABLE 6-continued

| Name | Sequence | SEQ ID NOs. |
|---|---|---|
| S1PR2_chr19:10341123-10341223 | AGGGGGACTGTGGGCTCAGCGCGTGGGCCCGGAGCATCTGACAAGGACAGAGACAGAGGAGGGGTG GAAATCCCCGGGTGAGTCAACCCGTGCTGAG | 1090 |
| S1PR2_chr19:10341223-10341323 | AAGGGGGCGAGTTCCGACGCTCCGCCCGGCTCGGGGCTCGGGCGAGGTCCGCGCCACGCGCCTTCACCC ACGACCCATCCCTGAGCCGGAGTTGAAAGA | 1091 |
| S1PR2_chr19:10341323-10341423 | GGAGGCGTCTGAGCCACCAGTCACTTTCTCTTTCCTTACAAACAAAGCCACGCCCCCCGCCGGGGAC CGGAGGAGGCAAACAACTTGGGAAACCGA | 1092 |
| NCOA3_chr20:46131072-46131172 | CCCACTTTCCCCTTTCTGTCCCTAAAGTTTTTTCTTCCTCTTGCCTCCCCCAGCCCTTTTGAAAGCTCCCGC GTCGTCCTCCTGCTCCCCGGCTCCTTA | 1093 |
| NCOA3_chr20:46131172-46131272 | GCAGCTTCTGGGACGACGGAGGGAAAAGCGCGGGAGGACCCCCCCACCCCAGCCTCCCAGCCGGGTG AGATTTGGTTGCTGTGTTTCCTCCTCACTTG | 1094 |
| NCOA3_chr20:46131217-46131317 | CCACCCCAGCCTCCCAGCCGGGTGAGATTTGGTTGCTGTGTTTCCTCCTCACTTGGGCATTTAAAAAATAT TTTAACACGAATTGTCCGCGGAATTTTCA | 1095 |
| IGLV4-69_chr22:22380472-22380572 | CATGGCCTGACACCCCTCTCTCCTCCAGCTTCTCCACCCTCTGCTCAGTGACTGCTGTGGAATGCCAAAG TGATTATTGGGGACACATGGGATGACTTT | 1096 |
| IGLV4-69_chr22:22380572-22380672 | TCTCTTATATTTTAACATTGTGGGTGGGTAGTGAACCCAGACTCACCTCTGTGCCTCTGCCTCTCTGTT CCAGGGTCCTGGGCACAGTCTGCGCTGAC | 1097 |
| IGLV4-69_chr22:22380672-22380772 | CCAGGAAGCCTCGTTGTCAGGAGACCGTGGGACAGAAGGTCACCCTCCTGTACTGGAAACAGCAACAAC GTTGGAAGTTATGCTGTGGGCTGGTACCAA | 1098 |
| IGLV4-69_chr22:22380772-22380872 | CAGATTTCTCACCGTGCTCCCAAAACTGTGATGTTTGGAAATTCTCTGCCCTCAGGGATCCCTGACCGCTT CTCTGGCTCAAAGTCTGGGACCACAGCCT | 1099 |
| IGLV4-69_chr22:22380872-22380972 | CCCTGACTATCTCGGGCTTCTAGCCTGGAGGACGAGGCTTGATATTATTGTTCAACATGGGACTACAGCCTC AGTGCTCACACAGTGCTGCAGGCACATGG | 1100 |
| IGLV4-69_chr22:22380972-22381072 | GGAACCGAGACAAAAACTGCCCTTGCCTGTCCCGAGGCTGATCACTCCATACTTGCCTATGACAAACA AAGAGGGTGCCTGGCTGATCGTACAGTT | 1101 |
| IGLV4-60_chr22:22516707-22516807 | GAAATGTTGTTGCTCTTGTCCTTCCTCAGGCCATAATGAGCGTCTCTGTTTTCAGGGTCTCTCTCCCAGC CTGTGCTGACTCAATCATCCTCTGCCTC | 1102 |
| IGLV4-60_chr22:22516827-22516927 | TCAAGCTCACCTGCACTCTGAGCAGTGGGACAGTAGCTAGCTACATCATCGCATGGCATCAGCAGCCAGG GAAGGCCCCTCCGGTACTTGATGAAGCTTGA | 1103 |
| IGLV4-60_chr22:22516927-22517027 | AGGTAGTGGAAGCTACAACAAGGGAGCGGAGTTCCTGATCGCTTCCAGGCTCCAGCTCTGGGCTGAC CGCTACCTCACCATCCCAACCTCCAGTTT | 1104 |
| IGLV4-60_chr22:22517027-22517127 | GAGGATGAGGCTGATTATTACTGTGAGACCTGGGACAGTAACACTCACACAGTGATACAGGCAGATGAG GAAGTGGGACAAAATCCTCAACCTGCTGAGG | 1105 |

TABLE 6-continued

| Name | Sequence | SEQ ID NOs. |
|---|---|---|
| IGLV1-51_chr22:22677077-22677177 | AAGGTCACCATTCCTGCTCTGGAAGCAGCTCCAACATTGGGAATAATTATGTATCCTGGTACCAGCAGC TCCCAGGAACAGCCCCCAAACTCCTCATTT | 1106 |
| IGLV1-51_chr22:22677177-22677277 | ATGACAATAATAAGCGACCCTCAGGGATTCCTGACCGATTCTCTGGCTCCAAGTCTGCACGTCAGCCAC CCTGGGCATCACCGACTCCAGACTGGGGA | 1107 |
| IGLV5-48_chr22:22707517-22707617 | TCAGCCAGACTCACCTGACCTTGCGCAGTGGCATCAATCTTGGTAGCTACAGGATATTCTGTACCAGC AGAAGCCAGAGAGCCCTCCCCGGTATCTCC | 1108 |
| IGLV5-48_chr22:22707617-22707717 | TGAGCTACTACTCAGACTCAAGTAAGCATCAGGGCTCTGGAGTCCCCAGCCGCTTCTCTGGATCCAAAGA TGCTTCGAGCAATGCAGGGATTTTAGTCAT | 1109 |
| IGLV1-47_chr22:22712077-22712177 | AGAGATCTGGGGAAGTCAGTTCAGCTGTGTAGAGAAGACAGGATTCAGGACAATCTCCAGCATGG CCGGCTTCCCCTCTTCCCTCTCACCCTCCTCAC | 1110 |
| IGLV1-47_chr22:22712177-22712277 | TCACTGTGCAGGTGCACAGGATGGGGACCCAAGAGAGGGGCCCTCGGGAAGCCCTGCTTTCTCC TCTTGTCTCCTTTTCGTCTCTTGTCAATCAC | 1111 |
| IGLV1-47_chr22:22712277-22712377 | CATGTCTGTCTCTCCACTTCCAGGTCTCTGGGCCCAGTCTGTGCTGACTCAGCCACCCTCAGCGTCTG GGACCCCCGGGCAGAGGGTCACCATCTCT | 1112 |
| IGLV1-47_chr22:22712377-22712477 | TGTTCTGAAAGCAGCTCAACATCGGAAGTAATTATGTATACTGGTACCAGCAGCTCCCAGGAACGGCCC CCAAACTCCTCATCTATAGTAATAATCAGC | 1113 |
| IGLV1-47_chr22:22712477-22712577 | GGCCCTCAGGGGTCCCTGACCGATTCTCTGGCTCCAAGTCTGGCACCTCAGCCTCCCTGGCCATCAGTGGG CTCCGGTCCGAGGATGAGGCTGATTATTA | 1114 |
| IGLV7-46_chr22:22723897-22723997 | ATTTGCATAAAGCAGCACACAGACACACCCCTCCGTGCGGAGAGCTCAATAGGAGATAAAGAGCCATAG AATCCAGCCCCAGCTCTGGCACCAGGGGTC | 1115 |
| IGLV7-46_chr22:22723997-22724097 | CCTTCCAATATCAGCACCATGGCCTGGACTCCTCCTCTTTCTGTTCCCTCACTTGCTGCCCAGGTTAAGA GAGATTTCAAATACCAGCCTTTGGAGGGA | 1116 |
| IGLV7-46_chr22:22724097-22724197 | TCCCTTTTCTCCCTTTCTAATTCCTAATATATGTCTGTTTTTTTTGTTTCAGGGTCCAATTCCCAGGCTGTG GTGACTCAGGAGCCCTCACTGACTGTG | 1117 |
| IGLV7-46_chr22:22724207-22724307 | GGACAGTCACTCTCCACCTGGCTCCAGCACTGGAGCTGTCACCAGTGCTGTCATTATCCTACTGGTTCCAG CAGAAGCCTGGCCAAGCCCCCAGGACACT | 1118 |
| IGLV7-46_chr22:22724307-22724407 | GATTTATGATACAGCAACAAACACTCCTGACCACCTGCCCGGTTCTCAGGCTGTCCCTCCTTGGGGGCAAA GCTGCCCTGACCCTTTTGGGTGCGCAGCCT | 1119 |
| IGLV7-46_chr22:22724407-22724507 | GAGGATGAGGCTGAGTATTACTGCTTGCTCTCCTATAGTGGTGCTCGGCACAGTGACAGACCCATGAGAG GAACCAAGACAATAAACCTCCCTCGGCCCTT | 1120 |
| IGLV5-45_chr22:22730452-22730552 | GGTCAGCCACCCAGCCTGATTCTGACTCTTCTGGCAAAGATCCCTGAAAAACTTTACCCTGTTTCTGCCT TAGCACCCCATTAATGTCTGTTTCCAG | 1121 |

TABLE 6-continued

| Name | Sequence | SEQ ID NOs. |
|---|---|---|
| IGLV5-45_chr22:22730552-22730652 | TTCCCTCTTCGCAGGCTGTGCTGACTCAGCCGTCTTCCCTCTGCATCTCCTGGAGCATCAGCCAGTCTCACCTGCACCTTGCCAGTGCCAGTCAATGTT | 1122 |
| IGLV5-45_chr22:22730607-22730707 | GCATCAGCCAGTCTCACCTGCACCTTGCGCAGTGGCATCAATGTTGTGTACCTACAGGATATACTGGTACCAGCAGAAGCCAGGGAGTCCTCCCAGTATC | 1123 |
| IGLV5-45_chr22:22730707-22730807 | TCCTGAGGTACAAATCAGACTCAGATAAGCAGCAGGGCTCTGGAGTCCCCAGCCGCTTCTCTGGATCCAAAGATGCTTCGGCCAATGCAGGGATTTTACT | 1124 |
| IGLV5-45_chr22:22730887-22730987 | ACAGAGATGGGAAGTGGGACAAAAACCTCACCCTGTCTCTTGCTCTGTACCAATTTTTAAATTTTAAAATAACTGGCCTAGGCACACAAACTATATTT | 1125 |
| IGLV1-44_chr22:22735417-22735517 | GCCCAGTCTGTGCTGACTCAGCCACCCTCAGCGTCTGGGACCCCCGGGCAGAGGGTCACCATCTCTTGTTCTGGAAGCAGCTCCAACATCGGAAGTAATA | 1126 |
| IGLV1-44_chr22:22735517-22735617 | CTGTAAACTGGTACCAGCAGCTCCCAGGAACGGCCCCCAAACTCCTCATCTATAGTAATAATCAGCGGCCCTCAGGGGTCCCTGACCGATTCTCTGGCTC | 1127 |
| IGLV1-44_chr22:22735792-22735892 | TGCTGCTCAGGCTCTGGCCTGTGCTGCTGCAGCTTCCTTCATGGGGTCCAGGGCATCCAGGGCCCTGCCTGAGAGTGGAGGCTCCTCCCCCT | 1128 |
| IGLV7-43_chr22:22749602-22749702 | TCCAGCACTGGAGCCAGTCACCAGTGGTTACTATCCAAACTGGTTCCAGCAGAAACCTGGACAAGCACCCAGGGCACTGATTTATAGTACAAGCAACAAAC | 1129 |
| IGLV7-43_chr22:22749732-22749832 | CCCTCCTTGGGGCAAAGCTGCCCTGACACTGTCAGTGTGCAGCCTGAGGACGAGGCTGAGTATTACTGCCTGCTTCTACTATGGTGTGCTCAGCACAG | 1130 |
| IGLV7-43_chr22:22749832-22749932 | TGACAGACTCATAAGAGAACCAAGAACATAAACCTCCCTCGGCCCTTGTGATGTGGAGATTGTGTGATCATACACCAGCTCTCAAGACACAGCCTATACACCAGCCTGAGCCATAGAAAGGGAAGG | 1131 |
| IGLV7-43_chr22:22749857-22749957 | ACATAAACCTCCCTCGGCCCTTGTGATGTGGAGATTGTGTGATCATACACCAGCTCTCAAGACACAGCCTACATGTGGACCAGCCATAGAAAGGGAAGG | 1132 |
| IGLV7-43_chr22:22749942-22750042 | ATAGAAAGGGAAGGAAGGAAAGGGTCTGAATTGATTTCTATCCCTCCTTGTGCCCTGAAGTGGAGGAAAATGTGAGAGTGATTTGCAGTAATTGAATGAGACAA | 1133 |
| IGLV7-43_chr22:22750042-22750142 | AGCAAAAGTTATTTGTTTTATATGAAAAAAAACAGAAAACAGCAGGATCAGATCTAAAGGCTGAGTCTAAATGCATTTCCTCCAGACAGAAGCTTCTT | 1134 |
| IGLV7-43_chr22:22750092-22750192 | CAGATCTAAAGGCTGAGTCTAAATGCATTTCCTCCAGACAGAAGCTTCTTCAAACGATGGGCTTTCTGAGCTAAGAGCAAAGAAAATAAACTCTCCACGG | 1135 |
| IGLV7-43_chr22:22750192-22750292 | GTATATTATTAAAGTTTATTTATTGAGTTACTTTCAAAGCAATCCATGACTATTATATAAAGTCAGAAAGTATTAAAAATCACCAAGTTCTCTGCTAAG | 1136 |
| IGLV7-43_chr22:22750292-22750392 | CTACCTTATCCCATGCAATCAAAATAAGTACTTTTCTTCATTTGGATGCATTTTTATTTCTGTTTTTAATATTTCCACAATGGTGATTAAACCTGGTGC | 1137 |

TABLE 6-continued

| Name | Sequence | SEQ ID NOs. |
|---|---|---|
| IGLV1-40_chr22:22758647-22758747 | ACAGGGTCAGGGAGGGGTCCAGGAAGCCCATGAGGCCCTGCTTTCTCCTTCTCTCTAGACCAAGAAT CACCGTGTCTGTCTTCTCCTGCTTCCACG | 1138 |
| IGLV1-40_chr22:22758747-22758847 | GTCCTGGGCCCAGTCTGTGTTGACGCAGCCGCCTTCAGTGTCTGCGGCCCCAGGACAGAAGTCACCATC TCCTGCTCTGGAAGCAGCTCCGACATGGGG | 1139 |
| IGLV1-40_chr22:22758847-22758947 | AATTATGCGGTATCCTGGTACCAGCAGCTCCCAGGAACAGCCCCCAAACTCCTCATCTATGAAAATAATA AGCGACCCTCAGGGATTCCTGACCGATTCT | 1140 |
| IGLV1-40_chr22:22758947-22759047 | CTGGCTCCAAGTCTGGCACCTCAGCCACCCTGGGCATCACTGGCCTCCTGGCCTGAGGACTAGGCCGATTA TTACTGCTTAGCACTGGATACCAGCCTGAG | 1141 |
| IGLV1-40_chr22:22759047-22759147 | AGCTTGCACAGTGCTCCAGGCCAATGGGGAACTGAGACAAGAACCCTCTTCCTCCTCCGCCAGGAGGTG AGTGCCTGCAGCTGCTGCTCACCCTGACC | 1142 |
| IGLV1-40_chr22:22759147-22759247 | TGTAGCTTCTGCTGCTGTAGCTTCCCCATGGCCTCCGGGGCATCCAGGGCCTTGCCTAGGAGTGGAGGC TCCACCACTTTGTCCTCAGAGTCAGGAAC | 1143 |
| IGLV1-40_chr22:22759247-22759347 | AGGGACCCCAGGAGACAGAATATCCTGCTCCTCAGCTTGGGACACAGGGTCTCTGCACTGAAATCGTGGG CTGAGGTGCAGCCGAGTCGAGGAAGTGTGG | 1144 |
| IGLV1-40_chr22:22759297-22759397 | CTCTGCACTGAAATCGTGGGCTGAGGTGCAGTTGGCAGTGGATACAGTTCCAACTGTGTCTTCACAGTCCTTCCTGTGCCTGCCCA TGGTGTGGGACGGAGTCGAGGAAGTGTGG | 1145 |
| IGLV1-40_chr22:22764167-22764267 | TCCTCACTCTCCTCGCTCGTCTCTCCCACTTCCAGGGTCCTGGGCCCAGTCGTGCTGACGCAGCCGCC GGATTCTTGCTTTCCTGTTGTCTCAGA | 1146 |
| IGLV1-40_chr22:22764267-22764367 | AGCCGAATAATGATGCCTGTCTCTCCCACTTCCAGGGTCCTGGGCCCAGTCGTGCTGACGCAGCCGCC CTCAGTGTCTGGGGCCCCAGGACAGAGGG | 1147 |
| IGLV1-40_chr22:22764367-22764467 | TCACCATCTCCTGCACTGGGAGCAGCTCCAACATCGGGGCAGGCAGTTATGATGTACACTGGTACCAGCAGCT TCCAGGAACAGCCCCCAAACTCCTCATCTA | 1148 |
| IGLV1-40_chr22:22764552-22764652 | CTCCAGCTGAGGATGAGGCTGATTATTACTGCCAGTCCTATGACACAGCCTGAGTGGTTCCACAGTGC TCCAGGGCCCGGGGGAACTGAGACAAGAAC | 1149 |
| IGLV2-23_chr22:23040452-23040552 | GCTTCCTCACTCTCCTCACTCAGGACACAGGTGACGCCTTCCAGGGAAGGGGTCTTGGGGACCTCTGGGCTG ATCCTTGGTCTCTCCTGCTTCCTCCAGGGTCACC | 1150 |
| IGLV2-23_chr22:23040592-23040692 | TTCCAGGGTCCTGGCCCCAGTCTGCCCTGACTCAGCCTCGCTCCGTGTCTGGGTCTCCTGGACAGTCGATC ACCATCTCCTGCACTGGAACCAGCAGTGA | 1151 |
| IGLV2-23_chr22:23040692-23040792 | TGTTGGGAGTTATAACCTTGTCTCTGGTACCAACAGCACCCAGGCAAAGCCCCCAAACTCATGATTTATG AGGGCAGTAAGCGGCCCTCAGGGGTTTCT | 1152 |
| IGLV2-23_chr22:23040792-23040892 | AATCGCTTCTCTGGCTCCAAGTCTGGCAACACGGCCTCCCTGACAATCTCTGGGCTCCAGGCTGAGGACG AGGCTGATTATTACTGCTGCTCATATGCAG | 1153 |

TABLE 6-continued

| Name | Sequence | SEQ ID NOs. |
|---|---|---|
| IGLV2-23_chr22:23040852-23040952 | GCTGAGGACGAGGCTGATTATTACTGCTGCTCATATGCAGGTAGTAGCACTTTCCACAGTGGTCCAAGTTCATGGGAACTGAGACCAAAACCTGCCAG | 1154 |
| IGLV2-23_chr22:23040952-23041052 | GGCCTTCAGACTTCCTCTGTCTGAAGATGCTTCCTCACCCGGTGCAAGAGGCTTGCTGCAGCGCGGCCTTGAGAATTCTTCTCTCTCAGCTCCTTCC | 1155 |
| IGLV2-23_chr22:23041052-23041152 | CTTTCCACCATGAATTCAACAGGAAAACCTGCCCTGTGGTTTCCCATCCAGGACAGGGACAGAGTTCCTGATGCTTGTGTGCTGTGGTCCCTGAATGTGCA | 1156 |
| IGLV2-23_chr22:23041152-23041252 | ACTCTTCCAGCTCTTCAAATGCAGGGACCAGTGACAAGGAGCAGTGACCTCGATTGTGCAGTCACTGCTTTTTTCAGGGATGTCTTCACCCTACACTATATCAT | 1157 |
| IGLV2-23_chr22:23041252-23041352 | CATCCCCTACACTGTGGGTAGAATTTTAGCAACTACATATTCTAATGGTTATCGCCACAACTTTGATCTTAGAAATAACAGTGCAGTGAACATCCCTATGCA | 1158 |
| IGLV2-23_chr22:23041352-23041452 | GGCTCCTTTGAGTTCCTGTGAATACGACATAGGATTCATTTCTAAAAGTGAAATTGCGGGTCAGAAAGATGTGTTTGTGATTTTCACCCAATGTT | 1159 |
| IGLV3-21_chr22:23055497-23055597 | ACCAGCAGAAGCCAGGCCAGGAGTCTCAACTCTGGAATGAGCGATTCTCTGGCTCACCCTCTTGCTCCAGCCCCGGGAAGCCCTGTTGATAAAGCCATGAGTGAATCTGGCCCTGAGCGATTCTCTGGATCTGAGCCTTTCAGGTTG | 1160 |
| IGLV3-21_chr22:23055827-23055927 | CCCAGTCTCGGTCACCCTCTTGCTCCAGCCCCCGGGAAGCCCTGTTGATAAAGCCATGAGTGAATCTGGCCCAGAATCATCTGGTGACTCTGAGCCTTTCAGGTTGT | 1161 |
| IGLV3-21_chr22:23101392-23101492 | GGTCCTGGGCCCAGTCTCGCCTGACTCAGCCTGCCTCCGTGTCTGGGGTCTCCTGGACAGTCGATCACCATCTCCTGCACTGGAACCAGCAGTGACGTTGG | 1162 |
| IGLV2-14_chr22:23101532-23101632 | CCCTTCCCTGGCCCCAGTCTGCCTGACTCAGCCTGCCTCCGTGTCTGGGGTCTCCTGGACAGTCGATCACCATCTCCTGCACTGGAACCAGCAGTGACGTTGT | 1163 |
| IGLV2-14_chr22:23154347-23154447 | AAAGCCCCCAAACTCATCGATTTATGAGGTCAGTAATCGGCTTCAGGGGGTTTCTAATCGCTTCTCTGGCTCCAAGTCTGGCAACGGCCTCCCTGACCA | 1164 |
| IGLV3-10_chr22:23154447-23154547 | AGCTCCAGTGCCCATAGACCCCAAGTTGGCCCTGCCCTGAACCCTGTGCAAAGCCCAGACACAGTCTTAGGGTAGGACCCCCTGGGAATGGGCTCTTGATC | 1165 |
| IGLV3-10_chr22:23154547-23154647 | TTCAAGCCCCCCTCCTCCTGTTTTCCTTGCAGTCTCTGAGGCCTTCCTATGAGCTGACACAGCCACCCTCCGTGTCAGTGTCCCAGGACAAACGGCCAGGAT | 1166 |
| IGLV3-10_chr22:23154697-23154797 | AGAAGTCAGGCCAGGCCCCTGTCTGTGCATCTATGAGGACAGCAAACGACCCTCCGGGATCCCTGAGAGATTCTCTGGCTCCAGGGACAATGGC | 1167 |
| IGLV3-10_chr22:23154797-23154897 | CACCTTGACTATCAGTGGGGCCAGGTGGAGGATGAAGCTGACTACTACTGTTACTCAACAGACAGCAGTGGTAATCATAGCACAGTGACACTGGCAGAT | 1168 |
| IGLV3-10_chr22:23154897- | GGGGAAGTGAGACACAAACCCTTCTTCATCTATTTTTACCCTCTCCCTCCAGCCCCCAGGACCCCGCTGTGGACCAACCCATAAGCAGGTCTGGCAGAATTCA | 1169 |

TABLE 6-continued

| Name | Sequence | SEQ ID NOs. |
|---|---|---|
| IGLV2-8_chr22:23165422-23165522 | AGGCTCACCTGGGCCCAGCACTGACTCACTAGACTGTGTTTCTCCCTTTCCAGGGTCTGGGCCCAGTCTG CCCTGACTCAGCCTCCCTCCCGCGTCCGGG | 1170 |
| IGLV2-8_chr22:23165542-23165642 | CATCTCCTGCACTGGAACCAGCAGTGACGTTGGTGGTTATAACTATGTCTCCTGGTACCAACAGCACCCA GGCAAAGCCCCCAAACTCATGATTTATGAG | 1171 |
| IGLV2-8_chr22:23165642-23165742 | GTCAGTAAGCGGCCCTCAGGGGTCCCTGATCGCTTCTCTGGCTCCAAGTCTGGCAACTCGGCCTCCCTGAC CGTCTCTGGGCTCCAGGCTGAGGATGAGG | 1172 |
| IGLV2-8_chr22:23165727-23165827 | AGGCTGAGGATGAGGCTGATTATTACTGCAGCTCATATGCAGGCAACAACAATTTCCACAGTGTTTTAAG TCAATGAGGAAGTAAGATCAAAACCTGCCC | 1173 |
| IGLV4-3_chr22:23192412-23192512 | TCAGGCTCAGAACCCATAGGATCCTGAGCTGGGCCTGCCCAAACATGAGTTCATCCAGGCACAACCTCA GGGTGGGACCCCCTGGGAACAGATTCATCA | 1174 |
| IGLV4-3_chr22:23192512-23192612 | TTTACAAGCCTCTCTCTCTCTCCTGCAAGCTCCTATGAGCTTACACAGCCACCCTCAGTGTCAGTG TCACCAGGACAGGCAGCCATGATCACCTG | 1175 |
| IGLV4-3_chr22:23192612-23192712 | CTCTTGAGATAACCTCAAAGATGAGTATGTTTACTGGTTCTGCAGAGACCAGCAGGCCCATACTGT GATATATGAAGGCAGCAAGCGGCCCTCAGG | 1176 |
| IGLV4-3_chr22:23192712-23192812 | AATTTCTGATTTTCTGAGTCCAGCTCAGGGAACATGGCCACCCTGACCATCAGCAGGCTCAGACTGAGG ACGAGGCTGACTATTACTGTCACAGGTACA | 1177 |
| IGLV4-3_chr22:23192812-23192912 | ATAGAAACAGTGATGAGCCCACAGTGACACAGGCAGATTAGGAAGTGAGACACAAACCCCTTCCAATCT GTGTCACCCTCTTTCTCCAGCCCCAGGATG | 1178 |
| IGLV4-3_chr22:23197917-23198017 | GGGATGAGAAGGACCAGGGCTGGGATTGAGCTGTGAAGGGAACCAAAAGCAGGAGGGACAGGGC AGGGGCTGTCAGCTATGACTCAGGGGAGGTTC | 1179 |
| IGLV4-3_chr22:23198017-23198117 | CTCGGGCCTCAGGATCCTCCCTCTGAGGCCACCAGGGGGCGGGGGTGGACACATGCCTGGACCTGGGAGTC CCTGCTGGGCTTCACCCTGGGTGGGTCCTA | 1180 |
| IGLV4-3_chr22:23198067-23198167 | ATGCCTGGACCTGGGAGTCCCTGCTGGGCTTCACCCTGGGTGGGTCCTAGGAGTCTCCTTCCTCCTAAGTC CCCTAAAGAGACAGAGGCATTCTGGGGT | 1181 |
| IGLV4-3_chr22:23198167-23198267 | CCTAAATCTGTCATGCCCCATAAATGCATTTCTACGAGGGCCAATAAATGAACTCCAGGTTTATCCAAGC AGCAGCTTCAGGCGCTGTGCAGACACAGAG | 1182 |
| IGLV4-3_chr22:23198267-23198367 | CGGGAGGAATTAGCCAACCTGAGGCCACCCTAGAAAGGGCTGAAGGGGGCTGAAGGGGACTGAAGGGTCC CTGTGGGGGCCGTGTGGTCCTGGGAGGGAGA | 1183 |
| IGLV4-3_chr22:23198367-23198467 | GCTGGGGTGTCTCCCAGGCCACTCTGGGCCCTGTCCTGACACTTCTCCCACAAAGAAGGGAAGGGAAATCC TGGGACCCCACAGCCAGGACCAACCGTGAA | 1184 |
| IGLV4-3_chr22:23198467-23198567 | CCCACAGGACAGGAAGGACAGGAGACCCCAAGGCTGGCTCCCATTTCCCAGGCACTGTCATGGGCTGAGTCT CAGGAAATCCAAGTCAAGGAGTTTCAATCC | 1185 |

TABLE 6-continued

| Name | Sequence | SEQ ID NOs. |
|---|---|---|
| IGLV4-3_chr22:23198587-23198687 | CCAAGGAAACAGAAGTCTACGGGCCCAGGCCCCAGTGAGGGTGGGGTAAGAGAGAGCTTAGGATGCAGATTTGCATGGAGGCCCGCCCTCCTCTGAG | 1186 |
| IGLV4-3_chr22:23198687-23198787 | GCATCAGGGTAAGACAAGGCTGGGGGCAGGCCCAGTGGGGTCTCAGGAGGCAGCGCTCTGGGACGTCTCCACATGGCCTGGCTCTGCCTCTCCT | 1187 |
| IGLV4-3_chr22:23198797-23198897 | CTCAGGGCACAGGTGACGCTCCAGGAAGGGCCTCGGGGACCCTTGGGCTGATCCTTGGTCTCCTGCTCCTCAGGCTCACCTGGGCCCAGCACTGACT | 1188 |
| IGLV4-3_chr22:23199022-23199122 | TTCGGAGTTATGACTATGTCTCTCGGTACCAACAGCACCCAGGCACAGTCCCCAAACCCATGATCTACAATGTCAATACTCAGCCCTCCAGGGGTCCCTGA | 1189 |
| IGLV4-3_chr22:23199122-23199222 | TCGTTTCTCTGGCTCCAAGTCTGGCAATACGGCCTCCATGACCATCTCTGGACTCCAGGCTGAGGACGAGGCTGATTATTAGTGCTGTCATATACAAGC | 1190 |
| IGLV4-3_chr22:23199182-23199282 | TGAGGACGAGGCTGATTATTAGTGTCTGCTCATATACAAGCAGTGCCACTTAACCACAGTGGTCCAAGTTCTTGGGGAACTGAGACGAAAACTGCCCTGG | 1191 |
| IGLV4-3_chr22:23199277-23199377 | CCTGGGCTCTCAGGCTCCTTTTGCTCTGAAGATGTTTCCTCACCCAGTGCAACGGGCTTCCTGAAGCACAGCCTTGAGAATTCTTCTCCCTCAGCAAC | 1192 |
| IGLV4-3_chr22:23199377-23199477 | TCTCTTTTTCCCACCATGAAATCAAAGGAAATCCTGCTCTGTGTTTCTCATCCAGGACAGGGACAGCTTCCTTTTGCTTGTGTGTGGTCCCTGAGTG | 1193 |
| IGLV4-3_chr22:23199477-23199577 | GGTGCAACTCTTCCTAGCTTTTTAAATTATGGAGGGTGACAATGAGCTCCCTGACTGGTGCAGTCCCTGCTGTTTTCAGGAACATCCTCATCCTAAATG | 1194 |
| IGLV4-3_chr22:23199577-23199677 | CATCTGAATCTCCCACTGTGTGCAGACAATCTGGACAGATGTTATTAGGGGGAGTTTCAGAAGCCACATCTTACTCAACTCTGTATCCACCACACTCT | 1195 |
| IGLV3-1_chr22:23222927-23223027 | TGCCTCAGCCAGCCATGGCATGATCCCTCTCTTCCTCTCGGGCTCGACTCTGACTCAGCAGGGCCCCCGCCTGTGGGCAGGATGCTCATGACCTCCTAGCAGGTGATGGCCTCGGCGGGCT | 1196 |
| IGLV3-1_chr22:23223027-23223127 | TGGGTCCAGCCTGGCCTGACTCTGACTCAGCAGGGCCCCCGCCTGTGGGCAGGATGCTCATGACCCTGCTGCAGGTGATGGCCTCGGCGGGCT | 1197 |
| IGLV3-1_chr22:23223077-23223177 | TGGGCAGGATGCTCATGACCTCTGCAGGTGGATGGGCTCGGCGGGGCTGAAATCCCCCACACAGTGCTCATGTGCTCACACTGCCTTAGGGCTCTTT | 1198 |
| IGLV3-1_chr22:23223177-23223277 | CATCCCTGACTCTGTCTGCAGGCCAGGCACGTGGGAAGATTTACTTGGAGTTCAGCTCCTCAGTTTCAAGCCTTTTCTCTCCCGTTTCTCTCCTGTAGG | 1199 |
| IGLV3-1_chr22:23223277-23223377 | ATCCGTGGCCTCTATGAGCTGACTCAGCCACCCTCAGTGTCCGTGTCCCCAGGACAGACAGCCAGCATCACCTGCTCTGGAGATAAATTGGGGGATAAA | 1200 |
| IGLV3-1_chr22:23223327-23223427 | CAGGACAGACAGCCAGCATCACCTGCTCTGGAGATAAATTGGGGGATAAATGCTTGCTGTATCAGCAGAAGCCAGGCCAGTCCCCTGTGTGCTGGTCAT | 1201 |

TABLE 6-continued

| Name | Sequence | SEQ ID NOs. |
|---|---|---|
| IGLV3-1_chr22:23223427-23223527 | CTATCAAGATAGCAAGCGGCCCTCAGGGATCCCTGAGCGATTCTCTGCTCCAACTCTGGGAACACAGCCACTCTGACCATCAGCGGACCCAGGCTATG | 1202 |
| IGLV3-1_chr22:23223527-23223627 | GATGAGGCTGACTATTACTGTCAGGCGTGGGACAGCACTGCACACAGTGACACAGGCAGATGCGAAGTGAGACAGAAACCAGCCACCTCGGCCTGG | 1203 |
| IGLV3-1_chr22:23223627-23223727 | CTCACAAGACCCTTCCCTCTCCTGCCCTGTCACACTGAGCAGGAGGGAGCCTTCATGTGAATGAAGTTTCCAGTCCTATCCCTGCCCTTATGTTC | 1204 |
| IGLV3-1_chr22:23223727-23223827 | CTCGAGAGCGGGAGCAAGTTCCTGCCCACCCTCTAGGCTCAGCTTATCCAGAATAAACTGAGCTAGTCATTTTGATGATCAAATGCCAGCTCCCAAAGA | 1205 |
| IGLV3-1_chr22:23223827-23223927 | CCCCAGAAACCCTGATATCTAAGTAGCACCGACTCTATTAGTATCAAGGGAGACTAGCCCCTAGGGTGAATCATTTTAGTGTCTCAGAAGGCACAGGCA | 1206 |
| IGLV3-1_chr22:23223927-23224027 | ATGGAAAGTGTTTATGAGGTTTCAGGATATGCACGTGAGCAGTTAAAGGCAGGTCTTACAAGGAAGGAACCTACTAGAATTGGGGCCCATCTGACATC | 1207 |
| IGLL5_chr22:23227062-23227162 | ACATCCCTGCTCTTGGGAGAGAAGGGCCAGGGTCGGGACCCAGAGAGCTCTGCAGAGGCACCACAGACCCTCAGCAGGGGTCGCCAAACAGGACAGCT | 1208 |
| IGLL5_chr22:23227162-23227262 | GGACTTGGCTGCTGTCTCTGCCCAGGCCTGATCCAGCCCTTGCACATCTCAGGGCAGGGGATAGGCCTGGGTGGCCAGAGCTGCAGCTGCACCTGCTGGGGA | 1209 |
| IGLL5_chr22:23227262-23227362 | GGCCTAGTCCAGTCCTCCAGGTCCCCAGACAGATCGGATTTCCGACTGCGCCACCATGGAAGAGATGTGGTCTGCGGTGACGATGTCTATCCAGAGGC | 1210 |
| IGLL5_chr22:23227567-23227667 | CCGAATATCCAAGGAGCCCAAGATCAGAGGCAGGAATAGGCCAAGCTCCCCAGTGGAGAAGCTGTGCTGGACCAGGGGTTTCCCAGGGCCCTCCCTTGTG | 1211 |
| IGLL5_chr22:23227667-23227767 | CCCTGAATGATGTCTGTTAGGGCACCTACACCCTGTTACTGCTCAGTGCCTTGCCTATTTGAAGGACAGGGATGTGTGGTGATTATTTGTATAATCCAG | 1212 |
| IGLL5_chr22:23227767-23227867 | CCCCCAGCCACCTGGTCCTCAAAGTTACCCAAGCAATGTGTATAAAGATCCAGCCTGGAGATCTTTGAAAACCGATTCGATGAGTCGAACCATTAAGTCA | 1213 |
| IGLL5_chr22:23227867-23227967 | TGATCACCATCCTCAACTTCATCTCTTTCTTCCCCTCATTATCACCTTCAAGAACTGTTAAGAGTCTGAGACTTCATCCTATTTGCAGACTAAGTCTGAGACTTCATCCTATTTGCAGAC | 1214 |
| IGLL5_chr22:23227897-23227997 | TCCTCCTCCTCCTCATTATCATCAAGACTTCAAGAGACTGTTAAGAGTCTGAGAGTCTATTTGCAGACTAAAAGTAAGCCTGCCACAGTGCCATGGA | 1215 |
| IGLL5_chr22:23227997-23228097 | TGCTGGGCAGAAGATACAAGACTCCTGGGTCAGAGAGACAACGAATAATCTGTTTTCACAGCAATAGCAGTTGCCAAGGTATCAGCATTGTCTTGCCACCAGT | 1216 |
| IGLL5_chr22:23228097-23228197 | TCCACAAGGTGATGCAAAGAGGGCCAGTGACATCTGCATGCCAGAGCTCAGGGATCCCAAATATTCATACTTGACAGTAAGCATATATCTGTGTTTG | 1217 |

TABLE 6-continued

| Name | Sequence | SEQ ID NOs. |
|---|---|---|
| IGLL5_chr22:23228197-23228297 | CTCCAAAGAGAGGCATTCTCTGTACCTTCCGAGGTTGTTCACTCCACAAACACTCTTGAAAAGATAATCCA CAATCAGTGCCTTTGCCCGAGAGACATGC | 1218 |
| IGLL5_chr22:23228297-23228397 | AGAAATGCAGAGATCCATAGTAGACCACTGTCTCCCACAACCATCAACTTTATCAATGAAATGAAGTCT CAGGCTATTTGTCTGTTACCATAGCCCACA | 1219 |
| IGLL5_chr22:23228397-23228497 | AAAATGTCTGGCTTGATTGTCACCAAATGTATCAAGGAAGTTAAGGAGTATCTGACACAAAATGTGAACC AAGCAATTCTCAAAGGAGCCTCCCAGAAA | 1220 |
| IGLL5_chr22:23228497-23228597 | TTCACTTTAGGAAGTCCTAGGAGGCTCTCTCTGAGAGTTGCTAAAACAAAACATTGAGAGTCCTAGAGGGC TGCAGATCTGAACTTGAGCAGATATTTTA | 1221 |
| IGLL5_chr22:23228597-23228697 | AAGATTTTGTGCAGAAAAAGAAACTGAAAGCAAGAAGGGCAGACCCTCATTGCAGTTCTGTAATGTAA GGGGGCAGAGCAGGGGCCTTTCTCACCAGAG | 1222 |
| IGLL5_chr22:23229332-23229432 | GATATTGGACCCTGCATTCATCTTCTCTGGATGGTAATTTCTCACCTGTAAAACAGAGACACTGGCCCCA AGGACACCCCACAAGTAGTTGTGAATCCC | 1223 |
| IGLL5_chr22:23229432-23229532 | AAAGTAAGAGAAGAACAAAAAAAGAACAGAATTTATTCAACACCCACTGAGTGCTTAGCAAACACATG GTTTCTTTAACTCTCATAAGCTTCATGCTGCC | 1224 |
| IGLL5_chr22:23229532-23229632 | AGAGGAACTCTCCCCATTTACAGATAAGGAACTGAGGCCCAGAGGTAACCTAGGTCTAGATAGACTCC ACATTATGACTTCACCACTCTTCCTTGCC | 1225 |
| IGLL5_chr22:23229562-23229662 | AAACTGAGGCCCAGAGGTAACCTAGGTCTAGATAGACTCCACATTTATGACTTCACCACTCTTCCTTGCCT GAAGGATATAGAATCACTCCCTGCAGGC | 1226 |
| IGLL5_chr22:23229662-23229762 | TCTTGCCTGACTCAGGAAAGGGCCACAGATAGCCAGCCAGGCTTAACCAACCCAGCCAAGAAAGGGCT GGTCCCAACTGGCTGGAGTGCAGTGTACAGG | 1227 |
| IGLL5_chr22:23230012-23230112 | GTTGGTAGATGCCCCTCTGGGAGGATCCCCAGGGGTGACAGCCCATGACCCTGGAAGGGGCCTGGGCTA GGGACAGGGACCAGAGCCAGTCCAGGGAGAG | 1228 |
| IGLL5_chr22:23230112-23230212 | GACAGAGCCAATGGACTGGGGTGTACTGTAACAGCCCTGCTGGCGAGAGGGACCAGGGCACCGTCCTCC AGGGAGCCCATGCTGCAAGTCGGGCCAGAGG | 1229 |
| IGLL5_chr22:23230212-23230312 | TGCCCCTGAACCTGAAGGCCAATGAGACCCAAGACAGGCCAAGTGGGTTGTGAGACCCCTGAGGAGCTG GGCCCTGGTCGTCCCAGGCAGCGCTGGCCCTGC | 1230 |
| IGLL5_chr22:23230312-23230412 | TGCTGCTGGGTGCTCTGGCCATGGTCGCCCATGGCCTGCTGCGCCCCAATGGTTGCACCCGCAAAGCGGGACCC AGACCCTGGAGCTGGAGCCTCAGTTGGAAGCAGCCG | 1231 |
| IGLL5_chr22:23230412-23230512 | ATCCAGCCTGCGGAGCCTGTGGGGGCAGGTAAGGGGCAAGAGATTCCAGGGGATGTGGGGGTCCTGCAGC AGAGCTGGGAAAGGGTGACCAAGGGAGACA | 1232 |
| IGLL5_chr22:23230512-23230612 | AGCCAGAGGAGTGAGGAGGAAGTTAACCCCTAAGAGGGGCTGGGCTGACACTGGCTTTAGTAATGGG TTGATATTTTGTCCATCACAGATTTGTTGA | 1233 |

TABLE 6-continued

| Name | Sequence | SEQ ID NOs. |
|---|---|---|
| IGLL5_chr22:23230612-23230712 | ATTACTGTTTTAATATCATATTACGATATTATTTTCTTGATTTCTGAGTTTTCTGCGCCACTTAAATTTTCACCAGGGTCAGTGCCTCAATCACCTA | 1234 |
| IGLL5_chr22:23230712-23230812 | GTCCTAGTCCTCTGGGTAGGGAAGGAACAGAGGCAGGGACACATTCCACAGGGGTGGTGCCACTGTCCCCACAGGGTGCCCAGGCCTGTTCCTCCC | 1235 |
| IGLL5_chr22:23230812-23230912 | CCTCCTCCTCTCTGCCCATGTGCCTCCTGCCCAGTGAGGGCAGGGGCACTCCCTGAGAAGGCAGCAAGGGCTTGGTTTGGTCTCCCCAAGGCTGTCT | 1236 |
| IGLL5_chr22:23230912-23231012 | GTTCACCAACTTGCACATAAATGCTTACTGGGGCCCAGGCTCAAGGACACACAGGGAGGGTGGGATGAACCGAGGGGAGCTGTCCAGTCATTGGAACAGGCCC | 1237 |
| IGLL5_chr22:23231012-23231112 | ACGGCCCATGTTTTGGAGCAATAAAGGGAGAGGGGATCTCCCTCTGGGATGATGCCCAGGCTGTCTCACAGATCGAGGGGCACTGGCTGGTGATGGGTGC | 1238 |
| IGLL5_chr22:23231072-23231172 | TGGTCTCACAGATCGAGGGGCACTGGCTGGTGATGGGTGCCCCCAAAGACAGCAGCGTCAGAGGAGAGGAGACACAGATGAGGCTGGGAGCTCCT | 1239 |
| IGLL5_chr22:23231172-23231272 | GGGTGACTGGGAAGGGAGGCAAGAAGACACATAGGGTCCGTGCACCATTCCCAGTCAGGACGAGTCCTTGGATGGATTTAGTGACTGGCCAAGTCCAGGGTAG | 1240 |
| IGLL5_chr22:23231272-23231372 | TCAGATTTGTGTTTTTGGAAAAATCAGCACCGGATTGGAGGTGATGCGAACCCGATTAGGAGGAGGAGGAGAGGGGTGATGGCCAAGTCCAGGGTAG | 1241 |
| IGLL5_chr22:23231372-23231472 | GTGGGGATCCTGGAGGAAGCCTGCCTTGGGAGGGGAGGACACTCCAGATTCAGAGCTCAGAGCCACCCAGGGGCCCAGTTTCCTATGAAATGGGAGCATGAAGTTG | 1242 |
| IGLL5_chr22:23231472-23231572 | AAGTGAGGGCTGAGCAGAGGGGAGCAGACACGCTCGGGGACTGTCTATGGGCATTAAAAATGTATAACCATTTTAGCAACAGGCGCGAGTCAAAAAACA | 1243 |
| IGLL5_chr22:23231572-23231672 | AAGTGTGTTTATCTAAACTGGGCAATTCCACTTCCACTTCTAGGAATTTATCCTAAGGGTTGTTGGGGAATAATCAAAGCTGTAACCAAATCTTTATACAAGG | 1244 |
| IGLL5_chr22:23231672-23231772 | GTGGTTAGCTCAGCATTATTAGTGATGGGAGAAAAACTGGAAAAAATCAAAATATCTACCAGAAAAGGGTGTGAAAAAACACAATTGTATTTGGGGGACTGT | 1245 |
| IGLL5_chr22:23231927-23232027 | TGGCTAATTTGATTAGGATTATTATTAGTTTAGAGACAGAGCCTCGCTATATTGCTCAGGCCTGTCTCAAATTCCTAAGCTCAAGCAATCTTTCTGCCT | 1246 |
| IGLL5_chr22:23232062-23232162 | ACTGCACCTGACCCAACTGTGTTTTAAAGTATATATGCATTTTCAAAAACCTGTCTGAAAATATAGAAAAATGTCAATGGTGTCTCGGCTGATG | 1247 |
| IGLL5_chr22:23232162-23232262 | GGATTTCACCTAATTTAATGTGGCTTTATAATTTCTGGTTTTGTGAAGTGTTCACAAAAAGAGACATTTCTTCTAATATAATTTTAATACAACAGT | 1248 |
| IGLL5_chr22:23232262-23232362 | AATGTACTCATGTGCATTACTCTTTTTGTAATGAGTATATTACAAAATGTAATGACTTTTGTACATTACTCTTTTTTCTTGCCAAAAAAAAAGATTA | 1249 |

TABLE 6-continued

| Name | Sequence | SEQ ID NOs. |
|---|---|---|
| IGLL5_chr22:23232362-23232462 | AGCAGAGAAGTATATAAAGTAAAAGCAAGTGCTTCTGCTTACCATCTCTCACCTCTTCCCAGAGATAGCCACTGTCAGGTTGGTCAATATATACTTCCAGAA | 1250 |
| IGLL5_chr22:23232462-23232562 | CTTTTCCTGTGTGTGTGTGTGTCCCTGAAAACACACACACACACACACACAGTTGGTGCTGGGATTTTATTTTGCAAAGTAAGAGCC | 1251 |
| IGLL5_chr22:23232517-23232617 | CACACACAGTTGGTGCTGGGATTTTATTTTGCAAAGTAAGAGCCATATTCTGCATATTACCAACTTTTAATCTATTATTGACACTTTCTGTATCAGTCC | 1252 |
| IGLL5_chr22:23232617-23232717 | ATATGGATTAACCACATTCATTGCTTATAAAACTTTGTTTTATAAGCAAAGTTTAGATGAGCCAGAATTTATTTCCACTAAAAATCTAAATGACAAATGA | 1253 |
| IGLL5_chr22:23232717-23232817 | TGCTGCAGTGGAAATTTGTGTGTGTGTGTGTGTGTGTGTGTGTGTGTGTGTGTATGTGTACAAAGTGCACTTATATATCTCCCCAGGATA | 1254 |
| IGLL5_chr22:23234612-23234712 | TGACCTGGGTGTTTTCTTTTTCTCTGTAGGATGTTAATAGTATCTTGTCTAGGATGTCTAGGACAGAGGGCAATACAATGAGGGGAAGGCATT | 1255 |
| IGLL5_chr22:23234712-23234812 | CTGCGATGTCCCCAGGCCTCTGCTTGAAGAGTAACTTGCTGAAGTGAGGACTCTGTGGAGGAGCAAGTTATACAGAGAAGAAGTTAGTTGTGATCTGTT | 1256 |
| IGLJ1_chr22:23234812-23234912 | GAGTTGGAGGTGTCTACAGGGCATCCAAGCAGACATAGGTTGAGGAGCAGAGATATATGTGAATCTGAAGCCAAGAGACAGAACCAGGGTAAGGGCTGGAAATAGG | 1257 |
| IGLJ1_chr22:23234912-23235012 | GATCTAAGACCCCTGGACAGTTGTGAGTGTGCACAATGAGGGTCAGATGCAGAGAAAATTAGGAGACTACAGAGCAGAAGGGGAGAGTGACTAGAAAGAAAAC | 1258 |
| IGLJ1_chr22:23235012-23235112 | AGTCAGCAGTTGGGCATGGCCTGGTAGAAAGGGAAGCCAAGGAGGAGGGGCAGTCTCAGACACCAAGGAGGGGAGAGTTGAGGGAGAGATGAGGCTG | 1259 |
| IGLJ1_chr22:23235112-23235212 | CTTCTTGCAGAGACATAGGGGATGGGGAAGAACTGCAGACTGAACTGGGGCAAAGGACTGTTGGCCTTAACCAGAGAGATTTGAGGGAGAGATGAGGCTG | 1260 |
| IGLJ1_chr22:23235212-23235312 | AGAGCCAGGGGATCCTGCCATGTCCCAGCATAAAAACAGTACCTGACACAGATGGGTGCTTGGGAGCTGTTGTCTGGATGAATGAGTGGACAGATGCATGG | 1261 |
| IGLJ1_chr22:23235312-23235412 | ATGGACGGATGGAAGGATGGAAGGATGATAGATTGATGGACAAACAGATGAACAGATGAATAGCTGGATGGACAACTGGATGGATGGAGACAGAGATGATCTC | 1262 |
| IGLJ1_chr22:23235412-23235512 | AGAGATCAGAAAAAGCTTCATGCACTAAGTGGGACTGAACCCGCTCCATGGGTAGAAAGCAGAGGAATCTCCACTTGAGTCAGGAATGACCCAGTGCT | 1263 |
| IGLJ1_chr22:23235512-23235612 | CTCAATCCAGGGAGAAAGCCAGCCTGGCTTCACTCTGGGGACACTTGTGTGGGGACTCAGAGGCCCTTTAAATGAGGCCAGACGACCAAGGTTGGACAGGTCAA | 1264 |
| IGLJ1_chr22:23235612-23235712 | GCCAACTTCAGCACTCCTCTGCCACACTGCACAGGAGGGGATGTGTCACTCAGGGAGTTGCTGGGACCTATGGGTCCCAGTGTTGTCATCAGCACCGACAG | 1265 |

TABLE 6-continued

| Name | Sequence | SEQ ID NOs. |
|---|---|---|
| IGLJ1_chr22:23235712-23235812 | CCTCAGAGGAGGAAAGACACACACTGGGGTAACTCCAAGGCTGTGTGTGGCACATTGCCTTGGACAGCAGACAGGCACAGGGACACCTCTAGGGGGCTGGCC | 1266 |
| IGLJ1_chr22:23235812-23235912 | ACCCCCCTGCCTCATGTCTAGGTCTCAGCCCCGCCCACTGCAACCCTGTGCCGTCATGCCCAGCAGGCTCCTGCTCCAGCCCAGCCCCGGGGTTTTGGTCTGAGC | 1267 |
| IGLJ1_chr22:23235847-23235947 | CACTGCAACCCTGTGCCCGTCATGCCCAGCAGGCTCCTGCTCCAGCCCCAGAGAGACAGACCCCAGGTGTCGCCCCGGGGTTTTGGTCTGAGC | 1268 |
| IGLJ1_chr22:23235947-23236047 | CTCAGTCACTGTGTTATGTCTTCGGAACTGGGACTCACCCGTCTCCTAGGTAAGTGGCTCTCAACCTTTCCCAGCCTGTCTCACCCTCTGCTGTCCCT | 1269 |
| IGLJ1_chr22:23236047-23236147 | GGAAAATCTGTTTTCTCTCTCTGGGGTTCCTCCCCTCTGTCCTCCCAGCCTTAAGCACTGACCCCTTACCTTTCTCCATGGGGCCTGGAGGAGGTGCATT | 1270 |
| IGLJ1_chr22:23236147-23236247 | AGTCTCCGGGTAACCGGCAGGAAGGGCCTCCACAGTGGGAGCAGCCGGATGCAGCCTGGTCCCGGGCCTGAGCTGGGATTGGGCAGGGTCAGGGCTCCT | 1271 |
| IGLJ1_chr22:23236247-23236347 | CCTCTCTTCCAGGGCAGATGTCTGAGTGAGGACAGAGAGTCTGGTTCTGATGAGGGGGCCCTGCAGTGTCCTTAGGGACATTGCCCAGTGACTCCTGGGGTC | 1272 |
| IGLJ1_chr22:23236277-23236377 | GGACAGAGGCTGGTTCTGATGAGGGGGCCCTGCAGTGTCCTTAGGGACATTGCCCAGTGACTCCTGGGTCAAGGACAGAGGCTGCTGGGGTGGGCCTGGG | 1273 |
| IGLJ1_chr22:23236377-23236477 | AGCTGCTGAGTCTCATAGTCTAGGGAGCAGCCCAAGAACAGCTGAGGGTCTAGGCTGAGGACTGGATGCCAATCCAGCCTGGGAGGGCCACACGGCCT | 1274 |
| IGLJ1_chr22:23236387-23236487 | TCTCATAGTCTAGGGAGCAGCCCAAGAACAGCTGAGGGTCTAGGCTGAGGACTGGATGCCAATCCAGCCTGGGAGGGCCACACGCCTGTGACACAG | 1275 |
| IGLJ1_chr22:23236487-23236587 | AGTGTCACCCAAGGGAGACCCCCAAGTGGGGACACAGAGGGGACCGGGTGAGACTGGGTGAGGTGCCAGAATCCAACCTGTGCTGGGTCATGAGGACATGGGACACA | 1276 |
| IGLJ1_chr22:23236557-23236657 | TGTGCTGGGTCATGAGGACATGGGACACAGAGGGGACACAGAGGGGACCGGGTGAGACTGGGTGAGGTGCCAGAATCCAACCCTCCCAGGACAGTCACCCAGAAAGGAGACAG | 1277 |
| IGLJ1_chr22:23236657-23236757 | TCTCTTAGGGCAGAGATGTCTGTCCTGGAGCCCCCAGTCACCCTGGGGCCCAGTGTCTCTCTGTTCACGGATCGGCCTCCTGCCTTCTCAAAGGCA | 1278 |
| IGLC1_chr22:23236757-23236857 | TGTTAGACTCAGAAATGACCAGAGGGAGTGAATGAGGGGTGCAGAGAACTCCATGCTACCAGGTGAAGTTTGGGTCATCACAGCCTGCTGGGGTGG | 1279 |
| IGLC1_chr22:23236877-23236977 | CATAGTCTGTGGAGCAGCCCAGGAACAGCTGAGGTGAAGGGTTCTGTGGTCGGCTTGTGAGACAGGAAACATCCAGAGCCTCAGAGAGCCCTGA | 1280 |
| IGLC1_chr22:23236977-23237077 | GGCTTGTCTAGTGGAGCCCACTCCTTGCCAGGAGAGCCAAGTGGGCTGGGGCAGAGCCCGTGCCTGTGAGGGATAGGAAGCTCCAGTTCAAAG | 1281 |

TABLE 6-continued

| Name | Sequence | SEQ ID NOs. |
|---|---|---|
| IGLC1_chr22:23237077-23237177 | CAGGCTTGGGTCTTCCCACACACTGCTTGCCTGCCAGGACAGTCCTACAGGATGAGCAGGGACCCACAGTTCA CGGAGGAGGCTCTAGGTCCTGGAAGAATAA | 1282 |
| IGLC1_chr22:23237177-23237277 | AGTGGGTGATGAGGGGGGTATAGGGATGGAAATGAGGGATCCAGGGGTCAAGGCCCAGATTCTAAACTC AGACTCCAGAGATCAGAGAAGAAGGAACACA | 1283 |
| IGLC1_chr22:23237277-23237377 | GCCTGCCCTGGGCTATATGGAGAAATTGAGGCTCTAGAGGAGGAGGGGTCGGGCCAGGACACCTGAAAG GTGACTTGGGAGGGCTCCTAGGAAGGCACAG | 1284 |
| IGLC2_chr22:23242602-23242702 | TGAAAGCCCCACTGCTATGACCAGGTAGCCGGACGTAGCCGGACGTGGGGTGATGCCAGAGACTCCACGGAATA AGAGAGAGCCCAGGACAGCAGGCAGGCTCTC | 1285 |
| IGLC2_chr22:23242702-23242802 | CGATCCCCCCAGGCCCTTGCCCATACACGGGCTCCAGAACACACATTTGGCTGGAACAGCCTGAGGGAC CAAAAGGCCCCAGTATCCCACAGAGCTGAG | 1286 |
| IGLC2_chr22:23242802-23242902 | GAGCCAGGCCAGAAAAGTAACCCCAGAGTTCGCTGTCGCAGGGGAGACACAGAGCTCTCTTTATCTGTCAG GATGGCAGGAGGGGACAGGGTCAGGGCGCT | 1287 |
| IGLC2_chr22:23242902-23243002 | GAGGGTCAGATGTCGGTCTTGGGGGGCCAAGGCCCCGAGAGATTCAGGACAGACAGTGGTCAGGTGTCTAAG GTAAAACAGCTCCCCGTCAGATCAGGGCAT | 1288 |
| IGLC2_chr22:23244157-23244257 | ATGCAGGACAGTCCATGTCTCAGCAGGAACACAGTTGAAAATCCCCATTCCACACAAGACCGTTTAGCAGAA GAGGCAGAAGTAAGGGTGAAGAGCACCTATG | 1289 |
| IGLC2_chr22:23244257-23244357 | AGTCAATGTCATGGTCTCAGCAGGAACACAGTTGAAAATCCCCATTCCACACAAGACCGTTTAGCAGAA AGGAGTCCATACTTGTGCTGCCACCAGGAT | 1290 |
| IGLC2_chr22:23244357-23244457 | GTCCTGAGAAGCCTTGAGAGAATGAAACATACAGGTGCATTTCCTAGACTTGACAATGCACGTTAGCCAAG TAAAGGCAATGAAAAGTTCTCTACTAGGGA | 1291 |
| IGLJ3_chr22:23247257-23247357 | TTTGTTTGTTTCTGTATCTTGTCTCAACTTGTGGTTCAGCCTTTCTCCCTGCATCCCAGGCCTGAGCAAGGAC CTCTGCCCCCTGTTCAGACCCTTGCT | 1292 |
| IGLJ3_chr22:23247357-23247457 | TGCCTCAGCAGGTCACTACAACACTTCACCTCTGACCGCAGGGGACTAGATAGAATGACCTAC TGAGCCCTGCTGTCTGTCTGTCTGTCTGT | 1293 |
| IGLJ3_chr22:23247467-23247567 | CTGTTTGTCTCTCTGTCTGTCTGACAGGCGCAGGCTGGGTCTTCTAAGCCTTGTTCTGTTCTGCCTCCTCA GTCTGGGTTCTTGTCGGAACAGCTTTGCC | 1294 |
| IGLJ3_chr22:23247567-23247667 | CTTGGGTTACCTGGGTTCCATCTCTGGGGAATTGGGAACAAGGGGTCTGAGGGAGGAGCACCTCCTGGGAG ACTTTAGAAGGACCCCAGTGCCCTCGGGGCT | 1295 |
| IGLC3_chr22:23248182-23248282 | AGAGTTCCTGTGCAGGGGAGACACAGAGCTCTCTTTATCTGTCAGGATGGCAGGAGGGGACAGGGTCA GGGCGCTGAGGGTCAGATGTCGGTGTTGGGG | 1296 |
| IGLC3_chr22:23248282-23248382 | GCCAAGGCCCCGAGAGATCTCAGGACAGGTGGTCAGGTGTCTAAGGTAAAACAGCTCCCCGTGCAGATCA GGACATAGTGGAAAACACCCTGACCCTCT | 1297 |

TABLE 6-continued

| Name | Sequence | SEQ ID NOs. |
|---|---|---|
| IGLC3_chr22:23248382-23248482 | GCCTGGGCATAGACCTTCAGACACAGAGCCCTGAACAAGGGCACCCAACACCTCATCATATACTGAGGT CAGGGGCTCCCCAGGTGGACACCAGGACTC | 1298 |
| IGLJ7_chr22:23263872-23263972 | AGAATATTCCGTGAGAAGGTGGCCCCACAGCGCTGGGTCACGCGCCATCCCCCAAGACAGGCCAGGACACC ACAGACAGGGTGGTGGGTCTCAGAAAACTC | 1299 |
| IGLJ7_chr22:23263972-23264072 | AGGCCCTAAACGTGGATCCTTACCAATTCCTCCACTGGAGGAAGACCTCAGAGACCAGATGCCCAGGACAGG GACTTCTGGTAGGGACGGTGACTGGGACGG | 1300 |
| IGLJ7_chr22:23264072-23264172 | GTCCCTGTTTGTCAGGGAAAACCCACTGGAGAGTCAGATCCCCCAGATAACTTCTCACGACATGGAGACT CTTTCGAACAGACAAAGCTCCACGTTCAGC | 1301 |
| IGLC7_chr22:23264172-23264272 | TCAGGGAGTAAAAAAAAAATGCTCAAATGGAGGCCTTTGATCTACTGGAATCCAGCCCCAGGACTGAC ACCCTGTCTCACCAGGCAGCCCAGAGGGGT | 1302 |
| IGLC7_chr22:23278157-23278257 | CAGGGTCCACCAGAAGGCATCTCAGAACCAGCCAGCAGTTGGCCCTGATTGTCAGCAGGACCCCAGGGAG GGGGGTGGCCAGGACAGGGCTCTGAAGCCCC | 1303 |
| IGLC7_chr22:23278257-23278357 | CACCCCAGGACCTTCCCTGGGACAGAACGAGTTGGTGAGGGAGTGATGAGCAACCACAGGCCTCCTAACTT CCCAAGCTGGCGATTCTGAGAGGCCTCAAG | 1304 |
| IGLC7_chr22:23278357-23278457 | GCTGAGACACGGTTCAGCCTTTTAGGCCCTCTGAAGCTGCCCCTGTCTCCACAGCCTGGGAATGCACTC TCTTTTGACCCAGAAATCCTGCTCATAAG | 1305 |
| IGLC7_chr22:23282767-23282867 | CTGTCATTGTACAACACATCATTTCACTTTGTTTTTCAAACATAGTGAATTCTTCCTAATTAAAGAAGAA AAGAGTATAAAGAAGAAAGTTTCCAGTGCA | 1306 |
| IGLC7_chr22:23282842-23282942 | GTATAAAGAAGAAAGTTTCCAGTGCAGCCTGAGATCTGTACTGGTTGTATCTGGAATTCCAGACTCAGCC TTGCATTTCACATAGCAGATAGATGATGAT | 1307 |
| IGLC7_chr22:23282942-23283042 | GATGGAGAAGGAAGAAGAAGAAGGAGGAGGAGGAAGAAGAAGAAGAAGAAGAAGAGGAGG AAGAAGAAGAACGAAGGGAAGAAGAAGAAGAAGGATG | 1308 |
| TBC1D22A_chr22:47570209-47570309 | TCCAGGTCTGCCAGGTGTAGGGAGGTGTGACTGGTTCCATCATGGACCGGTTCCTCCATGGACCGGTTC CTCCGTGACCGGTTCCCGCCATGACCCGGT | 1309 |
| TBC1D22A_chr22:47570309-47570409 | TCCGCCATGGACCACTCCTGCCCTGGACCACTCCTGCCCTGGACCGGTTCTGCCGTGGACTGGTTCCCGCC GTGGACCAGTTCCCGCTGTATACTGGTTC | 1310 |
| TBC1D22A_chr22:47570409-47570509 | TGCCCTGGACTGGTTCCCGCTGGTTCCTGGACTGGTTCCTTGGGGCTCTAAGTGCGGAAGGGCCCAGAGCTGGTC CCTGCCCAGCCGCCCCTGCTAGGGCTGTGTCC | 1311 |
| TMSB4X_chrX:12993264-12993364 | TCGTACTCGTGCGCCCTCGCTTCGGTGAGCCCCAGGGGCCCCTCCGCTCCTCCTGCCTCCGT CCCCGCCCTTTCATCATCCGCGTCCCTGT | 1312 |
| TMSB4X_chrX:12993364-12993464 | GAAGGCATTCCCTAAATCCGAGCCCGAGTGGTTCTCCCCGGAAGGCTACTTTGGGGAGCTGGGGGATG CGAAACACCCTAGATACTGGATAATGGGGT | 1313 |

TABLE 6-continued

| Name | Sequence | SEQ ID NOs. |
|---|---|---|
| TMSB4X_chrX:12993464-12993564 | GGGGAAATCGATGATTAAGAACAAAACCGAAAAACTGGCGTTTGCCGTGCCGCTCGGAGGGACATTAAAAAATTCTTAGTGTTTGCCCGCAAAGT | 1314 |
| TMSB4X_chrX:12993544-12993644 | TAGTGTTTGCCCGCAAAGGTATTGTGCGTTGCCTTGGAGGCTGAGATATGGGGAATAGACAAGTCCTTTGTTCTGAGGTTCATCTTCCGAGCCCCGAGC | 1315 |
| TMSB4X_chrX:12993644-12993744 | CTCCTCCCAGCCTCGGACGGCTGCGCGGGCTGCATCTGTGCAGCCTGCGGCGCGGGGCTGTGCTATGACATCTTTACAGTCCTTCTTGCAGAGACATG | 1316 |
| TMSB4X_chrX:12993744-12993844 | TGTGCCAGGGATGCCGAATTGCCGGAGAGCAGGCAAGACCGGCTTCGGGGCGCGGGCCCGCTTTGTGTGCGGGGCTGCATTGTGACGCGGGCGATG | 1317 |
| TMSB4X_chrX:12993844-12993944 | AAGCCGGTAGGGCGTGTCGGAAGCTCCAGCCGCGGCCGCCGCCTTTGTGAGAGGACTAGAAAGCCGGATCCGGGCCCGCATCCTTGCGGAGGGCCGCG | 1318 |
| TMSB4X_chrX:12993944-12994044 | GCTAGGAAATGGAAACGCTTTTCCTACCTGGGCTCCATTTTAGGAATTCTTGCCGATTTTCCCACTTGAATTTTGGAAGTGGCTTTCCTCTCTTTCCTT | 1319 |
| TMSB4X_chrX:12994044-12994144 | GTCCTAGCCAGCCTTTAATTTAAACGCTGTAATTAACAATTCGCAGTGGTCAATTCCTTTATTCTGCAAGATTCGGCTTTGAGAGGCATCCGCCTCT | 1320 |
| TMSB4X_chrX:12994144-12994244 | TTGGTCCACAGCGTTTGAAATATGGGAGGAGGGGCGCGGGGGGTGTCGCCTCTTTTTCTGTAGAAAGAGGAAGCTCGTGAGCGCGAACGGCAGCAGT | 1321 |
| TMSB4X_chrX:12994289-12994389 | AAGTGCAGTTCCCAGCCCAGAGACAGCGGGGCGGGTGGCTCTTCCTCCACGCTCGCTTGGCTTGCTCCCTGCAGCTTTTCCTCCGCAACCATGTCTGAC | 1322 |

TABLE 6-continued

| Name | Sequence | SEQ ID NOs. |
|---|---|---|
| TMSB4X_chrX:12994389-12994489 | AAACCCGATATGGCTGAGATCGAGAAATTCGATAAGTCGAAACTGAAGAAGACAGAGACGCAAGAGAAA AATCCACTGCCTTCCAAAGAAAGTGAGCTCC | 1323 |
| TMSB4X_chrX:12994444-12994544 | AGACGCAAGAGAAAAATCCACTGCCTTCCAAAGAAAGTGAGCTCCGACCCCACCCCATCTTTAGAAAGGC TGGGTGGGAGCGGCCGGTGGGAGGGCGGGA | 1324 |
| DMD_chrX:3146106-3146206 | TTTATAGAAAGGCATATGGAACAGGAGTCATCCAAATATATCCAGGGGTTGCAAATTGACCAAAAGAGT CACCTTTAGGGAAGCCTGCTTCTGAATGCT | 1325 |
| DMD_chrX:3146206-3146306 | TGTTGGAATTTATCATTCTTCTGAATGGCTGTTGCATTTATCTGCAGCTTTTACTCACCAGATGAGACCTCA GACATTTCAAATTCTGCGGAGGCTGGCTA | 1326 |
| DMD_chrX:3146306-3146406 | CACACCTTCATAGGAAAGCTTTTTGCTGATTTCCCTGTTGGTACTTTTCTCTTACACATTCTATGGGTATG GTAAACCTGGAGGTAGAGTCATAGCCAA | 1327 |
| DMD_chrX:3146406-3146506 | GCACAGATAAAGCAGGCACAGAATCTCTGACCAGCCTCACAAAAGCAGACAAACACACAATCTTTTGCA CCTGTTTCTTCCACTCCGTTGCCGTGAAT | 1328 |
| PABPC5_chrX:90026453-90026553 | TAGAAATGTTCAACCAGTTCCAATATCAATATAGCTGCTTATTACTCTATTCACTTACTTCAAAGTGGCAT TTGTTTTGAGTAAGACTTTATTTAATTCT | 1329 |
| PABPC5_chrX:90026553-90026653 | TACCGTTAGCTTGAAACCATAGAGATCTTCTCTCTATTTGCCCTACTTCCTCAAAAGTCAAATGACCTCC TACAAATAAAGACGTTCTTATTTCATT | 1330 |

What is claimed is:

1. A method comprising:
   (a) obtaining, by a computer system, sequencing data for at least 1,000 cell-free DNA molecules from a first sample of a human subject;
   (b) processing, by the computer system, the sequencing data of (a) to identify one or more cell-free DNA molecules of the at least 1,000 cell-free DNA molecules as phased variant-containing cell-free DNA molecules, wherein identifying the one or more cell-free DNA molecules as phased variant-containing cell-free DNA molecules comprises aligning reads corresponding to each of the at least 1,000 cell-free DNA molecules to a reference human genomic sequence of at least 10 kb in length, wherein each of the one or more cell-free nucleic acid molecules identified as phased variant-containing cell-free DNA molecules comprises a plurality of phased variants relative to a sequence derived from a second sample of the same subject, wherein at least 10% of the one or more cell-free nucleic acid molecules identified as phased variant-containing cell-free DNA molecules comprises a first phased variant of the plurality of phased variants and a second phased variant of the plurality of phased variants that are separated by at least one nucleotide; and
   (c) analyzing, by the computer system, the identified one or more cell-free nucleic acid molecules identified as phased variant-containing cell-free DNA molecules to determine a condition of the subject, wherein the condition comprises a cancer which is not a hematological malignancy.

2. The method of claim 1, further comprising separating, in silico, (i) at least a portion of the identified one or more cell-free nucleic acid molecules from (ii) one or more other cell-free nucleic acid molecules of the plurality of cell-free nucleic acid molecules that are not identified to comprise the plurality of phased variants.

3. The method of claim 2, further comprising analyzing, by the computer system, (i) and (ii) as different variables.

4. The method of claim 1, wherein the sequencing data is obtained without in silico removal or suppression of (i) background error or (ii) sequencing error.

5. The method of claim 1, wherein a number of the plurality of phased variants from the identified one or more cell-free nucleic acid molecules is indicative of the condition of the subject.

6. The method of claim 5, wherein a ratio of (i) the number of the plurality of phased variants from the identified one or more cell-free nucleic acid molecules and (ii) a number of single nucleotide variants (SNVs) from the identified one or more cell-free nucleic acid molecules is indicative of the condition of the subject.

7. The method of claim 1, wherein a frequency of the plurality of phased variants in the identified one or more cell-free nucleic acid molecules is indicative of the condition of the subject.

8. The method of claim 1, wherein the at least 10% of the one or more cell-free nucleic acid molecules comprises at least 50% of the one or more cell-free nucleic acid molecules.

9. The method of claim 8, wherein the at least 10% of the one or more cell-free nucleic acid molecules comprises 100% of the one or more cell-free nucleic acid molecules.

10. The method of claim 1, wherein the first and second phased variants are separated by at least 2 nucleotides.

11. The method of claim 1, wherein the first phased variant and the second phased variant are separated by at most 160 nucleotides.

12. The method of claim 1, wherein the reference human genomic sequence is derived from a reference cohort and comprises at least a portion of hg19 human genome, hg18 genome, hg17 genome, hg16 genome, or hg38 genome.

13. The method of claim 1, wherein the reference human genomic sequence is derived from a sample of the subject.

14. The method of claim 1, wherein the reference genomic sequence is derived from a healthy cell of the subject.

15. The method of claim 1, wherein the condition comprises a solid tumor.

16. The method of claim 1, wherein the cancer is not a lymphoma.

17. The method of claim 1, wherein the cancer is a lung cancer, a colorectal cancer, a gastrointestinal cancer, an esophageal cancer or a breast cancer.

18. The method of claim 1, further comprising determining, by the computer, that the subject has the condition or determining a degree or status of the condition of the subject, based on the identified one or more cell-free nucleic acid molecules comprising the plurality of phased variants, wherein the identified one or more cell-free nucleic acid molecules are derived from a sample associated with the condition, based on performing a statistical model analysis of the identified one or more cell-free nucleic acid molecules.

19. The method of claim 1, wherein the at least 1,000 cell-free DNA molecules from which sequencing data is derived are captured with a set of nucleic acid probes, wherein the set of nucleic acid probes is configured to hybridize to at least a portion of cell-free nucleic acid molecules comprising one or more genomic regions associated with the condition.

20. The method of claim 19, wherein the set of nucleic acid probes is designed based on the plurality of phased variants that are identified by comparing (i) sequencing data from a tumor sample of the subject and (ii) sequencing data from a healthy cell of the subject or a healthy cohort.

21. The method according to claim 1, wherein the first sample and the second sample are derived from separate components of a blood draw.

22. The method according to claim 21, wherein the first sample is derived from plasma.

23. The method according to claim 22, wherein the second sample is derived from peripheral blood mononuclear cells.

24. A method comprising:
(a) obtaining, by a computer system, sequencing data for at least 1,000 cell-free DNA molecules from a first sample of a human subject;
(b) processing, by the computer system, the sequencing data of (a) to identify one or more cell-free DNA molecules of the at least 1,000 cell-free DNA molecules as phased variant-containing cell-free DNA molecules, wherein identifying the one or more cell-free DNA molecules as phased variant-containing cell-free DNA molecules comprises aligning reads corresponding to each of the at least 1,000 cell-free DNA molecules to a reference human genomic sequence of at least 10 kb in length, wherein each of the one or more cell-free nucleic acid molecules identified as phased variant-containing cell-free DNA molecules comprises a plurality of phased variants relative to a sequence derived from a second sample of the same subject, wherein at least 10% of the one or more cell-free nucleic acid molecules identified as phased variant-containing cell-free DNA molecules comprises a first phased variant of the plurality of phased variants and a second phased variant of the plurality of phased variants that are separated by at least one nucleotide; and
(c) analyzing, by the computer system, the identified one or more cell-free nucleic acid molecules identified as phased variant-containing cell-free DNA molecules to determine a condition of the subject.

\* \* \* \* \*

SEQUENCE LISTING

```
Sequence total quantity: 1358
SEQ ID NO: 1                moltype = DNA  length = 100
FEATURE                     Location/Qualifiers
source                      1..100
                            mol_type = genomic DNA
                            organism = Homo sapiens
SEQUENCE: 1
tctcttctgg cccacagccg cagcaatggc gctgagttcc tctgctggag ttcatcctgc    60
tagctgggtt cccgagctgc cggtctgagc ctgaggcatg                         100

SEQ ID NO: 2                moltype = DNA  length = 100
FEATURE                     Location/Qualifiers
source                      1..100
                            mol_type = genomic DNA
                            organism = Homo sapiens
SEQUENCE: 2
gagcctcctg gagactgggg gcctcctccc tggagatcca cccccaaaac cgacgtcttg    60
aggctggtga gcccccgagc ctcctctccg tctgctcgca                         100

SEQ ID NO: 3                moltype = DNA  length = 100
FEATURE                     Location/Qualifiers
source                      1..100
                            mol_type = genomic DNA
                            organism = Homo sapiens
SEQUENCE: 3
gatcccagtt ctgaccccag ggcctccac agatctcttc cccatgcccc tgtcctggcc     60
gttgctggct ccggcgtcca gcccgtcccc tgctgcctgg                         100

SEQ ID NO: 4                moltype = DNA  length = 100
FEATURE                     Location/Qualifiers
source                      1..100
                            mol_type = genomic DNA
                            organism = Homo sapiens
SEQUENCE: 4
ccatgttgct ggcttacttg gcatttccca tgatctcaca ctgctggctt atttggcatt    60
tcccatgatc ccctgctgct ggtttacttg gcattccta                          100

SEQ ID NO: 5                moltype = DNA  length = 100
FEATURE                     Location/Qualifiers
source                      1..100
                            mol_type = genomic DNA
                            organism = Homo sapiens
SEQUENCE: 5
tgatcccatg ttgctggttt acttagcatt tcccatgatc ccatgttgct ggcttacttg    60
gcatttccca tgataccatg ttgctggctt acttggcatt                         100

SEQ ID NO: 6                moltype = DNA  length = 100
FEATURE                     Location/Qualifiers
source                      1..100
                            mol_type = genomic DNA
                            organism = Homo sapiens
SEQUENCE: 6
atagattaga ggaaggaatt ctagatgaaa ttaagtaaat gagttattta agtcaactaa    60
tacaagtcct caaaactttg attatataga gagctaaact                         100

SEQ ID NO: 7                moltype = DNA  length = 100
FEATURE                     Location/Qualifiers
source                      1..100
                            mol_type = genomic DNA
                            organism = Homo sapiens
SEQUENCE: 7
gataaatata gacaaatata gtgagcctat aaattaaagc tatactatga tgaaaaaata    60
aatgaataat tgtgaaatag ccaaaaatac taaaatacag                         100

SEQ ID NO: 8                moltype = DNA  length = 100
FEATURE                     Location/Qualifiers
source                      1..100
                            mol_type = genomic DNA
                            organism = Homo sapiens
SEQUENCE: 8
aatgaataat tgtgaaatag ccaaaaatac taaaatacag ctataaggtt aaaaataaat    60
ctgaataaaa aatgtaggag ggaaaagtga ttaccttacc                         100

SEQ ID NO: 9                moltype = DNA  length = 100
FEATURE                     Location/Qualifiers
source                      1..100
                            mol_type = genomic DNA
                            organism = Homo sapiens
```

-continued

```
SEQUENCE: 9
gacatgcatc aaatgtaaac aaatgattac agccatttta taaaaagtca tattctttaa    60
aacattttt gtcatcatta aaaattaaaa ggcaataaag                            100

SEQ ID NO: 10           moltype = DNA   length = 100
FEATURE                 Location/Qualifiers
source                  1..100
                        mol_type = genomic DNA
                        organism = Homo sapiens
SEQUENCE: 10
tgtcattgtc gtgaaacagt acgtgatctt aagggaagaa acatctcact agagtttgca    60
caagttcctt cttcttctaa ctgtagatct ggtggcaaag                          100

SEQ ID NO: 11           moltype = DNA   length = 100
FEATURE                 Location/Qualifiers
source                  1..100
                        mol_type = genomic DNA
                        organism = Homo sapiens
SEQUENCE: 11
gaggagcccc tgggtcccca ggtctgggaa gtgtagttga agagaagatg gtattttcag    60
ttctgcctac ttctagaaca ggcaaattca gagaagaatt                          100

SEQ ID NO: 12           moltype = DNA   length = 100
FEATURE                 Location/Qualifiers
source                  1..100
                        mol_type = genomic DNA
                        organism = Homo sapiens
SEQUENCE: 12
agtagaaaaa aagggcgtcg tgctggattc tccttctgga tggtacatga cagtggatgc    60
cctcagtttt tcagagaaat tactctcatc tgaatttgat                          100

SEQ ID NO: 13           moltype = DNA   length = 100
FEATURE                 Location/Qualifiers
source                  1..100
                        mol_type = genomic DNA
                        organism = Homo sapiens
SEQUENCE: 13
ctggagaggt tgttcgtggc tccatctgga aaaggttcac aactgctaca ttttagtcct    60
acaataaaat tattcagatg taaatgaaaa agtaactaaa                          100

SEQ ID NO: 14           moltype = DNA   length = 100
FEATURE                 Location/Qualifiers
source                  1..100
                        mol_type = genomic DNA
                        organism = Homo sapiens
SEQUENCE: 14
acccgagacc tctcactgag cccgagccgc gcgcgacatg agccacggga agggaaccga    60
catgctcccg gagatcgccg ccgccgtggg cttcctctcc                          100

SEQ ID NO: 15           moltype = DNA   length = 100
FEATURE                 Location/Qualifiers
source                  1..100
                        mol_type = genomic DNA
                        organism = Homo sapiens
SEQUENCE: 15
agcctcctga ggacccgggg ctgcgtgagc gagcagaggc ttaaggtctt cagcggggcg    60
ctccaggagg cactcacagg tgagcgcatg ccgaggggcc                          100

SEQ ID NO: 16           moltype = DNA   length = 100
FEATURE                 Location/Qualifiers
source                  1..100
                        mol_type = genomic DNA
                        organism = Homo sapiens
SEQUENCE: 16
tggcgccacc gggggtcggc cccatccctg ccagggccgt ctttcttcta ctcctgcggc    60
agggtgaccc acgggagcag ctttgggact cggtggccct                          100

SEQ ID NO: 17           moltype = DNA   length = 100
FEATURE                 Location/Qualifiers
source                  1..100
                        mol_type = genomic DNA
                        organism = Homo sapiens
SEQUENCE: 17
cctccgaccc ccgggcggc ccgcagtccc cagtttcctg ggtcctcctc cccagccctg    60
tgctcgggtc tcggccgtgg cggttctgat ggggcgcgcc                          100

SEQ ID NO: 18           moltype = DNA   length = 100
FEATURE                 Location/Qualifiers
source                  1..100
```

```
                         mol_type = genomic DNA
                         organism = Homo sapiens
SEQUENCE: 18
cctctacgct ctcggaggcg cagaccctgg tcctggagtg ccagcccgag tccccagctt    60
atgcccctgt ctcattacgg gctcgtctcc ctcgctggac                         100

SEQ ID NO: 19            moltype = DNA  length = 100
FEATURE                  Location/Qualifiers
source                   1..100
                         mol_type = genomic DNA
                         organism = Homo sapiens
SEQUENCE: 19
cctcgagatc ttaagaccct cgatggatgt tgttgcgggc cgcccggtcg gccgaggggt    60
cccgatgagg gaagaaggtg cagtcgagcc ttttcaacaa                         100

SEQ ID NO: 20            moltype = DNA  length = 100
FEATURE                  Location/Qualifiers
source                   1..100
                         mol_type = genomic DNA
                         organism = Homo sapiens
SEQUENCE: 20
tttggagtcc cagtgcggtt cttcctgccg gtcggggtgc gctgtgcctg gggtagtcca    60
ctggttgctg actggcttca agttggaatt tgggccccct                         100

SEQ ID NO: 21            moltype = DNA  length = 100
FEATURE                  Location/Qualifiers
source                   1..100
                         mol_type = genomic DNA
                         organism = Homo sapiens
SEQUENCE: 21
ttgtgttatc tttggttccc cttagccatc tgccacctat tgtggtaggg aggagagcct    60
cgtagctcgt gaccctgccg tgcgggcctt caagttggga                         100

SEQ ID NO: 22            moltype = DNA  length = 100
FEATURE                  Location/Qualifiers
source                   1..100
                         mol_type = genomic DNA
                         organism = Homo sapiens
SEQUENCE: 22
ggtgaagaga taagcagccc gctcgctggc tggggagaga cctctctccc agctgtttct    60
agctggttac tgtcagtttt gggaagcgat agccatctcg                         100

SEQ ID NO: 23            moltype = DNA  length = 100
FEATURE                  Location/Qualifiers
source                   1..100
                         mol_type = genomic DNA
                         organism = Homo sapiens
SEQUENCE: 23
gaacgcaccc acacagaccc tgccttctga ggaaaacaga tgtttcatca aaacaaccca    60
gttttcactc ccttaggcac tgctaaggaa ggttctctga                         100

SEQ ID NO: 24            moltype = DNA  length = 100
FEATURE                  Location/Qualifiers
source                   1..100
                         mol_type = genomic DNA
                         organism = Homo sapiens
SEQUENCE: 24
ctcttctgaa ggaagcagag ggaacacagg gtgggaggtc cagtgacttg ctgtggaccc    60
aacaatgttg gcagccttcc tggccctgaa acttcagctc                         100

SEQ ID NO: 25            moltype = DNA  length = 100
FEATURE                  Location/Qualifiers
source                   1..100
                         mol_type = genomic DNA
                         organism = Homo sapiens
SEQUENCE: 25
acaggtctcc agaggccctg cctggacatg ccagtcccag tcacaccctt cccttgcttt    60
gggggtgtgc caaaagcaat acactggcca ctagagagta                         100

SEQ ID NO: 26            moltype = DNA  length = 100
FEATURE                  Location/Qualifiers
source                   1..100
                         mol_type = genomic DNA
                         organism = Homo sapiens
SEQUENCE: 26
ccctagagct ctagaatccc ctcccaacac gcacacacac acacacacac actctctctc    60
tcacacacac acactcagtc acacacacac acacacacac                         100

SEQ ID NO: 27            moltype = DNA  length = 100
```

| FEATURE | Location/Qualifiers |
|---|---|
| source | 1..100 |
| | mol_type = genomic DNA |
| | organism = Homo sapiens |

SEQUENCE: 27
ctttcagatc tttcgcagcg tcccaacagg gcaaaggctc cagcattctg ccagaaggaa    60
ttcccgcctc cacattcccg gtccccggct gtgctgaggg                         100

| SEQ ID NO: 28 | moltype = DNA   length = 100 |
|---|---|
| FEATURE | Location/Qualifiers |
| source | 1..100 |
| | mol_type = genomic DNA |
| | organism = Homo sapiens |

SEQUENCE: 28
gctgccccca agcaagccca gcgttgggga ccctccctcc actctgtcgg agagctgcca    60
acgcccccg cccacggggg ccccacttcg ggcctcctca                          100

| SEQ ID NO: 29 | moltype = DNA   length = 100 |
|---|---|
| FEATURE | Location/Qualifiers |
| source | 1..100 |
| | mol_type = genomic DNA |
| | organism = Homo sapiens |

SEQUENCE: 29
gggcctacgg aggccagggc cctgggcagc ctggaccagc tcagggaatc agaggactct    60
gcgctttgca cgctcacagt cgtctcctct ggccttttgc                         100

| SEQ ID NO: 30 | moltype = DNA   length = 100 |
|---|---|
| FEATURE | Location/Qualifiers |
| source | 1..100 |
| | mol_type = genomic DNA |
| | organism = Homo sapiens |

SEQUENCE: 30
ccacttcagg ctccccagag cccggcatgc cacagggcag atatcctttc cccatcttcc    60
caggggttc tccatcgcgg ggcccgcccc tttctgggc                           100

| SEQ ID NO: 31 | moltype = DNA   length = 100 |
|---|---|
| FEATURE | Location/Qualifiers |
| source | 1..100 |
| | mol_type = genomic DNA |
| | organism = Homo sapiens |

SEQUENCE: 31
tgggcttgtc tcactgccca gaaactgccc ctgcctctcc accagggcct ctggggctg    60
caggtcctca agctcacggg ctctcccaga cggctcagtg                         100

| SEQ ID NO: 32 | moltype = DNA   length = 100 |
|---|---|
| FEATURE | Location/Qualifiers |
| source | 1..100 |
| | mol_type = genomic DNA |
| | organism = Homo sapiens |

SEQUENCE: 32
agggcaagat cctgtggacg gtgtggccca gtggatgtaa ctctcgctgc cacttccgtg    60
gccatcgtta agctagctcc gaacagcccc aatgagggag                         100

| SEQ ID NO: 33 | moltype = DNA   length = 100 |
|---|---|
| FEATURE | Location/Qualifiers |
| source | 1..100 |
| | mol_type = genomic DNA |
| | organism = Homo sapiens |

SEQUENCE: 33
ctaggcagct ccgagttccc ggggtaggag agcccctttt gtcaatttcc atagctgtgg    60
gtgagccaca gcggggactg gcagggatac ccttctccat                         100

| SEQ ID NO: 34 | moltype = DNA   length = 100 |
|---|---|
| FEATURE | Location/Qualifiers |
| source | 1..100 |
| | mol_type = genomic DNA |
| | organism = Homo sapiens |

SEQUENCE: 34
ccttacaaaa gcggatggac cctgagcctc tgatcctgta ggggcagccc ggccgggaag    60
aggtggcatt cctttcttca cctgcgagga gcataggctg                         100

| SEQ ID NO: 35 | moltype = DNA   length = 100 |
|---|---|
| FEATURE | Location/Qualifiers |
| source | 1..100 |
| | mol_type = genomic DNA |
| | organism = Homo sapiens |

SEQUENCE: 35
ggccctcctt tcctcccgga gtcggttcct gaagtctctg acattgctc ccccaggac     60
tttgtcctcc gttcctcgct ccgggcgccc tgaaccagga                         100

```
SEQ ID NO: 36           moltype = DNA   length = 100
FEATURE                 Location/Qualifiers
source                  1..100
                        mol_type = genomic DNA
                        organism = Homo sapiens
SEQUENCE: 36
cccttccagg gggctgactg ctgctgcgga aggggcacgg ggagggcgag cgagccctgc    60
ccaaacgcgg gctgcggggc gcttgaatgg cggagctctg                         100

SEQ ID NO: 37           moltype = DNA   length = 100
FEATURE                 Location/Qualifiers
source                  1..100
                        mol_type = genomic DNA
                        organism = Homo sapiens
SEQUENCE: 37
tgcctggatg tgcgcctcaa acatgcccac tttctggttc acctgcacgt tctgcaactc    60
gcgctgcaag atccgcagct tcctcttggc ctcctccggc                         100

SEQ ID NO: 38           moltype = DNA   length = 100
FEATURE                 Location/Qualifiers
source                  1..100
                        mol_type = genomic DNA
                        organism = Homo sapiens
SEQUENCE: 38
cctggcgggg agagggtacc ggctgccacc acctgctgcc ggtcccctcg caggcgacca    60
gcccaacttg ggctgctcac gctactgccg ctgctgccgc                         100

SEQ ID NO: 39           moltype = DNA   length = 100
FEATURE                 Location/Qualifiers
source                  1..100
                        mol_type = genomic DNA
                        organism = Homo sapiens
SEQUENCE: 39
tgccactgcc gctgctacta ttcagcctgc ccggccgct ccgccagccc ccggggctcc     60
ggggctcctc gggggacagc gactcggctg gggggaagag                         100

SEQ ID NO: 40           moltype = DNA   length = 100
FEATURE                 Location/Qualifiers
source                  1..100
                        mol_type = genomic DNA
                        organism = Homo sapiens
SEQUENCE: 40
gaaagaggcg cctctcccgg ggctgaaaac gctgccgggg ctcagcactg ccctcctcgg    60
gggcgggggc gtctcgctgc cactgggccc cgggccgccg                         100

SEQ ID NO: 41           moltype = DNA   length = 100
FEATURE                 Location/Qualifiers
source                  1..100
                        mol_type = genomic DNA
                        organism = Homo sapiens
SEQUENCE: 41
ccgctcttca tctcgttggc gctattcatg atcaccaggc tattgagcgc atagcagtac    60
acagccatag tactgggtcc cgcgctgccc gccgccgcgg                         100

SEQ ID NO: 42           moltype = DNA   length = 100
FEATURE                 Location/Qualifiers
source                  1..100
                        mol_type = genomic DNA
                        organism = Homo sapiens
SEQUENCE: 42
ctcccgctcc tgctccgccg ccggcgcctc ctcctcccgg cgctcccggc tcagccccgg    60
aggcccggca gccgcggctc cgcgcgcaga tggggcggca                         100

SEQ ID NO: 43           moltype = DNA   length = 100
FEATURE                 Location/Qualifiers
source                  1..100
                        mol_type = genomic DNA
                        organism = Homo sapiens
SEQUENCE: 43
aagtgcgaag gaagtgtcag gctggatgtc aaaatgaaca ccttggagaa ctggatgatg    60
gaacagacgg taaaaatcag ctaaacatca gagaaaatgg                         100

SEQ ID NO: 44           moltype = DNA   length = 100
FEATURE                 Location/Qualifiers
source                  1..100
                        mol_type = genomic DNA
                        organism = Homo sapiens
SEQUENCE: 44
```

```
aggaagaggt caaaactgtg aacaggaact agaagaaagt gtagcagaaa aagacttgtc   60
acaaacttcg agagatttgg agaaaatgat gtcaaaacac                        100

SEQ ID NO: 45            moltype = DNA   length = 100
FEATURE                  Location/Qualifiers
source                   1..100
                         mol_type = genomic DNA
                         organism = Homo sapiens
SEQUENCE: 45
atcttcctca agcccatgct gagtatctct gatttggtta atttcttggt aagtgttcca   60
agtacagaca acaaagcaga aaagcactga ttacagggaa                        100

SEQ ID NO: 46            moltype = DNA   length = 100
FEATURE                  Location/Qualifiers
source                   1..100
                         mol_type = genomic DNA
                         organism = Homo sapiens
SEQUENCE: 46
tatgcagaat gatccttcag atcatgtgaa cgctataatt aaatgttgct accaaatccc   60
cactaccctt tctcccacct agaaaaagtt aatgcatgaa                        100

SEQ ID NO: 47            moltype = DNA   length = 100
FEATURE                  Location/Qualifiers
source                   1..100
                         mol_type = genomic DNA
                         organism = Homo sapiens
SEQUENCE: 47
ttcagtatga gcaaattgtg atttataaaa acaaacaaac aaacaaacaa acaaaaccca   60
ccctattcac tccgtagggg aataaagctt tcttgcatta                        100

SEQ ID NO: 48            moltype = DNA   length = 100
FEATURE                  Location/Qualifiers
source                   1..100
                         mol_type = genomic DNA
                         organism = Homo sapiens
SEQUENCE: 48
aacaaacaaa acccacccta ttcactccgt aggggaataa agctttcttg cattaagtca   60
cgcatcatgg gggtaggaaa aaagcacagt actgaaagaa                        100

SEQ ID NO: 49            moltype = DNA   length = 100
FEATURE                  Location/Qualifiers
source                   1..100
                         mol_type = genomic DNA
                         organism = Homo sapiens
SEQUENCE: 49
gtgaagtgat ccaaatgtag cccagagatc ctaaagaaaa aacgatgctc atgtgttaca   60
aaacaaaatt ttaaggcaat cagtgaggaa tcacagacaa                        100

SEQ ID NO: 50            moltype = DNA   length = 100
FEATURE                  Location/Qualifiers
source                   1..100
                         mol_type = genomic DNA
                         organism = Homo sapiens
SEQUENCE: 50
atttccttag tgcttttatc aaggttgaat ctgaatataa attactagag gaaagcaaat   60
cagatttcac atctgaaaat taaaaacaaa attcttagct                        100

SEQ ID NO: 51            moltype = DNA   length = 100
FEATURE                  Location/Qualifiers
source                   1..100
                         mol_type = genomic DNA
                         organism = Homo sapiens
SEQUENCE: 51
aggcaacaaa atgagatcct gtccctagaa aacatttcaa aaaattaaca gcatggtgac   60
gcacacttgt agccctagct acttgggagg ctgagtggga                        100

SEQ ID NO: 52            moltype = DNA   length = 100
FEATURE                  Location/Qualifiers
source                   1..100
                         mol_type = genomic DNA
                         organism = Homo sapiens
SEQUENCE: 52
aagaacttaa gcagactagg atataaagta taggagcgta ttgtgtacag gaacgggaaa   60
tactgttttcc tggatctttt gtttcactta cgcacacacc                        100

SEQ ID NO: 53            moltype = DNA   length = 100
FEATURE                  Location/Qualifiers
source                   1..100
                         mol_type = genomic DNA
```

```
                         organism = Homo sapiens
SEQUENCE: 53
cacacccgcc agtagtgtac caggttgcga tggaaatctc tctctttctg tggatgagtt    60
tgtggaagcc cttgctccag catgccctcc ttcctgccca                         100

SEQ ID NO: 54           moltype = DNA   length = 100
FEATURE                 Location/Qualifiers
source                  1..100
                        mol_type = genomic DNA
                        organism = Homo sapiens
SEQUENCE: 54
cccctggacc attccttccc ttcacagcac tgtcccatgg gtaggccaca gcccagcaca    60
ggccccagcc tggcggctgc agcaggagcc ccatcccagg                         100

SEQ ID NO: 55           moltype = DNA   length = 100
FEATURE                 Location/Qualifiers
source                  1..100
                        mol_type = genomic DNA
                        organism = Homo sapiens
SEQUENCE: 55
gcctgagggg ccatgcgggg gtctgggtgg gagtgggaac cgctgaggaa ggtgaaggga    60
aatatggtga gatgacaggc ccgctgtcag ggagagtggg                         100

SEQ ID NO: 56           moltype = DNA   length = 100
FEATURE                 Location/Qualifiers
source                  1..100
                        mol_type = genomic DNA
                        organism = Homo sapiens
SEQUENCE: 56
aggagccctg gagtgcccta cctctgtggg gctggaactc cctgtatccg agctagggtc    60
ttccacacgc atgctactac cccaagtgcc acagctggag                         100

SEQ ID NO: 57           moltype = DNA   length = 100
FEATURE                 Location/Qualifiers
source                  1..100
                        mol_type = genomic DNA
                        organism = Homo sapiens
SEQUENCE: 57
tcatctccca ctggataaca gtgttgtcgg gaacttccat ccagcactgg cggacactcc    60
cgtcgcagct gctcctgact gagcaagtca tttaagggg                          100

SEQ ID NO: 58           moltype = DNA   length = 100
FEATURE                 Location/Qualifiers
source                  1..100
                        mol_type = genomic DNA
                        organism = Homo sapiens
SEQUENCE: 58
tccttggcac tcataagcac tcacagaatg gggctggcag tgcgcccggc ctccctggga    60
tgggtccaga atggtaggaa gcgcagtccg ggagggaccc                         100

SEQ ID NO: 59           moltype = DNA   length = 100
FEATURE                 Location/Qualifiers
source                  1..100
                        mol_type = genomic DNA
                        organism = Homo sapiens
SEQUENCE: 59
actgcttaga gctctcagcc ctagatggcg tatcacagtt aatgctctat aaaacccatc    60
atggcttttc cctagtaagc ctcaaatcgc tgcaagcaag                         100

SEQ ID NO: 60           moltype = DNA   length = 100
FEATURE                 Location/Qualifiers
source                  1..100
                        mol_type = genomic DNA
                        organism = Homo sapiens
SEQUENCE: 60
gcttcatata tgagagtttc tgctgtctcc tggagccatc tcacccaaag ccactgactc    60
tgggagacca gcccaggcca caaaccagca aagcaccagt                         100

SEQ ID NO: 61           moltype = DNA   length = 100
FEATURE                 Location/Qualifiers
source                  1..100
                        mol_type = genomic DNA
                        organism = Homo sapiens
SEQUENCE: 61
tatagttaga gctgcattat aaagtggcca gaggacattt ctttgcagtg agatgtgtat    60
cgtgaacgtt tggggcctgt gctcgcctag tcctcatctt                         100

SEQ ID NO: 62           moltype = DNA   length = 100
FEATURE                 Location/Qualifiers
```

```
source                          1..100
                                mol_type = genomic DNA
                                organism = Homo sapiens
SEQUENCE: 62
tgcttttcta ggtacacaaa gccatcccat ggctgcaaat gttagctggg ctgggctccc    60
tacttgcctc aagcccttc atagaccctt caggcacatg                           100

SEQ ID NO: 63                   moltype = DNA  length = 100
FEATURE                         Location/Qualifiers
source                          1..100
                                mol_type = genomic DNA
                                organism = Homo sapiens
SEQUENCE: 63
cttttctctg gacgtttaca gacaggtcct cagaggtcag agcaggttgt cctagggagc    60
agggaggctt cctagggagg tcagactcca aatagtggat                          100

SEQ ID NO: 64                   moltype = DNA  length = 100
FEATURE                         Location/Qualifiers
source                          1..100
                                mol_type = genomic DNA
                                organism = Homo sapiens
SEQUENCE: 64
atggcaaaaa tgcagctgca gactcatgag gagtcgccct gggctgccac tagggctccc    60
acagtgtgcg ctgccaacct gctgcccgtg cagaaactct                          100

SEQ ID NO: 65                   moltype = DNA  length = 100
FEATURE                         Location/Qualifiers
source                          1..100
                                mol_type = genomic DNA
                                organism = Homo sapiens
SEQUENCE: 65
caactgtgcc ctgcactgtt agggcccttg tcaaaacaac acatttctca gtgattctga    60
gactcttttct cttatctata gaagtcataa ctcaagagta                          100

SEQ ID NO: 66                   moltype = DNA  length = 100
FEATURE                         Location/Qualifiers
source                          1..100
                                mol_type = genomic DNA
                                organism = Homo sapiens
SEQUENCE: 66
aaatcatacc aatattttac ataaaccta gaattttttat agatctatta tttcttttta    60
gagtacatat tggaagtaac ttcacaagga acatttttctt                         100

SEQ ID NO: 67                   moltype = DNA  length = 100
FEATURE                         Location/Qualifiers
source                          1..100
                                mol_type = genomic DNA
                                organism = Homo sapiens
SEQUENCE: 67
tctggtcaaa ccactccaca aataaagtgg actgatcctc ttgactctat gtgtaagtgc    60
ccattgtgtg tgcacagagc tggtgagaac ggccatggtg                          100

SEQ ID NO: 68                   moltype = DNA  length = 100
FEATURE                         Location/Qualifiers
source                          1..100
                                mol_type = genomic DNA
                                organism = Homo sapiens
SEQUENCE: 68
ctaggtgggg gtggtgttgg tggagttgga ctagattatc tgggatcatg cgaaatggaa    60
attcatttct agctggctgg cttcagaagg tgccatctcc                          100

SEQ ID NO: 69                   moltype = DNA  length = 100
FEATURE                         Location/Qualifiers
source                          1..100
                                mol_type = genomic DNA
                                organism = Homo sapiens
SEQUENCE: 69
tattttata tgaagcgtgc tttggaactc agggcaacga agggtgggtg tgctgcacaa    60
ggacagcaga agagtgagct gactggtccc tgaaatcgca                          100

SEQ ID NO: 70                   moltype = DNA  length = 100
FEATURE                         Location/Qualifiers
source                          1..100
                                mol_type = genomic DNA
                                organism = Homo sapiens
SEQUENCE: 70
gttggaaagt ggattaccag tgcagtagaa ctcttcacgg aggcctggac catcaggtct    60
aatggtgttg ttccaggtgg gtggtcatgt ggagcaaaaa                          100
```

```
SEQ ID NO: 71               moltype = DNA  length = 100
FEATURE                     Location/Qualifiers
source                      1..100
                            mol_type = genomic DNA
                            organism = Homo sapiens
SEQUENCE: 71
tatttgaaat cagcgagcac gtacctgaga gatgactttt ccacttgggc tagtctcttg    60
atatttctgg tcctgtttct tcatctgtaa actgggttag                         100

SEQ ID NO: 72               moltype = DNA  length = 100
FEATURE                     Location/Qualifiers
source                      1..100
                            mol_type = genomic DNA
                            organism = Homo sapiens
SEQUENCE: 72
aaggagacca agaagcgtat ttaaaatctt gatgttttga gtttcttcct agcttccccc    60
tattccttaa taaagttcta aattgttttg ttggagctct                         100

SEQ ID NO: 73               moltype = DNA  length = 100
FEATURE                     Location/Qualifiers
source                      1..100
                            mol_type = genomic DNA
                            organism = Homo sapiens
SEQUENCE: 73
ttgcagccat tctgagggct ttgcatgctt ttctgacctt gcagtaaact caatgcttta    60
ggcaaagaat ggccacgtca tccgaccccc tcagagttta                         100

SEQ ID NO: 74               moltype = DNA  length = 100
FEATURE                     Location/Qualifiers
source                      1..100
                            mol_type = genomic DNA
                            organism = Homo sapiens
SEQUENCE: 74
gaattcagaa caggtctgaa gaagaccagg cagcggctga gtcaaggaaa gcctccgtcc    60
gcttttattt cccctgtgcc tcttccagga ctgtgctggg                         100

SEQ ID NO: 75               moltype = DNA  length = 100
FEATURE                     Location/Qualifiers
source                      1..100
                            mol_type = genomic DNA
                            organism = Homo sapiens
SEQUENCE: 75
ataacaggct cccgggggtt actttggctg ggctgggcta aaacctccct gcagagcagg    60
ccctgagccc tgcctctgcg cctgggtggt gtcagcccct                         100

SEQ ID NO: 76               moltype = DNA  length = 100
FEATURE                     Location/Qualifiers
source                      1..100
                            mol_type = genomic DNA
                            organism = Homo sapiens
SEQUENCE: 76
ccaccttctg actgttccag caactctcta agccctccca aaggcctcaa ggcctgtaac    60
catatgcagc aattttcagc cataccagga gaggtcaact                         100

SEQ ID NO: 77               moltype = DNA  length = 100
FEATURE                     Location/Qualifiers
source                      1..100
                            mol_type = genomic DNA
                            organism = Homo sapiens
SEQUENCE: 77
gtaatcttgg ccacctgcct aagaggaagt ggctagcttc acttctgacc ctcagcaact    60
gccaggtggc ctcttggaaa tcccctctg ggggattcca                          100

SEQ ID NO: 78               moltype = DNA  length = 100
FEATURE                     Location/Qualifiers
source                      1..100
                            mol_type = genomic DNA
                            organism = Homo sapiens
SEQUENCE: 78
cccgttgggt gggagagcag tagttaaaat gtaaataag aatctttgc tgggagaagt      60
caacagatag ggagaagtca gctgataaca gaaatagttt                         100

SEQ ID NO: 79               moltype = DNA  length = 100
FEATURE                     Location/Qualifiers
source                      1..100
                            mol_type = genomic DNA
                            organism = Homo sapiens
SEQUENCE: 79
taaaactaac ttcactgtta accaagcagt tcaacatgaa agactgaatc tcttatgttt    60
```

-continued

```
aatattttct tctcttttaa tcttcataac taatttttt                                100

SEQ ID NO: 80          moltype = DNA   length = 100
FEATURE                Location/Qualifiers
source                 1..100
                       mol_type = genomic DNA
                       organism = Homo sapiens
SEQUENCE: 80
cagataattg tataaaataa ccatggtagc aaaataatgt gatcactgga aaataagcag          60
ggaaaaacat gctatgaaga tactcctatc tgggtgaatt                              100

SEQ ID NO: 81          moltype = DNA   length = 100
FEATURE                Location/Qualifiers
source                 1..100
                       mol_type = genomic DNA
                       organism = Homo sapiens
SEQUENCE: 81
cttgatagct ttacattttt catctggcat ttaaacatta aacagttaat gtatttgaca          60
tgaaaattat ttcaagttat cttattagtt ttaatagagt                              100

SEQ ID NO: 82          moltype = DNA   length = 100
FEATURE                Location/Qualifiers
source                 1..100
                       mol_type = genomic DNA
                       organism = Homo sapiens
SEQUENCE: 82
ttaaaaagtg tttaaaagag ttttcaaaag gctctaaaat cattttgaaa tagtttaaaa          60
cagttttgaa tcgttgtaag ttagttttaa tagagcttta                              100

SEQ ID NO: 83          moltype = DNA   length = 100
FEATURE                Location/Qualifiers
source                 1..100
                       mol_type = genomic DNA
                       organism = Homo sapiens
SEQUENCE: 83
aaaaggccct aaaatagtcc tatcaagttg ttgcagacca aaataatctc cttaaatatc          60
acttttgaga tcagctgggg taaacgacag caacacaatg                              100

SEQ ID NO: 84          moltype = DNA   length = 100
FEATURE                Location/Qualifiers
source                 1..100
                       mol_type = genomic DNA
                       organism = Homo sapiens
SEQUENCE: 84
acaaatcatt aaactatttt agagattatg aaattaaaat actcagatta aaattttcct          60
atcacagaat taaggtactg gaaaatatgt ttaagttttt                              100

SEQ ID NO: 85          moltype = DNA   length = 100
FEATURE                Location/Qualifiers
source                 1..100
                       mol_type = genomic DNA
                       organism = Homo sapiens
SEQUENCE: 85
attaatcaca ttgctatagg tttagatatt ttgtacaact gaaataaaat cacacactgg          60
cagctacatt tttgaaagtt aaaaacatgg tcacgaatat                              100

SEQ ID NO: 86          moltype = DNA   length = 100
FEATURE                Location/Qualifiers
source                 1..100
                       mol_type = genomic DNA
                       organism = Homo sapiens
SEQUENCE: 86
atcttatttt aaaatcagtt aatataccct aatggtattt aatgccaaat tcaaagtgaa          60
ttgatcaagc cctcagtggc caggtcatgg gtgtgatttt                              100

SEQ ID NO: 87          moltype = DNA   length = 100
FEATURE                Location/Qualifiers
source                 1..100
                       mol_type = genomic DNA
                       organism = Homo sapiens
SEQUENCE: 87
tactctgaaa gaattacata tttctttctt tttggttgag cttttgttat ttaaatacat          60
ttgatgagag gatattgaaa taattaaata gcactgaaaa                              100

SEQ ID NO: 88          moltype = DNA   length = 100
FEATURE                Location/Qualifiers
source                 1..100
                       mol_type = genomic DNA
                       organism = Homo sapiens
```

```
SEQUENCE: 88
aaaaaaagct ttaaattatt tacaatcccc taatggaaat tttcactaat gagatatcat       60
aatgaatgtg aatttattt ctgaaatctc taataaatca                              100

SEQ ID NO: 89           moltype = DNA   length = 100
FEATURE                 Location/Qualifiers
source                  1..100
                        mol_type = genomic DNA
                        organism = Homo sapiens
SEQUENCE: 89
aagctttaaa ttatttacaa tccctaatg gaaattttca ctaatgagat atcataatga        60
atgtgaattt tatttctgaa atctctaata aatcagtctt                             100

SEQ ID NO: 90           moltype = DNA   length = 100
FEATURE                 Location/Qualifiers
source                  1..100
                        mol_type = genomic DNA
                        organism = Homo sapiens
SEQUENCE: 90
ctccctggtt ttcccagctc agcgcccatt acgtttctgt tctctttccc ttagtggcat       60
tatttgtatc actgtgcatc aggaaagctg gctacggcag                             100

SEQ ID NO: 91           moltype = DNA   length = 100
FEATURE                 Location/Qualifiers
source                  1..100
                        mol_type = genomic DNA
                        organism = Homo sapiens
SEQUENCE: 91
catcaatcgg gcagacacag ggtggccacg gccactagcg gcaaggcggc tgccccaaga       60
gcgcggtggg atggccacca aagccactca atcgagaaag                             100

SEQ ID NO: 92           moltype = DNA   length = 100
FEATURE                 Location/Qualifiers
source                  1..100
                        mol_type = genomic DNA
                        organism = Homo sapiens
SEQUENCE: 92
accgcggctc tgtctacagc tcgcggtgcc acggccttct tggcagaata aaatgtaga        60
caagtaataa cagaggataa tgaaagaaca tactctttaa                             100

SEQ ID NO: 93           moltype = DNA   length = 100
FEATURE                 Location/Qualifiers
source                  1..100
                        mol_type = genomic DNA
                        organism = Homo sapiens
SEQUENCE: 93
aatatttcct attttttca cagacccacg gtcattaaaa aatgcaatta tttacttttt       60
ttcatttaaa cacatttctt tgagattgag cttttgggaa                             100

SEQ ID NO: 94           moltype = DNA   length = 100
FEATURE                 Location/Qualifiers
source                  1..100
                        mol_type = genomic DNA
                        organism = Homo sapiens
SEQUENCE: 94
taaccacctt tccaccatta caataagaga taatttcacg tttagtctaa tgtacaaatt      60
ggattttta aaaatgagct ctatctgtga agcccttatt                             100

SEQ ID NO: 95           moltype = DNA   length = 100
FEATURE                 Location/Qualifiers
source                  1..100
                        mol_type = genomic DNA
                        organism = Homo sapiens
SEQUENCE: 95
aaaatgagct ctatctgtga agcccttatt cctatagaat gtgtctttt gagtttatta       60
cttattacag actctaaaaa caacattgct gctgattttc                             100

SEQ ID NO: 96           moltype = DNA   length = 100
FEATURE                 Location/Qualifiers
source                  1..100
                        mol_type = genomic DNA
                        organism = Homo sapiens
SEQUENCE: 96
aagtaagctg cctcttctac atagcaaata ggtacacttc acttttccct gattttcttt      60
agggcgtgct attgattttt attgttgtct gacaaaataa                             100

SEQ ID NO: 97           moltype = DNA   length = 100
FEATURE                 Location/Qualifiers
source                  1..100
```

```
                            mol_type = genomic DNA
                            organism = Homo sapiens
SEQUENCE: 97
tttatcaaac aaaagggaga aagactaaaa aatgtatttt tccacttttc tgtatcatgc    60
ataatcagca acaaccaata caatatttgg caagagtgaa                         100

SEQ ID NO: 98          moltype = DNA  length = 100
FEATURE                Location/Qualifiers
source                 1..100
                       mol_type = genomic DNA
                       organism = Homo sapiens
SEQUENCE: 98
caaaaataaa tttacttttg ctccttagaa atacaagggt tccttttag ttacactttt    60
ttttttact ttgtgtcatt cagtttagag caatttaatc                          100

SEQ ID NO: 99          moltype = DNA  length = 100
FEATURE                Location/Qualifiers
source                 1..100
                       mol_type = genomic DNA
                       organism = Homo sapiens
SEQUENCE: 99
tttttttctc caaatccatt tttgaagctg agtttaactt ttgcaaccca tggcaaatct    60
taaatgccct catttaccaa tctttaccaa actcctattt                         100

SEQ ID NO: 100         moltype = DNA  length = 100
FEATURE                Location/Qualifiers
source                 1..100
                       mol_type = genomic DNA
                       organism = Homo sapiens
SEQUENCE: 100
aagcctctaa aagtcaatac tggccatcag acccaaattt cagaagacaa tagtgaaaaa    60
ttacttacgt ttaatctcca gtcgtgtccc ttggccgaag                         100

SEQ ID NO: 101         moltype = DNA  length = 100
FEATURE                Location/Qualifiers
source                 1..100
                       mol_type = genomic DNA
                       organism = Homo sapiens
SEQUENCE: 101
gtgatccaca gtgttaactt aattactttc cccttaacaa aaatctcttt tcgctgttaa    60
tatcactaac ctgaccgatg cagagaaaat cttgcaattg                         100

SEQ ID NO: 102         moltype = DNA  length = 100
FEATURE                Location/Qualifiers
source                 1..100
                       mol_type = genomic DNA
                       organism = Homo sapiens
SEQUENCE: 102
agatgcctca cttaactggc tagcgcttgg ctgttcctta agatgaacta attttctatc    60
ccttactcat ctgactttt gaaagaatct ggtactcttt                          100

SEQ ID NO: 103         moltype = DNA  length = 100
FEATURE                Location/Qualifiers
source                 1..100
                       mol_type = genomic DNA
                       organism = Homo sapiens
SEQUENCE: 103
ggaattgacc tgagctaata tctcaaacac aaaaacgctc caaatttaaa accttataag    60
aaaaagcatt aggaaagtgc acttacgttt gatctccacc                         100

SEQ ID NO: 104         moltype = DNA  length = 100
FEATURE                Location/Qualifiers
source                 1..100
                       mol_type = genomic DNA
                       organism = Homo sapiens
SEQUENCE: 104
ttggtccctc cgccgaaagt gagccacagt gagggatctc acccttccc ctcaacaaaa     60
acctctcttg aagccaatca tatgagatag gctgcttgtt                         100

SEQ ID NO: 105         moltype = DNA  length = 100
FEATURE                Location/Qualifiers
source                 1..100
                       mol_type = genomic DNA
                       organism = Homo sapiens
SEQUENCE: 105
cagagaaaaa tctagctatt tcttccccat ttccccatg aatcctattc tcctctcaaa     60
cccaatgatt cgtctatttg ctcagctttt taagttcatt                         100

SEQ ID NO: 106         moltype = DNA  length = 100
```

```
FEATURE                 Location/Qualifiers
source                  1..100
                        mol_type = genomic DNA
                        organism = Homo sapiens
SEQUENCE: 106
ttctggtgtc ctgctattta cttctgggtc accaggttta ttcaaccaaa atatcacaaa    60
acttgcacaa atgatacaat ggcactaaaa tctcacgaat                         100

SEQ ID NO: 107          moltype = DNA  length = 100
FEATURE                 Location/Qualifiers
source                  1..100
                        mol_type = genomic DNA
                        organism = Homo sapiens
SEQUENCE: 107
aattgagaca gatgtactta cgtttgatat ccactttggt cccagggccg aaagtgaatc    60
acagtgattc gtcttaactt ttcccttttac aaaaacctcc                        100

SEQ ID NO: 108          moltype = DNA  length = 100
FEATURE                 Location/Qualifiers
source                  1..100
                        mol_type = genomic DNA
                        organism = Homo sapiens
SEQUENCE: 108
ctgaaagctc agcaagcctc tttcccccaa tgaagttatt ttgatttaga aatcttaaaa    60
attagccaca agctagcgtc ctgtggaaca atttcccctc                         100

SEQ ID NO: 109          moltype = DNA  length = 100
FEATURE                 Location/Qualifiers
source                  1..100
                        mol_type = genomic DNA
                        organism = Homo sapiens
SEQUENCE: 109
ctctgtacct aacctgggaa tgaagtttgt tagatccctg gcatccgact aatgaaaatc    60
cacacaaagg aacacaaagt aaactaatta gcaacagtga                         100

SEQ ID NO: 110          moltype = DNA  length = 100
FEATURE                 Location/Qualifiers
source                  1..100
                        mol_type = genomic DNA
                        organism = Homo sapiens
SEQUENCE: 110
agaatcagtg gaaaaagta cttacgtttg atctccagct tggtcccctg gccaaaagtg     60
tacacacaat ggttcctctt aacttccctc ctatacaaaa                         100

SEQ ID NO: 111          moltype = DNA  length = 100
FEATURE                 Location/Qualifiers
source                  1..100
                        mol_type = genomic DNA
                        organism = Homo sapiens
SEQUENCE: 111
actcccttc tgacaattga ccaaggctct gtccagaaca tgttatgttc cccaggacat     60
ttctgaagct attacttaga caagttattc tcacccaatg                         100

SEQ ID NO: 112          moltype = DNA  length = 100
FEATURE                 Location/Qualifiers
source                  1..100
                        mol_type = genomic DNA
                        organism = Homo sapiens
SEQUENCE: 112
actgaatctt gcttgctctt caaagaaaat gtgcaatcaa ttctcgagtt tgactacaga    60
cttatcttta tcttttccct gaaggatatc agaggctgat                         100

SEQ ID NO: 113          moltype = DNA  length = 100
FEATURE                 Location/Qualifiers
source                  1..100
                        mol_type = genomic DNA
                        organism = Homo sapiens
SEQUENCE: 113
tgcagagtca ccttatagat cacttcatag acacagggaa cagaagacac agacaactga    60
ggaagcaaag tttaaattct actcacgttt gatttccacc                         100

SEQ ID NO: 114          moltype = DNA  length = 100
FEATURE                 Location/Qualifiers
source                  1..100
                        mol_type = genomic DNA
                        organism = Homo sapiens
SEQUENCE: 114
ttggtccctt ggccgaacgt ccaccacagt gagagctctc cattgtcttg ctgaacaaaa    60
acccttctca ccaaagggga acagagtcct gggtcagctg                         100
```

```
SEQ ID NO: 115          moltype = DNA   length = 100
FEATURE                 Location/Qualifiers
source                  1..100
                        mol_type = genomic DNA
                        organism = Homo sapiens
SEQUENCE: 115
atcaacttaa ggctcataac tttgaaatgc attttgaaat gtagctccag atggtatacg    60
aaaccaaagt gaagactaat agagtagaaa agtagactt                          100

SEQ ID NO: 116          moltype = DNA   length = 100
FEATURE                 Location/Qualifiers
source                  1..100
                        mol_type = genomic DNA
                        organism = Homo sapiens
SEQUENCE: 116
acttggttgg tttgtctgtt ttcacagcac aggaagagct cagctcttac tgagctggac    60
caggcgcatg ccatctttgg agctgccatg gagtcccagt                         100

SEQ ID NO: 117          moltype = DNA   length = 100
FEATURE                 Location/Qualifiers
source                  1..100
                        mol_type = genomic DNA
                        organism = Homo sapiens
SEQUENCE: 117
gttccatagt gtttccatag taatctcatc aacaacactg aagacctttt cagtattttc    60
ttttgagtcc agctccattt ttgcagcctt gtatctctct                         100

SEQ ID NO: 118          moltype = DNA   length = 100
FEATURE                 Location/Qualifiers
source                  1..100
                        mol_type = genomic DNA
                        organism = Homo sapiens
SEQUENCE: 118
ccgcgcccag ccgagtgcct gttatttttt acctgctttc agattctctt ctacccttct    60
aaattataag ctgtttgatg ttttatttgc cctgtatttg                         100

SEQ ID NO: 119          moltype = DNA   length = 100
FEATURE                 Location/Qualifiers
source                  1..100
                        mol_type = genomic DNA
                        organism = Homo sapiens
SEQUENCE: 119
ggaggctccg tccagtatct ttacttagca aatgcttaac aaacattttc agaataaata    60
aaaaaaaata cctaattgaa agtcaataat agatcagaga                         100

SEQ ID NO: 120          moltype = DNA   length = 100
FEATURE                 Location/Qualifiers
source                  1..100
                        mol_type = genomic DNA
                        organism = Homo sapiens
SEQUENCE: 120
tgctatcata gaccaaagac taatactgac tgccacaaca gtaaccttta caacagaaat    60
cataactaca attctaaaga ttaggggtag gtttatttga                         100

SEQ ID NO: 121          moltype = DNA   length = 100
FEATURE                 Location/Qualifiers
source                  1..100
                        mol_type = genomic DNA
                        organism = Homo sapiens
SEQUENCE: 121
ttctgtcact ggcagctttg ctagttgcct tgaatagcag aattagcatt tggtctcacc    60
agaagatgag gaaggagagg gatcaagtta gaggtggaga                         100

SEQ ID NO: 122          moltype = DNA   length = 100
FEATURE                 Location/Qualifiers
source                  1..100
                        mol_type = genomic DNA
                        organism = Homo sapiens
SEQUENCE: 122
gttaacattg gcaagtgaaa tttaatgtgc aaaatagctg accaagggca tagtcctttt    60
ttaaggggga cacaaagtga ttttctctgc agacatacac                         100

SEQ ID NO: 123          moltype = DNA   length = 100
FEATURE                 Location/Qualifiers
source                  1..100
                        mol_type = genomic DNA
                        organism = Homo sapiens
SEQUENCE: 123
```

```
gcaataccaa tcataaaggg tgacatttat tgagcactta ctaagtgcca gacattgtac    60
atggatcatc acatttaatt attcccaaga ctctatgaac                         100

SEQ ID NO: 124           moltype = DNA  length = 100
FEATURE                  Location/Qualifiers
source                   1..100
                         mol_type = genomic DNA
                         organism = Homo sapiens
SEQUENCE: 124
tgagcactta ctaagtgcca gacattgtac atggatcatc acatttaatt attcccaaga    60
ctctatgaac taggaactaa tattatcccc tactttgtag                         100

SEQ ID NO: 125           moltype = DNA  length = 100
FEATURE                  Location/Qualifiers
source                   1..100
                         mol_type = genomic DNA
                         organism = Homo sapiens
SEQUENCE: 125
gtgcaaaaac ttgagggcag agaggtcaag gaactggctt atggcagtaa gtggcagagc    60
tgtgacctaa actcagatcc catgttttta actgaactat                         100

SEQ ID NO: 126           moltype = DNA  length = 100
FEATURE                  Location/Qualifiers
source                   1..100
                         mol_type = genomic DNA
                         organism = Homo sapiens
SEQUENCE: 126
atgcagatta tactccagga gtaaagtcac tcaacggaag caacaagcgt gacagggaat    60
gctgggatgg gggaaggtaa aaggaactcc ttagactggg                         100

SEQ ID NO: 127           moltype = DNA  length = 100
FEATURE                  Location/Qualifiers
source                   1..100
                         mol_type = genomic DNA
                         organism = Homo sapiens
SEQUENCE: 127
ataagtgtgt acagacgtat gtataagact acacatggaa atattgttta aagagtgaaa    60
aataactaaa atcctcatta ataggagttt ggttaaactg                         100

SEQ ID NO: 128           moltype = DNA  length = 100
FEATURE                  Location/Qualifiers
source                   1..100
                         mol_type = genomic DNA
                         organism = Homo sapiens
SEQUENCE: 128
tgctagagct ttacaatgta gcacaaagca gacattaagg ggaagacgta gacttctata    60
tagttacgtg gaaggtgttt gtgaaaatgc aggtcactga                         100

SEQ ID NO: 129           moltype = DNA  length = 100
FEATURE                  Location/Qualifiers
source                   1..100
                         mol_type = genomic DNA
                         organism = Homo sapiens
SEQUENCE: 129
agagtatgtg tggtgagata tcatgatccc atctacattg aatatatatg tatataaata    60
cgggctgaat tttaaaagac ataaattgtg cttggtagtt                         100

SEQ ID NO: 130           moltype = DNA  length = 100
FEATURE                  Location/Qualifiers
source                   1..100
                         mol_type = genomic DNA
                         organism = Homo sapiens
SEQUENCE: 130
aaatacgggc tgaattttaa aagacataaa ttgtgcttgg tagttatctc ctgggattgc    60
agaggaggaa caatgacact ttatgccatc tcctcctact                         100

SEQ ID NO: 131           moltype = DNA  length = 100
FEATURE                  Location/Qualifiers
source                   1..100
                         mol_type = genomic DNA
                         organism = Homo sapiens
SEQUENCE: 131
cttctgtatg gtgatgtgaa tatattcatt ttatagtttt tagaaataat aaaactgtac    60
taattttgaa aaacagtaaa ctctgacatt gcctattagc                         100

SEQ ID NO: 132           moltype = DNA  length = 100
FEATURE                  Location/Qualifiers
source                   1..100
                         mol_type = genomic DNA
```

```
                        organism = Homo sapiens
SEQUENCE: 132
attctcgata ttcctgtgca atgcataaac ataactttt aaaagatatg tacacacatg    60
tgtgagtttt ctttgtcaaa tactttcta taatctttaa                         100

SEQ ID NO: 133          moltype = DNA   length = 100
FEATURE                 Location/Qualifiers
source                  1..100
                        mol_type = genomic DNA
                        organism = Homo sapiens
SEQUENCE: 133
atcaagcatg ccaaaaaggt aaaagctttc ctgtttcagt gtaggagata gtcgtctgca    60
aaggaaagag atgtagggga tagaaacagg aatgaaaaag                         100

SEQ ID NO: 134          moltype = DNA   length = 100
FEATURE                 Location/Qualifiers
source                  1..100
                        mol_type = genomic DNA
                        organism = Homo sapiens
SEQUENCE: 134
atgactgagc tgttcgaggg acttatgttc ctaagtgagc taattggaaa tctaatatga    60
acagtgcaac cgataacta ttgtaaagca gtatttgtaa                          100

SEQ ID NO: 135          moltype = DNA   length = 100
FEATURE                 Location/Qualifiers
source                  1..100
                        mol_type = genomic DNA
                        organism = Homo sapiens
SEQUENCE: 135
acaataaaag atgattatca taagtaccat tgttgcaaaa actatttat tgatcacatg     60
cagtggtgat ctgtaggaat gattgttgtg atgtttgctg                         100

SEQ ID NO: 136          moltype = DNA   length = 100
FEATURE                 Location/Qualifiers
source                  1..100
                        mol_type = genomic DNA
                        organism = Homo sapiens
SEQUENCE: 136
taacataaaa tgaaacatgg gaagtggctg agatctttag gatgtgtgtg gttcattttt    60
tgaaagcaaa tgttgtctca gaagcatctg tgagactctg                         100

SEQ ID NO: 137          moltype = DNA   length = 100
FEATURE                 Location/Qualifiers
source                  1..100
                        mol_type = genomic DNA
                        organism = Homo sapiens
SEQUENCE: 137
ccaggatcca ccgttctaca aaatatctgt gatggacatt gataagattg atctgttgag    60
gaaaggcaag gtgtcagtaa gatagtctga gagcttcttg                         100

SEQ ID NO: 138          moltype = DNA   length = 100
FEATURE                 Location/Qualifiers
source                  1..100
                        mol_type = genomic DNA
                        organism = Homo sapiens
SEQUENCE: 138
gatttcatgt aaaagagtgc tggaaataga atttcttggg gaacattcca actaactcat    60
cactgaaggt gctttacatt gaaccctcag caaagttaga                         100

SEQ ID NO: 139          moltype = DNA   length = 100
FEATURE                 Location/Qualifiers
source                  1..100
                        mol_type = genomic DNA
                        organism = Homo sapiens
SEQUENCE: 139
ttatcagaaa aaaatataaa actgctgtgg aggggacagg aaggaaagtc agggagggag    60
ggggcaagg agagaaagag cgagagagag gagagaaaga                          100

SEQ ID NO: 140          moltype = DNA   length = 100
FEATURE                 Location/Qualifiers
source                  1..100
                        mol_type = genomic DNA
                        organism = Homo sapiens
SEQUENCE: 140
agagaggaga gagagagcac aagtacacac ttcaatgcac atctataaat catcctgaaa    60
actactgata aattatttta gcaatgttcc tcagatgtaa                         100

SEQ ID NO: 141          moltype = DNA   length = 100
FEATURE                 Location/Qualifiers
```

```
source                  1..100
                        mol_type = genomic DNA
                        organism = Homo sapiens
SEQUENCE: 141
catttcaaga aatatcattt ttgctttta tttggcataa tttactagcc aatttaggaa    60
gttccctca catcagtaac atacagtaca tcacccagta                         100

SEQ ID NO: 142          moltype = DNA  length = 100
FEATURE                 Location/Qualifiers
source                  1..100
                        mol_type = genomic DNA
                        organism = Homo sapiens
SEQUENCE: 142
tgtcagagga cacaatggca taagtttgcc ttttgcaagg tttgagggat ggccatttcc    60
ctacctgact caggaaagtc tgtagctgat atccatcttc                        100

SEQ ID NO: 143          moltype = DNA  length = 100
FEATURE                 Location/Qualifiers
source                  1..100
                        mol_type = genomic DNA
                        organism = Homo sapiens
SEQUENCE: 143
aagtttgtgg ttctttctct ctatatatat atttgagctc agcagtcatg ctggagtcca    60
gagtaggtga ttctttctgc tttagcttga ctcctcctta                        100

SEQ ID NO: 144          moltype = DNA  length = 100
FEATURE                 Location/Qualifiers
source                  1..100
                        mol_type = genomic DNA
                        organism = Homo sapiens
SEQUENCE: 144
tatatatttg agctcagcag tcatgctgga gtccagagta ggtgattctt tctgctttag    60
cttgactcct ccttaagatt gtaactctct cagttttaca                        100

SEQ ID NO: 145          moltype = DNA  length = 100
FEATURE                 Location/Qualifiers
source                  1..100
                        mol_type = genomic DNA
                        organism = Homo sapiens
SEQUENCE: 145
ttttttgtca gacgtaagct gacattccac aaggagagga ggaaattctg tggttcacat    60
ccagtggtgc ttggaacctg attggttgtc attcttccag                        100

SEQ ID NO: 146          moltype = DNA  length = 100
FEATURE                 Location/Qualifiers
source                  1..100
                        mol_type = genomic DNA
                        organism = Homo sapiens
SEQUENCE: 146
ctagtttgtc acgagtggat atctgtcctg gattcccaag gatcaaggct gccccattag    60
ccaggaagta gggagataga ggaggtcact tgagaaagag                        100

SEQ ID NO: 147          moltype = DNA  length = 100
FEATURE                 Location/Qualifiers
source                  1..100
                        mol_type = genomic DNA
                        organism = Homo sapiens
SEQUENCE: 147
ctgcttcttt gccgcctcca ggttgtgtct gtttcctctc atatctgaag acagatgtgc    60
tggcagaagc aaagtccttt gtccggccac gtgcaaatgc                        100

SEQ ID NO: 148          moltype = DNA  length = 100
FEATURE                 Location/Qualifiers
source                  1..100
                        mol_type = genomic DNA
                        organism = Homo sapiens
SEQUENCE: 148
atgggacata aatatgaaca gagattcttg tcccactcta gaaaatgtag atgttcatct    60
tgtttccaag gggacagtaa ggctgcaggt gttttttgac                        100

SEQ ID NO: 149          moltype = DNA  length = 100
FEATURE                 Location/Qualifiers
source                  1..100
                        mol_type = genomic DNA
                        organism = Homo sapiens
SEQUENCE: 149
cttttgtact cactggttgt ttttgcatag gcccctccag gccacgacca gctgtttgga    60
ttttataaac gggccgtttg cattgtgaac tgagctacaa                        100
```

```
SEQ ID NO: 150         moltype = DNA    length = 100
FEATURE                Location/Qualifiers
source                 1..100
                       mol_type = genomic DNA
                       organism = Homo sapiens
SEQUENCE: 150
caggcaggca ggggcagcaa gatggtgttg cagacccagg tcttcatttc tctgttgctc    60
tggatctctg gtgaggaatt aaaaagtgcc acagtctttt                          100

SEQ ID NO: 151         moltype = DNA    length = 100
FEATURE                Location/Qualifiers
source                 1..100
                       mol_type = genomic DNA
                       organism = Homo sapiens
SEQUENCE: 151
cagagtaata tctgtgtaga aataaaaaaa attaagatat agttggaaat aatgactatt    60
tccaatatgg atccaattat ctgctgactt ataatactac                          100

SEQ ID NO: 152         moltype = DNA    length = 100
FEATURE                Location/Qualifiers
source                 1..100
                       mol_type = genomic DNA
                       organism = Homo sapiens
SEQUENCE: 152
attaagatat agttggaaat aatgactatt tccaatatgg atccaattat ctgctgactt    60
ataatactac tagaaagcaa atttaaatga catatttcaa                          100

SEQ ID NO: 153         moltype = DNA    length = 100
FEATURE                Location/Qualifiers
source                 1..100
                       mol_type = genomic DNA
                       organism = Homo sapiens
SEQUENCE: 153
ttatatctga gacagcgtgt ataagtttat gtataatcat tgtccattac tgactacagg    60
tgcctacggg gacatcgtga tgacccagtc tccagactcc                          100

SEQ ID NO: 154         moltype = DNA    length = 100
FEATURE                Location/Qualifiers
source                 1..100
                       mol_type = genomic DNA
                       organism = Homo sapiens
SEQUENCE: 154
ctggctgtgt ctctgggcga gagggccacc atcaactgca agtccagcca gagtgtttta    60
tacagctcca acaataagaa ctacttagct tggtaccagc                          100

SEQ ID NO: 155         moltype = DNA    length = 100
FEATURE                Location/Qualifiers
source                 1..100
                       mol_type = genomic DNA
                       organism = Homo sapiens
SEQUENCE: 155
agaaaccagg acagcctcct aagctgctca tttactgggc atctacccgg gaatccgggg    60
tccctgaccg attcagtggc agcgggtctg ggacagattt                          100

SEQ ID NO: 156         moltype = DNA    length = 100
FEATURE                Location/Qualifiers
source                 1..100
                       mol_type = genomic DNA
                       organism = Homo sapiens
SEQUENCE: 156
cactctcacc atcagcagcc tgcaggctga agatgtggca gtttattact gtcagcaata    60
ttatagtact cctcccacag tgcttcagcc tcgaacacaa                          100

SEQ ID NO: 157         moltype = DNA    length = 100
FEATURE                Location/Qualifiers
source                 1..100
                       mol_type = genomic DNA
                       organism = Homo sapiens
SEQUENCE: 157
acctcctccc catacgctgg gccagtaggt ctttgctgca gcagctgctt cctctgcaca    60
cagcccccaa catgcatgct tcctctgtgt gttgggagg                           100

SEQ ID NO: 158         moltype = DNA    length = 100
FEATURE                Location/Qualifiers
source                 1..100
                       mol_type = genomic DNA
                       organism = Homo sapiens
SEQUENCE: 158
aatacatgaa aacaactacc gaaatgttat gaaattatag tttagtagaa ctaacaagtg    60
```

```
cattaatgca aaagaaaagt agggctcagt aatcagggaa                          100

SEQ ID NO: 159          moltype = DNA   length = 100
FEATURE                 Location/Qualifiers
source                  1..100
                        mol_type = genomic DNA
                        organism = Homo sapiens
SEQUENCE: 159
ccaagtgtgc attgtaaaag tgcagcctct ctaacactgg gtttcatcac aagtaacaga   60
acaggatgcc tgatgcaggg aaaaaagaaa ggcaattgtt                         100

SEQ ID NO: 160          moltype = DNA   length = 100
FEATURE                 Location/Qualifiers
source                  1..100
                        mol_type = genomic DNA
                        organism = Homo sapiens
SEQUENCE: 160
gatctctggt aagagaaaca cttcctctcc tctgtgccac caagtcccct gcatatccac   60
aaaaataata tattttcata aggaattgat tttcctcatt                         100

SEQ ID NO: 161          moltype = DNA   length = 100
FEATURE                 Location/Qualifiers
source                  1..100
                        mol_type = genomic DNA
                        organism = Homo sapiens
SEQUENCE: 161
ctctgcaaat atgatgcatt tgatttatgt ttttactttt gctccataat cagataccag   60
ggcagaaacg acactcacgc agtctccagc attcatgtca                         100

SEQ ID NO: 162          moltype = DNA   length = 100
FEATURE                 Location/Qualifiers
source                  1..100
                        mol_type = genomic DNA
                        organism = Homo sapiens
SEQUENCE: 162
gcgactccag gagacaaagt caacatctcc tgcaaagcca gccaagacat tgatgatgat   60
atgaactggt accaacagaa accaggagaa gctgctattt                         100

SEQ ID NO: 163          moltype = DNA   length = 100
FEATURE                 Location/Qualifiers
source                  1..100
                        mol_type = genomic DNA
                        organism = Homo sapiens
SEQUENCE: 163
tcattattca agaagctact actctcgttc ctggaatccc acctcgattc agtggcagcg   60
ggtatggaac agattttacc ctcacaatta ataacataga                         100

SEQ ID NO: 164          moltype = DNA   length = 100
FEATURE                 Location/Qualifiers
source                  1..100
                        mol_type = genomic DNA
                        organism = Homo sapiens
SEQUENCE: 164
atctgaggat gctgcatatt acttctgtct caacatgat aatttccctc tcacagtgat    60
acccctgtt acaaaaacct ccaagttctc tcagtgggat                          100

SEQ ID NO: 165          moltype = DNA   length = 100
FEATURE                 Location/Qualifiers
source                  1..100
                        mol_type = genomic DNA
                        organism = Homo sapiens
SEQUENCE: 165
gccctctgtc ctggagacac ggccaaggag gctggagact gggtcagcac aatgtcccca   60
ttgcagcctg aaatgataaa gacagataaa ttatatcaga                         100

SEQ ID NO: 166          moltype = DNA   length = 100
FEATURE                 Location/Qualifiers
source                  1..100
                        mol_type = genomic DNA
                        organism = Homo sapiens
SEQUENCE: 166
tatactgaga ctgtccccat gtaggccatg cattggtgac acttgtaacc acagtcatat   60
gcaacatctt gagtaaccag aaaacaaaag ataactgggg                         100

SEQ ID NO: 167          moltype = DNA   length = 100
FEATURE                 Location/Qualifiers
source                  1..100
                        mol_type = genomic DNA
                        organism = Homo sapiens
```

```
SEQUENCE: 167
aacttacaac ctacaatgag tgccctaaat ccaacaacca agaatccaga gacacaaaaa      60
acaatgatgg ccacatgagt ttgcccgatg tttccctata                           100

SEQ ID NO: 168          moltype = DNA   length = 100
FEATURE                 Location/Qualifiers
source                  1..100
                        mol_type = genomic DNA
                        organism = Homo sapiens
SEQUENCE: 168
taccaacacc atcagagtgt ggctgcatct gaggaccact ctcagctgat agaggcatca      60
ggaggagcag ctggggcagc cctgcctcac acatctgctt                           100

SEQ ID NO: 169          moltype = DNA   length = 100
FEATURE                 Location/Qualifiers
source                  1..100
                        mol_type = genomic DNA
                        organism = Homo sapiens
SEQUENCE: 169
ggggtttatg ttcgggtgtg taacactgtg ggagaataac tattatactg ttggcagtaa      60
taagttgcaa aatcatcagg ctgcaggctg ctgatggtga                           100

SEQ ID NO: 170          moltype = DNA   length = 100
FEATURE                 Location/Qualifiers
source                  1..100
                        mol_type = genomic DNA
                        organism = Homo sapiens
SEQUENCE: 170
gccgctgaac cttgatggga ccccactttc taaactagac gccttataga tcaggagctt      60
aggggctttc cctggtttct gctgatacca ggccaaccag                           100

SEQ ID NO: 171          moltype = DNA   length = 100
FEATURE                 Location/Qualifiers
source                  1..100
                        mol_type = genomic DNA
                        organism = Homo sapiens
SEQUENCE: 171
ctactaatac tctgactggc ccggcaagtg atggtgactc tgtctcctac agatgcagac      60
agggtggaag gagactgggt catctggatg tcacatttgg                           100

SEQ ID NO: 172          moltype = DNA   length = 100
FEATURE                 Location/Qualifiers
source                  1..100
                        mol_type = genomic DNA
                        organism = Homo sapiens
SEQUENCE: 172
ggatgtcaca tttggcacct gagattggaa atagaaacac aaatattcat actattgatc      60
atattatagg aagactccc tgaataacca ggcagtactg                            100

SEQ ID NO: 173          moltype = DNA   length = 100
FEATURE                 Location/Qualifiers
source                  1..100
                        mol_type = genomic DNA
                        organism = Homo sapiens
SEQUENCE: 173
agcacactgg gctgagtaaa ttcctagtgt tctccttcct tacctgggag ccagagcagc      60
aggagcccca ggagctgagc ggggaccctc atgtccatgc                           100

SEQ ID NO: 174          moltype = DNA   length = 100
FEATURE                 Location/Qualifiers
source                  1..100
                        mol_type = genomic DNA
                        organism = Homo sapiens
SEQUENCE: 174
gggactattt tattatgaga aacaattttt aggtattttt ttgagaattt taaatattcc      60
tcaggagccg atagagtaat gtatttcatt ggtgtatcag                           100

SEQ ID NO: 175          moltype = DNA   length = 100
FEATURE                 Location/Qualifiers
source                  1..100
                        mol_type = genomic DNA
                        organism = Homo sapiens
SEQUENCE: 175
gattatttag gagaatattc ttgttttgtag gaaacacata gtaaaatgtt agatggtagg      60
attctcaagt cttcaaaaga ctctcataag attccgggta                           100

SEQ ID NO: 176          moltype = DNA   length = 100
FEATURE                 Location/Qualifiers
source                  1..100
```

```
                        mol_type = genomic DNA
                        organism = Homo sapiens
SEQUENCE: 176
tattcttgtt tgtaggaaac acatagtaaa atgttagatg gtaggattct caagtcttca    60
aaagactctc ataagattcc gggtagggaa gggggtaatt                         100

SEQ ID NO: 177          moltype = DNA  length = 100
FEATURE                 Location/Qualifiers
source                  1..100
                        mol_type = genomic DNA
                        organism = Homo sapiens
SEQUENCE: 177
tgtaagtatt aggtaatggt gttatgcctt tgttcttact agtattagat caagcaattt    60
attacagata tacaaagatg ataccgtgtt gtctccatgc                         100

SEQ ID NO: 178          moltype = DNA  length = 100
FEATURE                 Location/Qualifiers
source                  1..100
                        mol_type = genomic DNA
                        organism = Homo sapiens
SEQUENCE: 178
atgcagcact cacagatcca ccactatcaa gaactgcagg tctctttaat acccagagac    60
taaatgaggt gcaccttatt cttgttttgg gtaccttcat                         100

SEQ ID NO: 179          moltype = DNA  length = 100
FEATURE                 Location/Qualifiers
source                  1..100
                        mol_type = genomic DNA
                        organism = Homo sapiens
SEQUENCE: 179
ttgggtgtgt aacactgtgg gagggtaact ataatactgt tgacagtaat aagttgcaaa    60
atcttcagac tgcaggcagc tgatggtgag agtgaaatct                         100

SEQ ID NO: 180          moltype = DNA  length = 100
FEATURE                 Location/Qualifiers
source                  1..100
                        mol_type = genomic DNA
                        organism = Homo sapiens
SEQUENCE: 180
ctgactcgcc cgacaagtga tggtgactct gtcctgta gatgcagaga atgaggatgg      60
agactgggtc atccggatgg cacatctggc acctgagatt                         100

SEQ ID NO: 181          moltype = DNA  length = 100
FEATURE                 Location/Qualifiers
source                  1..100
                        mol_type = genomic DNA
                        organism = Homo sapiens
SEQUENCE: 181
cttttccctg gagacaaaga cagggtgcct ggagactgcg tcaacacaat ttctccggtg    60
gtatctgaga ttggaaataa aacagaaaag tcacccatgt                         100

SEQ ID NO: 182          moltype = DNA  length = 100
FEATURE                 Location/Qualifiers
source                  1..100
                        mol_type = genomic DNA
                        organism = Homo sapiens
SEQUENCE: 182
aatctaaatc aaacccattg tcttcccaga agagccagaa ttattgcttt atattgagct    60
ttaattattg tattgactga gcagagttgc caggtaacag                         100

SEQ ID NO: 183          moltype = DNA  length = 100
FEATURE                 Location/Qualifiers
source                  1..100
                        mol_type = genomic DNA
                        organism = Homo sapiens
SEQUENCE: 183
gacttgagag ggttttcact gacatgcaaa accatcccat gttcccctca cctgggagcc    60
agagtagcag gaggaagaga agctgcgctg gggtttccat                         100

SEQ ID NO: 184          moltype = DNA  length = 100
FEATURE                 Location/Qualifiers
source                  1..100
                        mol_type = genomic DNA
                        organism = Homo sapiens
SEQUENCE: 184
agctcttctc cagagctctg acccaggcat tgatatgggc tctggactgc agggcggctg    60
ggagggacat gcaaagcagc tggggcgggt gctgggcttg                         100

SEQ ID NO: 185          moltype = DNA  length = 100
```

```
FEATURE                 Location/Qualifiers
source                  1..100
                        mol_type = genomic DNA
                        organism = Homo sapiens
SEQUENCE: 185
cagctgcaga gacaatctgc ctcccctttc tgctctcagc agcccatgcc caggtgatca    60
ggccagaaaa ggccgttggc tcagtctgag ggtagaactt                         100

SEQ ID NO: 186          moltype = DNA  length = 100
FEATURE                 Location/Qualifiers
source                  1..100
                        mol_type = genomic DNA
                        organism = Homo sapiens
SEQUENCE: 186
ctcccctgcg gccacagaat ttaacccctg tgtcctcttg tctcaccatc acctagattg    60
agccacagaa tgtttggtac aagtctgtta gaaacaaaat                         100

SEQ ID NO: 187          moltype = DNA  length = 100
FEATURE                 Location/Qualifiers
source                  1..100
                        mol_type = genomic DNA
                        organism = Homo sapiens
SEQUENCE: 187
agaaggctgt ggtttcattt ttctctttct gctccaactt gtgcccagtc agctccctaa    60
atgcatgatg gatcaggttg aaaggaagag tctattacaa                         100

SEQ ID NO: 188          moltype = DNA  length = 100
FEATURE                 Location/Qualifiers
source                  1..100
                        mol_type = genomic DNA
                        organism = Homo sapiens
SEQUENCE: 188
ctttatcttc cggatatact tgtatttact tgttagtgat ctttcctgag ggtccagaag    60
ctgtctcatt ctttgcagaa attaaaagag taacattcaa                         100

SEQ ID NO: 189          moltype = DNA  length = 100
FEATURE                 Location/Qualifiers
source                  1..100
                        mol_type = genomic DNA
                        organism = Homo sapiens
SEQUENCE: 189
ttaacctcag cactgtgggt gtgaggactt tcacaactgc acagataagt gagacctggg    60
ctccaaatcc tcagggtagt gataccattt ccctaaagac                         100

SEQ ID NO: 190          moltype = DNA  length = 100
FEATURE                 Location/Qualifiers
source                  1..100
                        mol_type = genomic DNA
                        organism = Homo sapiens
SEQUENCE: 190
agaagatggt tttgtccatg caggcaaaga actatttctt gggtgatcct ctaaactatc    60
cagtcttttt attctgtata gctggtatag tttaccctta                         100

SEQ ID NO: 191          moltype = DNA  length = 100
FEATURE                 Location/Qualifiers
source                  1..100
                        mol_type = genomic DNA
                        organism = Homo sapiens
SEQUENCE: 191
ggctatatat gtatttgttc atatttcaaa aatacacagt ttcaaaatgg aactcaaggg    60
atccaaggct caaaggggtc tccagaagac cccacaccat                         100

SEQ ID NO: 192          moltype = DNA  length = 100
FEATURE                 Location/Qualifiers
source                  1..100
                        mol_type = genomic DNA
                        organism = Homo sapiens
SEQUENCE: 192
cccctttctg tgtcagtctt ccccagagca cagatcctttg tttctgcttg aatcttcctc    60
actctcacag atctgatcat cacatgcccc actctggagg                         100

SEQ ID NO: 193          moltype = DNA  length = 100
FEATURE                 Location/Qualifiers
source                  1..100
                        mol_type = genomic DNA
                        organism = Homo sapiens
SEQUENCE: 193
acaacatgtg catgtccaat acaggaaagg aacacacata ggagtgtagt gagacccca    60
gagatcactg ttgttagagg cagtggggcc ccagaactca                         100
```

```
SEQ ID NO: 194          moltype = DNA  length = 100
FEATURE                 Location/Qualifiers
source                  1..100
                        mol_type = genomic DNA
                        organism = Homo sapiens
SEQUENCE: 194
ggagcagcag cgggtggaga ccccatgggc tggccgagac aagaggactc ctcagccagt   60
cctcctgacc tgagacaggt ctcaggaatg tgcggaggac                        100

SEQ ID NO: 195          moltype = DNA  length = 100
FEATURE                 Location/Qualifiers
source                  1..100
                        mol_type = genomic DNA
                        organism = Homo sapiens
SEQUENCE: 195
acaccgggac atacatttcc cttcatgctc ccaacataca catgcaaaca tacacagacc   60
catacaggca cgcgcgagca gccatgcccc accccctccc                        100

SEQ ID NO: 196          moltype = DNA  length = 100
FEATURE                 Location/Qualifiers
source                  1..100
                        mol_type = genomic DNA
                        organism = Homo sapiens
SEQUENCE: 196
ccaacacaca cacgtataaa agtgtgtgta tatgggcaaa ctgctcgcat ccccaaatgg   60
caggctcttt ccctagaggc gcccagtccg cggcggggag                        100

SEQ ID NO: 197          moltype = DNA  length = 100
FEATURE                 Location/Qualifiers
source                  1..100
                        mol_type = genomic DNA
                        organism = Homo sapiens
SEQUENCE: 197
aagctcactc actggggcca ttgactggga tccagtctgt ggccatgtca tggtttctat   60
ttttgaggtt atagctaatg agcaacatga ggttaagaca                        100

SEQ ID NO: 198          moltype = DNA  length = 100
FEATURE                 Location/Qualifiers
source                  1..100
                        mol_type = genomic DNA
                        organism = Homo sapiens
SEQUENCE: 198
cacttttcat aaggcccag ccagcatcat aaatatgtgt gtgagcatgt tcacactcag    60
gttatgtctt ctttatgtgc accctctacc acacacacac                        100

SEQ ID NO: 199          moltype = DNA  length = 100
FEATURE                 Location/Qualifiers
source                  1..100
                        mol_type = genomic DNA
                        organism = Homo sapiens
SEQUENCE: 199
gccaagaacc acgactctct aattttactt cccagcaggt attcagtgca taatagttcc   60
tacttagaag tatcatattt gcccaaacac aaggtgatac                        100

SEQ ID NO: 200          moltype = DNA  length = 100
FEATURE                 Location/Qualifiers
source                  1..100
                        mol_type = genomic DNA
                        organism = Homo sapiens
SEQUENCE: 200
ccaaaatgag gtaagtttcc tgttttctca gtgagatctt tgttgttgt tgttgttgtt    60
gttgttttgt tgtcgatgtt gttgtttttg gttttggtct                        100

SEQ ID NO: 201          moltype = DNA  length = 100
FEATURE                 Location/Qualifiers
source                  1..100
                        mol_type = genomic DNA
                        organism = Homo sapiens
SEQUENCE: 201
ccgggtcgtc cagccccggg ccgccgcggc tgcccactac acccacgcca accgcccgca   60
agcagcgctg caggggctcc gctgggcgac acgccaggct                        100

SEQ ID NO: 202          moltype = DNA  length = 100
FEATURE                 Location/Qualifiers
source                  1..100
                        mol_type = genomic DNA
                        organism = Homo sapiens
SEQUENCE: 202
```

```
ctgtcccaca gggtgctggg gagcgactgg gcggctccgc cgcgagcgtc tttgaattgc    60
gcgccgctgc aggaaaccaa aaactcccta gcaagagggt                        100

SEQ ID NO: 203           moltype = DNA   length = 100
FEATURE                  Location/Qualifiers
source                   1..100
                         mol_type = genomic DNA
                         organism = Homo sapiens
SEQUENCE: 203
ttcaaaaggt ttctggaaac caccgacggt taaacatcac aactggactc ggagagagcc    60
aaacggtttc cccacttgca cctgccagtc ttcgcggcgg                        100

SEQ ID NO: 204           moltype = DNA   length = 100
FEATURE                  Location/Qualifiers
source                   1..100
                         mol_type = genomic DNA
                         organism = Homo sapiens
SEQUENCE: 204
cgacctggca gcccaggtgc ggtcttaacc gcccccgccc ctcacccccgt acccgctcct    60
atccccggag cgcaaatctc agggctggca gctgcgcggt                        100

SEQ ID NO: 205           moltype = DNA   length = 100
FEATURE                  Location/Qualifiers
source                   1..100
                         mol_type = genomic DNA
                         organism = Homo sapiens
SEQUENCE: 205
ggaaggtttt cccctcaaa cccaaagcgc gcgggcggat caactcctag ctgctgccac      60
cactcgatcc cctcagagga tcggcgcggt gggtccaccc                        100

SEQ ID NO: 206           moltype = DNA   length = 100
FEATURE                  Location/Qualifiers
source                   1..100
                         mol_type = genomic DNA
                         organism = Homo sapiens
SEQUENCE: 206
gcctctcccg ccctctgcct actgtgctgg gagactggca cagctccgtc ggccgcacag    60
agtttaacaa acacgcaccc agtgtcaaga acagtcacca                        100

SEQ ID NO: 207           moltype = DNA   length = 100
FEATURE                  Location/Qualifiers
source                   1..100
                         mol_type = genomic DNA
                         organism = Homo sapiens
SEQUENCE: 207
ggcgcttaac cccgaagtta aagcgggcgc aatctcctcc tgggaactca gcccaggcac    60
gccgccctcc gcctctaaat tcagacaatg taactcgctc                        100

SEQ ID NO: 208           moltype = DNA   length = 100
FEATURE                  Location/Qualifiers
source                   1..100
                         mol_type = genomic DNA
                         organism = Homo sapiens
SEQUENCE: 208
caagacatcc ccgcttcccc aaggaagaga ccggtggtct gagtcccgag gcagcgcgca    60
cgccttctct gcacttgtgc acagaatgtt cttacgtttg                        100

SEQ ID NO: 209           moltype = DNA   length = 100
FEATURE                  Location/Qualifiers
source                   1..100
                         mol_type = genomic DNA
                         organism = Homo sapiens
SEQUENCE: 209
caaacagcgt gcaagccgcc gcgcgcggcg ggactcaagg gggagacaca tgcagccact    60
ggaacgctct ttccagtcgt ttctcctcga ctcacagaga                        100

SEQ ID NO: 210           moltype = DNA   length = 100
FEATURE                  Location/Qualifiers
source                   1..100
                         mol_type = genomic DNA
                         organism = Homo sapiens
SEQUENCE: 210
aaaagattcc aatcctgctc ccccccacc cacccgcact atataggcat ggtcaagaaa      60
actcctttcg gtgacccttt tttggagtac gggtacctcc                        100

SEQ ID NO: 211           moltype = DNA   length = 100
FEATURE                  Location/Qualifiers
source                   1..100
                         mol_type = genomic DNA
```

```
                        organism = Homo sapiens
SEQUENCE: 211
aatgtcctgg ccgcttctgc ccgctcggag aggggctgcg ctctaagttc aaacgtttgt    60
acatttatga caaagcaggt tgaaactgga cttacactga                         100

SEQ ID NO: 212          moltype = DNA   length = 100
FEATURE                 Location/Qualifiers
source                  1..100
                        mol_type = genomic DNA
                        organism = Homo sapiens
SEQUENCE: 212
tcccctccat ggtaaccgct ggttctccag atgcggtggc tactggagca ctcaggccct    60
cggcgtcact ttgctacctg ctgccgcagc caacaaactg                         100

SEQ ID NO: 213          moltype = DNA   length = 100
FEATURE                 Location/Qualifiers
source                  1..100
                        mol_type = genomic DNA
                        organism = Homo sapiens
SEQUENCE: 213
cccattgctg acatacttac tccctgagag tggctcttca tgcacctcca aggggttgct    60
ctccggtcca tccagtgtct tgctcacccc ctgtggtgaa                         100

SEQ ID NO: 214          moltype = DNA   length = 100
FEATURE                 Location/Qualifiers
source                  1..100
                        mol_type = genomic DNA
                        organism = Homo sapiens
SEQUENCE: 214
agttctccac catctccctc tccggagggt gagctgggct gcttggcgag gggcacctcc    60
cctctggggc ctgagctggg ctctgggctt tggtttctcc                         100

SEQ ID NO: 215          moltype = DNA   length = 100
FEATURE                 Location/Qualifiers
source                  1..100
                        mol_type = genomic DNA
                        organism = Homo sapiens
SEQUENCE: 215
cagccggagc actgcacaca tccccagtcc ccggtttctc attctccagt gacgcgtgat    60
ccccacgtgc gttttttgca tctctggcat cctcggtgct                         100

SEQ ID NO: 216          moltype = DNA   length = 100
FEATURE                 Location/Qualifiers
source                  1..100
                        mol_type = genomic DNA
                        organism = Homo sapiens
SEQUENCE: 216
atttgcaggt tatatcctgg atggtggcac gacagcgcct ggaacacaga aggttgggag    60
gcgtgacgct catcaggaag gctcttttgg ggagccagga                         100

SEQ ID NO: 217          moltype = DNA   length = 100
FEATURE                 Location/Qualifiers
source                  1..100
                        mol_type = genomic DNA
                        organism = Homo sapiens
SEQUENCE: 217
agagtccccc agaagcccac ttggcaccct atctataaca agttgctctt taagaatcat    60
gggaactcca gaatcatttt cacaaatacc ttccactcat                         100

SEQ ID NO: 218          moltype = DNA   length = 100
FEATURE                 Location/Qualifiers
source                  1..100
                        mol_type = genomic DNA
                        organism = Homo sapiens
SEQUENCE: 218
gattcaatta aatggcagaa aacacaaacc ttccgttccc actggcaaac tgggtctagc    60
taactgagca cagctagcac aaggcaggcc cctgctagc                          100

SEQ ID NO: 219          moltype = DNA   length = 100
FEATURE                 Location/Qualifiers
source                  1..100
                        mol_type = genomic DNA
                        organism = Homo sapiens
SEQUENCE: 219
agggcaagtg gcggcccggt ccccaaggcc caggggagcc tctgcagctc cctggaagga    60
cggtcaagtg aacagagagc tggctgccat ctgggttctt                         100

SEQ ID NO: 220          moltype = DNA   length = 100
FEATURE                 Location/Qualifiers
```

```
source                  1..100
                        mol_type = genomic DNA
                        organism = Homo sapiens
SEQUENCE: 220
atgagatcac cagtttatcg taactagagg cctctcccat ctaaagcatc tttgtaactg    60
ctttcccttt ccccacactg cctacacata aagaagcccc                         100

SEQ ID NO: 221          moltype = DNA  length = 100
FEATURE                 Location/Qualifiers
source                  1..100
                        mol_type = genomic DNA
                        organism = Homo sapiens
SEQUENCE: 221
taatttgtaa caagtcattt gacaactcca gaagaggggc cacatccttt ttctctatgt    60
ctgttgatta acaaagacaa cattatgttt ccaacaccag                         100

SEQ ID NO: 222          moltype = DNA  length = 100
FEATURE                 Location/Qualifiers
source                  1..100
                        mol_type = genomic DNA
                        organism = Homo sapiens
SEQUENCE: 222
tcagaccaag ggggaaaaaa gtccccatga cttcagtaat tttccatcct ttggaacaag    60
gaaatataca caaaaggttt actatagaat gtaagcattg                         100

SEQ ID NO: 223          moltype = DNA  length = 100
FEATURE                 Location/Qualifiers
source                  1..100
                        mol_type = genomic DNA
                        organism = Homo sapiens
SEQUENCE: 223
aactgttcaa gattgggctc tcacactaac acacctcttc cttgcaactt gcacccaatt    60
tgactctggt cctaggcatg ctgacctgaa atagttgctg                         100

SEQ ID NO: 224          moltype = DNA  length = 100
FEATURE                 Location/Qualifiers
source                  1..100
                        mol_type = genomic DNA
                        organism = Homo sapiens
SEQUENCE: 224
gctgcggcaa gcaccacgcg gtggcaggag aattcctgaa tgtccacaca caagatgaca    60
tctgtcagag cgttttccat tcgcagggtt tccaggccat                         100

SEQ ID NO: 225          moltype = DNA  length = 100
FEATURE                 Location/Qualifiers
source                  1..100
                        mol_type = genomic DNA
                        organism = Homo sapiens
SEQUENCE: 225
tctgaagaat taaggagagt cccgcgtcgt caaatttgac cttttcccca tttaagatct    60
cgaccaagtc tcctgttttc tgggagggct catctgtaga                         100

SEQ ID NO: 226          moltype = DNA  length = 100
FEATURE                 Location/Qualifiers
source                  1..100
                        mol_type = genomic DNA
                        organism = Homo sapiens
SEQUENCE: 226
aggtgccagg ggcccttcca aactcttctc gaccacatca cccatggtcc aggcgccct    60
ttgtcctgcc atcaacatcg agactgaagg agcgcccaag                         100

SEQ ID NO: 227          moltype = DNA  length = 100
FEATURE                 Location/Qualifiers
source                  1..100
                        mol_type = genomic DNA
                        organism = Homo sapiens
SEQUENCE: 227
ccttcctgtt ggccactaca tacgtgtccc ccgcttcttg cccctctctg cttgggtccc    60
tgctacactg gtatcctgca cttccacct tgtattgcca                          100

SEQ ID NO: 228          moltype = DNA  length = 100
FEATURE                 Location/Qualifiers
source                  1..100
                        mol_type = genomic DNA
                        organism = Homo sapiens
SEQUENCE: 228
gtttgtttcc aaggccatct ccactttgag cttgttcatg accacctcac acagcacact    60
tggtctgtgt ggtggtttga gggtcctgt ctgtacactg                          100
```

```
SEQ ID NO: 229          moltype = DNA   length = 100
FEATURE                 Location/Qualifiers
source                  1..100
                        mol_type = genomic DNA
                        organism = Homo sapiens
SEQUENCE: 229
tgctttggct gtgttggagg cgggcaggtg ggaaggaaga aatgtattct tggggagatt    60
tgttttttaga gacatgagac atggaaaata gttaagtaat                        100

SEQ ID NO: 230          moltype = DNA   length = 100
FEATURE                 Location/Qualifiers
source                  1..100
                        mol_type = genomic DNA
                        organism = Homo sapiens
SEQUENCE: 230
aatataatat gggaggcatg gactatcaga ggaggcaggc aggactgccc aacctcctca    60
ctgggcacgt tacgctactt cctcctgacc tctatagtcc                         100

SEQ ID NO: 231          moltype = DNA   length = 100
FEATURE                 Location/Qualifiers
source                  1..100
                        mol_type = genomic DNA
                        organism = Homo sapiens
SEQUENCE: 231
ctatcattgc cctttcttac cttgatatcc taaaaagctg gtggtctgtc ttctctatct    60
tttgtcctgg tcagttatcc taactatttt gtgtctgttt                         100

SEQ ID NO: 232          moltype = DNA   length = 100
FEATURE                 Location/Qualifiers
source                  1..100
                        mol_type = genomic DNA
                        organism = Homo sapiens
SEQUENCE: 232
ctgtggatta gtaaacgggg tccccacccc cactccacaa ggagaacatc tggcacccag    60
aagtcactga gagaatagct gttgctttgg tagaattctg                         100

SEQ ID NO: 233          moltype = DNA   length = 100
FEATURE                 Location/Qualifiers
source                  1..100
                        mol_type = genomic DNA
                        organism = Homo sapiens
SEQUENCE: 233
cctctgagtg gcttgttctt ttcccagacg gagaggtctc ctgacagcag ctctcttctt    60
tttcttttt ttttttttg agacagagtt ttgctcttgc                           100

SEQ ID NO: 234          moltype = DNA   length = 100
FEATURE                 Location/Qualifiers
source                  1..100
                        mol_type = genomic DNA
                        organism = Homo sapiens
SEQUENCE: 234
ctcctgtacc ctgtgggcct gagagaggag acaatgggac aagaagaccc agtggcttcc    60
ttggaagctt ttgtgctagc tggagagaga agacctactt                         100

SEQ ID NO: 235          moltype = DNA   length = 100
FEATURE                 Location/Qualifiers
source                  1..100
                        mol_type = genomic DNA
                        organism = Homo sapiens
SEQUENCE: 235
cctatatgcc tagcaacagt ccacactgac tggactgcaa ccaggacatt tccagattac    60
tcagtggggc ttatcttgaa ataatagttg atgccatttg                         100

SEQ ID NO: 236          moltype = DNA   length = 100
FEATURE                 Location/Qualifiers
source                  1..100
                        mol_type = genomic DNA
                        organism = Homo sapiens
SEQUENCE: 236
ttaaatatat tatatatacc atctaagggt cttacatgcc ttctctcatt tgatcttcat    60
ggcaaaccct gtgaggtatg accaccaacc accattttac                         100

SEQ ID NO: 237          moltype = DNA   length = 100
FEATURE                 Location/Qualifiers
source                  1..100
                        mol_type = genomic DNA
                        organism = Homo sapiens
SEQUENCE: 237
ctcagaactc aggctcccag agtttaagtt gctcacagga gcccagaaag taagcgacag    60
```

```
aggtgggatt tggttctagg tgtttgccac cagcacttta                          100

SEQ ID NO: 238          moltype = DNA   length = 100
FEATURE                 Location/Qualifiers
source                  1..100
                        mol_type = genomic DNA
                        organism = Homo sapiens
SEQUENCE: 238
aatcaccaaa gctttctgga agctccaact tttcttctca agatactgaa agacaggtat    60
ctggatgggt tggcagggcg ggtgggaggt gggcgagatt                         100

SEQ ID NO: 239          moltype = DNA   length = 100
FEATURE                 Location/Qualifiers
source                  1..100
                        mol_type = genomic DNA
                        organism = Homo sapiens
SEQUENCE: 239
tccatcaaca acgggtctaa aaccagcgat ggtgagctgg gtgatttga tggaacccct     60
gccatacagt ctattaatat cataattgga gctaaaattt                         100

SEQ ID NO: 240          moltype = DNA   length = 100
FEATURE                 Location/Qualifiers
source                  1..100
                        mol_type = genomic DNA
                        organism = Homo sapiens
SEQUENCE: 240
aatcatgatg gcaatcatga gttctggggc ttcttgattt gggccagcag acacagtctc    60
agtcactagt tctccgaatc agagaaagga tgccttcagg                         100

SEQ ID NO: 241          moltype = DNA   length = 100
FEATURE                 Location/Qualifiers
source                  1..100
                        mol_type = genomic DNA
                        organism = Homo sapiens
SEQUENCE: 241
ctgtgtcttc acatggcttt tcctctgtgc gtggtggaaa gagagagctc tgcgggtctc    60
ttcttgttgt aaggacactg gccccattgg attagggccc                         100

SEQ ID NO: 242          moltype = DNA   length = 100
FEATURE                 Location/Qualifiers
source                  1..100
                        mol_type = genomic DNA
                        organism = Homo sapiens
SEQUENCE: 242
caccacatga cacatttaat cctaattacc tccctcacag ccctatttcc aaacagggta    60
ttagtcacat tagggattag ggcttcaaca taggaattct                         100

SEQ ID NO: 243          moltype = DNA   length = 100
FEATURE                 Location/Qualifiers
source                  1..100
                        mol_type = genomic DNA
                        organism = Homo sapiens
SEQUENCE: 243
ggggcacac aattcagtct ataacagagg gaaaacagat tgagaagaa aaagtccaa       60
aatatgcaca gtggtaatat ctgaagatgt gcgtgcgtgc                         100

SEQ ID NO: 244          moltype = DNA   length = 100
FEATURE                 Location/Qualifiers
source                  1..100
                        mol_type = genomic DNA
                        organism = Homo sapiens
SEQUENCE: 244
tcaagggctc agcaaacgac aacttaagca tttagagtcc catccctatc caccaaaccc    60
agaataagtt agtcttttca agaaagcatt ggtataaaac                         100

SEQ ID NO: 245          moltype = DNA   length = 100
FEATURE                 Location/Qualifiers
source                  1..100
                        mol_type = genomic DNA
                        organism = Homo sapiens
SEQUENCE: 245
ccttcaaaac tgaaagaag aaggggcaa ttgagaatt cccactttt ctggctgtct        60
ccttcaagtc gcccagtttt tatgaacagc atctagcctt                         100

SEQ ID NO: 246          moltype = DNA   length = 100
FEATURE                 Location/Qualifiers
source                  1..100
                        mol_type = genomic DNA
                        organism = Homo sapiens
```

```
SEQUENCE: 246
actgtcacta tcaacaaccc ttaaaactag ccaatgcttc ggcctctagt attggaaagt    60
cttccaaata ggatactgga aacttctatt tataagcttg                         100

SEQ ID NO: 247          moltype = DNA   length = 100
FEATURE                 Location/Qualifiers
source                  1..100
                        mol_type = genomic DNA
                        organism = Homo sapiens
SEQUENCE: 247
gggtggcggg cggggcgggg aggtggagag agagttgcca tctacaggtt tctattttgg    60
cctgaagact caactgcagt cattagagta agggaatgcc                         100

SEQ ID NO: 248          moltype = DNA   length = 100
FEATURE                 Location/Qualifiers
source                  1..100
                        mol_type = genomic DNA
                        organism = Homo sapiens
SEQUENCE: 248
ttatttatta aaaccacaca caccttgcaa agaaaaaggg aaactggcag tctctgtaga    60
ggaagccggt ggcatcgctc agagccacaa actgtatttc                         100

SEQ ID NO: 249          moltype = DNA   length = 100
FEATURE                 Location/Qualifiers
source                  1..100
                        mol_type = genomic DNA
                        organism = Homo sapiens
SEQUENCE: 249
taaacagccc tttccctggt tccctctctc ctgccccact ttttttaaaa tccagactgt    60
aaaaaacaca tctactgaca ctcactttac tttaaaaaaa                         100

SEQ ID NO: 250          moltype = DNA   length = 100
FEATURE                 Location/Qualifiers
source                  1..100
                        mol_type = genomic DNA
                        organism = Homo sapiens
SEQUENCE: 250
gaagagaaaa agtaaagcgt tacaagactt tcctcctgga aactataaac tgaaaaaaaa    60
atccataaaa gattaaatcc tggcgggttg tggggtggcg                         100

SEQ ID NO: 251          moltype = DNA   length = 100
FEATURE                 Location/Qualifiers
source                  1..100
                        mol_type = genomic DNA
                        organism = Homo sapiens
SEQUENCE: 251
ggggccggcg gggagggggc gcggagtgga gattggctct ctgaggtggt caggggccct    60
gtgacagctt gggactttca gcacctggtt tggggtcatt                         100

SEQ ID NO: 252          moltype = DNA   length = 100
FEATURE                 Location/Qualifiers
source                  1..100
                        mol_type = genomic DNA
                        organism = Homo sapiens
SEQUENCE: 252
tatctgctca actgtcagga ccccccaccc ccaaacccca gccaccaaca caaccatcgt    60
agaagggaac acaacacaga gggtctttt tcattttttt                          100

SEQ ID NO: 253          moltype = DNA   length = 100
FEATURE                 Location/Qualifiers
source                  1..100
                        mol_type = genomic DNA
                        organism = Homo sapiens
SEQUENCE: 253
ttttaaaaa atcggtttgg ttgtgttttt gttttccatg ggggagcttt aaaactcatt    60
attgcaacac tagttccatt tttcgccagg gttccaataa                         100

SEQ ID NO: 254          moltype = DNA   length = 100
FEATURE                 Location/Qualifiers
source                  1..100
                        mol_type = genomic DNA
                        organism = Homo sapiens
SEQUENCE: 254
caagacattt accacggtca ctacatccgg cagcggggtg gcccctagct cctgctgccc    60
ccccgccctt tctccccgcc cgccccggga gctcagccga                         100

SEQ ID NO: 255          moltype = DNA   length = 100
FEATURE                 Location/Qualifiers
source                  1..100
```

```
                         mol_type = genomic DNA
                         organism = Homo sapiens
SEQUENCE: 255
tttctgaggc tccaactcta cccactccct ccccgggccg ccgccgccgc gccttccccc   60
attcttactc cctcgaggag agccacaggt tgcaaatcca                        100

SEQ ID NO: 256           moltype = DNA   length = 100
FEATURE                  Location/Qualifiers
source                   1..100
                         mol_type = genomic DNA
                         organism = Homo sapiens
SEQUENCE: 256
accaacctcg caatctattt ttgcaaaatc actcacaaag atctcccttt cgcgcccgcg   60
cccgctcctc ccgcgccggg tccctcagc cacggccaca                         100

SEQ ID NO: 257           moltype = DNA   length = 100
FEATURE                  Location/Qualifiers
source                   1..100
                         mol_type = genomic DNA
                         organism = Homo sapiens
SEQUENCE: 257
aagtgccctt ctctcctcct gagtcttgca cataaggaac gcgggctggg gctctgttcg   60
tctttctcct cgcccaaggt aaggacctcg ggaatctgaa                        100

SEQ ID NO: 258           moltype = DNA   length = 100
FEATURE                  Location/Qualifiers
source                   1..100
                         mol_type = genomic DNA
                         organism = Homo sapiens
SEQUENCE: 258
gcctggcgtc cactacgctc aggcccgcag ttccctttt acagagcttg caccatggga    60
aaaaataaaa taaatttag gaaagggagg caacagccat                         100

SEQ ID NO: 259           moltype = DNA   length = 100
FEATURE                  Location/Qualifiers
source                   1..100
                         mol_type = genomic DNA
                         organism = Homo sapiens
SEQUENCE: 259
taaaatttag gaaagggagg caacagccat tgggagccaa cacagagtca cgcagcgccc   60
aaaatacaaa caccgcagcg gccagaaatc ccgccacctt                        100

SEQ ID NO: 260           moltype = DNA   length = 100
FEATURE                  Location/Qualifiers
source                   1..100
                         mol_type = genomic DNA
                         organism = Homo sapiens
SEQUENCE: 260
tctcgttctc ccaggctgtc ctgtcgaggt tccctgagtc ccccgcaca ctgaaaggca    60
tcgcaggtgc agtgcgcacc cctttcccac ccaccccaag                        100

SEQ ID NO: 261           moltype = DNA   length = 100
FEATURE                  Location/Qualifiers
source                   1..100
                         mol_type = genomic DNA
                         organism = Homo sapiens
SEQUENCE: 261
aagccctgtc ccgccatcag tctctctcct cgggatgagc agggagagcg cgcggaggtt   60
cccgactccc tcgactacaa ccaagaaaga ataattttca                        100

SEQ ID NO: 262           moltype = DNA   length = 100
FEATURE                  Location/Qualifiers
source                   1..100
                         mol_type = genomic DNA
                         organism = Homo sapiens
SEQUENCE: 262
aagtgttcaa catccccgcc cccaagctcc ccaaaacaca ggggcaggga acaccaaaac   60
actcggctct cattaggaag atcacggctc tgaaaggaaa                        100

SEQ ID NO: 263           moltype = DNA   length = 100
FEATURE                  Location/Qualifiers
source                   1..100
                         mol_type = genomic DNA
                         organism = Homo sapiens
SEQUENCE: 263
tagtagacac gatacttcat ctcatctgga tttatgacca aaaaacaaa acaaaaaacc    60
caaagagttc gcttgcattt tttccttcca aatctcggtt                        100

SEQ ID NO: 264           moltype = DNA   length = 100
```

| FEATURE | Location/Qualifiers |
|---|---|
| source | 1..100 |
| | mol_type = genomic DNA |
| | organism = Homo sapiens |

SEQUENCE: 264
```
aacaaaaacc caaagagttc gcttgcattt tttccttcca aatctcggtt cggctcgaag    60
gcagggaatc taaaagaccg aggccgatgg aagagagcca                          100
```

| SEQ ID NO: 265 | moltype = DNA  length = 100 |
|---|---|
| FEATURE | Location/Qualifiers |
| source | 1..100 |
| | mol_type = genomic DNA |
| | organism = Homo sapiens |

SEQUENCE: 265
```
gcggggcgag cgagcgggca gcctcccttt ttgcctccg gagttaccca gaaggacagg    60
ggaagggaag gaagaagagg cgaggaaaaa gaggagggag                          100
```

| SEQ ID NO: 266 | moltype = DNA  length = 100 |
|---|---|
| FEATURE | Location/Qualifiers |
| source | 1..100 |
| | mol_type = genomic DNA |
| | organism = Homo sapiens |

SEQUENCE: 266
```
ggaagcggag gccaggagcg acggagcaag gaaagcagtt tgcaagcgag aaaagaggga    60
aaaaacacag ccgcacgaat ccagagagat cacaagccgt                          100
```

| SEQ ID NO: 267 | moltype = DNA  length = 100 |
|---|---|
| FEATURE | Location/Qualifiers |
| source | 1..100 |
| | mol_type = genomic DNA |
| | organism = Homo sapiens |

SEQUENCE: 267
```
acgcaagcag cagcagaaag agcgagagcg cgagcgcgcg tcctctccgc ggtctggggc    60
cagacagccc ccagactagc ccgaatcacc ccccaagcac                          100
```

| SEQ ID NO: 268 | moltype = DNA  length = 100 |
|---|---|
| FEATURE | Location/Qualifiers |
| source | 1..100 |
| | mol_type = genomic DNA |
| | organism = Homo sapiens |

SEQUENCE: 268
```
tgtctcgtcc tctctgctcc ggccgccccc taattcccct ccttcctctc ctccacctcc    60
tttccaaaaa ccaaaacaac acaagggagg gtggcaaaag                          100
```

| SEQ ID NO: 269 | moltype = DNA  length = 100 |
|---|---|
| FEATURE | Location/Qualifiers |
| source | 1..100 |
| | mol_type = genomic DNA |
| | organism = Homo sapiens |

SEQUENCE: 269
```
cctcccaaa ccggccgatt cactcaaaga caacaataat aataataaat acataacaat    60
ctatatccta tggtgggaga gacgtgggac taatcttcgg                          100
```

| SEQ ID NO: 270 | moltype = DNA  length = 100 |
|---|---|
| FEATURE | Location/Qualifiers |
| source | 1..100 |
| | mol_type = genomic DNA |
| | organism = Homo sapiens |

SEQUENCE: 270
```
acataacaat ctatatccta tggtgggaga gacgtgggac taatcttcgg catttatttt    60
aacacctgac agctagaata aataaatata tacatttata                          100
```

| SEQ ID NO: 271 | moltype = DNA  length = 100 |
|---|---|
| FEATURE | Location/Qualifiers |
| source | 1..100 |
| | mol_type = genomic DNA |
| | organism = Homo sapiens |

SEQUENCE: 271
```
aataaatata tacatttata tcaatagata cacatagaaa acttggagcc aaagcatttg    60
gcaagagcgg aaaaaaaaag aattaaaagg taaaataatg                          100
```

| SEQ ID NO: 272 | moltype = DNA  length = 100 |
|---|---|
| FEATURE | Location/Qualifiers |
| source | 1..100 |
| | mol_type = genomic DNA |
| | organism = Homo sapiens |

SEQUENCE: 272
```
atcatgagca gcggcggcgg cagcggcacc agcggcaaca gcggcggcgg cggcagtagc    60
agcagcagcg gcggcagcaa cagcaataat cacctggtgt                          100
```

```
SEQ ID NO: 273          moltype = DNA   length = 100
FEATURE                 Location/Qualifiers
source                  1..100
                        mol_type = genomic DNA
                        organism = Homo sapiens
SEQUENCE: 273
ccggcctttc ctagaaactt cttgcatcac cacttctaag aacccccagtt ctaagaatca    60
acagagctca attctcggaa tttgagcttc ggactttacc                          100

SEQ ID NO: 274          moltype = DNA   length = 100
FEATURE                 Location/Qualifiers
source                  1..100
                        mol_type = genomic DNA
                        organism = Homo sapiens
SEQUENCE: 274
actgctacgt ggcagggggag gacttggtgt cagctctccg agattttttac tgcccctggc    60
caaccaaaag ccctcaaagc cacaagattt tttcactggc                          100

SEQ ID NO: 275          moltype = DNA   length = 100
FEATURE                 Location/Qualifiers
source                  1..100
                        mol_type = genomic DNA
                        organism = Homo sapiens
SEQUENCE: 275
cggcatattt cgaggtcctc ataagcagag cgtctcggat ttggaggttc cggttcgagg    60
ctcgaggggc ctgaaggtgg ctctccctcc ccgggcccaa                          100

SEQ ID NO: 276          moltype = DNA   length = 100
FEATURE                 Location/Qualifiers
source                  1..100
                        mol_type = genomic DNA
                        organism = Homo sapiens
SEQUENCE: 276
gacgatggta tggcctgctc cgccaccatc acgtgggctc ctcctctgtg acgtcggcgc    60
cttcgctgta gcaaagctcg gcctctggaa ttctgagaac                          100

SEQ ID NO: 277          moltype = DNA   length = 100
FEATURE                 Location/Qualifiers
source                  1..100
                        mol_type = genomic DNA
                        organism = Homo sapiens
SEQUENCE: 277
gcacaaaagg gagcgagagg tttgaaccac tgggaaaagt atgttatata tatagtaggg    60
ttagagaggc gagtaagaga aaaataaaat aaaaataaaca                          100

SEQ ID NO: 278          moltype = DNA   length = 100
FEATURE                 Location/Qualifiers
source                  1..100
                        mol_type = genomic DNA
                        organism = Homo sapiens
SEQUENCE: 278
aaaataaaat aaacatcaca gctctttcca actagaatat taggcaccac gagaaaaata    60
tttgccaagc agttttcggt gggttcattt gctttatttt                          100

SEQ ID NO: 279          moltype = DNA   length = 100
FEATURE                 Location/Qualifiers
source                  1..100
                        mol_type = genomic DNA
                        organism = Homo sapiens
SEQUENCE: 279
tatttaggac aggggtttttt gctgttgttc tgggtttttt tctttctggt gtggtggctt    60
gggattttttg gttctgtat tttgatggtt tatggatttt                          100

SEQ ID NO: 280          moltype = DNA   length = 100
FEATURE                 Location/Qualifiers
source                  1..100
                        mol_type = genomic DNA
                        organism = Homo sapiens
SEQUENCE: 280
tgcttctgat tttttgcctt ttgcaagttt gtggtgttac gtaaatcaca ggatcggcat    60
cggttggatt ttttttgtacg tgccttttct ttccctatct                          100

SEQ ID NO: 281          moltype = DNA   length = 100
FEATURE                 Location/Qualifiers
source                  1..100
                        mol_type = genomic DNA
                        organism = Homo sapiens
SEQUENCE: 281
```

```
aatccctcaa gcgttttaaa gatgtattat ttcaatacta atactattga aagaagctta    60
aatttttggc catatgtaac aatcccagcc cccactttt                          100

SEQ ID NO: 282          moltype = DNA   length = 100
FEATURE                 Location/Qualifiers
source                  1..100
                        mol_type = genomic DNA
                        organism = Homo sapiens
SEQUENCE: 282
attatcatca tcaccaccaa catcctctgc cctggagacc aagagaattc aaacaggtca    60
gcacctctaa ttgctgtata gaacattgac cctactgtct                         100

SEQ ID NO: 283          moltype = DNA   length = 100
FEATURE                 Location/Qualifiers
source                  1..100
                        mol_type = genomic DNA
                        organism = Homo sapiens
SEQUENCE: 283
cccagttcct gaggatggtg tgataataat acatctcaga gttctgtagt ttcttcacca    60
ctgtgcaggt gtggttggtg ggagcaatgc cctggatgga                         100

SEQ ID NO: 284          moltype = DNA   length = 100
FEATURE                 Location/Qualifiers
source                  1..100
                        mol_type = genomic DNA
                        organism = Homo sapiens
SEQUENCE: 284
taagccaagc tcttgtgtcc tggcagataa acaaggtgaa ccctcaatcc gtgtagcagg    60
agtttccaga caaactcact ttgcatggaa ggacactaac                         100

SEQ ID NO: 285          moltype = DNA   length = 100
FEATURE                 Location/Qualifiers
source                  1..100
                        mol_type = genomic DNA
                        organism = Homo sapiens
SEQUENCE: 285
ccttccaggt gcatggaaat attttgtagt tttactgtc tcccccttcc tccactgcct     60
catctttttt gttttttccc ctgtgagact atttgctctg                         100

SEQ ID NO: 286          moltype = DNA   length = 100
FEATURE                 Location/Qualifiers
source                  1..100
                        mol_type = genomic DNA
                        organism = Homo sapiens
SEQUENCE: 286
cctttccaac actggcctgc cttagggact caccgtctgc actccgcctg cacaggtgga    60
actgagttca gatgagggag aattgctttc cattgttcag                         100

SEQ ID NO: 287          moltype = DNA   length = 100
FEATURE                 Location/Qualifiers
source                  1..100
                        mol_type = genomic DNA
                        organism = Homo sapiens
SEQUENCE: 287
taggcttttt gtaatttcta gttttgctta cctttcctac tcaccacaca cacaaaacag    60
tgtgagcttt ctcattctag tgcataaaca caggtcggtc                         100

SEQ ID NO: 288          moltype = DNA   length = 100
FEATURE                 Location/Qualifiers
source                  1..100
                        mol_type = genomic DNA
                        organism = Homo sapiens
SEQUENCE: 288
aatacccaca agtgttccaa aaggtgagct ggcattgctg cccaactggg cattatagtc    60
ccttctgtcc ctgcccatca ggcttgcctt cctcggcaac                         100

SEQ ID NO: 289          moltype = DNA   length = 100
FEATURE                 Location/Qualifiers
source                  1..100
                        mol_type = genomic DNA
                        organism = Homo sapiens
SEQUENCE: 289
ctttctagct tgaattgtac tgtgactcct tctcacggac cactcccgga gactggtgaa    60
agttgggccc attcttgaag cctctgcttc taaatcatgt                         100

SEQ ID NO: 290          moltype = DNA   length = 100
FEATURE                 Location/Qualifiers
source                  1..100
                        mol_type = genomic DNA
```

```
                        organism = Homo sapiens
SEQUENCE: 290
tttccataaa gtctccctca tcgtgcttgc ttccaccttc tcctatttgg aattactggt    60
gggctcttcc actgtcccat agcaagtgtt ctatacattc                         100

SEQ ID NO: 291          moltype = DNA  length = 100
FEATURE                 Location/Qualifiers
source                  1..100
                        mol_type = genomic DNA
                        organism = Homo sapiens
SEQUENCE: 291
tgaaggcaca tttgaatata tactttgtca tggttgcttg gaaccatgtc gtcttttcca    60
agtaggctgt gaacattcag tggcatggat cataccgtgc                         100

SEQ ID NO: 292          moltype = DNA  length = 100
FEATURE                 Location/Qualifiers
source                  1..100
                        mol_type = genomic DNA
                        organism = Homo sapiens
SEQUENCE: 292
cccattgttc aaagaaaggc attatggagt ctccaaaagc cattggcagg tggtgtctgt    60
gacttcctta gcctggaaat aaacaaataa acaagcacaa                         100

SEQ ID NO: 293          moltype = DNA  length = 100
FEATURE                 Location/Qualifiers
source                  1..100
                        mol_type = genomic DNA
                        organism = Homo sapiens
SEQUENCE: 293
aaacaaataa acaagcacaa attagaagtc tttgccctat tactgcacta ttagtattga    60
ttgcgcaaca tcatgcaaaa agtcacttta atttatctgg                         100

SEQ ID NO: 294          moltype = DNA  length = 100
FEATURE                 Location/Qualifiers
source                  1..100
                        mol_type = genomic DNA
                        organism = Homo sapiens
SEQUENCE: 294
caggtcctat gtaaacacca atacagtcaa gagggcttgg atgggtattt gctttcattt    60
ctaatgaaat ttcaggcctc tagggtagga tatcaaaatt                         100

SEQ ID NO: 295          moltype = DNA  length = 100
FEATURE                 Location/Qualifiers
source                  1..100
                        mol_type = genomic DNA
                        organism = Homo sapiens
SEQUENCE: 295
ggtagatcat ttgcaattta ttttatccca aacacctcac tttacagtca gagaaactga    60
ggcccagaga agtaaaatga gttgctcaag gtctcagaga                         100

SEQ ID NO: 296          moltype = DNA  length = 100
FEATURE                 Location/Qualifiers
source                  1..100
                        mol_type = genomic DNA
                        organism = Homo sapiens
SEQUENCE: 296
actgaggccc agagaagtaa aatgagttgc tcaaggtctc agagagcaag aaatagagat    60
gggacttgag cacctagatc tctggtattg ctgtcctgta                         100

SEQ ID NO: 297          moltype = DNA  length = 100
FEATURE                 Location/Qualifiers
source                  1..100
                        mol_type = genomic DNA
                        organism = Homo sapiens
SEQUENCE: 297
gttcatggag ctggcagatg gatacatctg tgacctggga tgatggagag actgctggac    60
ccttcagagg atctcatctc aaggtggggt ttatgtgtaa                         100

SEQ ID NO: 298          moltype = DNA  length = 100
FEATURE                 Location/Qualifiers
source                  1..100
                        mol_type = genomic DNA
                        organism = Homo sapiens
SEQUENCE: 298
atgatatctg tgtgtttcat tttcctttca taaactaatt taaaaatcct tttggtatca    60
aattttaagc caaaaagtag tgaggggaa catgggtagg                          100

SEQ ID NO: 299          moltype = DNA  length = 100
FEATURE                 Location/Qualifiers
```

```
source                  1..100
                        mol_type = genomic DNA
                        organism = Homo sapiens
SEQUENCE: 299
aatagcttac agcttgccta acaaggttgt tgactgcata agagtcagga gttttgggta    60
agagtgtgtg tgtgtgtgtg tgtgtgtgag                                    100

SEQ ID NO: 300          moltype = DNA  length = 100
FEATURE                 Location/Qualifiers
source                  1..100
                        mol_type = genomic DNA
                        organism = Homo sapiens
SEQUENCE: 300
cgtactgaat ttgactgctt tattttgtag ggaaggaaac tgatgtgcct agagtagttg    60
agagctttat tcaaactcat tccactgtta ttgagtagtt                         100

SEQ ID NO: 301          moltype = DNA  length = 100
FEATURE                 Location/Qualifiers
source                  1..100
                        mol_type = genomic DNA
                        organism = Homo sapiens
SEQUENCE: 301
aggatattag accagcaaca tatttgggta gaaactttca tataaaaaag cgtaatcata    60
actatccaat catgtcaact agtaaggctg ctcaggtggg                         100

SEQ ID NO: 302          moltype = DNA  length = 100
FEATURE                 Location/Qualifiers
source                  1..100
                        mol_type = genomic DNA
                        organism = Homo sapiens
SEQUENCE: 302
ataacacatc aaccttcttt gggattcttc cctcagacat ggttttggtg ggaggagcat    60
ggcaagggag gggcgagctc caaatgcagg gctgctctgt                         100

SEQ ID NO: 303          moltype = DNA  length = 100
FEATURE                 Location/Qualifiers
source                  1..100
                        mol_type = genomic DNA
                        organism = Homo sapiens
SEQUENCE: 303
cctcggcgac ctgagcagac acacgagcag agatcagaga cactcttagt gaatgaacct    60
ccctattggc tatattaaag taatgctctg aaaaagttcc                         100

SEQ ID NO: 304          moltype = DNA  length = 100
FEATURE                 Location/Qualifiers
source                  1..100
                        mol_type = genomic DNA
                        organism = Homo sapiens
SEQUENCE: 304
tatgtatgca tagtctaaag tgatgatttt agaggtagca agacagtgag aatgtcccta    60
catgtgaaat gggcacagtt ttatcaggga agtgtcaata                         100

SEQ ID NO: 305          moltype = DNA  length = 100
FEATURE                 Location/Qualifiers
source                  1..100
                        mol_type = genomic DNA
                        organism = Homo sapiens
SEQUENCE: 305
gagggttaat gttccacgta gtggctgcaa gaatgataag tggtcatggg gatagcctga    60
cactctagga gcagaaggtg gtgggtatgg atagaactac                         100

SEQ ID NO: 306          moltype = DNA  length = 100
FEATURE                 Location/Qualifiers
source                  1..100
                        mol_type = genomic DNA
                        organism = Homo sapiens
SEQUENCE: 306
tgatatagca tgaatccaac ctgctgttat ctgcgcaggc ctctctgcag ctgtttgccc    60
tgaagtacat gctgtacgtt tctccagctg atcctgcatg                         100

SEQ ID NO: 307          moltype = DNA  length = 100
FEATURE                 Location/Qualifiers
source                  1..100
                        mol_type = genomic DNA
                        organism = Homo sapiens
SEQUENCE: 307
actgggtata aacgcctgtc cgctgtgtgc tggacagccc cagacaccct cggcagcctg    60
ctgtgttttgt gtgagacatg ctgtgttagg gatttaagca                        100
```

```
SEQ ID NO: 308              moltype = DNA   length = 100
FEATURE                     Location/Qualifiers
source                      1..100
                            mol_type = genomic DNA
                            organism = Homo sapiens
SEQUENCE: 308
acagctttct catctacatg gacaacctat ttttaaagaa tcttcagaga gtcgttgact    60
ttgttataac tactactata tacgtaattt cagatgatag                         100

SEQ ID NO: 309              moltype = DNA   length = 100
FEATURE                     Location/Qualifiers
source                      1..100
                            mol_type = genomic DNA
                            organism = Homo sapiens
SEQUENCE: 309
aattgaaaat ttaacttgtt tttctagaaa gagtttattt tccctataac ttcaaagagt    60
aatggtgggg agtaggacat tctgaaaata agaagaaaca                         100

SEQ ID NO: 310              moltype = DNA   length = 100
FEATURE                     Location/Qualifiers
source                      1..100
                            mol_type = genomic DNA
                            organism = Homo sapiens
SEQUENCE: 310
tgtcaaatga atttctgact tccagctagg catatggaat aaaggtcttt attccagtga    60
cctctgctca ttggaaaact ttgggctggt agatttcatg                         100

SEQ ID NO: 311              moltype = DNA   length = 100
FEATURE                     Location/Qualifiers
source                      1..100
                            mol_type = genomic DNA
                            organism = Homo sapiens
SEQUENCE: 311
tctcttgcat tcttaacttg caatttagta ctgtttatat tctgcttgaa ggttagagac    60
attcgactaa atggtctttt ctccacattg ctgtcattca                         100

SEQ ID NO: 312              moltype = DNA   length = 100
FEATURE                     Location/Qualifiers
source                      1..100
                            mol_type = genomic DNA
                            organism = Homo sapiens
SEQUENCE: 312
ttaatgtcct ggtcctggac tttactcatt gaccacagga caagtggctc aactctctcc    60
tgccactacc caggctgtta gtcctgttgg gaggctcagg                         100

SEQ ID NO: 313              moltype = DNA   length = 100
FEATURE                     Location/Qualifiers
source                      1..100
                            mol_type = genomic DNA
                            organism = Homo sapiens
SEQUENCE: 313
gcccaactca ctcatctgta actctcatct ccattcagct gcagcctcta cagcccctgg    60
ttataccctg gatcttatca ttgcttcgct ctatttacc                          100

SEQ ID NO: 314              moltype = DNA   length = 100
FEATURE                     Location/Qualifiers
source                      1..100
                            mol_type = genomic DNA
                            organism = Homo sapiens
SEQUENCE: 314
tcctaaatcg taaaaattaa aaccagcctc ggaacacaac ccctcattct tccagcactc    60
tctctcattc aggtaactcc tattctactt ttcttcagca                         100

SEQ ID NO: 315              moltype = DNA   length = 100
FEATURE                     Location/Qualifiers
source                      1..100
                            mol_type = genomic DNA
                            organism = Homo sapiens
SEQUENCE: 315
ttgttttttt ttactttacc ttaatttctc tttttggact aagatgttaa aatgtttctt    60
aatgtgactg tctccgaaac tgttttgtgt ctaccactca                         100

SEQ ID NO: 316              moltype = DNA   length = 100
FEATURE                     Location/Qualifiers
source                      1..100
                            mol_type = genomic DNA
                            organism = Homo sapiens
SEQUENCE: 316
tcctagtggc agtcattgat ccttttcttg ttgcgagtgt ttgagtgtgg gtgtgtgtga    60
```

-continued

```
gtgtgtatat gtatttgtag agggaaaaac aagagagagg                          100

SEQ ID NO: 317         moltype = DNA  length = 100
FEATURE                Location/Qualifiers
source                 1..100
                       mol_type = genomic DNA
                       organism = Homo sapiens
SEQUENCE: 317
tgtgagtgtg tatatgtatt tgtagaggga aaaacaagag agagggaaac agacattgga    60
gccacctttc ccccactagc cacgtacctg ttgaaccttc                          100

SEQ ID NO: 318         moltype = DNA  length = 100
FEATURE                Location/Qualifiers
source                 1..100
                       mol_type = genomic DNA
                       organism = Homo sapiens
SEQUENCE: 318
aagcctctct atagaatcag atatacacaa gcacagtgac agaactacat gtgtcctaca    60
gtccagcttt taagatatga taaaaactct tgtattcaca                          100

SEQ ID NO: 319         moltype = DNA  length = 100
FEATURE                Location/Qualifiers
source                 1..100
                       mol_type = genomic DNA
                       organism = Homo sapiens
SEQUENCE: 319
gagctaaatg gcaataacca taggagattg catattgcta cattatgtaa agacagagtc    60
ccaagaaaat agtgagaact cagtttgatg tatgatgtga                          100

SEQ ID NO: 320         moltype = DNA  length = 100
FEATURE                Location/Qualifiers
source                 1..100
                       mol_type = genomic DNA
                       organism = Homo sapiens
SEQUENCE: 320
tatgtgatat cttactttac atggctaaca gttgacattc tttgtggatt ctatattgtc    60
taaggctaca gaagagccat atgataaatt catcggcaac                          100

SEQ ID NO: 321         moltype = DNA  length = 100
FEATURE                Location/Qualifiers
source                 1..100
                       mol_type = genomic DNA
                       organism = Homo sapiens
SEQUENCE: 321
cagtgaaaag gcttgggccg cttttgtttt cacctgcttt tgttgaacaa atttgatttc    60
cggagtcagt cattttactg tcaagacatt tcttcggcat                          100

SEQ ID NO: 322         moltype = DNA  length = 100
FEATURE                Location/Qualifiers
source                 1..100
                       mol_type = genomic DNA
                       organism = Homo sapiens
SEQUENCE: 322
tctgcaacag gtaaggattt tgcttcctta aaagtatttc tttggtgtca aaagaaattt    60
ttctaatttt atttagcttt tactctaggc caaacatcgt                          100

SEQ ID NO: 323         moltype = DNA  length = 100
FEATURE                Location/Qualifiers
source                 1..100
                       mol_type = genomic DNA
                       organism = Homo sapiens
SEQUENCE: 323
aatgactctg agctacctgc tgtaaggtgt agaatcaatt tacaggggga cgggggtcgg    60
gggggtgagt gttgctttga tattcactgc ccctcaccac                          100

SEQ ID NO: 324         moltype = DNA  length = 100
FEATURE                Location/Qualifiers
source                 1..100
                       mol_type = genomic DNA
                       organism = Homo sapiens
SEQUENCE: 324
agtcctaaca agattttga aacatgaaaa gttacaatag ttggcttttt ggttttccag     60
atattctaga gaatgcatat gcttgtgact gtggctgagc                          100

SEQ ID NO: 325         moltype = DNA  length = 100
FEATURE                Location/Qualifiers
source                 1..100
                       mol_type = genomic DNA
                       organism = Homo sapiens
```

```
SEQUENCE: 325
tcaactgtat gggtagttta aatactaccc aaggtttgat gaagtaaatc taaagatgct    60
ctaagttgtg caaatatgaa ttttaaagtt gtctagttca                         100

SEQ ID NO: 326          moltype = DNA   length = 100
FEATURE                 Location/Qualifiers
source                  1..100
                        mol_type = genomic DNA
                        organism = Homo sapiens
SEQUENCE: 326
gaaaagaaac agaaccgaag tctaaatgat gtagatttca atctggaatt tctagcttgt    60
gtttttcacc tattgccaat gttaatgacc atttcccaaa                         100

SEQ ID NO: 327          moltype = DNA   length = 100
FEATURE                 Location/Qualifiers
source                  1..100
                        mol_type = genomic DNA
                        organism = Homo sapiens
SEQUENCE: 327
agtgctctat gatgtataac atgtattttt taattaaatt taatctttct tctgaggtgg    60
tttgatttgg agatatgcta cgaggtacca gtcagtagcc                         100

SEQ ID NO: 328          moltype = DNA   length = 100
FEATURE                 Location/Qualifiers
source                  1..100
                        mol_type = genomic DNA
                        organism = Homo sapiens
SEQUENCE: 328
tgagttgtaa ctaaacaaag tttgggaaat caccggtttt aggtgcttta ctaaatgaaa    60
gttgccattg acgtattcaa gcaggcaaca agtagttggt                         100

SEQ ID NO: 329          moltype = DNA   length = 100
FEATURE                 Location/Qualifiers
source                  1..100
                        mol_type = genomic DNA
                        organism = Homo sapiens
SEQUENCE: 329
gtccccttat tggttctaag ctggtgccgt ggaggatata agagaaatat tttaaaaatc    60
tctactttga aggaccctat aatctggtag ttgtgataag                         100

SEQ ID NO: 330          moltype = DNA   length = 100
FEATURE                 Location/Qualifiers
source                  1..100
                        mol_type = genomic DNA
                        organism = Homo sapiens
SEQUENCE: 330
tttaaaaatc tctactttga aggaccctat aatctggtag ttgtgataag aagtaaaatt    60
taggaagcaa tgcaagatga gaattcagtg atgagtgggg                         100

SEQ ID NO: 331          moltype = DNA   length = 100
FEATURE                 Location/Qualifiers
source                  1..100
                        mol_type = genomic DNA
                        organism = Homo sapiens
SEQUENCE: 331
cagcacaggc ttgaagagtt ctgtgaattc catggagggg gcctgggggc aaactggagt    60
tgtcaggaag atctgggctt tggaagaatg cgaagtgtcg                         100

SEQ ID NO: 332          moltype = DNA   length = 100
FEATURE                 Location/Qualifiers
source                  1..100
                        mol_type = genomic DNA
                        organism = Homo sapiens
SEQUENCE: 332
gtagaaggag aagggcagg tgatttcaga ctgggaggac cttgtgggca aaggcacaaa     60
ggcgagactg acctggagat gataaggcca gttgaagaga                         100

SEQ ID NO: 333          moltype = DNA   length = 100
FEATURE                 Location/Qualifiers
source                  1..100
                        mol_type = genomic DNA
                        organism = Homo sapiens
SEQUENCE: 333
acattgcagg aaatcagatt agacagttag ggtgtggaca caaaagcgag gaccttgcag    60
gcactgggga gaagtgaccc cattcaatag tccttggtct                         100

SEQ ID NO: 334          moltype = DNA   length = 100
FEATURE                 Location/Qualifiers
source                  1..100
```

```
                        mol_type = genomic DNA
                        organism = Homo sapiens
SEQUENCE: 334
ccttctgccc tgcggctgcg cttcctcggc tctcacggca ccagcagaat tccatgtgag      60
agggagcttg tcgagcgtgg cctcttccca cttggggctg                            100

SEQ ID NO: 335          moltype = DNA   length = 100
FEATURE                 Location/Qualifiers
source                  1..100
                        mol_type = genomic DNA
                        organism = Homo sapiens
SEQUENCE: 335
cttttctgcat ccctgtgcct ggctgtgggc ctccatttgc cctctactgt cttcccttag     60
gacatcattt atgcagagaa aggttcgtgt ggctcgggt                             100

SEQ ID NO: 336          moltype = DNA   length = 100
FEATURE                 Location/Qualifiers
source                  1..100
                        mol_type = genomic DNA
                        organism = Homo sapiens
SEQUENCE: 336
ggacgttgtt tagagagtca gtagatcata ataattcaga cactttttt ctggaccata       60
aaatatctga acccatataa taacaaacat acagcacggt                            100

SEQ ID NO: 337          moltype = DNA   length = 100
FEATURE                 Location/Qualifiers
source                  1..100
                        mol_type = genomic DNA
                        organism = Homo sapiens
SEQUENCE: 337
gaataagaac ccaacttttg agccagatca ctttgcatgg aatccccatt ctatcattct      60
atcatttctg ggctgtggga acctcagaca agttacttaa                            100

SEQ ID NO: 338          moltype = DNA   length = 100
FEATURE                 Location/Qualifiers
source                  1..100
                        mol_type = genomic DNA
                        organism = Homo sapiens
SEQUENCE: 338
cttcttcaat gctcagatta aaaaaaaaat tcacaaaata tctctaataa cagtaataat      60
aactgaaaat acctacctca gagggttgtc gtagagatca                            100

SEQ ID NO: 339          moltype = DNA   length = 100
FEATURE                 Location/Qualifiers
source                  1..100
                        mol_type = genomic DNA
                        organism = Homo sapiens
SEQUENCE: 339
aaaattcaca aatatctct aataacagta ataataactg aaaataccta cctcagaggg       60
ttgtcgtaga gatcaaatga gataaaaata tgtaaagcat                            100

SEQ ID NO: 340          moltype = DNA   length = 100
FEATURE                 Location/Qualifiers
source                  1..100
                        mol_type = genomic DNA
                        organism = Homo sapiens
SEQUENCE: 340
gtagcctagt gcctgactga aaaaaaaatc tctcaataga tgcaactctt atgattctta      60
ttaaggactt ggctattgcc acaaatgaag gtgttatgag                            100

SEQ ID NO: 341          moltype = DNA   length = 100
FEATURE                 Location/Qualifiers
source                  1..100
                        mol_type = genomic DNA
                        organism = Homo sapiens
SEQUENCE: 341
ccctggctta agagcaagaa gcctgcaaag ctaactctcc taatcccaac attcctttcc      60
agggaaagta gggtgacagg tggaggctgg gaattaacgt                            100

SEQ ID NO: 342          moltype = DNA   length = 100
FEATURE                 Location/Qualifiers
source                  1..100
                        mol_type = genomic DNA
                        organism = Homo sapiens
SEQUENCE: 342
ttttttgagca ccaaatatgg acaaggcaca ggggttgggt gttttctag tgagaataca      60
tatgaaagaa ggaaaacaaa cttggaaacc gctattttaa                            100

SEQ ID NO: 343          moltype = DNA   length = 100
```

```
FEATURE                 Location/Qualifiers
source                  1..100
                        mol_type = genomic DNA
                        organism = Homo sapiens
SEQUENCE: 343
gccatttggt aacagtttct ctagcttatg agatgagaga ggtcctctca gtatccgctg    60
cattacttgt gggcctcctt ggttgacgtc gctctctgaa                          100

SEQ ID NO: 344          moltype = DNA  length = 100
FEATURE                 Location/Qualifiers
source                  1..100
                        mol_type = genomic DNA
                        organism = Homo sapiens
SEQUENCE: 344
cgcttggggt ggaattctag aggtgctttt cattagaggc agagagcatg acctttcttc    60
cttgcccagt ttaaattaaa ttattttatc ttacaatgtg                          100

SEQ ID NO: 345          moltype = DNA  length = 100
FEATURE                 Location/Qualifiers
source                  1..100
                        mol_type = genomic DNA
                        organism = Homo sapiens
SEQUENCE: 345
ttaattttag tgctagcaag gcacagctaa aattccattt ctacttagga gtggggatca    60
ttgtggcagt gagtgcttat ttgggtttgg gatgcttgga                          100

SEQ ID NO: 346          moltype = DNA  length = 100
FEATURE                 Location/Qualifiers
source                  1..100
                        mol_type = genomic DNA
                        organism = Homo sapiens
SEQUENCE: 346
tctgggtgaa agccaggatt aaaaagcatc ctccttcccc attccactct ctaggttata    60
aatattttt tggattaaaa gcctccttta aaaaaatgca                           100

SEQ ID NO: 347          moltype = DNA  length = 100
FEATURE                 Location/Qualifiers
source                  1..100
                        mol_type = genomic DNA
                        organism = Homo sapiens
SEQUENCE: 347
aatccacctg gcatgttaat tgtgcagggg attcctaatt atgtgtgcag atgacgtgag    60
tcacacggtg atagtgttcc ttctagagtc ccactggtgt                          100

SEQ ID NO: 348          moltype = DNA  length = 100
FEATURE                 Location/Qualifiers
source                  1..100
                        mol_type = genomic DNA
                        organism = Homo sapiens
SEQUENCE: 348
actaggcgtt catcctgtgt aatttgaaaa tatgtcacac gtggtgatga gaatctattt    60
gaggaacatg ggcagtttga aataatatat gcaatgtatg                          100

SEQ ID NO: 349          moltype = DNA  length = 100
FEATURE                 Location/Qualifiers
source                  1..100
                        mol_type = genomic DNA
                        organism = Homo sapiens
SEQUENCE: 349
actagtttat ataatgaaag gaagtattta aaaagataga atgacataga ctaatctaat    60
tgagaaatat gaaagtctaa cagaaatgat tgcttgtgaa                          100

SEQ ID NO: 350          moltype = DNA  length = 100
FEATURE                 Location/Qualifiers
source                  1..100
                        mol_type = genomic DNA
                        organism = Homo sapiens
SEQUENCE: 350
attttatgaa gaaatccaca gataaattct ccaccttgat ctatgtaatc cgaaatttag    60
atgttaaaaa tatgttgatt ctgaaaattt atatttattc                          100

SEQ ID NO: 351          moltype = DNA  length = 100
FEATURE                 Location/Qualifiers
source                  1..100
                        mol_type = genomic DNA
                        organism = Homo sapiens
SEQUENCE: 351
tttggtatga ataggtcaaa acaagtcacc attaactgac aggaagcaca gaattctcaa    60
ttagttttg gcaaagacat tattttataa atatgagttt                           100
```

-continued

```
SEQ ID NO: 352          moltype = DNA   length = 100
FEATURE                 Location/Qualifiers
source                  1..100
                        mol_type = genomic DNA
                        organism = Homo sapiens
SEQUENCE: 352
ttaaatgatt cttatgaaga aactagcacc aaagtgaatg cactctgcaa ataactccca    60
gcttctctga atttcaaaag cagccactaa atattattag                         100

SEQ ID NO: 353          moltype = DNA   length = 100
FEATURE                 Location/Qualifiers
source                  1..100
                        mol_type = genomic DNA
                        organism = Homo sapiens
SEQUENCE: 353
caaatcaatt tagctgaaag cgatgaatta cagaagtaaa tctttaggta caaagtagac    60
agctgacaca catgtagcat atacacacta gtgatctgcc                         100

SEQ ID NO: 354          moltype = DNA   length = 100
FEATURE                 Location/Qualifiers
source                  1..100
                        mol_type = genomic DNA
                        organism = Homo sapiens
SEQUENCE: 354
ttccttcttt accaacatag agtttcccat gagccctgaa tccggggcac ttttgctaac    60
ttcccctgca gcggcgacgc tgccactccc agtgcccccg                         100

SEQ ID NO: 355          moltype = DNA   length = 100
FEATURE                 Location/Qualifiers
source                  1..100
                        mol_type = genomic DNA
                        organism = Homo sapiens
SEQUENCE: 355
cagtggaagg ggctcgcgcc acctccattg ctcttggccc caaagccata gaggtgcccc    60
ccggaagggg cctggctgcc actgccattc tggtggccct                         100

SEQ ID NO: 356          moltype = DNA   length = 100
FEATURE                 Location/Qualifiers
source                  1..100
                        mol_type = genomic DNA
                        organism = Homo sapiens
SEQUENCE: 356
gaagcaggtc gtgcttgtcc ttcctggatt tccccgcatc cttatcccgc ttggcgcctc    60
ggctgctctg gcttttacct ggcttctcct ctttgctttt                         100

SEQ ID NO: 357          moltype = DNA   length = 100
FEATURE                 Location/Qualifiers
source                  1..100
                        mol_type = genomic DNA
                        organism = Homo sapiens
SEQUENCE: 357
cccacaggag cctgccccg cggtggcggc agaggtgctg gtgctggtac tattgctgtt     60
tgggttgccg ctgccgccgc tgctcacact ttgacccagc                         100

SEQ ID NO: 358          moltype = DNA   length = 100
FEATURE                 Location/Qualifiers
source                  1..100
                        mol_type = genomic DNA
                        organism = Homo sapiens
SEQUENCE: 358
gctgaattca tgccagttgc ctctccaggg cgcccttgga cttcctgcct cttgccagtg    60
ctgctgatct cgggaatccc atacaaggca gcagaaggca                         100

SEQ ID NO: 359          moltype = DNA   length = 100
FEATURE                 Location/Qualifiers
source                  1..100
                        mol_type = genomic DNA
                        organism = Homo sapiens
SEQUENCE: 359
gagatttatt agcatcctta gaagttttac tccttttcac ttttgatttg ctggtctctt    60
tgtgtgaatt cccctgggga gcagaggcct gaacagaagc                         100

SEQ ID NO: 360          moltype = DNA   length = 100
FEATURE                 Location/Qualifiers
source                  1..100
                        mol_type = genomic DNA
                        organism = Homo sapiens
SEQUENCE: 360
```

```
aaatttagg ccatcagcta aggctgcggt agcaccagcc ccactggagg ccggacctcc   60
acaatccttg gagttgctgc tactagtggt ggtggtggaa                       100

SEQ ID NO: 361          moltype = DNA  length = 100
FEATURE                 Location/Qualifiers
source                  1..100
                        mol_type = genomic DNA
                        organism = Homo sapiens
SEQUENCE: 361
ttattcatct caaatttctg tctgtccttc tccaaatcag cgtccaaatc aattattaaa   60
tttccaaccc cgatttccca atcatcgcca ctgtcataag                       100

SEQ ID NO: 362          moltype = DNA  length = 100
FEATURE                 Location/Qualifiers
source                  1..100
                        mol_type = genomic DNA
                        organism = Homo sapiens
SEQUENCE: 362
tatcaactgt atttggatcc acaccttttc ctgcagtaga aatgttcact gacatcctga   60
agatgagctc tctagaataa aaatccgatg aacttttctt                       100

SEQ ID NO: 363          moltype = DNA  length = 100
FEATURE                 Location/Qualifiers
source                  1..100
                        mol_type = genomic DNA
                        organism = Homo sapiens
SEQUENCE: 363
ttcctcagga atttgagctg gggatctgca tcctggccat tgcagtcctt tagcatcctc   60
gccgcgccct gagcgcgctg gaggctcgca ggctgcgccc                       100

SEQ ID NO: 364          moltype = DNA  length = 100
FEATURE                 Location/Qualifiers
source                  1..100
                        mol_type = genomic DNA
                        organism = Homo sapiens
SEQUENCE: 364
tcccagggct gatgccgcgt cctgctccgc cgttctggga cgtcggggac aaaagtggag   60
gagacgggag agcccgggca gaaaaagcag gacgcgcgtc                       100

SEQ ID NO: 365          moltype = DNA  length = 100
FEATURE                 Location/Qualifiers
source                  1..100
                        mol_type = genomic DNA
                        organism = Homo sapiens
SEQUENCE: 365
ccaggtgccc acctcttcgc tttgaggcgg gggcggtggg atggaatatg ggtgcgcgag   60
gtcggggctg gtaactctcg gaggggcacg gcctccacgc                       100

SEQ ID NO: 366          moltype = DNA  length = 100
FEATURE                 Location/Qualifiers
source                  1..100
                        mol_type = genomic DNA
                        organism = Homo sapiens
SEQUENCE: 366
tgggagggat gaatggacgc tgggccccgg caaatgaggc gctgtgggtc cccaggaagt   60
ggggtaccag gctctactcc caccccggcc tctgaaacgc                       100

SEQ ID NO: 367          moltype = DNA  length = 100
FEATURE                 Location/Qualifiers
source                  1..100
                        mol_type = genomic DNA
                        organism = Homo sapiens
SEQUENCE: 367
ggccaggagg ggtggcggct gggtggggag agagggtgca agacgagcgg cgcgtgtcgg   60
gagcctttgg gctgcgggtg cgttacagga gagcaggcgg                       100

SEQ ID NO: 368          moltype = DNA  length = 100
FEATURE                 Location/Qualifiers
source                  1..100
                        mol_type = genomic DNA
                        organism = Homo sapiens
SEQUENCE: 368
gtaggagcct tcgcgggggc cgagctcgga aggcggacgg ctgtgcccgc ccaggggatg   60
cgcccgggcc ggcgcgaag gtgccttctt ccggggcccc                        100

SEQ ID NO: 369          moltype = DNA  length = 100
FEATURE                 Location/Qualifiers
source                  1..100
                        mol_type = genomic DNA
```

```
                            organism = Homo sapiens
SEQUENCE: 369
ggacgaccct gacacggcac gcgcgcgctt cgcagcctca aagactccgg ggcctcgtgg    60
tcactggcgc aggggatcgg ggcggggtgc ccggagtgcg                         100

SEQ ID NO: 371            moltype = DNA  length = 100
FEATURE                   Location/Qualifiers
source                    1..100
                          mol_type = genomic DNA
                          organism = Homo sapiens
SEQUENCE: 370
cccgcagtgc agagcagagc gggcggagga ccccgggcgc gggcgcggac ggcacgcggg    60
gcatgaacct ggagggcggc ggccgaggcg gagagttcgg                         100

SEQ ID NO: 371            moltype = DNA  length = 100
FEATURE                   Location/Qualifiers
source                    1..100
                          mol_type = genomic DNA
                          organism = Homo sapiens
SEQUENCE: 371
catgagcgcg gtgagctgcg gcaacgggaa gctccgccag tggctgatcg accagatcga    60
cagcggcaag taccccgggc tggtgtggga aacgaggag                          100

SEQ ID NO: 372            moltype = DNA  length = 100
FEATURE                   Location/Qualifiers
source                    1..100
                          mol_type = genomic DNA
                          organism = Homo sapiens
SEQUENCE: 372
aagagcatct tccgcatccc ctggaagcac gcgggcaagc aggactacaa ccgcgaggag    60
gacgccgcgc tcttcaaggt ctccggcctc gggagccggc                         100

SEQ ID NO: 373            moltype = DNA  length = 100
FEATURE                   Location/Qualifiers
source                    1..100
                          mol_type = genomic DNA
                          organism = Homo sapiens
SEQUENCE: 373
cccgcgcgcc acagctctgc agctcgtggc agcggcgcag cgctccagcc atgtcgcgcg    60
gcctccagct tctgctcctg agctgcggta gggctcgcga                         100

SEQ ID NO: 374            moltype = DNA  length = 100
FEATURE                   Location/Qualifiers
source                    1..100
                          mol_type = genomic DNA
                          organism = Homo sapiens
SEQUENCE: 374
gcgcctgtct cgcctgtcgc cccccgcccc tccacgacac cccctcccgt cggtcgcttg    60
ctcacgacgc gctctctctt tcttgtagcc tacagcctgg                         100

SEQ ID NO: 375            moltype = DNA  length = 100
FEATURE                   Location/Qualifiers
source                    1..100
                          mol_type = genomic DNA
                          organism = Homo sapiens
SEQUENCE: 375
ctcccgcgac gccggaggtg aaggtggctt gctccgaaga tgtggacttg ccctgcaccg    60
cccccctggga tccgcaggtt ccctacacgg tctcctgggt                        100

SEQ ID NO: 376            moltype = DNA  length = 100
FEATURE                   Location/Qualifiers
source                    1..100
                          mol_type = genomic DNA
                          organism = Homo sapiens
SEQUENCE: 376
caaggtaggt gctgcgatac ccacgggctg gggtttggtg ggctcatttg aagacagcag    60
gaaccatctc ccctaggctg gcgaccctct gtggctgcca                         100

SEQ ID NO: 377            moltype = DNA  length = 100
FEATURE                   Location/Qualifiers
source                    1..100
                          mol_type = genomic DNA
                          organism = Homo sapiens
SEQUENCE: 377
ggtgggggcg aggggcgtct cccgcagctg aacttggagt acccagcctc ccgtcgcgcc    60
tcccccaccc catccgcatc caggtacagg gccgaattag                         100

SEQ ID NO: 378            moltype = DNA  length = 100
FEATURE                   Location/Qualifiers
```

```
source                  1..100
                        mol_type = genomic DNA
                        organism = Homo sapiens
SEQUENCE: 378
gttttgctct ccgcagacct caatcccctt cctgtcactg aaggtggcct gagatgaatg    60
atccacttaa gatgttttgg aagggcagag actctcattt                         100

SEQ ID NO: 379          moltype = DNA  length = 100
FEATURE                 Location/Qualifiers
source                  1..100
                        mol_type = genomic DNA
                        organism = Homo sapiens
SEQUENCE: 379
ggattaattc tggaggccac ctgtggttgt gggccagcag gtcaggaaga aagcaacagg    60
gacctagatt tgggcattgg acaggggaa tgtctccaga                          100

SEQ ID NO: 380          moltype = DNA  length = 100
FEATURE                 Location/Qualifiers
source                  1..100
                        mol_type = genomic DNA
                        organism = Homo sapiens
SEQUENCE: 380
ctctccagtt cctatattct aatacccctc cgccgccaaa taaaatttgg cgtctggcca    60
cagctctttt agtgggtatc tgggtggctc ttaaaagagc                         100

SEQ ID NO: 381          moltype = DNA  length = 100
FEATURE                 Location/Qualifiers
source                  1..100
                        mol_type = genomic DNA
                        organism = Homo sapiens
SEQUENCE: 381
cttttggggtt aggtgttaag acgcttactt ggaatgttta cttggagctg gtgtacttgg    60
tgacggcctt ggtgccctcc gacacggcgt gcttggccag                         100

SEQ ID NO: 382          moltype = DNA  length = 100
FEATURE                 Location/Qualifiers
source                  1..100
                        mol_type = genomic DNA
                        organism = Homo sapiens
SEQUENCE: 382
ctccggcccc tgccgagaag actcccgtga agaagaaggc ccgcaagtct gcaggtgcgg    60
ccaagcgcaa agcgtctggg ccccggtgt ccgagctcat                          100

SEQ ID NO: 383          moltype = DNA  length = 100
FEATURE                 Location/Qualifiers
source                  1..100
                        mol_type = genomic DNA
                        organism = Homo sapiens
SEQUENCE: 383
tactaaagct gttgccgcct ccaaggagcg cagcggcgta tctttggccg ctctcaagaa    60
agcgctggca gccgctggct atgacgtgga gaagaacaac                         100

SEQ ID NO: 384          moltype = DNA  length = 100
FEATURE                 Location/Qualifiers
source                  1..100
                        mol_type = genomic DNA
                        organism = Homo sapiens
SEQUENCE: 384
agccgcatca agctgggtct caagagcctg gtgagcaagg gcaccctggt gcagaccaag    60
ggcaccggcg cgtcgggttc cttcaaactc aacaagaagg                         100

SEQ ID NO: 385          moltype = DNA  length = 100
FEATURE                 Location/Qualifiers
source                  1..100
                        mol_type = genomic DNA
                        organism = Homo sapiens
SEQUENCE: 385
cggcctctgg ggaagccaag cctaaggcta aaaaggcagg cgcggccaag gccaagaagc    60
cagcaggagc ggcgaagaag cccaagaagg cgacgggggc                         100

SEQ ID NO: 386          moltype = DNA  length = 100
FEATURE                 Location/Qualifiers
source                  1..100
                        mol_type = genomic DNA
                        organism = Homo sapiens
SEQUENCE: 386
ggccaccccc aagaagagcg ccaagaagac cccaaagaag gcgaagaagc cggctgcagc    60
tgctggagcc aaaaaagcga aaagcccgaa aaaggcgaaa                         100
```

-continued

```
SEQ ID NO: 387        moltype = DNA   length = 100
FEATURE               Location/Qualifiers
source                1..100
                      mol_type = genomic DNA
                      organism = Homo sapiens
SEQUENCE: 387
gcagccaagc caaaaaaggc gcccaagagc ccagcgaagg ccaaagcagt taaacccaag   60
gcggctaaac caaagaccgc caagcccaag gcagccaagc                        100

SEQ ID NO: 388        moltype = DNA   length = 100
FEATURE               Location/Qualifiers
source                1..100
                      mol_type = genomic DNA
                      organism = Homo sapiens
SEQUENCE: 388
caaagaaggc ggcagccaag aaaaagtaga aagttccttt ggccaactgc ttagaagccc   60
aacacaaccc aaaggctctt ttcagagcca cccaccgctc                        100

SEQ ID NO: 389        moltype = DNA   length = 100
FEATURE               Location/Qualifiers
source                1..100
                      mol_type = genomic DNA
                      organism = Homo sapiens
SEQUENCE: 389
tcagtaaaag agctgttgca ctattagggg gcgtggctcg ggaaaacgct gctaagcagg   60
ggcgggtctc ccgggaacaa agtcggggag aggagtggga                        100

SEQ ID NO: 390        moltype = DNA   length = 100
FEATURE               Location/Qualifiers
source                1..100
                      mol_type = genomic DNA
                      organism = Homo sapiens
SEQUENCE: 390
ctccttagcc agactcgatt acaagcactg catgcattac tcagtgtgat aagatcatga   60
taatcccttt aaaaagatcg cccgaattta agcctggatt                        100

SEQ ID NO: 391        moltype = DNA   length = 100
FEATURE               Location/Qualifiers
source                1..100
                      mol_type = genomic DNA
                      organism = Homo sapiens
SEQUENCE: 391
aggaacacgt gtttacagct ctaatatcga taatttaagt ggctcttaaa agagcctttg   60
gggttgggct ttaagacgct tacttggcaa gtttacttag                        100

SEQ ID NO: 392        moltype = DNA   length = 100
FEATURE               Location/Qualifiers
source                1..100
                      mol_type = genomic DNA
                      organism = Homo sapiens
SEQUENCE: 392
cgctggtgta cttggtgacg gccttggtgc cctcggacac ggcgtgcttg gccaactccc   60
cgggcagcag caggcgcacg gccgtctgga tctccctgga                        100

SEQ ID NO: 393        moltype = DNA   length = 100
FEATURE               Location/Qualifiers
source                1..100
                      mol_type = genomic DNA
                      organism = Homo sapiens
SEQUENCE: 393
ccccggctcc ggctcctgcg gcagctcctc tgggcaccgt ccctgcgccg acatcctgga   60
ggttgggatg ctcttgtcca aaatcaactc gcttgcccac                        100

SEQ ID NO: 394        moltype = DNA   length = 100
FEATURE               Location/Qualifiers
source                1..100
                      mol_type = genomic DNA
                      organism = Homo sapiens
SEQUENCE: 394
ctgcgcgccg cgccctgcaa cgacctgcac gccaccaagc tggcgcccgg tgagagcacc   60
ccccgcctcc ggcccgggga tgcggggcgg cggcgggatc                        100

SEQ ID NO: 395        moltype = DNA   length = 100
FEATURE               Location/Qualifiers
source                1..100
                      mol_type = genomic DNA
                      organism = Homo sapiens
SEQUENCE: 395
tcctgggtgg ggagctggcg gctcgcgggc cggcactgag tccccgtgct tcccccttcc   60
```

-continued

```
ctaggcaagg agaaggagcc cctggagtcg cagtaccagg                          100

SEQ ID NO: 396         moltype = DNA   length = 100
FEATURE                Location/Qualifiers
source                 1..100
                       mol_type = genomic DNA
                       organism = Homo sapiens
SEQUENCE: 396
tgggcccgct actgggcagc ggcggcttcg gctcggtcta ctcaggcatc cgcgtctccg      60
acaacttgcc ggtgagtggg cgcccgcgg tggggagggc                            100

SEQ ID NO: 397         moltype = DNA   length = 100
FEATURE                Location/Qualifiers
source                 1..100
                       mol_type = genomic DNA
                       organism = Homo sapiens
SEQUENCE: 397
gcgccgggcg gggggcgcac gggcgtgctt tagcccggac gagggaacct gacggagacc      60
ctgggcttcc aggtggccat caaacacgtg gagaaggacc                           100

SEQ ID NO: 398         moltype = DNA   length = 100
FEATURE                Location/Qualifiers
source                 1..100
                       mol_type = genomic DNA
                       organism = Homo sapiens
SEQUENCE: 398
ggatttccga ctggggagag ctggtgagtg ccctgcagga gcgaccccca ggatgagtgg      60
gtggggtgag gggcgccccc gactcccgcc ctaacgcggc                           100

SEQ ID NO: 399         moltype = DNA   length = 100
FEATURE                Location/Qualifiers
source                 1..100
                       mol_type = genomic DNA
                       organism = Homo sapiens
SEQUENCE: 399
cccctcgccc ctgcagccta atggcactcg agtgcccatg gaagtggtcc tgctgaagaa      60
ggtgagctcg ggtttctccg gcgtcattag gctcctggac                           100

SEQ ID NO: 400         moltype = DNA   length = 100
FEATURE                Location/Qualifiers
source                 1..100
                       mol_type = genomic DNA
                       organism = Homo sapiens
SEQUENCE: 400
tggttcgaga ggcccgacag tttcgtcctg atcctggaga ggcccgagcc ggtgcaagat      60
ctcttcgact tcatcacgga aaggggagcc ctgcaagagg                           100

SEQ ID NO: 401         moltype = DNA   length = 100
FEATURE                Location/Qualifiers
source                 1..100
                       mol_type = genomic DNA
                       organism = Homo sapiens
SEQUENCE: 401
agctggcccg cagcttcttc tggcaggtgc tggaggccgt gcggcactgc cacaactgcg      60
gggtgctcca ccgcgacatc aaggacgaaa acatccttat                           100

SEQ ID NO: 402         moltype = DNA   length = 100
FEATURE                Location/Qualifiers
source                 1..100
                       mol_type = genomic DNA
                       organism = Homo sapiens
SEQUENCE: 402
cgacctcaat cgcggcgagc tcaagctcat cgacttcggg tcggggcgc tgctcaagga       60
caccgtctac acggacttcg atggtgagcc aggcccggga                           100

SEQ ID NO: 403         moltype = DNA   length = 100
FEATURE                Location/Qualifiers
source                 1..100
                       mol_type = genomic DNA
                       organism = Homo sapiens
SEQUENCE: 403
gggagctgcc caggtgactc ggcccggcc ggcccagtcc ggaggcctcg gccagtctcc       60
cgcgccagcc ttttgtaaag gtcattgggc cgcctggctc                           100

SEQ ID NO: 404         moltype = DNA   length = 100
FEATURE                Location/Qualifiers
source                 1..100
                       mol_type = genomic DNA
                       organism = Homo sapiens
```

```
SEQUENCE: 404
gatgctagcc ggggtgggac gcaggagagc ctcccagcgt agtaaagccg gggattttca    60
gccagctgaa cctgtaatgt ttctggcatg attttattct                         100

SEQ ID NO: 405          moltype = DNA  length = 100
FEATURE                 Location/Qualifiers
source                  1..100
                        mol_type = genomic DNA
                        organism = Homo sapiens
SEQUENCE: 405
tcaagtggaa ttcagttagt tccaggcttt cccgatgaat aagaggttgt gggcaaccgg    60
cggtagccca gattttcta aagtctgacc cagtttcccc                          100

SEQ ID NO: 406          moltype = DNA  length = 100
FEATURE                 Location/Qualifiers
source                  1..100
                        mol_type = genomic DNA
                        organism = Homo sapiens
SEQUENCE: 406
ctctaaacag acaaaagcaa aatatctcat taggcatcat ctccgccaag gttcccacta    60
ggcaggaaag gattttatc taaagtaatt acccttttta                          100

SEQ ID NO: 407          moltype = DNA  length = 100
FEATURE                 Location/Qualifiers
source                  1..100
                        mol_type = genomic DNA
                        organism = Homo sapiens
SEQUENCE: 407
gttaaataca ctcaacagat gaaatttaca gagagtgaga gactgcagca ctagacagcg    60
aaggtgaaaa ccaggaacgc cgcgtctcgc cgcccgcggg                         100

SEQ ID NO: 408          moltype = DNA  length = 100
FEATURE                 Location/Qualifiers
source                  1..100
                        mol_type = genomic DNA
                        organism = Homo sapiens
SEQUENCE: 408
cccgccggga gactgcgggt ccgtctcgcg ggtggggcgc cccggtccct ctcgtttcct    60
ggaggccaca ggtcacggcg acggcggtga ccgggagagc                         100

SEQ ID NO: 409          moltype = DNA  length = 100
FEATURE                 Location/Qualifiers
source                  1..100
                        mol_type = genomic DNA
                        organism = Homo sapiens
SEQUENCE: 409
cgggtctgac agctgctgcg gctcgcgcgg acgcgcgcct cctgcagccc gccctcccca    60
tgcctgactt attactctct gctcctcctc cctctgctgt                         100

SEQ ID NO: 410          moltype = DNA  length = 100
FEATURE                 Location/Qualifiers
source                  1..100
                        mol_type = genomic DNA
                        organism = Homo sapiens
SEQUENCE: 410
tccaaaacac ccttcgacgc cagcaaaata caatgcgcct cggccgccgt aaacagccgg    60
gagggagagc acacattcgg cgcggcgcgg ccgccggctc                         100

SEQ ID NO: 411          moltype = DNA  length = 100
FEATURE                 Location/Qualifiers
source                  1..100
                        mol_type = genomic DNA
                        organism = Homo sapiens
SEQUENCE: 411
ggctcccacc cccttcccgt tcctagaaaa tgccataaaa gcgggcaggg cgcggggagg    60
gcggctgcgc gcccggcggc cggggctccc ttcccgcgcc                         100

SEQ ID NO: 412          moltype = DNA  length = 100
FEATURE                 Location/Qualifiers
source                  1..100
                        mol_type = genomic DNA
                        organism = Homo sapiens
SEQUENCE: 412
tatgaaacag ccagtgctac gtctcctta taccaaaact ggtagcctga agagctctca    60
ggcttaccta taaacgatgt tcagtgaatg caggtagccc                         100

SEQ ID NO: 413          moltype = DNA  length = 100
FEATURE                 Location/Qualifiers
source                  1..100
```

```
                        mol_type = genomic DNA
                        organism = Homo sapiens
SEQUENCE: 413
aaggcactgg ctatttcagc agcatagaaa cgagcccgtg gttccaggaa gcagcgttcc    60
ctctggagat ggtagaacaa ctgcaggaga cagaacaaag                         100

SEQ ID NO: 414          moltype = DNA   length = 100
FEATURE                 Location/Qualifiers
source                  1..100
                        mol_type = genomic DNA
                        organism = Homo sapiens
SEQUENCE: 414
tcattctggg ttgcaaatga atttaattag ttttgacata cacagcaaaa gaacaactgc    60
aggaagtggc cccaagtaat ctattaacta taaacctgac                         100

SEQ ID NO: 415          moltype = DNA   length = 100
FEATURE                 Location/Qualifiers
source                  1..100
                        mol_type = genomic DNA
                        organism = Homo sapiens
SEQUENCE: 415
aggttgaagg aaatgctaat tctggtaaca ttctccccac caaaaatctt tgaaaacttt    60
tttctcaaac taaaacaaag caggctgtgc agagacacta                         100

SEQ ID NO: 416          moltype = DNA   length = 100
FEATURE                 Location/Qualifiers
source                  1..100
                        mol_type = genomic DNA
                        organism = Homo sapiens
SEQUENCE: 416
agagttgact tctatccccc ctgctcacct ctccaccatt aatgtagtct aggacaaagt    60
acaatttgtc agcagtctgg aaagagaagt gaaggcccac                         100

SEQ ID NO: 417          moltype = DNA   length = 100
FEATURE                 Location/Qualifiers
source                  1..100
                        mol_type = genomic DNA
                        organism = Homo sapiens
SEQUENCE: 417
caggaaaggg tgcttcacat tcttcaacag aacattccgc tccgacataa tatgcttctc    60
ctaggaaaat gacgattcag atttagtggc atgtttcaac                         100

SEQ ID NO: 418          moltype = DNA   length = 100
FEATURE                 Location/Qualifiers
source                  1..100
                        mol_type = genomic DNA
                        organism = Homo sapiens
SEQUENCE: 418
gaggacatga aggaagtgta ccaaaagatc ttcagatttg aaattacctt tccaaaactg    60
cccttttccga tcactttcaa gaagtgaaag tcagatggtt                         100

SEQ ID NO: 419          moltype = DNA   length = 100
FEATURE                 Location/Qualifiers
source                  1..100
                        mol_type = genomic DNA
                        organism = Homo sapiens
SEQUENCE: 419
tagcatgagg attggacgac gggccaaggt tgatttgctg agaaggactt ggctagaaaa    60
aaaaaaaaag aatttctttt aataccattg cttcaaagga                         100

SEQ ID NO: 420          moltype = DNA   length = 100
FEATURE                 Location/Qualifiers
source                  1..100
                        mol_type = genomic DNA
                        organism = Homo sapiens
SEQUENCE: 420
aatttctttt aataccattg cttcaaagga agacatctat aacataaacg atgtagaaaa    60
tgttacatct acaaatgact gatgcaaatg accatacatc                         100

SEQ ID NO: 421          moltype = DNA   length = 100
FEATURE                 Location/Qualifiers
source                  1..100
                        mol_type = genomic DNA
                        organism = Homo sapiens
SEQUENCE: 421
aataaaataa tactctgact caatacttaa atatttatat cacttgttat gccataatga    60
agcattcctg ccttgatact aatttctaga aatgctattt                         100

SEQ ID NO: 422          moltype = DNA   length = 100
```

-continued

| | | |
|---|---|---|
| FEATURE | Location/Qualifiers | |
| source | 1..100 | |
| | mol_type = genomic DNA | |
| | organism = Homo sapiens | |

SEQUENCE: 422
taatccatta atgtaggaat actaactgac tcccttacag ttctccacag atgcacggca    60
catacaaaaa cttactggag gagaagggtt ggcattcata                         100

| | | |
|---|---|---|
| SEQ ID NO: 423 | moltype = DNA  length = 100 | |
| FEATURE | Location/Qualifiers | |
| source | 1..100 | |
| | mol_type = genomic DNA | |
| | organism = Homo sapiens | |

SEQUENCE: 423
agctcaggct cctgaggttg ggagatcttc aagatggact gaacttcagg gctgcaggga    60
ataaagggca cgatttagaa tccagctcgc cactaggggg                         100

| | | |
|---|---|---|
| SEQ ID NO: 424 | moltype = DNA  length = 100 | |
| FEATURE | Location/Qualifiers | |
| source | 1..100 | |
| | mol_type = genomic DNA | |
| | organism = Homo sapiens | |

SEQUENCE: 424
cacaccaaca tcaaaagtga gtttctggct ctaccgactt ctaccggat aattcactgt     60
ttaaactgaa aatacccccaa tacattagtc agttaaagaa                        100

| | | |
|---|---|---|
| SEQ ID NO: 425 | moltype = DNA  length = 100 | |
| FEATURE | Location/Qualifiers | |
| source | 1..100 | |
| | mol_type = genomic DNA | |
| | organism = Homo sapiens | |

SEQUENCE: 425
aataataaac cccattaaat acagaaataa ggattgttgc tcatggagaa aggccgtgaa    60
ttcggccaac acgaaccatt tatcttacat ctccagttca                         100

| | | |
|---|---|---|
| SEQ ID NO: 426 | moltype = DNA  length = 100 | |
| FEATURE | Location/Qualifiers | |
| source | 1..100 | |
| | mol_type = genomic DNA | |
| | organism = Homo sapiens | |

SEQUENCE: 426
agccaaatca gcaaattaac tttaatgttt aaaatgtgtc aaatatatta gaatttaagg    60
agaaatgaga tccccacccc agaagaagtc ttcgccttcc                         100

| | | |
|---|---|---|
| SEQ ID NO: 427 | moltype = DNA  length = 100 | |
| FEATURE | Location/Qualifiers | |
| source | 1..100 | |
| | mol_type = genomic DNA | |
| | organism = Homo sapiens | |

SEQUENCE: 427
cgataaacgc cgtgatgaga atgtttaccg ctggcaaatt caaactatac tagttatttc    60
ctcaaatccg gtcaaactta ctgtttgcat gcataggagt                         100

| | | |
|---|---|---|
| SEQ ID NO: 428 | moltype = DNA  length = 100 | |
| FEATURE | Location/Qualifiers | |
| source | 1..100 | |
| | mol_type = genomic DNA | |
| | organism = Homo sapiens | |

SEQUENCE: 428
tattggcaat cttctgaata aagtcgttca gacccatcct cctctgcttc atgaaagctg    60
tggatgaagg aggagaaata aagaaacgtt tagacggctt                         100

| | | |
|---|---|---|
| SEQ ID NO: 429 | moltype = DNA  length = 100 | |
| FEATURE | Location/Qualifiers | |
| source | 1..100 | |
| | mol_type = genomic DNA | |
| | organism = Homo sapiens | |

SEQUENCE: 429
cataacgtcc ggcgccacac acactaatct gatccgggac tttcaaaaaa tttccacttt    60
gcgtctcctg gagcagaagt cccgcaagat tcctgcactc                         100

| | | |
|---|---|---|
| SEQ ID NO: 430 | moltype = DNA  length = 100 | |
| FEATURE | Location/Qualifiers | |
| source | 1..100 | |
| | mol_type = genomic DNA | |
| | organism = Homo sapiens | |

SEQUENCE: 430
accgatgaga attgccacca tgcccctcat cctggagtaa gtgagggtgc ccttagcagc    60
ctcagttttc accgtcatca ccaccgcggg gagacagaaa                         100

```
SEQ ID NO: 431         moltype = DNA   length = 100
FEATURE                Location/Qualifiers
source                 1..100
                       mol_type = genomic DNA
                       organism = Homo sapiens
SEQUENCE: 431
gacgttagcg ctcaaagacc ggctcggcgt atgctgcgcc aggccgcgcg ctcggcctta    60
taaaaaggc accgccgcgg gggcggggcc tgcgcgacag                           100

SEQ ID NO: 432         moltype = DNA   length = 100
FEATURE                Location/Qualifiers
source                 1..100
                       mol_type = genomic DNA
                       organism = Homo sapiens
SEQUENCE: 432
agggtgagag gagtcaccag gtaaagatgg gttggaagga cctggcaggc agagcaggga    60
gcaggacccc agtccaggga agcagggaag cgggagtctg                          100

SEQ ID NO: 433         moltype = DNA   length = 100
FEATURE                Location/Qualifiers
source                 1..100
                       mol_type = genomic DNA
                       organism = Homo sapiens
SEQUENCE: 433
ggcagagctg attccaggca gctcagtatt gctggcctgt gcatcctgag acttatccga    60
gtcgcaggtg aagctggtgg gaatcaggca gagtgcagag                          100

SEQ ID NO: 434         moltype = DNA   length = 100
FEATURE                Location/Qualifiers
source                 1..100
                       mol_type = genomic DNA
                       organism = Homo sapiens
SEQUENCE: 434
ctttagctgg ggcagggtta gccaagagcc tgtcatggag ctgctctctg ggcactggga    60
aacataagtc tggaggcttt ggctgcagct gcagataaag                          100

SEQ ID NO: 435         moltype = DNA   length = 100
FEATURE                Location/Qualifiers
source                 1..100
                       mol_type = genomic DNA
                       organism = Homo sapiens
SEQUENCE: 435
atgcaggggc ctctgacgat gggggcctta gtcatctcag aggtggtgca gagggtagaa    60
gcctgactgg ggtcagagat gaggaaggag agggtcagaa                          100

SEQ ID NO: 436         moltype = DNA   length = 100
FEATURE                Location/Qualifiers
source                 1..100
                       mol_type = genomic DNA
                       organism = Homo sapiens
SEQUENCE: 436
acagtgattc taaaccaatt tggttgaggc agaagatact aatggccgag gggaggagag    60
agggagcgta ggctctaaag gggaagcttg ttaggaatga                          100

SEQ ID NO: 437         moltype = DNA   length = 100
FEATURE                Location/Qualifiers
source                 1..100
                       mol_type = genomic DNA
                       organism = Homo sapiens
SEQUENCE: 437
agacagaggc gcaggcacag ccctttcatc agctgaccag gagtgctcgg cccggcctgc    60
caggaacctc ttatcaaact ccaccggctg cctgcatcta                          100

SEQ ID NO: 438         moltype = DNA   length = 100
FEATURE                Location/Qualifiers
source                 1..100
                       mol_type = genomic DNA
                       organism = Homo sapiens
SEQUENCE: 438
caattcaagt ccatggctaa ccttctgtta gagacagaaa ttctgctgca gccagcaagt    60
ttgctggtgt acagggcacc gcttcatggg cctagtagga                          100

SEQ ID NO: 439         moltype = DNA   length = 100
FEATURE                Location/Qualifiers
source                 1..100
                       mol_type = genomic DNA
                       organism = Homo sapiens
SEQUENCE: 439
```

```
agcgaagctg aaaggcaact tccgaaagcc agtctcctct cccaaacgcc ctttaatatc    60
tccccagttg gatctggggc gcctgtggtt tcggacccdtt                         100

SEQ ID NO: 440          moltype = DNA   length = 100
FEATURE                 Location/Qualifiers
source                  1..100
                        mol_type = genomic DNA
                        organism = Homo sapiens
SEQUENCE: 440
aggagctctg agaactggtg tgtgtggtcg gaagccatct gagtctccct gtgatttgga    60
cttttttaaga aacttctaag ttgtattact atacccttta                        100

SEQ ID NO: 441          moltype = DNA   length = 100
FEATURE                 Location/Qualifiers
source                  1..100
                        mol_type = genomic DNA
                        organism = Homo sapiens
SEQUENCE: 441
ttcccttgtc atatgacttc catcctcagc actacaatat tatcattaat gtttaaatca    60
ttgtcaagtc tgtgattgcc ttagagattt attaagaata                         100

SEQ ID NO: 442          moltype = DNA   length = 100
FEATURE                 Location/Qualifiers
source                  1..100
                        mol_type = genomic DNA
                        organism = Homo sapiens
SEQUENCE: 442
acatgctagg attaggaaag tttaactttt taccatcctt aaaattagat ttttgaaaac    60
tgtcttatcc ccattaaaga aaaaaataaa aaggatgaat                         100

SEQ ID NO: 443          moltype = DNA   length = 100
FEATURE                 Location/Qualifiers
source                  1..100
                        mol_type = genomic DNA
                        organism = Homo sapiens
SEQUENCE: 443
tatacatacc tgcacatata tacagcatat gtatatgtgt ctgtattata tgtattaaat    60
gaaagattat ccacattttg ttctttagga tcttcagcag                         100

SEQ ID NO: 444          moltype = DNA   length = 100
FEATURE                 Location/Qualifiers
source                  1..100
                        mol_type = genomic DNA
                        organism = Homo sapiens
SEQUENCE: 444
ctctcttccc atcacaatag aaaggcctga gctaacattt ccatttctgc aaaaggcaga    60
ttttgttcaa ttaaaaatta taatgcctta aatttccaca                         100

SEQ ID NO: 445          moltype = DNA   length = 100
FEATURE                 Location/Qualifiers
source                  1..100
                        mol_type = genomic DNA
                        organism = Homo sapiens
SEQUENCE: 445
gacatttaag agacttcgtt ttcactgtga taaacaggtt tgatttggac ttataacttt    60
tttctaaaat tatcaaatta ataacgacta taatgaaata                         100

SEQ ID NO: 446          moltype = DNA   length = 100
FEATURE                 Location/Qualifiers
source                  1..100
                        mol_type = genomic DNA
                        organism = Homo sapiens
SEQUENCE: 446
gaggcaaata ttttagagga ttcattcctt ggggtaacat ttgttctata atttatagtc    60
tcataatgtt gagagattaa agcatttaaa taacattgtc                         100

SEQ ID NO: 447          moltype = DNA   length = 100
FEATURE                 Location/Qualifiers
source                  1..100
                        mol_type = genomic DNA
                        organism = Homo sapiens
SEQUENCE: 447
aactaacttt cagcttacct ttcttaagga aaaaaacaa aaaatgttta aaatagaca      60
tgtatttttc aaacatacaa ttcatgtttt tatgtcatta                         100

SEQ ID NO: 448          moltype = DNA   length = 100
FEATURE                 Location/Qualifiers
source                  1..100
                        mol_type = genomic DNA
```

```
                            organism = Homo sapiens
SEQUENCE: 448
aagagatgtg agggacttat aaataatatt aagataacag gaattaaagt ctcggtgtgt      60
gaaaatactg tatatctagg atgcacataa aaactgccct                           100

SEQ ID NO: 449          moltype = DNA   length = 100
FEATURE                 Location/Qualifiers
source                  1..100
                        mol_type = genomic DNA
                        organism = Homo sapiens
SEQUENCE: 449
tacagatctt gcagggaaaa gtacctgact atactgtata agacttctgc tgtaccattt      60
aatcatacca aaaaaaatgg aatcaacaca caaatagatt                           100

SEQ ID NO: 450          moltype = DNA   length = 100
FEATURE                 Location/Qualifiers
source                  1..100
                        mol_type = genomic DNA
                        organism = Homo sapiens
SEQUENCE: 450
tcttttccac tgttctcaat ttaaaaataa ttggagaaat gtgtgctttg tttagaagag      60
taaggaaaa cattcattca atagtaccat gcagaatgat                            100

SEQ ID NO: 451          moltype = DNA   length = 100
FEATURE                 Location/Qualifiers
source                  1..100
                        mol_type = genomic DNA
                        organism = Homo sapiens
SEQUENCE: 451
cagaaaaata gaaagattat catcggattt gggaatcaaa gacagctcag caaaatacta      60
ggacatggct catataagat ggaataagcc tggaaataca                           100

SEQ ID NO: 452          moltype = DNA   length = 100
FEATURE                 Location/Qualifiers
source                  1..100
                        mol_type = genomic DNA
                        organism = Homo sapiens
SEQUENCE: 452
ctttagggga tagctctgca aggggagagg ttcgggactg tggcgcgcac tgcgcgctgc      60
gccaggtttc cgcaccaaga ccccttttaac tcaagactgc                          100

SEQ ID NO: 453          moltype = DNA   length = 100
FEATURE                 Location/Qualifiers
source                  1..100
                        mol_type = genomic DNA
                        organism = Homo sapiens
SEQUENCE: 453
ctcccgcttt gtgtgccccg ctccagcagc ctcccgcgac gatgcccctc aacgttagct      60
tcaccaacag gaactatgac ctcgactacg actcggtgca                           100

SEQ ID NO: 454          moltype = DNA   length = 100
FEATURE                 Location/Qualifiers
source                  1..100
                        mol_type = genomic DNA
                        organism = Homo sapiens
SEQUENCE: 454
gccgtatttc tactgcgacg aggaggagaa cttctaccag cagcagcagc agagcgagct      60
gcagcccccg gcgcccagcg aggatatctg gaagaaattc                           100

SEQ ID NO: 455          moltype = DNA   length = 100
FEATURE                 Location/Qualifiers
source                  1..100
                        mol_type = genomic DNA
                        organism = Homo sapiens
SEQUENCE: 455
gagctgctgc ccaccccgcc cctgtccct agccgccgct ccgggctctg ctcgccctcc       60
tacgttgcgg tcacacccct ctcccttcgg ggagacaacg                           100

SEQ ID NO: 456          moltype = DNA   length = 100
FEATURE                 Location/Qualifiers
source                  1..100
                        mol_type = genomic DNA
                        organism = Homo sapiens
SEQUENCE: 456
acggcggtgg cgggagcttc tccacggccg accagctgga gatggtgacc gagctgctgg      60
gaggagacat ggtgaaccag agtttcatct gcgacccgga                           100

SEQ ID NO: 457          moltype = DNA   length = 100
FEATURE                 Location/Qualifiers
```

```
source                  1..100
                        mol_type = genomic DNA
                        organism = Homo sapiens
SEQUENCE: 457
cgacgagacc ttcatcaaaa acatcatcat ccaggactgt atgtggagcg gcttctcggc    60
cgccgccaag ctcgtctcag agaagctggc ctcctaccag                         100

SEQ ID NO: 458          moltype = DNA  length = 100
FEATURE                 Location/Qualifiers
source                  1..100
                        mol_type = genomic DNA
                        organism = Homo sapiens
SEQUENCE: 458
gctgcgcgca aagacagcgg cagcccgaac cccgcccgcg gccacagcgt ctgctccacc    60
tccagcttgt acctgcagga tctgagcgcc gccgcctcag                         100

SEQ ID NO: 459          moltype = DNA  length = 100
FEATURE                 Location/Qualifiers
source                  1..100
                        mol_type = genomic DNA
                        organism = Homo sapiens
SEQUENCE: 459
agtgcatcga ccctcggtg gtcttcccct accctctcaa cgacagcagc tcgcccaagt    60
cctgcgcctc gcaagactcc agcgccttct ctccgtcctc                         100

SEQ ID NO: 460          moltype = DNA  length = 100
FEATURE                 Location/Qualifiers
source                  1..100
                        mol_type = genomic DNA
                        organism = Homo sapiens
SEQUENCE: 460
ggattctctg ctctcctcga cggagtcctc cccgcagggc agccccgagc ccctggtgct    60
ccatgaggag acaccgccca ccaccagcag cgactctggt                         100

SEQ ID NO: 461          moltype = DNA  length = 100
FEATURE                 Location/Qualifiers
source                  1..100
                        mol_type = genomic DNA
                        organism = Homo sapiens
SEQUENCE: 461
gctccccatc tgtccccaca gttgctcctt ggctgagcca agggcttgct cacctctcag    60
agcattgccc taactggttt gttttgggct tacattgcaa                         100

SEQ ID NO: 462          moltype = DNA  length = 100
FEATURE                 Location/Qualifiers
source                  1..100
                        mol_type = genomic DNA
                        organism = Homo sapiens
SEQUENCE: 462
gatcaggtcc tccccagagc caggctggag tccgaggcag aaaaggctgt ggagggcact    60
ggggtcacca cagactggaa accggttggg cgcaggcccc                         100

SEQ ID NO: 463          moltype = DNA  length = 100
FEATURE                 Location/Qualifiers
source                  1..100
                        mol_type = genomic DNA
                        organism = Homo sapiens
SEQUENCE: 463
aaaccttgag gaatcgtttg ggctgggacc agaacagggg gctcctctgc acagagctcc    60
ccaccgcttt ggtggattac ttcagactca gaaaattgac                         100

SEQ ID NO: 464          moltype = DNA  length = 100
FEATURE                 Location/Qualifiers
source                  1..100
                        mol_type = genomic DNA
                        organism = Homo sapiens
SEQUENCE: 464
acaaagagaa actgacctgc ccgcagccag ccctggctgc ctacacaagc tttcccctgc    60
ttgccaggcc actcagcact gcgtggcaga cacggacatg                         100

SEQ ID NO: 465          moltype = DNA  length = 100
FEATURE                 Location/Qualifiers
source                  1..100
                        mol_type = genomic DNA
                        organism = Homo sapiens
SEQUENCE: 465
ctcgccccgg gaagctcacc ttcactccag ccgggtctct gctgcctttg ttaaataggg    60
gacctgcggc taggaaaagct ggatcccagg ctgttgggat                        100
```

-continued

```
SEQ ID NO: 466          moltype = DNA   length = 100
FEATURE                 Location/Qualifiers
source                  1..100
                        mol_type = genomic DNA
                        organism = Homo sapiens
SEQUENCE: 466
gggggggagc gggtgggag gaccaggcat gggacggct cctagcccgg gagcaactcc     60
ctgacctgaa gcccgcagag accccgagcg gcacccgagc                         100

SEQ ID NO: 467          moltype = DNA   length = 100
FEATURE                 Location/Qualifiers
source                  1..100
                        mol_type = genomic DNA
                        organism = Homo sapiens
SEQUENCE: 467
cgaggctgcc gaagcctgtc accttcctcc agcctggctc tgcagcaaac agaaaggaaa   60
cgcgattcgt tccacttgga atttccttga aatctccgaa                         100

SEQ ID NO: 468          moltype = DNA   length = 100
FEATURE                 Location/Qualifiers
source                  1..100
                        mol_type = genomic DNA
                        organism = Homo sapiens
SEQUENCE: 468
tctaatccgg cgttaactca ccgtgagagg agcgctcatc tcacaggagg ctgtggtaat   60
gggtgaattg gcaggatccc tgcgggccag gcagccaggc                         100

SEQ ID NO: 469          moltype = DNA   length = 100
FEATURE                 Location/Qualifiers
source                  1..100
                        mol_type = genomic DNA
                        organism = Homo sapiens
SEQUENCE: 469
ttttcgtttc ttatcctctt tttttaaagg ggagaagcca tgagaaaagg cgtcctgcag   60
agaaggaccc aatggggtct ttaagggtct ctgtatgaac                         100

SEQ ID NO: 470          moltype = DNA   length = 100
FEATURE                 Location/Qualifiers
source                  1..100
                        mol_type = genomic DNA
                        organism = Homo sapiens
SEQUENCE: 470
tggccggctc ctaagcagaa gctgaactca gaaaccgcta cttccttgat ttttcaaagc   60
cccctcctca actccaggac gcctttggag ccctagcccc                         100

SEQ ID NO: 471          moltype = DNA   length = 100
FEATURE                 Location/Qualifiers
source                  1..100
                        mol_type = genomic DNA
                        organism = Homo sapiens
SEQUENCE: 471
tgtcgccgcc ggagccttga aaggctgcag ctcgctgccc aagctacgcg ttgccggagg   60
cgggattccc aggtgcctca gcccgggcgg ccaagtgcgt                         100

SEQ ID NO: 472          moltype = DNA   length = 100
FEATURE                 Location/Qualifiers
source                  1..100
                        mol_type = genomic DNA
                        organism = Homo sapiens
SEQUENCE: 472
tgtttcaggt cccctgcctg ggatccctgc actttgcaaa gttagctgcg cggctgcaga   60
ggtccgagat ccttccggcc ttagtacctg acccacggtc                         100

SEQ ID NO: 473          moltype = DNA   length = 100
FEATURE                 Location/Qualifiers
source                  1..100
                        mol_type = genomic DNA
                        organism = Homo sapiens
SEQUENCE: 473
cggcacccc aaccggtcc cggcgggaga gtgagagaag cgagctcgcc gcctacttac     60
tatgcatgga tgcaaacggg tcgtgcttac agtgtatttc                         100

SEQ ID NO: 474          moltype = DNA   length = 100
FEATURE                 Location/Qualifiers
source                  1..100
                        mol_type = genomic DNA
                        organism = Homo sapiens
SEQUENCE: 474
catcggggcg ctccagactg caggccggcc cacgccgccg cctcccggcg ccaagggget   60
```

-continued

```
gcccagggcg atagggagc ctcgccacca ggccaggcac                              100

SEQ ID NO: 475          moltype = DNA   length = 100
FEATURE                 Location/Qualifiers
source                  1..100
                        mol_type = genomic DNA
                        organism = Homo sapiens
SEQUENCE: 475
tgtgcgagct gggctcagaa aacactgctg gagcttcggg gtctctctca gagcctccct        60
gctggagacc gcccggagct gcgcggagag gcgggaaatg                             100

SEQ ID NO: 476          moltype = DNA   length = 100
FEATURE                 Location/Qualifiers
source                  1..100
                        mol_type = genomic DNA
                        organism = Homo sapiens
SEQUENCE: 476
gtgctagcgc acccgggcta ggagcgggtg cccaactccg gctggcttcc ctccctggct        60
ggctcaagca gcagctccgg gcccagcccg gggtagctgc                             100

SEQ ID NO: 477          moltype = DNA   length = 100
FEATURE                 Location/Qualifiers
source                  1..100
                        mol_type = genomic DNA
                        organism = Homo sapiens
SEQUENCE: 477
ggccaaggcg cccgcggctt cgggggcata gcgtaggggc ccgcctccgg gacagccagc        60
agcccccggc cccaggaagg agcagctttg aggaggccgc                             100

SEQ ID NO: 478          moltype = DNA   length = 100
FEATURE                 Location/Qualifiers
source                  1..100
                        mol_type = genomic DNA
                        organism = Homo sapiens
SEQUENCE: 478
cggaacaatc ggcccttgac ttcactcagg gggcggagag acccgggggc tgccaggctg        60
gttccgcggc ctcgatgctt ctgaggtccc tcctcgaccc                             100

SEQ ID NO: 479          moltype = DNA   length = 100
FEATURE                 Location/Qualifiers
source                  1..100
                        mol_type = genomic DNA
                        organism = Homo sapiens
SEQUENCE: 479
cacacaggca aacaactttt ggacacaaac tcatatattt ttacatcttt taaaaataca        60
tatactgtaa tgaacacact gagtcccttaa tataaacaca                            100

SEQ ID NO: 480          moltype = DNA   length = 100
FEATURE                 Location/Qualifiers
source                  1..100
                        mol_type = genomic DNA
                        organism = Homo sapiens
SEQUENCE: 480
caggccctaa cttgcagacc cccggaagga cgccagcgtg aacattcaga acagagaaa        60
aacacagaca aactcacaga tatttggact gatgcagaag                             100

SEQ ID NO: 481          moltype = DNA   length = 100
FEATURE                 Location/Qualifiers
source                  1..100
                        mol_type = genomic DNA
                        organism = Homo sapiens
SEQUENCE: 481
acagtttgaa gtgtgagcct gaacatgttt gatctaaggt ctggaggaag atgtgaagca        60
aatctgacct aaaaaaaatt ataggaaaaa agcaaattgt                             100

SEQ ID NO: 482          moltype = DNA   length = 100
FEATURE                 Location/Qualifiers
source                  1..100
                        mol_type = genomic DNA
                        organism = Homo sapiens
SEQUENCE: 482
tctggatttg tttcaccaag gaacaagtaa gcagagaacc agacactgga gaaaaaaagg        60
agtcaggaag tagacaagga aatgttaaaa gaaataatag                             100

SEQ ID NO: 483          moltype = DNA   length = 100
FEATURE                 Location/Qualifiers
source                  1..100
                        mol_type = genomic DNA
                        organism = Homo sapiens
```

```
SEQUENCE: 483
gataactgaa agaatgtagc ttccagattg ctagctatca gcagatagat agaaactttt    60
atacagcctt taaatcttcc ctagaaacct ttttaaaagt                         100

SEQ ID NO: 484          moltype = DNA   length = 100
FEATURE                 Location/Qualifiers
source                  1..100
                        mol_type = genomic DNA
                        organism = Homo sapiens
SEQUENCE: 484
caagggcctg ccaggatgag aacgggcaaa cctggccaag gtgacccat tagggactac     60
cctcctaggg acagcactca gggccgttcc caatcacccc                         100

SEQ ID NO: 485          moltype = DNA   length = 100
FEATURE                 Location/Qualifiers
source                  1..100
                        mol_type = genomic DNA
                        organism = Homo sapiens
SEQUENCE: 485
ggatttcctg tcctgctcgt ctcctgccac acctcctttt gatctacccc caagacaccc    60
ctacctttt attctgtgaa aatttactca tgctgtgggc                          100

SEQ ID NO: 486          moltype = DNA   length = 100
FEATURE                 Location/Qualifiers
source                  1..100
                        mol_type = genomic DNA
                        organism = Homo sapiens
SEQUENCE: 486
cctgctggaa atgccctcct actgtttccc caaaccccgt cagaaattcc acggggaaac    60
tcccttccct tctgctgcag gcaccgtcac tgtgtctctc                         100

SEQ ID NO: 487          moltype = DNA   length = 100
FEATURE                 Location/Qualifiers
source                  1..100
                        mol_type = genomic DNA
                        organism = Homo sapiens
SEQUENCE: 487
agctctgccc cccagcctct gagtaccacc ttatcctagc ccttagctac tggcttgtca    60
ttgtctcttt acgttctcag cctcccacag aagcctggga                         100

SEQ ID NO: 488          moltype = DNA   length = 100
FEATURE                 Location/Qualifiers
source                  1..100
                        mol_type = genomic DNA
                        organism = Homo sapiens
SEQUENCE: 488
aggcacactc gcccctggtc tccaaggctc tgggtcctca gactggctga gtactgggga    60
ccaaggtcac ccaagaagcc ctgagtggcc ctcttgaggg                         100

SEQ ID NO: 489          moltype = DNA   length = 100
FEATURE                 Location/Qualifiers
source                  1..100
                        mol_type = genomic DNA
                        organism = Homo sapiens
SEQUENCE: 489
ttagcagagc ttctctctgt ccaagacagg tcaggctctc tccccctggcc ccagctccac    60
cgtcactcag aggagtggcc taaacaaacg ctgcaggtga                         100

SEQ ID NO: 490          moltype = DNA   length = 100
FEATURE                 Location/Qualifiers
source                  1..100
                        mol_type = genomic DNA
                        organism = Homo sapiens
SEQUENCE: 490
ggctcccgag cccctgacat ggatgtttat ggaagaggac tcttggcatc agcacctggg    60
caaggtgggt agaggcagga gtgggcaaat gggaaagtct                         100

SEQ ID NO: 491          moltype = DNA   length = 100
FEATURE                 Location/Qualifiers
source                  1..100
                        mol_type = genomic DNA
                        organism = Homo sapiens
SEQUENCE: 491
ggagagccgt ttgagattca ccaggtgaat gaaccccggt ttttttctgg gtaacaggtc    60
gaatgtgaat tacttatttt cacaagctct tgacatgttc                         100

SEQ ID NO: 492          moltype = DNA   length = 100
FEATURE                 Location/Qualifiers
source                  1..100
```

```
                        mol_type = genomic DNA
                        organism = Homo sapiens
SEQUENCE: 492
cgtcaaattg ctgttcccca aagagtggac tctggtgaca tataagtgtg tgggaccatt    60
gcatcttacc ccagagatcc actcctgatc tggcattatt                         100

SEQ ID NO: 493          moltype = DNA   length = 100
FEATURE                 Location/Qualifiers
source                  1..100
                        mol_type = genomic DNA
                        organism = Homo sapiens
SEQUENCE: 493
caaaatctgc tgaattcaaa acgatcctgt acttcctgct caccaggtct gaaaagaaaa    60
aagaaaaaag aagaaggaaa gactacacct gacaaaagac                         100

SEQ ID NO: 494          moltype = DNA   length = 100
FEATURE                 Location/Qualifiers
source                  1..100
                        mol_type = genomic DNA
                        organism = Homo sapiens
SEQUENCE: 494
ttcacggttt ctctttagtt ttatctgaaa tacatttgta agcttagggt gcaatttgga    60
ttaaaacagt tttctttagt gtcaataatg gcctttacta                         100

SEQ ID NO: 495          moltype = DNA   length = 100
FEATURE                 Location/Qualifiers
source                  1..100
                        mol_type = genomic DNA
                        organism = Homo sapiens
SEQUENCE: 495
gagtgaatgg atattttcc attctggatt atcgtttaat cgaaactttg tttcctgtgg     60
aaattttct ggtttaagtt atttgatttg ggagataaat                          100

SEQ ID NO: 496          moltype = DNA   length = 100
FEATURE                 Location/Qualifiers
source                  1..100
                        mol_type = genomic DNA
                        organism = Homo sapiens
SEQUENCE: 496
catgtaactt aataaacttt ggcatcctgg ttaactgaaa ttgcttcatt caatatttga    60
agactgaaat ctgtattgtt gcctgtacct aaattatggg                         100

SEQ ID NO: 497          moltype = DNA   length = 100
FEATURE                 Location/Qualifiers
source                  1..100
                        mol_type = genomic DNA
                        organism = Homo sapiens
SEQUENCE: 497
ggacagacag ggagagatga ctgagttaga tgagacgagg gggcgggctg ggggtgcgag    60
aaggaagctt ggcaaggaga ctaggtctag ggggaccaca                         100

SEQ ID NO: 498          moltype = DNA   length = 100
FEATURE                 Location/Qualifiers
source                  1..100
                        mol_type = genomic DNA
                        organism = Homo sapiens
SEQUENCE: 498
gtggggcagg ctgcatggaa aatatccgca gggtccccca ggcagaacag ccacgctcca    60
ggccaggctg tccctactgc ctggtggagg gggaacttga                         100

SEQ ID NO: 499          moltype = DNA   length = 100
FEATURE                 Location/Qualifiers
source                  1..100
                        mol_type = genomic DNA
                        organism = Homo sapiens
SEQUENCE: 499
cctctgggag ggcgccgctc ttgcatagct gagcgagccc gggtgcgctg gtctgtgtgg    60
aaggaggaag gcagggagag gtagaagggg tggaggagtc                         100

SEQ ID NO: 500          moltype = DNA   length = 100
FEATURE                 Location/Qualifiers
source                  1..100
                        mol_type = genomic DNA
                        organism = Homo sapiens
SEQUENCE: 500
ggggcaggcg gagcttgagg aaaccgcaga taagtttttt tctctttgaa agatagagat    60
taatacaact acttaaaaaa tatagtcaat aggttactaa                         100

SEQ ID NO: 501          moltype = DNA   length = 100
```

| | | |
|---|---|---|
| FEATURE | Location/Qualifiers | |
| source | 1..100 | |
| | mol_type = genomic DNA | |
| | organism = Homo sapiens | |

SEQUENCE: 501
```
gatattgctt agcgttaagt ttttaacgta attttaatag cttaagattt taagagaaaa    60
tatgaagact tagaagagta gcatgaggaa ggaaaagata                         100
```

| | | |
|---|---|---|
| SEQ ID NO: 502 | moltype = DNA   length = 100 | |
| FEATURE | Location/Qualifiers | |
| source | 1..100 | |
| | mol_type = genomic DNA | |
| | organism = Homo sapiens | |

SEQUENCE: 502
```
aaaggtttct aaaacatgac ggaggttgag atgaagcttc ttcatggagt aaaaaatgta    60
tttaaaagaa aattgagaga aaggactaca gagccccgaa                         100
```

| | | |
|---|---|---|
| SEQ ID NO: 503 | moltype = DNA   length = 100 | |
| FEATURE | Location/Qualifiers | |
| source | 1..100 | |
| | mol_type = genomic DNA | |
| | organism = Homo sapiens | |

SEQUENCE: 503
```
ttaataccaa tagaagggca atgcttttag attaaaatga aggtgactta aacagcttaa    60
agtttagttt aaaagttgta ggtgattaaa ataatttgaa                         100
```

| | | |
|---|---|---|
| SEQ ID NO: 504 | moltype = DNA   length = 100 | |
| FEATURE | Location/Qualifiers | |
| source | 1..100 | |
| | mol_type = genomic DNA | |
| | organism = Homo sapiens | |

SEQUENCE: 504
```
ttggagaagt atagaagata gaaaatata aagccaaaaa ttggataaaa tagcactgaa     60
aaaatgagga aattattggt aaccaattta ttttaaaagc                         100
```

| | | |
|---|---|---|
| SEQ ID NO: 505 | moltype = DNA   length = 100 | |
| FEATURE | Location/Qualifiers | |
| source | 1..100 | |
| | mol_type = genomic DNA | |
| | organism = Homo sapiens | |

SEQUENCE: 505
```
ccatcaattt aatttctggt ggtgcagaag ttagaaggta aagcttgaga agatgagggt    60
gtttacgtag accagaacca atttagaaga atacttgaag                         100
```

| | | |
|---|---|---|
| SEQ ID NO: 506 | moltype = DNA   length = 100 | |
| FEATURE | Location/Qualifiers | |
| source | 1..100 | |
| | mol_type = genomic DNA | |
| | organism = Homo sapiens | |

SEQUENCE: 506
```
ctagaagggg aagttggtta aaaatcacat caaaaagcta ctaaaaggac tggtgtaatt    60
taaaaaaaac taaggcagaa ggcttttgga agagttagaa                         100
```

| | | |
|---|---|---|
| SEQ ID NO: 507 | moltype = DNA   length = 100 | |
| FEATURE | Location/Qualifiers | |
| source | 1..100 | |
| | mol_type = genomic DNA | |
| | organism = Homo sapiens | |

SEQUENCE: 507
```
tggtgtaaga gatgtgccag cggctggccg aggggcgctt agggctagag cccggggcgc    60
tgcagaggtt gagagtcagt gggtggggcg cagttatcaa                         100
```

| | | |
|---|---|---|
| SEQ ID NO: 508 | moltype = DNA   length = 100 | |
| FEATURE | Location/Qualifiers | |
| source | 1..100 | |
| | mol_type = genomic DNA | |
| | organism = Homo sapiens | |

SEQUENCE: 508
```
acaccagggc ccaaaagcag gctctagata ggttccaggt gctcaatttc tatttcacgt    60
ttggagtgag ccagtggaat tgtgaagttg tggcattttg                         100
```

| | | |
|---|---|---|
| SEQ ID NO: 509 | moltype = DNA   length = 100 | |
| FEATURE | Location/Qualifiers | |
| source | 1..100 | |
| | mol_type = genomic DNA | |
| | organism = Homo sapiens | |

SEQUENCE: 509
```
attcggttgc caagagttat cactgggcct tgcaggtgc caaataaatt tcaggacaga     60
gcctaaggca gagctctggc acaggaagga agtaaaacgt                         100
```

```
SEQ ID NO: 510        moltype = DNA  length = 100
FEATURE               Location/Qualifiers
source                1..100
                      mol_type = genomic DNA
                      organism = Homo sapiens
SEQUENCE: 510
ttaatgagca aatggacgca tgtttccaag cggtggtagg aagacagcag tttttggttg    60
tcttcctggt gatcagcatg gaaacctagt agtgctctta                         100

SEQ ID NO: 511        moltype = DNA  length = 100
FEATURE               Location/Qualifiers
source                1..100
                      mol_type = genomic DNA
                      organism = Homo sapiens
SEQUENCE: 511
ctctgatcaa tacattgtcg aaggcatgta cctgatgcta acgtaacaat aatattaaat    60
attgacttta tttgctatta tttattgcta acattaagta                         100

SEQ ID NO: 512        moltype = DNA  length = 100
FEATURE               Location/Qualifiers
source                1..100
                      mol_type = genomic DNA
                      organism = Homo sapiens
SEQUENCE: 512
ctgctacctg ctatgtgcta ggtttgtctc tgaagacttt acatgtattt ttcacgttta    60
attatcataa tcttaagaag caggtaccat aattatctcc                         100

SEQ ID NO: 513        moltype = DNA  length = 100
FEATURE               Location/Qualifiers
source                1..100
                      mol_type = genomic DNA
                      organism = Homo sapiens
SEQUENCE: 513
gggaaaaaga atgacgaaag gcaagacagt ggagcaagtg aggacacgct tcaccgagcc    60
agatctccac tcctcccagg gtatccacag ggacaagtca                         100

SEQ ID NO: 514        moltype = DNA  length = 100
FEATURE               Location/Qualifiers
source                1..100
                      mol_type = genomic DNA
                      organism = Homo sapiens
SEQUENCE: 514
cacctggcag aaagctaagt cactcagcta gaaacaggcc cagggaattc aacagaaggc    60
tgaagagcca ctgcttatgg aaataaagcc cctcctgtaa                         100

SEQ ID NO: 515        moltype = DNA  length = 100
FEATURE               Location/Qualifiers
source                1..100
                      mol_type = genomic DNA
                      organism = Homo sapiens
SEQUENCE: 515
agaactgcat ggcttttccc tcccaacccc aaacccatcc cacatctggc ttttgttgtg    60
tgaatcataa actgcccttt cttcaccaca gtgattcatg                         100

SEQ ID NO: 516        moltype = DNA  length = 100
FEATURE               Location/Qualifiers
source                1..100
                      mol_type = genomic DNA
                      organism = Homo sapiens
SEQUENCE: 516
aatcctctcc cactgtggat ctgtaaaatc tagacaggtc agtcagctcc cgcccttttaa   60
gagtttattt tccattctgt ggaagaagca gataaggaga                         100

SEQ ID NO: 517        moltype = DNA  length = 100
FEATURE               Location/Qualifiers
source                1..100
                      mol_type = genomic DNA
                      organism = Homo sapiens
SEQUENCE: 517
gctgctgtcc ttaggagaca tcctttagag gaagctggaa gacacgggtt caggccctgc    60
atcctcctct gagttgctat gtgactggga acaggatact                         100

SEQ ID NO: 518        moltype = DNA  length = 100
FEATURE               Location/Qualifiers
source                1..100
                      mol_type = genomic DNA
                      organism = Homo sapiens
SEQUENCE: 518
```

```
tcacctctcc attctttctc tcctttcct ttagggtcgg aatatggaac tagacaggaa    60
agtactttgg aggttttctt accgtaagga ggctggcatt                        100

SEQ ID NO: 519          moltype = DNA   length = 100
FEATURE                 Location/Qualifiers
source                  1..100
                        mol_type = genomic DNA
                        organism = Homo sapiens
SEQUENCE: 519
gggccctcca cccagcctca gttctatggg ggacgtggag tcaggcgatg atgtcctctg    60
aggcagcgtc catctcccct taacattaag gaataaggcc                        100

SEQ ID NO: 520          moltype = DNA   length = 100
FEATURE                 Location/Qualifiers
source                  1..100
                        mol_type = genomic DNA
                        organism = Homo sapiens
SEQUENCE: 520
agagggttct cgctcatttg ggaaaataaa aaaagcagga atggggcgct ggaaattcta    60
taagcttttc cccaccactc acaaaaacac agctgtgaaa                        100

SEQ ID NO: 521          moltype = DNA   length = 100
FEATURE                 Location/Qualifiers
source                  1..100
                        mol_type = genomic DNA
                        organism = Homo sapiens
SEQUENCE: 521
ataaatacca cccccaaac caagggtcta gggccaccaa cagtcctcct cctcctcctc    60
ctcctccttc cctcctcgt cctccagatc cagctgccaa                         100

SEQ ID NO: 522          moltype = DNA   length = 100
FEATURE                 Location/Qualifiers
source                  1..100
                        mol_type = genomic DNA
                        organism = Homo sapiens
SEQUENCE: 522
ccttctcctc ctcgtcctcc agatccagct gccaacagca tccccgctc ctgaagaaat    60
gcaccgccca gaagggaacg gcgaaagggg gaagaagtcc                        100

SEQ ID NO: 523          moltype = DNA   length = 100
FEATURE                 Location/Qualifiers
source                  1..100
                        mol_type = genomic DNA
                        organism = Homo sapiens
SEQUENCE: 523
aggggacccc cggcctctgg ccgagagctt gggtgggggc ctcggccgtc gccactcacc    60
cggggagggg aaaagctcca gatcgacttt ttccgtcttg                        100

SEQ ID NO: 524          moltype = DNA   length = 100
FEATURE                 Location/Qualifiers
source                  1..100
                        mol_type = genomic DNA
                        organism = Homo sapiens
SEQUENCE: 524
atgatggtga gagtcggctt gagatcgacg ccgccttca tggtgccagg agtgggggac    60
gtacgggatg gtagcaagtt tgcagttact gttgttttc                         100

SEQ ID NO: 525          moltype = DNA   length = 100
FEATURE                 Location/Qualifiers
source                  1..100
                        mol_type = genomic DNA
                        organism = Homo sapiens
SEQUENCE: 525
tttttaatga ggattagtaa caggggggaag gggacggggg aaatccgact tcttcccaa    60
aaatctcaaa ttcccgctgc ctttctttcc cccgcgcccg                        100

SEQ ID NO: 526          moltype = DNA   length = 100
FEATURE                 Location/Qualifiers
source                  1..100
                        mol_type = genomic DNA
                        organism = Homo sapiens
SEQUENCE: 526
gacggtgcgc gcccggcact ccaggggaag ttggcacttt gcggcgaagt gagcgcgctc    60
gggtcccagc ctcgccgcg ccgcgcccgc tcctcctgcc                         100

SEQ ID NO: 527          moltype = DNA   length = 100
FEATURE                 Location/Qualifiers
source                  1..100
                        mol_type = genomic DNA
```

```
                        organism = Homo sapiens
SEQUENCE: 527
gagtgagtag caaatattca tttatgaccc agtttttgtc caccctcagg cggggcatag    60
gactacagac attttttctag attacagcta ggatattatt                         100

SEQ ID NO: 528           moltype = DNA   length = 100
FEATURE                  Location/Qualifiers
source                   1..100
                         mol_type = genomic DNA
                         organism = Homo sapiens
SEQUENCE: 528
cctgagttta tgacaatgaa atggtttgag aaggcaatat tgtggggctt tcagagaggt    60
ttgctgagtg gctaggtgca tgcatgggtt taaccattaa                          100

SEQ ID NO: 529           moltype = DNA   length = 100
FEATURE                  Location/Qualifiers
source                   1..100
                         mol_type = genomic DNA
                         organism = Homo sapiens
SEQUENCE: 529
cttccctttt tgccttttta ttataagctg gttttgtctg tggctgtttt tttcttttaa    60
aattaattaa aacttctcaa aatttctaaa agtaaacaag                          100

SEQ ID NO: 530           moltype = DNA   length = 100
FEATURE                  Location/Qualifiers
source                   1..100
                         mol_type = genomic DNA
                         organism = Homo sapiens
SEQUENCE: 530
gcattctcta catacatcta catacatatt ttgcatttta aaaattggaa tatttgtcat    60
ttttctgtat tacccaaaag tatataaaca gttaccagag                          100

SEQ ID NO: 531           moltype = DNA   length = 100
FEATURE                  Location/Qualifiers
source                   1..100
                         mol_type = genomic DNA
                         organism = Homo sapiens
SEQUENCE: 531
atttatgtga gaagacagtt gtcacattac agatgtcaga ttagctataa aattgtttca    60
ttctagaaac ctaatatggt aaaaataaac cttacttatt                          100

SEQ ID NO: 532           moltype = DNA   length = 100
FEATURE                  Location/Qualifiers
source                   1..100
                         mol_type = genomic DNA
                         organism = Homo sapiens
SEQUENCE: 532
tagccattta tcagacaatt gcttttgttc agccagtttc ttgttctagc agtataaata    60
ttctttttat agaaagttac ttggtttgag aaataaacat                          100

SEQ ID NO: 533           moltype = DNA   length = 100
FEATURE                  Location/Qualifiers
source                   1..100
                         mol_type = genomic DNA
                         organism = Homo sapiens
SEQUENCE: 533
ataagcttaa ggtaggctag agatgaaaaa tttcagactt gtgtttgttt tggatttatt    60
gtacccttt c tactattatc tgagaaagct atttaggagt                         100

SEQ ID NO: 534           moltype = DNA   length = 100
FEATURE                  Location/Qualifiers
source                   1..100
                         mol_type = genomic DNA
                         organism = Homo sapiens
SEQUENCE: 534
ttaagaaata gtctagtttt aaaatagcaa tggtttgccg gacacagtgg ctcacccctg    60
taatcccagc attttgggag gccgaggtgg gcagattgct                          100

SEQ ID NO: 535           moltype = DNA   length = 100
FEATURE                  Location/Qualifiers
source                   1..100
                         mol_type = genomic DNA
                         organism = Homo sapiens
SEQUENCE: 535
gaatttgcca gttttcaata ttctgattca ctctgttaag ctagtaaggc agtctttaaa    60
ttacacagtc tgtgtgttat tttactactg ctcagagggc                          100

SEQ ID NO: 536           moltype = DNA   length = 100
FEATURE                  Location/Qualifiers
```

```
source                      1..100
                            mol_type = genomic DNA
                            organism = Homo sapiens
SEQUENCE: 536
attggagaag gttcccttgt gattagaact gttcatgttg agacatgaat cataaggcat    60
tccaaagttg gtttaaggtg tgtctgcttt agacactgtg                         100

SEQ ID NO: 537              moltype = DNA  length = 100
FEATURE                     Location/Qualifiers
source                      1..100
                            mol_type = genomic DNA
                            organism = Homo sapiens
SEQUENCE: 537
cccaggacta ttcttttgct ccagttttgc cttttgatta aatcaatatt atacctgagt    60
tttataaact actaagaatt tgttcccctt cctcactgtg                         100

SEQ ID NO: 538              moltype = DNA  length = 100
FEATURE                     Location/Qualifiers
source                      1..100
                            mol_type = genomic DNA
                            organism = Homo sapiens
SEQUENCE: 538
attttcttgc agtattttct tagaagagtc aactttaata acttaccccc aagtgcacgt    60
tcttgatatt atgaacttgc tattgttgtc ttcccagttt                         100

SEQ ID NO: 539              moltype = DNA  length = 100
FEATURE                     Location/Qualifiers
source                      1..100
                            mol_type = genomic DNA
                            organism = Homo sapiens
SEQUENCE: 539
tattgtagtt tttggaaggg ctcgttctgc ccaagagaag ttcctcctta cagctgattc    60
ggctgtctac catttgcacg ttggtgctgt tttgagtgct                         100

SEQ ID NO: 540              moltype = DNA  length = 100
FEATURE                     Location/Qualifiers
source                      1..100
                            mol_type = genomic DNA
                            organism = Homo sapiens
SEQUENCE: 540
acctcctgct ggtgaggctt catacagcac acagatggag ccatcctctc caattctgta    60
ggacacttca tagggtcaa cccagagtgt gagttcactt                          100

SEQ ID NO: 541              moltype = DNA  length = 100
FEATURE                     Location/Qualifiers
source                      1..100
                            mol_type = genomic DNA
                            organism = Homo sapiens
SEQUENCE: 541
gggagaagcc tgaacagctc ctgactgctc agtccaatcc gctgtgctgc ctgtccaatc    60
agaggatcca ttttatggtt gatgcgaata caacggtaac                        100

SEQ ID NO: 542              moltype = DNA  length = 100
FEATURE                     Location/Qualifiers
source                      1..100
                            mol_type = genomic DNA
                            organism = Homo sapiens
SEQUENCE: 542
ccgatcccctt gcatggcttt tctgggaacc agtgatgttt ataatgttct atagaagaaa    60
agaagaacag agaaacaacg cttaggatcg ttagctccca                        100

SEQ ID NO: 543              moltype = DNA  length = 100
FEATURE                     Location/Qualifiers
source                      1..100
                            mol_type = genomic DNA
                            organism = Homo sapiens
SEQUENCE: 543
ctgcggattc ctcctacccc aggctccttt gaggagcgaa atgaaaact atcaacttt     60
taaaatgtcc aggattgcat ccgttgttgt gcatgtgcgg                        100

SEQ ID NO: 544              moltype = DNA  length = 100
FEATURE                     Location/Qualifiers
source                      1..100
                            mol_type = genomic DNA
                            organism = Homo sapiens
SEQUENCE: 544
ggatggaaaa agcgggcagg gttttagaaa taacacagta gtaccggaca aaacaatctc    60
caggaaccaa ccggttgagc cgccaaaaca ggaatcaggc                        100
```

```
SEQ ID NO: 545          moltype = DNA   length = 100
FEATURE                 Location/Qualifiers
source                  1..100
                        mol_type = genomic DNA
                        organism = Homo sapiens
SEQUENCE: 545
gcgcagcctc ggccagtcgg gaagccactg gcacctatgg ccaggcgaga aactgtttac    60
tttctccacc ccaccccaga tgcacacaat ggagttgatg                          100

SEQ ID NO: 546          moltype = DNA   length = 100
FEATURE                 Location/Qualifiers
source                  1..100
                        mol_type = genomic DNA
                        organism = Homo sapiens
SEQUENCE: 546
gctttggaga tgagaagcgc caccggactg ttaaccccga agggaagaaa aacaagcaac    60
cctaaaccac gctctgggca gggctgttaa ttgtgccggt                          100

SEQ ID NO: 547          moltype = DNA   length = 100
FEATURE                 Location/Qualifiers
source                  1..100
                        mol_type = genomic DNA
                        organism = Homo sapiens
SEQUENCE: 547
acgcaacggt tggagggggc tgaggaaagg ggacgtcgaa cccaccccag ccccacggct    60
cctttgtccc caaatccgcc gacggtcctc ggaccgcagc                          100

SEQ ID NO: 548          moltype = DNA   length = 100
FEATURE                 Location/Qualifiers
source                  1..100
                        mol_type = genomic DNA
                        organism = Homo sapiens
SEQUENCE: 548
tcccgcctcg gtgggcttaa gtttctttgt tgtgcgtgtt gtcttctcct ctccgttttg    60
ccagctgggg ggaaggggggc gccctccgtc cagcccctaa                         100

SEQ ID NO: 549          moltype = DNA   length = 100
FEATURE                 Location/Qualifiers
source                  1..100
                        mol_type = genomic DNA
                        organism = Homo sapiens
SEQUENCE: 549
agcctcgcgg ggaaccgctg ttagcggcca cccagcgcaa ccacaccggt cccgcggcgg    60
ggcccaagcg cgaccggccc cggggcgctg ccgaggttcc                          100

SEQ ID NO: 550          moltype = DNA   length = 100
FEATURE                 Location/Qualifiers
source                  1..100
                        mol_type = genomic DNA
                        organism = Homo sapiens
SEQUENCE: 550
cgcagcccg acggccggac tctgacccag ggatgtgggg cccgcgtccc tccgacgccc     60
tcgccctgct cacctgccag cagctcctgc aggctctggc                          100

SEQ ID NO: 551          moltype = DNA   length = 100
FEATURE                 Location/Qualifiers
source                  1..100
                        mol_type = genomic DNA
                        organism = Homo sapiens
SEQUENCE: 551
tgaaggtctg cagctgtcgc tcgctcgtga gccccttggt gcggagaaac ttggagatga    60
aggacacggc ggcggcgatc tcgcctatca tggtggcggc                          100

SEQ ID NO: 552          moltype = DNA   length = 100
FEATURE                 Location/Qualifiers
source                  1..100
                        mol_type = genomic DNA
                        organism = Homo sapiens
SEQUENCE: 552
ccgggtgtag aagggatgca tgggggcggc gtgcggggggc ggcccggggc ggctggggct   60
cggcggcgcg gccccgacgg cggagcagcc accccgggct                          100

SEQ ID NO: 553          moltype = DNA   length = 100
FEATURE                 Location/Qualifiers
source                  1..100
                        mol_type = genomic DNA
                        organism = Homo sapiens
SEQUENCE: 553
acgccgcacc cctcccccgt gcgttctgcg gccacccagg ccttccagga caccgtggag    60
```

-continued

```
agggaacaag ggggcaggga cgcccccttc ggcaggagcc                          100

SEQ ID NO: 554          moltype = DNA  length = 100
FEATURE                 Location/Qualifiers
source                  1..100
                        mol_type = genomic DNA
                        organism = Homo sapiens
SEQUENCE: 554
gtcgagaag ggggcccaga ccggagggag gcgagaagcc ccactgaagc cgggcgcagg      60
gtctgggacg cagttgggag tgcaaagggc tggctgagag                         100

SEQ ID NO: 555          moltype = DNA  length = 100
FEATURE                 Location/Qualifiers
source                  1..100
                        mol_type = genomic DNA
                        organism = Homo sapiens
SEQUENCE: 555
ccgcaggagc agcaggctgt ggcccaggcc tcctgggtga caggccctgt ctggcgggga    60
agagggacca agagacaaca cggaagaggc tggacctcga                         100

SEQ ID NO: 556          moltype = DNA  length = 100
FEATURE                 Location/Qualifiers
source                  1..100
                        mol_type = genomic DNA
                        organism = Homo sapiens
SEQUENCE: 556
acagggcgg ctgcctcact ccctacctga gccagccgag ggggccaagg actttagagc     60
tgtttcctcc ggcataagag agacacttgc tttccagggc                         100

SEQ ID NO: 557          moltype = DNA  length = 100
FEATURE                 Location/Qualifiers
source                  1..100
                        mol_type = genomic DNA
                        organism = Homo sapiens
SEQUENCE: 557
agcacccttt atcggagaag gctctacagg gaagggtct ttgcagcctg gatggccatc     60
ccacattcct ttaacggagg tctctaggcc tcagagagaa                         100

SEQ ID NO: 558          moltype = DNA  length = 100
FEATURE                 Location/Qualifiers
source                  1..100
                        mol_type = genomic DNA
                        organism = Homo sapiens
SEQUENCE: 558
cccagagtta gaaaggaggc cagacggtcc ttgctgtccc cctggggaga gaggaagttg    60
ccgcctgctg ccaggcccag gaggagctgg gcctgcaata                         100

SEQ ID NO: 559          moltype = DNA  length = 100
FEATURE                 Location/Qualifiers
source                  1..100
                        mol_type = genomic DNA
                        organism = Homo sapiens
SEQUENCE: 559
gtgggggacc tggcccctga ggcagtggcg gccatgtcac ggccaggcca cggtgggctg    60
atgcctgtga atggtctggg cttcccaccg cagaacgtgg                         100

SEQ ID NO: 560          moltype = DNA  length = 100
FEATURE                 Location/Qualifiers
source                  1..100
                        mol_type = genomic DNA
                        organism = Homo sapiens
SEQUENCE: 560
cccgggtggt ggtgtgggag tggctgaatg agcacagccg ctggcggccc tacacggcca    60
ccgtgtgcca ccacattgag aacgtgctga aggaggacgc                         100

SEQ ID NO: 561          moltype = DNA  length = 100
FEATURE                 Location/Qualifiers
source                  1..100
                        mol_type = genomic DNA
                        organism = Homo sapiens
SEQUENCE: 561
tcgcggttcc gtggtcctgg ggcaggtgga cgcccagctt gtgccctaca tcatcgacct    60
gcagtccatg caccagtttc gccaggacac aggtgagcag                         100

SEQ ID NO: 562          moltype = DNA  length = 100
FEATURE                 Location/Qualifiers
source                  1..100
                        mol_type = genomic DNA
                        organism = Homo sapiens
```

```
SEQUENCE: 562
acacccaccc catgccaccc gccccgccga gccatcacta ccttgcagcg taggatgctg    60
aaaatcccag taaatctgct gatgccaaat cccttcccca                         100

SEQ ID NO: 563          moltype = DNA   length = 100
FEATURE                 Location/Qualifiers
source                  1..100
                        mol_type = genomic DNA
                        organism = Homo sapiens
SEQUENCE: 563
tctccctgcc tcacctccag aaaaacaggg cagtctaacc ttgtccagtt taagacttgg    60
attccaatgc agcctctgag caagctgtag ggccttgagc                         100

SEQ ID NO: 564          moltype = DNA   length = 100
FEATURE                 Location/Qualifiers
source                  1..100
                        mol_type = genomic DNA
                        organism = Homo sapiens
SEQUENCE: 564
gggtagatca atatctctca cagctgagtg aggattaaat aaaattgtgc tcactgagca    60
cagaacctag aacagcagta gcatgggatt gtagaataag                         100

SEQ ID NO: 565          moltype = DNA   length = 100
FEATURE                 Location/Qualifiers
source                  1..100
                        mol_type = genomic DNA
                        organism = Homo sapiens
SEQUENCE: 565
ggctttacat gcacttcctc atttgatttt tcccaagaat cacaggcagt aagtctgtgt    60
attgttgtat tattatgagt cccattttat agatgaagaa                         100

SEQ ID NO: 566          moltype = DNA   length = 100
FEATURE                 Location/Qualifiers
source                  1..100
                        mol_type = genomic DNA
                        organism = Homo sapiens
SEQUENCE: 566
tttatagatg aagaaaccga gtctcccaga agctgagtga tttaaactca gagctgggat    60
ttaaacccag gcggttgagt tccagaacca aagttcttaa                         100

SEQ ID NO: 567          moltype = DNA   length = 100
FEATURE                 Location/Qualifiers
source                  1..100
                        mol_type = genomic DNA
                        organism = Homo sapiens
SEQUENCE: 567
ctggtatcct atactggctc caagtgttgg tttgtggggt ggagtcgtgc tggtggtaat    60
taattgggga tggggggcgt tggtggtgtt gatggtgggg                         100

SEQ ID NO: 568          moltype = DNA   length = 100
FEATURE                 Location/Qualifiers
source                  1..100
                        mol_type = genomic DNA
                        organism = Homo sapiens
SEQUENCE: 568
tgaggtggca atgatggagg agacagtgtt agcggttgtg ttggtggtga ctcagtgata    60
gtattgatgg tggtggggtc ttggtgacaa tggagggatg                         100

SEQ ID NO: 569          moltype = DNA   length = 100
FEATURE                 Location/Qualifiers
source                  1..100
                        mol_type = genomic DNA
                        organism = Homo sapiens
SEQUENCE: 569
tgttggtgac attgatagtt gtgttggtgg tggtgctgga agtggtgtga tggggtggtg    60
atgatggaga aaatgagaga atgatgttgg tggcagtctt                         100

SEQ ID NO: 570          moltype = DNA   length = 100
FEATURE                 Location/Qualifiers
source                  1..100
                        mol_type = genomic DNA
                        organism = Homo sapiens
SEQUENCE: 570
cgtggccatg tggtggggct ggtagccctg tgtgtggctg ttacttagtg gtattggtga    60
tcctgttgtg gttgtaatga tggtgatgtt gatggttgcg                         100

SEQ ID NO: 571          moltype = DNA   length = 100
FEATURE                 Location/Qualifiers
source                  1..100
```

```
                        mol_type = genomic DNA
                        organism = Homo sapiens
SEQUENCE: 571
ttggtggtaa tgtgatggct gatgatggag ataaaatcga tgaggtccca ctctcaggcc    60
tactctcttt tgttctggag atttgtcatc gttggggaga                          100

SEQ ID NO: 572          moltype = DNA  length = 100
FEATURE                 Location/Qualifiers
source                  1..100
                        mol_type = genomic DNA
                        organism = Homo sapiens
SEQUENCE: 572
tgaaatggct gctgtcgggc tgtcatctcc aggcccgggg cgctgacatt tgggccactc    60
tcggtctccc tcttcattct gggcgcgcat tagctctggt                          100

SEQ ID NO: 573          moltype = DNA  length = 100
FEATURE                 Location/Qualifiers
source                  1..100
                        mol_type = genomic DNA
                        organism = Homo sapiens
SEQUENCE: 573
ccggccggtt ccgctgcagc tgaacagcaa gatgcggcac ccaggttacc ctgatcatcg    60
cagatttctc cccggggctc tgttctgagg cctcaaaagt                          100

SEQ ID NO: 574          moltype = DNA  length = 100
FEATURE                 Location/Qualifiers
source                  1..100
                        mol_type = genomic DNA
                        organism = Homo sapiens
SEQUENCE: 574
gctccttgta gatgggacca ggggtcattt gggcagtagc agcgcctggt ctcagtctgg    60
tactgaagtc aggaatggct taaggtgaaa tcgtggtcct                          100

SEQ ID NO: 575          moltype = DNA  length = 100
FEATURE                 Location/Qualifiers
source                  1..100
                        mol_type = genomic DNA
                        organism = Homo sapiens
SEQUENCE: 575
ctggtgaagc tcagcgaaga cccctcgcc ttgtttatga caagagaact tctgggggcg    60
ggaggaagag tccctgttac gatgctgatc atcattgagc                          100

SEQ ID NO: 576          moltype = DNA  length = 100
FEATURE                 Location/Qualifiers
source                  1..100
                        mol_type = genomic DNA
                        organism = Homo sapiens
SEQUENCE: 576
ttttgctgag cagaaaactc tttagtactc aaggtcgaga gtctctggtg gtctgcctgg    60
caccaggcac cttcctacaa ccctagtttt ccaaaaggac                          100

SEQ ID NO: 577          moltype = DNA  length = 100
FEATURE                 Location/Qualifiers
source                  1..100
                        mol_type = genomic DNA
                        organism = Homo sapiens
SEQUENCE: 577
aaagcctggg gcaggcgacg tcctagctcg catttgaaca gggccgcggg ccagcagaga    60
tgcgcgatgc ccaactcttt ccaagagcac ctcgcgtccc                          100

SEQ ID NO: 578          moltype = DNA  length = 100
FEATURE                 Location/Qualifiers
source                  1..100
                        mol_type = genomic DNA
                        organism = Homo sapiens
SEQUENCE: 578
gaaccggtgc cttcaactcg gagaagtcaa gagacccgca agaaacttgc acgactgcac    60
ccgccgccgc gctctggggg ctgggcaggg gcagctgggc                          100

SEQ ID NO: 579          moltype = DNA  length = 100
FEATURE                 Location/Qualifiers
source                  1..100
                        mol_type = genomic DNA
                        organism = Homo sapiens
SEQUENCE: 579
tggctcccgg ggaacgcgac cccccgcgc cccgcagacc ggctgtctcc catggacccc    60
tcggcacctg cagcctccga ggaagggtca gcgcgcgtgt                          100

SEQ ID NO: 580          moltype = DNA  length = 100
```

```
FEATURE                 Location/Qualifiers
source                  1..100
                        mol_type = genomic DNA
                        organism = Homo sapiens
SEQUENCE: 580
ggggggctcg ggccagccga tgtttttggc cagaagccgt tcgtcctggg ccgcggctgc    60
ctctccacac cgggagctcg tgtttgtttt gcggagggag                          100

SEQ ID NO: 581          moltype = DNA   length = 100
FEATURE                 Location/Qualifiers
source                  1..100
                        mol_type = genomic DNA
                        organism = Homo sapiens
SEQUENCE: 581
ctgttgtttt tgttctctgc accggggaga gggggacttg gtggcggccg cgcgtggttt    60
tcgggatcac attagcgtcc gcccggcgtg gcccggtcga                          100

SEQ ID NO: 582          moltype = DNA   length = 100
FEATURE                 Location/Qualifiers
source                  1..100
                        mol_type = genomic DNA
                        organism = Homo sapiens
SEQUENCE: 582
cattaagggg atcgaacctt tccgcggcct cgtcggggtc tgctcggaat cggcccctgg    60
gccaggcccg aggcgcaagc agatcgccag gttgggtcag                          100

SEQ ID NO: 583          moltype = DNA   length = 100
FEATURE                 Location/Qualifiers
source                  1..100
                        mol_type = genomic DNA
                        organism = Homo sapiens
SEQUENCE: 583
agttgttgaa aactcccgc tgcctgattt caactttatt attttttcc cacgccttca      60
ctggggtccc ggagggagag gagccgccgc aacgctggct                          100

SEQ ID NO: 584          moltype = DNA   length = 100
FEATURE                 Location/Qualifiers
source                  1..100
                        mol_type = genomic DNA
                        organism = Homo sapiens
SEQUENCE: 584
agtagcgcct cggtctctaa aagccactgg gggcgagcct ccggtgtggc ggtgtcacaa    60
gttagctgtc ctttctgagt caaacccaac aaaaaaggca                          100

SEQ ID NO: 585          moltype = DNA   length = 100
FEATURE                 Location/Qualifiers
source                  1..100
                        mol_type = genomic DNA
                        organism = Homo sapiens
SEQUENCE: 585
agaggaaaat caataaagtc cacgtgctcc ccggcctcct atggaaaggg ctggctgcga    60
tggccggatg cccggccgtg ggctgggttt ggctccagtg                          100

SEQ ID NO: 586          moltype = DNA   length = 100
FEATURE                 Location/Qualifiers
source                  1..100
                        mol_type = genomic DNA
                        organism = Homo sapiens
SEQUENCE: 586
ggacaaagaa ttttcagaac cgtgagaagg ggaggctttc caaagttgag atccaagtcg    60
tcggtgtctc gggagctccc ctggtacaca gggtgcccgg                          100

SEQ ID NO: 587          moltype = DNA   length = 100
FEATURE                 Location/Qualifiers
source                  1..100
                        mol_type = genomic DNA
                        organism = Homo sapiens
SEQUENCE: 587
tgcccgactg gagccattta aaaatggcag aaacagctgc aggccaacac acacacgctg    60
gaaaacaacc cgcagccccc tctactgtgg gattccccgc                          100

SEQ ID NO: 588          moltype = DNA   length = 100
FEATURE                 Location/Qualifiers
source                  1..100
                        mol_type = genomic DNA
                        organism = Homo sapiens
SEQUENCE: 588
gggaagcccg gagttgctcc cctccttgcc tcagcccctg tgcaaagaaa gaactggtgt    60
ctgtgcctgg gtcccttctg tcgccggcct ggaggttggg                          100
```

```
SEQ ID NO: 589         moltype = DNA  length = 100
FEATURE                Location/Qualifiers
source                 1..100
                       mol_type = genomic DNA
                       organism = Homo sapiens
SEQUENCE: 589
aaacagccgg caagccgcct ttctctgctc gaggaggcgt ggtggggcct cctactccag    60
gttcccggct ggacagaggc tcctgcaccc tgacagctgc                         100

SEQ ID NO: 590         moltype = DNA  length = 100
FEATURE                Location/Qualifiers
source                 1..100
                       mol_type = genomic DNA
                       organism = Homo sapiens
SEQUENCE: 590
ggaggccttc cagcccgctg accccgcggg gaccaggcct gtagttggag cttgaggggc    60
tgtacctctg cgcctccctg ggtttgggga acaacacat                          100

SEQ ID NO: 591         moltype = DNA  length = 100
FEATURE                Location/Qualifiers
source                 1..100
                       mol_type = genomic DNA
                       organism = Homo sapiens
SEQUENCE: 591
cgtgtcctct gaagacctca ggctttggga tctcatggtc cagcttccag ttcacttcgt    60
tgccgcgacc ttgggcatat cattgtcact tctctaacca                         100

SEQ ID NO: 592         moltype = DNA  length = 100
FEATURE                Location/Qualifiers
source                 1..100
                       mol_type = genomic DNA
                       organism = Homo sapiens
SEQUENCE: 592
tggtgacccg gggttttgtg cttggcttcc aggtcccctc gggttattga ggacgattga    60
ggtcatgcct ccgagagcac cgcgccctgg gcgcaggagg                         100

SEQ ID NO: 593         moltype = DNA  length = 100
FEATURE                Location/Qualifiers
source                 1..100
                       mol_type = genomic DNA
                       organism = Homo sapiens
SEQUENCE: 593
aatgcaaatt taacagggca ccctgtattt tacccagagg gaagccgaag tgtttggcag    60
atcatttggc cccatgagcc ttgggtgggt ttctcctcag                         100

SEQ ID NO: 594         moltype = DNA  length = 100
FEATURE                Location/Qualifiers
source                 1..100
                       mol_type = genomic DNA
                       organism = Homo sapiens
SEQUENCE: 594
ccctagtgac ccctaaaatt accccccccga cccacccact gtcccctgat gcttccccca    60
cccccggaaa aagctgtggc ctccctctca tttggggcag                         100

SEQ ID NO: 595         moltype = DNA  length = 100
FEATURE                Location/Qualifiers
source                 1..100
                       mol_type = genomic DNA
                       organism = Homo sapiens
SEQUENCE: 595
gctgcctcct gttctctttt tctggtgttt cagcaaggca ggccagtgga ggtgaggtga    60
ccagaagatg gctaaaggaa aaacaaaatg gtgggcctct                         100

SEQ ID NO: 596         moltype = DNA  length = 100
FEATURE                Location/Qualifiers
source                 1..100
                       mol_type = genomic DNA
                       organism = Homo sapiens
SEQUENCE: 596
ccagggtttg ggggccctgt gctggtggag gagagaagac cccagggcga tggtaggaga    60
cgaaagcttg ggctgcagcg taagcttgga ggcccgctgc                         100

SEQ ID NO: 597         moltype = DNA  length = 100
FEATURE                Location/Qualifiers
source                 1..100
                       mol_type = genomic DNA
                       organism = Homo sapiens
SEQUENCE: 597
```

```
ggtggctcac gcctgtaatc ccagagcttt gggaggctga gacaggagga ttgcttgagc    60
ccaggagttt gagaccagcc tgggtctcaa accaaaaaaa                         100

SEQ ID NO: 598          moltype = DNA   length = 100
FEATURE                 Location/Qualifiers
source                  1..100
                        mol_type = genomic DNA
                        organism = Homo sapiens
SEQUENCE: 598
taaatataat tttaacgcca atctgagaaa aatgacttat tagctgtgtg attttgagca    60
atgctcttaa cctcccccat gaaggatggt gtgagaacga                         100

SEQ ID NO: 599          moltype = DNA   length = 100
FEATURE                 Location/Qualifiers
source                  1..100
                        mol_type = genomic DNA
                        organism = Homo sapiens
SEQUENCE: 599
acagaattgt agcacgtgta tcagtctggt acacaatgtc ctatgaaggt tagctttatt    60
atcaccatca ttattattgc agaaagactt tcagttcaga                         100

SEQ ID NO: 600          moltype = DNA   length = 100
FEATURE                 Location/Qualifiers
source                  1..100
                        mol_type = genomic DNA
                        organism = Homo sapiens
SEQUENCE: 600
ataagacagc acagttacag agacctggtt ttattttcca gcttcttaac tgagtcatct    60
ttcagctcct tttaattaaa aagaaaaaac aatcagagat                         100

SEQ ID NO: 601          moltype = DNA   length = 100
FEATURE                 Location/Qualifiers
source                  1..100
                        mol_type = genomic DNA
                        organism = Homo sapiens
SEQUENCE: 601
tcaaagacct ggcagaaatg acttcccaac cccagatgcc cccagcagca gtatttagca    60
gtcatacaat tgcctgaaat gaagaatgag taatctggat                         100

SEQ ID NO: 602          moltype = DNA   length = 100
FEATURE                 Location/Qualifiers
source                  1..100
                        mol_type = genomic DNA
                        organism = Homo sapiens
SEQUENCE: 602
gagtcggccc tgaaatcgac ctgcaactta cccggaacgt gagctgtctc tctctgacct    60
ctgctggctg cttcacctgg agtctgagtc cgactcatgt                         100

SEQ ID NO: 603          moltype = DNA   length = 100
FEATURE                 Location/Qualifiers
source                  1..100
                        mol_type = genomic DNA
                        organism = Homo sapiens
SEQUENCE: 603
agcacttcac tgtccgcgtt agtttagcct tcactgtcag caactcgtca ccttgtcctc    60
ttgcagcgaa ggtttggaat cccatcacgg gtgtgcagtg                         100

SEQ ID NO: 604          moltype = DNA   length = 100
FEATURE                 Location/Qualifiers
source                  1..100
                        mol_type = genomic DNA
                        organism = Homo sapiens
SEQUENCE: 604
gttagtcctg agatcatggt ggtgctagga gaacctgcca accaatacag aaagttgtca    60
cgaatagaaa cctaagctct ggccgggtgc ggtggttcaa                         100

SEQ ID NO: 605          moltype = DNA   length = 100
FEATURE                 Location/Qualifiers
source                  1..100
                        mol_type = genomic DNA
                        organism = Homo sapiens
SEQUENCE: 605
agatatactg ttctagacat gtgtctgaaa ggaatcctgc aaattctgtc ttattgaaca    60
ggcataaggt gtcacgtcag gcgtaaggtg tcacagcagg                         100

SEQ ID NO: 606          moltype = DNA   length = 100
FEATURE                 Location/Qualifiers
source                  1..100
                        mol_type = genomic DNA
```

```
                          organism = Homo sapiens
SEQUENCE: 606
cgtaaggcgt cacgtcaggc gtaaggtgtc acagcaggcg taaggcatca cgtcaggcgt    60
aaggcgtcac gtcaggcgta aggtgtcaca agctcggtga                         100

SEQ ID NO: 607          moltype = DNA  length = 100
FEATURE                 Location/Qualifiers
source                  1..100
                        mol_type = genomic DNA
                        organism = Homo sapiens
SEQUENCE: 607
acgtcagggg tgtgccttgt gttctctgtt cgttgctttc agaagcagca gcatgtggca    60
gcatctctgt gcctatgacg atattgcagt gaatatgaga                         100

SEQ ID NO: 608          moltype = DNA  length = 100
FEATURE                 Location/Qualifiers
source                  1..100
                        mol_type = genomic DNA
                        organism = Homo sapiens
SEQUENCE: 608
aattgtacat ttcaacaaca taaataagct gttcaagact gtctcccatg cctccaaaac    60
aaataaaaac cccccacaac tcaaatgcat ataagctgtt                         100

SEQ ID NO: 609          moltype = DNA  length = 100
FEATURE                 Location/Qualifiers
source                  1..100
                        mol_type = genomic DNA
                        organism = Homo sapiens
SEQUENCE: 609
actatagtat aatggtgagt tatagccagt gtatgatggg attgttgata gaataatgca    60
tattagagct tttagttcaa aaatttgaga tagtgattca                         100

SEQ ID NO: 610          moltype = DNA  length = 100
FEATURE                 Location/Qualifiers
source                  1..100
                        mol_type = genomic DNA
                        organism = Homo sapiens
SEQUENCE: 610
gaaagaaaaa aaggaatgat tatcatgaat tctgtttatt agaattctgt ttattaaaga    60
gttaaagata tgttttattt ttttatcttt attatcatta                         100

SEQ ID NO: 611          moltype = DNA  length = 100
FEATURE                 Location/Qualifiers
source                  1..100
                        mol_type = genomic DNA
                        organism = Homo sapiens
SEQUENCE: 611
aattctaatg ttggtccctt aggatcagca ggggggggacc gggaatctgt aactgcaacc    60
accccaccga gaggattaca ggaacccagt cgagagctgg                         100

SEQ ID NO: 612          moltype = DNA  length = 100
FEATURE                 Location/Qualifiers
source                  1..100
                        mol_type = genomic DNA
                        organism = Homo sapiens
SEQUENCE: 612
ttcccaacaa tgaggttcat ttaaaaagtc gtgaggggg aggggggcca aagaaagaaa      60
tagatcaaag agcgggagag tcgagaaaag aaggaagaaa                         100

SEQ ID NO: 613          moltype = DNA  length = 100
FEATURE                 Location/Qualifiers
source                  1..100
                        mol_type = genomic DNA
                        organism = Homo sapiens
SEQUENCE: 613
tgttggggag cgctggcagc cgggctggca agtggagttt gggaatgtgc agggagggaa    60
ggaagctgaa aaattcaaac ttttaaatg ctactcttca                          100

SEQ ID NO: 614          moltype = DNA  length = 100
FEATURE                 Location/Qualifiers
source                  1..100
                        mol_type = genomic DNA
                        organism = Homo sapiens
SEQUENCE: 614
gctcctcggc gtccctgcac cccaaccctg cagccctggg gcgttggcag ctgcaccaac    60
aggagcagca agctgggaaa acagagcaac atgacccgac                         100

SEQ ID NO: 615          moltype = DNA  length = 100
FEATURE                 Location/Qualifiers
```

```
source                  1..100
                        mol_type = genomic DNA
                        organism = Homo sapiens
SEQUENCE: 615
gtgttaagag aaggcaaaac acttcagcaa ttaaaaagta gcccagcagc ttcacccttt    60
caaattggga gggggaggtt ggaaagaaat ttaacaacat                         100

SEQ ID NO: 616          moltype = DNA  length = 100
FEATURE                 Location/Qualifiers
source                  1..100
                        mol_type = genomic DNA
                        organism = Homo sapiens
SEQUENCE: 616
ccatagactt tgctatgta catttaaacc gcagtcctgg aacattccga gtttaaaact    60
tgctttttca acactggctg acaagcaaca tgttttaagg                         100

SEQ ID NO: 617          moltype = DNA  length = 100
FEATURE                 Location/Qualifiers
source                  1..100
                        mol_type = genomic DNA
                        organism = Homo sapiens
SEQUENCE: 617
agcccccat taaatcctta ctcgcgggac tctcgagttc aagccagcat tttgtcgcca    60
cctcccccc caaccccgcc cgcaatcgat gagccgcaat                          100

SEQ ID NO: 618          moltype = DNA  length = 100
FEATURE                 Location/Qualifiers
source                  1..100
                        mol_type = genomic DNA
                        organism = Homo sapiens
SEQUENCE: 618
gcctcggcaa cacaggtaag cgggtcaacc tgaatgcctc tttcaccca aagtttgctg    60
cacgatcggc tatcgcggga agaagcccaa cggagctagg                         100

SEQ ID NO: 619          moltype = DNA  length = 100
FEATURE                 Location/Qualifiers
source                  1..100
                        mol_type = genomic DNA
                        organism = Homo sapiens
SEQUENCE: 619
gcggactcaa gccccactgc aaacttgttc tgcaacatct ttttgaatca caacttggcc    60
tttcttcctc gcatatcccc agctcccccc aaagagtgga                         100

SEQ ID NO: 620          moltype = DNA  length = 100
FEATURE                 Location/Qualifiers
source                  1..100
                        mol_type = genomic DNA
                        organism = Homo sapiens
SEQUENCE: 620
ggaaaacatt gtcccgagac tcacttcccc gagggacctc ccactcccaa ccccacgggt    60
gggtaatgcc gctggacaga cctagggcgc agactgggaa                         100

SEQ ID NO: 621          moltype = DNA  length = 100
FEATURE                 Location/Qualifiers
source                  1..100
                        mol_type = genomic DNA
                        organism = Homo sapiens
SEQUENCE: 621
cccgatcaga ccagcaaacc tgggatccag cagcacgtta cgtaaaacag gatcgcccaa    60
aacttgtccc aatcccagcc ctccccccga agccccggg                          100

SEQ ID NO: 622          moltype = DNA  length = 100
FEATURE                 Location/Qualifiers
source                  1..100
                        mol_type = genomic DNA
                        organism = Homo sapiens
SEQUENCE: 622
ctgccctgcc aggcaaactt cgcccctcaa aaccctggcc tccagattca catgtaatcc    60
ccgccagcaa ctgttgaaac tcaaagggtg ggaaggacgg                         100

SEQ ID NO: 623          moltype = DNA  length = 100
FEATURE                 Location/Qualifiers
source                  1..100
                        mol_type = genomic DNA
                        organism = Homo sapiens
SEQUENCE: 623
ggccaaattc cttcaaactt gggagaaatg ccggaggaga aaagaatcat ctcgctgcac    60
cactttcccc attgccttcc aagacccaaa cttttggggg                         100
```

```
SEQ ID NO: 624          moltype = DNA  length = 100
FEATURE                 Location/Qualifiers
source                  1..100
                        mol_type = genomic DNA
                        organism = Homo sapiens
SEQUENCE: 624
ttctttctta aggcaaaaga aaaagacttt tgaaaagca aatgctccgc cccccttac      60
cttgcataaa acttcgctca agtcgaagat ggtggcagac                         100

SEQ ID NO: 625          moltype = DNA  length = 100
FEATURE                 Location/Qualifiers
source                  1..100
                        mol_type = genomic DNA
                        organism = Homo sapiens
SEQUENCE: 625
acgagggtgg tggtcatcct gtgcgttcgc gcgagccagg ggcgaggatc tggtgtgtcg    60
cgaaggtccc ggtgcgggga aggcgcagcc tctcctgtct                         100

SEQ ID NO: 626          moltype = DNA  length = 100
FEATURE                 Location/Qualifiers
source                  1..100
                        mol_type = genomic DNA
                        organism = Homo sapiens
SEQUENCE: 626
ttattttttt atattaagat ttattctaaa ttttgattct tctaaatata gtatatattt    60
agtatatata taatgcacct ctcttaccta atgatcattt                         100

SEQ ID NO: 627          moltype = DNA  length = 100
FEATURE                 Location/Qualifiers
source                  1..100
                        mol_type = genomic DNA
                        organism = Homo sapiens
SEQUENCE: 627
ctaaataatc ataacaacat cgagtaaaac tatgtaataa cacatattat tattaagata    60
agtataagaa atataataat aaattgtccc tgttctaaaa                         100

SEQ ID NO: 628          moltype = DNA  length = 100
FEATURE                 Location/Qualifiers
source                  1..100
                        mol_type = genomic DNA
                        organism = Homo sapiens
SEQUENCE: 628
ggtaattata taatgctgaa tgtgtcagag gcattcgaac cagagtgact ccattttgag    60
tgagggctag gaaaatgagg ctgagacttg ctgggatgca                         100

SEQ ID NO: 629          moltype = DNA  length = 100
FEATURE                 Location/Qualifiers
source                  1..100
                        mol_type = genomic DNA
                        organism = Homo sapiens
SEQUENCE: 629
tttaatttt atgctttctt cagtgtatgt ttggagagag tttgaacatt ttttgactct     60
ttttcattga gtaaatccaa atacttgtaa aagacttatc                         100

SEQ ID NO: 630          moltype = DNA  length = 100
FEATURE                 Location/Qualifiers
source                  1..100
                        mol_type = genomic DNA
                        organism = Homo sapiens
SEQUENCE: 630
tatttcttta acaaaaactt aacatggatt aaggacccat cttaaggcat cacacattaa    60
aaaagtcaat attgattcaa taccggcgct tatactacga                         100

SEQ ID NO: 631          moltype = DNA  length = 100
FEATURE                 Location/Qualifiers
source                  1..100
                        mol_type = genomic DNA
                        organism = Homo sapiens
SEQUENCE: 631
catcacttgt taaatttgtt ttctaaataa agcccagagg tagtggaaaa tacttcacac    60
tctaggccag tgtttgctat gcctggttga ccctaaactg                         100

SEQ ID NO: 632          moltype = DNA  length = 100
FEATURE                 Location/Qualifiers
source                  1..100
                        mol_type = genomic DNA
                        organism = Homo sapiens
SEQUENCE: 632
ttgagggttc ttttaaaaaa tacagatttc tgggacccac ctgagatgat tccgataatc    60
```

```
ggccatatgg atgagtcact tagagatacc cattttttaag                          100

SEQ ID NO: 633          moltype = DNA   length = 100
FEATURE                 Location/Qualifiers
source                  1..100
                        mol_type = genomic DNA
                        organism = Homo sapiens
SEQUENCE: 633
gattaggacc ccgaagccca gaaaatgcct gctgtagtca acattatagt cacactccac     60
aggcactggg tccacccctt tgaccgacat tcctttgcgg                          100

SEQ ID NO: 634          moltype = DNA   length = 100
FEATURE                 Location/Qualifiers
source                  1..100
                        mol_type = genomic DNA
                        organism = Homo sapiens
SEQUENCE: 634
tttcccacc cttcttccct gcctggagaa ctcctattca tcctccagag cccggctcaa      60
agtggcttca tctgtgggga tcctccctgc cccatagtga                          100

SEQ ID NO: 635          moltype = DNA   length = 100
FEATURE                 Location/Qualifiers
source                  1..100
                        mol_type = genomic DNA
                        organism = Homo sapiens
SEQUENCE: 635
gtgctccttg agtcctcgcc cttcctaggg catcccaagc tcccaggggc tgcccctgct     60
gcctcgccat ccgctccaaa gctggctgta cctcgatggt                          100

SEQ ID NO: 636          moltype = DNA   length = 100
FEATURE                 Location/Qualifiers
source                  1..100
                        mol_type = genomic DNA
                        organism = Homo sapiens
SEQUENCE: 636
taagggcagc caggcgtgct gcttctcgtc caaatacacg aacttctccc aggcccacag     60
gcggtccggg tggtcggtga ctgcctcccc gagtgtcggg                          100

SEQ ID NO: 637          moltype = DNA   length = 100
FEATURE                 Location/Qualifiers
source                  1..100
                        mol_type = genomic DNA
                        organism = Homo sapiens
SEQUENCE: 637
aggaatcaga tttcaaaatg aatatgtata agaaaagaac cggggatcag tgatcaggaa     60
cagggatcca tgatctggtc cagggctcag cggtcaggaa                          100

SEQ ID NO: 638          moltype = DNA   length = 100
FEATURE                 Location/Qualifiers
source                  1..100
                        mol_type = genomic DNA
                        organism = Homo sapiens
SEQUENCE: 638
ccctggcctg gagtcccaag tccccagccc atcctgcccc tggagcccag tttagcttgg     60
tcttgaagtc tgctctaggt accccaaaa tcacagtatc                           100

SEQ ID NO: 639          moltype = DNA   length = 100
FEATURE                 Location/Qualifiers
source                  1..100
                        mol_type = genomic DNA
                        organism = Homo sapiens
SEQUENCE: 639
cagccccgct ctgcccaccg ggacagccaa gttcagctga gactggccta ccgggggagt     60
cgccctctga agttcactct aagccagcct ggttcagcct                          100

SEQ ID NO: 640          moltype = DNA   length = 100
FEATURE                 Location/Qualifiers
source                  1..100
                        mol_type = genomic DNA
                        organism = Homo sapiens
SEQUENCE: 640
ggcccaggtc agcccaggac ctccccttgc aggcagcaaa ctcttatttc agtccagcca     60
gctcaaccag cttgcttctg actcagctcc tcttagccag                          100

SEQ ID NO: 641          moltype = DNA   length = 100
FEATURE                 Location/Qualifiers
source                  1..100
                        mol_type = genomic DNA
                        organism = Homo sapiens
```

```
SEQUENCE: 641
ttagctcagc aaagctggac ctaaagtagc cacctcaccc cagcttcatc cagatgaata    60
cagtccagat cagcttagtc agttaagcct agcctagcta                         100

SEQ ID NO: 642          moltype = DNA   length = 100
FEATURE                 Location/Qualifiers
source                  1..100
                        mol_type = genomic DNA
                        organism = Homo sapiens
SEQUENCE: 642
gttaaatcca gttacgacca gctcaactaa tcctgctcag gcctgctcag cccagcccag    60
ctgaacccag tttagccgag gccaggccag cccagctgaa                         100

SEQ ID NO: 643          moltype = DNA   length = 100
FEATURE                 Location/Qualifiers
source                  1..100
                        mol_type = genomic DNA
                        organism = Homo sapiens
SEQUENCE: 643
tacagttgcc cagtctagct cagcccagtc cagcactgcc cagtttagct gagctcagcc    60
tggcccagcc cagctcatat cagcccatct cagctgaacc                         100

SEQ ID NO: 644          moltype = DNA   length = 100
FEATURE                 Location/Qualifiers
source                  1..100
                        mol_type = genomic DNA
                        organism = Homo sapiens
SEQUENCE: 644
agtttgaccc agtctaaccc aaccccgctc agctgaaccc agcccagccc agcccagccc    60
agccaaaccc agtttagcct agctcagctc agcccatttc                         100

SEQ ID NO: 645          moltype = DNA   length = 100
FEATURE                 Location/Qualifiers
source                  1..100
                        mol_type = genomic DNA
                        organism = Homo sapiens
SEQUENCE: 645
cctgtcctag gggtggcagg cagtctgcac ccagcctagc cctgcccagc gtggggtctc    60
tgaccttctt ggtcttgggc ccagccaaga ttcccagccc                         100

SEQ ID NO: 646          moltype = DNA   length = 100
FEATURE                 Location/Qualifiers
source                  1..100
                        mol_type = genomic DNA
                        organism = Homo sapiens
SEQUENCE: 646
ttctagcttt cctgtgtccc catgcaggga agggatgcct agagtccacg cagtgaccaa    60
gaagcttggt tgatgctgtg agggtggccc aggagtcccc                         100

SEQ ID NO: 647          moltype = DNA   length = 100
FEATURE                 Location/Qualifiers
source                  1..100
                        mol_type = genomic DNA
                        organism = Homo sapiens
SEQUENCE: 647
cacctgctgt ccttggtcct ggctgagagg agggccctac ggccagctct gctgaccctg    60
ccctgggctc tggtgatgct gccggcctgg acaagcccct                         100

SEQ ID NO: 648          moltype = DNA   length = 100
FEATURE                 Location/Qualifiers
source                  1..100
                        mol_type = genomic DNA
                        organism = Homo sapiens
SEQUENCE: 648
gagctcaggt cggtcgtgcc catcctggca tcaccccaca gccggttctg ccgcatcccg    60
tcatgttcct cgtgctccca gcccggtcgt cctggaggcc                         100

SEQ ID NO: 649          moltype = DNA   length = 100
FEATURE                 Location/Qualifiers
source                  1..100
                        mol_type = genomic DNA
                        organism = Homo sapiens
SEQUENCE: 649
tgagcatgag tggggcgggc agaggcctcc gggtgaggag acagatgggg cctgccttgc    60
tgccctgggc tggggctgca cagccggggt gcgtccaggc                         100

SEQ ID NO: 650          moltype = DNA   length = 100
FEATURE                 Location/Qualifiers
source                  1..100
```

```
                          mol_type = genomic DNA
                          organism = Homo sapiens
SEQUENCE: 650
aggagggctg agcctggctt ccagcagaca ccctccctcc ctgagctggc ctctcaccaa      60
ctgtcttgtc caccttggtg ttgctgggct tgtgatctac                           100

SEQ ID NO: 651            moltype = DNA   length = 100
FEATURE                   Location/Qualifiers
source                    1..100
                          mol_type = genomic DNA
                          organism = Homo sapiens
SEQUENCE: 651
accaactgtc ttgtccacct tggtgttgct gggcttgtga tctacgttgc aggtgtaggt      60
ctgggtgccg aagttgctgg agggcacggt caccacgctg                           100

SEQ ID NO: 652            moltype = DNA   length = 100
FEATURE                   Location/Qualifiers
source                    1..100
                          mol_type = genomic DNA
                          organism = Homo sapiens
SEQUENCE: 652
ggactgtagg acagccggga aggtgtgcac gccgctggtc agagcgcctg agttccacga      60
caccgtcacc ggttcgggga agtagtcctt gaccaggcag                           100

SEQ ID NO: 653            moltype = DNA   length = 100
FEATURE                   Location/Qualifiers
source                    1..100
                          mol_type = genomic DNA
                          organism = Homo sapiens
SEQUENCE: 653
tgctacactg ccctgcacca cctccactca gcttcattgt gctggtggcc ctggctcctg      60
gcagcccatc ttgctccttc tggggcgcca gcctcagagg                           100

SEQ ID NO: 654            moltype = DNA   length = 100
FEATURE                   Location/Qualifiers
source                    1..100
                          mol_type = genomic DNA
                          organism = Homo sapiens
SEQUENCE: 654
ccttcctgcc tagggtccgc tggggccagc cctgggaccc tcctggtctc aagcacacat      60
tcccctgca gccacacctg cccctgcctg agagctcagc                            100

SEQ ID NO: 655            moltype = DNA   length = 100
FEATURE                   Location/Qualifiers
source                    1..100
                          mol_type = genomic DNA
                          organism = Homo sapiens
SEQUENCE: 655
cccgagccct ggaatgcctt cccttctcca tcccagctca cccttgccaa ctgctcagtg      60
ggatgggctc acactccctt cctggcacca ggaggctgca                           100

SEQ ID NO: 656            moltype = DNA   length = 100
FEATURE                   Location/Qualifiers
source                    1..100
                          mol_type = genomic DNA
                          organism = Homo sapiens
SEQUENCE: 656
ctgcactttc accagccctc agctgtctgc tgccagcaac tacccagctc ctgccaaaat      60
ctaggagctg agtgatgcct cccaccggcc ctgctcacct                           100

SEQ ID NO: 657            moltype = DNA   length = 100
FEATURE                   Location/Qualifiers
source                    1..100
                          mol_type = genomic DNA
                          organism = Homo sapiens
SEQUENCE: 657
gtggttgcct tgccctgagc tctagtgcct gtccctgct cgtcctgcct cccaccggcc       60
ctgctcacct gtggctgctc tgctctgatt ccctgaggct                           100

SEQ ID NO: 658            moltype = DNA   length = 100
FEATURE                   Location/Qualifiers
source                    1..100
                          mol_type = genomic DNA
                          organism = Homo sapiens
SEQUENCE: 658
aagcctcagt cctgctcacc ttctgatgct ctcctctgtc ccctgagctc caggggctgt      60
ccctgctcg tcctgcctcc tacctgcccc tgcttacctg                            100

SEQ ID NO: 659            moltype = DNA   length = 100
```

```
FEATURE                 Location/Qualifiers
source                  1..100
                        mol_type = genomic DNA
                        organism = Homo sapiens
SEQUENCE: 659
agggtgctct gccctggtgc tctgagctcc aggggctgtc ccctgctcct cctgcttcct    60
accagcccct gctcacctgt ggctgctctg ccctggtccc                         100

SEQ ID NO: 660          moltype = DNA  length = 100
FEATURE                 Location/Qualifiers
source                  1..100
                        mol_type = genomic DNA
                        organism = Homo sapiens
SEQUENCE: 660
ctctgccctg gtccctgag ctccaggggc ttccccctgc tcttcctgcc cccaccagcc    60
cctgttcacc ttcagatgcc ctccctggt cccctgaagt                         100

SEQ ID NO: 661          moltype = DNA  length = 100
FEATURE                 Location/Qualifiers
source                  1..100
                        mol_type = genomic DNA
                        organism = Homo sapiens
SEQUENCE: 661
cccagagctg ccctgttc ctcctgcctc ccaccagccc gtgctcacct gccgctgctc    60
tgccctggtc ccgagttcca ggggctgcac cctgttcgcc                         100

SEQ ID NO: 662          moltype = DNA  length = 100
FEATURE                 Location/Qualifiers
source                  1..100
                        mol_type = genomic DNA
                        organism = Homo sapiens
SEQUENCE: 662
cacctcccac tagccatgct cagctcttga tgctctgtcc tggtcccctg agctccagga    60
gctgtcccct actcgtcctg ccacccacca gcccctgctc                         100

SEQ ID NO: 663          moltype = DNA  length = 100
FEATURE                 Location/Qualifiers
source                  1..100
                        mol_type = genomic DNA
                        organism = Homo sapiens
SEQUENCE: 663
acctgaggca cctgaggctg ctctgccctg gtccctgag ctccagggtc ttccccctgc    60
tcatcctgcc tcccacctgc ccttgttcac cttcagttgc                         100

SEQ ID NO: 664          moltype = DNA  length = 100
FEATURE                 Location/Qualifiers
source                  1..100
                        mol_type = genomic DNA
                        organism = Homo sapiens
SEQUENCE: 664
tctgccctgg tctgctgagc tccaggaggt gccccctgct ccttctgccc ccacctgccc    60
tgctcacctg tggctgctcg gtcctggtac cctgaactcc                         100

SEQ ID NO: 665          moltype = DNA  length = 100
FEATURE                 Location/Qualifiers
source                  1..100
                        mol_type = genomic DNA
                        organism = Homo sapiens
SEQUENCE: 665
gcccctgct ccttctgccc ccacctgccc tgctcacctg tggctgctcg gtcctggtac    60
cctgaactcc aatgcctgcc ccctgctcac tctgccctcc                         100

SEQ ID NO: 666          moltype = DNA  length = 100
FEATURE                 Location/Qualifiers
source                  1..100
                        mol_type = genomic DNA
                        organism = Homo sapiens
SEQUENCE: 666
ctcaacccgg gcagcaatgt cactcaggtc actgttgccc ccctgcctgt cctggcaccc    60
tctgtccagg tttgggctgt ttttctggcc tcatttttgt                         100

SEQ ID NO: 667          moltype = DNA  length = 100
FEATURE                 Location/Qualifiers
source                  1..100
                        mol_type = genomic DNA
                        organism = Homo sapiens
SEQUENCE: 667
tgtccagtca ggtctcccca acagagcccc ttgcccttgc ccatgtgccc ctcctgggtg    60
agctcccaga tcctccgtc cctgcactgc tcctgctctg                         100
```

```
SEQ ID NO: 668          moltype = DNA  length = 100
FEATURE                 Location/Qualifiers
source                  1..100
                        mol_type = genomic DNA
                        organism = Homo sapiens
SEQUENCE: 668
gaagcctctc cagaacctca gctcctcagt ggcctctgct ctgctgggtc agctccctga    60
acgcacggag cctcaccccT cccctcgccc caggcctgct                         100

SEQ ID NO: 669          moltype = DNA  length = 100
FEATURE                 Location/Qualifiers
source                  1..100
                        mol_type = genomic DNA
                        organism = Homo sapiens
SEQUENCE: 669
gcactctggg cctttctggg cctccctgga ctcttccctc ctcccatctg tgcactcagc    60
acagctctcc cctccactcc gctgctgacc acagccctgc                         100

SEQ ID NO: 670          moltype = DNA  length = 100
FEATURE                 Location/Qualifiers
source                  1..100
                        mol_type = genomic DNA
                        organism = Homo sapiens
SEQUENCE: 670
cctttctggg cctccctgga ctcttccctc ctcccatctg tgcactcagc acagctctcc    60
cctccactcc gctgctgacc acagccctgc tccccgccag                         100

SEQ ID NO: 671          moltype = DNA  length = 100
FEATURE                 Location/Qualifiers
source                  1..100
                        mol_type = genomic DNA
                        organism = Homo sapiens
SEQUENCE: 671
cccacggcca gcactgctga ccctgccctg ggctccagtg atgctgctgg cctggacaag    60
cccctccgtt cacctggggc ctctcctcct ccctcgttct                         100

SEQ ID NO: 672          moltype = DNA  length = 100
FEATURE                 Location/Qualifiers
source                  1..100
                        mol_type = genomic DNA
                        organism = Homo sapiens
SEQUENCE: 672
actgcctcct cagctcaggt gggtcctgcc catgctggca tcaccccacg gccggctctg    60
ccgcatcccg tcaggttcct cgtgctccca gcctggtcgt                         100

SEQ ID NO: 673          moltype = DNA  length = 100
FEATURE                 Location/Qualifiers
source                  1..100
                        mol_type = genomic DNA
                        organism = Homo sapiens
SEQUENCE: 673
catggaggcc tcagtcagcc tctggtgtgt cctgccctgt tggcttggaa gccctgccc    60
acggtccccg tcatcttgca ctgggtgggc gttggtgcct                         100

SEQ ID NO: 674          moltype = DNA  length = 100
FEATURE                 Location/Qualifiers
source                  1..100
                        mol_type = genomic DNA
                        organism = Homo sapiens
SEQUENCE: 674
agctcagccc agcctagtcc agcccagccc agcacaggtc agcccagctt agcttagccc    60
aggtcagtcc agctcagctc agtccactta agctcaccca                         100

SEQ ID NO: 675          moltype = DNA  length = 100
FEATURE                 Location/Qualifiers
source                  1..100
                        mol_type = genomic DNA
                        organism = Homo sapiens
SEQUENCE: 675
ggtcagctcc gtccagctca gcccagccta gcccagctta gcccagccca gcccaacaca    60
ggtcagccca gctcagccta gcccagccca gctcagcaca                         100

SEQ ID NO: 676          moltype = DNA  length = 100
FEATURE                 Location/Qualifiers
source                  1..100
                        mol_type = genomic DNA
                        organism = Homo sapiens
SEQUENCE: 676
```

```
ggtcagacca gctcagtaca gctcaggtca gcccagacca gtccaaccca gcccagcgca    60
gtccaaccca gcccagctca gctcatccaa gcctagctca                         100

SEQ ID NO: 677          moltype = DNA   length = 100
FEATURE                 Location/Qualifiers
source                  1..100
                        mol_type = genomic DNA
                        organism = Homo sapiens
SEQUENCE: 677
gctcagccca gcccaggtca gcctagccca gccgaaccca gctcagccca ggtcaaccca    60
attcagctca gctcagccca ggtcaaccca accaagctca                         100

SEQ ID NO: 678          moltype = DNA   length = 100
FEATURE                 Location/Qualifiers
source                  1..100
                        mol_type = genomic DNA
                        organism = Homo sapiens
SEQUENCE: 678
gctcagccta gcccagtcca gctcagccca gctcagctca gcccagtcca gctcaatcca    60
cctaagctca cccagctcag cccagtctgg ctcagcttag                         100

SEQ ID NO: 679          moltype = DNA   length = 100
FEATURE                 Location/Qualifiers
source                  1..100
                        mol_type = genomic DNA
                        organism = Homo sapiens
SEQUENCE: 679
gtcagcccag cccagcctag cccagatcag tccagcttag cccagcccag gtcagcccag    60
cccaggtcag cccagctcag ctcagcccag cccagctcag                         100

SEQ ID NO: 680          moltype = DNA   length = 100
FEATURE                 Location/Qualifiers
source                  1..100
                        mol_type = genomic DNA
                        organism = Homo sapiens
SEQUENCE: 680
cccagcccag ctcagcgcag cccagcctag ctcaccccag ccaggtccag cttagcccag    60
ctcagcccag cccaactcag ctcagcccag ctcagcccaa                         100

SEQ ID NO: 681          moltype = DNA   length = 100
FEATURE                 Location/Qualifiers
source                  1..100
                        mol_type = genomic DNA
                        organism = Homo sapiens
SEQUENCE: 681
tctgagctcc aggggctgcc cacctgctcc tcctgcttcc caccggccct gctcacctgc    60
agctgctctg ccctggctcc ctgaggctga gcctcagtcc                         100

SEQ ID NO: 682          moltype = DNA   length = 100
FEATURE                 Location/Qualifiers
source                  1..100
                        mol_type = genomic DNA
                        organism = Homo sapiens
SEQUENCE: 682
tgctcacctt ctgatgctct ccccttgtcc cctgagctcc aggggctgac ccctgatctt    60
tctgcttcct acctgcccct gctcacctgt ggctgctctg                         100

SEQ ID NO: 683          moltype = DNA   length = 100
FEATURE                 Location/Qualifiers
source                  1..100
                        mol_type = genomic DNA
                        organism = Homo sapiens
SEQUENCE: 683
ccctgatccc ctgagctcca ggagctgcct cctgctcttc ctgcctccca cctgcccctg    60
ctcacctgca gatctgccct ggctctctga ggtccagggg                         100

SEQ ID NO: 684          moltype = DNA   length = 100
FEATURE                 Location/Qualifiers
source                  1..100
                        mol_type = genomic DNA
                        organism = Homo sapiens
SEQUENCE: 684
ctgcccctg ctcgcccacc tcccaccagc catgctgacg ttgtgatgct ctgccctggt    60
ctcctgaggt ccaggggctg tccctgctt attctgcctc                          100

SEQ ID NO: 685          moltype = DNA   length = 100
FEATURE                 Location/Qualifiers
source                  1..100
                        mol_type = genomic DNA
```

```
                          organism = Homo sapiens
SEQUENCE: 685
ccacctgccc cttctcacct gaggctcttc tgccctggtg ctctgagctc caaaagctgc    60
ccacttgctc ctcctgcttc ctaccagccc ctgctctcct                         100

SEQ ID NO: 686           moltype = DNA   length = 100
FEATURE                  Location/Qualifiers
source                   1..100
                         mol_type = genomic DNA
                         organism = Homo sapiens
SEQUENCE: 686
gtggatgatc tgccctggct ctctgagctc caggggctgc ccacctgctc cccatgcttc    60
ccacctgccc ctgctgacct gcggctgctc tgccttggct                         100

SEQ ID NO: 687           moltype = DNA   length = 100
FEATURE                  Location/Qualifiers
source                   1..100
                         mol_type = genomic DNA
                         organism = Homo sapiens
SEQUENCE: 687
ccctgagctc caggagcttc cccctgctca tcctgccccc cactggcccc tgttcacctt    60
cagatgccct ccctggtccc ctgaagtcca ggagctgccc                         100

SEQ ID NO: 688           moltype = DNA   length = 100
FEATURE                  Location/Qualifiers
source                   1..100
                         mol_type = genomic DNA
                         organism = Homo sapiens
SEQUENCE: 688
cctgttcctc ccgcctccca ccagcccgtg ctcacctgcg gctgctctgc cctggtcccc    60
tgagttccag gggctgcccc ctgctcgccc acctcccact                         100

SEQ ID NO: 689           moltype = DNA   length = 100
FEATURE                  Location/Qualifiers
source                   1..100
                         mol_type = genomic DNA
                         organism = Homo sapiens
SEQUENCE: 689
agccatgctc acctcctgat gctctgtcct ggtcccctga gctccagggg ctgcccctg     60
cttgcccatc tcccactagc catgctcacc ttctgatgct                         100

SEQ ID NO: 690           moltype = DNA   length = 100
FEATURE                  Location/Qualifiers
source                   1..100
                         mol_type = genomic DNA
                         organism = Homo sapiens
SEQUENCE: 690
ctgccctggt ccctgagct ccagggtctt cccctgctc atcctgccgc ccaccagccc      60
ctgctcacct gaggctgctc tgccctggtc ccctgagctc                         100

SEQ ID NO: 691           moltype = DNA   length = 100
FEATURE                  Location/Qualifiers
source                   1..100
                         mol_type = genomic DNA
                         organism = Homo sapiens
SEQUENCE: 691
cccctgagct ccaggtctt cccctgctc atcctgccgc ccaccagccc ctgctcacct      60
gaggctgctc tgccctggtc ccctgagctc caggaggtgc                         100

SEQ ID NO: 692           moltype = DNA   length = 100
FEATURE                  Location/Qualifiers
source                   1..100
                         mol_type = genomic DNA
                         organism = Homo sapiens
SEQUENCE: 692
ttctgccccc acctgccctg ctcacctgtg gctgcttggt cctggtccct gagctccaat    60
gcctgctccc tgctcactct gccctccctc aacccgggca                         100

SEQ ID NO: 693           moltype = DNA   length = 100
FEATURE                  Location/Qualifiers
source                   1..100
                         mol_type = genomic DNA
                         organism = Homo sapiens
SEQUENCE: 693
gcaatgtcac tcaggtcact gttgcccccc tgcctgtcct ggcaccctct gtccaggttt    60
gggctgtttt tctgccctca tttttgattt tgcagcactt                         100

SEQ ID NO: 694           moltype = DNA   length = 100
FEATURE                  Location/Qualifiers
```

```
source                  1..100
                        mol_type = genomic DNA
                        organism = Homo sapiens
SEQUENCE: 694
cctctgtcca ggtttgggct gtttttctgc cctcattttt gattttgcag cacttggcgt    60
gttccctatg ctgtggagca gccccagtgt ccagtcaggt                          100

SEQ ID NO: 695          moltype = DNA   length = 100
FEATURE                 Location/Qualifiers
source                  1..100
                        mol_type = genomic DNA
                        organism = Homo sapiens
SEQUENCE: 695
agtgtccagt caggtctccc aacagagcc ccttgccctt gcccatgtgc cctcctgaa     60
tgagctcccg gatcctcctg tccctgcact gctcctgctc                          100

SEQ ID NO: 696          moltype = DNA   length = 100
FEATURE                 Location/Qualifiers
source                  1..100
                        mol_type = genomic DNA
                        organism = Homo sapiens
SEQUENCE: 696
tggaagcctc tctggaacct cagctcctca gtggcctctg ctctgctggg tcagttccct    60
gaacgcacgg agcctcagcc cttccctcg ccccaggcct                           100

SEQ ID NO: 697          moltype = DNA   length = 100
FEATURE                 Location/Qualifiers
source                  1..100
                        mol_type = genomic DNA
                        organism = Homo sapiens
SEQUENCE: 697
gctgcactct gggcctttct gggcctccct ggactcttcc cttctcccgc ccgtgcactc    60
agcacagctc tccctcctc tccactgctg accacagccc                           100

SEQ ID NO: 698          moltype = DNA   length = 100
FEATURE                 Location/Qualifiers
source                  1..100
                        mol_type = genomic DNA
                        organism = Homo sapiens
SEQUENCE: 698
tgctccccgc cagcaggtgc cccaacccca tcagctggct ctgagcccag cccctgtgcc    60
tccctgtcc ctgcctctgc ctctgggctc cttggcttcc                           100

SEQ ID NO: 699          moltype = DNA   length = 100
FEATURE                 Location/Qualifiers
source                  1..100
                        mol_type = genomic DNA
                        organism = Homo sapiens
SEQUENCE: 699
acctgctgtc cttggtcctg gctgagagga gggccccacg gccagcactg ctgaccctgc    60
cctgggctcc ggtgatgctg ccggcctgga caagccccctc                         100

SEQ ID NO: 700          moltype = DNA   length = 100
FEATURE                 Location/Qualifiers
source                  1..100
                        mol_type = genomic DNA
                        organism = Homo sapiens
SEQUENCE: 700
cgttcacctg gggcctctcc tcctccctcg ctctgctgcc tcctgagctc aggtcggtcg    60
tgcccatcct ggcatcaccc cacggccggc tctgccgcat                          100

SEQ ID NO: 701          moltype = DNA   length = 100
FEATURE                 Location/Qualifiers
source                  1..100
                        mol_type = genomic DNA
                        organism = Homo sapiens
SEQUENCE: 701
ccagtcatgt tcctcgtgct cccagcccgg tcgtcctgga ggcctcagtc agcctctggt    60
gtgtcctgcc ctgttggctt ggaagcccct gcccacggtc                          100

SEQ ID NO: 702          moltype = DNA   length = 100
FEATURE                 Location/Qualifiers
source                  1..100
                        mol_type = genomic DNA
                        organism = Homo sapiens
SEQUENCE: 702
cccgtcgtct cgcactgggt gggcatcggt gcctgaaggc tgcccactc ccccgtgctg     60
gctccgcttg ggcctccatg tggggccggc ctcgacccca                          100
```

```
SEQ ID NO: 703          moltype = DNA   length = 100
FEATURE                 Location/Qualifiers
source                  1..100
                        mol_type = genomic DNA
                        organism = Homo sapiens
SEQUENCE: 703
cactgcactt tcaccagccc tcagctgtct gctgccggca actacccagc tcctgccaaa    60
gtctaggagc tgcgtgctgc ctcccaccgt ccctgctcac                          100

SEQ ID NO: 704          moltype = DNA   length = 100
FEATURE                 Location/Qualifiers
source                  1..100
                        mol_type = genomic DNA
                        organism = Homo sapiens
SEQUENCE: 704
ctgtggctgc tctgccctgg tgctctgagc tccaggagat gccccctgct cctcctgccc    60
cccacctgcc cctgctcacc tgcagcggct ctgccctggt                          100

SEQ ID NO: 705          moltype = DNA   length = 100
FEATURE                 Location/Qualifiers
source                  1..100
                        mol_type = genomic DNA
                        organism = Homo sapiens
SEQUENCE: 705
gagctccaag agctgccccc tgctcctcct gtccctgac cctgctcctg tttgcctatg     60
gctgctctgc ccttgtcccc tgagctccag gagctgcccc                          100

SEQ ID NO: 706          moltype = DNA   length = 100
FEATURE                 Location/Qualifiers
source                  1..100
                        mol_type = genomic DNA
                        organism = Homo sapiens
SEQUENCE: 706
tgctcattct gccgcccacc tgccctgtt cacctgtggc tgctcttccc tggtcctctg     60
agctccatga gctgcccctt gctcctcctg cttccacca                           100

SEQ ID NO: 707          moltype = DNA   length = 100
FEATURE                 Location/Qualifiers
source                  1..100
                        mol_type = genomic DNA
                        organism = Homo sapiens
SEQUENCE: 707
gccctgctc acctaccgat gatcttcccc ggctctctga gctccagggg ctgcccacct     60
gctaccctg cttcccacca gccctgctta cctgcagctg                           100

SEQ ID NO: 708          moltype = DNA   length = 100
FEATURE                 Location/Qualifiers
source                  1..100
                        mol_type = genomic DNA
                        organism = Homo sapiens
SEQUENCE: 708
ctctgccctg gctggcagag ctgcagaagc tgcccctgc tctgcaacct cccaccggcc     60
cttctcatct tctgatgttc tcccctgttc cctgagctcc                          100

SEQ ID NO: 709          moltype = DNA   length = 100
FEATURE                 Location/Qualifiers
source                  1..100
                        mol_type = genomic DNA
                        organism = Homo sapiens
SEQUENCE: 709
aggagctgcc ccctactcgt tctacctccc accaacccgt gctcacctgc gactgctctg    60
ccctggtccc ctgagctcca ggggctgccc cctgctcgcc                          100

SEQ ID NO: 710          moltype = DNA   length = 100
FEATURE                 Location/Qualifiers
source                  1..100
                        mol_type = genomic DNA
                        organism = Homo sapiens
SEQUENCE: 710
tgccctgatc ccctgagctc caggactgcc ccctgctcgt cctgcccctc acctgcccct    60
gctcacctga ggctgctctg ccctggtccc ctgagctaaa                          100

SEQ ID NO: 711          moltype = DNA   length = 100
FEATURE                 Location/Qualifiers
source                  1..100
                        mol_type = genomic DNA
                        organism = Homo sapiens
SEQUENCE: 711
ggggctgccc cttactcatc ctgcctccca ccagccctg ctcaccttct gatgcctcc      60
```

```
cctggtcccc tgagctccag gggctgcccc ctgctcgtcc                            100

SEQ ID NO: 712          moltype = DNA   length = 100
FEATURE                 Location/Qualifiers
source                  1..100
                        mol_type = genomic DNA
                        organism = Homo sapiens
SEQUENCE: 712
gggctgcccc ctgctcgtcc tgcctcccac cagcccctgc tcacctgcag ctacactgcc      60
ctggttccct gagctccagg agctgccacc tgcttgtcct                           100

SEQ ID NO: 713          moltype = DNA   length = 100
FEATURE                 Location/Qualifiers
source                  1..100
                        mol_type = genomic DNA
                        organism = Homo sapiens
SEQUENCE: 713
gccttccacc agccctgct cacctgcagc tacactgccc tggttccctg agctccggga       60
gctgccgcct gcttgtcctg cctcccacca gcccctgctc                           100

SEQ ID NO: 714          moltype = DNA   length = 100
FEATURE                 Location/Qualifiers
source                  1..100
                        mol_type = genomic DNA
                        organism = Homo sapiens
SEQUENCE: 714
acctgtggct acactgccct ggtgccctga gctccaggag ctgcccctg cttgcccatc       60
ttccactgag ccctgctcac ctgcaactgc tctgccctgg                           100

SEQ ID NO: 715          moltype = DNA   length = 100
FEATURE                 Location/Qualifiers
source                  1..100
                        mol_type = genomic DNA
                        organism = Homo sapiens
SEQUENCE: 715
ctctatgagc tccagggct gccccctgct ggtcctgcct cccacctgcc ctgcgcacct       60
gtggctgcct cctcacctgt ggctgctctg ccctggtccc                           100

SEQ ID NO: 716          moltype = DNA   length = 100
FEATURE                 Location/Qualifiers
source                  1..100
                        mol_type = genomic DNA
                        organism = Homo sapiens
SEQUENCE: 716
ctgagctcca gggtcttcct cctgctcatc ctgcccctcc accggctcct gttcaccttc      60
agatgctctc ccgtggtccc ctgagctcca ggagctgccc                           100

SEQ ID NO: 717          moltype = DNA   length = 100
FEATURE                 Location/Qualifiers
source                  1..100
                        mol_type = genomic DNA
                        organism = Homo sapiens
SEQUENCE: 717
cctgttcttc ctgcctccca cctgccctgt gcacctgtgg ctgcttggtc ctggtcccct      60
gaactccaat gcctgccccc tgctcactct gccctccctc                           100

SEQ ID NO: 718          moltype = DNA   length = 100
FEATURE                 Location/Qualifiers
source                  1..100
                        mol_type = genomic DNA
                        organism = Homo sapiens
SEQUENCE: 718
aacctggggc agcaacgtca ctcggtccac tgttgccccc ctgcctgtcc tggcaccctc      60
tgtccaggtt taggctgttt ttcttgcctc attttgttt                            100

SEQ ID NO: 719          moltype = DNA   length = 100
FEATURE                 Location/Qualifiers
source                  1..100
                        mol_type = genomic DNA
                        organism = Homo sapiens
SEQUENCE: 719
tggcaccctc tgtccaggtt taggctgttt tcttgcctc attttgttt ttgcagcact        60
tggcgtgttc cctatgctgt ggagcagccc cagtgtccag                           100

SEQ ID NO: 720          moltype = DNA   length = 100
FEATURE                 Location/Qualifiers
source                  1..100
                        mol_type = genomic DNA
                        organism = Homo sapiens
```

```
SEQUENCE: 720
tccagtcagg tctccccaac agagcccctt gcccttgccc atgtgcccct cctggatgag    60
ctcccggatc ctcccgtccc tgcactgctc ctgctctgga                          100

SEQ ID NO: 721         moltype = DNA  length = 100
FEATURE                Location/Qualifiers
source                 1..100
                       mol_type = genomic DNA
                       organism = Homo sapiens
SEQUENCE: 721
agcctctcca gaacctcagc tcctcagtgg cctctgctct gctgggtcag ttccctgaac    60
gcacggagcc tcagcccctc ccctcgcccc aggcctgctg                          100

SEQ ID NO: 722         moltype = DNA  length = 100
FEATURE                Location/Qualifiers
source                 1..100
                       mol_type = genomic DNA
                       organism = Homo sapiens
SEQUENCE: 722
cactctgggc ctttctgggc ctccctggac tcttccctcc tcccgcccgt gcactcagca    60
cagtctcccc ctcctctccg ctgctgacca cagccctgct                          100

SEQ ID NO: 723         moltype = DNA  length = 100
FEATURE                Location/Qualifiers
source                 1..100
                       mol_type = genomic DNA
                       organism = Homo sapiens
SEQUENCE: 723
gaccacagcc ctgctcccgg ccagcaggtg ccccaacccc atcagctggc tctgagccca    60
gcccctgtgc ctcccctgtc cctgcctctg cctctgggct                          100

SEQ ID NO: 724         moltype = DNA  length = 100
FEATURE                Location/Qualifiers
source                 1..100
                       mol_type = genomic DNA
                       organism = Homo sapiens
SEQUENCE: 724
gctctgctcc cagctcacct gctgtccttg gtcctggctg agaggagggc cctacggcca    60
gctctgctga ccctgccctg ggctccggtg atgctgccgg                          100

SEQ ID NO: 725         moltype = DNA  length = 100
FEATURE                Location/Qualifiers
source                 1..100
                       mol_type = genomic DNA
                       organism = Homo sapiens
SEQUENCE: 725
cctggacaag ccctcggtt cacctggggc ctctcctcct ccctctctct gctgcctcct     60
gagctcaggt cggtcatgcc catcctggca tcaccccatg                          100

SEQ ID NO: 726         moltype = DNA  length = 100
FEATURE                Location/Qualifiers
source                 1..100
                       mol_type = genomic DNA
                       organism = Homo sapiens
SEQUENCE: 726
gctggctctg ccccatcccg tcatgttcct cacactccca gcccggtcgt cctggaggcc    60
tcagtcagcc tctggtgtgt cctgccctgt tggcttggaa                          100

SEQ ID NO: 727         moltype = DNA  length = 100
FEATURE                Location/Qualifiers
source                 1..100
                       mol_type = genomic DNA
                       organism = Homo sapiens
SEQUENCE: 727
gggtagagcc cacctcgtgg cctgcaagcc agccagcccc tgccggtcga gaaggaagcc    60
tgtgtgagag cacacaactg gaggccgggc ggggaagaga                          100

SEQ ID NO: 728         moltype = DNA  length = 100
FEATURE                Location/Qualifiers
source                 1..100
                       mol_type = genomic DNA
                       organism = Homo sapiens
SEQUENCE: 728
aacacgtgcc aacaggccac gcaggccagg accccagacc cggaggcagc gcccctttga    60
gttcctctct ctggtctccg atgttcttct gttgggatca                          100

SEQ ID NO: 729         moltype = DNA  length = 100
FEATURE                Location/Qualifiers
source                 1..100
```

```
                        mol_type = genomic DNA
                        organism = Homo sapiens
SEQUENCE: 729
tttcacctac aggcaacaga gacagtgtga aatgctttcc ctgtggtcgg gaagggagcc      60
ggggcagaga tgacccagtg gggtggtgtg ggggcctccg                           100

SEQ ID NO: 730          moltype = DNA  length = 100
FEATURE                 Location/Qualifiers
source                  1..100
                        mol_type = genomic DNA
                        organism = Homo sapiens
SEQUENCE: 730
cttttgcacac cacgtgttcg tctgtgccct gcatgacgtc cttggaaggc agcagcacct    60
gtgaggtggc tgcgtacttg cccctctca ggactgatgg                            100

SEQ ID NO: 731          moltype = DNA  length = 100
FEATURE                 Location/Qualifiers
source                  1..100
                        mol_type = genomic DNA
                        organism = Homo sapiens
SEQUENCE: 731
gaagcccgg gtgctgctga tgtcagagtt gttcttgtat ttccaggaga aagtgatgga      60
gtcgggaagg aagtcctgtg cgaggcagcc aacggccacg                           100

SEQ ID NO: 732          moltype = DNA  length = 100
FEATURE                 Location/Qualifiers
source                  1..100
                        mol_type = genomic DNA
                        organism = Homo sapiens
SEQUENCE: 732
ctgctcgtat ccgacgggga attctcacag gagacgaggg ggaaaagggt tggggcggat      60
gcactccctg aggacccgca ggacaaaaga gaaagggagg                           100

SEQ ID NO: 733          moltype = DNA  length = 100
FEATURE                 Location/Qualifiers
source                  1..100
                        mol_type = genomic DNA
                        organism = Homo sapiens
SEQUENCE: 733
actccagcta ccctgaagtc tccccaggca gacaacccag gcctgggagt gagtataggg      60
agggtgggtg tgatggggaa cgcagtgtag actcagctga                           100

SEQ ID NO: 734          moltype = DNA  length = 100
FEATURE                 Location/Qualifiers
source                  1..100
                        mol_type = genomic DNA
                        organism = Homo sapiens
SEQUENCE: 734
ggctatccat ctatgtccaa caagatcatg aagattggcc cagtgccatg tcctccagtt      60
catcccagcc caggccagct caatccagtt catcccagcc                           100

SEQ ID NO: 735          moltype = DNA  length = 100
FEATURE                 Location/Qualifiers
source                  1..100
                        mol_type = genomic DNA
                        organism = Homo sapiens
SEQUENCE: 735
caggccagct caatccagcc cagcccaccc caccccagct cagcaaagcc aagctcagct      60
cagcccaact cagatgagct cagaccagct cagcccagcc                           100

SEQ ID NO: 736          moltype = DNA  length = 100
FEATURE                 Location/Qualifiers
source                  1..100
                        mol_type = genomic DNA
                        organism = Homo sapiens
SEQUENCE: 736
cagctcagct cagcccaacc cagcccagct cgctcaacct tgctcggctc agcttagccc      60
agcccagccc agctcaatcc agcctggctc agcccagccc                           100

SEQ ID NO: 737          moltype = DNA  length = 100
FEATURE                 Location/Qualifiers
source                  1..100
                        mol_type = genomic DNA
                        organism = Homo sapiens
SEQUENCE: 737
agcccagttt ggctcaaccc agcttggctc agcccaggtc agcctggctc aactcagccc      60
agcccagccc agctctgctc aacccagctc tgctcaactc                           100

SEQ ID NO: 738          moltype = DNA  length = 100
```

```
FEATURE            Location/Qualifiers
source             1..100
                   mol_type = genomic DNA
                   organism = Homo sapiens
SEQUENCE: 738
agcccagctc atcccagctc agccagcccc agcctagctt agctcaaccc agctcagctc    60
agttcagctc agccctgctc agcacagcac agcagagccc                         100

SEQ ID NO: 739     moltype = DNA   length = 100
FEATURE            Location/Qualifiers
source             1..100
                   mol_type = genomic DNA
                   organism = Homo sapiens
SEQUENCE: 739
agcccggatc ggctcaaccc agcttagctc agcccaggtc agcccagctt aactcagccc    60
aggtcagccc agcttaactc agcccagccc agcccagctc                         100

SEQ ID NO: 740     moltype = DNA   length = 100
FEATURE            Location/Qualifiers
source             1..100
                   mol_type = genomic DNA
                   organism = Homo sapiens
SEQUENCE: 740
tcagcccagt tcagcccagc tcagcccagc ccagcctagc ttggctcaac acagctcagc    60
tcagccagcc cagaccagct cagctcagcc cagtccagct                         100

SEQ ID NO: 741     moltype = DNA   length = 100
FEATURE            Location/Qualifiers
source             1..100
                   mol_type = genomic DNA
                   organism = Homo sapiens
SEQUENCE: 741
caacccagcc cagcccaacc cagctcggct taacccagct cggctcagcc cagatcagcc    60
tggctcaact cagcccagcc cagctcaacc cagcccagtt                         100

SEQ ID NO: 742     moltype = DNA   length = 100
FEATURE            Location/Qualifiers
source             1..100
                   mol_type = genomic DNA
                   organism = Homo sapiens
SEQUENCE: 742
cagctcagct gagcccagcc cagcccagtc cggctcagct cagccccgcc ccactcagcc    60
cagctcagct cagcccagct cagcccagct cagcttagcc                         100

SEQ ID NO: 743     moltype = DNA   length = 100
FEATURE            Location/Qualifiers
source             1..100
                   mol_type = genomic DNA
                   organism = Homo sapiens
SEQUENCE: 743
cagcccagat catcccagct cagctcagct cagctcggct tagcccagct caacctggcc    60
cagcctggtc caggtcagcc cagcctggac cacccagccc                         100

SEQ ID NO: 744     moltype = DNA   length = 100
FEATURE            Location/Qualifiers
source             1..100
                   mol_type = genomic DNA
                   organism = Homo sapiens
SEQUENCE: 744
agctcagctc agcccagctc atcctggttc agctcagctc aacccggctc agcccaggtc    60
tgctcaaccc agcccaaatc agctcagccc agcccaggtc                         100

SEQ ID NO: 745     moltype = DNA   length = 100
FEATURE            Location/Qualifiers
source             1..100
                   mol_type = genomic DNA
                   organism = Homo sapiens
SEQUENCE: 745
atcccagctc agcccagcac agcctacttc agctcagctc agctcagcct aggtcagctc    60
agttgaggtc agctcaactc agcccaatcc agcctggctc                         100

SEQ ID NO: 746     moltype = DNA   length = 100
FEATURE            Location/Qualifiers
source             1..100
                   mol_type = genomic DNA
                   organism = Homo sapiens
SEQUENCE: 746
agcccagctc accctagctc agcttagctc agcccaactc aacccagccc agccttgccc    60
aacccagctc agctcagccc agcccaggtt agccagcccc                         100
```

```
SEQ ID NO: 747        moltype = DNA  length = 100
FEATURE               Location/Qualifiers
source                1..100
                      mol_type = genomic DNA
                      organism = Homo sapiens
SEQUENCE: 747
agcctcggct tagctctgct cagctcggcc ctgctcgcct cagcccgttc agcccagttc    60
agctcagctc agctcagccc agctcagccc agccctggtt                         100

SEQ ID NO: 748        moltype = DNA  length = 100
FEATURE               Location/Qualifiers
source                1..100
                      mol_type = genomic DNA
                      organism = Homo sapiens
SEQUENCE: 748
agctcagccc agctaagctc agctcggctt ggctctgctg agcttggccc agcttggctt    60
agcctgatac aacctgctca gcccagttca gctcggctca                         100

SEQ ID NO: 749        moltype = DNA  length = 100
FEATURE               Location/Qualifiers
source                1..100
                      mol_type = genomic DNA
                      organism = Homo sapiens
SEQUENCE: 749
gcccagcgta gctcagctca gctgagccca gcccaggtta gctcagcccc agtccaggtc    60
agctcaactc agcccaaacc agcctggctc ggcccagctc                         100

SEQ ID NO: 750        moltype = DNA  length = 100
FEATURE               Location/Qualifiers
source                1..100
                      mol_type = genomic DNA
                      organism = Homo sapiens
SEQUENCE: 750
accctagttc agcttagctc agcccagccc agccctgccc aacccagctc agctcagccc    60
agcccaggtt agcccagccc agcctcggct tagctctgct                         100

SEQ ID NO: 751        moltype = DNA  length = 100
FEATURE               Location/Qualifiers
source                1..100
                      mol_type = genomic DNA
                      organism = Homo sapiens
SEQUENCE: 751
agcccagccc aggttagccc agcccagcct cggcttagct ctgctcagct cggcccagcc    60
caggttagcc cagcccagcc tcggcttagc tctgctcagc                         100

SEQ ID NO: 752        moltype = DNA  length = 100
FEATURE               Location/Qualifiers
source                1..100
                      mol_type = genomic DNA
                      organism = Homo sapiens
SEQUENCE: 752
tcggccctgc tcgcctcagc ccgttcagcc cagttcagct cagctcagct cagcccagct    60
cagcccagcc ctggttagct cagcccagct aagctcagct                         100

SEQ ID NO: 753        moltype = DNA  length = 100
FEATURE               Location/Qualifiers
source                1..100
                      mol_type = genomic DNA
                      organism = Homo sapiens
SEQUENCE: 753
cggctcagct ctgctgagct cggcccagct tggctcagcc cgacacagcc tgctcagccc    60
agttcagctc ggctcagccc agcccagccc agcgtagctc                         100

SEQ ID NO: 754        moltype = DNA  length = 100
FEATURE               Location/Qualifiers
source                1..100
                      mol_type = genomic DNA
                      organism = Homo sapiens
SEQUENCE: 754
agctgagccc agcccaggtt agctcagccc cagcccaggt tagctcagcc cagctcagct    60
ctgcccaggt tagctcagcc ccagtccagg ttagctcagc                         100

SEQ ID NO: 755        moltype = DNA  length = 100
FEATURE               Location/Qualifiers
source                1..100
                      mol_type = genomic DNA
                      organism = Homo sapiens
SEQUENCE: 755
```

```
ccagctcagc tctgcccagg ttagctcagc cccagtccag gttagctcag cccagctcag    60
ccttgcccag gttagctcag cccagctaag ctcaacttgg                         100

SEQ ID NO: 756        moltype = DNA   length = 100
FEATURE               Location/Qualifiers
source                1..100
                      mol_type = genomic DNA
                      organism = Homo sapiens
SEQUENCE: 756
ctcagctcag cctagcttgg ctcagcccag cacagcacgc tcaacccggt tcagcttggc    60
tcagcccagc ccagcccagc ctagctcagc tcagccccgc                         100

SEQ ID NO: 757        moltype = DNA   length = 100
FEATURE               Location/Qualifiers
source                1..100
                      mol_type = genomic DNA
                      organism = Homo sapiens
SEQUENCE: 757
ccagctcagc gcagcccagc tcagctcagc tcagcctagc cttgctcggc ccagctcagc    60
tcagcccagc tcagcctagc cttgctcagc ccagctcagc                         100

SEQ ID NO: 758        moltype = DNA   length = 100
FEATURE               Location/Qualifiers
source                1..100
                      mol_type = genomic DNA
                      organism = Homo sapiens
SEQUENCE: 758
tcagcccagc cctgcccagc tcagcccagc ttagtgcagc caagcccagc tcagctcagc    60
tcacctggtg caacttagcc cagctcagct cagctcagct                         100

SEQ ID NO: 759        moltype = DNA   length = 100
FEATURE               Location/Qualifiers
source                1..100
                      mol_type = genomic DNA
                      organism = Homo sapiens
SEQUENCE: 759
caacccagtt caactcagcc cagttcagct cagctcagcc cagttcagcc ttgtttagtc    60
taggtcagct taggtcagtt ttgcccatct gagtccattt                         100

SEQ ID NO: 760        moltype = DNA   length = 100
FEATURE               Location/Qualifiers
source                1..100
                      mol_type = genomic DNA
                      organism = Homo sapiens
SEQUENCE: 760
ctgaaagctg gatggagttg tcatggccag aaatggtcag cccaccagac ctgcttgtct    60
cagctaaagc catctcattg ccaggttcct gcacagccag                         100

SEQ ID NO: 761        moltype = DNA   length = 100
FEATURE               Location/Qualifiers
source                1..100
                      mol_type = genomic DNA
                      organism = Homo sapiens
SEQUENCE: 761
gctggcttcc atcttttgtc tccctctact tgataccca gttccctgca gtcctgcccc     60
agcgccacct gggttttggt tccaaagcat taccaatcat                         100

SEQ ID NO: 762        moltype = DNA   length = 100
FEATURE               Location/Qualifiers
source                1..100
                      mol_type = genomic DNA
                      organism = Homo sapiens
SEQUENCE: 762
taccaccctc cactacctgg gtggaatatt tctttgctgc tttaaagtca ttaaaacatc    60
ttgagaatga gaccaagaat ttaggagcct gtgctgtgat                         100

SEQ ID NO: 763        moltype = DNA   length = 100
FEATURE               Location/Qualifiers
source                1..100
                      mol_type = genomic DNA
                      organism = Homo sapiens
SEQUENCE: 763
aaaaatgagc aggtccccatt gctctagaag tggcagcata tcttctgcac caagaggagg    60
gtattgagat gctcagagcc tccaccttcc cggagcatcc                         100

SEQ ID NO: 764        moltype = DNA   length = 100
FEATURE               Location/Qualifiers
source                1..100
                      mol_type = genomic DNA
```

```
                              organism = Homo sapiens
SEQUENCE: 764
cctcccttct gagtctgcag taaacccctg cctttaaatt ccctctagat aacagtcatc    60
attggaaaca accaagaaat gcattttatc tgaatttgcc                         100

SEQ ID NO: 765          moltype = DNA  length = 100
FEATURE                 Location/Qualifiers
source                  1..100
                        mol_type = genomic DNA
                        organism = Homo sapiens
SEQUENCE: 765
acttaaaatt ctgccattta ccataaatcg ctttggaagg catgggctac tttcaagggt    60
gcgatgatga cctacagtca atgacttaga caagggcgat                         100

SEQ ID NO: 766          moltype = DNA  length = 100
FEATURE                 Location/Qualifiers
source                  1..100
                        mol_type = genomic DNA
                        organism = Homo sapiens
SEQUENCE: 766
gccagtgggg cttggtatgt tctcaagcat cattacccat gccatcccca ttcagaggtt    60
gtggagcagc tcgtgcgacc tctccttcaa atgggcttta                         100

SEQ ID NO: 767          moltype = DNA  length = 100
FEATURE                 Location/Qualifiers
source                  1..100
                        mol_type = genomic DNA
                        organism = Homo sapiens
SEQUENCE: 767
gggaaagtta aatgggagtg acccagacaa tggtcactca aaagactcac ataaatgagt    60
ctcctgctct tcatcaagca attaagacca gttcccttc                          100

SEQ ID NO: 768          moltype = DNA  length = 100
FEATURE                 Location/Qualifiers
source                  1..100
                        mol_type = genomic DNA
                        organism = Homo sapiens
SEQUENCE: 768
tagtggaaat aagacgtcaa atacaaagtt ttaagagaag caaatgcagc agcggcggct    60
gcctgtctct taccatgtcg ggcgcctggt cactgcgagc                         100

SEQ ID NO: 769          moltype = DNA  length = 100
FEATURE                 Location/Qualifiers
source                  1..100
                        mol_type = genomic DNA
                        organism = Homo sapiens
SEQUENCE: 769
cttgcaaagc tttggcatgg aatcattcct ccaagtccat taacaagggc tggggcctga    60
gcagccagtc ggcccggcag cagaagccac gcatcccagc                         100

SEQ ID NO: 770          moltype = DNA  length = 100
FEATURE                 Location/Qualifiers
source                  1..100
                        mol_type = genomic DNA
                        organism = Homo sapiens
SEQUENCE: 770
tctgggtagt ccggggagac ccaaagccca ggccgggcct ggcagccacc ctcccagagc    60
ctccgctagg ccagtcctgc tgacgccgca tcggtgattc                         100

SEQ ID NO: 771          moltype = DNA  length = 100
FEATURE                 Location/Qualifiers
source                  1..100
                        mol_type = genomic DNA
                        organism = Homo sapiens
SEQUENCE: 771
ggaacagaat ctgtccttct aaggtgtctc cacagtcctg tcttcagcac tatctgattg    60
agttttctct tatgccacca actaacatgc ttaactgaaa                         100

SEQ ID NO: 772          moltype = DNA  length = 100
FEATURE                 Location/Qualifiers
source                  1..100
                        mol_type = genomic DNA
                        organism = Homo sapiens
SEQUENCE: 772
taattcagga taatgatgca catttttacct aaaacttatc ctaaagtgag tagttgaaaa    60
gtggtcttga aaaatactaa aatgaaggcc actctatcag                         100

SEQ ID NO: 773          moltype = DNA  length = 100
FEATURE                 Location/Qualifiers
```

```
source                  1..100
                        mol_type = genomic DNA
                        organism = Homo sapiens
SEQUENCE: 773
aatatcaaag tgtttctcct taatcacaaa gagaaaacga gttaacctaa aaagattgtg    60
aacacagtca ttatgaaaat aatgctctga ggtatcgaaa                         100

SEQ ID NO: 774          moltype = DNA   length = 100
FEATURE                 Location/Qualifiers
source                  1..100
                        mol_type = genomic DNA
                        organism = Homo sapiens
SEQUENCE: 774
aagtatttga gattagttat cacatgaagg gataacaagc taatttaaaa aacttttttga   60
atacagtcat aaactctccc taagactgtt taatttctta                         100

SEQ ID NO: 775          moltype = DNA   length = 100
FEATURE                 Location/Qualifiers
source                  1..100
                        mol_type = genomic DNA
                        organism = Homo sapiens
SEQUENCE: 775
aacatcttac tttaaaaatg aatgcagttt agaagttgat atgctgtttg cacaaactag    60
cagttgataa gctaagattg gaaatgaaat tcagatagtt                         100

SEQ ID NO: 776          moltype = DNA   length = 100
FEATURE                 Location/Qualifiers
source                  1..100
                        mol_type = genomic DNA
                        organism = Homo sapiens
SEQUENCE: 776
aaaaaaagcc ttttcagttt cggtcagcct cgccttattt tagaaacgca aattgtccag    60
gtgttgtttt gctcagtaga gcactttcag atctgggcct                         100

SEQ ID NO: 777          moltype = DNA   length = 100
FEATURE                 Location/Qualifiers
source                  1..100
                        mol_type = genomic DNA
                        organism = Homo sapiens
SEQUENCE: 777
gggcaaaacc acctcttcac aaccagaagt gataaattta ccaattgtgt tttttttgctt   60
cctaaaatag actctcgcgg tgacctgctt cctgccacct                         100

SEQ ID NO: 778          moltype = DNA   length = 100
FEATURE                 Location/Qualifiers
source                  1..100
                        mol_type = genomic DNA
                        organism = Homo sapiens
SEQUENCE: 778
gctgtgggtg ccggagaccc ccatgcagcc atcttgactc taattcatca tctgcttcca    60
gcttcgctca attaattaaa aaaataaact tgatttatga                         100

SEQ ID NO: 779          moltype = DNA   length = 100
FEATURE                 Location/Qualifiers
source                  1..100
                        mol_type = genomic DNA
                        organism = Homo sapiens
SEQUENCE: 779
tggtcaaaac gcagtcccgc atcggggccg acagcactgt gctagtattt cttagctgag    60
cttgctttgg cctcaattcc agacacatat cactcatggg                         100

SEQ ID NO: 780          moltype = DNA   length = 100
FEATURE                 Location/Qualifiers
source                  1..100
                        mol_type = genomic DNA
                        organism = Homo sapiens
SEQUENCE: 780
tgttaatcaa atgataagaa tttcaaatac ttggacagtt aaaaaaatta atatacttga    60
aaatctctca cattttaag tcataatttt cttaaccatt                          100

SEQ ID NO: 781          moltype = DNA   length = 100
FEATURE                 Location/Qualifiers
source                  1..100
                        mol_type = genomic DNA
                        organism = Homo sapiens
SEQUENCE: 781
tttctcagaa gccacttcaa acatatcctg tcttttaaca gtaagcatgc ctcctaagat    60
aaacaatcct tttctcttgg aaaccagctt caaggcactg                         100
```

| SEQ ID NO: 782 | moltype = DNA length = 100 |
|---|---|
| FEATURE | Location/Qualifiers |
| source | 1..100 |
| | mol_type = genomic DNA |
| | organism = Homo sapiens |

SEQUENCE: 782
aggtcctgga gcctccctaa gcccctgtca ggacggcagc caccgtttct gggctacccc   60
tgcccccaac cctgctctca tcaagaccgg ggctacgcgt                          100

| SEQ ID NO: 783 | moltype = DNA length = 100 |
|---|---|
| FEATURE | Location/Qualifiers |
| source | 1..100 |
| | mol_type = genomic DNA |
| | organism = Homo sapiens |

SEQUENCE: 783
ccctcctggc tggattcacc cactccgaca gttctctttc cagccaataa agaatttaag   60
atgcaggttg acacacagcg cacctcataa ttctaaagaa                         100

| SEQ ID NO: 784 | moltype = DNA length = 100 |
|---|---|
| FEATURE | Location/Qualifiers |
| source | 1..100 |
| | mol_type = genomic DNA |
| | organism = Homo sapiens |

SEQUENCE: 784
aatatttcac gattcgctgc tgtgcagcga tcttgcagtc ctacagacac cgctcctgag   60
acacattcct cagccatcac taagacccct ggtttgttca                         100

| SEQ ID NO: 785 | moltype = DNA length = 100 |
|---|---|
| FEATURE | Location/Qualifiers |
| source | 1..100 |
| | mol_type = genomic DNA |
| | organism = Homo sapiens |

SEQUENCE: 785
ggcatctcgt ccaaatgtgg ctccccaagc ccccaggctc agttactcca tcagacgcac   60
ccaacctgag tcccattttc caaaggcatc ggaaaatcca                         100

| SEQ ID NO: 786 | moltype = DNA length = 100 |
|---|---|
| FEATURE | Location/Qualifiers |
| source | 1..100 |
| | mol_type = genomic DNA |
| | organism = Homo sapiens |

SEQUENCE: 786
cagaggctcc cagatcctca aggcacccca gtgcccgtcc cctcctggcc agtccgccca   60
ggtcccctcg gaacatgccc cgaggaccaa cctgcaatgc                         100

| SEQ ID NO: 787 | moltype = DNA length = 100 |
|---|---|
| FEATURE | Location/Qualifiers |
| source | 1..100 |
| | mol_type = genomic DNA |
| | organism = Homo sapiens |

SEQUENCE: 787
tcaggaaacc ccacaggcag tagcagaaaa caaaggccct agagtggcca ttcttacctg   60
aggagacggt gaccgtggtc cctttgcccc agacgtccat                         100

| SEQ ID NO: 788 | moltype = DNA length = 100 |
|---|---|
| FEATURE | Location/Qualifiers |
| source | 1..100 |
| | mol_type = genomic DNA |
| | organism = Homo sapiens |

SEQUENCE: 788
gtagtagtag tagtagtaat cacaatggca gaatgtccat cctcaccccca caaaaccca   60
gccacccaga gaccttctgt ctccgggcgt cacatggaag                         100

| SEQ ID NO: 789 | moltype = DNA length = 100 |
|---|---|
| FEATURE | Location/Qualifiers |
| source | 1..100 |
| | mol_type = genomic DNA |
| | organism = Homo sapiens |

SEQUENCE: 789
ctgactgtcc gtggcctgt cctgcccttc tcatggaacc ctctgctggc ctcccacgta    60
ccccacattc tggcctgacc cctcagaagc cagaccactg                         100

| SEQ ID NO: 790 | moltype = DNA length = 100 |
|---|---|
| FEATURE | Location/Qualifiers |
| source | 1..100 |
| | mol_type = genomic DNA |
| | organism = Homo sapiens |

SEQUENCE: 790
tcggcctggg aagtccaact gcaagcagac ggctgctaag tcacccccag gagtccaaaa   60

-continued

```
accccgggggg gcacccgtcc cagagagcgg gtgccttgga                           100

SEQ ID NO: 791          moltype = DNA   length = 100
FEATURE                 Location/Qualifiers
source                  1..100
                        mol_type = genomic DNA
                        organism = Homo sapiens
SEQUENCE: 791
gcgggacaga gtcccaccac gcaatcatca cgacagcccc tgagaatgct ccaggtgaag        60
cggagagagg tcaccccaga ccagccgaag gagcccccca                             100

SEQ ID NO: 792          moltype = DNA   length = 100
FEATURE                 Location/Qualifiers
source                  1..100
                        mol_type = genomic DNA
                        organism = Homo sapiens
SEQUENCE: 792
gctgccgaca tctgtggccg gacttgggga ggacaggctg ggttcccatt cgaagggtcc        60
ctctccccgg ctttctttcc tgacctccaa aatgcctcca                             100

SEQ ID NO: 793          moltype = DNA   length = 100
FEATURE                 Location/Qualifiers
source                  1..100
                        mol_type = genomic DNA
                        organism = Homo sapiens
SEQUENCE: 793
agactctgac cctgagaccc tggcaagctg agtctcccta agtggactca gagaggggggt       60
ggtgaggact cacctgagga gacggtgacc agggttccct                             100

SEQ ID NO: 794          moltype = DNA   length = 100
FEATURE                 Location/Qualifiers
source                  1..100
                        mol_type = genomic DNA
                        organism = Homo sapiens
SEQUENCE: 794
ggccccaggg gtcgaaccag ttgtcacatt gtgacaacaa tgccaggacc ccaggcaaga        60
actggcgccc cgctacgtcc ctgggaccct ctcagactga                             100

SEQ ID NO: 795          moltype = DNA   length = 100
FEATURE                 Location/Qualifiers
source                  1..100
                        mol_type = genomic DNA
                        organism = Homo sapiens
SEQUENCE: 795
gcccggggag ggcccggggg ttgttgggca ttggacccca gaggcctagg gtggccctgg        60
ccacagagag accgtgctg ctgggctcag gaggaaggag                              100

SEQ ID NO: 796          moltype = DNA   length = 100
FEATURE                 Location/Qualifiers
source                  1..100
                        mol_type = genomic DNA
                        organism = Homo sapiens
SEQUENCE: 796
catctggagc ccttgcccct cgtctgtgtg gccgctgttg cctcagggca tcctcctgag        60
cccccagga tgctccgggg ctctcttggc aggagaccca                              100

SEQ ID NO: 797          moltype = DNA   length = 100
FEATURE                 Location/Qualifiers
source                  1..100
                        mol_type = genomic DNA
                        organism = Homo sapiens
SEQUENCE: 797
gcaccttat ttcccccag aaatgcagca aaacccttca gagttaaagc aggagagagg          60
ttgtgaggac tcacctgagg agacggtgac cagggttccc                             100

SEQ ID NO: 798          moltype = DNA   length = 100
FEATURE                 Location/Qualifiers
source                  1..100
                        mol_type = genomic DNA
                        organism = Homo sapiens
SEQUENCE: 798
tggccccagt agtcaaagta gtcacattgt gggaggcccc attaaggggt gcacaaaaac        60
ctgactctcc gactgtcccg ggccggccgt ggcagccagc                             100

SEQ ID NO: 799          moltype = DNA   length = 100
FEATURE                 Location/Qualifiers
source                  1..100
                        mol_type = genomic DNA
                        organism = Homo sapiens
```

```
SEQUENCE: 799
cccgtgtccc aaggtcattt tgtccccagc acaagcatga ctctgcccac cctttgcccc     60
agcagcagag tcccagttcc caaagaaagg ccttctgctg                          100

SEQ ID NO: 800          moltype = DNA   length = 100
FEATURE                 Location/Qualifiers
source                  1..100
                        mol_type = genomic DNA
                        organism = Homo sapiens
SEQUENCE: 800
aacgtggtcc caaacagccg gagaaggagc cccggagggc cccacatggc ccagcgcaga     60
ccaaggagcc cccggacatt atctcccagc tccaggacag                          100

SEQ ID NO: 801          moltype = DNA   length = 100
FEATURE                 Location/Qualifiers
source                  1..100
                        mol_type = genomic DNA
                        organism = Homo sapiens
SEQUENCE: 801
aggacgctgg gcccagagaa aggaggcaga aggaaagcca tcttacctga agagacggtg     60
accattgtcc cttggcccca gatatcaaaa gcatcacaca                          100

SEQ ID NO: 802          moltype = DNA   length = 100
FEATURE                 Location/Qualifiers
source                  1..100
                        mol_type = genomic DNA
                        organism = Homo sapiens
SEQUENCE: 802
gggacacagt ccctgttcct gcccagacac aaacctgtgc ccgtgcagga cactcgaatg     60
ggtcacatgg cccaagcaca gagcagaggc agccggcgtc                          100

SEQ ID NO: 803          moltype = DNA   length = 100
FEATURE                 Location/Qualifiers
source                  1..100
                        mol_type = genomic DNA
                        organism = Homo sapiens
SEQUENCE: 803
cctgtcccca gccacacaga ccccgggct gagacccagg cagggagggg tgacgttccc      60
agggagacgg tggccgggct gccctggccc cagtgctcca                          100

SEQ ID NO: 804          moltype = DNA   length = 100
FEATURE                 Location/Qualifiers
source                  1..100
                        mol_type = genomic DNA
                        organism = Homo sapiens
SEQUENCE: 804
agcacttgta gccacactaa agcgcaggcc tggtccccgg cacatgaaca gccagcgccc     60
agccccagcc caggctctgc ccacaacttc tccttcccgt                          100

SEQ ID NO: 805          moltype = DNA   length = 100
FEATURE                 Location/Qualifiers
source                  1..100
                        mol_type = genomic DNA
                        organism = Homo sapiens
SEQUENCE: 805
ccctgccctc ggcctgcttg ctacctgtgg agggtccctg acggggctga agcccagcgg     60
ggtccctgcc tgtccttggg ggctccagct ggccccaggg                          100

SEQ ID NO: 806          moltype = DNA   length = 100
FEATURE                 Location/Qualifiers
source                  1..100
                        mol_type = genomic DNA
                        organism = Homo sapiens
SEQUENCE: 806
ctaagtgaca gcagggctct ggcatgcagc ccatggcgga gaccccaggg atggcagctg     60
gtgtggcctc aggccagacc caggccggct gcagacccca                          100

SEQ ID NO: 807          moltype = DNA   length = 100
FEATURE                 Location/Qualifiers
source                  1..100
                        mol_type = genomic DNA
                        organism = Homo sapiens
SEQUENCE: 807
gatacctggc ctggtgcctg gacagagaag actgggaggg ggctgcagtg ggactcacct     60
gaggagacag tgaccagggt gccacggccc cagagatcga                          100

SEQ ID NO: 808          moltype = DNA   length = 100
FEATURE                 Location/Qualifiers
source                  1..100
```

```
                        mol_type = genomic DNA
                        organism = Homo sapiens
SEQUENCE: 808
agtaccagta gcacagcctc tgccctcctg cttctcccat acaaaaacac accctccgcc    60
ctcctgccga cctcctttgc tgagcacctg tccccaagtc                          100

SEQ ID NO: 809          moltype = DNA  length = 100
FEATURE                 Location/Qualifiers
source                  1..100
                        mol_type = genomic DNA
                        organism = Homo sapiens
SEQUENCE: 809
tgaagccaaa gcccttgcct ggcccagtac acctggctcc ccgctatccc cagacagcag    60
actcacctga ggagacggtg accagggtgc cctggcccca                          100

SEQ ID NO: 810          moltype = DNA  length = 100
FEATURE                 Location/Qualifiers
source                  1..100
                        mol_type = genomic DNA
                        organism = Homo sapiens
SEQUENCE: 810
gtgctggaag tattcagcca cggtgagtca gccctgagcc aggggctaca gaaacccaca    60
gcccgggtc ccgggggagc atggtttttg tagagctgcc                           100

SEQ ID NO: 811          moltype = DNA  length = 100
FEATURE                 Location/Qualifiers
source                  1..100
                        mol_type = genomic DNA
                        organism = Homo sapiens
SEQUENCE: 811
aatcactgtg tccccagtta gcacagtggt tctcagctca gccaaaaccc tgcggctggt    60
aggggggcctg tggggctggg ggctgatgtg gctgcggtct                         100

SEQ ID NO: 812          moltype = DNA  length = 100
FEATURE                 Location/Qualifiers
source                  1..100
                        mol_type = genomic DNA
                        organism = Homo sapiens
SEQUENCE: 812
tgctgggtct gtcctctgtg ggaggggctg ctacccaggc ccaggactgc agtggagggc    60
tcactgaggg gcttttgggt ctggcctgag ccgctgtggg                          100

SEQ ID NO: 813          moltype = DNA  length = 100
FEATURE                 Location/Qualifiers
source                  1..100
                        mol_type = genomic DNA
                        organism = Homo sapiens
SEQUENCE: 813
gctctcaggt ctactgcggg gacactcggg tctgccctg gcttaggtgg acagtgtccg     60
tgcccacctg tgccctgagg ctccatttca ggctgatatc                          100

SEQ ID NO: 814          moltype = DNA  length = 100
FEATURE                 Location/Qualifiers
source                  1..100
                        mol_type = genomic DNA
                        organism = Homo sapiens
SEQUENCE: 814
tgtctgtatt gtccctaccc gctgcatggc catgtccttt tgggtttata aattgccccc    60
aaatcacgca ggcatcattc aggctttta tattccctgg                           100

SEQ ID NO: 815          moltype = DNA  length = 100
FEATURE                 Location/Qualifiers
source                  1..100
                        mol_type = genomic DNA
                        organism = Homo sapiens
SEQUENCE: 815
tattccctgg gccaccaggt gcctccaccc agaaagctga gatgtgggag gttctagagt    60
cattctgcaa ccctggatga gccctgcag cctcagtgct                           100

SEQ ID NO: 816          moltype = DNA  length = 100
FEATURE                 Location/Qualifiers
source                  1..100
                        mol_type = genomic DNA
                        organism = Homo sapiens
SEQUENCE: 816
actgaggttc cagcaagacc tggagcaggt gcagatgagg cctgaggcca ggtgaagccc    60
aggccaggta aggtccaggc cagtgaggcc caggtcagat                          100

SEQ ID NO: 817          moltype = DNA  length = 100
```

```
FEATURE                 Location/Qualifiers
source                  1..100
                        mol_type = genomic DNA
                        organism = Homo sapiens
SEQUENCE: 817
gaggcccagg tcaggtgaag cccaggtcag gtgaaaccca ggtcaggtga ggcccagatc    60
atgtgagctc aggacaggca aggtccaagt caggtgaggc                         100

SEQ ID NO: 818          moltype = DNA  length = 100
FEATURE                 Location/Qualifiers
source                  1..100
                        mol_type = genomic DNA
                        organism = Homo sapiens
SEQUENCE: 818
cgagctcagg tgaagcccag aggtgaggtc taggccaggt gaggtccagg ccaggtgagg    60
tccaggtcag gtgaggccca ggtcaggcaa ggctgaggta                         100

SEQ ID NO: 819          moltype = DNA  length = 100
FEATURE                 Location/Qualifiers
source                  1..100
                        mol_type = genomic DNA
                        organism = Homo sapiens
SEQUENCE: 819
tccaggtcag gtgaggccca ggtcaggcaa ggctgaggta gatgtatgag acttctgtaa    60
ttttcagttg gtgccaaccc tgcctggtgt ccctgcccct                         100

SEQ ID NO: 820          moltype = DNA  length = 100
FEATURE                 Location/Qualifiers
source                  1..100
                        mol_type = genomic DNA
                        organism = Homo sapiens
SEQUENCE: 820
cctcccagcc catgctctgt gcctgccaga tggcggcccc tgcacaggtg ctgctggctg    60
tggaggagct gggctctgcc tccctgtgca tgggcgtccc                         100

SEQ ID NO: 821          moltype = DNA  length = 100
FEATURE                 Location/Qualifiers
source                  1..100
                        mol_type = genomic DNA
                        organism = Homo sapiens
SEQUENCE: 821
gcctgcagcc tgtccgggga tgcccaggga ggtgagtgcc accacatatc aggccttttc    60
tctttaaagt catttctttg gggatacatc atcaatgtct                         100

SEQ ID NO: 822          moltype = DNA  length = 100
FEATURE                 Location/Qualifiers
source                  1..100
                        mol_type = genomic DNA
                        organism = Homo sapiens
SEQUENCE: 822
tctaaacaca gctgtgtgca ttttcctctt cttgcaattt agaattttaa ctgctgtttt    60
caaggtactg taatgtattt gttctcttct tgttaggaga                         100

SEQ ID NO: 823          moltype = DNA  length = 100
FEATURE                 Location/Qualifiers
source                  1..100
                        mol_type = genomic DNA
                        organism = Homo sapiens
SEQUENCE: 823
cttgccaacc ctgtgtgtct cagttcatac cctcttcctt ccccagtaga agtaacgacc    60
actgtgttta tgtgatcatc cttttcttga ttttccttat                         100

SEQ ID NO: 824          moltype = DNA  length = 100
FEATURE                 Location/Qualifiers
source                  1..100
                        mol_type = genomic DNA
                        organism = Homo sapiens
SEQUENCE: 824
tgtgatcatc cttttcttga ttttccttat agttttccta gtggaaagtt tatcccttaa    60
gaagatagtt cattttgccg gctgtaaatt ttatttagaa                         100

SEQ ID NO: 825          moltype = DNA  length = 100
FEATURE                 Location/Qualifiers
source                  1..100
                        mol_type = genomic DNA
                        organism = Homo sapiens
SEQUENCE: 825
ctgccatcgt ttatttgcct gttttccttc agatggctgt tgcttcatt ctcagtttgg     60
ggctatgaca aacatatgtt ctgcacatct ttgcccatga                         100
```

```
SEQ ID NO: 826           moltype = DNA  length = 100
FEATURE                  Location/Qualifiers
source                   1..100
                         mol_type = genomic DNA
                         organism = Homo sapiens
SEQUENCE: 826
ggctctcagg gagggctctg gagctggcat tgcctgcagg gctctgcttt gttgcaggga    60
gttcctgcca aggcttttca gagtgtctgt gcccagcctg                         100

SEQ ID NO: 827           moltype = DNA  length = 100
FEATURE                  Location/Qualifiers
source                   1..100
                         mol_type = genomic DNA
                         organism = Homo sapiens
SEQUENCE: 827
aaggtacaca ctgtactttg cccttgcatc aggcactttc cttgtgcttg cttctgtgtg    60
gctccacatt ctggagaatt tattcagatc tgtgctgcaa                         100

SEQ ID NO: 828           moltype = DNA  length = 100
FEATURE                  Location/Qualifiers
source                   1..100
                         mol_type = genomic DNA
                         organism = Homo sapiens
SEQUENCE: 828
cttcccacac tgtcctcctg ggctcactcc cagccatcga tcttgaacac cagtttatgg    60
aactatctgc acaggaaagc agaaacagca aaaggccctg                         100

SEQ ID NO: 829           moltype = DNA  length = 100
FEATURE                  Location/Qualifiers
source                   1..100
                         mol_type = genomic DNA
                         organism = Homo sapiens
SEQUENCE: 829
ttgcgtggac cctgtttttg gtcaagggaa gtacttgctg gtgaaggaga cctcccctcc    60
tttctttctc aggagccccc tctgatgccg ttgcctggtg                         100

SEQ ID NO: 830           moltype = DNA  length = 100
FEATURE                  Location/Qualifiers
source                   1..100
                         mol_type = genomic DNA
                         organism = Homo sapiens
SEQUENCE: 830
tttctcaggg ctggtgctgg gggctcagca gtgtctgccc tgttccaggt gggaatgtgg    60
gtctgttctg tttccacgcg gtgttctggg gccgccagtg                         100

SEQ ID NO: 831           moltype = DNA  length = 100
FEATURE                  Location/Qualifiers
source                   1..100
                         mol_type = genomic DNA
                         organism = Homo sapiens
SEQUENCE: 831
cagcagtgtc tgccctgttc caggtgggaa tgtgggtctg ttctgtttcc acgcggtgtt    60
ctggggccgc cagtgagggg ctcgggatgt cagcggctgg                         100

SEQ ID NO: 832           moltype = DNA  length = 100
FEATURE                  Location/Qualifiers
source                   1..100
                         mol_type = genomic DNA
                         organism = Homo sapiens
SEQUENCE: 832
tctctgtccc tatggtctgg gctccggttc actgctcccc tgccctccag gtcggtcact    60
gactcagtta ctatccagcg ggctccgtgg ctgttcagtg                         100

SEQ ID NO: 833           moltype = DNA  length = 100
FEATURE                  Location/Qualifiers
source                   1..100
                         mol_type = genomic DNA
                         organism = Homo sapiens
SEQUENCE: 833
gggagcaaat ggagagggaa gtggcagcgg cccgagtgcc aggcggtccc ggtttggggt    60
tgatctttgt ggaacagctc cctggcccgt gtgtaagtgg                         100

SEQ ID NO: 834           moltype = DNA  length = 100
FEATURE                  Location/Qualifiers
source                   1..100
                         mol_type = genomic DNA
                         organism = Homo sapiens
SEQUENCE: 834
```

```
tcggggagg cacggaggtc tggagctaca agcggtggca ggaaggcagg tcccagtctt    60
gggggtctgg agcttatctt cttcctgtga actgagtgtg                        100
```

SEQ ID NO: 835         moltype = DNA  length = 100
FEATURE                Location/Qualifiers
source                 1..100
                       mol_type = genomic DNA
                       organism = Homo sapiens
SEQUENCE: 835
```
atggaggacc tgcctcggat gacacccta tcttaagaag gtcatggtgg gttccagctg    60
ggaggaaggg aagtgggcca cctcctgggg gtcttccacc                        100
```

SEQ ID NO: 836         moltype = DNA  length = 100
FEATURE                Location/Qualifiers
source                 1..100
                       mol_type = genomic DNA
                       organism = Homo sapiens
SEQUENCE: 836
```
gtcttccacc cccaccacct cagcctgggg cctctgtgat tcctctctgc acagacccca    60
aagtctgtgc tgccgcaggg caggaaggaa gggcctgtgg                        100
```

SEQ ID NO: 837         moltype = DNA  length = 100
FEATURE                Location/Qualifiers
source                 1..100
                       mol_type = genomic DNA
                       organism = Homo sapiens
SEQUENCE: 837
```
tcgaggttgg ggccacagtg gtgttccta agcccgagtc tggtctcatg gcccgccccg    60
cagcaggtcc tgagtgaggg acagagaccg gggcggggtc                        100
```

SEQ ID NO: 838         moltype = DNA  length = 100
FEATURE                Location/Qualifiers
source                 1..100
                       mol_type = genomic DNA
                       organism = Homo sapiens
SEQUENCE: 838
```
tttggtcctg gtggactctg gggtggattc cagtggggag tcatcagggt cggtgtcccc    60
cagggtactg gggtgtctct gctcctggag tcggctctgg                        100
```

SEQ ID NO: 839         moltype = DNA  length = 100
FEATURE                Location/Qualifiers
source                 1..100
                       mol_type = genomic DNA
                       organism = Homo sapiens
SEQUENCE: 839
```
cctgggtttt tgtacaggag gtgccctggg ctgtgtcttt gtggtctgtg tgcacagtaa    60
tatgtggctg tgtccacagg gtccatgttg gtcattgtaa                        100
```

SEQ ID NO: 840         moltype = DNA  length = 100
FEATURE                Location/Qualifiers
source                 1..100
                       mol_type = genomic DNA
                       organism = Homo sapiens
SEQUENCE: 840
```
gtgtccttgg tgatggtgag cctgctcttc agagatgggc tgtagcgctt atcatcattc    60
caataaatga gtgcaagcca ctccagggcc tttcctgggg                        100
```

SEQ ID NO: 841         moltype = DNA  length = 100
FEATURE                Location/Qualifiers
source                 1..100
                       mol_type = genomic DNA
                       organism = Homo sapiens
SEQUENCE: 841
```
gctgacggat ccagcccaca cccactccac tagtgctgag tgagaaccca gagaaggtgc    60
aggtcagcgt gagggtctgt gtgggtttca ccagcgtagg                        100
```

SEQ ID NO: 842         moltype = DNA  length = 100
FEATURE                Location/Qualifiers
source                 1..100
                       mol_type = genomic DNA
                       organism = Homo sapiens
SEQUENCE: 842
```
ctgtggagaa agcataagaa gatgaagccc acaaacaaga aaactgatgt ttcacccgtg    60
aaggagtccc tgaccacagc actcacatga agggatggtc                        100
```

SEQ ID NO: 843         moltype = DNA  length = 100
FEATURE                Location/Qualifiers
source                 1..100
                       mol_type = genomic DNA

```
SEQUENCE: 843
agcagcagga gcgtggagca aagtgtgtcc atggtggggc acaggagtca ctgagctggg    60
acctgtgctc ggcttttca acccagagga gggtggagct                          100

SEQ ID NO: 844              moltype = DNA   length = 100
FEATURE                     Location/Qualifiers
source                      1..100
                            mol_type = genomic DNA
                            organism = Homo sapiens
SEQUENCE: 844
aagtgtgtcc atggtggggc acaggagtca ctgagctggg acctgtgctc ggcttttca    60
acccagagga gggtggagct ggtggagatt tgcattcccc                         100

SEQ ID NO: 845              moltype = DNA   length = 100
FEATURE                     Location/Qualifiers
source                      1..100
                            mol_type = genomic DNA
                            organism = Homo sapiens
SEQUENCE: 845
agatttgcat tccctcatc tgtgccctac tctatgggat ggagtcaggt ttcaggactc     60
aggagggtgt tgcatctgtg gtgaggacca gtgatagtaa                         100

SEQ ID NO: 846              moltype = DNA   length = 100
FEATURE                     Location/Qualifiers
source                      1..100
                            mol_type = genomic DNA
                            organism = Homo sapiens
SEQUENCE: 846
catgatcagt gtaattcaga tggcattaat ctaaggctgg gcaagtagat tctgagtaga    60
agtctttgca gaagtcatga ttatgaggtc atgttggtct                         100

SEQ ID NO: 847              moltype = DNA   length = 100
FEATURE                     Location/Qualifiers
source                      1..100
                            mol_type = genomic DNA
                            organism = Homo sapiens
SEQUENCE: 847
gcccttcaca gagtccacat agtatttctc acttccatct tgctttatgt tggccaccca    60
ctccagcccc ttccctggag cctggcggac ccagctcatc                         100

SEQ ID NO: 848              moltype = DNA   length = 100
FEATURE                     Location/Qualifiers
source                      1..100
                            mol_type = genomic DNA
                            organism = Homo sapiens
SEQUENCE: 848
tgagtcctct gtgctcagtg ctgatcacca agtggaaagg ccttggagtc cagggctaag    60
gctcctctct gagacctgca gggtcagggt tgggttggtt                         100

SEQ ID NO: 849              moltype = DNA   length = 100
FEATURE                     Location/Qualifiers
source                      1..100
                            mol_type = genomic DNA
                            organism = Homo sapiens
SEQUENCE: 849
ttcatcagta gagggagggc cctatttgca tgtctcctac tatataagaa gctctagtgg    60
gatgctggag gaataggctg tacccatata agaagacggt                         100

SEQ ID NO: 850              moltype = DNA   length = 100
FEATURE                     Location/Qualifiers
source                      1..100
                            mol_type = genomic DNA
                            organism = Homo sapiens
SEQUENCE: 850
agggccctat ttgcatgtct cctactatat aagaagctct agtgggatgc tggaggaata    60
ggctgtaccc atataagaag acggtgctct gcagaagttt                         100

SEQ ID NO: 851              moltype = DNA   length = 100
FEATURE                     Location/Qualifiers
source                      1..100
                            mol_type = genomic DNA
                            organism = Homo sapiens
SEQUENCE: 851
gctgacaatg atggtatttg gaaaatatgc tgtcttatga aattgtgctg tgataaacac    60
tttgccctga tcaccctatt acatttttta aaaaatgtgt                         100

SEQ ID NO: 852              moltype = DNA   length = 100
FEATURE                     Location/Qualifiers
```

```
source                  1..100
                        mol_type = genomic DNA
                        organism = Homo sapiens
SEQUENCE: 852
caaacacaga gacaacctag tcagaaactg ccacatatat tcactgctta tctcactcac    60
gtccactcaa tgtctctagt tctccataaa tcaccttta                          100

SEQ ID NO: 853          moltype = DNA  length = 100
FEATURE                 Location/Qualifiers
source                  1..100
                        mol_type = genomic DNA
                        organism = Homo sapiens
SEQUENCE: 853
taatagcaac aaggaaaacc cagctcagcc caaactccat ggtgagtcct ctgtgttcag    60
tgctgatcac cgaatggaaa ctcctgggaa ttctggggct                         100

SEQ ID NO: 854          moltype = DNA  length = 100
FEATURE                 Location/Qualifiers
source                  1..100
                        mol_type = genomic DNA
                        organism = Homo sapiens
SEQUENCE: 854
gtcctctgtg ttcagtgctg atcaccgaat ggaaactcct gggaattctg ggctggggc    60
tcttctccca gagctgcagg gtctgggctc ggctggtttt                         100

SEQ ID NO: 855          moltype = DNA  length = 100
FEATURE                 Location/Qualifiers
source                  1..100
                        mol_type = genomic DNA
                        organism = Homo sapiens
SEQUENCE: 855
tatcagcaga gggagggccc tatttgcatg tctcctacta tatagcaagc tctagtggga    60
cgctggagga gagggcagtg cccagagcag atgagagggt                         100

SEQ ID NO: 856          moltype = DNA  length = 100
FEATURE                 Location/Qualifiers
source                  1..100
                        mol_type = genomic DNA
                        organism = Homo sapiens
SEQUENCE: 856
cccggaaaac actggaggta atcctatctc tcaggaaaat ataacttcag attatgtgat    60
tgtgacttga tgatcaatta gcagtcatca tcttatttaa                         100

SEQ ID NO: 857          moltype = DNA  length = 100
FEATURE                 Location/Qualifiers
source                  1..100
                        mol_type = genomic DNA
                        organism = Homo sapiens
SEQUENCE: 857
tgtttacata tttgcagaat atattcagtg caagtgtcaa tgttacattt ttagagaaga    60
tgaattacat acataacaga gcagttgtgc aatgtgtcca                         100

SEQ ID NO: 858          moltype = DNA  length = 100
FEATURE                 Location/Qualifiers
source                  1..100
                        mol_type = genomic DNA
                        organism = Homo sapiens
SEQUENCE: 858
actcacactt aatctctcta gttctccata aatcaccttt taaaatagca gcaaggaaaa    60
tccagctcag cccaaactcc atggtgagtc tctgtgttc                          100

SEQ ID NO: 859          moltype = DNA  length = 100
FEATURE                 Location/Qualifiers
source                  1..100
                        mol_type = genomic DNA
                        organism = Homo sapiens
SEQUENCE: 859
gatgctattt aatagcccaa ttcctgaccc aggatgagaa agagcaaata catgacacat    60
ggacgacaca attgtagaag ctgagggttc aagccgtaat                         100

SEQ ID NO: 860          moltype = DNA  length = 100
FEATURE                 Location/Qualifiers
source                  1..100
                        mol_type = genomic DNA
                        organism = Homo sapiens
SEQUENCE: 860
cctgttagag gccacgcatc ccctacccat ccctgaactc tgtgttgaca gagcttcccc    60
cactggagaa caagctcccc caggacacgc acctcactta                         100
```

```
SEQ ID NO: 861           moltype = DNA   length = 100
FEATURE                  Location/Qualifiers
source                   1..100
                         mol_type = genomic DNA
                         organism = Homo sapiens
SEQUENCE: 861
ggcccttcac ggagtctgcg tagtatgtgc taccaccact accactaata gctgagaccc     60
actccagccc cttccctgga gcctggcgga cccagctcat                          100

SEQ ID NO: 862           moltype = DNA   length = 100
FEATURE                  Location/Qualifiers
source                   1..100
                         mol_type = genomic DNA
                         organism = Homo sapiens
SEQUENCE: 862
ggcatagctg ctaaaggtga atccagaggc tgcacaggag agtctcaggg accccccagg     60
ctgtaccaag cctcccccag actccaacag ctgcacctca                          100

SEQ ID NO: 863           moltype = DNA   length = 100
FEATURE                  Location/Qualifiers
source                   1..100
                         mol_type = genomic DNA
                         organism = Homo sapiens
SEQUENCE: 863
actgtttctc tcactcttat ccattcacac tcaattttc tatttctcca tgaattacct      60
tttaaaatag ccacaagaaa aagccagctc agcccaaact                          100

SEQ ID NO: 864           moltype = DNA   length = 100
FEATURE                  Location/Qualifiers
source                   1..100
                         mol_type = genomic DNA
                         organism = Homo sapiens
SEQUENCE: 864
ccatggtgag ttctctctgt tcagtcctga tcaccaaatg aaaacacctg aaaatcccag     60
ggctgggctc ctctctcaga gctgcagggt cagggctggg                          100

SEQ ID NO: 865           moltype = DNA   length = 100
FEATURE                  Location/Qualifiers
source                   1..100
                         mol_type = genomic DNA
                         organism = Homo sapiens
SEQUENCE: 865
tttgcatatc tcctactata tagtaagctc tggggtgaga ggcctttgga gatagtgggg     60
ctcagagcat gtcagaatgt cctcggggag atctgtgata                          100

SEQ ID NO: 866           moltype = DNA   length = 100
FEATURE                  Location/Qualifiers
source                   1..100
                         mol_type = genomic DNA
                         organism = Homo sapiens
SEQUENCE: 866
ttgaaagcat tgggaaattg tgctttccta ttgtcagttt gttttgtgat aaacttaaac     60
cttaaaacct aaaaatctta taattttgta attttattt                           100

SEQ ID NO: 867           moltype = DNA   length = 100
FEATURE                  Location/Qualifiers
source                   1..100
                         mol_type = genomic DNA
                         organism = Homo sapiens
SEQUENCE: 867
gaggtaccat agatctacat aaactgcata tttttaaagt tagcaccaat catcttttat     60
ttttacatac gcagagaaac catggtatat agtatcaata                          100

SEQ ID NO: 868           moltype = DNA   length = 100
FEATURE                  Location/Qualifiers
source                   1..100
                         mol_type = genomic DNA
                         organism = Homo sapiens
SEQUENCE: 868
ttatttccat gttaaagatg aaaaattatc agcaaaagca caggtgggtt ttacaatgtc     60
cccagtgctc acttttggtc agagtgagcc tgggcatctg                          100

SEQ ID NO: 869           moltype = DNA   length = 100
FEATURE                  Location/Qualifiers
source                   1..100
                         mol_type = genomic DNA
                         organism = Homo sapiens
SEQUENCE: 869
tcctacataa tgacagtgta cacatctttc cattgctgtt ttactcaatt actcaaccca    60
```

```
                                                       -continued tttttctaaac agatttaaac ttcataaatc ctgtcatctc                                    100

SEQ ID NO: 870          moltype = DNA   length = 100
FEATURE                 Location/Qualifiers
source                  1..100
                        mol_type = genomic DNA
                        organism = Homo sapiens
SEQUENCE: 870
ctcagcctca gcacagctgc ctcattcctc agggtttctg acgctctcag gatgtgggtt              60
ttcacactgt gtctgttgca cagtaataca cggccgtgtc                                   100

SEQ ID NO: 871          moltype = DNA   length = 100
FEATURE                 Location/Qualifiers
source                  1..100
                        mol_type = genomic DNA
                        organism = Homo sapiens
SEQUENCE: 871
gctcagctcc atgtaggctg tgtctgtaga tgtgtcctcg gtcatggtga ctctgccctg              60
gaacttctgt gcgtagattg tttcaccatc ttcaggatca                                   100

SEQ ID NO: 872          moltype = DNA   length = 100
FEATURE                 Location/Qualifiers
source                  1..100
                        mol_type = genomic DNA
                        organism = Homo sapiens
SEQUENCE: 872
ttcaggatca aaacctccca tccactcaag ccctttcca ggagcctgtc gcacccagtg               60
catggataat tcagtgaggg tgtatccgga aaccttgcag                                   100

SEQ ID NO: 873          moltype = DNA   length = 100
FEATURE                 Location/Qualifiers
source                  1..100
                        mol_type = genomic DNA
                        organism = Homo sapiens
SEQUENCE: 873
gagaccttca ctgaggcccc aggcttcttc acctcagccc cagactgtac cagctggacc              60
tgggcgtggg tgcctgtgga gaggacagag gagtggatga                                   100

SEQ ID NO: 874          moltype = DNA   length = 100
FEATURE                 Location/Qualifiers
source                  1..100
                        mol_type = genomic DNA
                        organism = Homo sapiens
SEQUENCE: 874
gacaccactt aactggaccc agtcccctca tcagccctgg aactcaggat tctcttgcct              60
gtagctgctg ccaccaagaa gaggatcctc caggtgcagt                                   100

SEQ ID NO: 875          moltype = DNA   length = 100
FEATURE                 Location/Qualifiers
source                  1..100
                        mol_type = genomic DNA
                        organism = Homo sapiens
SEQUENCE: 875
gagggtggga atctgggaga gcaaggggct tcccataagt gttctgataa aaatcctctt              60
tgtttagggg gaaagtgatg attttttga atgatagaga                                    100

SEQ ID NO: 876          moltype = DNA   length = 100
FEATURE                 Location/Qualifiers
source                  1..100
                        mol_type = genomic DNA
                        organism = Homo sapiens
SEQUENCE: 876
atacatcacc caaacattta aaatgtatt gtgtaaagaa gtgtaaatgg catctcagcc               60
atttacacac tgcaagacac acagcttatt agtgtgcctg                                   100

SEQ ID NO: 877          moltype = DNA   length = 100
FEATURE                 Location/Qualifiers
source                  1..100
                        mol_type = genomic DNA
                        organism = Homo sapiens
SEQUENCE: 877
tggtgaatcg gcccttcacg gagtctgcat agtatttatt acttccatca tatgatataa              60
ctgccaccca ctccagcccc ttgcctggag cctggcggac                                   100

SEQ ID NO: 878          moltype = DNA   length = 100
FEATURE                 Location/Qualifiers
source                  1..100
                        mol_type = genomic DNA
                        organism = Homo sapiens
```

-continued

```
SEQUENCE: 878
acaatcactt gagttcagac acaccaggat tcacttaatg ttattttag ttcagaacct    60
ctatcaggtt tagagggaat cgctctgtcc cagggagtgg                         100

SEQ ID NO: 879          moltype = DNA   length = 100
FEATURE                 Location/Qualifiers
source                  1..100
                        mol_type = genomic DNA
                        organism = Homo sapiens
SEQUENCE: 879
atcttacaat agcaaaacgg tcttagaaaa cccaacataa tctacagcga gacctcagca    60
tggcaagcaa ggaatcacta aagccaccag ggagatccgg                         100

SEQ ID NO: 880          moltype = DNA   length = 100
FEATURE                 Location/Qualifiers
source                  1..100
                        mol_type = genomic DNA
                        organism = Homo sapiens
SEQUENCE: 880
cactaaagcc accagggaga tccggatgca ctgatacgat ccagaaacat agcgagtccg    60
ggaactgatg cggactttga ggcagcctct ttttttttt                          100

SEQ ID NO: 881          moltype = DNA   length = 100
FEATURE                 Location/Qualifiers
source                  1..100
                        mol_type = genomic DNA
                        organism = Homo sapiens
SEQUENCE: 881
gatggtgaat cggcccttca cggagtctgc atagtattta ttacttccat cataccatat    60
aactgccacc cactccagcc ccttgcctgg agcctggcgg                         100

SEQ ID NO: 882          moltype = DNA   length = 100
FEATURE                 Location/Qualifiers
source                  1..100
                        mol_type = genomic DNA
                        organism = Homo sapiens
SEQUENCE: 882
acccagtgca tgccatagct actgaaggtg aatccagacg ctgcacagga gagtctcagg    60
gacctcccag gctggaccac gcctccccca gactccacca                         100

SEQ ID NO: 883          moltype = DNA   length = 100
FEATURE                 Location/Qualifiers
source                  1..100
                        mol_type = genomic DNA
                        organism = Homo sapiens
SEQUENCE: 883
ctcgactctt gagggacggg ttgtagttgg tgcttccact atgattgatt tccccaatcc    60
actccagccc cttccctggg ggctggcgga tccagctcca                         100

SEQ ID NO: 884          moltype = DNA   length = 100
FEATURE                 Location/Qualifiers
source                  1..100
                        mol_type = genomic DNA
                        organism = Homo sapiens
SEQUENCE: 884
ggctggcgga tccagctcca gtagtaacca ctgaaggacc caccatagac agcgcaggtg    60
agggacaggg tctccgaagg cttcaacagt cctgcgcccc                         100

SEQ ID NO: 885          moltype = DNA   length = 100
FEATURE                 Location/Qualifiers
source                  1..100
                        mol_type = genomic DNA
                        organism = Homo sapiens
SEQUENCE: 885
actgctgtag ctgcacctgg gacaggaccc ctgtgaacag agaaacccac agtgagccct    60
gggatcagag gcagcatctc atatcttcat atccgcattc                         100

SEQ ID NO: 886          moltype = DNA   length = 100
FEATURE                 Location/Qualifiers
source                  1..100
                        mol_type = genomic DNA
                        organism = Homo sapiens
SEQUENCE: 886
ctgagacact cacatctggg agctgccacc aggaggagga agaaccacag gtgtttcatg    60
ttcttgtgca ggaggtccat gactctcaga aagcacttcc                         100

SEQ ID NO: 887          moltype = DNA   length = 100
FEATURE                 Location/Qualifiers
source                  1..100
```

```
                        mol_type = genomic DNA
                        organism = Homo sapiens
SEQUENCE: 887
gaggatttgc atgtgggtgg tgcctttgta tggataggta aaaagggatg agggaggccc    60
cagtcttttg ggctcaccct gggaggtgta tgctggctgt                         100

SEQ ID NO: 888          moltype = DNA   length = 100
FEATURE                 Location/Qualifiers
source                  1..100
                        mol_type = genomic DNA
                        organism = Homo sapiens
SEQUENCE: 888
agttctcttc ctgtggcctc ccctcaccaa acccagagtc ctcttcttcc aggtaggaaa    60
tgtgctgaag gagctggtct gggagacaag tgtgatcatg                         100

SEQ ID NO: 889          moltype = DNA   length = 100
FEATURE                 Location/Qualifiers
source                  1..100
                        mol_type = genomic DNA
                        organism = Homo sapiens
SEQUENCE: 889
ggtctgggag acaagtgtga tcatggatca aagacagatt ttggaataca gttaatactg    60
ttctacattt aaagattcat ataacaccaa ccatacaccc                         100

SEQ ID NO: 890          moltype = DNA   length = 100
FEATURE                 Location/Qualifiers
source                  1..100
                        mol_type = genomic DNA
                        organism = Homo sapiens
SEQUENCE: 890
aggtcaccta aattgtcatt taccccttca gacatattga aacagctgct gagtgtaata    60
atcacagtga attgagacaa acctggatcc atgcaatgtg                         100

SEQ ID NO: 891          moltype = DNA   length = 100
FEATURE                 Location/Qualifiers
source                  1..100
                        mol_type = genomic DNA
                        organism = Homo sapiens
SEQUENCE: 891
tactgtagtt cagaacatcc atcatggtta gaaggatgct acctgtccca ggaagtgggt    60
tattttaaa tagtacctga gagctgccct tctgagacct                          100

SEQ ID NO: 892          moltype = DNA   length = 100
FEATURE                 Location/Qualifiers
source                  1..100
                        mol_type = genomic DNA
                        organism = Homo sapiens
SEQUENCE: 892
tttgaaattt gagattgtgt gtgagatctc aggagaaggt agtagaatat atctccatcc    60
ttctcaatgt gtaaccctga gaatatggcc tgacctctaa                         100

SEQ ID NO: 893          moltype = DNA   length = 100
FEATURE                 Location/Qualifiers
source                  1..100
                        mol_type = genomic DNA
                        organism = Homo sapiens
SEQUENCE: 893
acatttctgt gtgaaaagat gtacattggg gatagcagtg acagcttcag atgaaaactc    60
tatagtacat cagcactgga ggatagtctc atcaccaaga                         100

SEQ ID NO: 894          moltype = DNA   length = 100
FEATURE                 Location/Qualifiers
source                  1..100
                        mol_type = genomic DNA
                        organism = Homo sapiens
SEQUENCE: 894
ttagtgaaat tacctttcct gggaaccaga gaggacctct gtgagctcta ccctctgaga    60
gaacaaggaa ctctggttct tccctgacag gtcacacctg                         100

SEQ ID NO: 895          moltype = DNA   length = 100
FEATURE                 Location/Qualifiers
source                  1..100
                        mol_type = genomic DNA
                        organism = Homo sapiens
SEQUENCE: 895
aacaagtggg ctggccttct atgagacgac agagggaaag agacagactc aatatccaga    60
gcgaggtgag ctccttacct acctaccagg tggtctctgg                         100

SEQ ID NO: 896          moltype = DNA   length = 100
```

```
FEATURE                 Location/Qualifiers
source                  1..100
                        mol_type = genomic DNA
                        organism = Homo sapiens
SEQUENCE: 896
gccatttgtt tgagcagacc cagaagtacc ttcctcaccc tcaggagaat tatgaacatt      60
gagagaaact gagatacttt ttttatttac agggaatatt                          100

SEQ ID NO: 897          moltype = DNA  length = 100
FEATURE                 Location/Qualifiers
source                  1..100
                        mol_type = genomic DNA
                        organism = Homo sapiens
SEQUENCE: 897
tcatcggcgt gtttacatct acctgggtgt gtacagggat gctaggatgt gctcatacac      60
agaagagcaa gaattatatt tcgtggaaag aaaaccaaag                          100

SEQ ID NO: 898          moltype = DNA  length = 100
FEATURE                 Location/Qualifiers
source                  1..100
                        mol_type = genomic DNA
                        organism = Homo sapiens
SEQUENCE: 898
agcttctgaa tttgtaggta ttgtttgctg caaatgtgtc aggtcactag atcatgttat      60
gctgctagaa gaaaaacttc ccaacattgt catggagaca                          100

SEQ ID NO: 899          moltype = DNA  length = 100
FEATURE                 Location/Qualifiers
source                  1..100
                        mol_type = genomic DNA
                        organism = Homo sapiens
SEQUENCE: 899
aaatgcaaaa cagtaaagat tcaactgaga ttcccttgaa aatcaccagt aatgaacagg      60
ccaaaagaaa tcaaccattg tggaaagagt ggtcattaag                          100

SEQ ID NO: 900          moltype = DNA  length = 100
FEATURE                 Location/Qualifiers
source                  1..100
                        mol_type = genomic DNA
                        organism = Homo sapiens
SEQUENCE: 900
cccagtgtca ccttacacat cctgcaggtc acctcacaca tccaccaggt caccgcacat      60
atccccaca tcacctcaga cacaccctgg tcacctcata                           100

SEQ ID NO: 901          moltype = DNA  length = 100
FEATURE                 Location/Qualifiers
source                  1..100
                        mol_type = genomic DNA
                        organism = Homo sapiens
SEQUENCE: 901
catacgtcag gtcacctcac gctcacccaa ggtcacctca cacatcccgc aggtcacctc      60
gtaaatcccc caggtcacca catacatgca ccagttcacc                          100

SEQ ID NO: 902          moltype = DNA  length = 100
FEATURE                 Location/Qualifiers
source                  1..100
                        mol_type = genomic DNA
                        organism = Homo sapiens
SEQUENCE: 902
ctcttgaggg acgggttgta gtaggtgctc ccactataat agatactccc aatccactcc      60
agccccttcc ctgggggctg gcggatccag ccccagtagt                          100

SEQ ID NO: 903          moltype = DNA  length = 100
FEATURE                 Location/Qualifiers
source                  1..100
                        mol_type = genomic DNA
                        organism = Homo sapiens
SEQUENCE: 903
aactactact gctgatggag ccaccagaga cagtgcaggt gagggacagg gtctccgaag      60
gcttcaccag tcctgggccc gactcctgca gctgcagctg                          100

SEQ ID NO: 904          moltype = DNA  length = 100
FEATURE                 Location/Qualifiers
source                  1..100
                        mol_type = genomic DNA
                        organism = Homo sapiens
SEQUENCE: 904
gaacagaaaa acccacagtg agccctggga tcagaggcag cctcccatat ctccatgtct      60
gcatcctaga aacactcaca tctgggagcc gccaccagca                          100
```

| SEQ ID NO: 905 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 905
ggaggaagaa ccacaggtgc ttcattttct tgcacatgag atccatgact ctcagaaagc 60
atttccctta tgagttggac ctgaatttaa ggaaatgtgt 100

| SEQ ID NO: 906 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 906
ggtggcttcc tgtgggcgcc taagtgagga tttgcatggg ggtggtgcgt ttgtacggag 60
cagtgaaaag ggatgagaga ggcgccagtc ttttgagctc 100

| SEQ ID NO: 907 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 907
accctgggag gagaatgctg gctgtgccct ttgagaactc agttctcttc ttgggcctcc 60
cctctccaag cccagagtcc tcttcttcca ggtaaagaga 100

| SEQ ID NO: 908 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 908
tgtgctgaag gagctggtct gagagatgag tgtgatcctg gatcaaggac agattttgga 60
atagggtcag tactgttcaa cccttaaaga ttcatataaa 100

| SEQ ID NO: 909 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 909
acccaccaca cacccaggcc atctaaatag tcatttaccc tttcagacac attgaaacaa 60
cagctgaatg taataatgac agtgacttca aacaatactg 100

| SEQ ID NO: 910 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 910
atgtttattg tagttcagaa catccaccat ggttacaggg aagctcactg tccctggaag 60
tgggtcattt tttaaaagca cctgagagct gtccttctgt 100

| SEQ ID NO: 911 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 911
aaggtagtgg gacatatctc catacttctc aatgtgtgac cttgaagatg tgtcctgccc 60
tctaaacact tctgattgaa aatatgtaga ttggggatta 100

| SEQ ID NO: 912 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 912
gtggaaatgc cttggaatcc agggctaagg cacctctctg agagctgcag ggtcagggtt 60
gggttggttt tcatcagtag agggagggcc ctatttgcat 100

| SEQ ID NO: 913 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 913

```
ggacccttga ggagtaggct gtacccagat aagacgacgg tgccctgtag aagtttgctg    60
gcaatgattg catttggaaa atatgctgtc ttattatgaa                         100

SEQ ID NO: 914          moltype = DNA   length = 100
FEATURE                 Location/Qualifiers
source                  1..100
                        mol_type = genomic DNA
                        organism = Homo sapiens
SEQUENCE: 914
attgtgctgt gataaacact ttgcactaat caccctattt cattttaaat attcatgtaa    60
actatgttct gtaggagaca atattttctc catttacaga                         100

SEQ ID NO: 915          moltype = DNA   length = 100
FEATURE                 Location/Qualifiers
source                  1..100
                        mol_type = genomic DNA
                        organism = Homo sapiens
SEQUENCE: 915
acactttgca ctaatcaccc tatttcattt taaatattca gtaaactat gttctgtagg     60
agacaatatt ttctccattt acagaagtgg aagtaaaccc                         100

SEQ ID NO: 916          moltype = DNA   length = 100
FEATURE                 Location/Qualifiers
source                  1..100
                        mol_type = genomic DNA
                        organism = Homo sapiens
SEQUENCE: 916
ctgtatgcat ctaggagctc atgtctggga tgagtgaacc ccggtatctg gccctgtgct    60
cttcatcact gtctctgaca tccccctaaa ccaactccag                         100

SEQ ID NO: 917          moltype = DNA   length = 100
FEATURE                 Location/Qualifiers
source                  1..100
                        mol_type = genomic DNA
                        organism = Homo sapiens
SEQUENCE: 917
gacaaagctg gatgtgtcta gtgtttttat cagaacccac tttccgtaat aagagcatgt    60
gtggttttgc tgccctccag cactcttctg aaaatatgga                         100

SEQ ID NO: 918          moltype = DNA   length = 100
FEATURE                 Location/Qualifiers
source                  1..100
                        mol_type = genomic DNA
                        organism = Homo sapiens
SEQUENCE: 918
gagaactagg atccaggcac attaattttc aggtacttct gacattgaac ttattttttc    60
tatctttcta ttactctttc cttgtctaag tttccatttg                         100

SEQ ID NO: 919          moltype = DNA   length = 100
FEATURE                 Location/Qualifiers
source                  1..100
                        mol_type = genomic DNA
                        organism = Homo sapiens
SEQUENCE: 919
agagagaccc acagtgagcc ctgggatcag aggcacctcc catatcccca tgtctggatc    60
cctgagatac tcacatctgg gagctgccac caggagaagg                         100

SEQ ID NO: 920          moltype = DNA   length = 100
FEATURE                 Location/Qualifiers
source                  1..100
                        mol_type = genomic DNA
                        organism = Homo sapiens
SEQUENCE: 920
aagaaccaca gatgtttcat gttcttgcac aggaggtcca ggactctcag aaagtatttc    60
ccatgtgagc tggaacctga atttaaggaa atgtgtggtg                         100

SEQ ID NO: 921          moltype = DNA   length = 100
FEATURE                 Location/Qualifiers
source                  1..100
                        mol_type = genomic DNA
                        organism = Homo sapiens
SEQUENCE: 921
atttgcatgt gggtggtgcc tttgtatgga gaggtgaaaa aggaggaggg aggccccagt    60
cttttgggct cgccctggga gtaggatgct ggctgtgccc                         100

SEQ ID NO: 922          moltype = DNA   length = 100
FEATURE                 Location/Qualifiers
source                  1..100
                        mol_type = genomic DNA
```

```
                       organism = Homo sapiens
SEQUENCE: 922
tttgagaact cagttgtctt cttggggtct ccctctcca agcccagagt cctcttcttt    60
caggtaaaga gacgtgctga aggacctggt ctgggagatg                         100

SEQ ID NO: 923          moltype = DNA   length = 100
FEATURE                 Location/Qualifiers
source                  1..100
                        mol_type = genomic DNA
                        organism = Homo sapiens
SEQUENCE: 923
ctgacagtgg tgaccatggt tgagaacttt tcatctcctc tgtgaggatc aatctgcatt    60
ttctgcatag gagaataggt tttcatatta aaacaatcat                          100

SEQ ID NO: 924          moltype = DNA   length = 100
FEATURE                 Location/Qualifiers
source                  1..100
                        mol_type = genomic DNA
                        organism = Homo sapiens
SEQUENCE: 924
tttaaaaata tgtagaaatg accctagtaa tcacagaatt ccgaacttag gttcagtaga    60
gaaactttaa gaagatgaag tcccacatcg tgacaggaaa                          100

SEQ ID NO: 925          moltype = DNA   length = 100
FEATURE                 Location/Qualifiers
source                  1..100
                        mol_type = genomic DNA
                        organism = Homo sapiens
SEQUENCE: 925
tggagatggt gaatctgccc ttcacagagt ctgcataata tgtgctaccc ccattactac    60
taatagctga aacatattcc agtcccttcc ctggagcctg                          100

SEQ ID NO: 926          moltype = DNA   length = 100
FEATURE                 Location/Qualifiers
source                  1..100
                        mol_type = genomic DNA
                        organism = Homo sapiens
SEQUENCE: 926
gcggacccag tgcatagcat agctactgaa ggtgaatcca gaggctgcac aggagagtct    60
cagggacccc ccaggctgga ccaagccttc cccagactcc                          100

SEQ ID NO: 927          moltype = DNA   length = 100
FEATURE                 Location/Qualifiers
source                  1..100
                        mol_type = genomic DNA
                        organism = Homo sapiens
SEQUENCE: 927
ttctctcact catgtccact cacactcaat atctctatt cctcatgaat caccttaaa     60
aatagcaaca aggaaaaccc agctcagccc aaactccatc                          100

SEQ ID NO: 928          moltype = DNA   length = 100
FEATURE                 Location/Qualifiers
source                  1..100
                        mol_type = genomic DNA
                        organism = Homo sapiens
SEQUENCE: 928
atgactcttc tgtgttcagt gctgatcacc aaatgaaaac acctgggaat cccagggcgg    60
gggctcctct cccagagctg cggagtcagg gctgggctgg                          100

SEQ ID NO: 929          moltype = DNA   length = 100
FEATURE                 Location/Qualifiers
source                  1..100
                        mol_type = genomic DNA
                        organism = Homo sapiens
SEQUENCE: 929
tagggcacat ccttcccatc cactcaagcc cttgtgcatg ggcctggcgc acctagtgca    60
tagagtaact ggtgaaggta ggtgtatcca caagtcttgc                          100

SEQ ID NO: 930          moltype = DNA   length = 100
FEATURE                 Location/Qualifiers
source                  1..100
                        mol_type = genomic DNA
                        organism = Homo sapiens
SEQUENCE: 930
aggagacttt cactgatgcc ccagccttct tcatctcatc cccagactgc accagctgca    60
cctgggactg ggcacctgtg gagaggacac gggagtggat                          100

SEQ ID NO: 931          moltype = DNA   length = 100
FEATURE                 Location/Qualifiers
```

```
source                  1..100
                        mol_type = genomic DNA
                        organism = Homo sapiens
SEQUENCE: 931
gaaaacttgt tcacagtagc accttcatgg aatgtttgta tcaacgttat agagtgtggc    60
cttttccact ctgtgaattt ggcttatatt acgactcttg                          100

SEQ ID NO: 932          moltype = DNA   length = 100
FEATURE                 Location/Qualifiers
source                  1..100
                        mol_type = genomic DNA
                        organism = Homo sapiens
SEQUENCE: 932
aatggaatat ttatcttaaa attagagtat gtacttgttt ctactgttct tttttttctca   60
aatatataac ccattttgta aacagcctta aacctaataa                          100

SEQ ID NO: 933          moltype = DNA   length = 100
FEATURE                 Location/Qualifiers
source                  1..100
                        mol_type = genomic DNA
                        organism = Homo sapiens
SEQUENCE: 933
ctgctcagct ccatgtaggc tgtgctcgtg gatttgtccg cggtaatcgt gactctgccc    60
tggaacttct gtgcgtagtt tgctgtacca aagataggga                          100

SEQ ID NO: 934          moltype = DNA   length = 100
FEATURE                 Location/Qualifiers
source                  1..100
                        mol_type = genomic DNA
                        organism = Homo sapiens
SEQUENCE: 934
tgatccctcc catccactca agcccttgtc caggggcctg tcgcacccag ctgatagcat    60
agctgctgaa ggtgcctcca gaagccttgc aggagacctt                          100

SEQ ID NO: 935          moltype = DNA   length = 100
FEATURE                 Location/Qualifiers
source                  1..100
                        mol_type = genomic DNA
                        organism = Homo sapiens
SEQUENCE: 935
caccgaggac ccaggcttct tcacctcagc cccagactgc accagctgca cctgggactg    60
gacacctgtg gagaggacac aggggtgaat aaaatcctct                          100

SEQ ID NO: 936          moltype = DNA   length = 100
FEATURE                 Location/Qualifiers
source                  1..100
                        mol_type = genomic DNA
                        organism = Homo sapiens
SEQUENCE: 936
cctgggactg gacacctgtg gagaggacac aggggtgaat aaaatcctct ttaactaaac    60
caggatccct tcctcagcct taggactagg aagccccttA                          100

SEQ ID NO: 937          moltype = DNA   length = 100
FEATURE                 Location/Qualifiers
source                  1..100
                        mol_type = genomic DNA
                        organism = Homo sapiens
SEQUENCE: 937
cctgtagctg ctgccaccac aaagaggaac ctccaggtcc agtccatggt gatgagctgt    60
gctcccaggg gcttcttcag aggaggaatg tggttgttat                          100

SEQ ID NO: 938          moltype = DNA   length = 100
FEATURE                 Location/Qualifiers
source                  1..100
                        mol_type = genomic DNA
                        organism = Homo sapiens
SEQUENCE: 938
gtgatgctct cagggcacca atatatctat atttatctca gaagacctca ggttatttgc    60
atatgcatga ggcagggtat ttcacagctc aaagcctgat                          100

SEQ ID NO: 939          moltype = DNA   length = 100
FEATURE                 Location/Qualifiers
source                  1..100
                        mol_type = genomic DNA
                        organism = Homo sapiens
SEQUENCE: 939
tttgcatatg catgaggcag ggtatttcac agctcaaagc ctgatctagg atgagaaaga    60
aaacacagat gccacatcag ctgtacaagt gtgggatgct                          100
```

| SEQ ID NO: 940 | moltype = DNA length = 100 |
|---|---|
| FEATURE | Location/Qualifiers |
| source | 1..100 |
| | mol_type = genomic DNA |
| | organism = Homo sapiens |

SEQUENCE: 940
cagaacaaac cccaacccca ggatgcactc ctcactgtga acccacattt tattggccta  60
aagattacct gggttttttg tgggaccatt gctgtctctg                        100

| SEQ ID NO: 941 | moltype = DNA length = 100 |
|---|---|
| FEATURE | Location/Qualifiers |
| source | 1..100 |
| | mol_type = genomic DNA |
| | organism = Homo sapiens |

SEQUENCE: 941
acattgagca ggcacctaga cccatcctgg tcccattagg aacactcaga gctcactggt  60
aacactgaaa aggtggccac tcgttaccct acatgagtgt                        100

| SEQ ID NO: 942 | moltype = DNA length = 100 |
|---|---|
| FEATURE | Location/Qualifiers |
| source | 1..100 |
| | mol_type = genomic DNA |
| | organism = Homo sapiens |

SEQUENCE: 942
ccagcaggac ccatggagag ttctgagatc tgctgggcac tcccaagaca gggtccccag  60
cactttcctg agggtcctga cctcccaggt ccttcagtgg                        100

| SEQ ID NO: 943 | moltype = DNA length = 100 |
|---|---|
| FEATURE | Location/Qualifiers |
| source | 1..100 |
| | mol_type = genomic DNA |
| | organism = Homo sapiens |

SEQUENCE: 943
ttatccattt ctatgtgttc ttttgaaaat gtctactcat gtcctttgct cattttaacg  60
gagttatttg gttcttgttg ctgttgttgt tgtagagttg                        100

| SEQ ID NO: 944 | moltype = DNA length = 100 |
|---|---|
| FEATURE | Location/Qualifiers |
| source | 1..100 |
| | mol_type = genomic DNA |
| | organism = Homo sapiens |

SEQUENCE: 944
ttgcaaattc ttcatattag ttccctgtca caggcaaagt gtgcaaaagt tttctgtcat  60
tctgtaaatt gcgtattcac tctgttgttg tgaaaaaaat                        100

| SEQ ID NO: 945 | moltype = DNA length = 100 |
|---|---|
| FEATURE | Location/Qualifiers |
| source | 1..100 |
| | mol_type = genomic DNA |
| | organism = Homo sapiens |

SEQUENCE: 945
tatttaggtt aattaaatct catctgtcta tttttttttta ggtagcagga cctttcatgc  60
tgaatctttg tcaaacagga tacagcttct gcttgcatga                        100

| SEQ ID NO: 946 | moltype = DNA length = 100 |
|---|---|
| FEATURE | Location/Qualifiers |
| source | 1..100 |
| | mol_type = genomic DNA |
| | organism = Homo sapiens |

SEQUENCE: 946
accactaaca ggggacatgc catttattag taaagaaaaa ggaggaaaac aaggctctga  60
gtcagatggg gatgggaaac gcacgccctg ggcaggaaat                        100

| SEQ ID NO: 947 | moltype = DNA length = 100 |
|---|---|
| FEATURE | Location/Qualifiers |
| source | 1..100 |
| | mol_type = genomic DNA |
| | organism = Homo sapiens |

SEQUENCE: 947
ggcatctcag ccacactatc ctgttctgca gaagtgggga gggagcacca ctgaaaaaca  60
cctgggttct tgtacaggaa gcgccctggg ctgtgtctct                        100

| SEQ ID NO: 948 | moltype = DNA length = 100 |
|---|---|
| FEATURE | Location/Qualifiers |
| source | 1..100 |
| | mol_type = genomic DNA |
| | organism = Homo sapiens |

SEQUENCE: 948
gtggtatccg tgcacaataa tacgtggctg tgtccacagg gtccatgttg gtcattgtaa  60

```
                                              -continued ggaccacctg gttttggag gtgtccttgg agatggtgag                            100

SEQ ID NO: 949          moltype = DNA  length = 100
FEATURE                 Location/Qualifiers
source                  1..100
                        mol_type = genomic DNA
                        organism = Homo sapiens
SEQUENCE: 949
acctggtttt tggaggtgtc cttggagatg gtgagcctgg tcttcagaga tgtgctgtag     60
tatttatcat catcccaatc aatgagtgca agccactcca                          100

SEQ ID NO: 950          moltype = DNA  length = 100
FEATURE                 Location/Qualifiers
source                  1..100
                        mol_type = genomic DNA
                        organism = Homo sapiens
SEQUENCE: 950
gggccttccc tgggggctga cggatccagc tcacacacat tccactagtg ctgagtgaga     60
acccagagaa ggtgcaggtc agtgtgaggg tctgtgtggg                          100

SEQ ID NO: 951          moltype = DNA  length = 100
FEATURE                 Location/Qualifiers
source                  1..100
                        mol_type = genomic DNA
                        organism = Homo sapiens
SEQUENCE: 951
tttcaccagc gcaggaccag actccctcaa ggtgacctgg gataagaccc ctgtggagaa     60
gacataagaa gatgaagccc acaaaggaga gaatagattt                          100

SEQ ID NO: 952          moltype = DNA  length = 100
FEATURE                 Location/Qualifiers
source                  1..100
                        mol_type = genomic DNA
                        organism = Homo sapiens
SEQUENCE: 952
ctgtggagaa gacataagaa gatgaagccc acaaaggaga gaatagattt tttgcttctg     60
aagtactacc tgaccacagc actcacagga cgggacagtc                          100

SEQ ID NO: 953          moltype = DNA  length = 100
FEATURE                 Location/Qualifiers
source                  1..100
                        mol_type = genomic DNA
                        organism = Homo sapiens
SEQUENCE: 953
agtagcagga gcgtggaaca aagtatgtcc atggtggaga gcaggattca ctgagcgagg     60
ccctgtcctc gtcttttgaa cccaggggag ggtggagctg                          100

SEQ ID NO: 954          moltype = DNA  length = 100
FEATURE                 Location/Qualifiers
source                  1..100
                        mol_type = genomic DNA
                        organism = Homo sapiens
SEQUENCE: 954
gtggagattt gcatcccctc atctgagccc tactctatgg ggtgcactca ggtctcagga     60
ctcagtaggg gagtgcatct gtggtgagga gcagtgagcc                          100

SEQ ID NO: 955          moltype = DNA  length = 100
FEATURE                 Location/Qualifiers
source                  1..100
                        mol_type = genomic DNA
                        organism = Homo sapiens
SEQUENCE: 955
tactctatgg ggtgcactca ggtctcagga ctcagtaggg gagtgcatct gtggtgagga     60
gcagtgagcc ctcaggtgtg ggggtccacg tgtgctctcc                          100

SEQ ID NO: 956          moltype = DNA  length = 100
FEATURE                 Location/Qualifiers
source                  1..100
                        mol_type = genomic DNA
                        organism = Homo sapiens
SEQUENCE: 956
atcagggaat ctatctcatt tcagcaccat ggctctcagt caagtcttga cgctcctgct     60
tctacagaca ggatcttctt cgatgctccc gcaccggaca                          100

SEQ ID NO: 957          moltype = DNA  length = 100
FEATURE                 Location/Qualifiers
source                  1..100
                        mol_type = genomic DNA
                        organism = Homo sapiens
```

-continued

```
SEQUENCE: 957
tgcaaccttc tggttttagt cctagaggat tagagtagaa atcaagagag ctgccgttcc    60
tcctcccttc aagaataatg atggtgggca tctgggggc                          100

SEQ ID NO: 958            moltype = DNA   length = 100
FEATURE                   Location/Qualifiers
source                    1..100
                          mol_type = genomic DNA
                          organism = Homo sapiens
SEQUENCE: 958
aagggctcc ccacaagcat tctgatcaaa atcctctttg attatgggga aaagtgatga     60
atttgtgtaa aaaaattgga gagaataaat aagaaaatac                         100

SEQ ID NO: 959            moltype = DNA   length = 100
FEATURE                   Location/Qualifiers
source                    1..100
                          mol_type = genomic DNA
                          organism = Homo sapiens
SEQUENCE: 959
agttacaagt aattatgtaa agaagtgtgt gcttagcagt gtgtgtgcac acagctgcat    60
tcctagaggc atgttccatg aaaaatcgat gttgtccttg                         100

SEQ ID NO: 960            moltype = DNA   length = 100
FEATURE                   Location/Qualifiers
source                    1..100
                          mol_type = genomic DNA
                          organism = Homo sapiens
SEQUENCE: 960
tgccccgtca gttctgtgga gagagtagac tgcatgaatg acttcccttt tctcagccca    60
tgaatgagcg gatgctttgg acaagggaat tggaagactc                         100

SEQ ID NO: 961            moltype = DNA   length = 100
FEATURE                   Location/Qualifiers
source                    1..100
                          mol_type = genomic DNA
                          organism = Homo sapiens
SEQUENCE: 961
ctgagggagc agcaggctga ctgttgcagc cttgctctgc acctgcactg gatgtggtct    60
ctgtgctcat aaggccgtgg aaactcatca atccaggttc                         100

SEQ ID NO: 962            moltype = DNA   length = 100
FEATURE                   Location/Qualifiers
source                    1..100
                          mol_type = genomic DNA
                          organism = Homo sapiens
SEQUENCE: 962
caaaaagggg ttaaatgatt ttggaaaagt aagtagaaaa taaagaaagg agggagtaag    60
agcggacaga agggaggaag gcaagcaagc aatgatgaac                         100

SEQ ID NO: 963            moltype = DNA   length = 100
FEATURE                   Location/Qualifiers
source                    1..100
                          mol_type = genomic DNA
                          organism = Homo sapiens
SEQUENCE: 963
tgtgtaaaat tttcactaat taaaagacta ttatattgaa gaggtgccta ttaggcagcc    60
ttttgatgtt aaccatgtaa tatacaccat gaacaacctt                         100

SEQ ID NO: 964            moltype = DNA   length = 100
FEATURE                   Location/Qualifiers
source                    1..100
                          mol_type = genomic DNA
                          organism = Homo sapiens
SEQUENCE: 964
gaacaacctt gtagaacaca caagagcccc ctcagagaac tggatgggtc aggtctccca    60
tccagttgcc ttaggggtta ggaacgctcc catgttgttc                         100

SEQ ID NO: 965            moltype = DNA   length = 100
FEATURE                   Location/Qualifiers
source                    1..100
                          mol_type = genomic DNA
                          organism = Homo sapiens
SEQUENCE: 965
tctggttttt gctcctgagg acacaaacag ccagtgtttc ctccccggat gaatagagag    60
gccctgggg agggtgtgtc tggcagctca ctctgcacct                          100

SEQ ID NO: 966            moltype = DNA   length = 100
FEATURE                   Location/Qualifiers
source                    1..100
```

```
                          mol_type = genomic DNA
                          organism = Homo sapiens
SEQUENCE: 966
gtttcctccc cggatgaata gagaggcccc tggggagggt gtgtctggca gctcactctg    60
cacctgcacc gcggaaggtt ttagatggtc cctctcacac                         100

SEQ ID NO: 967            moltype = DNA  length = 100
FEATURE                   Location/Qualifiers
source                    1..100
                          mol_type = genomic DNA
                          organism = Homo sapiens
SEQUENCE: 967
aataatacat ggcggcgtcc gaggccttca ggctgctcca ctgcaggtag gcggtgctgc    60
tggagctgtc ggctgagatg gtgacgtggc cttggaagga                        100

SEQ ID NO: 968            moltype = DNA  length = 100
FEATURE                   Location/Qualifiers
source                    1..100
                          mol_type = genomic DNA
                          organism = Homo sapiens
SEQUENCE: 968
tgggctgtat ctggtatcag agttcccagg atagatgctc cccatccact ccagttcttt    60
cccgggcatc tggcgcaccc agtggatcca gtagctggta                        100

SEQ ID NO: 969            moltype = DNA  length = 100
FEATURE                   Location/Qualifiers
source                    1..100
                          mol_type = genomic DNA
                          organism = Homo sapiens
SEQUENCE: 969
acaggagatc ctcagagact ccccgggtct tttcacctct gctgcagact gcaacagctg    60
cacctcggca aagacacctg tgtgggagac acaaaatttg                        100

SEQ ID NO: 970            moltype = DNA  length = 100
FEATURE                   Location/Qualifiers
source                    1..100
                          mol_type = genomic DNA
                          organism = Homo sapiens
SEQUENCE: 970
gtgtctggag tatgaaccat gtatcagcac cgaaaggttc tagaagtcag actttcgggc    60
agtgtgtcac taactctcag catgctggcc tggctcggcc                        100

SEQ ID NO: 971            moltype = DNA  length = 100
FEATURE                   Location/Qualifiers
source                    1..100
                          mol_type = genomic DNA
                          organism = Homo sapiens
SEQUENCE: 971
cacagcaagg tcttctcgcc tccctttggg taaatactga ggggtgcctc tgcaggacgg    60
gacctctgcc agactccact ccatacccag agaagcaggg                        100

SEQ ID NO: 972            moltype = DNA  length = 100
FEATURE                   Location/Qualifiers
source                    1..100
                          mol_type = genomic DNA
                          organism = Homo sapiens
SEQUENCE: 972
aaaccaaaat tggagtcagc cttgaggtgt agctgttgag ccctcagcag ctggggagag    60
ctggcggatg ctgccctccc cccagtttcc taatggtgtt                        100

SEQ ID NO: 973            moltype = DNA  length = 100
FEATURE                   Location/Qualifiers
source                    1..100
                          mol_type = genomic DNA
                          organism = Homo sapiens
SEQUENCE: 973
gtttaaaaag ggtcagggga cgggggaaca gatggtggga agagcacagt gcagacacct    60
ggcaccggct ctgaaggcag catggcagct acaccgttgg                        100

SEQ ID NO: 974            moltype = DNA  length = 100
FEATURE                   Location/Qualifiers
source                    1..100
                          mol_type = genomic DNA
                          organism = Homo sapiens
SEQUENCE: 974
ctgggaaggg tgtgccnctg aagaagtcgt ttacattctc gagtcaattt tcctggagtg    60
tacaatggac ctgtgggaaa gcctgtatga aagggtaatg                        100

SEQ ID NO: 975            moltype = DNA  length = 100
```

```
FEATURE             Location/Qualifiers
source              1..100
                    mol_type = genomic DNA
                    organism = Homo sapiens
SEQUENCE: 975
atgagggacc tagcacagtg tccaatattt tataggaact ggaattgagc tcataggagc    60
tcaattttat tggcattgct gttgttggat ggttaaaggg                          100

SEQ ID NO: 976      moltype = DNA   length = 100
FEATURE             Location/Qualifiers
source              1..100
                    mol_type = genomic DNA
                    organism = Homo sapiens
SEQUENCE: 976
gtggtatccc ttttctcaga ctcccctgaa atgtatggtt tgctttgaac ccagagactg    60
atgacaggtc tgccggtgtg gttgggtgca gccttaagtt                          100

SEQ ID NO: 977      moltype = DNA   length = 100
FEATURE             Location/Qualifiers
source              1..100
                    mol_type = genomic DNA
                    organism = Homo sapiens
SEQUENCE: 977
gctacgggaa agtgttggag ggggagaagt cagaggtaac cttgcccct ccctcaattc     60
cagatgagga aattcaggcc tgaaaaggga aagtgaccac                          100

SEQ ID NO: 978      moltype = DNA   length = 100
FEATURE             Location/Qualifiers
source              1..100
                    mol_type = genomic DNA
                    organism = Homo sapiens
SEQUENCE: 978
ctcaaagtct catgccttgg aggacccagc aggaatccaa gacctctgaa aaggaccggc    60
agggctcttg ccacggctgg gggtgtggtc atggtaacac                          100

SEQ ID NO: 979      moltype = DNA   length = 100
FEATURE             Location/Qualifiers
source              1..100
                    mol_type = genomic DNA
                    organism = Homo sapiens
SEQUENCE: 979
aggttttcca tccatggaag gtacctgagg gattttctct tcctccctag ggccagcatc    60
agaggagtga atagctcagt tagctcatct caggggccat                          100

SEQ ID NO: 980      moltype = DNA   length = 100
FEATURE             Location/Qualifiers
source              1..100
                    mol_type = genomic DNA
                    organism = Homo sapiens
SEQUENCE: 980
gtgccctcgg aggtggtttg ccactttcac ggttggactg agttggagag aaacagagac    60
ccacccaggg gtggggacaa gctccctgca actcaggact                          100

SEQ ID NO: 981      moltype = DNA   length = 100
FEATURE             Location/Qualifiers
source              1..100
                    mol_type = genomic DNA
                    organism = Homo sapiens
SEQUENCE: 981
tgcagatcac ttgcccaagt ggctccctag ctcctggctc ctggcccggg gcctgggact    60
ctccccgaag tggggctggc cactgtgagg aaccgactgg                          100

SEQ ID NO: 982      moltype = DNA   length = 100
FEATURE             Location/Qualifiers
source              1..100
                    mol_type = genomic DNA
                    organism = Homo sapiens
SEQUENCE: 982
aggcagggac ctcttggatg ccccaggcag ttgggatgcc acttctgata aagcacgtgg    60
tggccacagt aggtgcttgg ttgctccaca gcctggcccg                          100

SEQ ID NO: 983      moltype = DNA   length = 100
FEATURE             Location/Qualifiers
source              1..100
                    mol_type = genomic DNA
                    organism = Homo sapiens
SEQUENCE: 983
agctcagcgc tgcagaaaga aagtgaaagg gaaaaagaac tgcggggagg cggggaggta    60
ggatgaccag cggacgagct gccacagact tgccgcggcc                          100
```

```
SEQ ID NO: 984           moltype = DNA  length = 100
FEATURE                  Location/Qualifiers
source                   1..100
                         mol_type = genomic DNA
                         organism = Homo sapiens
SEQUENCE: 984
ccagagctgg cgggagggag aggccaccag cagcgcgcgc gggagcccgg ggaacagcgg    60
taggtgacca aagtctcctc tgtaacccct aaggtcgggc                         100

SEQ ID NO: 985           moltype = DNA  length = 100
FEATURE                  Location/Qualifiers
source                   1..100
                         mol_type = genomic DNA
                         organism = Homo sapiens
SEQUENCE: 985
tgagaatcga ggctccgaga ctgtcagcta cttgctcaag gtcacacagc aagtctggga    60
ggatggggggg atggaatatg caaaatgtag ggccggaaaa                        100

SEQ ID NO: 986           moltype = DNA  length = 100
FEATURE                  Location/Qualifiers
source                   1..100
                         mol_type = genomic DNA
                         organism = Homo sapiens
SEQUENCE: 986
cacctcgttt ccagcatccc cgcaacgact ctgcgcggga accaggagcc gggaacccgg    60
agcttggctt gctgtgccca gagctccggg gccgtgggcg                         100

SEQ ID NO: 987           moltype = DNA  length = 100
FEATURE                  Location/Qualifiers
source                   1..100
                         mol_type = genomic DNA
                         organism = Homo sapiens
SEQUENCE: 987
ggtggcagga aagcctggcg gcagcttctg cagagaagcc ggagcgcaga ctgggagcgc    60
ggagcagaca cactcccccg gccacccttg gccgactccg                         100

SEQ ID NO: 988           moltype = DNA  length = 100
FEATURE                  Location/Qualifiers
source                   1..100
                         mol_type = genomic DNA
                         organism = Homo sapiens
SEQUENCE: 988
cgcgcccggg atcctgcaga ggtgcgcgcc cttcttgtac gccagacttt ggaccagggc    60
cgccgttccc tgagcttcac tttccctgtt gggtcatatt                         100

SEQ ID NO: 989           moltype = DNA  length = 100
FEATURE                  Location/Qualifiers
source                   1..100
                         mol_type = genomic DNA
                         organism = Homo sapiens
SEQUENCE: 989
ccatctctaa ctctggaatc ttgggtattg ggctctccag gcggggggcc ctgctcaggg    60
aggcagtagg gagccaaacc tttaaccaga ggatgggata                         100

SEQ ID NO: 990           moltype = DNA  length = 100
FEATURE                  Location/Qualifiers
source                   1..100
                         mol_type = genomic DNA
                         organism = Homo sapiens
SEQUENCE: 990
agtcctcaac tctcgttgaa catcttggcg aaggtgtgtg ttgttgggag gggtggggga    60
gggatccccc cggactgaac cgatctcttg atctctcact                         100

SEQ ID NO: 991           moltype = DNA  length = 100
FEATURE                  Location/Qualifiers
source                   1..100
                         mol_type = genomic DNA
                         organism = Homo sapiens
SEQUENCE: 991
tctctacctc gctttggggc cctgagtcac accctctaag gagagaggct aaagcgcccc    60
ggaaagccag cgtgcgaatg ccggggtggg agtgggagat                         100

SEQ ID NO: 992           moltype = DNA  length = 100
FEATURE                  Location/Qualifiers
source                   1..100
                         mol_type = genomic DNA
                         organism = Homo sapiens
SEQUENCE: 992
```

```
tggatctccc tggggtccag gaaagccgga atcggagcca ccatgcttag cttagtctgg    60
aactcttaaa agccgcggtc ctcctgagtc ccacagcccc                         100

SEQ ID NO: 993          moltype = DNA  length = 100
FEATURE                 Location/Qualifiers
source                  1..100
                        mol_type = genomic DNA
                        organism = Homo sapiens
SEQUENCE: 993
tctccaccct aggtggcaca ggagaggtgg caaaagccta gaagttcaag gcatggctcc    60
ctccccagcc gcagcctgga gtgtctaact ttggcaggaa                        100

SEQ ID NO: 994          moltype = DNA  length = 100
FEATURE                 Location/Qualifiers
source                  1..100
                        mol_type = genomic DNA
                        organism = Homo sapiens
SEQUENCE: 994
gtcttccgtt tctgctcccc actccagaga aaaataaat aaatacttct ccggagtgag    60
attaaggaaa caggtacttc ttcctcttgg agaagagga                         100

SEQ ID NO: 995          moltype = DNA  length = 100
FEATURE                 Location/Qualifiers
source                  1..100
                        mol_type = genomic DNA
                        organism = Homo sapiens
SEQUENCE: 995
cttctccgga gtgagattaa ggaaacaggt acttcttcct cttggagaaa gaggagccaa    60
aggaacttga ctccaacaaa tgatcacctt gcaaaccccc                        100

SEQ ID NO: 996          moltype = DNA  length = 100
FEATURE                 Location/Qualifiers
source                  1..100
                        mol_type = genomic DNA
                        organism = Homo sapiens
SEQUENCE: 996
ggctccctta ggggatgacc tggtctccaa caatctcaga gcgtttggag gcagggtctt    60
tggagatgac tgagtgggga atcccaggct ccccacacat                        100

SEQ ID NO: 997          moltype = DNA  length = 100
FEATURE                 Location/Qualifiers
source                  1..100
                        mol_type = genomic DNA
                        organism = Homo sapiens
SEQUENCE: 997
gaacatcacc tgggatgatc aacctgttca ggatgtaggt tcccgggctc accccaggc    60
ccggttggct aggcctgggg tgaggctgag atcctgcagg                        100

SEQ ID NO: 998          moltype = DNA  length = 100
FEATURE                 Location/Qualifiers
source                  1..100
                        mol_type = genomic DNA
                        organism = Homo sapiens
SEQUENCE: 998
ttaaaccatc tatcccaggt gactccaatg ttcgtttgtg gggcaaaagt ccctcaagtc    60
agagacactg ggaggcgctg atgtggtctc atctctttac                        100

SEQ ID NO: 999          moltype = DNA  length = 100
FEATURE                 Location/Qualifiers
source                  1..100
                        mol_type = genomic DNA
                        organism = Homo sapiens
SEQUENCE: 999
caagaggtga gaaggggtct gcggcctcgt ctccagccga gggcgggagg cgcctcgccc    60
ctacacccat ccgctccctc caacccaggc cggggagggt                        100

SEQ ID NO: 1000         moltype = DNA  length = 100
FEATURE                 Location/Qualifiers
source                  1..100
                        mol_type = genomic DNA
                        organism = Homo sapiens
SEQUENCE: 1000
acccacatgg ttccaggcaa gtaataacaa aataacacgg catcccagtt aatgctgcgt    60
gcacggcggg cgctgccggt caaatctgga aggggaagga                        100

SEQ ID NO: 1001         moltype = DNA  length = 100
FEATURE                 Location/Qualifiers
source                  1..100
                        mol_type = genomic DNA
```

```
                    organism = Homo sapiens
SEQUENCE: 1001
gctcaggtag tcgcggagga cggggttgag ggggatgcga gccaggttct cgcggcccac    60
ggtggccacg atgcgctggc ggcacagctc ctgcagcggc                          100

SEQ ID NO: 1002         moltype = DNA   length = 100
FEATURE                 Location/Qualifiers
source                  1..100
                        mol_type = genomic DNA
                        organism = Homo sapiens
SEQUENCE: 1002
cgcacgcggc gctggcgcag cggggccccc agcatgcggc gcggcgccgc cacgtagtgc    60
tccagcagct cgaagaggca gtcgaagctc tcgcggctgc                          100

SEQ ID NO: 1003         moltype = DNA   length = 100
FEATURE                 Location/Qualifiers
source                  1..100
                        mol_type = genomic DNA
                        organism = Homo sapiens
SEQUENCE: 1003
catccaggtg aaagcggccg gcctgaaagt gcacgcggat gctcgtgggt cccgaggcca    60
tcttcacgct aagggcgaaa aagcagttcc gctggcggct                          100

SEQ ID NO: 1004         moltype = DNA   length = 100
FEATURE                 Location/Qualifiers
source                  1..100
                        mol_type = genomic DNA
                        organism = Homo sapiens
SEQUENCE: 1004
gtcgcgcacc aggaaggtgc ccacgggctc ggcgcgcagc cgctcgtgcg ccccgtgcac    60
gctcaggggc ccccagtaga atccgcaggc gtccaggagc                          100

SEQ ID NO: 1005         moltype = DNA   length = 100
FEATURE                 Location/Qualifiers
source                  1..100
                        mol_type = genomic DNA
                        organism = Homo sapiens
SEQUENCE: 1005
gcgctggcgc gcgtgatgcg ccggtaatcg gcgtgcgaac ggaatgtgcg gaagtgcgtg    60
tcgccggggg ccggggccgg daccgcgggg cacggccgcg                          100

SEQ ID NO: 1006         moltype = DNA   length = 100
FEATURE                 Location/Qualifiers
source                  1..100
                        mol_type = genomic DNA
                        organism = Homo sapiens
SEQUENCE: 1006
ggcgcgcggg ggccgcgggc gaggaggagg aagaggagga aggttctggc cgccgtcggg    60
gctctgctgc tgtggagact gcattgtcgg ctgccacctg                          100

SEQ ID NO: 1007         moltype = DNA   length = 100
FEATURE                 Location/Qualifiers
source                  1..100
                        mol_type = genomic DNA
                        organism = Homo sapiens
SEQUENCE: 1007
tttaaaatca cccaaatcaa aataatttta tcttcattaa taaataatca tcagaagttt    60
aactaatttt tactttataa tactaggttt aaaaattctt                          100

SEQ ID NO: 1008         moltype = DNA   length = 100
FEATURE                 Location/Qualifiers
source                  1..100
                        mol_type = genomic DNA
                        organism = Homo sapiens
SEQUENCE: 1008
aatctgaatg cccaagtcgt tgattgtcgt ttgcctgttt ccaaagattg gtagatagat    60
gcctttttaa aaatctcatt tttctttaaa tctggtttac                          100

SEQ ID NO: 1009         moltype = DNA   length = 100
FEATURE                 Location/Qualifiers
source                  1..100
                        mol_type = genomic DNA
                        organism = Homo sapiens
SEQUENCE: 1009
atggaaaacg ttaggagagc tcatataatg aacggcaata gcaaccccct atcttgaaac    60
gcgctctatc atcccactga aattctacca cgtggaataa                          100

SEQ ID NO: 1010         moltype = DNA   length = 100
FEATURE                 Location/Qualifiers
```

```
source                          1..100
                                mol_type = genomic DNA
                                organism = Homo sapiens
SEQUENCE: 1010
tgcttggagg gtcagagttg tggaactgcc caataaccag tcgttactga gggttagttt    60
gtgaaggagg ggacagactg cttctaaaat tctgtttaat                          100

SEQ ID NO: 1011                 moltype = DNA   length = 100
FEATURE                         Location/Qualifiers
source                          1..100
                                mol_type = genomic DNA
                                organism = Homo sapiens
SEQUENCE: 1011
gacagtcaat taagatttct gagtctggct tgagggcctt tgcttccatc acagcccagt    60
cgtccttggc aagagagtct gtatatgggc cacagctcac                          100

SEQ ID NO: 1012                 moltype = DNA   length = 100
FEATURE                         Location/Qualifiers
source                          1..100
                                mol_type = genomic DNA
                                organism = Homo sapiens
SEQUENCE: 1012
aaaagcattg tttgaaaaaa tttattgaaa gaacattgtt tgtaaaatga gtcccaatac    60
ataggacaga ctttcctaag gtgagatgtg ttacttaccc                          100

SEQ ID NO: 1013                 moltype = DNA   length = 100
FEATURE                         Location/Qualifiers
source                          1..100
                                mol_type = genomic DNA
                                organism = Homo sapiens
SEQUENCE: 1013
agagctgtga aaggctttac ggatggaaac tagagactga attttccaga attttaagaa    60
gtctccccaa ccaatggccc cccactttct ttttttaaac                          100

SEQ ID NO: 1014                 moltype = DNA   length = 100
FEATURE                         Location/Qualifiers
source                          1..100
                                mol_type = genomic DNA
                                organism = Homo sapiens
SEQUENCE: 1014
ggcgtgatct ccgaagccca cagtacactc atccataaag taggaaacac tacaccctcc    60
agtgctgtta gtagtgcttt ctactttatg ggtgactgca                          100

SEQ ID NO: 1015                 moltype = DNA   length = 100
FEATURE                         Location/Qualifiers
source                          1..100
                                mol_type = genomic DNA
                                organism = Homo sapiens
SEQUENCE: 1015
ctgtctgtct gtccgtcggc gtgtactctt caggctgccc aggcctcctg actcctgctc    60
caagagcccc ccagccctcc ttgtggcttc ctaagatccc                          100

SEQ ID NO: 1016                 moltype = DNA   length = 100
FEATURE                         Location/Qualifiers
source                          1..100
                                mol_type = genomic DNA
                                organism = Homo sapiens
SEQUENCE: 1016
ccctcttccc ttcccctaa aggctccacc ccatccccc agtttcagag acactcaggt      60
agagactagg gcctctggag gcctcacctt cagttctgtg                          100

SEQ ID NO: 1017                 moltype = DNA   length = 100
FEATURE                         Location/Qualifiers
source                          1..100
                                mol_type = genomic DNA
                                organism = Homo sapiens
SEQUENCE: 1017
aaccctggc tggccgcttc cagccacgct agccaccctc cagcgtccaa atgaggcagc      60
cacagctccc ctgccaaggt cttggtctcc agtccacccc                          100

SEQ ID NO: 1018                 moltype = DNA   length = 100
FEATURE                         Location/Qualifiers
source                          1..100
                                mol_type = genomic DNA
                                organism = Homo sapiens
SEQUENCE: 1018
aaccgtgagg tcctgactgc ccagagcctc agtccccacc cttcagcctc cccaccagcc    60
caagatcctg acccccagg gcctaagtcc ccagcctccc                           100
```

```
SEQ ID NO: 1019         moltype = DNA  length = 100
FEATURE                 Location/Qualifiers
source                  1..100
                        mol_type = genomic DNA
                        organism = Homo sapiens
SEQUENCE: 1019
caacagccca gggtcctgac ccccagggc ctcaggccct ggcctcccca ccagcccaag    60
gtcttgaaca caccagggcc tcaattccca gcctccccac                        100

SEQ ID NO: 1020         moltype = DNA  length = 100
FEATURE                 Location/Qualifiers
source                  1..100
                        mol_type = genomic DNA
                        organism = Homo sapiens
SEQUENCE: 1020
cagctcaagg tcctgactcc cccagagcct cagtcccagc ctccatagca gcccaaggtc    60
ctgaccccc agggcctcag tcccagcca ctccaccagc                          100

SEQ ID NO: 1021         moltype = DNA  length = 100
FEATURE                 Location/Qualifiers
source                  1..100
                        mol_type = genomic DNA
                        organism = Homo sapiens
SEQUENCE: 1021
cccaaagtcc tgactcccca gagccttgat tctcggcctc ccaccagcc caaagtcctg    60
actccctcac tgccctgctg ttcccctggc aggagcccaa                        100

SEQ ID NO: 1022         moltype = DNA  length = 100
FEATURE                 Location/Qualifiers
source                  1..100
                        mol_type = genomic DNA
                        organism = Homo sapiens
SEQUENCE: 1022
ggctatccca acaaaaatgg tggccatgtt gggcggagga agaggctggc gccccttgag    60
acactggtcc cacttctcag cctctgcgta ccctctgcca                        100

SEQ ID NO: 1023         moltype = DNA  length = 100
FEATURE                 Location/Qualifiers
source                  1..100
                        mol_type = genomic DNA
                        organism = Homo sapiens
SEQUENCE: 1023
tccccgcctt actctccagc cctcctcctt ggacacctct ttccccgcct ggggtcccgg    60
agccattta ccttccttca ctagagaggg tttcaaggcg                         100

SEQ ID NO: 1024         moltype = DNA  length = 100
FEATURE                 Location/Qualifiers
source                  1..100
                        mol_type = genomic DNA
                        organism = Homo sapiens
SEQUENCE: 1024
ctaagatttt caagaagtta aacgtagaat taagattgtt ctaattctgg ttgtaaactg    60
ctatttaaa aacaaaaca aacagaaaac atcaaaaaca                         100

SEQ ID NO: 1025         moltype = DNA  length = 100
FEATURE                 Location/Qualifiers
source                  1..100
                        mol_type = genomic DNA
                        organism = Homo sapiens
SEQUENCE: 1025
aaacaaacag aaaacatcaa aaacacaaaa agatattaaa acagcaagtc ttttgtacat    60
cactgtagca taagctgctt gaggttgtca tgcagaatag                        100

SEQ ID NO: 1026         moltype = DNA  length = 100
FEATURE                 Location/Qualifiers
source                  1..100
                        mol_type = genomic DNA
                        organism = Homo sapiens
SEQUENCE: 1026
tatccttcac gtcacggaaa acaaggcgga tgttctccgt gttgatagca gtggtgaagt    60
ggtggtataa gggcttctgt tgctggtccc ggcgtttgtt                        100

SEQ ID NO: 1027         moltype = DNA  length = 100
FEATURE                 Location/Qualifiers
source                  1..100
                        mol_type = genomic DNA
                        organism = Homo sapiens
SEQUENCE: 1027
ccggaaacat tccaccagga attttggac gtctcttaag cagtggggat cccctcaaa    60
```

-continued

```
ttctaggaaa tagtctttga tgctcacaat ttgcaccttc                                100

SEQ ID NO: 1028         moltype = DNA  length = 100
FEATURE                 Location/Qualifiers
source                  1..100
                        mol_type = genomic DNA
                        organism = Homo sapiens
SEQUENCE: 1028
tcctcaagca agtctgtctt gtttaagaac agaattatgg agacattgct gaaaacccgg           60
ttattgacga ttgtttcaaa aatgttcaga gactctgtaa                                100

SEQ ID NO: 1029         moltype = DNA  length = 100
FEATURE                 Location/Qualifiers
source                  1..100
                        mol_type = genomic DNA
                        organism = Homo sapiens
SEQUENCE: 1029
ggcgattggt cagtcgatct tccataagca cctggtcaaa ttcacttgag gaaacaagga           60
aaagtattga tgtcacactg tcgaaacatt caaaccaacg                                100

SEQ ID NO: 1030         moltype = DNA  length = 100
FEATURE                 Location/Qualifiers
source                  1..100
                        mol_type = genomic DNA
                        organism = Homo sapiens
SEQUENCE: 1030
tttcctttct gatctctgac cacctacatc aaccattttg aaaggaacat ttttatttc            60
aaagtcgtat tcatggatgc ctttggtggg tcttctggca                                100

SEQ ID NO: 1031         moltype = DNA  length = 100
FEATURE                 Location/Qualifiers
source                  1..100
                        mol_type = genomic DNA
                        organism = Homo sapiens
SEQUENCE: 1031
agcagaatat cttgttgtga tggaatataa tcctggaaaa gaaaaaactt gttttatacc           60
tattaatccc gaagtaatgc gaatttttaa tggactacta                                100

SEQ ID NO: 1032         moltype = DNA  length = 100
FEATURE                 Location/Qualifiers
source                  1..100
                        mol_type = genomic DNA
                        organism = Homo sapiens
SEQUENCE: 1032
tgtaaatatt tggccaacta agctgagtgg ctaagttctc ctgctgcccg gagcttcttg           60
gaacatgttt cctttcgca aggggtttcc ctggcttcca                                 100

SEQ ID NO: 1033         moltype = DNA  length = 100
FEATURE                 Location/Qualifiers
source                  1..100
                        mol_type = genomic DNA
                        organism = Homo sapiens
SEQUENCE: 1033
ggagggccag gaagaaattc gaattggcca ccgctttctc taaaatcact ccgctcaagt           60
tatcacccct ctgggctccc gaagaccggc tggctggagg                                100

SEQ ID NO: 1034         moltype = DNA  length = 100
FEATURE                 Location/Qualifiers
source                  1..100
                        mol_type = genomic DNA
                        organism = Homo sapiens
SEQUENCE: 1034
ctggagatag tctcaatgct cgaaatgccg taaccgaagc tccccgcggc gccggcactg           60
ggatccaggg agctgctgct acagcgcagc tctggattcc                                100

SEQ ID NO: 1035         moltype = DNA  length = 100
FEATURE                 Location/Qualifiers
source                  1..100
                        mol_type = genomic DNA
                        organism = Homo sapiens
SEQUENCE: 1035
tggatgtgtt ggatatgtgc agggcgttcc tgggaggagc ggggagggag ggtgctgctg           60
gcggggctgg tctgcgtgtg ctttgcttct ctacaatggc                                100

SEQ ID NO: 1036         moltype = DNA  length = 100
FEATURE                 Location/Qualifiers
source                  1..100
                        mol_type = genomic DNA
                        organism = Homo sapiens
```

```
SEQUENCE: 1036
atgctgcgtg tcggccatgc agaggcatgt cagtgagcag gggctgaggg atctccctaa    60
cggacctgct ttcagagggt cttttcatgc tgggagaacc                         100

SEQ ID NO: 1037         moltype = DNA  length = 100
FEATURE                 Location/Qualifiers
source                  1..100
                        mol_type = genomic DNA
                        organism = Homo sapiens
SEQUENCE: 1037
ccagagacta aatcatgcag ccaacggggt ggtccccggc ctcaaagcag ggagggggcga   60
ggagctttgt aggcaatgcc atctgctcct gaaacgccgt                         100

SEQ ID NO: 1038         moltype = DNA  length = 100
FEATURE                 Location/Qualifiers
source                  1..100
                        mol_type = genomic DNA
                        organism = Homo sapiens
SEQUENCE: 1038
cagcctcctt agtagctacc gccttagtaa gtaccactta gtaagtaccg ccttagtaag    60
taccacttag tagctacctc cttagtaagt accacttagt                         100

SEQ ID NO: 1039         moltype = DNA  length = 100
FEATURE                 Location/Qualifiers
source                  1..100
                        mol_type = genomic DNA
                        organism = Homo sapiens
SEQUENCE: 1039
aagtacctcc ttagtaagta ccacttagta ctaccaccac gcctggctaa tttcgtattt    60
tttttttttt agtagagacg gggtttctcc atattggtca                         100

SEQ ID NO: 1040         moltype = DNA  length = 100
FEATURE                 Location/Qualifiers
source                  1..100
                        mol_type = genomic DNA
                        organism = Homo sapiens
SEQUENCE: 1040
aggtcaggcg catactgcat gcgggtctcg cggtcgtgct ccagccacag cacggacatc    60
tggaagagcg ccagctccga ctccacgggg ggcggcagcg                         100

SEQ ID NO: 1041         moltype = DNA  length = 100
FEATURE                 Location/Qualifiers
source                  1..100
                        mol_type = genomic DNA
                        organism = Homo sapiens
SEQUENCE: 1041
agtccagcag ggcgcgcatc tcctcgaagt tgagcagcag cacatcctcc accaggtact    60
tgttggccag cttcttggtc tcctccaggc cgtgcagcgc                         100

SEQ ID NO: 1042         moltype = DNA  length = 100
FEATURE                 Location/Qualifiers
source                  1..100
                        mol_type = genomic DNA
                        organism = Homo sapiens
SEQUENCE: 1042
ggcgatcttg cacacctgct tgtagttctg caccgagatc tggtcgttga ggaactgcac    60
gcagagcttg gtgacctggg ggatgtgcag gatcttgctg                         100

SEQ ID NO: 1043         moltype = DNA  length = 100
FEATURE                 Location/Qualifiers
source                  1..100
                        mol_type = genomic DNA
                        organism = Homo sapiens
SEQUENCE: 1043
accgacagca cctcctccac cgtgtccagg gacagggtca cgttggccgt gtagaggtac    60
tcgagcacca ggcgcagccc gatggacgag cagccctgca                         100

SEQ ID NO: 1044         moltype = DNA  length = 100
FEATURE                 Location/Qualifiers
source                  1..100
                        mol_type = genomic DNA
                        organism = Homo sapiens
SEQUENCE: 1044
gcaccaggtt gttgatggcc cgggggctgg tcagcagctt gtcgtcgggg gaggaagaag    60
gagtcccggg ctcctcctgc ggcggcggct gctgctgctg                         100

SEQ ID NO: 1045         moltype = DNA  length = 100
FEATURE                 Location/Qualifiers
source                  1..100
```

```
                        mol_type = genomic DNA
                        organism = Homo sapiens
SEQUENCE: 1045
tgacggctgc tgctgcggcg gctgctgctg gtccttgggg gcccccaggc cgtcctggcc    60
gccgacccct cccccgagag gggggtggct ggagaagagc                         100

SEQ ID NO: 1046         moltype = DNA  length = 100
FEATURE                 Location/Qualifiers
source                  1..100
                        mol_type = genomic DNA
                        organism = Homo sapiens
SEQUENCE: 1046
gagacttcag ccggagctgg ctattccaga gatggacctc agaggattcc ttagtctaat    60
taccttctgg gctggggtag aagatggtgt ctggagggaa                         100

SEQ ID NO: 1047         moltype = DNA  length = 100
FEATURE                 Location/Qualifiers
source                  1..100
                        mol_type = genomic DNA
                        organism = Homo sapiens
SEQUENCE: 1047
gcacagaacc aagttcccta ctgccgcact agctatgcaa atactgcagg gcacctgtgg    60
gctcatgtcc ctcctgcaag aaggtgtggt cagtccagta                         100

SEQ ID NO: 1048         moltype = DNA  length = 100
FEATURE                 Location/Qualifiers
source                  1..100
                        mol_type = genomic DNA
                        organism = Homo sapiens
SEQUENCE: 1048
attcaaaaga cgtacttctg aaataggtgg agaaatgcat ttatagcaaa aagtgctaaa    60
aatatgttaa tagttatgct atttggttca ccaggttagt                         100

SEQ ID NO: 1049         moltype = DNA  length = 100
FEATURE                 Location/Qualifiers
source                  1..100
                        mol_type = genomic DNA
                        organism = Homo sapiens
SEQUENCE: 1049
gtaataaacc ataacaagag agactaaagg ccgtatctat atgaccttga aatctcatct    60
tcagcgggct tattcattca gtaaccaaac tatttttgta                         100

SEQ ID NO: 1050         moltype = DNA  length = 100
FEATURE                 Location/Qualifiers
source                  1..100
                        mol_type = genomic DNA
                        organism = Homo sapiens
SEQUENCE: 1050
aggtgctgag tatttagctt aaagctaaat aagacacatg ccctgcccta tagtaactgc    60
ttggtaatat tcccagtggc ttccatgggc ctgataattt                         100

SEQ ID NO: 1051         moltype = DNA  length = 100
FEATURE                 Location/Qualifiers
source                  1..100
                        mol_type = genomic DNA
                        organism = Homo sapiens
SEQUENCE: 1051
tcttagtact gaattcaaag cactttgtgt cttgtctgca ggcccatttg cccagcagtg    60
gccttgccag gagagaacag gcccatgctc ctgtcctcat                         100

SEQ ID NO: 1052         moltype = DNA  length = 100
FEATURE                 Location/Qualifiers
source                  1..100
                        mol_type = genomic DNA
                        organism = Homo sapiens
SEQUENCE: 1052
caaacaaaca attcaagaag aggatttaaa ttttagaaat ttaaattggg gcatttagt     60
taatcttact tttaaacacc aaacagtggc atcaatattt                         100

SEQ ID NO: 1053         moltype = DNA  length = 100
FEATURE                 Location/Qualifiers
source                  1..100
                        mol_type = genomic DNA
                        organism = Homo sapiens
SEQUENCE: 1053
tgtcaacttt ggtcaaataa gatcagatgt tcacatcaat catctacttt tcttggcctt    60
ttctctattt ggcctcctag tatgagcaca ctttgtaaaa                         100

SEQ ID NO: 1054         moltype = DNA  length = 100
```

| | | |
|---|---|---|
| FEATURE | Location/Qualifiers | |
| source | 1..100 | |
| | mol_type = genomic DNA | |
| | organism = Homo sapiens | |

SEQUENCE: 1054

```
tgtaataaaa acatgtggtg tgcttcttga catctaatcc acttgcagta atttctaggc   60
tttttgctcc tgttaggtcc tataaaataa tgacattagt                        100
```

| | | |
|---|---|---|
| SEQ ID NO: 1055 | moltype = DNA length = 100 | |
| FEATURE | Location/Qualifiers | |
| source | 1..100 | |
| | mol_type = genomic DNA | |
| | organism = Homo sapiens | |

SEQUENCE: 1055

```
atagatacct agatgcaaat ttttttcagc cgaccacaaa attaggtcca ctctgagtgg   60
tgaaaaacaa aagattctaa cattctagca aactggtaaa                        100
```

| | | |
|---|---|---|
| SEQ ID NO: 1056 | moltype = DNA length = 100 | |
| FEATURE | Location/Qualifiers | |
| source | 1..100 | |
| | mol_type = genomic DNA | |
| | organism = Homo sapiens | |

SEQUENCE: 1056

```
ccatacacaa attatagaat acaaagaatg cagccgatgc aaattctgtc actgacaagg   60
tagcaaagcc atagcctgat actcctcagg acacctcatc                        100
```

| | | |
|---|---|---|
| SEQ ID NO: 1057 | moltype = DNA length = 100 | |
| FEATURE | Location/Qualifiers | |
| source | 1..100 | |
| | mol_type = genomic DNA | |
| | organism = Homo sapiens | |

SEQUENCE: 1057

```
acgcccactg ggaacatggc acacactgga gattccagtc caaggacttt ggaatgtcaa   60
cttagctctt tacaaacaca actaagtttt tcagggaaaa                        100
```

| | | |
|---|---|---|
| SEQ ID NO: 1058 | moltype = DNA length = 100 | |
| FEATURE | Location/Qualifiers | |
| source | 1..100 | |
| | mol_type = genomic DNA | |
| | organism = Homo sapiens | |

SEQUENCE: 1058

```
agacttacat tggttttcct cttttggaaa attttaccga ttgatgatgc ccttggtctt   60
ctgtggagtc tattcttcta atcgggttgt tctccaattt                        100
```

| | | |
|---|---|---|
| SEQ ID NO: 1059 | moltype = DNA length = 100 | |
| FEATURE | Location/Qualifiers | |
| source | 1..100 | |
| | mol_type = genomic DNA | |
| | organism = Homo sapiens | |

SEQUENCE: 1059

```
tagtgtacaa cgggcttgtt tcaggggagc ttgtttggga tgcagactgt caagacccaa   60
cctggtatct ggttcataag cagtccctga aacctccctc                        100
```

| | | |
|---|---|---|
| SEQ ID NO: 1060 | moltype = DNA length = 100 | |
| FEATURE | Location/Qualifiers | |
| source | 1..100 | |
| | mol_type = genomic DNA | |
| | organism = Homo sapiens | |

SEQUENCE: 1060

```
cggttccaac aagctgctca agccaggaaa cggtggtcct ggggactcct ggaccttcag   60
cttgagaaac actgaagggg taccatttac caccacatcc                        100
```

| | | |
|---|---|---|
| SEQ ID NO: 1061 | moltype = DNA length = 100 | |
| FEATURE | Location/Qualifiers | |
| source | 1..100 | |
| | mol_type = genomic DNA | |
| | organism = Homo sapiens | |

SEQUENCE: 1061

```
tactggatta caaacgctag atctttggat ctccacgact agcaagcaag ttaaagactt   60
ttagatggca ggcgttatcg gtcaggttgg gagtgaacgc                        100
```

| | | |
|---|---|---|
| SEQ ID NO: 1062 | moltype = DNA length = 100 | |
| FEATURE | Location/Qualifiers | |
| source | 1..100 | |
| | mol_type = genomic DNA | |
| | organism = Homo sapiens | |

SEQUENCE: 1062

```
tttgtccaga ggaggaggta gggacgccgg gaagcaacaa ctctgatttt atttcgccgg   60
ctccacagcc tcccattgcc ccaggagccc acccgcactc                        100
```

```
SEQ ID NO: 1063         moltype = DNA  length = 100
FEATURE                 Location/Qualifiers
source                  1..100
                        mol_type = genomic DNA
                        organism = Homo sapiens
SEQUENCE: 1063
caaccccgc atctcggacc tgtggcctca gcccagactc acatcaccaa gtgcacctac    60
ccagcctccg ttatcctgga tccaggtgtg caggtgccgg                        100

SEQ ID NO: 1064         moltype = DNA  length = 100
FEATURE                 Location/Qualifiers
source                  1..100
                        mol_type = genomic DNA
                        organism = Homo sapiens
SEQUENCE: 1064
ttcaggtact cagtcatcca cagggcgatg ttgtccacca ggggcgacat ctcccggttg    60
acgtctcca cacacatgac cccaccgaac tcaaagaagg                          100

SEQ ID NO: 1065         moltype = DNA  length = 100
FEATURE                 Location/Qualifiers
source                  1..100
                        mol_type = genomic DNA
                        organism = Homo sapiens
SEQUENCE: 1065
ccacaatcct cccccagttc accccgtccc tgaagagctc ctccaccacc gtggcaaagc    60
gtccccgcgc ggtgaagggc gtcaggtgca gctggctgga                         100

SEQ ID NO: 1066         moltype = DNA  length = 100
FEATURE                 Location/Qualifiers
source                  1..100
                        mol_type = genomic DNA
                        organism = Homo sapiens
SEQUENCE: 1066
catctcggcg aagtcgcggc ggtagcggcg ggagaagtcg tcgccggcct ggcggagggt    60
caggtggacc acaggtggca ccgggctgag cgcaggcccc                         100

SEQ ID NO: 1067         moltype = DNA  length = 100
FEATURE                 Location/Qualifiers
source                  1..100
                        mol_type = genomic DNA
                        organism = Homo sapiens
SEQUENCE: 1067
gcggcggcgc cggggcagc cggggtctgc agcggcgagg tcctggcgac cgggtcccgg    60
gatgcggctg gatggggcgt gtgcccgggc tgggaggaga                         100

SEQ ID NO: 1068         moltype = DNA  length = 100
FEATURE                 Location/Qualifiers
source                  1..100
                        mol_type = genomic DNA
                        organism = Homo sapiens
SEQUENCE: 1068
agatgcccgg tgcgggggcg gcccccgggg gcgcggcgcc cacatctccc gcatcccact    60
cgtagcccct ctgcgacagc ttataatgga tgtacttcat                         100

SEQ ID NO: 1069         moltype = DNA  length = 100
FEATURE                 Location/Qualifiers
source                  1..100
                        mol_type = genomic DNA
                        organism = Homo sapiens
SEQUENCE: 1069
cactatctcc cggttatcgt accctgttct cccagcgtgc gccatccttc ccagaggaaa    60
agcaacgggg gccaacggca cctctcgccc cagctcccac                         100

SEQ ID NO: 1070         moltype = DNA  length = 100
FEATURE                 Location/Qualifiers
source                  1..100
                        mol_type = genomic DNA
                        organism = Homo sapiens
SEQUENCE: 1070
cccacggccc ccagagaaag aagaggagtt ataatccagc tattttattg gatgtgcttt    60
gcattcttgg acgaggggt gtcttcaatc acgcggaaca                          100

SEQ ID NO: 1071         moltype = DNA  length = 100
FEATURE                 Location/Qualifiers
source                  1..100
                        mol_type = genomic DNA
                        organism = Homo sapiens
SEQUENCE: 1071
```

```
cttgattctg gtgtttcccc cttggcatga gatgcaggaa attttttattc caattccttt    60
cggatcttta tttcatgagg cacgttatta ttagtaagta                          100

SEQ ID NO: 1072         moltype = DNA  length = 100
FEATURE                 Location/Qualifiers
source                  1..100
                        mol_type = genomic DNA
                        organism = Homo sapiens
SEQUENCE: 1072
ttgttaatat cagtctactt cctctgtgat gctgaaaggt taaagaaaaa acaaactaat    60
aagtaaaaaa tcaggtgcgt ttccctgtac acactgagtg                         100

SEQ ID NO: 1073         moltype = DNA  length = 100
FEATURE                 Location/Qualifiers
source                  1..100
                        mol_type = genomic DNA
                        organism = Homo sapiens
SEQUENCE: 1073
aaagcagggc atacacacta caagtaacac ggctaaaaag aatgtattaa gctgcctgga    60
aattaaattt actcgaatgc actttaagta aaaaatctca                         100

SEQ ID NO: 1074         moltype = DNA  length = 100
FEATURE                 Location/Qualifiers
source                  1..100
                        mol_type = genomic DNA
                        organism = Homo sapiens
SEQUENCE: 1074
aaggtttcca ttgaaagtta cattaaacca atttcctgtg cagagaactt acttgtattt    60
tttaagtaca gcatgatcct ctgtcaagtt tccttttttgt                        100

SEQ ID NO: 1075         moltype = DNA  length = 100
FEATURE                 Location/Qualifiers
source                  1..100
                        mol_type = genomic DNA
                        organism = Homo sapiens
SEQUENCE: 1075
aaaaccaaaa caaatgcata aggcaacgat cccatcaatc ttcagcactc tccagttata    60
gctgatttga aacttcccaa tgaatcagga gtcgcgggga                         100

SEQ ID NO: 1076         moltype = DNA  length = 100
FEATURE                 Location/Qualifiers
source                  1..100
                        mol_type = genomic DNA
                        organism = Homo sapiens
SEQUENCE: 1076
gagggagtaa aaattaggag gatttccaga tcgattccca gacttctgct tcacagaaat    60
gtcaatccgc aggaatccca accggagatc tcaagagctc                         100

SEQ ID NO: 1077         moltype = DNA  length = 100
FEATURE                 Location/Qualifiers
source                  1..100
                        mol_type = genomic DNA
                        organism = Homo sapiens
SEQUENCE: 1077
gagaaaaaaa aaaggcagcg gcggcggcag atgaattaca attttcagtc cggtattcgc    60
agaagtcctg tgatgttttc cccttctcgg caatttacac                         100

SEQ ID NO: 1078         moltype = DNA  length = 100
FEATURE                 Location/Qualifiers
source                  1..100
                        mol_type = genomic DNA
                        organism = Homo sapiens
SEQUENCE: 1078
tgaaggagcc ggggacggag gcaggaatcc tcttctgatt aaactccgaa cagcaaatgc    60
attttccgaa aagctgctgg ataaatgaag gcaggacgcg                         100

SEQ ID NO: 1079         moltype = DNA  length = 100
FEATURE                 Location/Qualifiers
source                  1..100
                        mol_type = genomic DNA
                        organism = Homo sapiens
SEQUENCE: 1079
cctggcccgc cggtgccgag cgctagaagc ccgcgctgtg tgtggtgcgg cgaggggtgg    60
ggagaaggag gtggtggggg agggttttat tttttccctc                         100

SEQ ID NO: 1080         moltype = DNA  length = 100
FEATURE                 Location/Qualifiers
source                  1..100
                        mol_type = genomic DNA
```

```
                        organism = Homo sapiens
SEQUENCE: 1080
ttttcctaaa aaggatgact gctacgaagt tctccccct ggaccccctc ttccgctgca    60
ccccaccggc gcaccccgcc tccgggctgc gcacccttc                         100

SEQ ID NO: 1081          moltype = DNA   length = 100
FEATURE                  Location/Qualifiers
source                   1..100
                         mol_type = genomic DNA
                         organism = Homo sapiens
SEQUENCE: 1081
gtgtgtgtct cgcctggacc ttttctagcc gtgtatgtgg gagtgtgtgt gtcgcctgga    60
cccttctag ccgtgtatga gagtgtgtac acgcgcctac                          100

SEQ ID NO: 1082          moltype = DNA   length = 100
FEATURE                  Location/Qualifiers
source                   1..100
                         mol_type = genomic DNA
                         organism = Homo sapiens
SEQUENCE: 1082
acacacacac gttgtgttac cggcgctcgg ccgccggggg aagacccagg ccaatgccgc    60
cccccaccgc ccccagcagt gggacctcag cgctgccctg                         100

SEQ ID NO: 1083          moltype = DNA   length = 100
FEATURE                  Location/Qualifiers
source                   1..100
                         mol_type = genomic DNA
                         organism = Homo sapiens
SEQUENCE: 1083
ctgtgaagac aggtgactct gcacgtttta agcaatgtct agggacgccc cgagcgtggt    60
gtttactttc aagtagcttc ctaggtgtcc gcgcactaca                         100

SEQ ID NO: 1084          moltype = DNA   length = 100
FEATURE                  Location/Qualifiers
source                   1..100
                         mol_type = genomic DNA
                         organism = Homo sapiens
SEQUENCE: 1084
cacgcacgcg catccccgcc cgtgtccacc tgaacaccta gtccgtggcc caggccatgc    60
agaactcagc gctccaggga aggggtttat caagggcttt                         100

SEQ ID NO: 1085          moltype = DNA   length = 100
FEATURE                  Location/Qualifiers
source                   1..100
                         mol_type = genomic DNA
                         organism = Homo sapiens
SEQUENCE: 1085
acgacagttt aagtcaatgt tttccctctg tccctaacac cttttacact ggtttagtgc    60
tacacgatga ggacttccat atagtaactt tcaggcccac                         100

SEQ ID NO: 1086          moltype = DNA   length = 100
FEATURE                  Location/Qualifiers
source                   1..100
                         mol_type = genomic DNA
                         organism = Homo sapiens
SEQUENCE: 1086
cgtcctaacg ctggggtggg tgggctccta aaggtctcca cctttgcctc gtagccaatc    60
ctagttggcc gcactttctc aaatgaggta catagataca                         100

SEQ ID NO: 1087          moltype = DNA   length = 100
FEATURE                  Location/Qualifiers
source                   1..100
                         mol_type = genomic DNA
                         organism = Homo sapiens
SEQUENCE: 1087
gtgtctccat ggagatggca gcaggacccg acccgtgct ggcccgcact ctcggcctcc     60
ttatctggtt taggaatgcg cggtatccac gctcgctcgc                         100

SEQ ID NO: 1088          moltype = DNA   length = 100
FEATURE                  Location/Qualifiers
source                   1..100
                         mol_type = genomic DNA
                         organism = Homo sapiens
SEQUENCE: 1088
gcgggagcca cgcctcctct cccccccgcc cccgagaccg ccacgcgcg ggggccccca     60
cgtctccaag cggcactgga aggattcctc tccgtcccgc                         100

SEQ ID NO: 1089          moltype = DNA   length = 100
FEATURE                  Location/Qualifiers
```

```
source                  1..100
                        mol_type = genomic DNA
                        organism = Homo sapiens
SEQUENCE: 1089
cagggggtccc gcctcgagat tctgggaaga ctgggggtgg gggaccagat cgcagcagca    60
gctgcaccgc gagttccgcg cctggccgtg tcgcccacg                           100

SEQ ID NO: 1090         moltype = DNA   length = 100
FEATURE                 Location/Qualifiers
source                  1..100
                        mol_type = genomic DNA
                        organism = Homo sapiens
SEQUENCE: 1090
aggggggactg tgggctcagc gcgtggggcc cggagcatct gacaaggaca gagacagagg    60
aggggggtgga aatccccggg tgagtcaacc cgtgcctgag                          100

SEQ ID NO: 1091         moltype = DNA   length = 100
FEATURE                 Location/Qualifiers
source                  1..100
                        mol_type = genomic DNA
                        organism = Homo sapiens
SEQUENCE: 1091
aaggggggcga gttccgacgc tccgcccggc tcggggccac gcgaggtccg cgccacgcgc    60
gccttcaccc acgacccatc cctgagccgg agttgaaaga                           100

SEQ ID NO: 1092         moltype = DNA   length = 100
FEATURE                 Location/Qualifiers
source                  1..100
                        mol_type = genomic DNA
                        organism = Homo sapiens
SEQUENCE: 1092
ggaggcgtct gagccacgca gtcactttct ctttccttac aaacaaagc cacgccccc      60
gccgggggac cggaggaggc aaacaacttg gggaaaccga                           100

SEQ ID NO: 1093         moltype = DNA   length = 100
FEATURE                 Location/Qualifiers
source                  1..100
                        mol_type = genomic DNA
                        organism = Homo sapiens
SEQUENCE: 1093
cccactttcc ccttctgtcc ctaaagtttt ttcttcctct tgcctccccc agcccttttg    60
aaagctcccc gcgtcgtcct cctgctgccc cggctcctta                           100

SEQ ID NO: 1094         moltype = DNA   length = 100
FEATURE                 Location/Qualifiers
source                  1..100
                        mol_type = genomic DNA
                        organism = Homo sapiens
SEQUENCE: 1094
gcagcttctg ggacgcacgg gagggaaaag ccgcggggac ccccccacc ccagcctccc     60
agccgggtga gatttggttg ctgtgtttcc tcctcacttg                           100

SEQ ID NO: 1095         moltype = DNA   length = 100
FEATURE                 Location/Qualifiers
source                  1..100
                        mol_type = genomic DNA
                        organism = Homo sapiens
SEQUENCE: 1095
ccacccccagc ctcccagccg ggtgagattt ggttgctgtg tttcctcctc acttgggcat    60
ttaaaaaata ttttaacacg aattgtccgc ggaattttca                           100

SEQ ID NO: 1096         moltype = DNA   length = 100
FEATURE                 Location/Qualifiers
source                  1..100
                        mol_type = genomic DNA
                        organism = Homo sapiens
SEQUENCE: 1096
catggcctgg acccctctcc tcctccagct tctcaccctc tgctcaggtg actgcctgtg     60
gaatgccaaa gtgattattg gggacacatg ggatgacttt                            100

SEQ ID NO: 1097         moltype = DNA   length = 100
FEATURE                 Location/Qualifiers
source                  1..100
                        mol_type = genomic DNA
                        organism = Homo sapiens
SEQUENCE: 1097
tctcttatat tttaacattg tggggtgggt agtgaaccca gactcacctc tctgtgcctg     60
cctcctctgt tccagggtcc tgggcacagt ctgcgctgac                            100
```

| SEQ ID NO: 1098 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 1098
ccaggaagcc tcggtgtcag ggaccgtggg acagaaggtc accctctcct gtactggaaa 60
cagcaacaac gttggaagtt atgctgtggg ctggtaccaa 100

| SEQ ID NO: 1099 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 1099
cagatttctc acgtgctcc caaaactgtg atgtttggaa attctctgcc ctcagggatc 60
cctgaccgct tctctggctc aaagtctggg accacagcct 100

| SEQ ID NO: 1100 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 1100
ccctgactat ctcgggcctc tagcctgagg acgaggctga ttattactgt tcaacatggg 60
actacagcct cagtgctcac acagtgctgc aggcacatgg 100

| SEQ ID NO: 1101 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 1101
ggaaccgaga caaaaacctg cccttggcct gtcccgaggc tgatcactcc atacttgcct 60
atgacaaaca aagagggtgc ctgtggctga tcgtacagtt 100

| SEQ ID NO: 1102 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 1102
gaaatgttgt ttgctcttgt ccttccttca ggccataatg agcgtctctg ttttcagggt 60
ctctctccca gcctgtgctg actcaatcat cctctgcctc 100

| SEQ ID NO: 1103 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 1103
tcaagctcac ctgcactctg agcagtgggc acagtagcta catcatcgca tggcatcagc 60
agcagccagg gaaggcccct cggtacttga tgaagcttga 100

| SEQ ID NO: 1104 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 1104
aggtagtgga agctcaaaca aggggagcgg agttcctgat cgcttctcag gctccagctc 60
tggggctgac cgctacctca ccatctccaa cctccagttt 100

| SEQ ID NO: 1105 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 1105
gaggatgagg ctgattatta ctgtgagacc tgggacagta acactcacac agtgatacag 60
gcagatgagg aagtgggaca aaatcctcaa cctgctgagg 100

| SEQ ID NO: 1106 | moltype = DNA length = 100 |
| --- | --- |
| FEATURE | Location/Qualifiers |
| source | 1..100 |
| | mol_type = genomic DNA |
| | organism = Homo sapiens |

SEQUENCE: 1106
aaggtcacca tctcctgctc tggaagcagc tccaacattg gaataatta tgtatcctgg 60

```
taccagcagc tcccaggaac agcccccaaa ctcctcattt                         100

SEQ ID NO: 1107        moltype = DNA   length = 100
FEATURE                Location/Qualifiers
source                 1..100
                       mol_type = genomic DNA
                       organism = Homo sapiens
SEQUENCE: 1107
atgacaataa taagcgaccc tcagggattc ctgaccgatt ctctggctcc aagtctggca    60
cgtcagccac cctgggcatc accggactcc agactgggga                        100

SEQ ID NO: 1108        moltype = DNA   length = 100
FEATURE                Location/Qualifiers
source                 1..100
                       mol_type = genomic DNA
                       organism = Homo sapiens
SEQUENCE: 1108
tcagccagac tcacctgcac cttgcgcagt ggcatcaatc ttggtagcta caggatattc    60
tggtaccagc agaagccaga gagccctccc cggtatctcc                        100

SEQ ID NO: 1109        moltype = DNA   length = 100
FEATURE                Location/Qualifiers
source                 1..100
                       mol_type = genomic DNA
                       organism = Homo sapiens
SEQUENCE: 1109
tgagctacta ctcagactca agtaagcatc agggctctgg agtccccagc cgcttctctg    60
gatccaaaga tgcttcgagc aatgcaggga ttttagtcat                        100

SEQ ID NO: 1110        moltype = DNA   length = 100
FEATURE                Location/Qualifiers
source                 1..100
                       mol_type = genomic DNA
                       organism = Homo sapiens
SEQUENCE: 1110
agagatctgg gggaagctca gcttcagctg tggtagagaa gacaggattc aggacaatct    60
ccagcatggc cggcttccct ctcctcctca ccctcctcac                        100

SEQ ID NO: 1111        moltype = DNA   length = 100
FEATURE                Location/Qualifiers
source                 1..100
                       mol_type = genomic DNA
                       organism = Homo sapiens
SEQUENCE: 1111
tcactgtgca ggtgacagga tggggaccaa gagaggggcc ctgggaagcc catggggccc    60
tgctttctcc tcttgtctcc tttcgtctct tgtcaatcac                        100

SEQ ID NO: 1112        moltype = DNA   length = 100
FEATURE                Location/Qualifiers
source                 1..100
                       mol_type = genomic DNA
                       organism = Homo sapiens
SEQUENCE: 1112
catgtctgtg tctctctcac ttccagggtc ctgggcccag tctgtgctga ctcagccacc    60
ctcagcgtct gggaccccg ggcagagggt caccatctct                         100

SEQ ID NO: 1113        moltype = DNA   length = 100
FEATURE                Location/Qualifiers
source                 1..100
                       mol_type = genomic DNA
                       organism = Homo sapiens
SEQUENCE: 1113
tgttctggaa gcagctccaa catcggaagt aattatgtat actggtacca gcagctccca    60
ggaacggccc ccaaactcct catctatagt aataatcagc                        100

SEQ ID NO: 1114        moltype = DNA   length = 100
FEATURE                Location/Qualifiers
source                 1..100
                       mol_type = genomic DNA
                       organism = Homo sapiens
SEQUENCE: 1114
ggccctcagg ggtccctgac cgattctctg gctccaagtc tggcacctca gcctccctgg    60
ccatcagtgg gctccggtcc gaggatgagg ctgattatta                        100

SEQ ID NO: 1115        moltype = DNA   length = 100
FEATURE                Location/Qualifiers
source                 1..100
                       mol_type = genomic DNA
                       organism = Homo sapiens
```

```
SEQUENCE: 1115
atttgcataa agcagcacac agcacacccc ctccgtgcgg agagctcaat aggagataaa    60
gagccatcag aatccagccc cagctctggc accaggggtc                         100

SEQ ID NO: 1116        moltype = DNA  length = 100
FEATURE                Location/Qualifiers
source                 1..100
                       mol_type = genomic DNA
                       organism = Homo sapiens
SEQUENCE: 1116
ccttccaata tcagcaccat ggcctggact cctctctttc tgttcctcct cacttgctgc    60
ccaggttaag agagatttca aataccagcc tttggaggga                         100

SEQ ID NO: 1117        moltype = DNA  length = 100
FEATURE                Location/Qualifiers
source                 1..100
                       mol_type = genomic DNA
                       organism = Homo sapiens
SEQUENCE: 1117
tccctttttc tccctttcta attcctaata tatgtctgtt ttttttgttt cagggtccaa    60
ttcccaggct gtggtgactc aggagccctc actgactgtg                         100

SEQ ID NO: 1118        moltype = DNA  length = 100
FEATURE                Location/Qualifiers
source                 1..100
                       mol_type = genomic DNA
                       organism = Homo sapiens
SEQUENCE: 1118
ggacagtcac tctcacctgt ggctccagca ctggagctgt caccagtggt cattatccct    60
actggttcca gcagaagcct ggccaagccc caggacact                          100

SEQ ID NO: 1119        moltype = DNA  length = 100
FEATURE                Location/Qualifiers
source                 1..100
                       mol_type = genomic DNA
                       organism = Homo sapiens
SEQUENCE: 1119
gatttatgat acaagcaaca aacactcctg gacacctgcc cggttctcag gctccctcct    60
tgggggcaaa gctgccctga ccctttggg tgcgcagcct                          100

SEQ ID NO: 1120        moltype = DNA  length = 100
FEATURE                Location/Qualifiers
source                 1..100
                       mol_type = genomic DNA
                       organism = Homo sapiens
SEQUENCE: 1120
gaggatgagg ctgagtatta ctgcttgctc tcctatagtg gtgctcggca cagtgacaga    60
cccatgagag gaaccaagac ataaacctcc ctcggccctt                         100

SEQ ID NO: 1121        moltype = DNA  length = 100
FEATURE                Location/Qualifiers
source                 1..100
                       mol_type = genomic DNA
                       organism = Homo sapiens
SEQUENCE: 1121
ggtcagccac ccagcctgat tctgactctt ctggcaaaga tccctgaaaa actttaccct    60
ggtttctgcc ttagcaccca ttaatgtctg tgtttccagg                         100

SEQ ID NO: 1122        moltype = DNA  length = 100
FEATURE                Location/Qualifiers
source                 1..100
                       mol_type = genomic DNA
                       organism = Homo sapiens
SEQUENCE: 1122
ttccctctcg caggctgtgc tgactcagcc gtcttccctc tctgcatctc ctggagcatc    60
agccagtctc acctgcacct tgcgcagtgg catcaatgtt                         100

SEQ ID NO: 1123        moltype = DNA  length = 100
FEATURE                Location/Qualifiers
source                 1..100
                       mol_type = genomic DNA
                       organism = Homo sapiens
SEQUENCE: 1123
gcatcagcca gtctcacctg caccttgcgc agtggcatca atgttggtac ctacaggata    60
tactggtacc agcagaagcc agggagtcct ccccagtatc                         100

SEQ ID NO: 1124        moltype = DNA  length = 100
FEATURE                Location/Qualifiers
source                 1..100
```

```
                        mol_type = genomic DNA
                        organism = Homo sapiens
SEQUENCE: 1124
tcctgaggta caaatcagac tcagataagc agcagggctc tggagtcccc agccgcttct     60
ctggatccaa agatgcttcg gccaatgcag ggatttttact                          100

SEQ ID NO: 1125         moltype = DNA   length = 100
FEATURE                 Location/Qualifiers
source                  1..100
                        mol_type = genomic DNA
                        organism = Homo sapiens
SEQUENCE: 1125
acagatgggg aagtgggaca aaaacctcac cctgctctgg gtcttgctct gtaccaattt     60
ttaaatttta aaataactgg cctaggcaca aactatattt                           100

SEQ ID NO: 1126         moltype = DNA   length = 100
FEATURE                 Location/Qualifiers
source                  1..100
                        mol_type = genomic DNA
                        organism = Homo sapiens
SEQUENCE: 1126
gcccagtctg tgctgactca gccaccctca gcgtctggga ccccgggca gagggtcacc      60
atctcttgtt ctggaagcag ctccaacatc ggaagtaata                           100

SEQ ID NO: 1127         moltype = DNA   length = 100
FEATURE                 Location/Qualifiers
source                  1..100
                        mol_type = genomic DNA
                        organism = Homo sapiens
SEQUENCE: 1127
ctgtaaactg gtaccagcag ctcccaggaa cggccccaa actcctcatc tatagtaata      60
atcagcggcc ctcaggggtc cctgaccgat tctctggctc                           100

SEQ ID NO: 1128         moltype = DNA   length = 100
FEATURE                 Location/Qualifiers
source                  1..100
                        mol_type = genomic DNA
                        organism = Homo sapiens
SEQUENCE: 1128
tgctgctcag gcctggcctg tggcttctgc tgctgcagct tccttcatgg gtccaggggc     60
atccagggcc ctgcctgaga gtggaggctc ctcctcccct                           100

SEQ ID NO: 1129         moltype = DNA   length = 100
FEATURE                 Location/Qualifiers
source                  1..100
                        mol_type = genomic DNA
                        organism = Homo sapiens
SEQUENCE: 1129
tccagcactg gagcagtcac cagtggttac tatccaaact ggttccagca gaaacctgga    60
caagcaccca gggcactgat ttatagtaca agcaacaaac                           100

SEQ ID NO: 1130         moltype = DNA   length = 100
FEATURE                 Location/Qualifiers
source                  1..100
                        mol_type = genomic DNA
                        organism = Homo sapiens
SEQUENCE: 1130
ccctccttgg gggcaaagct gccctgacac tgtcaggtgt gcagcctgag gacgaggctg     60
agtattactg cctgctctac tatggtggtg ctcagcacag                           100

SEQ ID NO: 1131         moltype = DNA   length = 100
FEATURE                 Location/Qualifiers
source                  1..100
                        mol_type = genomic DNA
                        organism = Homo sapiens
SEQUENCE: 1131
tgacagactc ataagaggaa ccaagacata aacctccctc ggcccttgtg atgtggagat     60
tgtgtgatca tacacaccag ctctcaagac agcctacatg                           100

SEQ ID NO: 1132         moltype = DNA   length = 100
FEATURE                 Location/Qualifiers
source                  1..100
                        mol_type = genomic DNA
                        organism = Homo sapiens
SEQUENCE: 1132
acataaacct ccctcggccc ttgtgatgtg gagattgtgt gatcatacac accagctctc    60
aagacagcct acatgtggac cagccataga aaggggaagg                          100

SEQ ID NO: 1133         moltype = DNA   length = 100
```

```
FEATURE                 Location/Qualifiers
source                  1..100
                        mol_type = genomic DNA
                        organism = Homo sapiens
SEQUENCE: 1133
atagaaaggg gaaggaaagg gtctgaattg atttctatcc ctccttgtgc cctgaagtgg    60
aggaaatgtg agagtgattt gcagtaattg aatgagacaa                         100

SEQ ID NO: 1134         moltype = DNA   length = 100
FEATURE                 Location/Qualifiers
source                  1..100
                        mol_type = genomic DNA
                        organism = Homo sapiens
SEQUENCE: 1134
agcaaaagtt atttgtttta tatgaaaaaa aaaaacagaa acagcaggat cagatctaaa    60
ggctgagtct aaatgcattt cctccagaca gaagcttctt                         100

SEQ ID NO: 1135         moltype = DNA   length = 100
FEATURE                 Location/Qualifiers
source                  1..100
                        mol_type = genomic DNA
                        organism = Homo sapiens
SEQUENCE: 1135
cagatctaaa ggctgagtct aaatgcattt cctccagaca gaagcttctt caaacgatgg    60
gctttctgag ctaagagcaa agaaaataaa ctctccacgg                         100

SEQ ID NO: 1136         moltype = DNA   length = 100
FEATURE                 Location/Qualifiers
source                  1..100
                        mol_type = genomic DNA
                        organism = Homo sapiens
SEQUENCE: 1136
gtatattatt aaagtttatt ttattgagtt actttcaaag caatccatga ctattatata    60
aagtcagaaa gtattaaaaa tcaccaagtt ctctgctaag                         100

SEQ ID NO: 1137         moltype = DNA   length = 100
FEATURE                 Location/Qualifiers
source                  1..100
                        mol_type = genomic DNA
                        organism = Homo sapiens
SEQUENCE: 1137
ctaccttatc ccatgcaatc aaaataagta cttttcttca tttggatgca ttttttattt    60
ctgttttaa tatttccaca atggtgatta aacctggtgc                          100

SEQ ID NO: 1138         moltype = DNA   length = 100
FEATURE                 Location/Qualifiers
source                  1..100
                        mol_type = genomic DNA
                        organism = Homo sapiens
SEQUENCE: 1138
acagggtcag gggaggggtc caggaagccc atgaggccct gctttctcct tctctctcta    60
gaccaagaat caccgtgtct gtgtctctcc tgcttccacg                         100

SEQ ID NO: 1139         moltype = DNA   length = 100
FEATURE                 Location/Qualifiers
source                  1..100
                        mol_type = genomic DNA
                        organism = Homo sapiens
SEQUENCE: 1139
gtcctgggcc cagtctgtgt tgacgcagcc gccttcagtg tctgcggccc caggacagaa    60
ggtcaccatc tcctgctctg gaagcagctc cgacatgggg                         100

SEQ ID NO: 1140         moltype = DNA   length = 100
FEATURE                 Location/Qualifiers
source                  1..100
                        mol_type = genomic DNA
                        organism = Homo sapiens
SEQUENCE: 1140
aattatgcgg tatcctggta ccagcagctc ccaggaacag cccccaaact cctcatctat    60
gaaaataata agcgaccctc agggattcct gaccgattct                         100

SEQ ID NO: 1141         moltype = DNA   length = 100
FEATURE                 Location/Qualifiers
source                  1..100
                        mol_type = genomic DNA
                        organism = Homo sapiens
SEQUENCE: 1141
ctggctccaa gtctggcacc tcagccaccc tgggcatcac tggcctctgg cctgaggact    60
aggccgatta ttactgctta gcatgggata ccagcctgag                         100
```

```
SEQ ID NO: 1142        moltype = DNA  length = 100
FEATURE                Location/Qualifiers
source                 1..100
                       mol_type = genomic DNA
                       organism = Homo sapiens
SEQUENCE: 1142
agcttgcaca gtgctccagg ccaatgggga actgagacaa gaaccctctt cctcctccgc      60
caggagggtg agtgcctgca gctgctgctc acacctgacc                          100

SEQ ID NO: 1143        moltype = DNA  length = 100
FEATURE                Location/Qualifiers
source                 1..100
                       mol_type = genomic DNA
                       organism = Homo sapiens
SEQUENCE: 1143
tgtagcttct gctgctgtag cttcccccat gggcctcggg gcatccaggg ccttgcctag      60
gagtggaggc tccaccactt ttgtcctcag agtcaggaac                          100

SEQ ID NO: 1144        moltype = DNA  length = 100
FEATURE                Location/Qualifiers
source                 1..100
                       mol_type = genomic DNA
                       organism = Homo sapiens
SEQUENCE: 1144
agggacccca ggagacagaa tatcctgctc ctcagcttgg gacacagggt ctctgcactg      60
aaatcgtggg ctgaggtggc aggtccaact gtgtcttcac                          100

SEQ ID NO: 1145        moltype = DNA  length = 100
FEATURE                Location/Qualifiers
source                 1..100
                       mol_type = genomic DNA
                       organism = Homo sapiens
SEQUENCE: 1145
ctctgcactg aaatcgtggg ctgaggtggc aggtccaact gtgtcttcac agtccttcct      60
gtgcctgccc atggtgtggg gacggagtga ggaagtgtgg                          100

SEQ ID NO: 1146        moltype = DNA  length = 100
FEATURE                Location/Qualifiers
source                 1..100
                       mol_type = genomic DNA
                       organism = Homo sapiens
SEQUENCE: 1146
tcctcactct cctcgctcac tgcacaggtg actggataca ggtccagggg aggggccctg      60
ggaagcctat ggattcttgc tttctcctgt tgtctctaga                          100

SEQ ID NO: 1147        moltype = DNA  length = 100
FEATURE                Location/Qualifiers
source                 1..100
                       mol_type = genomic DNA
                       organism = Homo sapiens
SEQUENCE: 1147
agccgaataa tgatgcctgt gtctctccca cttccaggt cctgggccca gtctgtgctg      60
acgcagccgc cctcagtgtc tggggcccca gggcagaggg                          100

SEQ ID NO: 1148        moltype = DNA  length = 100
FEATURE                Location/Qualifiers
source                 1..100
                       mol_type = genomic DNA
                       organism = Homo sapiens
SEQUENCE: 1148
tcaccatctc ctgcactggg agcagctcca acatcgggc aggttatgat gtacactggt       60
accagcagct tccaggaaca gcccccaaac tcctcatcta                          100

SEQ ID NO: 1149        moltype = DNA  length = 100
FEATURE                Location/Qualifiers
source                 1..100
                       mol_type = genomic DNA
                       organism = Homo sapiens
SEQUENCE: 1149
ctccaggctg aggatgaggc tgattattac tgccagtcct atgacagcag cctgagtggt      60
tccacagtgc tccaggcccg gggggaactg agacaagaac                          100

SEQ ID NO: 1150        moltype = DNA  length = 100
FEATURE                Location/Qualifiers
source                 1..100
                       mol_type = genomic DNA
                       organism = Homo sapiens
SEQUENCE: 1150
```

```
gctcctcact ctcctcactc aggacacagg tgacgcctcc agggaagggg tcttggggac    60
ctctgggctg atccttggtc tcctgctcct caggctcacc                         100

SEQ ID NO: 1151         moltype = DNA  length = 100
FEATURE                 Location/Qualifiers
source                  1..100
                        mol_type = genomic DNA
                        organism = Homo sapiens
SEQUENCE: 1151
ttccagggtc ctgggcccag tctgccctga ctcagcctgc ctccgtgtct gggtctcctg    60
gacagtcgat caccatctcc tgcactggaa ccagcagtga                         100

SEQ ID NO: 1152         moltype = DNA  length = 100
FEATURE                 Location/Qualifiers
source                  1..100
                        mol_type = genomic DNA
                        organism = Homo sapiens
SEQUENCE: 1152
tgttgggagt tataaccttg tctcctggta ccaacagcac ccaggcaaag cccccaaact    60
catgatttat gagggcagta agcggccctc aggggtttct                         100

SEQ ID NO: 1153         moltype = DNA  length = 100
FEATURE                 Location/Qualifiers
source                  1..100
                        mol_type = genomic DNA
                        organism = Homo sapiens
SEQUENCE: 1153
aatcgcttct ctggctccaa gtctggcaac acgcctccc tgacaatctc tgggctccag     60
gctgaggacg aggctgatta ttactgctgc tcatatgcag                         100

SEQ ID NO: 1154         moltype = DNA  length = 100
FEATURE                 Location/Qualifiers
source                  1..100
                        mol_type = genomic DNA
                        organism = Homo sapiens
SEQUENCE: 1154
gctgaggacg aggctgatta ttactgctgc tcatatgcag gtagtagcac tttccacagt    60
ggtccaagtt catggggaac tgagaccaaa acctgcccag                         100

SEQ ID NO: 1155         moltype = DNA  length = 100
FEATURE                 Location/Qualifiers
source                  1..100
                        mol_type = genomic DNA
                        organism = Homo sapiens
SEQUENCE: 1155
ggccttcaga cttcctcctt gctctgaaga tgcttcctca cccggtgcaa gaggcttgct    60
gcagcgcggc cttgagaatt cttctctctc agctccttcc                         100

SEQ ID NO: 1156         moltype = DNA  length = 100
FEATURE                 Location/Qualifiers
source                  1..100
                        mol_type = genomic DNA
                        organism = Homo sapiens
SEQUENCE: 1156
ctttccacca tgaattccaa caggaaacct gccctgtggt ttcccatcca ggacagggac    60
agcttcctga tgcttgtgtg ctgtggtccc tgaatgtgca                         100

SEQ ID NO: 1157         moltype = DNA  length = 100
FEATURE                 Location/Qualifiers
source                  1..100
                        mol_type = genomic DNA
                        organism = Homo sapiens
SEQUENCE: 1157
actcttccca gctcttcaaa tgcagggaca gtgacaagga gctgcctgat tggtgcagtc    60
actgctttttt tcagggatgt cttcacccta catgtatcat                        100

SEQ ID NO: 1158         moltype = DNA  length = 100
FEATURE                 Location/Qualifiers
source                  1..100
                        mol_type = genomic DNA
                        organism = Homo sapiens
SEQUENCE: 1158
catcccctac actgtgggta gaattttagc aactacattc taatggttat cgccacaact    60
ttgatcttag aaataacagt gcagtgaaca tccctatgca                         100

SEQ ID NO: 1159         moltype = DNA  length = 100
FEATURE                 Location/Qualifiers
source                  1..100
                        mol_type = genomic DNA
```

```
                          organism = Homo sapiens
SEQUENCE: 1159
ggctcctttg agttcctgtg tgaatacgac cataggattc atttctaaaa gtgaaattgc    60
gggtcagaaa gatgtgtgtt tgtgattttc acccaatgtt                         100

SEQ ID NO: 1160         moltype = DNA   length = 100
FEATURE                 Location/Qualifiers
source                  1..100
                        mol_type = genomic DNA
                        organism = Homo sapiens
SEQUENCE: 1160
accagcagaa gccaggccag gcccctgtgc tggtcgtcta tgatgatagc gaccggccct    60
cagggatccc tgagcgattc tctggctcca actctgggaa                         100

SEQ ID NO: 1161         moltype = DNA   length = 100
FEATURE                 Location/Qualifiers
source                  1..100
                        mol_type = genomic DNA
                        organism = Homo sapiens
SEQUENCE: 1161
cccagcctcg gtcaccctct tgctccagcc ccgggaagcc tgttgataaa gccatgagtg    60
aatctggccc agttcacctg gatctgagcc tttcaggttg                         100

SEQ ID NO: 1162         moltype = DNA   length = 100
FEATURE                 Location/Qualifiers
source                  1..100
                        mol_type = genomic DNA
                        organism = Homo sapiens
SEQUENCE: 1162
cccttccctc cagcccctc caggagtctc tacagaagat acatcaggca taaatatggc    60
ctggaagggc cagaatcatc tggtgacttg gggctgttgt                         100

SEQ ID NO: 1163         moltype = DNA   length = 100
FEATURE                 Location/Qualifiers
source                  1..100
                        mol_type = genomic DNA
                        organism = Homo sapiens
SEQUENCE: 1163
ggtcctgggc ccagtctgcc ctgactcagc ctgcctccgt gtctgggtct cctggacagt    60
cgatcaccat ctcctgcact ggaaccagca gtgacgttgg                         100

SEQ ID NO: 1164         moltype = DNA   length = 100
FEATURE                 Location/Qualifiers
source                  1..100
                        mol_type = genomic DNA
                        organism = Homo sapiens
SEQUENCE: 1164
aaagccccca aactcatgat ttatgaggtc agtaatcggc cctcagggt ttctaatcgc     60
ttctctggct ccaagtctgg caacacggcc tccctgacca                         100

SEQ ID NO: 1165         moltype = DNA   length = 100
FEATURE                 Location/Qualifiers
source                  1..100
                        mol_type = genomic DNA
                        organism = Homo sapiens
SEQUENCE: 1165
aggctcagtg cccatagacc ccaagttggc cctgccctga accctgtgca aagcccagac    60
acagtcttag ggtaggaccc ctgggaatgg gctcttgatc                         100

SEQ ID NO: 1166         moltype = DNA   length = 100
FEATURE                 Location/Qualifiers
source                  1..100
                        mol_type = genomic DNA
                        organism = Homo sapiens
SEQUENCE: 1166
ttcaagcccc ctctcctgtt ttccttgcag tctctgaggc ctcctatgag ctgacacagc    60
caccctcggt gtcagtgtcc ccaggacaaa cggccaggat                         100

SEQ ID NO: 1167         moltype = DNA   length = 100
FEATURE                 Location/Qualifiers
source                  1..100
                        mol_type = genomic DNA
                        organism = Homo sapiens
SEQUENCE: 1167
agaagtcagg ccaggcccct gtgctggtca tctatgagga cagcaaacga ccctccggga    60
tccctgagag attctctggc tccagctcag ggacaatggc                         100

SEQ ID NO: 1168         moltype = DNA   length = 100
FEATURE                 Location/Qualifiers
```

```
source                  1..100
                        mol_type = genomic DNA
                        organism = Homo sapiens
SEQUENCE: 1168
caccttgact atcagtgggg cccaggtgga ggatgaagct gactactact gttactcaac   60
agacagcagt ggtaatcata gcacagtgac actggcagat                        100

SEQ ID NO: 1169         moltype = DNA  length = 100
FEATURE                 Location/Qualifiers
source                  1..100
                        mol_type = genomic DNA
                        organism = Homo sapiens
SEQUENCE: 1169
ggggaagtga gacacaaacc ccttcttcat ctattttacc ctctccctcc agccccagga   60
ccgctgtgga ccaacccata agcaggtctg gcagaattca                        100

SEQ ID NO: 1170         moltype = DNA  length = 100
FEATURE                 Location/Qualifiers
source                  1..100
                        mol_type = genomic DNA
                        organism = Homo sapiens
SEQUENCE: 1170
aggctcacct gggcccagca ctgactcact agactgtgtt tctcccttc caggqtcctg    60
ggcccagtct gccctgactc agcctccctc cgcgtccggg                        100

SEQ ID NO: 1171         moltype = DNA  length = 100
FEATURE                 Location/Qualifiers
source                  1..100
                        mol_type = genomic DNA
                        organism = Homo sapiens
SEQUENCE: 1171
catctcctgc actggaacca gcagtgacgt tggtggttat aactatgtct cctggtacca   60
acagcaccca ggcaaagccc ccaaactcat gatttatgag                        100

SEQ ID NO: 1172         moltype = DNA  length = 100
FEATURE                 Location/Qualifiers
source                  1..100
                        mol_type = genomic DNA
                        organism = Homo sapiens
SEQUENCE: 1172
gtcagtaagc ggccctcagg ggtccctgat cgcttctctg gctccaagtc tggcaacacg   60
gcctccctga ccgtctctgg gctccaggct gaggatgagg                        100

SEQ ID NO: 1173         moltype = DNA  length = 100
FEATURE                 Location/Qualifiers
source                  1..100
                        mol_type = genomic DNA
                        organism = Homo sapiens
SEQUENCE: 1173
aggctgagga tgaggctgat tattactgca gctcatatgc aggcagcaac aatttccaca   60
gtgttttaag tcaatgagga agtaagatca aaacctgccc                        100

SEQ ID NO: 1174         moltype = DNA  length = 100
FEATURE                 Location/Qualifiers
source                  1..100
                        mol_type = genomic DNA
                        organism = Homo sapiens
SEQUENCE: 1174
tcaggctcag aacccatagg atcctgagct gggcctgccc aaacatgagt tcatcccagg   60
cacaacctca gggtgggacc ccctgggaac agattcatca                        100

SEQ ID NO: 1175         moltype = DNA  length = 100
FEATURE                 Location/Qualifiers
source                  1..100
                        mol_type = genomic DNA
                        organism = Homo sapiens
SEQUENCE: 1175
tttacaagcc tcctctcctg tcctctcttg caagctccta tgagcttaca cagccaccct   60
cagtgtcagt gtcaccagga caggcagcca tgatcacctg                        100

SEQ ID NO: 1176         moltype = DNA  length = 100
FEATURE                 Location/Qualifiers
source                  1..100
                        mol_type = genomic DNA
                        organism = Homo sapiens
SEQUENCE: 1176
ctcttgagat aacctcaaag atgagtatgt ttactggttc tggcagaagc cagaccaggc   60
ccatactggt gatatatgaa ggcagcaagc ggccctcagg                        100
```

| SEQ ID NO: 1177 | moltype = DNA length = 100 |
|---|---|
| FEATURE | Location/Qualifiers |
| source | 1..100 |
| | mol_type = genomic DNA |
| | organism = Homo sapiens |

SEQUENCE: 1177
aatttctgat tttctgagtc cagctcaggg aacatggcca ccctgaccat cagcagggct   60
cagactgagg acgaggctga ctattactgt cacaggtaca                         100

| SEQ ID NO: 1178 | moltype = DNA length = 100 |
|---|---|
| FEATURE | Location/Qualifiers |
| source | 1..100 |
| | mol_type = genomic DNA |
| | organism = Homo sapiens |

SEQUENCE: 1178
atagaaacag tgatgagccc acagtgacac aggcagatta ggaagtgaga cacaaacccc   60
ttcccaatct gtgtcaccct ctttctccag ccccaggatg                         100

| SEQ ID NO: 1179 | moltype = DNA length = 100 |
|---|---|
| FEATURE | Location/Qualifiers |
| source | 1..100 |
| | mol_type = genomic DNA |
| | organism = Homo sapiens |

SEQUENCE: 1179
gggatgagaa gggaccaggg gcctgggatt gagctgtgaa gggaaccaaa aggcaggagg   60
gacagggcag gggctgtcag ctatgactca ggggaggttc                         100

| SEQ ID NO: 1180 | moltype = DNA length = 100 |
|---|---|
| FEATURE | Location/Qualifiers |
| source | 1..100 |
| | mol_type = genomic DNA |
| | organism = Homo sapiens |

SEQUENCE: 1180
ctgggcctca ggatcctccc tctgaggcca ccaggggggcg ggggtggcac atgcctggac  60
ctgggaggtc cctgctgggc ttcaccctgg gtgggtccta                         100

| SEQ ID NO: 1181 | moltype = DNA length = 100 |
|---|---|
| FEATURE | Location/Qualifiers |
| source | 1..100 |
| | mol_type = genomic DNA |
| | organism = Homo sapiens |

SEQUENCE: 1181
atgcctggac ctgggaggtc cctgctgggc ttcaccctgg gtgggtccta ggagctcctt   60
cctcctaagt cccccctaaag agacagaggc attctggggt                        100

| SEQ ID NO: 1182 | moltype = DNA length = 100 |
|---|---|
| FEATURE | Location/Qualifiers |
| source | 1..100 |
| | mol_type = genomic DNA |
| | organism = Homo sapiens |

SEQUENCE: 1182
cctaaatctg tcatgccccc ataaatgcat ttctacgagg gccaataaat gaactccagg   60
tttatccaag cagcagcttc aggcgtctgc agacacagag                         100

| SEQ ID NO: 1183 | moltype = DNA length = 100 |
|---|---|
| FEATURE | Location/Qualifiers |
| source | 1..100 |
| | mol_type = genomic DNA |
| | organism = Homo sapiens |

SEQUENCE: 1183
cggggaggaa ttagccaacc tgaggcaccc tagaagggct gaaggggggct gaagggggact 60
gaagggtccc tgtgggggcct gtggtcctgg ggagggggaga                       100

| SEQ ID NO: 1184 | moltype = DNA length = 100 |
|---|---|
| FEATURE | Location/Qualifiers |
| source | 1..100 |
| | mol_type = genomic DNA |
| | organism = Homo sapiens |

SEQUENCE: 1184
gctggggtgt ctcccagcca ctctgggccc tgtcctgaca cttctcccac aaagaaggga   60
agggaaatcc tgggaccccca cagccaggac caaccgtgaa                        100

| SEQ ID NO: 1185 | moltype = DNA length = 100 |
|---|---|
| FEATURE | Location/Qualifiers |
| source | 1..100 |
| | mol_type = genomic DNA |
| | organism = Homo sapiens |

SEQUENCE: 1185
ccacaggaca ggaaggacag gaccccccaa ggctggctcc atttcccagg cactgtcatg   60

-continued

```
ggctgagtct caggaaatcc aagtcaagga gtttcaatcc                           100

SEQ ID NO: 1186        moltype = DNA   length = 100
FEATURE                Location/Qualifiers
source                 1..100
                       mol_type = genomic DNA
                       organism = Homo sapiens
SEQUENCE: 1186
ccaaggaaac agaagtctac gggcccaggc ccaggtgagg gtggggtaag aagaggagct     60
taggatgcag atttgcatgg aggccccgcc ctcctctgag                          100

SEQ ID NO: 1187        moltype = DNA   length = 100
FEATURE                Location/Qualifiers
source                 1..100
                       mol_type = genomic DNA
                       organism = Homo sapiens
SEQUENCE: 1187
gcatcagggt aagacaaggc tgggggcagg cccagtgctg gggtctcagg aggcagcgct     60
ctggggacgt ctccaccatg gcctgggctc tgctcctcct                          100

SEQ ID NO: 1188        moltype = DNA   length = 100
FEATURE                Location/Qualifiers
source                 1..100
                       mol_type = genomic DNA
                       organism = Homo sapiens
SEQUENCE: 1188
ctcagggcac aggtgacgcc tccaggaag gggcctcggg gacccttggg ctgatccttg      60
gtctcctgct cctcaggctc acctgggccc agcactgact                          100

SEQ ID NO: 1189        moltype = DNA   length = 100
FEATURE                Location/Qualifiers
source                 1..100
                       mol_type = genomic DNA
                       organism = Homo sapiens
SEQUENCE: 1189
ttgggagtta tgactatgtc tcctggtacc aacagcaccc aggcacagtc cccaaaccca    60
tgatctacaa tgtcaatact cagccctcag gggtccctga                          100

SEQ ID NO: 1190        moltype = DNA   length = 100
FEATURE                Location/Qualifiers
source                 1..100
                       mol_type = genomic DNA
                       organism = Homo sapiens
SEQUENCE: 1190
tcgtttctct ggctccaagt ctggcaatac ggcctccatg accatctctg gactccaggc    60
tgaggacgag gctgattatt agtgctgctc atatacaagc                          100

SEQ ID NO: 1191        moltype = DNA   length = 100
FEATURE                Location/Qualifiers
source                 1..100
                       mol_type = genomic DNA
                       organism = Homo sapiens
SEQUENCE: 1191
tgaggacgag gctgattatt agtgctgctc atatacaagc agtgccactt aaccacagtg    60
gtccaagttc ttggggaact gagacgaaaa cctgccctgg                          100

SEQ ID NO: 1192        moltype = DNA   length = 100
FEATURE                Location/Qualifiers
source                 1..100
                       mol_type = genomic DNA
                       organism = Homo sapiens
SEQUENCE: 1192
cctgggctct caggctccct ttttgctctg aagatgtttc ctcacccagt gcaacgggct    60
tcctgaagca cagccttgag aattcttctc cctcagcaac                          100

SEQ ID NO: 1193        moltype = DNA   length = 100
FEATURE                Location/Qualifiers
source                 1..100
                       mol_type = genomic DNA
                       organism = Homo sapiens
SEQUENCE: 1193
tctcttttcc caccatgaaa tccaaaggaa acctgctctg tggtttctca tccaggacag    60
ggacagcttc cttttgcttg tgtgttgtgg tccctgagtg                          100

SEQ ID NO: 1194        moltype = DNA   length = 100
FEATURE                Location/Qualifiers
source                 1..100
                       mol_type = genomic DNA
                       organism = Homo sapiens
```

-continued

```
SEQUENCE: 1194
ggtgcaactc ttcctagctt tttaaattat gggagggtga caatgagctc cctgactggt    60
gcagtccctg ctgttttcag gaacatcctc atcctaaatg                          100

SEQ ID NO: 1195          moltype = DNA   length = 100
FEATURE                  Location/Qualifiers
source                   1..100
                         mol_type = genomic DNA
                         organism = Homo sapiens
SEQUENCE: 1195
catctgaatc tcccactgtg tgcagaccaa tctggacaga tgttattagg gggagtttcc    60
agaagccaca tcttactcaa ctctgtatcc accacactct                          100

SEQ ID NO: 1196          moltype = DNA   length = 100
FEATURE                  Location/Qualifiers
source                   1..100
                         mol_type = genomic DNA
                         organism = Homo sapiens
SEQUENCE: 1196
tgcctcagcc atggcatgga tccctctctt cctcggcgtc cttgcttact gcacaggtgc    60
tgccctagg gtcctagcca ctggtccagt cccagggctc                           100

SEQ ID NO: 1197          moltype = DNA   length = 100
FEATURE                  Location/Qualifiers
source                   1..100
                         mol_type = genomic DNA
                         organism = Homo sapiens
SEQUENCE: 1197
tgggtccagc ctggccctga ctctgagctc agcagggccc ccgcctgtgg tgggcaggat    60
gctcatgacc ctgctgcagg tggatgggct cggcggggct                          100

SEQ ID NO: 1198          moltype = DNA   length = 100
FEATURE                  Location/Qualifiers
source                   1..100
                         mol_type = genomic DNA
                         organism = Homo sapiens
SEQUENCE: 1198
tgggcaggat gctcatgacc ctgctgcagg tggatgggct cggcggggct gaaatccccc    60
cacacagtgc tcatgtgctc acactgcctt agggctcttt                          100

SEQ ID NO: 1199          moltype = DNA   length = 100
FEATURE                  Location/Qualifiers
source                   1..100
                         mol_type = genomic DNA
                         organism = Homo sapiens
SEQUENCE: 1199
catccctgga tctgtgtcca ggccaggcac gtgggaagat ttacttggag ttcagctcct    60
cagtttcaag ccttttctct cccgttttct ctcctgtagg                          100

SEQ ID NO: 1200          moltype = DNA   length = 100
FEATURE                  Location/Qualifiers
source                   1..100
                         mol_type = genomic DNA
                         organism = Homo sapiens
SEQUENCE: 1200
atccgtggcc tcctatgagc tgactcagcc accctcagtg tccgtgtccc caggacagac    60
agccagcatc acctgctctg gagataaatt ggggggataaa                         100

SEQ ID NO: 1201          moltype = DNA   length = 100
FEATURE                  Location/Qualifiers
source                   1..100
                         mol_type = genomic DNA
                         organism = Homo sapiens
SEQUENCE: 1201
caggacagac agccagcatc acctgctctg gagataaatt ggggggataaa tatgcttgct    60
ggtatcagca gaagccaggc cagtcccctg tgctggtcat                          100

SEQ ID NO: 1202          moltype = DNA   length = 100
FEATURE                  Location/Qualifiers
source                   1..100
                         mol_type = genomic DNA
                         organism = Homo sapiens
SEQUENCE: 1202
ctatcaagat agcaagcggc cctcagggat ccctgagcga ttctctggct ccaactctgg    60
gaacacagcc actctgacca tcagcgggac ccaggctatg                          100

SEQ ID NO: 1203          moltype = DNA   length = 100
FEATURE                  Location/Qualifiers
source                   1..100
```

```
                              mol_type = genomic DNA
                              organism = Homo sapiens
SEQUENCE: 1203
gatgaggctg actattactg tcaggcgtgg gacagcagca ctgcacacag tgacacaggc     60
agatgcggaa gtgagacaga aaccagccac ctcggcctgg                          100

SEQ ID NO: 1204               moltype = DNA   length = 100
FEATURE                       Location/Qualifiers
source                        1..100
                              mol_type = genomic DNA
                              organism = Homo sapiens
SEQUENCE: 1204
ctcacaagac ccttccctct ctcctgccct gtcacactga gcaggaggga gccttccatg     60
tggaatggaa gtttccagtc ctatccctgc ccttatgttc                          100

SEQ ID NO: 1205               moltype = DNA   length = 100
FEATURE                       Location/Qualifiers
source                        1..100
                              mol_type = genomic DNA
                              organism = Homo sapiens
SEQUENCE: 1205
ctgagagacg ggagcaagtt cctgcccacc tctaggctca gcttatccca gaataaactg     60
agctagtcat tttgatgatc aaatgccagc tcccaaaaga                          100

SEQ ID NO: 1206               moltype = DNA   length = 100
FEATURE                       Location/Qualifiers
source                        1..100
                              mol_type = genomic DNA
                              organism = Homo sapiens
SEQUENCE: 1206
ccccagaaac cctgtatatct aagtagcacc gactctatta gtatcaaggg agactagccc    60
tagggtggaa tcattttagt gtctcagaag gcacagggca                          100

SEQ ID NO: 1207               moltype = DNA   length = 100
FEATURE                       Location/Qualifiers
source                        1..100
                              mol_type = genomic DNA
                              organism = Homo sapiens
SEQUENCE: 1207
atggaaagtg tttatgaggt ttcaggatat gcacgtgagc agttaaaggc aggtcttaca     60
aggaaggaac ctactagaat tggggcccat ctgtgacatc                          100

SEQ ID NO: 1208               moltype = DNA   length = 100
FEATURE                       Location/Qualifiers
source                        1..100
                              mol_type = genomic DNA
                              organism = Homo sapiens
SEQUENCE: 1208
acatccctct gctttgggag agaagggcca gggcgggacc cagagagctc tgcagaggca     60
ccacagaccc tcagcagggg gtctgccaaa caggacagct                          100

SEQ ID NO: 1209               moltype = DNA   length = 100
FEATURE                       Location/Qualifiers
source                        1..100
                              mol_type = genomic DNA
                              organism = Homo sapiens
SEQUENCE: 1209
ggacttggct gcttctgccc aggcctggat ccagcccttg cacatctcag ggcaggggat     60
aggcctgggt ggccagagct gcagctgcac ctgctgggga                          100

SEQ ID NO: 1210               moltype = DNA   length = 100
FEATURE                       Location/Qualifiers
source                        1..100
                              mol_type = genomic DNA
                              organism = Homo sapiens
SEQUENCE: 1210
ggcctagtcc agtcctccag ggtccccaga cagactcgga tttccgactg cagccaccat     60
ggaaggatgt ggtctgcggt gacgatgtct atccagaggc                          100

SEQ ID NO: 1211               moltype = DNA   length = 100
FEATURE                       Location/Qualifiers
source                        1..100
                              mol_type = genomic DNA
                              organism = Homo sapiens
SEQUENCE: 1211
ccgaatatcc aaggagccca agatcagagg caggaatagg ccaagctccc cagtggagaa     60
gctgtgctgg accaggggtt tcccagggcc ctcccttgtg                          100

SEQ ID NO: 1212               moltype = DNA   length = 100
```

```
FEATURE              Location/Qualifiers
source               1..100
                     mol_type = genomic DNA
                     organism = Homo sapiens
SEQUENCE: 1212
ccctgaatga tgtctgttag ggcacctaca ccctgttact gctcagtgcc ttgcctattt   60
tgaaggacag ggatgtgtgg tgattatttg tataatccag                        100

SEQ ID NO: 1213      moltype = DNA   length = 100
FEATURE              Location/Qualifiers
source               1..100
                     mol_type = genomic DNA
                     organism = Homo sapiens
SEQUENCE: 1213
cccccagcac ctggtcctca aaagttaccc aagcaatgtg tataaagatc cagcctggag   60
atctttgaaa accgattcga tgagtcgaac cattaagtca                        100

SEQ ID NO: 1214      moltype = DNA   length = 100
FEATURE              Location/Qualifiers
source               1..100
                     mol_type = genomic DNA
                     organism = Homo sapiens
SEQUENCE: 1214
tgatcaccat cctcaacttc atctctttct tcctcctcct cctcattatc atcaccttca   60
agaactgtta agagtctgag acttcatcct atttgcagac                        100

SEQ ID NO: 1215      moltype = DNA   length = 100
FEATURE              Location/Qualifiers
source               1..100
                     mol_type = genomic DNA
                     organism = Homo sapiens
SEQUENCE: 1215
tcctcctcct cctcattatc atcaccttca agaactgtta agagtctgag acttcatcct   60
atttgcagac taaaaagtaa gcctgccaca gtgccatgga                        100

SEQ ID NO: 1216      moltype = DNA   length = 100
FEATURE              Location/Qualifiers
source               1..100
                     mol_type = genomic DNA
                     organism = Homo sapiens
SEQUENCE: 1216
tgctggcaga agatacaaga ctcctgggtc agagacaacg aataatctgt ttttcacagc   60
aatagcagtt gccaaggtat cagcattgtc ttgcaccagt                        100

SEQ ID NO: 1217      moltype = DNA   length = 100
FEATURE              Location/Qualifiers
source               1..100
                     mol_type = genomic DNA
                     organism = Homo sapiens
SEQUENCE: 1217
tccacaaggt gatgcaaaga gggccaggtg acatctgcat gccagagctc agggatccca   60
aatatttcat acttgacagt aagcatatat ctgtgttttg                        100

SEQ ID NO: 1218      moltype = DNA   length = 100
FEATURE              Location/Qualifiers
source               1..100
                     mol_type = genomic DNA
                     organism = Homo sapiens
SEQUENCE: 1218
ctccaaagag aggcattctc tgtaccttcc gaggttgttc actccacaaa cactcttgaa   60
aagataatcc acaatcagtg cctttgcccg agagacatgc                        100

SEQ ID NO: 1219      moltype = DNA   length = 100
FEATURE              Location/Qualifiers
source               1..100
                     mol_type = genomic DNA
                     organism = Homo sapiens
SEQUENCE: 1219
agaaatgcag agatccatag tagaccactg tctcccaaca accatcaact ttatcaatga   60
aatgaagtct caggctattt gtctgttacc atagcccaca                        100

SEQ ID NO: 1220      moltype = DNA   length = 100
FEATURE              Location/Qualifiers
source               1..100
                     mol_type = genomic DNA
                     organism = Homo sapiens
SEQUENCE: 1220
aaaatgtctg gcttgattgt caccaaatgt atcaaggaag ttaaggagta tctgacacaa   60
aatgtgaacc aagcaattct caaaggagcc tcccaggaaa                        100
```

```
SEQ ID NO: 1221         moltype = DNA   length = 100
FEATURE                 Location/Qualifiers
source                  1..100
                        mol_type = genomic DNA
                        organism = Homo sapiens
SEQUENCE: 1221
ttcactttag gaagtcctag gaggctcctc tgagagttgc taaaacaaaa cattgagagt    60
cctagagggc tgcagatctg aacttgagca gatattttta                         100

SEQ ID NO: 1222         moltype = DNA   length = 100
FEATURE                 Location/Qualifiers
source                  1..100
                        mol_type = genomic DNA
                        organism = Homo sapiens
SEQUENCE: 1222
aagattttgt ggcagaaaaa gaaactggaa agcaagaggg cagaccctca ttgcagttct    60
gtaatgtaag ggggcagagc aggggccttt ctcaccagag                         100

SEQ ID NO: 1223         moltype = DNA   length = 100
FEATURE                 Location/Qualifiers
source                  1..100
                        mol_type = genomic DNA
                        organism = Homo sapiens
SEQUENCE: 1223
gatattggac cctgcattca tcttctctgg atggtaattt tctcacctgt aaaacagaga    60
cactggcccc aaggacaccc cacaagtagt tgtgaatccc                         100

SEQ ID NO: 1224         moltype = DNA   length = 100
FEATURE                 Location/Qualifiers
source                  1..100
                        mol_type = genomic DNA
                        organism = Homo sapiens
SEQUENCE: 1224
aaagtaagag aagaacaaaa aaagaaccag aatttattca acacccactg agtgcttagc    60
aaacacatgg tttctttaac tctcataagc ttcatgctgc                         100

SEQ ID NO: 1225         moltype = DNA   length = 100
FEATURE                 Location/Qualifiers
source                  1..100
                        mol_type = genomic DNA
                        organism = Homo sapiens
SEQUENCE: 1225
agaggaactc tccccatttt acagataagg aaactgaggc ccagaggtaa cctaggtcta    60
gatagactcc acatttatga cttcaccact cttccttgcc                         100

SEQ ID NO: 1226         moltype = DNA   length = 100
FEATURE                 Location/Qualifiers
source                  1..100
                        mol_type = genomic DNA
                        organism = Homo sapiens
SEQUENCE: 1226
aaactgaggc ccagaggtaa cctaggtcta gatagactcc acatttatga cttcaccact    60
cttccttgcc tgaaggatat agaatcactc cctgcagggc                         100

SEQ ID NO: 1227         moltype = DNA   length = 100
FEATURE                 Location/Qualifiers
source                  1..100
                        mol_type = genomic DNA
                        organism = Homo sapiens
SEQUENCE: 1227
tcttgcctga ctcaggaaag ggccacagga tagccagcca ggcttaacca acccagccaa    60
gaaagggctg gtcccaactg gctggagtgc agtgtacagg                         100

SEQ ID NO: 1228         moltype = DNA   length = 100
FEATURE                 Location/Qualifiers
source                  1..100
                        mol_type = genomic DNA
                        organism = Homo sapiens
SEQUENCE: 1228
gttggtagat gccctctgg gagagatccc cagggtgac agccatggac cctggaaggg      60
cctgggctag ggacagggac cagagccagt ccagggagag                         100

SEQ ID NO: 1229         moltype = DNA   length = 100
FEATURE                 Location/Qualifiers
source                  1..100
                        mol_type = genomic DNA
                        organism = Homo sapiens
SEQUENCE: 1229
```

```
gacagagcca atggactggg gtgtactgta acagccctgc tggcgagagg gaccagggca   60
ccgtcctcca gggagcccat gctgcaagtc gggccagagg                         100

SEQ ID NO: 1230         moltype = DNA  length = 100
FEATURE                 Location/Qualifiers
source                  1..100
                        mol_type = genomic DNA
                        organism = Homo sapiens
SEQUENCE: 1230
tgccctgaa cctgaaggcc aatgagaccc aagacaggcc aagtgggttg tgagacccct    60
gaggagctgg gccctggtcc caggcagcgc tggcccctgc                         100

SEQ ID NO: 1231         moltype = DNA  length = 100
FEATURE                 Location/Qualifiers
source                  1..100
                        mol_type = genomic DNA
                        organism = Homo sapiens
SEQUENCE: 1231
tgctgctggg tctggccatg gtcgcccatg gcctgctgcg cccaatggtt gcaccgcaaa   60
gcggggaccc agaccctgga gcctcagttg gaagcagccg                         100

SEQ ID NO: 1232         moltype = DNA  length = 100
FEATURE                 Location/Qualifiers
source                  1..100
                        mol_type = genomic DNA
                        organism = Homo sapiens
SEQUENCE: 1232
atccagcctg cggagcctgt ggggcaggta aggggcaaga gattccaggg gatgtggggg   60
tcctgcagca gagctgggaa agggtgacca aggggagaca                         100

SEQ ID NO: 1233         moltype = DNA  length = 100
FEATURE                 Location/Qualifiers
source                  1..100
                        mol_type = genomic DNA
                        organism = Homo sapiens
SEQUENCE: 1233
agccagagga gtgaggagga aggttaaccc ctaagagggg cctgggctga cactggcttt   60
agtaatgggt tgatattttg tccatcacag atttgtttga                         100

SEQ ID NO: 1234         moltype = DNA  length = 100
FEATURE                 Location/Qualifiers
source                  1..100
                        mol_type = genomic DNA
                        organism = Homo sapiens
SEQUENCE: 1234
attactgttt ttaatatcat attacgatat tattttcctt gatttctgag ttttctggcg   60
ccacttaaat tttcaccagg gtcagtgcct caatcaccta                         100

SEQ ID NO: 1235         moltype = DNA  length = 100
FEATURE                 Location/Qualifiers
source                  1..100
                        mol_type = genomic DNA
                        organism = Homo sapiens
SEQUENCE: 1235
gtcctagtcc tctgggtagg gaaggaacag aggcagggac aggacatcca caggggtgg    60
tggcactgt ccccacaggg tgcccaggcc tgttcctccc                          100

SEQ ID NO: 1236         moltype = DNA  length = 100
FEATURE                 Location/Qualifiers
source                  1..100
                        mol_type = genomic DNA
                        organism = Homo sapiens
SEQUENCE: 1236
cctcctcctc tctgcccatg tgcctcctgc ccagtgaggg caggggccac tccctggaga   60
aggcagcaag ggcttggttt ggtctccccc aaggctgtct                         100

SEQ ID NO: 1237         moltype = DNA  length = 100
FEATURE                 Location/Qualifiers
source                  1..100
                        mol_type = genomic DNA
                        organism = Homo sapiens
SEQUENCE: 1237
gttcaccaac ttgcacataa atgcttactg gggccaggct caaggacaca gggagggtgg   60
gatgaaccga ggggagctgt ccagtcattg gaacaggccc                         100

SEQ ID NO: 1238         moltype = DNA  length = 100
FEATURE                 Location/Qualifiers
source                  1..100
                        mol_type = genomic DNA
```

```
                         organism = Homo sapiens
SEQUENCE: 1238
acggcccatg tttggagcaa taaagggaga ggggatctcc ctctgggatg atgcccaggc      60
tggtctcaca gatcgagggg cactggctgg tgatgggtgc                           100

SEQ ID NO: 1239          moltype = DNA   length = 100
FEATURE                  Location/Qualifiers
source                   1..100
                         mol_type = genomic DNA
                         organism = Homo sapiens
SEQUENCE: 1239
tggtctcaca gatcgagggg cactggctgg tgatgggtgc ccccaaaaga cagagcagcg      60
tcagaggaga ggagagcaca ggatgaggct gggagctcct                           100

SEQ ID NO: 1240          moltype = DNA   length = 100
FEATURE                  Location/Qualifiers
source                   1..100
                         mol_type = genomic DNA
                         organism = Homo sapiens
SEQUENCE: 1240
gggtgactgg gaaggggagg caagaagacc atagggtccg tgcaccattc ccagtccagg      60
acgagtcctt ggatggattt aggtagattg attatcagag                           100

SEQ ID NO: 1241          moltype = DNA   length = 100
FEATURE                  Location/Qualifiers
source                   1..100
                         mol_type = genomic DNA
                         organism = Homo sapiens
SEQUENCE: 1241
tcagatttgt gtttttggaa aaatcagcac cggattggag gctgatgcga cgcccgatta     60
gaggagggag gagaggggt gatggccaag tccagggtag                            100

SEQ ID NO: 1242          moltype = DNA   length = 100
FEATURE                  Location/Qualifiers
source                   1..100
                         mol_type = genomic DNA
                         organism = Homo sapiens
SEQUENCE: 1242
gtggggatcc tggaggaagc cgtgccttgg ggatggggag gacactcaga ttcagagcac      60
ccaggggccc agtttcctat gaaatgggag catgaagttg                           100

SEQ ID NO: 1243          moltype = DNA   length = 100
FEATURE                  Location/Qualifiers
source                   1..100
                         mol_type = genomic DNA
                         organism = Homo sapiens
SEQUENCE: 1243
aagtgagggc tgagcagagg ggagcagaca cgctcgggga ctgtctatgg gcattaaaaa      60
tgtataacca ttttagcaac aggcggcgag tcaaaaaaca                           100

SEQ ID NO: 1244          moltype = DNA   length = 100
FEATURE                  Location/Qualifiers
source                   1..100
                         mol_type = genomic DNA
                         organism = Homo sapiens
SEQUENCE: 1244
aagtgtgttt atctaaactg ggcaattcca cttctaggaa tttatcctaa gggttggttg      60
ggggaataat caaagctgta accaaatctt tataacaagg                           100

SEQ ID NO: 1245          moltype = DNA   length = 100
FEATURE                  Location/Qualifiers
source                   1..100
                         mol_type = genomic DNA
                         organism = Homo sapiens
SEQUENCE: 1245
gtggttagct cagcattatt agtgatggga gaaaactgga aaaatccaa atatctacca       60
gaaagggtgt gaaaaaacac aattgtattt gggggactgt                           100

SEQ ID NO: 1246          moltype = DNA   length = 100
FEATURE                  Location/Qualifiers
source                   1..100
                         mol_type = genomic DNA
                         organism = Homo sapiens
SEQUENCE: 1246
tggctaattt tgattaggat tattattagt ttagagacag agcctcgcta tattgctcag      60
gcctgtctca aattcctaag ctcaagcaat ctttctgcct                           100

SEQ ID NO: 1247          moltype = DNA   length = 100
FEATURE                  Location/Qualifiers
```

| | | |
|---|---|---|
| source | 1..100<br>mol_type = genomic DNA<br>organism = Homo sapiens | |
| SEQUENCE: 1247 | | |
| actgcacctg acccaactgt gttttttaaag tatatatgca ttttcaaaaa cctgtcagaa | | 60 |
| aatatagaaa aatgtcaatg gtgtgtctgg ctggctgatg | | 100 |
| | | |
| SEQ ID NO: 1248 | moltype = DNA  length = 100 | |
| FEATURE | Location/Qualifiers | |
| source | 1..100<br>mol_type = genomic DNA<br>organism = Homo sapiens | |
| SEQUENCE: 1248 | | |
| ggatttcacc taattttaat gtggctttat aattttctgg ttttgtgaag ttgttcacaa | | 60 |
| aaagagacat ttcttctaat ataatttta atacaacagt | | 100 |
| | | |
| SEQ ID NO: 1249 | moltype = DNA  length = 100 | |
| FEATURE | Location/Qualifiers | |
| source | 1..100<br>mol_type = genomic DNA<br>organism = Homo sapiens | |
| SEQUENCE: 1249 | | |
| aatgtactca tgtgcattac tcttttttgta atgagtatat tacaaaatgt aatgactttt | | 60 |
| gtacattact ctttttcttt gccaaaaaaa aaaagatta | | 100 |
| | | |
| SEQ ID NO: 1250 | moltype = DNA  length = 100 | |
| FEATURE | Location/Qualifiers | |
| source | 1..100<br>mol_type = genomic DNA<br>organism = Homo sapiens | |
| SEQUENCE: 1250 | | |
| agcagagaag tatataaagt aaaagcaagt gcttctgctt accatctctc acctcttccc | | 60 |
| agagatagcc actgtcaggt tggtcaatat acttccagaa | | 100 |
| | | |
| SEQ ID NO: 1251 | moltype = DNA  length = 100 | |
| FEATURE | Location/Qualifiers | |
| source | 1..100<br>mol_type = genomic DNA<br>organism = Homo sapiens | |
| SEQUENCE: 1251 | | |
| cttttcctgt gtgtgtgtgt gtccctgaaa acacacacac acacacacac acacacacac | | 60 |
| acagttggtg ctgggatttt attttgcaaa agtaagagcc | | 100 |
| | | |
| SEQ ID NO: 1252 | moltype = DNA  length = 100 | |
| FEATURE | Location/Qualifiers | |
| source | 1..100<br>mol_type = genomic DNA<br>organism = Homo sapiens | |
| SEQUENCE: 1252 | | |
| cacacacagt tggtgctggg attttatttt gcaaaagtaa gagccatatt ctgcatatta | | 60 |
| ccaactttta atctattatt gacactttct gtatcagtcc | | 100 |
| | | |
| SEQ ID NO: 1253 | moltype = DNA  length = 100 | |
| FEATURE | Location/Qualifiers | |
| source | 1..100<br>mol_type = genomic DNA<br>organism = Homo sapiens | |
| SEQUENCE: 1253 | | |
| atatggatta accacattca ttgcttataa actttgtttt ataagcaaag tttagatgag | | 60 |
| ccagaattta tttccactaa aaaatctaaa tgacaaatga | | 100 |
| | | |
| SEQ ID NO: 1254 | moltype = DNA  length = 100 | |
| FEATURE | Location/Qualifiers | |
| source | 1..100<br>mol_type = genomic DNA<br>organism = Homo sapiens | |
| SEQUENCE: 1254 | | |
| tgctgcagtg gaaatttgtg tgtgtgtgtg tgtgtgtgtg tgtgtgtgtg tgtgtgtgtg | | 60 |
| tgtatgtgta caaagtgcac ttatatatct ccccaggata | | 100 |
| | | |
| SEQ ID NO: 1255 | moltype = DNA  length = 100 | |
| FEATURE | Location/Qualifiers | |
| source | 1..100<br>mol_type = genomic DNA<br>organism = Homo sapiens | |
| SEQUENCE: 1255 | | |
| tgacctgggt gttttctttt ttctctgtag gatgttaata gtatcttgtg tcatgctagg | | 60 |
| atgtctagga cagagggcaa tacaatgagg ggaaggcatt | | 100 |

```
SEQ ID NO: 1256            moltype = DNA  length = 100
FEATURE                    Location/Qualifiers
source                     1..100
                           mol_type = genomic DNA
                           organism = Homo sapiens
SEQUENCE: 1256
ctgcgatgtc cccaggcctc tggcttgaag agtaacttgc tgaagtgagg actctgtgga    60
ggagcaagtt atacagaaag aagtttagtt gtgatctgtt                         100

SEQ ID NO: 1257            moltype = DNA  length = 100
FEATURE                    Location/Qualifiers
source                     1..100
                           mol_type = genomic DNA
                           organism = Homo sapiens
SEQUENCE: 1257
gagttggagg tgtctacagg gcatccaagc agacataggt tgaggaggca gaatatatgt    60
gaatctggag ccaagaagag aggtaagggc tggaaatagg                         100

SEQ ID NO: 1258            moltype = DNA  length = 100
FEATURE                    Location/Qualifiers
source                     1..100
                           mol_type = genomic DNA
                           organism = Homo sapiens
SEQUENCE: 1258
gatctaagac ccctggacag ttgtgagtgt gcacaatgag ggtcagatgc agagaaaatt    60
aggagactac agagagcaga acccagggtg gggatctggg                         100

SEQ ID NO: 1259            moltype = DNA  length = 100
FEATURE                    Location/Qualifiers
source                     1..100
                           mol_type = genomic DNA
                           organism = Homo sapiens
SEQUENCE: 1259
agtcagcagt tgggcatggg cctggtagaa agggaagcca aggaggagga gaggggcag    60
tctcagacac caaggagggg agagtgacta gaaagaaaac                         100

SEQ ID NO: 1260            moltype = DNA  length = 100
FEATURE                    Location/Qualifiers
source                     1..100
                           mol_type = genomic DNA
                           organism = Homo sapiens
SEQUENCE: 1260
cttcttgcag agacataggg gatgggaag aactgcagac tgaactgggg caaaggactg    60
ttggccttaa ccagagagat ttgagggaga gatgaggctg                         100

SEQ ID NO: 1261            moltype = DNA  length = 100
FEATURE                    Location/Qualifiers
source                     1..100
                           mol_type = genomic DNA
                           organism = Homo sapiens
SEQUENCE: 1261
agagccaggg gatcctgcca tgtcccagca taaaaacagt acctgacaca gatgggtgct    60
tgggagctgt tgtcggatga atgagtggac agatgcatgg                         100

SEQ ID NO: 1262            moltype = DNA  length = 100
FEATURE                    Location/Qualifiers
source                     1..100
                           mol_type = genomic DNA
                           organism = Homo sapiens
SEQUENCE: 1262
atggacggat ggatggaagg atgatagatt gatggacaaa cagatgaaca gatgaatagc    60
tgatggaca actggatgga tgggtagaca gaatgatctc                         100

SEQ ID NO: 1263            moltype = DNA  length = 100
FEATURE                    Location/Qualifiers
source                     1..100
                           mol_type = genomic DNA
                           organism = Homo sapiens
SEQUENCE: 1263
agagatcaga aaaagcttca tgcactaagt gggactgaac cgcgtctcca tgggtagaaa    60
gcagaggaat ctccacttga gtcaggaatg acccagtgct                         100

SEQ ID NO: 1264            moltype = DNA  length = 100
FEATURE                    Location/Qualifiers
source                     1..100
                           mol_type = genomic DNA
                           organism = Homo sapiens
SEQUENCE: 1264
ctcaatccag ggagaaagcc agcctggctt cactggggac acttgtgtgg gggactcaga    60
```

-continued

```
ggcccttta  atgaggccag  acgaggttgg  acaggtccaa                           100

SEQ ID NO: 1265           moltype = DNA   length = 100
FEATURE                   Location/Qualifiers
source                    1..100
                          mol_type = genomic DNA
                          organism = Homo sapiens
SEQUENCE: 1265
gccaactcag  cactcctctg  ccacactgca  caggagggga  tgtgtcactc  agggagttgc   60
tgggacctat  gggtcccagt  gttgtcatca  gcaccgacag                          100

SEQ ID NO: 1266           moltype = DNA   length = 100
FEATURE                   Location/Qualifiers
source                    1..100
                          mol_type = genomic DNA
                          organism = Homo sapiens
SEQUENCE: 1266
cctcagagag  gaaagacaca  cactggggta  actccaaggc  tgtgtgtggc  acttgccttg   60
gacagcagac  aggcacaggg  acacctctag  ggggctggcc                          100

SEQ ID NO: 1267           moltype = DNA   length = 100
FEATURE                   Location/Qualifiers
source                    1..100
                          mol_type = genomic DNA
                          organism = Homo sapiens
SEQUENCE: 1267
acccccctgc  ctcatgtcta  ggtcccagcc  ccgcccactg  caaccctgtg  cccgtcatgc   60
ccagcaggct  cctgctccag  cccagccccc  agagagcaga                          100

SEQ ID NO: 1268           moltype = DNA   length = 100
FEATURE                   Location/Qualifiers
source                    1..100
                          mol_type = genomic DNA
                          organism = Homo sapiens
SEQUENCE: 1268
cactgcaacc  ctgtgcccgt  catgcccagc  aggctcctgc  tccagcccag  ccccagaga    60
gcagacccca  ggtgctggcc  ccgggggttt  tggtctgagc                          100

SEQ ID NO: 1269           moltype = DNA   length = 100
FEATURE                   Location/Qualifiers
source                    1..100
                          mol_type = genomic DNA
                          organism = Homo sapiens
SEQUENCE: 1269
ctcagtcact  gtgttatgtc  ttcggaactg  ggaccaaggt  caccgtccta  ggtaagtggc   60
tctcaacctt  tccagcctg   tctcaccctc  tgctgtccct                          100

SEQ ID NO: 1270           moltype = DNA   length = 100
FEATURE                   Location/Qualifiers
source                    1..100
                          mol_type = genomic DNA
                          organism = Homo sapiens
SEQUENCE: 1270
ggaaaatctg  ttttctctct  ctggggcttc  ctccccctctg tcctcccagc  cttaagcact   60
gacccttacc  tttctccatg  gggcctggag  gaggtgcatt                          100

SEQ ID NO: 1271           moltype = DNA   length = 100
FEATURE                   Location/Qualifiers
source                    1..100
                          mol_type = genomic DNA
                          organism = Homo sapiens
SEQUENCE: 1271
agtctccggg  taaccggcag  gaagggcctc  cacagtggga  gcagccggat  gcagcctggt   60
cccgggggcct gagctgggat  tgggcagggt  cagggctcct                          100

SEQ ID NO: 1272           moltype = DNA   length = 100
FEATURE                   Location/Qualifiers
source                    1..100
                          mol_type = genomic DNA
                          organism = Homo sapiens
SEQUENCE: 1272
cctctcttcc  agggcagatg  tctgagtgag  ggacagaggc  tggttctgat  gaggggccct   60
gcagtgtcct  tagggacatt  gcccagtgac  tcctggggtc                          100

SEQ ID NO: 1273           moltype = DNA   length = 100
FEATURE                   Location/Qualifiers
source                    1..100
                          mol_type = genomic DNA
                          organism = Homo sapiens
```

```
SEQUENCE: 1273
ggacagaggc tggttctgat gaggggccct gcagtgtcct tagggacatt gcccagtgac    60
tcctggggtc aaggacagag gctgctgggg tgggcctggg                         100

SEQ ID NO: 1274         moltype = DNA  length = 100
FEATURE                 Location/Qualifiers
source                  1..100
                        mol_type = genomic DNA
                        organism = Homo sapiens
SEQUENCE: 1274
agctgctgag tctcatagtc tagggagca gccccaagaa cagctgaggg tctaggctga     60
ggactggatg ccaatccagc ctgggagggc cacacggcct                         100

SEQ ID NO: 1275         moltype = DNA  length = 100
FEATURE                 Location/Qualifiers
source                  1..100
                        mol_type = genomic DNA
                        organism = Homo sapiens
SEQUENCE: 1275
tctcatagtc tagggagca gccccaagaa cagctgaggg tctaggctga ggactggatg     60
ccaatccagc ctgggagggc cacacggcct ggtgacacag                         100

SEQ ID NO: 1276         moltype = DNA  length = 100
FEATURE                 Location/Qualifiers
source                  1..100
                        mol_type = genomic DNA
                        organism = Homo sapiens
SEQUENCE: 1276
aggtcacccc aagggagac caatggaggg cacagagagg gctctgggtc taggctgcag     60
ctctgtggcc tgtgctgggt catgaggaca tggggacaca                         100

SEQ ID NO: 1277         moltype = DNA  length = 100
FEATURE                 Location/Qualifiers
source                  1..100
                        mol_type = genomic DNA
                        organism = Homo sapiens
SEQUENCE: 1277
tgtgctgggt catgaggaca tggggacaca gagggacggg tgagactggg tgaggtgcca    60
gaatccaacc ctcccaggac agtcaccaga aaggagacag                         100

SEQ ID NO: 1278         moltype = DNA  length = 100
FEATURE                 Location/Qualifiers
source                  1..100
                        mol_type = genomic DNA
                        organism = Homo sapiens
SEQUENCE: 1278
tctcttaggg cagagatgtg tctgtccctg gagcccgtc acctctgggg cccagtgtct     60
ctctgttcac ggatcggcct cctgccttcc tcaaagggca                         100

SEQ ID NO: 1279         moltype = DNA  length = 100
FEATURE                 Location/Qualifiers
source                  1..100
                        mol_type = genomic DNA
                        organism = Homo sapiens
SEQUENCE: 1279
tgttagactc aggaaatgac cagaggggag tgaatgaggg gtgcagagaa ctccatggct    60
accaggtgaa gtttggggtc atcacaggct gctggggtgg                         100

SEQ ID NO: 1280         moltype = DNA  length = 100
FEATURE                 Location/Qualifiers
source                  1..100
                        mol_type = genomic DNA
                        organism = Homo sapiens
SEQUENCE: 1280
catagtctgt gggagcagcc ccaggaacag ctgaggtgaa gggttctgtg gtcgggcttg    60
tggagacagg aaacatctca gagcctcaga ggagccctga                         100

SEQ ID NO: 1281         moltype = DNA  length = 100
FEATURE                 Location/Qualifiers
source                  1..100
                        mol_type = genomic DNA
                        organism = Homo sapiens
SEQUENCE: 1281
ggcttgtcta ggtgagccc actccttgcc aggagagcca agtgggctgg gctggggcag     60
agcccggtgc ctgtgaggga taggaagctc cagttcaaag                         100

SEQ ID NO: 1282         moltype = DNA  length = 100
FEATURE                 Location/Qualifiers
source                  1..100
```

```
                        mol_type = genomic DNA
                        organism = Homo sapiens
SEQUENCE: 1282
caggcttggg tctccccaca cactgcctgc caggacagtc ctacaggatg agcaggggac    60
ccacagttca cggaggaggc tctaggtcct ggaagaataa                         100

SEQ ID NO: 1283         moltype = DNA  length = 100
FEATURE                 Location/Qualifiers
source                  1..100
                        mol_type = genomic DNA
                        organism = Homo sapiens
SEQUENCE: 1283
agtgggtgat ggaggggggt atagggatgg aaatgaggga tccaggggtc aaggccagat    60
tctaaactca gactccagag atcagagaag aaggaacaca                         100

SEQ ID NO: 1284         moltype = DNA  length = 100
FEATURE                 Location/Qualifiers
source                  1..100
                        mol_type = genomic DNA
                        organism = Homo sapiens
SEQUENCE: 1284
gcctgccctg ggtatatgga gaaattgagg ctgtagagga gaggggctgg gccaggacac    60
ctgtgaaagg tgacttggga gggctcctag gaaggcacag                         100

SEQ ID NO: 1285         moltype = DNA  length = 100
FEATURE                 Location/Qualifiers
source                  1..100
                        mol_type = genomic DNA
                        organism = Homo sapiens
SEQUENCE: 1285
tgaaagcccc actgctatga ccaggtagcc gggacgtggg gtggatgcca gaaaagactc    60
cacggaataa gagagagccc aggacagcag gcaggctctc                         100

SEQ ID NO: 1286         moltype = DNA  length = 100
FEATURE                 Location/Qualifiers
source                  1..100
                        mol_type = genomic DNA
                        organism = Homo sapiens
SEQUENCE: 1286
cgatccccca aggcccttgc cccatacacg ggctccagaa cacacatttg gctggaacag    60
cctgagggac caaaaggccc cagtatccca cagagctgag                         100

SEQ ID NO: 1287         moltype = DNA  length = 100
FEATURE                 Location/Qualifiers
source                  1..100
                        mol_type = genomic DNA
                        organism = Homo sapiens
SEQUENCE: 1287
gagccaggcc agaaaagtaa ccccagagtt cgctgtgcag gggagacaca gagctctctt    60
tatctgtcag gatggcagga ggggacaggg tcagggcgct                         100

SEQ ID NO: 1288         moltype = DNA  length = 100
FEATURE                 Location/Qualifiers
source                  1..100
                        mol_type = genomic DNA
                        organism = Homo sapiens
SEQUENCE: 1288
gagggtcaga tgtcggtgtt gggggccaag gccccgagag atctcaggac aggtggtcag    60
gtgtctaagg taaacagct ccccgtgcag atcagggcat                          100

SEQ ID NO: 1289         moltype = DNA  length = 100
FEATURE                 Location/Qualifiers
source                  1..100
                        mol_type = genomic DNA
                        organism = Homo sapiens
SEQUENCE: 1289
atgcaggaca gtccggagag ggaaatcagg agaagtgaag gggtctctgg ggagcccaga    60
tgtgggctag aggcagaagt aagggtgaag agcacctatg                         100

SEQ ID NO: 1290         moltype = DNA  length = 100
FEATURE                 Location/Qualifiers
source                  1..100
                        mol_type = genomic DNA
                        organism = Homo sapiens
SEQUENCE: 1290
agtcaatgtc atggtctcag caggaacaca gttgaaaatc cccattccac acaagaccgt    60
ttagcaggaa aggagtccat acttgtgctg ccaccaggat                         100

SEQ ID NO: 1291         moltype = DNA  length = 100
```

| FEATURE | Location/Qualifiers |
|---|---|
| source | 1..100<br>mol_type = genomic DNA<br>organism = Homo sapiens |

SEQUENCE: 1291

```
gtcctgagaa gccttggaga atgaaacata caggtgcatt tcctagactt gacaatgcac    60
gttagccaag taaaggcaat gaaaagttct ctactaggga                         100
```

| SEQ ID NO: 1292 | moltype = DNA   length = 100 |
|---|---|
| FEATURE | Location/Qualifiers |
| source | 1..100<br>mol_type = genomic DNA<br>organism = Homo sapiens |

SEQUENCE: 1292

```
tttgtttgtt tctgtatctt gtctcaactt gtggtcagcc tttctccctg catcccaggc    60
ctgagcaagg acctctgccc tccctgttca gacccttgct                         100
```

| SEQ ID NO: 1293 | moltype = DNA   length = 100 |
|---|---|
| FEATURE | Location/Qualifiers |
| source | 1..100<br>mol_type = genomic DNA<br>organism = Homo sapiens |

SEQUENCE: 1293

```
tgcctcagca ggtcactaca accacttcac ctctgaccgc aggggcaggg gactagatag    60
aatgacctac tgagcctcgt ctgtctgtct gtctgtctgt                         100
```

| SEQ ID NO: 1294 | moltype = DNA   length = 100 |
|---|---|
| FEATURE | Location/Qualifiers |
| source | 1..100<br>mol_type = genomic DNA<br>organism = Homo sapiens |

SEQUENCE: 1294

```
ctgtttgtct ctctgtctgt ctgacaggcg caggctgggt ctctaagcct tgttctgttc    60
tggcctcctc agtctgggtt cttgtcggaa cagctttgcc                         100
```

| SEQ ID NO: 1295 | moltype = DNA   length = 100 |
|---|---|
| FEATURE | Location/Qualifiers |
| source | 1..100<br>mol_type = genomic DNA<br>organism = Homo sapiens |

SEQUENCE: 1295

```
cttgggttac ctgggttcca tctcctgggg aattgggaac aaggggtctg agggaggcac    60
ctcctgggag actttagaag gacccagtgc cctcggggct                         100
```

| SEQ ID NO: 1296 | moltype = DNA   length = 100 |
|---|---|
| FEATURE | Location/Qualifiers |
| source | 1..100<br>mol_type = genomic DNA<br>organism = Homo sapiens |

SEQUENCE: 1296

```
agagttcgct gtgcagggga gacacagagc tctctttatc tgtcaggatg gcaggagggg    60
acagggtcag ggcgctgagg gtcagatgtc ggtgttgggg                         100
```

| SEQ ID NO: 1297 | moltype = DNA   length = 100 |
|---|---|
| FEATURE | Location/Qualifiers |
| source | 1..100<br>mol_type = genomic DNA<br>organism = Homo sapiens |

SEQUENCE: 1297

```
gccaaggccc cgagagatct caggacaggt ggtcaggtgt ctaaggtaaa acagctcccc    60
gtgcagatca ggacatagtg gaaaacaccc tgacccctct                         100
```

| SEQ ID NO: 1298 | moltype = DNA   length = 100 |
|---|---|
| FEATURE | Location/Qualifiers |
| source | 1..100<br>mol_type = genomic DNA<br>organism = Homo sapiens |

SEQUENCE: 1298

```
gcctggcata gaccttcaga cacagagccc ctgaacaagg gcaccccaac acctcatcat    60
atactgaggt cagggctcc ccaggtggac accaggactc                          100
```

| SEQ ID NO: 1299 | moltype = DNA   length = 100 |
|---|---|
| FEATURE | Location/Qualifiers |
| source | 1..100<br>mol_type = genomic DNA<br>organism = Homo sapiens |

SEQUENCE: 1299

```
agaatattcc gtgagaaggt ggccccacag cgctgggtca cacgccatcc cccaagacag    60
gcaggacacc acagacaggg tggtgggtct cagaaaactc                         100
```

```
SEQ ID NO: 1300         moltype = DNA  length = 100
FEATURE                 Location/Qualifiers
source                  1..100
                        mol_type = genomic DNA
                        organism = Homo sapiens
SEQUENCE: 1300
aggccctaaa cgtggatgct taccaattcc tccactggag gaagacctca gagcagatgc    60
ccaggacagg gacttctggt agggacggtg actgggacgg                         100

SEQ ID NO: 1301         moltype = DNA  length = 100
FEATURE                 Location/Qualifiers
source                  1..100
                        mol_type = genomic DNA
                        organism = Homo sapiens
SEQUENCE: 1301
gtgcctgttt gtcagggaaa acccactgga gagtcagatc ccccagataa cttctcacga    60
catgagagact ctttcgaaca gacaaagctc cacgttcagc                        100

SEQ ID NO: 1302         moltype = DNA  length = 100
FEATURE                 Location/Qualifiers
source                  1..100
                        mol_type = genomic DNA
                        organism = Homo sapiens
SEQUENCE: 1302
tcagggagta aaaaaaaat gcctcaaatg gaggcctttg atctactgga atccagcccc     60
caggactgac accctgtctc accaggcagc ccagaggggt                         100

SEQ ID NO: 1303         moltype = DNA  length = 100
FEATURE                 Location/Qualifiers
source                  1..100
                        mol_type = genomic DNA
                        organism = Homo sapiens
SEQUENCE: 1303
cagggtccac cagaaggcat ctcagaacca gccagcagtg gccctgattg tcagcaggac    60
cccaggagg ggggtggcca ggacagggct ctgaagcccc                          100

SEQ ID NO: 1304         moltype = DNA  length = 100
FEATURE                 Location/Qualifiers
source                  1..100
                        mol_type = genomic DNA
                        organism = Homo sapiens
SEQUENCE: 1304
cacccccagga ccttccctgg gcagaacgag ttggtgaggg agtgatgagc aaccacaggc   60
ctcctaactt cccaagctgg cgattctgag aggcctcaag                         100

SEQ ID NO: 1305         moltype = DNA  length = 100
FEATURE                 Location/Qualifiers
source                  1..100
                        mol_type = genomic DNA
                        organism = Homo sapiens
SEQUENCE: 1305
gctgagacac ggttcagcct tttaggccct cctgaacgtg tccctgtct ccacagcctg     60
ggaatgcact ctcttttgac ccagaaatcc tgctcataag                         100

SEQ ID NO: 1306         moltype = DNA  length = 100
FEATURE                 Location/Qualifiers
source                  1..100
                        mol_type = genomic DNA
                        organism = Homo sapiens
SEQUENCE: 1306
ctgtcattgt acaacacatc atttcacttt gttttttcaaa catagtgaat tctttcctaa   60
ttaaagaaga aaagagtata aagagaaagt ttccagtgca                         100

SEQ ID NO: 1307         moltype = DNA  length = 100
FEATURE                 Location/Qualifiers
source                  1..100
                        mol_type = genomic DNA
                        organism = Homo sapiens
SEQUENCE: 1307
gtataaagag aaagtttcca gtgcagcctg gagatctgta ctggttgtat ctggaattcc    60
agctcagcc ttgcatttca catagcagat agatgatgat                          100

SEQ ID NO: 1308         moltype = DNA  length = 100
FEATURE                 Location/Qualifiers
source                  1..100
                        mol_type = genomic DNA
                        organism = Homo sapiens
SEQUENCE: 1308
```

```
gatggagaag gagaagaaga aggaggagga ggaggaaaga aggaagaaga agaagaagag    60
gaggaggaag aagaagacga agggaagaag aagaaggatg                         100

SEQ ID NO: 1309         moltype = DNA   length = 100
FEATURE                 Location/Qualifiers
source                  1..100
                        mol_type = genomic DNA
                        organism = Homo sapiens
SEQUENCE: 1309
tccaggtctg ccaggtgtag gggaggtgtg actggttcca tcatggaccg gttcctccat    60
ggaccggttc ctccgtggac cggttccgcc atggaccggt                         100

SEQ ID NO: 1310         moltype = DNA   length = 100
FEATURE                 Location/Qualifiers
source                  1..100
                        mol_type = genomic DNA
                        organism = Homo sapiens
SEQUENCE: 1310
tccgccatgg accactcctg ccctggacca ctcctgccct ggaccggttc tgccgtggac    60
tggttcccgc cgtggaccag ttcccgctgt atactggttc                         100

SEQ ID NO: 1311         moltype = DNA   length = 100
FEATURE                 Location/Qualifiers
source                  1..100
                        mol_type = genomic DNA
                        organism = Homo sapiens
SEQUENCE: 1311
tgccctggac tggttcccgc tgtggactgg ttccttgggg ctctaagtgc ggaagggccc    60
agagctggtc cctgcccagc gccctgctag ggctgtgtcc                         100

SEQ ID NO: 1312         moltype = DNA   length = 100
FEATURE                 Location/Qualifiers
source                  1..100
                        mol_type = genomic DNA
                        organism = Homo sapiens
SEQUENCE: 1312
tcgtactcgt gcgcctcgct tcggtgagcc ccagggcccc tgcctccttc ctcctgccgt    60
cctgcctccg tcccgccct ttcatcatcc gcgtccctgt                          100

SEQ ID NO: 1313         moltype = DNA   length = 100
FEATURE                 Location/Qualifiers
source                  1..100
                        mol_type = genomic DNA
                        organism = Homo sapiens
SEQUENCE: 1313
gaaggcattc cctaaatccg agcccgagtg gttctccccg ggaaggctac tttggggagc    60
tgggggatg cgaaacaccc tagatactgg ataatgggt                           100

SEQ ID NO: 1314         moltype = DNA   length = 100
FEATURE                 Location/Qualifiers
source                  1..100
                        mol_type = genomic DNA
                        organism = Homo sapiens
SEQUENCE: 1314
ggggaaatcg atgatttaag aacaaaaccg aaaaactggc gttttgccgt gccgctcgga    60
ggggacatta aaaatttct tagtgtttgc ccgcaaaggt                          100

SEQ ID NO: 1315         moltype = DNA   length = 100
FEATURE                 Location/Qualifiers
source                  1..100
                        mol_type = genomic DNA
                        organism = Homo sapiens
SEQUENCE: 1315
tagtgtttgc ccgcaaaggt attgtgcgtt gccttggagg ctgagatatg ggggaataga    60
caagtccttt gttctgaggt tcatcttccg agccccgagc                         100

SEQ ID NO: 1316         moltype = DNA   length = 100
FEATURE                 Location/Qualifiers
source                  1..100
                        mol_type = genomic DNA
                        organism = Homo sapiens
SEQUENCE: 1316
ctcctcccag cctcggacgg ctgcgcgggc tgcatctgtg cagcctggcg gcggcgggc     60
tgtgctatga catctttaca gtccttcttg cagagacatg                         100

SEQ ID NO: 1317         moltype = DNA   length = 100
FEATURE                 Location/Qualifiers
source                  1..100
                        mol_type = genomic DNA
```

```
                        organism = Homo sapiens
SEQUENCE: 1317
tgtgccaggg atgccgaatt gccgggagag caggcaagac cggcttcggg gcgcgcggcg    60
gccgctttgt gtgcggggct gcattgtgac gcgggcgatg                         100

SEQ ID NO: 1318         moltype = DNA   length = 100
FEATURE                 Location/Qualifiers
source                  1..100
                        mol_type = genomic DNA
                        organism = Homo sapiens
SEQUENCE: 1318
aagccggtag ggcggtggtc ggaagctcca gccgcggccg ccgcctttgt gagaggacta    60
gaaagccgga tccggcccgc atccttgcgg agaggccgcg                         100

SEQ ID NO: 1319         moltype = DNA   length = 100
FEATURE                 Location/Qualifiers
source                  1..100
                        mol_type = genomic DNA
                        organism = Homo sapiens
SEQUENCE: 1319
gctaggaaat ggaaacgctt ttcctacctg ggctccattt taggaattct tgccgatttt    60
tcccacttga atttggaagt ggctttcctc ttctttcctt                         100

SEQ ID NO: 1320         moltype = DNA   length = 100
FEATURE                 Location/Qualifiers
source                  1..100
                        mol_type = genomic DNA
                        organism = Homo sapiens
SEQUENCE: 1320
gtcctagcca gcctttaatt ttaaacgctg taattaacaa ttcgcagtgg tcaatttcct    60
ttattctgca agattcggct ttgagaggca tccgccctct                         100

SEQ ID NO: 1321         moltype = DNA   length = 100
FEATURE                 Location/Qualifiers
source                  1..100
                        mol_type = genomic DNA
                        organism = Homo sapiens
SEQUENCE: 1321
ttggtccaca gcgttttgaa atatggggag gaggggcgcg ggggtgtcg cctcttttc     60
tgtagaaaga ggaagctcgt gagcgcggaa cggcagcagt                         100

SEQ ID NO: 1322         moltype = DNA   length = 100
FEATURE                 Location/Qualifiers
source                  1..100
                        mol_type = genomic DNA
                        organism = Homo sapiens
SEQUENCE: 1322
aagtgcagtt cccagcccag agacagcggg gcgggtggct cttcctcacg ctcgctcttg    60
gcttgctccc tgcagctttt cctccgcaac catgtctgac                         100

SEQ ID NO: 1323         moltype = DNA   length = 100
FEATURE                 Location/Qualifiers
source                  1..100
                        mol_type = genomic DNA
                        organism = Homo sapiens
SEQUENCE: 1323
aaacccgata tggctgagat cgagaaattc gataagtcga aactgaagaa gacagagacg    60
caagagaaaa atccactgcc ttccaaagaa agtgagctcc                         100

SEQ ID NO: 1324         moltype = DNA   length = 100
FEATURE                 Location/Qualifiers
source                  1..100
                        mol_type = genomic DNA
                        organism = Homo sapiens
SEQUENCE: 1324
agacgcaaga gaaaatcca ctgccttcca agaaagtga gctccgaccc accccatct      60
ttagaaaggc tgggtgggag cggccggtgg gagggcggga                         100

SEQ ID NO: 1325         moltype = DNA   length = 100
FEATURE                 Location/Qualifiers
source                  1..100
                        mol_type = genomic DNA
                        organism = Homo sapiens
SEQUENCE: 1325
tttatagaaa ggcatatgga acaggagtca tccaaatata tcccaggggt tgcaaattga    60
ccaaaagagt cacctttagg gaagcctgct tctgaatgct                         100

SEQ ID NO: 1326         moltype = DNA   length = 100
FEATURE                 Location/Qualifiers
```

```
source                  1..100
                        mol_type = genomic DNA
                        organism = Homo sapiens
SEQUENCE: 1326
tgtggaattt atcattcttc tgaatggctg ttgcatttat ctgcagcttt tactcaccag    60
atgagacctc agacatttca aattctgcgg aggctggcta                         100

SEQ ID NO: 1327         moltype = DNA  length = 100
FEATURE                 Location/Qualifiers
source                  1..100
                        mol_type = genomic DNA
                        organism = Homo sapiens
SEQUENCE: 1327
cacaccttca taggaaagct ttttgctgat ttccctgttg gtacttttct cttacacatt    60
ctatggggta tggtaaacct ggaggtagag tcatagccaa                         100

SEQ ID NO: 1328         moltype = DNA  length = 100
FEATURE                 Location/Qualifiers
source                  1..100
                        mol_type = genomic DNA
                        organism = Homo sapiens
SEQUENCE: 1328
gcacagataa agcaggcaca gaatctctga ccagcctcac aaaagcagac aaacacacaa    60
tcttttgca cctgtttctt ccactccggt tgccgtgaat                          100

SEQ ID NO: 1329         moltype = DNA  length = 100
FEATURE                 Location/Qualifiers
source                  1..100
                        mol_type = genomic DNA
                        organism = Homo sapiens
SEQUENCE: 1329
tagaaatggt tcaaccagtc caatatcaat atagctgctt attactctat tcacttactt    60
caaagtggca tttgttttga gtaagacttt atttaattct                         100

SEQ ID NO: 1330         moltype = DNA  length = 100
FEATURE                 Location/Qualifiers
source                  1..100
                        mol_type = genomic DNA
                        organism = Homo sapiens
SEQUENCE: 1330
taccgttagc ttgaaaccat agagatcttc tctctatttg ccctacttcc ttcaaaagtc    60
aaatgacctc ctacaaataa aagacgttct tattttcatt                         100

SEQ ID NO: 1331         moltype = DNA  length = 150
FEATURE                 Location/Qualifiers
source                  1..150
                        mol_type = genomic DNA
                        organism = Homo sapiens
SEQUENCE: 1331
cgactacgac tcggtgcagc cgtatttcta ctgcgacgag gaggagaact tctaccagca    60
gcagcagcag agcgagctgc agccccggc gcccagcgag gatatctgga agaaattcga   120
gctgctgccc accccgcccc tgtcccctag                                    150

SEQ ID NO: 1332         moltype = DNA  length = 150
FEATURE                 Location/Qualifiers
source                  1..150
                        mol_type = genomic DNA
                        organism = Homo sapiens
SEQUENCE: 1332
cgactacgac tcggtgcagc cgtagttcta ctgcgacgag gaggaaaact tctaccagca    60
gcagcagcag agcgagctgc agccctggc gcccagcgag gatatctgga agaacttcga   120
gctgctgccc accccgcccc tgtcccctag                                    150

SEQ ID NO: 1333         moltype = DNA  length = 150
FEATURE                 Location/Qualifiers
source                  1..150
                        mol_type = genomic DNA
                        organism = Homo sapiens
SEQUENCE: 1333
cgactacgac tcggtgcagc cgtagttcta ctgcgacgag gaggaatact tctaccagca    60
gcagccgcag agcgagctgc agccctggc gcccagcgag ggtatctgga agaacttcga   120
gctactgccc accccgcccc tgtcccctag                                    150

SEQ ID NO: 1334         moltype = DNA  length = 150
FEATURE                 Location/Qualifiers
source                  1..150
                        mol_type = genomic DNA
                        organism = Homo sapiens
SEQUENCE: 1334
```

```
cgactacgac tcgttgcagc cgtagttcta ctgcgacgag gaggaatact tctaccagca    60
gcagccgcag agcgagctgc agcgcctggc gcccagcgag ggtatctgga agaacttcga   120
gctacagccc accccgcccc tgtcccctag                                    150

SEQ ID NO: 1335         moltype = DNA   length = 150
FEATURE                 Location/Qualifiers
source                  1..150
                        mol_type = genomic DNA
                        organism = Homo sapiens
SEQUENCE: 1335
cgactacgac tcgttgcagc cgtagatcta ctgcgacgag gaggaatact tctacctgca    60
gcagccgcag agcgagctgc agcgcctggc gcccagcgag cgtatctgga agaacttcga   120
gctacagccc accccgccct tgtcccctag                                    150

SEQ ID NO: 1336         moltype = DNA   length = 150
FEATURE                 Location/Qualifiers
source                  1..150
                        mol_type = genomic DNA
                        organism = Homo sapiens
SEQUENCE: 1336
cgacaacgac tcgttgcacc cgtagatcta ctgcgacgag gaggaatact tctacctgca    60
gcagccgcag agcgagctgc agcgcctggc gcccagcgag cgtatctgaa agaacttcga   120
gctacagccc acgccgccct tgtcccctag                                    150

SEQ ID NO: 1337         moltype = DNA   length = 150
FEATURE                 Location/Qualifiers
source                  1..150
                        mol_type = genomic DNA
                        organism = Homo sapiens
SEQUENCE: 1337
cgacaacgac tcgttgcacc cgtagatcta ctgcgacgag gaggaatact tctacctgca    60
gcagccgcag agcgagctgc agcgcctggc gcccagcgag cgtatctgaa agaacttcga   120
gctacagccc acgccgccct tgtcccctag                                    150

SEQ ID NO: 1338         moltype = DNA   length = 150
FEATURE                 Location/Qualifiers
source                  1..150
                        mol_type = genomic DNA
                        organism = Homo sapiens
SEQUENCE: 1338
gctcacctgt acaaatctgg ctccgcaggt ttcgcatttg tagggcttct ctccagagtg    60
aattcgagtg tgggttttca ggttggctgg ccggttgaac tgggcccac agatgttgca   120
acgatagggt ttctcaccta ttaccaagaa                                    150

SEQ ID NO: 1339         moltype = DNA   length = 150
FEATURE                 Location/Qualifiers
source                  1..150
                        mol_type = genomic DNA
                        organism = Homo sapiens
SEQUENCE: 1339
gctcacctgt acaaatctgc ctccgcaggt ttcgcatttg tagggctcct ctccagagtg    60
aattcgagtg tgggttttca ggttggctgg gcggttgaac tgggcccac agatgttgca   120
acgctagggt ttctcaccta ttaccaagaa                                    150

SEQ ID NO: 1340         moltype = DNA   length = 150
FEATURE                 Location/Qualifiers
source                  1..150
                        mol_type = genomic DNA
                        organism = Homo sapiens
SEQUENCE: 1340
gctcacctgt acaaatctgc ctccgcaggt ttcgcctttg tagggctcct ctccagagtg    60
aattcgagtg taggttttca agttggctgg gcggttgaac tgggcccac ggatgttgca   120
acgctagggt ttctcaccta ttaccaagaa                                    150

SEQ ID NO: 1341         moltype = DNA   length = 150
FEATURE                 Location/Qualifiers
source                  1..150
                        mol_type = genomic DNA
                        organism = Homo sapiens
SEQUENCE: 1341
gctcacctgt acaaatctgc ctccgccggt ttcgcctttt tagggctcct ctccagagtg    60
aattcgagtg taggttttca agttggctgg gcggttgaac tgggcccac ggatgttgca   120
acgctagggt ttctcaccta tttccaagaa                                    150

SEQ ID NO: 1342         moltype = DNA   length = 150
FEATURE                 Location/Qualifiers
source                  1..150
                        mol_type = genomic DNA
                        organism = Homo sapiens
```

```
SEQUENCE: 1342
gctcacctgt acaagtctgc ctccgccggt tacgccttt tagggctcct ctccagagtg    60
aattcgagtg taggttttca agttggctgg gcggttgaac tgggctccac ggatgttgca   120
acgctaggga ttctcaccta tttccaagaa                                    150

SEQ ID NO: 1343         moltype = DNA   length = 150
FEATURE                 Location/Qualifiers
source                  1..150
                        mol_type = genomic DNA
                        organism = Homo sapiens
SEQUENCE: 1343
gctcacctgg acaagtctgc ctccgccggt tacgactttt tagggctcct ctccagagtg    60
aattcgagtg taggctttca agttggctgg gcggttgaac tgggctccac ggctgttgca   120
acgctaggga ttctcaccta tttccaagaa                                    150

SEQ ID NO: 1344         moltype = DNA   length = 150
FEATURE                 Location/Qualifiers
source                  1..150
                        mol_type = genomic DNA
                        organism = Homo sapiens
SEQUENCE: 1344
gctcacctgg acaagtctgc ctccgccggt tacgactttt tagggcacct ctccagagtg    60
aattcgagtg taggctttca agttggctgg gagcttgaac tgggctgcac ggctgttgca   120
acgctaggga ttctcaccta tttccaagaa                                    150

SEQ ID NO: 1345         moltype = DNA   length = 150
FEATURE                 Location/Qualifiers
source                  1..150
                        mol_type = genomic DNA
                        organism = Homo sapiens
SEQUENCE: 1345
ctaggggaca ggggcggggt gggcagcagc tcgaatttct tccagatatc ctcgctgggc    60
gccgggggct gcagctcgct ctgctgctgc tgctggtaga agttctcctc ctcgtcgcag   120
tagaaatacg gctgcaccga gtcgtagtcg                                    150

SEQ ID NO: 1346         moltype = DNA   length = 150
FEATURE                 Location/Qualifiers
source                  1..150
                        mol_type = genomic DNA
                        organism = Homo sapiens
SEQUENCE: 1346
ctaggggaca ggggcggggt gggcagcagc tcgaagttct tccagatatc ctcgctgggc    60
gccaggggct gcagctcgct ctgctgctgc tgctggtaga agttttcctc ctcgtcgcag   120
tagaactacg gctgcaccga gtcgtagtcg                                    150

SEQ ID NO: 1347         moltype = DNA   length = 150
FEATURE                 Location/Qualifiers
source                  1..150
                        mol_type = genomic DNA
                        organism = Homo sapiens
SEQUENCE: 1347
ctaggggaca ggggcggggt gggcagtagc tcgaagttct tccagatacc ctcgctgggc    60
gccaggggct gcagctcgct ctgcggctgc tgctggtaga agtattcctc ctcgtcgcag   120
tagaactacg gctgcaccga gtcgtagtcg                                    150

SEQ ID NO: 1348         moltype = DNA   length = 150
FEATURE                 Location/Qualifiers
source                  1..150
                        mol_type = genomic DNA
                        organism = Homo sapiens
SEQUENCE: 1348
ctaggggaca ggggcggggt gggctgtagc tcgaagttct tccagatacc ctcgctgggc    60
gccaggcgct gcagctcgct ctgcggctgc tgctggtaga agtattcctc ctcgtcgcag   120
tagaactacg gctgcaacga gtcgtagtcg                                    150

SEQ ID NO: 1349         moltype = DNA   length = 150
FEATURE                 Location/Qualifiers
source                  1..150
                        mol_type = genomic DNA
                        organism = Homo sapiens
SEQUENCE: 1349
ctaggggaca agggcggggt gggctgtagc tcgaagttct tccagatacg ctcgctgggc    60
gccaggcgct gcagctcgct ctgcggctgc tgcaggtaga agtattcctc ctcgtcgcag   120
tagatctacg gctgcaacga gtcgtagtcg                                    150

SEQ ID NO: 1350         moltype = DNA   length = 150
FEATURE                 Location/Qualifiers
source                  1..150
                        mol_type = genomic DNA
```

```
                        organism = Homo sapiens
SEQUENCE: 1350
ctagggaca  agggcggcgt  gggctgtagc  tcgaagttct  ttcagatacg  ctcgctgggc    60
gccaggcgct  gcagctcgct  ctgcggctgc  tgcaggtaga  agtattcctc  ctcgtcgcag   120
tagatctacg  ggtgcaacga  gtcgttgtcg                                      150

SEQ ID NO: 1351         moltype = DNA   length = 150
FEATURE                 Location/Qualifiers
source                  1..150
                        mol_type = genomic DNA
                        organism = Homo sapiens
SEQUENCE: 1351
ctaggcgaca  agggcggcgt  gggctgtagc  tcgaagttct  ttcagatacg  ctcggtgggc    60
gccaggcgct  gcagcacgct  ctgcggctgc  tgcaggtaga  agtattcctc  ctcgtcgcag   120
tagatctacg  ggtgcaacga  gtcgctgtcg                                      150

SEQ ID NO: 1352         moltype = DNA   length = 150
FEATURE                 Location/Qualifiers
source                  1..150
                        mol_type = genomic DNA
                        organism = Homo sapiens
SEQUENCE: 1352
ttcttggtaa  taggtgagaa  accctatcgt  tgcaacatct  gtggggccca  gttcaaccgg    60
ccagccaacc  tgaaaaccca  cactcgaatt  cactctggag  agaagcccta  caaatgcgaa   120
acctgcggag  ccagatttgt  acaggtgagc                                      150

SEQ ID NO: 1353         moltype = DNA   length = 150
FEATURE                 Location/Qualifiers
source                  1..150
                        mol_type = genomic DNA
                        organism = Homo sapiens
SEQUENCE: 1353
ttcttggtaa  taggtgagaa  accctagcgt  tgcaacatct  gtggggccca  gttcaaccgc    60
ccagccaacc  tgaaaaccca  cactcgaatt  cactctggag  aggagcccta  caaatgcgaa   120
acctgcggag  gcagatttgt  acaggtgagc                                      150

SEQ ID NO: 1354         moltype = DNA   length = 150
FEATURE                 Location/Qualifiers
source                  1..150
                        mol_type = genomic DNA
                        organism = Homo sapiens
SEQUENCE: 1354
ttcttggtaa  taggtgagaa  accctagcgt  tgcaacatcc  gtggggccca  gttcaaccgc    60
ccagccaact  tgaaaaccta  cactcgaatt  cactctggag  aggagcccta  caaaggcgaa   120
acctgcggag  gcagatttgt  acaggtgagc                                      150

SEQ ID NO: 1355         moltype = DNA   length = 150
FEATURE                 Location/Qualifiers
source                  1..150
                        mol_type = genomic DNA
                        organism = Homo sapiens
SEQUENCE: 1355
ttcttggaaa  taggtgagaa  accctagcgt  tgcaacatcc  gtggggccca  gttcaaccgc    60
ccagccaact  tgaaaaccta  cactcgaatt  cactctggag  aggagcccta  aaaaggcgaa   120
accggcggag  gcagatttgt  acaggtgagc                                      150

SEQ ID NO: 1356         moltype = DNA   length = 150
FEATURE                 Location/Qualifiers
source                  1..150
                        mol_type = genomic DNA
                        organism = Homo sapiens
SEQUENCE: 1356
ttcttggaaa  taggtgagaa  tccctagcgt  tgcaacatcc  gtggagccca  gttcaaccgc    60
ccagccaact  tgaaaaccta  cactcgaatt  cactctggag  aggagcccta  aaaaggcgta   120
accggcggag  gcagacttgt  acaggtgagc                                      150

SEQ ID NO: 1357         moltype = DNA   length = 150
FEATURE                 Location/Qualifiers
source                  1..150
                        mol_type = genomic DNA
                        organism = Homo sapiens
SEQUENCE: 1357
ttcttggaaa  taggtgagaa  tccctagcgt  tgcaacagcc  gtggagccca  gttcaaccgc    60
ccagccaact  tgaaagccta  cactcgaatt  cactctggag  aggagcccta  aaaagtcgta   120
accggcggag  gcagacttgt  ccaggtgagc                                      150

SEQ ID NO: 1358         moltype = DNA   length = 150
FEATURE                 Location/Qualifiers
source                  1..150
```

```
                    mol_type = genomic DNA
                    organism = Homo sapiens
SEQUENCE: 1358
ttcttggaaa taggtgagaa tccctagcgt tgcaacagcc gtgcagccca gttcaagctc    60
ccagccaact tgaaagccta cactcgaatt cactctggag aggtgcccta aaaagtcgta   120
accggcggag gcagacttgt ccaggtgagc                                    150
```